US012807578B2

(12) United States Patent
Jones et al.

(10) Patent No.: US 12,807,578 B2
(45) Date of Patent: Nov. 24, 2026

(54) METHYL-SUBSTITUTED PYRIDINE AND PYRIDAZINE COMPOUNDS, DERIVATIVES THEREOF, AND METHODS OF THEIR USE

(71) Applicants: LATIGO BIOTHERAPEUTICS, INC., Thousand Oaks, CA (US); LIEBER INSTITUTE, INC., Baltimore, MD (US)

(72) Inventors: Robert M. Jones, Oakley, UT (US); Ashok Bajji, Thousand Oaks, CA (US); Nathaniel Julius Thomas Monck, Abingdon (GB); Suzanne J. O'Connor, Abingdon (GB); William H. Gardiner, Oxfordshire (GB); Robert James Townsend, Oxfordshire (GB); Andreina Pacheco Pita, Abingdon (GB); Michael Brunavs, Oxfordshire (GB); Abdul Kadar Shaikh, Abingdon (GB); Jonathan Paul Shine, Oxfordshire (GB); Ian James Wigginton, Oxfordshire (GB); Jonathan Philip Richards, Oxfordshire (GB); Marco Michele Mastandrea, Oxfordshire (GB); Adam James Davenport, Abingdon (GB); Bryan Moyer, Thousand Oaks, CA (US); Michael Poslusney, Baltimore, MD (US); James Barrow, Baltimore, MD (US); Richard Edmund Rathmell, Abingdon (GB)

(73) Assignees: LATIGO BIOTHERAPEUTICS, INC., Thousand Oaks, CA (US); LIEBER INSTITUTE, INC., Baltimore, MD (US)

( * ) Notice: Subject to any disclaimer, the term of this patent is extended or adjusted under 35 U.S.C. 154(b) by 406 days.

(21) Appl. No.: 18/280,891

(22) PCT Filed: Mar. 10, 2022

(86) PCT No.: PCT/US2022/019673

§ 371 (c)(1),
(2) Date: Sep. 7, 2023

(87) PCT Pub. No.: WO2022/192487

PCT Pub. Date: Sep. 15, 2022

(65) Prior Publication Data

US 2024/0336574 A1 Oct. 10, 2024

Related U.S. Application Data

(60) Provisional application No. 63/252,469, filed on Oct. 5, 2021, provisional application No. 63/252,459, filed (Continued)

(51) Int. Cl.

| | |
|---|---|
| ***C07D 237/24*** | (2006.01) |
| ***A61K 31/455*** | (2006.01) |

(Continued)

(52) U.S. Cl.

CPC .......... *C07D 237/24* (2013.01); *A61K 31/455* (2013.01); *A61K 31/4725* (2013.01);

(Continued)

(58) Field of Classification Search

CPC .. C07D 237/24; C07D 213/82; C07D 237/26; C07D 239/26; C07D 241/24; C07D 401/04; C07D 401/12; C07D 403/04; C07D 403/12; C07D 403/14; C07D 405/04; C07D 405/12; C07D 413/12; C07D 417/04; C07D 417/12; C07D 471/04; A61K 31/5377; A61K 31/455; A61K 31/4725;

(Continued)

(56) References Cited

U.S. PATENT DOCUMENTS

| | | | |
|---|---|---|---|
| 4,166,452 | A | 9/1979 | Generales, Jr. |
| 4,256,108 | A | 3/1981 | Theeuwes |

(Continued)

FOREIGN PATENT DOCUMENTS

| | | | |
|---|---|---|---|
| WO | 2011/026240 | A1 | 3/2011 |
| WO | 2012/106499 | A1 | 8/2012 |

(Continued)

OTHER PUBLICATIONS

Flynn, G. L., and Samuel H. Yalkowsky. "Correlation and prediction of mass transport across membranes I: Influence of alkyl chain length on flux-determining properties of barrier and diffusant." Journal of pharmaceutical sciences 61, No. 6 (1972): 838-852 (Year: 1972).*

Akopian, 1999, The tetrodotoxin-resistant sodium channel SNS has a specialized function in pain pathways, Nat Neurosci, 2(6):541-548.

Bagal, 2014, Recent progress in sodium channel modulators for pain, Bioorganic & Medicinal Chemistry Letters, 24(16):3690-3699.

(Continued)

*Primary Examiner* — James H Alstrum-Acevedo
*Assistant Examiner* — Carolyn L. Ladd
(74) *Attorney, Agent, or Firm* — Brown Rudnick LLP; Adam M. Schoen

(57) ABSTRACT

The invention provides methyl-substituted pyridine and pyridazine compounds, derivatives thereof, and methods of their use. The compounds of the invention are useful for treatment of conditions associated with $NaV_{1.8}$ sodium channels. The compounds are useful as pharmacological agents to treat a variety of conditions, including various pain states, itch, and cough for patients suffering from these conditions.

12 Claims, 1 Drawing Sheet

Related U.S. Application Data on Oct. 5, 2021, provisional application No. 63/237,368, filed on Aug. 26, 2021, provisional application No. 63/196,715, filed on Jun. 4, 2021, provisional application No. 63/196,713, filed on Jun. 4, 2021, provisional application No. 63/185,692, filed on May 7, 2021, provisional application No. 63/185,164, filed on May 6, 2021, provisional application No. 63/159,720, filed on Mar. 11, 2021, provisional application No. 63/159,718, filed on Mar. 11, 2021.

(51) Int. Cl.

| | |
|---|---|
| ***A61K 31/4725*** | (2006.01) |
| ***A61K 31/50*** | (2006.01) |
| ***A61K 31/501*** | (2006.01) |
| ***A61K 31/502*** | (2006.01) |
| ***A61K 31/506*** | (2006.01) |
| ***A61K 31/5377*** | (2006.01) |
| ***A61K 45/06*** | (2006.01) |
| ***C07D 213/82*** | (2006.01) |
| ***C07D 237/26*** | (2006.01) |
| ***C07D 239/26*** | (2006.01) |
| ***C07D 241/24*** | (2006.01) |
| ***C07D 401/04*** | (2006.01) |
| ***C07D 401/12*** | (2006.01) |
| ***C07D 403/04*** | (2006.01) |
| ***C07D 403/12*** | (2006.01) |
| ***C07D 403/14*** | (2006.01) |
| ***C07D 405/04*** | (2006.01) |
| ***C07D 405/12*** | (2006.01) |
| ***C07D 413/12*** | (2006.01) |
| ***C07D 417/04*** | (2006.01) |
| ***C07D 417/12*** | (2006.01) |
| ***C07D 471/04*** | (2006.01) |

(52) U.S. Cl.

CPC ............ *A61K 31/50* (2013.01); *A61K 31/501* (2013.01); *A61K 31/502* (2013.01); *A61K 31/506* (2013.01); *A61K 31/5377* (2013.01); *A61K 45/06* (2013.01); *C07D 213/82* (2013.01); *C07D 237/26* (2013.01); *C07D 239/26* (2013.01); *C07D 241/24* (2013.01); *C07D 401/04* (2013.01); *C07D 401/12* (2013.01); *C07D 403/04* (2013.01); *C07D 403/12* (2013.01); *C07D 403/14* (2013.01); *C07D 405/04* (2013.01); *C07D 405/12* (2013.01); *C07D 413/12* (2013.01); *C07D 417/04* (2013.01); *C07D 417/12* (2013.01); *C07D 471/04* (2013.01)

(58) Field of Classification Search

CPC .... A61K 31/50; A61K 31/501; A61K 31/502; A61K 31/506; A61K 45/06

See application file for complete search history.

(56) References Cited

U.S. PATENT DOCUMENTS

| | | | |
|---|---|---|---|
| 4,265,874 | A | 5/1981 | Bonsen et al. |
| 6,214,841 | B1 | 4/2001 | Jackson et al. |
| 7,705,031 | B2 | 4/2010 | Wilson et al. |
| 7,989,481 | B2 | 8/2011 | Neubert et al. |
| 8,236,829 | B2 | 8/2012 | Neubert et al. |
| 8,236,833 | B2 | 8/2012 | Martinborough et al. |
| 8,309,543 | B2 | 11/2012 | Gonzalez, III et al. |
| 8,314,125 | B2 | 11/2012 | Termin et al. |
| 8,466,188 | B2 | 6/2013 | Chafeev et al. |
| 8,492,403 | B2 | 7/2013 | Kawatkar et al. |
| 8,536,195 | B2 | 9/2013 | Termin et al. |
| 8,883,840 | B2 | 11/2014 | Chafeev et al. |
| 9,783,501 | B2 | 10/2017 | Hadida-Ruah et al. |
| 9,828,397 | B2 | 11/2017 | Anderson et al. |
| 9,969,693 | B2 | 5/2018 | Bogdan et al. |
| 10,000,475 | B2 | 6/2018 | Tadesse et al. |
| 10,005,724 | B2 | 6/2018 | Andrez et al. |
| 10,005,768 | B2 | 6/2018 | Yao et al. |
| 12,234,221 | B2 * | 2/2025 | Poslusney ............... A61P 29/00 |
| 2003/0232877 | A1 | 12/2003 | Sikorski et al. |
| 2016/0152561 | A1 | 6/2016 | Hadida-Ruah et al. |

FOREIGN PATENT DOCUMENTS

| | | | |
|---|---|---|---|
| WO | 2012/112743 | A1 | 8/2012 |
| WO | 2012/116440 | A1 | 9/2012 |
| WO | 2012/125613 | A1 | 9/2012 |
| WO | 2020/014243 | A1 | 1/2020 |
| WO | 2020/014246 | A1 | 1/2020 |
| WO | 2020/092187 | A1 | 5/2020 |
| WO | 2020/146682 | A1 | 7/2020 |
| WO | 2021/140425 | A1 | 7/2021 |

OTHER PUBLICATIONS

Bagal, 2015, Discovery and Optimization of Selective Nav1.8 Modulator Series that Demonstrate Efficacy in Preclinical Models of Pain, Acs Med Chem Lett, 6(6):650-654.

Black, 2000, Sensory neuron-specific sodium channel SNS is abnormally expressed in the brains of mice with experimental allergic encephalomyelitis and humans with multiple sclerosis, P Natl Acad Sci USA, 97(21):11598-11602.

Bucknill, 2002, Nerve fibers in lumbar spine structures and injured spinal roots express the sensory neuron-specific sodium channels SNS/PN3 and NaN/SNS2, Spines, 27(2):135-140.

Catterall, 2012, Voltage-gated sodium channels at 60: structure, function and pathophysiology, J Physiol-London, 590 (11):2577-2589.

Deuis, 2017, The pharamcology of voltage-gated sodium channel activators, Neuropharmacology, 127:109 pages.

Eijkelkamp, 2012, Neurological perspectives on voltage-gated sodium channels, Brain, 135:2585-2612.

Faber, 2012, Gain-of-function Nav1.8 mutations in painful neuropathy, Proceedings of the National Academy of Sciences, 107(47):19444-19449.

Flynn, 1972, Correlation and Prediction of Mass Transport across Membranes I:Influence of Alky Chain Length on Flux-Determining Properties of Barrier and Diffusant, Journal of Pharmaceutical Sciences, 61(6):838-852.

International Search Report and Written Opinion issued in International Application No. PCT/US2022/19673, date of mailing: Jul. 7, 2022, 11 pages.

Jarvis, 2007, A-803467, a potent and selective Nav1.8 sodium channel blocker, attenuates neuropathic and inflammatory pain in the rat, P Natl Acad Sci USA, 104(20):8520-8525.

Kort, 2008, Discovery and biological evaluation of 5-aryl-2-furfuramides, potent and selective blockers of the Nav1.8 sodium channel with efficacy in models of neuropathic and inflammatory pain, J Med Chem, 51(3):407-416.

Kull, 1961, Mixtures of Quaternary Ammonium Compounds and Long-chain Fatty Acids as Antifungal Agents, Applied Microbiology, 9:538-541.

Payne, 2015, A novel selective and orally bioavailable Nav1.8 channel blocker, PF-01247324, attenuates nociception and sensory neuron excitability, Brit J Pharmacol, 172(10):2654-2670.

PubChem-SID-378917918, Modify Date: Jun. 3, 2016, 7 pages.

Rannals, 2016, Psychiatric Risk Gene Transcription Factor 4 Regulates Intrinsic Excitability of Prefrontal Neurons via Repression of SCN10a and KCNQ1, Neuron, 90(1):43-55.

Renton, 2005, Sodium channel Nav1.8 immunoreactivity in painful human dental pulp, BMC oral health, 5(5):1-6.

Ruiz, 2015, Voltage-Gated Sodium Channels: Structure, Function, Pharmacology, and Clinical Indications, J Med Chem, 58(18):7093-7118.

(56) References Cited

OTHER PUBLICATIONS

Shields, 2015, Oral Administration of PF-01247324, a Subtype-Selective Nav1.8 Blocker, Reverses Cerebellar Deficits in a Mouse Model of Multiple Sclerosis, Plos One, 10(3):1-8.
Skolnick, 2018, The Opioid Epidemic: Crisis and Solutions, Annual Review of Pharmacology and Toxicology, 58:143-159.
Sweatt, 2013, Pitt-Hopkins Syndrome: intellectual disability due to loss of TCF4-regulated gene transcription, Exp Mol Med, 45, e21, 15 pages.
Vetter, 2017, Na(V)1.7 as a pain target—From gene to pharmacology, Pharmacology & Therapeutics, 172, 117 pages.
Yekkirala, 2017, Breaking barriers to novel analgesic drug development, Nat Rev Discov, 16(8):544-563.
Yu, 2003, Overview of the voltage-gated sodium channel family, Genome Biol, 4(207)1-7.
Zakrzewska, 2017, Safety and efficacy of a Nav1.7 selective sodium channel blocker in patients with trigeminal neuralgia: a double-blind, pacebo-controlled, randomised withdrawal phase 2a trial, The Lancet Neurology, 16(4):291-300.
Zhang, 2010, A-887826 is a structurally novel, potent and voltage-dependent Nav1.8 sodium channel blocker that attenuates neuropathic tactile allodynia in rats, Neuropharmacology, 59(3):201-207.

* cited by examiner

PROTOCOL 1
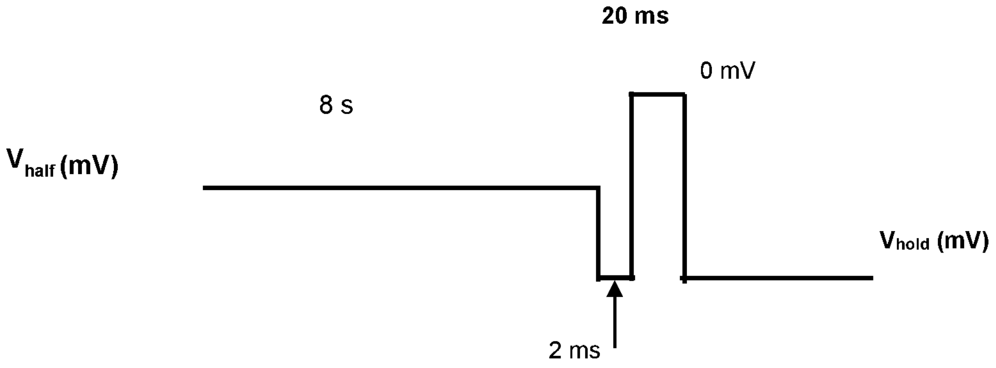

METHYL-SUBSTITUTED PYRIDINE AND PYRIDAZINE COMPOUNDS, DERIVATIVES THEREOF, AND METHODS OF THEIR USE

I. FIELD OF THE INVENTION

The application relates generally to methyl-substituted pyridine and pyridazine compounds, derivatives thereof, and the use of such compounds as pharmacological agents.

II. BACKGROUND

Millions of people suffer from conditions associated with pain, itch, and/or cough. In many cases, drugs used to treat such condition fail to provide relief or produce intolerable side effects. Therefore, existing treatments are inadequate for many patients who suffer from a variety of conditions.

III. SUMMARY

The invention provides compounds that are useful for treatment of conditions associated with aberrant activity of voltage-gated $Na_V1.8$ sodium channels, such as pain, itch, and cough.

A. First Set of Compounds

In an aspect, the invention provides compounds of Formula (I):

(I)

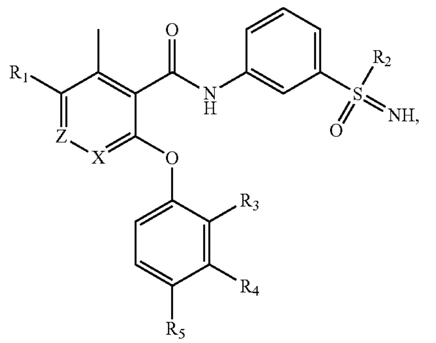

wherein:

- $R_1$ is —CN, —$CF_3$, an optionally substituted 5 or 6 ring membered ring, including aryl or heteroaryl rings, wherein the 5 or 6 ring membered ring optionally includes one or more N or S in the ring, wherein the substitutions on the 5 or 6 ring membered ring are selected from halogen, alkyl, haloalkyl, alkoxy, haloalkoxy, alkyl sulphonyl, alkyl sulfoximinyl, alkyl sulfonamide, cyano, $CF_3$, $OCF_3$, a fused heterocyclyl in which each ring has 5 or 6 members, a heteroaryl having 5 or 6 ring members, a saturated heterocyclyl, or a partially unsaturated heterocyclyl, each of which is optionally substituted where valency permits
- $R_2$ is alkyl, haloalkyl, alkoxy, or haloalkoxy;
- $R_3$ is halogen, alkyl, or alkoxy;
- $R_4$ is halogen, alkyl, or H;
- $R_5$ is H, halogen, alkyl, haloalkyl, alkoxy, haloalkoxy, alkyl sulphonyl, alkyl sulfoximinyl, alkyl sulfonamide, cyano, $CF_3$, $OCF_3$, a fused heterocyclyl in which each ring has 5 or 6 members, a heteroaryl having 5 or 6 ring members, a saturated heterocyclyl, or a partially unsaturated heterocyclyl, each of which is optionally substituted where valency permits;
- X is CH or N; and
- Z is CH or N, with the proviso that X and Z cannot both be CH, or a pharmaceutically acceptable salt thereof.

$R_2$ may be —$CH_3$, —$CD_3$, or —$CT_3$, wherein D is deuterium and T is tritium.

$R_3$ may be —$CH_3$, —$CD_3$, or —$CT_3$, wherein D is deuterium and T is tritium.

The moieties in $R_5$ may be substituted with alkyl, haloalkyl, alkoxy, haloalkoxy, hydroxyl, or halogen.

The compound of Formula (I) may have the sulfoximine group in the R stereochemical configuration, the S stereochemical configuration, or a mixture of R and S stereochemical configurations.

In another aspect, the invention provides compounds of Formula (II):

(II)

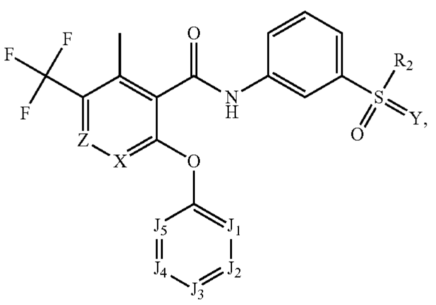

wherein:

- each of $J_1$, $J_2$, $J_4$, and $J_5$ is independently N, N—O, or $CR_6$;
- $J_3$ is N, N—O, or $CR_7$;
- X is CH or N;
- Y is $NR_8$ or O;
- Z is CH, N, or N—O,
- $R_2$ is alkyl, haloalkyl, alkoxy, or haloalkoxy;
- each instance of $R_6$ is independently H, halogen, $C_{1-3}$ alkyl, $C_{3-5}$ cycloalkyl, $C_{1-3}$ alkoxy, $CD_3$ or $CT_3$; and
- $R_7$ is H, halogen, —$CD_3$, alkyl, haloalkyl, alkoxy, haloalkoxy, alkyl sulphonyl, alkyl sulfoximinyl, alkyl sulfonamide, cyano, —$CF_3$, —$OCF_3$, heterocyclyl in which each ring has 5 or 6 members, heteroaryl having 5 or 6 ring members, saturated heterocyclyl, or partially unsaturated heterocyclyl, O-aryl in which each ring has 5 or 6 members, O-heteroaryl in which each ring has 5 or 6 members, O-cycloalkyl, O-cycloheteroalkyl, each of which is optionally substituted where valency permits,
- $R_8$ is H, $C_{1-3}$ alkyl, or $C_{3-5}$ cycloalkyl, acyl, with the provisos that:

- X and Z cannot both be CH; and
- not more than two of $J_1$, $J_2$, $J_3$, $J_4$, and $J_5$ are N or N—O, or a pharmaceutically acceptable salt thereof.

$R_2$ may be —$CH_3$, —$CD_3$, or —$CT_3$, wherein D is deuterium and T is tritium.

The compound of Formula (II) may have the sulfoximine group in the R stereochemical configuration, the S stereochemical configuration, or a mixture of R and S stereochemical configurations.

In another aspect, the invention provides compounds of Formula (III):

(III)

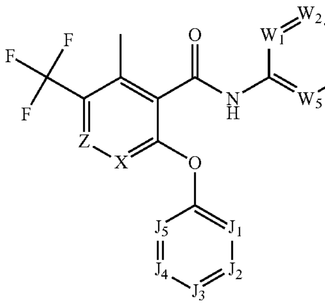

wherein:

each of $J_1$, $J_2$, $J_4$, and $J_5$ is independently N, N—O, or $CR_6$;

$J_3$ is N, N—O, or $CR_7$;

each of $W_1$, $W_2$, $W_3$, $W_4$, and $W_5$ is independently N, CH, or $CR_9$;

X is CH or N;

Z is CH, N, or N—O, each instance of $R_6$ is independently —H, halogen, $C_{1-3}$ alkyl, $C_{3-5}$ cycloalkyl, $C_{1-3}$ alkoxy, $CD_3$ or $CT_3$; and $R_7$ is —H, halogen, —$CD_3$, alkyl, haloalkyl, alkoxy, haloalkoxy, alkyl sulphonyl, alkyl sulfoximinyl, alkyl sulfonamide, cyano, —$CF_3$, —$OCF_3$, carbocyclyl in which each ring has 3-6 members, heterocyclyl in which each ring has 5 or 6 members, heteroaryl having 5 or 6 ring members, saturated heterocyclyl in which each ring has 3 to 6 members, or partially unsaturated heterocyclyl, O-aryl in which each ring has 5 or 6 members, O-heteroaryl in which each ring has 5 or 6 members, O-cycloalkyl, O-cycloheteroalkyl, each of which is optionally substituted where valency permits, each instance of $R_9$ is independently —$C(O)NR_{10}R_{11}$, —$S(O)_2C_{1-6}$ alkyl, —$S(O)(NH)C_{1-6}$ alkyl, $C_{1-3}$ alkyl, or $C_{3-5}$ cycloalkyl; and each of $R_{10}$ and $R_{11}$ is independently selected from —H and $C_{1-5}$ alkyl, or $R_{10}$ and $R_{11}$ together with the nitrogen atom to which they are attached form a heterocyclyl having 3-6 members, in which each of the $C_{1-5}$ alkyl and heterocyclyl is optionally substituted where valency permits, with the provisos that:

not more than two of $J_1$, $J_2$, $J_3$, $J_4$, and $J_5$ are N or N—O;

not more than two of $W_1$, $W_2$, $W_3$, $W_4$, and $W_5$ are N;

not more than three of $W_1$, $W_2$, $W_3$, $W_4$, and $W_5$ are $CR_9$; and

X and Z cannot both be CH, or a pharmaceutically acceptable salt thereof.

In another aspect, the invention provides compounds of Formula (IV), (IV)

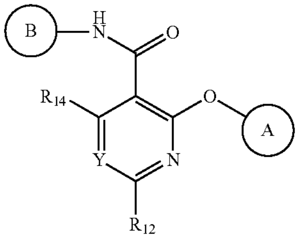

wherein:

Y is N or $CR_{13}$;

A and B are independently aryl, heteroaryl, or a 3-6 membered ring containing one or more heteroatoms independently selected from O, S, and N; wherein A is unsubstituted or substituted with one or more substituents selected from:

H, halo, $C_1$-$C_6$-alkyl, branched alkyl, alkenyl, alkynyl, haloalkyl, alkoxy, cycloalkoxy, haloalkoxy, nitro, cyano, SR', —$CH_2$-cycloalkyl, —$CF_2$-cycloalky, —$CH(CH_3)$-cycloalkyl, —$CH_2$-aryl, —$CF_2$-aryl, —CH(—$CH_3$)-aryl, C(═O)-alkyl, —C(═O)cycloalkyl, —C(═O)—NH-alkyl, —C(═O)$NH_2$, hydroxy, —COOH (and ester thereof), alkylsulfonyl, arylsulfonyl, sulfonamide, amino, NR'R"—NHSOR', —NHC(═O)-alkyl-NH(C═O)NR'R", $SO_2R'$, trifluoromethyl, bromo, chloro, fluoro, cyclopropylmethyl, sufonylmethyl, 3-6 membered cycloalkyl; 3-6 membered heterocycloalkyl, any of which may have one or more substituents, wherein the 3-6 membered heterocycloalkyl comprises at least one heteroatom independently selected from O, S, and N;

$R_{12}$, $R_{13}$, and $R_{14}$ are individually selected from: H, $CF_3$, halo, $C_1$-$C_6$-alkyl, branched alkyl, alkenyl, alkynyl, haloalkyl, alkoxy, cycloalkoxy, haloalkoxy, nitro, cyano, —$CH_2$—cycloalkyl, —$CF_2$-cycloalky, —$CH(CH_3)$-cycloalkyl, —$CH_2$-aryl, —$CF_2$-aryl, —CH(—$CH_3$)-aryl, C(═O)-alkyl, —C(═O)cycloalkyl, —C(═O)—NH-alkyl, —C(═O)$NH_2$, hydroxy, —COOH (and ester thereof), alkylsulfonyl, arylsulfonyl, sulfonamide, amino, NR'R"—$NHSO_2R1$, —NHC(═O)-alkyl-NH(C═O)NR'R", spirocyclyl, morpholinyl, pyrrolidinyl, piperidinyl, carbocyclyl, heterocyclyl, aryl or heteroaryl, wherein the 5 or 6 ring membered ring optionally includes one or more N or S in the ring, wherein the substitutions on the 5 or 6 ring membered ring are selected from halogen, alkyl, haloalkyl, alkoxy, haloalkoxy, alkyl sulphonyl, alkyl sulfoximinyl, alkyl sulfonamide, —C(═O)—NH-alkyl, —C(═O)$NH_2$ cyano, $CF_3$, $CHF_2$, $OCH_3$, $OCF_3$, a fused heterocyclyl in which each ring has 5 or 6 members, a heteroaryl having 5 or 6 ring members, a saturated heterocyclyl, or a partially unsaturated heterocyclyl, each of which is optionally substituted where valency permits;

the substituents R' and R" may be independently selected from hydrogen, substituted or unsubstituted alkyl, substituted or unsubstituted cycloalkyl, substituted or unsubstituted heterocycloalkyl, substituted or unsubstituted aryl, and substituted, unsubstituted heteroaryl, or $CD_3$.

In selected embodiments, A is $CH_2CF_3$ or

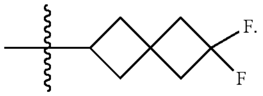 [SMILES: *C1CC2(C1)CC(F)(F)C2]

In another aspect, the invention provides compounds of Formula (V), (V)

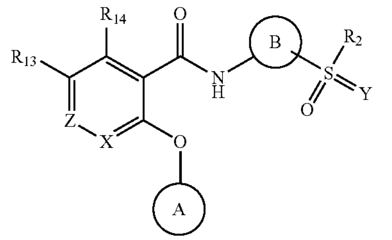

A, and B are as described in for Formula (IV)

$R_2$ is as described in for Formula (II)

$R_{13}$ and $R_{14}$ are as described in Formula (IV)

X is CH or N;

Y is $NR_8$ or O;

Z is CH, N, or N—O.

B. Second Set of Compounds

In an aspect, the invention provides compounds of Formula (I):

(I)

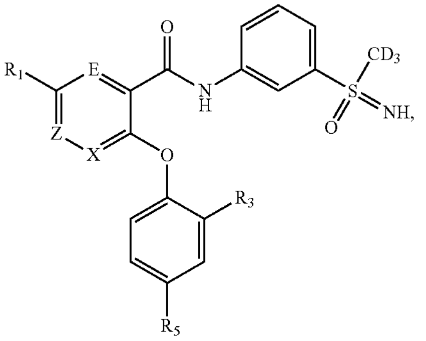

wherein:

$R_1$ is —CN or —$CF_3$;

$R_3$ is halogen, alkyl, alkoxy, or —$CD_3$;

$R_5$ is H, halogen, alkyl, haloalkyl, alkoxy, haloalkoxy, alkyl sulphonyl, alkyl sulfoximinyl, alkyl sulfonamide, cyano, $CF_3$, $OCF_3$, a fused heterocyclyl in which each ring has 5 or 6 members, a heteroaryl having 5 or 6 ring members, a saturated heterocyclyl, or a partially unsaturated heterocyclyl, each of which is optionally substituted where valency permits;

E is CH or CF;

X is CH or N;

Z is CH or N; and

—$CD_3$ is fully deuterated methyl group, with the proviso that X and Z cannot both be CH, or a pharmaceutically acceptable salt thereof.

The moieties in $R_5$ may be substituted with alkyl, haloalkyl, alkoxy, haloalkoxy, hydroxyl, or halogen.

The compound of Formula (I) may have the sulfoximine group in the R stereochemical configuration, the S stereochemical configuration, or a mixture of R and S stereochemical configurations.

C. Third Set of Compounds

In an aspect, the invention provides compounds of Formula (I):

(I)

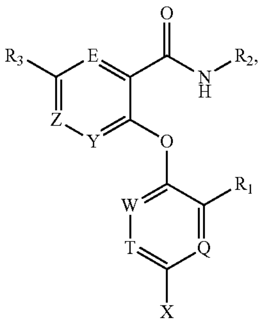

wherein:

$R_1$ is halogen, $C_1$-$C_3$ alkyl, $C_1$-$C_3$ alkoxy, $C_3$-$C_4$ cycloalkyl, haloalkyl, halocycloalkyl, or H;

$R_2$ is selected from the group consisting of aryl, heteroaryl, and unsaturated heterocyclyl, wherein:

each of the aryl, heteroaryl, and unsaturated heterocyclyl is optionally fused to one selected from the group consisting of optionally saturated carbocyclyl containing 5-6 ring members and optionally saturated heterocyclyl containing 5-6 ring members and 1-3 hetereoatoms;

each of the aryl, heteroaryl, and unsaturated heterocyclyl is optionally substituted with one or more groups selected from the group consisting of —$(CH_2)_nNR^eC(O)N(R^e)_2$, —$(CH_2)_nNR^eC(O)N(R^j)_2$, —$(CH_2)_nNR^eC(O)NR^eR^j$, —$(CH_2)_nNR^eC(O)OR^j$, —$(CH_2)_nNR^eC(O)R^j$, —$(CH_2)_nNR^eR^j$, —$(CH_2)_nNR^eS(O)_mN(R^e)_2$, —$(CH_2)_nNR^eS(O)_mN(R^j)_2$, —$(CH_2)_nNR^eS(O)_mNR^eR^j$, —$(CH_2)_nNR^eS(O)_mR^j$, alkyliminosulfanonyl, alkylsulfinyl, alkylsulfonamidyl, alkylsulfonyl, alkylsulfoxide, alkylsulfoximine, alkylthioether, amino, aryl, arylalkoxyl, aryloxyl, —$C(O)NH_2$, —$C(O)NR^eR^j$, —$C(O)R^j$, $C_1$-$C_4$ alkoxyl, $C_1$-$C_6$ alkyl, $C_1$-$C_6$alkyl, $C_2$-$C_6$alkenyl, $C_2$-$C_6$cycloheteroalkyl, $C_3$-$C_{10}$ cycloalkyl, $C_3$-$C_6$cycloalkyl, —$CF_3$, —CN, —$CO_2H$, —$CO_2R^j$, cyano, —H, halogen, heteroaryl, mono-, di-, and trihalo-$C_1$-$C_4$ alkyl, mono-, di-, or trihaloalkoxyl, morpholinyl, nitro, O-aryl, —$OC(O)N(R^j)_2$, —$OC(O)NR^eR^j$, —$OC(O)R^j$, —$OC_1$-$C_6$alkyl, —$OC_2$-$C_6$alkenyl, —$OC_2$-$C_6$cycloheteroalkyl, —$OC_3$-$C_6$cycloalkyl, —OH, O-heteroaryl, oxazolyl, oxo, —$S(O)_2R^j$, —$SO_2$aryl, —$SO_2C_1$-$C_6$alkenyl, —$SO_2C_1$-$C_6$alkyl, —$SO_2C_2$-$C_6$cycloheteroalkyl, —$SO_2C_3$-$C_6$cycloalkyl, $SO_2$heteroaryl, —$SO_2NH_2$, —$SO_2NR^e$-aryl, —$SO_2NR^eC(O)C_1$-$C_6$alkyl, —$SO_2NR^eC(O)C_2$-$C_6$cycloheteroalkyl, —$SO_2NR^eC(O)C_3$-$C_6$cycloalkyl, —$SO_2NR^eC_1$-$C_6$alkyl, —$SO_2NR^eC_2$-$C_6$alkenyl, —$SO_2NR^eC_2$-$C_6$cycloheteroalkyl, —$SO_2NR^eC_3$-$C_6$cycloalkyl, —$SO_2NR^e$-heteroary 1, —$SO_3H$, —$SR^j$, sulfoximinyl —$S(O)({=}NR^a)R^a$, sulfonimidamide —$S(O)({=}NR^a)N(R^a)_2$, sulfonimidoyl fluoride —$S(O)({=}NR^a)F$, and sulfondiimine —$S({=}NR^a)_2R^a$, wherein each alkenyl, alkyl, aryl, cycloalkyl, cycloheteroalkyl, and heteroaryl substituent is itself optionally substituted with one or more substituents selected from the group consisting of halogen, —OH, —$NH_2$, —$NH(C_1$-$C_6alkyl)$ and —$N(C_1$-$C_6alkyl)_2$;

the unsaturated heterocyclyl is optionally substituted with $R^kR^l$; and each heteroatom in the heteroaryl, unsaturated heterocyclyl, and optionally saturated heterocyclyl is independently O, S or $N(R^h)_q$, each of which may be in its oxidized or unoxidized state;

$R_3$ is selected from the group consisting of —H, cyano, halogen, $C_1$-$C_4$ alkoxyl, mono-, di-, and trihalo-$C_1$-$C_4$ alkyl, mono-, di-, and trihalo-$C_1$-$C_4$ alkoxyl, optionally substituted $C_1$-$C_8$ alkyl, and $C_3$-$C_8$ cycloalkyl optionally substituted with 1-4 fluorine atoms;

each $R^a$ is independently halogen, $C_1$-$C_3$ alkyl, $C_3$-$C_4$ cycloalkyl, haloalkyl, halocycloalkyl, or H;

each $R^e$ is independently —H, $C_1$-$C_6$ alkyl, or $C_2$-$C_6$ alkenyl;

each $R^h$ is independently —H, or $C_1$-$C_6$ alkyl;

each $R^j$ is independently $C_1$-$C_6$ alkyl, $C_2$-$C_6$ alkenyl, $C_3$-$C_6$ cycloalkyl, $C_2$-$C_6$ cycloheteroalkyl, aryl, or heteroaryl, wherein each alkyl, alkenyl, cycloalkyl, cycloheteroalkyl, aryl and heteroaryl in $R^j$ is optionally substituted with one or more substituents independently selected from the group consisting of $C_1$-$C_6$ alkyl, $C_3$-$C_6$ cycloalkyl, —OH, —$OC_1$-$C_6$alkyl, —$OC_3$-$C_6$cycloalkyl, halogen, cyano, and —$S(O)_2CH_3$;

$R^k$ and $R^l$, together with the atom to which they are attached, form a cylcloalkyl or cycloheteroalkyl containing 3-7 ring members;

E is CH, CF, or N;

Q is CH, CF, or N;

T is CH, CF or N;

W is CH, CF, or N;

X is halogen, alkyl, haloalkyl, cycloalkyl, or halocycloalkyl,

Y is N or $N^+O^-$;

Z is N, $N^+O^-$, or CH;

each m is independently 0-2;

each n is independently 0-4; and each q is independently 0 or 1, or a pharmaceutically acceptable salt thereof.

$R_2$ may be an optionally substituted aryl, an optionally substituted heteroaryl, or an optionally substituted unsaturated heterocyclyl.

$R_1$ may be H, halogen, $C_1$-$C_3$ alkyl, $C_3$-$C_4$ cycloalkyl, haloalkyl, or halocycloalkyl.

$R_3$ may be a mono-, di-, or trihalo-$C_1$-$C_4$ alkyl. $R_3$ may be —$CF_3$.

E may be CH, CF, or N.

Q may be CH, CF, or N.

T may be CH, CF, or N.

W may be CH, CF, or N.

D. Fourth Set of Compounds

In an aspect, the invention provides compounds of Formula (I):

(I)

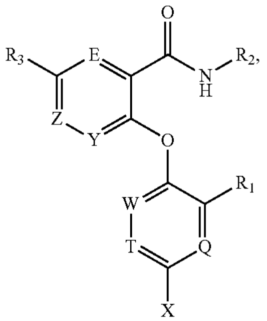

wherein:

$R_1$ is halogen, $C_1$-$C_3$ alkyl, $C_3$-$C_4$ cycloalkyl, haloalkyl, halocycloalkyl, or H;

$R_2$ is selected from the group consisting of aryl, heteroaryl, and unsaturated heterocyclyl, wherein:

each of the aryl, heteroaryl, and unsaturated heterocyclyl is optionally fused to one selected from the group consisting of optionally saturated carbocyclyl containing 5-6 ring members and optionally saturated heterocyclyl containing 5-6 ring members and 1-3 hetereoatoms;

each of the aryl, heteroaryl, and unsaturated heterocyclyl is optionally substituted with one or more groups selected from the group consisting of —$(CH_2)_nNR^eC(O)N(R^e)_2$, —$(CH_2)_nNR^eC(O)N(R^j)_2$, —$(CH_2)_nNR^eC(O)NR^eR^j$, —$(CH_2)_nNR^eC(O)OR^j$, —$(CH_2)_nNR^eC(O)R^j$, —$(CH_2)_nNR^eR^j$, —$(CH_2)_nNR^eS(O)_mN(R^e)_2$, —$(CH_2)_nNR^eS(O)_mN(R^j)_2$, —$(CH_2)_nNR^eS(O)_mNR^eR^j$, —$(CH_2)_nNR^eS(O)_mR^j$, alkyliminosulfanonyl, alkylsulfinyl, alkylsulfonamidyl, alkylsulfonyl, alkylsulfoxide, alkylsulfoximine, alkylthioether, amino, aryl, arylalkoxyl, aryloxyl, —$C(O)NH_2$, —$C(O)NR^eR^j$, —$C(O)R^j$, $C_1$-$C_4$ alkoxyl, $C_1$-$C_6$ alkyl, $C_1$-$C_6$alkyl, $C_2$-$C_6$alkenyl, $C_2$-$C_6$cycloheteroalkyl, $C_3$-$C_{10}$ cycloalkyl, $C_3$-$C_6$cycloalkyl, —$CF_3$, —CN, —$CO_2H$, —$CO_2R^j$, cyano, —H, halogen, heteroaryl, mono-, di-, and trihalo-$C_1$-$C_4$ alkyl, mono-, di-, or trihaloalkoxyl, morpholinyl, nitro, O-aryl, —$OC(O)N(R^j)_2$, —$OC(O)NR^eR^j$, —$OC(O)R^j$, —$OC_1$-$C_6$alkyl, —$OC_2$-$C_6$alkenyl, —$OC_2$-$C_6$cycloheteroalkyl, —$OC_3$-$C_6$cycloalkyl, —OH, O-heteroaryl, oxazolyl, oxo, —$S(O)_2R^j$, —$SO_2$aryl, —$SO_2C_1$-$C_6$alkenyl, —$SO_2C_1$-$C_6$alkyl, —$SO_2C_2$-$C_6$cycloheteroalkyl, —$SO_2C_3$-$C_6$cycloalkyl, $SO_2$heteroaryl, —$SO_2NH_2$, —$SO_2NR^e$-aryl, —$SO_2NR^eC(O)C_1$-$C_6$alkyl, —$SO_2NR^eC(O)C_2$-$C_6$cycloheteroalkyl, —$SO_2NR^eC(O)C_3$-$C_6$cycloalkyl, —$SO_2NR^eC_1$-$C_6$alkyl, —$SO_2NR^eC_2$-$C_6$alkenyl, —$SO_2NR^eC_2$-$C_6$cycloheteroalkyl, —$SO_2NR^eC_3$-$C_6$cycloalkyl, —$SO_2NR^e$-heteroary 1, —$SO_3H$, —$SR^j$, sulfoximinyl —$S(O)({=}NR^a)R^a$, sulfonimidamide —$S(O)({=}NR^a)N(R^a)_2$, sulfonimidoyl fluoride —$S(O)({=}NR^a)F$, and sulfondiimine —$S({=}NR^a)_2R^a$, wherein each alkenyl, alkyl, aryl, cycloalkyl, cycloheteroalkyl, and heteroaryl substituents itself optionally substituted with one or more substituents selected from the group consisting of halogen, —OH, —$NH_2$, —$NH(C_1$-$C_6$alkyl) and —$N(C_1$-$C_6$alkyl$)_2$;

the unsaturated heterocyclyl is optionally substituted with $R^kR^l$; and each heteroatom in the heteroaryl, unsaturated heterocyclyl, and optionally saturated heterocyclyl is independently O, S or $N(R^h)_q$, each of which may be in its oxidized or unoxidized state;

$R_3$ is selected from the group consisting of —H, cyano, halogen, $C_1$-$C_4$ alkoxyl, mono-, di-, and trihalo-$C_1$-$C_4$ alkyl, mono-, di-, and trihalo-$C_1$-$C_4$ alkoxyl, optionally substituted $C_1$-$C_8$ alkyl, and $C_3$-$C_8$ cycloalkyl optionally substituted with 1-4 fluorine atoms;

each $R^a$ is independently halogen, $C_1$-$C_3$ alkyl, $C_3$-$C_4$ cycloalkyl, haloalkyl, halocycloalkyl, or H;

each $R^e$ is independently —H, $C_1$-$C_6$ alkyl, or $C_2$-$C_6$ alkenyl; each $R^h$ is independently —H, or $C_1$-$C_6$ alkyl;

each $R^j$ is independently $C_1$-$C_6$ alkyl, $C_2$-$C_6$ alkenyl, $C_3$-$C_6$ cycloalkyl, $C_2$-$C_6$ cycloheteroalkyl, aryl, or heteroaryl, wherein each alkyl, alkenyl, cycloalkyl, cycloheteroalkyl, aryl and heteroaryl in $R^j$ is optionally substituted with one or more substituents independently selected from the group consisting of $C_1$-$C_6$ alkyl, $C_3$-$C_6$ cycloalkyl, —OH, —$OC_1$-$C_6$alkyl, —$OC_3$-$C_6$cycloalkyl, halogen, cyano, and —$S(O)_2CH_3$;

$R^k$ and $R^l$, together with the atom to which they are attached, form a cylcloalkyl or cycloheteroalkyl containing 3-7 ring members;

E is CH or CF;

Q is CH, CF, or N;

T is CH, CF or N;

W is CH, CF, or N;

X is halogen, alkyl, haloalkyl, cycloalkyl, or halocycloalkyl,

Y is N or $N^+O^-$;

Z is N or $N^+O^-$, each m is independently 0-2;

each n is independently 0-4; and each q is independently 0 or 1, or a pharmaceutically acceptable salt thereof.

$R_2$ may be an optionally substituted aryl, an optionally substituted heteroaryl, or an optionally substituted unsaturated heterocyclyl.

$R_1$ may be H, halogen, $C_1$-$C_3$ alkyl, $C_3$-$C_4$ cycloalkyl, haloalkyl, or halocycloalkyl.

$R_3$ may be a mono-, di-, ortrihalo-$C_1$-$C_4$ alkyl. $R_3$ may be —$CF_3$.

E may be CH, CF, or N.

Q may be CH, CF, or N.

T may be CH, CF, or N.

W may be CH, CF, or N.

E. Fifth Set of Compounds

In some aspects, the presently disclosed subject matter provides a compound of formula (I).

(I)

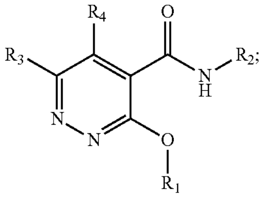

wherein:

$R_1$ is aryl or heteroaryl, wherein the aryl or heteroaryl is unsubstituted or substituted with one or more groups selected from the group consisting of mono-, di-, and trihalo-$C_1$-$C_4$ alkyl, substituted or unsubstituted $C_1$-$C_8$ alkyl, $C_3$-$C_{10}$ cycloalkyl, halogen, heteroaryl, cyano, amino, nitro, aryloxyl, aryl, $C_1$-$C_8$ alkoxyl, mono-, di-, or trihaloalkoxyl, sulfanyl, trifluoromethylsulfanyl, and arylalkoxyl;

$R_2$ is selected from the group consisting of aryl, heteroaryl, and heterocycle, wherein the aryl, heteroaryl, and heterocycle unsubstituted or are substituted with one or more groups selected from the group consisting of mono-, di-, andtrihalo-$C_1$-$C_4$ alkyl, substituted or unsubstituted $C_1$-$C_8$ alkyl, $C_3$-$C_{10}$ cycloalkyl, halogen, heteroaryl, cyano, amino, nitro, aryloxyl, aryl, $C_1$-$C_8$ alkoxyl, mono-, di-, or trihaloalkoxyl, arylalkoxyl, oxo, alkylsulfinyl, alkylsulfonyl, alkyliminosulfanonyl, alkylsulfoxide, sulfonamide, morpholinyl, and oxazolyl;

$R_3$ is selected from the group consisting of hydrogen, cyano, halogen, $C_1$-$C_8$ alkoxyl, mono-, di-, and trihalo-$C_1$-$C_4$ alkyl, mono-, di-, and trihalo-$C_1$-$C_4$ alkoxyl, substituted or unsubstituted $C_1$-$C_8$ alkyl, $C_3$-$C_5$ cycloalkyl, —$NO_2$;

$R_4$ is selected from the group consisting of hydrogen, cyano, halogen, $C_1$-$C_8$ alkoxyl, mono-, di-, and trihalo-$C_1$-$C_4$ alkyl, mono-, di-, and trihalo-$C_1$-$C_4$ alkoxyl, substituted or unsubstituted $C_1$-$C_8$ alkyl, and morpholinyl, provided that $R_3$ and $R_4$ are not hydrogen at the same time; or $R_3$ and $R_4$ together form a $C_3$-$C_5$ carbocyclic ring including carbon atoms to which $R_3$ and $R_4$ are attached; and pharmaceutically acceptable salts thereof.

In some aspects of the compound of formula (I), $R_1$ is phenyl or pyridinyl, wherein the phenyl or pyridinyl is unsubstituted or substituted with one or more groups selected from the group consisting of substituted or unsubstituted $C_1$-$C_8$ alkyl, halogen, —O—$R_5$, wherein $R_5$ is selected from the group consisting of $C_1$-$C_8$ alkyl, —$CF_3$, —$CHF_2$, and —$(CH_2)_p$—$CF_3$, wherein p is an integer selected from the group consisting of 1, 2, 3, 4, 5, 6, 7, and 8, and —S—$CF_3$;

$R_2$ is selected from the group consisting of phenyl, pyridyl, pyrimidinyl, pyridazinyl, pyrazolyl, pyridine-1-oxide, 1,2,3-thiadiazolyl, 1,2,4-triazolyl, and 1,3-benzothiazolyl, wherein the phenyl, pyridyl, pyrimidinyl, pyridazinyl, pyridine-1-oxide, 1,2,3-thiadiazolyl, 1,2,4-triazolyl, and 1,3-benzothiazolyl are unsubstituted or are substituted with one or more groups selected from the group consisting of unsubstituted or substituted $C_1$-$C_8$ alkyl, halogen, cyano, oxo, —O—$R_5$, wherein $R_5$ is selected from the group consisting of $C_1$-$C_8$ alkyl, —$CF_3$, and —$CHF_2$, —$(CH_2)_q$—OH, wherein q is an integer selected from the group consisting of 1, 2, 3, 4, 5, 6, 7, and 8, —$NR_6R_7$, wherein $R_6$ and $R_7$ are selected from the group consisting of H and $C_1$-$C_4$ alkyl, morpholinyl, oxazolyl, —C(=O)—$R_8$, wherein $R_8$ is selected from the group consisting of —$NR_6R_7$, wherein $R_6$ and $R_7$ are selected from the group consisting of H and $C_1$-$C_4$ alkyl, and $C_1$-$C_4$ alkyl, —S(=O)—$R_9$, —$S(=O)_2$—$R_9$, —S(=O)(=$NR_{10}$)—$R_{11}$, and —N=S(=O)—$(R_1)_2$, wherein each $R_9$ is independently $C_1$-$C_4$ alkyl, —$CF_3$, or —$NR_6R_7$, wherein $R_6$ and $R_7$ are selected from the group consisting of H and $C_1$-$C_4$ alkyl, $R_{10}$ is H or $C_1$-$C_4$ alkyl, and Rn is $C_1$-$C_4$ alkyl, provided that when Y is nitrogen and $R_2$ is phenyl or pyridyl, $R_8$ cannot be —$NR_6R_7$;

$R_3$ is selected from the group consisting of hydrogen, cyano, halogen, —$CF_3$, $C_1$-$C_8$ alkoxyl, —O—$CH(F)_2$, substituted or unsubstituted $C_1$-$C_8$ alkyl, $C_3$-$C_8$ cycloalkyl, —$N^+$(=O)—$O^-$;

$R_4$ is selected from the group consisting of hydrogen, cyano, halogen, $C_1$-$C_8$ alkoxyl, —$CF_3$, substituted or unsubstituted $C_1$-$C_8$ alkyl, and morpholinyl, provided that $R_3$ and $R_4$ are not hydrogen at the same time; or $R_3$ and $R_4$ together form a $C_3$-$C_5$ carbocyclic ring including carbon atoms to which $R_3$ and $R_4$ are attached.

In certain aspects, the compound of formula (I) comprises a compound of formula (II):

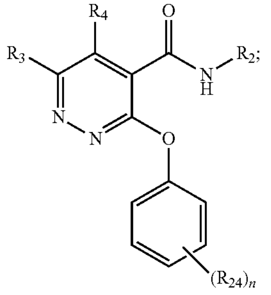

(II)

wherein:

$R_2$ is selected from the group consisting of aryl, heteroaryl, and heterocycle, wherein the aryl, heteroaryl, and heterocycle unsubstituted or are substituted with one or more groups selected from the group consisting of mono-, di-, andtrihalo-$C_1$-$C_4$ alkyl, substituted or unsubstituted $C_1$-$C_8$ alkyl, $C_3$-$C_{10}$ cycloalkyl, halogen, heteroaryl, cyano, amino, nitro, aryloxyl, aryl, $C_1$-$C_8$ alkoxyl, mono-, di-, or trihaloalkoxyl, arylalkoxyl, oxo, alkylsulfinyl, alkylsulfonyl, alkyliminosulfanonyl, alkylsulfoxide, sulfonamide, morpholinyl, and oxazolyl;

$R_3$ is selected from the group consisting of hydrogen, cyano, halogen, $C_1$-$C_8$ alkoxyl, mono-, di-, and trihalo-$C_1$-$C_4$ alkyl, mono-, di-, and trihalo-$C_1$-$C_4$ alkoxyl, substituted or unsubstituted $C_1$-$C_8$ alkyl, $C_3$-$C_8$ cycloalkyl, —$NO_2$;

$R_4$ is selected from the group consisting of hydrogen, cyano, halogen, $C_1$-$C_8$ alkoxyl, mono-, di-, and trihalo-$C_1$-$C_4$ alkyl, mono-, di-, and trihalo-$C_1$-$C_4$ alkoxyl, substituted or unsubstituted $C_1$-$C_8$ alkyl, and morpholinyl, provided that $R_3$ and $R_4$ are not hydrogen at the same time; or $R_3$ and $R_4$ together form a $C_3$-$C_5$ carbocyclic ring including carbon atoms to which $R_3$ and $R_4$ are attached;

n is an integer selected from 0, 1, 2, 3, 4, and 5;

each $R_{24}$ is independently selected from the group consisting of mono-, di-, and trihalo-$C_1$-$C_4$ alkyl, substituted or unsubstituted $C_1$-$C_8$ alkyl, $C_3$-$C_{10}$ cycloalkyl, halogen, heteroaryl, cyano, amino, nitro, aryloxyl, aryl, $C_1$-$C_8$ alkoxyl, mono-, di-, or trihaloalkoxyl, sulfanyl, trifluoromethylsulfanyl, and arylalkoxyl.

In some aspects of the compound of formula (II), $R_2$ is selected from the group consisting of:

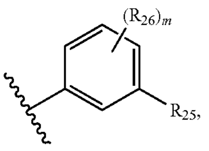

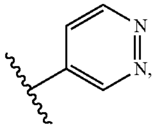

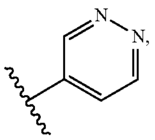

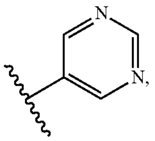

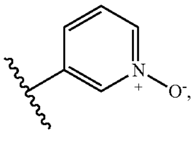

-continued

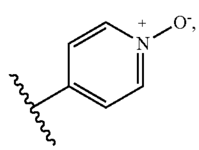

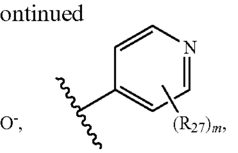

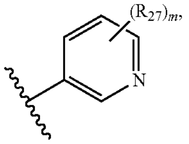

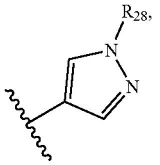

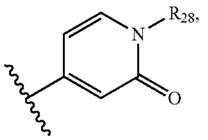

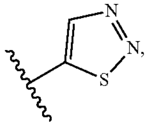

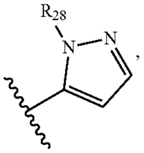

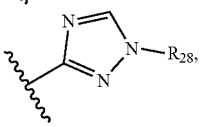

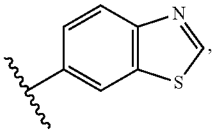

and

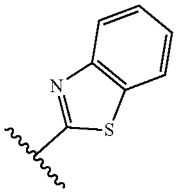

wherein:

m is an integer selected from the group consisting of 0, 1, 2, 3, and 4;

$R_{25}$ is selected from the group consisting of H, morpholinyl, oxazolyl, halogen, cyano, —$(CH_2)_q$—OH, wherein q is an integer selected from the group consisting of 1, 2, 3, 4, 5, 6, 7, and 8, —C(═O)—$R_8$, wherein $R_8$ is selected from the group consisting of —$NR_6R_7$ and $C_1$-$C_4$ alkyl, wherein $R_6$ and $R_7$ are selected from the group consisting of H and $C_1$-$C_4$ alkyl, —S(═O)—$R_9$, —S(═O)$_2$—$R_9$, —S(═O)(═$NR_{10}$)—$R_{11}$, and —N═S(═O)—$(R_1)_2$, wherein each $R_9$ is independently $C_1$-$C_4$ alkyl, —$CF_3$, or —$NR_6R_7$, wherein $R_6$ and $R_7$ are selected from the group consisting of H and $C_1$-$C_4$ alkyl, $R_{10}$ is H or $C_1$-$C_4$ alkyl, and $R_{11}$ is $C_1$-$C_4$ alkyl, provided that when Y is nitrogen and $R_2$ is phenyl or pyridyl, $R_8$ cannot be —$NR_6R_7$;

$R_{26}$ is halogen or cyano;

each $R_{27}$ is independently selected from the group consisting of H, halogen, $C_1$-$C_8$ alkoxyl, cyano, -and $NR_6R_7$; and each $R_{28}$ is independently H or $C_1$-$C_4$ alkyl.

In some aspects, the compound of formula (I) comprises a compound of formula (III):

(III)

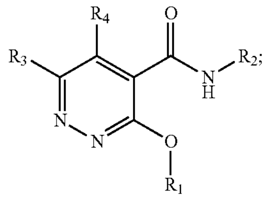

wherein:

$R_1$ is selected from the group consisting of phenyl, pyridyl, and 1,3-benzothiazol-4yl, wherein the phenyl and pyridyl can be unsubstituted or substituted with one or more of halogen, $C_1$-$C_8$ alkyl, —O—$R_5$, wherein $R_5$ is selected from the group consisting of $C_1$-$C_8$ alkyl, —$CF_3$, —$CHF_2$, and —$(CH_2)_p$—$CF_3$, wherein p is an integer selected from the group consisting of 1, 2, 3, 4, 5, 6, 7, and 8, —S—$CF_3$, —$NR_6R_7$, wherein $R_6$ and $R_7$ are selected from the group consisting of H and $C_1$-$C_4$ alkyl;

$R_2$ is selected from the group consisting of:

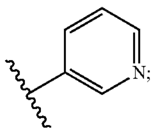

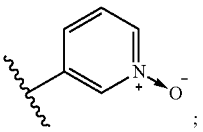

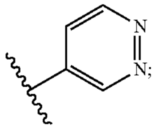

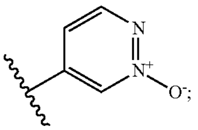

and $R_3$ and $R_4$ are H or —$CF_3$, provided that if $R_3$ is H, then $R_4$ is —$CF_3$ and if $R_4$ is H, then $R_3$ is —$CF_3$.

In some aspects, the compound of formula (I), comprises a compound of formula (IV):

(IV)

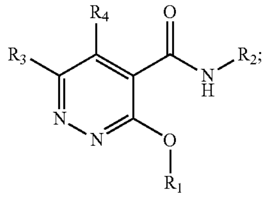

wherein $R_2$ is selected from the group consisting of:

(i)

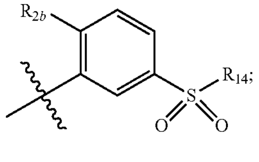

wherein $R_{2b}$ is selected from the group consisting of H, $C_1$-$C_4$ alkyl, and halogen; and $R_{14}$ is $C_1$-$C_4$ alkyl;

(ii)

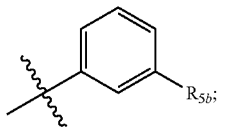

wherein $R_{5b}$ is selected from the group consisting of —C(═O)—$R_8$, —$(CH_2)_n$OH, and cyano, wherein $R_8$ is $C_1$-$C_4$ alkyl and n is an integer selected from 1, 2, 3, 4, 5, 6, 7 and 8;

(iii)

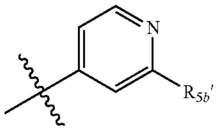

wherein $R_{5b'}$ is selected from the group consisting of H, halogen, and $C_1$-$C_4$ alkyl;

(iv)

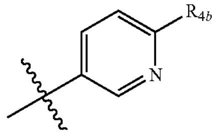

wherein $R_{4b}$ is H or halogen;

(v)

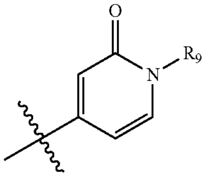

wherein $R_9$ is H or $C_1$-$C_4$ alkyl; and (vi)

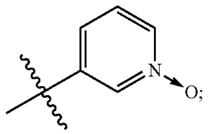

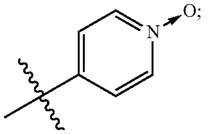

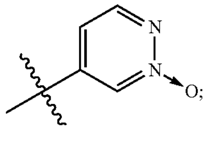

and

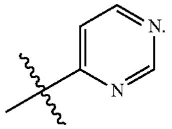

F. Methods of Using the Compounds

In another aspect, the invention provides inhibitors of a $Na_V$ 1.8 sodium channel. The inhibitors may have a defined chemical structure, such as the structure of any of the compounds described above.

In another aspect, the invention provides methods of treating a condition in a subject by providing to a subject having a condition a compound of the invention, such as any of those described above.

The condition may be associated with aberrant activity of $Na_V$1.8 sodium channels. The condition may be abdominal cancer pain, acute cough, acute idiopathic transverse myelitis, acute itch, acute pain, acute pain in major trauma/injury, airways hyperreactivity, allergic dermatitis, allergies, ankylosing spondylitis, asthma, atopy, Behcet disease, bladder pain syndrome, bone cancer pain, brachial plexus injury, burn injury, burning mouth syndrome, calcium pyrophosphate deposition disease, cervicogenic headache, Charcot-neuropathic osteoarthropathy, chemotherapy-induced oral mucositis, chemotherapy-induced peripheral neuropathy, cholestasis, chronic cough, chronic itch, chronic low back pain, chronic pain, chronic pancreatitis, chronic post-traumatic headache, chronic widespread pain, cluster headache, complex regional pain syndrome, complex regional pain syndromes, constant unilateral facial pain with additional attacks, contact dermatitis, cough, dental pain, diabetic neuropathy, diabetic peripheral neuropathy, diffuse idiopathic skeletal hyperostosis, disc degeneration pain, distal sensory polyneuropathy (DSP) associated with highly active antiretroviral therapy (HAART), Ehlers-Danlos syndrome, endometriosis, epidermolysis bullosa, epilepsy, erythromelalgia, Fabry disease, facetjoint syndrome, failed back surgery syndrome, familial hemiplegic migraine, fibromyalgia, glossopharyngeal neuralgia, glossopharyngeal neuropathic pain, gout, head and neck cancer pain, inflammatory bowel disease, inflammatory pain, inherited erythromelalgia, irritable bowel syndrome, irritable bowel syndrome, itch, juvenile idiopathic arthritis, mastocytosis, melorheostosis, migraine, multiple sclerosis, musculoskeletal damage, myofascial orofacial pain, neurodegeneration following ischemia, neurofibromatosis type II, neuropathic ocular pain, neuropathic pain, neuropathic pain, nociceptive pain, non-cardiac chest pain, optic neuritis, oral mucosal pain, orofacial pain, osteoarthritis, o steoarthritis, overactive bladder, pachyonychia congenita, pain, pain resulting from cancer, pain resulting from chemotherapy, pain resulting from diabetes, pain syndrome, painful joint arthroplasties, pancreatitis, Parkinson disease, paroxysmal extreme pain disorder, pemphigus, perioperative pain, peripheral neuropathy, persistent idiopathic dentoalveolar pain, persistent idiopathic facial pain, phantom limb pain, phantom limb pain, polymyalgia rheumatica, postherpetic neuralgia, post-mastectomy pain syndrome, postoperative pain, post-stroke pain, post-surgical pain, post-thoracotomy pain syndrome, post-traumatic stress disorder, preoperative pain, pruritus, psoriasis, psoriatic arthritis, pudendal neuralgia, pyoderma gangrenosum, radiotherapy-induced peripheral neuropathy, Raynaud disease, renal colic, renal colic, renal failure, rheumatoid arthritis, salivary gland pain, sarcoidosis, sciatica, scleroderma, sickle cell disease, small fiber neuropathy, spinal cord injury pain, spondylolisthesis, spontaneous pain, stump pain, subacute cough, temporomandibular joint disorders, tension-type headache, trigeminal neuralgia, vascular leg ulcers, vulvodynia, or whiplash associated disorder. In another aspect, the invention provides methods of making a medicament using a compound of the invention, such as any of those described above.

In another aspect the invention provides products comprising a compound of the invention, such as any of those described above, for treatment of a condition, such as any of those described above, in a subject.

IV. DETAILED DESCRIPTION

A. Definitions

Unless otherwise defined, all technical and scientific terms used herein have the same meaning as commonly understood by one of ordinary skill in the art to which this presently described subject matter belongs. The definitions provided below are intended to supplement and illustrate, not preclude, the definitions that would be apparent to one of ordinary skill in the art upon review of the present disclosure.

Unless otherwise stated, the moieties described below are optionally substituted, i.e., they may be substituted at one or more positions. The terms substituted, whether preceded by the term "optionally" or not, and substituent, as used herein, refer to the ability to change one or more functional groups for another functional group or groups on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

When the term "independently selected" is used, the substituents being referred to (e.g., R groups, such as groups $R^h$, $R^j$, and the like, or variables, such as "m" and "n"), can be identical or different. For example, both $R^h$ and $R^j$ can be substituted alkyls, or $R^h$ can be hydrogen and $R^j$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein.

The term hydrocarbon, as used herein, refers to any chemical group comprising hydrogen and carbon. The hydrocarbon may be substituted or unsubstituted. As would be known to one skilled in tins art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, ally 1, vinyl, n-butyl, tert-butyl, ethynyl, cyclohexyl, and the like.

The term "alkyl" by itself or as part of another substituent, means, unless otherwise stated, a straight (i.e., unbranched) or branched chain, acyclic or cyclic saturated hydrocarbon group, or combination thereof, and can include di- and multivalent groups, having the number of carbon atoms designated (e.g., $C_{1-10}$ means one to ten carbons, including 1, 2, 3, 4, 5, 6, 7, 8, 9, and 10 carbons). In particular embodiments, the term "alkyl" refers to $C_{1-10}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic saturated hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl, or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, cyano, and mercapto.

The term "heteroalkyl," by itself or in combination with another term, means, unless otherwise stated, a stable straight or branched chain having from 1 to 20 carbon atoms or heteroatoms or a cyclic hydrocarbon group having from 3 to 15 carbon atoms or heteroatoms, or combinations thereof, consisting of at least one carbon atom and at least one heteroatom, such as O, N, P, Si or S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, $—CH{=}CH—N(CH_3)—CH_3$, $O—CH_3$, $—O—CH_2—CH_3$, and —CN. Up to two or three heteroatoms may be consecutive, such as, for example, —CH2-$NH—OCH_3$ and $—CH_2—O—Si(CH_3)_3$.

As described above, heteroalkyl groups, as used herein, include those groups that are attached to the remainder of the molecule through a heteroatom, such as —C(O)NR', —NR'R", —OR', —SR, —S(O)R, and/or $—S(O_2)R'$.

"Cycloalkyl" refers to a saturated monocyclic or multicyclic ring system of from about 3 to about 15 carbon atoms, e.g., 3, 4, 5, 6, 7, 8, 9, or 10 carbon atoms. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Examples of cycloalkyl include, but are not limited to, cyclopentyl, cyclohexyl, 1-cyclohexenyl, 3-cyeiohexenyl, cycloheptyl, and the like.

The term "cycloalkylalkyl," as used herein, refers to a cycloalkyl group as defined above, which is attached to the parent molecular moiety through an alkylene moiety, also as defined above, e.g., a $C_{1-20}$ alkylene moiety. Examples of cycloalkylalkyl groups include cyclopropylmethyl and cyclopentylethyl.

The term "carbocyclyl" refers to a monocyclic or multicyclic ring system of from about 3 to about 15 ring members in which all ring members are carbon atoms. Unless otherwise specified, a carbocyclyl may be saturated, partially saturated (i.e., have one or more double or triple bonds), or aromatic.

The term "heterocyclyl" refers to a monocyclic or multicyclic ring system of from about 3 to about 15 ring members in which at least one ring member is a heteroatom, such as N, O, or S. Unless otherwise specified, a heterocyclyl may be saturated, partially saturated (i.e., have one or more double or triple bonds), or aromatic. Examples of saturated and partially unsaturated non-aromatic heterocyclic groups include, but are not limited to, 3-oxetanyl, 2-oxetanyl, azetidinyl, thietanyl, tetrahydrofuranyl, tetrahydrothiophenyl, pyrrolidinyl, dihydropyranyl, tetrahydropyranyl, thio-dihydropyranyl, thio-tetrahydropyranyl, piperidinyl, piperazinyl, morpholinyl, 1,3-oxazinanyl, 1,3-thiazinanyl, 4,5,6-tetrahydropyrimidinyl, 2,3-dihydrofuranyl, dihydrothienyl, dihydropyridinyl, tetrahydropyridinyl, isoxazolidinyl, pyrazolidinyl, tetrazolyl, imidazolyl, isothiozolyl, triazolyl, azabicyclo-octanyl, diazabicyclo-octanyl, and all alkyl, alkoxy, haloalkyl and haloalkoxy substituted derivatives of any of the aforementioned groups.

The terms "cycloheteroalkyl" and "heterocycloalkyl" refer to a saturated ring system, such as a 3- to 10-member cycloalkyl ring system, that include one or more heteroatoms. The heteroatoms may be the same or different and may be nitrogen (N), oxygen (O), or sulfur (S). Examples of heterocycloalkyl include, but are not limited to, 1-(1,2,5,6-tetrahydropyridyi), 1-piperidmyl, 2-piperidinyl, 3-piperidinyl, 4-morpholinyl, 3-morpholinyl, tetrahydrofuran-3-yl, tetrahydrofuran-3-yl, tetrahydrothien-2-yl, tetrahydrothien-3-yl, 1-piperazinyl, 2-piperazinyl, and the like.

The cycloheteroalkyl ring can be optionally fused to or otherwise attached to other cycloheteroalkyl rings and/or non-aromatic hydrocarbon rings. Heterocyclic rings include those having from one to three heteroatoms, such as oxygen, sulfur, and nitrogen, in which the nitrogen and sulfur heteroatoms may optionally be oxidized and the nitrogen heteroatom may optionally be quaternized. Examples include, but are not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quatemized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidinyl, piperazinyl, indolinyl, quinuclidinyl, morpholinyl, thiomorpholinyl, thiadiazinanyl, tetrahydrofuranyl, and the like.

An unsaturated hydrocarbon, carbocyclyl, or heterocyclyl has one or more double bonds or triple bonds. Examples of unsaturated hydrocarbons include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkenyl" as used herein refers to a monovalent group derived from a $C_{2-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{2-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched, or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene ($—CH_2—$); ethylene ($—CH_2—CH_2—$); propylene $(CH_2)_3$, cyclohexylene ($—C_6H_{10}—$, $—CH{=}CH—CH{=}CH—$, $—CH{=}CH—CH_2—$, $—CH_2CH_2CH_2CH_2—$, $—CH_2CH_2CH(CH_2CH_2CH_3)CH_2—$, $—(CH_2)_q—N(R)—(CH_2)_r—$, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl ($—O—CH_2—O—$); and ethylenedioxyl ($—O—(CH_2)_2—O—$).

The term "heteroalkylene" by itself or as part of another substituent means a divalent group derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "spirocyclyl" refers to a polycyclic compound in which two rings have a single atom, e.g., carbon, as the only common member of two rings. Thus, a "spirocycloalkyl" refers to a cycloalkyl group with two rings having a single carbon in common, and a "spiroheterocycloalkyl" or "spiroheterocycloalkyl" refers to a cycloheteroalkyl group with two rings having a single carbon or other atom, e.g., nitrogen, in common.

The term "aryl" means, unless otherwise stated, an aromatic hydrocarbon substituent that can be a single ring or multiple rings (such as from 1 to 3 rings), which are fused together or linked covalently.

The term "heteroaryl" refers to and groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyndyl, 4-pyridyl, 2-pyrimidyl, 4-pyrimidyl, 5-benzoihiazolyl, purinyl, 2-benzimidazolyl, 5-indolyl, 1-isoquinolyl, 5-isoquinolyl, 2-quinoxalinyl, 5-quinoxalinyl, 3-qumolyl, and 6-quinolyl. Substituents for each of above noted aryl and heteroaryl ring systems are selected from the group of acceptable substituents described below.

The terms "arylene" and "heteroarylene" refer to the divalent forms of aryl and heteroaryl, respectively.

Where a heteroalkyl, heterocycloalkyl, or heteroaryl includes a specific number of members (e.g. "3 to 7 membered"), the term "member" refers to a carbon atom or heteroatom.

Each of the above terms is meant to include both substituted and unsubstituted forms of the indicated group. Optional substituents are provided below.

Substituents can be one or more of a variety of groups selected from, but not limited to: —OR', =O, =NR', =N—OR', —NR'R"—SR', -halogen, —SiR'R"R", —OC(O)R, —C(O)R, $—CO_2R$—C(O)NR'R", —OC(O)NR'R", —NR"C(O)R, —NR'—C(O)NR"R', —NR"C(O)OR', —NR—C(NR'R")=NR'", —S(O)R, $—S(O)_2R'$, $—S(O)_2NR'R"$, $—NRSO_2R'$, —CN, $CF_3$, fluorinated $C_{1-4}$ alkyl, and $—NO_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. Other non-limiting examples of substituents include $(C_1-C_6)$alkyl, $(C_2-C_5)$alkenyl, $(C_3-C_8)$alkynyl, halogen, halo$(C_1-C_6)$alkyl, hydroxy, —$O(C_1-C_6)$alkyl, halo$(C_1-C_6)$alkoxy, $(C_3-C_8)$cycloalkyl, $(C_6-C_{10})$aryl, heterocyclyl, heteroaryl, amino, cyano, nitro, $(C_1-C_6)$alkyl-OH, $(C_1-C_6)$alkyl-O—$(C_1-C_6)$alkyl, $(C_1-C_6)$alkyl$(C_6-C_{10})$aryl, —$C(O)(C_1-C_6)$alkyl, —C(O)NR'R", —$S(O)(C_1-C_6)$alkyl, —S(O)NR'R", —$S(O)_2(C_1-C_6)$alkyl, —$S(O)_2$NR'R", —$O(C_1-C_6)$alkyl-S$(O)(C_1-C_6)$alkyl, —$O(C_1-C_6)$alkyl-S(O)NR'R", —$O(C_1-C_6)$alkyl-$S(O)_2(C_1-C_6)$alkyl, and —$O(C_1-C_6)$alkyl-$S(O)_2$NR'R".

As used herein, an "alkoxy" group is an alkyl attached to the remainder of the molecule through a divalent oxygen.

When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of ordinary skill in the art will understand that the term "alkyl" is meant to include groups including carbon atoms bound to groups other than hydrogen groups, such as haloalkyl (e. g., —$CF_3$ and —$CH_2CF_3$) and acyl (e.g., —$C(O)CH_3$, —$C(O)CF_3$, —$C(O)CH_2OCH_3$, and the like).

Two of the substituents on adjacent atoms of aryl or heteroaryl ring may optionally form a ring of the formula -T-C(O)—$(CRR')_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-$(CH2)_r$—B—, wherein A and B are independently —CRR'—, —O—, —NR—, —S—, —S(O)—, —$S(O)_2$—, —$S(O)_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')s-X'—(C"R'")d-, where s and d are independently integers of from 0 to 3, and X' is —O—, —NR'—, —S—, —S(O)—, —$S(O)_2$—, or —$S(O)_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(═O)—, wherein R is an alkyl, alkenyl, alkynyl, aryl, carbocyclic, heterocyclic, or aromatic heterocyclic group as defined herein). As such, the term "acyl" specifically includes aryl acyl groups, such as a 2-(furan-2-yl)acetyl)- and a 2-phenylacetyl group. Specific examples of acyl groups include acetyl and benzoyl. Acyl groups also are intended to include amides, —RC(═O)NR, esters, —RC(═O)OR', ketones, —RC(═O)R', and aldehydes, —RC(═O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxy alkyl" as used herein refers to an alkyl-O-alkyl ether, for example, a methoxy ethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described and includes substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplar) □a ralkyloxyl group is benzyloxyl, i.e., $C_6H_5CH_2$—O—. An aralkyloxyl group can optionally be substituted.

"Alkoxycarbonyl" refers to an alkyl-O—C(═O)— group. Exemplary alkoxy carbonyl groups include methoxycarbonyl, ethoxy carbonyl, butyloxycarbonyl, and tert-butyloxycarbonyl.

"Aryloxycarbonyl" refers to an aryl-O—C(═O)— group. Exemplary aryloxy carbonyl groups include phenoxy- and naphthoxy-carbonyl.

"Aralkoxycarbonyl" refers to an aralkyl-O—C(═O)— group. An exemplary aralkoxycarbonyl group is benzyloxycarbonyl.

"Carbamoyl" refers to an amide group of the formula —$C(═O)NH_2$.

"Alkylcarbamoyl" refers to a R'RN—C(═O) group wherein one of R and R' is hydrogen and the other of R and R' is alkyl and/or substituted alkyl as previously described. "Dialkylcarbamoyl" refers to a R'RN—C(═O)— group wherein each of R and R' is independently alkyl and/or substituted alkyl as previously described.

The term "carbonyldioxyl," as used herein, refers to a carbonate group of the formula —OC(═O)—OR.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic groups. For example, the terms "acyl amino" and "alkylamino" refer to specific N-substituted organic groups with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —$(CH_2)_k$ where k is an integer from 2 to 6. Examples include, but are not limited to, methylamino, dimethylamino, ethylamino, diethylamino, diethylaminocarbonyl, methylethylamino, isopropyl amino, piperidino, trimethylamino, and propylamine.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(═O)— group, and can include an aldehyde group represented by the general formula R—C(═O)H.

The term "carboxyl" refers to the COOH group. Such groups also are referred to herein as a "carboxylic acid" moiety.

The term "cyano" refers to the —CN group.

The terms "halo," "halide," and "halogen" refer to fluoro, chloro, bromo, and iodo groups.

The term "haloalkyl" refer to an alkyl group substituted with one or more halogens. Additionally, the term "haloalkyl," includes monohaloalkyl and polyhaloalkyl. For example, the term "halo($C_{1-4}$)alkyl" includes, but is not limited to, trifluoromethyl, 2,2,2-trifluoroethyl, 4-chlorobutyl, 3-bromopropyl, and the like.

The terms "halocycloalky" and "cyclohaloalkyl" refer to a cycloalkly group with one or more halogens.

The term "hydroxyl" refers to the —OH group.

The term "hydroxy alkyl" refers to an alkyl group substituted with an —OH group.

The term "mercapto" refers to the —SH group.

The term "oxo" refers to an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —$S(O_2)R'$.

The term "sulfoxide" refers to a compound having a sulfinyl group —S(O)R

The term ureido refers to a urea group of the formula —NH—CO—$NH_2$.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

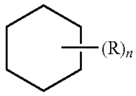
or
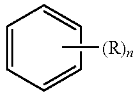

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

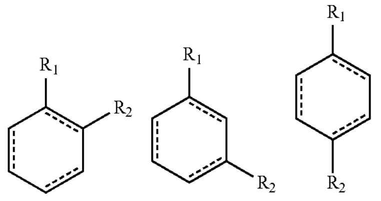

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol () denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', ═O, ═NR', ═N—OR', —NR'R", —SR', -halogen, —SiR'R"R', —OC(O)R', —C(O)R', —$CO_2$R', —C(O)NR'R", —OC(O)NR'R", —NR"C(O)R', —NR'—C(O)NR"R', —NR"C(O)OR', —NR—C(NR'R")=NR', —S(O)R', —$S(O)_2R'$, —$S(O)_2NR'R"$, —$NRSO_2R'$, —CN, $CF_3$, fluorinated $C_{1-4}$ alkyl, and —$NO_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of ordinary skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R', —OC(O)R', —C(O)R', —$CO_2R'$, —C(O)NR'R", —OC(O)NR'R", —NR"C(O)R', —NR'—C(O)NR"R', —NR"C(O)OR', —NR—C(NR'R"R'")=NR"", —NR—C(NR'R")=NR'—S(O)R', —$S(O)_2R'$, —$S(O)_2NR'R"$, —$NRSO_2R'$, —CN and —$NO_2$, —R', —$N_3$, —$CH(Ph)_2$, fluoro($C_{1-4}$)alkoxo, and fluoro($C_{1-4}$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—$(CRR')_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-$(CH_2)_r$—B—, wherein A and B are independently —CRR'—, —O—, —NR—, —S—, —S(O)—, —$S(O)_2$—, —$S(O)_2NR'$— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —$(CRR')_s$—X'—$(C"R'")_d$—, where s and d are independently integers of from 0 to 3, and X' is —O—, —NR'—, —S—, —S(O)—, —$S(O)_2$—, or —$S(O)_2NR'$—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., $C_6H_5$—$CH_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)$NH_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic groups. For example, the terms "acylamino" and "alkylamino" refer to specific N-substituted organic groups with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R"', wherein R', R", and R"' are each independently selected from the group consisting of alkyl groups. Additionally, R', R", and/or R"' taken together may optionally be $—(CH_2)_k—$ where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(═O)— group, and can include an aldehyde group represented by the general formula R—C(═O)H.

The term "carboxyl" refers to the —COOH group. Such groups also are referred to herein as a "carboxylic acid" moiety.

The term "cyano" refers to the —C≡N group.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_{1-4}$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element, including to the nitrogen of a pyridine ring to make a pyridine N-oxide.

The term "nitro" refers to the $—NO_2$ group, which also can be represented as $—N^+(═O)—O—$.

The term "thio" refers to a compound described previously herein wherein a carbon or oxygen atom is replaced by a sulfur atom.

The term "sulfate" refers to the $—SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group $—S(O_2)R$.

The term "sulfoxide" refers to a compound having a sulfinyl group —S(O)R

The term ureido refers to a urea group of the formula $—NH—CO—NH_2$.

Throughout the specification and claims, a given chemical formula or name shall encompass all tautomers, congeners, and optical- and stereoisomers, as well as racemic mixtures where such isomers and mixtures exist.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisomeric forms that may be defined, m terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example deuterium ($^2H$), tritium ($^3H$), iodine-125 ($^{125}I$) or carbon-14 ($^4C$). All isotopic variations of the compounds of the present disclosure, whether radioactive or not, are encompassed within the scope of the present disclosure.

The compounds of the present disclosure may exist as salts, and, in particular, as pharmaceutically acceptable salts.

The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates, and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or m a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow t he compounds to be converted into either base or acid addition salts.

The neutral forms of the compounds may be regenerated by contacting the salt with a base or acid and isolating the parent compound in the conventional manner.

The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds that are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups.

For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

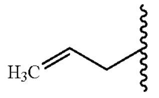
allyl

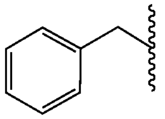
Bn

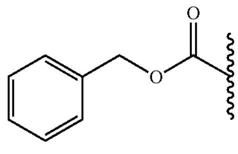
Cbz

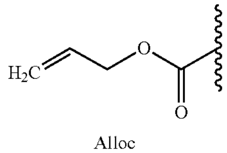
Alloc

Me

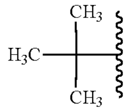
t-butyl

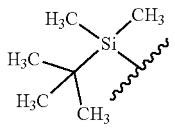
TBDMS

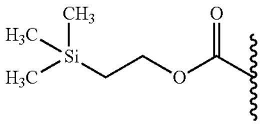
Teoc

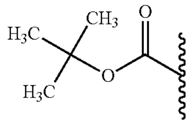
Boc

-continued

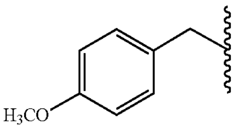

pMB

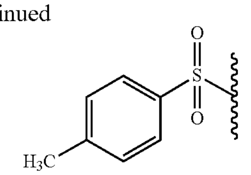

tosyl

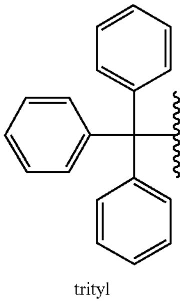

trityl

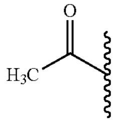

acetyl

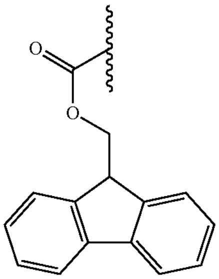

Fmoc

Following long-standing patent law convention, the terms "a," an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of ordinary skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Compounds

The invention provides compounds that modulate, e.g., inhibit, the activity of voltage-gated $Na_V1.8$ sodium channels.

A. First Set of Compounds

In certain embodiments, the compounds have the structure of Formula (I):

(I)

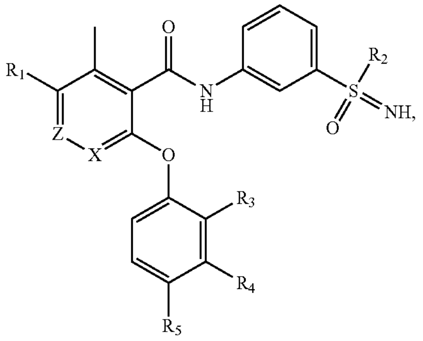

wherein:

- $R_1$ is —CN, —$CF_3$, an optionally substituted 5 or 6 ring membered ring, including aryl or heteroaryl rings, wherein the 5 or 6 ring membered ring optionally includes one or more N or S in the ring, wherein the substitutions on the 5 or 6 ring membered ring are selected from halogen, alkyl, haloalkyl, alkoxy, haloalkoxy, alkyl sulphonyl, alkyl sulfoximinyl, alkyl sulfonamide, cyano, $CF_3$, $OCF_3$, a fused heterocyclyl in which each ring has 5 or 6 members, a heteroaryl having 5 or 6 ring members, a saturated heterocyclyl, or a partially unsaturated heterocyclyl, each of which is optionally substituted where valency permits;
- $R_2$ is alkyl, haloalkyl, alkoxy, or haloalkoxy;
- $R_3$ is halogen, alkyl, or alkoxy;
- $R_4$ is halogen, alkyl, or H;
- $R_5$ is H, halogen, alkyl, haloalkyl, alkoxy, haloalkoxy, alkyl sulphonyl, alkyl sulfoximinyl, alkyl sulfonamide, cyano, $CF_3$, $OCF_3$, a fused heterocyclyl in which each ring has 5 or 6 members, a heteroaryl having 5 or 6 ring members, a saturated heterocyclyl, or a partially unsaturated heterocyclyl, each of which is optionally substituted where valency permits;
- X is CH or N; and
- Z is CH or N, with the proviso that X and Z cannot both be CH, or a pharmaceutically acceptable salt thereof.

$R_2$ may be —$CH_3$, —$CD_3$, or —$CT_3$, wherein D is deuterium and T is tritium.

$R_3$ may be —$CH_3$, —$CD_3$, or —$CT_3$, wherein D is deuterium and T is tritium.

The moieties in $R_5$ may be substituted with alkyl, haloalkyl, alkoxy, haloalkoxy, hydroxyl, or halogen.

The compound of Formula (I) may have the sulfoximine group in the R stereochemical configuration, the S stereochemical configuration, or a mixture of R and S stereochemical configurations.

In certain embodiments, the compounds have the structure of Formula (II):

(II)

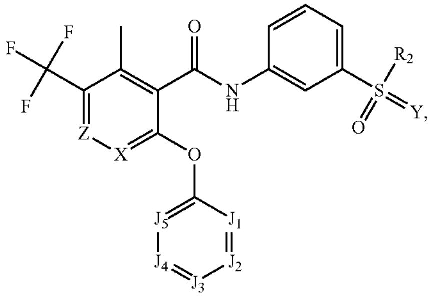

wherein:

each of $J_1$, $J_2$, $J_4$, and $J_5$ is independently N, N—O, or $CR_6$;

$J_3$ is N, N—O, or $CR_7$;

X is CH or N;

Y is $NR_8$ or O;

Z is CH, N, or N—O, $R_2$ is alkyl, haloalkyl, alkoxy, or haloalkoxy;

each instance of $R_6$ is independently H, halogen, $C_{1-3}$ alkyl, $C_{3-5}$ cycloalkyl, $C_{1-3}$ alkoxy, $CD_3$ or $CT_3$; and $R_7$ is H, halogen, —$CD_3$, alkyl, haloalkyl, alkoxy, haloalkoxy, alkyl sulphonyl, alkyl sulfoximinyl, alkyl sulfonamide, cyano, —$CF_3$, —$OCF_3$, heterocyclyl in which each ring has 5 or 6 members, heteroaryl having 5 or 6 ring members, saturated heterocyclyl, or partially unsaturated heterocyclyl, O-aryl in which each ring has 5 or 6 members, O-heteroaryl in which each ring has 5 or 6 members, O-cycloalkyl, O-cycloheteroalkyl, each of which is optionally substituted where valency permits, $R_8$ is H, $C_{1-3}$ alkyl, or $C_{3-5}$ cycloalkyl, with the provisos that:

X and Z cannot both be CH; and not more than two of $J_1$, $J_2$, $J_3$, $J_4$, and $J_5$ are N or N—O, or a pharmaceutically acceptable salt thereof.

$R_2$ may be —$CH_3$, —$CD_3$, or —$CT_3$, wherein D is deuterium and T is tritium.

The compound of Formula (II) may have the sulfoximine group in the R stereochemical configuration, the S stereochemical configuration, or a mixture of R and S stereochemical configurations.

In certain embodiments, the compounds have the structure of Formula (III):

(III)

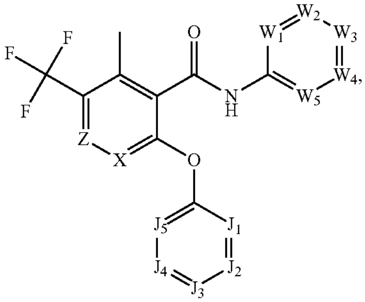

wherein:

each of $J_1$, $J_2$, $J_4$, and $J_5$ is independently N, N—O, or $CR_6$;

$J_3$ is N, N—O, or $CR_7$;

each of $W_1$, $W_2$, $W_3$, $W_4$, and $W_5$ is independently N, CH, or $CR_9$;

X is CH or N;

Z is CH, N, or N—O, each instance of $R_6$ is independently —H, halogen, $C_{1-3}$ alkyl, $C_{3-5}$ cycloalkyl, $C_{1-3}$ alkoxy, $CD_3$ or $CT_3$; and $R_7$ is —H, halogen, —$CD_3$, alkyl, haloalkyl, alkoxy, haloalkoxy, alkyl sulphonyl, alkyl sulfoximinyl, alkyl sulfonamide, cyano, —$CF_3$, —$OCF_3$, carbocyclyl in which each ring has 3-6 members, heterocyclyl in which each ring has 5 or 6 members, heteroaryl having 5 or 6 ring members, saturated heterocyclyl in which each ring has 3 to 6 members, or partially unsaturated heterocyclyl, O-aryl in which each ring has 5 or 6 members, O-heteroaryl in which each ring has 5 or 6 members, O-cycloalkyl, O-cycloheteroalkyl, each of which is optionally substituted where valency permits, each instance of $R_9$ is independently —$C(O)NR_{10}R_{11}$, —$S(O)_2C_{1-6}$ alkyl, —$S(O)(NH)C_{1-6}$ alkyl, $C_{1-3}$ alkyl, or $C_{3-5}$ cycloalkyl; and each of $R_{10}$ and $R_{11}$ is independently selected from —H and $C_{1-5}$ alkyl, or $R_{10}$ and $R_{11}$ together with the nitrogen atom to which they are attached form a heterocyclyl having 3-6 members, in which each of the $C_{1-5}$ alkyl and heterocyclyl is optionally substituted where valency permits, with the provisos that:

not more than two of $J_1$, $J_2$, $J_3$, $J_4$, and $J_5$ are N or N—O;

not more than two of $W_1$, $W_2$, $W_3$, $W_4$, and $W_5$ are N;

not more than three of $W_1$, $W_2$, $W_3$, $W_4$, and $W_5$ are $CR_9$; and

X and Z cannot both be CH, or a pharmaceutically acceptable salt thereof.

The compounds of the invention may be enriched for an isotope at any position for which an atomic mass is not otherwise specified. For example, the compounds may have one or more hydrogen atoms replaced with deuterium atoms or tritium atoms. Isotopic substitution or enrichment may occur at carbon, sulfur, or phosphorus, or other atoms. For example and without limitation, fluorine atoms can be enriched for $^{19}F$, carbon atoms can be enriched for $^{14}C$, and nitrogen atoms can be enriched for $^{15}N$. The compounds may be isotopically substituted or enriched for a given atom at one or more positions within the compound, or the compounds may be isotopically substituted or enriched at all instances of a given atom within the compound.

In certain embodiments, the compounds have the structure of Formula (IV), (IV)

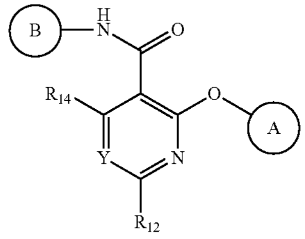

wherein:

Y is N or $CR_{13}$;

A and B are independently aryl, heteroaryl, or a 3-6 membered ring containing one or more heteroatoms independently selected from O, S, and N; wherein A is unsubstituted or substituted with one or more substituents selected from:

H, halo, $C_1$-$C_6$-alkyl, branched alkyl, alkenyl, alkynyl, haloalkyl, alkoxy, cycloalkoxy, haloalkoxy, nitro, cyano, SR', —$CH_2$-cycloalkyl, —$CF_2$-cycloalky, —$CH(CH_3)$-cycloalkyl, —$CH_2$— aryl, —$CF_2$-aryl, —CH(—$CH_3$)-aryl, C(═O)-alkyl, —C(═O)cycloalkyl, —C(═O)—NH-alkyl, —C(═O)$NH_2$, hydroxy, —COOH (and ester thereof), alkylsulfonyl, arylsulfonyl, sulfonamide, amino, NR'R"—NHSOR', —NHC(═O)-alkyl-NH(C═O)NR'R", $SO_2R'$, trifluoromethyl, bromo, chloro, fluoro, cyclopropylmethyl, sulfonylmethyl, 3-6 membered cycloalkyl; 3-6 membered heterocycloalkyl, any of which may have one or more substituents, wherein the 3-6 membered heterocycloalkyl comprises at least one heteroatom independently selected from O, S, and N;

$R_{12}$, $R_{13}$, and $R_{14}$ are individually selected from: H, $CF_3$, halo, $C_1$-$C_6$-alkyl, branched alkyl, alkenyl, alkynyl, haloalkyl, alkoxy, cycloalkoxy, haloalkoxy, nitro, cyano; —$CH_2$-cycloalkyl, —$CF_2$-cycloalky, —CH($CH_3$)-cycloalkyl, —$CH_2$-aryl, —$CF_2$-aryl, —CH(—$CH_3$)-aryl, C(═O)-alkyl, —C(═O)cycloalkyl, —C(═O)—NH-alkyl, —C(═O)$NH_2$, hydroxy, —COOH (and ester thereof), alkylsulfonyl, arylsulfonyl, sulfonamide, amino, NR'R"—$NHSO_2R1$, —NHC(═O)-alkyl-NH(C═O)NR'R", spirocyclyl, morpholinyl, pyrrolidinyl, piperidinyl, carbocyclyl, heterocyclyl, aryl or heteroaryl, wherein the 5 or 6 ring membered ring optionally includes one or more N or S in the ring, wherein the substitutions on the 5 or 6 ring membered ring are selected from halogen, alkyl, haloalkyl, alkoxy, haloalkoxy, alkyl sulphonyl, alkyl sulfoximinyl, alkyl sulfonamide, —C(═O)—NH-alkyl, —C(═O)$NH_2$ cyano, $CF_3$, $CHF_2$, $OCH_3$, $OCF_3$, a fused heterocyclyl in which each ring has 5 or 6 members, a heteroaryl having 5 or 6 ring members, a saturated heterocyclyl, or a partially unsaturated heterocyclyl, each of which is optionally substituted where valency permits;

the substituents R' and R" may be independently selected from hydrogen, substituted or unsubstituted alkyl, substituted or unsubstituted cycloalkyl, substituted or unsubstituted heterocycloalkyl, substituted or unsubstituted aryl, and substituted, unsubstituted heteroaryl, or $CD_3$.

In selected embodiments, A is $CH_2CF_3$ or

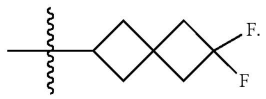 [SMILES: *C1CC2(C1)CC(F)(F)C2]

In another aspect, the invention provides compounds of Formula (V), (V)

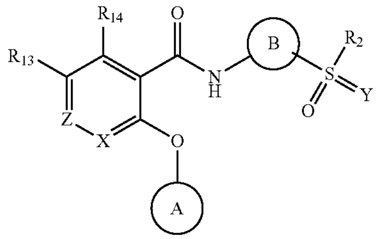

A, and B are as described in for Formula (IV)
$R_2$ is as described in for Formula (II)
$R_{13}$ and $R_{14}$ are as described in Formula (IV)
X is CH or N;
Y is $NR_8$ or O;
Z is CH, N, or N—O.

B. Second Set of Compounds

The compounds have the structure of Formula (I):

(I)

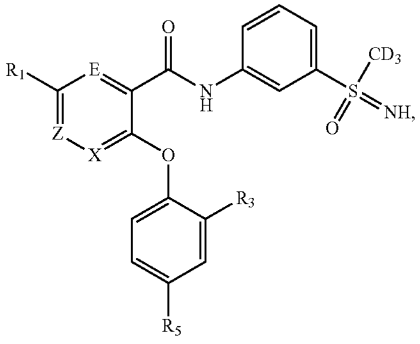

wherein:

$R_1$ is —CN or —$CF_3$;

$R_3$ is halogen, alkyl, alkoxy, or —$CD_3$;

$R_5$ is H, halogen, alkyl, haloalkyl, alkoxy, haloalkoxy, alkyl sulphonyl, alkyl sulfoximinyl, alkyl sulfonamide, cyano, $CF_3$, $OCF_3$, a fused heterocyclyl in which each ring has 5 or 6 members, a heteroaryl having 5 or 6 ring members, a saturated heterocyclyl, or a partially unsaturated heterocyclyl, each of which is optionally substituted where valency permits;

E is CH or CF;

X is CH or N;

Z is CH or N; and

—$CD_3$ is fully deuterated methyl group, with the proviso that X and Z cannot both be CH, or a pharmaceutically acceptable salt thereof.

The moieties in $R_5$ may be substituted with alkyl, haloalkyl, alkoxy, haloalkoxy, hydroxyl, or halogen.

The compound of Formula (I) may have the sulfoximine group in the R stereochemical configuration, the S stereochemical configuration, or a mixture of R and S stereochemical configurations.

The compounds of Formula (I) contain a deuterated methyl group (—$CD_3$) on the sulfoximine moiety. For other atoms of the compounds, however, the atomic mass is not specified. Thus, compounds of the invention may be enriched for an isotope at any position for which an atomic mass is not otherwise specified. For example, the compounds may have one or more hydrogen atoms replaced with deuterium or tritium. Isotopic substitution or enrichment may occur at carbon, sulfur, or phosphorus, or other atoms. For example and without limitation, fluorine atoms can be enriched for $^{19}F$, carbon atoms can be enriched for $^{14}C$, and nitrogen atoms can be enriched for $^{15}N$. The compounds may be isotopically substituted or enriched for a given atom at one or more positions within the compound, or the compounds may be isotopically substituted or enriched at all instances of a given atom within the compound.

C. Third Set of Compounds

The compounds have the structure of Formula (I):

(I)

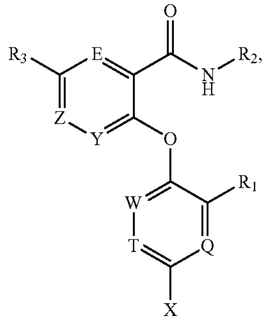

wherein:

$R_1$ is halogen, $C_1$-$C_3$ alkyl, $C_1$-$C_3$ alkoxy, $C_3$-$C_4$ cycloalkyl, haloalkyl, halocycloalkyl, or H;

$R_2$ is selected from the group consisting of aryl, heteroaryl, and unsaturated heterocyclyl, wherein:

each of the aryl, heteroaryl, and unsaturated heterocyclyl is optionally fused to one selected from the group consisting of optionally saturated carbocyclyl containing 5-6 ring members and optionally saturated heterocyclyl containing 5-6 ring members and 1-3 hetereoatoms;

each of the aryl, heteroaryl, and unsaturated heterocyclyl is optionally substituted with one or more groups selected from the group consisting of —$(CH_2)_nNR^eC(O)N(R^e)_2$, —$(CH_2)_nNR^eC(O)N(R^j)_2$, —$(CH_2)_nNR^eC(O)NR^eR^j$, —$(CH_2)_nNR^eC(O)OR^j$, —$(CH_2)_nNR^eC(O)R^j$, —$(CH_2)_nNR^eR^j$, —$(CH_2)_nNR^eS(O)_mN(R^e)_2$, —$(CH_2)_nNR^eS(O)_mN(R^j)_2$, —$(CH_2)_nNR^eS(O)_mNR^eR^j$, —$(CH_2)_nNR^eS(O)_mR^j$, alkyliminosulfanonyl, alkylsulfinyl, alkylsulfonamidyl, alkylsulfonyl, alkylsulfoxide, alkylsulfoximine, alkylthioether, amino, aryl, arylalkoxyl, aryloxyl, —$C(O)NH_2$, —$C(O)NR^eR^j$, —$C(O)R^j$, $C_1$-$C_4$ alkoxyl, $C_1$-$C_6$ alkyl, $C_1$-$C_6$alkyl, $C_2$-$C_6$alkenyl, $C_2$-$C_6$cycloheteroalkyl, $C_3$-$C_{10}$ cycloalkyl, $C_3$-$C_6$cycloalkyl, —$CF_3$, —CN, —$CO_2H$, —$CO_2R^j$, cyano, —H, halogen, heteroaryl, mono-, di-, and trihalo-$C_1$-$C_4$ alkyl, mono-, di-, or trihaloalkoxyl, morpholinyl, nitro, O-aryl, —$OC(O)N(R^j)_2$, —$OC(O)NR^eR^j$, —$OC(O)R^j$, —$OC_1$-$C_6$alkyl, —$OC_2$-$C_6$alkenyl, —$OC_2$-$C_6$cycloheteroalkyl, —$OC_3$-$C_6$cycloalkyl, —OH, O-heteroaryl, oxazolyl, oxo, —$S(O)_2R^j$, —$SO_2$aryl, —$SO_2C_1$-$C_6$alkenyl, —$SO_2C_1$-$C_6$alkyl, —$SO_2C_2$-$C_6$cycloheteroalkyl, —$SO_2C_3$-$C_6$cycloalkyl, $SO_2$heteroaryl, —$SO_2NH_2$, —$SO_2NR^e$-aryl, —$SO_2NR^eC(O)C_1$-$C_6$alkyl, —$SO_2NR^eC(O)C_2$-$C_6$cycloheteroalkyl, —$SO_2NR^eC(O)C_3$-$C_6$cycloalkyl, —$SO_2NR^eC_1$-$C_6$alkyl, —$SO_2NR^eC_2$-$C_6$alkenyl, —$SO_2NR^eC_2$-$C_6$cycloheteroalkyl, —$SO_2NR^eC_3$-$C_6$cycloalkyl, —$SO_2NR^e$-heteroary 1, —$SO_3H$, —$SR^j$, sulfoximinyl —$S(O)({=}NR^a)R^a$, sulfonimidamide —$S(O)({=}NR^a)N(R^a)_2$, sulfonimidoyl fluoride —$S(O)({=}NR^a)F$, and sulfondiimine —$S({=}NR^a)_2R^a$, wherein each alkenyl, alkyl, aryl, cycloalkyl, cycloheteroalkyl, and heteroaryl substituent is itself optionally substituted with one or more substituents selected from the group consisting of halogen, —OH, —$NH_2$, —$NH(C_1$-$C_6$alkyl) and —$N(C_1$-$C_6$alkyl$)_2$;

the unsaturated heterocyclyl is optionally substituted with $R^kR^l$; and each heteroatom in the heteroaryl, unsaturated heterocyclyl, and optionally saturated heterocyclyl is independently O, S or $N(R^h)_q$, each of which may be in its oxidized or unoxidized state;

$R_3$ is selected from the group consisting of —H, cyano, halogen, $C_1$-$C_4$ alkoxyl, mono-, di-, and trihalo-$C_1$-$C_4$ alkyl, mono-, di-, and trihalo-$C_1$-$C_4$ alkoxyl, optionally substituted $C_1$-$C_8$ alkyl, and $C_3$-$C_8$ cycloalkyl optionally substituted with 1-4 fluorine atoms; each $R^a$ is independently halogen, $C_1$-$C_3$ alkyl, $C_3$-$C_4$ cycloalkyl, haloalkyl, halocycloalkyl, or H;

each $R^e$ is independently —H, $C_1$-$C_6$ alkyl, or $C_2$-$C_6$ alkenyl; each $R^h$ is independently —H, or $C_1$-$C_6$ alkyl;

each $R^j$ is independently $C_1$-$C_6$ alkyl, $C_2$-$C_6$ alkenyl, $C_3$-$C_6$ cycloalkyl, $C_2$-$C_6$ cycloheteroalkyl, aryl, or heteroaryl, wherein each alkyl, alkenyl, cycloalkyl, cycloheteroalkyl, aryl and heteroaryl in $R^j$ is optionally substituted with one or more substituents independently selected from the group consisting of $C_1$-$C_6$ alkyl, $C_3$-$C_6$ cycloalkyl, —OH, —$OC_1$-$C_6$alkyl, —$OC_3$-$C_6$cycloalkyl, halogen, cyano, and —$S(O)_2CH_3$;

$R^k$ and $R^l$, together with the atom to which they are attached, form a cylcloalkyl or cycloheteroalkyl containing 3-7 ring members;

E is CH, CF, or N;

Q is CH, CF, or N;

T is CH, CF or N;

W is CH, CF, or N;

X is halogen, alkyl, haloalkyl, cycloalkyl, or halocycloalkyl,

Y is N or $N^+O^-$;

Z is N, $N^+O^-$, or CH;

each m is independently 0-2;

each n is independently 0-4; and each q is independently 0 or 1, or a pharmaceutically acceptable salt thereof.

$R_2$ may be an optionally substituted aryl, an optionally substituted heteroaryl, or an optionally substituted unsaturated heterocyclyl.

$R_1$ may be H, halogen, $C_1$-$C_3$ alkyl, $C_3$-$C_4$ cycloalkyl, haloalkyl, or halocycloalkyl.

$R_3$ may be a mono-, di-, ortrihalo-$C_1$-$C_4$ alkyl. $R_3$ may be —$CF_3$.

E may be CH, CF, or N.

Q may be CH, CF, or N.

T may be CH, CF, or N.

W may be CH, CF, or N, or pharmaceutically acceptable salts thereof.

D. Fourth Set of Compounds

The compounds have the structure of Formula (I):

(I)

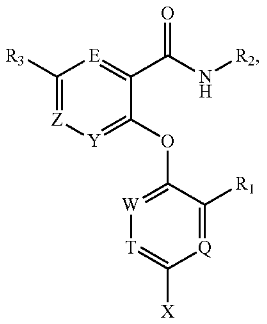

wherein:

$R_1$ is halogen, $C_1$-$C_3$ alkyl, $C_3$-$C_4$ cycloalkyl, haloalkyl, halocycloalkyl, or H;

$R_2$ is selected from the group consisting of aryl, heteroaryl, and unsaturated heterocyclyl, wherein:

each of the aryl, heteroaryl, and unsaturated heterocyclyl is optionally fused to one selected from the group consisting of optionally saturated carbocyclyl containing 5-6 ring members and optionally saturated heterocyclyl containing 5-6 ring members and 1-3 hetereoatoms;

each of the aryl, heteroaryl, and unsaturated heterocyclyl is optionally substituted with one or more groups selected from the group consisting of —$(CH_2)_n NR^e C(O)N(R^e)_2$, —$(CH_2)_n NR^e C(O)N(R^j)_2$, —$(CH_2)_n NR^e C(O)NR^e R^j$, —$(CH_2)_n NR^e C(O)OR^j$, —$(CH_2)_n NR^e C(O)R^j$, —$(CH_2)_n NR^e R^j$, —$(CH_2)_n NR^e S(O)_m N(R^e)_2$, —$(CH_2)_n NR^e S(O)_m N(R^j)_2$, —$(CH_2)_n NR^e S(O)_m NR^e R^j$, —$(CH_2)_n NR^e S(O)_m R^j$, alkyliminosulfanonyl, alkylsulfinyl, alkylsulfonamidyl, alkylsulfonyl, alkylsulfoxide, alkylsulfoximine, alkylthioether, amino, aryl, arylalkoxyl, aryloxyl, —$C(O)NH_2$, —$C(O)NR^e R^j$, —$C(O)R^j$, $C_1$-$C_4$ alkoxyl, $C_1$-$C_6$ alkyl, $C_1$-$C_6$alkyl, $C_2$-$C_6$alkenyl, $C_2$-$C_6$cycloheteroalkyl, $C_3$-$C_{10}$ cycloalkyl, $C_3$-$C_6$cycloalkyl, —$CF_3$, —CN, —$CO_2H$, —$CO_2R^j$, cyano, —H, halogen, heteroaryl, mono-, di-, and trihalo-$C_1$-$C_4$ alkyl, mono-, di-, or trihaloalkoxyl, morpholinyl, nitro, O-aryl, —$OC(O)N(R^j)_2$, —$OC(O)NR^e R^j$, —$OC(O)R^j$, —$OC_1$-$C_6$alkyl, —$OC_2$-$C_6$alkenyl, —$OC_2$-$C_6$cycloheteroalkyl, —$OC_3$-$C_6$cycloalkyl, —OH, O-heteroaryl, oxazolyl, oxo, —$S(O)_2R^j$, —$SO_2$aryl, —$SO_2C_1$-$C_6$alkenyl, —$SO_2C_1$-$C_6$alkyl, —$SO_2C_2$-$C_6$cycloheteroalkyl, —$SO_2C_3$-$C_6$cycloalkyl, $SO_2$heteroaryl, —$SO_2NH_2$, —$SO_2NR^e$-aryl, —$SO_2NR^e C(O)C_1$-$C_6$alkyl, —$SO_2NR^e C(O)C_2$-$C_6$cycloheteroalkyl, —$SO_2NR^e C(O)C_3$-$C_6$cycloalkyl, —$SO_2NR^e C_1$-$C_6$alkyl, —$SO_2NR^e C_2$-$C_6$alkenyl, —$SO_2NR^e C_2$-$C_6$cycloheteroalkyl, —$SO_2NR^e C_3$-$C_6$cycloalkyl, —$SO_2NR^e$-heteroary 1, —$SO_3H$, —$SR^j$, sulfoximinyl —$S(O)(=NR^a)R^a$, sulfonimidamide —$S(O)(=NR^a)N(R^a)_2$, sulfonimidoyl fluoride —$S(O)(=NR^a)F$, and sulfondiimine —$S(=NR^a)_2R^a$, wherein each alkenyl, alkyl, aryl, cycloalkyl, cycloheteroalkyl, and heteroaryl substituent is itself optionally substituted with one or more substituents selected from the group consisting of halogen, —OH, —$NH_2$, —$NH(C_1$-$C_6$alkyl) and —$N(C_1$-$C_6$alkyl$)_2$;

the unsaturated heterocyclyl is optionally substituted with $R^k R^l$; and each heteroatom in the heteroaryl, unsaturated heterocyclyl, and optionally saturated heterocyclyl is independently O, S or $N(R^h)_q$, each of which may be in its oxidized or unoxidized state;

$R_3$ is selected from the group consisting of —H, cyano, halogen, $C_1$-$C_4$ alkoxyl, mono-, di-, and trihalo-$C_1$-$C_4$ alkyl, mono-, di-, and trihalo-$C_1$-$C_4$ alkoxyl, optionally substituted $C_1$-$C_8$ alkyl, and $C_3$-$C_8$ cycloalkyl optionally substituted with 1-4 fluorine atoms;

each $R^a$ is independently halogen, $C_1$-$C_3$ alkyl, $C_3$-$C_4$ cycloalkyl, haloalkyl, halocycloalkyl, or H;

each $R^e$ is independently —H, $C_1$-$C_6$ alkyl, or $C_2$-$C_6$ alkenyl; each $R^h$ is independently —H, or $C_1$-$C_6$ alkyl;

each $R^j$ is independently $C_1$-$C_6$ alkyl, $C_2$-$C_6$ alkenyl, $C_3$-$C_6$ cycloalkyl, $C_2$-$C_6$ cycloheteroalkyl, aryl, or heteroaryl, wherein each alkyl, alkenyl, cycloalkyl, cycloheteroalkyl, aryl and heteroaryl in $R^j$ is optionally substituted with one or more substituents independently selected from the group consisting of $C_1$-$C_6$ alkyl, $C_3$-$C_6$ cycloalkyl, —OH, —$OC_1$-$C_6$alkyl, —$OC_3$-$C_6$cycloalkyl, halogen, cyano, and —$S(O)_2CH_3$;

$R^k$ and $R^l$, together with the atom to which they are attached, form a cylcloalkyl or cycloheteroalkyl containing 3-7 ring members;

E is CH or CF;

Q is CH, CF, or N;

T is CH, CF or N;

W is CH, CF, or N;

X is halogen, alkyl, haloalkyl, cycloalkyl, or halocycloalkyl,

Y is N or $N^+O^-$;

Z is N or $N^+O^-$, each m is independently 0-2;

each n is independently 0-4; and each q is independently 0 or 1, or a pharmaceutically acceptable salt thereof.

$R_2$ may be an optionally substituted aryl, an optionally substituted heteroaryl, or an optionally substituted unsaturated heterocyclyl.

$R_1$ may be H, halogen, $C_1$-$C_3$ alkyl, $C_3$-$C_4$ cycloalkyl, haloalkyl, or halocycloalkyl.

$R_3$ may be a mono-, di-, ortrihalo-$C_1$-$C_4$ alkyl. $R_3$ may be —$CF_3$.

E may be CH, CF, or N.

Q may be CH, CF, or N.

T may be CH, CF, or N.

W may be CH, CF, or N;

or pharmaceutically acceptable salts thereof.

E. Fifth Set of Compounds

In some embodiments, the presently disclosed subject matter provides a compound of formula (I):

(I)

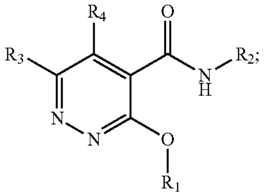

wherein:

$R_1$ is aryl or heteroaryl, wherein the aryl or heteroaryl is unsubstituted or substituted with one or more groups selected from the group consisting of mono-, di-, and trihalo-$C_1$-$C_4$ alkyl, substituted or unsubstituted $C_1$-$C_8$ alkyl, $C_3$-$C_{10}$ cycloalkyl, halogen, heteroaryl, cyano, amino, nitro, aryloxyl, aryl, $C_1$-$C_8$ alkoxyl, mono-, di-, or trihaloalkoxyl, sulfanyl, trifluoromethylsulfanyl, and arylalkoxyl;

$R_2$ is selected from the group consisting of aryl, heteroaryl, and heterocycle, wherein the aryl, heteroaryl, and heterocycle unsubstituted or are substituted with one or more groups selected from the group consisting of mono-, di-, andtrihalo-$C_1$-$C_4$ alkyl, substituted or unsubstituted $C_1$-$C_8$ alkyl, $C_3$-$C_{10}$ cycloalkyl, halogen, heteroaryl, cyano, amino, nitro, aryloxyl, aryl, $C_1$-$C_8$ alkoxyl, mono-, di-, or trihaloalkoxyl, arylalkoxyl, oxo, alkylsulfinyl, alkylsulfonyl, alkyliminosulfanonyl, alkylsulfoxide, sulfonamide, morpholinyl, and oxazolyl;

$R_3$ is selected from the group consisting of hydrogen, cyano, halogen, $C_1$-$C_8$ alkoxyl, mono-, di-, and trihalo-$C_1$-$C_4$ alkyl, mono-, di-, and trihalo-$C_1$-$C_4$ alkoxyl, substituted or unsubstituted $C_1$-$C_8$ alkyl, $C_3$-$C_8$ cycloalkyl, —$NO_2$;

$R_4$ is selected from the group consisting of hydrogen, cyano, halogen, $C_1$-$C_8$ alkoxyl, mono-, di-, and trihalo-$C_1$-$C_4$ alkyl, mono-, di-, and trihalo-$C_1$-$C_4$ alkoxyl, substituted or unsubstituted $C_1$-$C_8$ alkyl, and morpholinyl, provided that $R_3$ and $R_4$ are not hydrogen at the same time; or $R_3$ and $R_4$ together form a $C_3$-$C_5$ carbocyclic ring including carbon atoms to which $R_3$ and $R_4$ are attached;

and pharmaceutically acceptable salts thereof.

In some embodiments of the compound of formula (I), $R_1$ is phenyl or pyridinyl, wherein the phenyl or pyridinyl is unsubstituted or substituted with one or more groups selected from the group consisting of substituted or unsubstituted $C_1$-$C_8$ alkyl, halogen, —O—$R_5$, wherein $R_5$ is selected from the group consisting of $C_1$-$C_8$ alkyl, —$CF_3$, —$CHF_2$, and —$(CH_2)_p$—$CF_3$, wherein p is an integer selected from the group consisting of 1, 2, 3, 4, 5, 6, 7, and 8, and —S—$CF_3$;

$R_2$ is selected from the group consisting of phenyl, pyridyl, pyrimidinyl, pyridazinyl, pyrazolyl, pyridine-1-oxide, 1,2,3-thiadiazolyl, 1,2,4-triazolyl, and 1,3-benzothiazolyl, wherein the phenyl, pyridyl, pyrimidinyl, pyridazinyl, pyridine-1-oxide, 1,2,3-thiadiazolyl, 1,2,4-triazolyl, and 1,3-benzothiazolyl are unsubstituted or are substituted with one or more groups selected from the group consisting of unsubstituted or substituted $C_1$-$C_8$ alkyl, halogen, cyano, oxo, —O—$R_5$, wherein $R_5$ is selected from the group consisting of $C_1$-$C_8$ alkyl, —$CF_3$, and —$CHF_2$, —$(CH_2)_q$—OH, wherein q is an integer selected from the group consisting of 1, 2, 3, 4, 5, 6, 7, and 8, —$NR_6R_7$, wherein $R_6$ and $R_7$ are selected from the group consisting of H and $C_1$-$C_4$ alkyl, morpholinyl, oxazolyl, —C(═O)—$R_8$, wherein $R_8$ is selected from the group consisting of —$NR_6R_7$, wherein $R_6$ and $R_7$ are selected from the group consisting of H and $C_1$-$C_4$ alkyl, and $C_1$-$C_4$ alkyl, —S(═O)—$R_9$, —$S(=O)_2$—$R_9$, —S(═O)(═$NR_{10}$)—$R_{11}$, and —N═S(═O)—$(R_{11})_2$, wherein each $R_9$ is independently $C_1$-$C_4$ alkyl, —$CF_3$, or —$NR_6R_7$, wherein $R_6$ and $R_7$ are selected from the group consisting of H and $C_1$-$C_4$ alkyl, $R_{10}$ is H or $C_1$-$C_4$ alkyl, and $R_{11}$ is $C_1$-$C_4$ alkyl, provided that when Y is nitrogen and $R_2$ is phenyl or pyridyl, $R_8$ cannot be —$NR_6R_7$;

$R_3$ is selected from the group consisting of hydrogen, cyano, halogen, —$CF_3$, $C_1$-$C_8$ alkoxyl, —O—$CH(F)_2$, substituted or unsubstituted $C_1$-$C_8$ alkyl, $C_3$-$C_8$ cycloalkyl, —$N^+$(═O)—$O^-$;

$R_4$ is selected from the group consisting of hydrogen, cyano, halogen, $C_1$-$C_8$ alkoxyl, —$CF_3$, substituted or unsubstituted $C_1$-$C_8$ alkyl, and morpholinyl, provided that $R_3$ and $R_4$ are not hydrogen at the same time; or $R_3$ and $R_4$ together form a $C_3$-$C_5$ carbocyclic ring including carbon atoms to which $R_3$ and $R_4$ are attached.

In certain embodiments, the compound of formula (I) comprises a compound of formula (II):

(II)

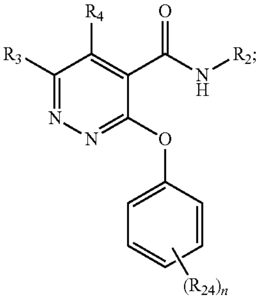

wherein:

$R_2$ is selected from the group consisting of aryl, heteroaryl, and heterocycle, wherein the aryl, heteroaryl, and heterocycle unsubstituted or are substituted with one or more groups selected from the group consisting of mono-, di-, andtrihalo-$C_1$-$C_4$ alkyl, substituted or unsubstituted $C_1$-$C_8$ alkyl, $C_3$-$C_{10}$ cycloalkyl, halogen, heteroaryl, cyano, amino, nitro, aryloxyl, aryl, $C_1$-$C_8$ alkoxyl, mono-, di-, or trihaloalkoxyl, arylalkoxyl, oxo, alkylsulfinyl, alkylsulfonyl, alkyliminosulfanonyl, alkylsulfoxide, sulfonamide, morpholinyl, and oxazolyl;

$R_3$ is selected from the group consisting of hydrogen, cyano, halogen, $C_1$-$C_8$ alkoxyl, mono-, di-, and trihalo-$C_1$-$C_4$ alkyl, mono-, di-, and trihalo-$C_1$-$C_4$ alkoxyl, substituted or unsubstituted $C_1$-$C_8$ alkyl, $C_3$-$C_8$ cycloalkyl, —$NO_2$;

$R_4$ is selected from the group consisting of hydrogen, cyano, halogen, $C_1$-$C_8$ alkoxyl, mono-, di-, and trihalo-$C_1$-$C_4$ alkyl, mono-, di-, and trihalo-$C_1$-$C_4$ alkoxyl, substituted or unsubstituted $C_1$-$C_8$ alkyl, and morpholinyl, provided that $R_3$ and $R_4$ are not hydrogen at the same time; or $R_3$ and $R_4$ together form a $C_3$-$C_5$ carbocyclic ring including carbon atoms to which $R_3$ and $R_4$ are attached;

n is an integer selected from 0, 1, 2, 3, 4, and 5;

each $R_{24}$ is independently selected from the group consisting of mono-, di-, and trihalo-$C_1$-$C_4$ alkyl, substituted or unsubstituted $C_1$-$C_8$ alkyl, $C_3$-$C_{10}$ cycloalkyl, halogen, heteroaryl, cyano, amino, nitro, aryloxyl, aryl, $C_1$-$C_8$ alkoxyl, mono-, di-, or trihaloalkoxyl, sulfanyl, trifluoromethylsulfanyl, and arylalkoxyl.

In some embodiments of the compound of formula (II), $R_2$ is selected from the group consisting of:

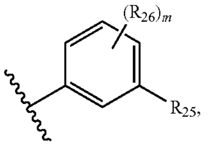
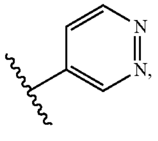
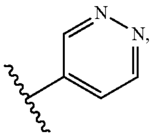
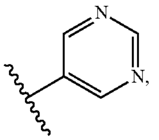
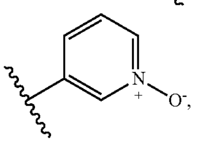
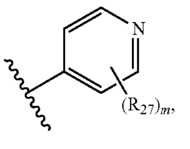
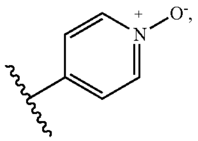
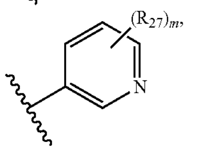
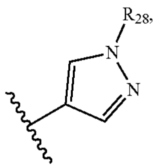
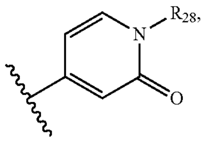
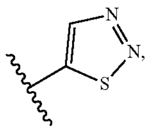
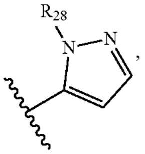
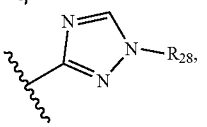
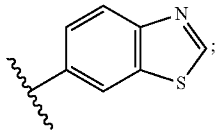 ; and
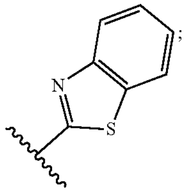 ;

wherein:

m is an integer selected from the group consisting of 0, 1, 2, 3, and 4;

$R_{25}$ is selected from the group consisting of H, morpholinyl, oxazolyl, halogen, cyano, —$(CH_2)_q$—OH, wherein q is an integer selected from the group consisting of 1, 2, 3, 4, 5, 6, 7, and 8, —C(═O)—$R_8$, wherein $R_8$ is selected from the group consisting of —$NR_6R_7$ and $C_1$-$C_4$ alkyl, wherein $R_6$ and $R_7$ are selected from the group consisting of H and $C_1$-$C_4$ alkyl, —S(═O)—$R_9$, —S(═O)$_2$—$R_9$, —S(═O)(═$NR_{10}$)—$R_{11}$, and —N═S(═O)—$(R_{11})_2$, wherein each $R_9$ is independently $C_1$-$C_4$ alkyl, —$CF_3$, or —$NR_6R_7$, wherein $R_6$ and $R_7$ are selected from the group consisting of H and $C_1$-$C_4$ alkyl, $R_{10}$ is H or $C_1$-$C_4$ alkyl, and $R_{11}$ is $C_1$-$C_4$ alkyl, provided that when Y is nitrogen and $R_2$ is phenyl or pyridyl, $R_8$ cannot be —$NR_6R_7$;

$R_{26}$ is halogen or cyano;

each $R_{27}$ is independently selected from the group consisting of H, halogen, $C_1$-$C_8$ alkoxyl, cyano, -and $NR_6R_7$; and each $R_{28}$ is independently H or $C_1$-$C_4$ alkyl.

In certain embodiments of the compound of formula (II), the compound is a compound of formula (II-a):

(II-a)

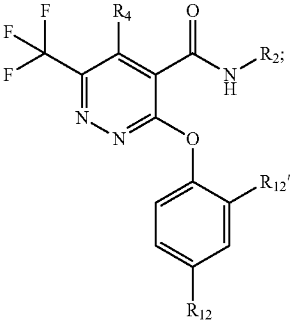

wherein:

$R_2$ is selected from the group consisting of aryl and heteroaryl, wherein the aryl or heteroaryl is optionally substituted with a substituent group selected from the group consisting of unsubstituted or substituted $C_1$-$C_8$ alkyl, halogen, cyano, oxo, heterocycloalkyl, —O—$R_5$, wherein $R_5$ is selected from the group consisting of $C_1$-$C_8$ alkyl, —$CF_3$, —$CH_2F$, and —$CHF_2$, —$(CH_2)_q$—OH, wherein q is an integer selected from the group consisting of 1, 2, 3, 4, 5, 6, 7, and 8, —$NR_6R_7$, wherein $R_6$ and $R_7$ are selected from the group consisting of H and $C_1$-$C_4$ alkyl, morpholinyl, oxazolyl, —C(═O)—$R_8$, wherein $R_8$ is selected from the group consisting of —$NR_6R_7$, wherein $R_6$ and $R_7$ are selected from the group consisting of H and $C_1$-$C_4$ alkyl, and $C_1$-$C_4$ alkyl, —S(═O)—$R_9$, —S(═O)$_2$—$R_9$, —S(═O)(═$NR_{10}$)—$R_{11}$, and —N═S(═O)—$(R_{11})_2$, wherein each $R_9$ is independently $C_1$-$C_4$ alkyl, —$CF_3$, or —$NR_6R_7$, wherein $R_6$ and $R_7$ are selected from the group consisting of H and $C_1$-$C_4$ alkyl, $R_{10}$ is H or $C_1$-$C_4$ alkyl, and Ru is $C_1$-$C_4$ alkyl;

$R_{12}$ is selected from the group consisting of halogen, —$OR_{23}$, wherein $R_{23}$ is selected from the group consisting of $C_1$-$C_8$ alkyl, —$CF_3$, —$CH_2F$, and —$CHF_2$; and $R_{12'}$ is selected from the group consisting of H, halogen, —$OR_{13}$, wherein $R_{13}$ is selected from the group consisting of $C_1$-$C_8$ alkyl, —$CF_3$, —$CH_2F$, and —$CHF_2$.

In certain embodiments of the compound of formula (II-a), the aryl and heteroaryl are selected from the group consisting of phenyl, benzothiazolyl, pyridyl, pyridyl N-oxide, pyridazinyl, and pyrimidinyl.

In certain embodiments of the compound of formula (II-a), $R_2$ is selected from the group consisting of (trifluorosulfonyl)phenyl, 1,2,4-triazolyl, 1,3-benzothiazol-2-yl, 1,3-benzothiazol-6-yl, 2-fluoro-5-methylsulfonylphenyl, 2-methoxy-4-pyridyl, 2-methyl-4-pyridyl, 3-(dimethylsulfamoyl)phenyl, 3-(methylsulfonimidoyl)phenyl, 3-(N,S-dimethylsulfonimidoyl)phenyl, 3-carbamoylphenyl, 3-cyanophenyl, 3-dimethylsulfamoylphenyl, 3-methylsulfinylphenyl, 3-methylsulfonylphenyl, 3-morpholinophenyl, 3-oxazol-5-ylphenyl, 3-pyridyl, 4-cyanophenyl, 4-pyridyl, 6-cyano-3-pyridyl, 6-methyl-3-pyridyl, dimethyl(oxo)-λ6-sulfanylidene]amino]phenyl, phenyl, pyrazolyl, pyridazine-4-yl, pyridazinyl, pyridizin-4-yl, pyridyl, pyrimidin-4-yl, pyrimidinyl, and thiadiazolyl.

In some embodiments, the compound of formula (I) comprises a compound of formula (III):

(III)

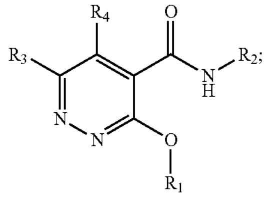

wherein:

$R_1$ is selected from the group consisting of phenyl, pyridyl, and 1,3-benzothiazol-4yl, wherein the phenyl and pyridyl can be unsubstituted or substituted with one or more of halogen, $C_1$-$C_8$ alkyl, —O—$R_5$, wherein $R_5$ is selected from the group consisting of $C_1$-$C_8$ alkyl, —$CF_3$, —$CHF_2$, and —$(CH_2)_p$—$CF_3$, wherein p is an integer selected from the group consisting of 1, 2, 3, 4, 5, 6, 7, and 8, —S—$CF_3$, —$NR_6R_7$, wherein $R_6$ and $R_7$ are selected from the group consisting of H and $C_1$-$C_4$ alkyl;

$R_2$ is selected from the group consisting of:

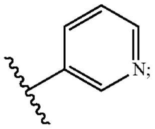
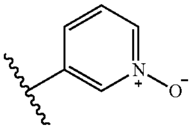
;

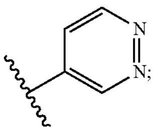
and
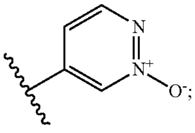

and $R_3$ and $R_4$ are H or —$CF_3$, provided that if $R_3$ is H, then $R_4$ is —$CF_3$ and if $R_4$ is H, then $R_3$ is —$CF_3$.

In certain embodiments of the compound of formula (III), the compound is a compound of formula (III-a):

(III-a)

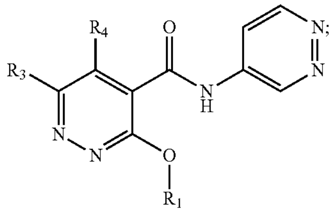

wherein:

$R_1$ is selected from the group consisting of phenyl, pyridyl, and 1,3-benzothiazol-4yl, wherein the phenyl and pyridyl can be unsubstituted or substituted with one or more of halogen, $C_1$-$C_8$ alkyl, —O—$R_5$, wherein $R_5$ is selected from the group consisting of $C_1$-$C_8$ alkyl, —$CF_3$, —$CHF_2$, and —$(CH_2)_p$—$CF_3$, wherein p is an integer selected from the group consisting of 1, 2, 3, 4, 5, 6, 7, and 8, —S—$CF_3$, —$NR_6R_7$, wherein $R_6$ and $R_7$ are selected from the group consisting of H and $C_1$-$C_4$ alkyl; and $R_3$ and $R_4$ are H or —$CF_3$, provided that if $R_3$ is H, then $R_4$ is —$CF_3$ and if $R_4$ is H, then $R_3$ is —$CF_3$.

In certain embodiments of the compound of formula (IIIa), $R_1$ is selected from the group consisting of 2,4-dichlorophenyl, 4-difluoromethoxyphenyl, and 2-chloro-4-methoxyphenyl.

In certain embodiments of the compound of formula (III), the compound is a compound of formula (III-b):

(III-b)

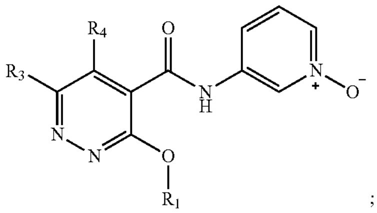
;

wherein:

$R_1$ is selected from the group consisting of phenyl, pyridyl, and 1,3-benzothiazol-4yl, wherein the phenyl and pyridyl can be unsubstituted or substituted with one or more of halogen, $C_1$-$C_8$ alkyl, —O—$R_5$, wherein $R_5$ is selected from the group consisting of $C_1$-$C_8$ alkyl, —$CF_3$, —$CHF_2$, and —$(CH_2)_p$—$CF_3$, wherein p is an integer selected from the group consisting of 1, 2, 3, 4, 5, 6, 7, and 8, —S—$CF_3$, —$NR_6R_7$, wherein $R_6$ and $R_7$ are selected from the group consisting of H and $C_1$-$C_4$ alkyl; and $R_3$ and $R_4$ are H or —$CF_3$, provided that if $R_3$ is H, then $R_4$ is —$CF_3$ and if $R_4$ is H, then $R_3$ is —$CF_3$.

In certain embodiments of the compound of formula (IIIc), the compound is a compound of formula (III-c):

(III-c)

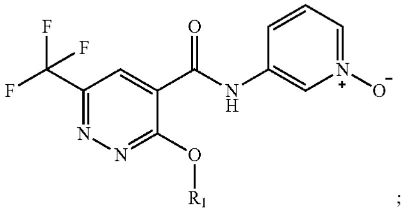

;

wherein:

$R_1$ is phenyl substituted with one or more of halogen, $C_1$-$C_8$ alkyl, —O—$R_5$, wherein $R_5$ is selected from the group consisting of $C_1$-$C_8$ alkyl, —$CF_3$, —$CHF_2$, and —$(CH_2)_p$—$CF_3$, wherein p is an integer selected from the group consisting of 1, 2, 3, 4, 5, 6, 7, and 8.

In certain embodiments of the compound of formula (IIIc), $R_1$ is selected from the group consisting of 4-fluoro-2-methoxyphenyl, 4-fluoro-2-methylphenyl, 4-difluoromethoxyphenyl, 4-trifluoromethoxyphenyl, 2,4-dimethoxyphenyl, 2,4-difluorophenyl, and 3,4-difluorophenyl.

In certain embodiments of the compound of formula (III), the compound is a compound of formula (III-d):

(III-d)

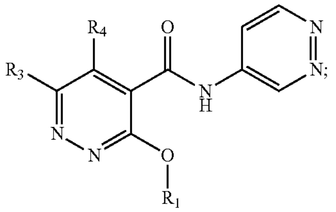

wherein:

$R_1$ is selected from the group consisting of phenyl, pyridyl, and 1,3-benzothiazol-4yl, wherein the phenyl and pyridyl can be unsubstituted or substituted with one or more of halogen, $C_1$-$C_8$ alkyl, —O—$R_5$, wherein $R_5$ is selected from the group consisting of $C_1$-$C_8$ alkyl, —$CF_3$, —$CHF_2$, and —$(CH_2)_p$—$CF_3$, wherein p is an integer selected from the group consisting of 1, 2, 3, 4, 5, 6, 7, and 8, —S—$CF_3$, —$NR_6R_7$, wherein $R_6$ and $R_7$ are selected from the group consisting of H and $C_1$-$C_4$ alkyl; and $R_3$ and $R_4$ are H or —$CF_3$, provided that if $R_3$ is H, then $R_4$ is —$CF_3$ and if $R_4$ is H, then $R_3$ is —$CF_3$.

In certain embodiments of the compound of formula (III-d), the compound is a compound of formula (III-d'):

(III-d')

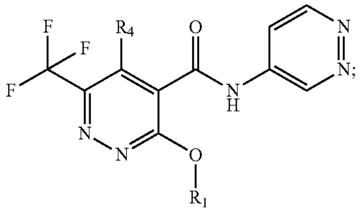

wherein $R_1$ is selected from the group consisting of 4-trifluoromethoxyphenyl, 4-difluoromethoxyphenyl, 2-chloro-4-trifluoromethoxyphenyl, 2,4-dimethoxyphenyl, and 2,4-difluorophenyl.

In certain embodiments of the compound of formula (III), the compound is a compound of formula (III-e):

(III-e)

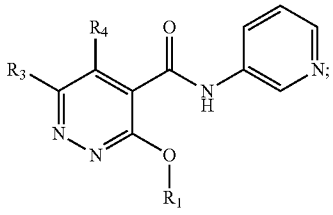

wherein:

$R_1$ is selected from the group consisting of phenyl, pyridyl, and 1,3-benzothiazol-4yl, wherein the phenyl and pyridyl can be unsubstituted or substituted with one or more of halogen, $C_1$-$C_8$ alkyl, —O—$R_5$, wherein $R_5$ is selected from the group consisting of $C_1$-$C_8$ alkyl, —$CF_3$, —$CHF_2$, and —$(CH_2)_p$—$CF_3$, wherein p is an integer selected from the group consisting of 1, 2, 3, 4, 5, 6, 7, and 8, —S—$CF_3$, —$NR_6R_7$, wherein $R_6$ and $R_7$ are selected from the group consisting of H and $C_1$-$C_4$ alkyl; and $R_3$ and $R_4$ are H or —$CF_3$, provided that if $R_3$ is H, then $R_4$ is —$CF_3$ and if $R_4$ is H, then $R_3$ is —$CF_3$.

In certain embodiments of the compound of formula (III-e), the compound is a compound of formula (III-e'):

(III-e')

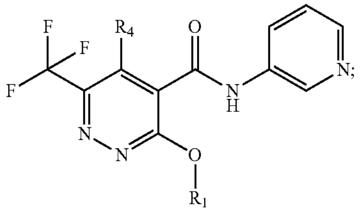

wherein $R_1$ is selected from the group consisting of 4-difluoromethoxyphenyl, 4-trifluoromethoxyphenyl, 2-chloro-4-trifluoromethoxyphenyl, 2,4-dimethoxyphenyl, and 2,4-difluorophenyl.

In certain embodiments of the compound of formula (III), the compound is a compound of formula (III-f):

(III-f)

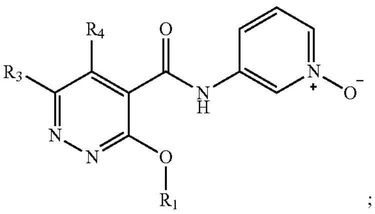

;

wherein:

$R_1$ is selected from the group consisting of phenyl, pyridyl, and 1,3-benzothiazol-4yl, wherein the phenyl and pyridyl can be unsubstituted or substituted with one or more of halogen, $C_1$-$C_8$ alkyl, —O—$R_5$, wherein $R_5$ is selected from the group consisting of $C_1$-$C_8$ alkyl, —$CF_3$, —$CHF_2$, and —$(CH_2)_p$—$CF_3$, wherein p is an integer selected from the group consisting of 1, 2, 3, 4, 5, 6, 7, and 8, —S—$CF_3$, —$NR_6R_7$, wherein $R_6$ and $R_7$ are selected from the group consisting of H and $C_1$-$C_4$ alkyl; and $R_3$ and $R_4$ are H or —$CF_3$, provided that if $R_3$ is H, then $R_4$ is —$CF_3$ and if $R_4$ is H, then $R_3$ is —$CF_3$.

In certain embodiments of the compound of formula (III-f), the compound is a compound of formula (III-f'):

(III-f')

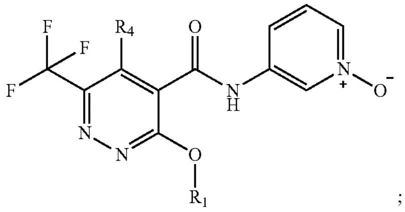

;

wherein:

$R_1$ is selected from the group consisting of 4-fluoro-2-methylphenyl, 4-fluoro-2-methoxyphenyl, 2,4-difluorophenyl, 4-difluoromethoxyphenyl, 2,4-dimethoxyphenyl, 2-chloro-4-methoxylphenyl, 3,4-difluorphenyl, and 2-chloro-4-fluorophenyl.

In certain embodiments of the compound of formula (III), the compound is a compound of formula (III-g):

(III-g)

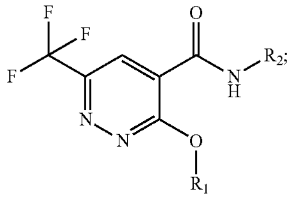

wherein:

$R_1$ is

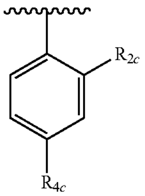

wherein $R_{2c}$ is selected from the group consisting of H, $C_1$-$C_4$ alkyl, halogen, and $C_1$-$C_4$ alkoxyl; and $R_{4c}$ is selected from the group consisting of —$OCF_3$, $C_1$-$C_4$ alkoxyl, and halogen; and $R_2$ is selected from the group consisting of:

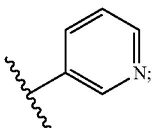

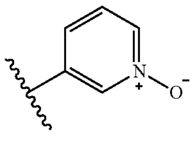

;

-continued

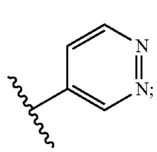

and

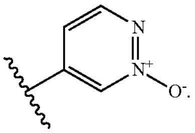

In certain embodiments of the compound of formula (III-g), $R_1$ is selected from the group consisting of:

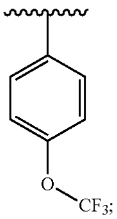

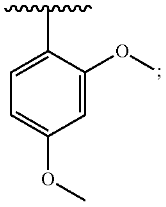

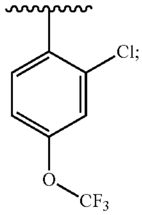

and

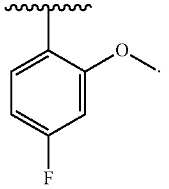

In certain embodiments, the compound of formula (III-g) is selected from the group consisting of:

3-(3-(4-(trifluoromethoxy)phenoxy)-6-(trifluoromethyl)pyridazine-4-carboxamido)pyridine 1-oxide;

3-(3-(2,4-dimethoxyphenoxy)-6-(trifluoromethyl)pyridazine-4-carboxamido)pyridine 1-oxide;

3-(3-(2-chloro-4-(trifluoromethoxy)phenoxy)-6-(trifluoromethyl)pyridazine-4-carboxamido)pyridine 1-oxide;

3-(2-chloro-4-(trifluoromethoxy)phenoxy)-N-(pyridazin-4-yl)-6-(trifluoromethyl)pyridazine-4-carboxamide;

3-(4-fluoro-2-methoxyphenoxy)-N-(pyridazin-4-yl)-6-(trifluoromethyl)pyridazine-4-carboxamide;

N-(pyridazin-4-yl)-3-(4-(trifluoromethoxy)phenoxy)-6-(trifluoromethyl)pyridazine-4-carboxamide;

3-(2,4-dimethoxyphenoxy)-N-(pyridazin-4-yl)-6-(trifluoromethyl)pyridazine-4-carboxamide;

5-(3-(2,4-dimethoxyphenoxy)-6-(trifluoromethyl)pyridazine-4-carboxamido)pyridazine 1-oxide;

5-(3-(4-(trifluoromethoxy)phenoxy)-6-(trifluoromethyl)pyridazine-4-carboxamido)pyridazine 1-oxide;

5-(3-(4-fluoro-2-methoxyphenoxy)-6-(trifluoromethyl)pyridazine-4-carboxamido)pyridazine 1-oxide; and 5-(3-(2-chloro-4-(trifluoromethoxy)phenoxy)-6-(trifluoromethyl)pyridazine-4-carboxamido)pyridazine 1-oxide.

In some embodiments, the compound of formula (I), comprises a compound of formula (IV):

(IV)

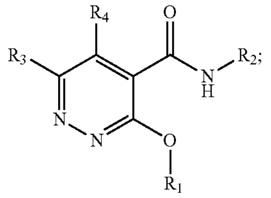

wherein $R_2$ is selected from the group consisting of:

(i)

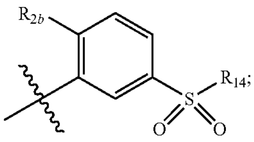

wherein $R_{2b}$ is selected from the group consisting of H, $C_1$-$C_4$ alkyl, and halogen; and $R_{14}$ is $C_1$-$C_4$ alkyl;

(ii)

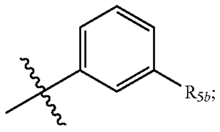

wherein $R_{5b}$ is selected from the group consisting of $-C(=O)-R_8$, $-(CH_2)_nOH$, and cyano, wherein $R_8$ is $C_1$-$C_4$ alkyl and n is an integer selected from 1, 2, 3, 4, 5, 6, 7 and 8;

(iii)

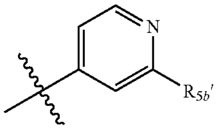

wherein $R_{5b'}$ is selected from the group consisting of H, halogen, and $C_1$-$C_4$ alkyl;

(iv)

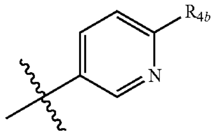

wherein $R_{4b}$ is H or halogen;

(v)

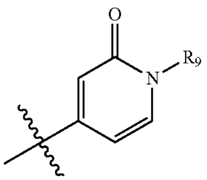

wherein $R_9$ is H or $C_1$-$C_4$ alkyl; and (vi)

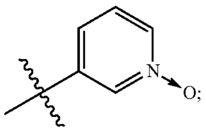

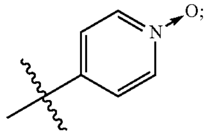

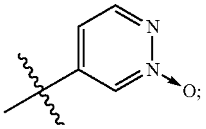

and

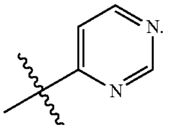

In certain embodiments of the compound of formula (IV), the compound is a compound of formula (IV-a):

(IV-a)

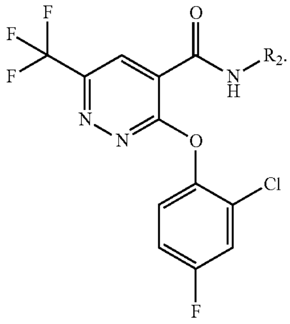

In certain embodiments of the compound of formula (IV-a), $R_2$ is selected from the group consisting of:

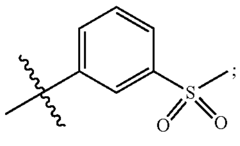

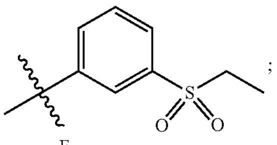

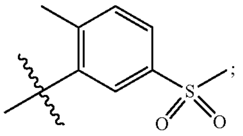

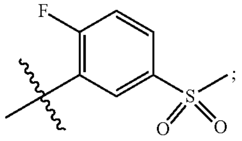

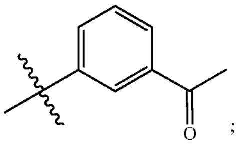

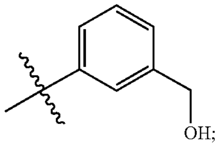

-continued

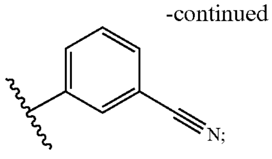

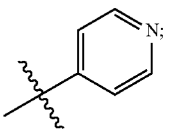

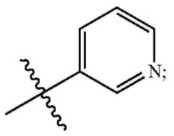

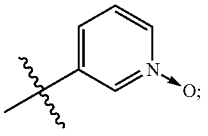

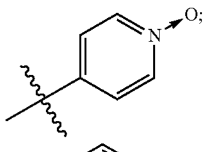

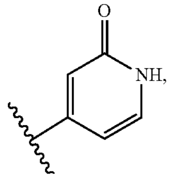

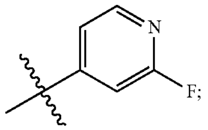

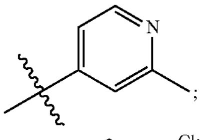

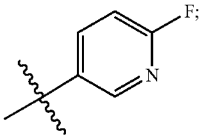

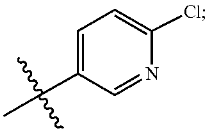

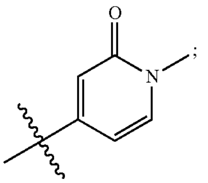

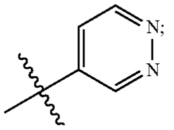

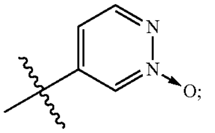

and

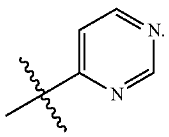

In certain embodiments of the compound of formula (IV-a), the compound is selected from the group consisting of:

3-(2-chloro-4-fluorophenoxy)-N-(3-methylsulfonylphenyl)-6-(trifluoromethyl)pyridazine-4-carboxamide;

3-(2-chloro-4-fluorophenoxy)-N-(3-ethylsulfonylphenyl)-6-(trifluoromethyl)pyridazine-4-carboxamide;

3-(2-chloro-4-fluorophenoxy)-N-(3-methylsulfonyl-6-methyl-phenyl)-6-(trifluoromethyl)pyridazine-4-carboxamide;

3-(2-chloro-4-fluorophenoxy)-N-(3-methylsulfonyl-6-fluoro-phenyl)-6-(trifluoromethyl)pyridazine-4-carboxamide;

N-(3-acetylphenyl)-3-(2-chloro-4-fluoro-phenoxy)-6-(trifluoromethyl)pyridazine-4-carboxamide;

3-(2-chloro-4-fluoro-phenoxy)-N-[3-(hydroxymethyl)phenyl]-6-(trifluoromethyl)pyridazine-4-carboxamide;

3-(2-chloro-4-fluoro-phenoxy)-N-[3-cyanophenyl]-6-(trifluoromethyl)pyridazine-4-carboxamide;

3-(2-chloro-4-fluoro-phenoxy)-N-(4-pyridyl)-6-(trifluoromethyl)pyridazine-4-carboxamide;

3-(2-chloro-4-fluoro-phenoxy)-N-(3-pyridyl)-6-(trifluoromethyl)pyridazine-4-carboxamide;

3-(2-chloro-4-fluoro-phenoxy)-N-(3-pyridyl-N-oxide)-6-(trifluoromethyl)pyridazine-4-carboxamide;

3-(2-chloro-4-fluoro-phenoxy)-N-(4-pyridyl-N-oxide)-6-(trifluoromethyl)pyridazine-4-carboxamide;

3-(2-chloro-4-fluoro-phenoxy)-N-(2-oxo-1H-pyridin-4-yl)-6-(trifluoromethyl)pyridazine-4-carboxamide;

3-(2-chloro-4-fluoro-phenoxy)-N-(2-fluoro-4-pyridyl)-6-(trifluoromethyl)pyridazine-4-carboxamide;

3-(2-chloro-4-fluoro-phenoxy)-N-(2-methyl-4-pyridyl)-6-(trifluoromethyl)pyridazine-4-carboxamide;

3-(2-chloro-4-fluoro-phenoxy)-N-(6-fluoro-3-pyridyl)-6-(trifluoromethyl)pyridazine-4-carboxamide;

3-(2-chloro-4-fluoro-phenoxy)-N-(6-chloro-3-pyridyl)-6-(trifluoromethyl)pyridazine-4-carboxamide;

3-(2-chloro-4-fluoro-phenoxy)-N-(1-methyl-2-oxo-4-pyridyl)-6-(trifluoromethyl)pyridazine-4-carboxamide;

3-(2-chloro-4-fluoro-phenoxy)-N-pyridazin-4-yl-6-(trifluoromethyl)pyridazine-4-carboxamide;

3-(2-chloro-4-fluoro-phenoxy)-N-(2-oxidopyridazin-2-ium-4-yl)-6-(trifluoromethyl)pyridazine-4-carboxamide; and 3-(2-chloro-4-fluoro-phenoxy)-N-pyrimidin-4-yl-6-(trifluoromethyl)pyridazine-4-carboxamide.

In certain embodiments of the compound of formula (IV), the compound is a compound of formula (IV-b):

(IV-b)

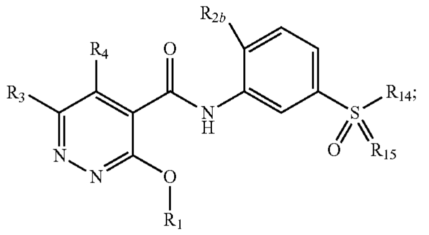

wherein:

$R_1$ is selected from the group consisting of phenyl, pyridyl, and 1,3-benzothiazol-4yl, wherein the phenyl and pyridyl can be unsubstituted or substituted with one or more of halogen, $C_1$-$C_8$ alkyl, —O—$R_5$, wherein $R_5$ is selected from the group consisting of $C_1$-$C_8$ alkyl, —$CF_3$, —$CHF_2$, and —$(CH_2)_p$—$CF_3$, wherein p is an integer selected from the group consisting of 1, 2, 3, 4, 5, 6, 7, and 8, —S—$CF_3$, —$NR_6R_7$, wherein $R_6$ and $R_7$ are selected from the group consisting of H and $C_1$-$C_4$ alkyl;

$R_3$ and $R_4$ are H or —$CF_3$, provided that if $R_3$ is H, then $R_4$ is —$CF_3$ and if $R_4$ is H, then $R_3$ is —$CF_3$;

$R_{2b}$ is selected from the group consisting of H, $C_1$-$C_4$ alkyl, and halogen; and $R_{14}$ is $C_1$-$C_4$ alkyl;

$R_{14}$ is $C_1$-$C_4$ alkyl; and $R_{15}$ is O or $NR_{10}$, wherein $R_{10}$ is H or $C_1$-$C_4$ alkyl.

In certain embodiments of the compound of formula (IV-b), $R_1$ is selected from the group consisting of phenyl, 4-fluorophenyl, 2,4-dichlorophenyl, 2,4-dimethylphenyl, 2-propylphenyl, 2-methoxy-4-methylphenyl, 2-methoxy-4-chlorophenyl, 2-isopropoxyphenyl, 4-fluoro-2-methoxyphenyl, 2-chloro-4-fluorophenyl, 2-methyl-4-trifluromethoxyphenyl, 4-trifluoromethoxyphenyl, difluoromethoxyphenyl, 3-fluoro-4-trifluoromethoxyphenyl, 3-fluorophenyl, 2,5-difluorophenyl, 4-methylphenyl, 3-chloro-5-flurophenyl, 2-isopropylphenyl, 3,4-difluorophenyl, 2,4-difluorophenyl, 3,5-difluorophenyl, 4-(2,2,2-trifluoroethoxy)phenyl, 4-(trifluoromethylsulfanyl)phenyl, 2-dimethylaminophenyl, 2-trifluromethylphenyl, 2,4-dimethoxyphenyl, 3,4,5-trifluorophenyl, 3,5-dichlorophenyl, 6-trifluoromethyl-3-pyridyl, 1,3-benzothiazol-4-yl, 4-difluoromethoxyphenyl, 2-chloro-4-methoxyphenyl, and 2-chlorophenyl.

In certain embodiments of the compound of formula (IV), the compound is a compound of formula (IV-c):

(IV-c)

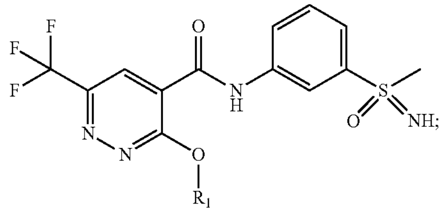

wherein:

$R_1$ is

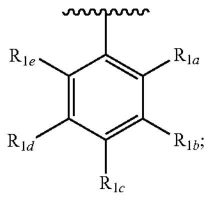

wherein:

$R_{1a}$, $R_{1b}$, $R_{1c}$, $R_{1d}$, and $R_{1e}$ are each independently selected from the group consisting of H, $C_1$-$C_4$ alkyl, halogen, $C_1$-$C_4$ alkoxyl, —$OCF_3$, —$OCHF_2$, —$OCH_2F$, —$OCH_2CF_3$, and —$NR_5R_6$, wherein $R_5$ and $R_6$ are $C_1$-$C_4$ alkyl, provided that at least one of $R_{1a}$, $R_{1b}$, $R_{1c}$, $R_{1d}$, and $R_{1e}$ are not H; and pharmaceutically acceptable salts thereof.

In certain embodiments of the compound of formula (IV-c):

(i) $R_{4a}$ is halogen; $R_{2a}$ is selected from the group consisting of H, $C_1$-$C_4$ alkyl, halogen, and $C_1$-$C_4$ alkoxyl; $R_{3a}$ is H or halogen; $R_{5a}$ is H or halogen; and $R_{6a}$ is H;

(ii) $R_{2a}$ and $R_{4a}$ are each $C_1$-$C_4$ alkoxyl;

(iii) $R_{4a}$ is —$OF_3$; $R_{2a}$ is selected from the group consisting of H, halogen, and $C_1$-$C_4$ alkyl; $R_{3a}$ and $R_{6a}$ are each H; $R_{5a}$ is H or halogen;

(iv) $R_{4a}$ is —$OCHF_2$; $R_{2a}$ is selected from the group consisting of H, halogen, and $C_1$-$C_4$ alkyl; $R_{3a}$ and $R_{6a}$ are each H; $R_{5a}$ is H or halogen;

(v) $R_{4a}$ is —$OCH_2F$; $R_{2a}$ is selected from the group consisting of H, halogen, and $C_1$-$C_4$ alkyl; $R_{3a}$ and $R_{6a}$ are each H; $R_{5a}$ is H or halogen;

(vi) $R_{4a}$ is —$OCH_2F_3$; $R_{2a}$ is selected from the group consisting of H, halogen, and $C_1$-$C_4$ alkyl; $R_{3a}$, $R_{5a}$, and $R_{6a}$ are each H;

(vii) $R_{3a}$ is halogen; $R_{2a}$ is H or halogen; $R_{4a}$ and $R_{5a}$ are H; and $R_{6a}$ is H or halogen; and (viii) $R_2$ is —$NR_5R_6$; and $R_{3a}$, $R_{4a}$, $R_{5a}$, and $R_{6a}$ are each H.

In certain embodiments of the compound of formula (IV-c), $R_1$ is selected from the group consisting of:

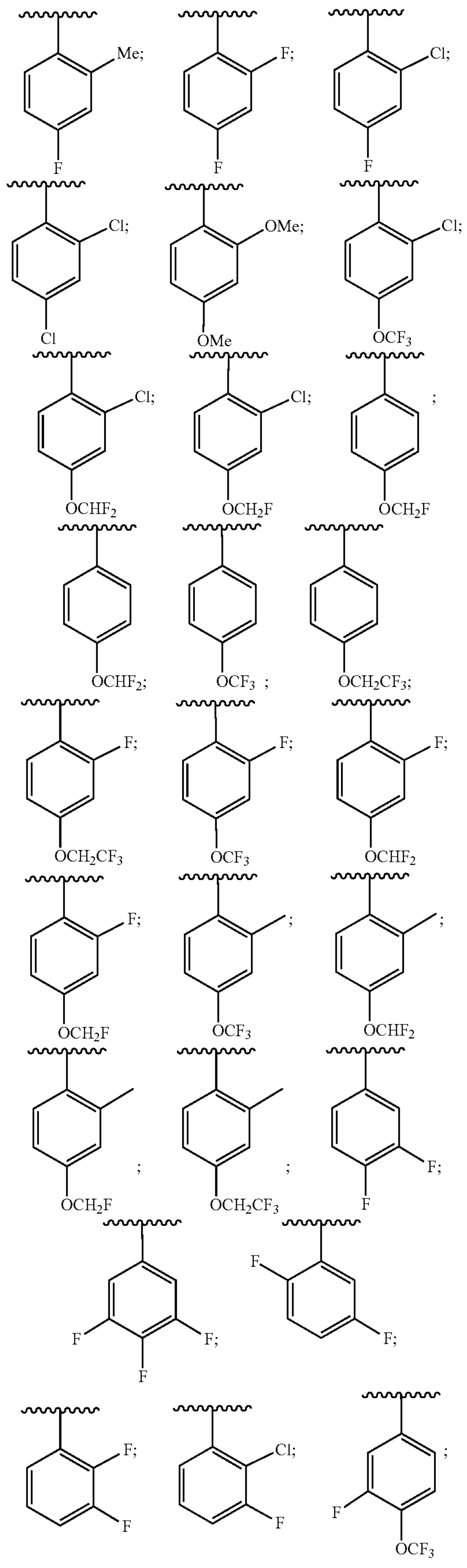

-continued

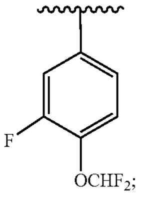 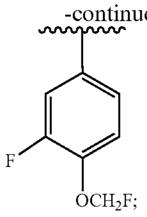 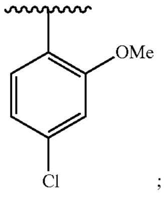 ; and

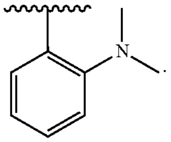

In certain embodiments of the compound of formula (IV-c), the compound is selected from the group consisting of:

3-(4-fluoro-2-methylphenoxy)-N-(3-(S-methylsulfonimidoyl)phenyl)-6-(trifluoromethyl)pyridazine-4-carboxamide;

3-(2,4-difluorophenoxy)-N-(3-(S-methylsulfonimidoyl)phenyl)-6-(trifluoromethyl)pyridazine-4-carboxamide;

3-(2-chloro-4-fluorophenoxy)-N-(3-(S-methylsulfonimidoyl)phenyl)-6-(trifluoromethyl)pyridazine-4-carboxamide;

3-(2,4-dichlorophenoxy)-N-(3-(S-methylsulfonimidoyl)phenyl)-6-(trifluoromethyl)pyridazine-4-carboxamide;

3-(2,4-dimethoxyphenoxy)-N-(3-(S-methylsulfonimidoyl)phenyl)-6-(trifluoromethyl)pyridazine-4-carboxamide;

3-(2-chloro-4-trifluoromethoxyphenoxy)-N-(3-(S-methylsulfonimidoyl)phenyl)-6-(trifluoromethyl)pyridazine-4-carboxamide;

3-(2-chloro-4-difluoromethoxyphenoxy)-N-(3-(S-methylsulfonimidoyl)phenyl)-6-(trifluoromethyl)pyridazine-4-carboxamide;

3-(2-chloro-4-fluoromethoxyphenoxy)-N-(3-(S-methylsulfonimidoyl)phenyl)-6-(trifluoromethyl)pyridazine-4-carboxamide;

3-(4-fluoromethoxyphenoxy)-N-(3-(S-methylsulfonimidoyl)phenyl)-6-(trifluoromethyl)pyridazine-4-carboxamide;

3-(4-difluoromethoxyphenoxy)-N-(3-(S-methylsulfonimidoyl)phenyl)-6-(trifluoromethyl)pyridazine-4-carboxamide;

3-(4-trifluoromethoxyphenoxy)-N-(3-(S-methylsulfonimidoyl)phenyl)-6-(trifluoromethyl)pyridazine-4-carboxamide;

3-(4-(2,2,2-trifluoroethoxy)phenoxy)-N-(3-(S-methylsulfonimidoyl)phenyl)-6-(trifluoromethyl)pyridazine-4-carboxamide;

3-(2-fluoro-4-(2,2,2-trifluoroethoxy)phenoxy)-N-(3-(S-methylsulfonimidoyl)phenyl)-6-(trifluoromethyl)pyridazine-4-carboxamide;

3-(2-fluoro-4-trifluoromethoxyphenoxy)-N-(3-(S-methylsulfonimidoyl)phenyl)-6-(trifluoromethyl)pyridazine-4-carboxamide;

3-(2-fluoro-4-difluoromethoxyphenoxy)-N-(3-(S-methylsulfonimidoyl)phenyl)-6-(trifluoromethyl)pyridazine-4-carboxamide;

3-(2-fluoro-4-fluoromethoxyphenoxy)-N-(3-(S-methylsulfonimidoyl)phenyl)-6-(trifluoromethyl)pyridazine-4-carboxamide;

3-(2-methyl-4-trifluoromethoxyphenoxy)-N-(3-(S-methylsulfonimidoyl)phenyl)-6-(trifluoromethyl)pyridazine-4-carboxamide;

3-(2-methyl-4-difluoromethoxyphenoxy)-N-(3-(S-methylsulfonimidoyl)phenyl)-6-(trifluoromethyl)pyridazine-4-carboxamide;

3-(2-methyl-4-fluoromethoxyphenoxy)-N-(3-(S-methylsulfonimidoyl)phenyl)-6-(trifluoromethyl)pyridazine-4-carboxamide;

3-(2-methyl-4-(2,2,2-trifluoroethoxy)phenoxy)-N-(3-(S-methylsulfonimidoyl)phenyl)-6-(trifluoromethyl)pyridazine-4-carboxamide;

3-(3,4-difluorophenoxy)-N-(3-(S-methylsulfonimidoyl)phenyl)-6-(trifluoromethyl)pyridazine-4-carboxamide;

3-(3,4,5-trifluorophenoxy)-N-(3-(S-methylsulfonimidoyl)phenyl)-6-(trifluoromethyl)pyridazine-4-carboxamide;

3-(3,6-difluorophenoxy)-N-(3-(S-methylsulfonimidoyl)phenyl)-6-(trifluoromethyl)pyridazine-4-carboxamide;

3-(2,3-difluorophenoxy)-N-(3-(S-methylsulfonimidoyl)phenyl)-6-(trifluoromethyl)pyridazine-4-carboxamide;

3-(2-chloro-3-fluorophenoxy)-N-(3-(S-methylsulfonimidoyl)phenyl)-6-(trifluoromethyl)pyridazine-4-carboxamide;

3-(3-fluoro-4-trifluoromethoxyphenoxy)-N-(3-(S-methylsulfonimidoyl)phenyl)-6-(trifluoromethyl)pyridazine-4-carboxamide;

3-(3-fluoro-4-difluoromethoxyphenoxy)-N-(3-(S-methylsulfonimidoyl)phenyl)-6-(trifluoromethyl)pyridazine-4-carboxamide;

3-(3-fluoro-4-fluoromethoxyphenoxy)-N-(3-(S-methylsulfonimidoyl)phenyl)-6-(trifluoromethyl)pyridazine-4-carboxamide;

3-(4-chloro-2-methoxyphenoxy)-N-(3-(S-methylsulfonimidoyl)phenyl)-6-(trifluoromethyl)pyridazine-4-carboxamide; and 3-(2-dimethylaminophenoxy)-N-(3-(S-methylsulfonimidoyl)phenyl)-6-(trifluoromethyl)pyridazine-4-carboxamide.

In certain embodiments of the compound of formula (IV), the compound is a compound of formula (IV-d):

(IV-d)

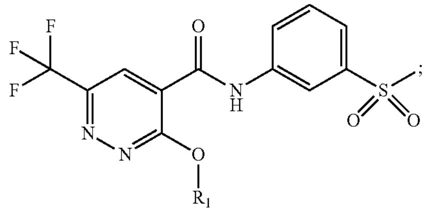

wherein:

$R_1$ is

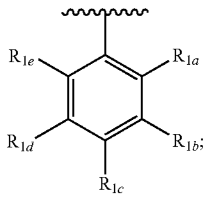

wherein:

$R_{1a}$, $R_{1b}$, $R_{1c}$, $R_{1d}$, and $R_{1e}$ are each independently selected from the group consisting of H, $C_1$-$C_4$ alkyl, halogen, $C_1$-$C_4$ alkoxyl, —$OCF_3$, —$OCHF_2$, —$OCH_2F$, —$OCH_2CF_3$, and —$NR_5R_6$, wherein $R_5$ and $R_6$ are $C_1$-$C_4$ alkyl, provided that at least one of $R_{1a}$, $R_{1b}$, $R_{1c}$, $R_{1d}$, and $R_{1e}$ are not H; and pharmaceutically acceptable salts thereof.

In certain embodiments of the compound of formula (IV-d):

(i) $R_{4a}$ is halogen; $R_{2a}$ is selected from the group consisting of H, $C_1$-$C_4$ alkyl, halogen, and $C_1$-$C_4$ alkoxyl; $R_{3a}$ is H or halogen; $R_{5a}$ is H or halogen; and $R_{6a}$ is H;

(ii) $R_{2a}$ and $R_{4a}$ are each $C_1$-$C_4$ alkoxyl;

(iii) $R_{4a}$ is —$OF_3$; $R_{2a}$ is selected from the group consisting of H, halogen, and $C_1$-$C_4$ alkyl; $R_{3a}$ and $R_{6a}$ are each H; $R_{5a}$ is H or halogen;

(iv) $R_{4a}$ is —$OCHF_2$; $R_{2a}$ is selected from the group consisting of H, halogen, and $C_1$-$C_4$ alkyl; $R_{3a}$ and $R_{6a}$ are each H; $R_{5a}$ is H or halogen;

(v) $R_{4a}$ is —$OCH_2F$; $R_{2a}$ is selected from the group consisting of H, halogen, and $C_1$-$C_4$ alkyl; $R_{3a}$ and $R_{6a}$ are each H; $R_{5a}$ is H or halogen;

(vi) $R_{4a}$ is —$OCH_2F_3$; $R_{2a}$ is selected from the group consisting of H, halogen, and $C_1$-$C_4$ alkyl; $R_{3a}$, $R_{5a}$, and $R_{6a}$ are each H;

(vii) $R_{3a}$ is halogen; $R_{2a}$ is H or halogen; $R_{4a}$ and $R_{5a}$ are H; and $R_{6a}$ is H or halogen; and (viii) $R_2$ is —$NR_5R_6$; and $R_{3a}$, $R_{4a}$, $R_{5a}$, and $R_{6a}$ are each H.

In certain embodiments of the compound of formula (IV-d), $R_1$ is selected from the group consisting of:

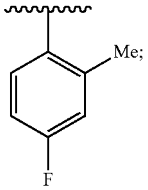
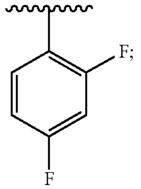
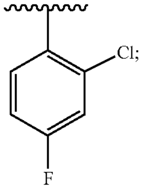
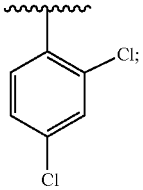
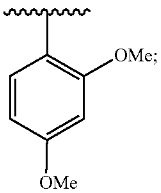
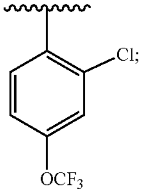
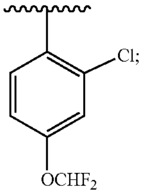
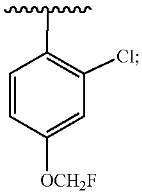
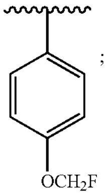
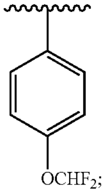
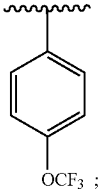
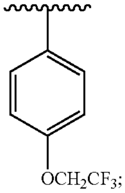
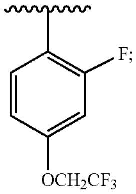
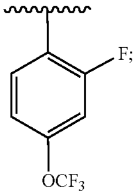
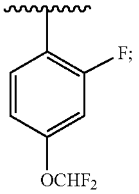

-continued

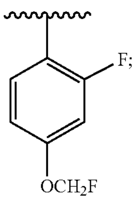
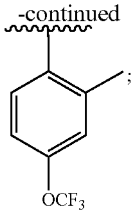
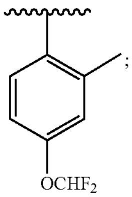
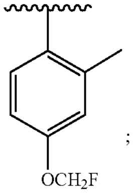
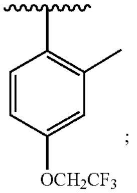
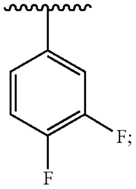
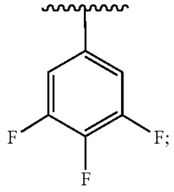
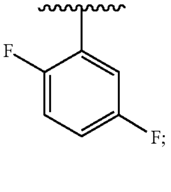
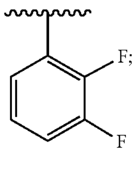
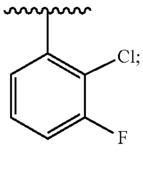
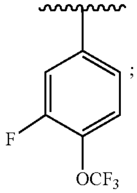
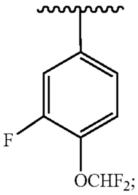
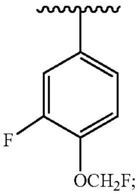
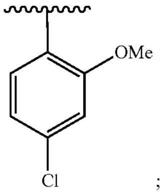

and

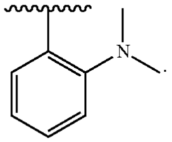

In certain embodiments of the compound of formula (IV-d), the compound is selected from the group consisting of:

3-(4-fluoro-2-methylphenoxy)-N-(3-(methylsulfonyl)phenyl)-6-(trifluoromethyl)pyridazine-4-carboxamide;

3-(2,4-difluorophenoxy)-N-(3-(methylsulfonyl)phenyl)-6-(trifluoromethyl)pyridazine-4-carboxamide;

3-(2-chloro-4-fluorophenoxy)-N-(3-(methylsulfonyl)phenyl)-6-(trifluoromethyl)pyridazine-4-carboxamide;

3-(2,4-dichlorophenoxy)-N-(3-(methylsulfonyl)phenyl)-6-(trifluoromethyl)pyridazine-4-carboxamide;

3-(2,4-dimethoxyphenoxy)-N-(3-(methylsulfonyl)phenyl)-6-(trifluoromethyl)pyridazine-4-carboxamide;

3-(2-chloro-4-(trifluoromethoxy)phenoxy)-N-(3-(methylsulfonyl)phenyl)-6-(trifluoromethyl)pyridazine-4-carboxamide;

3-(2-chloro-4-(difluoromethoxy)phenoxy)-N-(3-(methylsulfonyl)phenyl)-6-(trifluoromethyl)pyridazine-4-carboxamide;

3-(2-chloro-4-(fluoromethoxy)phenoxy)-N-(3-(methylsulfonyl)phenyl)-6-(trifluoromethyl)pyridazine-4-carboxamide;

3-(4-(fluoromethoxy)phenoxy)-N-(3-(methylsulfonyl)phenyl)-6-(trifluoromethyl)pyridazine-4-carboxamide;

3-(4-(difluoromethoxy)phenoxy)-N-(3-(methylsulfonyl)phenyl)-6-(trifluoromethyl)pyridazine-4-carboxamide;

N-(3-(methylsulfonyl)phenyl)-3-(4-(trifluoromethoxy)phenoxy)-6-(trifluoromethyl)pyridazine-4-carboxamide;

N-(3-(methylsulfonyl)phenyl)-3-(4-(2,2,2-trifluoroethoxy)phenoxy)-6-(trifluoromethyl)pyridazine-4-carboxamide;

3-(2-fluoro-4-(2,2,2-trifluoroethoxy)phenoxy)-N-(3-(methylsulfonyl)phenyl)-6-(trifluoromethyl)pyridazine-4-carboxamide;

3-(2-fluoro-4-(trifluoromethoxy)phenoxy)-N-(3-(methylsulfonyl)phenyl)-6-(trifluoromethyl)pyridazine-4-carboxamide;

3-(4-(difluoromethoxy)-2-fluorophenoxy)-N-(3-(methylsulfonyl)phenyl)-6-(trifluoromethyl)pyridazine-4-carboxamide;

3-(2-fluoro-4-(fluoromethoxy)phenoxy)-N-(3-(methylsulfonyl)phenyl)-6-(trifluoromethyl)pyridazine-4-carboxamide;

3-(2-methyl-4-(trifluoromethoxy)phenoxy)-N-(3-(methylsulfonyl)phenyl)-6-(trifluoromethyl)pyridazine-4-carboxamide;

3-(4-(difluoromethoxy)-2-methylphenoxy)-N-(3-(methylsulfonyl)phenyl)-6-(trifluoromethyl)pyridazine-4-carboxamide;

3-(4-(fluoromethoxy)-2-methylphenoxy)-N-(3-(methylsulfonyl)phenyl)-6-(trifluoromethyl)pyridazine-4-carboxamide;

3-(2-methyl-4-(2,2,2-trifluoroethoxy)phenoxy)-N-(3-(methylsulfonyl)phenyl)-6-(trifluoromethyl)pyridazine-4-carboxamide;

3-(3,4-difluorophenoxy)-N-(3-(methylsulfonyl)phenyl)-6-(trifluoromethyl)pyridazine-4-carboxamide;

N-(3-(methylsulfonyl)phenyl)-6-(trifluoromethyl)-3-(3,4,5-trifluorophenoxy)pyridazine-4-carboxamide;

3-(2,5-difluorophenoxy)-N-(3-(methylsulfonyl)phenyl)-6-(trifluoromethyl)pyridazine-4-carboxamide;

3-(2,3-difluorophenoxy)-N-(3-(methylsulfonyl)phenyl)-6-(trifluoromethyl)pyridazine-4-carboxamide;

3-(2-chloro-3-fluorophenoxy)-N-(3-(methylsulfonyl)phenyl)-6-(trifluoromethyl)pyridazine-4-carboxamide;

3-(3-fluoro-4-(trifluoromethoxy)phenoxy)-N-(3-(methylsulfonyl)phenyl)-6-(trifluoromethyl)pyridazine-4-carboxamide;

3-(4-(difluoromethoxy)-3-fluorophenoxy)-N-(3-(methylsulfonyl)phenyl)-6-(trifluoromethyl)pyridazine-4-carboxamide;

3-(3-fluoro-4-(fluoromethoxy)phenoxy)-N-(3-(methylsulfonyl)phenyl)-6-(trifluoromethyl)pyridazine-4-carboxamide;

3-(4-chloro-2-methoxyphenoxy)-N-(3-(methylsulfonyl)phenyl)-6-(trifluoromethyl)pyridazine-4-carboxamide; and 3-(2-(dimethylamino)phenoxy)-N-(3-(methylsulfonyl)phenyl)-6-(trifluoromethyl)pyridazine-4-carboxamide.

In certain embodiments of the compound of formula (IV), the compound is a compound of formula (IV-e):

(IV-e)

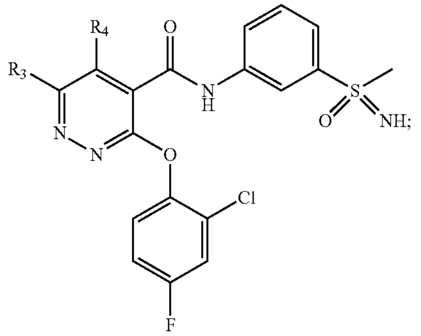

wherein:

$R_3$ is selected from the group consisting of —$CF_2H$, —$CH_2F$, halogen, —$OCF_3$, —$OCHF_2$, —$OCFH_2$, cyclopropyl, branched or straight chain $C_1$-$C_4$ alkyl, $C_1$-$C_4$ alkoxyl, cyano, nitro, —$SCF_3$, and $SF_5$; and $R_4$ is selected from the group consisting of H and branched or straightchain $C_1$-$C_4$ alkyl.

In certain embodiments of the compound of formula (IV-e), the compound is selected from the group consisting of:

3-(2-chloro-4-fluorophenoxy)-N-(3-(S-methylsulfonimidoyl)phenyl)-6-(difluoromethyl)pyridazine-4-carboxamide;

3-(2-chloro-4-fluorophenoxy)-N-(3-(S-methylsulfonimidoyl)phenyl)-6-(fluoromethyl)pyridazine-4-carboxamide;

3-(2-chloro-4-fluorophenoxy)-N-(3-(S-methylsulfonimidoyl)phenyl)-6-chloro-pyridazine-4-carboxamide;

3-(2-chloro-4-fluorophenoxy)-N-(3-(S-methylsulfonimidoyl)phenyl)-6-(trifluoromethoxy)pyridazine-4-carboxamide;

3-(2-chloro-4-fluorophenoxy)-N-(3-(S-methylsulfonimidoyl)phenyl)-6-(difluoromethoxy)pyridazine-4-carboxamide;

3-(2-chloro-4-fluorophenoxy)-N-(3-(S-methylsulfonimidoyl)phenyl)-6-(fluoromethoxy)pyridazine-4-carboxamide;

3-(2-chloro-4-fluorophenoxy)-N-(3-(S-methylsulfonimidoyl)phenyl)-6-bromo-pyridazine-4-carboxamide;

3-(2-chloro-4-fluorophenoxy)-N-(3-(S-methylsulfonimidoyl)phenyl)-6-cyclopropyl-pyridazine-4-carboxamide;

3-(2-chloro-4-fluorophenoxy)-N-(3-(S-methylsulfonimidoyl)phenyl)-6-tert-butyl-pyridazine-4-carboxamide;

3-(2-chloro-4-fluorophenoxy)-N-(3-(S-methylsulfonimidoyl)phenyl)-6-isopropyl-pyridazine-4-carboxamide;

3-(2-chloro-4-fluorophenoxy)-N-(3-(S-methylsulfonimidoyl)phenyl)-6-methyl-pyridazine-4-carboxamide;

3-(2-chloro-4-fluorophenoxy)-N-(3-(S-methylsulfonimidoyl)phenyl)-5,6-dimethyl-pyridazine-4-carboxamide;

3-(2-chloro-4-fluorophenoxy)-N-(3-(S-methylsulfonimidoyl)phenyl)-6-methoxy-pyridazine-4-carboxamide;

3-(2-chloro-4-fluorophenoxy)-N-(3-(S-methylsulfonimidoyl)phenyl)-5-methyl-6-methoxy-pyridazine-4-carboxamide;

3-(2-chloro-4-fluorophenoxy)-N-(3-(S-methylsulfonimidoyl)phenyl)-6-cyano-pyridazine-4-carboxamide;

3-(2-chloro-4-fluorophenoxy)-N-(3-(S-methylsulfonimidoyl)phenyl)-6-nitro-pyridazine-4-carboxamide;

3-(2-chloro-4-fluorophenoxy)-N-(3-(S-methylsulfonimidoyl)phenyl)-6-((trifluoromethyl)thio)pyridazine-4-carboxamide; and 3-(2-chloro-4-fluorophenoxy)-N-(3-(S-methylsulfonimidoyl)phenyl)-6-(pentafluoro-16-sulfaneyl)pyridazine-4-carboxamide.

In certain embodiments of the compound of formula (IV), the compound is a compound of formula (IV-f):

(IV-f)

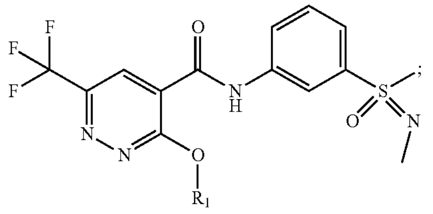

wherein:

$R_1$ is

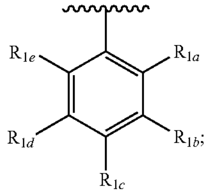

wherein:

$R_{1a}$, $R_{1b}$, $R_{1c}$, $R_{1d}$, and $R_{1e}$ are each independently selected from the group consisting of H, $C_1$-$C_4$ alkyl, halogen, $C_1$-$C_4$ alkoxyl, —$OCF_3$, —$OCHF_2$, —$OCH_2F$, —$OCH_2CF_3$, and —$NR_5R_6$, wherein $R_5$ and $R_6$ are $C_1$-$C_4$ alkyl, provided that at least one of $R_{1a}$, $R_{1b}$, $R_{1c}$, $R_{1d}$, and $R_{1e}$ are not H.

In certain embodiments of the compound of formula (IV-f):

(i) $R_{4a}$ is halogen; $R_{2a}$ is selected from the group consisting of H, $C_1$-$C_4$ alkyl, halogen, and $C_1$-$C_4$ alkoxyl; $R_{3a}$ is H or halogen; $R_{5a}$ is H or halogen; and $R_{6a}$ is H;

(ii) $R_{2a}$ is $C_1$-$C_4$ alkoxyl and $R_{4a}$ is selected from the group consisting of $C_1$-$C_4$ alkoxyl and halogen;

(iii) $R_{4a}$ is —$OF_3$; $R_{2a}$ is selected from the group consisting of H, halogen, and $C_1$-$C_4$ alkyl; $R_{3a}$ and $R_{6a}$ are each H; $R_{5a}$ is H or halogen;

(iv) $R_{4a}$ is —$OCHF_2$; $R_{2a}$ is selected from the group consisting of H, halogen, and $C_1$-$C_4$ alkyl; $R_{3a}$ and $R_{6a}$ are each H; $R_{5a}$ is H or halogen;

(v) $R_{4a}$ is —$OCH_2F$; $R_{2a}$ is selected from the group consisting of H, halogen, and $C_1$-$C_4$ alkyl; $R_{3a}$ and $R_{6a}$ are each H; $R_{5a}$ is H or halogen;

(vi) $R_{4a}$ is —$OCH_2F_3$; $R_{2a}$ is selected from the group consisting of H, halogen, and $C_1$-$C_4$ alkyl;

$R_{3a}$, $R_{5a}$, and $R_{6a}$ are each H;

(vii) $R_{3a}$ is halogen; $R_{2a}$ is H or halogen; $R_{4a}$ and $R_{5a}$ are H; and $R_{6a}$ is H or halogen; and (viii) $R_2$ is —$NR_5R_6$; and $R_{3a}$, $R_{4a}$, $R_{5a}$, and $R_{6a}$ are each H.

In certain embodiments of the compound of formula (IV-f), $R_1$ is selected from the group consisting of:

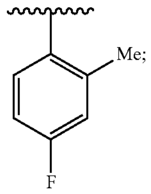
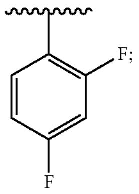
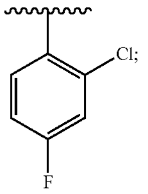
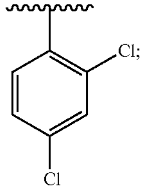
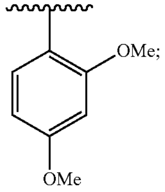
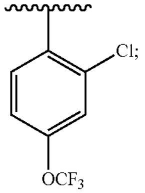
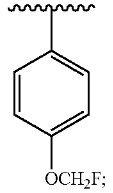
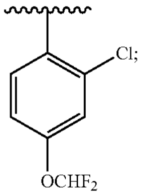
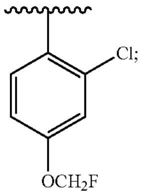
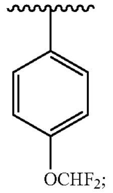
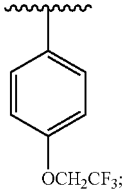
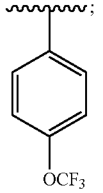
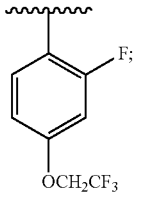
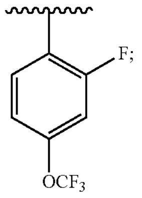
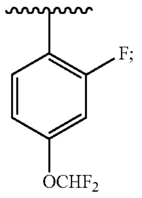
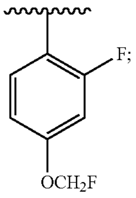
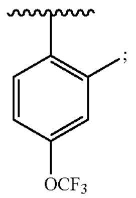
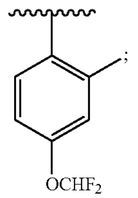
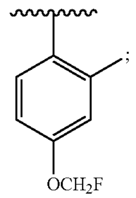

-continued

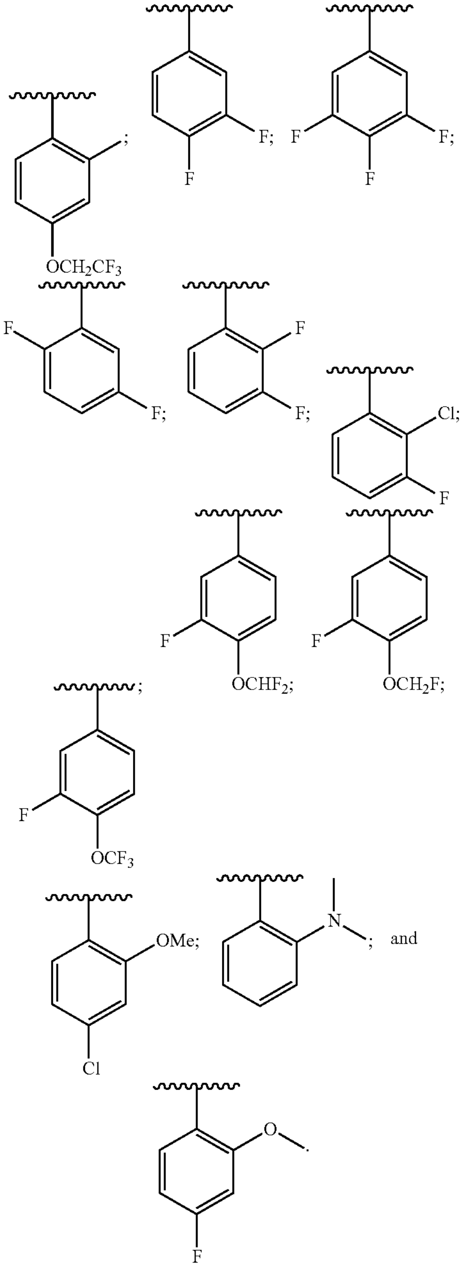

and

In certain embodiments of the compound of formula (IV), the compound is selected from the group consisting of:

N-(3-(N,S-dimethylsulfonimidoyl)phenyl)-3-(4-fluoro-2-methylphenoxy)-6-(trifluoromethyl)pyridazine-4-carboxamide;

3-(2,4-difluorophenoxy)-N-(3-(N,S-dimethylsulfonimidoyl)phenyl)-6-(trifluoromethyl)pyridazine-4-carboxamide;

3-(2-chloro-4-fluorophenoxy)-N-(3-(N,S-dimethylsulfonimidoyl)phenyl)-6-(trifluoromethyl)pyridazine-4-carboxamide;

3-(2,4-dichlorophenoxy)-N-(3-(N,S-dimethylsulfonimidoyl)phenyl)-6-(trifluoromethyl)pyridazine-4-carboxamide;

3-(2,4-dimethoxyphenoxy)-N-(3-(N,S-dimethylsulfonimidoyl)phenyl)-6-(trifluoromethyl)pyridazine-4-carboxamide;

3-(2-chloro-4-(trifluoromethoxy)phenoxy)-N-(3-(N,S-dimethylsulfonimidoyl)phenyl)-6-(trifluoromethyl)pyridazine-4-carboxamide;

3-(2-chloro-4-(difluoromethoxy)phenoxy)-N-(3-(N,S-dimethylsulfonimidoyl)phenyl)-6-(trifluoromethyl)pyridazine-4-carboxamide;

3-(2-chloro-4-(fluoromethoxy)phenoxy)-N-(3-(N,S-dimethylsulfonimidoyl)phenyl)-6-(trifluoromethyl)pyridazine-4-carboxamide;

N-(3-(N,S-dimethylsulfonimidoyl)phenyl)-3-(4-(fluoromethoxy)phenoxy)-6-(trifluoromethyl)pyridazine-4-carboxamide hydrochloride;

3-(4-(difluoromethoxy)phenoxy)-N-(3-(N,S-dimethylsulfonimidoyl)phenyl)-6-(trifluoromethyl)pyridazine-4-carboxamide;

N-(3-(N,S-dimethylsulfonimidoyl)phenyl)-3-(4-(trifluoromethoxy)phenoxy)-6-(trifluoromethyl)pyridazine-4-carboxamide;

N-(3-(N,S-dimethylsulfonimidoyl)phenyl)-3-(4-(2,2,2-trifluoroethoxy)phenoxy)-6-(trifluoromethyl)pyridazine-4-carboxamide;

N-(3-(N,S-dimethylsulfonimidoyl)phenyl)-3-(2-fluoro-4-(2,2,2-trifluoroethoxy)phenoxy)-6-(trifluoromethyl)pyridazine-4-carboxamide;

N-(3-(N,S-dimethylsulfonimidoyl)phenyl)-3-(2-fluoro-4-(trifluoromethoxy)phenoxy)-6-(trifluoromethyl)pyridazine-4-carboxamide;

3-(4-(difluoromethoxy)-2-fluorophenoxy)-N-(3-(N,S-dimethylsulfonimidoyl)phenyl)-6-(trifluoromethyl)pyridazine-4-carboxamide;

N-(3-(N,S-dimethylsulfonimidoyl)phenyl)-3-(2-fluoro-4-(fluoromethoxy)phenoxy)-6-(trifluoromethyl)pyridazine-4-carboxamide;

N-(3-(N,S-dimethylsulfonimidoyl)phenyl)-3-(2-methyl-4-(trifluoromethoxy)phenoxy)-6-(trifluoromethyl)pyridazine-4-carboxamide;

3-(4-(difluoromethoxy)-2-methylphenoxy)-N-(3-(N,S-dimethylsulfonimidoyl)phenyl)-6-(trifluoromethyl)pyridazine-4-carboxamide;

N-(3-(N,S-dimethylsulfonimidoyl)phenyl)-3-(4-(fluoromethoxy)-2-methylphenoxy)-6-(trifluoromethyl)pyridazine-4-carboxamide;

N-(3-(N,S-dimethylsulfonimidoyl)phenyl)-3-(2-methyl-4-(2,2,2-trifluoroethoxy)phenoxy)-6-(trifluoromethyl)pyridazine-4-carboxamide;

3-(3,4-difluorophenoxy)-N-(3-(N,S-dimethylsulfonimidoyl)phenyl)-6-(trifluoromethyl)pyridazine-4-carboxamide;

N-(3-(N,S-dimethylsulfonimidoyl)phenyl)-6-(trifluoromethyl)-3-(3,4,5-trifluorophenoxy)pyridazine-4-carboxamide;

3-(2,5-difluorophenoxy)-N-(3-(N,S-dimethylsulfonimidoyl)phenyl)-6-(trifluoromethyl)pyridazine-4-carboxamide;

3-(2,3-difluorophenoxy)-N-(3-(N,S-dimethylsulfonimidoyl)phenyl)-6-(trifluoromethyl)pyridazine-4-carboxamide;

3-(2-chloro-3-fluorophenoxy)-N-(3-(N,S-dimethylsulfonimidoyl)phenyl)-6-(trifluoromethyl)pyridazine-4-carboxamide;

N-(3-(N,S-dimethylsulfonimidoyl)phenyl)-3-(3-fluoro-4-(trifluoromethoxy)phenoxy)-6-(trifluoromethyl)pyridazine-4-carboxamide;

3-(4-(difluoromethoxy)-3-fluorophenoxy)-N-(3-(N,S-dimethylsulfonimidoyl)phenyl)-6-(trifluoromethyl)pyridazine-4-carboxamide;

N-(3-(N,S-dimethylsulfonimidoyl)phenyl)-3-(3-fluoro-4-(fluoromethoxy)phenoxy)-6-(trifluoromethyl)pyridazine-4-carboxamide;

3-(4-chloro-2-methoxyphenoxy)-N-(3-(N,S-dimethylsulfonimidoyl)phenyl)-6-(trifluoromethyl)pyridazine-4-carboxamide;

3-(2-(dimethylamino)phenoxy)-N-(3-(N,S-dimethylsulfonimidoyl)phenyl)-6-(trifluoromethyl)pyridazine-4-carboxamide; and N-(3-(N,S-dimethylsulfonimidoyl)phenyl)-3-(4-fluoro-2-methoxyphenoxy)-6-(trifluoromethyl)pyridazine-4-carboxamide.

In certain embodiments of the compound of formula (IV), the compound is a compound of formula (IV-g):

(IV-g)

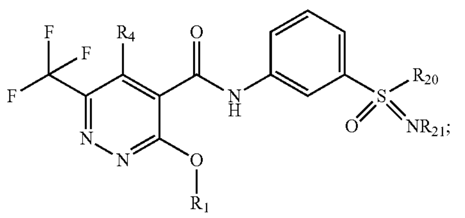

wherein:

$R_1$ is selected from the group consisting of 4-difluoromethoxyphenyl, 2,4-dimethoxyphenyl, and 2,4-difluorophenyl;

$R_{20}$ is $C_1$-$C_4$ alkyl; and $R_{21}$ is H or $C_1$-$C_4$ alkyl.

In other embodiments, the presently disclosed subject matter provides the use of a compound of formula (I-IV) in the manufacture of a medicament for treating a condition, disease, or disorder associated with an increased $Na_v1.8$ activity or expression in a subject afflicted with such a disorder.

F. Compositions

The invention provides pharmaceutical compositions containing compounds of the inventions, such as those described above. The pharmaceutical composition may be in a form suitable for oral use, for example, as tablets, troches, lozenges, fast-melts, aqueous or oily suspensions, dispersible powders or granules, emulsions, hard or soft capsules, syrups, or elixirs. Compositions intended for oral use may be prepared according to any method known in the art for the manufacture of pharmaceutical compositions and such compositions may contain one or more agents selected from sweetening agents, flavoring agents, coloring agents, and preserving agents, in order to provide pharmaceutically elegant and palatable preparations. Tablets contain the compounds in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid, or talc. The tablets may be uncoated, or they may be coated by known techniques to delay disintegration in the stomach and absorption lower down in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,166,452; and 4,265,874, the contents of which are incorporated herein by reference, to form osmotic therapeutic tablets for control release. Preparation and administration of compounds is discussed in U.S. Pat. No. 6,214,841 and U.S. Pub. No. 2003/0232877, the contents of which are incorporated herein by reference.

Formulations for oral use may also be presented as hard gelatin capsules in which the compounds are mixed with an inert solid diluent, for example calcium carbonate, calcium phosphate or kaolin, or as soft gelatin capsules in which the compounds are mixed with water or an oil medium, for example peanut oil, liquid paraffin, or olive oil.

An alternative oral formulation, where control of gastrointestinal tract hydrolysis of the compound is sought, can be achieved using a controlled-release formulation, where a compound of the invention is encapsulated in an enteric coating.

Aqueous suspensions may contain the compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents such as a naturally occurring phosphatide, for example lecithin, or condensation products of an alkylene oxide with fatty acids, for example, polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the compounds in a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the compounds in admixture with a dispersing or wetting agent, suspending agent and one or more preservatives. Suitable dispersing or wetting agents and suspending agents are exemplified, for example sweetening, flavoring, and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavoring agents.

Syrups and elixirs may be formulated with sweetening agents, such as glycerol, propylene glycol, sorbitol, or sucrose. Such formulations may also contain a demulcent, a preservative, and agents for flavoring and/or coloring. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

In certain embodiments, the formulation is a sustained release formulation. In certain embodiments, the formulation is not a sustained release formulation. In certain embodiments, the formulation is not injectable. In certain embodiments, the formulation does not contain particles having a D50 (volume weighted median diameter) of less than 10 microns. In certain embodiments, the formulation does not contain a polymer surface stabilizer. In certain embodiments, the formulation is not an aqueous suspension.

The composition may be formulated for administration by a particular mechanism. The composition may be formulated for oral, intravenous, enteral, parenteral, dermal, buccal, topical, nasal, or pulmonary administration. The composition may be formulated for administration by injection or on an implantable medical device (e.g., stent or drug-eluting stent or balloon equivalents).

The composition may be formulated a single daily dosage. The composition may be formulated for multiple daily dosages, e.g., two, three, four, five, six or more daily dosages.

In another aspect, the present disclosure provides a pharmaceutical composition including one or more compounds of the invention alone or in combination with one or more additional therapeutic agents in admixture with a pharmaceutically acceptable excipient. One of ordinary skill in the art will recognize that the pharmaceutical compositions include the pharmaceutically acceptable salts of the compounds described above. Pharmaceutically acceptable salts are generally well known to those of ordinary skill in the art and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intrasternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of ordinary skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

G. Methods of Treating Conditions

The invention provides method of treating a condition in a subject using compounds of the invention. The methods are useful for treating any condition associated with aberrant, e.g., increased, activity of voltage-gated $Na_V1.8$ sodium channels. Conditions associated with increased activity of $Na_V1.8$ and the use of $Na_V1.8$ to treat such conditions is known in the art and described in, for example, International Patent Publication Nos. WO 2020/014243, WO 2020/014246, WO 2020/092187, the contents of each of which are incorporated herein by reference.

For example and without limitation, the condition may be abdominal cancer pain, acute cough, acute idiopathic transverse myelitis, acute itch, acute pain, acute pain in major trauma/injury, airways hyperreactivity, allergic dermatitis, allergies, ankylosing spondylitis, asthma, atopy, Behcets disease, bladder pain syndrome, bone cancer pain, brachial plexus injury, burn injury, burning mouth syndrome, calcium pyrophosphate deposition disease, cervicogenic headache, Charcotneuropathic osteoarthropathy, chemotherapy-induced oral mucositis, chemotherapy-induced peripheral neuropathy, cholestasis, chronic cough, chronic itch, chronic low back pain, chronic pain, chronic pancreatitis, chronic post-traumatic headache, chronic widespread pain, cluster headache, complex regional pain syndrome, complex regional pain syndromes, constant unilateral facial pain with additional attacks, contact dermatitis, cough, dental pain, diabetic neuropathy, diabetic peripheral neuropathy, diffuse idiopathic skeletal hyperostosis, disc degeneration pain, distal sensory polyneuropathy (DSP) associated with highly active antiretroviral therapy (HAART), Ehlers-Danlos syndrome, endometriosis, epidermolysis bullosa, epilepsy, erythromelalgia, Fabry ⓢ disease, facet joint syndrome, failed back surgery syndrome, familial hemiplegic migraine, fibromyalgia, glossopharyngeal neuralgia, glossopharyngeal neuropathic pain, gout, head and neck cancer pain, inflammatory bowel disease, inflammatory pain, inherited erythromelalgia, irritable bowel syndrome, irritable bowel syndrome, itch, juvenile idiopathic arthritis, mastocytosis, melorheostosis, migraine, multiple sclerosis, musculoskeletal damage, myofascial orofacial pain, neurodegeneration following ischemia, neurofibromatosis type II, neuropathic ocular pain, neuropathic pain, neuropathic pain, nociceptive pain, non-cardiac chest pain, optic neuritis, oral mucosal pain, orofacial pain, osteoarthritis, osteoarthritis, overactive bladder, pachyonychia congenita, pain, pain resulting from cancer, pain resulting from chemotherapy, pain resulting from diabetes, pain syndrome, painful joint arthroplasties, pancreatitis, Parkinson ⓢ disease, paroxysmal extreme pain disorder, pemphigus, perioperative pain, peripheral neuropathy, persistent idiopathic dentoalveolar pain, persistent idiopathic facial pain, phantom limb pain, phantom limb pain, polymyalgia rheumatica, postherpetic neuralgia, post-mastectomy pain syndrome, postoperative pain, post-stroke pain, post-surgical pain, post-thoracotomy pain syndrome, post-traumatic stress disorder, preoperative pain, pruritus, psoriasis, psoriatic arthritis, pudendal neuralgia, pyoderma gangrenosum, radiotherapy-induced peripheral neuropathy, Raynaud ⓢ disease, renal colic, renal colic, renal failure, rheumatoid arthritis, salivary gland pain, sarcoidosis, sciatica, scleroderma, sickle cell disease, small fiber neuropathy, spinal cord injury pain, spondylolisthesis, spontaneous pain, stump pain, subacute cough, temporomandibular joint disorders, tension-type headache, trigeminal neuralgia, vascular leg ulcers, vulvodynia, or whiplash associated disorder.

Methods of treating a condition in a subject may include providing a composition of the invention to a subject. The composition may be provided to a subject by any suitable route or mode of administration. For example and without limitation, the composition may be provided buccally, dermally, enterally, intraarterially, intramuscularly, intraocularly, intravenously, nasally, orally, parenterally, pulmonarily, rectally, subcutaneously, topically, transdermally, by injection, or with or on an implantable medical device.

The composition may be provided according to a dosing regimen. A dosing regimen may include one or more of a dosage, a dosing frequency, and a duration.

Doses may be provided at any suitable interval. For example and without limitation, doses may be provided once per day, twice per day, three times per day, four times per day, five times per day, six times per day, eight times per day, once every 48 hours, once every 36 hours, once every 24 hours, once every 12 hours, once every 8 hours, once every 6 hours, once every 4 hours, once every 3 hours, once every two days, once every three days, once every four days, once every five days, once every week, twice per week, three times per week, four times per week, or five times per week.

The dose may be provided in a single dosage, i.e., the dose may be provided as a single tablet, capsule, pill, etc. Alternatively, the dose may be provided in a divided dosage, i.e., the dose may be provided as multiple tablets, capsules, pills, etc.

The dosing may continue for a defined period. For example and without limitation, doses may be provided for at least 1 week, at least 2 weeks, at least 3 weeks, at least 4 weeks, at least 6 weeks, at least 8 weeks, at least 10 weeks, at least 12 weeks, at least 4 months, at least 5 months, at least 6 months, at least 8 months, at least 10 months, at least 12 months or more.

In some embodiments, the presently disclosed subject matter provides a method for modulating a $Na_V1.8$ sodium ion channel, the method comprising administering to a subject in need thereof, a modulating-effective amount of a compounds disclosed herein to the subject.

In other embodiments, the presently disclosed subject matter provides a method for inhibiting $Na_V1.8$, the method comprising administering to a subject in need thereof, an inhibiting-effective amount of a compounds disclosed herein to the subject.

As used herein, the term "inhibit," and grammatical derivations thereof, refers to the ability of a presently disclosed compound, e.g., a presently disclosed compound of formula (I-IV), to block, partially block, interfere, decrease, or reduce the activity or expression of $Na_V1.8$ in a subject. Thus, one of ordinary skill in the art would appreciate that the term "inhibit" encompasses a complete and/or partial decrease in the function of the channel, e.g., a decrease by at least 10%, in some embodiments, a decrease by at least 20%, 30%, 50%, 75%, 95%, 98%, and up to and including 100%.

In particular embodiments, the presently disclosed subject matter provides a method for treating a condition, disease, or disorder associated with an increased $Na_V1.8$ activity or expression. In more particular embodiments, the condition, disease, or disorder associated with an increased $Na_V1.8$ activity or expression is selected from the group consisting of pain, especially inflammatory, visceral, and neuropathic pain, neurological disorders, especially multiple sclerosis, autism, especially Pitt Hopkins Syndrome, and psychiatric diseases, and combinations thereof, wherein the method comprises administering to the subject in need thereof a therapeutically effective amount of a compounds disclosed herein, or a pharmaceutically acceptable salt thereof.

In particular embodiments, the disease or condition is selected from the group consisting of neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, dental pain, peripheral nerve injury or a combination thereof.

In other embodiments, the disease or condition is selected from the group consisting of pain associated with HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritis, rheumatoid arthritis, osteoarthritis, atherosclerosis, paroxysmal dystonia, myasthenia syndromes, myotonia, malignant hyperthermia, cy stic fibrosis, pseudoaldosteronism, rhabdomyolysis, hypothyroidism, bipolar depression, anxiety, schizophrenia, sodium channel toxi related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions caused by stroke or neural trauma, tach-arrhythmias, atrial fibrillation and ventricular fibrillation.

In some embodiments, the disease or condition is Pitt Hopkins Syndrome (PTHS).

The presently disclosed subject matter also includes use of the compounds disclosed herein, in the manufacture of a medicament for treating a condition, disease, or disorder associated with an increased $Na_V1.8$ activity or expression in a subject afflicted with such a disorder.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

The term "combination" is used in its broadest sense and means that a subject is administered at least two agents, more particularly the compounds disclosed herein and at least one analgesic; and, optionally, one or more analgesic agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the compounds described herein can be administered alone or in combination with adjuvants that enhance stability of the compounds described herein, alone or in combination with one or more analgesic agents, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of the compounds disclosed herein and at least one additional therapeutic agent can be varied so long as the beneficial effects of the combination of these agents are achieved. Accordingly, the phrase "in combination with" refers to the administration of the compounds disclosed herein and at least one additional therapeutic agent either simultaneously, sequentially, or a combination thereof. Therefore, a subject administered a combination of the compounds disclosed herein and at least one additional therapeutic agent can receive a compound from the compounds disclosed herein and at least one additional therapeutic agent at the same time (i.e., simultaneously) or at different times (i.e., sequentially, in either order, on the same day or on different days), so long as the effect of the combination of both agents is achieved in the subject.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound selected from compounds disclosed herein and at least one additional therapeutic agent are administered simultaneously, they can be administered to the subject as separate pharmaceutical compositions, each comprising either a compound selected from the compounds disclosed herein or at least one additional therapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents m ay be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of a compound selected from the compounds disclosed herein and at least one additional therapeutic agent is greater than the sum of the biological activities of the respective agents when administered individually.

Synergy can be expressed in terms of a "Synergy Index (SI)," which generally can be determined by the method described by F. C. Kull et al., Applied Microbiology 9, 538 (1961), from the ratio determined by:

$$Q_a/Q_A + Q_b/Q_B = \text{Synergy Index }(SI)$$

wherein:

- $Q_A$ is the concentration of a component A, acting alone, which produced an end point in relation to component A;
- $Q_a$ is the concentration of component A, in a mixture, which produced an end point;
- $Q_B$ is the concentration of a component B, acting alone, which produced an end point in relation to component B; and
- $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

More particularly, in some embodiments, the presently disclosed methods include co-administering to the subject a compound selected from the compounds disclosed herein and/or a pharmaceutically acceptable salt thereof with one or more compounds selected from the group consisting of one or more:

- nonsteroidal anti-inflammatory drugs (NSAIDs), including, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin, and zomepirac; opioid analgesics, including, but not limited to, morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine, and pentazocine; barbiturates, including, but not limited to, amobarbital, aprobarbital, butabarbital, butabital, mephobarbital, metharbital, methohexital, pentobarbital, phenobartital, secobarbital, talbutal, thiamylal, and thiopental; benzodiazapines, including, but not limited to, chlordiazepoxide, clorazepate, diazepam, flurazepam, lorazepam, oxazepam, temazepam, and triazolam; histamine $H_1$ antagonists, including, but not limited to, diphenhydramine, pyrilamine, promethazine, chlorpheniramine, and chlorcyclizine; sedatives, including, but not limited to, glutethimide, meprobamate, methaqualone, and dichloralphenazone; a skeletal muscle relaxant, including, but not limited to, baclofen, carisoprodol, chlorzoxazone, cyclobenzaprine, methocarbamol, and orphrenadine; an NMDA receptor antagonist, including, but not limited to, dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®), a combination formulation of morphine and dextromethorphan), topiramate, neramexane or perzinfotel including an NR2B antagonist, e.g. ifenprodil, traxoprodil, and (−)—(R)-6-{2-[4-(3-fluorophenyl)-4-hydroxy-1-piperidinyl]-1-hydroxyethyl-3,4-dihydro-2(1H)-quinolinone; transient receptor potential ion channel antagonists; α-adrenergics, including, but not limited to, doxazosin, tamsulosin, clonidine, guanfacine, dexmetatomidine, modafinil, and 4-amino-6,7-dimethoxy-2-(5-methane-sulfonamido-1,2,3,4-tetrahydroisoquinol-2-yl)-5-(2-pyridyl) quinazoline; tricyclic antidepressants, including, but not limited to, desipramine, imipramine, amitriptyline, and nortriptyline; anticonvulsants, including, but not limited to, carbamazepine (Tegretol®), lamotrigine, topiramate, lacosamide (Vimpat®), andvalproate; tachykinin antagonists, particularly an NK-3, NK-2 or NK-1 antagonist, including, but not limited to, (alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-di-one (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant, and 3-[[2-methoxy-5-(trifluoromethoxy)phenyl]-methylamino]-2-phenylpiperidine (2S,3S); muscarinic antagonists, including, but not limited to, oxybutynin, tolterodine, propiverine, tropsium chloride, darifenacin, solifenacin, temiverine, and ipratropium; cyclooxygenase-2 selective (COX-2) inhibitors, including, but not limited to, celecoxib, rofecoxib, parecoxib, valdecoxib, deracoxib, etoricoxib, and lumiracoxib; a coal-tar analgesic, including, but not limited to, paracetamol; neuroleptics, including, but not limited to, droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion®, and sarizotan; vanilloid receptor agonists, including, but not limited to, resinferatoxin or civamide); vanilloid receptor antagonists, including, but not limited to, capsazepine or GRC-15300); β-adrenergics, including, but not limited to, propranolol; local anaesthetics, including, but not limited to, mexiletine; corticosteroids, including, but not limited to, dexamethasone and prednisone; 5-HT receptor agonists or antagonists, in particular a $5\text{-HT}_{1B/1D}$ agonist, including, but not limited to, eletriptan, sumatriptan, naratriptan, zolmitriptan or rizatriptan; $5\text{-HT}_2$A receptor antagonists, including, but not limited to, R(+)-alpha-(2,3-dimethoxy-phenyl)-1-[2-(4-fluorophenylethyl)]-4-piperidinemethanol (MDL-100907), eplivanserin, ketanserin, and pimavanserin; cholinergic (nicotinic) analgesics, including, but not limited to, ispronicline (TC-1734), (E)-N-methyl-4-(3-pyridinyl)-3-buten-1-amine (RJR-2403), (R)-5-(2-azetidinylmethoxy)-2-chloropyridine (ABT-594), and nicotine; $\alpha_2\delta$ ligands, including, but not limited to, gabapentin (Neurontin®), gabapentin GR (Gralise®), gabapentin, enacarbil (Horizant®), pregabalin (Lyrica®), 3-methyl gabapentin, (1[alpha],3[alpha],5[alpha])(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3 S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid; cannabinoid receptor ligands, including, but not limited to, cannabidiol, KHK-6188; metabotropic glutamate subtype 1 receptor antagonists; serotonin reuptake inhibitors, including, but not limited to, sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, and trazodone; noradrenaline (norepinephrine) reuptake inhibitors, including, but not limited to, maprotiline, lofepramine, mirtazepine, oxaprotiline, fezolamine, tomoxetine, mianserin, buproprion, buproprion metabolite hydroxybuproprion, nomifensine and viloxazine (Vivalan®), especially a selective noradrenaline reuptake inhibitor, such as reboxetine, in particular (S,S)-reboxetine; dual serotonin-noradrenaline reuptake inhibitors, including, but not limited to, venlafaxine, venlafaxine metabolite O-desmethylvenlafaxine, clomipramine, clomipramine metabolite desmethylclomipramine, duloxetine (Cymbalta®), milnacipran and imipramine; Rho kinase inhibitors; inducible nitric oxide synthase (iNOS) inhibitors, including, but not limited to, S-[2-[(1-iminoethyl)amino]ethyl]-L-homocysteine, S-[2-[(1-iminoethyl)- amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-S-chloro-S-pyridinecarbonitrile; 2-[[(1R, 3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl) butyl] thio]-6-(trifluoromethyl)-3-pyridinecarbonitrile, 2-[[(1R,3S)-3-amino-4-hydroxy-1-(5-thiazolyl)butyl] thio]-5-chlorobenzonit-rile, N-[4-[2-(3-chlorobenzylamino)ethyl]phenyl]thiophene-2-carboxamidine, NXN-462, and guanidinoethyldisulfide; acetylcholinesterase inhibitors, including, but not limited to, donepezil; prostaglandin $E_2$ subtype 4 antagonists, including, but not limited to, N-[({2-[4-(2-ethyl-4,6-dimethyl-1H-imidazo[4,5-c]pyridin-1-yl)phenyl] ethyl}amino)-carbonyl]-4-methylbenzenesulfonamide, and 4-[(15)-1-({[5-chloro-2-(3-fluorophenoxy)pyridin-3-yl]carbonyl}amino)ethyl]benzoic acid; leukotriene B4 antagonists, including, but not limited to, 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl] oxyphenoxy]-valeric acid (ONO-4057), and DPC-11870; 5-lipoxygenase inhibitors, including, but not limited to, zileuton, 6-[(3-fluoro-5-[4-methoxy-3,4,5,6-tetrahydro-2H-pyran-4-yl])phenoxy-methyl]-1-methyl-2-quinolone (ZD-2138), and 2,3,5-trimethyl-6-(3-pyridylmethyl)-1,4-benzoquinone (CV-6504); sodium channel blockers, including, but not limited to, lidocaine, lidocaine plus tetracaine cream (ZRS-201), and eslicarbazepine acetate; 5-$HT_3$ antagonists, including, but not limited to, ondansetron; N-methyl-D-aspartic acid receptor antagonists; voltage-gated calcium channel blockers (e.g., N-type and T-type), including, but not limited to ziconctide, Z-160, (R)-2-(4-cyclopropylphenyl)-N-(1-(5-(2,2,2-trifluoroethoxy)pyridin-2-yl)ethyl) acetamide; KCNQ openers (e.g., KCNQ2/3 (K, 7.2/3)); TPRV 1 receptor agonists, including, but not limited to, capsaicin (Neuroges®, Qutenza®); and the pharmaceutically acceptable salts and solvates thereof; nicotinic receptor antagonists, including, but not limited to, varenicline; nerve growth factor antagonists, including, but not limited to, tanezumab; endopeptidase stimulants, including, but not limited to, senrebotase; angiotensin II antagonists, including, but not limited to, EMA-401; Tramadol®, Tramadol ER (Ultram ER®), Tapentadol ER (Nucynta®); PDE5 inhibitors, including, but not limited to, 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2′,1′:6,1]-pyrido[3,4-b]indole-1,4-dione (IC-351 ortadalafil), 2-[2-ethoxy-5-(4-ethyl-piperazin-1-yl-1-sulphonyl)-phenyl]-5-methyl-7-propyl-3H-imidazo [5,1-f][1,2,4]triazin-4-one (vardenafil), 5-(5-acetyl-2-butoxy-3-pyridinyl)-3-ethyl-2-(1-ethyl-3-azetidinyl)-2, 6-di-hydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d] pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

$Na_V$1.7 blockers, including, but not limited to, XEN-402, XEN403, TV-45070, PF-05089771, CNV1014802, GDC-0276, RG7893 and such as those disclosed in WO2011/140425; WO2012/106499; WO2012/112743; WO2012/125613, WO2012/116440, WO2011026240, U.S. Pat. No. 8,883,840, or 8,466,188, or PCT/US2013/21535 the entire contents of each application hereby incorporated by reference; and $Na_V$1.7 blockers, including, but not limited to, (2-benzylspiro[3,4-dihydropyrrolo[1,2-a]pyrazine-1,4′-piperidine]-1′-yl)-(4-isopropoxy-3-methyl-phenyl)methanone, 2,2,2-trifluoro-1-[1′-[3-methoxy-4-[2-(trifluoromethoxy)ethoxy]benzoyl]-2-,4-dimethyl-spiro[3,4-dihydropyrrolo[1,2-a]pyrazine-1,4′-piperidine]-6-yl]-ethanone, [8-fluoro-2-methyl-6-(trifluoromethyl)spiro[3,4-dihydropyrrolo[1-,2-a]pyrazine-1,4′-piperidine]-1′-yl]-(4-isobutoxy-3-methoxy-phenyl)methanone, 1-(4-benzhydrylpiperazin-1-yl)-3-[2-(3,4-dimethylphenoxy)ethoxy]propan-2-ol, (4-butoxy-3-methoxy-phenyl)-[2-methyl-6-(trifluoromethyl)spiro [3,4-dihydropyrrolo[1,2-a]pyrazine-1,41′-piperidine]-1′-yl]methanone, [8-fluoro-2-methyl-6-(trifluoromethyl)spiro[3,4-dihydropyrrolo[1,2-a]pyrazine-1,4′-piperidine]-1′-yl]-(5-isopropoxy-6-methyl-2-pyridyl)methanone, (4-isopropoxy-3-methyl-phenyl)-[2-methyl-6-(1,1,2,2,2-pentafluoroethyl)spiro [3,4-dihydropyrrolo[1,2-a]pyrazine-1,4′-piperidine]-1′-yl]methanone, 5-[2-methyl-4-[2-methyl-6-(2,2,2-trifluoroacetyl)spiro[3,4-dihydropyrrolo-[1,2-a]pyrazine-1,4′-piperidine]-1′-carbonyl] phenyl]pyridine-2-carbonitrile, (4-isopropoxy-3-methyl-phenyl)-[6-(trifluoromethyl)spiro[3,4-dihydro-2H-pyrrolo[1,2-a]pyrazine-1,4′-piperidine]-1′-yl] methanone, 2,2,2-trifluoro-1-[1′-[3-methoxy-4-[2-(trifluoromethoxy)ethoxy]benzoyl]-2-′-methyl-spiro [3,4-dihydropyrrolo[1,2-a]pyrazine-1,4′-piperidine]-6-yl]ethanone, 2,2,2-trifluoro-1-[1′-(5-isopropoxy-6-methyl-pyridine-2-carbonyl)-3, -3-dimethyl-spiro[2,4-dihydropyrrolo[1,2-a]pyrazine-1,4′-piperidine]-6-yl] ethanone, 2,2,2-trifluoro-1-[1′-(5-isopentyloxypyridine-2-carbonyl)-2-methy-1-spiro[3, 4-dihydropyrrolo[1,2-a]pyrazine-1,4′-piperidine]-6-yl]ethanone, (4-isopropoxy-3-methoxy-phenyl)-[2-methyl-6-(trifluoromethyl)spiro[3,4-di-hydropyrrolo [1,2-a]pyrazine-1,4′-piperidine]-1′-yl]methanone, 2,2,2-trifluoro-1-[1′-(5-isopentyloxypyridine-2-carbonyl)-2,4-dimethyl-sp-iro[3,4-dihydropyrrolo[1,2-a] pyrazine-1,4′-piperidine]-6-yl]ethanone, 1-[(3 S)-2,3-dimethyl-1′-[4-(3,3,3-trifluoropropoxymethyl) benzoyl]spiro[3, -4-dihydropyrrolo[1,2-a]pyrazine-1,4′-piperidine]-6-yl]-2,2,2-trifluoro-ethanone, [8-fluoro-2-methyl-6-(trifluoromethyl)spiro[3,4-dihydropyrrolo [1,2-a]pyrazine-1,4′-piperidine]-1′-yl]-[3-methoxy-4-[(1R)-1-methylpropoxy]phenyl]methanone, 2,2,2-trifluoro-1-[1′-(5-isopropoxy-6-methyl-pyridine-2-carbonyl)-2,4-dimethyl-spiro[3,4-dihydropyrrolo[1,2-a]pyrazine-1,4′-piperidine]-6-yl]ethanone, 1-[1′-[4-methoxy-3-(trifluoromethyl)benzoyl]-2-methyl-spiro [3,4-dihydropyrrolo[1,2-a]pyrazine-1,4′-piperidine]-

6-yl]-2,2-dimethyl-propan-1-one, (4-isopropoxy-3-methyl-phenyl)-[2-methyl-6-(trifluoromethyl)spiro[3, 4-dihydropyrrolo[1,2-a]pyrazine-1,4′-piperidine]-1′-y yl]methanone, [2-methyl-6-(1-methylcyclopropanecarbonyl)spiro[3,4-dihydropyrrolo[1,2-a]-pyrazine-1,4′-p piperidine]-1′-y yl]-[4-(3,3,3-trifluoropropoxymethyl)phenyl]methanone, 4-bromo-N-(4-bromophenyl)-3-[(1-methyl-2-oxo-4-piperidyl) sulfamoyl]benzamide or (3-chloro-4-isopropoxy-phenyl)-[2-methyl-6-(1,1,2,2,2-pentafluoroethyl)sp-iro [34-dihydropyrrolo[1,2-a]pyrazine-1,4′-p piperidine]-1′-y yl]methanone.

In some embodiments, the method comprises administering to the subject a therapeutically effective amount of a compound described herein, or a pharmaceutically acceptable salt, with or without a pharmaceutically acceptable carrier, in combination with a second therapeutic agent selected from the group consisting of acetaminophen, NSAIDs, opioid analgesics, and combinations thereof.

In some embodiments, the method comprises administering to the subject a therapeutically effective amount of a compound described herein, or a pharmaceutically acceptable salt, with or without a pharmaceutically acceptable carrier, in combination with one or more additional therapeutic agents for treating pain. In one embodiment, the additional therapeutic agent is selected from the group consisting of acetaminophen, NSAIDs (such as aspirin, ibuprofen, and naproxen), and opioid analgesics. In another embodiment, the additional therapeutic agent is acetaminophen. In another embodiment, the additional therapeutic agent is an NSAID. In another embodiment, the additional therapeutic agent is an opioid analgesic.

BRIEF DESCRIPTION OF DRAWINGS

FIG. 1: A depiction of Protocol 1 for conducting the $Na_V1.8$ Inhibition Assay.

V. EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

A. Examples for First Set of Compounds

Example 1

Methods of making the compounds of the present invention, and intermediates used in their synthesis, are provided in the General Synthetic Schemes and Specific Syntheses Procedures below. Chemicals were purchased from standard commercial vendors and used as received unless otherwise noted. Otherwise, their preparation is facile and known to one of ordinary skill in the art, or it is referenced or described herein. Abbreviations are consistent with those in the ACS Style Guide. "dry" glassware means oven/desiccator dried. Solvents were ACS grade unless otherwise noted.

All reactions were performed in flame-dried or oven-dried glassware under a positive pressure of dry nitrogen or dry argon and were stirred magnetically unless otherwise indicated. Chemicals were purchased from standard commercial vendors and used as received unless otherwise noted. Yields are not optimized. The chemical names were generated using the ChemDraw Professional 19.1, available from PerkinElmer or ChemAxon.

Reactions were monitored by thin layer chromatography (TLC) using 0.25 mm silica gel 60 F254 plates purchased from EMD MILLIPORE™. Purification was performed with CombiFlash NextGen 300 Automated Flash Chromatography System or purified using one of the preparative HPLC methods mentioned below. Analytical data was collected using one of the analytical methods described below.

Example 2

Prep Method 1 (P1): Acidic Early Method

Purification (METCR/Prep004) (P1) LC were performed using a Waters Sunfire C18 column (30 mm×100 mm, 5 μm; temperature: room temperature), with an injection volume of 1500 μL at flow rate of 40 mL/min at 100% B (A=0.1% formic acid in water; B=0.1% formic acid in acetonitrile) for 0.55 min then a gradient of 10-95% B over 13.89 min and held for 2.11 min. A second gradient of 95-10% B was then applied over 0.2 min. UV spectra were recorded at 215 nm using a Gilson detector.

Prep Method 2 (P2): Acidic Standard Method

Purification (METCR/Prep001) (P2) LC were performed using a Waters Sunfire C18 column (30 mm×100 mm, 5 μm; temperature: room temperature), with an injection volume of 1500 μL at flow rate of 40 mL/min at 30% B (A=0.10% formic acid in water; B=0.1% formic acid in acetonitrile) for 0.55 min then a gradient of 30-95% B over 10.45 min and held for 2.10 min. A second gradient of 95-30% B was then applied over 0.21 min. UV spectra were recorded at 215 nm using a Gilson detector.

Prep Method 3 (P3): Basic Early Method

Purification (METCR/Prep002) (P3) LC were performed using a Waters X-Bridge C18 column (30 mm×100 mm, 5 μm; temperature: room temperature), with an injection volume of 1500 μL at flow rate of 40 mL/min at 10% B (A=0.2% ammonium hydroxide in water; B=0.2% ammonium hydroxide in acetonitrile) for 0.55 min then a gradient of 10-95% B over 13.89 min and held for 2.11 min. A second gradient of 95-10% B was then applied over 0.2 min. UV spectra were recorded at 215 nm using a Gilson detector.

Prep Method 4 (P4): Basic Standard Method

Purification (METCR/Prep003) (P4) LC were performed using a Waters X-Bridge C18 column (30 mm×100 mm, 5 μm; temperature: room temperature), with an injection volume of 1500 μL at flow rate of 40 mL/min at 30% B (A=0.2% ammonium hydroxide in water; B=0.2% ammonium hydroxide in acetonitrile) for 0.55 min then a gradient of 30-95% B over 10.45 min and held for 2.10 min. A second gradient of 95-30% B was then applied over 0.21 min. UV spectra were recorded at 215 nm using a Gilson detector.

Analytical LCMC were collected using one of following methods—

Method 1 (M1): Acidic IPC Method (METCR1410—MS17, MS18, MS19) Analytical (MET/CR/1410) (M1) HPLC-MS were performed using a Kinetex Core shell C18 column (2.1 mm×50 mm, 5 μm; temperature: 40 °C), with an injection volume of 3 μL at a flow rate of 1.2 mL/min and a gradient of 5-100% B (A=0.1% formic acid in water; B=0.10% formic acid in acetonitrile) over 1.2 min, then 100% B for 0.1 min. A second gradient of 100-5% B was then applied over 0.01 min and held for 0.39 min. UV spectra were recorded at 215 nm using a SPD-M20A PDA detector, spectrum range: 210-400 nm. Mass spectra were obtained using a 2010EV detector. Data were integrated and reported using Shimadzu LCMS-Solutions and PsiPort software.

Method 3 (M3): Basic IPC Method (MET-uPLC-AB-2005—MS16, MSQ5) Analytical (MET/uPLC/AB2005) (M14) uHPLC-MS were performed using a Waters uPLC® BEHTM C18 column (2.1 mm×30 mm, 1.7 μm; temperature 40 °C), with an injection volume of 1 μL at a flow rate of 1.0 mL/min and a gradient of 1-100% B (A=2 mM ammonium bicarbonate in water, buffered to pH 10; B=acetonitrile) over 1.1 min, then 100% B for 0.25 min. A second gradient of 100-1% B was then applied over 0.05 min and held for 0.4 min. UV spectra were recorded at 215 nm using a Waters ACQUITY PDA detector, spectrum range: 200-400 nm. Mass spectra were obtained using a Waters Quattro Premier XE mass detector or a Waters SQD2. Data were integrated and reported using Waters MassLynx and OpenLynx software.

Method 4 (M4): Acidic Final Analysis Method (METCR-uPLC-AB101—MSQ1, MSQ2, MSQ4)

Analytical (MET/uPLC/AB101) (M4) uHPLC-MS were performed using a Phenomenex Kinetex-XB C18 column (2.1 mm×100 mm, 1.7 μm; temperature: 40 °C), with an injection volume of 1 μL at flow rate of 0.6 mL/min and a gradient of 5-100% B (A=0.1% formic acid in water; B=0.1% formic acid in acetonitrile) over 5.3 min, then 100% B for 0.5 min. A second gradient of 100-5% B was then applied over 0.02 min and held for 1.18 min. UV spectra were recorded at 215 nm using a Waters ACQUITY PDA detector, spectrum range: 200-400 nm, ELS data was collected on a Waters ACQUITY ELS detector when reported. Mass spectra were obtained using a Waters SQD or Waters ACQUITY QDA. Data were integrated and reported using Waters MassLynx and OpenLynx software.

Method 5 (M5): Acidic Final Analysis Method (METCR1416—MS18, MS19) Analytical (MET/CR/1416) (M5) HPLC-MS were performed using a Waters Atlantis dC18 column (2.1 mm×100 mm, 3 μm; temperature: 40 °C), with an injection volume of 3 μL at flow rate of 0.6 mL/min and a gradient of 5-100% B (A=0.1% formic acid in water; B=0.1% formic acid in acetonitrile) over 5 min, then 100% B for 0.4 min. A second gradient of 100-5% B was then applied over 0.02 min and held for 1.58 min. UV spectra were recorded at 215 nm using a SPD-M20A PDA detector, spectrum range: 210-400 nm. Mass spectra were obtained using a 2010EV detector. Data were integrated and reported using Shimadzu LCMS-Solutions and PsiPort software.

Method 6 (M6): Basic Final Analysis Method (MET-uPLC-AB105—MS16, MSQ5) Analytical (MET/uHPLC/AB105) (M8) uHPLC-MS were performed using a Waters uPLC® BEHTM C18 column (2.1 mm×100 mm, 1.7 μm column; temperature: 40 °C), with an injection volume of 1 μL and at flow rate of 0.6 mL/min and a gradient of 5-100% B (A=2 mM ammonium bicarbonate in water, buffered to pH 10; B=acetonitrile) over 5.3 min, then 100% B for 0.5 min. A second gradient of 100-5% B was then applied over 0.02 min and held for 1.18 min. UV spectra were recorded at 215 nm using a Waters ACQUITY PDA detector, spectrum range: 200-400 nm. Mass spectra were obtained using a Waters Quattro Premier XE mass detector or a Waters SQD2. Data were integrated and reported using Waters MassLynx and OpenLynx software.

Method 7

Mass spectrometry data were collected using a Waters Acquity H-class ultra-high pressure liquid chromatograph coupled to a Waters Acquity TQD mass spectrometer. An Acquity UPLC BEH C18 column (2.1×50 mm) was used for separation and resolving samples. The compounds were eluted from the column using a 10 minutes linear solvent gradient: 0-0.5 min, 5% B; 0.5-6.5 min, 100% B, 6.5-7.5 min; 100% B, 7.5-8.1 min; 5% B, 8.1-10 min; 5% B. The solvent flow rate is 0.45 mL per minute. Solvent A was water and solvent B was acetonitrile. Mass spectra were collected in positive or negative ion mode, with following parameters: 2.5 kV capillary voltage; 25 V sampling cone voltage; 140 C source temperature; 400 C desolvation temperature; nitrogen desolvation at 800 L/hr.

Unless otherwise stated, $^1$H nuclear magnetic resonance spectroscopy (NMR) spectra were recorded on a Bruker™ 300 MHz, or 500 MHz, 400 MHz or 250 MHz on either a Bruker Avance III HD 500 MHz spectrometer Bruker Avance III HD 400 MHz spectrometer. Chemical shifts, 6, are quoted in parts per million (ppm) relative to TMS and calibrated using residual un-deuterated solvent as an internal reference. The following abbreviations are used to denote the multiplicities and general assignments: s (singlet), d (doublet), t (triplet), q (quartet), dd (doublet of doublets), ddd (doublet of doublet of doublets), dt (doublet of triplets), dq (doublet of quartets), hep (heptet), m (multiplet), pent (pentet), td (triplet of doublets), qd (quartet of doublets), app. (apparent) and br. (broad). Coupling constants, J, are quoted to the nearest 0.1 Hz.

Example 3

Purification Methods are as follows:

Prep Method 1 (P1): Acidic Early Method

Purification (METCR/Prep004) (P1) LC were performed using a Waters Sunfire C18 column (30 mm×100 mm, 5 μm; temperature: room temperature), with an injection volume of 1500 μL at flow rate of 40 mL/min at 100% B (A=0.1% formic acid in water; B=0.1% formic acid in acetonitrile) for 0.55 min then a gradient of 10-95% B over 13.89 min and held for 2.11 min. A second gradient of 95-10% B was then applied over 0.2 min. UV spectra were recorded at 215 nm using a Gilson detector.

Prep Method 2 (P2): Acidic Standard Method

Purification (METCR/Prep001) (P2) LC were performed using a Waters Sunfire C18 column (30 mm×100 mm, 5 μm; temperature: room temperature), with an injection volume of 1500 μL at flow rate of 40 mL/min at 30% B (A=0.10% formic acid in water; B=0.10% formic acid in acetonitrile) for 0.55 min then a gradient of 30-95% B over 10.45 min and held for 2.10 min. A second gradient of 95-30% B was then applied over 0.21 min. UV spectra were recorded at 215 nm using a Gilson detector.

Prep Method 3 (P3): Basic Early Method

Purification (METCR/Prep002) (P3) LC were performed using a Waters X-Bridge C18 column (30 mm×100 mm, 5 μm; temperature: room temperature), with an injection volume of 1500 μL at flow rate of 40 mL/min at 10% B (A=0.2% ammonium hydroxide in water; B=0.2% ammonium hydroxide in acetonitrile) for 0.55 min then a gradient of 10-95% B over 13.89 min and held for 2.11 min. A second gradient of 95-10% B was then applied over 0.2 min. UV spectra were recorded at 215 nm using a Gilson detector.

Prep Method 4 (P4): Basic Standard Method

Purification (METCR/Prep003) (P4) LC were performed using a Waters X-Bridge C18 column (30 mm×100 mm, 5 μm; temperature: room temperature), with an injection volume of 1500 μL at flow rate of 40 mL/min at 30% B (A=0.2% ammonium hydroxide in water; B=0.2% ammonium hydroxide in acetonitrile) for 0.55 min then a gradient of 30-95% B over 10.45 min and held for 2.10 min. A second gradient of 95-30% B was then applied over 0.21 min. UV spectra were recorded at 215 nm using a Gilson detector.

Example 4

Abbreviations and Acronyms

When the following abbreviations are used herein, they have the following meaning:

| | |
|---|---|
| Ac2O | acetic anhydride |
| anhy | Anhydrous |
| n-BuOH | n-butanol |
| t-BuOH | t-butanol |
| $CD_3OD$ | methanol-$d_4$ |
| Celite ® | diatomaceous earth filter agent, ® Celite Corp. |
| $CH_2Cl_2$ | methylene chloride |
| DCM | dichloromethane |
| CI-MS | chemical ionization mass spectroscopy |
| conc | concentrated |
| dec | decomposition |
| bs | broad singlet |
| br | broad |
| DME | dimethoxyethane |
| DMF | N,N-dimethylformamide |
| DMSO | dimethylsulfoxide |
| DMSO-$d_6$ | dimethylsulfoxide-$d_6$ |
| ELSD | evaporative light scattering device |
| EtOAc | ethyl acetate |
| EtOH | ethanol (100%) |
| $Et_2O$ | diethyl ether |
| $Et_3N$ | triethylamine |
| HPLC ESI-MS | high performance liquid chromatography-electrospray mass spectroscopy |
| MPLC | medium pressure liquid chromatography |
| NMR | nuclear magnetic resonance spectroscopy |
| TOF-MS | time-of-flight-mass spectroscopy |
| NMM | 4-methylmorpholine |
| $Ph_3P$ | triphenylphosphine |
| $Pd(dppf)Cl_2$ | [1,1'-bis(diphenylphosphino)ferrocene]dichloro-palladium(II) |
| $Pd(PPh_3)_4$ | tetrakis(triphenylphosphine)palladium(0) |
| $Pd(OAc)_2$ | palladium(II) acetate |
| $P(O)Cl_3$ | phosphorous oxychloride |
| Rf | TLC retention factor |
| RT | retention time (HPLC) |
| rt | room temperature |
| MS | Mass spectra |
| THF | tetrahydrofuran |
| TFA | trifluoroacetic acid |
| TLC | thin layer chromatography |
| LC-MS (ESI) | liquid chromatography-mass spectroscopy (electrospray ionization) |
| DIEA | diisopropylethylamine |
| $Et_3N$ | triethylamine |
| MsCl | Methanesulfonylchloride |
| HATU | N-[(dimethylamino)-1H-1,2,3-triazolo-[4,5-b]pyridin-1-ylmethylene]-N-methylmethanaminium hexafluorophosphate N-oxide |
| EDC | N-(3-dimethylaminopropyl)-N'-ethylcarbodiimide hydrochloride |
| AcOH | acetic acid |
| HCl | hydrochloric acid |
| $H_2SO_4$ | sulfuric acid |
| $HNO_3$ | nitric acid |
| HBr | hydrobromic acid |
| $CDCl_3$ | chloroform-d |
| $CHCl_3$ | chloroform |
| $H_2O$ | water |

-continued

| | |
|---|---|
| NaOAc | sodium acetate |
| KOH | potassium hydroxide |
| NaOH | sodium hydroxide |
| NaCl | sodium chloride |
| $NaHCO_3$ | sodium bicarbonate |
| $Na_2CO_3$ | sodium carbonate |
| $K_2CO_3$ | potassium carbonate |
| $Na_2SO_4$ | sodium sulfate |
| $MgSO_4$ | magnesium sulfate |
| MeOH | methanol |
| $SiO_2$ | silica gel |
| $K_3PO_4$ | potassium phosphate |
| $NH_4Cl$ | ammonium chloride |
| DMAP | N,N-dimethylpyridin-4-amine |
| LG | leaving group |
| TsCl | p-toluenesulfonyl chloride |
| PG | protecting group |
| AIBN | 2,2'-axo bisisobutyronitrile |

Example 5

General Synthetic Schemes

Methods for preparing the compounds of this invention are illustrated in the following Schemes and Examples. The present invention further provides processes for the preparation of compounds of structural Formula (I) and Formula (II) as defined above. In some cases, the order of carrying out the foregoing reaction schemes may be varied to facilitate the reaction or to avoid unwanted reaction products. The following exemplary compounds are provided for the purpose of illustration only and are not to be construed as limitations on the disclosed invention.

Scheme 1

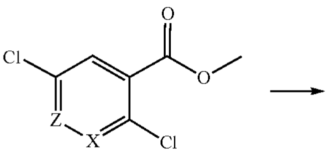

A-1

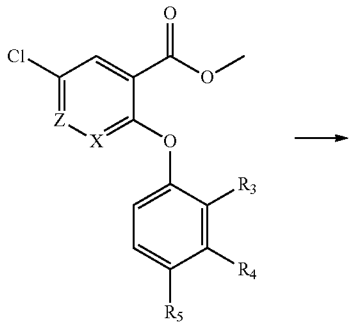

A-2

-continued

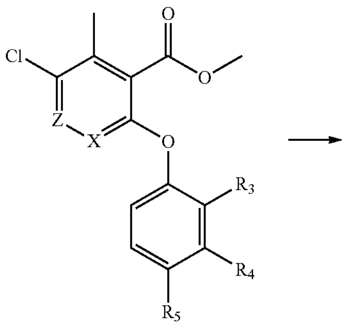

A-3

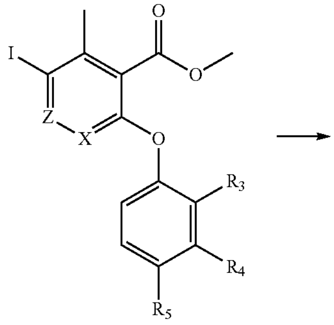

A-4

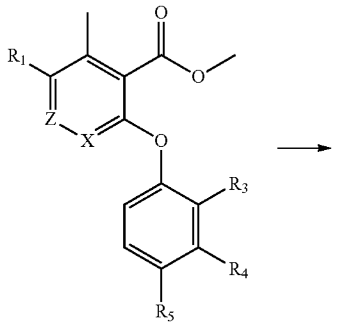

A-5

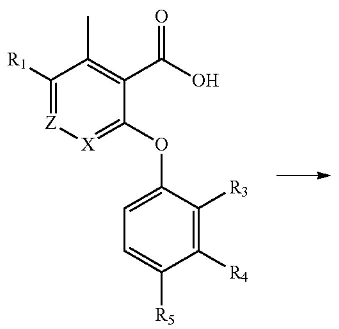

A-6

-continued

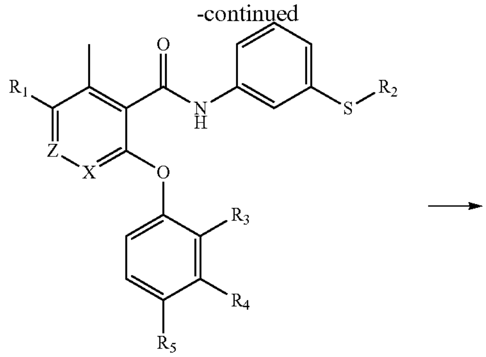

A-7

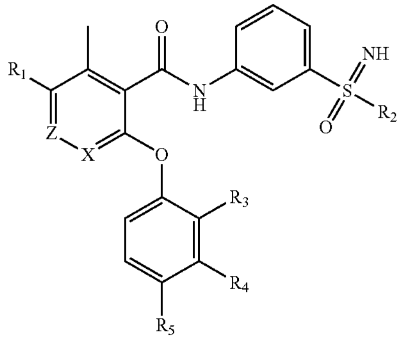

Formula(I)

Compounds of the Formula (I) may be synthesized in seven step linear synthesis starting from a heteroaromatic dichlorocarboxylic acid ester A-1 by nucleophilic displacement of Cl adjacent to the carboxylic acid using various substituted phenols in the presence of base, such as $K_2CO_3$, $Cs_2CO_3$, NaOH, KOH or other organic bases to provide intermediates of type A-2. Intermediates of type A-2 may be further treated with nitromethane in DMSO using organic base to produce A-3. A-3 can be converted to corresponding iodo compound by treating with HI (50%), HI(57%) or HI (40%) to furnish intermediates of type A-4. Variously substituted $R_1$ groups can be introduced either by Pd mediated or Cu mediated coupling with intermediates of type A-4 to produce intermediates of type A-5. The carboxylic acid of intermediates type A-6 can be prepared by hydrolyzing ester intermediates of type A-5 using a base, such as aqueous NaOH, KOH, or LiOH. Alternatively, intermediates of type A-6 can be prepared by treating intermediates A-5 using aqueous 1 to 6N HCl. The carboxylic acids (A-6) can be converted to the corresponding acid chlorides and followed by reacting with 3-(substitutedthio)aniline to afford A-7. Alternatively, A-7 can be prepared from carboxylic acids (A-6) and 3-(substitutedthio)aniline using standard amide coupling agents, not limited to HATU, TBTU, EDC or $T_3P$ in organic solvents and base, such as DIEA. The compounds of the Formula (I) may be prepared by reacting intermediates of type A-7 with ammonium carbonate and (diacetoxyiodo)benzene in organic solvents such as methanol.

Scheme 2

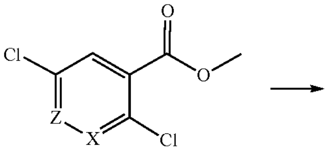

A-1

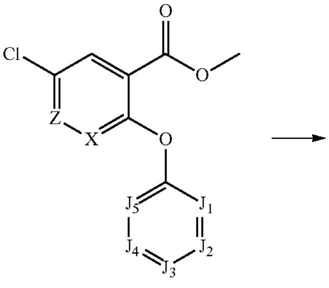

B-1

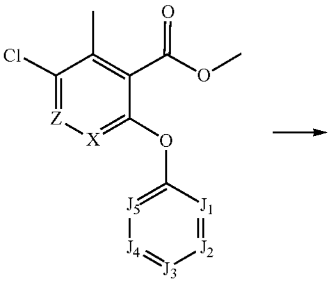

B-2

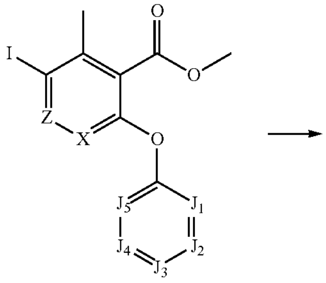

B-3

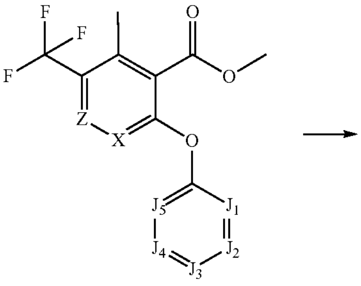

B-4

-continued

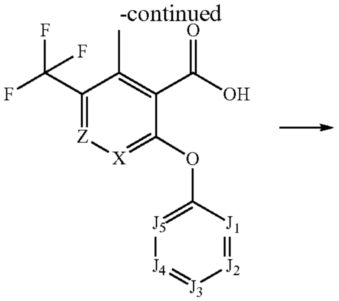

B-5

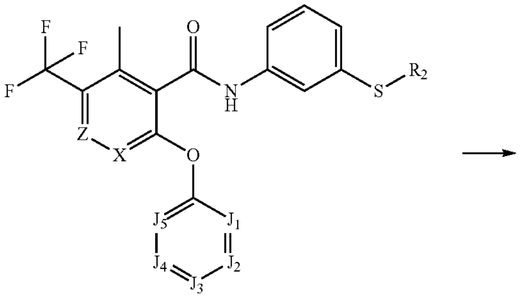

B-6

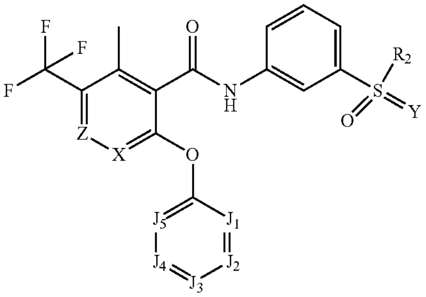

Formula(II)

The intermediates of type B-3 can be prepared analogous to the steps described for A-4 in Scheme 1. Intermediates of type B-3 were further reacted with methyl 2,2-difluoro-2-(fluorosulfonyl) acetate, TBAI, CuI using DMF or HMPA as a solvent and heating at 25 °C-120 °C for a period of 1-12 h to furnish B-4. The acid intermediates (B-5) can be prepared by similar hydrolysis procedures as described in scheme 1 from B-4. Intermediates of type B-6 may be prepared using standard coupling conditions described in scheme 1 from the corresponding acids. Compounds of Formula (II) may be prepared by treating B-6 with Oxone in organic solvents or mCPBA in DCM. Alternatively, the of compounds of the Formula (II) can be prepared from carboxylic acids (B-5) and appropriately 3-substituted aniline using standard coupling conditions as described in scheme 1. The compounds of the Formula (II) can also be prepared by reacting intermediates of type B-6 with ammonium carbonate and (diacetoxyiodo)benzene in organic solvents such as methanol.

Scheme 3

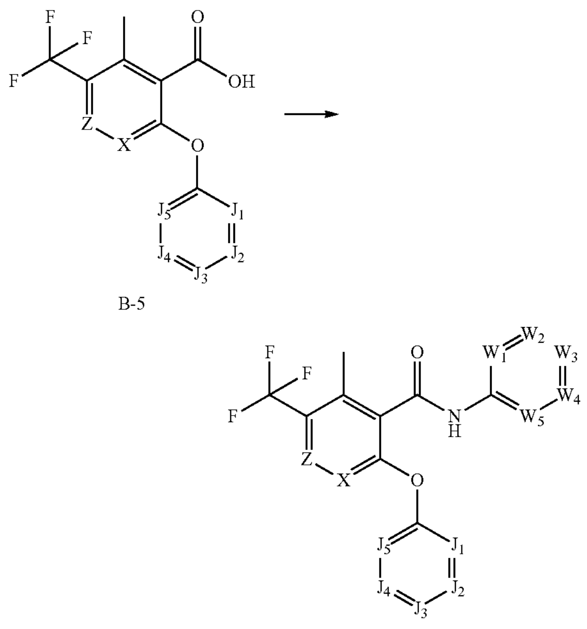

B-5

Formula(III)

Compounds of Formula (III) may be prepared by treating B-5 with substituted aniline or heteroaryl aniline using standard amide coupling agents, not limited to HATU, TBTU, EDC or T3P in organic solvents and base, such as DIEA.

Example 6

Specific Synthesis

Scheme 4, Intermediates 1-5

3-(4-Fluoro-2-methylphenoxy)-5-methyl-6-(trifluoromethyl)pyridazine-4-carboxylic Acid

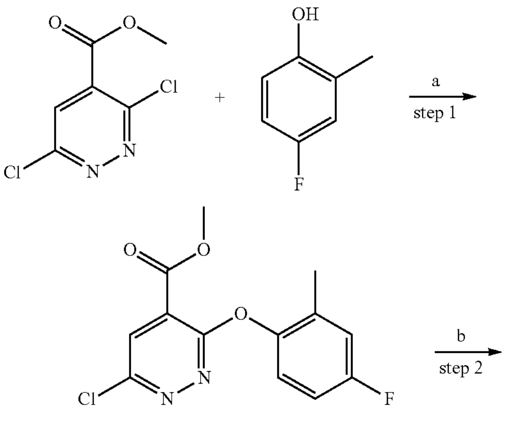

-continued

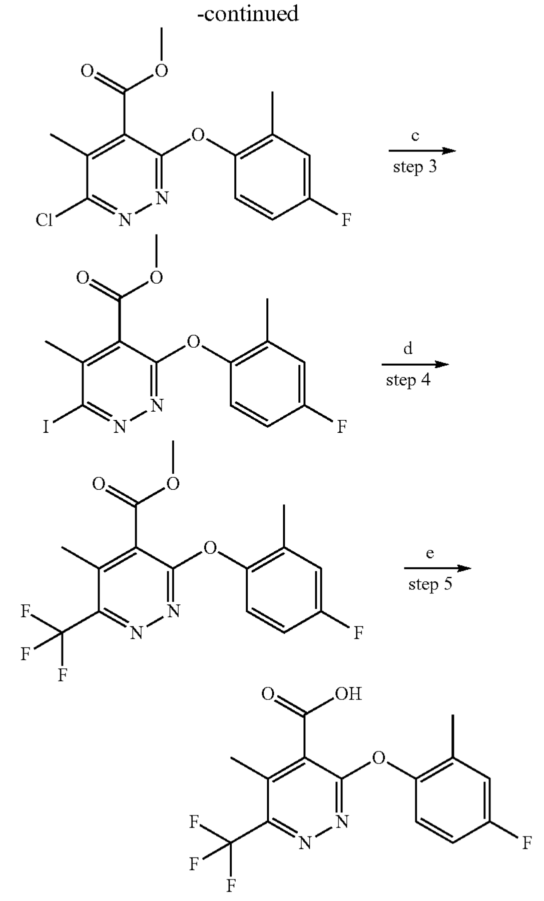

Reagents & conditions: a) 4-fluoro-2-methylphenol, $K_2CO_3$, $CH_3CN$, 80 °C, 3 h; b) nitromethane, $Et_3N$, DMSO, rt, 48 h; c) HI (57%), 55 °C, 16 h; d) methyl 2,2-difluoro-2-(fluorosulfonyl) acetate, TBAI, CuI, DMF, 90 °C, 2 h; e) LiOH, THF:$H_2O$ (5:1), rt.

Intermediate 1

Step 1: methyl 6-chloro-3-(4-fluoro-2-methylphenoxy) pyridazine-4-carboxylate: A mixture of 4-fluoro-2-methylphenol (3.01 g, 23.8 mmol), methyl 3,6-dichloropyridazine-4-carboxylate (4.70 g, 22.7 mmol) and $K_2CO_3$ (4.71 g, 34.1 mmol) in $CH_3CN$ (47 mL) was stirred at 80 °C for 3 h. The reaction was cooled to room temperature, filtered, and washed with $CH_3CN$ (20 mL). Filtrate was concentrated in vacuo to obtain the crude residue. Purification by chromatography on silica eluting with a gradient of 0 to 15% EtOAc in heptane afforded the title compound methyl 6-chloro-3-(4-fluoro-2-methyl-phenoxy)pyridazine-4-carboxylate (95.0%) (4.10 g, 58%) as a pale yellow oil. $^1H$ NMR (500 MHz, DMSO-$d_6$) δ 8.26 (s, 1H), 7.29-7.20 (m, 2H), 7.16-7.06 (m, 1H), 3.94 (s, 3H), 2.11 (s, 3H). LC-MS: m/z: 297/299 $[M+H]^+$, (ESI+), RT=4.26 LCMS Method 5.

Intermediate 2

Step 2: methyl 6-chloro-3-(4-fluoro-2-methylphenoxy)-5-methylpyridazine-4-carboxylate: To a mixture of methyl 6-chloro-3-(4-fluoro-2-methylphenoxy)pyridazine-4-carboxylate (1.20 g, 4.04 mmol) in DMSO (3.6 mL), nitromethane (1.1 mL, 20.2 mmol) was added and the mixture was stirred for 30 min at rt, triethylamine (0.85 mL, 6.07 mmol) was added to the reaction and stirred at rt for 48 h. The reaction was diluted with water (100 mL) and brine (25 mL) extracted with EtOAc (2×50 mL). Organic layers were dried ($MgSO_4$), filtered, concentrated under reduced pressure to obtain the crude residue. Purification by chromatography on silica eluting with a gradient of 0 to 100% EtOAc in heptane afforded the title compound (1.110 g, 85%) as a white solid. $^1$H NMR (400 MHz, DMSO-$d_6$) δ 7.26-7.19 (m, 2H), 7.15-7.08 (m, 1H), 3.99 (s, 3H), 2.38 (s, 3H), 2.08 (s, 3H). LC-MS: m/z 310.95, 312.9 $[M+H]^+$, (ESI+), RT=1.27 LCMS Method 5.

Intermediate 3

Step 3: methyl 3-(4-fluoro-2-methylphenoxy)-6-iodo-5-methylpyridazine-4-carboxylate: A mixture of methyl 6-chloro-3-(4-fluoro-2-methyl-phenoxy)-5-methyl-pyridazine-4-carboxylate (1.10 g, 3.54 mmol) in 55% aqueous hydrogen iodide (55%, 24 mL, 0.177 mol) was stirred at 40 °C for 16 h. The reaction was diluted with water (50 mL) and sat. sodium thiosulphate (100 mL), extracted with EtOAc (2×100 mL). Organic layer separated, dried over sodium sulphate and concentrated under reduced pressure to obtain the title compound methyl 3-(4-fluoro-2-methylphenoxy)-6-iodo-5-methylpyridazine-4-carboxylate (42.0%) (1153 mg, 34%) as a brown oil. LC-MS: m/z 403.0 [M+H]+, (ESI+), RT=1.29 LCMS Method 1.

Intermediate 4

Step 4: methyl 3-(4-fluoro-2-methylphenoxy)-5-methyl-6-(trifluoromethyl)pyridazine-4-carboxylate: To a mixture of methyl 3-(4-fluoro-2-methyl-phenoxy)-6-iodo-5-methylpyridazine-4-carboxylate (42%, 1.153 g, 1.20 mmol), iodocopper (0.35 g, 1.81 mmol), and tetrabutylammonium iodide (0.18 g, 0.482 mmol) in DMF (6.4023 mL), methyl difluoro(fluorosulfonyl)acetate (1.16 g, 6.02 mmol) was added and stirred at 70 °C for 2 h. The reaction was cooled to rt, filtered and washed with EtOAc (2×20 mL). The filtrate was washed with brine (50 mL) and dried over $MgSO_4$, filtered, concentrated under reduced pressure to obtain the crude residue. Purification by chromatography on silica eluting with a gradient of 0 to 20% EtOAc in heptane afforded the title compound (97.0%) (425 mg, 99%) as a pale yellow oil. LC-MS: m/z 345.0 [M+H]+, (ESI+), RT=1.33 LCMS Method 1. $^1$H NMR (400 MHz, DMSO-$d_6$) δ7.31-7.23 (m, 2H), 7.14 (td, J=8.6, 3.2 Hz, 1H), 4.02 (s, 3H), 2.48-2.44 (m, 3H), 2.09 (s, 3H).

Intermediate 5

Step 5: 3-(4-fluoro-2-methylphenoxy)-5-methyl-6-(trifluoromethyl)pyridazine-4-carboxylic acid: To a mixture of methyl 3-(4-fluoro-2-methyl-phenoxy)-5-methyl-6-(trifluoromethyl)pyridazine-4-carboxylate (97%, 425 mg, 1.20 mmol) in THF (4.5806 mL):Water (0.9161 mL), lithium hydroxide (149 mg, 5.99 mmol) was added and the mixture was stirred at rt for 16 h. The reaction was diluted with water (10 mL) and the pH was adjusted to 1 by dropwise addition of 1M HCl. The aqueous layer was extracted with EtOAc (20 mL), dried over sodium sulphate and concentrated under reduced pressure to obtain the title compound (407 mg, 99%) as a pale-yellow solid.

The intermediates 6-15 listed in Table 1 were prepared by a similar procedure as described for step 1 of scheme 4 using appropriate starting materials.

TABLE 1

| Intermediate | Structure & Name | Analytical data |
|---|---|---|
| 6 | 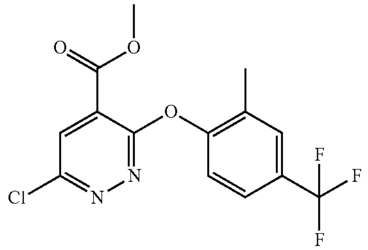 [SMILES: COC(=O)c1cc(Cl)nnc1Oc1ccc(C(F)(F)F)cc1C] Methyl 6-chloro-3-(2-methyl-4-(trifluoromethyl)phenoxy)pyridazine-4-carboxylate | $^1$H NMR (500 MHZ, DMSO-$d_6$) δ 8.32 (s, 1H), 7.81-7.77 (m, 1H), 7.68-7.64 (m, 1H), 7.43 (d, J = 8.4 Hz, 1H), 3.94 (s, 3H), 2.22 (s, 3H). LC-MS: m/z 346.9 $[M + H]^+$, (ESI+), RT = 1.25 LCMS Method 1 |
| 7 | 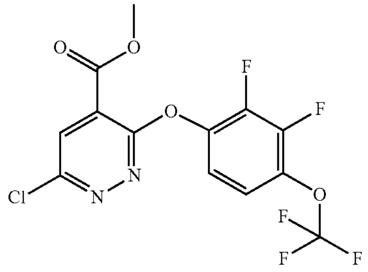 [SMILES: COC(=O)c1cc(Cl)nnc1Oc1ccc(OC(F)(F)F)c(F)c1F] Methyl 6-chloro-3-[2,3-difluoro-4-(trifluoromethoxy)phenoxy]pyridazine-4-carboxylate | $^1$H NMR (400 MHZ, DMSO-$d_6$) δ 8.37 (s, 1H), 7.65-7.55 (m, 1H), 7.52-7.44 (m, 1H), 3.99-3.89 (m, 3H). LC-MS: m/z 384.9 $[M + H]^+$, (ESI+), RT = 1.37 LCMS Method 1 |

TABLE 1-continued

| Intermediate | Structure & Name | Analytical data |
|---|---|---|
| 8 | 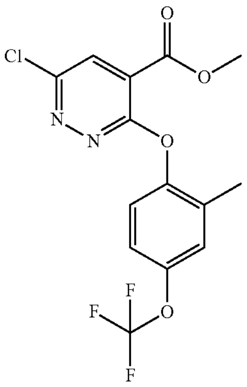 [SMILES: COC(=O)c1cc(Cl)nnc1Oc1ccc(OC(F)(F)F)cc1C] Methyl 6-chloro-3-[2-methyl-4-(trifluoromethoxy)phenoxy] pyridazine-4-carboxylate | $^1$H NMR (500 MHZ, DMSO-$d_6$) δ 8.29 (s, 1H), 7.44-7.41 (m, 1H), 7.35-7.29 (m, 2H), 3.94 (s, 3H), 2.15 (s, 3H). LC-MS: m/z 362.95/364.90 $[M + H]^+$, (ESI+), RT = 1.33 LCMS Method 1 |
| 9 | 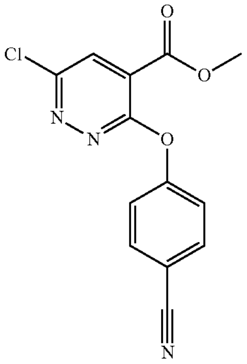 [SMILES: COC(=O)c1cc(Cl)nnc1Oc1ccc(C#N)cc1] Methyl 6-chloro-3-(4-cyano-phenoxy)pyridazine-4-carboxylate | $^1$H NMR (400 MHZ, DMSO-$d_6$) δ 8.33 (s, 1H), 7.99-7.93 (m, 2H), 7.50-7.45 (m, 2H), 3.91 (s, 3H). LC-MS: m/z 289.9 $[M + H]^+$, (ESI+), RT = 1.07 LCMS Method 1 |
| 10 | 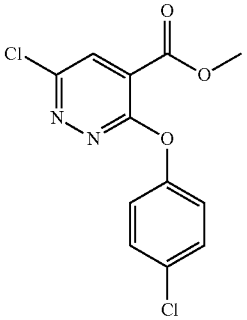 [SMILES: COC(=O)c1cc(Cl)nnc1Oc1ccc(Cl)cc1] Methyl 6-chloro-3-(4-chlorophenoxy)pyridazine-4-carboxylate | $^1$H NMR (500 MHZ, DMSO-$d_6$) δ 8.28 (s, 1H), 7.54-7.51 (m, 2H), 7.32-7.29 (m, 2H), 3.92 (s, 3H). LC-MS: m/z 298.8/300.9 $[M + H]^+$, (ESI+), RT = 1.16 LCMS Method 1 |
| 11 | 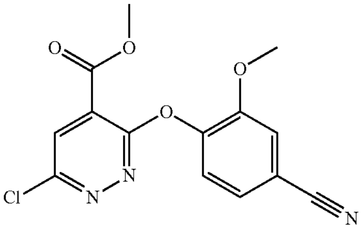 [SMILES: COC(=O)c1cc(Cl)nnc1Oc1ccc(C#N)cc1OC] Methyl 6-chloro-3-(4-cyano-2-methoxyphenoxy)pyridazine-4-carboxylate | $^1$H NMR (300 MHZ, $CDCl_3$) δ 7.96 (s, 1H), 7.40-7.18 (m, 5H), 4.02 (s, 3H), 3.76 (s, 3H). |

TABLE 1-continued

| Intermediate | Structure & Name | Analytical data |
|---|---|---|
| 12 | 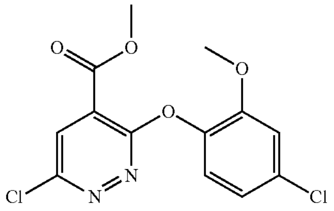 [SMILES: COC(=O)c1cc(Cl)nnc1Oc1ccc(Cl)cc1OC] Methyl 6-chloro-3-(4-chloro-2-methoxyphenoxy)pyridazine-4-carboxylate | $^1$H NMR (300 MHZ, $CDCl_3$) δ 7.91 (s, 1H), 7.16-7.10 (m, 1H), 6.98 (dd, J = 6.9, 2.2 Hz, 2H), 4.01 (d, J = 1.2 Hz, 3H), 3.72 (s, 3H). |
| 13 | 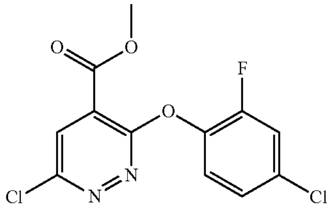 [SMILES: COC(=O)c1cc(Cl)nnc1Oc1ccc(Cl)cc1F] Methyl 6-chloro-3-(4-chloro-2-fluorophenoxy)pyridazine-4-carboxylate | $^1$H NMR (300 MHZ, $CDCl_3$) δ 7.95 (s, 1H), 7.27-7.24 (m, 1H), 7.21 (d, J = 1.2 Hz, 2H), 4.02 (s, 3H). |
| 14 | 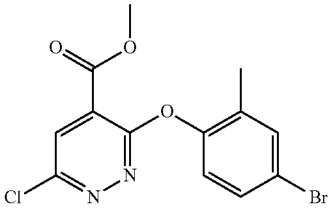 [SMILES: COC(=O)c1cc(Cl)nnc1Oc1ccc(Br)cc1C] Methyl 3-(4-bromo-2-methylphenoxy)-6-chloropyridazine-4-carboxylate | $^1$H NMR (300 MHZ, $CDCl_3$) δ 7.90 (s, 1H), 7.43 (td, J = 2.9, 2.4, 1.6 Hz, 1H), 7.36 (ddd, J = 8.5, 2.5, 0.7 Hz, 1H), 6.99 (dd, J = 8.5, 6.4 Hz, 1H), 4.02 (d, J = 1.5 Hz, 3H), 2.17 (s, 3H). |
| 15 | 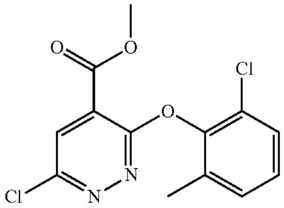 [SMILES: COC(=O)c1cc(Cl)nnc1Oc1c(C)cccc1Cl] Methyl 6-chloro-3-(2-chloro-6-methylphenoxy)pyridazine-4-carboxylate | $^1$H NMR (300 MHZ, $CDCl_3$) δ 7.94 (s, 1H), 7.34-7.27 (m, 1H), 7.23-7.09 (m, 2H), 4.03 (d, J = 1.6 Hz, 3H), 2.23 (d, J = 4.8 Hz, 3H). |

The intermediates 16-24 listed in Table 2 were prepared by a similar procedure as described for step 2 of scheme 4 using appropriate starting materials.

TABLE 2

| Intermediate | Structure & Name | Analytical data |
|---|---|---|
| 16 | 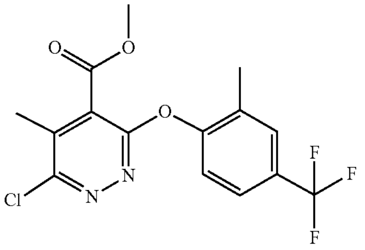 [SMILES: COC(=O)c1c(Oc2ccc(C(F)(F)F)cc2C)nnc(Cl)c1C] Methyl 6-chloro-5-methyl-3-(2-methyl-4-(trifluoromethyl)phenoxy)pyridazine-4-carboxylate | $^1$H NMR (400 MHZ, DMSO-$d_6$) δ 7.80-7.76 (m, 1H), 7.66 (dd, J = 8.5, 2.3 Hz, 1H), 7.43 (d, J = 8.5 Hz, 1H), 3.99 (s, 3H), 2.40 (s, 3H), 2.18 (s, 3H). LC-MS: m/z 360.9 $[M + H]^+$, (ESI+), RT = 1.27 LCMS Method 1 |
| 17 | 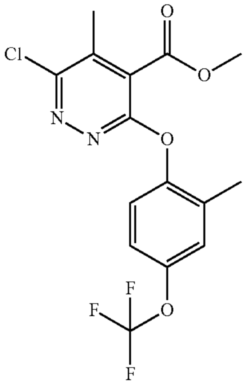 [SMILES: COC(=O)c1c(Oc2ccc(OC(F)(F)F)cc2C)nnc(Cl)c1C] Methyl 6-chloro-5-methyl-3-[2-methyl-4-(trifluoromethoxy) phenoxy]pyridazine-4-carboxylate | $^1$H NMR (400 MHZ, DMSO-$d_6$) δ 7.43-7.39 (m, 1H), 7.36-7.27 (m, 2H), 3.99 (s, 3H), 2.39 (s, 3H), 2.12 (s, 3H). LC-MS: m/z 377.35/378.95 $[M + H]^+$, (ESI+), RT = 1.38 LCMS Method 1 |
| 18 | 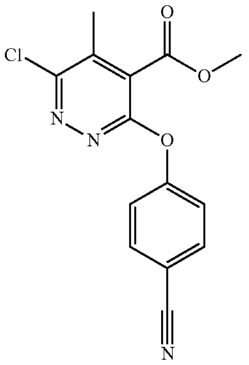 [SMILES: COC(=O)c1c(Oc2ccc(C#N)cc2)nnc(Cl)c1C] Methyl 6-chloro-3-(4-cyanophenoxy)-5-methyl-pyridazine-4-carboxylate | $^1$H NMR (500 MHZ, DMSO-$d_6$) δ 7.96 (dd, J = 8.9, 2.2 Hz, 2H), 7.47 (dd, J = 8.9, 2.2 Hz, 2H), 3.96 (d, J = 2.3 Hz, 3H), 2.40 (d, J = 2.3 Hz, 3H). LC-MS: m/z 304.0/305.95 $[M + H]^+$, (ESI+), RT = 1.17 LCMS Method 1 |
| 19 | 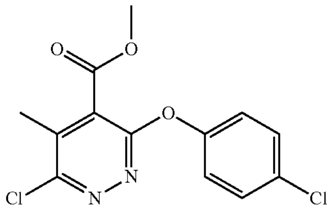 [SMILES: COC(=O)c1c(Oc2ccc(Cl)cc2)nnc(Cl)c1C] | $^1$H NMR (500 MHZ, DMSO-$d_6$) δ 7.53-7.50 (m, 2H), 7.30-7.27 (m, 2H), 3.97 (s, 3H), 2.38 (s, 3H) LC-MS: m/z 312.9/314.85 $[M + H]^+$, (ESI+), RT = 1.28 LCMS Method 1 |

TABLE 2-continued

| Intermediate | Structure & Name | Analytical data |
| --- | --- | --- |
| | Methyl 6-chloro-3-(4-chlorophenoxy)-5-methyl-pyridazine-4-carboxylate | |
| 20 | 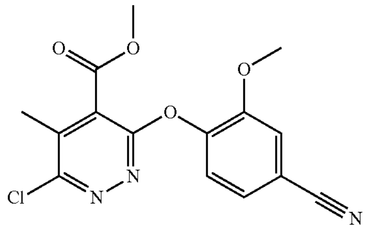 [SMILES: COC(=O)c1c(Oc2ccc(C#N)cc2OC)nnc(Cl)c1C] Methyl 6-chloro-3-(4-cyano-2-methoxyphenoxy)-5-methylpyridazine-4-carboxylate | $^1$H NMR (300 MHz, $CDCl_3$) δ 7.39-7.19 (m, 3H), 4.02 (s, 3H), 3.77 (s, 3H), 2.43 (s, 3H) |
| 21 | 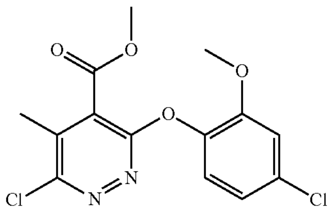 [SMILES: COC(=O)c1c(Oc2ccc(Cl)cc2OC)nnc(Cl)c1C] Methyl 6-chloro-3-(4-chloro-2-methoxyphenoxy)-5-methylpyridazine-4-carboxylate | $^1$H NMR (300 MHz, $CDCl_3$) δ 7.15-7.05 (m, 1H), 7.04-6.86 (m, 2H), 4.02 (s, 3H), 3.73 (s, 3H), 2.41 (s, 3H). |
| 22 | 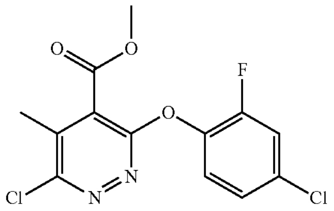 [SMILES: COC(=O)c1c(Oc2ccc(Cl)cc2F)nnc(Cl)c1C] Methyl 6-chloro-3-(4-chloro-2-fluorophenoxy)-5-methylpyridazine-4-carboxylate | $^1$H NMR (300 MHz, $CDCl_3$) δ 7.24-7.21 (m, 1H), 7.21-7.12 (m, 2H), 4.02 (d, J = 2.4 Hz, 3H), 2.40 (d, J = 6.7 Hz, 3H). |
| 23 | 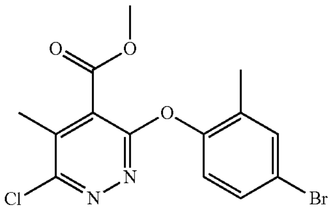 [SMILES: COC(=O)c1c(Oc2ccc(Br)cc2C)nnc(Cl)c1C] Methyl 3-(4-bromo-2-methylphenoxy)-6-chloro-5-methylpyridazine-4-carboxylate | $^1$H NMR (300 MHz, $CDCl_3$) δ 7.42 (ddd, J = 5.4, 2.4, 0.9 Hz, 1H), 7.36 (dddd, J = 8.5, 4.6, 2.5, 0.7 Hz, 1H), 6.99 (dd, J = 12.6, 8.6 Hz, 1H), 4.02 (s, 3H), 2.42 (s, 3H), 2.14 (d, J = 2.5 Hz, 3H). |
| 24 | 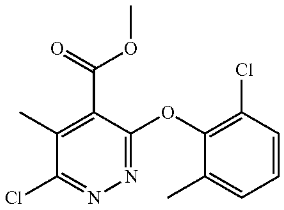 [SMILES: COC(=O)c1c(Oc2c(C)cccc2Cl)nnc(Cl)c1C] Methyl 6-chloro-3-(2-chloro-6-methylphenoxy)-5-methylpyridazine-4-carboxylate | $^1$H NMR (300 MHz, $CDCl_3$) δ 7.33-7.27 (m, 1H), 7.21-7.08 (m, 2H), 4.04 (d, J = 1.6 Hz, 3H), 2.44 (d, J = 5.1 Hz, 3H), 2.27-2.16 (m, 3H) |

The intermediates 25-35 listed in Table 3 were prepared by a similar procedure as described for step 3 of scheme 4 using appropriate starting materials.

TABLE 3

| Intermediate | Structure & Name | Analytical data |
| --- | --- | --- |
| 25 | 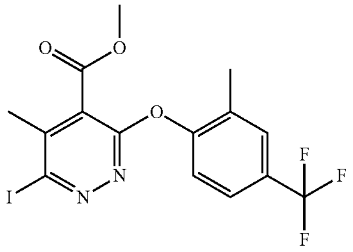 [SMILES: COC(=O)c1c(Oc2ccc(C(F)(F)F)cc2C)nnc(I)c1C] Methyl 6-iodo-5-methyl-3-(2-methyl-4-(trifluoromethyl)phenoxy)pyridazine-4-carboxylate | $^1$H NMR (400 MHz, DMSO-$d_6$) δ 7.80-7.74 (m, 1H), 7.70-7.61 (m, 1H), 7.47-7.38 (m, 1H), 3.97 (s, 3H), 2.39 (s, 3H), 2.17 (s, 3H) LC-MS: m/z 452.8 [M + H]$^+$, (ESI+), RT = 1.29 LCMS Method 1 |
| 26 | 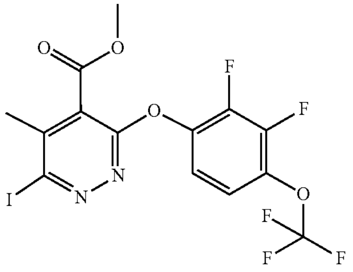 [SMILES: COC(=O)c1c(Oc2ccc(OC(F)(F)F)c(F)c2F)nnc(I)c1C] Methyl 3-(2,3-difluoro-4-(trifluoromethoxy)phenoxy)-6-iodo-5-methylpyridazine-4-carboxylate | $^1$H NMR (400 MHz, DMSO-$d_6$) δ 7.63-7.55 (m, 1H), 7.53-7.44 (m, 1H), 3.98 (s, 3H), 2.43-2.39 (m, 3H). LC-MS: m/z 490.9 [M + H]$^+$, (ESI+), RT = 1.40 LCMS Method 1 |
| 27 | 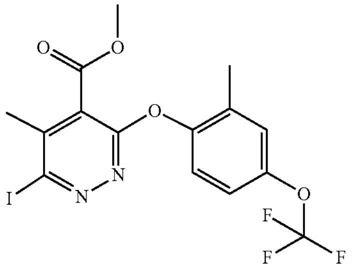 [SMILES: COC(=O)c1c(Oc2ccc(OC(F)(F)F)cc2C)nnc(I)c1C] Methyl 6-iodo-5-methyl-3-[2-methyl-4-(trifluoromethoxy)phenoxy]pyridazine-4-carboxylate | $^1$H NMR (500 MHz, DMSO)-$d_6$ δ 7.41-7.40 (m, 1H), 7.31-7.27 (m, 2H), 3.97 (s, 3H), 2.38 (s, 3H), 2.11 (s, 3H). LC-MS: m/z 468.95 [M + H]$^+$, (ESI+), RT = 1.40 LCMS Method 1 |
| 28 | 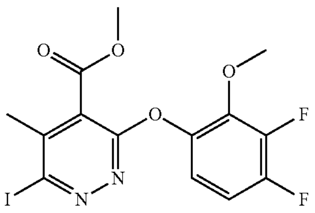 [SMILES: COC(=O)c1c(Oc2ccc(F)c(F)c2OC)nnc(I)c1C] Methyl 3-(3,4-difluoro-2-methoxy-phenoxy)-6-iodo-5-methyl-pyridazine-4-carboxylate | $^1$H NMR (500 MHz, DMSO-$d_6$) δ 7.32-7.25 (m, 1H), 7.25-7.21 (m, 1H), 4.01 (s, 3H), 3.81 (d, J = 1.4 Hz, 3H), 2.38 (s, 3H). LC-MS: m/z 437.3 [M + H]$^+$, (ESI+), RT = 1.28 LCMS Method 1 |

TABLE 3-continued

| Intermediate | Structure & Name | Analytical data |
|---|---|---|
| 29 | 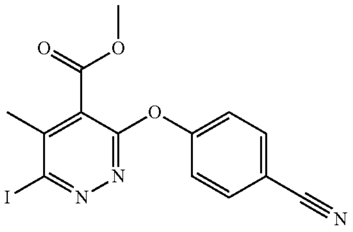 [SMILES: COC(=O)c1c(Oc2ccc(C#N)cc2)nnc(I)c1C] Methyl 3-(4-cyanophenoxy)-6-iodo-5-methyl-pyridazine-4-carboxylate | $^{1}$H NMR (500 MHz, DMSO-$d_6$) δ 7.99-7.90 (m, 2H), 7.49-7.40 (m, 2H), 3.94 (s, 3H), 2.39 (s, 3H). LC-MS: m/z 395.8 $[M + H]^+$, (ESI+), RT = 1.12 LCMS Method 1 |
| 30 | 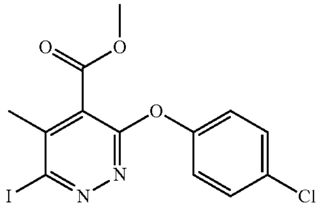 [SMILES: COC(=O)c1c(Oc2ccc(Cl)cc2)nnc(I)c1C] Methyl 3-(4-chlorophenoxy)-6-iodo-5-methyl-pyridazine-4-carboxylate | 1H NMR (500 MHz, DMSO) δ 7.52-7.49 (m, 2H), 7.28-7.25 (m, 2H), 3.95 (s, 3H), 2.37 (s, 3H). LC-MS: m/z 404.8 $[M + H]^+$, (ESI+), RT = 1.19 LCMS Method 1 |
| 31 | 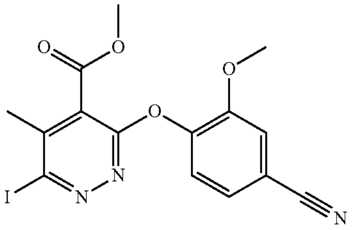 [SMILES: COC(=O)c1c(Oc2ccc(C#N)cc2OC)nnc(I)c1C] Methyl 3-(4-cyano-2-methoxyphenoxy)-6-iodo-5-methylpyridazine-4-carboxylate | MS: m/z 426.1 $[M + H]^+$ |
| 32 | 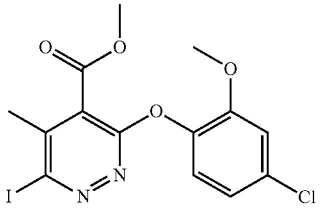 [SMILES: COC(=O)c1c(Oc2ccc(Cl)cc2OC)nnc(I)c1C] Methyl 3-(4-chloro-2-methoxyphenoxy)-6-iodo-5-methylpyridazine-4-carboxylate | MS: m/z 457.0 $[M + Na]^+$ |
| 33 | 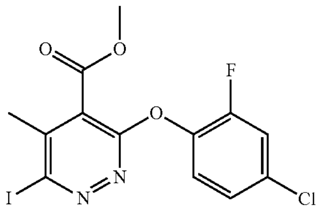 [SMILES: COC(=O)c1c(Oc2ccc(Cl)cc2F)nnc(I)c1C] Methyl 3-(4-chloro-2-fluorophenoxy)-6-iodo-5-methylpyridazine-4-carboxylate | MS: m/z 445.0 $[M + Na]^+$ |

TABLE 3-continued

| Intermediate | Structure & Name | Analytical data |
|---|---|---|
| 34 | 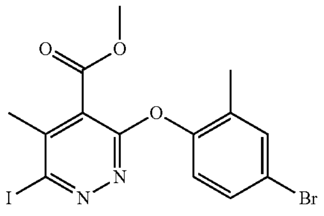 [SMILES: COC(=O)c1c(Oc2ccc(Br)cc2C)nnc(I)c1C]<br>Methyl 3-(4-bromo-2-methylphenoxy)-6-iodo-5-methylpyridazine-4-carboxylate | MS: m/z 463.0, 465.0 $[M + H]^+$ |
| 35 | 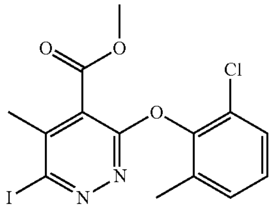<br>Methyl 3-(2-chloro-6-methylphenoxy)-6-iodo-5-methylpyridazine-4-carboxylate | MS: m/z 463.0, 465.0 $[M + H]^+$ |

The intermediates 36-46 listed in Table 4 were prepared by a similar procedure as described for step 4 of scheme 4 using appropriate starting materials.

TABLE 4

| Intermediate | Structure & Name | Analytical data |
|---|---|---|
| 36 | 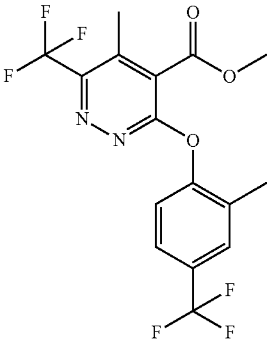<br>Methyl 5-methyl-3-[2-methyl-4-(trifluoromethyl)phenoxy]-6-(trifluoromethyl)pyridazine-4-carboxylate | $^1$H NMR (400 MHz, DMSO-$d_6$) δ 7.81 (d, J = 1.9 Hz, 1H), 7.69 (dd, J = 8.5, 2.1 Hz, 1H), 7.49 (d, J = 8.4 Hz, 1H), 4.02 (s, 3H), 2.49-2.47 (m, 3H), 2.19 (s, 3H).<br>LC-MS: m/z 394.9 $[M + H]^+$, (ESI+), RT = 1.31 LCMS Method 1 |
| 37 | 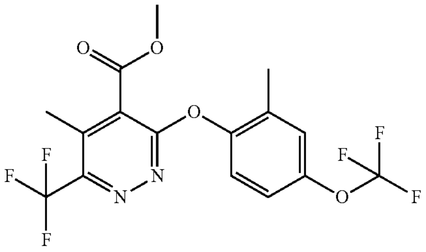<br>Methyl 5-methyl-3-[2-methyl-4-(trifluoromethoxy)phenoxy]-6-(trifluoromethyl) pyridazine-4-carboxylate | $^1$H NMR (500 MHz, DMSO-$d_6$) δ 7.46-7.42 (m, 1H), 7.39 (d, J = 8.9 Hz, 1H), 7.34-7.29 (m, 1H), 4.02 (s, 3H), 2.48-2.45 (m, 3H), 2.14 (s, 3H).<br>LC-MS: m/z 410.9 $[M + H]^+$, (ESI+), RT = 1.34 LCMS Method 1 |

TABLE 4-continued

| Intermediate | Structure & Name | Analytical data |
|---|---|---|
| 38 | 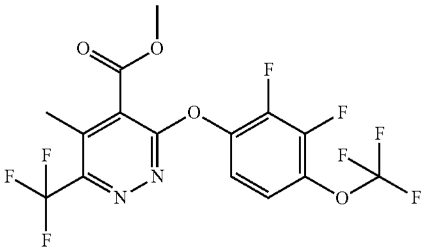<br>Methyl 3-[2,3-difluoro-4-(trifluoromethoxy)phenoxy]-5-methyl-6-(trifluoromethyl) pyridazine-4-carboxylate | $^{1}H$ NMR (400 MHz, DMSO-$d_6$) δ 7.67-7.60 (m, 1H), 7.55 (ddd, J = 9.6, 7.8, 2.2 Hz, 1H), 4.02 (s, 3H), 2.51-2.48 (m, 3H). Me peak hidden under DMSO, identified in HSQC. LC-MS: m/z 432.95 $[M + H]^+$, (ESI+), RT = 1.43 LCMS Method 1 |
| 39 | 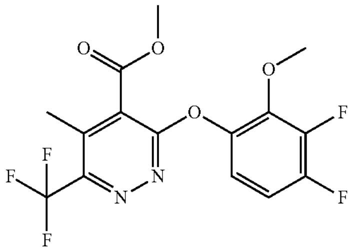<br>Methyl 3-(3,4-difluoro-2-methoxy-phenoxy)-5-methyl-6-(trifluoromethyl) pyridazine-4-carboxylate | $^{1}H$ NMR (400 MHz, DMSO-$d_6$) δ 7.34-7.21 (m, 2H), 4.02 (s, 3H), 3.80 (d, J = 1.3 Hz, 3H), 2.49-2.47 (m, 3H). LC-MS: m/z 379.35 $[M + H]^+$, (ESI+), RT = 1.32 LCMS Method 1 |
| 40 | 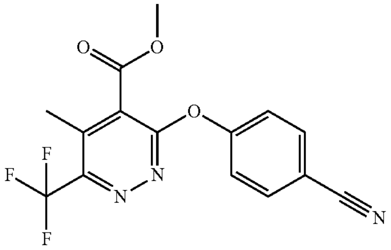<br>Methyl 3-(4-cyanophenoxy)-5-methyl-6-(trifluoromethyl)pyridazine-4-carboxylate | $^{1}H$ NMR (400 MHz, DMSO-$d_6$) δ 8.02-7.96 (m, 2H), 7.56-7.51 (m, 2H), 4.00 (s, 3H), 2.49-2.47 (m, 3H) LC-MS: m/z 338.5 $[M + H]^+$, (ESI+), RT = 1.16 LCMS Method 1 |
| 41 | 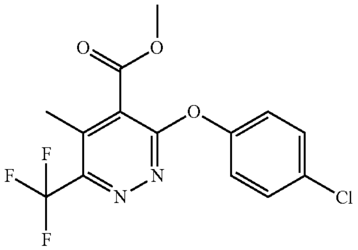<br>Methyl 3-(4-chlorophenoxy)-5-methyl-6-(trifluoromethyl)pyridazine-4-carboxylate | $^{1}H$ NMR (500 MHz, DMSO-$d_6$) δ 7.58-7.51 (m, 2H), 7.38-7.31 (m, 2H), 4.00 (s, 3H), 2.48-2.43 (m, 3H) LC-MS: m/z 346.95/348.95 $[M + H]^+$, (ESI+), RT = 1.34 LCMS Method 1 |

TABLE 4-continued

| Intermediate | Structure & Name | Analytical data |
|---|---|---|
| 42 | 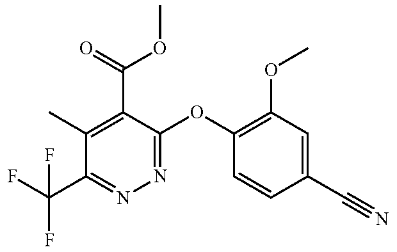 Methyl 3-(4-cyano-2-methoxyphenoxy)-5-methyl-6-(trifluoromethyl)pyridazine-4-carboxylate | $^1$H NMR (300 MHz, $CDCl_3$) δ 7.27 (d, J = 1.7 Hz, 2H), 7.17 (d, J = 1.7 Hz, 1H), 3.98 (s, 3H), 3.71 (s, 3H), 2.44 (q, J = 1.4 Hz, 3H). |
| 43 | 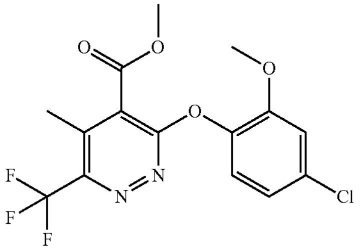 Methyl 3-(4-chloro-2-methoxyphenoxy)-5-methyl-6-(trifluoromethyl)pyridazine-4-carboxylate | $^1$H NMR (300 MHz, $CDCl_3$) δ 7.15-7.09 (m, 1H), 7.00-6.93 (m, 2H), 4.04 (s, 3H), 3.73 (s, 3H), 2.49 (q, J = 1.5 Hz, 3H). |
| 44 | 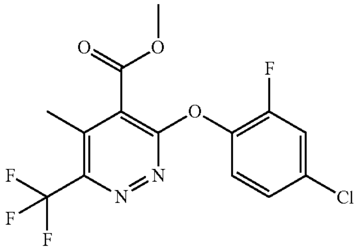 Methyl 3-(4-chloro-2-fluorophenoxy)-5-methyl-6-(trifluoromethyl)pyridazine-4-carboxylate | $^1$H NMR (300 MHz, $CDCl_3$) δ 7.29-7.24 (m, 1H), 7.23 (dd, J = 1.6, 0.8 Hz, 1H), 7.22-7.19 (m, 1H), 4.06 (s, 3H), 2.51 (q, J = 1.4 Hz, 3H) |
| 45 | 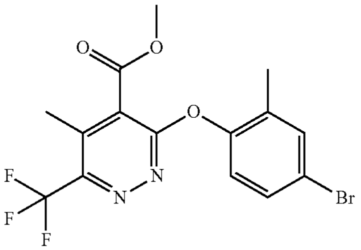 Methyl 3-(4-bromo-2-methylphenoxy)-5-methyl-6-(trifluoromethyl)pyridazine-4-carboxylate | $^1$H NMR (300 MHz, $CDCl_3$) δ 7.48-7.31 (m, 2H), 7.03 (d, J = 8.5 Hz, 1H), 4.05 (s, 3H), 2.50 (q, J = 1.4 Hz, 3H), 2.15 (s, 3H). |

TABLE 4-continued

| Intermediate | Structure & Name | Analytical data |
|---|---|---|
| 46 | 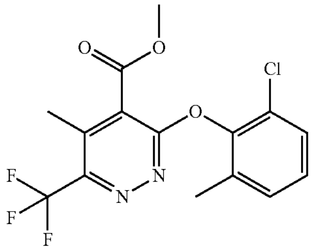<br>Methyl 3-(2-chloro-6-methylphenoxy)-5-methyl-6-(trifluoromethyl)pyridazine-4-carboxylate | $^1$H NMR (300 MHz, $CDCl_3$) δ 7.36-7.26 (m, 1H), 7.26-7.08 (m, 2H), 4.07 (s, 3H), 2.52 (q, J = 1.5 Hz, 3H), 2.21 (s, 3H). |

The intermediates 47-56 listed in Table 5 were prepared by a similar procedure as described for step 5 of scheme 4 using appropriate starting materials.

TABLE 5

| Intermediate | Structure & name | Analytical data |
|---|---|---|
| 47 | 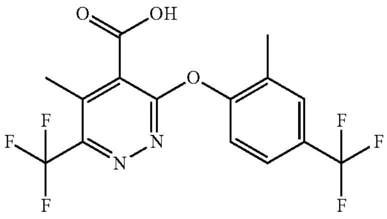<br>5-Methyl-3-(2-methyl-4-(trifluoromethyl)phenoxy)-6-(trifluoromethyl) pyridazine-4-carboxylic acid | $^1$H NMR (400 MHz, DMSO-$d_6$) δ 7.79 (d, J = 1.9 Hz, 1H), 7.67 (dd, J = 8.5, 2.1 Hz, 1H), 7.45 (d, J = 8.4 Hz, 1H), 2.48-2.45 (m, 3H), 2.18 (s, 3H) LC-MS: m/z 380.9 $[M + H]^+$, (ESI+), RT = 1.14 LCMS Method 1 |
| 48 | 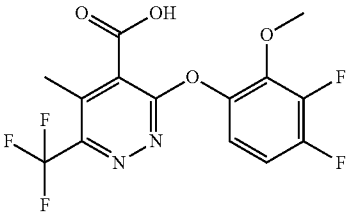<br>3-(3,4-Difluoro-2-methoxy-phenoxy)-5-methyl-6-(trifluoromethyl) pyridazine-4-carboxylic acid | LC-MS: m/z 365.0 $[M + H]^+$, (ESI+), RT = 1.02 LCMS Method 1 |
| 49 | 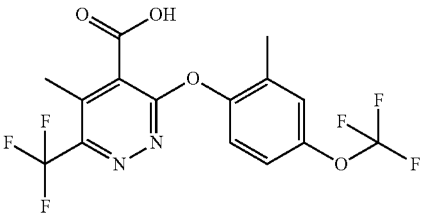<br>5-Methyl 3-[2-methyl-4-(trifluoromethoxy)phenoxy]-6-(trifluoromethyl)pyridazine-4-carboxylic acid | LC-MS: m/z 397.0 $[M + H]^+$, (ESI+), RT = 1.18 LCMS Method 1 |

TABLE 5-continued

| Intermediate | Structure & name | Analytical data |
| --- | --- | --- |
| 50 | 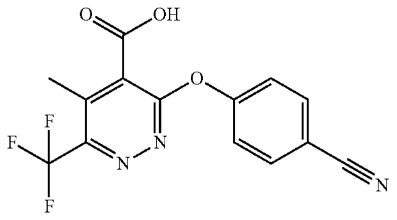 3-(4-Cyanophenoxy)-5-methyl-6-(trifluoromethyl) pyridazine-4-carboxylic acid | $^1H$ NMR (400 MHz, DMSO-$d_6$) δ 8.03-7.92 (m, 2H), 7.55-7.46 (m, 2H), 2.50 (s, 3H, from HSQC analysis).. LC-MS: m/z 323.9 $[M + H]^+$, (ESI+), RT = 0.88 LCMS Method 1 |
| 51 | 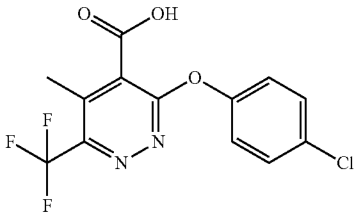 3-(4-Chlorophenoxy)-5-methyl-6-(trifluoromethyl)pyridazine-4-carboxylic acid | $^1H$ NMR (400 MHz, DMSO-$d_6$) δ 7.57-7.49 (m, 2H), 7.35-7.27 (m, 2H), 2.45 (d, J = 1.5 Hz, 3H). LC-MS: m/z 332.95 $[M + H]^+$, (ESI+), RT = 1.02 LCMS Method 1 |
| 52 | 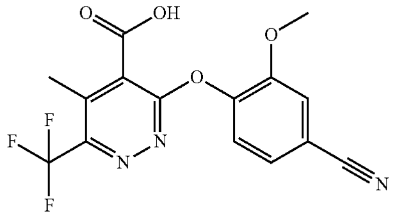 3-(4-Cyano-2-methoxyphenoxy)-5-methyl-6-(trifluoromethyl)pyridazine-4-carboxylic acid | $^1H$ NMR (300 MHz, DMSO-$d_6$) δ 7.76 (d, J = 1.8 Hz, 1H), 7.62-7.46 (m, 2H), 3.78 (s, 3H), 2.54 (s, 3H). |
| 53 | 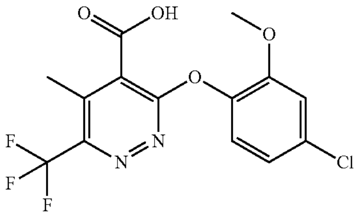 3-(4-Chloro-2-methoxyphenoxy)-5-methyl-6-(trifluoromethyl) pyridazine-4-carboxylic acid | $^1H$ NMR (300 MHz, DMSO-$d_6$) δ 7.42-7.25 (m, 2H), 7.10 (dd, J = 8.5, 2.4 Hz, 1H), 3.74 (s, 3H), 2.49-2.41 (m, 3H). |
| 54 | 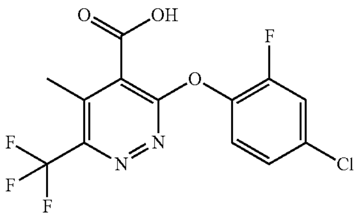 3-(4-Chloro-2-fluorophenoxy)-5-methyl-6-(trifluoromethyl) pyridazine-4-carboxylic acid | $^1H$ NMR (300 MHz, $CD_3OD$) δ 7.47-7.35 (m, 2H), 7.31 (ddd, J = 8.7, 2.4, 1.2 Hz, 1H), 2.56 (q, J = 1.5 Hz, 3H). |

TABLE 5-continued

| Intermediate | Structure & name | Analytical data |
| --- | --- | --- |
| 55 | 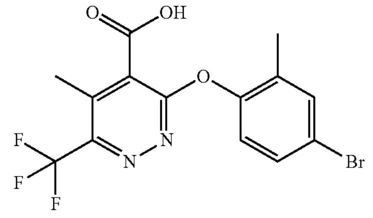 3-(4-Bromo-2-methylphenoxy)-5-methyl-6-(trifluoromethyl) pyridazine-4-carboxylic acid | $^1$H NMR (300 MHz, $CD_3OD$) δ 7.57-7.32 (m, 2H), 7.11 (d, J = 8.6 Hz, 1H), 2.54 (q, J = 1.5 Hz, 3H), 2.14 (s, 3H). |
| 56 | 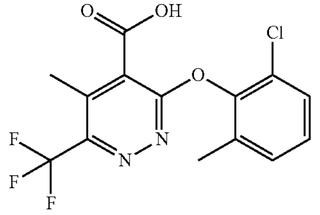 3-(2-Chloro-6-methylphenoxy)-5-methyl-6-(trifluoromethyl)pyridazine-4-carboxylic acid | $^1$H NMR (300 MHz, $CD_3OD$) δ 7.42-7.32 (m, 1H), 7.32-7.17 (m, 2H), 2.57 (q, J = 1.5 Hz, 3H), 2.20 (s, 3H) |

Intermediate 57

4-(cyclobutoxy)-2,3-difluoro-phenol

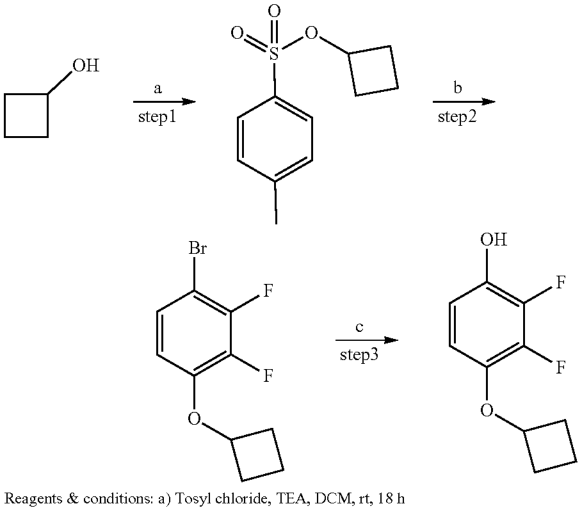

Reagents & conditions: a) Tosyl chloride, TEA, DCM, rt, 18 h
b) 4-bromo-2,3-difluorophenol, $K_2CO_3$, DMF, 90 °C, 4 h
c) KOH, (1{E},4{E})-1,5-diphenylpenta-1,4-dien-3-one; palladium, di-tert-butyl[3,4,5,6-tetramethyl-2,4,6-tri(propan-2-yl)biphenyl-2-yl]phosphane, 1:1 1,4-dioxane/water, 100 °C, 18 h Step 1: cyclobutyl 4-methylbenzenesulfonate: To a solution of cyclobutanol (0.22 mL, 2.77 mmol) in DCM (6 mL) under an atmosphere of nitrogen was added 4-methylbenzenesulfonyl chloride (635 mg, 3.33 mmol) followed by triethylamine (0.46 mL, 3.33 mmol). The mixture was stirred at room temperature for 18 h. The reaction mixture was diluted with water (5 mL) and extracted with DCM (2×5 mL). The organic phases were dried ($MgSO_4$), filtered and concentrated to afford a clear oil. Purification by FCC (Biotage isolera, $SiO_2$ gradient elution, 0 to 20% EtOAc in heptane) afforded cyclobutyl 4-methylbenzenesulfonate (97%) (362 mg, 1.599 mmol, 58%) as a clear oil. m/z: 227.1 $[M+H]^+$, (ESI+), RT=0.91 METCR1704 (2 minute uPLC gradient method for IPCs).

Step 2: 1-bromo-4-(cyclobutoxy)-2,3-difluoro-benzene: To a solution of 4-bromo-2,3-difluorophenol (1.40 g, 6.70 mmol) and cyclobutyl 4-methylbenzenesulfonate (1.82 g, 8.04 mmol) in DMF (10 mL) was added dipotassium; carbonate (1.39 g, 10.0 mmol). The mixture was heated at 90 °C for 4 h. The mixture was allowed to cool to room temperature, then diluted with ethyl acetate (60 mL) and washed with water (3×30 mL) and brine (30 mL). The organics were dried ($MgSO_4$), filtered and concentrated to afford an orange oil. Purification by FCC (Biotage isolera, $SiO_2$ gradient elution, 0 to 10% EtOAc in heptane) afforded 1-bromo-4-(cyclobutoxy)-2,3-difluoro-benzene (76%) (0.983 g, 3.737 mmol, 43%) as a clear oil. LC-MS: m/z 263.2 $[M]^+$, (ESI+), RT=1.10 METCR1704 (2 minute uPLC gradient method for IPCs).

Step 3: 4-(cyclobutoxy)-2,3-difluoro-phenol: A mixture of 1-bromo-4-(cyclobutoxy)-2,3-difluoro-benzene (980 mg, 3.73 mmol) and potassium hydroxide (418 mg, 7.45 mmol) in 1,4-Dioxane (5 mL) and Water (5 mL) was degassed by nitrogen bubbling for 10 min then, di-tert-butyl[3,4,5,6-tetramethyl-2,4 4,6 6 -tri(propan-2-yl)biphenyl-2-yl] phosphane (143 mg, 0.298 mmol) and (1{E},4{E})-1,5-diphenylpenta-1,4-dien-3-one; palladium (68 mg, 0.0745 mmol) were added and the reaction was stirred at 100 C for 18 h. The pH was adjusted to ~3 with 1M HCl, and the mixture extracted with ethyl acetate (3×8 mL). The combined organics were dried (MgSO4), filtered and concentrated to afford a brown oil. Purification by FCC (Biotage isolera, SiO2 gradient elution, 0 to 5% EtOAc) in heptane afforded 4-(cyclobutoxy)-2,3-difluoro-phenol (90%) (622 mg, 3.107 mmol, 75%) as a pale orange solid. LC-MS: m/z 199.1 $[M-H]^-$, (ESI−), RT=0.82 METCR1704 (2 minute uPLC gradient method for IPCs).

Intermediate 58 and Intermediate 59 tert-butyl (S)-((3-aminophenyl)(methyl)(oxo)-$\lambda^6$-sulfaneylidene) carbamate [Intermediate 58] and tert-butyl (R)-((3-aminophenyl)(methyl)(oxo)-$\lambda^6$-sulfaneylidene) carbamate [Intermediate 59]

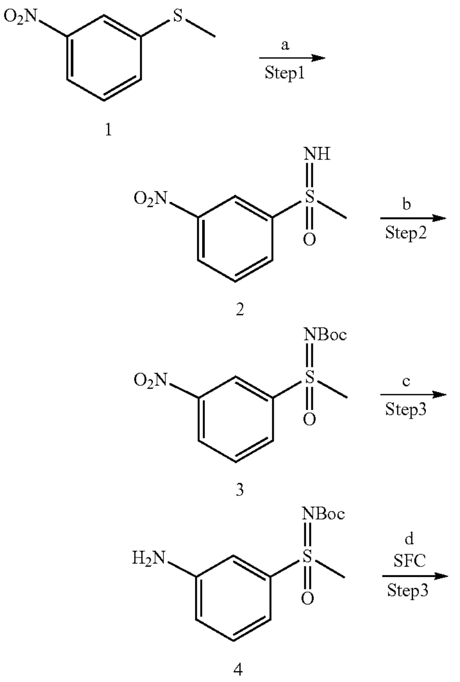

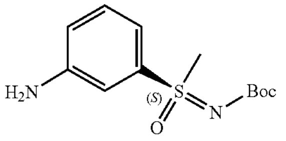

and

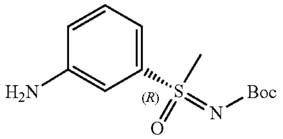

Reagents & conditions: $NH_4(OAc)$, $PhI(OAc)_2$, EtOH, rt, 16 h; b)t-BuOK, $(Boc)_2O$, t-BuOH, reflux, 10 h; c) $Pd(OH)_2$, $H_2$, MeOH, rt, 2 h; d) SFC purification Step 1: imino(methyl)(3-nitrophenyl)-$\lambda^6$-sulfanone: To a mixture of methyl(3-nitrophenyl) sulfane (8.2 g, 48.5 mmol) and ammonium acetate (5.6 g, 72.7 mmol) in EtOH (120 mL) was added $PhI(OAc)_2$ (31.2 g, 97 mmol) in one portion. The reaction mixture was stirred at room temperature under atmosphere for 16 h. The mixture was concentrated directly to give a residue which was purified by silica gel chromatography column (PE:EA=5:1 to 1:3) to afford imino (methyl)(3-nitrophenyl)-$\lambda^6$-sulfanone as a white solid (7.0 g, 72%). MS (ESI+): m/z found 201.03 $[M+H]^+$.

Step 2: tert-butyl (methyl(3-nitrophenyl)(oxo)-$\lambda^6$-sulfaneylidene)carbamate: To a solution of imino(methyl)(3-nitrophenyl)-$\lambda^6$-sulfanone (3.5 g, 17.5 mmol) in t-BuOH (200 mL) cooled with ice water bath was added t-BuOK (3.9 g, 35.0 mmol) under $N_2$ protection. Subsequently, $(Boc)_2O$ (7.6 g, 35.0 mmol) was added slowly and the reaction mixture was then refluxed for 10 h. The reaction mixture was quenched with saturated $NH_4Cl$ solution (200 mL) and extracted with EA (200 mL×2). The combined organic layer was washed with brine, dried over $Na_2SO_4$ and concentrated to give a residue which was purified with silica gel chromatography column (PE:EA=5:1 to 1:1) to afford tert-butyl (methyl(3-nitrophenyl)(oxo)-$\lambda^6$-sulfaneylidene)carbamate as yellow solid (1.8 g, 34%). LC-MS(ESI+): m/z 301.09 $[M+H]^+$.

Step 3: (3-aminophenyl)(imino)(methyl)-$\lambda^6$-sulfanone: To a solution of tert-butyl (methyl(3-nitrophenyl)(oxo)-$\lambda^6$-sulfaneylidene)carbamate (1.8 g, 6 mmol) in MeOH (30 mL) was added $Pd(OH)_2$ (300 mg) and the reaction mixture was stirred at room temperature for 2 h. The reaction mixture was filtered through celite and washed with MeOH (100 mL). The filtrate was concentrated to give a residue which was re-dissolved in EA (30 mL) and the resulting solution was filtered through celite again and washed with EA (100 mL). The filtrate was concentrated to give tert-butyl ((3-aminophenyl)(methyl)(oxo)-$\lambda^6$-sulfaneylidene) carbamate (1.4 g, 86%) as off-white solid. MS (ESI+): m/z found 271.10 $[M+H]^+$.

Step 4: SFC separation: The racemic product was separated by chiral HPLC with the Chiral separation condition: Column: Daicel CHIRALPAK IG, 250 mm×20 mm I.D., 5 μm; Mobile Phase A: $CO_2$/MeOH [0.2% $NH_3$ (7M Solution in MeOH)]=70/30; Flow rate: 60 g/min; 214 nm. Temperature: 35 °C. The first eluting isomer tert-butyl (S)-((3-aminophenyl)(methyl)(oxo)-$\lambda^6$-sulfaneylidene) carbamate [Intermediate 58]. $^1H$ NMR (DMSO-$d_6$) δ7.26 (t, 1H), 7.08 (s, 1H), 6.97 (d, 1H), 6.83 (d, 1H), 5.71 (s, 2H), 3.28 (s, 3H), 1.27 (s. 9H) and the second eluting isomer tert-butyl (R)-((3-aminophenyl)(methyl)(oxo)-$\lambda^6$-sulfaneylidene) carbamate [Intermediate 59]. $^1H$ NMR (DMSO-$d_6$) δ7.26 (t, 1H), 7.08 (s, 1H), 6.97 (d, 1H), 6.83 (d, 1H), 5.71 (s, 2H), 3.28 (s, 3H), 1.27 (s. 9H).

Example 7

Compound 1: 3-(4-Fluoro-2-methylphenoxy)-5-methyl-N-(3-(methylsulfonyl)phenyl)-6-(trifluoromethyl)pyridazine-4-carboxamide

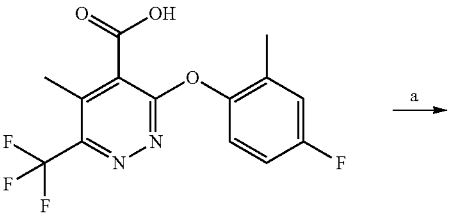

-continued

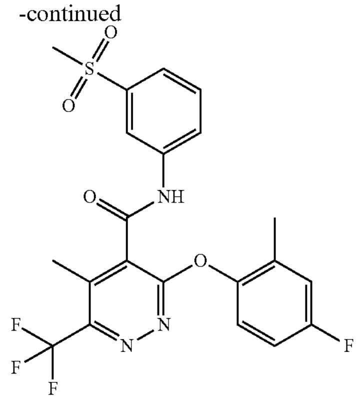

Reagents & conditions: a) 3-(methylsulfonyl)aniline, 50% Propylphosphonic anhydride solution in EtOAc, N,N-diisopropylethylamine(DIEA), DCM, rt.

A mixture of N,N-diisopropylethylamine(DIEA) (0.16 mL, 0.908 mmol), 3-(4-fluoro-2-methylphenoxy)-5-methyl-6-(trifluoromethyl)pyridazine-4-carboxylic acid (0.100 g, 0.303 mmol) and 3-(methylsulfonyl)aniline (0.062 g, 0.363 mmol) were dissolved in DCM (4.8 mL) under nitrogen at rt. To the above mixture 50% Propylphosphonic anhydride solution in EtOAc (50%, 0.36 mL, 0.606 mmol) was added in one portion. The reaction mixture was stirred at rt for 4 h. The reaction was then stirred at 55 °C for 16 h. The reaction mixture was cooled to room temperature and the solvent was removed in vacuo to obtain the crude residue. Purification by Prep LC Method P1 to afford the title compound (0.025 g, 17%) as a white solid. $^1$H NMR (500 MHz, DMSO-$d_6$) δ 11.39 (s, 1H), 8.38 (t, J=1.8 Hz, 1H), 7.90 (ddd, J=7.9, 2.0, 1.2 Hz, 1H), 7.78-7.73 (m, 1H), 7.70 (t, J=7.9 Hz, 1H), 7.29 (dd, J=8.9, 5.0 Hz, 1H), 7.24 (dd, J=9.4, 3.1 Hz, 1H), 7.14 (td, J=8.5, 3.1 Hz, 1H), 3.24 (s, 3H), 2.54-2.51 (m, 3H), 2.12 (s, 3H). LC-MS: m/z 484.0 [M+H]$^+$, (ESI+), RT=4.24 LCMS Method 5.

Example 8

Compound 2: 5-Methyl-N-(3-methylsulfonylphenyl)-3-[2-methyl-4-(trifluoromethyl)phenoxy]-6-(trifluoromethyl)pyridazine-4-carboxamide

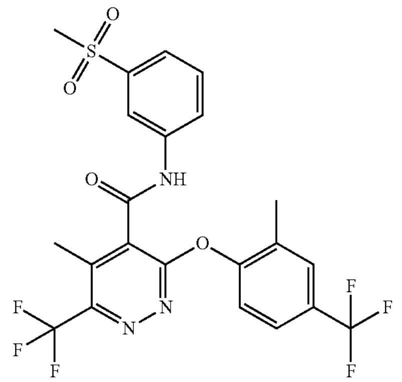 [SMILES: Cc1cc(C(F)(F)F)ccc1Oc1nnc(C(F)(F)F)c(C)c1C(=O)Nc1cccc(S(C)(=O)=O)c1]

The title compound was prepared by a similar method as described for compound 1 using 5-methyl-3-(2-methyl-4-(trifluoromethyl)phenoxy)-6-(trifluoromethyl)pyridazine-4-carboxylic acid and 3-(methylsulfonyl)aniline. $^1$H NMR (400 MHz, DMSO-$d_6$) δ 11.42 (s, 1H), 8.37 (t, J=1.8 Hz, 1H), 7.93-7.87 (m, 1H), 7.80-7.66 (m, 4H), 7.51 (d, J=8.4 Hz, 1H), 3.24 (s, 3H), 2.56-2.53 (m, 3H), 2.21 (s, 3H). m/z: 534.1 [M+H]$^+$, (ESI+), RT=3.81 LCMS Method 4

Example 9

Compound 3: 5-Methyl-3-(2-methyl-4-(trifluoromethoxy)phenoxy)-N-(3-(methylsulfonyl)phenyl)-6-(trifluoromethyl)pyridazine-4-carboxamide

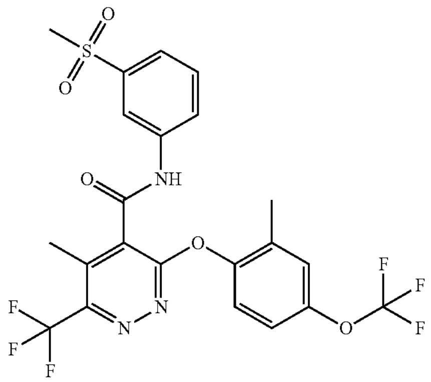 [SMILES: Cc1cc(OC(F)(F)F)ccc1Oc1nnc(C(F)(F)F)c(C)c1C(=O)Nc1cccc(S(C)(=O)=O)c1]

A mixture of 3-(methyl sulfonyl)aniline (41 mg, 0.242 mmol), using 5-methyl-3-(2-methyl-4-(methyl-4-(trifluoromethoxy)phenoxy)-6-(trifluoromethyl)pyridazine-4-carboxylic acid (85 mg, 0.202 mmol) were dissolved in DMF (0.5085 mL) under nitrogen at rt. Then N-ethyl-N-isopropyl-propan-2-amine (0.070 mL, 0.403 mmol) was added followed by N-[(dimethylamino)(3H-[1,2,3]triazolo[4,5-b]pyridin-3-yloxy)methylidene]-N-methylmethanaminium hexafluorophosphate (77 mg, 0.202 mmol). The reaction mixture was stirred at rt for 1 h. The reaction was diluted with brine (10 mL) extracted with EtOAc (2×10 mL). Organics washed with 1M HCl (10 mL), dried over $MgSO_4$, filtered, concentrated under reduced pressure to obtain the crude residue, which was purified using preparative method Prep1 to afford the 5-methyl-3-(2-methyl-4-(trifluoromethoxy)phenoxy)-N-(3-(methylsulfonyl)phenyl)-6-(trifluoromethyl)pyridazine-4-carboxamide (51 mg, 46%) as an off white solid. $^1$H NMR (500 MHz, $CD_3OD$) δ 8.41 (t, J=1.9 Hz, 1H), 7.97 (ddd, J=8.1, 2.1, 1.1 Hz, 1H), 7.79 (ddd, J=7.8, 1.7, 1.0 Hz, 1H), 7.68 (t, J=8.0 Hz, 1H), 7.32 (d, J=8.9 Hz, 1H), 7.29-7.25 (m, 1H), 7.21 (dd, J=8.8, 2.7 Hz, 1H), 3.15 (s, 3H), 2.62-2.57 (m, 3H), 2.21 (s, 3H). m/z: 550.5 [M+H]$^+$, (ESI+), RT=4.50 LCMS Method 5.

Example 10

Compound 4: 3-(4-Cyano-2-methoxyphenoxy)-5-methyl-N-(3-(methylsulfonyl)phenyl)-6-(trifluoromethyl)pyridazine-4-carboxamide

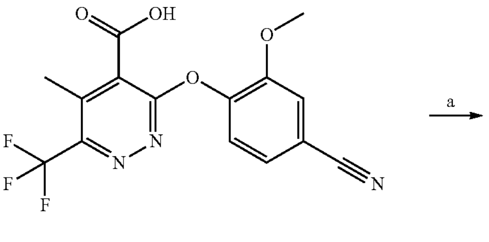

-continued

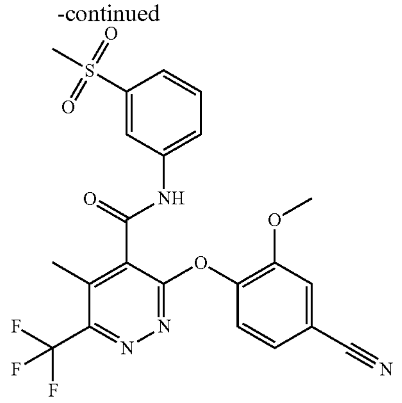

To a mixture of 3-(4-cyano-2-methoxyphenoxy)-5-methyl-6-(trifluoromethyl)pyridazine-4-carboxylic acid (0.060, 0.170 mmol), 3-methanesulfonylaniline (0.029 g, 0.170 mmol), HATU (0.097 g, 0.255 mmol) in DMF (3 mL) was added DIEA (0.089 mL, 0.510 mmol) at 25 °C and stirring continue for further 16 h at 25 °C. The reaction mixture was diluted with water (5 mL) and extracted with EtOAc (2x30 mL). The combined EtOAc layer was washed with 1M LiCl (10 mL) followed by brine (20 mL). The EtOAc layer was dried over $Na_2SO_4$, filtered and the solvent evaporated. The crude product was chromatographed over $SiO_2$ with a gradient of 0 to 10% EtOAc in DCM to afford 3-(4-cyano-2-methoxyphenoxy)-N-(3-methanesulfonylphenyl)-5-methyl-6-(trifluoromethyl)pyridazine-4-carboxamide (0.028 g, 33%). $^1H$ NMR (300 MHz, $CDCl_3$) δ 8.52 (s, 1H), 8.15-7.97 (m, 2H), 7.77 (dt, J=7.9, 1.3 Hz, 1H), 7.63 (t, J=8.0 Hz, H), 7.41 (d, J=1.5 Hz, 2H), 7.30 (s, 1H), 3.89 (s, 3H), 3.09 (s, 3H), 2.67 (q, J=1.5 Hz, 3H). LC-MS: m/z 505.3 $[M-H]^+$ The compounds 5-7 listed in Table 6 were prepared by a similar procedure as described for compound 4.

TABLE 6

| Compound | Structure & Name | Analytical data |
| --- | --- | --- |
| 5 | 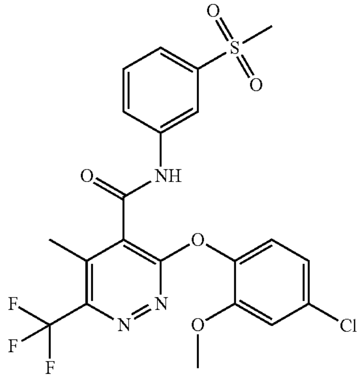<br>3-(4-Chloro-2-methoxyphenoxy)-5-methyl-N-(3-(methylsulfonyl)phenyl)-6-(trifluoromethyl)pyridazine-4-carboxamide | $^1H$ NMR (300 MHz, DMSO-$d_6$) δ 11.37 (s, 1H), 8.39 (t, J = 1.8 Hz, 1H), 7.91 (dt, J = 7.7, 1.8 Hz, 1H), 7.81-7.64 (m, 2H), 7.39-7.29 (m, 2H), 7.11 (dd, J = 8.5, 2.3 Hz, 1H), 3.76 (s, 3H), 3.25 (s, 3H), 2.53(s, 3H). Methyl peak at 2.53 peak buried under residual DMSO solvent. LC-MS: m/z 516.3 $[M + H]^+$ |
| 6 | 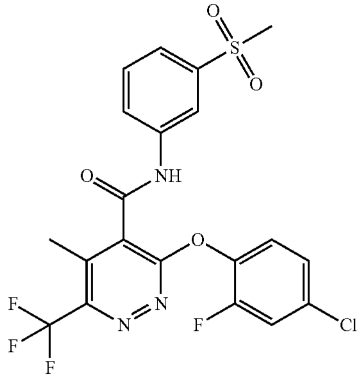<br>3-(4-Chloro-2-fluorophenoxy)-5-methyl-N-(3-(methylsulfonyl)phenyl)-6-(trifluoromethyl)pyridazine-4-carboxamide | $^1H$ NMR (300 MHz, $CDCl_3$) δ 8.79 (s, 1H), 8.26 (ddd, J = 8.0, 2.3, 1.2 Hz, 1H), 8.00 (t, J = 1.9 Hz, 1H), 7.75-7.57 (m, 2H), 7.24 (dd, J = 2.6, 1.7 Hz, 1H), 7.21-7.15 (m, 2H), 3.02 (s, 3H), 2.59 (q, J = 1.5 Hz, 3H). LC-MS: m/z 504.2$[M + H]^+$ |

TABLE 6-continued

| Compound | Structure & Name | Analytical data |
| --- | --- | --- |
| 7 | 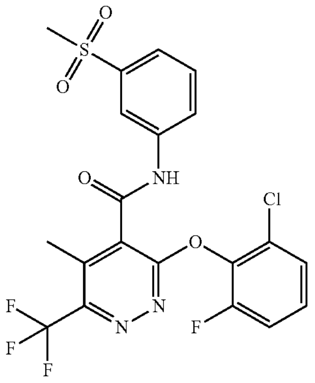 3-(2-Chloro-6-methylphenoxy)-5-methyl-N-(3-(methylsulfonyl)phenyl)-6-(trifluoromethyl)pyridazine-4-carboxamide | LC-MS: m/z 500.3 $[M + H]^+$ |

Example 11

Compound 8: 3-(4-Fluoro-2-methylphenoxy)-5-methyl-N-(3-(methylthio)phenyl)-6-(trifluoromethyl)pyridazine-4-carboxamide

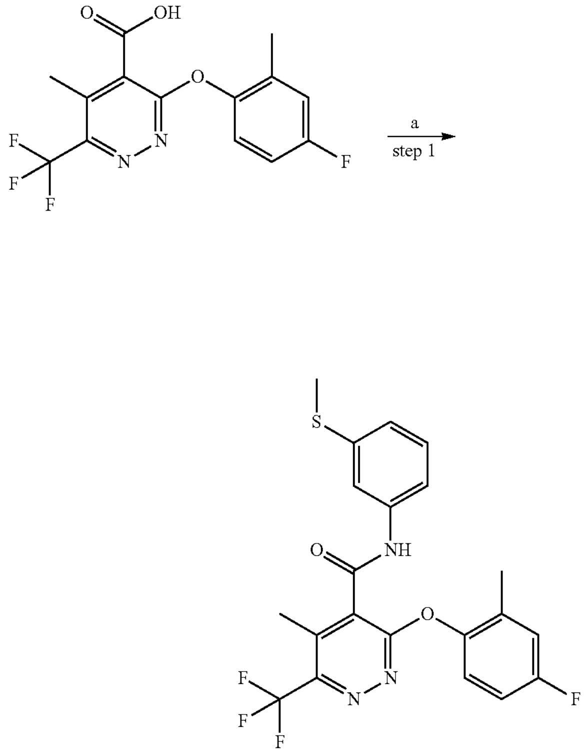

Reagents & conditions: DIEA, propylphosphonic anhydride solution in EtOAc (50%; v/v), DMAP, 3-(methylsulfanyl)aniline, DCM, 55 °C, 16 h.

To a mixture of 3-(4-fluoro-2-methylphenoxy)-5-methyl-6-(trifluoromethyl)pyridazine-4-carboxylic acid (100 mg, 0.303 mmol) in DCM (1.9151 mL) at RT, N-ethyl-N-isopropyl-propan-2-amine (0.12 mL, 0.666 mmol) and N,N-dimethylpyridin-4-amine (7.4 mg, 0.0606 mmol) were added followed by 5000 Propylphosphonic anhydride solution in EtOAc (500%, 0.36 mL, 0.606 mmol) the mixture was stirred at me for 15 min. 3-(methylsulfanyl)aniline (51 mg, 0.363 mmol) was added to the reaction. The reaction mixture was stirred at rt for 10 min and then at 55 °C for 16 h. The volatiles were removed in vacuo. Purification by chromatography on silica eluting with a gradient of 0 to 100% EtOAc in heptane followed by 0-60% MeOH in EtOAC afforded 3-(4-fluoro-2-methylphenoxy)-5-methyl-N-(3-(methylthio)phenyl)-6-(trifluoromethyl)pyridazine-4-carboxamide (43.00) (110 mg, 350) as a yellow solid. LC-MS: m/z 452.6 $[M+H]^+$, (ESI+), RT=4.81 LCMS Method 5.

The compounds 9-13 listed in Table 7 were prepared by a similar procedure as described for compound 8.

TABLE 7

| Compound | Structure and name | Analytical data |
|---|---|---|
| 9 | 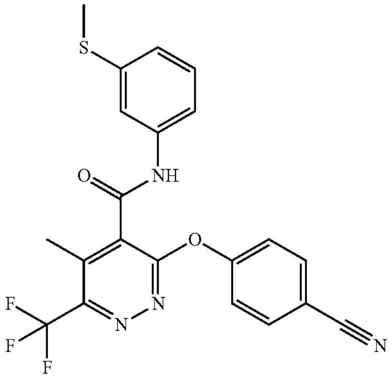 3-(4-Cyanophenoxy)-5-methyl-N-(3-(methylthio) phenyl)-6-(trifluoromethyl)pyridazine-4-carboxamide | $^1$H NMR (500 MHz, DMSO-$d_6$) δ 10.97 (s, 1H), 8.01-7.95 (m, 2H), 7.63-7.58 (m, 1H), 7.56-7.49 (m, 2H), 7.39 (ddd, J = 8.1, 1.9, 0.9 Hz, 1H), 7.32 (t, J = 7.9 Hz, 1H), 7.06 (ddd, J = 7.8, 1.7, 0.9 Hz, 1H), 2.51-2.50 (m, 3H), 2.46 (s, 3H). LC-MS: m/z 445.05 $[M + H]^+$, (ESI+), RT = 1.33 LCMS Method 1 |
| 10 | 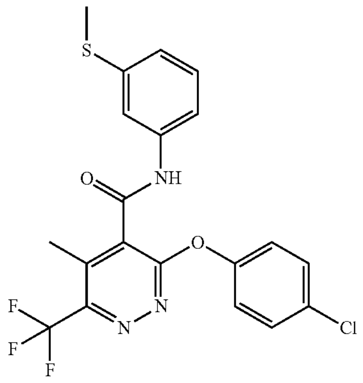 3-(4-Chlorophenoxy)-5-methyl-N-(3-(methylthio) phenyl)-6-(trifluoromethyl)pyridazine-4-carboxamide | LC-MS: m/z 453.95 $[M + H]^+$, (ESI+), RT = 1.41 LCMS Method 1 |

TABLE 7-continued

| Compound | Structure and name | Analytical data |
|---|---|---|
| 11 | 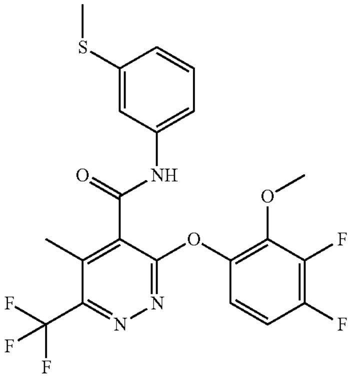 3-(3,4-Difluoro-2-methoxyphenoxy)-5-methyl-N-(3-(methylthio)phenyl)-6-(trifluoromethyl)pyridazine-4-carboxamide | $^{1}H$ NMR (500 MHz, DMSO-$d_6$) δ 11.00 (s, 1H), 7.43-7.39 (m, 1H), 7.34 (t, J = 7.9 Hz, 1H), 7.29 (dd, J = 8.9, 5.0 Hz, 1H), 7.24 (dd, J = 9.4, 3.0 Hz, 1H), 7.14 (td, J = 8.5, 3.2 Hz, 1H), 7.09-7.06 (m, 1H), 2.89 (s, 3H), 2.73 (s, 3H), 2.48 (s, 3H). LC-MS: m/z 486.5 $[M + H]^+$, (ESI+), RT = 4.75 LCMS Method 5 |
| 12 | 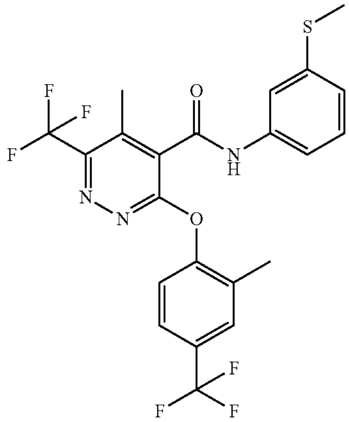 5-Methyl-N-(3-methylsulfanylphenyl)-3-[2-methyl-4-(trifluoromethyl)phenoxy]-6-(trifluoromethyl)pyridazine-4-carboxamide | $^{1}H$ NMR (400 MHz, DMSO-$d_6$) δ 11.02 (s, 1H), 7.79 (d, J = 2.0 Hz, 1H), 7.70 (dd, J = 8.5, 2.2 Hz, 1H), 7.65 (t, J = 1.8 Hz, 1H), 7.50 (d, J = 8.4 Hz, 1H), 7.41 (ddd, J = 8.1, 1.9, 1.1 Hz, 1H), 7.34 (t, J = 7.9 Hz, 1H), 7.08 (ddd, J = 7.8, 1.8, 1.1 Hz, 1H), 2.53-2.51 (m, 3H), 2.48 (s, 3H), 2.21 (s, 3H). LC-MS: m/z 502.0 $[M + H]^+$, (ESI+), RT = 1.47 LCMS Method 1 |
| 13 | 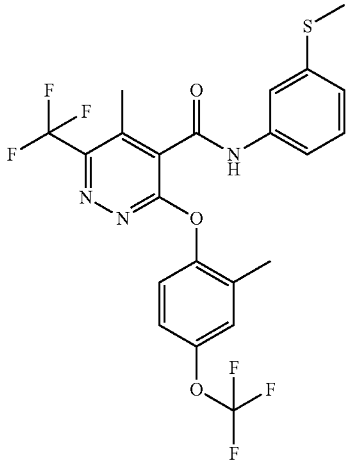 5-Methyl-N-(3-methylsulfanylphenyl)-3-[2-methyl-4-(trifluoromethoxy)phenoxy]-6-(trifluoromethyl)pyridazine-4-carboxamide | $^{1}H$ NMR (400 MHz, DMSO-$d_6$) δ 11.00 (s, 1H), 7.65 (t, J = 1.8 Hz, 1H), 7.41 (d, J = 5.3 Hz, 2H), 7.37 (d, J = 9.5 Hz, 1H), 7.33 (d, J = 7.9 Hz, 2H), 7.08 (d, J = 7.8 Hz, 1H), 2.51 (s, 3H), 2.48 (s, 3H), 2.16 (s, 3H). LC-MS: m/z 517.9 $[M + H]^+$, (ESI+), RT = 1.14 LCMS Method 1 |

Example 12

Compound 14: 3-(4-Cyano-2-methylphenoxy)-5-methyl-N-[3-(methylsulfanyl)phenyl]-6-(trifluoromethyl)pyridazine-4-carboxamide

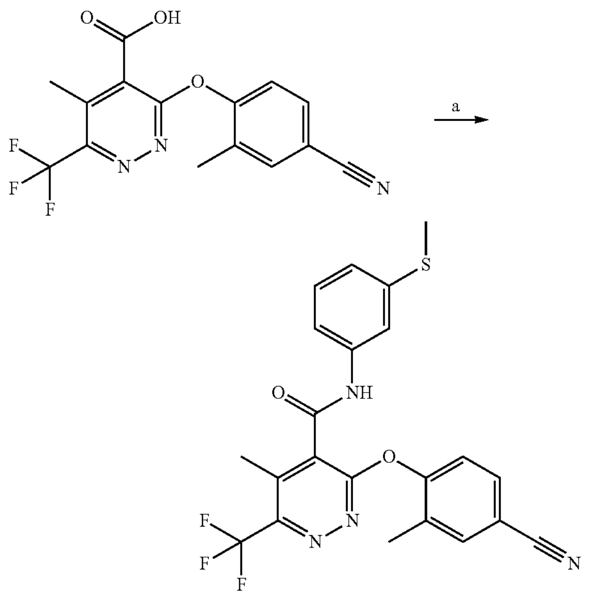

Reagents & conditions: HATU, 3-(methyl sulfanyl)aniline, DIEA, DMVF, rt, 16 h.

To a mixture of 3-(4-cyano-2-methylphenoxy)-5-methyl-6-(trifluoromethyl)pyridazine-4-carboxylic acid (0.300 g, 0.890 mmol), 3-(methylsulfanyl)aniline (0.124 g, 0.890 mmol) and HATU (0.676 g, 1.78 mmol) in DMF (10 mL) was added DIEA (0.0345 g, 2.67 mmol) at rt. The resulting mixture was stirred further for 16 h, at the end of this period water (10 mL) was added and extracted with EtOAc (2×40 mL). The combined EtOAc layer was washed with 1M LiCl (20 mL) followed by brine (30 mL). The EtOAc layer was dried over $Na_2SO_4$, filtered and the solvent evaporated. The crude material was chromatographed over $SiO_2$ with a gradient of 0-50% EtOAc in hexane to afford 3-(4-cyano-2-methylphenoxy)-5-methyl-N-[3-(methylsulfanyl)phenyl]-6-(trifluoromethyl)pyridazine-4-carboxamide (0.165 g, 40.46%). $^1H$ NMR (300 MHz, CDCl3) δ 7.72-7.49 (m, 3H), 7.37-7.21 (m, 4H), 7.19-7.06 (m, 1H), 2.63 (q, J=1.5 Hz, 3H), 2.52 (s, 3H), 2.23 (s, 3H). LC-MS: m/z 457.3[M−H]$^+$.

The compounds 15-19 listed in Table 8 were prepared by a similar procedure as described for compound 14.

TABLE 8

| Compound | Structure and name | Analytical data |
|---|---|---|
| 15 | 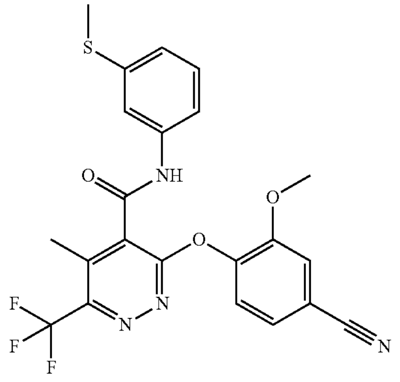 3-(4-Cyano-2-methoxyphenoxy)-5-methyl-N-(3-(methylthio)phenyl)-6-(trifluoromethyl)pyridazine-4-carboxamide | $^1H$ NMR (300 MHz, $CDCl_3$) δ 8.07 (s, 1H), 7.62 (q, J = 1.5 Hz, 1H), 7.39 (d, J = 1.4 Hz, 2H), 7.32-7.24 (m, 4H), 7.09 (ddd, J = 6.4, 2.8, 1.8 Hz, 1H), 3.85 (s, 3H), 2.66 (q, J = 1.5 Hz, 3H), 2.51 (s, 3H). |

TABLE 8-continued

| Compound | Structure and name | Analytical data |
| --- | --- | --- |
| 16 | 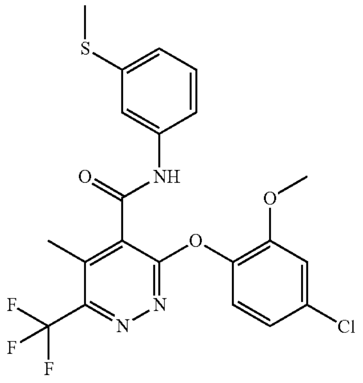 3-(4-Chloro-2-methoxyphenoxy)-5-methyl-N-(3-(methylthio)phenyl)-6-(trifluoromethyl)pyridazine-4-carboxamide | $^1$H NMR (300 MHz, $CDCl_3$) δ 8.20 (s, 1H), 7.63 (q, J = 1.5 Hz, 1H), 7.31-7.27 (m, 2H), 7.26-7.21 (m, 1H), 7.12-6.99 (m, 3H), 3.83 (s, 3H), 2.66(q, J = 1.5 Hz, 3H), 2.51 (s, 3H). |
| 17 | 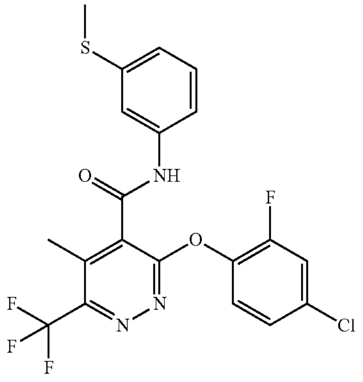 3-(4-Chloro-2-fluorophenoxy)-5-methyl-N-(3-(methylthio)phenyl)-6-(trifluoromethyl)pyridazine-4-carboxamide | $^1$H NMR (300 MHz, $CDCl_3$) δ 7.73-7.57 (m, 2H), 7.39-7.18 (m, 6H), 7.11 (dt, J = 6.3, 1.9 Hz, 1H), 2.63 (q, J = 1.5 Hz, 3H), 2.52 (s, 3H). |
| 18 | 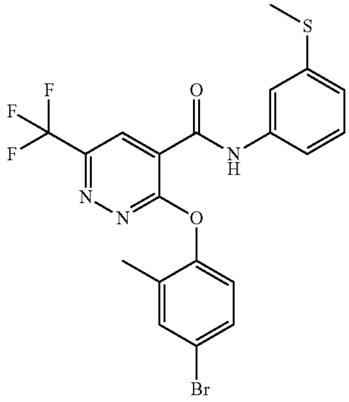 3-(4-Bromo-2-methylphenoxy)-N-(3-(methylthio)phenyl)-6-(trifluoromethyl)pyridazine-4-carboxamide | $^1$H NMR (300 MHz, DMSO-$d_6$) δ 10.90 (s, 1H), 8.66 (s, 1H), 7.65 (dt, J = 12.5, 2.0 Hz, 2H), 7.56-7.22 (m, 4H), 7.07 (dt, J = 7.9, 1.5 Hz, 1H), 2.49 (s, 3H), 2.13 (s, 3H) |

TABLE 8-continued

| Compound | Structure and name | Analytical data |
| --- | --- | --- |
| 19 | 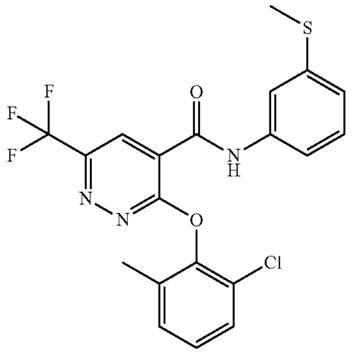 3-(2-Chloro-6-methylphenoxy)-N-(3-(methylthio)phenyl)-6-(trifluoromethyl)pyridazine-4-carboxamide | $^1$H NMR (300 MHz, $CDCl_3$) δ 7.99 (s, 1H), 7.67 (t, J = 2.0 Hz, 1H), 7.38-7.28 (m, 3H), 7.23-7.13 (m, 2H), 7.10 (dt, J = 7.3, 1.7 Hz, 1H), 2.67 (q, J = 1.5 Hz, 3H), 2.52 (s, 3H), 2.24 (s, 3H). |

Example 13

Compound 20: 3-(4-Fluoro-2-methylphenoxy)-5-methyl-N-(3-(S-methylsulfonimidoyl)phenyl)-6-(trifluoromethyl)pyridazine-4-carboxamide

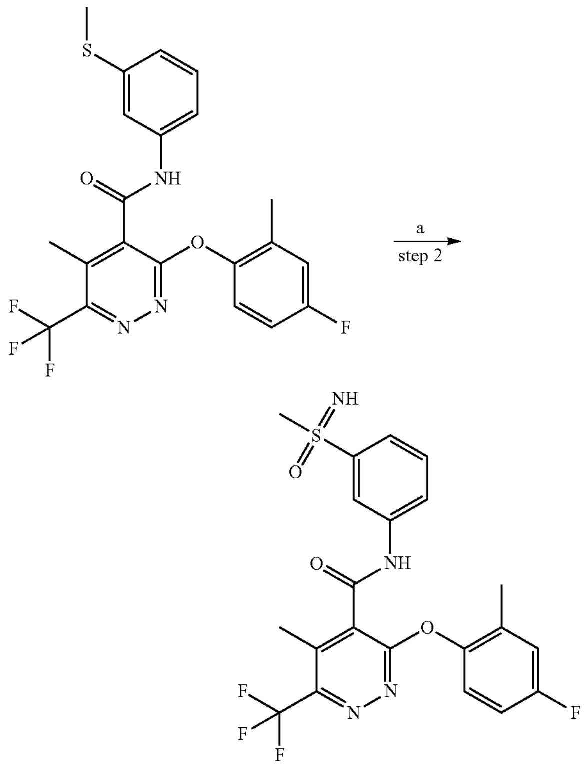

Reagents & conditions: a) ammonium carbonate, (diacetoxyiodo)benzene, MeOH, rt, 24 h To a solution of 3-(4-fluoro-2-methylphenoxy)-5-methyl-N-(3-(methylthio)phenyl)-6-(trifluoromethyl)pyridazine-4-carboxamide (43%) (0.090 g, 0.0857 mmol) was dissolved in Methanol (0.3518 mL) and treated with ammonium carbonate (0.012 g, 0.13 mmol) and (diacetoxyiodo)benzene (0.064 mg, 0.197 mmol), each added in one portion. The resulting mixture was stirred at rt for 24 h. The solvent was removed in vacuo. Purification by chromatography afforded the title compound (0.032 g, 75%) as a light brown solid. $^1$H NMR (400 MHz, DMSO-$d_6$) δ 11.35 (s, 1H), 8.36 (t, J=1.9 Hz, 1H), 7.90-7.84 (m, 1H), 7.76-7.71 (m, 1H), 7.64 (t, J=7.9 Hz, 1H), 7.29 (dd, J=8.9, 5.0 Hz, 1H), 7.24 (dd, J=9.3, 3.0 Hz, 1H), 7.14 (td, J=8.5, 3.1 Hz, 1H), 4.25 (s, 1H), 3.07 (s, 3H), 2.52 (s, 3H), 2.12 (s, 3H). LC-MS: m/z 482.9 $[M+H]^+$, (ESI+), RT=3.83 LCMS Method 5.

The compounds 21-29 listed in Table 9 were prepared by a similar procedure as described for compound 20.

TABLE 9

| Compound | Structure & name | Analytical data |
|---|---|---|
| 21 | 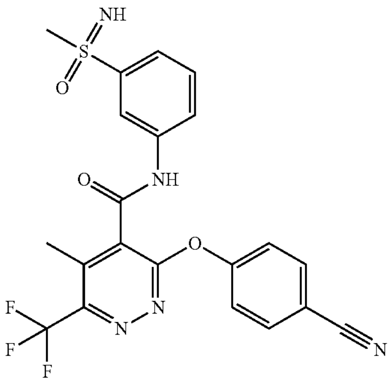 3-(4-Cyanophenoxy)-5-methyl-N-[3-(methylsulfonimidoyl)phenyl]-6-(trifluoromethyl)pyridazine-4-carboxamide | $^1$H NMR (500 MHz, DMSO-$d_6$) δ 11.32 (s, 1H), 8.33 (t, J = 1.9 Hz, 1H), 8.03-7.97 (m, 2H), 7.87 (ddd, J = 8.1, 2.1, 1.0 Hz, 1H), 7.76-7.70 (m, 1H), 7.68-7.60 (m, 1H), 7.57-7.50 (m, 2H), 4.26 (s, 1H), 3.07 (d, J = 0.8 Hz, 3H), 2.54-2.53 (m, 3H). m/z: 475.9 $[M + H]^+$, (ESI+), RT = 3.58 LCMS Method 5 |
| 22 | 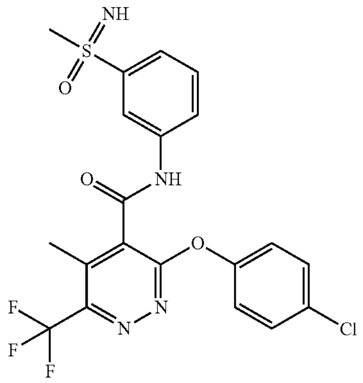 3-(4-Chlorophenoxy)-5-methyl-N-[3-(methylsulfonimidoyl)phenyl]-6-(trifluoromethyl)pyridazine-4-carboxamide | $^1$H NMR (500 MHz, DMSO-$d_6$) δ 11.34 (s, 1H), 8.35 (t, J = 1.8 Hz, 1H), 7.93-7.85 (m, 1H), 7.76-7.70 (m, 1H), 7.63 (t, J = 7.9 Hz, 1H), 7.59-7.52 (m, 2H), 7.41-7.30 (m, 2H), 4.26 (s, 1H), 3.07 (s, 3H), 2.52-2.51 (m, 3H). m/z: 484.9 $[M + H]^+$, (ESI+), RT = 3.89 LCMS Method 5 |

TABLE 9-continued

| Compound | Structure & name | Analytical data |
|---|---|---|
| 23 | 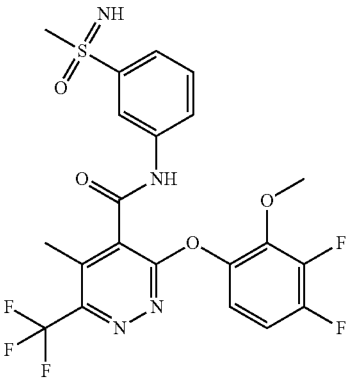 3-(3,4-Difluoro-2-methoxy-phenoxy)-5-methyl-N-[3-(methylsulfonimidoyl)phenyl]-6-(trifluoromethyl)pyridazine-4-carboxamide | $^1$H NMR (500 MHz, DMSO-$d_6$) δ 11.34 (s, 1H), 8.36 (t, J = 1.9 Hz, 1H), 7.88 (ddd, J = 8.1, 2.1, 1.0 Hz, 1H), 7.75-7.71 (m, 1H), 7.64 (t, J = 7.9 Hz, 1H), 7.33-7.26 (m, 1H), 7.24 (ddd, J = 9.3, 5.2, 1.8 Hz, 1H), 4.27 (s, 1H), 3.81 (d, J = 1.1 Hz, 3H), 3.07 (d, J = 0.8 Hz, 3H), 2.54-2.51 (m, 3H). m/z: 516.9 $[M + H]^+$, (ESI+), RT = 3.85 LCMS Method 5 |
| 24 | 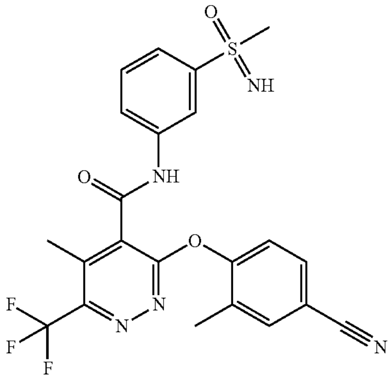 3-(4-Cyano-2-methylphenoxy)-5-methyl-N-(3-(S-(methylsulfonimidoyl)phenyl)-6-(trifluoromethyl)pyridazine-4-carboxamide | $^1$H NMR (300 MHz, DMSO-$d_6$) δ 11.34 (s, 1H), 8.35 (t, J = 1.9 Hz, 1H), 7.97-7.79 (m, 3H), 7.75 (dt, J = 8.0, 1.3 Hz, 1H), 7.65 (t, J = 7.9 Hz, 1H), 7.51 (d, J = 8.4 Hz, 1H), 4.28 (d, J = 1.3 Hz, 1H), 3.08 (d, J = 1.1 Hz, 3H), 2.54 (d, J = 1.7 Hz, 3H), 2.18 (s, 3H). LC-MS: m/z 488.2$[M + H]^+$ |
| 25 | 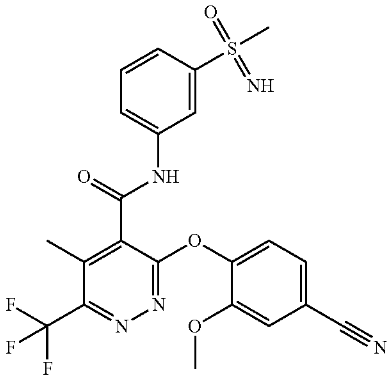 3-(4-Cyano-2-methoxyphenoxy)-5-methyl-N-(3-(S-methylsulfonimidoyl)phenyl)-6-(trifluoromethyl)pyridazine-4-carboxamide | $^1$H NMR (300 MHz, DMSO-$d_6$) δ 11.32 (s, 1H), 8.36 (t, J = 1.9 Hz, 1H), 7.88 (ddd, J = 8.0, 2.2, 1.2 Hz, 1H), 7.74 (dd, J = 8.8, 1.7 Hz, 2H), 7.70-7.48(m, 3H), 4.28 (d, J = 1.4 Hz, 1H), 3.80 (s, 3H), 3.08 (d, J = 1.1 Hz, 3H), 2.51(s, 3H). LC-MS: m/z 504.2 $[M - H]^+$ |

TABLE 9-continued

| Compound | Structure & name | Analytical data |
|---|---|---|
| 26 | 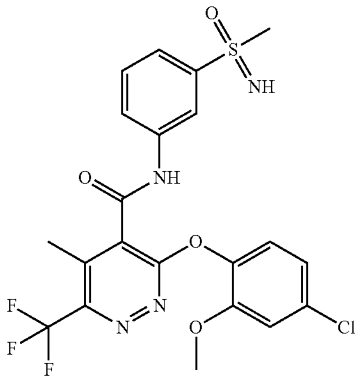 3-(4-Chloro-2-methoxyphenoxy)-5-methyl-N-(3-(S-methylsulfonimidoyl)phenyl)-6-(trifluoromethyl)pyridazine-4-carboxamide | $^1H$ NMR (300 MHz, DMSO-$d_6$) δ 11.30 (s, 1H), 8.37 (t, J = 1.9 Hz, 1H), 7.88 (dd, J = 8.2, 1.7 Hz, 1H), 7.78-7.58 (m, 2H), 7.32 (dd, J = 5.5, 3.1 Hz, 2H), 7.11 (dd, J = 8.5, 2.3 Hz, 1H), 4.32-4.19 (m, 1H), 3.76 (s, 3H), 3.08 (d, J = 1.1 Hz, 3H). A peak at 2.51 is buried under DMSO residual solvent peak. LC-MS: m/z 515.4[M + H]$^+$ |
| 27 | 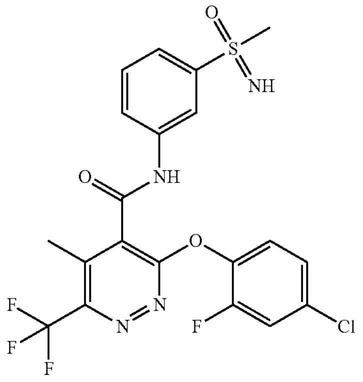 3-(4-Chloro-2-fluorophenoxy)-5-methyl-N-(3-(S-methylsulfonimidoyl)phenyl)-6-(trifluoromethyl)pyridazine-4-carboxamide | $^1H$ NMR (300 MHz, DMSO-$d_6$) δ 11.37 (s, 1H), 8.36 (t, J = 1.9 Hz, 1H), 7.89 (ddd, J = 8.0, 2.2, 1.2 Hz, 1H), 7.80-7.70 (m, 2H), 7.70-7.49 (m, 2H), 7.44 (ddd, J = 8.8, 2.5, 1.2 Hz, 1H), 4.29 (s, 1H), 3.08 (d, J = 1.1 Hz, 3H), 2.54 (d, J = 1.3 Hz, 3H). LC-MS: 503.3 [M + H]$^+$ |
| 28 | 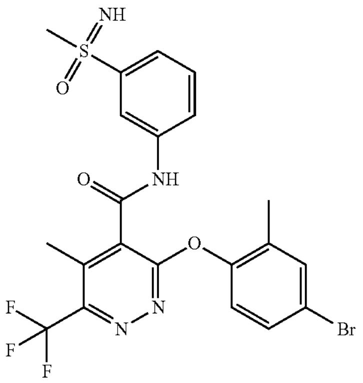 3-(4-Bromo-2-methylphenoxy)-5-methyl-N-(3-(S-methylsulfonimidoyl)phenyl)-6-(trifluoromethyl)pyridazine-4-carboxamide | LC-MS: m/z 543.4, 545.3[M + H]$^+$ |

TABLE 9-continued

| Compound | Structure & name | Analytical data |
|---|---|---|
| 29 | 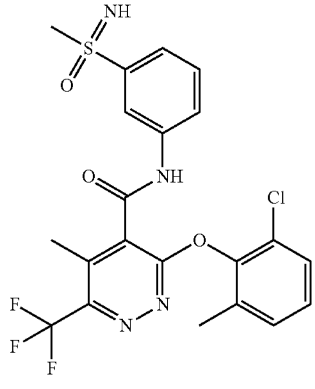 3-(2-Chloro-6-methylphenoxy)-5-methyl-N-(3-(S-methylsulfonimidoyl)phenyl)-6-(trifluoromethyl)pyridazine-4-carboxamide | LC-MS: m/z 499.4[M + H]$^+$ |

Example 14

Compounds 30 and 31: 3-(4-Fluoro-2-methylphenoxy)-5-methyl-N-(3-(S-methylsulfonimidoyl)phenyl)-6-(trifluoromethyl)pyridazine-4-carboxamide Chiral Separation

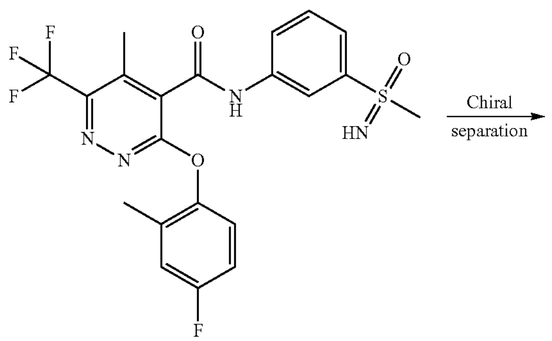

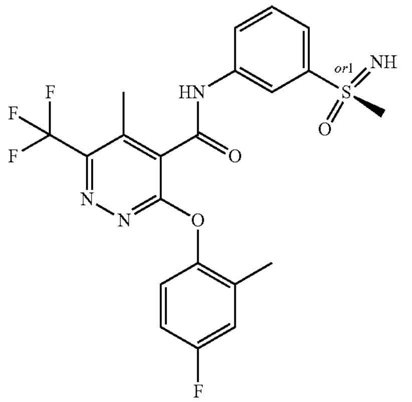

and

-continued

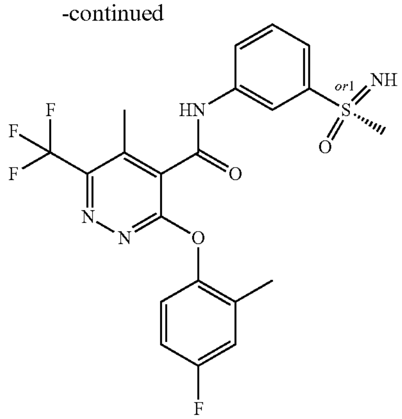

The chiral purification of 3-(4-fluoro-2-methylphenoxy)-5-methyl-N-(3-(S-methylsulfonimidoyl)phenyl)-6-(trifluoromethyl)pyridazine-4-carboxamide (compound 20) was performed using preparative chiral HPLC on a Chiralpak AD-H, (20×250 m) 5 μm eluting with a mixture of Heptane: Ethanol (70:30), flow rate 18 mL/min. Fractions containing product were evaporated and isolated as sticky oils, these were re-dissolved in 1:1 MeCN:water (1 mL) and lyophilized to afford first eluting isomer (compound 30) (39 mg, 32%) as an off white solid. LC-MS: m/z: 483.2 [M+H]$^+$, (ESI+), RT=3.15 LCMS Method 6. $^1$H NMR (400 MHz, DMSO-$d_6$) δ 11.31 (s, 1H), 8.38-8.33 (m, 1H), 7.90-7.83 (m, 1H), 7.77-7.70 (m, 1H), 7.64 (t, J=7.9 Hz, 1H), 7.29 (dd, J=8.8, 5.0 Hz, 1H), 7.24 (dd, J=9.4, 3.0 Hz, 1H), 7.14 (td, J=8.7, 3.2 Hz, 1H), 4.25 (s, 1H), 3.07 (s, 3H), 2.52-2.52 (m, 3H), 2.12 (s, 3H). Analytical method: Mobile phase 70:30 Heptane:Ethanol, Column Chiralpak AD-H, 4.6×250 mm, 5 μm Flow rate 1 mL/min. and the second eluting isomer (compound 31) (0.038 mg, 32%) as an off white solid. $^1$H NMR (400 MHz, $CD_3OD$) δ 8.45 (t, J=1.9 Hz, 1H), 7.96 (ddd, J=8.1, 2.1, 1.0 Hz, 1H), 7.84 (ddd, J=7.9, 1.8, 1.0 Hz, 1H), 7.66 (t, J=8.0 Hz, 1H), 7.21 (dd, J=8.8, 4.9 Hz, 1H), 7.09 (dd, J=9.1, 3.1 Hz, 1H), 7.01 (td, J=8.5, 3.1 Hz, 1H), 3.17 (s, 3H), 2.62-2.55 (m, 3H), 2.17 (s, 3H). m/z: 483.5 [M+H]$^+$, (ESI+), RT=3.82 LCMS Method 5.

Example 15

Compounds 32 and 33: 5-Methyl-3-(2-methyl-4-(trifluoromethoxy)phenoxy)-N-(3-(S-methylsulfonimidoyl)phenyl)-6-(trifluoromethyl)pyridazine-4-carboxamide Chiral Separation

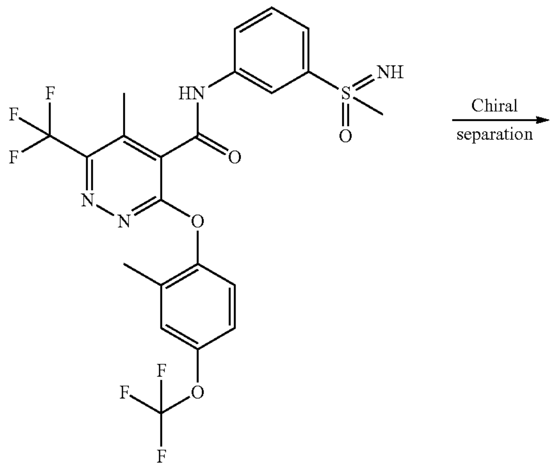

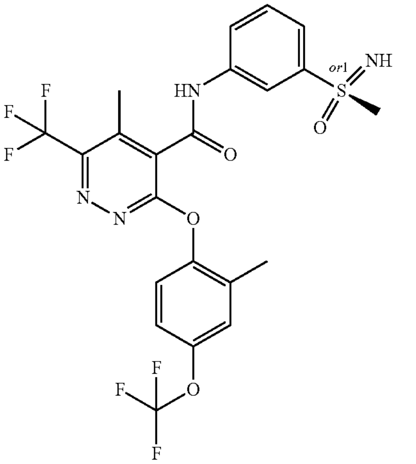

and

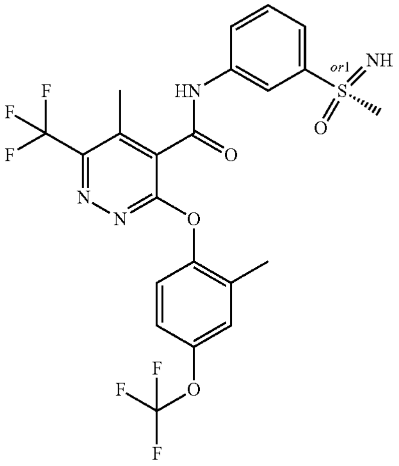

5-Methyl-3-(2-methyl-4-(trifluoromethoxy)phenoxy)-N-(3-(S-methylsulfonimidoyl)phenyl)-6-(trifluoromethyl) pyridazine-4-carboxamide was prepared by similar procedure described for compound 20 and was purified using preparative chiral HPLC on a Chiralpak AD-H, (20×250 m) 5 μm eluting with a mixture of Heptane:Ethanol (70:30), flow rate 18 mL/min. Fractions containing product were evaporated to and isolated as sticky oils, these were re-dissolved in 1:1 MeCN:water (1 mL) and lyophilized to afford first eluting isomer (compound 32) (63 mg, 37%) as a beige solid. $^{1}H$ NMR (400 MHz, DMSO-$d_6$) δ 11.33 (s, 1H), 8.35 (t, J=1.8 Hz, 1H), 7.90-7.83 (m, 1H), 7.73 (d, J=7.7 Hz, 1H), 7.64 (t, J=8.0 Hz, 1H), 7.44-7.38 (m, 2H), 7.35-7.30 (m, 1H), 4.25 (s, 1H), 3.07 (d, J=0.8 Hz, 3H), 2.54-2.52 (m, 3H), 2.16 (s, 3H). m/z: 549.2 $[M+H]^+$, (ESI+), RT=3.60 LCMS method 6 and the second eluting isomer (compound 33) (54 mg, 31%) as a beige solid. $^{1}H$ NMR (400 MHz, DMSO-$d_6$) δ 11.33 (s, 1H), 8.35 (t, J=1.9 Hz, 1H), 7.89-7.83 (m, 1H), 7.73 (d, J=7.8 Hz, 1H), 7.63 (t, J=7.8 Hz, 1H), 7.45-7.37 (m, 2H), 7.35-7.29 (m, 1H), 4.25 (s, 1H), 3.10-3.01 (m, 3H), 2.53-2.52 (m, 3H), 2.16 (s, 3H). m/z: 549.2 $[M+H]^+$, (ESI+), RT=3.60 LCMS method 6.

Example 16

Compounds 34 and 35: 5-Methyl-3-(2-methyl-4-(trifluoromethyl)phenoxy)-N-(3-(S-methylsulfonimidoyl)phenyl)-6-(trifluoromethyl)pyridazine-4-carboxamide Chiral Separation

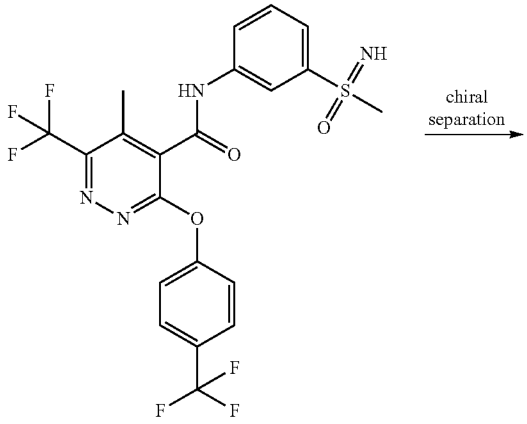

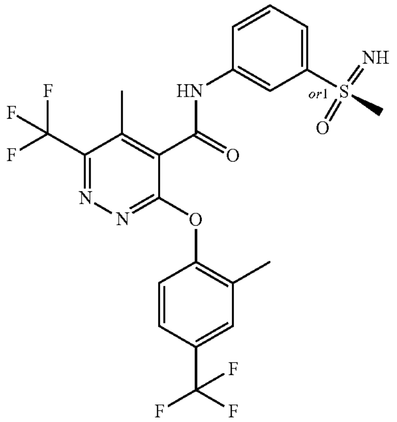

and

-continued

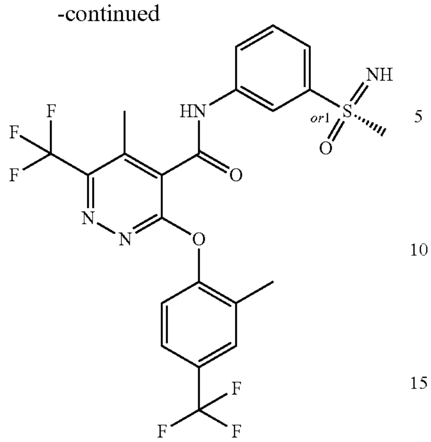

5-Methyl-3-(2-methyl-4-(trifluoromethyl)phenoxy)-N-(3-(S-methylsulfonimidoyl)phenyl)-6-(trifluoromethyl) pyridazine-4-carboxamide was prepared by similar procedure described for compound 20 and was purified using preparative chiral HPLC on a Chiralpak AD-H, (20×250 m) 10 μm eluting with a mixture of HPLC on a Chiralpak AD-H, (20×250 m) 5 μm eluting with a mixture of Heptane: Ethanol (85:15), flow rate 18 mL/min. Fractions containing product were evaporated to afford first eluting isomer (compound 34) (99 mg, 29%). $^1H$ NMR (400 MHz, DMSO-$d_6$) δ 11.33 (s, 1H), 8.35 (t, J=1.8 Hz, 1H), 7.91-7.84 (m, 1H), 7.81-7.77 (m, 1H), 7.76-7.68 (m, 2H), 7.64 (t, J=7.9 Hz, 1H), 7.51 (d, J=8.4 Hz, 1H), 4.25 (s, 1H), 3.10-3.04 (m, 3H), 2.55-2.53 (m, 3H), 2.21 (s, 3H). LC-MS: m/z 533.6 $[M+H]^+$, (ESI+), RT=4.15 LCMS method 5 and second eluting isomer (compound 35) (92 mg, 27%) as white solids. $^1H$ NMR (400 MHz, DMSO-$d_6$) δ 11.33 (s, 1H), 8.35 (t, J=1.8 Hz, 1H), 7.90-7.85 (m, 1H), 7.81-7.77 (m, 1H), 7.76-7.67 (m, 2H), 7.64 (t, J=7.9 Hz, 1H), 7.51 (d, J=8.5 Hz, 1H), 4.25 (s, 1H), 3.11-3.05 (m, 3H), 2.55-2.52 (m, 3H), 2.21 (s, 3H). LC-MS: m/z: 533.6 $[M+H]^+$, (ESI+), RT=4.14 LCMS method 5.

Example 17

The compounds 1401-1429 listed in Table 10 were prepared by a similar procedure as described for compound 14.

TABLE 10

| Compound | Structure & Name | Analytical data |
|---|---|---|
| 1401 | 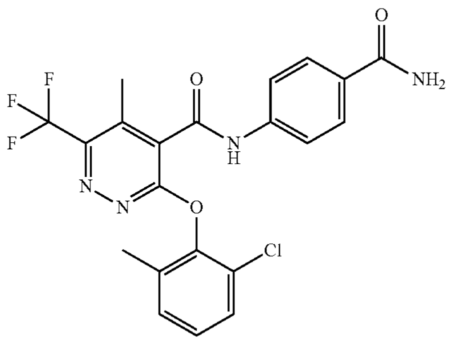 N-(4-Carbamoylphenyl)-3-(2-chloro-6-methylphenoxy)-5-methyl-6-(trifluoromethyl)pyridazine-4-carboxamide | LC-MS: m/z 465.4$[M + H]^+$ |
| 1402 | 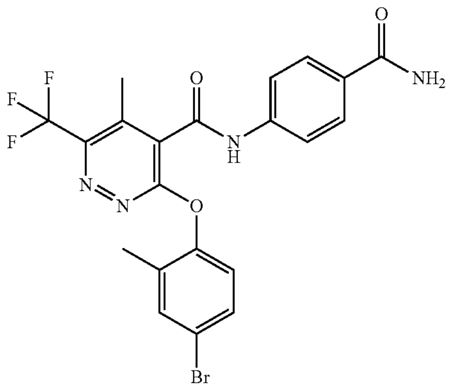 3-(4-Bromo-2-methylphenoxy)-N-(4-carbamoylphenyl)-5-methyl-6-(trifluoromethyl)pyridazine-4-carboxamide | $^1H$ NMR (300 MHz, DMSO-$d_6$) δ 11.19 (s, 1H), 8.01-7.85 (m, 3H), 7.81-7.67 (m, 2H), 7.61 (dd, J = 2.5, 0.9 Hz, 1H), 7.51 (dd, J = 8.7, 2.5 Hz, 1H), 7.34 (s, 1H), 7.25 (d, J = 8.6 Hz, 1H), 2.51 (s, 3H; buried under DMSO residual solvent), 2.12 (s, 3H). LC-MS: m/z 509.3, 511.3 $[M + H]^+$ |

TABLE 10-continued

| Compound | Structure & Name | Analytical data |
|---|---|---|
| 1403 | 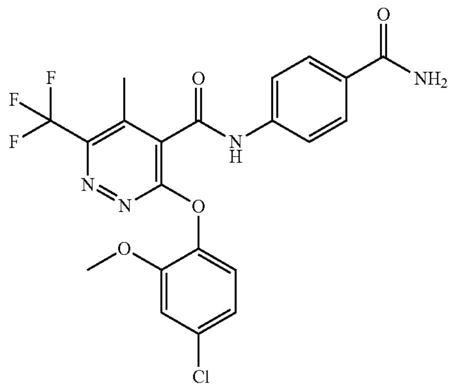 N-(4-Carbamoylphenyl)-3-(4-chloro-2-methoxyphenoxy)-5-methyl-6-(trifluoromethyl)pyridazine-4-carboxamide | $^1$H NMR (300 MHz, DMSO-$d_6$) δ 11.16 (s, 1H), 7.93 (d, J = 8.8 Hz, 3H), 7.81-7.67 (m, 2H), 7.40-7.23 (m, 3H), 7.11 (dd, J = 8.5, 2.4 Hz, 1H), 3.76 (s, 3H), 2.50 (s, 3H). 2.50 peak buried under residual DMSO solvent). LC-MS: m/z 481.4[M + H]$^+$ |
| 1404 | 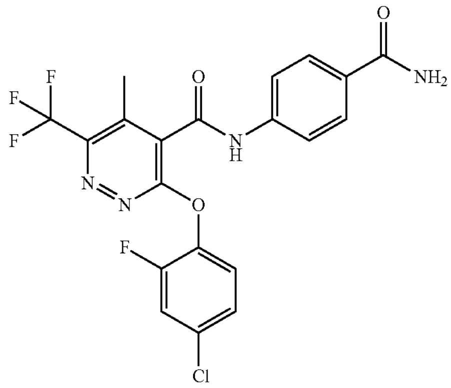 N-(4-Carbamoylphenyl)-3-(4-chloro-2-fluorophenoxy)-5-methyl-6-(trifluoromethyl)pyridazine-4-carboxamide | $^1$H NMR (300 MHz, DMSO-$d_6$) δ 11.23 (s, 1H), 8.01-7.88 (m, 3H), 7.74 (dd, J = 9.5, 2.4 Hz, 3H), 7.55 (t, J = 8.5 Hz, 1H), 7.48-7.32 (m, 2H), 2.53(s, 3H). LC-MS: m/z 469.3 [M + H]$^+$ |
| 1405 | 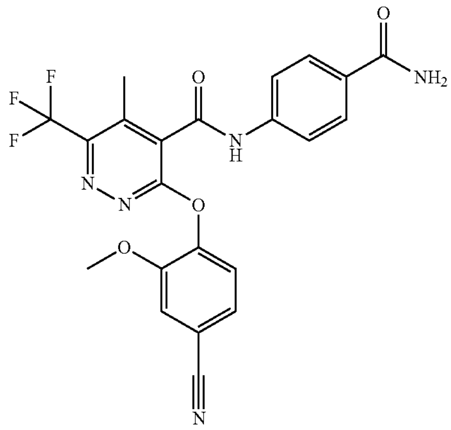 N-(4-Carbamoylphenyl)-3-(4-cyano-2-methoxyphenoxy)-5-methyl-6-(trifluoromethyl)pyridazine-4-carboxamide | $^1$H NMR (300 MHz, DMSO-$d_6$) δ 11.18 (s, 1H), 8.00-7.86 (m, 3H), 7.81-7.67 (m, 3H), 7.63-7.47 (m, 2H), 7.35 (s, 1H), 3.80 (s, 3H), 2.50(s, 3H). LC-MS: m/z 470.3 [M − H]$^+$ |

TABLE 10-continued

| Compound | Structure & Name | Analytical data |
|---|---|---|
| 1406 | 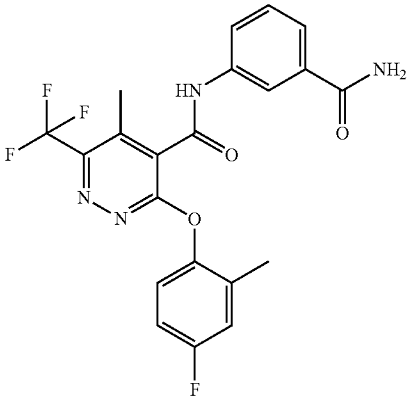 N-(3-Carbamoylphenyl)-3-(4-fluoro-2-methoxyphenoxy)-5-methyl-6-(trifluoromethyl)pyridazine-4-carboxamide | $^1$H NMR (400 MHz, DMSO-$d_6$) δ 11.08 (s, 1H), 8.17 (t, J = 1.8 Hz, 1H), 8.01 (s, 1H), 7.84-7.77 (m, 1H), 7.69-7.63 (m, 1H), 7.48 (t, J = 7.9 Hz, 1H), 7.40 (s, 1H), 7.29 (dd, J = 8.9, 5.1 Hz, 1H), 7.24 (dd, J = 9.4, 3.0 Hz, 1H), 7.14 (td, J = 8.6, 3.1 Hz, 1H), 2.52 (s, 3H), 2.12 (s, 3H). LC-MS: m/z: 449.5 $[M + H]^+$, (ESI+), RT = 3.88 METCR1416 Hi res 7 min |
| 1407 | 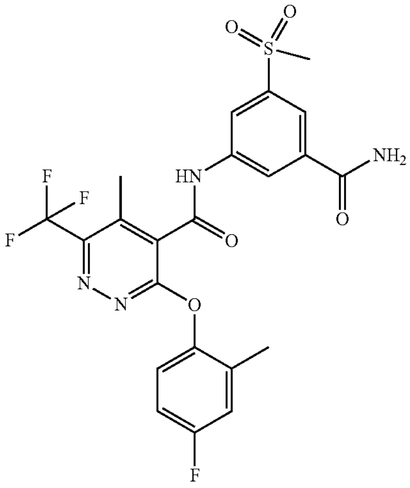 N-(3-Carbamoyl-5-(methylsulfonyl)phenyl)-3-(4-fluoro-2-methylphenoxy)-5-methyl-6-(trifluoromethyl)pyridazine-4-carboxamide | $^1$H NMR (500 MHz, DMSO-$d_6$) δ 11.54 (s, 1H), 8.47 (t, J = 1.8 Hz, 1H), 8.39-8.35 (m, 1H), 8.30 (s, 1H), 8.21 (t, J = 1.4 Hz, 1H), 7.68 (s, 1H), 7.30 (dd, J = 8.9, 5.1 Hz, 1H), 7.24 (dd, J = 9.4, 3.0 Hz, 1H), 7.14 (td, J = 8.5, 3.1 Hz, 1H), 3.29 (s, 3H), 2.55-2.52 (m, 3H), 2.12 (s, 3H). LC-MS: m/z: 527.5 $[M + H]^+$, (ESI+), RT = 3.82 METCR1416 Hi res 7 min |
| 1408 | 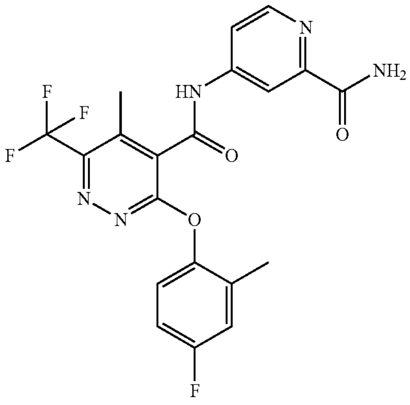 N-(2-Carbamoylpyridin-4-yl)-3-(4-fluoro-2-methylphenoxy)-5-methyl-6-(trifluoromethyl)pyridazine-4-carboxamide | $^1$H NMR (400 MHz, DMSO-$d_6$) δ 11.54 (s, 1H), 8.60 (d, J = 5.5 Hz, 1H), 8.33 (d, J = 2.0 Hz, 1H), 8.12 (d, J = 2.3 Hz, 1H), 7.82 (dd, J = 5.4, 2.1 Hz, 1H), 7.69 (d, J = 2.0 Hz, 1H), 7.30 (dd, J = 8.9, 5.0 Hz, 1H), 7.24 (dd, J = 9.4, 3.0 Hz, 1H), 7.14 (td, J = 8.6, 3.1 Hz, 1H), 2.53-2.51 (m, 3H), 2.11 (s, 3H). LC-MS: m/z: 449.9 $[M + H]^+$, (ESI+), RT = 3.94 METCR1416 Hi res 7 min |

TABLE 10-continued

| Compound | Structure & Name | Analytical data |
|---|---|---|
| 1409 | 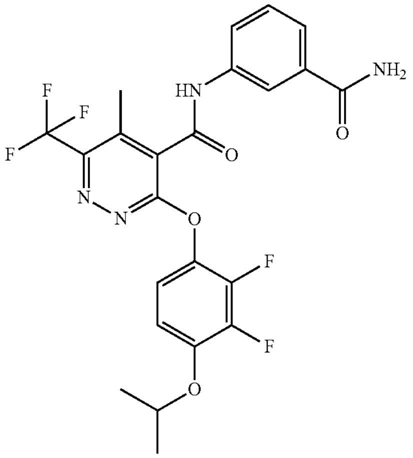 N-(3-Carbamoylphenyl)-3-(2,3-difluoro-4-isopropoxyphenoxy)-5-methyl-6-(trifluoromethyl)pyridazine-4-carboxamide | $^1$H NMR (500 MHz, DMSO-$d_6$) δ 11.12 (s, 1H), 8.17 (t, J = 1.8 Hz, 1H), 8.02 (br.s, 1H), 7.84-7.79 (m, 1H), 7.70-7.65 (m, 1H), 7.48 (t, J = 7.9 Hz, 1H), 7.41 (br.s, 1H), 7.28-7.21 (m, 1H), 7.17-7.11 (m, 1H), 4.71 (hept, J = 6.0 Hz, 1H), 2.54-2.51 (m, 3H), 1.32 (d, J = 6.0 Hz, 6H). LC-MS: m/z: 511.2 [M + H]$^+$, (ESI+), RT = 3.42 |
| 1410 | 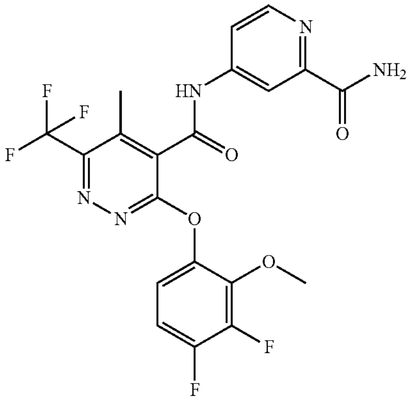 N-(2-Carbamoylpyridin-4-yl)-3-(3,4-difluoro-2-methoxyphenoxy)-5-methyl-6-(trifluoromethyl)pyridazine-4-carboxamide | $^1$H NMR (400 MHz, DMSO-$d_6$) δ 11.59 (s, 1H), 8.59 (m, 1H), 8.34 (s, 1H), 8.13 (s, 1H), 7.83 (m, 1H), 7.69 (s, 1H), 7.29 (m, 3H), 3.81 (s, 3H), 2.53 (s, 3H). LC-MS: m/z: 484.2 [M + H]$^+$, (ESI+), RT = 3.18 LCMS Method 7 |
| 1411 | 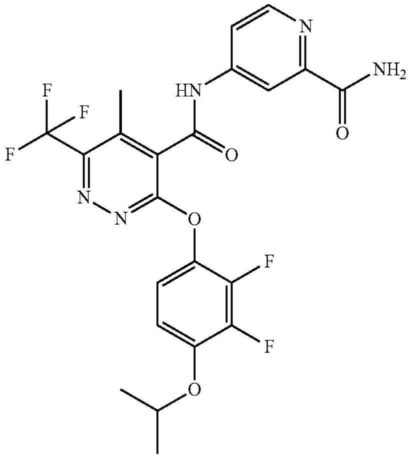 N-(2-Carbamoylpyridin-4-yl)-3-(2,3-difluoro-4-isopropoxyphenoxy)-5-methyl-6-(trifluoromethyl)pyridazine-4-carboxamide | $^1$H NMR (500 MHz, DMSO-$d_6$) δ 11.60 (s, 1H), 8.60 (d, J = 5.5 Hz, 1H), 8.33 (d, J = 2.0 Hz, 1H), 8.13 (d, J = 2.3 Hz, 1H), 7.83 (dd, J = 5.4, 2.1 Hz, 1H), 7.69 (d, J = 2.2 Hz, 1H), 7.29-7.22 (m, 1H), 7.17-7.11 (m, 1H), 4.70 (hept, J = 6.0 Hz, 1H), 2.53-2.52 (m, 3H), 1.31 (d, J = 6.0 Hz, 6H). LC-MS: m/z: 512.2 [M + H]$^+$, (ESI+), RT = 3.54 LCMS Method 4 |

TABLE 10-continued

| Compound | Structure & Name | Analytical data |
|---|---|---|
| 1412 | 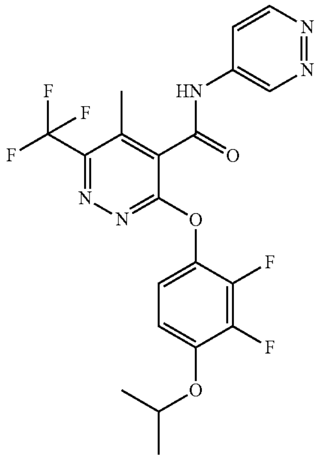 3-(2,3-Difluoro-4-isopropoxyphenoxy)-5-methyl-N-(pyridazin-4-yl)-6-(trifluoromethyl)pyridazine-4-carboxamide | $^1$H NMR (500 MHz, DMSO-$d_6$) δ 11.71 (s, 1H), 9.36-9.32 (m, 1H), 9.17 (d, J = 5.8 Hz, 1H), 8.06 (dd, J = 5.9, 2.7 Hz, 1H), 7.28-7.23 (m, 1H), 7.17-7.11 (m, 1H), 4.71 (hept, J = 6.0 Hz, 1H), 2.54-2.51 (m, 3H), 1.32 (d, J = 6.0 Hz, 6H). LC-MS: m/z: 470.2 [M + H]$^+$, (ESI+), RT = 3.42 LCMS Method 4 |
| 1413 | 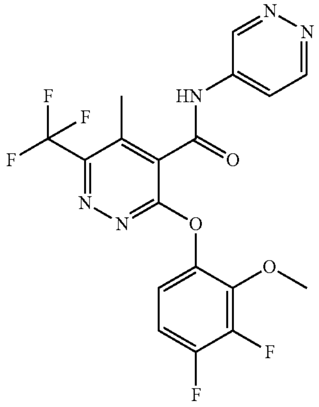 3-(3,4-Difluoro-2-methoxyphenoxy)-5-methyl-N-(pyridazin-4-yl)-6-(trifluoromethyl)pyridazine-4-carboxamide | $^1$H NMR (500 MHz, MeOH-$d_4$) δ 9.35 (dd, J = 2.7, 1.0 Hz, 1H), 9.12 (dd, J = 5.9, 1.1 Hz, 1H), 8.22 (dd, J = 6.0, 2.7 Hz, 1H), 7.15-7.03 (m, 2H), 3.85 (d, J = 1.7 Hz, 3H), 2.58 (q, J = 1.5 Hz, 3H). LC-MS: m/z: 442.0 [M + H]$^+$, (ESI+), RT = 3.41 LCMS Method 4 |
| 1414 | 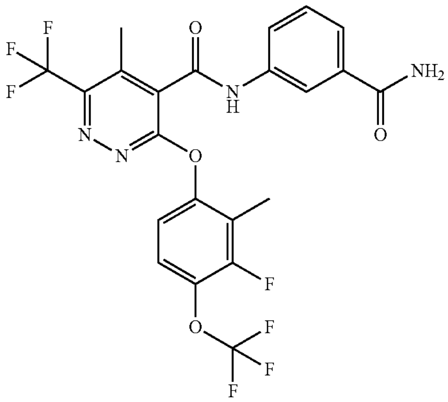 N-(3-carbamoylphenyl)-3-(3-fluoro-2-methyl-4-(trifluoromethoxy)phenoxy)-5-methyl-6-(trifluoromethyl)pyridazine-4-carboxamide | $^1$H NMR (500 MHz, DMSO-$d_6$) δ 11.14 (br.s, 1H), 8.17 (t, J = 1.8 Hz, 1H), 8.02 (br.s, 1H), 7.83-7.78 (m, 1H), 7.69-7.65 (m, 1H), 7.56 (t, J = 8.8 Hz, 1H), 7.48 (t, J = 7.9 Hz, 1H), 7.42 (br.s, 1H), 7.30 (dd, J = 9.1, 1.5 Hz, 1H), 2.55-2.52 (m, 3H), 2.14-2.10 (m, 3H). LC-MS: m/z 550.3 [M + $NH_4$]$^+$ RT 3.66 min, LCMS Method 6 |

TABLE 10-continued

| Compound | Structure & Name | Analytical data |
|---|---|---|
| 1415 | 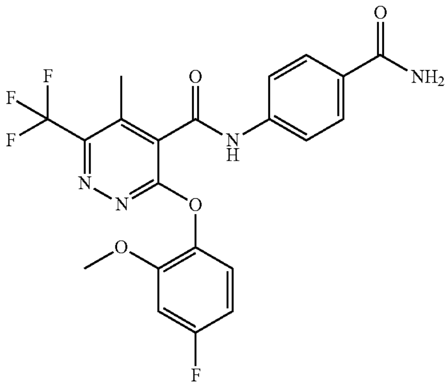 N-(4-Carbamoylphenyl)-3-(4-fluoro-2-methoxyphenoxy)-5-methyl-6-(trifluoromethyl)pyridazine-4-carboxamide | $^1$H NMR (400 MHz, DMSO-$d_6$) δ 11.14 (s, 1H), 7.96-7.84 (m, 3H), 7.77-7.68 (m, 2H), 7.35-7.22 (m, 2H), 7.15 (dd, J = 10.7, 2.9 Hz, 1H), 6.86 (td, J = 8.5, 2.9 Hz, 1H), 3.74 (s, 3H), 2.54-2.45 (m, 3H). m/z: 465.2 $[M + H]^+$, (ESI+), RT = 2.93 LCMS Method 4 |
| 1416 | 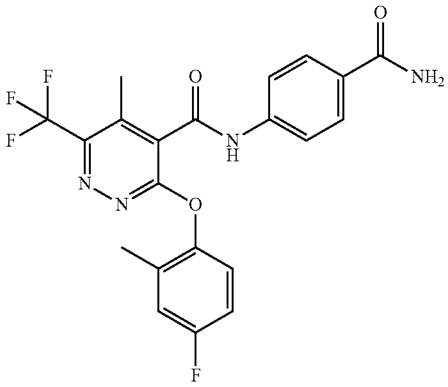 N-(4-Carbamoylphenyl)-3-(4-fluoro-2-methylphenoxy)-5-methyl-6-(trifluoromethyl)pyridazine-4-carboxamide | $^1$H NMR (500 MHz, DMSO-$d_6$) δ 11.18 (s, 1H), 7.96-7.87 (m, 3H), 7.79-7.68 (m, 2H), 7.35-7.27 (m, 2H), 7.24 (dd, J = 9.3, 3.2 Hz, 1H), 7.14 (td, J = 8.5, 3.2 Hz, 1H), 2.55-2.44 (m, 3H), 2.12 (s, 3H). m/z: 449.3 [M + H]+, (ESI+), RT = 3.08 LCMS Method 6 |
| 1417 | 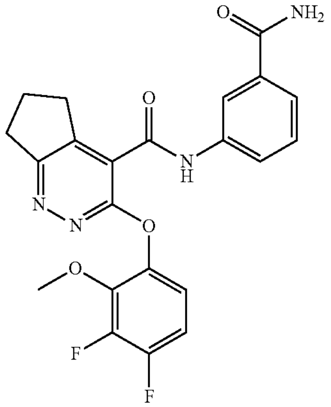 N-(3-carbamoylphenyl)-3-(3,4-difluoro-2-methoxyphenoxy)-6,7-dihydro-5H-cyclopenta[c]pyridazine-4-carboxamide | $^1$H NMR (400 MHz, DMSO-$d_6$) δ 10.88 (s, 1H), 8.18 (t, J = 1.8 Hz, 1H), 7.99 (br.s, 1H), 7.82 (ddd, J = 8.1, 2.1, 0.8 Hz, 1H), 7.63 (dt, J = 7.7, 1.0 Hz, 1H), 7.45 (t, J = 7.9 Hz, 1H), 7.39 (br.s, 1H), 7.31-7.20 (m, 1H), 7.17 (ddd, J = 9.3, 5.3, 2.1 Hz, 1H), 3.82-3.77 (m, 3H), 3.12-3.02 (m, 4H), 2.22-2.12 (m, 2H). LC-MS: m/z 441.2 $[M + H]^+$, (ESI+), RT = 2.50 MET-uPLC-AB-101 (7 min, low pH) |

TABLE 10-continued

| Compound | Structure & Name | Analytical data |
|---|---|---|
| 1418 | 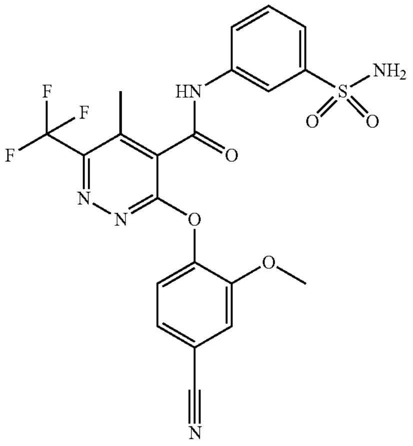 3-(4-cyano-2-methoxy-phenoxy)-5-methyl-N-(3-sulfamoylphenyl)-6-(trifluoromethyl)pyridazine-4-carboxamide | $^1$H NMR (400 MHz, DMSO-$d_6$) δ 11.29 (s, 1H), 8.31 (s, 1H), 7.78 (dt, J = 7.0, 2.0 Hz, 1H), 7.75 (d, J = 1.7 Hz, 1H), 7.66-7.59 (m, 2H), 7.57 (dd, J = 8.3, 1.8 Hz, 1H), 7.51 (d, J = 8.2 Hz, 1H), 7.43 (s, 2H), 3.79 (s, 3H), 2.52 (s, 3H). LC-MS: m/z 508.1 $[M + H]^+$, (ESI+), RT = 2.93 LCMS Method 6 |
| 1419 | 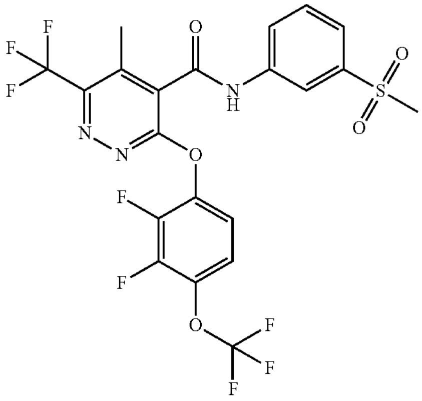 3-[2,3-difluoro-4-(trifluoromethoxy)phenoxy]-5-methyl-N-(3-methylsulfonylphenyl)-6-(trifluoromethyl)pyridazine-4-carboxamide | $^1$H NMR (400 MHz, DMSO-$d_6$) δ 11.35 (s, 1H), 8.36 (t, J = 1.8 Hz, 1H), 7.96-7.87 (m, 1H), 7.76 (dt, J = 7.9, 1.4 Hz, 1H), 7.70 (t, J = 7.9 Hz, 1H), 7.68-7.59 (m, 1H), 7.54 (ddd, J = 9.6, 7.7, 2.1 Hz, 1H), 3.24 (s, 3H), 2.59-2.53 (m, 3H). LC-MS: m/z 572.0 $[M + H]^+$, (ESI+), RT = 3.88 LCMS Method 4 |
| 1420 | 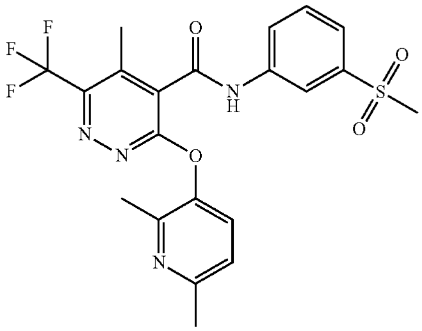 3-((2,6-dimethylpyridin-3-yl)oxy)-5-methyl-N-(3-methylsulfonyl)phenyl)-6-(trifluoromethyl)pyridazine-4-carboxamide | $^1$H NMR (400 MHz, DMSO-$d_6$) δ 11.40 (s, 1H), 8.38 (t, J = 1.8 Hz, 1H), 7.92-7.85 (m, 1H), 7.78-7.66 (m, 2H), 7.59 (d, J = 8.3 Hz, 1H), 7.21 (d, J = 8.3 Hz, 1H), 3.24 (s, 3H), 2.53-2.52 (m, 3H), 2.46 (s, 3H), 2.28 (s, 3H). LC-MS: m/z 481.2 $[M + H]^+$, (ESI+), RT = 3.05 LCMS Method 6 |

TABLE 10-continued

| Compound | Structure & Name | Analytical data |
|---|---|---|
| 1421 | 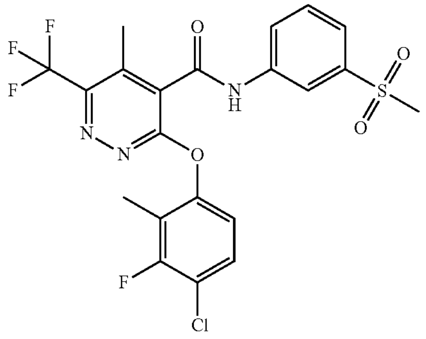 3-(4-chloro-3-fluoro-2-methyl-phenoxy)-5-methyl-N-(3-methylsulfonylphenyl)-6-(trifluoromethyl)pyridazine-4-carboxamide | $^1$H NMR (500 MHz, DMSO-$d_6$) δ 11.41 (s, 1H), 8.38 (t, J = 1.8 Hz, 1H), 7.90 (d, J = 8.7 Hz, 1H), 7.76 (d, J = 7.9 Hz, 1H), 7.71 (t, J = 7.9 Hz, 1H), 7.57 (t, J = 8.6 Hz, 1H), 7.23 (dd, J = 8.9, 1.2 Hz, 1H), 3.25 (s, 3H), 2.57-2.52 (m, 3H), 2.11 (d, J = 1.7 Hz, 3H). LC-MS: m/z 516.2, 518.3 $[M - H]^-$, (ESI−), RT = 3.94 LCMS Method 6 |
| 1422 | 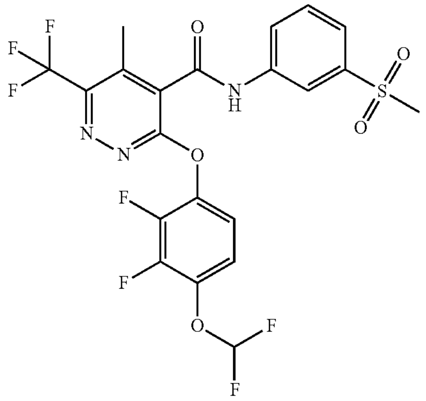 3-[4-(difluoromethoxy)-2,3-difluoro-phenoxy]-5-methyl-N-(3-methylsulfonylphenyl)-6-(trifluoromethyl)pyridazine-4-carboxamide | $^1$H NMR (500 MHz, DMSO-$d_6$) δ 11.45 (s, 1H), 8.37 (s, 1H), 7.91 (d, J = 7.9 Hz, 1H), 7.80-7.65 (m, 2H), 7.54-7.18 (m, 3H), 3.25 (s, 3H), 2.57-2.53 (m, 3H). LC-MS: m/z 553.9 $[M + H]^+$, (ESI+), RT = 3.73 LCMS Method 4 |
| 1423 | 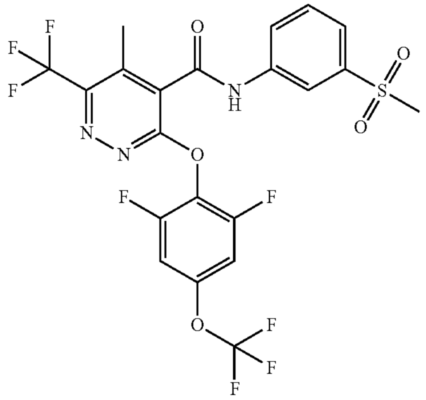 3-(2,6-difluoro-4-(trifluoromethoxy)phenoxy)-5-methyl-N-(3-methylsulfonyl)phenyl)-6-(trifluoromethyl)pyridazine-4-carboxamide | $^1$H NMR (400 MHz, $CDCl_3$) δ 8.36 (s, 1H), 8.20-8.08 (m, 2H), 7.76 (d, J = 8.0 Hz, 1H), 7.64 (t, J = 8.0 Hz, 1H), 6.98 (d, J = 8.2 Hz, 2H), 3.05 (s, 3H), 2.69-2.56 (m, 3H). LC-MS: m/z 572 $[M + H]^+$, (ESI+), RT = 3.83 LCMS Method 4 |

TABLE 10-continued

| Compound | Structure & Name | Analytical data |
|---|---|---|
| 1424 | 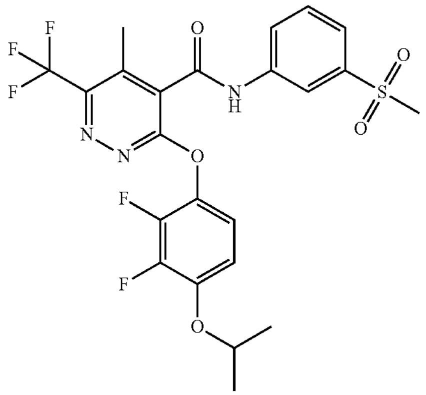 3-(2,3-difluoro-4-isopropoxyphenoxy)-5-methyl-N-(3-(methylsulfonyl)phenyl)-6-(trifluoromethyl)pyridazine-4-carboxamide | $^1$H NMR (400 MHz, DMSO-$d_6$) δ 11.42 (s, 1H), 8.37 (t, J = 1.8 Hz, 1H), 7.91 (ddd, J = 7.9, 2.0, 1.3 Hz, 1H), 7.76 (dt, J = 7.8, 1.3 Hz, 1H), 7.70 (t, J = 7.9 Hz, 1H), 7.25 (td, J = 8.9, 8.2, 2.1 Hz, 1H), 7.18-7.10 (m, 1H), 4.71 (hept, J = 6.0 Hz, 1H), 3.25 (s, 3H), 2.54-2.52 (m, 3H), 1.32 (d, J = 6.0 Hz, 6H). LC-MS: m/z 546.1 [M + H]$^+$, (ESI+), RT = 3.80 LCMS Method 4 |
| 1425 | 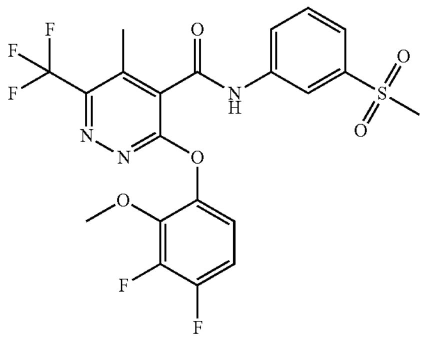 [SMILES: COc1c(Oc2nnc(C(F)(F)F)c(C)c2C(=O)Nc2cccc(S(C)(=O)=O)c2)ccc(F)c1F] | $^1$H NMR (400 MHz, $CDCl_3$) δ 8.60 (s, 1H), 8.16 (t, J = 1.8 Hz, 1H), 8.07 (m, 1H), 7.81-7.73 (m, 1H), 7.64 (t, J = 8.0 Hz, 1H), 7.05 (ddd, J = 9.2, 4.9, 2.2 Hz, 1H), 7.02-6.91 (m, 1H), 3.90 (d, J = 2.4 Hz, 3H), 3.09 (s, 3H), 2.67 (m, 3H). LC-MS: m/z 518.1 [M + H]$^+$, (ESI+), RT = 3.47 ET-uPLC-AB-101 (7 min, low pH) LCMS Method 4 |
| 1426 | 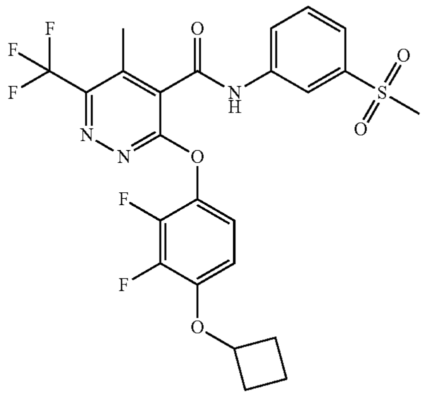 3-(4-cyclobutoxy-2,3-difluorophenoxy)-5-methyl-N-(3-(methylsulfonyl)phenyl)-6-(trifluoromethyl)pyridazine-4-carboxamide | $^1$H NMR (400 MHz, DMSO-$d_6$) δ 11.43 (s, 1H), 8.37 (m, 1H), 7.91 (m, 1H), 7.76 (m, 1H), 7.71 (m, 1H), 7.24 (m, 1H), 6.97 (m, 1H), 4.88-4.77 (m, 1H), 3.25 (s, 3H), 2.44 (m, 2H), 2.19-2.05 (m, 2H), 1.82 (m, 1H), 1.73-1.57 (m, 1H). LC-MS: m/z: 558.2 [M + H]$^+$, (ESI+), RT = 3.92 MET-uPLC-AB-101 (7 min, low pH) LCMS Method 4 |

TABLE 10-continued

| Compound | Structure & Name | Analytical data |
|---|---|---|
| 1427 | 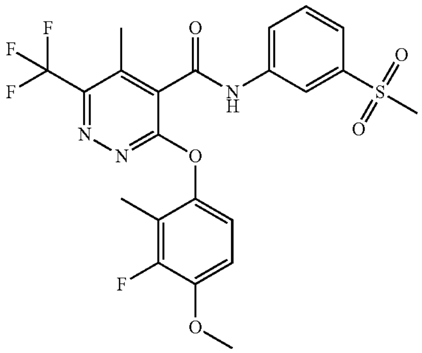 3-(3-fluoro-4-methoxy-2-methyl-phenoxy)-5-methyl-N-(3-(methylsulfonylphenyl)-6-(trifluoromethyl)pyridazine-4-carboxamide | $^1$H NMR (400 MHz, $CD_3OD$) δ 8.28 (t, J = 2.0 Hz, 1H), 7.85 (ddd, J = 8.1, 2.1, 1.0 Hz, 1H), 7.67 (ddd, J = 7.9, 1.8, 1.1 Hz, 1H), 7.56 (t, J = 8.0 Hz, 1H), 6.91-6.84 (m, 2H), 3.76 (s, 3H), 3.03 (s, 3H), 2.46 (q, J = 1.5 Hz, 3H), 1.96 (d, J = 2.3 Hz, 3H). LC-MS: m/z 514.0 $[M + H]^+$, (ESI+), RT = 3.55 MET-uPLC-AB-101 (7 min, low pH) |
| 1428 | 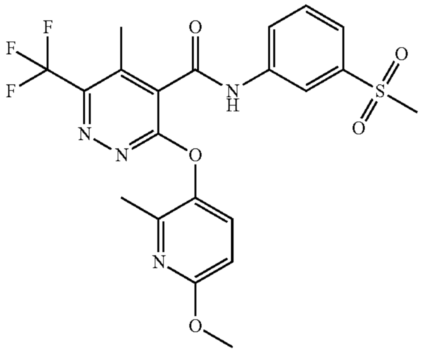 3-[(6-methoxy-2-methyl-3-pyridyl)oxy]-5-methyl-N-(3-methylsulfonylphenyl)-6-(trifluoromethyl)pyridazine-4-carboxamide | $^1$H NMR (500 MHz, $CD_3OD$) δ 8.41 (t, J = 1.9 Hz, 1H), 7.97 (ddd, J = 8.2, 2.2, 1.0 Hz, 1H), 7.79 (ddd, J = 7.9, 1.8, 1.1 Hz, 1H), 7.68 (t, J = 8.0 Hz, 1H), 7.54 (d, J = 8.7 Hz, 1H), 6.70 (d, J = 8.7 Hz, 1H), 3.90 (s, 3H), 3.15 (s, 3H), 2.59 (q, J = 1.5 Hz, 3H), 2.28 (s, 3H). LC-MS: m/z 497.3 $[M + H]^+$, (ESI+), RT = 3.30 LCMS Method 6 |
| 1429 | 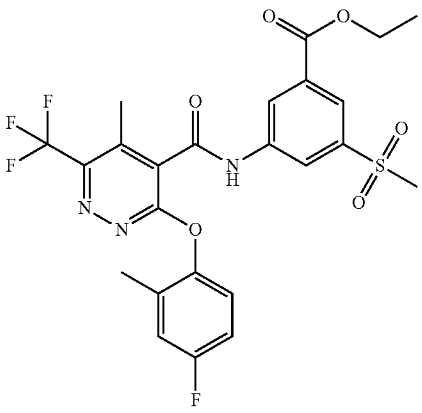 ethyl 3-(3-(4-fluoro-2-methylphenoxy)-5-methyl-6-(trifluoromethyl)pyridazine-4-carboxamido-5-(methylsulfonyl)benzoate | $^1$H NMR (400 MHz, DMSO-$d_6$) δ 11.61 (s, 1H), 8.57 (t, J = 1.9 Hz, 1H), 8.53-8.48 (m, 1H), 8.21 (t, J = 1.6 Hz, 1H), 7.30 (dd, J = 9.0, 5.1 Hz, 1H), 7.24 (dd, J = 9.4, 3.0 Hz, 1H), 7.14 (td, J = 8.6, 3.2 Hz, 1H), 4.39 (q, J = 7.1 Hz, 2H), 3.32 (s, 3H), 2.55-2.53 (m, 3H), 2.12 (s, 3H), 1.36 (t, J = 7.1 Hz, 3H). LC-MS: m/z 556.6 $[M + H]^+$, (ESI+), RT = 4.46 LCMS Method 5 |

Example 18

Compound 1430: 6-(3-Fluoroazetidin-1-yl)-3-(4-fluoro-2-methyl-phenoxy)-5-methyl-N-pyridazin-4-yl-pyridazine-4-carboxamide

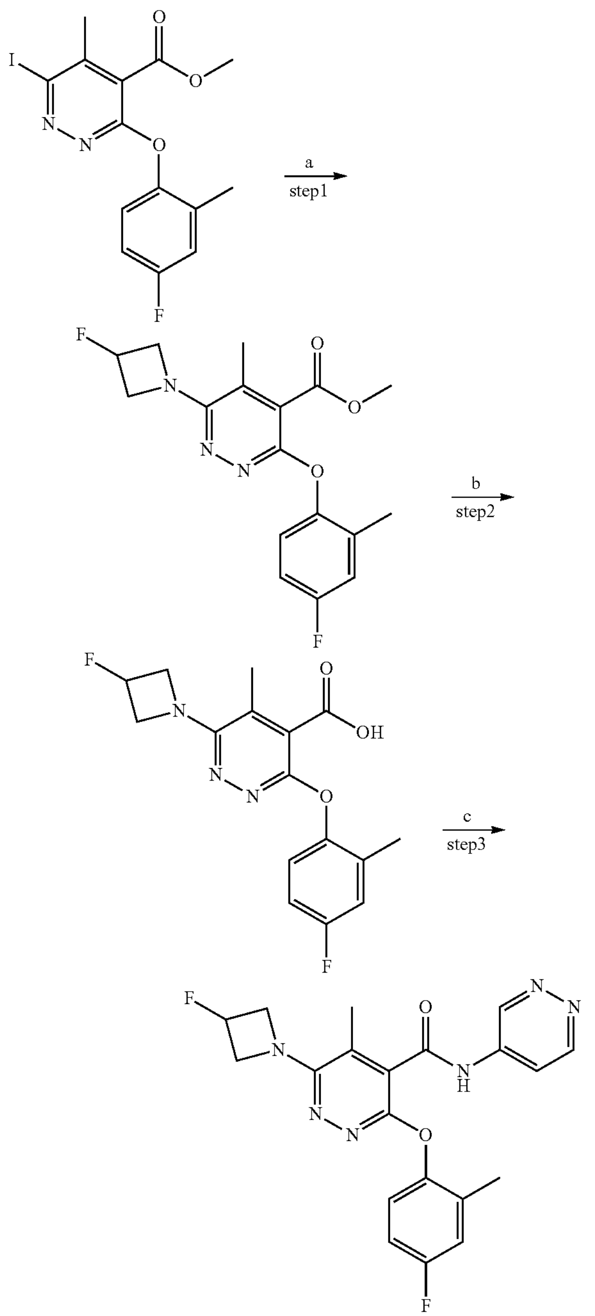

Reagents & conditions:
a) (4R)-4-hydroxy-L-proline, 3-fluoroazetidine hydrochloride, tripotassium phosphate, copper iodide, $CH_3CN$, DMSO, 50 °C, 104 h;
b) LiOH, THF:$H_2O$(7:1, v/v), rt, 2 h;
c) HATU, pyridazin-4-amine, DIPEA, DMF, rt, 2 h.

Step 1: methyl 6-(3-fluoroazetidin-1-yl)-3-(4-fluoro-2-methyl-phenoxy)-5-methyl-pyridazine-4-carboxylate: (4R)-4-hydroxy-L-proline (16 mg, 0.124 mmol) was added to a $N_2$ degassed mixture of methyl 3-(4-fluoro-2-methyl-phenoxy)-6-iodo-5-methyl-pyridazine-4-carboxylate (250 mg, 0.622 mmol), 3-fluoroazetidine hydrochloride (139 mg, 1.24 mmol), copper iodide (12 mg, 0.0622 mmol) and tripotassium phosphate (396 mg, 1.86 mmol) in anhydrous Acetonitrile (2.5 mL) and anhydrous DMSO (2 mL) and the reaction was stirred at 50 °C for 80 hr. Additional reagents (4R)-4-hydroxy-L-proline (16 mg, 0.124 mmol), methyl 3-(4-fluoro-2-methyl-phenoxy)-6-iodo-5-methyl-pyridazine-4-carboxylate (250 mg, 0.622 mmol), 3-fluoroazetidine hydrochloride (1:1) (139 mg, 1.24 mmol), copper(1+) iodide (12 mg, 0.0622 mmol) and tripotassium phosphate (396 mg, 1.86 mmol) were added and the reaction was stirred at 70 °C for a further 24 h. The reaction was diluted in EtOAc (~60 mL) and washed successively with 1M aq. HCl, water and brine, dried over sodium sulfate and concentrated to dryness in vacuum to give crude title compound methyl 6-(3-fluoroazetidin-1-yl)-3-(4-fluoro-2-methyl-phenoxy)-5-methyl-pyridazine-4-carboxylate (699 mg, 100%) as a brown gum, assumed 100% molar yield, that was used as such in the next step without further analysis or purification. m/z: 350 $[M+H]^+$, (ESI+), RT=0.89 min METCR1704 (2 minute uPLC gradient method for IPCs).

Step 2: 6-(3-fluoroazetidin-1-yl)-3-(4-fluoro-2-methyl-phenoxy)-5-methyl-pyridazine-4-carboxylic acid: Lithium hydroxide (93 mg, 3.73 mmol) was added to a mixture of methyl 6-(3-fluoroazetidin-1-yl)-3-(4-fluoro-2-methyl-phenoxy)-5-methyl-pyridazine-4-carboxylate (217 mg 0.622 mmol) in THF (4.2 mL) and Water (0.6 mL) and the mixture was stirred at rt for 16 h. The reaction was stirred for a further 24 h, then heated at 40 °C for a further 8 h (56 h total). The reaction was diluted with water (20 mL) and the pH was adjusted to ~1-2 by dropwise addition of 2M HCl (aq). The aqueous layer was extracted with EtOAc (3×20 mL). The organic phase was washed with brine, dried over sodium sulfate, filtered and concentrated to dryness in vacuum to give the title compound 6-(3-fluoroazetidin-1-yl)-3-(4-fluoro-2-methyl-phenoxy)-5-methyl-pyridazine-4-carboxylic acid (59.0%) (353 mg, 100%) as a brown solid, which was used in the next step without further analysis or purification. LC-MS: m/z 336 $[M+H]^+$, (ESI+), RT=0.46 min METCR1704 (2 minute uPLC gradient method for IPCs).

Step 3: 6-(3-fluoroazetidin-1-yl)-3-(4-fluoro-2-methyl-phenoxy)-5-methyl-N-pyridazin-4-yl-pyridazine-4-carboxamide: HATU (130 mg, 0.342 mmol) was added to a mixture of 6-(3-fluoroazetidin-1-yl)-3-(4-fluoro-2-methyl-phenoxy)-5-methyl-pyridazine-4-carboxylic acid (104 mg, 0.311 mmol) and N-ethyl-N-isopropyl-propan-2-amine (119 uL, 0.684 mmol) in DMF (2 mL) at rt and the reaction was stirred at rt for 5 min, then pyridazin-4-amine (44 mg, 0.466 mmol) was added and the reaction was stirred at rt for 2 h. The reaction mixture was diluted with EtOAc (50 mL) and washed with water (3×50 mL). The organic phase was washed with brine, dried over sodium sulfate, filtered, and concentrated to dryness to give crude product. Purification by high pH prep HPLC (early method) to give the title compound 6-(3-fluoroazetidin-1-yl)-3-(4-fluoro-2-methyl-phenoxy)-5-methyl-N-pyridazin-4-yl-pyridazine-4-carboxamide (20 mg, 0.0478 mmol, 15%) as an off-white solid. $^1H$ NMR (400 MHz, MeOH-$d_4$) δ 9.31 (d, J=1.9 Hz, 1H), 9.08 (d, J=5.9 Hz, 1H), 8.19 (dd, J=5.9, 2.7 Hz, 1H), 7.11 (dd, J=8.9, 4.9 Hz, 1H), 7.00 (dd, J=9.2, 3.0 Hz, 1H), 6.97-6.88 (m, 1H), 5.43 (dm, J=57.8, 9.4, 5.9, 3.5 Hz, 1H), 4.55-4.41 (m, 2H), 4.31-4.18 (m, 2H), 2.30 (s, 3H), 2.15 (s, 3H). m/z: 413.3 $[M+H]^+$, (ESI+), RT=2.45 LCMS Method 6

Example 19

Compound 1431: 6-(3-Fluoroazetidin-1-yl)-3-(4-fluoro-2-methyl-phenoxy)-5-methyl-N-[3-(methyl-sulfonimidoyl)phenyl]pyridazine-4-carboxamide

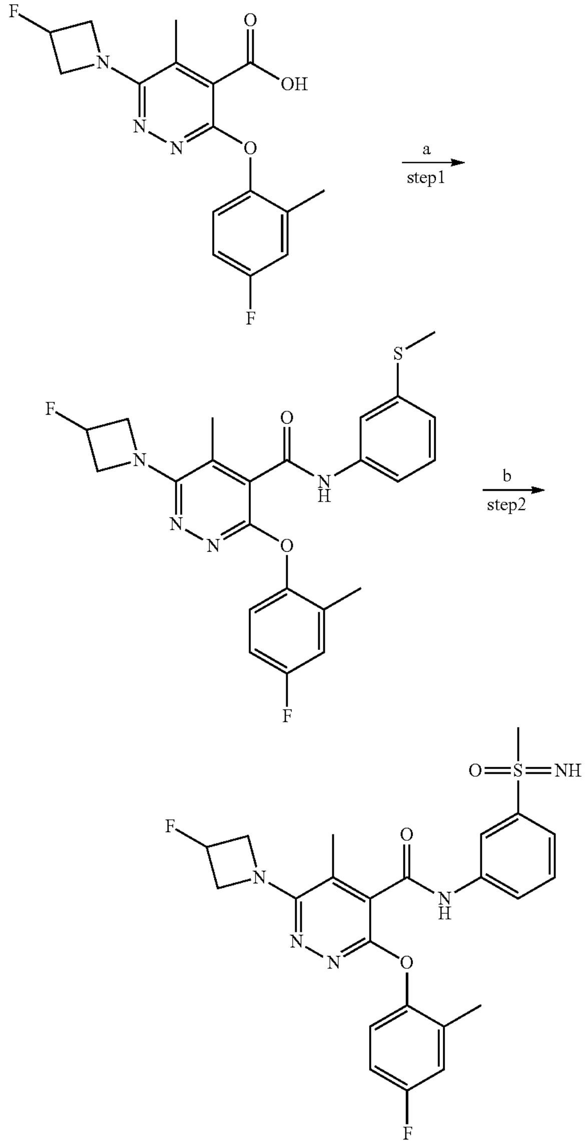

Reagents & conditions: a) HATU, 3-(methylsulfanyl)aniline, DIPEA, DMF, rt, 2 h. b) PIDA, (NH4)$_2$CO$_3$, MeOH, rt, 3 d.

Step 1: 6-(3-fluoroazetidin-1-yl)-3-(4-fluoro-2-methyl-phenoxy)-5-methyl-N-(3-methylsulfanylphenyl)pyridazine-4-carboxamide: HATU (130 mg, 0.342 mmol) was added to a mixture of 6-(3-fluoroazetidin-1-yl)-3-(4-fluoro-2-methyl-phenoxy)-5-methyl-pyridazine-4-carboxylic acid (104 mg, 0.311 mmol) and N-ethyl-N-isopropyl-propan-2-amine (119 uL, 0.684 mmol) in DMF (2 mL) at rt and the reaction was stirred at rt for 5 min, then 3-(methylsulfanyl)aniline (57 uL, 0.466 mmol) was added and the reaction was stirred at rt for 2 h. The reaction mixture was diluted with EtOAc (~50 mL) and washed with water (3×~50 mL). The organic phase was washed with brine, dried over sodium sulfate, filtered and concentrated to dryness to give crude product. Purification by FCC (Biotage Isolera, SiO2, gradient elution 10-50% EtOAc:Heptanes) gave the title compound 6-(3-fluoroazetidin-1-yl)-3-(4-fluoro-2-methyl-phenoxy)-5-methyl-N-(3-methylsulfanylphenyl)pyridazine-4-carboxamide (90.0%) (30 mg, 0.0591 mmol, 19%) as a yellow gum. LC-MS: m/z: 457 $[M+H]^+$, (ESI+), RT=0.95 min METCR1704 (2 minute uPLC gradient method for IPCs)

Step 2: 6-(3-fluoroazetidin-1-yl)-3-(4-fluoro-2-methyl-phenoxy)-5-methyl-N-[3-(methylsulfonimidoyl)phenyl] pyridazine-4-carboxamide: Phenyl Iodonium Di-Acetate (PIDA) (49 mg, 0.151 mmol) and diammonium carbonate (10 mg, 0.105 mmol) were added to a solution of 6-(3-fluoroazetidin-1-yl)-3-(4-fluoro-2-methyl-phenoxy)-5-methyl-N-(3-methylsulfanylphenyl)pyridazine-4-carboxamide (30 mg, 0.0657 mmol) in Methanol (1 mL) at rt and the reaction was stirred at rt for 3 days. The reaction mixture was concentrated to dryness in vacuum to give crude product. The residue was purified by low pH prep HPLC (early method). The product containing fractions were combined and the solvent was removed in vacuum, to give the title compound 6-(3-fluoroazetidin-1-yl)-3-(4-fluoro-2-methyl-phenoxy)-5-methyl-N-[3-(methylsulfonimidoyl)phenyl] pyridazine-4-carboxamide (100.0%)) (12 mg, 0.0246 mmol, 37%) as an off white solid. $^1$H NMR (400 MHz, $CD_3OD$) δ 8.43 (t, J=1.9 Hz, 1H), 7.99-7.90 (m, 1H), 7.86-7.76 (m, 1H), 7.64 (t, J=8.0 Hz, 1H), 7.11 (dd, J=8.9, 4.9 Hz, 1H), 7.01 (dd, J=9.1, 3.0 Hz, 1H), 6.99-6.93 (m, 1H), 5.52-5.34 (dm, J=57.8, Hz, 1H), 4.48 m, 2H), 4.24-4.19 (m, 2H), 3.17 (s, 3H), 2.30 (s, 3H), 2.16 (s, 3H). m/z: 488.3 $[M+H]^+$, (ESI+), RT=2.65 min LCMS Method 6.

Example 20

Compound 1432: 6-Cyano-3-(4-fluoro-2-methyl-phenoxy)-5-methyl-N-[3(methylsulfonimidoyl)phenyl]pyridazine-4-carboxamide

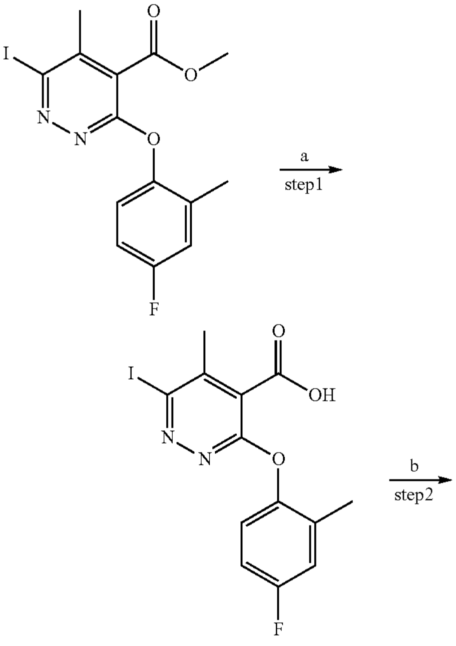

-continued

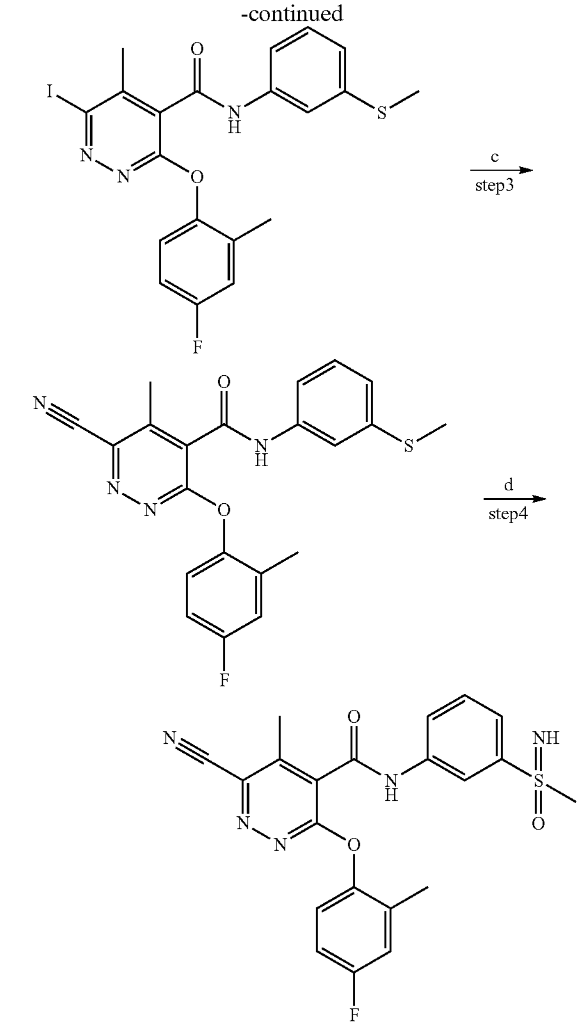

Reagents & conditions:
a) LiOH, THF, water, rt, 40 h.
b) 3-(methylsulfanyl)aniline, HATU, DIPEA, DMF, rt, 40 h.
b) HATU, 3-(methylsulfanyl)aniline, DIPEA, DMF, rt, 16 h.
c) $Pd(OAc)_2$, DPEphos, $K_4[Fe(CN)_6]•3H_2O$, $Na_2CO_3$, 1,4-dioxane, water, NMP 70 °C, 21 h. d) PIDA, $(NH_4)_2CO_3$, MeOH, rt, 16 h.

Step 1: 3-(2-fluoro-4-methyl-phenoxy)-6-iodo-5-methyl-pyridazine-4-carboxylic acid:Lithium; hydroxide (126 mg, 5.05 mmol) was added to a mixture of methyl 3-(2-fluoro-4-methyl-phenoxy)-6-iodo-5-methyl-pyridazine-4-carboxylate (677 mg, 1.68 mmol) in THF (11 mL) and Water (1.7 mL) and the mixture was stirred at rt for 40 h. The reaction was diluted with water (20 mL) and the pH was adjusted to 1 by dropwise addition of 2M HCl (aq). The aqueous layer was extracted with EtOAc (3×20 mL). The organic phase was dried over sodium sulfate, filtered and concentrated to dryness in vacuum to give the title compound 3-(2-fluoro-4-methyl-phenoxy)-6-iodo-5-methyl-pyridazine-4-carboxylic acid (617 mg, 1.59 mmol, 94%) as a pale yellow solid which was used as such in the next step. LC-MS: m/z: 389 $[M+H]^+$, (ESI+), RT=0.61 METCR1410 Generic 2 min Step 2: 3-[2,6-difluoro-4-(trifluoromethoxy)phenoxy]-5-methyl-N-(3-methylsulfanylphenyl)-6-(trifluoromethyl) pyridazine-4-carboxamide: HATU (665 mg, 1.75 mmol) was added to a mixture of 3-(4-fluoro-2-methyl-phenoxy)-6-iodo-5-methyl-pyridazine-4-carboxylic acid (617 mg, 1.59 mmol) and N-ethyl-N-isopropyl-propan-2-amine (555 uL, 3.18 mmol) in DMF (11.5 mL) at rt and the reaction was stirred at rt for 5 min, then 3-(methylsulfanyl)aniline (235 uL, 1.91 mmol) was added and the reaction was stirred at rt for 16 h. The reaction mixture was diluted with EtOAc (50 mL) and washed with water (3×50 ml). The organic phase was washed with brine, dried over sodium sulfate, filtered and concentrated to dryness to give crude product. Purification by FCC (Biotage Isolera, $SiO_2$ gradient elution 10-30% EtOAc:Heptanes) gave the title compound 3-(4-fluoro-2-methyl-phenoxy)-6-iodo-5-methyl-N-(3-methylsulfanylphenyl)pyridazine-4-carboxamide (682 mg, 68%) as a yellow solid. $^1H$ NMR (400 MHz, $CDCl_3$) δ 7.63 (s, 1H), 7.37-7.26 (m, 3H), 7.19-7.04 (m, 2H), 6.94 (dd, J=8.8, 3.0 Hz, 1H), 6.86 (td, J=8.3, 3.1 Hz, 1H), 2.69-2.52 (m, 3H), 2.50 (s, 3H), 2.15 (d, J=4.6 Hz, 3H). m/z: 510 $[M+H]^+$, (ESI+), RT=1.02 min METCR1410 Generic 2 min Step 3: 6-cyano-3-(4-fluoro-2-methyl-phenoxy)-5-methyl-N-(3-methylsulfanylphenyl)pyridazine-4-carboxamide: Palladium acetate (4.4 mg, 0.0196 mmol) was added to a stirred, $N_2$ degassed solution of 3-(4-fluoro-2-methyl-phenoxy)-6-iodo-5-methyl-N-(3-methylsulfanylphenyl) pyridazine-4-carboxamide (50 mg, 0.0982 mmol), potassium hexacyanoferrate(II) trihydrate (36 mg, 0.0982 mmol), sodium carbonate (21 mg, 0.196 mmol) and [2-(2-diphenylphosphanylphenoxy)phenyl]-diphenyl-phosphane (21 mg, 0.0393 mmol) in 1,4-Dioxane (0.28 mL) and Water (0.28 mL). The reaction mixture was heated at 70 °C for 1 h in a pressure vial. Reaction seemed inhomogeneous, therefore NMP (0.25 mL) was added and the reaction was stirred overnight (20 h) at 70 °C. The reaction mixture was diluted with EtOAc (30 mL) and washed with water (3×20 mL) and brine, dried over sodium sulfate, filtered and concentrated to dryness in vacuum to give crude product (~130 mg). Purification by FCC (Biotage Isolera, $SiO_2$, gradient elution 0-50% EtOAc:Heptanes) gave the title compound 6-cyano-3-(4-fluoro-2-methyl-phenoxy)-5-methyl-N-(3-methylsulfanylphenyl)pyridazine-4-carboxamide (99.0%) (30 mg, 0.0727 mmol, 74%) as a yellow solid. LC-MS: m/z: 409 $[M+H]^+$, (ESI+), RT=0.99 min METCR1410 Generic 2 min Step 4: 6-cyano-3-(4-fluoro-2-methyl-phenoxy)-5-methyl-[3(methylsulfonimidoyl)phenyl]pyridazine-4-carboxamide: Phenyl Iodonium Di-Acetate (PIDA) (54 mg, 0.169 mmol) and diammonium carbonate (10 mg, 0.110 mmol) were added to a solution of 6-cyano-3-(4-fluoro-2-methyl-phenoxy)-5-methyl-N-(3-methylsulfanylphenyl) pyridazine-4-carboxamide (30 mg, 0.0734 mmol) in Methanol (1 mL) at rt and the reaction was stirred at rt for 16 h. The reaction mixture was concentrated to dryness in vacuum to give crude product. Purification by FCC (Biotage isolera, gradient elution 0-100% EtOAc:Heptanes,) gave the title compound below required % purity therefore the product was further purified by low pH prep HPLC (early method). The product containing fractions were combined and the solvent was removed in vacuo by freeze drying overnight, to give the title compound 6-cyano-3-(4-fluoro-2-methyl-phenoxy)-5-methyl-N-[3-(methylsulfonimidoyl)phenyl] pyridazine-4-carboxamide (99.0%) (6.1 mg, 0.0137 mmol, 19%) as an off white solid. $^1H$ NMR (400 MHz, $CD_3OD$) δ 8.44 (t, J=1.9 Hz, 1H), 7.99-7.92 (m, 1H), 7.87-7.81 (m, 1H), 7.67 (t, J=8.0 Hz, 1H), 7.21 (dd, J=8.9, 4.9 Hz, 1H), 7.09 (dd, J=9.0, 3.0 Hz, 1H), 7.06-6.97 (m, 1H), 3.17 (s, 3H), 2.62 (s, 3H), 2.16 (s, 3H). LC-MS: m/z 440 $[M+H]^+$, (ESI+), RT=2.83 min MET-uPLC-AB-101 (7 min, low pH).

Example 21

Compound 1433: 6-Cyclopropyl-3-(4-fluoro-2-methyl-phenoxy)-5-methyl-N-[(methylsulfonimidoyl)phenyl]pyridazine-4-carboxamide

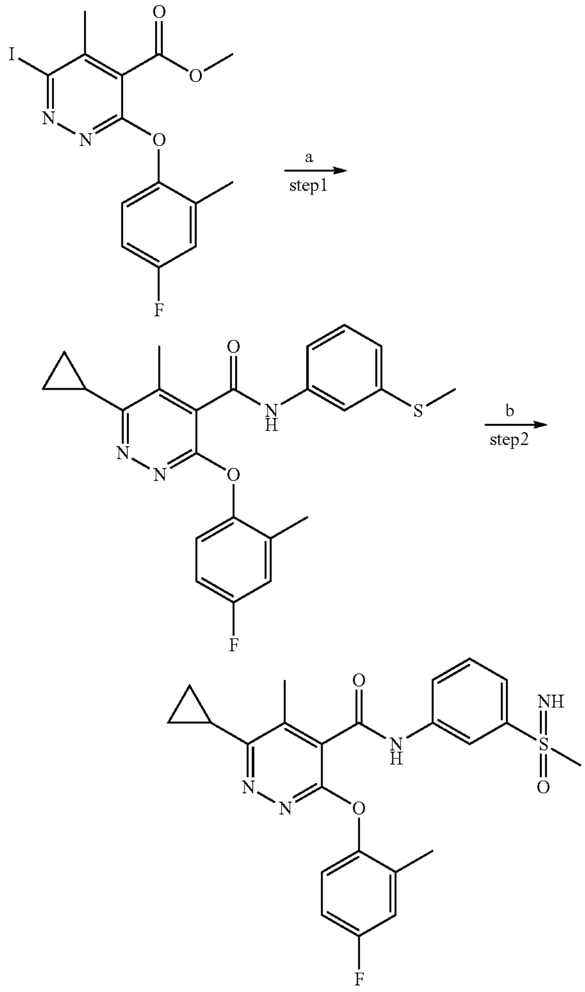

Reagents & conditions: a) $Pd(PPh_3)_4$, $CyclopropylSnBu_3$, toluene, 70 °C, 16 h. b) PIDA, $(NH_4)_2CO_3$, MeOH, rt, 4 days.

Step 1: 6-cyclopropyl-3-(4-fluoro-2-methyl-phenoxy)-5-methyl-N-(3-methylsulfanylphenyl)pyridazine-4-carboxamide: Palladium-triphenylphosphane (1:4) (18 mg, 0.0159 mmol) was added to a stirred, $N_2$ degassed solution of 3-(4-fluoro-2-methyl-phenoxy)-6-iodo-5-methyl-N-(3-methylsulfanylphenyl)pyridazine-4-carboxamide (81 mg, 0.159 mmol) and tributyl(cyclopropyl)stannane in Toluene Anhydrous (0.5 mL) and the reaction mixture was stirred at 70 °C for 16 h in a pressure vial. The reaction mixture was concentrated to dryness in vacuum to give crude product. Purification by FCC (Biotage Isolera, $SiO_2$, gradient elution 0-30% EtOAc:Heptanes) gave the title compound 6-cyclopropyl-3-(4-fluoro-2-methyl-phenoxy)-5-methyl-N-(3-methylsulfanylphenyl)pyridazine-4-carboxamide (66.0%) (98 mg, 0.153 mmol, 96%) as a pale yellow oil. LC-MS: m/z 424 $[M+H]^+$, (ESI+), RT=1.00 min METCR1410 Generic 2 min Step 2: 6-cyclopropyl-3-(4-fluoro-2-methyl-phenoxy)-5-methyl-N-[(methylsulfonimidoyl)phenyl]pyridazine-4-carboxamide:Phenyl Iodonium Di-Acetate (PIDA) (226 mg, 0.703 mmol) and diammonium carbonate (43 mg, 0.458 mmol) were added to a solution of 6-cyclopropyl-3-(4-fluoro-2-methyl-phenoxy)-5-methyl-N-(3-methylsulfanylphenyl)pyridazine-4-carboxamide (66%, 98 mg, 0.153 mmol) in methanol (2.2 mL) at rt and the reaction was stirred at rt for 4 days. The reaction mixture was concentrated under reduced pressure and purified by column chromatography Biotage Isolera $SiO_2$, gradient elution (0-100% EtOAc: Heptanes). The product was below required purity, therefore the product was purified by low pH prep HPLC (early method). The product containing fractions were combined and the solvent was removed in vacuum by freeze drying overnight, to give the title compound 6-cyclopropyl-3-(4-fluoro-2-methyl-phenoxy)-5-methyl-N-[3-(methylsulfonimidoyl)phenyl]pyridazine-4-carboxamide (100.0%) (22 mg, 0.0477 mmol, 31%) as an off-white solid. $^1H$ NMR (500 MHz, $CD_3OD$) δ 8.45 (t, J=1.9 Hz, 1H), 7.99-7.92 (m, 1H), 7.87-7.78 (m, 1H), 7.65 (t, J=8.0 Hz, 1H), 7.13 (dd, J=8.9, 4.9 Hz, 1H), 7.03 (dd, J=9.1, 3.0 Hz, 1H), 6.95 (td, J=8.5, 3.1 Hz, 1H), 3.17 (s, 3H), 2.54 (s, 3H), 2.24 (p, J=6.6 Hz, 1H), 2.15 (s, 3H), 1.09 (d, J=6.4 Hz, 4H). LC-MS: m/z 455 $[M+H]^+$, (ESI+), RT=2.63 min MET-uPLC-AB-101 (7 min, low pH).

Example 22

Compound 1434: 3-(4-Fluoro-2-methylphenoxy)-5-methyl-N-(3-(S-methylsulfonimidoyl)phenyl)-6-(prop-1-yn-1-yl)pyridazine-4-carboxamide

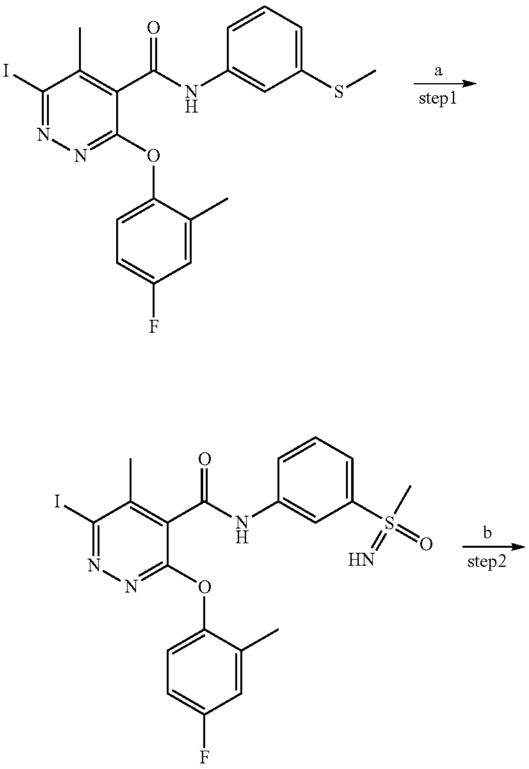

-continued

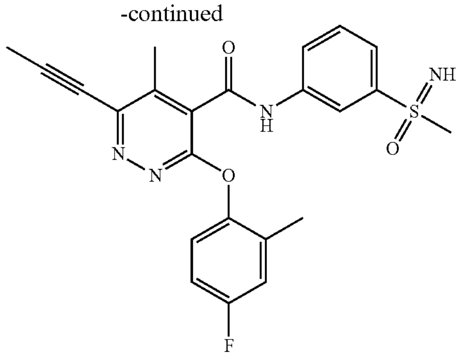

Reagents & conditions: a) PIDA, $(NH_4)_2CO_3$, MeOH, rt, 5 h. b) prop-1-yne (1M in THF), $PdCl_2(dppf)$, CuI, THF 70 °C Step 1: 3-(4-fluoro-2-methyl-phenoxy)-6-iodo-5-methyl-N-[3-(methylsulfonimidoyl)phenyl]pyridazine-4-carboxamide: Phenyl Iodonium Di-Acetate (PIDA) (780 mg, 2.42 mmol) and diammonium carbonate (158 mg, 1.68 mmol) were added to a solution of 3-(4-fluoro-2-methyl-phenoxy)-6-iodo-5-methyl-N-(3-methylsulfanylphenyl)pyridazine-4-carboxamide (536 mg, 1.05 mmol) in Methanol (15 mL) at rt and the reaction was stirred at rt for 5 h. The reaction mixture was concentrated to dryness in vacuum to give crude product. Purification by FCC (Biotage Isolera, gradient elution 10-100% EtOAc:Heptanes) gave the title compound 3-(4-fluoro-2-methyl-phenoxy)-6-iodo-5-methyl-N-[3-(methylsulfonimidoyl)phenyl]pyridazine-4-carboxamide (89.0%) (520 mg, 0.856 mmol, 81%) as a pale yellow solid. LC-MS: m/z 541 $[M+H]^+$, (ESI+), RT=0.75 METCR1410 Generic 2 min Step 2: 3-(4-fluoro-2-methylphenoxy)-5-methyl-N-(3-(S-methylsulfonimidoyl)phenyl)-6-(prop-1-yn-1-yl)pyridazine-4-carboxamide: A solution of 1 M prop-1-yne (1 Min THF) (925 uL, 0.925 mmol) was added to a stirred, N2 degassed mixture of 3-(4-fluoro-2-methyl-phenoxy)-6-iodo-5-methyl-N-[3-(methylsulfonimidoyl)phenyl]pyridazine-4-carboxamide (50 mg, 0.0925 mmol), copper(1+) iodide (21 mg, 0.111 mmol) and 1,1□ bis(diphenylphosphanyl)ferrocene-dichloropalladium (1:1) (6.8 mg, 9.25 μmol) in THF-Anhydrous (0.5 mL) and the reaction mixture was stirred at rt for 20 h in a pressure vial. The reaction mixture was concentrated to dryness in vacuum to give crude product. Purification by FCC (Biotage Isolera, $SiO_2$, gradient elution 0-30% EtOAc:Heptanes) gave the title compound which was below required purity spec, therefore the product was purified by low pH prep HPLC (standard method). The product containing fractions were combined and the solvent was removed in vacuum, to give the title compound 3-(4-fluoro-2-methyl-phenoxy)-5-methyl-N-[3-(methylsulfonimidoyl)phenyl]-6-prop-1-ynyl-pyridazine-4-carboxamide (100.0%) (15 mg, 0.0340 mmol, 37%) as an off white solid. $^1H$ NMR (400 MHz, $CD_3OD$) δ 8.44 (t, J=1.9 Hz, 1H), 7.99-7.92 (m, 1H), 7.85-7.78 (m, 1H), 7.65 (t, J=8.0 Hz, 1H), 7.17 (dd, J=8.9, 4.9 Hz, 1H), 7.05 (dd, J=9.1, 3.0 Hz, 1H), 7.02-6.94 (m, 1H), 3.17 (s, 3H), 2.51 (s, 3H), 2.19 (s, 3H), 2.16 (s, 3H). LC-MS: m/z 453.3 $[M+H]^+$, (ESI+), RT=2.78 MET-uPLC-AB-107 (7 min, high pH).

Example 23

Compound 1435: 3-(3,4-difluoro-2-methoxyphenoxy)-5,6-dimethyl-N-(3-(S-methylsulfonimidoyl)phenyl)pyridazine-4-carboxamide

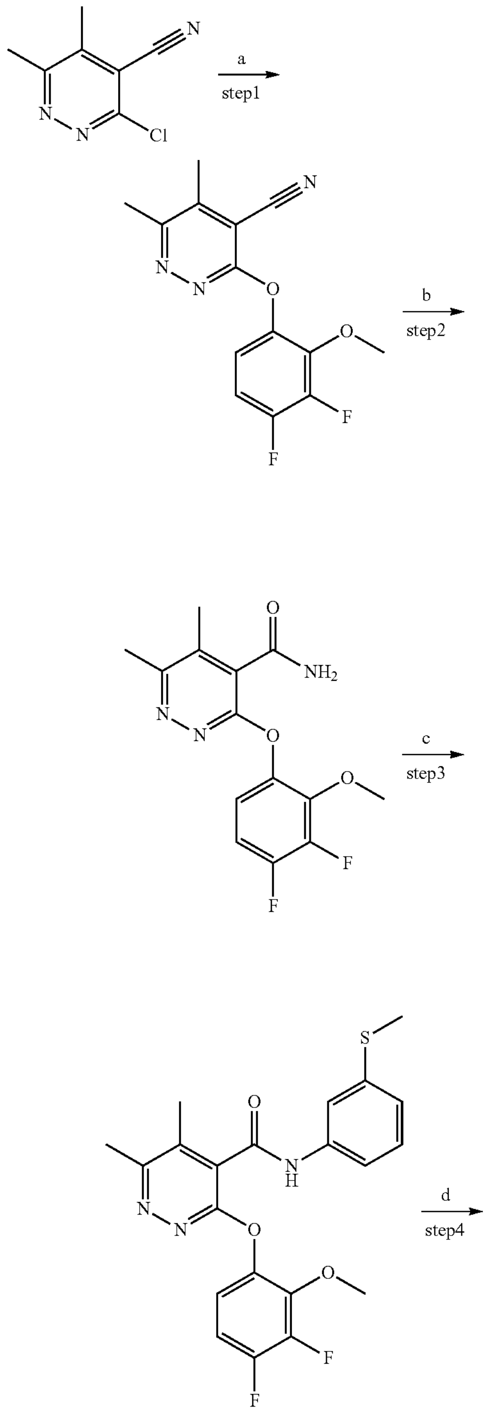

-continued

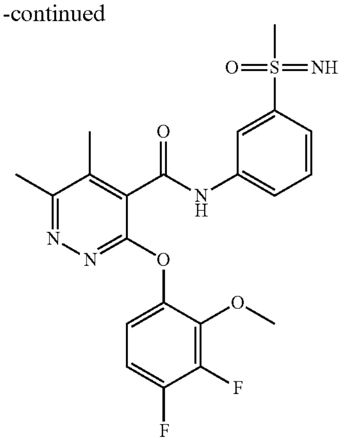

Reagents & conditions:
a) 3-chloro-5,6-dimethylpyridazine-4-carbonitrile, $K_2CO_3$, MeCN, 70 °C, 18 h
b) barium dihydroxide, $H_2O$, 80 °C, 17 h
c) 1-bromo-3-(methylsulfanyl)benzene, dicaesium carbonate, $Pd_2(dba)_3$, XantPhos, 1,4-Dioxane, 100 °C, 4 h
d) PIDA, diammonium carbonate, MeOH, rt, 17 h Step 1: 3-(3,4-difluoro-2-methoxy-phenoxy)-5,6-dimethyl-pyridazine-4-carbonitrile A mixture of 3,4-difluoro-2-methoxy-phenol (1.00 g, 6.25 mmol), 3-chloro-5,6-dimethylpyridazine-4-carbonitrile (1.00 g, 5.97 mmol) and dipotassium; carbonate (1.25 g, 9.04 mmol) in Acetonitrile (8.5 mL) was stirred at 70 °C for 18 h. The reaction was filtered, washed with EtOAc (2×) and the filtrate was washed with brine, the organics separated, dried over MgSO4, filtered and concentrated under reduced pressure. The crude material was then purified using the Biotage Isolena 4 flash purification system (Sfar Duo 50 g, 0-45% EtOAc in heptanes). Fractions containing the product were combined and evaporated in vacuo to the desired product 3-(3,4-difluoro-2-methoxy-phenoxy)-5,6-dimethyl-pyridazine-4-carbonitrile (97.0%) (1.70 g, 5.66 mmol, 95%) as an off-white powder.

Step 2: 3-(3,4-difluoro-2-methoxy-phenoxy)-5,6-dimethyl-pyridazine-4-carboxamide: 3-(3,4-difluoro-2-methoxy-phenoxy)-5,6-dimethyl-pyridazine-4-carbonitrile (97%, 200 mg, 0.666 mmol) was dissolved in Water (6 mL) and barium dihydroxide (560 mg, 3.27 mmol) was added. The resulting solution was stirred at 80 °C for 17 h. The solution was neutralised to pH 7 with 2M hydrochloric acid (aq) and the precipitate was filtered off and washed with water (×3) and EtOAc (×2). The solid was dried in a vacuum oven overnight to yield the desired product 3-(3,4-difluoro-2-methoxy-phenoxy)-5,6-dimethyl-pyridazine-4-carboxamide (98.0%) (200 mg, 0.634 mmol, 95%) as a white powder.

Step 3: 3-(3,4-difluoro-2-methoxy-phenoxy)-5,6-dimethyl-N-(3-methylsulfanylphenyl)pyridazine-4-carboxamide: To a degassed solution of 3-(3,4-difluoro-2-methoxy-phenoxy)-5,6-dimethyl-pyridazine-4-carboxamide (180 mg, 0.582 mmol), 1-bromo-3-(methylsulfanyl)benzene (142 mg, 0.699 mmol) and dicaesium carbonate (567 mg, 1.74 mmol) in anhydrous 1,4-Dioxane (3 mL) was added (1E,4E)-1,5-diphenylpenta-1,4-dien-3-one-palladium (3:2) (27 mg, 0.0295 mmol) and (9,9-dimethyl-9H-xanthene-4,5-diyl)bis(diphenylphosphane) (34 mg, 0.0588 mmol) and the reaction was degassed for a further 5 minutes. The vial was then sealed, and reaction stirred at 100 °C for 4 hours. The reaction mixture was then diluted with DCM and filtered through a phase separator. The filtrate was then washed with aq sat sodium bicarbonate solution, followed by brine. The organic extract was then dried with anhydrous sodium sulfate, filtered and concentrated under vacuum. The crude product was purified by column chromatography (Sfar Duo 10 g, eluting in 0-100% EtOAc in Heptanes). Fractions containing the product (F41-54) were combined to give the desired product, 3-(3,4-difluoro-2-methoxy-phenoxy)-5,6-dimethyl-N-(3-methylsulfanylphenyl)pyridazine-4-carboxamide (109 mg, 0.174 mmol, 30%) as a yellow solid.

Step 4: 3-(3,4-difluoro-2-methoxyphenoxy)-5,6-dimethyl-N-(3-(S-methylsulfonimidoyl)phenyl)pyridazine-4-carboxamide: diammonium carbonate (26 mg, 0.276 mmol) and bis(acetyloxy)(phenyl)-lambda~3~-iodane (PIDA) (130 mg, 0.404 mmol) were added to a solution of 3-(3,4-difluoro-2-methoxy-phenoxy)-5,6-dimethyl-N-(3-methylsulfanylphenyl)pyridazine-4-carboxamide (69%, 109 mg, 0.174 mmol) in Methanol (2 mL) at rt and the reaction was stirred at rt for 17 h. The reaction mixture was concentrated to dryness in vacuo to give crude product which was purified by prep-HPLC (Acidic Early Elute Method). Combination of fractions containing the product, evaporation in vacuo and freeze drying overnight gave the title compound, 3-(3,4-difluoro-2-methoxy-phenoxy)-5,6-dimethyl-N—[3-(methylsulfonimidoyl)phenyl]pyridazine-4-carboxamide (41 mg, 51%) as an off-white powder. $^1H$ NMR (400 MHz, DMSO-$d_6$) δ 11.18 (s, 1H), 8.42-8.36 (m, 1H), 7.90-7.83 (m, 1H), 7.74-7.67 (m, 1H), 7.64-7.58 (m, 1H), 7.30-7.20 (m, 1H), 7.17-7.10 (m, 1H), 4.24 (s, 1H), 3.81-3.76 (m, 3H), 3.08-3.04 (m, 3H), 2.58 (s, 3H), 2.33 (s, 3H). m/z: 463.2 $[M+H]^+$, (ESI+), RT=2.46 LCMS Method 6.

Example 24

Compound 1436: 3-(4-cyano-2-methoxyphenoxy)-5-methyl-N-(3-(S-methylsulfonimidoyl)phenyl)-6-phenylpyridazine-4-carboxamide

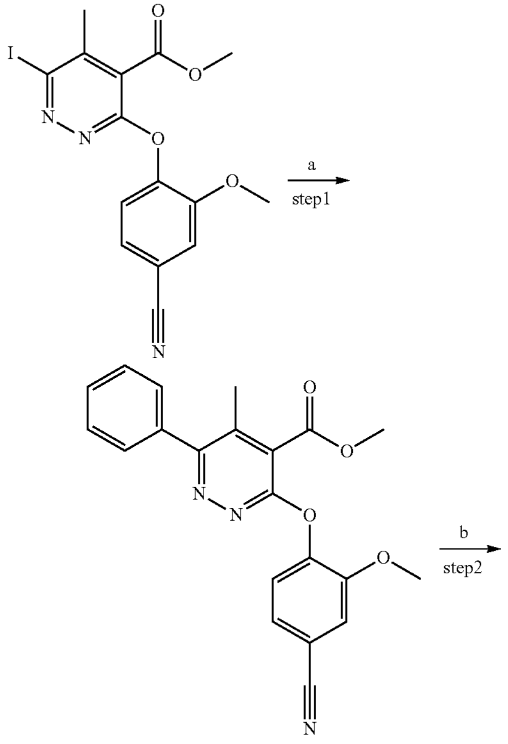

-continued

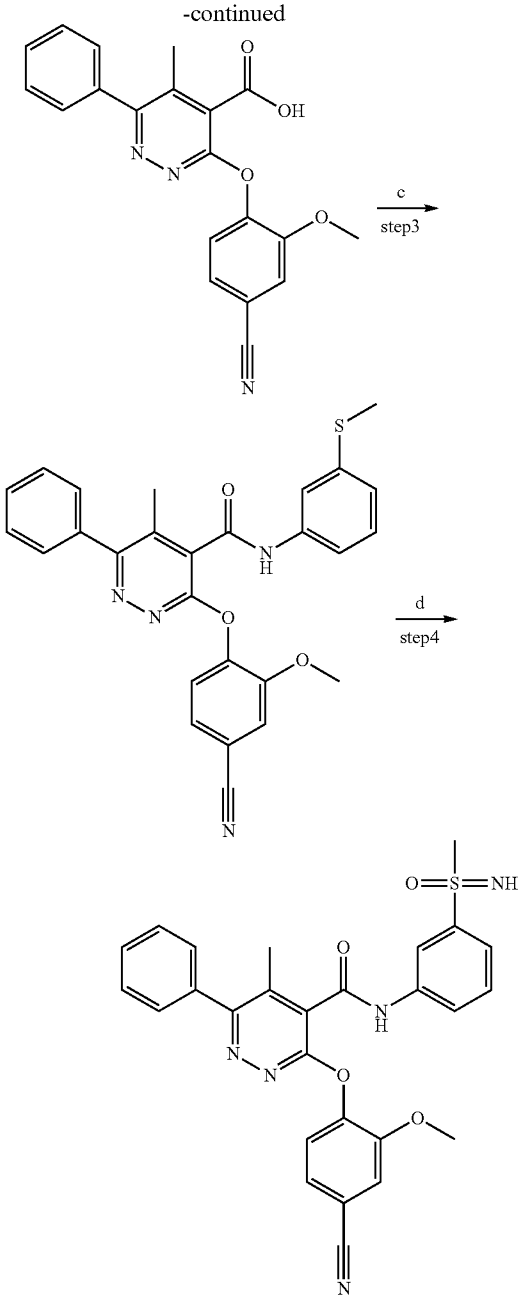

Reagents & conditions:

a) $PdCl_2(dppf)$, $PhB(OH)_3$, $Na_2CO_3$, 1,4-dioxane, water, 90 °C, 1 h.

b) LiOH, THF, water, rt, 2 days.

c) HATU, 3-(methylsufanyl)aniline, DIPEA, DMF, rt, 2 h.

d) PIDA, $(NH_4)_2CO_3$, MeOH, rt, 16 h,

Step 1: methyl 3-(4-cyano-2-methoxy-phenoxy)-5-methyl-6-phenyl-pyridazine-4-carboxylate: 1,1'-bis(diphenylphosphanyl)ferrocene-dichloropalladium (1:1) (17 mg, 0.0235 mmol) was added to a stirred, N2 degassed solution of methyl 3-(4-cyano-2-methoxy-phenoxy)-6-iodo-5-methyl-pyridazine-4-carboxylate (100 mg, 0.235 mmol), phenylboronic acid (43 mg, 0.353 mmol) and, 2 M disodium carbonate (0.35 mL, 0.706 mmol) in 1,4-Dioxane (3.5 mL). The reaction mixture was stirred at 90 °C for 1 h in a pressure vial. The reaction mixture was diluted with EtOAc (30 mL) and washed with water (3×20 ml) and brine, dried over sodium sulfate, filtered and concentrated to dryness in vacuo to give crude product. The residue was purified by FCC (Biotage Isolera, SiO2, gradient elution 10-100% EtOAc:Heptanes) gave the title compound methyl 3-(4-cyano-2-methoxy-phenoxy)-5-methyl-6-phenyl-pyridazine-4-carboxylate (85 mg, 0.226 mmol, 96%) as an off white solid. LC-MS: m/z: 376 $[M+H]^+$, (ESI+), RT=0.92 METCR1704 (2 minute uPLC gradient method for IPCs).

Step 2: 3-(4-cyano-2-methoxy-phenoxy)-5-methyl-6-phenyl-pyridazine-4-carboxylic acid: Lithium hydroxide (20 mg, 0.835 mmol) was added to a stirred solution of methyl 3-(4-cyano-2-methoxy-phenoxy)-5-methyl-6-phenyl-pyridazine-4-carboxylate (85 mg, 0.226 mmol) in THF (2 mL) and Water (0.25 mL) The reaction mixture was stirred at rt for 2 days. 1M HCl aq. was added to the reaction mixture to pH ~2 and the reaction was extracted with EtOAc (3×20 mL). The organic phase was dried with sodium sulfate, filtered and concentrated to dryness in vacuum to give crude product 3-(4-cyano-2-methoxy-phenoxy)-5-methyl-6-phenyl-pyridazine-4-carboxylic acid (83.0%) (64 mg, 0.147 mmol, 65%) as an off white solid, which was used as such in the next step. Assumed 100% molar yield. LC-MS: m/z 362 $[M+H]^+$, (ESI+), RT=0.65 METCR1704 (2 minute uPLC gradient method for IPCs).

Step 3: 3-(4-cyano-2-methoxy-phenoxy)-5-methyl-N-(3-methylsulfanylphenyl)-6-phenyl-pyridazine-4-carboxamide: HATU (74 mg, 0.195 mmol) was added to a mixture of 3-(4-cyano-2-methoxy-phenoxy)-5-methyl-6-phenyl-pyridazine-4-carboxylic acid (64 mg, 0.177 mmol) and N-ethyl-N-isopropyl-propan-2-amine (68 uL, 0.390 mmol) in DMF (1.1 mL) at rt and the reaction was stirred at rt for 5 min then 3-(methylsulfanyl)aniline (33 uL, 0.266 mmol) was added and the reaction was stirred at rt for 2 h. The reaction mixture was diluted with EtOAc (~50 mL) and washed with water (3×50 ml). The organic phase was washed with brine, dried over sodium sulfate, filtered and concentrated to dryness to give crude product. Purification by FCC (Biotage Isolera, $SiO_2$ gradient elution 10-80% EtOAc:Heptanes) gave the title compound 3-(4-cyano-2-methoxy-phenoxy)-5-methyl-N-(3-methylsulfanylphenyl)-6-phenyl-pyridazine-4-carboxamide (76.0%)(79 mg, 0.124 mmol, 70%) as a yellow gum. LC-MS: m/z 483 $[M+H]^+$, (ESI+), RT=1.03 METCR1704 (2 minute uPLC gradient method for IPCs).

Step 4: 3-(4-cyano-2-methoxy phenoxy)-5-methyl-N-(3-(S-methylsulfonimidoyl)phenyl)-6-phenylpyridazine-4-carboxamide: 3-(4-cyano-2-methoxy-phenoxy)-5-methyl-N-[3-(methylsulfonimidoyl)phenyl]-6-phenyl-pyridazine-4-carboxamide, Phenyl Iodonium Di-Acetate (PIDA) (121 mg, 0.377 mmol) and diammonium carbonate (25 mg, 0.262 mmol) were added to a solution of 3-(4-cyano-2-methoxy-phenoxy)-5-methyl-N-(3-methylsulfanylphenyl)-6-phenyl-pyridazine-4-carboxamide (79 mg, 0.164 mmol) in methanol (2.5 mL) at rt and the reaction was stirred at rt for 16 h. The reaction mixture was concentrated to dryness in vacuum to give crude product. The residue was purified by low pH prep HPLC (early method). The product containing fractions were combined and the solvent was removed in vacuum, to give the title compound 3-(4-cyano-2-methoxy-phenoxy)-5-methyl-N-[3-(methylsulfonimidoyl)phenyl]-6-phenyl-pyridazine-4-carboxamide (17 mg, 0.0327 mmol, 20%) as an off white solid. $^1H$ NMR (400 MHz, $CD_3OD$) δ 8.46 (t, J=1.9 Hz, 1H), 8.00-7.95 (m, 1H), 7.85-7.80 (m, 1H), 7.66 (t, J=8.0 Hz, 1H), 7.59-7.49 (m, 6H), 7.48-7.39 (m, 2H), 3.83 (s, 3H), 3.17 (s, 3H), 2.41 (s, 3H). LC-MS: m/z 514 $[M+H]^+$, (ESI+), RT=2.78 min MET-uPLC-AB-107 (7 min, high pH).

Example 25

Compound 1437: 3-(4-cyano-2-methoxy-phenoxy)-N-[3-(3-hydroxyazetidine-1-carbonyl)phenyl]-5-methyl-6-(trifluoromethyl)pyridazine-4-carboxamid

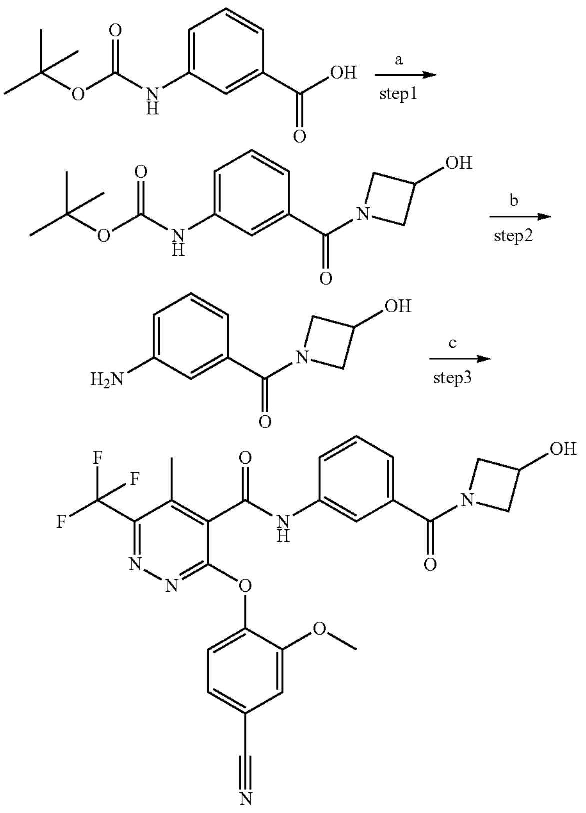

Reagents & conditions:
a) 3-hydroxyazetidine hydrochloride, HATU, DIPEA, DCM. RT, 18 h
b) TFA, DCM, RT, 66 h
c) 3-(4-cyano-2-methoxy-phenoxy)-5-methyl-6-(trifluoromethyl)pyridazine-4-carboxylic acid, HATU, DIPEA, DMF, RT, 16 h Step 1: tert-butyl N-[3-(3-hydroxyazetidine-1-carbonyl)phenyl]carbamate: To a mixture of 3-[(tert-butoxycarbonyl)amino]benzoic acid (200 mg, 0.843 mmol), HATU (385 mg, 1.01 mmol) and DIPEA (442 uL, 2.53 mmol) in DCM (3 mL) was added 3-hydroxyazetidine·HCl (111 mg, 1.01 mmol). The reaction mixture was stirred at room temperature for 18 h then partitioned between DCM (10 mL) and water (10 mL). The layers were separated, and the aqueous phase extracted with DCM (2×10 mL). The combined organics were washed with brine (10 mL), dried using a phase separator and concentrated under reduced pressure. The resulting crude product was purified by FCC (Biotage Isolera 4, 25 g Sfar Duo, lambda-all collect) using a 0-100% EtOAc/heptane followed by a 0-20% MeOH/EtOAc gradient to afford tert-butyl N-[3-(3-hydroxyazetidine-1-carbonyl)phenyl]carbamate (68.0%) (312 mg, 0.726 mmol, 86%) as a colorless gum. $^1$H NMR (500 MHz, DMSO-$d_6$) δ 9.49 (s, 1H), 7.75 (s, 1H), 7.58-7.53 (m, 1H), 7.31 (t, J=7.9 Hz, 1H), 7.18 (dt, J=7.7, 1.2 Hz, 1H), 5.74 (d, J=6.3 Hz, 1H), 4.52-4.45 (m, 1H), 4.39 (t, J=7.7 Hz, 1H), 4.27-4.18 (m, 1H), 4.01-3.96 (m, 1H), 3.80-3.71 (m, 1H), 1.48 (s, 9H). m/z: 293.1 $[M+H]^+$, (ESI+), RT=0.66 LCMS Method M2.

Step 2: (3-aminophenyl)-(3-hydroxyazetidin-1-yl)methanone: To a solution of tert-butyl N-[3-(3-hydroxyazetidine-1-carbonyl)phenyl]carbamate (68%, 312 mg, 0.726 mmol) in DCM (3 mL) was added trifluoroacetic acid (1.1 mL, 14.5 mmol). The reaction mixture was stirred at room temperature for 66 h then concentrated under reduced pressure. The resulting residue was co-evaporated with DCM-heptane (1:1) three times. The crude product was dissolved in MeOH (~1 mL) and loaded to a pre-wet SCX-2 cartridge (5 g, 25 mL). After washing with MeOH the product was eluted with ~2.5M $NH_3$ in MeOH. The product fractions were combined and concentrated under reduced pressure to afford (3-aminophenyl)-(3-hydroxyazetidin-1-yl)methanone (80.0%) (138 mg, 0.574 mmol, 79%) as a pale yellow opaque gum. $^1$H NMR (400 MHz, DMSO-$d_6$) δ 7.05 (t, J=7.8 Hz, 1H), 6.83-6.79 (m, 1H), 6.69 (dt, J=7.6, 1.2 Hz, 1H), 6.65 (ddd, J=8.0, 2.3, 0.9 Hz, 1H), 5.71 (br.s, 1H), 5.23 (br.s, 2H), 4.51-4.42 (m, 1H), 4.41-4.32 (m, 1H), 4.24-4.14 (m, 1H), 4.00-3.91 (m, 1H), 3.78-3.67 (m, 1H). m/z: 193.1 $[M+H]^+$, (ESI+), RT=0.23 LCMS Method M2.

Step 3: 3-(4-cyano-2-methoxy-phenoxy)-N-[3-(3-hydroxyazetidine-1-carbonyl)phenyl]-5-methyl-6-(trifluoromethyl)pyridazine-4-carboxamide: To a mixture of 3-(4-cyano-2-methoxy-phenoxy)-5-methyl-6-(trifluoromethyl)pyridazine-4-carboxylic acid (93%, 50 mg, 0.132 mmol), HATU (60 mg, 0.158 mmol) and DIPEA (46 uL, 0.263 mmol) in DMF (0.5 mL) was added (3-aminophenyl)-(3-hydroxyazetidin-1-yl)methanone (80%, 38 mg, 0.158 mmol). The reaction mixture was stirred at room temperature for 16 h then diluted with DMSO-MeCN-water (3:2:1, 1 mL), filtered and purified by prep HPLC (Prep Method 4). Product fractions were combined and concentrated under reduced pressure. The resulting residue was freeze-dried from MeCN-water (1:1) to afford 3-(4-cyano-2-methoxy-phenoxy)-N-[3-(3-hydroxyazetidine-1-carbonyl)phenyl]-5-methyl-6-(trifluoromethyl)pyridazine-4-carboxamide (99.0%) (32 mg, 0.0595 mmol, 45%) as a white powder. $^1$H NMR (400 MHz, DMSO-$d_6$) δ 11.13 (s, 1H), 8.00 (t, J=1.9 Hz, 1H), 7.79-7.72 (m, 2H), 7.56 (dd, J=8.2, 1.8 Hz, 1H), 7.53-7.45 (m, 2H), 7.40 (dt, J=7.8, 1.3 Hz, 1H), 5.77 (s, 1H), 4.57-4.39 (m, 2H), 4.31-4.21 (m, 1H), 4.08-3.97 (m, 1H), 3.85-3.76 (m, 4H), 2.52-2.51 (m, 3H). m/z: 528.2 $[M+H]^+$, (ESI+), RT=2.71 LCMS Method M4.

Example 26

Compound 1438: 3-(4-cyano-2-methoxy-phenoxy)-5-methyl-N-[3-(piperazine-1-carbonyl)phenyl]-6-(trifluoromethyl)pyridazine-4-carboxamide

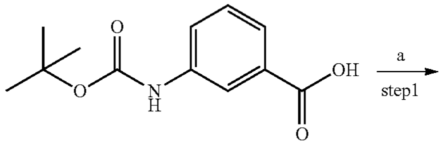

-continued

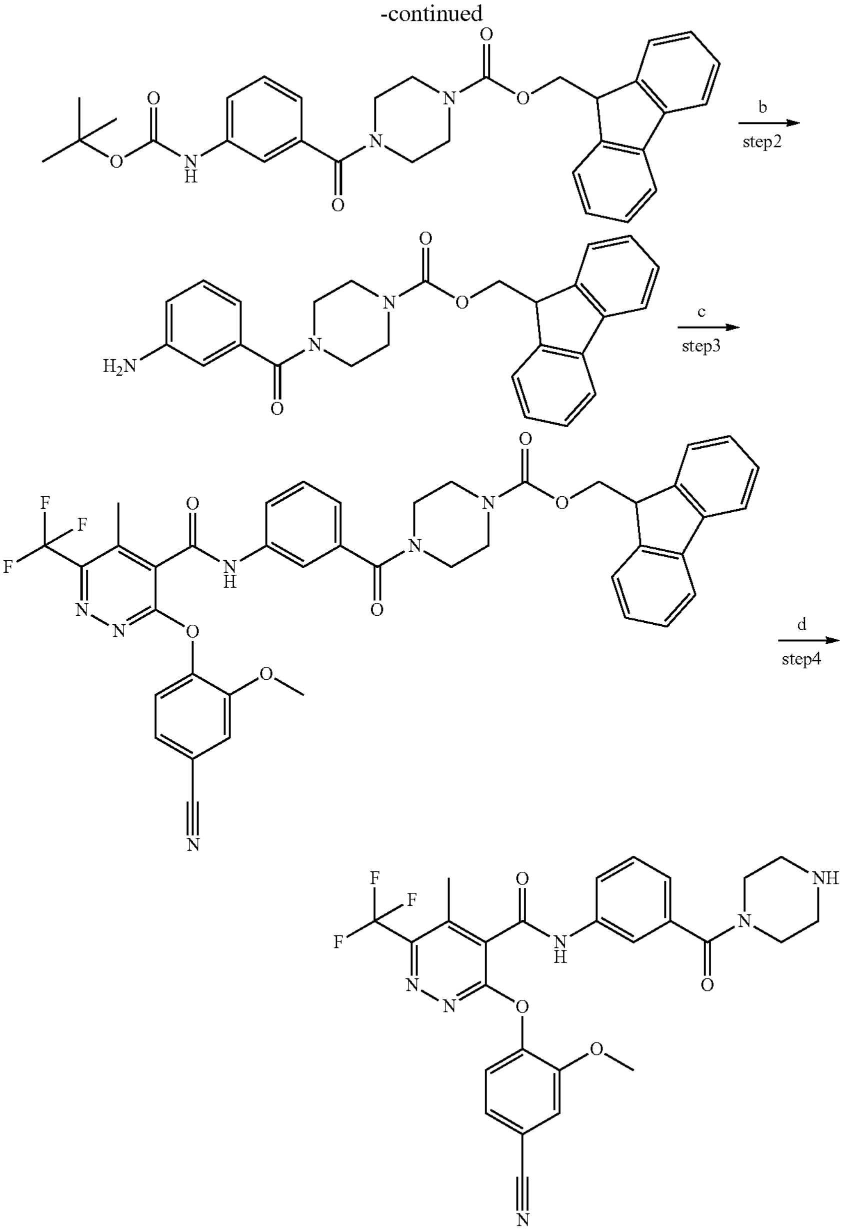

Reagents & conditions:
a) Fmoc-piperazine hydrochloride, HATU, DIPEA, DCM, RT, 66 h
b) 4M HCl in dioxane, RT, 4 h
c) 3-(4-cyano-2-methoxy-phenoxy)-5-methyl-6-(trifluoromethyl)pyridazine-4-carboxylic acid, HATU, DIPEA, DMF, RT, 16 h
d) piperidine, MeCN, RT, 16 h Step 1: 9H-fluoren-9-ylmethyl 4-[3-(tert-butoxycarbonylamino)benzoyl]piperazine-1-carboxylate: To a mixture of 3-[(tert-butoxycarbonyl)amino]benzoic acid (500 mg, 2.11 mmol), HATU (962 mg, 2.53 mmol) and DIPEA (1.1 mL, 6.32 mmol) in DCM (7.5 mL) was added Fmoc-piperazine hydrochloride (872 mg, 2.53 mmol). The reaction mixture was stirred at room temperature for 66 h then partitioned between DCM (20 mL) and water (20 mL). The layers were separated and the aqueous phase extracted with DCM (2×10 mL). The combined organics were washed with brine (20 mL), dried using a phase separator and concentrated under reduced pressure. The resulting residue was purified by FCC (Biotage Isolera 4, 25 g Sfar Duo, lambda-all collect) using a 0-75% EtOAc/heptane gradient. Product fractions were combined and concentrated under reduced pressure to afford 9H-fluoren-9-ylmethyl 4-[3-(tert-butoxycarbonylamino)benzoyl]piperazine-1-carboxylate (90.0%) (1.19 g, 2.03 mmol, 96%) as a white solid. $^1$H NMR (400 MHz, DMSO-$d_6$) δ 9.50 (d, J=10.9 Hz, 1H), 7.92-7.86 (m, 2H), 7.86-7.82 (m, 1H), 7.63 (d, J=7.4 Hz, 1H), 7.56-7.45 (m, 2H), 7.45-7.38 (m, 2H), 7.38-7.27 (m, 3H), 7.01-6.91 (m, 1H), 4.40 (d, J=6.5 Hz, 1H), 4.32-4.22 (m, 1H), 3.63-3.45 (m, 3H), 3.30-3.14 (m, 3H), 2.77-2.55 (m, 2H), 1.66-1.55 (m, 1H), 1.51-1.45 (m, 9H). LC-MS: m/z 550.3 $[M+Na]^+$, (ESI+), RT=1.08 LCMS Method M2.

Step 2: 9H-fluoren-9-ylmethyl 4-(3-aminobenzoyl)piperazine-1-carboxylate: 9H-fluoren-9-ylmethyl 4-[3-(tert-butoxycarbonylamino)benzoyl]piperazine-1-carboxylate (1.19 g, 2.26 mmol) was dissolved in 4M HCl in dioxane (25 mL). The reaction mixture was allowed to stir at room temp for 4 h then concentrated under reduced pressure. The solvent was co-evaporated with DCM-heptane (1:1) to give 9H-fluoren-9-ylmethyl 4-(3-aminobenzoyl)piperazine-1-carboxylate hydrochloride (85.0%) (1.23 g, 2.25 mmol, 100%) as a pink solid. $^1$H NMR (400 MHz, DMSO-$d_6$) δ 7.90 (d, J=7.4 Hz, 2H), 7.63 (d, J=7.4 Hz, 2H), 7.49 (t, J=8.0 Hz, 1H), 7.42 (t, J=7.4 Hz, 2H), 7.34 (t, J=7.8 Hz, 3H), 7.30-7.24 (m, 2H), 4.39 (d, J=6.5 Hz, 2H), 4.32-4.24 (m, 1H), 3.73-3.64 (m, 2H), 3.55-3.43 (m, 4H), 3.35-3.11 (m, 4H). LC-MS: m/z 428.3 $[M+H]^+$, (ESI+), room temperature=0.88 LCMS Method M2.

Step 3: 9H-fluoren-9-ylmethyl 4-[3-[[3-(4-cyano-2-methoxy-phenoxy)-5-methyl-6-(trifluoromethyl) pyridazine-4-carbonyl]amino]benzoyl]piperazine-1-carboxylate: To a mixture of 3-(4-cyano-2-methoxy-phenoxy)-5-methyl-6-(trifluoromethyl)pyridazine-4-carboxylic acid (93%, 100 mg, 0.263 mmol), HATU (120 mg, 0.316 mmol) and DIPEA (138 uL, 0.790 mmol) in DMF (1 mL) was added 9H-fluoren-9-ylmethyl 4-(3-aminobenzoyl)piperazine-1-carboxylate; hydrochloride (85%, 172 mg, 0.316 mmol). The reaction mixture was stirred at room temperature for 16 h then poured into water (10 mL) and extracted with EtOAc (15 mL). The organic phase was washed with water (2×10 mL) then 5% aq LiCl solution (2×10 mL), dried over $MgSO_4$ and concentrated under reduced pressure. The crude pro duct was purified by FCC (Biotage Isolera 4, 10 g Sfar Duo, lambda-all collect) using a 0-100% EtOAc/heptane gradient. Product fractions were combined and concentrated under reduced pressure to afford 9H-fluoren-9-ylmethyl 4-[3-[[3-(4-cyano-2-methoxy-phenoxy)-5-methyl-6-(trifluoromethyl)pyridazine-4-carbonyl]amino] benzoyl]piperazine-1-carboxylate (88.0%) (184 mg, 0.212 mmol, 81%) as a yellow glass. $^1$H NMR (500 MHz, $CDCl_3$) δ 8.89 (s, 1H), 7.83-7.79 (m, 1H), 7.79-7.74 (m, 2H), 7.68-7.66 (m, 1H), 7.58-7.52 (m, 2H), 7.44 (t, J=7.9 Hz, 1H), 7.42-7.38 (m, 2H), 7.38-7.36 (m, 2H), 7.34-7.29 (m, 2H), 7.27 (s, 1H), 7.11 (d, J=7.7 Hz, 1H), 4.54-4.50 (m, 2H), 4.26-4.20 (m, 1H), 3.82 (s, 3H), 3.57-3.27 (m, 8H), 2.60-2.55 (m, 3H). LC-MS: m/z 785.1 $[M+Na]^+$, (ESI+), RT=1.11 LCMS Method M2.

Step 4: 3-(4-cyano-2-methoxy-phenoxy)-5-methyl-N-[3-(piperazine-1-carbonyl)phenyl]-6-(trifluoromethyl) pyridazine-4-carboxamide: A solution of 9H-fluoren-9-ylmethyl 4-[3-[[3-(4-cyano-2-methoxy-phenoxy)-5-methyl-6-(trifluoromethyl)pyridazine-4-carbonyl]amino]benzoyl] piperazine-1-carboxylate (184 mg, 0.241 mmol) in Acetonitrile (3 mL) was treated with piperidine (95 uL, 0.965 mmol) and the mixture stirred at room temp for 16 h. The reaction mixture was then concentrated under reduced pressure and purified by prep HPLC (Prep Method 3). Product fractions were combined and concentrated under reduced pressure. The resulting residue was freeze-dried from MeCN-water (1:1) to afford 3-(4-cyano-2-methoxy-phenoxy)-5-methyl-N-[3-(piperazine-1-carbonyl)phenyl]-6-(trifluoromethyl)pyridazine-4-carboxamide (60 mg, 0.111 mmol, 46%) as an off-white powder. $^1$H NMR (500 MHz, DMSO-$d_6$) δ 11.11 (s, 1H), 7.76 (t, J=1.7 Hz, 1H), 7.74 (d, J=1.8 Hz, 1H), 7.67 (ddd, J=8.2, 2.0, 0.9 Hz, 1H), 7.56 (dd, J=8.2, 1.8 Hz, 1H), 7.51 (d, J=8.2 Hz, 1H), 7.46 (t, J=7.9 Hz, 1H), 7.20-7.14 (m, 1H), 3.79 (s, 3H), 3.58-3.47 (m, 2H), 3.29-3.21 (m, 2H), 2.80-2.57 (m, 4H), 2.53-2.51 (m, 3H). Piperazine NH not observed. LC-MS: m/z 541.2 $[M+H]^+$, (ESI+), RT=2.69 LCMS Method M6.

Example 27

Compound 1439: 3-(4-cyano-2-methoxy-phenoxy)-N-[3-(2-methoxyethylsulfamoyl)phenyl]-5-methyl-6-(trifluoromethyl)pyridazine-4-carboxamide

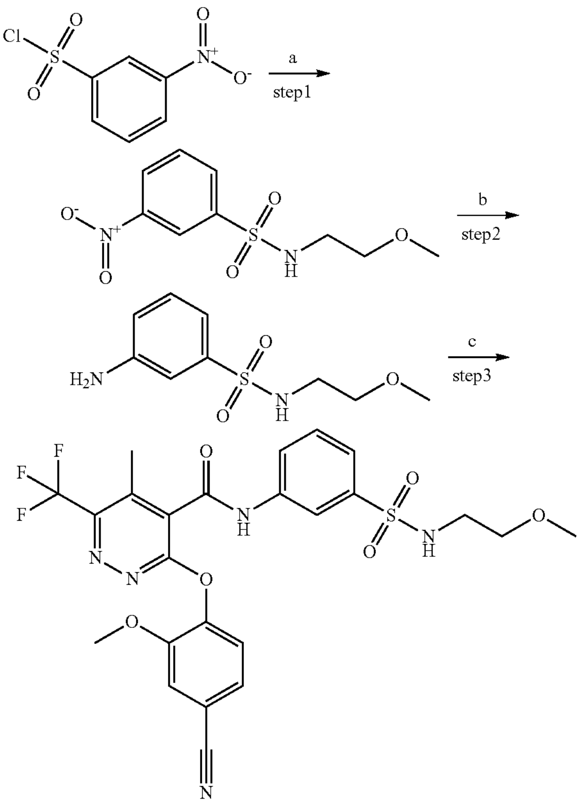

Reagents & conditions:
a) 2-methoxyethanamine, TEA, DCM, rt, 17 h
b) iron, ammonium chloride, EtOH, 90 °C, 22 h
c) 3-(4-cyano-2-methoxy-phenoxy)-5-methyl-6-(trifluoromethyl)pyridazine-4-carboxylic acid, EDC—HCl, pyridine, rt, 4 h Step 1: N-(2-methoxyethyl)-3-nitro-benzenesulfonamide: To a mixture of 2-methoxyethanamine (94 uL, 1.09 mmol) and triethylamine (0.25 mL, 1.79 mmol) in DCM (4.5 mL) was added 3-nitrobenzenesulfonyl chloride (200 mg, 0.902 mmol). The reaction was stirred at rt for 17 h. The reaction mixture was then poured into aq $NaHCO_3$ and extracted with DCM (2×). The combined organic phases were filtered through a phase separator and concentrated under reduced pressure to give the desired product, N-(2-methoxyethyl)-3-nitro-benzenesulfonamide (99.0%) (216 mg, 0.822 mmol, 91%) as a brown oil.

Step 2: 3-amino-N-(2-methoxyethyl)benzenesulfonamide: To a solution of 3-amino-N-(2-methoxyethyl)benzenesulfonamide (92.0%) (166 mg, 0.663 mmol, 81%) in Ethanol (6 mL) were added iron (459 mg, 8.22 mmol) and Ammonium chloride (440 mg, 8.23 mmol) at room temperature. The resulting mixture was then stirred at 90 °C for 22 hours. The reaction was filtered through celite, washed with methanol (2×20 mL) and evaporated under reduced pressure gave the crude material. The residue was diluted with water (20 mL) and extracted with ethyl acetate (3×20 mL), the combined organic phases were dried over anhydrous sodium sulfate and concentrated under a reduced pressure to give 3-amino-N-(2-methoxyethyl)benzenesulfonamide (92.0%) (166 mg, 0.663 mmol, 81%) as an off-white powder.

Step 3: 3-(4-cyano-2-methoxy-phenoxy)-N-[3-(2-methoxyethylsulfamoyl)phenyl]-5-methyl-6-(trifluoromethyl)pyridazine-4-carboxamide: To a solution of 3-(4-cyano-2-methoxy-phenoxy)-5-methyl-6-(trifluoromethyl) pyridazine-4-carboxylic acid (93%, 50 mg, 0.132 mmol) and N-[3-(dimethylamino)propyl]-N⊟e thylcarbodiimide hydrochloride (1:1) (51 mg, 0.266 mmol) in Pyridine (1 mL) was added 3-amino-N-(2-methoxyethyl)benzenesulfonamide (92%, 66 mg, 0.264 mmol). The mixture was stirred at room temperature for 4 h. The solvents were removed (co-evaporated with MeCN) and the residue purified by prep HPLC (Acidic Early Elute Method). Fractions containing the desired product were combined, evaporated and freeze dried overnight to afford the desired product, 3-(4-cyano-2-methoxy-phenoxy)-N-[3-(2-methoxyethylsulfamoyl)phenyl]-5-methyl-6-(trifluoromethyl)pyridazine-4-carboxamide (99.0%) (21 mg, 0.0368 mmol, 28%), as an off-white powder. $^1$H NMR (500 MHz, DMSO-$d_6$) δ 11.31 (s, 1H), 8.29-8.25 (m, 1H), 7.88-7.82 (m, 1H), 7.82-7.79 (m, 1H), 7.76-7.73 (m, 1H), 7.64-7.58 (m, 2H), 7.56 (dd, J=8.2, 1.8 Hz, 1H), 7.52-7.49 (m, 1H), 3.79 (s, 3H), 3.32-3.28 (m, 2H, overlap with $H_2O$ peak), 3.15 (s, 3H), 2.96-2.91 (m, 2H), 2.53-2.51 (m, 3H, overlap with DMSO peak). m/z: 566.1 $[M+H]^+$, (ESI+), RT=3.25 LCMS Method 4.

The compounds 1440-1445 listed in Table 11 were prepared by a similar procedure as described for compound 1439, using appropriate acids and substituted anilines

TABLE 11

| Compound | Structure | Analytical Data |
|---|---|---|
| 1440 | 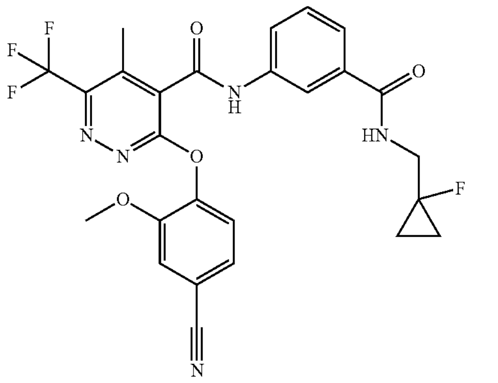 [SMILES: COc1cc(C#N)ccc1Oc1nnc(C(F)(F)F)c(C)c1C(=O)Nc1cccc(C(=O)NCC2(F)CC2)c1] 3-(4-cyano-2-methoxy-phenoxy)-N-[3-[(1-fluorocyclopropyl)methylcarbamoyl]phenyl]-5-methyl-6-(trifluoromethyl)pyridazine-4-carboxamide | $^1$H NMR (500 MHz, DMSO-$d_6$) δ 11.11 (s, 1H), 8.87 (t, J = 5.8 Hz, 1H), 8.19-8.15 (m, 1H), 7.86-7.81 (m, 1H), 7.77-7.73 (m, 1H), 7.68 (d, J = 7.8 Hz, 1H), 7.57 (dd, J = 8.2, 1.8 Hz, 1H), 7.54-7.47 (m, 2H), 3.80 (s, 3H), 3.70 (dd, J = 21.0, 5.9 Hz, 2H), 2.54-2.50 (m, 3H, overlap with DMSO peak), 1.04-0.94 (m, 2H), 0.85-0.77 (m, 2H). LC-MS: m/z 561.3 $[M + NH4]^+$, (ESI+), RT = 3.64 LCMS Method 6 |
| 1441 | 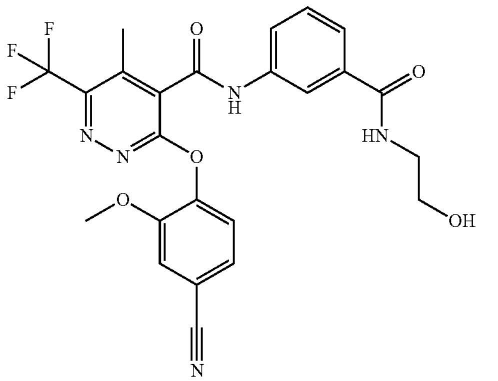 [SMILES: COc1cc(C#N)ccc1Oc1nnc(C(F)(F)F)c(C)c1C(=O)Nc1cccc(C(=O)NCCO)c1] 3-(4-cyano-2-methoxy-phenoxy)-N-[3-(2-hydroxyethylcarbamoyl)phenyl]-5-methyl-6-(trifluoromethyl)pyridazine-4-carboxamide | $^1$H NMR (500 MHz, DMSO-$d_6$) δ 7.36 (s, 1H), 7.07 (d, J = 8.0 Hz, 1H), 6.86 (d, J = 7.8 Hz, 1H), 6.75 (s, 1H), 6.71 (t, J = 7.9 Hz, 2H), 6.65 (s, 2H), 3.02 (s, 3H), 2.92 (t, J = 5.8 Hz, 2H), 2.72 (t, J = 5.8 Hz, 2H), 1.80 (s, 3H). LC-MS: m/z: 516.2 $[M + H]^+$, (ESI+), RT = 3.03 LCMS Method 6 |

TABLE 11-continued

| Compound | Structure | Analytical Data |
| --- | --- | --- |
| 1442 | 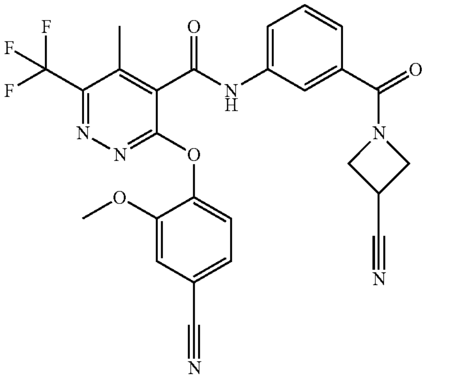 [SMILES: COc1cc(C#N)ccc1Oc1nnc(C(F)(F)F)c(C)c1C(=O)Nc1cccc(C(=O)N2CC(C#N)C2)c1] N-[3-(3-cyanoazetidine-1-carbonyl)phenyl]-3-(4-cyano-2-methoxy-phenoxy)-5-methyl-6-(trifluoromethyl)pyridazine-4-carboxamide | $^1$H NMR (500 MHz, DMSO-$d_6$) δ 11.16 (s, 1H), 8.02 (t, J = 1.8 Hz, 1H), 7.78 (ddd, J = 8.1, 2.1, 1.0 Hz, 1H), 7.74 (d, J = 1.8 Hz, 1H), 7.56 (dd, J = 8.2, 1.8 Hz, 1H), 7.53-7.47 (m, 2H), 7.42 (dt, J = 7.7, 1.2 Hz, 1H), 4.60-4.46 (m, 2H), 4.39-4.28 (m, 1H), 4.24-4.13 (m, 1H), 3.85 (p, J = 7.7 Hz, 1H), 3.79 (s, 3H), 2.52 (d, J = 1.4 Hz, 3H). LC-MS: m/z 537.1 [M + H]$^+$, (ESI+), RT = 3.06 MET-uPLC-AB-101 (7 min, low pH) |
| 1443 | 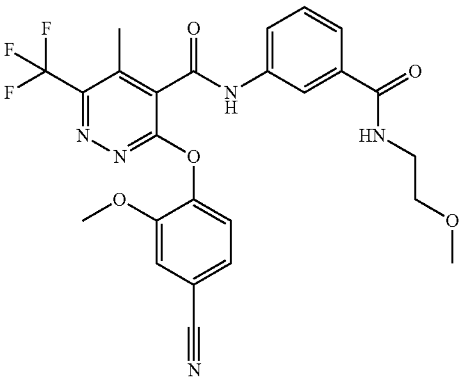 [SMILES: COCCNC(=O)c1cccc(NC(=O)c2c(Oc3ccc(C#N)cc3OC)nnc(C(F)(F)F)c2C)c1] 3-(4-cyano-2-methoxy-phenoxy)-N-[3-(2-methoxyethylcarbamoyl)phenyl]-5-methyl-6-(trifluoromethyl)pyridazine-4-carboxamide | $^1$H NMR (500 MHz, DMSO-$d_6$) δ 11.10 (s, 1H), 8.57 (t, J = 5.4 Hz, 1H), 8.14 (t, J = 1.9 Hz, 1H), 7.83-7.79 (m, 1H), 7.74 (d, J = 1.9 Hz, 1H), 7.65-7.62 (m, 1H), 7.56 (dd, J = 8.2, 1.8 Hz, 1H), 7.53-7.45 (m, 2H), 3.79 (s, 3H), 3.47-3.40 (m, 4H), 3.26 (s, 3H), 2.52-2.51 (m, 3H). LC-MS: m/z 530.0 [M + H]+, (ESI+), RT = 3.12 MET-uPLC-AB-101 (7 min, low pH) |
| 1444 | 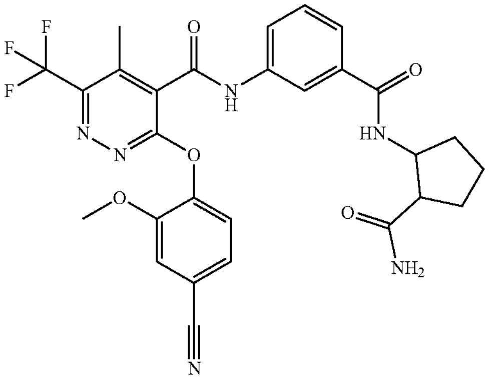 [SMILES: COc1cc(C#N)ccc1Oc1nnc(C(F)(F)F)c(C)c1C(=O)Nc1cccc(C(=O)NC2CCCC2C(N)=O)c1] N-[3-[(2-carbamoylcyclopentyl)carbamoyl]phenyl]-3-(4-cyano-2-methoxy-phenoxy)-5-methyl-6-(trifluoromethyl)pyridazine-4-carboxamide | $^1$H NMR (500 MHz, DMSO-$d_6$) δ 11.09 (s, 1H), 8.19 (d, J = 7.4 Hz, 1H), 8.04 (t, J = 1.9 Hz, 1H), 7.86 (ddd, J = 8.0, 2.2, 1.0 Hz, 1H), 7.74 (d, J = 1.8 Hz, 1H), 7.58-7.53 (m, 2H), 7.51 (d, J = 8.3 Hz, 1H), 7.48 (t, J = 7.9 Hz, 1H), 7.37-7.30 (m, 1H), 6.88-6.82 (m, 1H), 4.43 (p, J = 6.9 Hz, 1H), 3.79 (s, 3H), 2.86 (q, J = 7.9 Hz, 1H), 2.53-2.51 (m, 3H), 1.95-1.75 (m, 5H), 1.57-1.46 (m, 1H). LC-MS: m/z 583.5 [M + H]$^+$, (ESI+), RT = 3.06 MET-uPLC-AB-101 (7 min, low pH) |

TABLE 11-continued

| Compound | Structure | Analytical Data |
|---|---|---|
| 1445 | 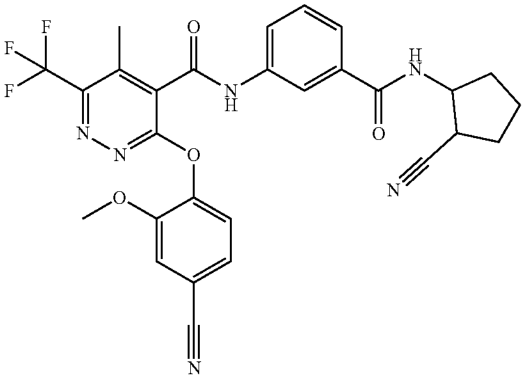 [SMILES: COc1cc(C#N)ccc1Oc1nnc(C(F)(F)F)c(C)c1C(=O)Nc1cccc(C(=O)NC2CCCC2C#N)c1] N-[3-[(2-cyanocyclopentyl)carbamoyl]phenyl]-3-(4-cyano-2-methoxy-phenoxy)-5-methyl-6-(trifluoromethyl)pyridazine-4-carboxamide | $^1$H NMR (500 MHz, DMSO-$d_6$) δ 11.11 (s, 1H), 8.70 (d, J = 7.8 Hz, 1H), 8.15 (t, J = 1.9 Hz, 1H), 7.85 (ddd, J = 8.1, 2.2, 1.0 Hz, 1H), 7.75 (d, J = 1.8 Hz, 1H), 7.66-7.62 (m, 1H), 7.56 (dd, J = 8.2, 1.8 Hz, 1H), 7.54-7.49 (m, 2H), 4.49 (p, J = 7.9 Hz, 1H), 3.79 (s, 3H), 3.00 (q, J = 8.3 Hz, 1H), 2.52 (q, J = 1.5 Hz, 3H), 2.19-2.10 (m, 1H), 2.09-1.99 (m, 1H), 1.89-1.80 (m, 1H), 1.80-1.70 (m, 2H), 1.68-1.57 (m, 1H). LC-MS: m/z 565.5 [M + H]$^+$, (ESI+), RT = 3.44 MET-uPLC-AB-101 (7 min, low pH) |

Example 28

Compound 1446: 3-(4-cyano-2-methoxy-phenoxy)-6-(4-cyanophenyl)-5-methyl-N-[3-(methylsulfonimidoyl)phenyl]pyridazine-4-carboxamide

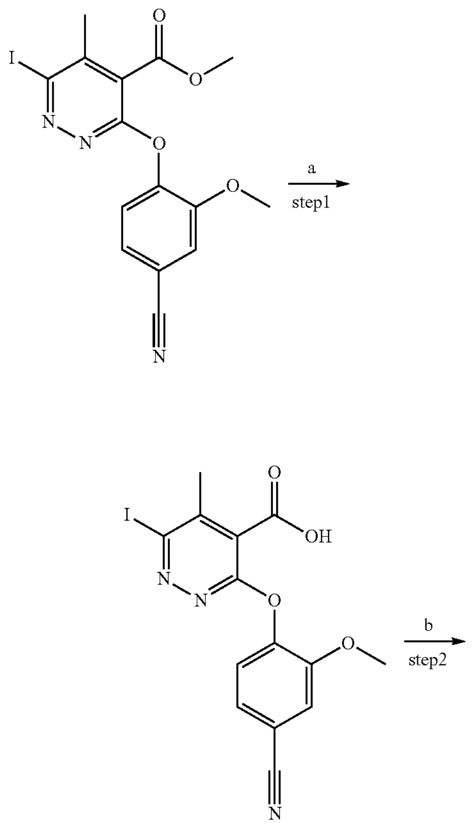

-continued

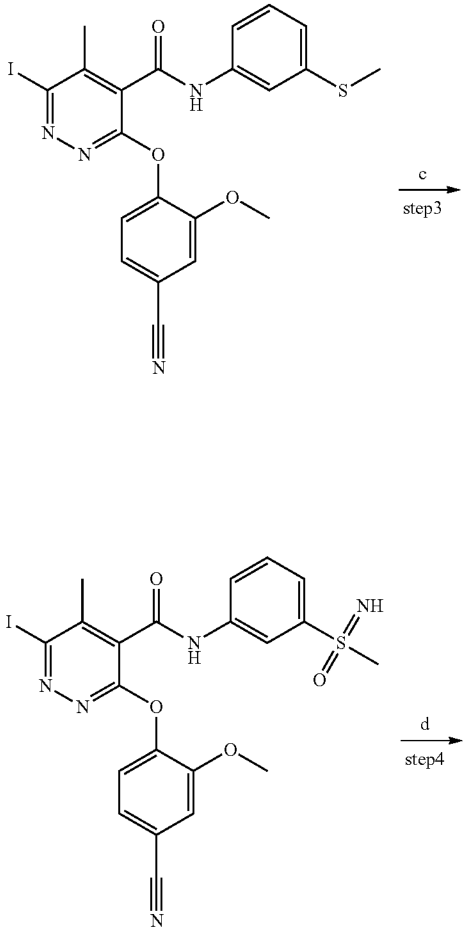

-continued

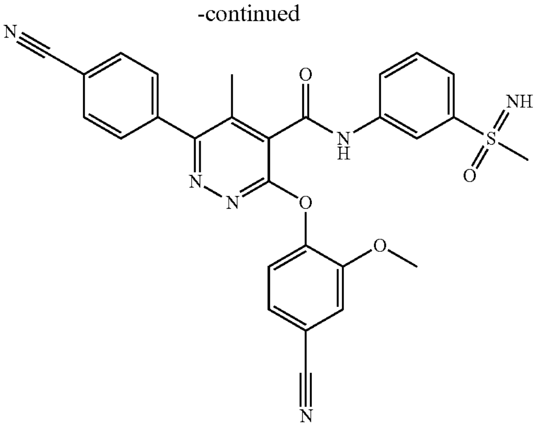

Reagents & conditions:
a) LiOH, THF/$H_2O$ rt;
b) 3-(methylsulfanyl)aniline, HATU, DIEA, DMF, rt;
c) Phenyl iodomium diacetate, $(NH_4)_2CO_3$, MeOH, rt;
d) 4-cyanophenyl)boronic acid, Pd(dppf)$Cl_2$•DCM, 2M $Na_2CO_3$, dioxane, 80 °C.

Step 1: 3-(4-cyano-2-methoxy-phenoxy)-6-iodo-5-methyl-pyridazine-4-carboxylic acid: Lithium hydroxide (37 mg, 1.55 mmol) was added to a solution of methyl 3-(4-cyano-2-methoxy-phenoxy)-6-iodo-5-methyl-pyridazine-4-carboxylate (200 mg, 0.470 mmol) in THF (4 mL) and Water (0.6 mL) at rt and the reaction was stirred at rt for 2 d. 1M HCl aq. was added to the reaction mixture to pH ~2 and the reaction was extracted with EtOAc (3×20 mL). The organic phase was dried with sodium sulfate, filtered and concentrated to dryness in vacuum to give crude product 3-(4-cyano-2-methoxy-phenoxy)-6-iodo-5-methyl-pyridazine-4-carboxylic acid (91.0%) (193 mg, 0.428 mmol, 91%) which was used as such in the next step. Assumed 100% molar yield. LC-MS: m/z 412 $[M+H]^+$, (ESI+), RT=0.55 min LCMS Method 1.

Step 2: 3-(4-cyano-2-methoxy-phenoxy)-6-iodo-5-methyl-N-(3-methylsulfanylphenyl)pyridazine-4-carboxamide: N-[(dimethylamino)(3H-[1,2,3]triazolo[4,5-b]pyridin-3-yloxy)methylidene]-N-methylmethanaminium hexafluorophosphate (HATU) (196 mg, 0.516 mmol) was added to a mixture of 3-(4-cyano-2-methoxy-phenoxy)-6-iodo-5-methyl-pyridazine-4-carboxylic acid (193 mg, 0.469 mmol) and N-ethyl-N-isopropyl-propan-2-amine (180 uL, 1.03 mmol) in DMF (3 mL) at rt and the reaction was stirred at rt for 5 min, then 3-(methylsulfanyl)aniline (87 uL, 0.704 mmol) was added and the reaction was stirred at rt for 16 h. The reaction mixture was diluted with EtOAc (~50 mL) and washed with water (3×~50 ml). The organic phase was washed with brine, dried over sodium sulfate, filtered and concentrated to dryness to give crude product. Purification by FCC (Biotage isolera, $SiO_2$ gradient elution 10-50% EtOAc:Heptanes) gave 3-(4-cyano-2-methoxy-phenoxy)-6-iodo-5-methyl-N-(3-methylsulfanylphenyl)pyridazine-4-carboxamide (80.0%) (239 mg, 0.359 mmol, 77%) as a yellow gum. LC-MS: m/z 533 $[M+H]^+$, (ESI+), RT=1.01 min LCMS Method 1.

Step 3: 3-(4-cyano-2-methoxy-phenoxy)-6-iodo-5-methyl-N-[3-(methylsulfonimidoyl)phenyl]pyridazine-4-carboxamide: Phenyl Iodonium Di-Acetate (PIDA) (1044 mg, 3.24 mmol) and diammonium carbonate (212 mg, 2.25 mmol) were added to a solution of 3-(4-cyano-2-methoxy-phenoxy)-6-iodo-5-methyl-N-(3-methylsulfanylphenyl)pyridazine-4-carboxamide (750 mg, 1.41 mmol) in Methanol (22 mL) at rt and the reaction was stirred at rt for 16 h. The reaction mixture was concentrated to dryness in vacuum to give crude product. The residue was purified by FCC (Biotage Isolera $SiO_2$, gradient elution 10-100% EtOAc: heptane) 3-(4-cyano-2-methoxy-phenoxy)-6-iodo-5-methyl-N-[3-(methylsulfonimidoyl)phenyl]pyridazine-4-carboxamide (83.0%) (773 mg, 1.14 mmol, 81%). LC-MS: m/z 564 $[M+H]^+$, (ESI+), RT=0.71 min LCMS Method 1.

Step 4: 3-(4-cyano-2-methoxy-phenoxy)-6-(4-cyanophenyl)-5-methyl-N-[3-(methylsulfonimidoyl)phenyl]pyridazine-4-carboxamide: 1,1 bis(diphenylphosphanyl)ferrocene-dichloropalladium (1:1) (5.8 mg, 7.99 V mol) was added to a stirred, $N_2$ degassed solution of 3-(4-cyano-2-methoxy-phenoxy)-6-iodo-5-methyl-N-[3-(methylsulfonimidoyl)phenyl]pyridazine-4-carboxamide (45 mg, 0.0799 mmol), 4-cyanophenyl)boronic acid (23 mg, 0.160 mmol) and 2 M disodium carbonate (2M aq.) (120 uL, 0.240 mmol) in 1,4-Dioxane (1.8 mL). The reaction mixture was stirred at 80 °C for 2 h in a pressure vial. The reaction mixture was diluted with EtOAc (~3 mL) and washed with water (~2 ml). The organic phase was dried over sodium sulfate, filtered and concentrated to dryness to give crude product. The residue was purified by high pH prep HPLC (early method). The product containing fractions were combined and the solvent was removed in vacuo by freeze drying, to give 3-(4-cyano-2-methoxy-phenoxy)-6-(4-cyanophenyl)-5-methyl-N-[3-(methylsulfonimidoyl)phenyl]pyridazine-4-carboxamide (99.0%) (12 mg, 0.0224 mmol, 28%) as an off white solid. $^1H$ NMR (400 MHz, DMSO-$d_6$) δ 11.30 (s, 1H), 8.39 (s, 1H), 8.02 (d, J=8.3 Hz, 2H), 7.87 (d, J=8.5 Hz, 1H), 7.81 (d, J=8.3 Hz, 2H), 7.74-7.67 (m, 2H), 7.65-7.59 (m, 1H), 7.58-7.53 (m, 1H), 7.49 (d, J=8.2 Hz, 1H), 4.24 (s, 1H), 3.80 (s, 3H), 3.07 (s, 3H), 2.35 (s, 3H). LC-MS: m/z 539.1 $[M+H]^+$, (ESI+), RT=2.60 LCMS Method 7.

The compounds 1447-1457 listed in Table 12 were prepared by a similar procedure described for step 4 of example 28, using 3-(4-cyano-2-methoxy-phenoxy)-6-iodo-5-methyl-N-[3-(methylsulfonimidoyl)phenyl]pyridazine-4-carboxamide coupling with the appropriate boronate(s) or boronic acids.

TABLE 12

| Compound | Structure | Analytical Data |
| --- | --- | --- |
| 1447 | 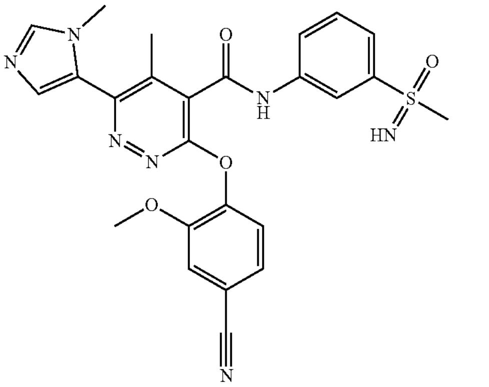 [SMILES: COc1cc(C#N)ccc1Oc1nnc(-c2cncn2C)c(C)c1C(=O)Nc1cccc(S(C)(=N)=O)c1] 3-(4-cyano-2-methoxy-phenoxy)-5-methyl-6-(3-methylimidazol-4-yl)-N-[3-(methylsulfonimidoyl)phenyl]pyridazine-4-carboxamide | $^1$H NMR (400 MHz, $CD_3OD$) δ 8.46 (t, J = 1.9 Hz, 1H), 8.00-7.94 (m, 1H), 7.90-7.78 (m, 2H), 7.66 (t, J = 8.0 Hz, 1H), 7.53 (d, J = 1.2 Hz, 1H), 7.50-7.41 (m, 2H), 7.37 (s, 1H), 3.82 (s, 3H), 3.74 (s, 3H), 3.18 (s, 3H), 2.50 (s, 3H) 2 exchangeable Hs not seen. LC-MS: m/z 518.1 [M + H]$^+$, (ESI+), RT = 2.01 LCMS Method 6 |
| 1448 | 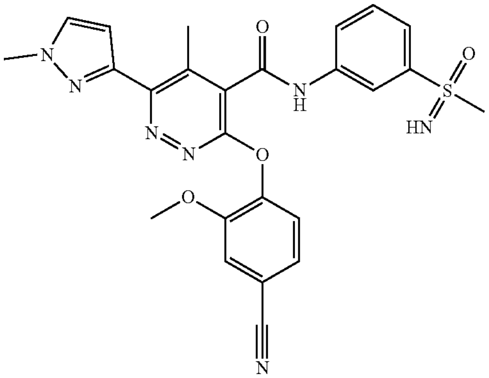 3-(4-cyano-2-methoxy-phenoxy)-5-methyl-6-(1-methylpyrazol-3-yl)-N-[3-(methylsulfonimidoyl)phenyl]pyridazine-4-carboxamide | $^1$H NMR (400 MHz, DMSO-$d_6$) δ 11.24 (s, 1H), 8.40 (s, 1H), 7.88 (d, J = 8.8 Hz, 1H), 7.85 (d, J = 2.2 Hz, 1H), 7.71 (d, J = 6.9 Hz, 2H), 7.62 (t, J = 7.9 Hz, 1H), 7.54 (dd, J = 8.2, 1.8 Hz, 1H), 7.46 (d, J = 8.2 Hz, 1H), 6.81 (d, J = 2.2 Hz, 1H), 4.24 (s, 1H), 3.95 (s, 3H), 3.79 (s, 3H), 3.07 (s, 3H), 2.63 (s, 3H). LC-MS: m/z 518.1 [M + H]$^+$, (ESI+), RT = 2.24 LCMS Method 6 |
| 1449 | 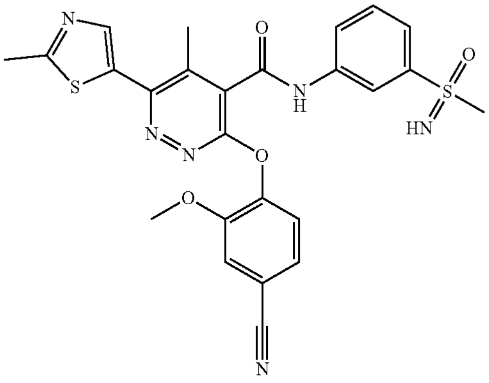 3-(4-cyano-2-methoxy-phenoxy)-5-methyl-N-[3-(methylsulfonimidoyl)phenyl]-6-(2-methylthiazol-5-yl)pyridazine-4-carboxamide | $^1$H NMR (400 MHz, DMSO-$d_6$) δ 11.34 (s, 1H), 8.39 (d, J = 2.2 Hz, 1H), 8.20 (s, 1H), 7.88 (d, J = 8.9 Hz, 1H), 7.80-7.66 (m, 2H), 7.62 (t, J = 7.9 Hz, 1H), 7.54 (dd, J = 8.2, 1.7 Hz, 1H), 7.47 (d, J = 8.2 Hz, 1H), 4.25 (s, 1H), 3.79 (s, 3H), 3.07 (s, 3H), 2.71 (s, 3H), 2.59 (s, 3H). LC-MS: m/z 535.1 [M + H]$^+$, (ESI+), RT = 2.40 LCMS Method 6 |

TABLE 12-continued

| Compound | Structure | Analytical Data |
|---|---|---|
| 1450 | 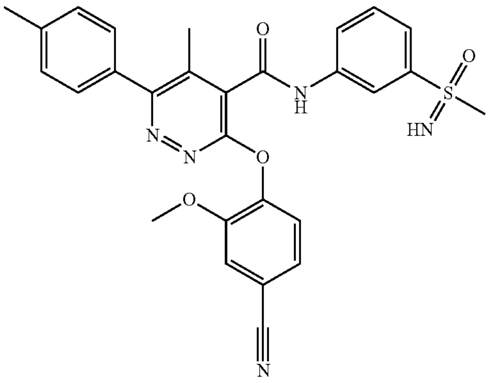 3-(4-cyano-2-methoxy-phenoxy)-5-methyl-N-[3-(methylsulfonimidoyl)phenyl]-6-(p-tolyl)pyridazine-4-carboxamide | $^1$H NMR (400 MHz, $CD_3OD$) δ 8.46 (t, J = 1.9 Hz, 1H), 8.00-7.94 (m, 1H), 7.83 (dd, J = 6.9, 1.7 Hz, 1H), 7.65 (t, J = 8.0 Hz, 1H), 7.51 (d, J = 1.4 Hz, 1H), 7.45-7.40 (m, 4H), 7.36 (d, J = 8.0 Hz, 2H), 3.83 (s, 3H), 3.17 (s, 3H), 2.43 (s, 3H), 2.41 (s, 3H). 2 exchangeable Hs not seen. LC-MS: m/z: 528.1 [M + H]$^+$, (ESI+), RT = 2.93 LCMS Method 6 |
| 1451 | 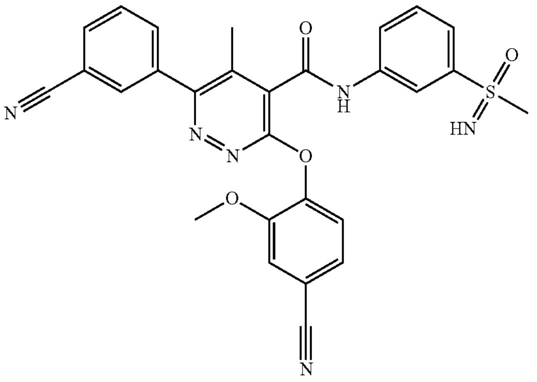 [SMILES: COc1cc(C#N)ccc1Oc1nnc(-c2cccc(C#N)c2)c(C)c1C(=O)Nc1cccc(S(C)(=N)=O)c1] 3-(4-cyano-2-methoxy-phenoxy)-6-(3-cyanophenyl)-5-methyl-N-[3-(methylsulfonimidoyl)phenyl]pyridazine-4-carboxamide | $^1$H NMR (400 MHz, DMSO-$d_6$) δ 11.34 (s, 1H), 8.40 (s, 1H), 8.10 (s, 1H), 8.06-7.98 (m, 1H), 7.97-7.92 (m, 1H), 7.88 (d, J = 8.4 Hz, 1H), 7.77 (t, J = 7.8 Hz, 1H), 7.74-7.67 (m, 2H), 7.62 (t, J = 7.9 Hz, 1H), 7.56 (dd, J = 8.2, 1.8 Hz, 1H), 7.50 (d, J = 8.2 Hz, 1H), 4.25 (s, 1H), 3.81 (s, 3H), 3.07 (s, 3H), 2.37 (s, 3H). LC-MS: m/z 539 [M + H]$^+$, (ESI+), RT = 2.58 LCMS Method 6 |
| 1452 | 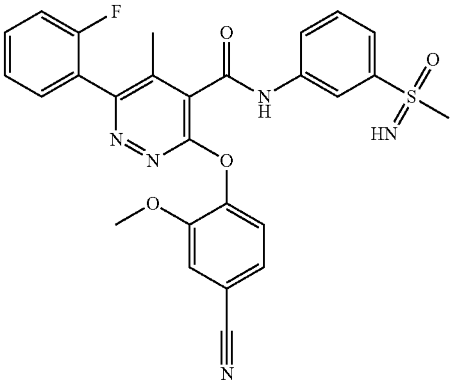 [SMILES: COc1cc(C#N)ccc1Oc1nnc(-c2ccccc2F)c(C)c1C(=O)Nc1cccc(S(C)(=N)=O)c1] 3-(4-cyano-2-methoxy-phenoxy)-6-(2-fluorophenyl)-5-methyl-N-[3-(methylsulfonimidoyl)phenyl]pyridazine-4-carboxamide | $^1$H NMR (400 MHz, DMSO-$d_6$) δ 11.35 (s, 1H), 8.40 (t, J = 1.8 Hz, 1H), 7.89 (d, J = 9.0 Hz, 1H), 7.81-7.68 (m, 2H), 7.67-7.58 (m, 2H), 7.58-7.47 (m, 3H), 7.47-7.36 (m, 2H), 4.25 (s, 1H), 3.81 (s, 3H), 3.07 (s, 3H), 2.23 (d, J = 1.2 Hz, 3H). LC-MS: m/z 532 [M + H]$^+$, (ESI+), RT = 2.73 LCMS Method 6 |

TABLE 12-continued

| Compound | Structure | Analytical Data |
|---|---|---|
| 1453 | 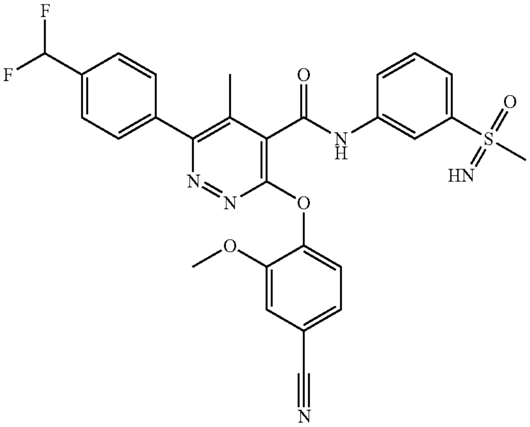 3-(4-cyano-2-methoxy-phenoxy)-6-[4-(difluoromethyl)phenyl]-5-methyl-N-[3-(methylsulfonimidoyl)phenyl]pyridazine-4-carboxamide | $^{1}$H NMR (400 MHz, $CD_3OD$) δ 8.46 (t, J = 2.0 Hz, 1H), 8.01-7.94 (m, 1H), 7.83 (m, 1H), 7.74 (d, J = 8.2 Hz, 2H), 7.71-7.62 (m, 3H), 7.53 (m, 1H), 7.49-7.40 (m, 2H), 6.88 (t, J = 56.1 Hz, 1H), 3.83 (s, 3H), 3.18 (s, 3H), 2.42 (s, 3H). LC-MS: m/z 564.2 $[M + H]^+$, (ESI+), RT = 2.84 LCMS Method 4 |
| 1454 | 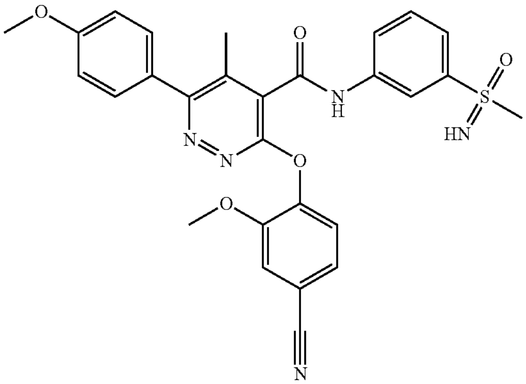 3-(4-cyano-2-methoxy-phenoxy)-6-(4-methoxyphenyl)-5-methyl-N-[3-(methylsulfonimidoyl)phenyl]pyridazine-4-carboxamide | $^{1}$H NMR (400 MHz, $CD_3OD$) δ 8.46 (t, J = 2.0 Hz, 1H), 8.01-7.93 (m, 1H), 7.83 (m, 1H), 7.65 (t, J = 8.0 Hz, 1H), 7.54-7.38 (m, 5H), 7.12-7.06 (m, 2H), 3.87 (s, 3H), 3.83 (s, 3H), 3.17 (s, 3H), 2.43 (s, 3H). LC-MS: m/z 544.2 $[M + H]^+$, (ESI+), RT = 2.68 LCMS Method 4 |
| 1455 | 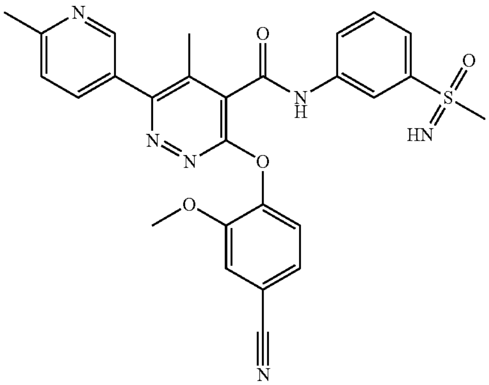 3-(4-cyano-2-methoxy-phenoxy)-5-methyl-6-(6-methyl-3-pyridyl)-N-[3-(methylsulfonimidoyl)phenyl]pyridazine-4-carboxamide | $^{1}$H NMR (400 MHz, $CD_3OD$) δ 8.62 (d, J = 2.0 Hz, 1H), 8.46 (t, J = 1.9 Hz, 1H), 8.02-7.94 (m, 2H), 7.86-7.80 (m, 1H), 7.66 (t, J = 8.0 Hz, 1H), 7.56-7.48 (m, 2H), 7.47-7.37 (m, 2H), 3.83 (s, 3H), 3.18 (s, 3H), 2.64 (s, 3H), 2.44 (s, 3H). LC-MS: m/z 529.2 $[M + H]^+$, (ESI+), RT = 2.35 LCMS Method 6 |

TABLE 12-continued

| Compound | Structure | Analytical Data |
| --- | --- | --- |
| 1456 | 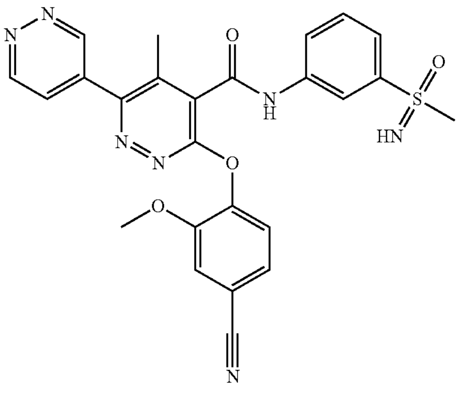 [SMILES: COc1cc(C#N)ccc1Oc1nnc(-c2ccnnc2)c(C)c1C(=O)Nc1cccc(S(C)(=N)=O)c1] 3-(4-cyano-2-methoxy-phenoxy)-5-methyl-N-[3-(methylsulfonimidoyl)phenyl]-6-pyridazin-4-yl-pyridazine-4-carboxamide | $^{1}$H NMR (500 MHz, $CD_3OD$) δ 9.49 (dd, J = 2.3, 1.2 Hz, 1H), 9.39 (dd, J = 5.3, 1.2 Hz, 1H), 8.46 (t, J = 1.9 Hz, 1H), 8.02 (dd, J = 5.3, 2.4 Hz, 1H), 7.98 (ddd, J = 8.1, 2.1, 0.9 Hz, 1H), 7.84 (ddd, J = 7.9, 1.7, 1.0 Hz, 1H), 7.67 (t, J = 8.0 Hz, 1H), 7.54 (d, J = 1.5 Hz, 1H), 7.48-7.43 (m, 2H), 3.83 (s, 3H), 3.18 (s, 3H), 2.51 (s, 3H). LC-MS: m/z 516.1 $[M + H]^+$, (ESI+), RT = 1.94 LCMS Method 6 |
| 1457 | 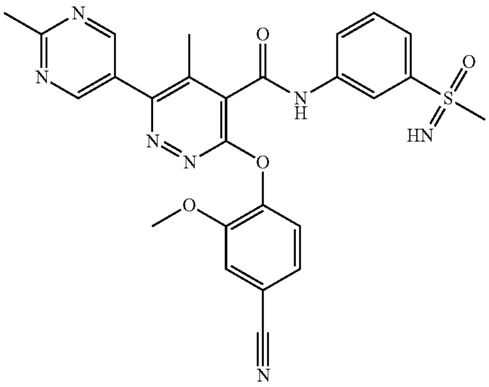 3-(4-cyano-2-methoxy-phenoxy)-5-methyl-6-(2-methylpyrimidin-5-yl)-N-[3-(methylsulfonimidoyl)phenyl]pyridazine-4-carboxamide | $^{1}$H NMR (400 MHz, $CD_3OD$) δ 8.95 (s, 2H), 8.46 (t, J = 1.9 Hz, 1H), 8.01-7.95 (m, 1H), 7.86-7.81 (m, 1H), 7.66 (t, J = 8.0 Hz, 1H), 7.53 (d, J = 1.3 Hz, 1H), 7.48-7.41 (m, 2H), 3.82 (s, 3H), 3.18 (s, 3H), 2.80 (s, 3H), 2.49 (s, 3H). LC-MS: m/z 530.2 $[M + H]^+$, (ESI+), RT = 2.16 LCMS Method 6 |

Example 29

Compound 1458: 3-(4-cyano-2-methoxyphenoxy)-5-methyl-N-(3-(S-methylsulfonimidoyl)phenyl)-6-(pyridin-2-yl)pyridazine-4-carboxamide

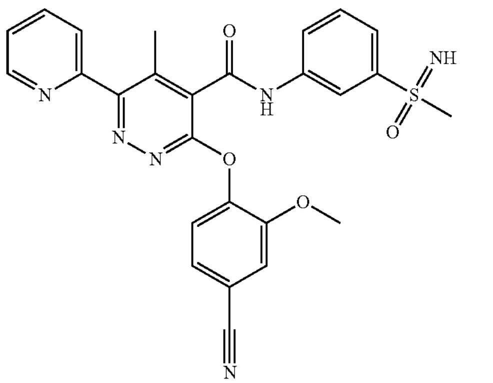 [SMILES: COc1cc(C#N)ccc1Oc1nnc(-c2ccccn2)c(C)c1C(=O)Nc1cccc(S(C)(=N)=O)c1]

2-(tributylstannanyl)pyridine (82 mg, 0.224 mmol) was added to a mixture of 3-(4-cyano-2-methoxy-phenoxy)-6-iodo-5-methyl-N-[3-(methylsulfonimidoyl)phenyl]pyridazine-4-carboxamide (63 mg, 0.112 mmol) and CuI (2.1 mg, 0.0112 mmol) in 1,4-Dioxane (2.5 mL) at rt and the reaction was stirred at rt for 5 min then palladium-triphenylphosphane (1:4) (13 mg, 0.0112 mmol) was added and the reaction was stirred at 110 °C for 16 h. The reaction mixture was diluted with EtOAc (~3 mL) and washed with 1M aq. KF, the mixture was stirred at rt for 15 min and filtered thru a pad of celite. The layers were separated and the organic phase was dried over sodium sulfate, filtered and concentrated to dryness in vacuum to give crude product. The residue was purified by low pH prep HPLC (early method). The product containing fractions were combined and the solvent was removed in vacuum by freeze drying. The crude product was diluted in $CH_3CN$ (3 mL) and MP-TMT (200 mg, 0.132 mmol, 0.66 mmol/g) and stirred at rt for ~16 h. The product was diluted in 1:1 ACN:$H_2O$ (~3 ml) and concentrated to dryness by freeze drying overnight to give 3-(4-cyano-2-methoxy-phenoxy)-5-methyl-N-[3-(methylsulfonimidoyl)phenyl]-6-(2-pyridyl)pyridazine-4-carboxamide (98.0%) (21 mg, 0.0404 mmol, 36%) as an off white solid. $^1H$ NMR (500 MHz, $CD_3OD$) δ 8.79-8.65 (m, 1H), 8.47 (t, J=1.9 Hz, 1H), 8.06-8.01 (m, 1H), 8.01-7.95 (m, 1H), 7.88-7.80 (m, 2H), 7.66 (t, J=8.0 Hz, 1H), 7.58-7.50 (m, 2H), 7.49-7.38 (m, 2H), 3.83 (s, 3H), 3.18 (s, 3H), 2.51 (s, 3H).

The compounds 1459-1464 listed in Table 13 were prepared by similar procedure described for example 29 using appropriate substituted R-SnBu3 and 3-(4-cyano-2-methoxy-phenoxy)-6-iodo-5-methyl-N-[3-(methylsulfonimidoyl)phenyl]pyridazine-4-carboxamide

TABLE 13

| Compound | Structure | Analytical Data |
| --- | --- | --- |
| 1459 | 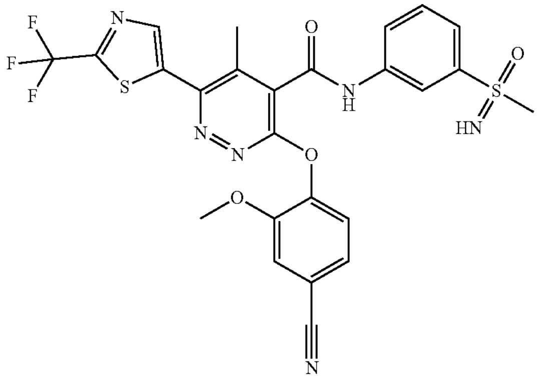 [SMILES: COc1cc(C#N)ccc1Oc1nnc(-c2cnc(C(F)(F)F)s2)c(C)c1C(=O)Nc1cccc(S(C)(=N)=O)c1] 3-(4-cyano-2-methoxy-phenoxy)-5-methyl-N-[3-(methylsulfonimidoyl)phenyl]-6-[2-(trifluoromethyl)thiazol-5-yl]pyridazine-4-carboxamide | $^1H$ NMR (400 MHz, $CD_3OD$) δ 8.56-8.41 (m, 2H), 7.97 (d, J = 8.0 Hz, 1H), 7.84 (d, J = 8.0 Hz, 1H), 7.66 (t, J = 8.0 Hz, 1H), 7.53 (s, 1H), 7.44 (s, 2H), 4.58 (s, 1H), 3.81 (s, 3H), 3.18 (s, 3H), 2.70 (s, 3H). LC-MS: m/z 589.1 [M + H]$^+$, (ESI+), RT = 3.06 LCMS Method 4 |

TABLE 13-continued

| Compound | Structure | Analytical Data |
|---|---|---|
| 1460 | 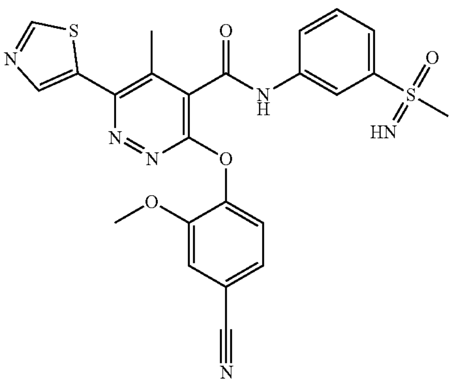 [SMILES: COc1cc(C#N)ccc1Oc1nnc(-c2cncs2)c(C)c1C(=O)Nc1cccc(S(C)(=N)=O)c1] 3-(4-cyano-2-methoxy-phenoxy)-5-methyl-N-[3-(methylsulfonimidoyl)phenyl]-6-thiazol-5-yl-pyridazine-4-carboxamide | $^{1}H$ NMR (400 MHz, $CD_3OD$) δ 9.16 (s, 1H), 8.46 (t, J = 2.0 Hz, 1H), 8.39 (s, 1H), 8.01-7.94 (m, 1H), 7.83 (m, 1H), 7.66 (t, J = 8.0 Hz, 1H), 7.52 (s, 1H), 7.44 (m, 2H), 3.82 (s, 3H), 3.18 (s, 3H), 2.67 (s, 3H). LC-MS: m/z 521.2 $[M + H]^+$, (ESI+), RT = 2.31 LCMS Method 6 |
| 1461 | 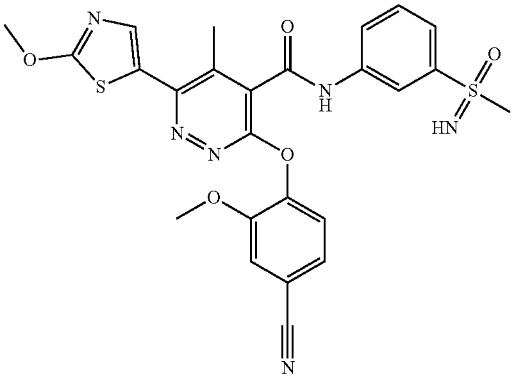 3-(4-cyano-2-methoxy-phenoxy)-6-(2-methoxythiazol-5-yl)-5-methyl-N-[3-(methylsulfonimidoyl)phenyl]pyridazine-4-carboxamide; formic acid | $^{1}H$ NMR (400 MHz, DMSO-$d_6$) δ 11.39 (s, 1H), 8.43 (s, 2H), 8.39 (s, 1H), 7.89 (d, J = 8.9 Hz, 1H), 7.83 (s, 1H), 7.71 (d, J = 8.6 Hz, 2H), 7.62 (t, J = 7.9 Hz, 1H), 7.55-7.51 (m, 1H), 7.47 (d, J = 8.2 Hz, 1H), 4.25 (s, 1H), 4.09 (s, 3H), 3.78 (s, 3H), 3.07 (s, 3H), 2.59 (s, 3H). Bis formic acid salt. LC-MS: LC-MS: m/z 551.2 $[M + H]^+$, (ESI+), RT = 2.72 LCMS Method 6 |
| 1462 | 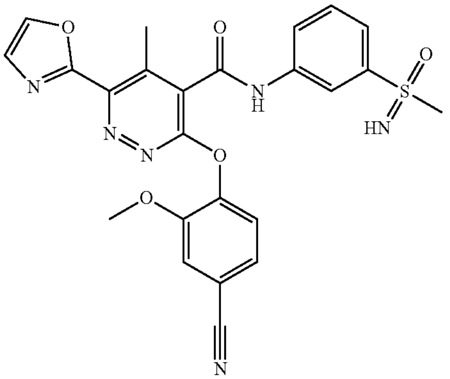 [SMILES: COc1cc(C#N)ccc1Oc1nnc(-c2ncco2)c(C)c1C(=O)Nc1cccc(S(C)(=N)=O)c1] 3-(4-cyano-2-methoxy-phenoxy)-5-methyl-N-[3-(methylsulfonimidoyl)phenyl]-6-oxazol-2-yl-pyridazine-4-carboxamide; formic acid | $^{1}H$ NMR (400 MHz, $CD_3OD$) δ 8.54 (s, 3H), 8.46 (s, 1H), 8.15 (s, 1H), 7.98 (d, J = 9.4 Hz, 1H), 7.84 (d, J = 7.9 Hz, 1H), 7.66 (t, J = 8.0 Hz, 1H), 7.53 (s, 1H), 7.50-7.41 (m, 3H), 3.81 (s, 3H), 3.18 (s, 3H), 2.79 (s, 3H). TRIS FORMATE SALT. LC-MS: m/z 505.1 $[M + H]^+$, (ESI+), RT = 2.23 LCMS Method 6 |

TABLE 13-continued

| Compound | Structure | Analytical Data |
|---|---|---|
| 1463 | 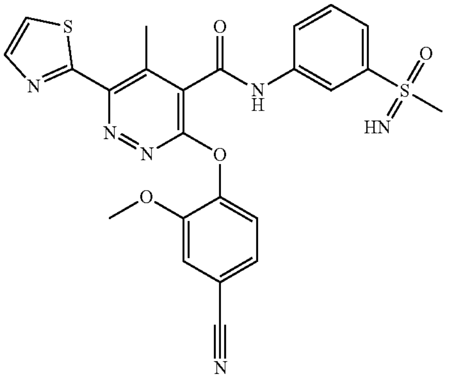 3-(4-cyano-2-methoxy-phenoxy)-5-methyl-N-[3-(methylsulfonimidoyl)phenyl]-6-thiazol-2-yl-pyridazine-4-carboxamide | $^1$H NMR (400 MHz, $CD_3OD$) δ 8.46 (t, J = 1.9 Hz, 1H), 8.04 (d, J = 3.3 Hz, 1H), 8.00-7.95 (m, 1H), 7.86-7.79 (m, 1H), 7.73 (d, J = 3.3 Hz, 1H), 7.66 (t, J = 8.0 Hz, 1H), 7.53 (s, 1H), 7.48-7.41 (m, 2H), 3.82 (s, 3H), 3.18 (s, 3H), 2.89 (s, 3H). LC-MS: m/z 521.1 $[M + H]^+$, (ESI+), RT = 2.65 LCMS Method 6 |
| 1464 | 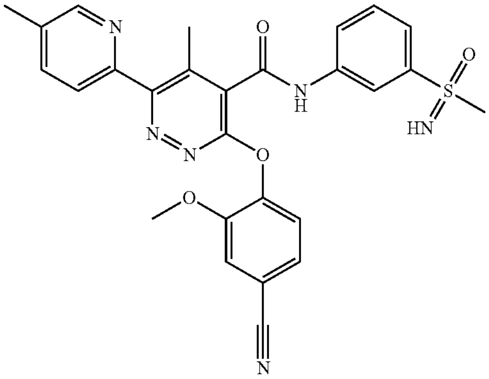 3-(4-cyano-2-methoxy-phenoxy)-5-methyl-6-(5-methyl-2-pyridyl)-N-[3-(methylsulfonimidoyl)phenyl]pyridazine-4-carboxamide | $^1$H NMR (400 MHz, MeOD) δ 8.57 (m, 1H), 8.47 (m, 1H), 7.98 (m, 1H), 7.84 (m, 2H), 7.71 (d, J = 8.0 Hz, 1H), 7.66 (t, J = 8.0 Hz, 1H), 7.52 (m, 1H), 7.49-7.39 (m, 2H), 3.82 (s, 3H), 3.18 (s, 3H), 2.50 (s, 3H), 2.46 (s, 3H). LC-MS: m/z 529.2 $[M + H]^+$, (ESI+), RT = 2.39 LCMS Method 4 |

Example 30

Compound 1465: 3-(4-cyano-2-methylphenoxy)-N-(3-methanesulfonylphenyl)-5-methyl-6-(trifluoromethyl)pyridazine-4-carboxamide

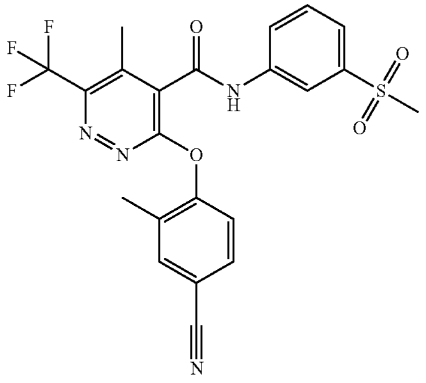 [SMILES: Cc1cc(C#N)ccc1Oc1nnc(C(F)(F)F)c(C)c1C(=O)Nc1cccc(S(C)(=O)=O)c1]

$^1H$ NMR (400 MHz, DMSO-$d_6$) δ 11.42 (br.s, 1H), 8.39-8.33 (m, 1H), 7.93-7.85 (m, 2H), 7.81 (dd, J=8.4, 1.8 Hz, 1H), 7.77-7.66 (m, 2H), 7.50 (d, J=8.4 Hz, 1H), 3.24 (s, 3H), 2.56-2.53 (m, 3H), 2.17 (s, 3H). m/z: 491.0 $[M+H]^+$, (ESI+), RT=3.28 LCMS Method 4.

Example 31

Compound 1466: 3-(4-fluoro-2-methylphenoxy)-5-methyl-N-(3-sulfamoylphenyl)-6-(trifluoromethyl)pyridazine-4-carboxamide

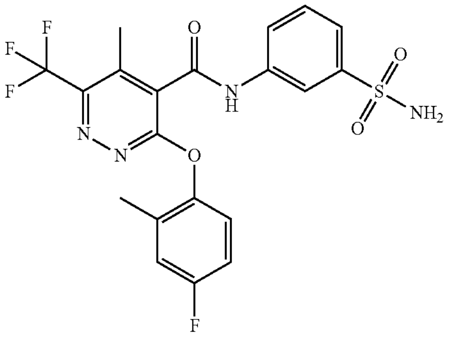 [SMILES: Cc1cc(F)ccc1Oc1nnc(C(F)(F)F)c(C)c1C(=O)Nc1cccc(S(N)(=O)=O)c1]

$^1H$ NMR (500 MHz, DMSO-$d_6$) δ 11.30 (s, 1H), 8.34-8.29 (m, 1H), 7.77 (dt, J=7.5, 1.8 Hz, 1H), 7.67-7.58 (m, 2H), 7.44 (s, 2H), 7.29 (dd, J=8.9, 5.1 Hz, 1H), 7.24 (dd, J=9.4, 3.0 Hz, 1H), 7.14 (td, J=8.6, 3.2 Hz, 1H), 2.53-2.51 (m, 3H), 2.12 (s, 3H). m/z: 485.0 $[M+H]^+$, (ESI+), RT=3.97 LCMS Method 5.

Example 32

Compound 1467: 3-[2-fluoro-4-(trifluoromethoxy)phenoxy]-N-(3-methanesulfonylphenyl)-5-methyl-6-(trifluoromethyl)pyridazine-4-carboxamide

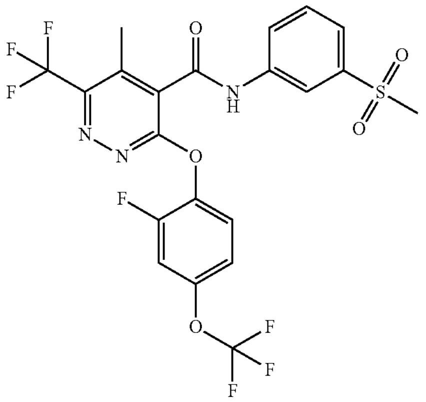 [SMILES: Cc1c(C(F)(F)F)nnc(Oc2ccc(OC(F)(F)F)cc2F)c1C(=O)Nc1cccc(S(C)(=O)=O)c1]

$^1H$ NMR (400 MHz, $CD_3OD$) δ 8.41 (t, J=1.9 Hz, 1H), 7.98 (ddd, J=8.1, 2.1, 1.0 Hz, 1H), 7.79 (ddd, J=7.8, 1.6, 1.0 Hz, 1H), 7.68 (t, J=8.0 Hz, 1H), 7.54 (t, J=8.8 Hz, 1H), 7.37 (dd, J=10.5, 2.4 Hz, 1H), 7.28-7.22 (m, 1H), 3.15 (s, 3H), 2.62-2.58 (m, 3H). 1 proton (NH) not observed. m/z: 554.0 $[M+H]^+$, (ESI+), RT=3.78 LCMS Method 4.

Example 33

Compound 1468: N-(3-methanesulfonylphenyl)-5-methyl-3-{[2-methyl-6-(trifluoromethyl)pyridin-3-yl]oxy}-6-(trifluoromethyl)pyridazine-4-carboxamide

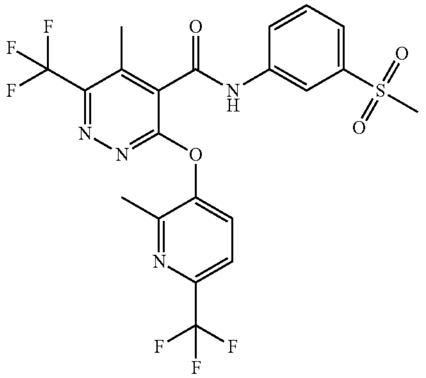 [SMILES: Cc1nc(C(F)(F)F)ccc1Oc1nnc(C(F)(F)F)c(C)c1C(=O)Nc1cccc(S(C)(=O)=O)c1]

$^1H$ NMR (400 MHz, $CD_3OD$) δ 8.41 (t, J=1.9 Hz, 1H), 7.97 (ddd, J=8.2, 2.2, 1.0 Hz, 1H), 7.94 (d, J=8.5 Hz, 1H), 7.81-7.76 (m, 2H), 7.69 (t, J=8.0 Hz, 1H), 3.15 (s, 3H), 2.62 (q, J=1.5 Hz, 3H), 2.47 (s, 3H). m/z: 535.5 $[M+H]^+$, (ESI+), RT=3.62 LCMS Method 4.

Example 34

Compound 1469: 3-[(6-bromo-2-methylpyridin-3-yl)oxy]-N-(3-methanesulfonylphenyl)-5-methyl-6-(trifluoromethyl)pyridazine-4-carboxamide

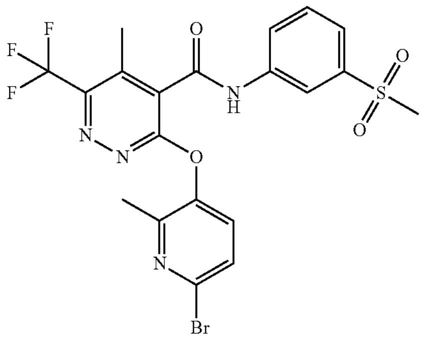 [SMILES: Cc1nc(Br)ccc1Oc1nnc(C(F)(F)F)c(C)c1C(=O)Nc1cccc(S(C)(=O)=O)c1]

$^1H$ NMR (400 MHz, $CD_3OD$) δ 8.40 (t, J=2.0 Hz, 1H), 7.96 (ddd, J=8.1, 2.2, 1.1 Hz, 1H), 7.79 (ddd, J=7.8, 1.7, 1.0 Hz, 1H), 7.71-7.62 (m, 2H), 7.56-7.51 (m, 1H), 3.15 (s, 3H), 2.60 (q, J=1.5 Hz, 3H), 2.37 (s, 3H). m/z: 545.3, 547.3 $[M+H]^+$, (ESI+), RT=3.44 LCMS Method 4.

Example 35

Compound 1470: 3-[(3-fluoro-1-bicyclo[1.1.1]pentanyl)methoxy]-5-methyl-N-[3-(methylsulfonimidoyl)phenyl]-6-(trifluoromethyl)pyridazine-4-carboxamide

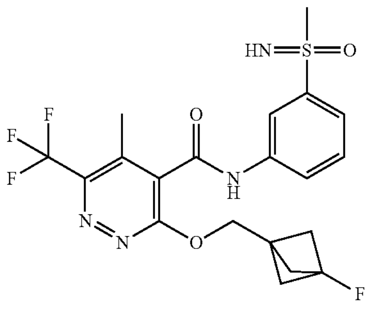 [SMILES: Cc1c(C(F)(F)F)nnc(OCC23CC(F)(C2)C3)c1C(=O)Nc1cccc(S(C)(=N)=O)c1]

$^1H$ NMR (400 MHz, $CD_3OD$) δ 8.41 (t, J=2.0 Hz, 1H), 7.93 (ddd, J=8.1, 2.2, 1.0 Hz, 1H), 7.85 (ddd, J=7.9, 1.9, 1.0 Hz, 1H), 7.67 (t, J=8.0 Hz, 1H), 4.88 (s, 2H), 3.18 (s, 3H), 2.52-2.49 (m, 3H), 2.02 (d, J=2.5 Hz, 7H). m/z: 473.4 $[M+H]^+$, (ESI+), RT=2.94 LCMS Method 4

Example 36

Compounds: 1471 and 1472

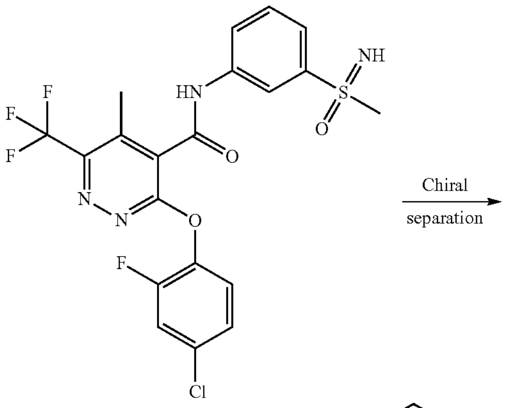

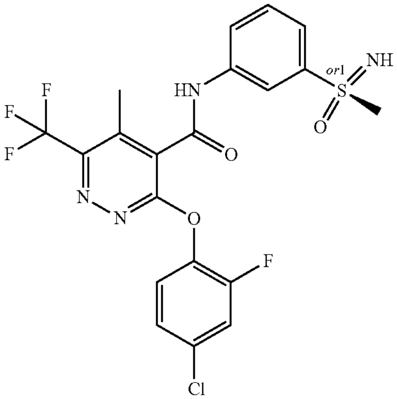

and

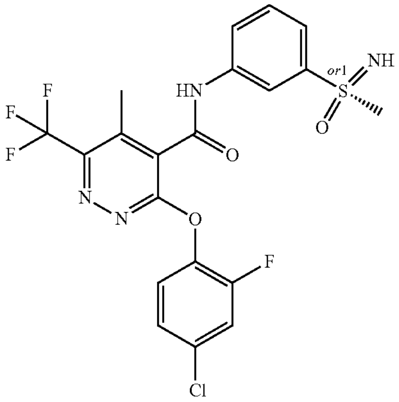

Racemic mixture of 3-(4-chloro-2-fluoro-phenoxy)-5-methyl-N-[3-(methylsulfonimidoyl)phenyl]-6-(trifluoromethyl)pyridazine-4-carboxamide was separated using following Chiral Separation conditions. Mobile phase: 85% Heptane, 15% Ethanol. Column: Chiralpak AS, 20×250 mm, 10 μm Flow rate: 18 mL/min. First eluting isomer $^1H$ NMR (500 MHz, DMSO-$d_6$) δ 11.35 (s, 1H), 8.35 (t, J=1.8 Hz, 1H), 7.91-7.86 (m, 1H), 7.76-7.71 (m, 2H), 7.64 (t, J=7.9 Hz, 1H), 7.54 (t, J=8.6 Hz, 1H), 7.45-7.41 (m, 1H), 4.26 (s, 1H), 3.11-3.04 (m, 3H), 2.54-2.52 (m, 3H). m/z: 503.1, 505.1 $[M+H]^+$, (ESI+), RT=3.13 MET-uPLC-AB-101 (7 min, low pH) and the second eluting isomer $^1H$ NMR (500 MHz, DMSO-$d_6$) δ 11.36 (s, 1H), 8.35 (t, J=1.8 Hz, 1H), 7.91-7.86 (m, 1H), 7.76-7.70 (m, 2H), 7.64 (t, J=7.9 Hz, 1H), 7.54 (t, J=8.6 Hz, 1H), 7.45-7.41 (m, 1H), 4.27 (s, 1H), 3.13-3.03 (m, 3H), 2.54-2.52 (m, 3H). m/z: 503.1, 505.1 $[M+H]^+$, (ESI+), RT=3.13 MET-uPLC-AB-101 (7 min, low pH).

Example 37

Compounds: 1473 and 1474

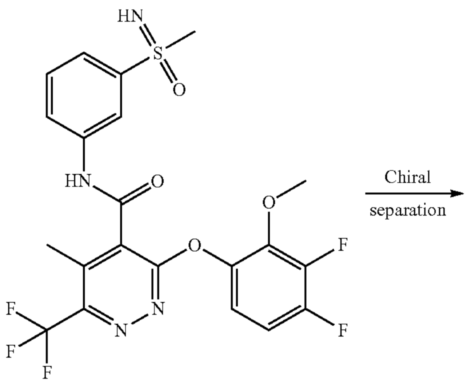

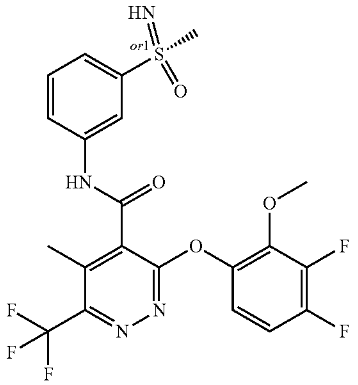

and

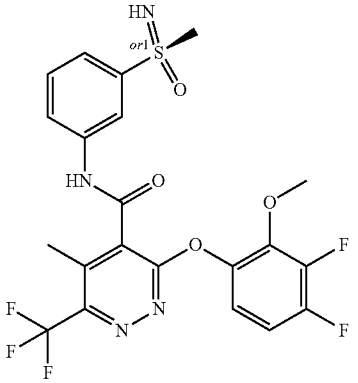

Racemic mixture of 3-(3,4-difluoro-2-methoxy-phenoxy)-5-methyl-N-[3-(methylsulfonimidoyl)phenyl]-6-(trifluoromethyl)pyridazine-4-carboxamide was separated using following Chiral Separation conditions: Mobile phase 85:15 Heptane:Ethanol. Column Chiralpak AS, 20×250 mm, 10 μm. Flow rate (mL/min) 18. First eluting isomer $^1H$ NMR (500 MHz, DMSO-$d_6$) δ 11.33 (s, 1H), 8.35 (t, J=1.8 Hz, 1H), 7.87 (d, J=8.1 Hz, 1H), 7.73 (d, J=7.9 Hz, 1H), 7.64 (t, J=7.8 Hz, 1H), 7.33-7.26 (m, 1H), 7.24 (ddd, J=9.3, 5.3, 1.8 Hz, 1H), 4.26 (s, 1H), 3.87-3.76 (m, 3H), 3.11-2.99 (m, 3H), 2.54-2.52 (m, 3H). m/z: 516.9 $[M+H]^+$, (ESI+), RT=3.85 METCR1416 Hi res 7 min and the second eluting isomer $^1H$ NMR (500 MHz, DMSO-$d_6$) δ 11.32 (s, 1H), 8.36 (t, J=1.9 Hz, 1H), 7.90-7.84 (m, 1H), 7.73 (d, J=7.9 Hz, 1H), 7.64 (t, J=7.9 Hz, 1H), 7.34-7.26 (m, 1H), 7.24 (ddd, J=9.3, 5.3, 1.9 Hz, 1H), 4.26 (s, 1H), 3.85-3.76 (m, 3H), 3.10-3.02 (m, 3H), 2.54-2.52 (m, 3H). m/z: 516.9 $[M+H]^+$, (ESI+), RT=3.86 METCR1416 Hi res 7 min.

Example 38

Compounds: 1475 and 1476

Compound 1475: 3-(3,4-difluoro-2-methoxy-phenoxy)-5-methyl-N-(3-pyridyl)-6-(trifluoromethyl)pyridazine-4-carboxamide

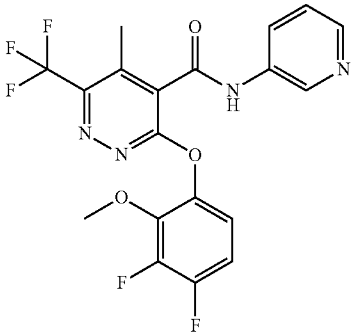 [SMILES: COc1c(Oc2nnc(C(F)(F)F)c(C)c2C(=O)Nc2cccnc2)ccc(F)c1F]

$^1H$ NMR (500 MHz, DMSO-$d_6$) δ 11.24 (br.s, 1H), 8.82 (d, J=2.3 Hz, 1H), 8.39 (dd, J=4.7, 1.4 Hz, 1H), 8.16 (ddd, J=8.3, 2.6, 1.5 Hz, 1H), 7.45 (dd, J=8.1, 4.5 Hz, 1H), 7.34-7.20 (m, 2H), 3.84-3.78 (m, 3H), 2.54-2.52 (m, 3H). m/z: 441.1 $[M+H]^+$, (ESI+), RT=3.00 MET-uPLC-AB-101 (7 min, low pH).

Compound 1476: 3-(3,4-difluoro-2-methoxy-phenoxy)-5-methyl-N-(1-oxidopyridin-1-ium-3-yl)-6-(trifluoromethyl)pyridazine-4-carboxamide

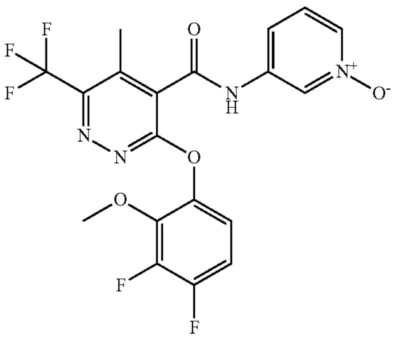 [SMILES: COc1c(Oc2nnc(C(F)(F)F)c(C)c2C(=O)Nc2ccc[n+]([O-])c2)ccc(F)c1F]

$^1H$ NMR (400 MHz, DMSO-$d_6$) δ 11.48 (br.s, 1H), 8.72 (t, J=1.6 Hz, 1H), 8.11-8.05 (m, 1H), 7.54-7.48 (m, 1H), 7.44 (dd, J=8.4, 6.3 Hz, 1H), 7.36-7.20 (m, 2H), 3.85-3.78 (m, 3H), 2.54-2.52 (m, 3H). m/z: 457.1 $[M+H]^+$, (ESI+), RT=2.77 MET-uPLC-AB-101 (7 min, low pH).

Example 39

Compounds: 1477 and 1478

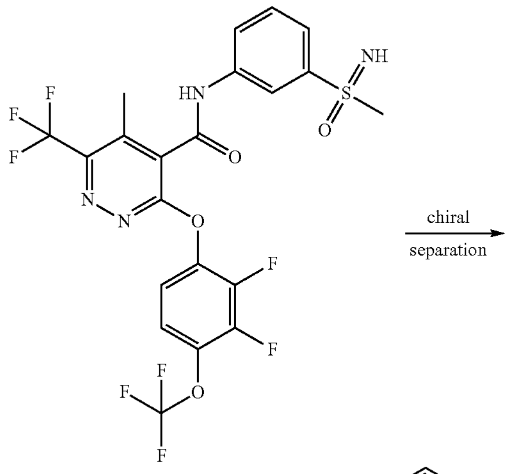

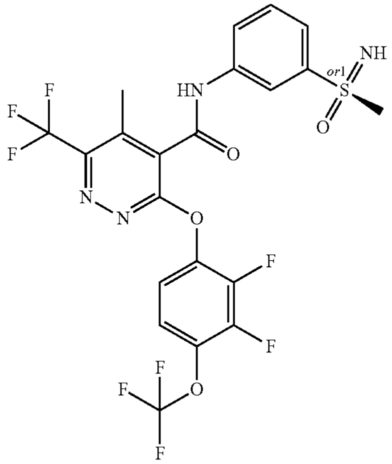

and

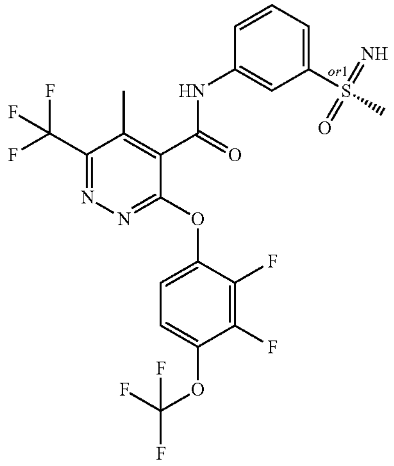

Racemic mixture of 3-[2,3-difluoro-4-(trifluoromethoxy) phenoxy]-5-methyl-N-[3-(methylsulfonimidoyl)phenyl]-6-(trifluoromethyl)pyridazine-4-carboxamide was separated using following Chiral Separation conditions: 10% IPA, 90% $CO_2$, Chiralpak IC, 10×250 mm, 5 μm, 15 mL/min, sample in Methanol, IPA. First eluting isomer $^{1}H$ NMR (500 MHz, DMSO-$d_6$) δ 11.38 (s, 1H), 8.34 (t, J=1.8 Hz, 1H), 7.92-7.84 (m, 1H), 7.74 (d, J=7.8 Hz, 1H), 7.70-7.59 (m, 2H), 7.58-7.49 (m, 1H), 4.26 (s, 1H), 3.12-3.03 (m, 3H), 2.56-2.53 (m, 3H). LC-MS: m/z 571.6 $[M+H]^+$, (ESI+), RT=4.24 LCMS Method 5 and the second eluting isomer $^{1}H$ NMR (500 MHz, DMSO-$d_6$) δ 11.41 (s, 1H), 8.35 (s, 1H), 7.88 (d, J=7.8 Hz, 1H), 7.79-7.70 (m, 1H), 7.64 (t, J=8.0 Hz, 2H), 7.57-7.50 (m, 1H), 4.27 (s, 1H), 3.08 (s, 3H), 2.57-2.53 (m, 3H). LC-MS: m/z 571.1 $[M+H]^+$, (ESI+), RT=3.48 LCMS LCMS Method M2.

Example 40

Compounds: 1479 and 1480

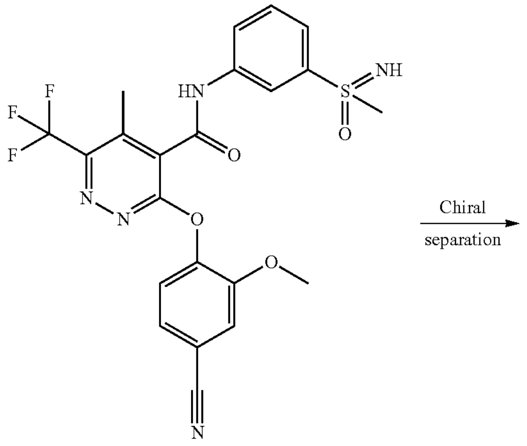

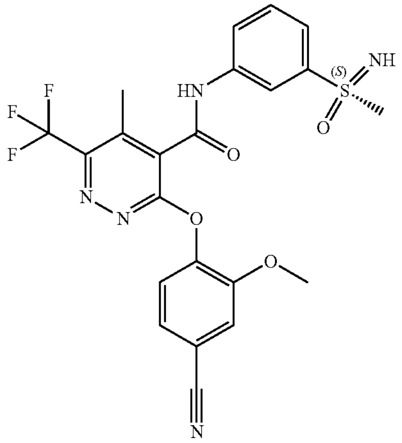

and

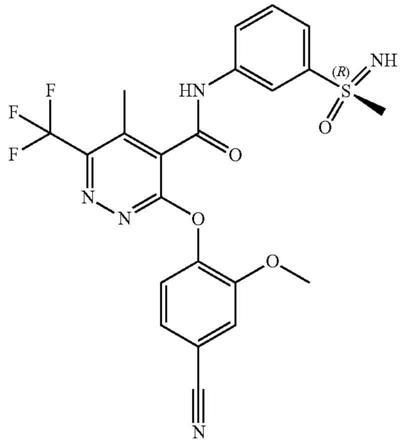

Racemic mixture of 3-(4-cyano-2-methoxyphenoxy)-5-methyl-N-(3-(S-methylsulfonimidoyl)phenyl)-6-(trifluoromethyl)pyridazine-4-carboxamide was separated using following Chiral Separation conditions: Mobile phase 20% Methanol: 80% $CO_2$ Column Chiralpak IC, 10×250 mm, 5 µm Flow rate (mL/min) 15. First eluting isomer (S)-3-(4-cyano-2-methoxyphenoxy)-5-methyl-N-(3-(S-methylsulfonimidoyl)phenyl)-6-(trifluoromethyl)pyridazine-4-carboxamide $^1$H NMR (400 MHz, DMSO-$d_6$) δ 11.29 (s, 1H), 8.33 (t, J=2.0 Hz, 1H), 7.88-7.83 (m, 1H), 7.75-7.68 (m, 2H), 7.62 (t, J=7.9 Hz, 1H), 7.55 (dd, J=8.3, 1.8 Hz, 1H), 7.49 (d, J=8.2 Hz, 1H), 4.24 (s, 1H), 3.77 (s, 3H), 3.05 (d, J=1.1 Hz, 3H), 2.51-2.50 (m, 3H). m/z: 506.3 $[M+H]^+$, (ESI+), RT=2.89 LCMS Method 6 and the second eluting isomer (R)-3-(4-cyano-2-methoxyphenoxy)-5-methyl-N-(3-(S-methylsulfonimidoyl)phenyl)-6-(trifluoromethyl)pyridazine-4-carboxamide $^1$H NMR (400 MHz, DMSO-$d_6$) δ 11.29 (s, 1H), 8.33 (t, J=2.0 Hz, 1H), 7.89-7.82 (m, 1H), 7.75-7.68 (m, 2H), 7.62 (t, J=7.9 Hz, 1H), 7.55 (dd, J=8.2, 1.8 Hz, 1H), 7.49 (d, J=8.2 Hz, 1H), 4.24 (s, 1H), 3.77 (s, 3H), 3.05 (d, J=1.1 Hz, 3H), 2.51-2.50 (m, 3H). m/z: 506.3 $[M+H]^+$, (ESI+), RT=2.89 LCMS Method 6.

Example 41

Compounds: 1481 and 1482

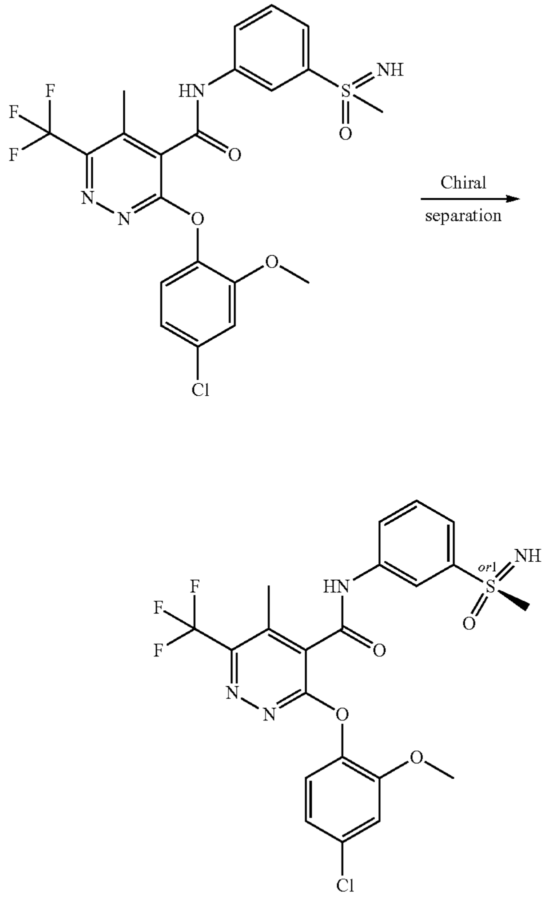

and

-continued

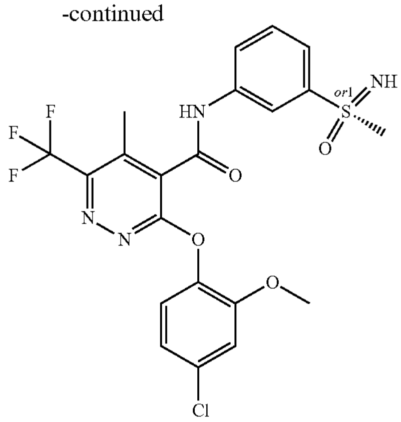

Racemic mixture of 3-(4-chloro-2-methoxyphenoxy)-5-methyl-N-(3-(S-methylsulfonimidoyl)phenyl)-6-(trifluoromethyl)pyridazine-4-carboxamide was separated using following Chiral Separation conditions: Chiral Separation: 85% Heptane, 15% Ethanol, Chiralpak AS, 20×250 mm, 10 µm, 18 mL/min, sample in Methanol, Ethanol. First eluting isomer 1H NMR (500 MHz, DMSO-$d_6$) δ 11.29 (s, 1H), 8.36 (t, J=1.8 Hz, 1H), 7.89-7.85 (m, 1H), 7.75-7.70 (m, 1H), 7.63 (t, J=7.9 Hz, 1H), 7.33-7.29 (m, 2H), 7.10 (dd, J=8.6, 2.3 Hz, 1H), 4.26 (s, 1H), 3.75 (s, 3H), 3.09-3.05 (m, 3H). 3H (one Me) not observed—hidden by DMSO signal. m/z: 503.1, 505.1 $[M+H]^+$, (ESI+), RT=3.06 LCMS Method 4 and the second eluting isomer $^1$H NMR (500 MHz, DMSO-$d_6$) δ 11.29 (s, 1H), 8.36 (t, J=1.8 Hz, 1H), 7.90-7.85 (m, 1H), 7.75-7.70 (m, 1H), 7.63 (t, J=7.9 Hz, 1H), 7.33-7.28 (m, 2H), 7.10 (dd, J=8.6, 2.3 Hz, 1H), 4.26 (s, 1H), 3.75 (s, 3H), 3.10-3.04 (m, 3H). 3H (one $CH_3$) not observed—hidden by DMSO signal m/z: 503.1, 505.1 $[M+H]^+$, (ESI+), RT=3.13 LCMS Method 4.

Example 42

Compound 1483: 3-[(2,6-dimethylpyridin-3-yl)oxy]-N-{3-[imino(methyl)oxo-λ$^6$-sulfanyl]phenyl}-5-methyl-6-(trifluoromethyl)pyridazine-4-carboxamide

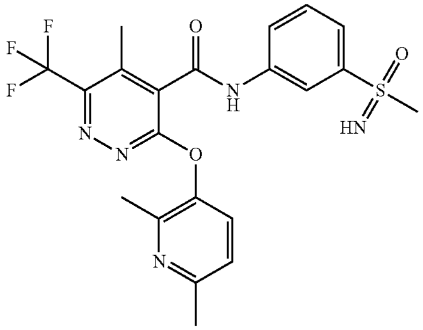

$^1$H NMR (500 MHz, DMSO-$d_6$) δ 11.34 (s, 1H), 8.37 (t, J=1.9 Hz, 1H), 8.13 (s, 1H), 7.89-7.84 (m, 1H), 7.77-7.71 (m, 1H), 7.65 (t, J=7.9 Hz, 1H), 7.61 (d, J=8.2 Hz, 1H), 7.23 (d, J=8.2 Hz, 1H), 3.17 (s, 1H), 3.12 (s, 3H), 2.54-2.52 (m, 3H), 2.47 (s, 3H), 2.28 (s, 3H). m/z: 480.3 $[M+H]^+$, (ESI+), RT=2.74 LCMS Method 6.

Example 43

Compounds: 1484 and 1485

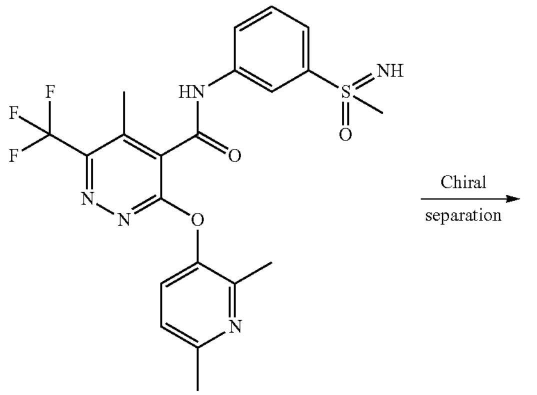

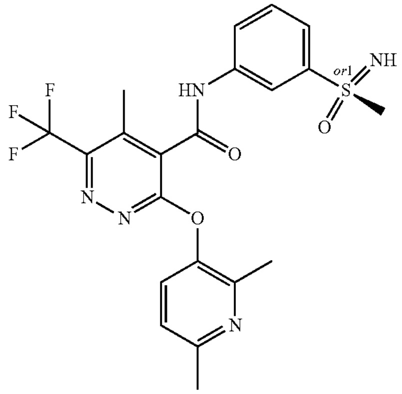

and

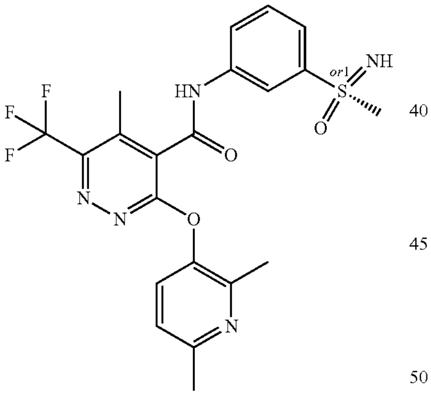

Racemic mixture of 3-[(2,6-dimethylpyridin-3-yl)oxy]-N-{3-[imino(methyl)oxo-$\lambda^6$-sulfanyl]phenyl}-5-methyl-6-(trifluoromethyl)pyridazine-4-carboxamide was separated using following Chiral Separation conditions: Mobile phase 70:30 Heptane: IPA+0.2% DEA Column Cellulose-4, 21.2×250 mm, 5 μm Flow rate (mL/min) 9. First eluting isomer $^1$H NMR (500 MHz, $CD_3OD$) δ 8.33 (t, J=2.0 Hz, 1H), 7.84 (ddd, J=8.2, 2.2, 1.0 Hz, 1H), 7.72 (ddd, J=7.8, 1.8, 1.0 Hz, 1H), 7.54 (t, J=8.0 Hz, 1H), 7.48 (d, J=8.3 Hz, 1H), 7.12 (d, J=8.4 Hz, 1H), 3.05 (s, 3H), 2.47 (q, J=1.5 Hz, 3H), 2.41 (s, 3H), 2.24 (s, 3H). m/z: 480.3 $[M+H]^+$, (ESI+), RT=2.55 LCMS Method 6 and the second eluting isomer $^1$H NMR (500 MHz, $CD_3OD$) δ 8.33 (t, J=2.0 Hz, 1H), 7.84 (ddd, J=8.1, 2.2, 1.0 Hz, 1H), 7.72 (ddd, J=7.9, 1.9, 1.0 Hz, 1H), 7.55 (t, J=8.0 Hz, 1H), 7.48 (d, J=8.4 Hz, 1H), 7.12 (d, J=8.3 Hz, 1H), 3.05 (s, 3H), 2.48 (q, J=1.5 Hz, 3H), 2.41 (s, 3H), 2.24 (s, 3H). m/z: 480.3 $[M+H]^+$, (ESI+), RT=2.54 LCMS Method 6.

Example 44

Compound 1486: 3-(4-chloro-3-fluoro-2-methylphenoxy)-5-methyl-N-[3-(methylsulfonimidoyl)phenyl]-6-(trifluoromethyl)pyridazine-4-carboxamide

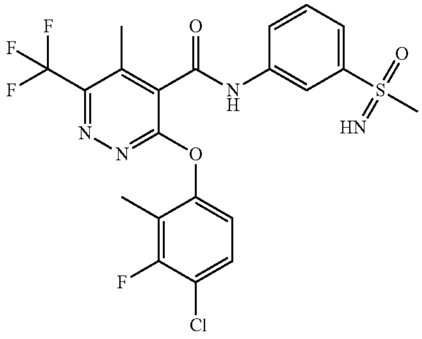 [SMILES: Cc1c(Oc2nnc(C(F)(F)F)c(C)c2C(=O)Nc2cccc(S(C)(=N)=O)c2)ccc(Cl)c1F]

$^1$H NMR (400 MHz, DMSO) δ 11.35 (s, 1H), 8.36 (s, 1H), 7.87 (d, J=8.7 Hz, 1H), 7.74 (d, J=7.9 Hz, 1H), 7.64 (t, J=7.9 Hz, 1H), 7.57 (t, J=8.6 Hz, 1H), 7.23 (d, J=8.9 Hz, 1H), 4.27 (s, 1H), 3.08 (s, 3H), 2.56-2.51 (m, 3H), 2.11 (d, J=1.9 Hz, 3H). m/z: 517.1, 519.1 $[M+H]^+$, (ESI+), RT=3.30 LCMS Method 4

Example 45

Compound: 1487 and 1488

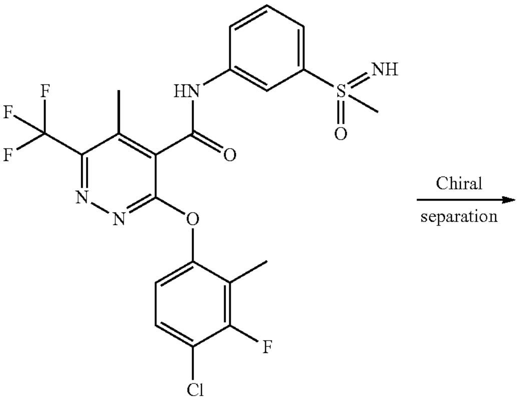

-continued

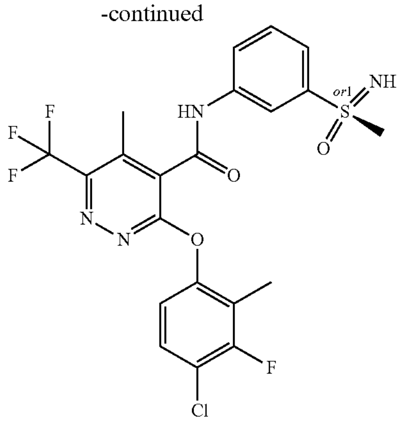

and

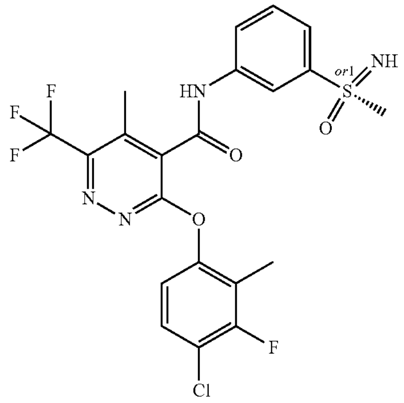

Racemic mixture of 3-(4-chloro-3-fluoro-2-methyl-phenoxy)-5-methyl-N-[3-(methylsulfonimidoyl)phenyl]-6-(trifluoromethyl)pyridazine-4-carboxamide was separated using following Chiral Separation conditions: Mobile phase 15% Methanol, 85% $CO_2$ Column Chiralpak AS-H, 10×250 mm, 5 μm Flow rate (mL/min) 15. First eluting isomer $^1$H NMR (500 MHz, DMSO-$d_6$) δ 11.34 (s, 1H), 8.35 (t, J=2.0 Hz, 1H), 7.90-7.81 (m, 1H), 7.73 (d, J=7.7 Hz, 1H), 7.64 (t, J=7.9 Hz, 1H), 7.56 (t, J=8.6 Hz, 1H), 7.22 (dd, J=8.9, 1.6 Hz, 1H), 4.26 (s, 1H), 3.07 (d, J=1.1 Hz, 3H), 2.54-2.51 (m, 3H), 2.10 (d, J=2.2 Hz, 3H). m/z: 517.4, 519.4 $[M+H]^+$, (ESI+), RT=3.42 LCMS Method 4 and the second eluting isomer $^1$H NMR (500 MHz, DMSO-$d_6$) δ 11.34 (s, 1H), 8.35 (t, J=2.0 Hz, 1H), 7.89-7.80 (m, 1H), 7.73 (d, J=7.8 Hz, 1H), 7.63 (t, J=7.9 Hz, 1H), 7.56 (t, J=8.6 Hz, 1H), 7.22 (dd, J=8.9, 1.6 Hz, 1H), 4.26 (s, 1H), 3.07 (d, J=1.1 Hz, 3H), 2.54-2.52 (m, 3H), 2.12-2.08 (m, 3H). m/z: 517.4, 519.4 $[M+H]^+$, (ESI+), RT=3.42 LCMS Method 4.

Example 46

Compound 1489: 3-(4-chloro-3-fluoro-2-methoxy-phenoxy)-5-methyl-N-[3-(methylsulfonimidoyl)phenyl]-6-(trifluoromethyl)pyridazine-4-carboxamide

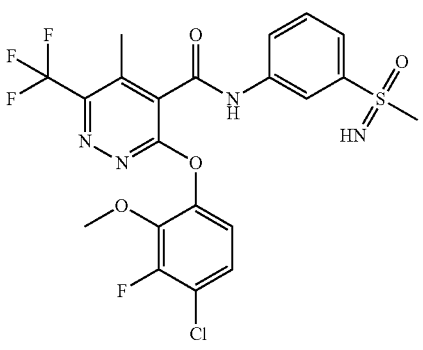 [SMILES: COc1c(Oc2nnc(C(F)(F)F)c(C)c2C(=O)Nc2cccc(S(C)(=N)=O)c2)ccc(Cl)c1F]

$^1$H NMR (400 MHz, DMSO-$d_6$) δ 11.34 (s, 1H), 8.36 (t, J=1.9 Hz, 1H), 7.93-7.84 (m, 1H), 7.74 (d, J=8.1 Hz, 1H), 7.65 (t, J=7.9 Hz, 1H), 7.45 (dd, J=9.0, 7.8 Hz, 1H), 7.28 (dd, J=9.0, 2.0 Hz, 1H), 4.27 (s, 1H), 3.80 (d, J=1.3 Hz, 3H), 3.08 (d, J=0.8 Hz, 3H), 2.56-2.51 (m, 3H). m/z: 533.1, 535.1 $[M+H]^+$, (ESI+), RT=3.21 LCMS Method 4.

Example 47

Compounds: 1490 and 1491

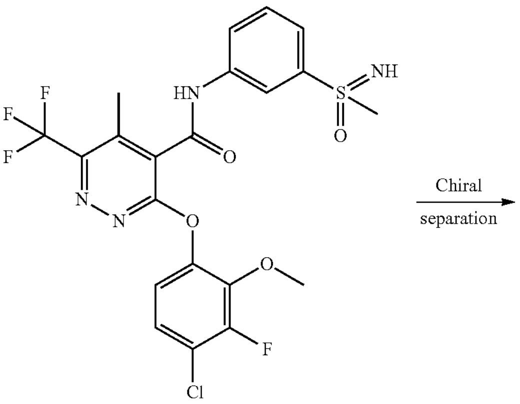

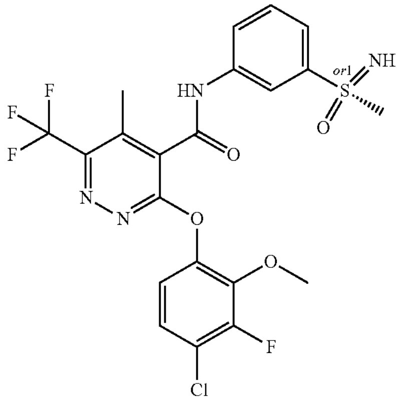

and

-continued

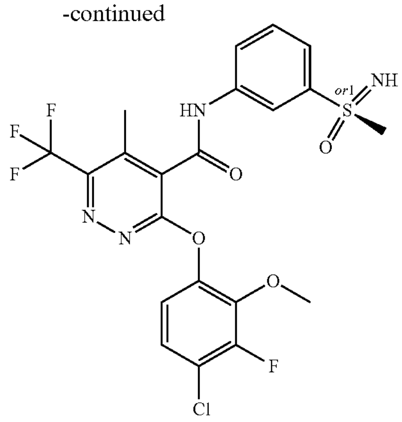

Racemic mixture of 3-(4-chloro-3-fluoro-2-methoxy-phenoxy)-5-methyl-N-[3-(methylsulfonimidoyl)phenyl]-6-(trifluoromethyl)pyridazine-4-carboxamide was separated using following Chiral Separation conditions: Mobile phase 15% Methanol, 85% $CO_2$ Column Chiralpak AS-H, 10×250 mm, 5 μm Flow rate (mL/min) 15. First eluting isomer $^1$H NMR (400 MHz, DMSO-$d_6$) δ 11.33 (s, 1H), 8.35 (s, 1H), 7.87 (d, J=8.0 Hz, 1H), 7.73 (d, J=7.8 Hz, 1H), 7.63 (t, J=7.9 Hz, 1H), 7.44 (dd, J=9.0, 7.7 Hz, 1H), 7.27 (dd, J=9.0, 1.9 Hz, 1H), 4.26 (s, 1H), 3.79 (d, J=1.3 Hz, 3H), 3.07 (d, J=1.1 Hz, 3H), 2.54-2.52 (m, 3H). m/z: 533.1, 535.1 $[M+H]^+$, (ESI+), RT=3.22 LCMS Method 4 and the second eluting isomer $^1$H NMR (400 MHz, DMSO-$d_6$) δ 11.34 (s, 1H), 8.35 (t, J=1.9 Hz, 1H), 7.92-7.83 (m, 1H), 7.73 (d, J=7.8 Hz, 1H), 7.64 (t, J=7.9 Hz, 1H), 7.44 (dd, J=9.0, 7.7 Hz, 1H), 7.27 (dd, J=9.0, 2.0 Hz, 1H), 4.27 (s, 1H), 3.79 (d, J=1.3 Hz, 3H), 3.07 (d, J=1.1 Hz, 3H), 2.55-2.52 (m, 3H). m/z: 533.1, 535.1 $[M+H]^+$, (ESI+), RT=3.22 LCMS Method 4.

Example 48

Compound 1492: 3-[4-(cyclobutoxy)-2,3-difluoro-phenoxy]-5-methyl-N-[3-(methylsulfonimidoyl)phenyl]-6-(trifluoromethyl)pyridazine-4-carboxamide

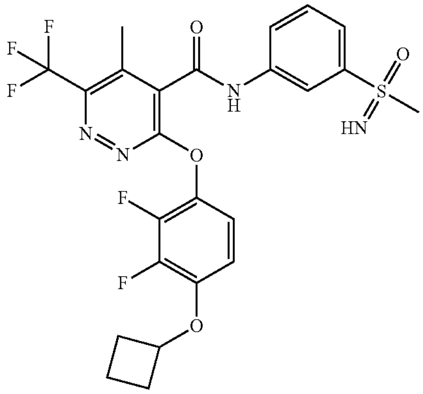 [SMILES: Cc1c(C(F)(F)F)nnc(Oc2ccc(OC3CCC3)c(F)c2F)c1C(=O)Nc1cccc(S(C)(=N)=O)c1]

$^1$H NMR (400 MHz, $CD_3OD$) δ 8.47 (t, J=1.9 Hz, 1H), 7.98 (m, 1H), 7.86 (m, 1H), 7.68 (t, J=8.0 Hz, 1H), 7.11 (td, J=8.7, 2.4 Hz, 1H), 6.90-6.81 (m, 1H), 4.80 (p, J=6.9 Hz, 1H), 3.19 (s, 3H), 2.61 (d, J=1.4 Hz, 3H), 2.57-2.45 (m, 2H), 2.29-2.15 (m, 2H), 1.90 (m, 1H), 1.84-1.67 (m, 1H). m/z: 557.3 $[M+H]^+$, (ESI+), RT=3.63 LCMS Method 6.

Example 49

Compounds: 1493 and 1494

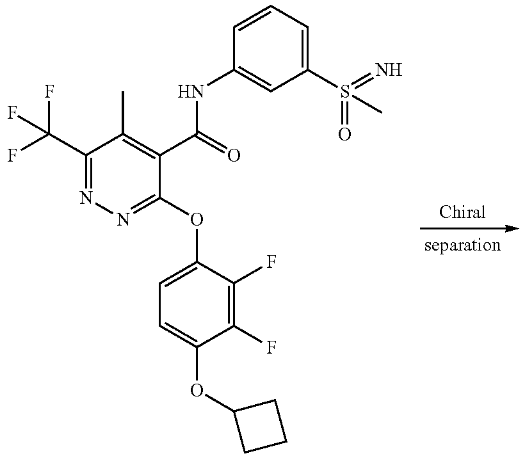

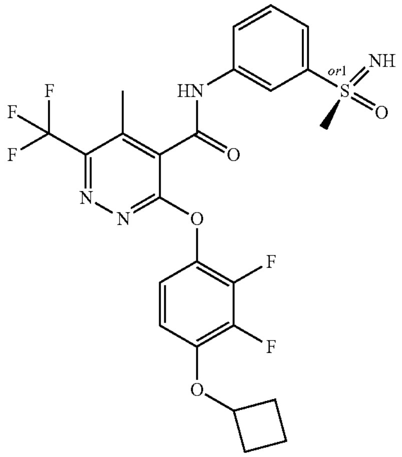

and

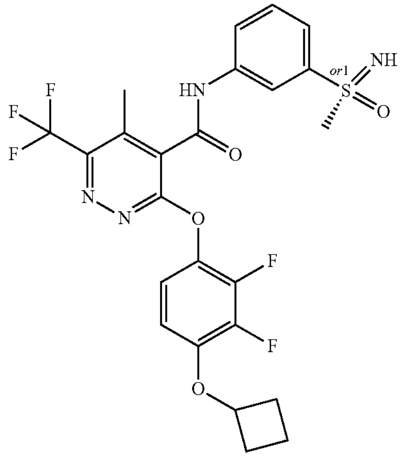

Racemic mixture of 3-(4-cyclobutoxy-2,3-difluorophenoxy)-N-{3-[imino(methyl)oxo-$\lambda^6$-sulfanyl]phenyl}-5-methyl-6-(trifluoromethyl)pyridazine-4-carboxamide was separated using following Chiral Separation conditions: Mobile phase 15% Methanol, 85% $CO_2$ Column Chiralpak AS-H, 10×250 mm, 5 μm Flow rate (mL/min) 15. First eluting isomer $^1$H NMR (400 MHz, $CD_3OD$) δ 8.47 (t, J=1.9 Hz, 2H), 8.02-7.94 (m, 1H), 7.86 (d, J=8.6 Hz, 1H), 7.68 (t, J=8.0 Hz, 1H), 7.16-7.07 (m, 1H), 6.90-6.81 (m, 1H), 4.86-4.74 (m, 1H), 3.19 (s, 3H), 2.61 (d, J=1.4 Hz, 3H), 2.57-2.45 (m, 2H), 2.29-2.15 (m, 2H), 1.91 (m, 1H), 1.84-1.68 (m, 1H). m/z: 557.2 $[M+H]^+$, (ESI+), RT=2.16 and the second $^1H$ NMR (400 MHz, $CD_3OD$) δ 8.47 (t, J=1.9 Hz, 1H), 7.98 (m, 1H), 7.86 (d, J=7.9 Hz, 1H), 7.68 (t, J=8.0 Hz, 1H), 7.16-7.07 (m, 1H), 6.90-6.81 (m, 1H), 4.80 (p, J=7.1 Hz, 1H), 3.19 (s, 3H), 2.63-2.58 (m, 3H), 2.51 (m, 2H), 2.29-2.15 (m, 2H), 1.90 (m, 1H), 1.76 (m, 1H). m/z: 557.2 $[M+H]^+$, (ESI+), RT=3.81 Chiral LC.

Example 50

Compound 1495: 3-[2-fluoro-4-(trifluoromethoxy)phenoxy]-5-methyl-N-[3-(methylsulfonimidoyl)phenyl]-6-(trifluoromethyl)pyridazine-4-carboxamide

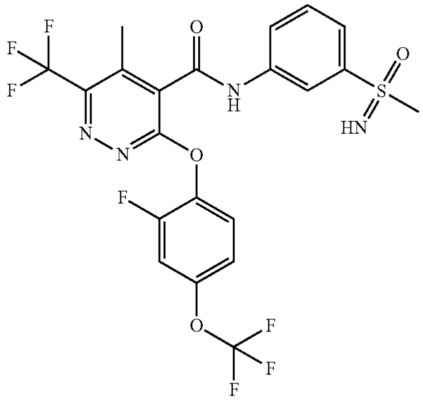 [SMILES: Cc1c(C(F)(F)F)nnc(Oc2ccc(OC(F)(F)F)cc2F)c1C(=O)Nc1cccc(S(C)(=N)=O)c1]

$^1H$ NMR (500 MHz, DMSO-$d_6$) δ 11.37 (s, 1H), 8.35 (t, J=1.9 Hz, 1H), 7.89 (ddd, J=8.0, 2.0, 0.9 Hz, 1H), 7.77-7.69 (m, 2H), 7.69-7.61 (m, 2H), 7.44-7.37 (m, 1H), 4.26 (s, 1H), 3.10-3.06 (m, 3H), 2.55-2.52 (m, 3H). m/z: 553.1 $[M+H]^+$, (ESI+), RT=3.36 LCMS Method 4.

Example 51

Compounds: 1496 and 1497

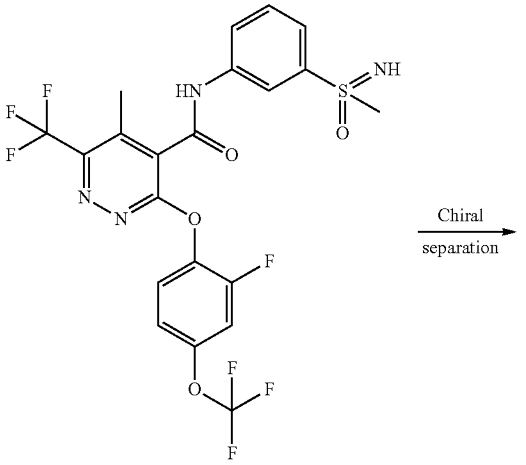

-continued

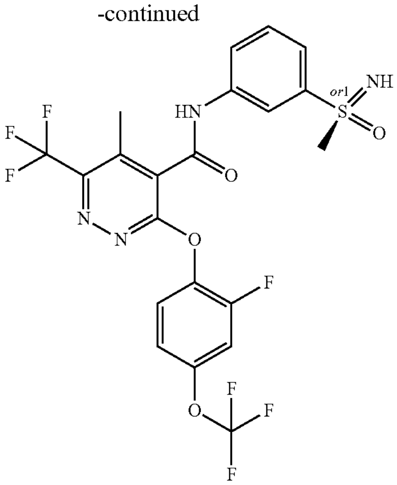

and

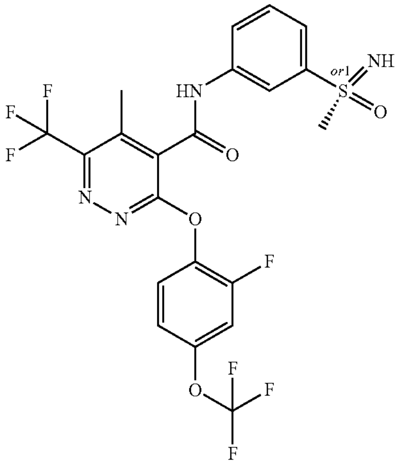

Racemic mixture of 3-[2-fluoro-4-(trifluoromethoxy)phenoxy]-N-{3-[imino(methyl)oxo-$\lambda^6$-sulfanyl]phenyl}-5-methyl-6-(trifluoromethyl)pyridazine-4-carboxamide was separated using following Chiral Separation conditions: Chiral Separation: 10% Methanol, 90% $CO_2$, Chiralpak IC, 10×250 mm, 5 μm, 15 mL/min, sample in Methanol. First eluting isomer $^1H$ NMR (500 MHz, DMSO-$d_6$) δ 11.37 (s, 1H), 8.38-8.32 (m, 1H), 7.92-7.85 (m, 1H), 7.76-7.70 (m, 2H), 7.68-7.61 (m, 2H), 7.40 (d, J=9.0 Hz, 1H), 4.26 (s, 1H), 3.07 (s, 3H), 2.55-2.52 (m, 3H). m/z: 553.1 $[M+H]^+$, (ESI+), RT=3.36 LCMS Method 4 and the second eluting isomer $^1H$ NMR (500 MHz, DMSO-$d_6$) δ 11.37 (s, 1H), 8.37-8.33 (m, 1H), 7.91-7.86 (m, 1H), 7.77-7.69 (m, 2H), 7.69-7.61 (m, 2H), 7.40 (d, J=9.1 Hz, 1H), 4.26 (s, 1H), 3.08 (s, 3H), 2.55-2.52 (m, 3H). m/z: 553.1 $[M+H]^+$, (ESI+), RT=3.36 LCMS Method 4.

Example 52

Compound 1498: 3-[(6-cyclobutoxy-2-methylpyridin-3-yl)oxy]-N-{3-[imino(methyl)oxo-$\lambda^6$-sulfanyl]phenyl}-5-methyl-6-(trifluoromethyl)pyridazine-4-carboxamide

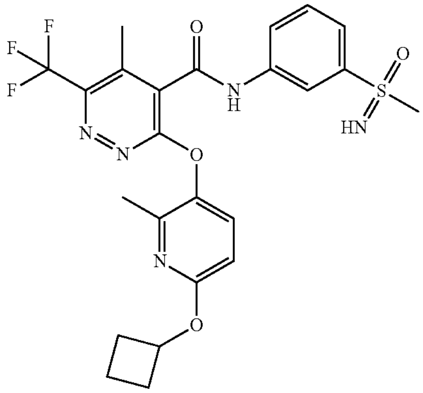 [SMILES: Cc1nc(OC2CCC2)ccc1Oc1nnc(C(F)(F)F)c(C)c1C(=O)Nc1cccc(S(C)(=N)=O)c1]

$^1$H NMR (500 MHz, DMSO-$d_6$) δ 11.40 (s, 1H), 8.37 (s, 1H), 7.88 (d, J=8.0 Hz, 1H), 7.74 (d, J=8.0 Hz, 1H), 7.69-7.60 (m, 2H), 6.72 (d, J=8.7 Hz, 1H), 5.10 (p, J=7.2 Hz, 1H), 4.27 (s, 1H), 3.08 (s, 3H), 2.45-2.36 (m, 2H), 2.22 (s, 3H), 2.05 (m, 2H), 1.78 (m, 1H), 1.64 (m, 1H). m/z: 536.2 $[M+H]^+$, (ESI+), RT=3.35 LCMS Method 4.

Example 53

Compounds: 1499 and 1500

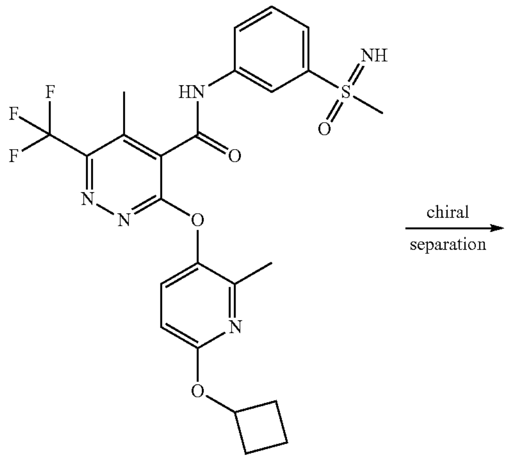

-continued

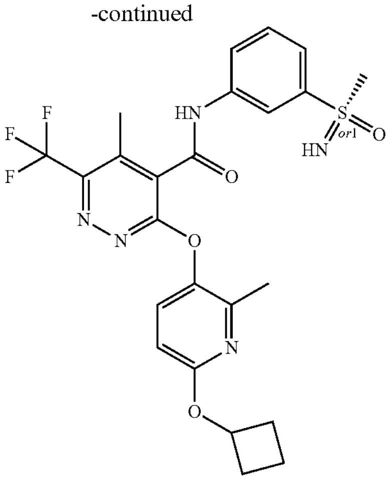

and

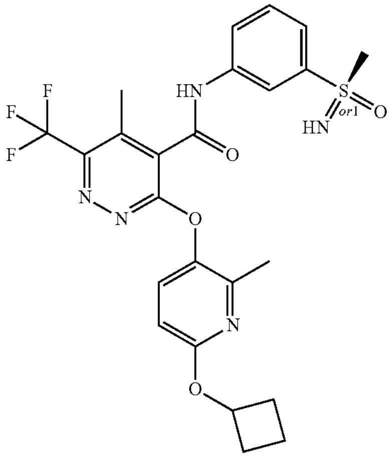

Racemic mixture of 3-((6-cyclobutoxy-2-methylpyridin-3-yl)oxy)-5-methyl-N-(3-(S-methylsulfonimidoyl)phenyl)-6-(trifluoromethyl)pyridazine-4-carboxamide was separated using following Chiral Separation conditions: 100% Ethanol, Chirapak AD-H, 20×250 mm, 5 μm, 9 mL/min. First eluting isomer $^1$H NMR (500 MHz, $CD_3OD$) δ δ 8.47 (t, J=1.9 Hz, 1H), 7.98 (m, 1H), 7.89-7.83 (m, 1H), 7.68 (t, J=8.0 Hz, 1H), 7.55 (d, J=8.8 Hz, 1H), 6.66 (d, J=8.8 Hz, 1H), 5.13 (p, J=7.3 Hz, 1H), 3.19 (s, 3H), 2.61 (d, J=1.3 Hz, 3H), 2.53-2.42 (m, 2H), 2.28 (s, 3H), 2.14 (m, 2H), 1.93-1.80 (m, 1H), 1.72 (m, 1H). m/z: 536.2 $[M+H]^+$, (ESI+), RT=3.35 MET-uPLC-AB-101 (7 min, low pH LCMS Method 4 and the second eluting isomer $^1$H NMR (500 MHz, $CD^3OD$) δ 8.47 (t, J=1.9 Hz, 1H), 7.98 (m, 1H), 7.86 (m, 1H), 7.69 (t, J=8.0 Hz, 1H), 7.55 (d, J=8.8 Hz, 1H), 6.67 (d, J=8.8 Hz, 1H), 5.14 (p, J=7.2 Hz, 1H), 3.19 (s, 1H), 2.61 (d, J=1.3 Hz, 3H), 2.54-2.43 (m, 2H), 2.28 (s, 3H), 2.14 (m, 2H), 1.93-1.81 (m, 1H), 1.72 (m, 1H).

Example 54

Compound 1501: 3-[2,3-difluoro-4-(propan-2-yloxy)phenoxy]-N-{3-[imino(methyl)oxo-$\lambda^6$-sulfanyl]phenyl}-5-methyl-6-(trifluoromethyl)pyridazine-4-carboxamide

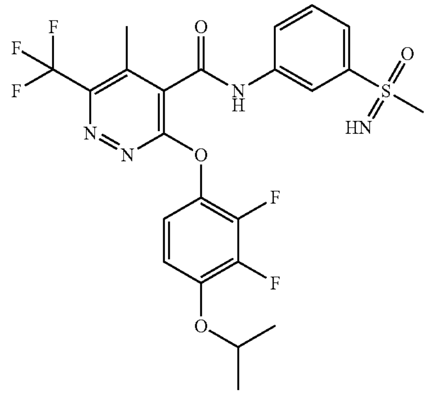 [SMILES: Cc1c(C(F)(F)F)nnc(Oc2ccc(OC(C)C)c(F)c2F)c1C(=O)Nc1cccc(S(C)(=N)=O)c1]

$^1$H NMR (400 MHz, DMSO-$d_6$) δ 11.37 (s, 1H), 8.35 (t, J=1.8 Hz, 1H), 7.92-7.85 (m, 1H), 7.78-7.70 (m, 1H), 7.64 (t, J=7.9 Hz, 1H), 7.29-7.20 (m, 1H), 7.18-7.11 (m, 1H), 4.71 (hept, J=6.0 Hz, 1H), 4.27 (s, 1H), 3.08 (s, 3H), 2.54-2.51 (m, 3H), 1.32 (d, J=6.0 Hz, 6H). m/z: 545.3 $[M+H]^+$, (ESI+), RT=3.53 LCMS Method 6.

Example 55

Compounds: 1502 and 1503

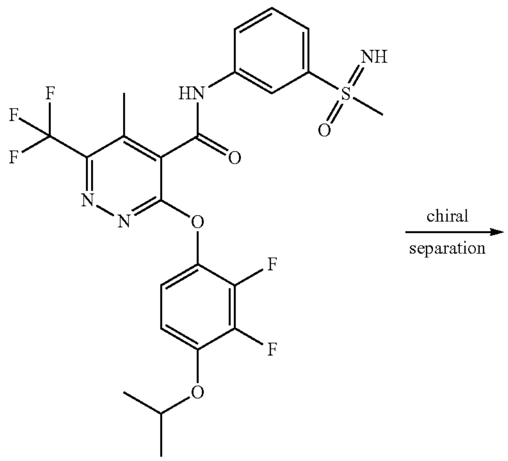

-continued

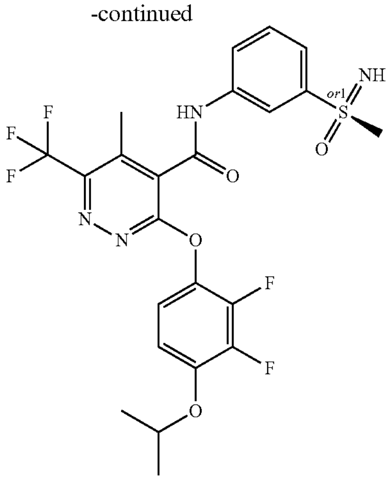

and

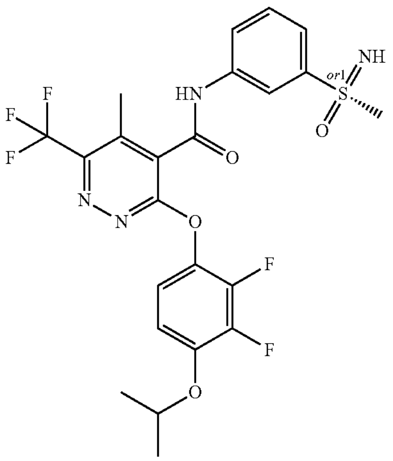

Racemic mixture of 3-(2,3-difluoro-4-isopropoxyphenoxy)-5-methyl-N-(3-(S-methylsulfonimidoyl)phenyl)-6-(trifluoromethyl)pyridazine-4-carboxamide was separated using following chiral conditions: 80% Heptane, 20% IPA, Chiralpak AS, 20×250 mm, 10 μm, 18 mL/min, sample in Methanol, IPA. First eluting isomer $^1$H NMR (400 MHz, DMSO-$d_6$) δ 11.36 (br.s, 1H), 8.37-8.33 (m, 1H), 7.91-7.85 (m, 1H), 7.77-7.71 (m, 1H), 7.64 (t, J=7.9 Hz, 1H), 7.29-7.20 (m, 1H), 7.18-7.10 (m, 1H), 4.71 (hept, J=5.9 Hz, 1H), 4.27 (s, 1H), 3.10-3.05 (m, 3H), 2.55-2.51 (m, 3H), 1.32 (d, J=6.0 Hz, 6H). LC-MS: m/z 545.3 $[M+H]^+$, (ESI+), RT=3.50 LCMS Method 6 and the second eluting isomer $^1$H NMR (400 MHz, DMSO-$d_6$) δ 11.36 (br.s, 1H), 8.37-8.33 (m, 1H), 7.91-7.85 (m, 1H), 7.77-7.71 (m, 1H), 7.64 (t, J=7.9 Hz, 1H), 7.29-7.20 (m, 1H), 7.19-7.10 (m, 1H), 4.71 (hept, J=5.9 Hz, 1H), 4.27 (s, 1H), 3.08 (s, 3H), 2.54-2.52 (m, 3H), 1.32 (d, J=6.0 Hz, 6H). LC-MS: m/z 545.3 $[M+H]^+$, (ESI+), RT=3.51 LCMS Method 6.

Example 56

Compound 1504: 3-(3-fluoro-4-methoxy-2-methylphenoxy)-N-{3-[imino(methyl)oxo-λ$^6$-sulfanyl]phenyl}-5-methyl-6-(trifluoromethyl)pyridazine-4-carboxamide

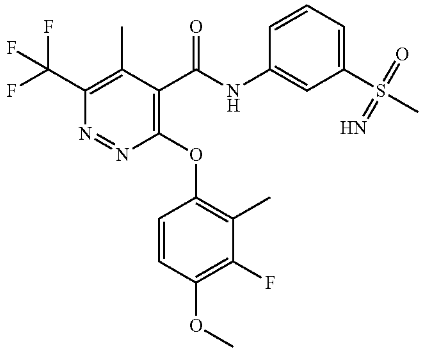 [SMILES: COc1ccc(Oc2nnc(C(F)(F)F)c(C)c2C(=O)Nc2cccc(S(C)(=N)=O)c2)c(C)c1F]

$^1$H NMR (400 MHz, $CD_3OD$) δ 8.45 (t, J=2.0 Hz, 1H), 7.96 (ddd, J=8.1, 2.1, 1.0 Hz, 1H), 7.84 (ddd, J=7.9, 1.9, 1.0 Hz, 1H), 7.66 (t, J=8.0 Hz, 1H), 7.04-6.95 (m, 2H), 3.88 (s, 3H), 3.17 (s, 3H), 2.58 (q, J=1.5 Hz, 3H), 2.07 (d, J=2.2 Hz, 3H). m/z: 513.3 $[M+H]^+$, (ESI+), RT=3.12 LCMS Method 6.

Example 57

Compounds: 1505 and 1506

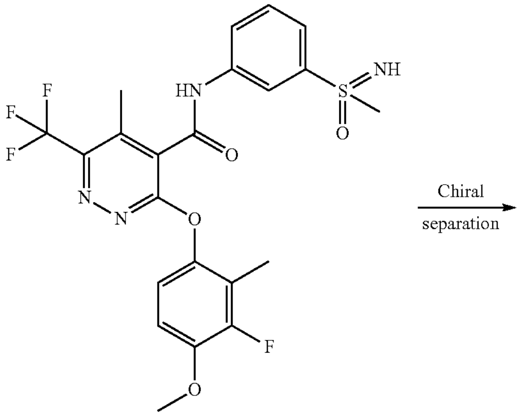

-continued

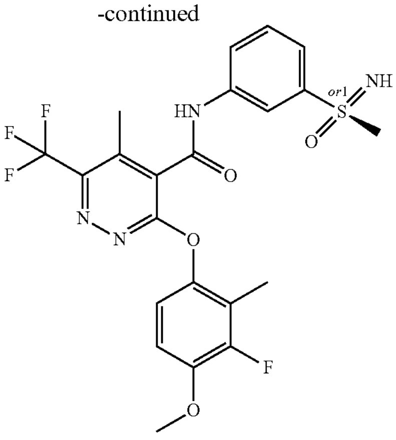

and

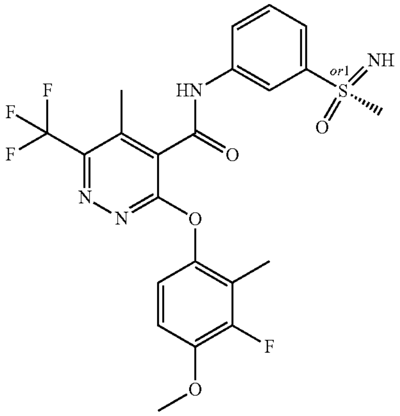

Racemic mixture of 3-(3-fluoro-4-methoxy-2-methylphenoxy)-N-{3-[imino(methyl)oxo-λ$^6$-sulfanyl]phenyl}-5-methyl-6-(trifluoromethyl)pyridazine-4-carboxamide was separated using following chiral conditions: Mobile phase: 10% Methanol: 90% $CO_2$ Column: Chiralpak AS-H, 10×250 mm, 5 μm Flow rate (mL/min) 15. First eluting isomer. $^1$H NMR (500 MHz, DMSO-$d_6$) δ 11.31 (s, 1H), 8.34 (t, J=1.8 Hz, 1H), 7.90-7.80 (m, 1H), 7.72 (d, J=7.8 Hz, 1H), 7.62 (t, J=7.9 Hz, 1H), 7.13-7.01 (m, 2H), 4.25 (s, 1H), 3.83 (s, 3H), 3.06 (d, J=1.1 Hz, 3H), 2.51-2.50 (m, 3H), 2.01 (d, J=2.2 Hz, 3H). m/z: 513.3 $[M+H]^+$, (ESI+), RT=3.13 LCMS Method 6. and the second $^1$H NMR (500 MHz, DMSO-$d_6$) δ 11.31 (s, 1H), 8.34 (t, J=2.0 Hz, 1H), 7.88-7.81 (m, 1H), 7.72 (d, J=7.8 Hz, 1H), 7.62 (t, J=7.9 Hz, 1H), 7.13-7.02 (m, 2H), 4.25 (s, 1H), 3.83 (s, 3H), 3.06 (d, J=1.1 Hz, 3H), 2.51-2.50 (m, 3H), 2.01 (d, J=2.1 Hz, 3H). m/z: 513.3 $[M+H]^+$, (ESI+), RT=3.13 LCMS Method 6.

Example 58

Compound 1507: N-{3-[imino(methyl)oxo-λ$^6$-sulfanyl]phenyl}-3-[(6-methoxy-2-methylpyridin-3-yl)oxy]-5-methyl-6-(trifluoromethyl)pyridazine-4-carboxamide

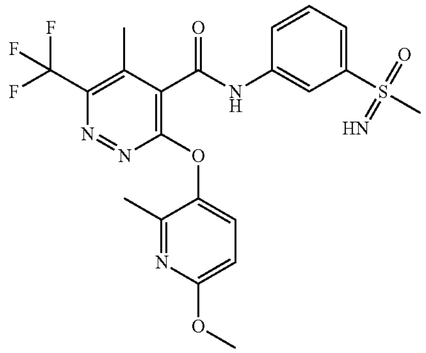 [SMILES: COc1ccc(Oc2nnc(C(F)(F)F)c(C)c2C(=O)Nc2cccc(S(C)(=N)=O)c2)c(C)n1]

$^1$H NMR (500 MHz, $CD_3OD$) δ 8.45 (t, J=2.0 Hz, 1H), 7.96 (ddd, J=8.2, 2.2, 1.0 Hz, 1H), 7.84 (ddd, J=7.8, 1.8, 1.0 Hz, 1H), 7.66 (t, J=8.0 Hz, 1H), 7.54 (d, J=8.8 Hz, 1H), 6.70 (d, J=8.7 Hz, 1H), 3.91 (s, 3H), 3.17 (s, 3H), 2.59 (q, J=1.6 Hz, 3H), 2.28 (s, 3H). m/z: 496.3 $[M+H]^+$, (ESI+), RT=2.96 LCMS Method 6.

Example 59

Compounds: 1508 and 1509

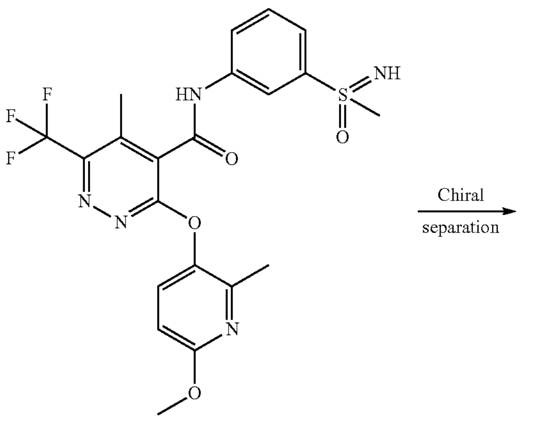

-continued

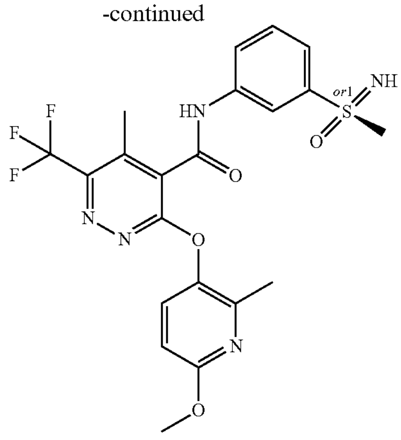

and

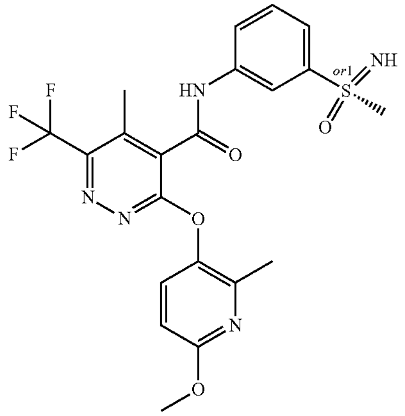

Racemic mixture of N-{3-[imino(methyl)oxo-λ$^6$-sulfanyl]phenyl}-3-[(6-methoxy-2-methylpyridin-3-yl)oxy]-5-methyl-6-(trifluoromethyl)pyridazine-4-carboxamide was separated using following chiral conditions: Mobile phase: 85:15 heptane: ethanol Column: Chiralpak AS, 20×250 mm, 10 m Flow rate (mL/min) 18. First eluting isomer $^1$H NMR (500 MHz, DMSO-$d_6$) δ 11.30 (s, 1H), 8.34 (t, J=2.0 Hz, 1H), 7.89-7.83 (m, 1H), 7.72 (d, J=7.8 Hz, 1H), 7.65-7.59 (m, 2H), 6.75 (d, J=8.5 Hz, 1H), 4.25 (s, 1H), 3.84 (s, 3H), 3.06 (d, J=1.1 Hz, 3H), 2.51-2.50 (m, 3H), 2.23 (s, 3H). m/z: 496.3 $[M+H]^+$, (ESI+), RT=2.95 LCMS Method 6 and the second eluting isomer $^1$H NMR (400 MHz, DMSO-$d_6$) δ 11.31 (s, 1H), 8.34 (t, J=2.0 Hz, 1H), 7.87-7.81 (m, 1H), 7.75-7.68 (m, 1H), 7.66-7.57 (m, 2H), 6.75 (d, J=8.8 Hz, 1H), 4.25 (s, 1H), 3.84 (s, 3H), 3.06 (d, J=1.2 Hz, 3H), 2.51-2.50 (m, 3H), 2.23 (s, 3H). m/z: 496.3 $[M+H]^+$, (ESI+), RT=2.95 LCMS Method 6.

Example 60

Compound 1510: 3-[4-(difluoromethoxy)-2,3-difluoro-phenoxy]-5-methyl-N-(3-methylsulfonylphenyl)-6-(trifluoromethyl)pyridazine-4-carboxamide

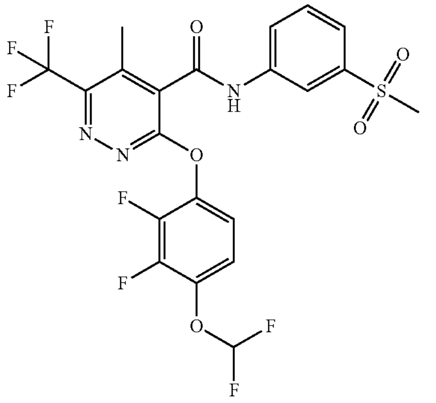 [SMILES: Cc1c(C(F)(F)F)nnc(Oc2ccc(OC(F)F)c(F)c2F)c1C(=O)Nc1cccc(S(C)(=O)=O)c1]

$^1$H NMR (500 MHz, DMSO-$d_6$) δ 11.39 (s, 1H), 8.36 (t, J=1.8 Hz, 1H), 7.89 (dd, J=8.1, 1.1 Hz, 1H), 7.78-7.72 (m, 1H), 7.65 (t, J=7.9 Hz, 1H), 7.53-7.17 (m, 3H), 4.28 (s, 1H), 3.09 (s, 3H), 2.57-2.53 (m, 3H). m/z: 553.1 [M+H]$^+$, (ESI+), RT=3.18 LCMS Method 4.

Example 61

Compounds: 1511 and 1512

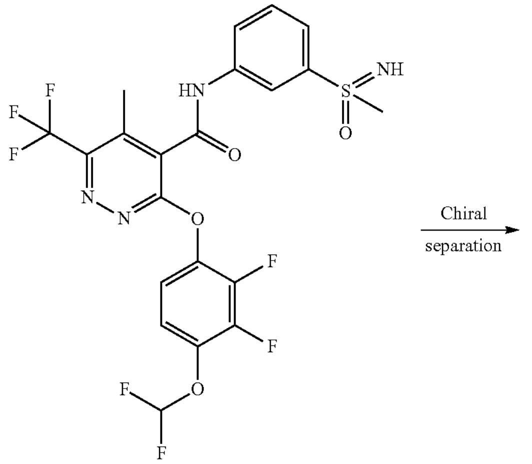

-continued

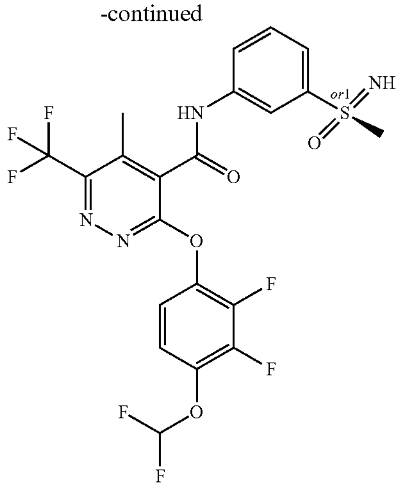

and

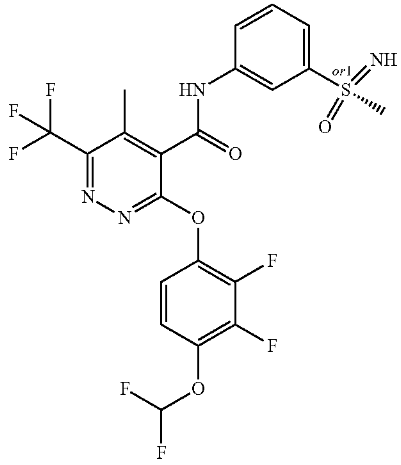

Racemic mixture of 3-[4-(difluoromethoxy)-2,3-difluoro-phenoxy]-N-{3-[imino(methyl)oxo-$\lambda^6$-sulfanyl]phenyl}-5-methyl-6-(trifluoromethyl)pyridazine-4-carboxamide was separated using following chiral conditions: Mobile phase: 85:15 Heptane:Ethanol Column: Chiralpak AD-H, 20×250 mm, 5 μm Flow rate (mL/min):18 mL/min, sample in Ethanol, Methanol & Acetonitrile. First eluting isomer $^1$H NMR (400 MHz, DMSO-$d_6$) δ 11.37 (s, 1H), 8.34 (t, J=2.0 Hz, 1H), 7.88 (ddd, J=8.0, 2.2, 1.1 Hz, 1H), 7.78-7.70 (m, 1H), 7.64 (t, J=7.9 Hz, 1H), 7.55-7.14 (m, 3H), 4.27 (d, J=1.4 Hz, 1H), 3.08 (d, J=1.1 Hz, 3H), 2.56-2.53 (m, 3H). m/z: 553.1 [M+H]$^+$, (ESI+), RT=3.19 LCMS Method 4 and the second eluting isomer $^1$H NMR (400 MHz, DMSO-$d_6$) δ 11.39 (s, 1H), 8.34 (t, J=2.0 Hz, 1H), 7.88 (ddd, J=7.9, 2.2, 1.1 Hz, 1H), 7.76-7.70 (m, 1H), 7.64 (t, J=7.9 Hz, 1H), 7.54-7.14 (m, 3H), 4.27 (s, 1H), 3.08 (d, J=1.2 Hz, 3H), 2.56-2.53 (m, 3H). m/z: 553.1 [M+H]$^+$, (ESI+), RT=3.19 LCMS Method 4.

Example 62

Compound 1513: 3-(4-carbamoylphenoxy)-N-{3-[imino(methyl)oxo-λ$^6$-sulfanyl]phenyl}-5-methyl-6-(trifluoromethyl)pyridazine-4-carboxamide

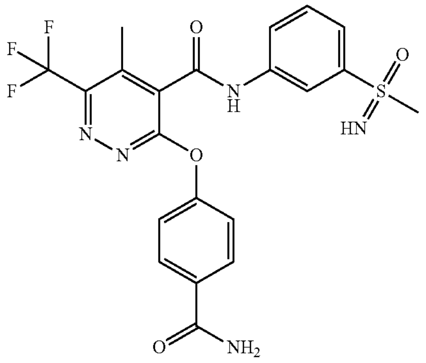 [SMILES: Cc1c(C(F)(F)F)nnc(Oc2ccc(C(N)=O)cc2)c1C(=O)Nc1cccc(S(C)(=N)=O)c1]

$^1$H NMR (500 MHz, DMSO-$d_6$) δ 11.32 (s, 1H), 8.33 (t, J=2.0 Hz, 1H), 8.01 (s, 1H), 7.99-7.94 (m, 2H), 7.87 (ddd, J=8.1, 2.1, 1.1 Hz, 1H), 7.71 (ddd, J=7.8, 1.8, 1.1 Hz, 1H), 7.62 (t, J=8.0 Hz, 1H), 7.40 (s, 1H), 7.38-7.34 (m, 2H), 4.29-4.18 (m, 1H), 3.11-3.01 (m, 3H), 2.51-2.50 (m, 3H). m/z: 494.5 $[M+H]^+$, (ESI+), RT=2.19 LCMS Method 4.

Example 63

Compound 1514: 3-[2,6-difluoro-4-(trifluoromethoxy)phenoxy]-N-{3-[imino(methyl)oxo-λ$^6$-sulfanyl]phenyl}-5-methyl-6-(trifluoromethyl)pyridazine-4-carboxamide

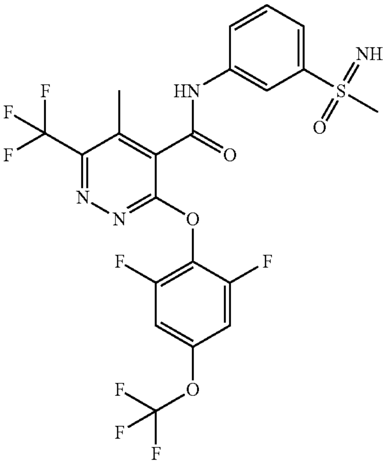 [SMILES: Cc1c(C(F)(F)F)nnc(Oc2c(F)cc(OC(F)(F)F)cc2F)c1C(=O)Nc1cccc(S(C)(=N)=O)c1]

$^1$H NMR (400 MHz, CD3OD) δ 8.46 (t, J=1.9 Hz, 1H), 7.96 (ddd, J=8.1, 2.1, 0.9 Hz, 1H), 7.85 (ddd, J=7.9, 1.7, 1.0 Hz, 1H), 7.67 (t, J=8.0 Hz, 1H), 7.29 (d, J=8.6 Hz, 2H), 3.18 (s, 3H), 2.61 (d, J=1.4 Hz, 3H) 2 NH not seen. m/z: 571 $[M+H]^+$, (ESI+), RT=3.55 LCMS Method 4.

Example 64

Compound 1515: 3-[3-fluoro-2-methyl-4-(trifluoromethoxy)phenoxy]-N-{3-[imino(methyl)oxo-λ$^6$-sulfanyl]phenyl}-5-methyl-6-(trifluoromethyl)pyridazine-4-carboxamide

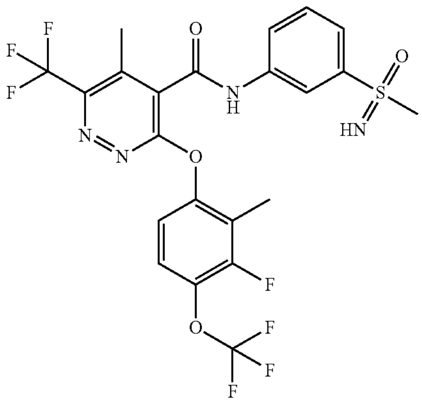 [SMILES: Cc1c(Oc2nnc(C(F)(F)F)c(C)c2C(=O)Nc2cccc(S(C)(=N)=O)c2)ccc(OC(F)(F)F)c1F]

$^1$H NMR (400 MHz, DMSO-$d_6$) δ 11.38 (br.s, 1H), 8.35 (t, J=1.8 Hz, 1H), 7.90-7.84 (m, 1H), 7.77-7.70 (m, 1H), 7.64 (t, J=7.9 Hz, 1H), 7.56 (t, J=8.8 Hz, 1H), 7.30 (dd, J=9.1, 1.6 Hz, 1H), 4.26 (s, 1H), 3.07 (s, 3H), 2.55-2.52 (m, 3H), 2.14-2.10 (m, 3H). m/z: 567.3 $[M+H]^+$, (ESI+), RT=3.66 LCMS Method 6.

Example 65

Compound 1516: 3-(3,4-difluoro-2-methoxyphenoxy)-N-{3-[imino(methyl)oxo-λ$^6$-sulfanyl]phenyl}-5H,6H,7H-cyclopenta[c]pyridazine-4-carboxamide

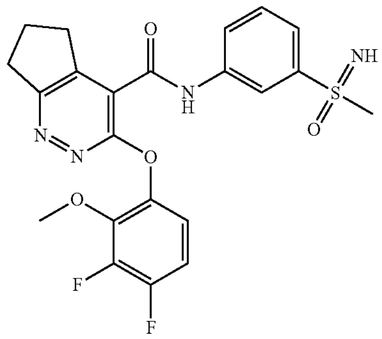 [SMILES: COc1c(Oc2nnc3c(c2C(=O)Nc2cccc(S(C)(=N)=O)c2)CCC3)ccc(F)c1F]

$^1$H NMR (400 MHz, DMSO-$d_6$) δ 11.12 (s, 1H), 8.38 (t, J=1.8 Hz, 1H), 7.88 (ddd, J=8.0, 2.0, 1.0 Hz, 1H), 7.70 (dt, J=7.8, 1.1 Hz, 1H), 7.61 (t, J=7.9 Hz, 1H), 7.30-7.21 (m, 1H), 7.17 (ddd, J=9.3, 5.3, 2.0 Hz, 1H), 4.24 (s, 1H), 3.82-3.75 (m, 3H), 3.12-3.02 (m, 7H), 2.22-2.12 (m, 2H). m/z: 475.3 $[M+H]^+$, (ESI+), RT=2.54 LCMS Method 6.

Example 66

Compound 1517: (S)-3-(4-fluoro-2-methoxyphenoxy)-5-methoxy-N-(3-(S-methylsulfonimidoyl)phenyl)-6-(trifluoromethyl)pyridazine-4-carboxamide

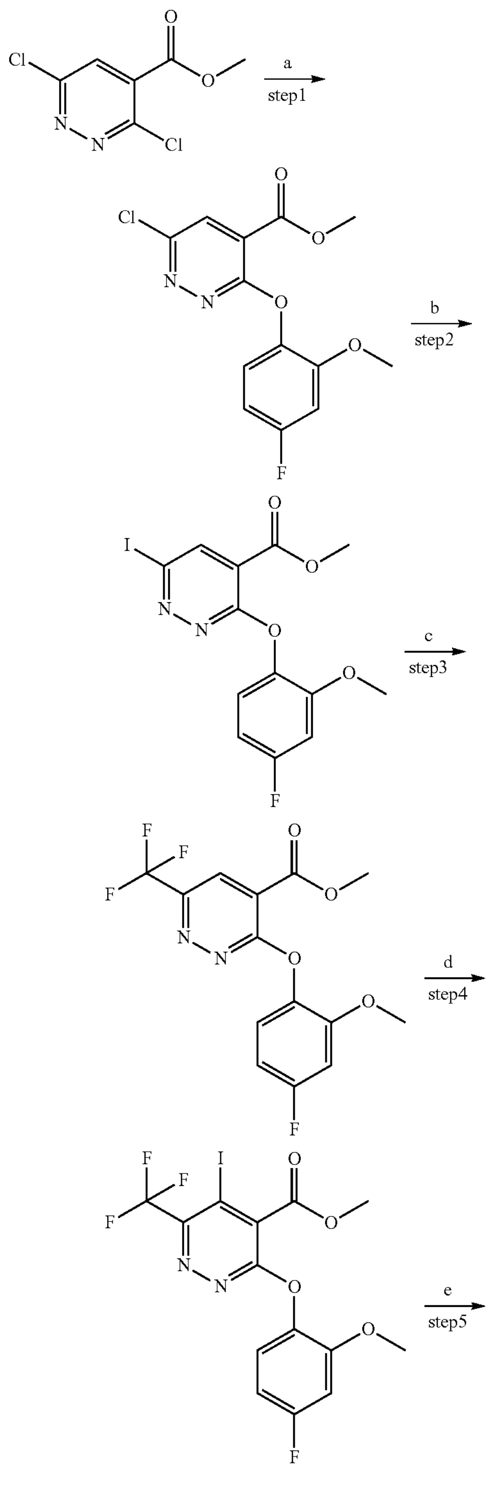

-continued

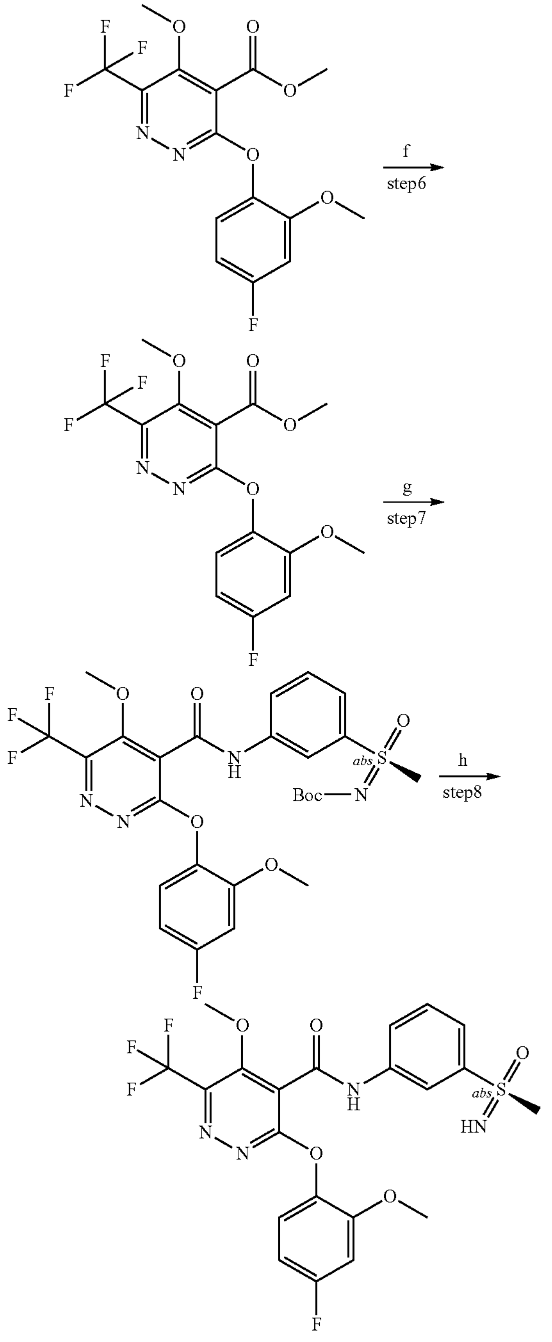

Reagents & conditions:
a) 4-fluoro-2-methoxyphenol, $K_2CO_3$, acetonitrile, 70 °C;
b) NaI, $CH_3COCl$, acetonitrile, 0 °C;
c) methyl difluoro(fluorosulfonyl)acetate, CuI, TBAI, DMF, 70 °C;
d) 2,2,6,6-tetramethylpiperidine, n-BuLi (2.5M in hexane), 1-iodopyrrolidine-2,5-dione, THF, -78 °C;
e) 5.4M NaOMe in MeOH, MeOH, 0 °C to rt;
f) LiOH, THF:$H_2O$ (8:2, v/v), rt;
g) tert-butyl (S)-((3-aminophenyl)(methyl)(oxo)-$\lambda^6$-sulfaneylidene)carbamate;
h) 4M HCl in dioxane, 1,4-dioxane.

Step 1: methyl 6-chloro-3-(4-fluoro-2-methoxy-phenoxy)pyridazine-4-carboxylate A mixture of 4-fluoro-2-methoxy-phenol (98%, 3.86 g, 26.6 mmol), methyl 3,6-dichloro-pyridazine-4-carboxylate (5.25 g, 25.4 mmol) and $K_2CO_3$ (5.26 g, 38.0 mmol) in Acetonitrile (52 mL) was stirred at 70

°C for 3.5 h. The reaction mixture was cooled to room temperature, filtered through a phase separator, washed with DCM (3×50 mL) and concentrated in vacuo. The compound was purified by FCC using 0-100% EtOAc in heptane over silica (on a Biotage Sfar 100 g column, compound wet-loaded using DCM) and concentrated in vacuo to afford methyl 6-chloro-3-(4-fluoro-2-methoxy-phenoxy) pyridazine-4-carboxylate (71.0%) (6.26 g, 56%) as a pale yellow solid. $^1$H NMR (500 MHz, DMSO-$d_6$) δ 8.26 (s, 1H), 7.29 (dd, J=8.8, 5.8 Hz, 1H), 7.14 (dd, J=10.8, 2.9 Hz, 1H), 6.88-6.82 (m, 1H), 3.94 (s, 3H), 3.72 (s, 3H). LC-MA: m/z 313.0, 315.0 [M+H]$^+$, (ESI+), RT=0.88 LCMS Method M2.

Step 2: methyl 3-(4-fluoro-2-methoxy-phenoxy)-6-iodo-pyridazine-4-carboxylate To a stirring solution of methyl 6-chloro-3-(4-fluoro-2-methoxy-phenoxy)pyridazine-4-carboxylate (84%, 6.19 g, 16.6 mmol) and sodium iodide (12.55 g, 83.1 mmol) in Acetonitrile (120 mL) was added acetyl chloride (1.3 mL, 18.3 mmol) dropwise at 0 °C. The reaction was subsequently stirred at 0 °C for 1 h. The reaction was diluted with EtOAc (200 mL), washed with sat. aq $Na_2CO_3$ (200 mL) and sat. sodium sulfite aq (50 mL). The aqueous was re-extracted with EtOAc (2×200 mL), passed through a phase separator and concentrated in vacuo. The compound was purified by FCC using 0-100% EtOAc in heptane over silica (using a Biotage Sfar 100 g column, compound wet-loaded using DCM) and concentrated in vacuo to afford methyl 3-(4-fluoro-2-methoxy-phenoxy)-6-iodo-pyridazine-4-carboxylate (84.0%) (3.54 g, 44%) a as a yellow solid. $^1$H NMR (400 MHz, DMSO-$d_6$) δ 8.35 (s, 1H), 7.25 (dd, J=8.8, 5.8 Hz, 1H), 7.11 (dd, J=10.7, 2.9 Hz, 1H), 6.86-6.80 (m, 1H), 3.91 (s, 3H), 3.70 (s, 3H). LC-MS: m/z 405.1 [M+H]$^+$, (ESI+), RT=0.91 LCMS Method M2.

Step 3: methyl 3-(4-fluoro-2-methoxy-phenoxy)-6-(trifluoromethyl)pyridazine-4-carboxylate: To a mixture of methyl 3-(4-fluoro-2-methoxy-phenoxy)-6-iodo-pyridazine-4-carboxylate (84%, 3.54 g, 7.36 mmol), iodocopper (2.11 g, 11.0 mmol), and tetrabutylammonium; iodide (1.09 g, 2.94 mmol) in DMF (38 mL), methyl difluoro(fluorosulfonyl)acetate (4.7 mL, 36.8 mmol) was added and stirred at 70 °C for 4 h. The reaction was cooled to room temperature, poured into water (200 mL) and extracted with EtOAc (3×200 mL). The combined organic phases were passed through a phase separator and concentrated in vacuo (high vac for DMF removal). The compound was purified by FCC using 0-50% EtOAc in heptane over silica (on a Biotage Sfar 100 g column, compound wet-loaded using DCM), concentrated in vacuo to afford methyl 3-(4-fluoro-2-methoxy-phenoxy)-6-(trifluoromethyl) pyridazine-4-carboxylate (93.0%) (2.52 g, 6.77 mmol, 92%) as a yellow solid. $^1$H NMR (400 MHz, DMSO-$d_6$) δ 8.53 (s, 1H), 7.33 (dd, J=8.9, 5.8 Hz, 1H), 7.16 (dd, J=10.7, 2.9 Hz, 1H), 6.87 (ddd, J=8.9, 8.2, 2.9 Hz, 1H), 3.96 (s, 3H), 3.72 (s, 3H). m/z: 347.0 [M+H]$^+$, (ESI+), RT=0.95 LCMS Method M2.

Step 4: methyl 3-(4-fluoro-2-methoxy-phenoxy)-5-iodo-6-(trifluoromethyl)pyridazine-4-carboxylate: To a stirring solution of 2,2,6,6-tetramethylpiperidine (0.68 mL, 4.03 mmol) in THF-Anhydrous (24 mL), butyllithium (2.5M in hexanes) (1.1 mL, 2.69 mmol) was added dropwise at 0 °C and stirred for 30 mins. The reaction was cooled to −78 °C and treated with a dropwise addition of methyl 3-(4-fluoro-2-methoxy-phenoxy)-6-(trifluoromethyl)pyridazine-4-carboxylate (93%, 500 mg, 1.34 mmol) in THF-Anhydrous (5 mL) at −78 °C. (over 40 minutes) and stirred for 30 mins at −78 °C. The reaction was cooled again to −78 °C and 1-iodopyrrolidine-2,5-dione (332 mg, 1.48 mmol) in THF-Anhydrous (5 mL) was added dropwise (over 20 mins) at −78 °C and stirred at this temperature for 30 mins. The reaction was quenched with sat. aq. NH4Cl (2 mL) at −78 °C and allowed to warm to room temperature, stirring for 30 mins. The reaction mixture was poured into water (100 mL) and extracted with EtOAc (3×100 mL), passed through a phase separator and concentrated in vacuo. The compound was purified by FCC using 0-50% EtOAc in heptane over silica (on a Biotage Sfar 10 g column, compound wet-loaded using DCM), concentrated in vacuo to afford methyl 3-(4-fluoro-2-methoxy-phenoxy)-5-iodo-6-(trifluoromethyl) pyridazine-4-carboxylate (82.0%) (216 mg, 0.375 mmol, 28%) as an orange solid. $^1$H NMR (500 MHz, DMSO-$d_6$) δ 7.32 (dd, J=8.8, 5.8 Hz, 1H), 7.16 (dd, J=10.7, 2.9 Hz, 1H), 6.85 (td, J=8.5, 2.9 Hz, 1H), 4.02 (s, 3H), 3.73 (s, 3H). LC-MS: m/z 473.1 [M+H]$^+$, (ESI+), RT=1.03 LCMS Method M2.

Step 5: methyl 3-(4-fluoro-2-methoxy-phenoxy)-5-methoxy-6-(trifluoromethyl)pyridazine-4-carboxylate: To a stirring solution of methyl 3-(4-fluoro-2-methoxy-phenoxy)-5-iodo-6-(trifluoromethyl)pyridazine-4-carboxylate (82%, 216 mg, 0.375 mmol) in Methanol-Anhydrous (3.3 mL), 5.4 MNaOMe in MeOH (0.069 mL, 0.375 mmol) was added at 0 °C dropwise. The reaction was subsequently allowed to stir at room temperature for 0.5 h. The reaction was re-treated with 5.4 MNaOMe in MeOH (0.035 mL, 0.188 mmol) at 0 °C and stirred for 0.5 h. The reaction was re-treated further time with 5.4 MNaOMe in MeOH (0.017 mL, 0.0938 mmol) and stirred at room temperature for 0.5 h. The reaction was quenched with sat. NH4Cl (aq) (1 mL) and acidified to pH 1 using 2M HCl (aq). The reaction mixture was concentrated in vacuo, poured into water (10 mL) and extracted with EtOAc (3×10 mL). The combined organic phases were passed through a phase separator and concentrated in vacuo. The compound was purified by FCC using 0-100% EtOAc in heptane followed by 0-80% MeOH in EtOAc (on a Biotage Sfar 5 g column, compound wet-loaded using DCM), concentrated in vacuo to afford methyl 3-(4-fluoro-2-methoxy-phenoxy)-5-methoxy-6-(trifluoromethyl)pyridazine-4-carboxylate (68.0%) (148 mg, 0.267 mmol, 71%) as a pale yellow solid. LC-MS: m/z 377.1 [M+H]$^+$, (ESI+), RT=3.75 LCMS Method 4.

Step 6: 3-(4-fluoro-2-methoxy-phenoxy)-5-methoxy-6-(trifluoromethyl)pyridazine-4-carboxylic acid: To a mixture of methyl 3-(4-fluoro-2-methoxy-phenoxy)-5-methoxy-6-(trifluoromethyl)pyridazine-4-carboxylate (68%, 143 mg, 0.258 mmol) in THF (0.8 mL):Water (0.2 mL), lithium hydroxide (12 mg, 0.517 mmol) was added and the mixture was stirred at room temperature for 18 h. The reaction mixture was quenched with 2M HCl (aqueous) to pH 1, poured into water (10 mL) and extracted with EtOAc (3×10 mL). The combined organic phases were passed through a phase separator and concentrated in vacuo. The compound was purified by FCC using 0-100% EtOAc in heptane followed by 0-60% MeOH in EtOAc over silica (on a Biotage Sfar 5 g column, compound wet-loaded using EtOAc) and concentrated in vacuo to afford 3-(4-fluoro-2-methoxy-phenoxy)-5-methoxy-6-(trifluoromethyl) pyridazine-4-carboxylic acid (82.0%) (71 mg, 0.161 mmol, 62%) as a pale yellow solid. $^1$H NMR (400 MHz, DMSO-$d_6$) δ 7.25 (dd, J=8.8, 5.8 Hz, 1H), 7.14 (dd, J=10.7, 2.9 Hz, 1H), 6.84 (ddd, J=8.9, 8.2, 2.9 Hz, 1H), 4.17 (s, 3H), 3.73 (s, 3H). LC-MS: m/z 363.1 [M+H]$^+$, (ESI+), RT=3.03 LCMS Method 4.

Step 7: tert-butyl (S)-((3-(3-(4-fluoro-2-methoxyphenoxy)-5-methoxy-6-(trifluoromethyl)pyridazine-4-carboxamido)phenyl)(methyl)(oxo)-λ$^6$-sulfaneylidene)carbamate: To a stirring solution of 3-(4-fluoro-2-methyl-phenoxy)-5-methoxy-6-(trifluoromethyl)pyridazine-4-carboxylic acid (82%, 95 mg, 0.225 mmol) in DMF-Anhydrous (1.0 mL) was added N-ethyl-N-isopropyl-propan-2-amine (0.079 mL, 0.450 mmol) and HATU (103 mg, 0.270 mmol) at room temperature followed by tert-butyl N—[(S)-(3-aminophenyl)(methyl)oxo-$\lambda^6$-sulfanylidene]carbamate (79 mg, 0.292 mmol) in DMF-Anhydrous (0.5 mL). The reaction was stirred at room temperature for 18 h. The reaction was poured into water (10 mL) and extracted with EtOAc (3×15 mL). The combined organic phases were passed through a phase separator and concentrated in vacuo. The compound was purified by FCC firstly using 0-100% EtOAc in heptane over silica (on a Biotage Sfar 5 g column, compound wet-loaded using DCM), concentrated in vacuo and then purified again using 0-100% DCM in heptane, then 0-100% EtOAc in DCM and flushed with 0-20% MeOH in EtOAc over silica (on a Biotage Sfar 10 g column, compound wet-loaded using DCM) and concentrated in vacuo to afford tert-butyl (S)-((3-(3-(4-fluoro-2-methoxyphenoxy)-5-methoxy-6-(trifluoromethyl)pyridazine-4-carboxamido) phenyl)(methyl)(oxo)-$\lambda^6$-sulfaneylidene)carbamate. (88.0%) (74 mg, 0.106 mmol, 47%) as a white solid. $^1$H NMR (500 MHz, DMSO-$d_6$) δ 11.50 (s, 1H), 8.35 (s, 1H), 7.98-7.87 (m, 1H), 7.77-7.65 (m, 2H), 7.26 (dd, J=8.9, 5.8 Hz, 1H), 7.12 (dd, J=10.7, 2.9 Hz, 1H), 6.83 (td, J=8.5, 2.9 Hz, 1H), 4.18 (s, 3H), 3.74 (s, 3H), 3.39 (s, 3H), 1.21 (s, 9H). LC-MS: m/z 615.3 $[M+H]^+$, (ESI+), RT=0.84 LCMS Method M2.

Step 8: (S)-3-(4-fluoro-2-methoxyphenoxy)-5-methoxy-N-(3-(S-methylsulfonimidoyl)phenyl)-6-(trifluoromethyl) pyridazine-4-carboxamide: To a stirring solution of tert-butyl (S)-((3-(3-(4-fluoro-2-methoxyphenoxy)-5-methoxy-6-(trifluoromethyl)pyridazine-4-carboxamido)phenyl) (methyl)(oxo)-$\lambda^6$-sulfaneylidene)carbamate (74 mg, 0.120 mmol) in 1,4-Dioxane (0.5 mL) was added 4 M HCl in dioxane (0.50 mL, 2.00 mmol) was added and the reaction was stirred at room temperature for 4 h. The reaction was quenched with sat, $Na_2CO_3$ (aq) (2 mL), poured into water (10 mL) and extracted with EtOAc (3×15 mL). The combined organic phases were passed through a phase separator and concentrated in vacuo. The compound was purified by FCC using 0-100% EtOAc in heptane followed by 0-80% MeOH in EtOAc over silica (on a Biotage Sfar 5 g column, compound wet-loaded using DCM) and concentrated in vacuo. The compound was further purified by reverse-phase FCC using 10-100% MeCN+0.1% formic acid in water+0.1% formic acid (on a C18 Biotage Sfar 6 g column, compound loaded using a sample preloaded with a MeOH solution), concentrated in vacuo to afford 3-(4-fluoro-2-methoxy-phenoxy)-5-methoxy-N-[3-(methylsulfonimidoyl) phenyl]-6-(trifluoromethyl)pyridazine-4-carboxamide (99.0%) (9.0 mg, 14%) as a white solid and (S)-3-(4-fluoro-2-methoxyphenoxy)-5-methoxy-N-(3-(S-methylsulfonimidoyl)phenyl)-6-(trifluoromethyl)pyridazine-4-carboxamide (99.0%) (18 mg, 29%) as a white solid. $^1$H NMR (400 MHz, DMSO-$d_6$) δ 11.43 (s, 1H), 8.33 (t, J=2.0 Hz, 1H), 7.87 (ddd, J=8.0, 2.2, 1.1 Hz, 1H), 7.73 (dt, J=8.0, 1.3 Hz, 1H), 7.64 (t, J=7.9 Hz, 1H), 7.28 (dd, J=8.8, 5.8 Hz, 1H), 7.13 (dd, J=10.7, 2.9 Hz, 1H), 6.84 (td, J=8.5, 2.9 Hz, 1H), 4.28-4.23 (m, 1H), 4.19 (s, 3H), 3.74 (s, 3H), 3.07 (d, J=1.0 Hz, 3H). LC-MS: m/z 515.1 $[M+H]^+$, (ESI+), RT=3.06, LC-MS Method 4.

Example 67

Compound 1518: (S)-5-ethyl-3-(4-fluoro-2-methoxyphenoxy)-N-(3-(S-methylsulfonimidoyl) phenyl)-6-(trifluoromethyl)pyridazine-4-carboxamide

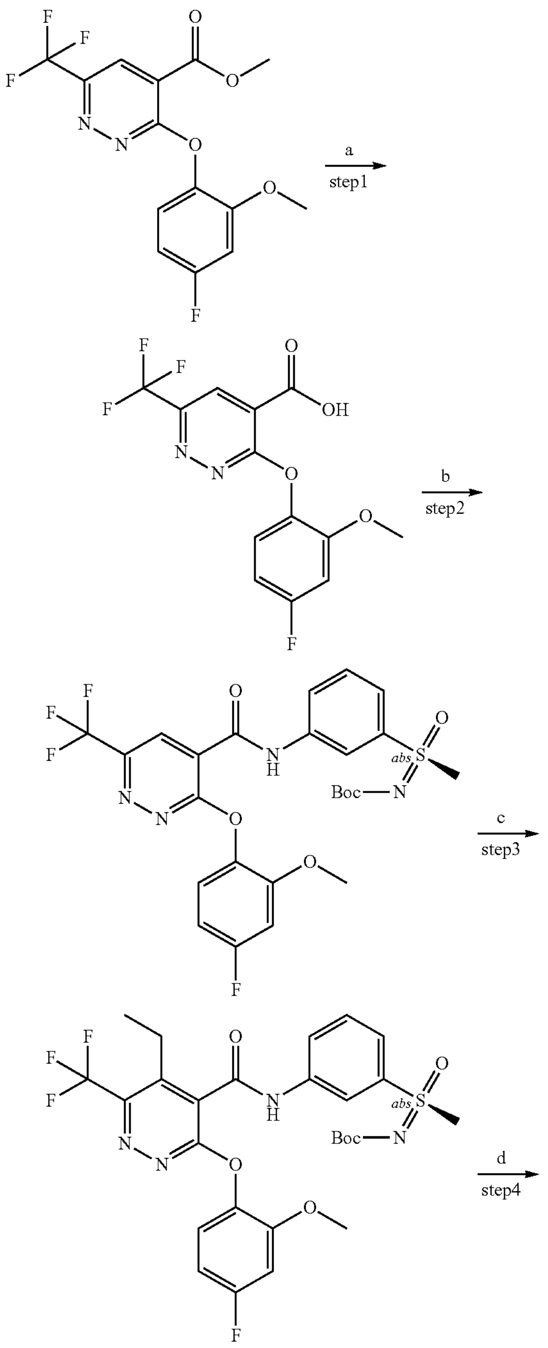

-continued

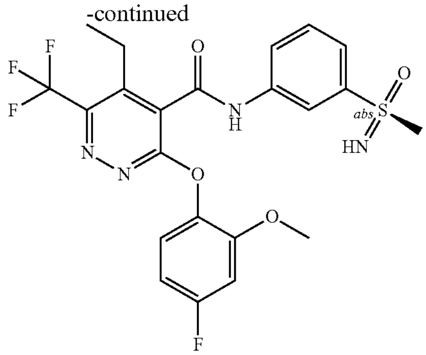

Reagents & conditions:
a) LiOH, THF/$H_2O$, rt;
b) tert-butyl N-[(S)-(3-aminophenyl)(methyl)oxo-$\lambda^6$-sulfanylidene]carbamate, EDC, pyridine;
c) bromo(ethyl)magnesium (3M in $Et_2O$), THF, -78 °C, NBS;
d) DCM, TFA Step 1: 3-(4-fluoro-2-methoxy-phenoxy)-6-(trifluoromethyl)pyridazine-4-carboxylic acid To a mixture of methyl 3-(4-fluoro-2-methoxy-phenoxy)-6-(trifluoromethyl) pyridazine-4-carboxylate (500 mg, 1.44 mmol) in THF (4.5 mL):Water (1 mL), lithium hydroxide (173 mg, 7.22 mmol) was added and the mixture was stirred at room temperature for 1 h. The reaction mixture was quenched with 2M HCl (aq) to pH1, poured into water (50 mL) and extracted with EtOAc (3×50 mL). The combined organic phases were passed through a phase separator and concentrated in vacuo to afford 3-(4-fluoro-2-methoxy-phenoxy)-6-(trifluoromethyl)pyridazine-4-carboxylic acid (69.0%) (509 mg, 73%) as a pale yellow solid. $^1$H NMR (400 MHz, DMSO-$d_6$) δ 8.47 (s, 1H), 7.32 (dd, J=8.8, 5.8 Hz, 1H), 7.15 (dd, J=10.7, 2.9 Hz, 1H), 6.87 (td, J=8.5, 2.9 Hz, 1H), 3.71 (s, 3H). LC_MS: m/z 333.0 $[M+H]^+$, (ESI+), RT=2.96 LCMS Method 4.

Step 2: tert-butyl (S)-((3-(3-(4-fluoro-2-methoxyphenoxy)-6-(trifluoromethyl)pyridazine-4-carboxamido)phenyl)(methyl)(oxo) $\lambda^6$-sulfaneylidene)carbamate: A mixture of 3-(4-fluoro-2-methoxy-phenoxy)-6-(trifluoromethyl) pyridazine-4-carboxylic acid (100 mg, 0.301 mmol), tert-butyl N—[(S)-(3-aminophenyl)(methyl)oxo-$\lambda^6$-sulfanylidene]carbamate (98 mg, 0.361 mmol) and 3-(ethyliminomethyleneamino)-N,N-dimethyl-propan-1-amine hydrochloride (69 mg, 0.361 mmol) were dissolved in Pyridine (2 mL) and stirred at room temperature for 2 h. The reaction was re-treated with tert-butyl N—[(S)-(3-aminophenyl)(methyl)oxo-$\lambda^6$-sulfanylidene]carbamate (20 mg, 0.072 mmol) and stirred at room temperature for 2 h. The reaction was re-treated with 3-(ethyliminomethyleneamino)-N,N-dimethyl-propan-1-amine hydrochloride (14 mg, 0.072 mmol) and stirred at room temperature for 3 h. The reaction was poured into water (30 mL) and extracted with DCM (3×40 mL). The combined organic phases were passed through a phase separator, concentrated in vacuo, purified by FCC using 0-100% EtOAc in heptane over silica (on a Biotage Sfar 10 g column, compound wet-loaded using DCM) and concentrated in vacuo to afford tert-butyl (S)-((3-(3-(4-fluoro-2-methoxyphenoxy)-6-(trifluoromethyl) pyridazine-4-carboxamido)phenyl)(methyl)(oxo)-$\lambda^6$-sulfaneylidene)carbamate (95.0%) (175 mg, 0.284 mmol, 94%) as a pale yellow solid. $^1$H NMR (500 MHz, DMSO-$d_6$) δ 11.26 (s, 1H), 8.64 (s, 1H), 8.37-8.31 (m, 1H), 8.03-7.95 (m, 1H), 7.75-7.67 (m, 2H), 7.37 (dd, J=8.8, 5.9 Hz, 1H), 7.15 (dd, J=10.7, 2.9 Hz, 1H), 6.88 (td, J=8.5, 2.9 Hz, 1H), 3.72 (s, 3H), 3.40 (s, 3H), 1.25 (s, 9H). LC-MS: m/z 585.2 $[M+H]^+$, (ESI+), RT=1.00 LCMS Method M2.

Step 3: tert-butyl (S)-((3-(5-ethyl-3-(4-fluoro-2-methoxyphenoxy)-6-(trifluoromethyl)pyridazine-4-carboxamido) phenyl)(methyl)(oxo)-$\lambda^6$-sulfaneylidene)carbamate: To a stirring solution of tert-butyl (S)-((3-(3-(4-fluoro-2-methoxyphenoxy)-6-(trifluoromethyl)pyridazine-4-carboxamido)phenyl)(methyl)(oxo)-$\lambda^6$-sulfaneylidene)carbamate (72 mg, 0.123 mmol) in THF-Anhydrous (1.5 mL), bromo (ethyl)magnesium (3M in $Et_2O$) (0.21 mL, 0.616 mmol) was added at −78 °C and stirred for 2.5 h. The reaction was re-treated with bromo(ethyl)magnesium (3M in $Et_2O$) (0.21 mL, 0.616 mmol) and stirred at −78 °C for 1 h. The reaction was quenched with methanol (0.40 mL, 9.85 mmol). NBS (39 mg, 0.222 mmol) was subsequently added to the reaction, allowed to warm to room temperature and stirred for 26 h. The reaction was re-treated with NBS (13 mg, 0.073 mmol, 0.6 eq) and stirred at room temperature for 15.5 h. The reaction was re-treated with NBS (13 mg, 0.073 mmol, 0.6 eq) and stirred at room temperature for 2 h. The reaction mixture was poured into water (20 mL) and extracted with EtOAc (3×20 mL). The combined organic phases were passed through a phase separator and concentrated in vacuo. The compound was purified by FCC using 0-100% EtOAc in heptane over silica and flushed with 0-20% MeOH in EtOAc (on a Biotage Sfar 5 g column, compound wet-loaded using DCM) and concentrated in vacuo to afford tert-butyl (S)-((3-(5-ethyl-3-(4-fluoro-2-methoxyphenoxy)-6-(trifluoromethyl)pyridazine-4-carboxamido)phenyl) (methyl)(oxo)-$\lambda^6$-sulfaneylidene)carbamate (60.0%) (66 mg, 52%) as a yellow oil. $^1$H NMR (500 MHz, DMSO-$d_6$) δ 11.41 (s, 1H), 8.39 (t, J=2.0 Hz, 1H), 7.93 (dt, J=6.8, 2.2 Hz, 1H), 7.76-7.70 (m, 2H), 7.31 (dd, J=8.8, 5.9 Hz, 1H), 7.16 (dd, J=10.7, 2.9 Hz, 1H), 6.86 (td, J=8.5, 2.9 Hz, 1H), 3.75 (s, 3H), 3.40 (d, J=1.4 Hz, 3H), 2.85 (q, J=7.3 Hz, 2H), 1.29-1.24 (m, 3H), 1.23 (s, 9H). m/z: 613.3$[M+H]^+$, (ESI+), RT=0.91 LCMS Method M3.

Step 4: (S)-5-ethyl-3-(4-fluoro-2-methoxyphenoxy)-N-(3-(S-methylsulfonimidoyl)phenyl)-6-(trifluoromethyl) pyridazine-4-carboxamide: To a stirring solution of tert-butyl (S)-((3-(5-ethyl-3-(4-fluoro-2-methoxyphenoxy)-6-(trifluoromethyl)pyridazine-4-carboxamido)phenyl) (methyl)(oxo)-$\lambda^6$-sulfaneylidene)carbamate (60%, 66 mg, 0.0646 mmol) in DCM (0.8 mL), TFA (0.048 mL, 0.646 mmol) was added dropwise and stirred at room temperature for 2 h. The reaction was basified with sat. $NaHCO_3$ aq solution (2 mL), poured into water (10 mL) and extracted with DCM (3×20 mL). The combined organic phases were passed through a phase separator, concentrated in vacuo and purified by reverse phase using 10-100% MeCN+01% formic acid in water+0.1% formic acid (on a Biotage Sfar C18 6 g column, compound loaded onto a sampler pre-loaded with the compound solution in MeOH and dried in a 40 °C oven), concentrated in vacuo and freeze-dried overnight to afford (S)-5-ethyl-3-(4-fluoro-2-methoxyphenoxy)-N-(3-(S-methylsulfonimidoyl)phenyl)-6-(trifluoromethyl) pyridazine-4-carboxamide (90.0%) (14 mg, 38%) as a white solid. $^1$H NMR (400 MHz, DMSO-$d_6$) δ 11.31 (s, 1H), 8.36 (t, J=2.0 Hz, 1H), 7.89-7.83 (m, 1H), 7.77-7.69 (m, 1H), 7.64 (t, J=7.9 Hz, 1H), 7.32 (dd, J=8.9, 5.8 Hz, 1H), 7.15 (dd, J=10.7, 2.9 Hz, 1H), 6.86 (td, J=8.5, 2.9 Hz, 1H), 4.26 (s, 1H), 3.74 (s, 3H), 3.08 (d, J=1.1 Hz, 3H), 2.84 (q, J=7.2 Hz, 2H), 1.27 (t, J=7.5 Hz, 3H). LC-MS: m/z 513.2 1 [M+H]+, (ESI+), RT=3.04 LCMS Method 4.

Example 68

Compound 1519: (S)-5-cyclopropyl-3-(4-fluoro-2-methylphenoxy)-N-(3-(S-methylsulfonimidoyl)phenyl)-6-(trifluoromethyl)pyridazine-4-carboxamide

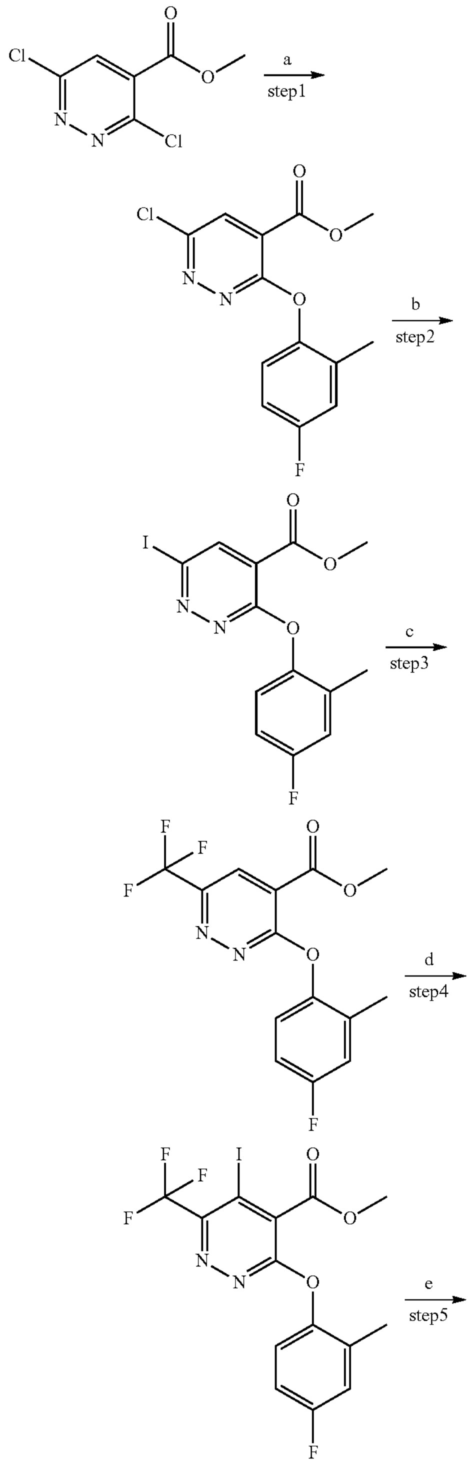

-continued

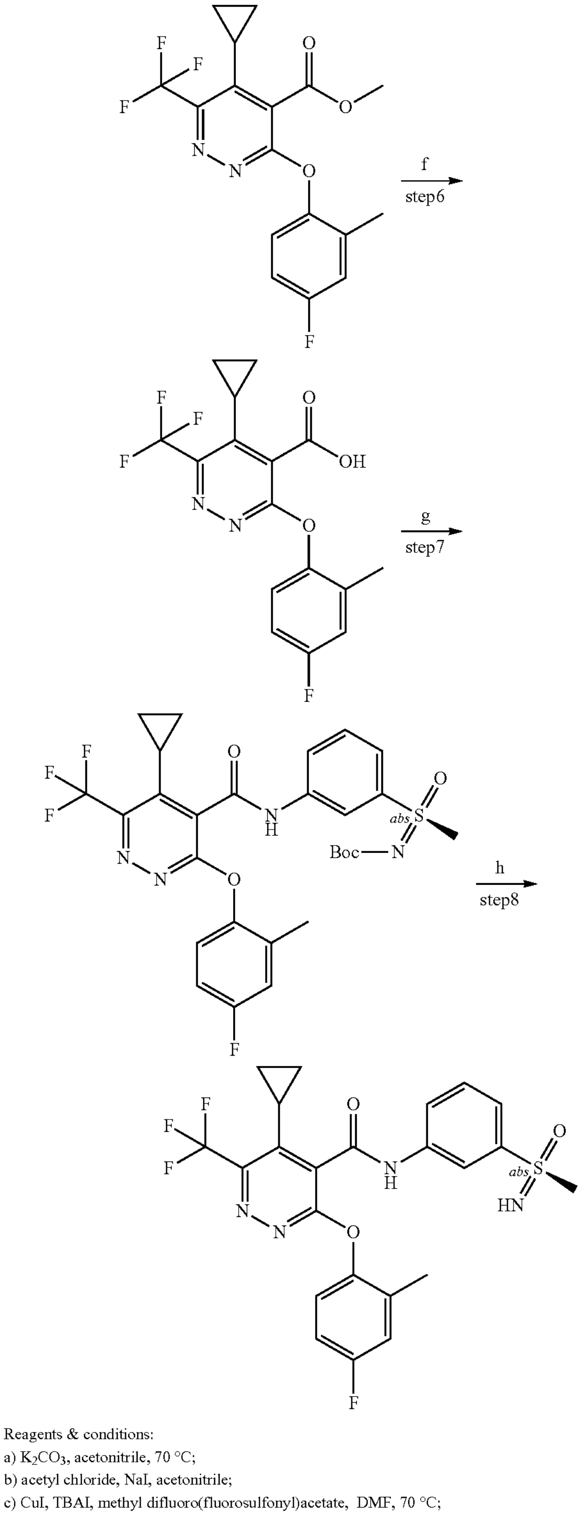

Reagents & conditions:
a) $K_2CO_3$, acetonitrile, 70 °C;
b) acetyl chloride, NaI, acetonitrile;
c) CuI, TBAI, methyl difluoro(fluorosulfonyl)acetate, DMF, 70 °C;
d) THF, 2,2,6,6-tetramethylpiperidine, n-BiLi (2.5M in hexanes), -78 °C, 1-iodopyrrolidine-2,5-dione;
e) cyclopropylboronic acid, bis[3-(diphenylphosphanyl)cyclopenta-2,4-dien-1-yl]iron; dichloromethane; dichloropalladium, $K_2CO_3$, 100 °C;
f) LiOH, THF/$H_2O$, 40 °C 20 h;
g) oxalyl chloride, tert-butyl N-[(S)-(3-aminophenyl)(methyl)oxo-$\lambda^6$-sulfanylidene]carbamate, DIEA, DMF, rt;
h) DCM, TFA Step 1: methyl 6-chloro-3-(4-fluoro-2-methyl-phenoxy)pyridazine-4-carboxylate: A mixture of 4-fluoro-2-methylphenol (5.05 g, 40.1 mmol), methyl 3,6-dichloropyridazine-4-carboxylate (7.90 g, 38.2 mmol) and dipotassium carbonate (7.91 g, 57.2 mmol) in Acetonitrile (79 mL) was stirred at 70 °C for 14.5 h. The reaction was cooled to room temperature, filtered and washed with DCM (2×100 mL) and concentrated in vacuo. The compound was purified by FCC using 0-50% EtOAc in heptane over silica (on a Biotage Sfar 350 g column, compound wet-loaded using DCM) and concentrated in vacuo to afford methyl 6-chloro-3-(4-fluoro-2-methyl-phenoxy)pyridazine-4-carboxylate (9.12 g, 20.9 mmol, 55%) as a pale yellow solid. H NMR (400 MHz, DMSO-$d_6$) δ 8.27 (s, 1H), 7.26-7.21 (m, 2H), 7.16-7.07 (m, 1H), 3.94 (s, 3H), 2.11 (s, 3H). LC-MS: m/z 297.0, 299.0 $[M+H]^+$, (ESI+), RT=0.93 LCMS Method M2.

Step 2: methyl 3-(4-fluoro-2-methyl-phenoxy)-6-iodo-pyridazine-4-carboxylate: To a stirring solution of methyl 6-chloro-3-(4-fluoro-2-methyl-phenoxy)pyridazine-4-carboxylate (3.00 g, 10.1 mmol) and sodium iodide (15.16 g, 0.101 mol) in Acetonitrile-Anhydrous (34 mL) was added a solution of acetyl chloride (0.79 mL, 11.1 mmol) in Acetonitrile-Anhydrous (34 mL) dropwise over 30 mins at 0 to 5 °C. The reaction was subsequently stirred at 5 °C for 30 mins then at room temperature for 2 h. The reaction was re-treated with acetyl chloride (0.10 mL, 1.41 mmol) at 0 °C and stirred at room temperature for 2 h. The reaction mixture was diluted with sat. aq. $NaHCO_3$ (20 mL) and stirred for 5 min. Water (100 mL) was added and the resulting solution extracted with EtOAc (3×100 mL). The combined organic phases were washed with sat. aq sodium thiosulfate (2×50 ml), passed through a phase separator, concentrated in vacuo and purified by FCC using 0-100% EtOAc in heotane over silica (on a Biotage Sfar 200 g column, compound wet-loaded using DCM) and concentrated in vacuo to afford methyl 3-(4-fluoro-2-methyl-phenoxy)-6-iodo-pyridazine-4-carboxylate (95.0%) (2.19 g, 5.36 mmol, 53%) as a pale yellow oil. LC-MS: m/z 389.0 $[M+H]^+$, (ESI+), RT=1.04 LCMS Method M2.

Step 3: methyl 3-(4-fluoro-2-methyl-phenoxy)-6-(trifluoromethyl)pyridazine-4-carboxylate: To a mixture of methyl 3-(4-fluoro-2-methyl-phenoxy)-6-iodo-pyridazine-4-carboxylate (2.19 g, 5.64 mmol), iodocopper (1.62 g, 8.46 mmol), and tetrabutylammonium iodide (836 mg, 2.26 mmol) in DMF (29.14 mL), methyl difluoro(fluorosulfonyl)acetate (3.6 mL, 28.2 mmol) was added and stirred at 70 °C for 4 h. The reaction was cooled to room temperature, poured into water (200 mL) and extracted with EtOAc (3×200 mL). The combined organic phases were passed through a phase separator and concentrated in vacuo (high vac for DMF removal). The compound was purified by FCC using 0-50% EtOAc in heptane over silica (on a Biotage Sfar 200 g column, compound wet-loaded using DCM), concentrated in vacuo to afford methyl 3-(4-fluoro-2-methyl-phenoxy)-6-(trifluoromethyl)pyridazine-4-carboxylate (76.0%) (1.49 g, 3.43 mmol, 61%) as a yellow solid. $^1$H NMR (400 MHz, DMSO-$d_6$) δ 8.54 (s, 1H), 7.34-7.24 (m, 2H), 7.18-7.11 (m, 1H), 3.97 (s, 3H), 2.13 (s, 3H). LC-MS: m/z 331.1 $[M+H]^+$, (ESI+), RT=0.98 LCMS Method M2.

Step 4: methyl 3-(4-fluoro-2-methyl-phenoxy)-5-iodo-6-(trifluoromethyl)pyridazine-4-carboxylate: To a stirring solution of 2,2,6,6-tetramethylpiperidine (0.58 mL, 3.45 mmol) in THF-Anhydrous (12 mL), butyllithium (2.5M in hexanes) (0.92 mL, 2.30 mmol) was added dropwise at 0 °C and stirred for 30 minutes. The reaction was cooled to −78 °C and a pre-cooled mixture of methyl 3-(4-fluoro-2-methyl-phenoxy)-6-(trifluoromethyl)pyridazine-4-carboxylate (76%, 500 mg, 1.15 mmol) in THF-Anhydrous (12 mL) was transferred by cannula to the LiTMP mixture, both at −78 °C. A pre-cooled mixture of 1-iodopyrrolidine-2,5-dione (259 mg, 1.15 mmol) in THF-Anhydrous (6 mL) was immediately added afterwards at −78 °C and stirred at this temperature for 30 mins. The reaction was quenched with sat. $NH_4Cl$ (aq) (1 mL) and allowed to warm to rt. The reaction was poured into water (30 mL), extracted with EtOAc (3×50 mL), combined organic phases passed through a phase separator and concentrated in vacuo. The compound was purified by FCC using 0-100% EtOAc in heptane over silica and flushed with 0-60% MeOH in EtOAc (on a Biotage Sfar 25 g column, compound wet-loaded using DCM) and concentrated in vacuo to afford methyl 3-(4-fluoro-2-methyl-phenoxy)-5-iodo-6-(trifluoromethyl)pyridazine-4-carboxylate (85.0%) (342 mg, 0.637 mmol, 55%) as a orange solid. $^1$H NMR (500 MHz, DMSO-$d_6$) δ 7.32 (dd, J=9.0, 5.0 Hz, 1H), 7.26 (dd, J=9.4, 3.1 Hz, 1H), 7.15 (td, J=8.5, 3.2 Hz, 1H), 4.04 (s, 3H), 2.10 (s, 3H). LC-MS: m/z 457.0 $[M+H]^+$, (ESI+), RT=1.06 LCMS Method M2.

Step 5: methyl 5-cyclopropyl-3-(4-fluoro-2-methyl-phenoxy)-6-(trifluoromethyl)pyridazine-4-carboxylate: A mixture of methyl 3-(4-fluoro-2-methyl-phenoxy)-5-iodo-6-(trifluoromethyl)pyridazine-4-carboxylate (75%, 203 mg, 0.334 mmol), cyclopropylboronic acid (34 mg, 0.401 mmol), bis[3-(diphenylphosphanyl)cyclopenta-2,4-dien-1-yl]iron; dichloromethane; dichloropalladium (14 mg, 0.0167 mmol) and dipotassium carbonate (92 mg, 0.668 mmol) in 1,4-Dioxane (1.8 mL):Water (0.2 mL) was degassed with nitrogen and heated to 100 °C for 3 h. The reaction was re-treated with and bis[3-(diphenylphosphanyl)cyclopenta-2,4-dien-1-yl]iron; dichloromethane; dichloropalladium (14 mg, 0.0167 mmol), degassed with nitrogen and stirred at 100 °C for 1 h. The reaction was re-treated with cyclopropylboronic acid (34 mg, 0.401 mmol), bis[3-(diphenylphosphanyl)cyclopenta-2,4-dien-1-yl]iron; dichloromethane; dichloropalladium (14 mg, 0.0167 mmol) and dipotassium carbonate (51 mg, 0.334 mmol), degassed with nitrogen and stirred at 100 °C for 4 h. The reaction mixture was allowed to warm to room temperature, poured into water (20 mL) and extracted with DCM (3×20 mL). The combined organic phases were passed through a phase separator, concentrated in vacuo and purified by FCC using 0-100% EtOAc in heptane over silica and flushed with 0-60% MeOH in EtOAc (on a Biotage Sfar 10 g column, compound wet-loaded using DCM) and concentrated in vacuo to afford methyl 5-cyclopropyl-3-(4-fluoro-2-methyl-phenoxy)-6-(trifluoromethyl)pyridazine-4-carboxylate (81.0%) (114 mg, 0.249 mmol, 75%) as a yellow sticky oil. $^1$H NMR (500 MHz, DMSO-$d_6$-) δ 7.28-7.22 (m, 2H), 7.13 (td, J=8.5, 3.5 Hz, 1H), 4.00 (s, 3H), 2.18-2.12 (m, 1H), 2.08 (s, 3H), 1.12-1.06 (m, 2H), 0.82-0.75 (m, 2H). LC-MS: m/z 371.2 $[M+H]^+$, (ESI+), RT=1.04 LCMS Method M2.

Step 6: 5-cyclopropyl-3-(4-fluoro-2-methyl-phenoxy)-6-(trifluoromethyl)pyridazine-4-carboxylic acid: To a mixture of methyl 5-cyclopropyl-3-(4-fluoro-2-methyl-phenoxy)-6-(trifluoromethyl)pyridazine-4-carboxylate (113 mg, 0.305 mmol) in THF (1 mL):Water (0.25 mL), lithium hydroxide (15 mg, 0.610 mmol) was added and the mixture was stirred at room temperature for 16 h. The reaction was re-treated with LiOH (29 mg, 1.22 mmol) and stirred at room temperature for 1 h. The reaction was re-treated with LiOH (29 mg, 1.22 mmol) and stirred at room temperature for 16 h. The reaction was re-treated with LiOH (29 mg, 1.22 mmol) and stirred at 40 °C. 20 h. The reaction was re-treated with LiOH (29 mg, 1.22 mmol) and stirred at 60 °C for 6.5 h. The reaction was re-treated with lithium hydroxide (29 mg, 1.22 mmol) and stirred at 40 °C for 3 h. The reaction mixture was acidified with 2M HCl (aqueous) to pH 1, poured into water (10 mL) and extracted with EtOAc (3×10 mL). The combined organic phases were passed through a phase separator and concentrated in vacuo. The compound was purified by FCC using 0-100% EtOAc in heptane followed by 0-80% MeOH in EtOAc over silica (on a Biotage Sfar 5 g column, compound wet-loaded using EtOAc) and concentrated in vacuo to afford 5-cyclopropyl-3-(4-fluoro-2-methyl-phenoxy)-6-(trifluoromethyl)pyridazine-4-carboxylic acid (62 mg, 0.174 mmol, 57%) as a as a orange solid. LC-MS: m/z 357.2 $[M+H]^+$, (ESI+), RT=0.74 LCMS Method M2.

Step 7: tert-butyl N—[(S)-{3-[5-cyclopropyl-3-(4-fluoro-2-methylphenoxy)-6-(trifluoromethyl)pyridazine-4-amido]phenyl}(methyl)oxo-$\lambda^6$-sulfanylidene]carbamate: To a stirring solution of 5-cyclopropyl-3-(4-fluoro-2-methylphenoxy)-6-(trifluoromethyl)pyridazine-4-carboxylic acid (92%, 52 mg, 0.134 mmol) in DCM (0.6 mL), N,N-dimethylformamide (2.1 uL, 0.0269 mmol) was added followed by oxalyl chloride (13 uL, 0.148 mmol) under nitrogen and at rt. The reaction was stirred for 1 h. Subsequently tert-butyl N—[(S)-(3-aminophenyl)(methyl)oxo-$\lambda^6$-sulfanylidene]carbamate (44 mg, 0.161 mmol) in DCM (0.2 mL) was added followed by DIEA (47 uL, 0.269 mmol) and the reaction was stirred at room temperature for 1.5 h. Water (2 mL) was added to the reaction and the reaction mixture passed through a phase separator and rinsed with DCM (3×3 mL). The combined organic phases were combined, concentrated in vacuo and purified by FCC using 0-100% EtOAc in Heptane over silica and flushed with 0-60% MeOH in EtOAc (on a Biotage Sfar 5 g column, compound wet-loaded using DCM) and concentrated in vacuo to tert-butyl N—[(S)-{3-[5-cyclopropyl-3-(4-fluoro-2-methylphenoxy)-6-(trifluoromethyl)pyridazine-4-amido]phenyl}(methyl)oxo-$\lambda^6$-sulfanylidene]carbamate (94.0%) (79 mg, 0.122 mmol, 91%) as a white sticky solid. m/z: 509.1 $[M-Boc+H]^+$, (ESI+), RT=0.99 LCMS Method M2.

Step 8: (S)-5-cyclopropyl-3-(4-fluoro-2-methylphenoxy)-N-(3-(S-methylsulfonimidoyl)phenyl)-6-(trifluoromethyl)pyridazine-4-carboxamide: To a stirring solution of tert-butyl N—[(S)-{3-[5-cyclopropyl-3-(4-fluoro-2-methylphenoxy)-6-(trifluoromethyl)pyridazine-4-amido]phenyl}(methyl)oxo-$\lambda^6$-sulfanylidene]carbamate (94%, 79 mg, 0.122 mmol) in DCM (1.5 mL), TFA (0.091 mL, 1.22 mmol) was added dropwise and stirred at room temperature for 3 h. The reaction was basified with sat. $NaHCO_3$ aq solution (2 mL), poured into water (10 mL) and extracted with DCM (3×20 mL). The combined organic phases were passed through a phase separator, concentrated in vacuo and purified using 0-100% EtOAc in heptane over silica (on a Biotage Sfar 5 g column, compound wet-loaded using DCM), concentrated in vacuo and freeze-dried overnight in 1:1 MeCN/Water to afford (S)-5-cyclopropyl-3-(4-fluoro-2-methylphenoxy)-N-(3-(S-methylsulfonimidoyl)phenyl)-6-(trifluoromethyl)pyridazine-4-carboxamide (95.0%) (28 mg, 42%) as a white solid. $^1H$ NMR (400 MHz, DMSO-$d_6$) δ 11.21 (s, 1H), 8.29 (t, J=2.0 Hz, 1H), 7.93-7.84 (m, 1H), 7.73 (d, J=7.8 Hz, 1H), 7.64 (t, J=7.9 Hz, 1H), 7.29-7.21 (m, 2H), 7.13 (td, J=8.5, 3.2 Hz, 1H), 4.26 (s, 1H), 3.12-3.03 (m, 3H), 2.23-2.16 (m, 1H), 2.11 (s, 3H), 1.10-1.02 (m, 2H), 0.99-0.91 (m, 2H). LC-MS: m/z 509.1 $[M+H]^+$, (ESI+), RT=3.11 LCMS Method 4.

Example 69

Compound 1520: (S)-3-(4-fluoro-2-methylphenoxy)-N-(3-(S-methylsulfonimidoyl)phenyl)-5-phenyl-6-(trifluoromethyl)pyridazine-4-carboxamide

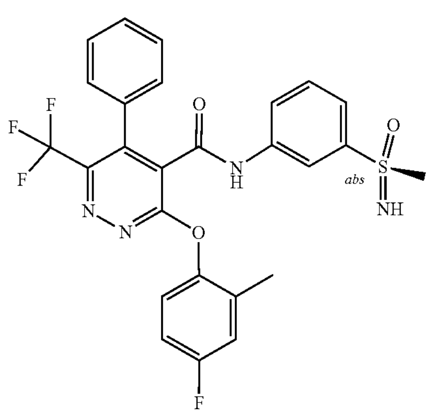 [SMILES: Cc1cc(F)ccc1Oc1nnc(C(F)(F)F)c(-c2ccccc2)c1C(=O)Nc1cccc([S@@](C)(=N)=O)c1]

The title compound was prepared by a similar procedure described for compound 1519 using appropriate reagents. $^1H$ NMR (400 MHz, DMSO-$d_6$) δ 11.06 (s, 1H), 8.03 (t, J=2.0 Hz, 1H), 7.67-7.61 (m, 1H), 7.60-7.55 (m, 1H), 7.53 (d, J=7.7 Hz, 1H), 7.51-7.44 (m, 5H), 7.34 (dd, J=8.9, 5.0 Hz, 1H), 7.28 (dd, J=9.4, 3.2 Hz, 1H), 7.18 (td, J=8.7, 3.3 Hz, 1H), 4.21 (s, 1H), 3.04-2.95 (m, 3H), 2.19 (s, 3H). m/z: 545.3 $[M+H]^+$, (ESI+), RT=3.37 LCMS Method 4.

Compound 1521: (S)-3-(4-fluoro-2-methylphenoxy)-5-(1-methyl-1H-pyrazol-4-yl)-N-(3-(S-methylsulfonimidoyl)phenyl)-6-(trifluoromethyl)pyridazine-4-carboxamide

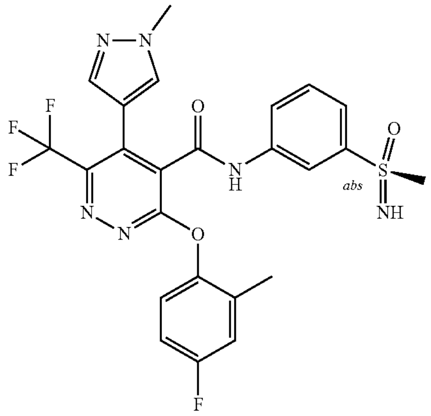 [SMILES: Cc1cc(F)ccc1Oc1nnc(C(F)(F)F)c(-c2cnn(C)c2)c1C(=O)Nc1cccc([S@@](C)(=N)=O)c1]

The title compound was prepared by a similar procedure described for compound 1519 using appropriate reagents. $^1H$ NMR (400 MHz, DMSO-$d_6$) δ 11.20 (s, 1H), 8.17 (t, J=2.0 Hz, 1H), 8.06 (s, 1H), 7.74-7.67 (m, 2H), 7.65 (s, 1H), 7.58 (t, J=7.9 Hz, 1H), 7.31 (dd, J=8.9, 5.0 Hz, 1H), 7.26 (dd, J=9.4, 3.2 Hz, 1H), 7.16 (td, J=8.6, 3.2 Hz, 1H), 4.24 (s, 1H), 3.89 (s, 3H), 3.05 (s, 3H), 2.15 (s, 3H). m/z: 549.3 $[M+H]^+$, (ESI+), RT=2.88 LCMS Method 4.

Example 70

Compound 1522: (S)-5-(cyclopropylamino)-3-(4-fluoro-2-methylphenoxy)-N-(3-(S-methylsulfonimidoyl)phenyl)-6-(trifluoromethyl)pyridazine-4-carboxamide

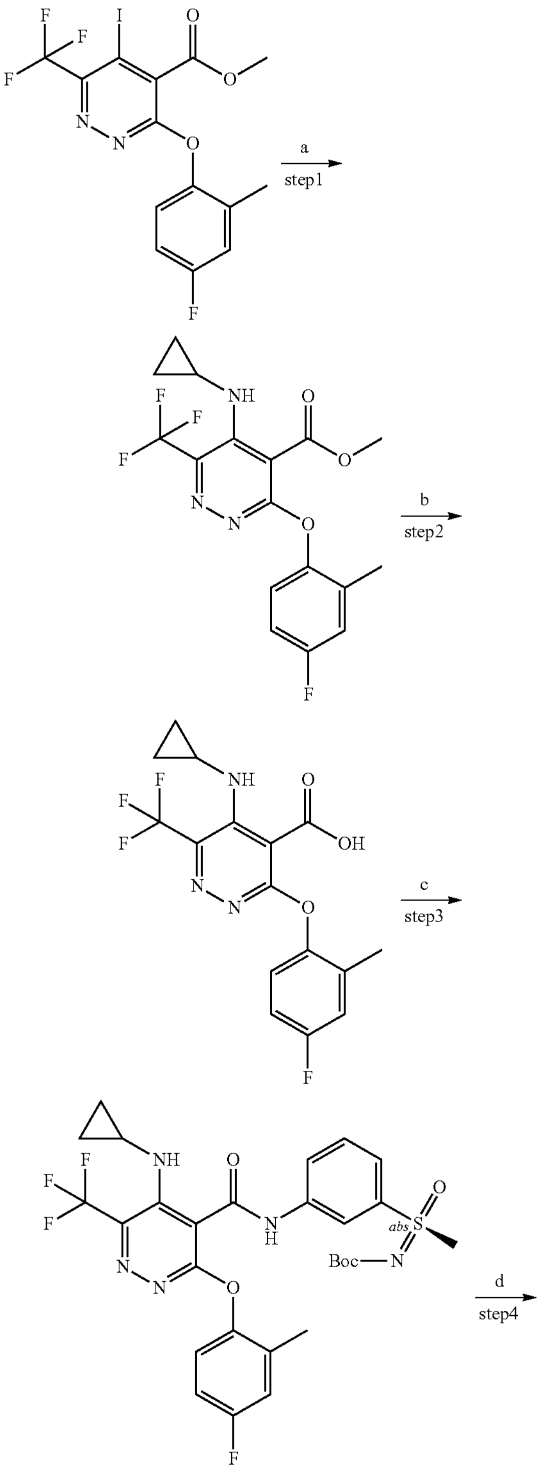

-continued

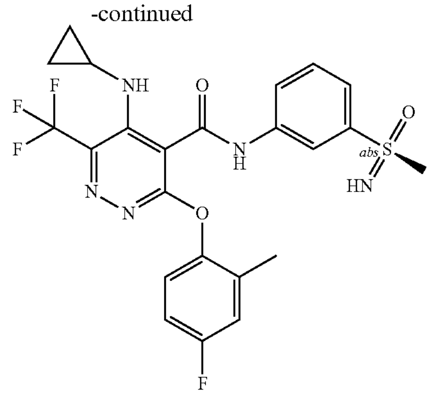

Reagents & conditions:
a) cyclopropanamine, DIEA, acetonitrile, 50 °C;
b) LiOH, THF/$H_2O$, rt;
c) TCFH, 1-methylimidazole, acetonitrile, tert-butyl N-[(S)-(3-aminophenyl)(methyl)oxo-$\lambda^6$-sulfanylidene]carbamate, rt;
c) DCM, TFA, rt.

Step 1: methyl 5-(cyclopropylamino)-3-(4-fluoro-2-methyl-phenoxy)-6-(trifluoromethyl)pyridazine-4-carboxylate: A mixture containing methyl 3-(4-fluoro-2-methyl-phenoxy)-5-iodo-6-(trifluoromethyl)pyridazine-4-carboxylate (75%, 203 mg, 0.334 mmol), N-ethyl-N-(propan-2-yl)propan-2-amine (87 uL, 0.501 mmol) and cyclopropanamine (35 uL, 0.501 mmol) in Acetonitrile-Anhydrous (2 mL) was stirred at 50 °C for 3.5 h. The reaction was combined with trial from concentrated in vacuo and purified by FCC using 0-100% EtOAc in heptane over silica and flushed with 0-60% MeOH in EtOAc (on a Biotage Sfar 5 g column, compound wet-loaded using DCM) and concentrated in vacuo to afford methyl 5-(cyclopropylamino)-3-(4-fluoro-2-methyl-phenoxy)-6-(trifluoromethyl)pyridazine-4-carboxylate (75.0%) (182 mg, 0.354 mmol, 106%) as a orange solid. $^1$H NMR (500 MHz, DMSO-$d_6$) δ 7.31-7.25 (m, 1H), 7.22-7.15 (m, 2H), 7.08 (td, J=8.5, 3.2 Hz, 1H), 3.91 (s, 3H), 2.57-2.52 (m, 1H), 2.07 (s, 3H), 0.79-0.73 (m, 2H), 0.68-0.62 (m, 2H). LC-MS: m/z 386.2 [M+H]+, (ESI+), RT=1.00 LCMS Method M2.

Step 2: 5-(cyclopropylamino)-3-(4-fluoro-2-methyl-phenoxy)-6-(trifluoromethyl)pyridazine-4-carboxylic acid: To a mixture of methyl 5-(cyclopropylamino)-3-(4-fluoro-2-methyl-phenoxy)-6-(trifluoromethyl)pyridazine-4-carboxylate (75%, 182 mg, 0.354 mmol) in THF (1 mL):Water (0.3 mL), lithium hydroxide (17 mg, 0.709 mmol) was added and the mixture was stirred at room temperature for 65 h. The reaction mixture was quenched with 2M HCl (aqueous) to pH1, poured into water (10 mL) and extracted with EtOAc (3×20 mL). The combined organic phases were passed through a phase separator and concentrated in vacuo. The compound was purified by FCC using 0-100% EtOAc in heptane followed by 0-80% MeOH in EtOAc over silica (on a Biotage Sfar 5 g column, compound wet-loaded using EtOAc) and concentrated in vacuo to afford 5-(cyclopropylamino)-3-(4-fluoro-2-methyl-phenoxy)-6-(trifluoromethyl)pyridazine-4-carboxylic acid (86.0%) (164 mg, 0.380 mmol, 107%) as a pale yellow sticky oil. LC-MS: m/z 372.2 [M+H]+, (ESI+), RT=0.78 LCMS Method M2.

Step 3: tert-butyl N—[(S)-{3-[5-(cyclopropylamino)-3-(4-fluoro-2-methylphenoxy)-6-(trifluoromethyl)pyridazine-4-amido]phenyl}(methyl)oxo-$\lambda^6$-sulfanylidene]carbamate: To a stirring solution of 5-(cyclopropylamino)-3-(4-fluoro-2-methyl-phenoxy)-6-(trifluoromethyl)pyridazine-4-carboxylic acid (78 mg, 0.210 mmol), tert-butyl N—[(S)-(3-aminophenyl)(methyl)oxo-λ$^6$-sulfanylidene]carbamate (74 mg, 0.273 mmol) and 1-methylimidazole (NMI) (59 uL, 0.735 mmol) in Acetonitrile-Anhydrous (0.5528 mL), N-[chloro(dimethylamino)methylidene]-N-methylmethanaminium hexafluorophosphate (TCFH) (71 mg, 0.252 mmol) was added in a single portion and the reaction was stirred at room temperature for 15.5 h. The reaction was re-treated with 1-methylimidazole (NMI) (59 uL, 0.735 mmol) and N-[chloro(dimethylamino)methylidene]-N-methylmethanaminium hexafluorophosphate (TCFH) (71 mg, 0.252 mmol) and stirred at room temperature for 24 h. The reaction mixture was poured into water (20 mL) and extracted with EtOAc (3×20 mL). The combined organic phases were passed through a phase separator and concentrated in vacuo. The compound was purified by FCC using 0-100% EtOAc in heptane and flushed with 0-60% MeOH in EtOAc (on a Biotage Sfar 5 g column, compound wet-loaded using DCM and a few drops of EtOAc) and concentrated in vacuo to afford tert-butyl N—[(S)-{3-[5-(cyclopropylamino)-3-(4-fluoro-2-methylphenoxy)-6-(trifluoromethyl)pyridazine-4-amido]phenyl}(methyl)oxo-λ$^6$-sulfanylidene]carbamate (138 mg, 0.153 mmol, 73%) as a pale yellow. $^1$H NMR (400 MHz, DMSO-d$_6$) δ 11.23 (s, 1H), 8.38-8.32 (m, 1H), 7.96-7.86 (m, 1H), 7.70-7.62 (m, 2H), 7.23-7.13 (m, 2H), 7.13-7.03 (m, 2H), 3.36 (s, 3H), 2.68-2.65 (m, 1H), 2.09 (s, 3H), 1.17 (s, 9H), 0.74-0.69 (m, 2H), 0.63-0.54 (m, 2H). m/z: 624.2 1 [M+H]$^+$, (ESI+), RT=0.93 LCMS Method M2.

Step 4: (S)-5-(cyclopropylamino)-3-(4-fluoro-2-methylphenoxy)-N-(3-(S-methylsulfonimidoyl)phenyl)-6-(trifluoromethyl)pyridazine-4-carboxamide: To a stirring solution of tert-butyl N—[(S)-{3-[5-(cyclopropylamino)-3-(4-fluoro-2-methylphenoxy)-6-(trifluoromethyl)pyridazine-4-amido]phenyl}(methyl)oxo-λ$^6$-sulfanylidene]carbamate (69%, 138 mg, 0.153 mmol) in DCM (2.7 mL), TFA (0.11 mL, 1.53 mmol) was added dropwise and stirred at room temperature for 3 h. The reaction was basified with sat. $NaHCO_3$ aq solution (2 mL), poured into water (10 mL) and extracted with DCM (3×20 mL). The combined organic phases were passed through a phase separator, concentrated in vacuo and purified using 0-100% EtOAc in heptane over silica (on a Biotage Sfar 5 g column, compound wet-loaded using DCM), concentrated in vacuo. The compound was further purified by reverse-phase FCC using 10-100% MeCN+0.1% formic acid in water+0.1% formic acid (on a C18 Biotage Sfar 6 g column, compound loaded on a sampler pre-loaded with a compound solution in MeOH), concentrated in vacuo and freeze-dried overnight to afford (S)-5-(cyclopropylamino)-3-(4-fluoro-2-methylphenoxy)-N-(3-(S-methylsulfonimidoyl)phenyl)-6-(trifluoromethyl)pyridazine-4-carboxamide (100.0%) (44 mg, 0.0840 mmol, 55%) as a white solid. $^1$H NMR (500 MHz, DMSO-d$_6$) δ 11.13 (s, 1H), 8.33 (t, J=1.9 Hz, 1H), 7.87 (ddd, J=8.0, 2.2, 1.1 Hz, 1H), 7.70-7.64 (m, 1H), 7.59 (t, J=7.9 Hz, 1H), 7.23-7.14 (m, 2H), 7.13-7.03 (m, 2H), 4.22 (d, J=1.3 Hz, 1H), 3.05 (d, J=1.0 Hz, 3H), 2.73-2.66 (m, 1H), 2.10 (s, 3H), 0.75-0.68 (m, 2H), 0.66-0.58 (m, 2H). LC-MS: m/z 524.1 [M+H]$^+$, (ESI+), RT=2.79 LCMS Method 4.

The following compounds were synthesised in the same manner as described above.

Compound 1523: (S)-5-(azetidin-3-ylamino)-3-(4-fluoro-2-methylphenoxy)-N-(3-(S-methylsulfonimidoyl)phenyl)-6-(trifluoromethyl)pyridazine-4-carboxamide

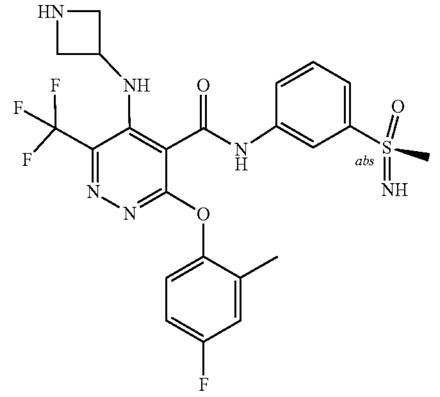

$^1$H NMR (400 MHz, DMSO-d$_6$) δ 11.21 (s, 1H), 8.35 (t, J=2.0 Hz, 1H), 7.94-7.85 (m, 1H), 7.75-7.67 (m, 1H), 7.63 (t, J=7.9 Hz, 1H), 7.23-7.12 (m, 2H), 7.08 (td, J=8.5, 3.1 Hz, 1H), 4.56-4.44 (m, 1H), 4.27 (s, 1H), 3.68-3.58 (m, 2H), 3.49-3.41 (m, 2H), 3.07 (s, 3H), 2.08 (s, 3H). m/z: 539.2 [M+H]$^+$, (ESI+), RT=1.71 LCMS Method 4.

Compound 1524: (S)-3-(4-fluoro-2-methylphenoxy)-N-(3-(S-methylsulfonimidoyl)phenyl)-5-morpholino-6-(trifluoromethyl)pyridazine-4-carboxamide

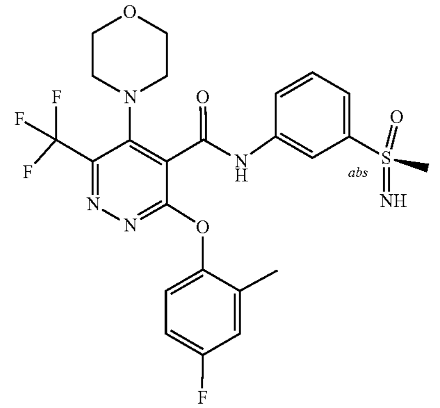 [SMILES: Cc1cc(F)ccc1Oc1nnc(C(F)(F)F)c(N2CCOCC2)c1C(=O)Nc1cccc([S@@](C)(=N)=O)c1]

Example 71

Compound 1525:3-(4-cyano-2-methylphenoxy)-N-{3-[(S)-imino(methyl)oxo-λ$^6$-sulfanyl]phenyl}-5-methyl-6-(trifluoromethyl)pyridazine-4-carboxamide

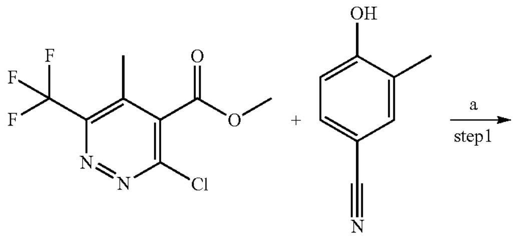

-continued

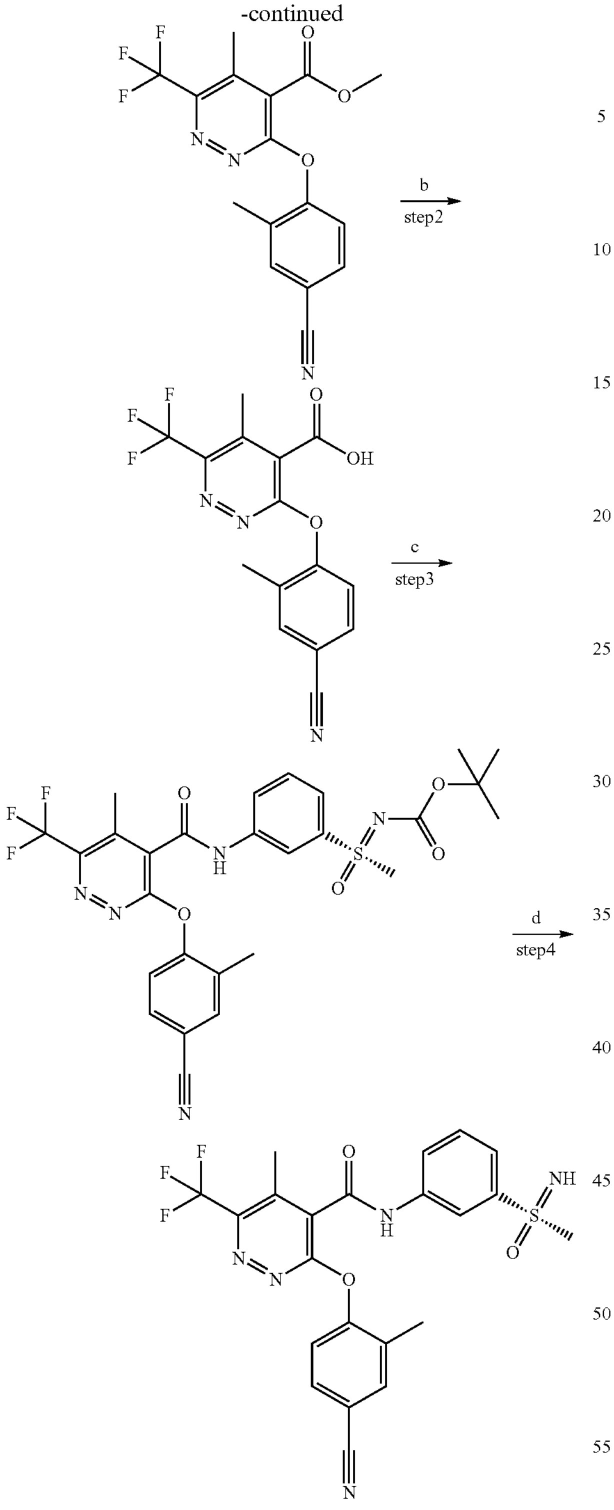

Reagents & conditions:
a) $K_2CO_3$, acetonitrile, 70 °C;
b) LiOH, THF/$H_2O$, rt;
c) tert-butyl (S)-((3-aminophenyl)(methyl)(oxo)-$\lambda^6$-sulfaneylidene)carbamate, HATU, DIEA, DMF, rt;
d) TFA, DCM.

Step 1: methyl 3-(4-cyano-2-methyl-phenoxy)-5-methyl-6-(trifluoromethyl)pyridazine-4-carboxylate: A mixture of 4-hydroxy-3-methylbenzonitrile (650 mg, 4.88 mmol), methyl 3-chloro-5-methyl-6-(trifluoromethyl)pyridazine-4-carboxylate (94%, 1.20 g, 4.43 mmol) and $K_2CO_3$ (920 mg, 6.66 mmol) in Acetonitrile (11.5 mL) was stirred at 70 °C for 17 h. The reaction was cooled to room temperature, filtered and washed with EtOAc (60 mL). Filtrate was washed with water (60 mL) and brine (60 mL), organic separated, passed through phase separator and concentrated in vacuo to obtain methyl 3-(4-cyano-2-methyl-phenoxy)-5-methyl-6-(trifluoromethyl)pyridazine-4-carboxylate (90.0%) (1.68 g, 4.30 mmol, 97%) as an off-white powder. $^1$H NMR (500 MHz, DMSO-$d_6$) δ 7.94 (d, J=1.5 Hz, 1H), 7.82 (dd, J=8.4, 2.1 Hz, 1H), 7.50 (d, J=8.4 Hz, 1H), 4.02 (s, 3H), 2.51-2.47 (m, 16H), 2.16 (s, 3H). m/z: 352.1 $[M-BOC+H]^+$, (ESI+), RT=0.94 LCMS Method 2.

Step 2: 3-(4-cyano-2-methyl-phenoxy)-5-methyl-6-(trifluoromethyl)pyridazine-4-carboxylic acid: To a solution of methyl 3-(4-cyano-2-methyl-phenoxy)-5-methyl-6-(trifluoromethyl)pyridazine-4-carboxylate (90%, 1.68 g, 4.30 mmol) in THE (15 mL):Water (3 mL), lithium hydroxide (236 mg, 9.46 mmol) was added, and the mixture stirred at rt for 18 h. The reaction was diluted with EtOAc and the product was extracted with water (×3). The pH of the aqueous phase was adjusted to 1 by dropwise addition of 1M HCl (aq). The aqueous layer was then extracted with EtOAc (3×), dried ($MgSO_4$), filtered and concentrated in vacuo to afford 3-(4-cyano-2-methyl-phenoxy)-5-methyl-6-(trifluoromethyl)pyridazine-4-carboxylic acid (99.0%) (1.48 g, 100%) as an off-white solid. $^1$H NMR (500 MHz, DMSO-$d_6$) δ 7.95-7.91 (m, 1H), 7.81 (dd, J=8.4, 2.1 Hz, 1H), 7.47 (d, J=8.4 Hz, 1H), 2.51-2.47 (m, 3H, overlap with DMSO peak), 2.16 (s, 3H). m/z: 338.1 $[M+H]^+$, (ESI+), RT=2.67 LCMS Method 4.

Step 3: tert-butyl N—[(S)-{3-[3-(4-cyano-2-methylphenoxy)-5-methyl-6-(trifluoromethyl)pyridazine-4-amido]phenyl}(methyl)oxo-$\lambda^6$-sulfanylidene]carbamate: N-[(dimethylamino)(3H-[1,2,3]triazolo[4,5-b]pyridin-3-yloxy)methylidene]-N-methylmethanaminium hexafluorophosphate (1000 mg, 2.63 mmol) was added to a solution of intermediate 3-(4-cyano-2-methyl-phenoxy)-5-methyl-6-(trifluoromethyl)pyridazine-4-carboxylic acid (740 mg, 2.19 mmol) and N-ethyl-N-isopropyl-propan-2-amine (0.77 mL, 4.41 mmol) in DMF-Anhydrous (15 mL). tert-butyl (S)-((3-aminophenyl)(methyl)(oxo)-$\lambda^6$-sulfaneylidene)carbamate (98%, 787 mg, 2.85 mmol) was then added and the mixture was stirred at rt for 18 h. The mixture was diluted with ethyl acetate (50 mL) and washed with brine (3×50 mL). The organics were dried ($MgSO_4$), filtered and concentrated to afford tert-butyl N-[[33-[[3-(4-cyano-2-methyl-phenoxy)-5-methyl-6-(trifluoromethyl)pyridazine-4-carbonyl]amino]phenyl]-methyl-oxo-$\lambda^6$-sulfanylidene]carbamate (48.0%)(1.95 g, 72%) as a brown oil. The material was used in the next reaction without further purification. $^1$H NMR (500 MHz, DMSO-$d_6$) δ 11.44 (s, 1H), 8.40-8.36 (m, 1H), 7.95-7.87 (m, 2H), 7.85-7.80 (m, 1H), 7.78-7.69 (m, 2H), 7.50 (d, J=8.4 Hz, 1H), 3.40 (s, 3H), 2.69 (s, 3H), 2.17 (s, 3H), 1.22 (s, 9H). m/z: 490.1 $[M-BOC+H]^+$, (ESI+), RT=0.91 LCMS Method 2.

Step 4: 3-(4-cyano-2-methylphenoxy)-N-{3-[(S)-imino(methyl)oxo-$\lambda^6$-sulfanyl]phenyl}-5-methyl-6-(trifluoromethyl)pyridazine-4-carboxamide: To a solution of tert-butyl N—[(S)-{3-[3-(4-cyano-2-methylphenoxy)-5-methyl-6-(trifluoromethyl)pyridazine-4-amido]phenyl}(methyl)oxo-$\lambda^6$-sulfanylidene]carbamate (48%, 1.95 g, 1.59 mmol) in DCM (12 mL) was added 2,2,2-trifluoroacetic acid (2.4 mL, 32.3 mmol). The mixture was stirred at RT for 4 h. The reaction was diluted with sat. $NaHCO_3$, extracted with DCM (3×), dried ($MgSO_4$), filtered and concentrated to afford a yellow oil. Purification by basic (0.1% $NH_3$) reverse phase chromatography (Sfar C18 60 g D Duo 30, 10-40% MeCN in $H_2O$, fractions 14 to 16 combined), evaporation and freeze drying over the weekend gave 3-(4-cyano-2-methylphenoxy)-N-{3-[(S)-imino(methyl)oxo-$\lambda^6$-sulfanyl]phenyl}-5-methyl-6-(trifluoromethyl)pyridazine-4-carboxamide (141 mg, 0.282 mmol, 18%) as an off-white powder. Impure fractions were evaporated to a yellow oil (471 mg) and purified further by Prep Method 1. Earlier obtained material and the material obtained from Prep Method 1 were combined and freeze dried overnight to give 3-(4-cyano-2-methylphenoxy)-N-{3-[(S)-imino(methyl)oxo-$\lambda^6$-sulfanyl]phenyl}-5-methyl-6-(trifluoromethyl)pyridazine-4-carboxamide (463 mg, 60%) as a white powder. $^1H$ NMR (400 MHz, $CD_3OD$) δ 8.44 (t, J=1.9 Hz, 1H), 7.98-7.94 (m, 1H), 7.87-7.82 (m, 1H), 7.77-7.73 (m, 1H), 7.71-7.64 (m, 2H), 7.43 (d, J=8.4 Hz, 1H), 3.17 (s, 3H), 2.62-2.59 (m, 3H), 2.23 (s, 3H). m/z: 490.2 $[M+H]^+$, (ESI+), RT=2.80 LCMS Method 4.

Example 72

Compound 1526: 3-(4-cyano-2-methylphenoxy)-N-{3-[(R)-imino(methyl)oxo-$\lambda^6$-sulfanyl]phenyl}-5-methyl-6-(trifluoromethyl)pyridazine-4-carboxamide

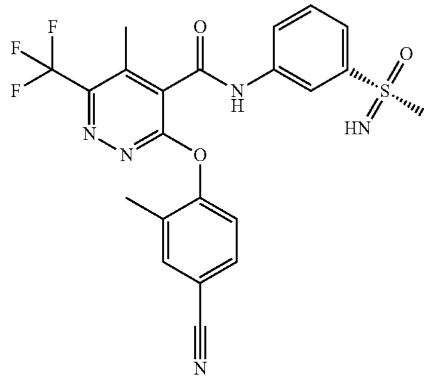 [SMILES: Cc1cc(C#N)ccc1Oc1nnc(C(F)(F)F)c(C)c1C(=O)Nc1cccc([S@](C)(=N)=O)c1]

The title compound was prepared by a similar reaction sequence as described for compound xx using 3-(4-cyano-2-methyl-phenoxy)-5-methyl-6-(trifluoromethyl) pyridazine-4-carboxylic and tert-butyl N—[(R)-(3-amino-phenyl)(methyl)oxo-$\lambda^6$-sulfanylidene]carbamate. $^1H$ NMR (500 MHz, $CD_3OD$) δ 8.44 (t, J=1.9 Hz, 1H), 7.98-7.93 (m, 1H), 7.86-7.82 (m, 1H), 7.77-7.73 (m, 1H), 7.71-7.64 (m, 2H), 7.43 (d, J=8.4 Hz, 1H), 3.17 (s, 3H, overlap with $CD_3OD$ satellite), 2.63-2.58 (m, 3H), 2.23 (s, 3H). m/z: 490.2 $[M+H]^+$, (ESI+), RT=2.80 LCMS Method 4.

Example 73

Compound 1527: 3-(4-cyano-2-methoxy-phenoxy)-6-(4-cyanophenyl)-5-methyl-N-(1-oxidopyridin-1-ium-3-yl)pyridazine-4-carboxamide

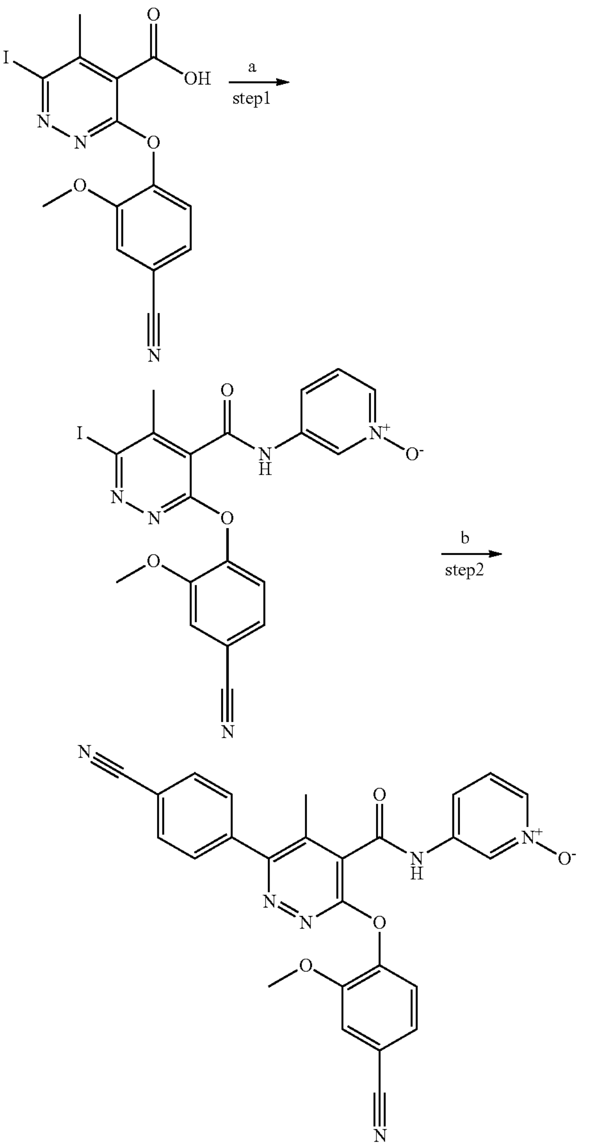

Reagents & conditions:
1-oxidopyridin-1-ium-3-amine hydrochloride, HATU, DIEA, DMF;
b) of 4-(4,4,5,5-tetramethyl-1,3,2,-dioxaborolan-2-yl)benzonitrile, 2M $Na_2CO_3$, 1,4-dioxane Pd(dppf)$Cl_2$.

Step 1: 3-(4-cyano-2-methoxy-phenoxy)-6-iodo-5-methyl-N-(1-oxidopyridin-1-ium-3-yl)pyridazine-4-carboxamide: To a mixture of 3-(4-cyano-2-methoxy-phenoxy)-6-iodo-5-methyl-pyridazine-4-carboxylic acid (64 mg, 0.156 mmol), HATU (71 mg, 0.187 mmol) DIEA (0.082 mL, 0.467 mmol) in DMF (1.5 mL) was added 1-oxidopyridin-1-ium-3-amine; hydrochloride (25 mg, 0.171 mmol). The reaction mixture was stirred at 40 °C for 3 h, then at rt overnight. LCMS analysis indicated the reaction was complete. The mixture was diluted with ethyl acetate (10 mL) and washed with water (3x5 mL) and brine (5 mL). Dried (MgSO4), filtered and concentrated to afford an orange oil. The residue was purified by FCC (5 g, 0 to 100% MeOH in EA) to afford 3-(4-cyano-2-methoxy-phenoxy)-6-iodo-5-methyl-N-(1-oxidopyridin-1-ium-3-yl)pyridazine-4-carboxamide (80.0%) (32 mg, 33%) as an orange solid. m/z: 504.0 $[M+H]^+$, (ESI+), RT=0.62 min LCMS Method 2.

Step 2: 3-(4-cyano-2-methoxy-phenoxy)-6-(4-cyanophenyl)-5-methyl-N-(1-oxidopyridin-1-ium-3-yl)pyridazine-4-carboxamide: 2M $Na_2CO_3$ (2M aq.) (170 uL, 0.340 mmol) was added to a mixture of 4-(4,4,5,5-tetramethyl-1,3,2-dioxaborolan-2-yl)benzonitrile (29 mg, 0.115 mmol), 3-(4-cyano-2-methoxy-phenoxy)-6-iodo-5-methyl-N-[3-(methylsulfonimidoyl)phenyl]pyridazine-4-carboxamide (50 mg, 0.0888 mmol) and Pd(dppf)$Cl_2$ (6.5 mg, 8.88 μmol) in 1,4-Dioxane (2 mL). The mixture was degassed with nitrogen for 5 minutes, then heated at 90 °C for 6 h. LCMS analysis indicated the reaction was complete. The mixture was diluted with ethyl acetate (10 mL) and washed with water (5 mL) and brine (5 mL). The organics were dried ($MgSO_4$), filtered and concentrated to afford a brown oil. Purification by prep. HPLC (standard method) afforded 3-(4-cyano-2-methoxy-phenoxy)-6-(4-cyanophenyl)-5-methyl-N-(1-oxidopyridin-1-ium-3-yl)pyridazine-4-carboxamide (99.0%) (10 mg, 18%) as a white solid. $^1H$ NMR (500 MHz, $CD_3OD$) δ 9.06 (t, J=1.9 Hz, 1H), 8.18 (m, 1H), 7.95-7.89 (m, 2H), 7.81-7.73 (m, 3H), 7.57 (dd, J=8.6, 6.4 Hz, 1H), 7.53 (d, J=1.6 Hz, 1H), 7.49-7.41 (m, 2H), 3.82 (s, 3H), 2.41 (s, 3H). m/z: 479.2 $[M+H]^+$, (ESI+), RT=2.36 LCMS Method 4.

Example 74

Compound 1528: 3-(4-cyano-2-methoxyphenoxy)-6-(2,2-difluorocyclopropyl)-N-{3-[(S)-imino(methyl)oxo-$\lambda^6$-sulfanyl]phenyl}-5-methylpyridazine-4-carboxamide

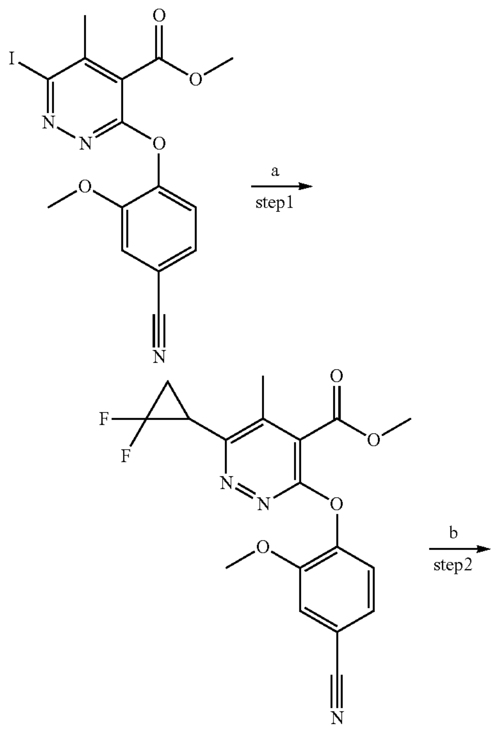

-continued

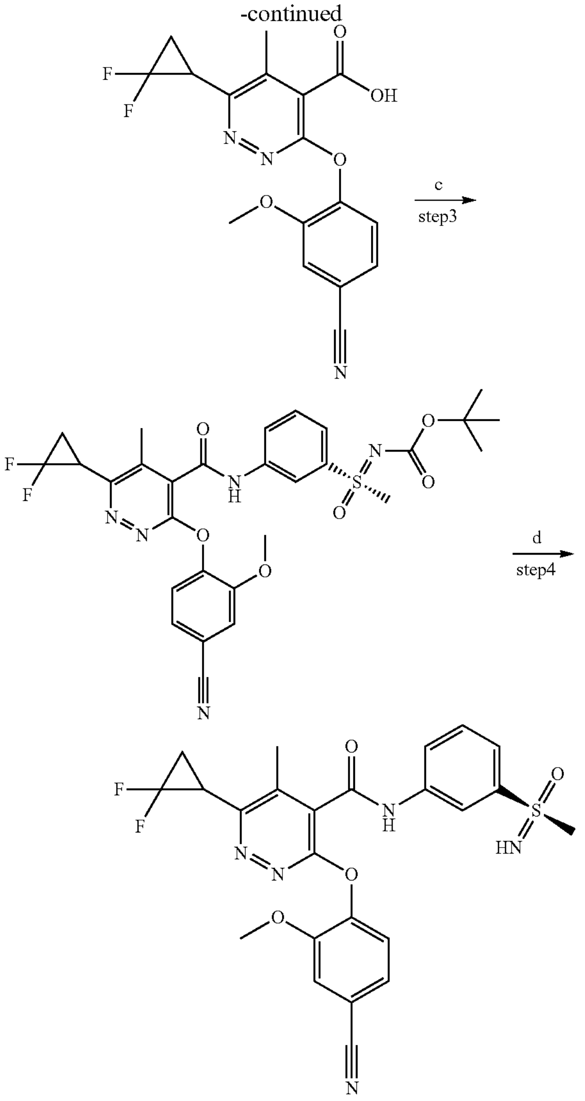

Reagents & conditions:
a) potassium; (2,2-difluorocyclopropyl)-trifluoro-boranuide, Pd Amphos, 2M $Na_2CO_3$, 1,4-dioxane, 100 °C;
b) 1M sodium trimethylsilanolate, THF;
c) (S)-tert-butyl N-[(3-aminophenyl)-methyl-oxo-$\lambda^6$-sulfanylidene], HATU, DIEA, DMF, rt;
d) TFA, DCM, rt Step 1: methyl 3-(4-cyano-2-methoxy-phenoxy)-6-(2,2-difluorocyclopropyl)-5-methyl-pyridazine-4-carboxylate: methyl 3-(4-cyano-2-methoxy-phenoxy)-6-iodo-5-methyl-pyridazine-4-carboxylate (250 mg, 0.588 mmol), potassium; (2,2-difluorocyclopropyl)-trifluoro-boranuide (130 mg, 0.706 mmol) and, 2 M disodium carbonate (882 uL, 1.76 mmol) in 1,4-Dioxane (2 mL) was degassed with nitrogen. Pd Amphos (42 mg, 0.0588 mmol) was added and the solution heated at 100 °C overnight for 3 days. No additional boronate was available to retreat. The solution was cooled and the material purified using FCC (10 g silica, 0-100% EtOAc in heptane; directly loading reaction mixture). Clean fractions were evaporated in vacuo to afford methyl 3-(4-cyano-2-methoxy-phenoxy)-6-(2,2-difluorocyclopropyl)-5-methyl-pyridazine-4-carboxylate (45 mg, 0.120 mmol, 20%) as an off white solid. m/z: 376.2 $[M+H]^+$, (ESI+), RT=0.87 min LCMS Method 2.

Step 2: 3-(4-cyano-2-methoxy-phenoxy)-6-(2,2-difluoro-cyclopropyl)-5-methyl-pyridazine-4-carboxylic acid: To a solution of methyl 3-(4-cyano-2-methoxy-phenoxy)-6-(2,2-difluorocyclopropyl)-5-methyl-pyridazine-4-carboxylate (35 mg, 0.0933 mmol) in THF-Anhydrous (3 mL) was added 1 M sodium trimethylsilanolate (140 uL, 0.140 mmol) and the solution stirred for 3 h at ambient. The solvent was removed in vacuo to afford 3-(4-cyano-2-methoxy-phenoxy)-6-(2,2-difluorocyclopropyl)-5-methyl-pyridazine-4-carboxylic acid (75.0%) (45 mg, 0.0934 mmol, 100%) as a tan solid. Material used in next step without further purification. m/z: 362.1 $[M+H]^+$, (ESI+), RT=0.61 min LCMS Method 2.

Step 3: tert-butyl N—[(S)-{3-[3-(4-cyano-2-methoxyphenoxy)-6-(2,2-difluorocyclopropyl)-5-methylpyridazine-4-amido]phenyl}(methyl)oxo-$\lambda^6$-sulfanylidene]carbamate: A mixture of 3-(4-cyano-2-methoxy-phenoxy)-6-(2,2-difluorocyclopropyl)-5-methyl-pyridazine-4-carboxylic acid (45 mg, 0.125 mmol), (S)-tert-butyl N-[(3-aminophenyl)-methyl-oxo-$\lambda^6$-sulfanylidene]carbamate (22 mg, 0.0830 mmol), HATU (35 mg, 0.0913 mmol) and N-ethyl-N-iso-propyl-propan-2-amine (0.032 mL, 0.183 mmol) was stirred at ambient in DMF-Anhydrous (3.3672 mL) for 4 h. IPC indicated formation of the desired product. The mixture was directly purified using FCC (0-100% EtOAc followed by 0-20% MeOH in DCM, 10 g silica). Clean fractions were evaporated in vacuo to afford tert-butyl N—[(S)-{3-[3-(4-cyano-2-methoxyphenoxy)-6-(2,2-difluorocyclopropyl)-5-methylpyridazine-4-amido]phenyl}(methyl)oxo-$\lambda^6$-sulfanylidene]carbamate (11 mg, 0.0142 mmol, 110%) as a white solid. m/z: 614.2 $[M+H]^+$, (ESI+), RT=0.87 min LCMS Method 2.

Step 4 3-(4-cyano-2-methoxyphenoxy)-6-(2,2-difluoro-cyclopropyl)-N-{3-[(S)-imino(methyl)oxo-$\lambda^6$-sulfanyl]phenyl}-5-methylpyridazine-4-carboxamide: To a solution of tert-butyl N-[[3-[[3-(4-cyano-2-methoxy-phenoxy)-6-(2,2-difluorocyclopropyl)-5-methyl-pyridazine-4-carbonyl]amino]phenyl]-methyl-oxo-$\lambda^6$-sulfanylidene]carbamate (11 mg, 0.0179 mmol) in DCM (0.2423 mL) was added TFA (0.2423 mL) and the solution stirred at ambient for 4 h. IPC indicated formation of the desired product. The solvent was removed under a stream of nitrogen. saturated sodium carbonate aq (1 mL) was added and the solution extracted with DCM (3×1 mL). The combined organics were washed again with saturated sodium carbonate passed through a phase separating frit and the solvent removed in vacuo to afford the crude solid. Purification was attempted with reverse phase standard acidic gradient. Compound eluted ~90% purity. Purification using standard FCC (10 g silica; 0-100% EtOAc in heptanes followed by 0-30% MeOH in DCM eluted the title compound and impurities ~10% MeOH). The solvent was removed in vacuo and the solid freeze dried to afford 3 3-(4-cyano-2-methoxyphenoxy)-6-(2,2-difluorocyclopropyl)-N-{3-[(S)-imino(methyl)oxo-$\lambda^6$-sulfanyl]phenyl}-5-methylpyridazine-4-carboxamide (90.0%) (8.3 mg, 0.0145 mmol, 81%) as an off white solid. $^1H$ NMR (500 MHz, $CD_3OD$) δ 8.47-8.43 (m, 1H), 7.98-7.93 (m, 1H), 7.82 (ddd, J=7.9, 1.8, 1.0 Hz, 1H), 7.65 (t, J=8.0 Hz, 1H), 7.50 (s, 1H), 7.43-7.39 (m, 2H), 3.79 (s, 3H), 3.26-3.21 (m, 1H), 3.17 (s, 3H), 2.52 (s, 3H), 2.48-2.39 (m, 1H), 2.04-1.97 (m, 1H). m/z: 514.2 $[M+H]^+$, (ESI+), RT=2.57 LCMS Method 4.

Example 75

Compound 1529: 3-(4-cyano-2-methoxyphenoxy)-N-{3-[(R)-imino(methyl)oxo-λ6-sulfanyl]phenyl}-5-methyl-6-(4-methylphenyl)pyridazine-4-carboxamide

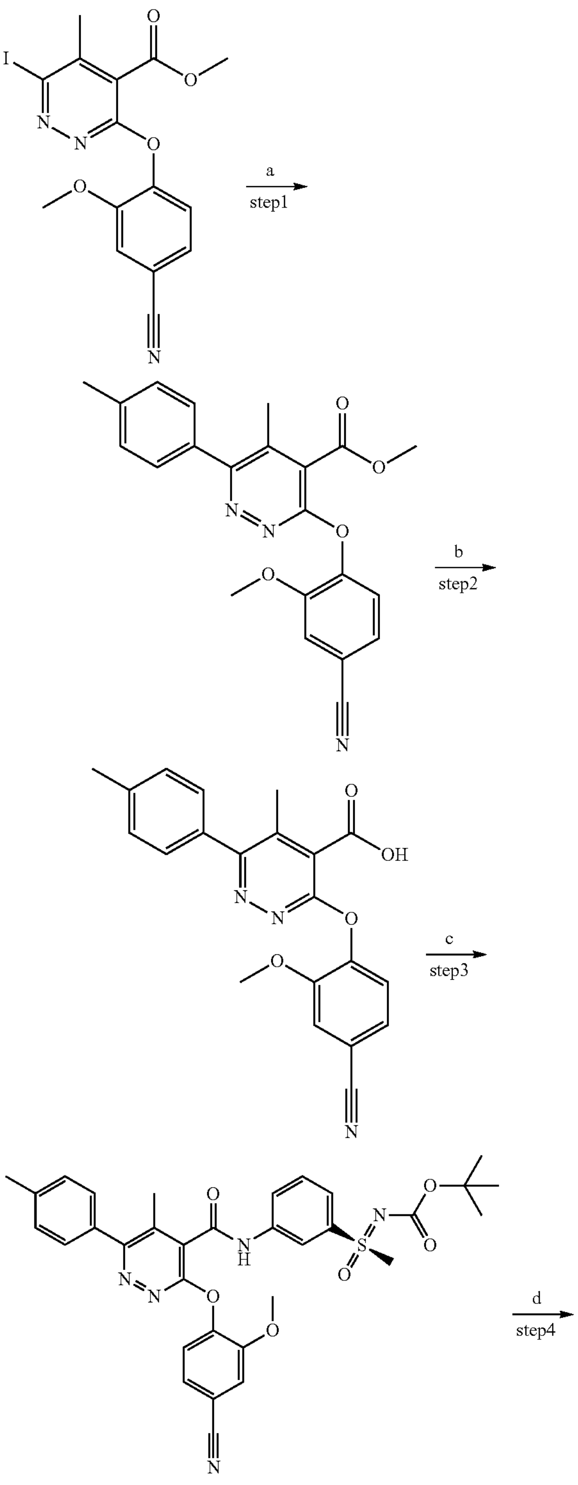

-continued

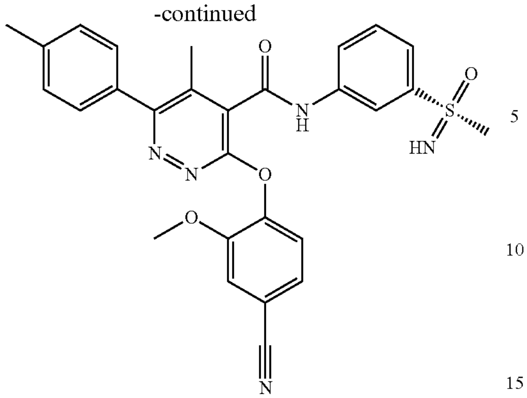

Reagents & conditions:
a) Pd(dppf)$Cl_2$•DCM, (4-methylphenyl)boronic acid, 2M $Na_2CO_3$, 1,4-dioane, 80 °C;
b) LiOH, THF/$H_2O$, rt; ) tert-butyl N-[(R)-(3-aminophenyl)(methyl)oxo-$\lambda^6$-sulfanylidene]carbamate, HATU, DIEA, DMF;
d) 4M HCl in dioxane, 1,-4-dioxane, rt.

Step 1: methyl 3-(4-cyano-2-methoxy-phenoxy)-5-methyl-6-(p-tolyl)pyridazine-4-carboxylate: 1,1′-bis(diphenylphosphanyl)ferrocene-dichloropalladium (1:1) (0.17 g, 0.235 mmol) was added to a stirred, N2 degassed solution of methyl 3-(4-cyano-2-methoxy-phenoxy)-6-iodo-5-methyl-pyridazine-4-carboxylate (1.00 g, 2.35 mmol), (4-methylphenyl)boronic acid (0.64 g, 4.70 mmol) and 2 M disodium carbonate (2M aq.) (3.5 mL, 7.06 mmol) in 1,4-Dioxane (12 mL). The reaction mixture was stirred at 80 °C for 2 h in a pressure vial. LCMS analysis indicated the reaction was complete. The mixture was diluted with ethyl acetate (30 mL) and washed with water (15 mL) and brine (15 mL). The organics were dried (MgSO4), filtered and concentrated to afford a brown solid. Purification by FCC (25 g, 0 to 40% EA in heptane) afforded methyl 3-(4-cyano-2-methoxy-phenoxy)-5-methyl-6-(p-tolyl)pyridazine-4-carboxylate (77.0%)(1.20 g, 100%) as a pale yellow solid. LCMS and $^1$H-NMR analysis indicated this was the desired product, with excess tolyl boronic acid. Used directly in the next step.

Step 2: 3-(4-cyano-2-methoxy-phenoxy)-5-methyl-6-(p-tolyl)pyridazine-4-carboxylic acid: To a solution of methyl 3-(4-cyano-2-methoxy-phenoxy)-5-methyl-6-(p-tolyl) pyridazine-4-carboxylate (0.92 g, 2.35 mmol) in THF (6 mL):Water (2 mL), lithium hydroxide (0.13 g, 5.17 mmol) was added, and the mixture was stirred at RT for 18 h. LCMS analysis indicated ca. 50% conversion. Additional lithium hydroxide (0.13 g, 5.17 mmol) in Water (2 mL) was added, and the mixture stirred at rt for 18 h. LCMS analysis indicated ca. 75% conversion with 18% carboxamide at 215 nm. The mixture was diluted with water (30 mL) and extracted with ethyl acetate (2×15 mL). The organics were concentrated to afford a yellow semi-solid, 565 mg. The the pH was then adjusted to 1 by dropwise addition of 2M HCl (aq), and the aqueous layer was extracted with EtOAc (2×15 mL) and the organics concentrated to afford 3-(4-cyano-2-methoxy-phenoxy)-5-methyl-6-(p-tolyl)pyridazine-4-carboxylic acid (93.0%) (0.69 g, 73%) as a white solid. $^1$H NMR (400 MHz, DMSO-$d_6$) δ 7.72 (d, J=1.8 Hz, 1H), 7.53 (dd, J=8.2, 1.8 Hz, 1H), 7.49-7.40 (m, 3H), 7.32 (d, J=7.9 Hz, 2H), 3.79 (s, 3H), 2.38 (s, 3H), 2.30 (s, 3H). m/z: 376.2 $[M+H]^+$, (ESI+), RT=0.71 min LCMS Method 2.

Step 3: tert-butyl N—[(R)-{3-[3-(4-cyano-2-methoxy-phenoxy)-5-methyl-6-(4-methylphenyl)pyridazine-4-amido]phenyl}(methyl)oxo-$\lambda^6$-sulfanylidene]carbamate: N-[(dimethylamino)(3H-[1,2,3]triazolo[4,5-b]pyridin-3-yloxy)methylidene]-N-methylmethanaminium hexafluorophosphate (0.79 g, 2.08 mmol) was added to a solution of 3-(4-cyano-2-methoxy-phenoxy)-5-methyl-6-(p-tolyl) pyridazine-4-carboxylic acid (0.65 g, 1.73 mmol) and N-ethyl-N-isopropyl-propan-2-amine (0.60 mL, 3.46 mmol) in DMF-Anhydrous (7 mL). The mixture was stirred at rt for 5 minutes, before the addition of tert-butyl N—[(R)-(3-aminophenyl)(methyl)oxo-$\lambda^6$-sulfanylidene]carbamate (0.51 g, 1.90 mmol) as a solution in DMF-Anhydrous (4 mL). The mixture was stirred at RT for 18 h. LCMS analysis indicated the reaction was mostly complete. The mixture was diluted with ethyl acetate (30 mL) and washed with water (3×15 mL) and brine (15 mL). Organics were dried ($MgSO_4$), filtered and concentrated to afford a yellow foam. Purification by FCC (25 g, 0 to 100% EA in heptane) tert-butyl N—[(R)-{3-[3-(4-cyano-2-methoxyphenoxy)-5-methyl-6-(4-methylphenyl)pyridazine-4-amido]phenyl}(methyl)oxo-$\lambda^6$-sulfanylidene]carbamate (90.0%) (0.90 g, 74%) as a pale yellow foam. $^1$H NMR (400 MHz, $CD_3OD$) δ 8.49 (t, J=2.0 Hz, 1H), 8.02-7.95 (m, 1H), 7.78 (m, 1H), 7.70 (t, J=8.0 Hz, 1H), 7.51 (m, 1H), 7.47-7.39 (m, 4H), 7.36 (d, J=8.0 Hz, 2H), 3.83 (s, 3H), 3.35 (s, 3H), 2.43 (s, 3H), 2.40 (s, 3H), 1.27 (s, 9H). m/z: 628.2 $[M+H]^+$, (ESI+), RT=0.94 min LCMS Method 2.

Step 4: 3-(4-cyano-2-methoxyphenoxy)-N-{3-[(R)-imino(methyl)oxo-λ6-sulfanyl]phenyl}-5-methyl-6-(4-methylphenyl)pyridazine-4-carboxamide: To a solution of tert-butyl N—[(R)-{3-[3-(4-cyano-2-methoxyphenoxy)-5-methyl-6-(4-methylphenyl)pyridazine-4-amido]phenyl}(methyl)oxo-$\lambda^6$-sulfanylidene]carbamate (898 mg, 1.43 mmol) in 1,4-Dioxane-Anhydrous (8 mL) was added 4 M hydrogen chloride 4m in dioxane (18 mL, 71.5 mmol). The mixture was stirred at rt for 2 h. LCMS analysis indicated the reaction was complete. The mixture was cooled to 0'C, diluted with ethyl acetate (20 mL) and the pH adjusted to ~9 with sat. $NaHCO_3$. Extracted with ethyl acetate (3×30 mL), and the organics dried ($MgSO_4$), filtered and concentrated to afford an orange solid. Purification by acidic (0.10% Formic acid) reverse phase chromatography (Sfar C18 30 g D Duo, 10% MeCN in $H_2O$ 2 CV 10-25% MeCN in $H_2O$ 2 CV, 25-40% MeCN in $H_2O$ 12 CV, 40% MeCN in $H_2O$ 8 CV THEN 40-100%®6CV) afforded a white solid (~480 mg) which was taken up in MeCN (20 mL) and scavenged with Si TMT (TCI chemicals, 0.5 mmol/g, 1.41 g) for 30 min at rt. The mixture was filtered and concentrated, then freeze dried to afford 3-(4-cyano-2-methoxyphenoxy)-N-{3-[(R)-imino(methyl)oxo-$\lambda^6$-sulfanyl]phenyl}-5-methyl-6-(4-methylphenyl)pyridazine-4-carboxamide (100.0%)(435 mg, 58%) as a white solid. $^1$H NMR (500 MHz, $CD_3OD$) δ 8.46 (t, J=2.0 Hz, 1H), 7.97 (m, 1H), 7.83 (m, 1H), 7.65 (t, J=8.0 Hz, 1H), 7.51 (d, J=1.6 Hz, 1H), 7.47-7.39 (m, 4H), 7.36 (d, J=7.8 Hz, 2H), 3.83 (s, 3H), 3.17 (s, 3H), 2.43 (s, 3H), 2.41 (s, 3H). m/z: 528.2 $[M+H]^+$, (ESI+), RT=2.88 LCMS Method 4.

Example 76

Compound 1530: 3-(4-cyano-2-methoxyphenoxy)-N-{3-[(S)-imino(methyl)oxo-$\lambda^6$-sulfanyl]phenyl}-5-methyl-6-(4-methylphenyl)pyridazine-4-carboxamide

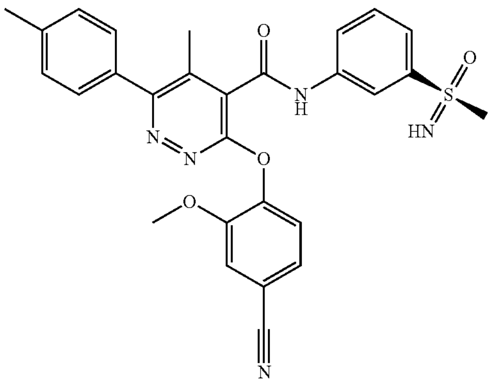

Title compound was made using a similar method to that above but using tert-butyl N—[(S)-(3-aminophenyl)(methyl)oxo-$\lambda^6$-sulfanylidene]carbamate. This route yields 3-(4-cyano-2-methoxyphenoxy)-N-{3-[(S)-imino(methyl)oxo-$\lambda^6$-sulfanyl]phenyl}-5-methyl-6-(4-methylphenyl)pyridazine-4-carboxamide (0.52 g, 0.984 mmol) as a white solid $^1$H NMR (400 MHz, $CD_3OD$) δ 8.46 (t, J=2.0 Hz, 1H), 8.01-7.93 (m, 1H), 7.83 (m, 1H), 7.65 (t, J=8.0 Hz, 1H), 7.51 (m, 1H), 7.47-7.40 (m, 4H), 7.36 (d, J=8.0 Hz, 2H), 3.83 (s, 3H), 3.17 (s, 3H), 2.43 (s, 3H), 2.41 (s, 3H). m/z: 528.2 $[M+H]^+$, (ESI+), RT=2.88 LCMS Method 4.

Example 77

Compound 1531: (R)-3-(4-cyano-2-methoxyphenoxy)-6-(4-cyanophenyl)-5-methyl-N-(3-(S-methylsulfonimidoyl)phenyl)pyridazine-4-carboxamide

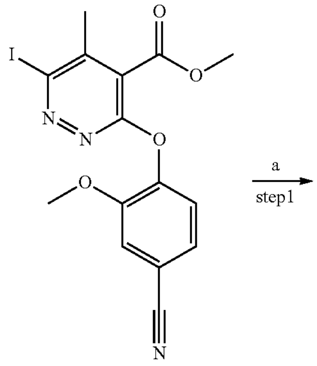

-continued

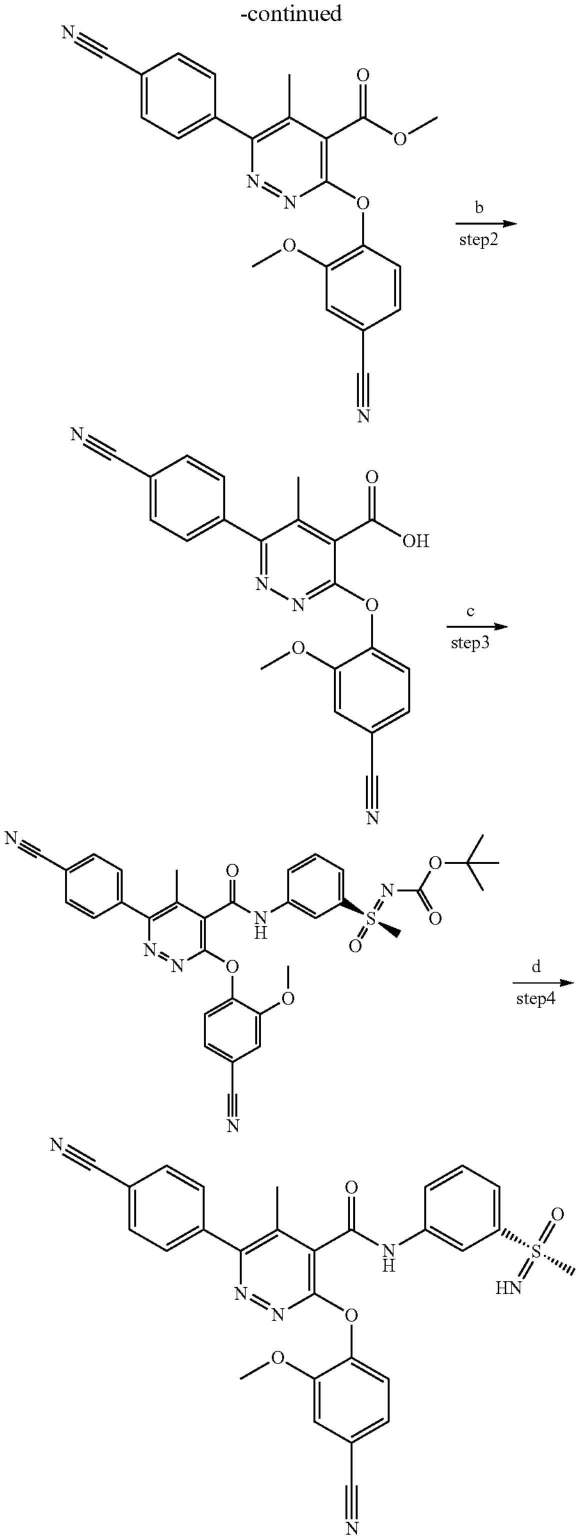

Reagents & conditions:
a) Pd(dppf)$Cl_2$•DCM, (4-cyanophenyl)boronic acid, 2M $Na_2CO_3$, 1,4-dioxane, 80 °C;
b) LiOH, THF/$H_2O$, rt;
c) tert-butyl N-[(R)-(3-aminophenyl)(methyl)oxo-$\lambda^6$-sulfanylidene]carbamate, HATU, DIEA, DMF;
d) 4M HCl in dioxane, 2-propanol, 1,-4-dioxane.

Step 1: methyl 3-(4-cyano-2-methoxy-phenoxy)-6-(4-cyanophenyl)-5-methyl-pyridazine-4-carboxylate: Pd(dppf)

$Cl_2$·DCM (1:1) (172 mg, 0.23 5 mmol) was added to a stirred, $N_2$ degassed solution of methyl 3-(4-cyano-2-methoxy-phenoxy)-6-iodo-5-methyl-pyridazine-4-carboxylate (1000 mg, 2.35 mmol), (4-cyanophenyl)boronic acid (691 mg, 4.70 mmol) and 2 M disodium carbonate (2M aq.) (3.5 mL, 7.06 mmol) in 1,4-Dioxane (40 mL). The reaction mixture was stirred at 80 °C for 4 h. The reaction mixture was diluted with EtOAc (~80 mL) and washed with water (~20 ml). The organic phase was washed with brine, dried over sodium sulfate, filtered and concentrated to dryness to give crude product. Purification by FCC (Biotage isolera, $SiO_2$, gradient elution 10-100% EtOAc:Heptanes gave methyl 3-(4-cyano-2-methoxy-phenoxy)-6-(4-cyanophenyl)-5-methyl-pyridazine-4-carboxylate (92.0%) (891 mg, 87%) as an off white solid. $^1H$ NMR (400 MHz, $CDCl_3$) δ 7.82 (dd, J=16.0, 8.2 Hz, 2H), 7.65 (d, J=8.3 Hz, 2H), 7.39-7.31 (m, 2H), 7.26-7.19 (m, 1H), 4.05 (s, 3H), 3.80 (s, 3H), 2.37 (s, 3H). m/z: 401 $[M+H]^+$, (ESI+), RT=0.87 LCMS Method 2.

Step 2: 3-(4-cyano-2-methoxyphenoxy)-6-(4-cyanophenyl)-5-methylpyridazine-4-carboxylic acid: lithium hydroxide (117 mg, 4.90 mmol) was added to a solution of methyl 3-(4-cyano-2-methoxy-phenoxy)-6-(4-cyanophenyl)-5-methyl-pyridazine-4-carboxylate (891 mg, 2.23 mmol) in THF-Anhydrous (19 mL) and water (2.5 mL) at rt and the reaction was stirred at rt for 16 h. The reaction mixture was concentrated to low volume (remove THF), diluted in water (~20 ml) and washed with TBME (~20 ml). The basic aqueous phase was cooled to OC and acidified to pH 2-3 by addition of 2M HCl aq. The organic phase was extracted with EtOAc (3×50 ml). The organic phase was dried with sodium sulfate, filtered and concentrated to dryness in vacuum. to give crude product 3-(4-cyano-2-methoxyphenoxy)-6-(4-cyanophenyl)-5-methylpyridazine-4-carboxylic acid (91.0%) (674 mg, 1.745 mmol) which was used as such in the next step. Assumed 100% molar yield.

Step 3: tert-butyl (R)-((3-(3-(4-cyano-2-methoxyphenoxy)-6-(4-cyanophenyl)-5-methylpyridazine-4-carboxamido)phenyl)(methyl)(oxo)-$\lambda^6$-sulfaneylidene)carbamate: N-[(dimethylamino)(3H-[1,2,3]triazolo[4,5-b]pyridin-3-yloxy)methylidene]-N-methylmethanaminium hexafluorophosphate (HATU) (730 mg, 1.92 mmol) was added to a mixture of 3-(4-cyano-2-methoxy-phenoxy)-6-(4-cyanophenyl)-5-methyl-pyridazine-4-carboxylic acid (674 mg, 1.74 mmol) and N-ethyl-N-isopropyl-propan-2-amine (670 uL, 3.84 mmol) in DMF (6 mL) at rt and the reaction was stirred at rt for 5 min then a solution of) tert-butyl N—[(R)-(3-aminophenyl)(methyl)oxo-$\lambda^6$-sulfanylidene]carbamate (472 mg, 1.74 mmol) in DMF (6 mL) was added and the reaction was stirred at rt for 16 h. The reaction mixture was diluted with EtOAc (~50 mL) and washed with water (3×~50 ml). The organic phase was washed with brine, dried over sodium sulfate, filtered and concentrated to dryness to give crude product. Purification by FCC (Biotage isolera, $SiO_2$ gradient elution 10-50% EtOAc:Heptanes) to provide tert-butyl (R)-((3-(3-(4-cyano-2-methoxyphenoxy)-6-(4-cyanophenyl)-5-methylpyridazine-4-carboxamido)phenyl)(methyl)(oxo)-$\lambda^6$-sulfaneylidene)carbamate (887 mg, 80%) as a yellow gum. Material used in the next step without further purification.

Step 4: (R)-3-(4-cyano-2-methoxyphenoxy)-6-(4-cyanophenyl)-5-methyl-N-(3-(S-methylsulfonimidoyl)phenyl)pyridazine-4-carboxamide: 4 M hydrogen chloride (4M in dioxane) (12 mL, 46.8 mmol) was added to a solution tert-butyl (R)-((3-(3-(4-cyano-2-methoxyphenoxy)-6-(4-cyanophenyl)-5-methylpyridazine-4-carboxamido)phenyl)(methyl)(oxo)-$\lambda^6$-sulfaneylidene)carbamate (598 mg, 0.936 mmol) in 1,4-Dioxane (5.5 mL) and 2-Propanol (5.5 mL). The mixture was stirred at rt for 4 h. The reaction wad cooled to °C, diluted in EtOAc, −50 ml. Basified to pH9 by the dropwise addition of satd aq $NaHCO_3$. The aq. phase was extracted with EtOAc (3×50 mL). The org. phase was washed with brine, dried over sodium sulfate, filtered and concentrated to dryness in vacuum to give crude desired product which was purified by low pH reverse phase Biotage 2×(Sfar C18 12 g D Duo, 10% MeCN in H2O 2 CV, 10-25% MeCN in $H_2O$ 2 CV, 25-40% MeCN in $H_2O$ 12 CV, 40% MeCN in $H_2O$ 8 CV, then 40-100% ACN 6CV) The product containing fractions were combined and the solvent was removed in vacuo, to give the desired product 381 mg as a white solid, which was diluted in ACN (30 ml) and scavenged with Si TMT, TCI chemicals, 0.5 mmol/g, 1.85 g) for 30 min at rt. The scavenger was filtered thru a douche tube and concentrated to dryness in vacuum. The residue was diluted in 3:2 water:ACN (10 ml) and freeze dried overnight to give (R)-3-(4-cyano-2-methoxyphenoxy)-6-(4-cyanophenyl)-5-methyl-N-(3-(S-methylsulfonimidoyl)phenyl)pyridazine-4-carboxamide (100.0%)(331 mg, 66%). $^1H$ NMR (400 MHz, DMSO-$d_6$) δ 11.31 (s, 1H), 8.39 (s, 1H), 8.02 (d, J=8.3 Hz, 2H), 7.87 (d, J=8.6 Hz, 1H), 7.81 (d, J=8.3 Hz, 2H), 7.75-7.68 (m, 2H), 7.62 (t, J=7.9 Hz, 1H), 7.55 (dd, J=8.2, 1.7 Hz, 1H), 7.49 (d, J=8.2 Hz, 1H), 4.25 (s, 1H), 3.80 (s, 3H), 3.07 (s, 3H), 2.35 (s, 3H). m/z: 539.2 $[M+H]^+$, (ESI+), RT=2.67 LCMS Method 6.

Example 78

Compound 1532: 3-(4-cyano-2-methoxyphenoxy)-6-(4-cyanophenyl)-N-{3-[(S)-imino(methyl)oxo-$\lambda^6$-sulfanyl]phenyl}-5-methylpyridazine-4-carboxamide

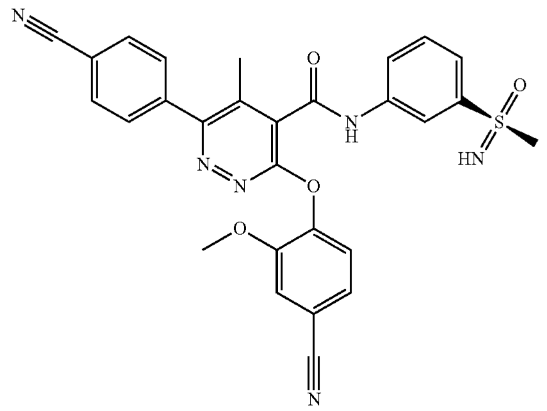 [SMILES: COc1cc(C#N)ccc1Oc1nnc(-c2ccc(C#N)cc2)c(C)c1C(=O)Nc1cccc([S@@](C)(=N)=O)c1]

The title compound was made with a similar method to that described for example 77, compound 1531 but using 3-(4-cyano-2-methoxy-phenoxy)-6-(4-cyanophenyl)-5-methyl-pyridazine-4-carboxylic acid and tert-butyl N—[(S)-(3-aminophenyl)(methyl)oxo-λ6-sulfanylidene]carbamate to eventually yield 3-(4-cyano-2-methoxyphenoxy)-6-(4-cyanophenyl)-N-{3-[(S)-imino(methyl)oxo-$\lambda^6$-sulfanyl]phenyl}-5-methylpyridazine-4-carboxamide (279 mg, 0.513 mmol). $^1H$ NMR (400 MHz, DMSO-$d_6$) δ 11.29 (s, 1H), 8.40 (s, 1H), 8.02 (d, J=8.2 Hz, 2H), 7.88 (d, J=8.5 Hz, 1H), 7.81 (d, J=8.3 Hz, 2H), 7.75-7.68 (m, 2H), 7.62 (t, J=7.9 Hz, 1H), 7.55 (dd, J=8.2, 1.7 Hz, 1H), 7.49 (d, J=8.2 Hz, 1H), 4.26 (s, 1H), 3.80 (s, 3H), 3.07 (s, 3H), 2.35 (s, 3H). 0.3 WT % ACN. m/z: 539.0 $[M+H]^+$, (ESI+), RT=2.67 MET-uPLC-AB-101 (7 min, low pH).

Compounds 1533 to 1537 were prepared using a related route, but using appropriate commercially available boronic acids/esters/BF3 salts for the Suzuki step and the appropriate chiral intermediates tert-butyl N—[(S)-(3-aminophenyl)(methyl)oxo-$\lambda^6$-sulfanylidene]carbamate or tert-butyl N—[(R)-(3-aminophenyl)(methyl)oxo-$\lambda^6$-sulfanylidene]carbamate for the relevant chiral sulfoximine products.

Compounds 1533: 3-(4-cyano-2-methoxyphenoxy)-6-[4-(difluoromethyl)phenyl]-N-{3-[(S)-imino(methyl)oxo-$\lambda^6$-sulfanyl]phenyl}-5-methylpyridazine-4-carboxamide

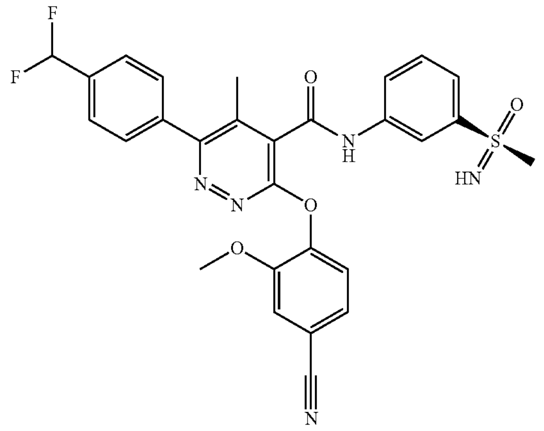 [SMILES: COc1cc(C#N)ccc1Oc1nnc(-c2ccc(C(F)F)cc2)c(C)c1C(=O)Nc1cccc([S@@](C)(=N)=O)c1]

$^1$H NMR (400 MHz, DMSO-$d_6$)) δ 11.29 (s, 1H), 8.40 (s, 1H), 7.88 (d, J=8.0 Hz, 1H), 7.83-7.68 (m, 6H), 7.62 (t, J=7.9 Hz, 1H), 7.55 (dd, J=8.2, 1.6 Hz, 1H), 7.49 (d, J=8.2 Hz, 1H), 7.14 (t, J=55.8 Hz, 1H), 4.25 (s, 1H), 3.81 (s, 3H), 3.07 (s, 3H), 2.35 (s, 3H). m/z: 564.0 [M+H]$^+$, (ESI+), RT=2.91 LCMS Method 4.

Compound 1534: 3-(4-cyano-2-methoxyphenoxy)-6-[4-(difluoromethyl)phenyl]-N-{3-[(R)-imino(methyl)oxo-$\lambda^6$-sulfanyl]phenyl}-5-methylpyridazine-4-carboxamide

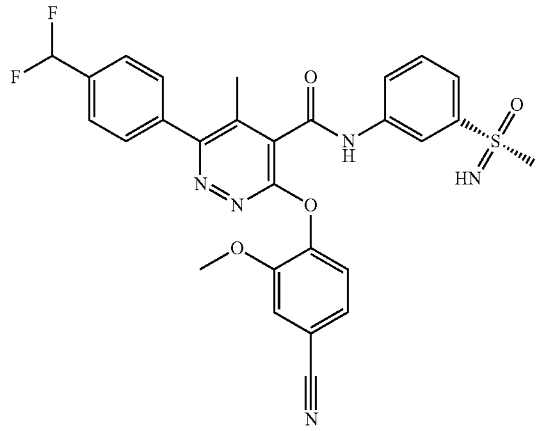 [SMILES: COc1cc(C#N)ccc1Oc1nnc(-c2ccc(C(F)F)cc2)c(C)c1C(=O)Nc1cccc([S@](C)(=N)=O)c1]

$^1$H NMR (400 MHz, DMSO-$d_6$)) δ 11.29 (s, 1H), 8.40 (s, 1H), 7.88 (d, J=8.6 Hz, 1H), 7.81-7.67 (m, 6H), 7.62 (t, J=7.9 Hz, 1H), 7.55 (dd, J=8.2, 1.7 Hz, 1H), 7.49 (d, J=8.2 Hz, 1H), 7.14 (t, J=55.8 Hz, 1H), 4.25 (s, 1H), 3.81 (s, 3H), 3.07 (s, 3H), 2.35 (s, 3H). m/z: 564.0 [M+H]$^+$, (ESI+), RT=2.91 LCMS Method 4.

Compound 1535: 3-(4-cyano-2-methoxyphenoxy)-N-{3-[(R)-imino(methyl)oxo-$\lambda^6$-sulfanyl]phenyl}-6-(4-methoxyphenyl)-5-methylpyridazine-4-carboxamide

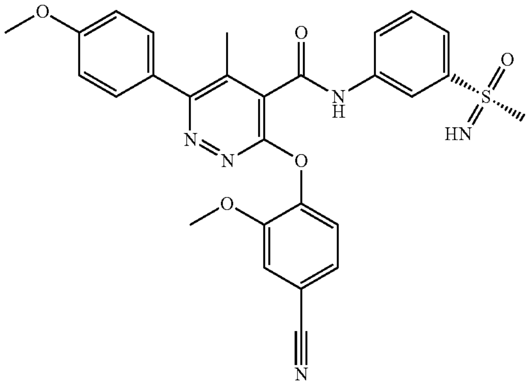

$^1$H NMR (500 MHz, $CD_3OD$) δ 8.46 (t, J=2.0 Hz, 1H), 7.97 (m, 1H), 7.83 (m, 1H), 7.65 (t, J=8.0 Hz, 1H), 7.54-7.46 (m, 3H), 7.46-7.38 (m, 2H), 7.12-7.06 (m, 2H), 3.87 (s, 3H), 3.83 (s, 3H), 3.17 (s, 3H), 2.42 (s, 3H). m/z: 544.1 [M+H]$^+$, (ESI+), RT=2.68 LCMS Method 4.

Compound 1536: 3-(4-cyano-2-methoxyphenoxy)-N-{3-[(S)-imino(methyl)oxo-$\lambda^6$-sulfanyl]phenyl}-6-(4-methoxyphenyl)-5-methylpyridazine-4-carboxamide

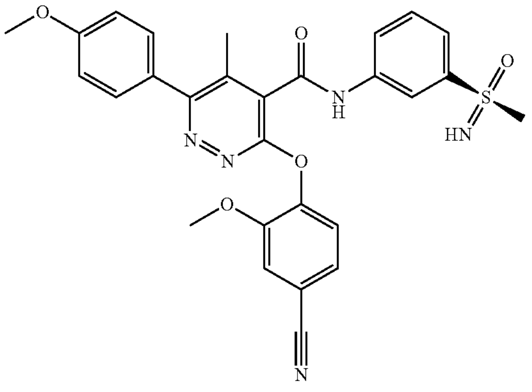

$^1$H NMR (500 MHz, $CD_3OD$) δ 8.46 (t, J=2.0 Hz, 1H), 7.97 (m, 1H), 7.82 (m, 1H), 7.65 (t, J=8.0 Hz, 1H), 7.53-7.46 (m, 3H), 7.45-7.36 (m, 2H), 7.13-7.04 (m, 2H), 3.87 (s, 3H), 3.82 (s, 3H), 3.17 (s, 3H), 2.42 (s, 3H). m/z: 544.4 [M+H]$^+$, (ESI+), RT=2.77 LCMS Method 4.

Compound 1537: 3-(4-cyano-2-methoxyphenoxy)-6-(2-fluorophenyl)-N-{3-[(R)-imino(methyl)oxo-$\lambda^6$-sulfanyl]phenyl}-5-methylpyridazine-4-carboxamide

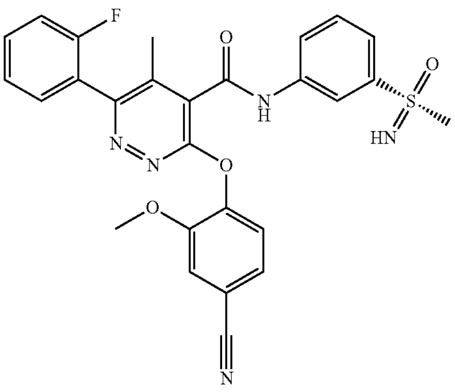 [SMILES: COc1cc(C#N)ccc1Oc1nnc(-c2ccccc2F)c(C)c1C(=O)Nc1cccc([S@](C)(=N)=O)c1]

$^1$H NMR (500 MHz, $CD_3OD$) δ 8.46 (t, J=2.0 Hz, 1H), 7.97 (m, 1H), 7.83 (m, J=7.8, 1.8, 1.0 Hz, 1H), 7.65 (t, J=8.0 Hz, 1H), 7.59 (m, 1H), 7.52 (d, J=1.7 Hz, 1H), 7.51-7.41 (m, 3H), 7.38 (td, J=7.5, 1.1 Hz, 1H), 7.31 (m, 1H), 3.84 (s, 3H), 3.17 (s, 3H), 2.33 (d, J=1.4 Hz, 3H). m/z: 532.1 [M+H]$^+$, (ESI+), RT=2.71 LCMS Method 4.

Example 79

Compound 1538: 5-[[3-(4-cyano-2-methoxy-phenoxy)-5-methyl-6-(trifluoromethyl)pyridazine-4-carbonyl]amino]thiazole-2-carboxamide

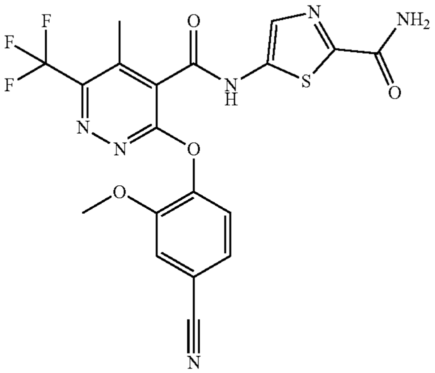 [SMILES: COc1cc(C#N)ccc1Oc1nnc(C(F)(F)F)c(C)c1C(=O)Nc1cnc(C(N)=O)s1]

$^1$H NMR (500 MHz, DMSO-$d_6$) δ 12.70 (s, 1H), 8.05 (s, 1H), 7.77 (s, 1H), 7.76-7.73 (m, 2H), 7.57 (dd, J=8.2, 1.8 Hz, 1H), 7.51 (d, J=8.2 Hz, 1H), 3.78 (s, 3H), 2.48 (m, 3H). m/z: 479.1 [M+H]$^+$, (ESI+), RT=2.73 MET-uPLC-AB-101 (7 min, low pH).

Compound 1539: N-(6-carbamoyl-3-pyridyl)-3-(4-cyano-2-methoxy-phenoxy)-5-methyl-6-(trifluoromethyl)pyridazine-4-carboxamide

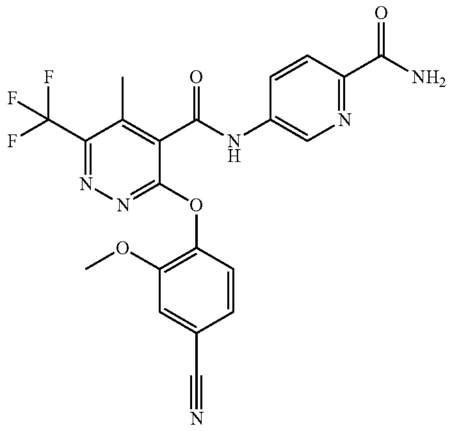 [SMILES: COc1cc(C#N)ccc1Oc1nnc(C(F)(F)F)c(C)c1C(=O)Nc1ccc(C(N)=O)nc1]

$^1$H NMR (500 MHz, DMSO-$d_6$) δ 11.47 (s, 1H), 8.87 (d, J=2.4 Hz, 1H), 8.32 (dd, J=8.6, 2.5 Hz, 1H), 8.10 (d, J=8.5 Hz, 1H), 8.08-8.01 (m, 1H), 7.75 (d, J=1.8 Hz, 1H), 7.61 (s, 1H), 7.57 (dd, J=8.2, 1.8 Hz, 1H), 7.53 (d, J=8.2 Hz, 1H), 3.80 (s, 3H), 2.54 (d, J=1.4 Hz, 3H). m/z: 473.1 [M+H]$^+$, (ESI+), RT=2.69 MET-uPLC-AB-107 (7 min, high pH)

Compound 1540: 3-(4-cyano-2-methoxy-phenoxy)-N-(5-cyano-3-pyridyl)-5-methyl-6-(trifluoromethyl) pyridazine-4-carboxamide

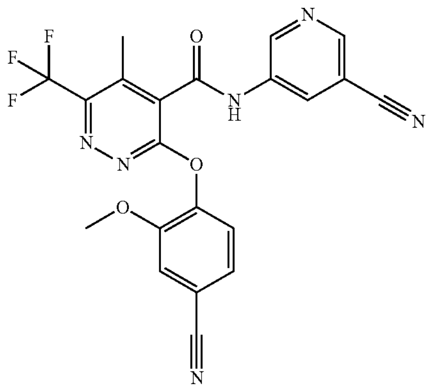 [SMILES: COc1cc(C#N)ccc1Oc1nnc(C(F)(F)F)c(C)c1C(=O)Nc1cncc(C#N)c1]

$^1$H NMR (500 MHz, $CD_3OD$) δ 8.98 (d, J=2.5 Hz, 1H), 8.71 (d, J=1.8 Hz, 1H), 8.68 (dd, J=2.5, 1.8 Hz, 1H), 7.54 (d, J=1.4 Hz, 1H), 7.45 (t, J=1.3 Hz, 2H), 3.81 (s, 3H), 2.59 (q, J=1.5 Hz, 3H). m/z: 455.0 [M+H]$^+$, (ESI+), RT=3.35 MET-uPLC-AB-101 (7 min, low pH)

Compound 1541: N-(3-carbamoyl-4-methoxy-phenyl)-3-(4-cyano-2-methoxy-phenoxy)-5-methyl-6-(trifluoromethyl)pyridazine-4-carboxamide

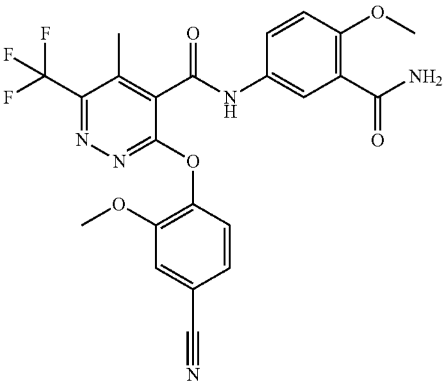 [SMILES: COc1cc(C#N)ccc1Oc1nnc(C(F)(F)F)c(C)c1C(=O)Nc1ccc(OC)c(C(N)=O)c1]

$^1$H NMR (500 MHz, $CD_3OD$) δ 8.14 (d, J=2.8 Hz, 1H), 8.01 (dd, J=9.0, 2.8 Hz, 1H), 7.53 (d, J=1.6 Hz, 1H), 7.46-7.42 (m, 2H), 7.22 (d, J=9.0 Hz, 1H), 4.00 (s, 3H), 3.81 (s, 3H), 2.61-2.55 (m, 3H). m/z: 502.0 $[M+H]^+$, (ESI+), RT=3.00 MET-uPLC-AB-101 (7 min, low pH)

Compound 1542: 3-(4-cyano-2-methoxy-phenoxy)-5-methyl-N-[3-(methylsulfonylcarbamoyl)phenyl]-6-(trifluoromethyl)pyridazine-4-carboxamide

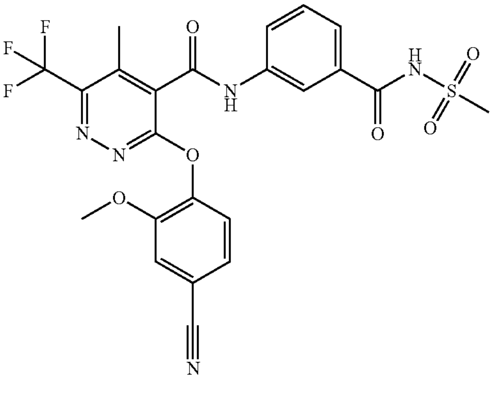 [SMILES: COc1cc(C#N)ccc1Oc1nnc(C(F)(F)F)c(C)c1C(=O)Nc1cccc(C(=O)NS(C)(=O)=O)c1]

$^1$H NMR (500 MHz, $CD_3OD$) δ 8.12 (s, 1H), 7.88-7.83 (m, 1H), 7.66-7.61 (m, 1H), 7.46-7.41 (m, 2H), 7.38-7.32 (m, 2H), 3.72 (s, 3H), 3.23 (s, 3H), 2.50 (d, J=1.4 Hz, 3H). m/z: 550.0 $[M+H]^+$, (ESI+), RT=1.97 MET-uPLC-AB-107 (7 min, high pH)

Compound 1543: 3-(4-cyano-2-methoxy-phenoxy)-5-methyl-N-(3-pyridyl)-6-(trifluoromethyl)pyridazine-4-carboxamide

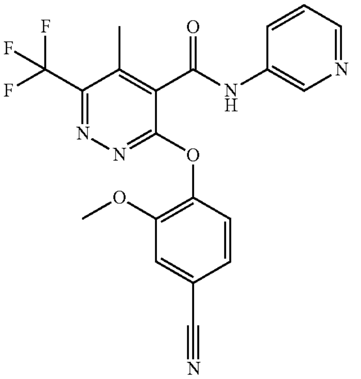 [SMILES: COc1cc(C#N)ccc1Oc1nnc(C(F)(F)F)c(C)c1C(=O)Nc1cccnc1]

$^1$H NMR (400 MHz, DMSO-$d_6$) δ 11.21 (br.s, 1H), 8.82 (d, J=2.4 Hz, 1H), 8.39 (dd, J=4.7, 1.3 Hz, 1H), 8.16 (ddd, J=8.3, 2.6, 1.5 Hz, 1H), 7.74 (d, J=1.7 Hz, 1H), 7.56 (dd, J=8.2, 1.8 Hz, 1H), 7.51 (d, J=8.2 Hz, 1H), 7.45 (dd, J=8.3, 4.7 Hz, 1H), 3.79 (s, 3H), 2.53-2.51 (m, 3H). m/z: 430.2 $[M+H]^+$, (ESI+), RT=2.99 MET-uPLC-AB-101 (7 min, low pH)

Compound 1544: 3-(4-cyano-2-methoxy-phenoxy)-5-methyl-N-(1-oxidopyridin-1-ium-3-yl)-6-(trifluoromethyl)pyridazine-4-carboxamide

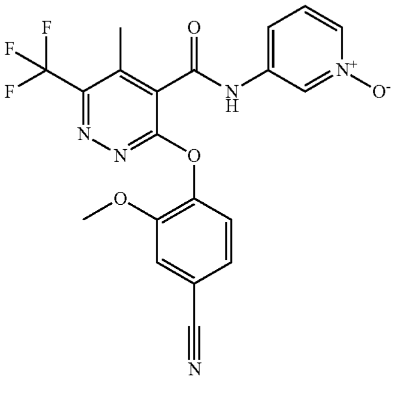 [SMILES: COc1cc(C#N)ccc1Oc1nnc(C(F)(F)F)c(C)c1C(=O)Nc1ccc[n+]([O-])c1]

$^1$H NMR (400 MHz, $CD_3OD$) δ 9.04 (t, J=1.9 Hz, 1H), 8.21-8.15 (m, 1H), 7.76 (m, 1H), 7.60-7.52 (m, 2H), 7.45 (s, 2H), 3.81 (s, 3H), 2.58 (m, 3H). m/z: 446.2 $[M+H]^+$, (ESI+), RT=2.44 MET-uPLC-AB-101 (7 min, low pH).

Compound 1545: 3-(4-cyano-2-methoxy-phenoxy)-N-[3-[(E)-N-methoxy-C-methyl-carbonimidoyl]phenyl]-5-methyl-6-(trifluoromethyl)pyridazine-4-carboxamide

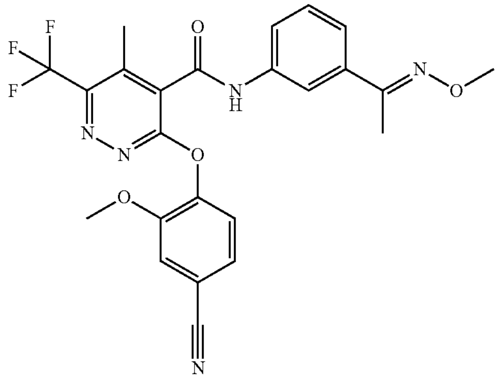 [SMILES: CO/N=C(\C)c1cccc(NC(=O)c2c(Oc3ccc(C#N)cc3OC)nnc(C(F)(F)F)c2C)c1]

$^1$H NMR (400 MHz, DMSO-$d_6$) δ 11.06 (s, 1H), 8.03-7.98 (m, 1H), 7.78-7.71 (m, 2H), 7.56 (dd, J=8.2, 1.8 Hz, 1H), 7.50 (d, J=8.2 Hz, 1H), 7.47-7.42 (m, 2H), 3.92 (s, 3H), 3.79 (s, 3H), 2.52-2.51 (m, 3H), 2.18 (s, 3H). m/z: 500.0 [M+H]$^+$, (ESI+), RT=4.09 MET-uPLC-AB-101 (7 min, low pH).

Compound 1546: methyl 3-[[3-(4-cyano-2-methoxy-phenoxy)-5-methyl-6-(trifluoromethyl)pyridazine-4-carbonyl]amino]benzoate

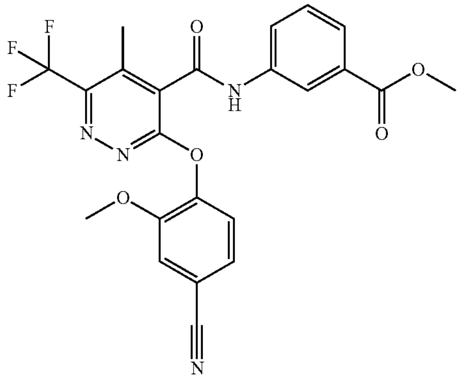 [SMILES: COC(=O)c1cccc(NC(=O)c2c(Oc3ccc(C#N)cc3OC)nnc(C(F)(F)F)c2C)c1]

$^{19}$F NMR (376 MHz, DMSO-$d_6$) δ −63.30. m/z: 487.1 [M+H]$^+$, (ESI+), RT=3.57 MET-uPLC-AB-107 (7 min, high pH)

Compound 1547: 3-(4-fluoro-2-methyl-phenoxy)-6-(1-hydroxyethyl)-5-methyl-N-[3-(methylsulfonimidoyl)phenyl]pyridazine-4-carboxamide

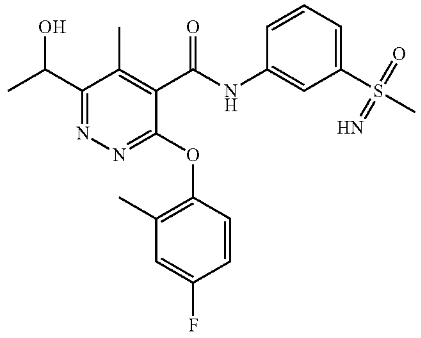 [SMILES: Cc1cc(F)ccc1Oc1nnc(C(C)O)c(C)c1C(=O)Nc1cccc(S(C)(=N)=O)c1]

$^1$H NMR (500 MHz, $CD_3OD$) δ, 8.46 (t, J=1.9 Hz, 1H), 8.02-7.89 (m, 1H), 7.86-7.77 (m, 1H), 7.65 (t, J=8.0 Hz, 1H), 7.16 (dd, J=8.9, 4.9 Hz, 1H), 7.05 (dd, J=9.1, 2.9 Hz, 1H), 7.01-6.93 (m, 1H), 5.23 (q, J=6.5 Hz, 1H), 3.17 (s, 3H), 2.56 (s, 3H), 2.16 (s, 3H), 1.61 (d, J=6.6 Hz, 3H) 3 exchangeable Hs not seen. m/z: 459.1 [M+H]$^+$, (ESI+), RT=2.25 MET-uPLC-AB-107 (7 min, high pH)

Compound 1548: 3-(4-cyano-2-methoxy-phenoxy)-N-(3-cyanophenyl)-5-methyl-6-(trifluoromethyl)pyridazine-4-carboxamide

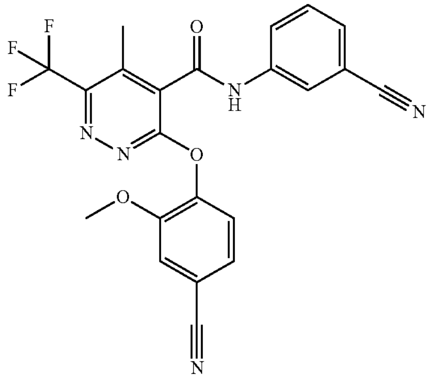 [SMILES: COc1cc(C#N)ccc1Oc1nnc(C(F)(F)F)c(C)c1C(=O)Nc1cccc(C#N)c1]

$^1$H NMR (500 MHz, DMSO-$d_6$) δ 11.35 (s, 1H), 8.18 (d, J=1.6 Hz, 1H), 7.91 (d, J=8.0 Hz, 1H), 7.76 (d, J=1.8 Hz, 1H), 7.65 (dt, J=15.6, 7.7 Hz, 3H), 7.57 (dd, J=8.2, 1.8 Hz, 1H), 7.52 (d, J=8.2 Hz, 1H), 3.80 (s, 3H). m/z: 454.2 [M+H]$^+$, (ESI+), RT=3.52 MET-uPLC-AB-101 (7 min, low pH).

Compound 1549: N-(3-carbamoylphenyl)-3-(3,4-difluoro-2-methoxy-phenoxy)-5-methyl-6-(trifluoromethyl)pyridazine-4-carboxamide

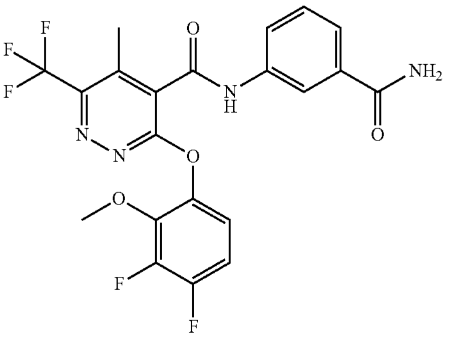 [SMILES: COc1c(Oc2nnc(C(F)(F)F)c(C)c2C(=O)Nc2cccc(C(N)=O)c2)ccc(F)c1F]

$^1$H NMR (500 MHz, DMSO-$d_6$) δ 11.10 (s, 1H), 8.18 (t, J=1.8 Hz, 1H), 8.01 (br.s, 1H), 7.81 (ddd, J=8.1, 2.2, 0.9 Hz, 1H), 7.67 (dt, J=7.8, 1.0 Hz, 1H), 7.48 (t, J=7.9 Hz, 1H), 7.41 (br.s, 1H), 7.33-7.26 (m, 1H), 7.24 (ddd, J=9.3, 5.2, 1.9 Hz, 1H), 3.83-3.79 (m, 3H), 2.54-2.52 (m, 3H). m/z: 483.1 $[M+H]^+$, (ESI+), RT=3.09 MET-uPLC-AB-101 (7 min, low pH).

Compound 1550: 3-[(6-cyclopropyl-2-methoxy-3-pyridyl)oxy]-5-methyl-N-[3-(methylsulfonimidoyl)phenyl]-6-(trifluoromethyl)pyridazine-4-carboxamide

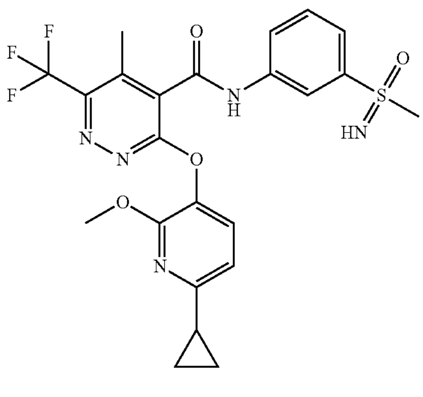 [SMILES: COc1nc(C2CC2)ccc1Oc1nnc(C(F)(F)F)c(C)c1C(=O)Nc1cccc(S(C)(=N)=O)c1]

$^1$H NMR (500 MHz, $CD_3OD$) δ 8.46-8.43 (m, 1H), 7.98-7.94 (m, 1H), 7.85-7.81 (m, 1H), 7.68-7.63 (m, 1H), 7.46-7.44 (m, 1H), 6.93-6.90 (m, 1H), 3.81 (s, 3H), 3.17 (s, 3H), 2.59-2.55 (m, 3H), 2.07-2.01 (m, 1H), 1.04-0.99 (m, 2H), 0.96-0.91 (m, 2H). m/z: 522.3 $[M+H]^+$, (ESI+), RT=3.48 MET-uPLC-AB-107 (7 min, high pH).

Compound 1551: 3-(3,4-difluoro-2-methoxy-phenoxy)-5-methyl-N-(tetrazolo[1,5-a]pyridin-7-yl)-6-(trifluoromethyl)pyridazine-4-carboxamide

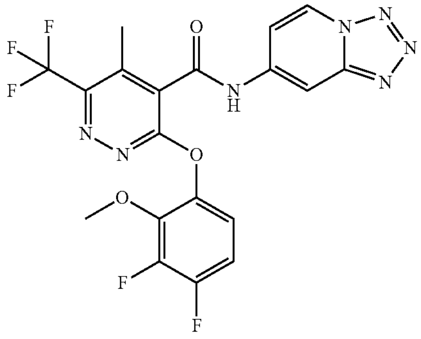 [SMILES: COc1c(Oc2nnc(C(F)(F)F)c(C)c2C(=O)Nc2ccn3nnnc3c2)ccc(F)c1F]

$^1$H NMR (400 MHz, $CD_3OD$) δ 9.09 (d, J=7.5 Hz, 1H), 8.67 (s, 1H), 7.48-7.39 (m, 1H), 7.18-7.01 (m, 2H), 3.86 (s, 3H), 2.61 (s, 3H). m/z: 481.9 $[M+H]^+$, (ESI+), RT=3.98 MET-uPLC-AB-101 (7 min, low pH).

Compound 1552: 3-(4-chloro-3-fluoro-2-methoxy-phenoxy)-5-methyl-N-(3-methylsulfonylphenyl)-6-(trifluoromethyl)pyridazine-4-carboxamide

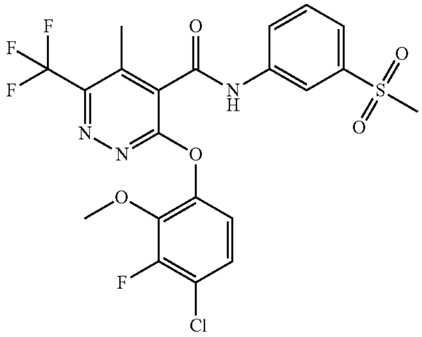 [SMILES: COc1c(Oc2nnc(C(F)(F)F)c(C)c2C(=O)Nc2cccc(S(C)(=O)=O)c2)ccc(Cl)c1F]

$^1$H NMR (400 MHz, DMSO) δ 11.40 (s, 1H), 8.38 (d, J=1.8 Hz, 1H), 7.91 (d, J=7.9 Hz, 1H), 7.79-7.66 (m, 2H), 7.45 (dd, J=9.0, 7.8 Hz, 1H), 7.28 (dd, J=9.0, 1.9 Hz, 1H), 3.80 (d, J=1.2 Hz, 3H), 3.25 (s, 3H), 2.57-2.52 (m, 3H). m/z: 534.1, 536.0 $[M+H]^+$, (ESI+), RT=3.65 MET-uPLC-AB-101 (7 min, low pH).

Compound 1553: 3-(4-fluoro-2-methyl-phenoxy)-5-methyl-N-[3-(methylsulfonimidoyl)phenyl]pyridazine-4-carboxamide

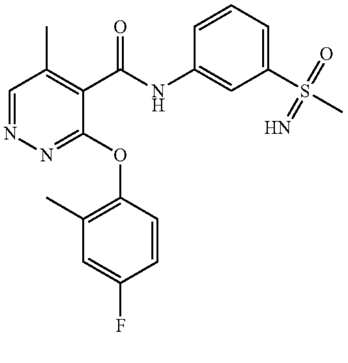 [SMILES: Cc1cc(F)ccc1Oc1nncc(C)c1C(=O)Nc1cccc(S(C)(=N)=O)c1]

¹H NMR (400 MHz, DMSO-$d_6$) δ 11.19 (s, 1H), 9.06 (s, 1H), 8.38 (t, J=1.9 Hz, 1H), 7.92-7.84 (m, 1H), 7.74-7.68 (m, 1H), 7.61 (t, J=7.9 Hz, 1H), 7.28-7.16 (m, 2H), 7.10 (td, J=8.5, 3.1 Hz, 1H), 4.23 (s, 1H), 3.08-3.05 (m, 3H), 2.39 (s, 3H), 2.10 (s, 3H) m/z: 414.9 $[M+H]^+$, (ESI+), RT=3.19 MET-uPLC-AB-101 (7 min, low pH).

Example 80

The compounds 1554, 1555 and 1556 were prepared by a similar procedure described for example 77, using 3-(4-cyano-2-methoxy-phenoxy)-6-iodo-5-methyl-N-[3-(methylsulfonimidoyl)phenyl]pyridazine-4-carboxamide coupling with the appropriate boronate(s) or boronic acids.

Compound 1554: 6-(1-acetyl-3,6-dihydro-2H-pyridin-4-yl)-3-(4-cyano-2-methoxy-phenoxy)-5-methyl-N-[3-(methylsulfonimidoyl)phenyl]pyridazine-4-carboxamide

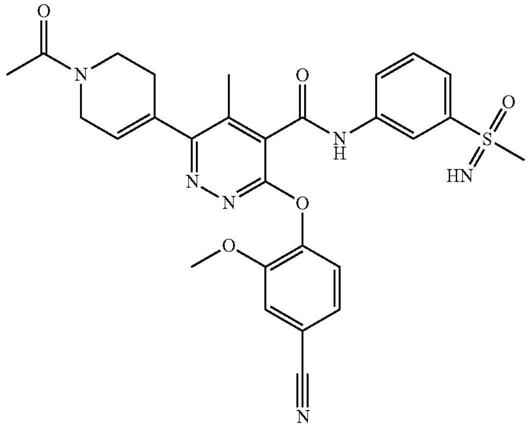 [SMILES: COc1cc(C#N)ccc1Oc1nnc(C2=CCN(C(C)=O)CC2)c(C)c1C(=O)Nc1cccc(S(C)(=N)=O)c1]

¹H NMR (400 MHz, $CD_3OD$) δ 8.44 (t, J=1.9 Hz, 1H), 7.99-7.92 (m, 1H), 7.86-7.78 (m, 1H), 7.65 (t, J=8.0 Hz, 1H), 7.50 (s, 1H), 7.41 (s, 2H), 6.05-5.96 (m, 1H), 4.31-4.22 (m, 2H), 3.89-3.76 (m, 5H), 3.17 (s, 3H), 2.68-2.59 (m, 1H), 2.57-2.49 (m, 1H), 2.46 (s, 3H), 2.18 (2×s, amide rotamers, 3H).2 exchangeable Hs not seen. m/z: 561.1 $[M+H]^+$, (ESI+), RT=2.05 MET-uPLC-AB-107 (7 min, high pH)

Compound 1555: 3-(4-cyano-2-methoxy-phenoxy)-5-methyl-6-(1-methyl-3,6-dihydro-2H-pyridin-4-yl)-N-[3-(methylsulfonimidoyl)phenyl]pyridazine-4-carboxamide

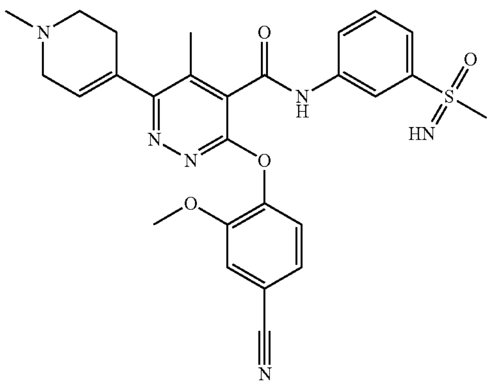

¹H NMR (400 MHz, $CD_3OD$) δ 8.44 (t, J=1.9 Hz, 1H), 8.00-7.90 (m, 1H), 7.85-7.77 (m, 1H), 7.65 (t, J=8.0 Hz, 1H), 7.50 (s, 1H), 7.41 (s, 2H), 5.95 (dt, J=2.5, 1.1 Hz, 1H), 3.80 (s, 3H), 3.27-3.19 (m, 2H), 3.17 (s, 3H), 2.77 (t, J=5.7 Hz, 2H), 2.63-2.56 (m, 2H), 2.47 (s, 3H), 2.44 (s, 3H). 2 exchangeable Hs not seen. m/z: 533.1 $[M+H]^+$, (ESI+), RT=2.20 MET-uPLC-AB-107 (7 min, high pH).

Compound 1556: 3-(4-cyano-2-methoxy-phenoxy)-6-(2,5-dihydrofuran-3-yl)-5-methyl-N-[3-(methylsulfonimidoyl)phenyl]pyridazine-4-carboxamide

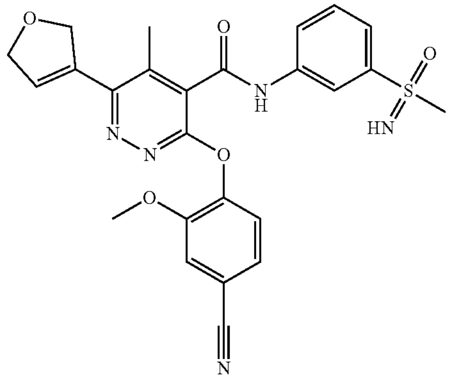 [SMILES: COc1cc(C#N)ccc1Oc1nnc(C2=CCOC2)c(C)c1C(=O)Nc1cccc(S(C)(=N)=O)c1]

¹H NMR (400 MHz, $CD_3OD$) δ 8.45 (t, J=1.9 Hz, 1H), 8.01-7.92 (m, 1H), 7.86-7.79 (m, 1H), 7.65 (t, J=8.0 Hz, 1H), 7.50 (s, 1H), 7.41 (s, 2H), 6.70-6.62 (m, 1H), 5.13 (td, J=4.7, 2.1 Hz, 2H), 4.94 (td, J=4.7, 1.9 Hz, 2H), 3.80 (s, 3H), 3.17 (s, 3H), 2.60 (s, 3H) 2 exchangeable Hs not seen. m/z: 506.1 $[M+H]^+$, (ESI+), RT=2.24 MET-uPLC-AB-107 (7 min, high pH).

Example 81

Exemplary compounds of the invention are provided below. The number of each compound is provided directly below its structural formula.

TABLE 14

| | |
|---|---|
| 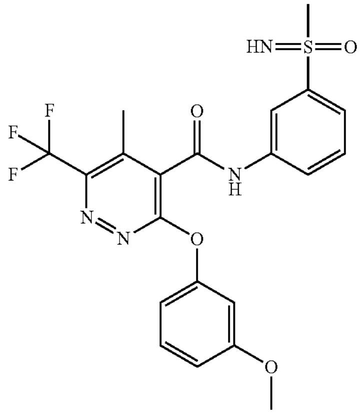 [SMILES: COc1cccc(Oc2nnc(C(F)(F)F)c(C)c2C(=O)Nc2cccc(S(C)(=N)=O)c2)c1] | 36 |

TABLE 14-continued
37
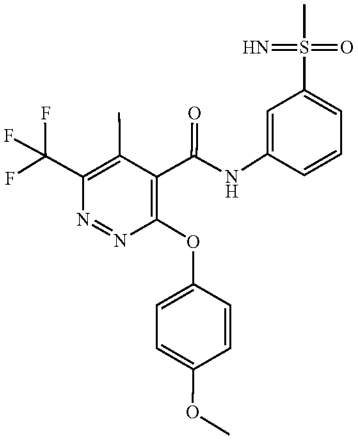 [SMILES: COc1ccc(Oc2nnc(C(F)(F)F)c(C)c2C(=O)Nc2cccc(S(C)(=N)=O)c2)cc1]
38
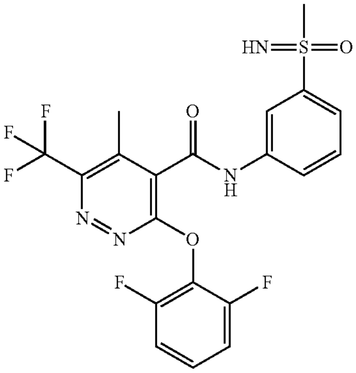 [SMILES: Cc1c(C(F)(F)F)nnc(Oc2c(F)cccc2F)c1C(=O)Nc1cccc(S(C)(=N)=O)c1]
39
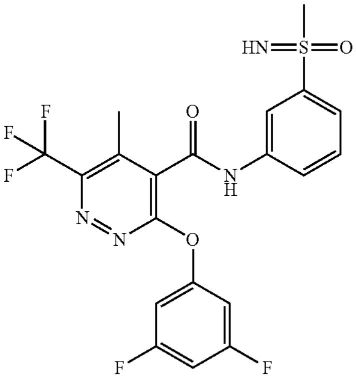 [SMILES: Cc1c(C(F)(F)F)nnc(Oc2cc(F)cc(F)c2)c1C(=O)Nc1cccc(S(C)(=N)=O)c1]
40
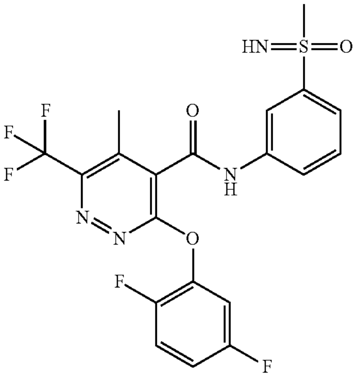 [SMILES: Cc1c(C(F)(F)F)nnc(Oc2cc(F)ccc2F)c1C(=O)Nc1cccc(S(C)(=N)=O)c1]
TABLE 14-continued
41
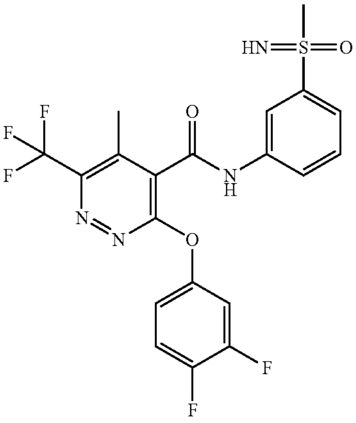 [SMILES: Cc1c(C(F)(F)F)nnc(Oc2ccc(F)c(F)c2)c1C(=O)Nc1cccc(S(C)(=N)=O)c1]
42
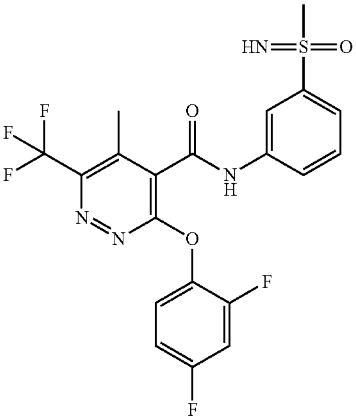 [SMILES: Cc1c(C(F)(F)F)nnc(Oc2ccc(F)cc2F)c1C(=O)Nc1cccc(S(C)(=N)=O)c1]
43
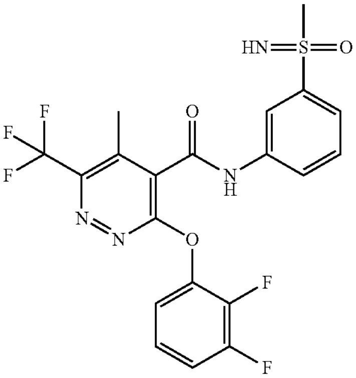 [SMILES: Cc1c(C(F)(F)F)nnc(Oc2cccc(F)c2F)c1C(=O)Nc1cccc(S(C)(=N)=O)c1]
44
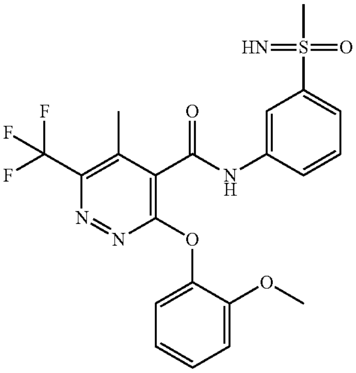 [SMILES: COc1ccccc1Oc1nnc(C(F)(F)F)c(C)c1C(=O)Nc1cccc(S(C)(=N)=O)c1]

TABLE 14-continued
46
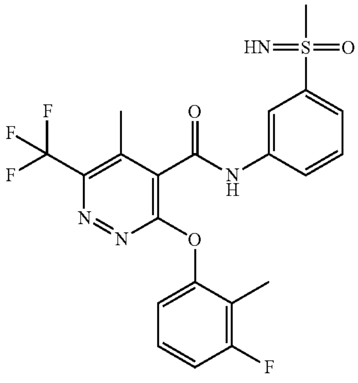 [SMILES: Cc1c(F)cccc1Oc1nnc(C(F)(F)F)c(C)c1C(=O)Nc1cccc(S(C)(=N)=O)c1]
47
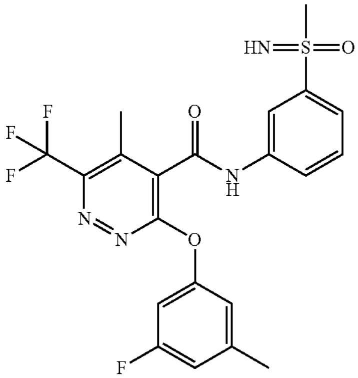
48
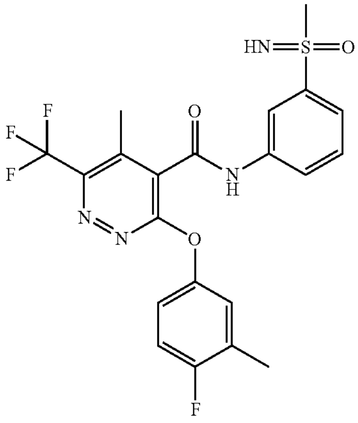 [SMILES: Cc1cc(Oc2nnc(C(F)(F)F)c(C)c2C(=O)Nc2cccc(S(C)(=N)=O)c2)ccc1F]
49
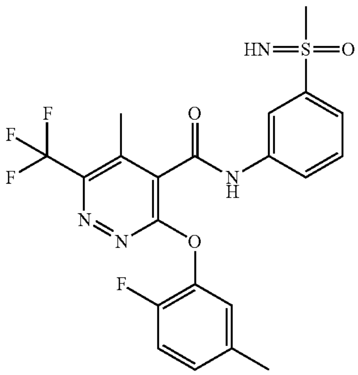 [SMILES: Cc1ccc(F)c(Oc2nnc(C(F)(F)F)c(C)c2C(=O)Nc2cccc(S(C)(=N)=O)c2)c1]
TABLE 14-continued
50
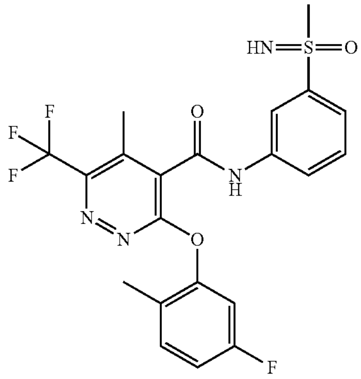
51
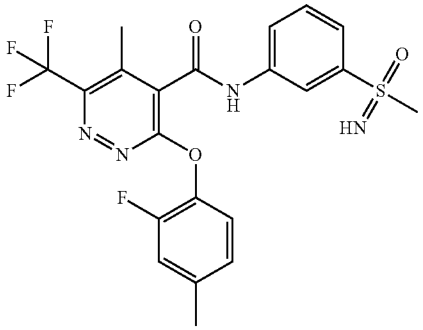 [SMILES: Cc1ccc(Oc2nnc(C(F)(F)F)c(C)c2C(=O)Nc2cccc(S(C)(=N)=O)c2)c(F)c1]
52
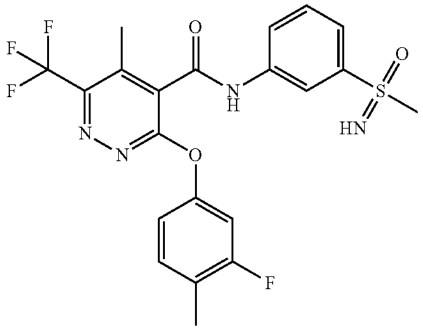
53
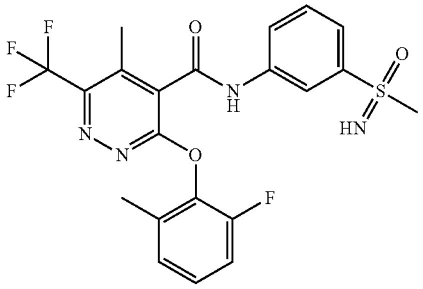 [SMILES: Cc1cccc(F)c1Oc1nnc(C(F)(F)F)c(C)c1C(=O)Nc1cccc(S(C)(=N)=O)c1]

TABLE 14-continued
54
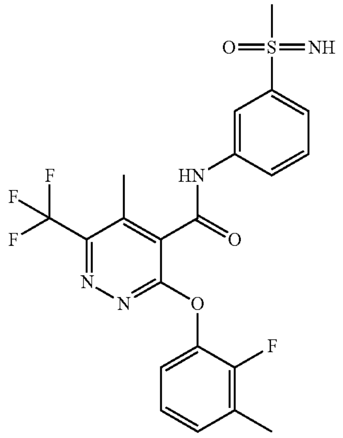 [SMILES: Cc1cccc(Oc2nnc(C(F)(F)F)c(C)c2C(=O)Nc2cccc(S(C)(=N)=O)c2)c1F]
55
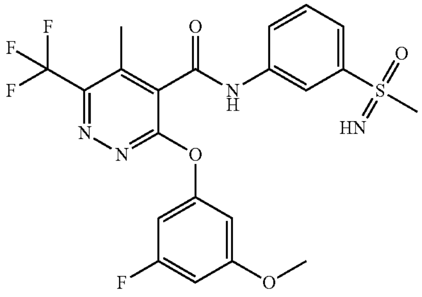 [SMILES: COc1cc(F)cc(Oc2nnc(C(F)(F)F)c(C)c2C(=O)Nc2cccc(S(C)(=N)=O)c2)c1]
56
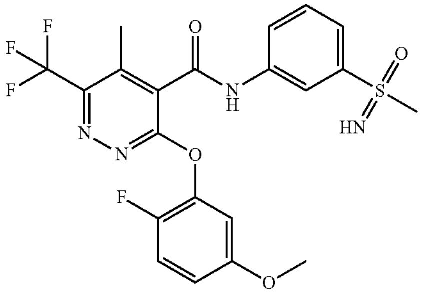 [SMILES: COc1ccc(F)c(Oc2nnc(C(F)(F)F)c(C)c2C(=O)Nc2cccc(S(C)(=N)=O)c2)c1]
57
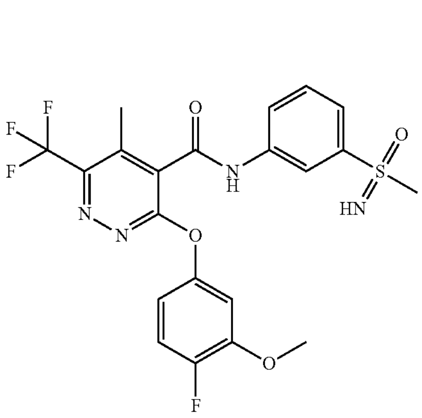 [SMILES: COc1cc(Oc2nnc(C(F)(F)F)c(C)c2C(=O)Nc2cccc(S(C)(=N)=O)c2)ccc1F]
TABLE 14-continued
58
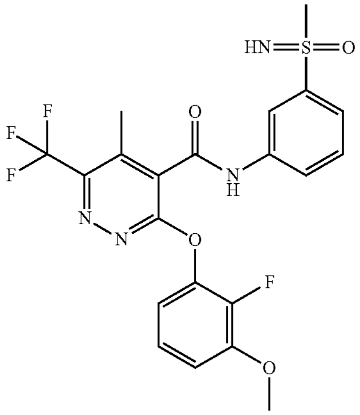 [SMILES: COc1cccc(Oc2nnc(C(F)(F)F)c(C)c2C(=O)Nc2cccc(S(C)(=N)=O)c2)c1F]
59
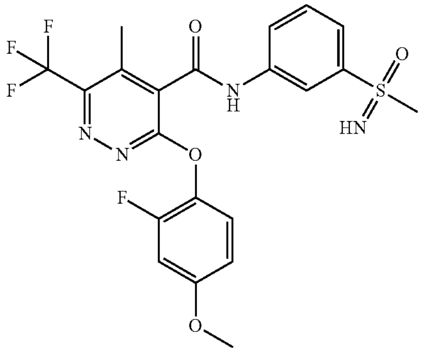 [SMILES: COc1ccc(Oc2nnc(C(F)(F)F)c(C)c2C(=O)Nc2cccc(S(C)(=N)=O)c2)c(F)c1]
60
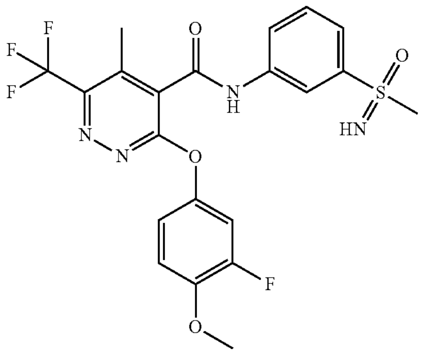 [SMILES: COc1ccc(Oc2nnc(C(F)(F)F)c(C)c2C(=O)Nc2cccc(S(C)(=N)=O)c2)cc1F]
61
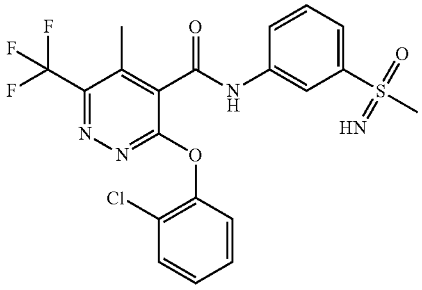 [SMILES: Cc1c(C(F)(F)F)nnc(Oc2ccccc2Cl)c1C(=O)Nc1cccc(S(C)(=N)=O)c1]

TABLE 14-continued
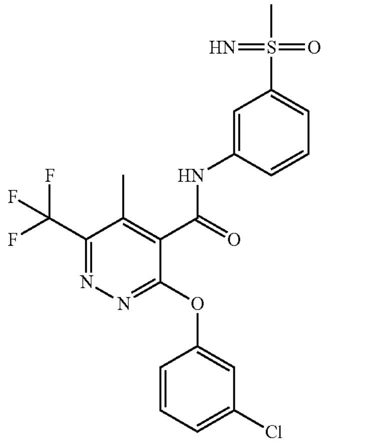 [SMILES: Cc1c(C(F)(F)F)nnc(Oc2cccc(Cl)c2)c1C(=O)Nc1cccc(S(C)(=N)=O)c1]
62
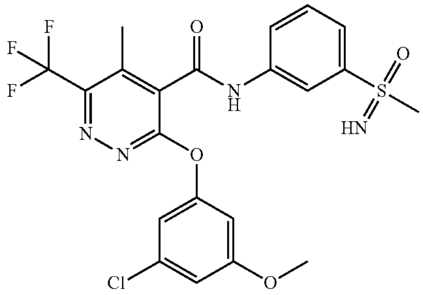 [SMILES: COc1cc(Cl)cc(Oc2nnc(C(F)(F)F)c(C)c2C(=O)Nc2cccc(S(C)(=N)=O)c2)c1]
63
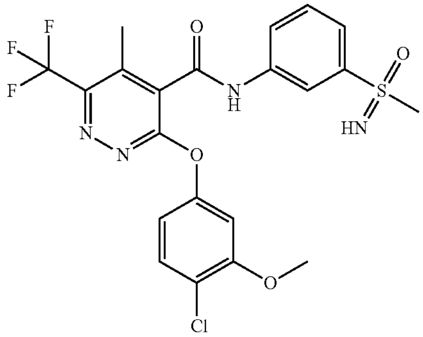 [SMILES: COc1cc(Oc2nnc(C(F)(F)F)c(C)c2C(=O)Nc2cccc(S(C)(=N)=O)c2)ccc1Cl]
64
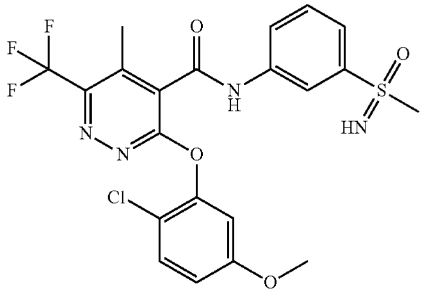 [SMILES: COc1ccc(Cl)c(Oc2nnc(C(F)(F)F)c(C)c2C(=O)Nc2cccc(S(C)(=N)=O)c2)c1]
65
TABLE 14-continued
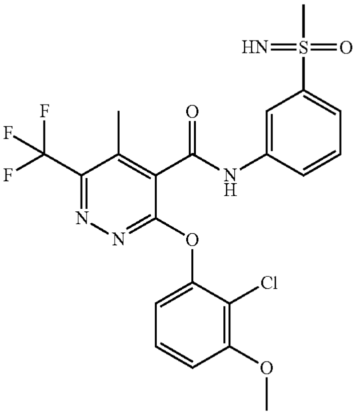
66
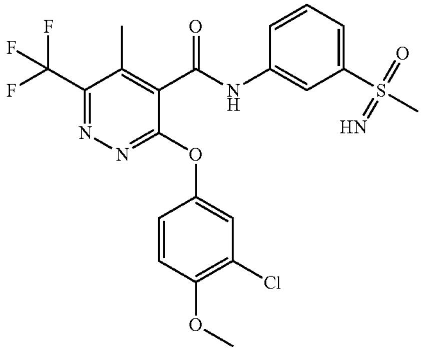
67
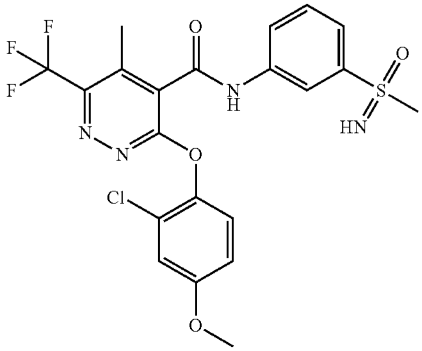
68
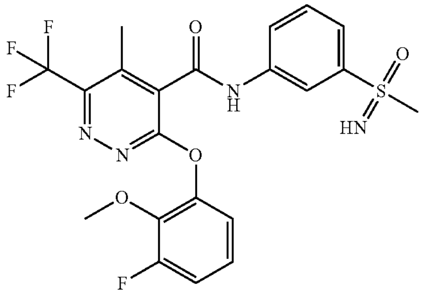 [SMILES: COc1c(F)cccc1Oc1nnc(C(F)(F)F)c(C)c1C(=O)Nc1cccc(S(C)(=N)=O)c1]
69

TABLE 14-continued
70
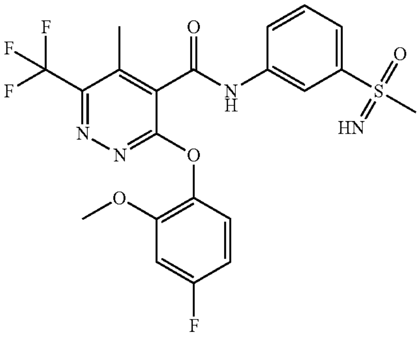
71
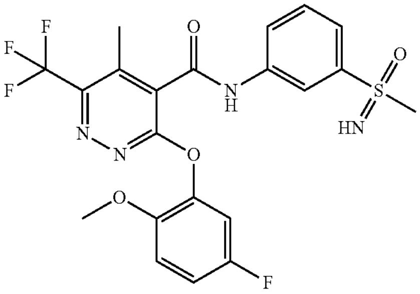 [SMILES: COc1ccc(F)cc1Oc1nnc(C(F)(F)F)c(C)c1C(=O)Nc1cccc(S(C)(=N)=O)c1]
72
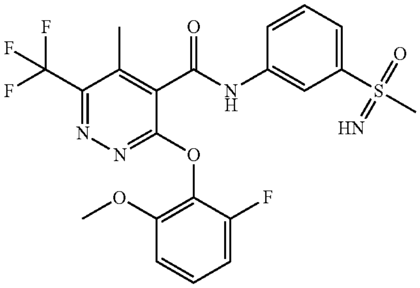
74
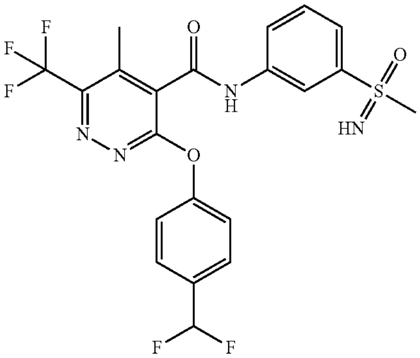 [SMILES: Cc1c(C(F)(F)F)nnc(Oc2ccc(C(F)F)cc2)c1C(=O)Nc1cccc(S(C)(=N)=O)c1]
TABLE 14-continued
77
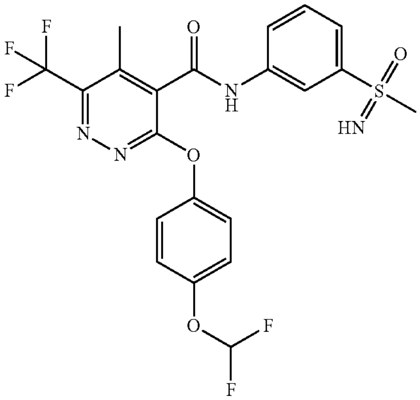 [SMILES: Cc1c(C(F)(F)F)nnc(Oc2ccc(OC(F)F)cc2)c1C(=O)Nc1cccc(S(C)(=N)=O)c1]
79
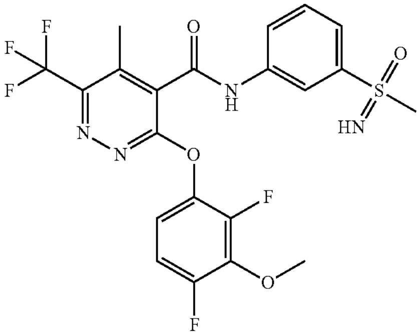 [SMILES: COc1c(F)ccc(Oc2nnc(C(F)(F)F)c(C)c2C(=O)Nc2cccc(S(C)(=N)=O)c2)c1F]
80
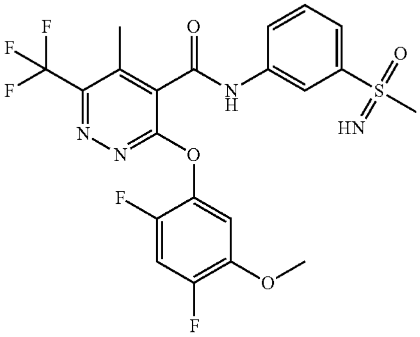 [SMILES: COc1cc(Oc2nnc(C(F)(F)F)c(C)c2C(=O)Nc2cccc(S(C)(=N)=O)c2)c(F)cc1F]
81
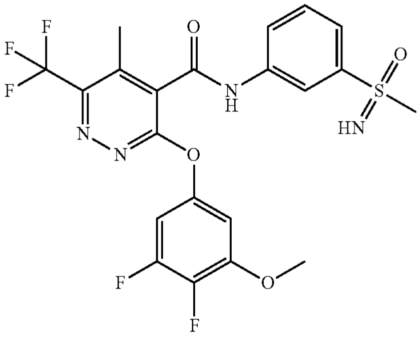 [SMILES: COc1cc(Oc2nnc(C(F)(F)F)c(C)c2C(=O)Nc2cccc(S(C)(=N)=O)c2)cc(F)c1F]

TABLE 14-continued
82
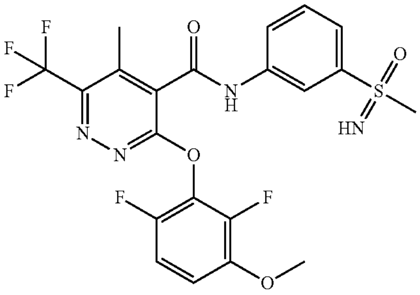 [SMILES: COc1ccc(F)c(Oc2nnc(C(F)(F)F)c(C)c2C(=O)Nc2cccc(S(C)(=N)=O)c2)c1F]
83
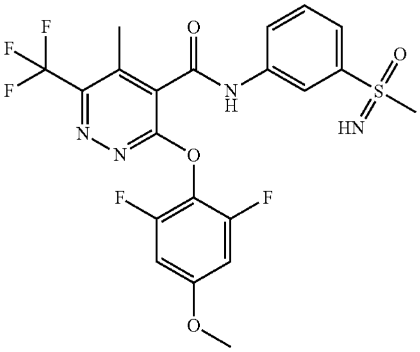
84
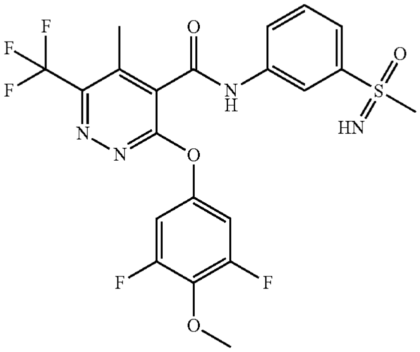 [SMILES: COc1c(F)cc(Oc2nnc(C(F)(F)F)c(C)c2C(=O)Nc2cccc(S(C)(=N)=O)c2)cc1F]
85
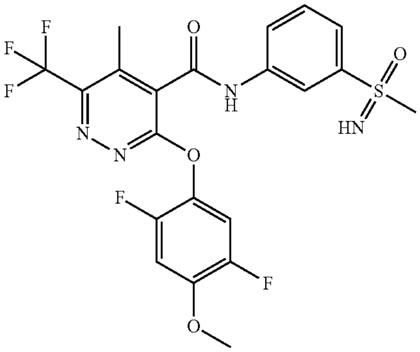 [SMILES: COc1cc(F)c(Oc2nnc(C(F)(F)F)c(C)c2C(=O)Nc2cccc(S(C)(=N)=O)c2)cc1F]
TABLE 14-continued
86
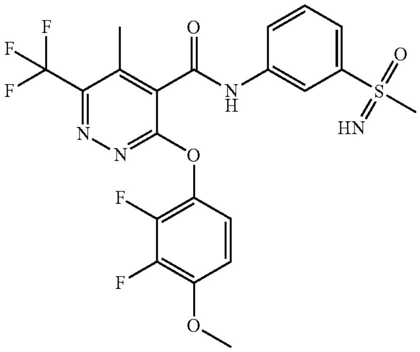
87
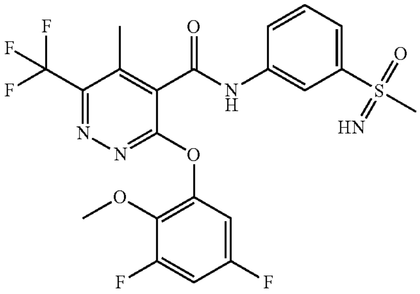 [SMILES: COc1c(F)cc(F)cc1Oc1nnc(C(F)(F)F)c(C)c1C(=O)Nc1cccc(S(C)(=N)=O)c1]
88
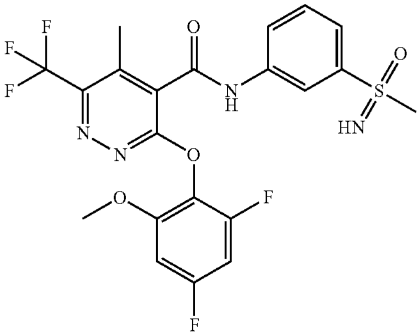 [SMILES: COc1cc(F)cc(F)c1Oc1nnc(C(F)(F)F)c(C)c1C(=O)Nc1cccc(S(C)(=N)=O)c1]
89
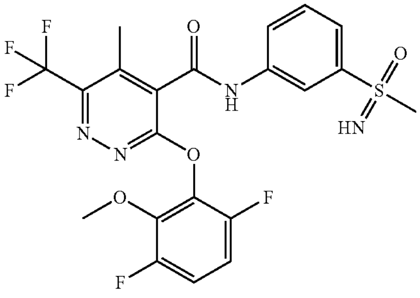 [SMILES: COc1c(F)ccc(F)c1Oc1nnc(C(F)(F)F)c(C)c1C(=O)Nc1cccc(S(C)(=N)=O)c1]
90
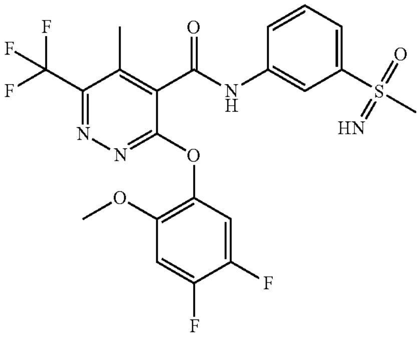

TABLE 14-continued
91
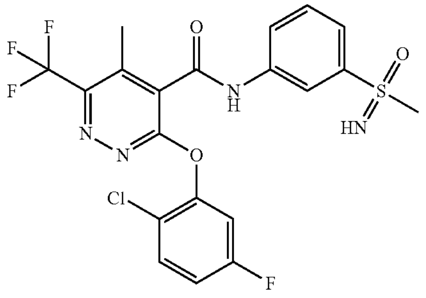 [SMILES: Cc1c(C(F)(F)F)nnc(Oc2cc(F)ccc2Cl)c1C(=O)Nc1cccc(S(C)(=N)=O)c1]
92
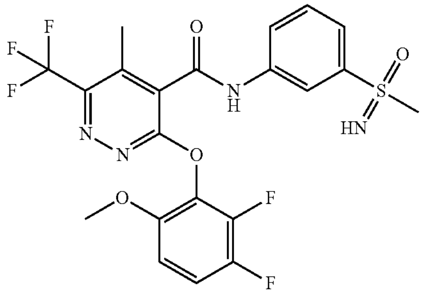 [SMILES: COc1ccc(F)c(F)c1Oc1nnc(C(F)(F)F)c(C)c1C(=O)Nc1cccc(S(C)(=N)=O)c1]
93
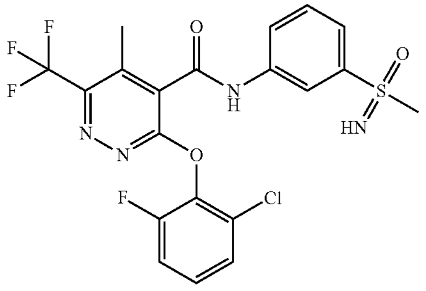 [SMILES: Cc1c(C(F)(F)F)nnc(Oc2c(F)cccc2Cl)c1C(=O)Nc1cccc(S(C)(=N)=O)c1]
94
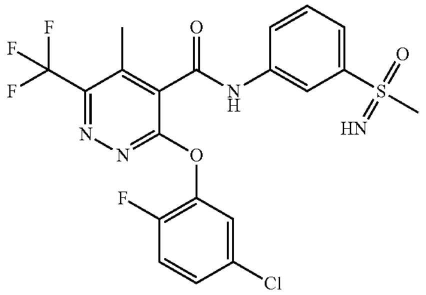
95
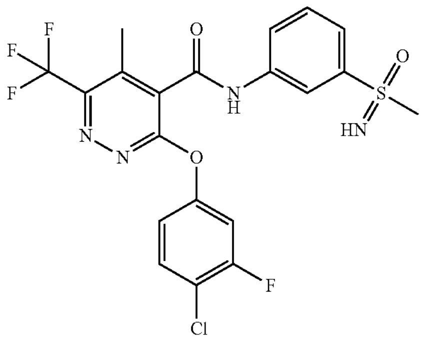 [SMILES: Cc1c(C(F)(F)F)nnc(Oc2ccc(Cl)c(F)c2)c1C(=O)Nc1cccc(S(C)(=N)=O)c1]
TABLE 14-continued
96
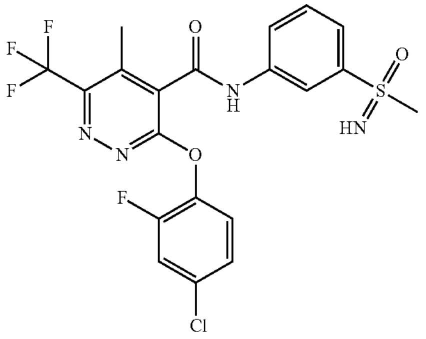
97
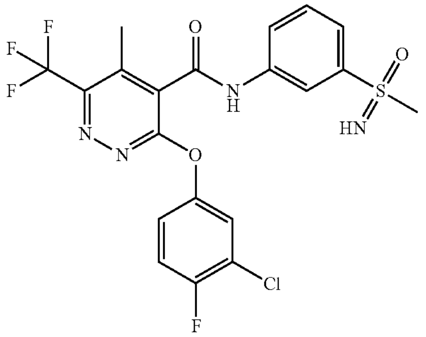 [SMILES: Cc1c(C(F)(F)F)nnc(Oc2ccc(F)c(Cl)c2)c1C(=O)Nc1cccc(S(C)(=N)=O)c1]
98
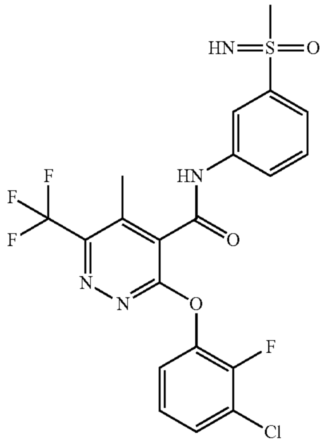 [SMILES: Cc1c(C(F)(F)F)nnc(Oc2cccc(Cl)c2F)c1C(=O)Nc1cccc(S(C)(=N)=O)c1]
99
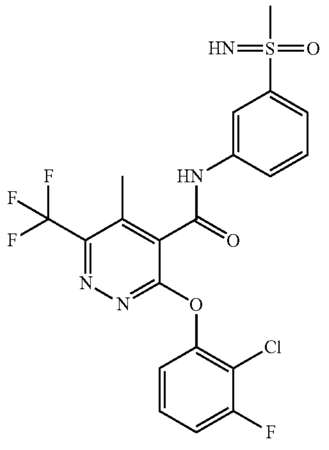 [SMILES: Cc1c(C(F)(F)F)nnc(Oc2cccc(F)c2Cl)c1C(=O)Nc1cccc(S(C)(=N)=O)c1]

TABLE 14-continued
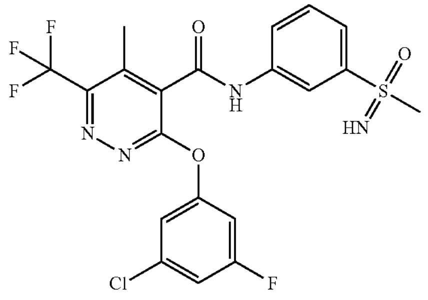
100
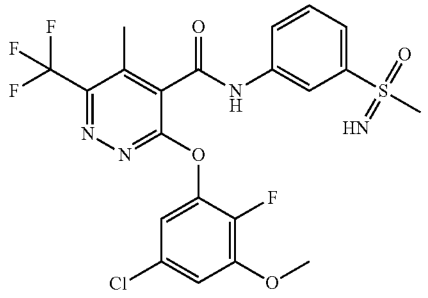 [SMILES: COc1cc(Cl)cc(Oc2nnc(C(F)(F)F)c(C)c2C(=O)Nc2cccc(S(C)(=N)=O)c2)c1F]
101
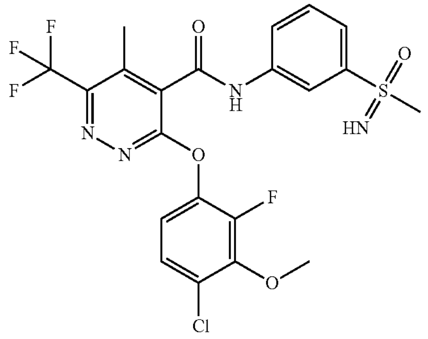 [SMILES: COc1c(Cl)ccc(Oc2nnc(C(F)(F)F)c(C)c2C(=O)Nc2cccc(S(C)(=N)=O)c2)c1F]
102
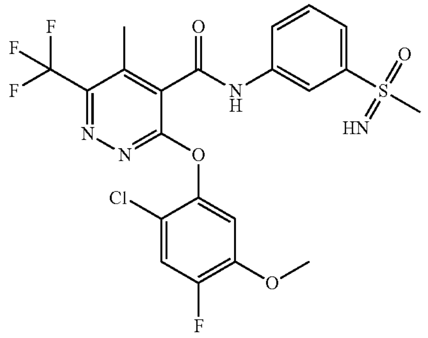 [SMILES: COc1cc(Oc2nnc(C(F)(F)F)c(C)c2C(=O)Nc2cccc(S(C)(=N)=O)c2)c(Cl)cc1F]
103
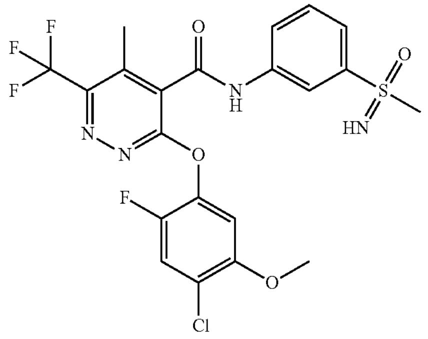 [SMILES: COc1cc(Oc2nnc(C(F)(F)F)c(C)c2C(=O)Nc2cccc(S(C)(=N)=O)c2)c(F)cc1Cl]
104
TABLE 14-continued
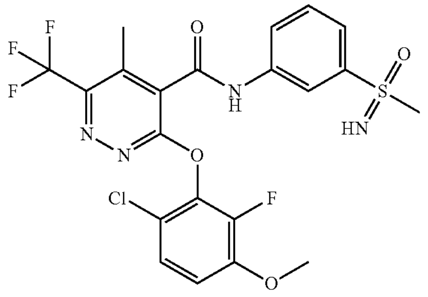 [SMILES: COc1ccc(Cl)c(Oc2nnc(C(F)(F)F)c(C)c2C(=O)Nc2cccc(S(C)(=N)=O)c2)c1F]
105
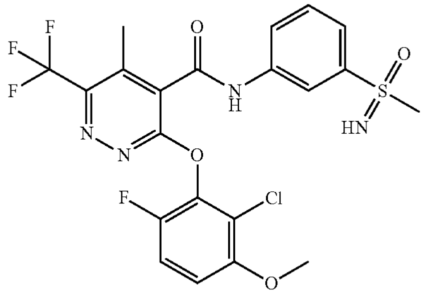 [SMILES: COc1ccc(F)c(Oc2nnc(C(F)(F)F)c(C)c2C(=O)Nc2cccc(S(C)(=N)=O)c2)c1Cl]
106
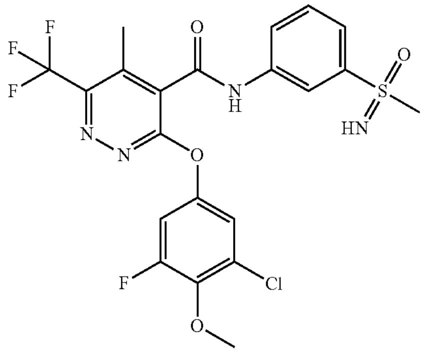 [SMILES: COc1c(F)cc(Oc2nnc(C(F)(F)F)c(C)c2C(=O)Nc2cccc(S(C)(=N)=O)c2)cc1Cl]
107
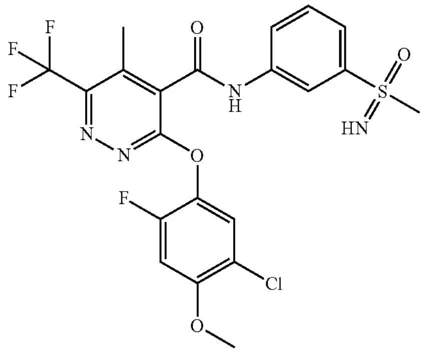 [SMILES: COc1cc(F)c(Oc2nnc(C(F)(F)F)c(C)c2C(=O)Nc2cccc(S(C)(=N)=O)c2)cc1Cl]
108
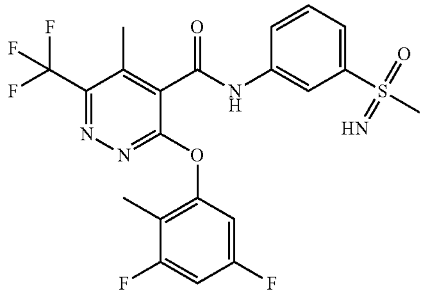 [SMILES: Cc1c(F)cc(F)cc1Oc1nnc(C(F)(F)F)c(C)c1C(=O)Nc1cccc(S(C)(=N)=O)c1]
110

TABLE 14-continued
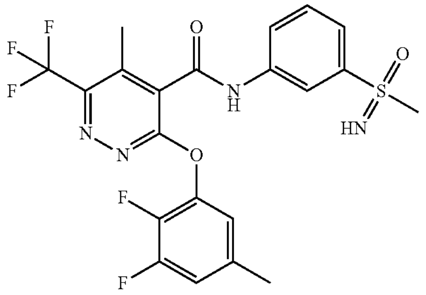 [SMILES: Cc1cc(F)c(F)c(Oc2nnc(C(F)(F)F)c(C)c2C(=O)Nc2cccc(S(C)(=N)=O)c2)c1]
111
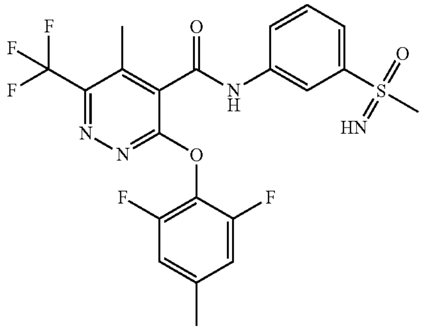 [SMILES: Cc1cc(F)c(Oc2nnc(C(F)(F)F)c(C)c2C(=O)Nc2cccc(S(C)(=N)=O)c2)c(F)c1]
112
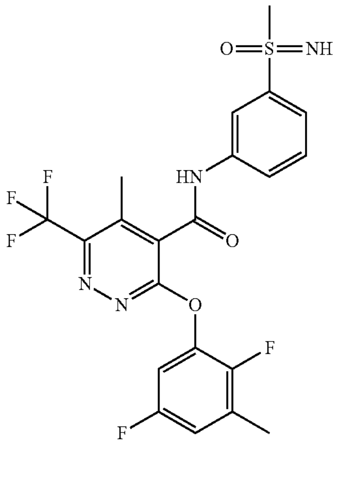 [SMILES: Cc1cc(F)cc(Oc2nnc(C(F)(F)F)c(C)c2C(=O)Nc2cccc(S(C)(=N)=O)c2)c1F]
113
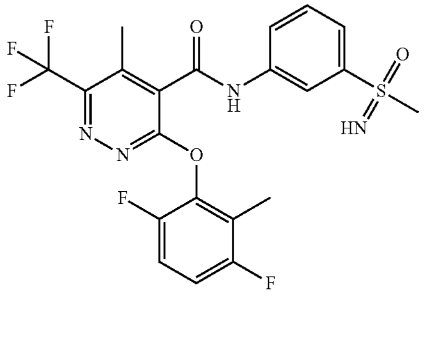 [SMILES: Cc1c(F)ccc(F)c1Oc1nnc(C(F)(F)F)c(C)c1C(=O)Nc1cccc(S(C)(=N)=O)c1]
114
TABLE 14-continued
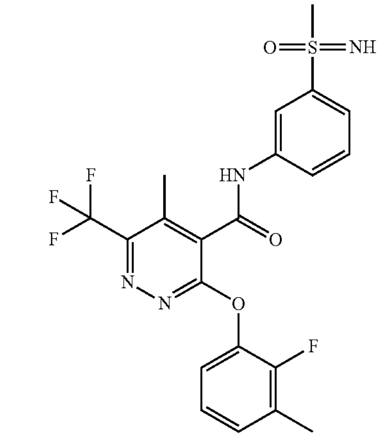 [SMILES: Cc1cccc(Oc2nnc(C(F)(F)F)c(C)c2C(=O)Nc2cccc(S(C)(=N)=O)c2)c1F]
115
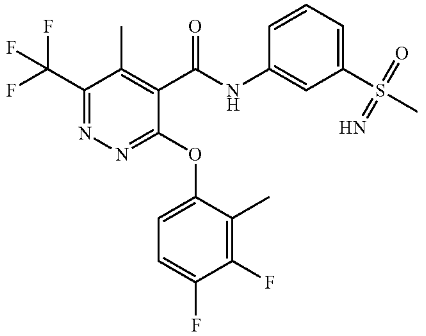 [SMILES: Cc1c(Oc2nnc(C(F)(F)F)c(C)c2C(=O)Nc2cccc(S(C)(=N)=O)c2)ccc(F)c1F]
116
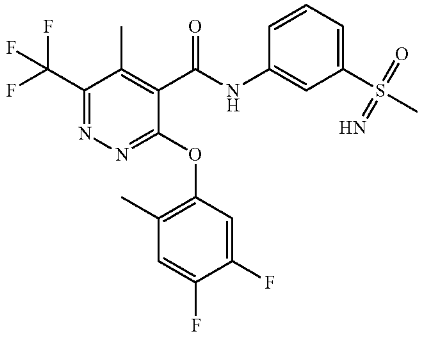 [SMILES: Cc1cc(F)c(F)cc1Oc1nnc(C(F)(F)F)c(C)c1C(=O)Nc1cccc(S(C)(=N)=O)c1]
117
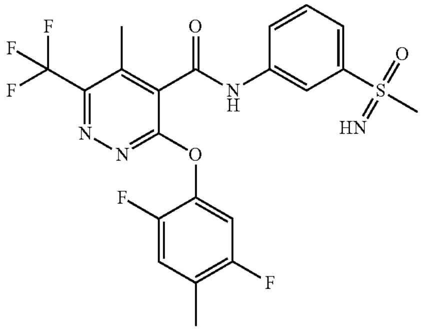 [SMILES: Cc1cc(F)c(Oc2nnc(C(F)(F)F)c(C)c2C(=O)Nc2cccc(S(C)(=N)=O)c2)cc1F]
118

TABLE 14-continued
119
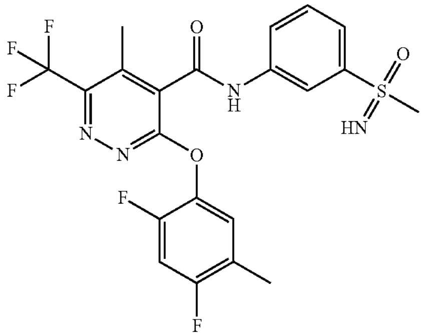 [SMILES: Cc1cc(Oc2nnc(C(F)(F)F)c(C)c2C(=O)Nc2cccc(S(C)(=N)=O)c2)c(F)cc1F]
120
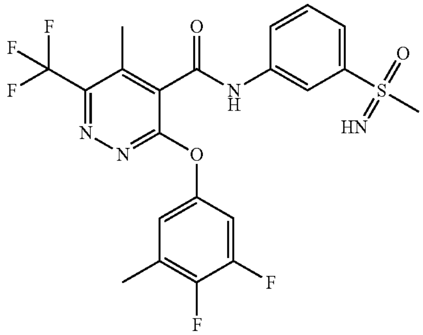
121
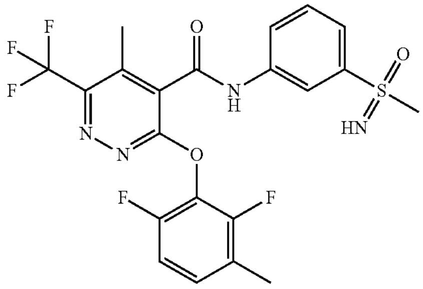
122
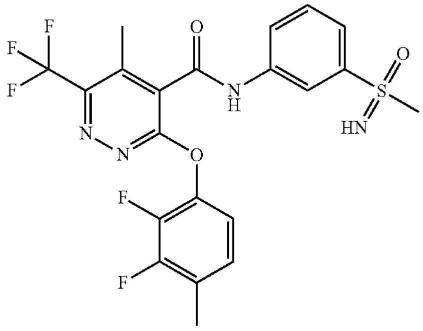 [SMILES: Cc1ccc(Oc2nnc(C(F)(F)F)c(C)c2C(=O)Nc2cccc(S(C)(=N)=O)c2)c(F)c1F]
131
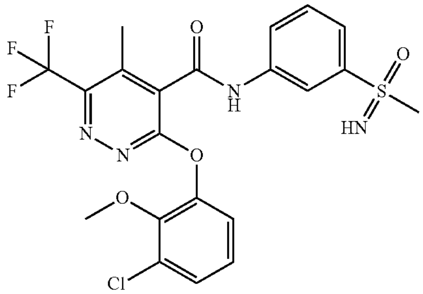
TABLE 14-continued
132
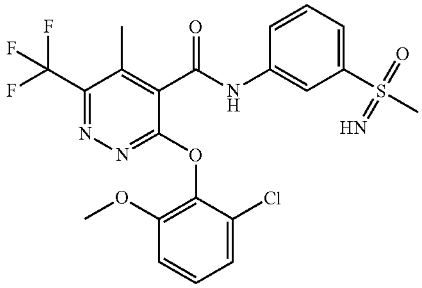 [SMILES: COc1cccc(Cl)c1Oc1nnc(C(F)(F)F)c(C)c1C(=O)Nc1cccc(S(C)(=N)=O)c1]
133
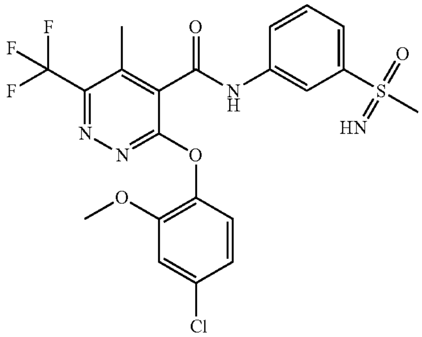
134
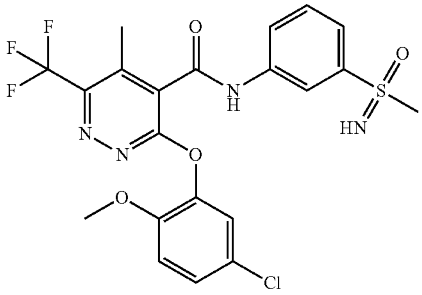 [SMILES: COc1ccc(Cl)cc1Oc1nnc(C(F)(F)F)c(C)c1C(=O)Nc1cccc(S(C)(=N)=O)c1]
144
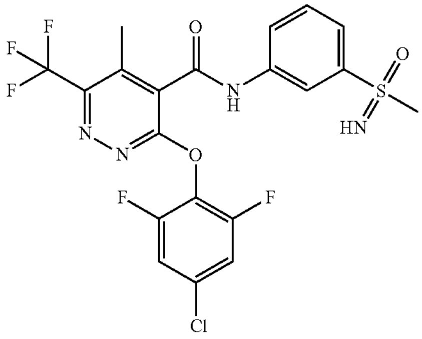 [SMILES: Cc1c(C(F)(F)F)nnc(Oc2c(F)cc(Cl)cc2F)c1C(=O)Nc1cccc(S(C)(=N)=O)c1]
145
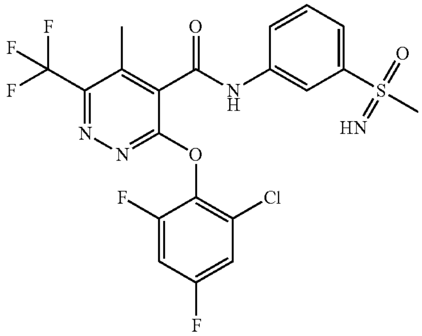 [SMILES: Cc1c(C(F)(F)F)nnc(Oc2c(F)cc(F)cc2Cl)c1C(=O)Nc1cccc(S(C)(=N)=O)c1]

146
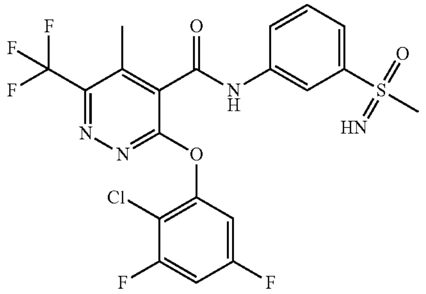 [SMILES: Cc1c(C(F)(F)F)nnc(Oc2cc(F)cc(F)c2Cl)c1C(=O)Nc1cccc(S(C)(=N)=O)c1]
147
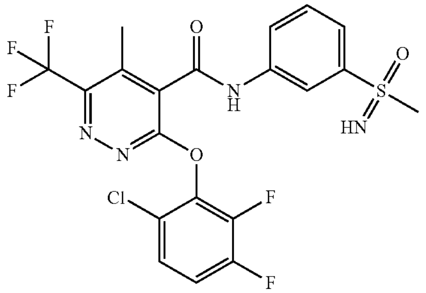 [SMILES: Cc1c(C(F)(F)F)nnc(Oc2c(Cl)ccc(F)c2F)c1C(=O)Nc1cccc(S(C)(=N)=O)c1]
148
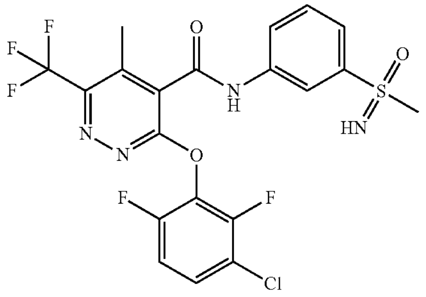 [SMILES: Cc1c(C(F)(F)F)nnc(Oc2c(F)ccc(Cl)c2F)c1C(=O)Nc1cccc(S(C)(=N)=O)c1]
149
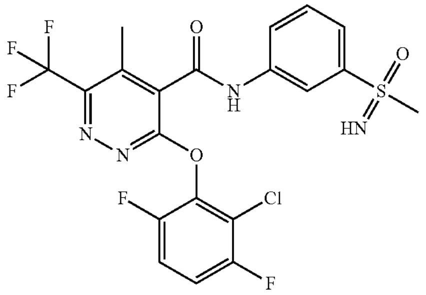 [SMILES: Cc1c(C(F)(F)F)nnc(Oc2c(F)ccc(F)c2Cl)c1C(=O)Nc1cccc(S(C)(=N)=O)c1]
150
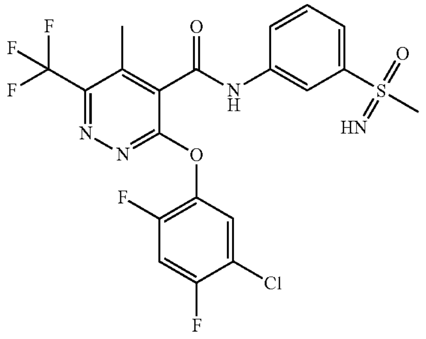 [SMILES: Cc1c(C(F)(F)F)nnc(Oc2cc(Cl)c(F)cc2F)c1C(=O)Nc1cccc(S(C)(=N)=O)c1]
151
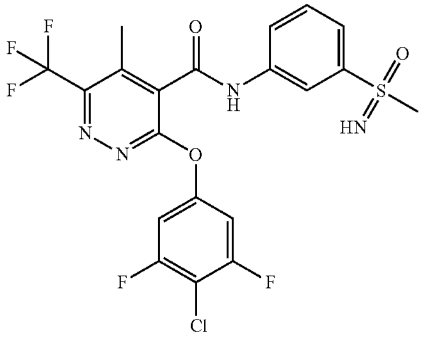 [SMILES: Cc1c(C(F)(F)F)nnc(Oc2cc(F)c(Cl)c(F)c2)c1C(=O)Nc1cccc(S(C)(=N)=O)c1]
152
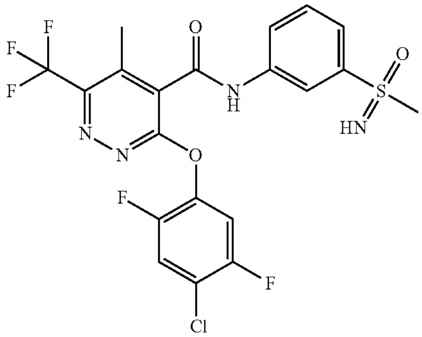 [SMILES: Cc1c(C(F)(F)F)nnc(Oc2cc(F)c(Cl)cc2F)c1C(=O)Nc1cccc(S(C)(=N)=O)c1]
153
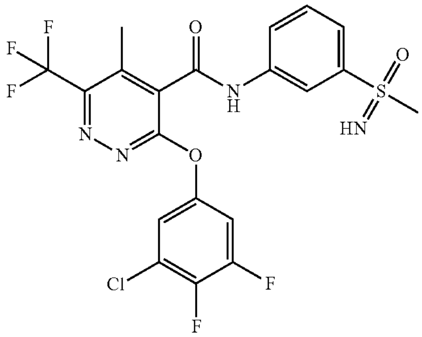
154
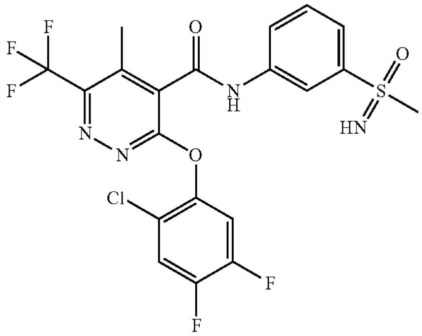 [SMILES: Cc1c(C(F)(F)F)nnc(Oc2cc(F)c(F)cc2Cl)c1C(=O)Nc1cccc(S(C)(=N)=O)c1]

TABLE 14-continued
155
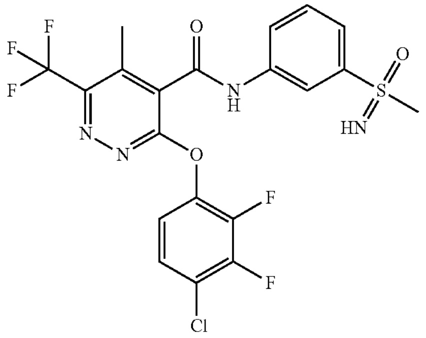 [SMILES: Cc1c(C(F)(F)F)nnc(Oc2ccc(Cl)c(F)c2F)c1C(=O)Nc1cccc(S(C)(=N)=O)c1]
156
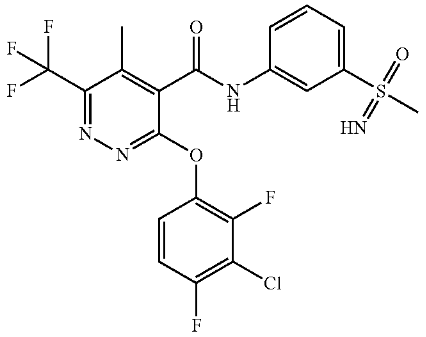 [SMILES: Cc1c(C(F)(F)F)nnc(Oc2ccc(F)c(Cl)c2F)c1C(=O)Nc1cccc(S(C)(=N)=O)c1]
157
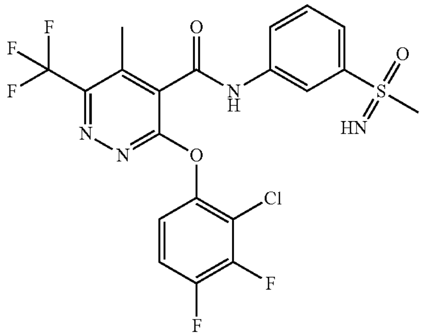 [SMILES: Cc1c(C(F)(F)F)nnc(Oc2ccc(F)c(F)c2Cl)c1C(=O)Nc1cccc(S(C)(=N)=O)c1]
164
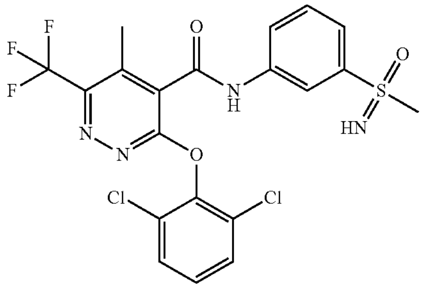 [SMILES: Cc1c(C(F)(F)F)nnc(Oc2c(Cl)cccc2Cl)c1C(=O)Nc1cccc(S(C)(=N)=O)c1]
165
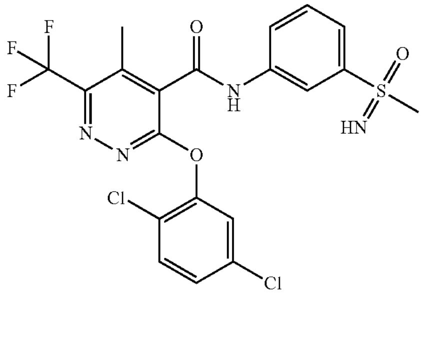 [SMILES: Cc1c(C(F)(F)F)nnc(Oc2cc(Cl)ccc2Cl)c1C(=O)Nc1cccc(S(C)(=N)=O)c1]
TABLE 14-continued
166
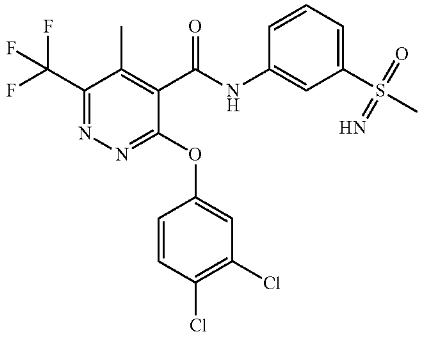 [SMILES: Cc1c(C(F)(F)F)nnc(Oc2ccc(Cl)c(Cl)c2)c1C(=O)Nc1cccc(S(C)(=N)=O)c1]
167
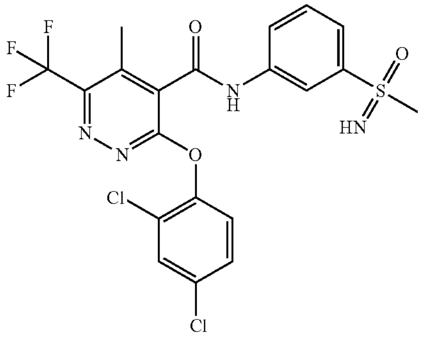 [SMILES: Cc1c(C(F)(F)F)nnc(Oc2ccc(Cl)cc2Cl)c1C(=O)Nc1cccc(S(C)(=N)=O)c1]
168
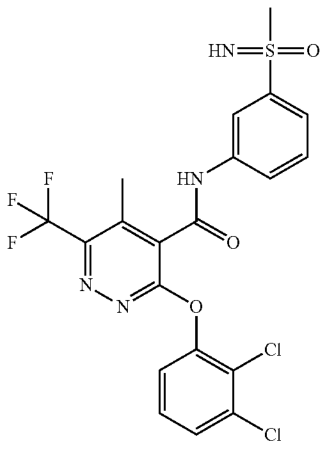 [SMILES: Cc1c(C(F)(F)F)nnc(Oc2cccc(Cl)c2Cl)c1C(=O)Nc1cccc(S(C)(=N)=O)c1]
169
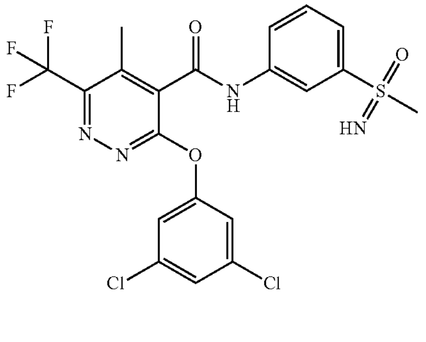 [SMILES: Cc1c(C(F)(F)F)nnc(Oc2cc(Cl)cc(Cl)c2)c1C(=O)Nc1cccc(S(C)(=N)=O)c1]

TABLE 14-continued
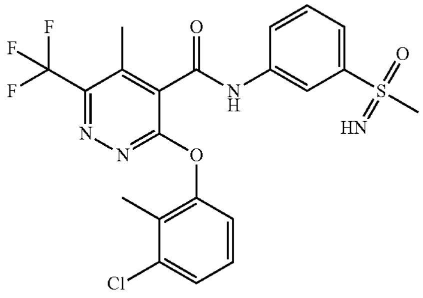
170
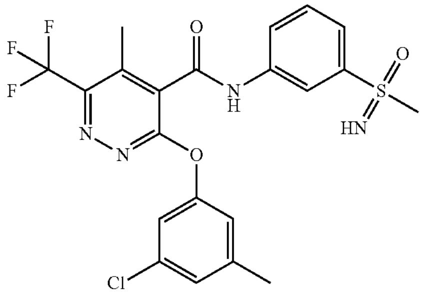
171
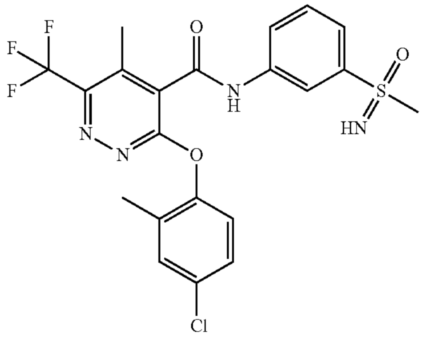
172
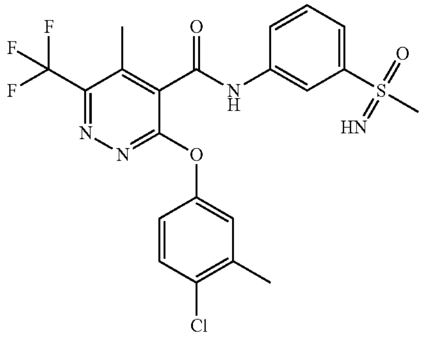 [SMILES: Cc1cc(Oc2nnc(C(F)(F)F)c(C)c2C(=O)Nc2cccc(S(C)(=N)=O)c2)ccc1Cl]
173
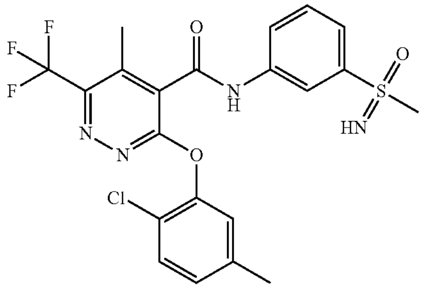 [SMILES: Cc1ccc(Cl)c(Oc2nnc(C(F)(F)F)c(C)c2C(=O)Nc2cccc(S(C)(=N)=O)c2)c1]
174
TABLE 14-continued
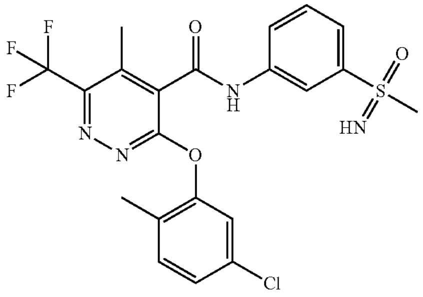 [SMILES: Cc1ccc(Cl)cc1Oc1nnc(C(F)(F)F)c(C)c1C(=O)Nc1cccc(S(C)(=N)=O)c1]
175
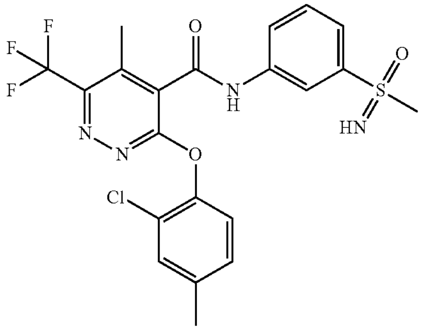 [SMILES: Cc1ccc(Oc2nnc(C(F)(F)F)c(C)c2C(=O)Nc2cccc(S(C)(=N)=O)c2)c(Cl)c1]
176
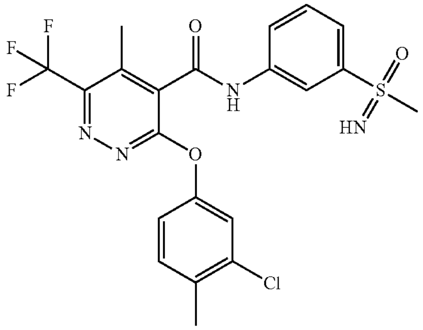 [SMILES: Cc1ccc(Oc2nnc(C(F)(F)F)c(C)c2C(=O)Nc2cccc(S(C)(=N)=O)c2)cc1Cl]
177
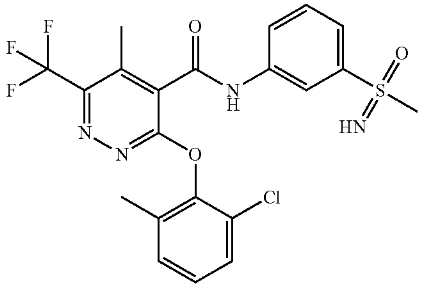 [SMILES: Cc1cccc(Cl)c1Oc1nnc(C(F)(F)F)c(C)c1C(=O)Nc1cccc(S(C)(=N)=O)c1]
178

TABLE 14-continued
179
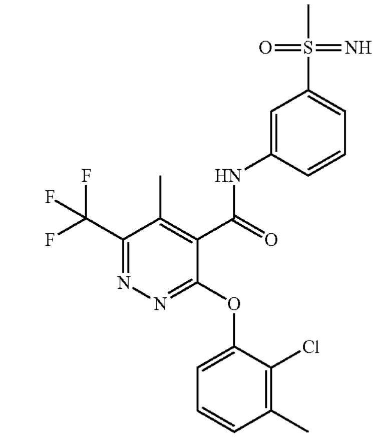
180
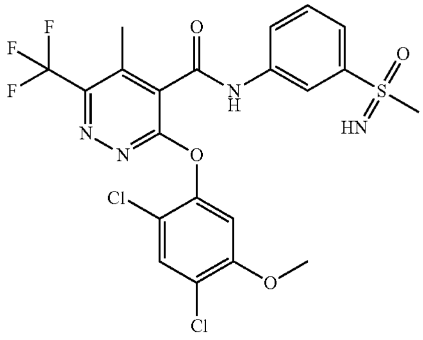 [SMILES: COc1cc(Oc2nnc(C(F)(F)F)c(C)c2C(=O)Nc2cccc(S(C)(=N)=O)c2)c(Cl)cc1Cl]
181
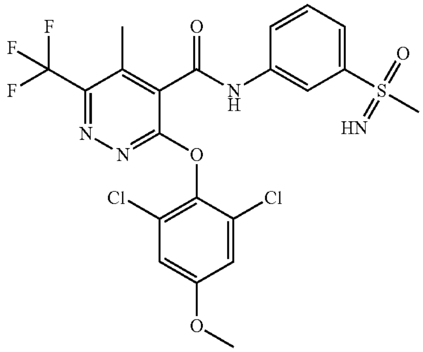 [SMILES: COc1cc(Cl)c(Oc2nnc(C(F)(F)F)c(C)c2C(=O)Nc2cccc(S(C)(=N)=O)c2)c(Cl)c1]
182
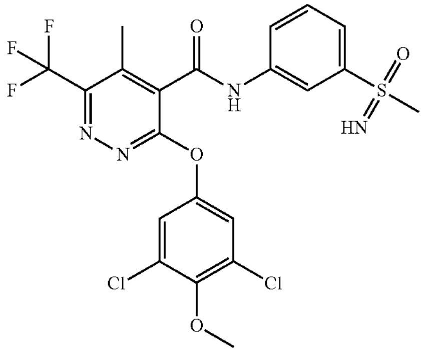 [SMILES: COc1c(Cl)cc(Oc2nnc(C(F)(F)F)c(C)c2C(=O)Nc2cccc(S(C)(=N)=O)c2)cc1Cl]
TABLE 14-continued
183
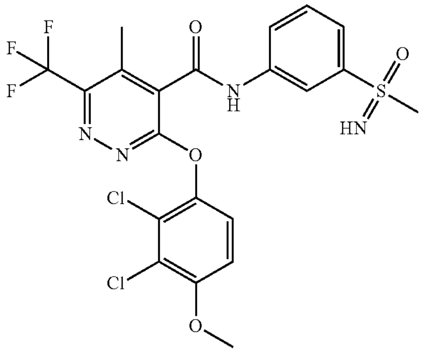 [SMILES: COc1ccc(Oc2nnc(C(F)(F)F)c(C)c2C(=O)Nc2cccc(S(C)(=N)=O)c2)c(Cl)c1Cl]
184
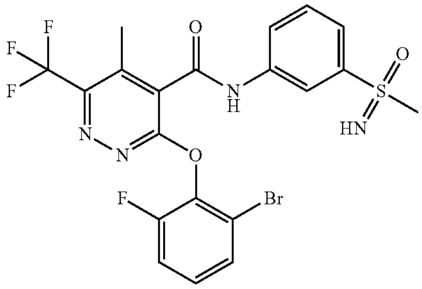 [SMILES: Cc1c(C(F)(F)F)nnc(Oc2c(F)cccc2Br)c1C(=O)Nc1cccc(S(C)(=N)=O)c1]
185
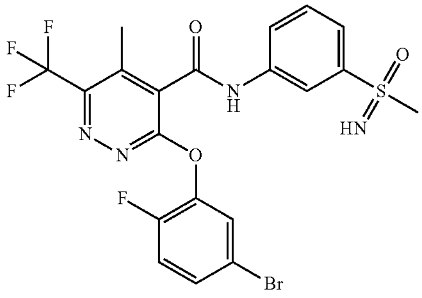
186
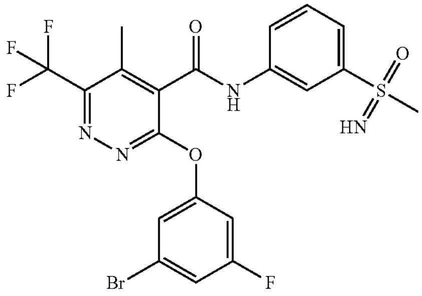 [SMILES: Cc1c(C(F)(F)F)nnc(Oc2cc(F)cc(Br)c2)c1C(=O)Nc1cccc(S(C)(=N)=O)c1]
187
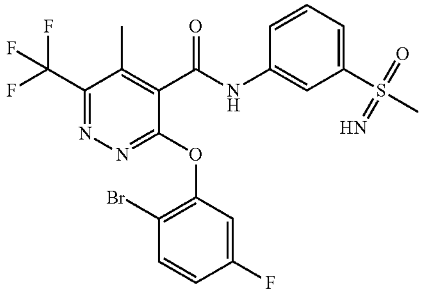 [SMILES: Cc1c(C(F)(F)F)nnc(Oc2cc(F)ccc2Br)c1C(=O)Nc1cccc(S(C)(=N)=O)c1]

TABLE 14-continued
188
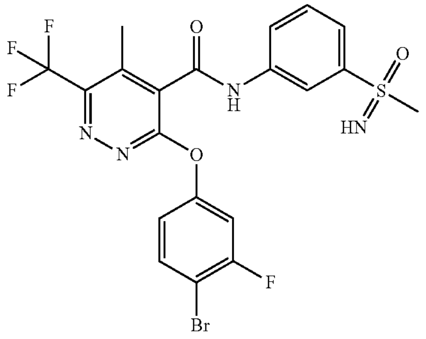
189
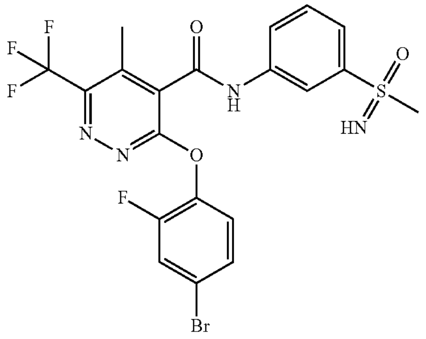
190
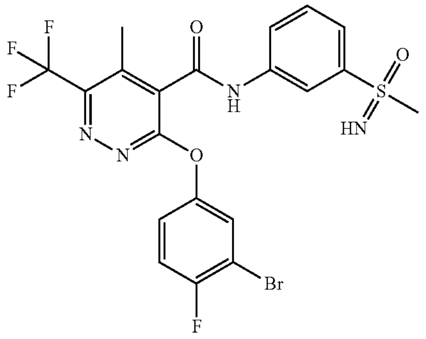 [SMILES: Cc1c(C(F)(F)F)nnc(Oc2ccc(F)c(Br)c2)c1C(=O)Nc1cccc(S(C)(=N)=O)c1]
191
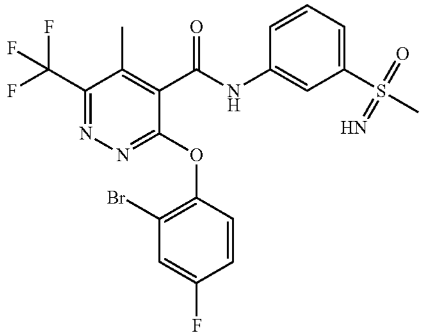 [SMILES: Cc1c(C(F)(F)F)nnc(Oc2ccc(F)cc2Br)c1C(=O)Nc1cccc(S(C)(=N)=O)c1]
TABLE 14-continued
192
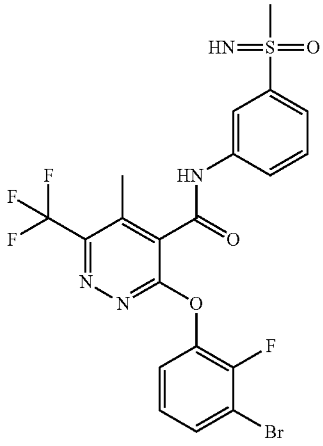 [SMILES: Cc1c(C(F)(F)F)nnc(Oc2cccc(Br)c2F)c1C(=O)Nc1cccc(S(C)(=N)=O)c1]
193
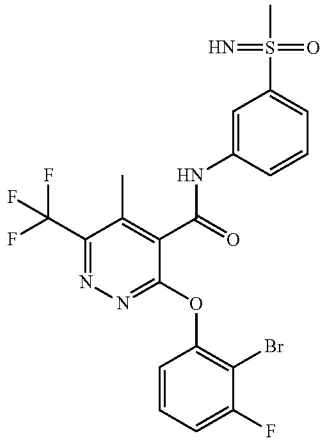 [SMILES: Cc1c(C(F)(F)F)nnc(Oc2cccc(F)c2Br)c1C(=O)Nc1cccc(S(C)(=N)=O)c1]
194
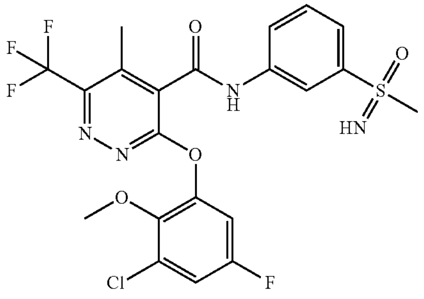 [SMILES: COc1c(Cl)cc(F)cc1Oc1nnc(C(F)(F)F)c(C)c1C(=O)Nc1cccc(S(C)(=N)=O)c1]
195
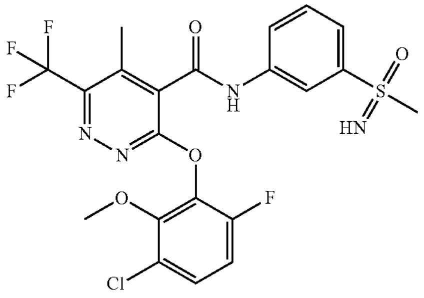 [SMILES: COc1c(Cl)ccc(F)c1Oc1nnc(C(F)(F)F)c(C)c1C(=O)Nc1cccc(S(C)(=N)=O)c1]

TABLE 14-continued
199
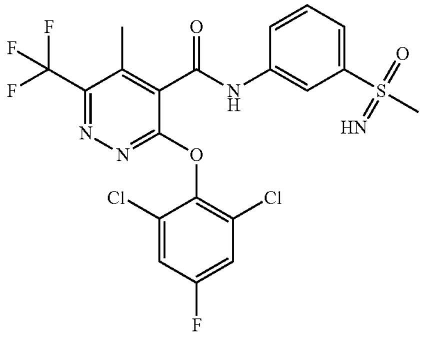 [SMILES: Cc1c(C(F)(F)F)nnc(Oc2c(Cl)cc(F)cc2Cl)c1C(=O)Nc1cccc(S(C)(=N)=O)c1]
200
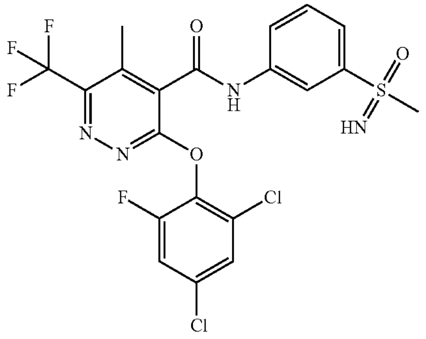 [SMILES: Cc1c(C(F)(F)F)nnc(Oc2c(F)cc(Cl)cc2Cl)c1C(=O)Nc1cccc(S(C)(=N)=O)c1]
201
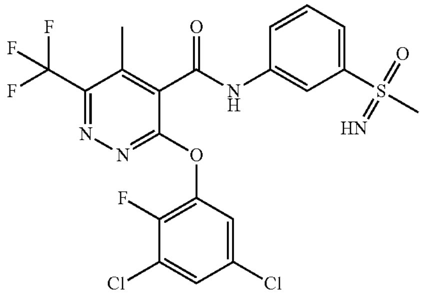 [SMILES: Cc1c(C(F)(F)F)nnc(Oc2cc(Cl)cc(Cl)c2F)c1C(=O)Nc1cccc(S(C)(=N)=O)c1]
202
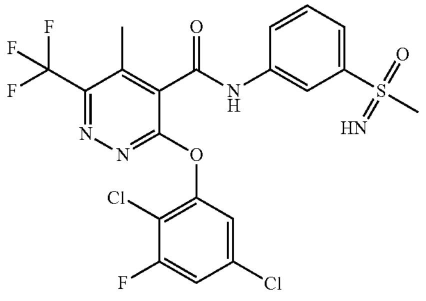 [SMILES: Cc1c(C(F)(F)F)nnc(Oc2cc(Cl)cc(F)c2Cl)c1C(=O)Nc1cccc(S(C)(=N)=O)c1]
203
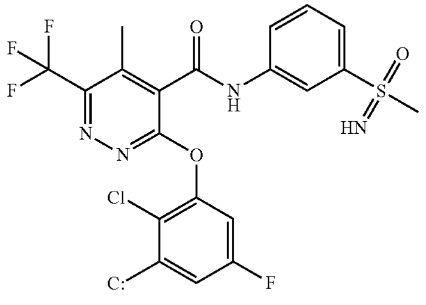
TABLE 14-continued
204
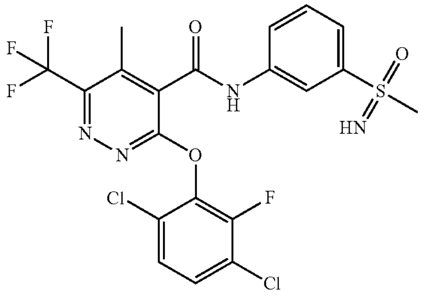 [SMILES: Cc1c(C(F)(F)F)nnc(Oc2c(Cl)ccc(Cl)c2F)c1C(=O)Nc1cccc(S(C)(=N)=O)c1]
205
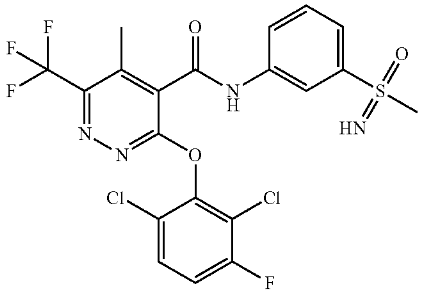 [SMILES: Cc1c(C(F)(F)F)nnc(Oc2c(Cl)ccc(F)c2Cl)c1C(=O)Nc1cccc(S(C)(=N)=O)c1]
206
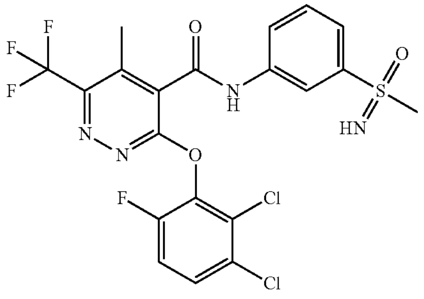 [SMILES: Cc1c(C(F)(F)F)nnc(Oc2c(F)ccc(Cl)c2Cl)c1C(=O)Nc1cccc(S(C)(=N)=O)c1]
207
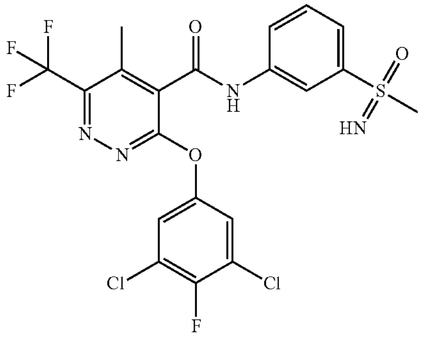 [SMILES: Cc1c(C(F)(F)F)nnc(Oc2cc(Cl)c(F)c(Cl)c2)c1C(=O)Nc1cccc(S(C)(=N)=O)c1]
208
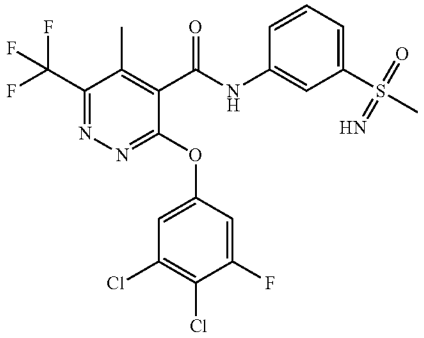 [SMILES: Cc1c(C(F)(F)F)nnc(Oc2cc(F)c(Cl)c(Cl)c2)c1C(=O)Nc1cccc(S(C)(=N)=O)c1]

TABLE 14-continued
209
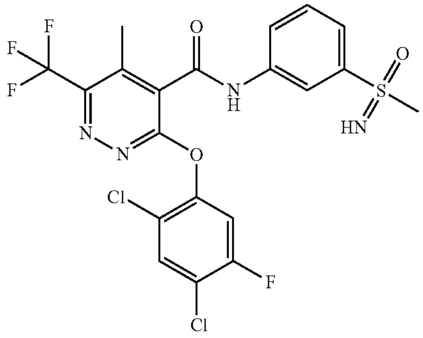 [SMILES: Cc1c(C(F)(F)F)nnc(Oc2cc(F)c(Cl)cc2Cl)c1C(=O)Nc1cccc(S(C)(=N)=O)c1]
210
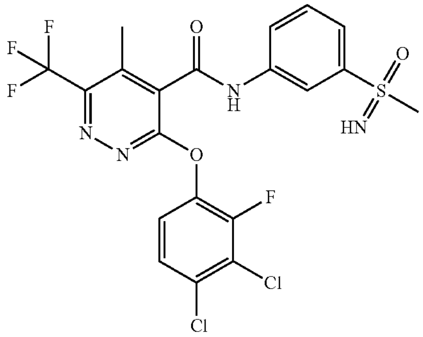 [SMILES: Cc1c(C(F)(F)F)nnc(Oc2ccc(Cl)c(Cl)c2F)c1C(=O)Nc1cccc(S(C)(=N)=O)c1]
211
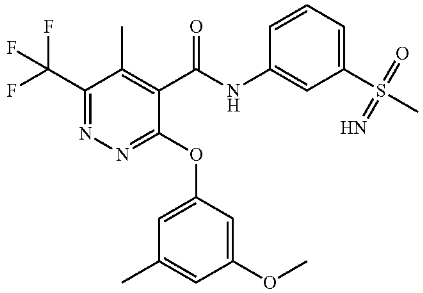
212
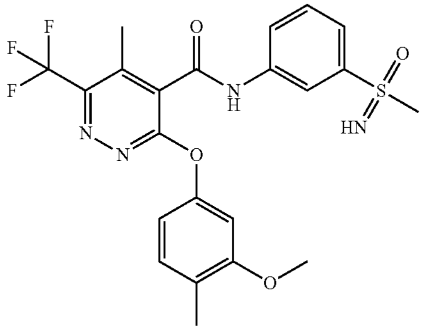 [SMILES: COc1cc(Oc2nnc(C(F)(F)F)c(C)c2C(=O)Nc2cccc(S(C)(=N)=O)c2)ccc1C]
213
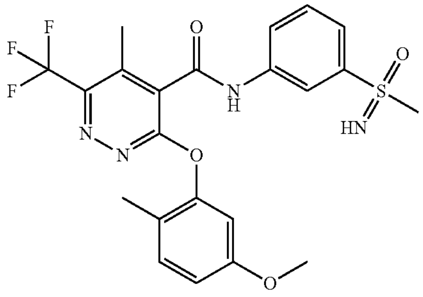 [SMILES: COc1ccc(C)c(Oc2nnc(C(F)(F)F)c(C)c2C(=O)Nc2cccc(S(C)(=N)=O)c2)c1]
TABLE 14-continued
214
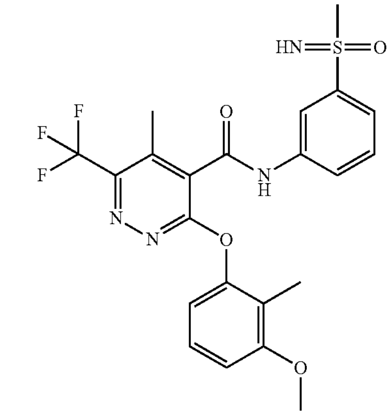 [SMILES: COc1cccc(Oc2nnc(C(F)(F)F)c(C)c2C(=O)Nc2cccc(S(C)(=N)=O)c2)c1C]
215
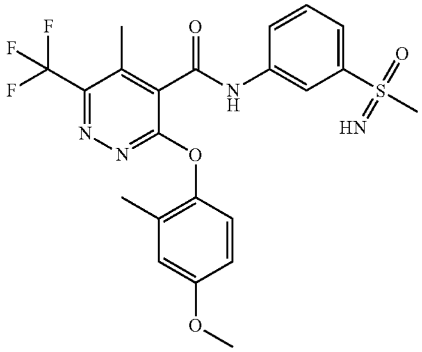 [SMILES: COc1ccc(Oc2nnc(C(F)(F)F)c(C)c2C(=O)Nc2cccc(S(C)(=N)=O)c2)c(C)c1]
216
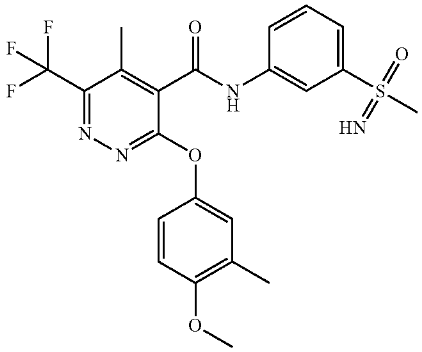 [SMILES: COc1ccc(Oc2nnc(C(F)(F)F)c(C)c2C(=O)Nc2cccc(S(C)(=N)=O)c2)cc1C]
220
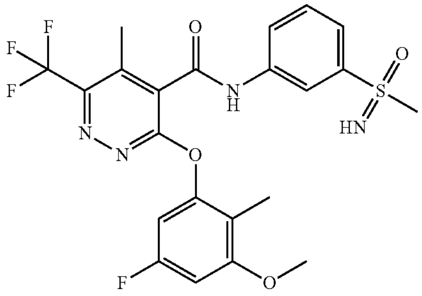 [SMILES: COc1cc(F)cc(Oc2nnc(C(F)(F)F)c(C)c2C(=O)Nc2cccc(S(C)(=N)=O)c2)c1C]

TABLE 14-continued
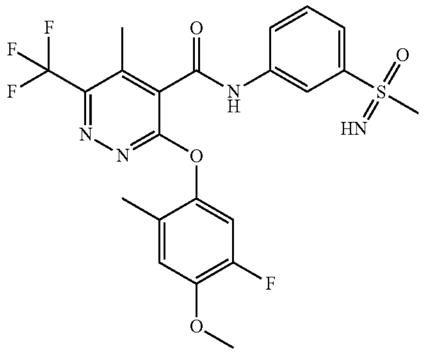
221
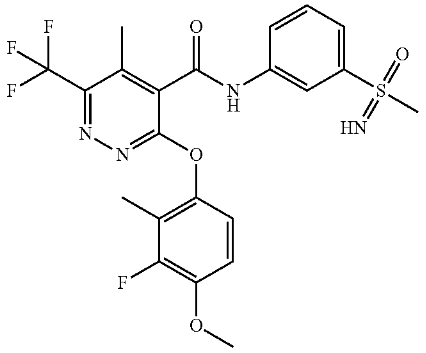 [SMILES: COc1ccc(Oc2nnc(C(F)(F)F)c(C)c2C(=O)Nc2cccc(S(C)(=N)=O)c2)c(C)c1F]
222
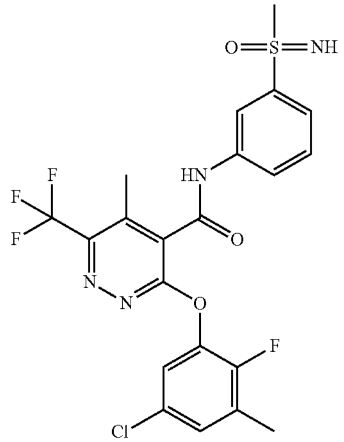 [SMILES: Cc1cc(Cl)cc(Oc2nnc(C(F)(F)F)c(C)c2C(=O)Nc2cccc(S(C)(=N)=O)c2)c1F]
224
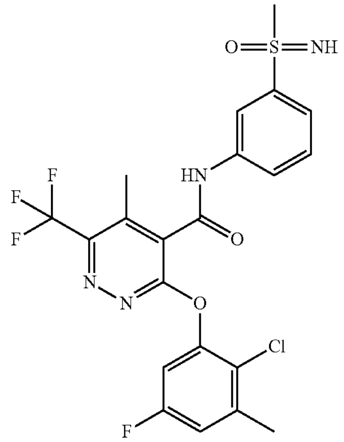 [SMILES: Cc1cc(F)cc(Oc2nnc(C(F)(F)F)c(C)c2C(=O)Nc2cccc(S(C)(=N)=O)c2)c1Cl]
225
TABLE 14-continued
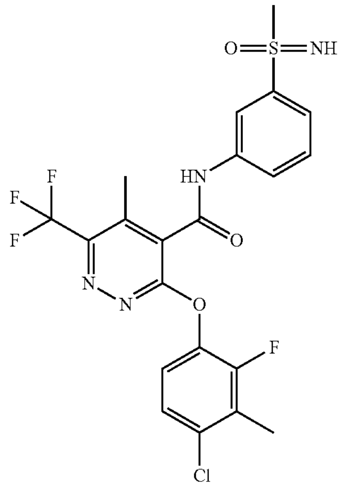 [SMILES: Cc1c(Cl)ccc(Oc2nnc(C(F)(F)F)c(C)c2C(=O)Nc2cccc(S(C)(=N)=O)c2)c1F]
226
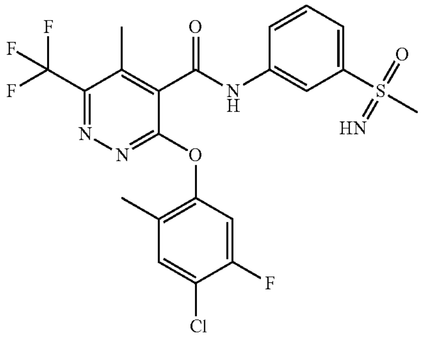 [SMILES: Cc1cc(Cl)c(F)cc1Oc1nnc(C(F)(F)F)c(C)c1C(=O)Nc1cccc(S(C)(=N)=O)c1]
227
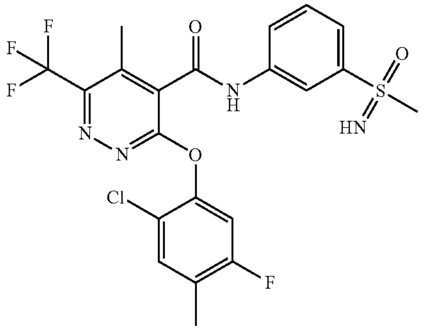
228
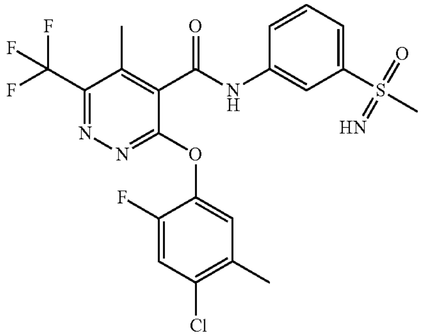
229

TABLE 14-continued
230
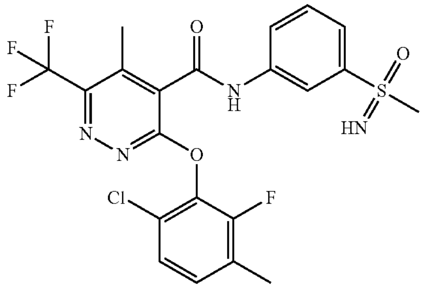
231
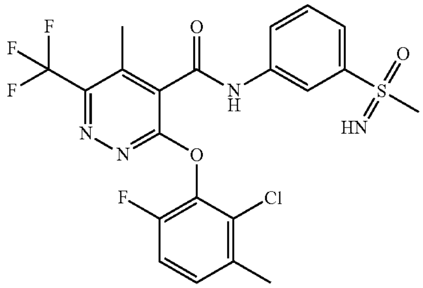 [SMILES: Cc1ccc(F)c(Oc2nnc(C(F)(F)F)c(C)c2C(=O)Nc2cccc(S(C)(=N)=O)c2)c1Cl]
236
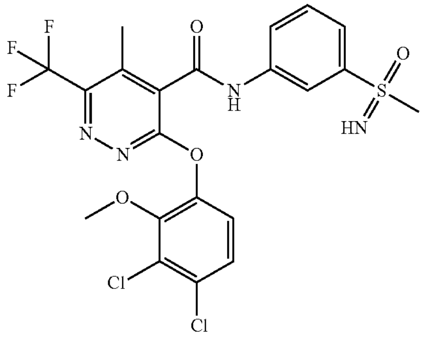
237
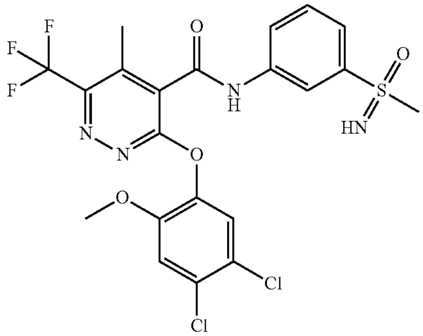
238
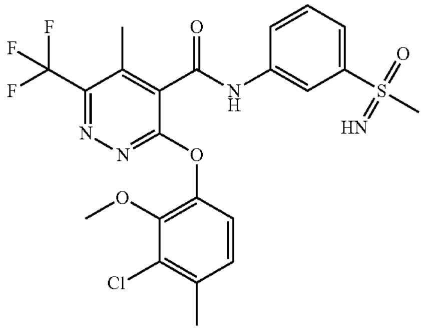 [SMILES: COc1c(Oc2nnc(C(F)(F)F)c(C)c2C(=O)Nc2cccc(S(C)(=N)=O)c2)ccc(C)c1Cl]
TABLE 14-continued
239
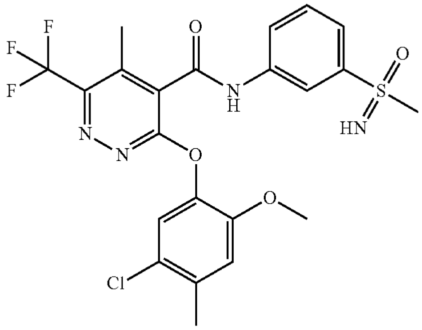 [SMILES: COc1cc(C)c(Cl)cc1Oc1nnc(C(F)(F)F)c(C)c1C(=O)Nc1cccc(S(C)(=N)=O)c1]
241
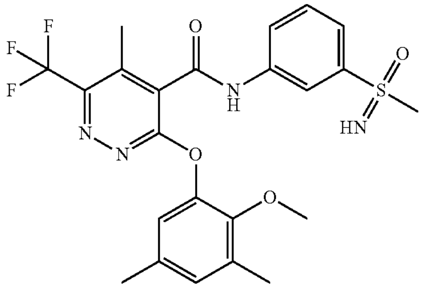 [SMILES: COc1c(C)cc(C)cc1Oc1nnc(C(F)(F)F)c(C)c1C(=O)Nc1cccc(S(C)(=N)=O)c1]
242
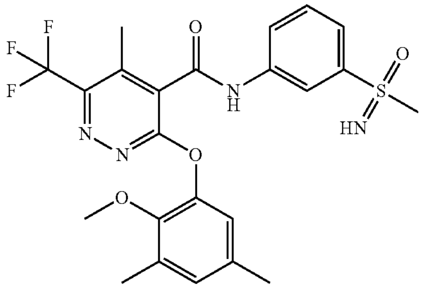 [SMILES: COc1c(C)cc(C)cc1Oc1nnc(C(F)(F)F)c(C)c1C(=O)Nc1cccc(S(C)(=N)=O)c1]
243
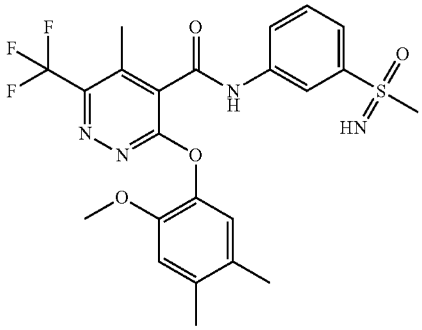 [SMILES: COc1cc(C)c(C)cc1Oc1nnc(C(F)(F)F)c(C)c1C(=O)Nc1cccc(S(C)(=N)=O)c1]
244
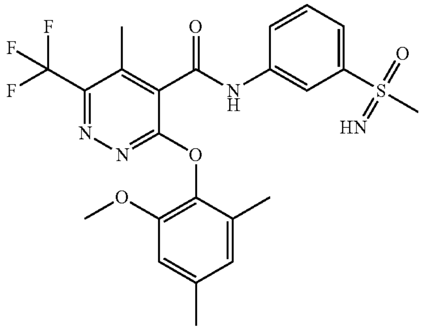

245
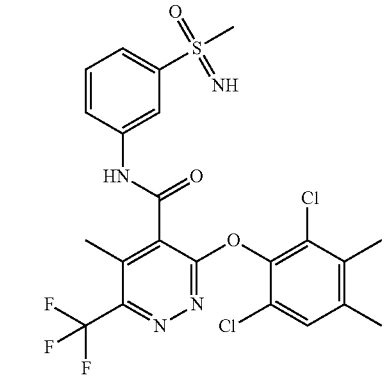 [SMILES: Cc1cc(Cl)c(Oc2nnc(C(F)(F)F)c(C)c2C(=O)Nc2cccc(S(C)(=N)=O)c2)c(Cl)c1C]
246
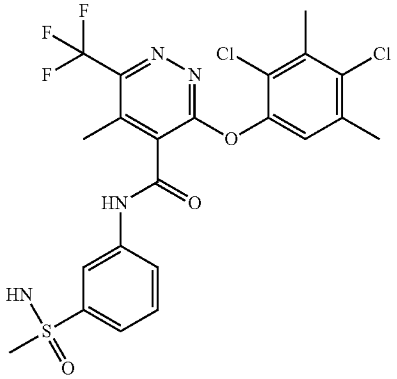
247
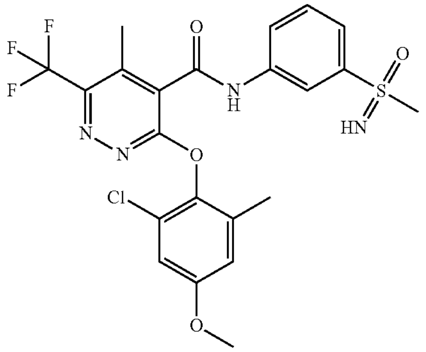 [SMILES: COc1cc(C)c(Oc2nnc(C(F)(F)F)c(C)c2C(=O)Nc2cccc(S(C)(=N)=O)c2)c(Cl)c1]
248
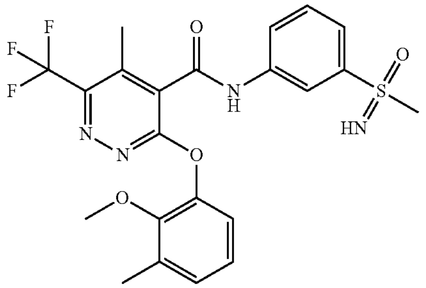 [SMILES: COc1c(C)cccc1Oc1nnc(C(F)(F)F)c(C)c1C(=O)Nc1cccc(S(C)(=N)=O)c1]
249
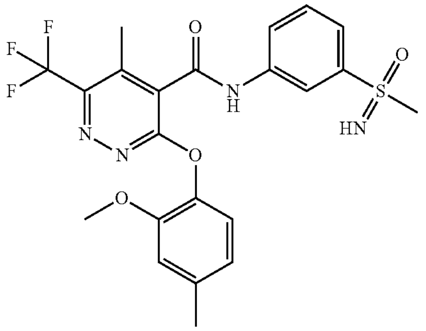
250
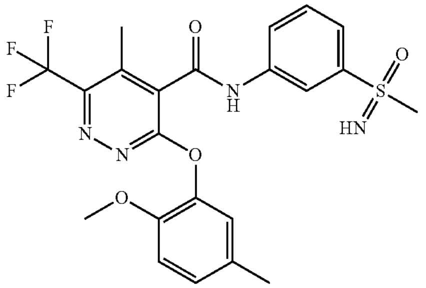
251
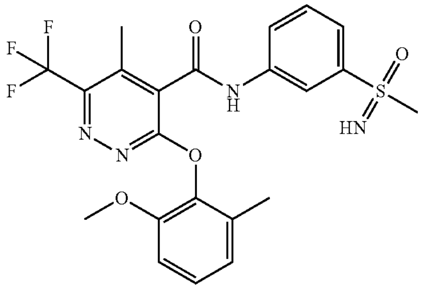 [SMILES: COc1cccc(C)c1Oc1nnc(C(F)(F)F)c(C)c1C(=O)Nc1cccc(S(C)(=N)=O)c1]
252
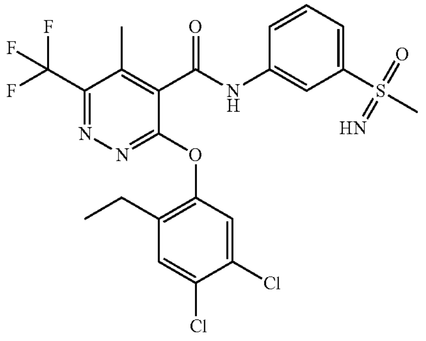

TABLE 14-continued
258
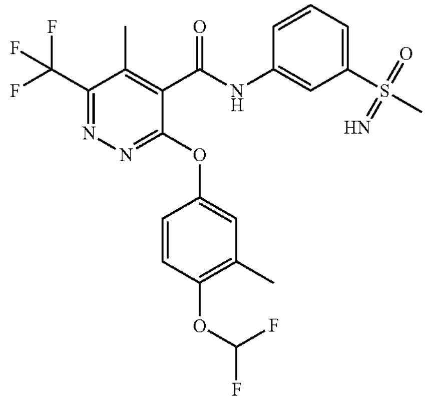 [SMILES: Cc1cc(Oc2nnc(C(F)(F)F)c(C)c2C(=O)Nc2cccc(S(C)(=N)=O)c2)ccc1OC(F)F]
259
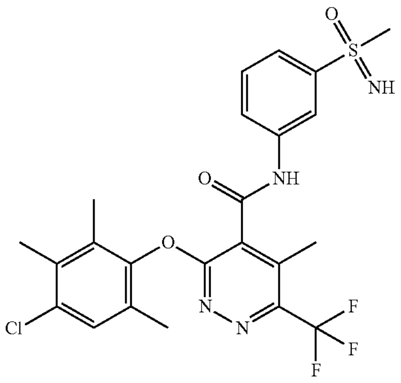 [SMILES: Cc1cc(Cl)c(C)c(C)c1Oc1nnc(C(F)(F)F)c(C)c1C(=O)Nc1cccc(S(C)(=N)=O)c1]
260
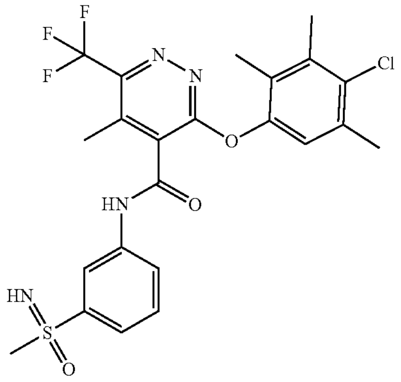 [SMILES: Cc1cc(Oc2nnc(C(F)(F)F)c(C)c2C(=O)Nc2cccc(S(C)(=N)=O)c2)c(C)c(C)c1Cl]
261
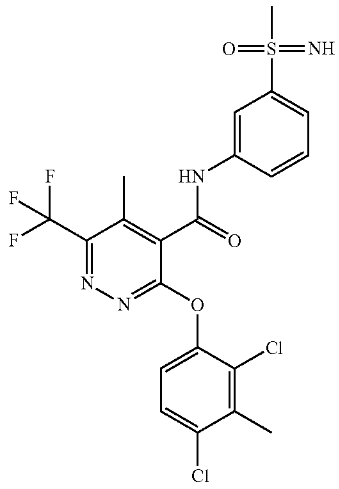 [SMILES: Cc1c(Cl)ccc(Oc2nnc(C(F)(F)F)c(C)c2C(=O)Nc2cccc(S(C)(=N)=O)c2)c1Cl]
TABLE 14-continued
262
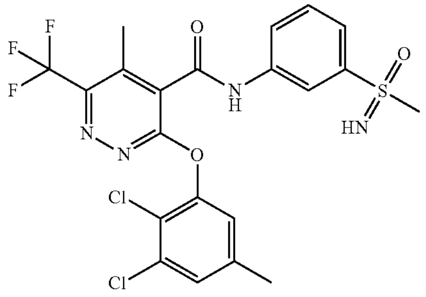 [SMILES: Cc1cc(Cl)c(Cl)c(Oc2nnc(C(F)(F)F)c(C)c2C(=O)Nc2cccc(S(C)(=N)=O)c2)c1]
263
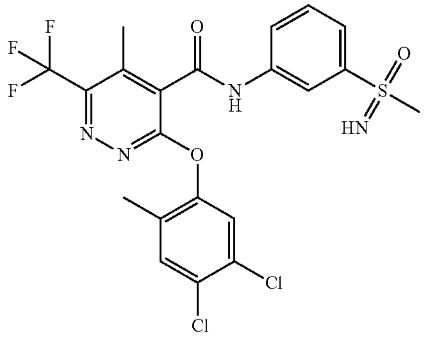
264
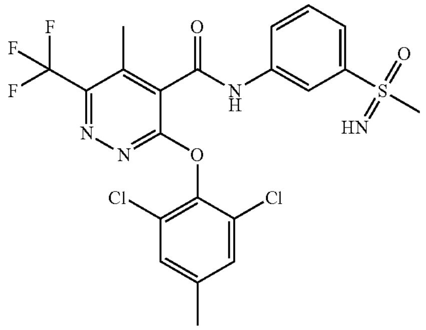 [SMILES: Cc1cc(Cl)c(Oc2nnc(C(F)(F)F)c(C)c2C(=O)Nc2cccc(S(C)(=N)=O)c2)c(Cl)c1]
265
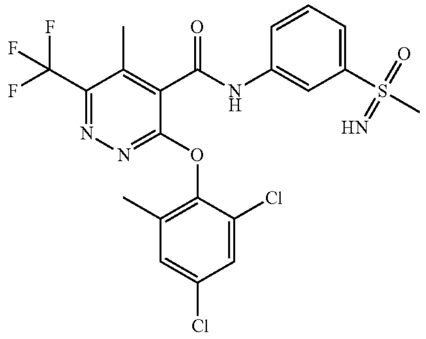

TABLE 14-continued
266
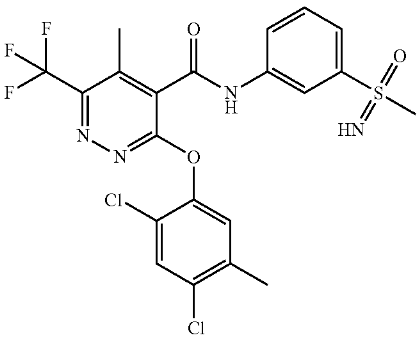 [SMILES: Cc1cc(Oc2nnc(C(F)(F)F)c(C)c2C(=O)Nc2cccc(S(C)(=N)=O)c2)c(Cl)cc1Cl]
267
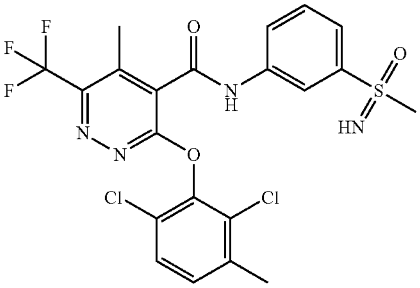 [SMILES: Cc1ccc(Cl)c(Oc2nnc(C(F)(F)F)c(C)c2C(=O)Nc2cccc(S(C)(=N)=O)c2)c1Cl]
268
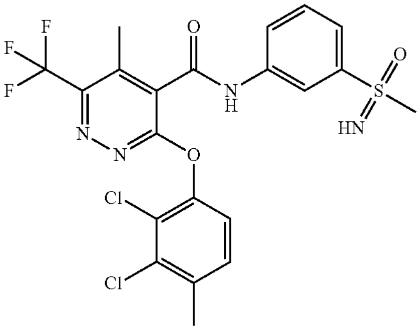
269
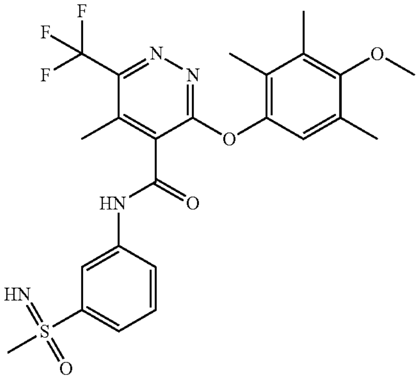
TABLE 14-continued
270
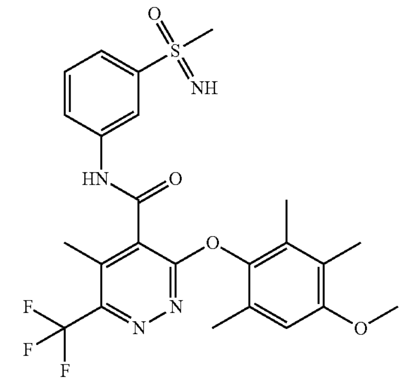 [SMILES: COc1cc(C)c(Oc2nnc(C(F)(F)F)c(C)c2C(=O)Nc2cccc(S(C)(=N)=O)c2)c(C)c1C]
271
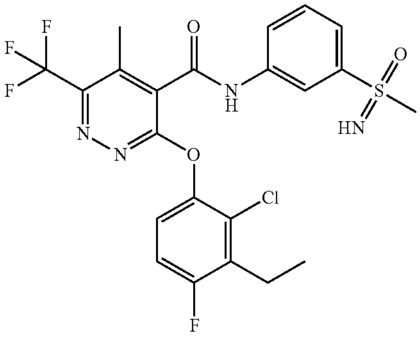 [SMILES: CCc1c(F)ccc(Oc2nnc(C(F)(F)F)c(C)c2C(=O)Nc2cccc(S(C)(=N)=O)c2)c1Cl]
272
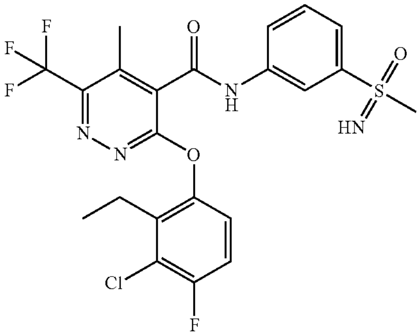 [SMILES: CCc1c(Oc2nnc(C(F)(F)F)c(C)c2C(=O)Nc2cccc(S(C)(=N)=O)c2)ccc(F)c1Cl]
273
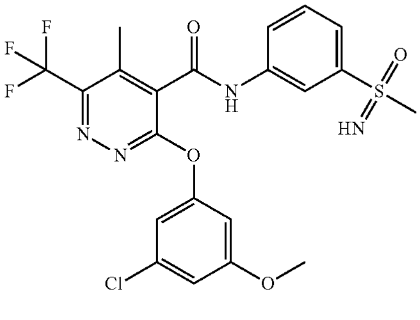 [SMILES: COc1cc(Cl)cc(Oc2nnc(C(F)(F)F)c(C)c2C(=O)Nc2cccc(S(C)(=N)=O)c2)c1]

TABLE 14-continued
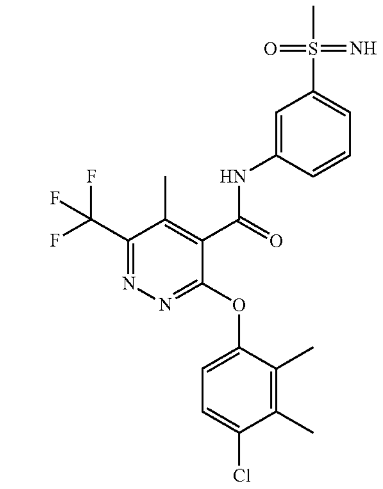 [SMILES: Cc1c(Cl)ccc(Oc2nnc(C(F)(F)F)c(C)c2C(=O)Nc2cccc(S(C)(=N)=O)c2)c1C]
274
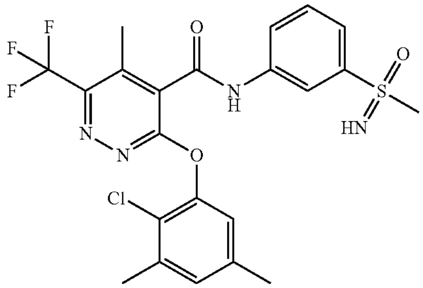 [SMILES: Cc1cc(C)c(Cl)c(Oc2nnc(C(F)(F)F)c(C)c2C(=O)Nc2cccc(S(C)(=N)=O)c2)c1]
275
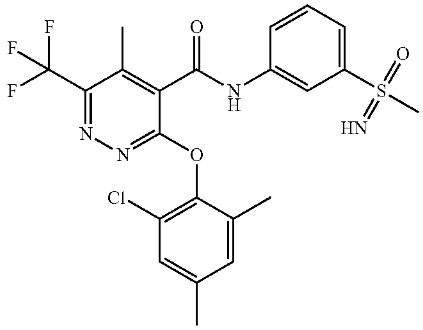 [SMILES: Cc1cc(C)c(Oc2nnc(C(F)(F)F)c(C)c2C(=O)Nc2cccc(S(C)(=N)=O)c2)c(Cl)c1]
276
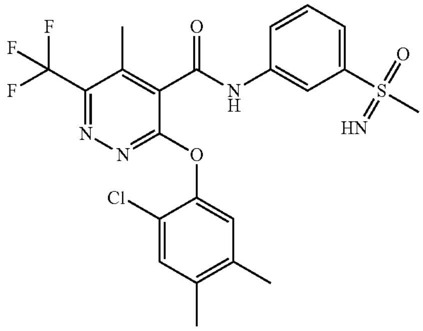 [SMILES: Cc1cc(Cl)c(Oc2nnc(C(F)(F)F)c(C)c2C(=O)Nc2cccc(S(C)(=N)=O)c2)cc1C]
277
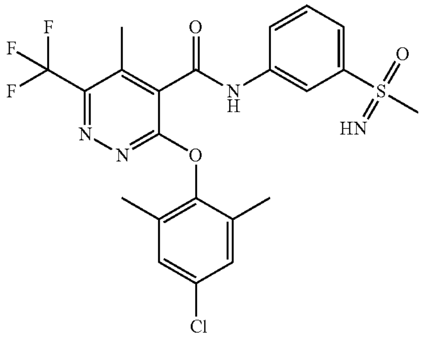 [SMILES: Cc1cc(Cl)cc(C)c1Oc1nnc(C(F)(F)F)c(C)c1C(=O)Nc1cccc(S(C)(=N)=O)c1]
278
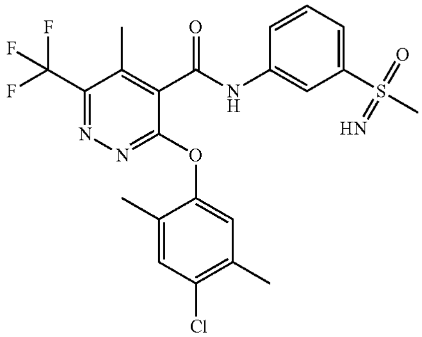 [SMILES: Cc1cc(Oc2nnc(C(F)(F)F)c(C)c2C(=O)Nc2cccc(S(C)(=N)=O)c2)c(C)cc1Cl]
279
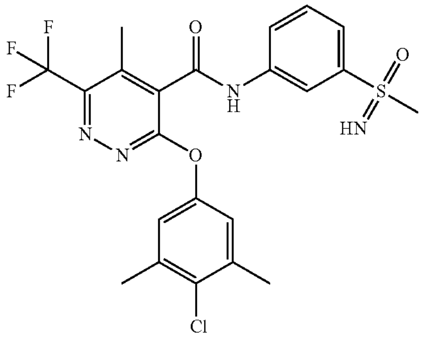 [SMILES: Cc1cc(Oc2nnc(C(F)(F)F)c(C)c2C(=O)Nc2cccc(S(C)(=N)=O)c2)cc(C)c1Cl]
280
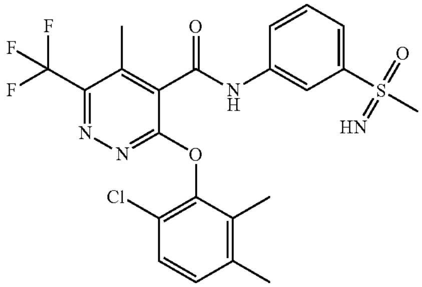 [SMILES: Cc1ccc(Cl)c(Oc2nnc(C(F)(F)F)c(C)c2C(=O)Nc2cccc(S(C)(=N)=O)c2)c1C]
281
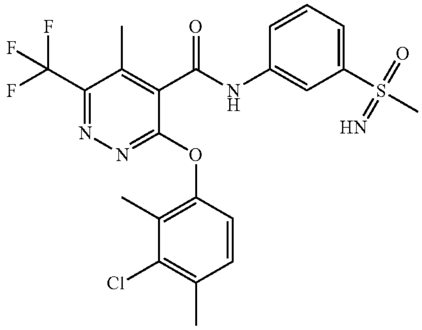 [SMILES: Cc1ccc(Oc2nnc(C(F)(F)F)c(C)c2C(=O)Nc2cccc(S(C)(=N)=O)c2)c(C)c1Cl]
282

TABLE 14-continued
283
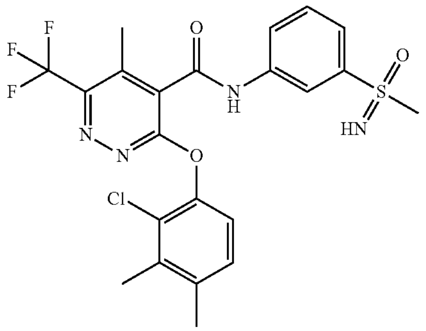 [SMILES: Cc1ccc(Oc2nnc(C(F)(F)F)c(C)c2C(=O)Nc2cccc(S(C)(=N)=O)c2)c(Cl)c1C]
284
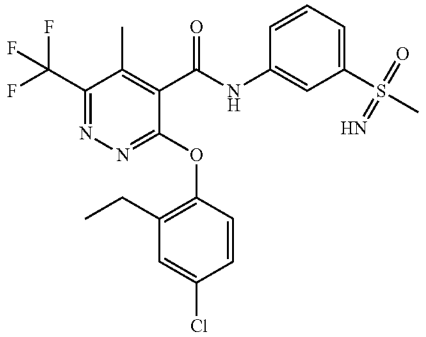 [SMILES: CCc1cc(Cl)ccc1Oc1nnc(C(F)(F)F)c(C)c1C(=O)Nc1cccc(S(C)(=N)=O)c1]
285
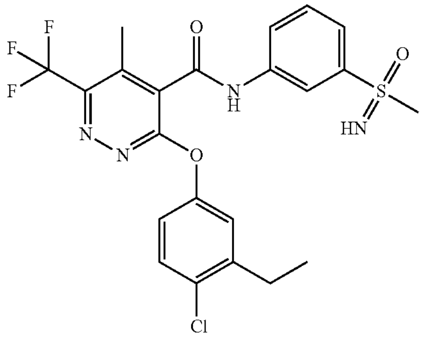 [SMILES: CCc1cc(Oc2nnc(C(F)(F)F)c(C)c2C(=O)Nc2cccc(S(C)(=N)=O)c2)ccc1Cl]
286
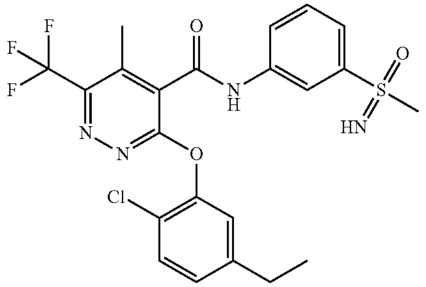 [SMILES: CCc1ccc(Cl)c(Oc2nnc(C(F)(F)F)c(C)c2C(=O)Nc2cccc(S(C)(=N)=O)c2)c1]
287
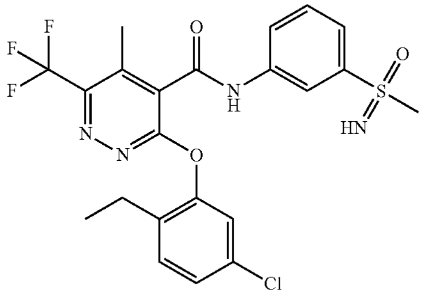 [SMILES: CCc1ccc(Cl)cc1Oc1nnc(C(F)(F)F)c(C)c1C(=O)Nc1cccc(S(C)(=N)=O)c1]
TABLE 14-continued
288
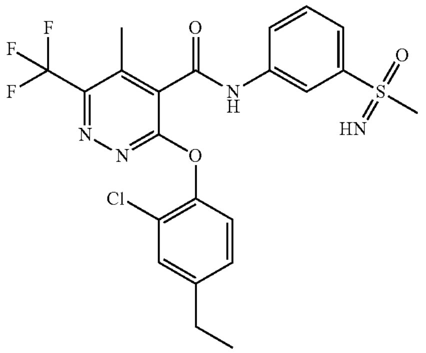 [SMILES: CCc1ccc(Oc2nnc(C(F)(F)F)c(C)c2C(=O)Nc2cccc(S(C)(=N)=O)c2)c(Cl)c1]
289
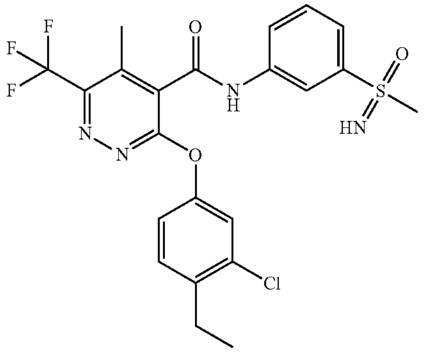
290
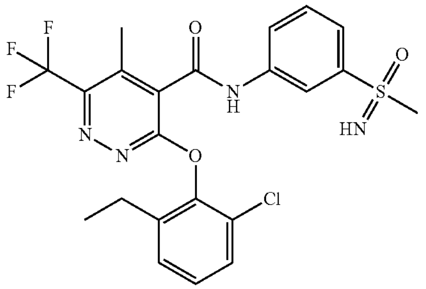
291
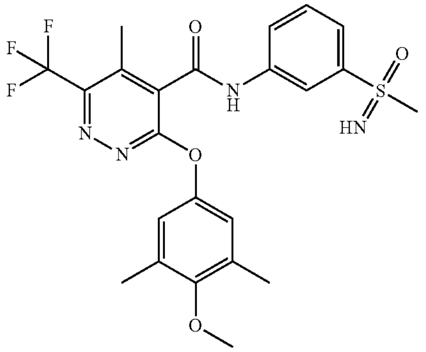 [SMILES: COc1c(C)cc(Oc2nnc(C(F)(F)F)c(C)c2C(=O)Nc2cccc(S(C)(=N)=O)c2)cc1C]

TABLE 14-continued
292
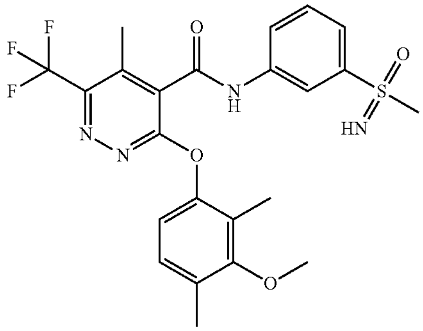 [SMILES: COc1c(C)ccc(Oc2nnc(C(F)(F)F)c(C)c2C(=O)Nc2cccc(S(C)(=N)=O)c2)c1C]
293
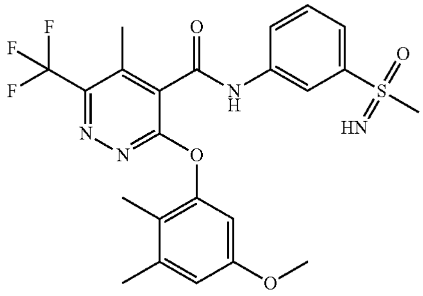 [SMILES: COc1cc(C)c(C)c(Oc2nnc(C(F)(F)F)c(C)c2C(=O)Nc2cccc(S(C)(=N)=O)c2)c1]
294
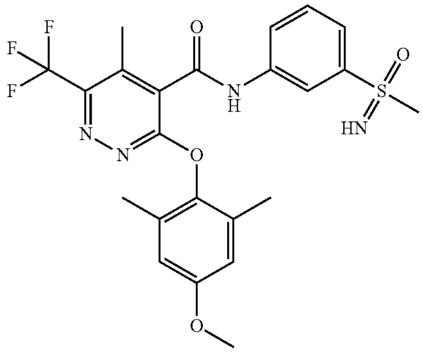 [SMILES: COc1cc(C)c(Oc2nnc(C(F)(F)F)c(C)c2C(=O)Nc2cccc(S(C)(=N)=O)c2)c(C)c1]
295
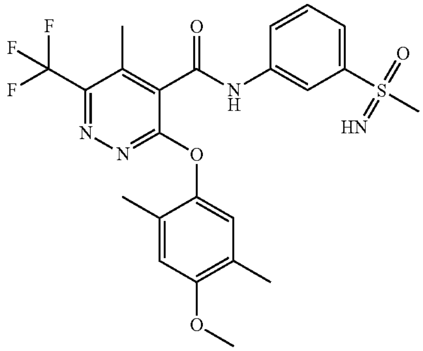 [SMILES: COc1cc(C)c(Oc2nnc(C(F)(F)F)c(C)c2C(=O)Nc2cccc(S(C)(=N)=O)c2)cc1C]
296
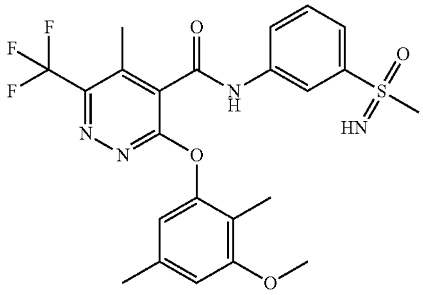 [SMILES: COc1cc(C)cc(Oc2nnc(C(F)(F)F)c(C)c2C(=O)Nc2cccc(S(C)(=N)=O)c2)c1C]
TABLE 14-continued
297
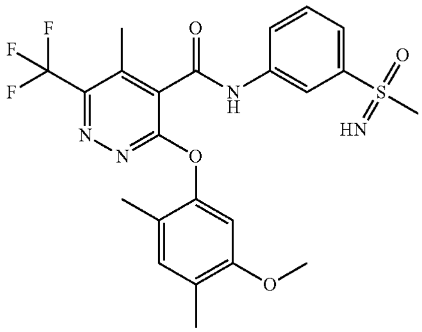 [SMILES: COc1cc(Oc2nnc(C(F)(F)F)c(C)c2C(=O)Nc2cccc(S(C)(=N)=O)c2)c(C)cc1C]
298
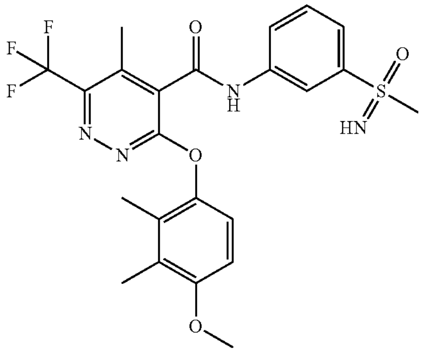 [SMILES: COc1ccc(Oc2nnc(C(F)(F)F)c(C)c2C(=O)Nc2cccc(S(C)(=N)=O)c2)c(C)c1C]
299
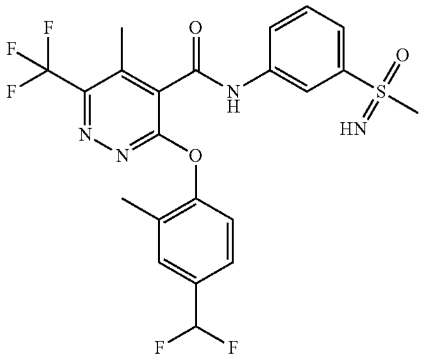 [SMILES: Cc1cc(C(F)F)ccc1Oc1nnc(C(F)(F)F)c(C)c1C(=O)Nc1cccc(S(C)(=N)=O)c1]
300
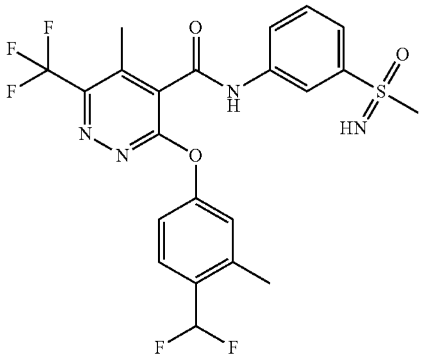 [SMILES: Cc1cc(Oc2nnc(C(F)(F)F)c(C)c2C(=O)Nc2cccc(S(C)(=N)=O)c2)ccc1C(F)F]

TABLE 14-continued
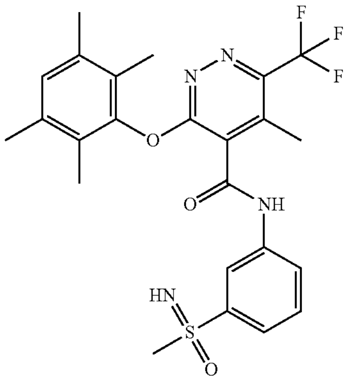 [SMILES: Cc1cc(C)c(C)c(Oc2nnc(C(F)(F)F)c(C)c2C(=O)Nc2cccc(S(C)(=N)=O)c2)c1C]
301
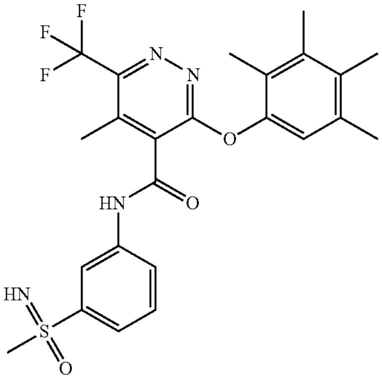
302
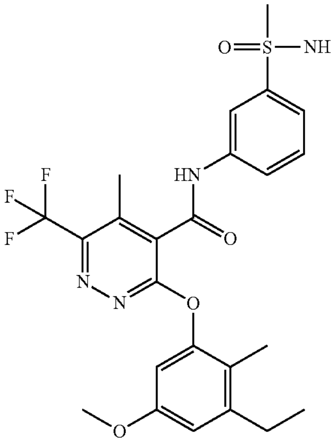
304
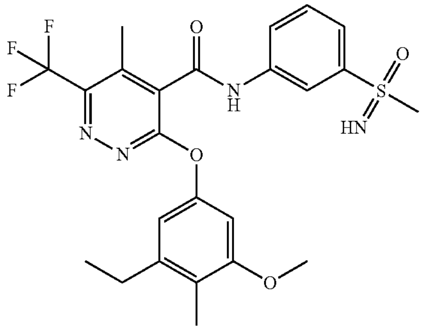 [SMILES: CCc1cc(Oc2nnc(C(F)(F)F)c(C)c2C(=O)Nc2cccc(S(C)(=N)=O)c2)cc(OC)c1C]
305
TABLE 14-continued
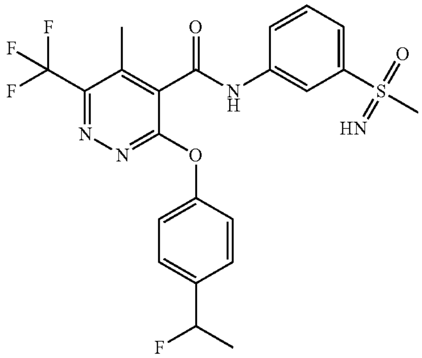 [SMILES: Cc1c(C(F)(F)F)nnc(Oc2ccc(C(C)F)cc2)c1C(=O)Nc1cccc(S(C)(=N)=O)c1]
306
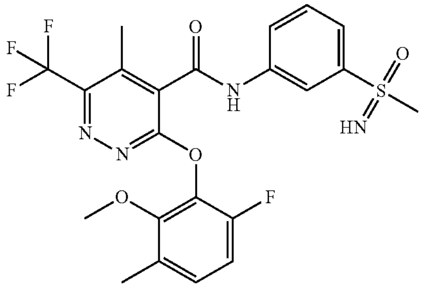 [SMILES: COc1c(C)ccc(F)c1Oc1nnc(C(F)(F)F)c(C)c1C(=O)Nc1cccc(S(C)(=N)=O)c1]
308
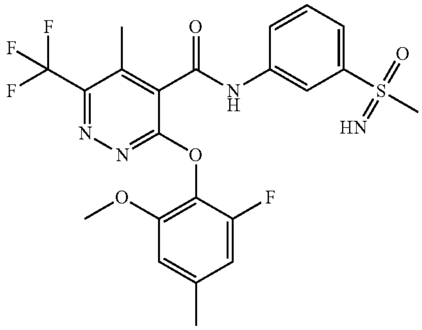 [SMILES: COc1cc(C)cc(F)c1Oc1nnc(C(F)(F)F)c(C)c1C(=O)Nc1cccc(S(C)(=N)=O)c1]
309
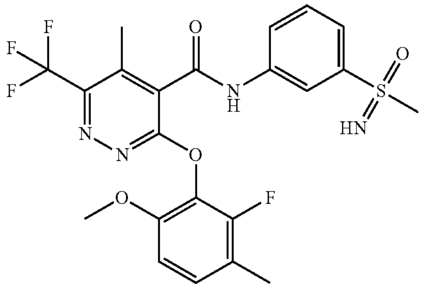 [SMILES: COc1ccc(C)c(F)c1Oc1nnc(C(F)(F)F)c(C)c1C(=O)Nc1cccc(S(C)(=N)=O)c1]
310
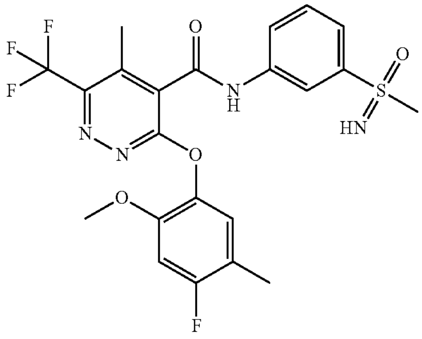 [SMILES: COc1cc(F)c(C)cc1Oc1nnc(C(F)(F)F)c(C)c1C(=O)Nc1cccc(S(C)(=N)=O)c1]
311

TABLE 14-continued
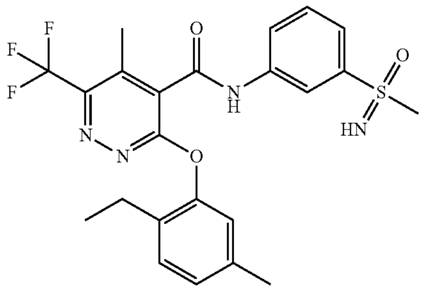 [SMILES: CCc1ccc(C)cc1Oc1nnc(C(F)(F)F)c(C)c1C(=O)Nc1cccc(S(C)(=N)=O)c1]
312
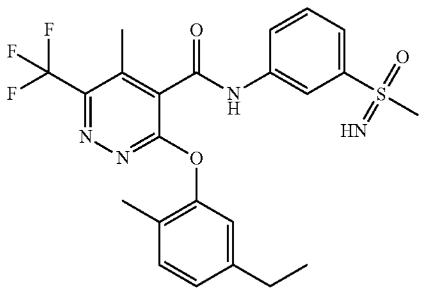 [SMILES: CCc1ccc(C)c(Oc2nnc(C(F)(F)F)c(C)c2C(=O)Nc2cccc(S(C)(=N)=O)c2)c1]
313
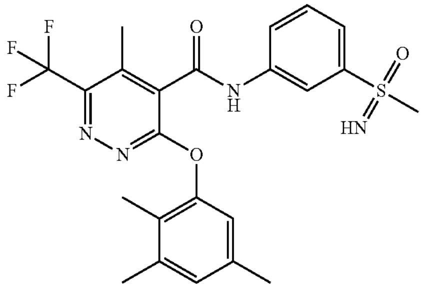 [SMILES: Cc1cc(C)c(C)c(Oc2nnc(C(F)(F)F)c(C)c2C(=O)Nc2cccc(S(C)(=N)=O)c2)c1]
314
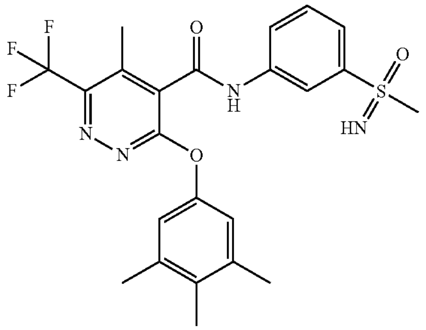 [SMILES: Cc1cc(Oc2nnc(C(F)(F)F)c(C)c2C(=O)Nc2cccc(S(C)(=N)=O)c2)cc(C)c1C]
315
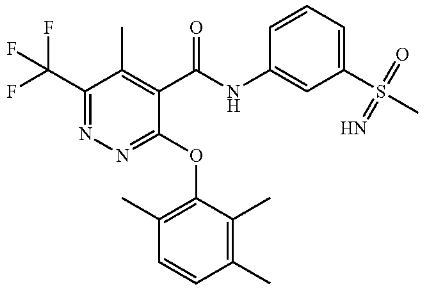 [SMILES: Cc1ccc(C)c(Oc2nnc(C(F)(F)F)c(C)c2C(=O)Nc2cccc(S(C)(=N)=O)c2)c1C]
316
TABLE 14-continued
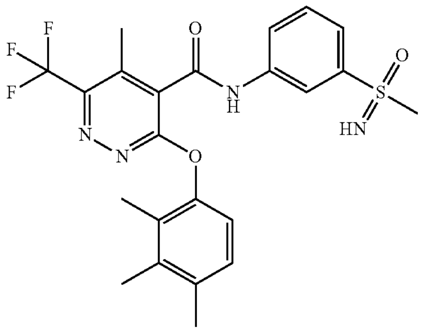 [SMILES: Cc1ccc(Oc2nnc(C(F)(F)F)c(C)c2C(=O)Nc2cccc(S(C)(=N)=O)c2)c(C)c1C]
317
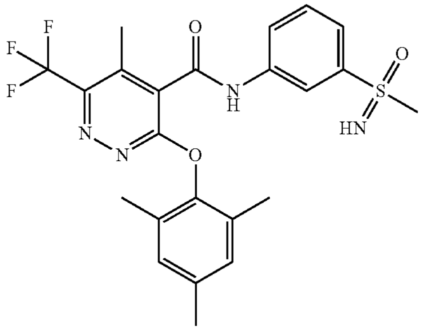 [SMILES: Cc1cc(C)c(Oc2nnc(C(F)(F)F)c(C)c2C(=O)Nc2cccc(S(C)(=N)=O)c2)c(C)c1]
318
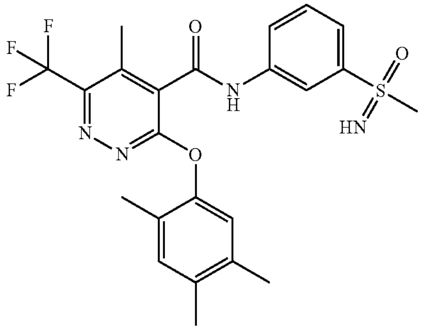 [SMILES: Cc1cc(C)c(Oc2nnc(C(F)(F)F)c(C)c2C(=O)Nc2cccc(S(C)(=N)=O)c2)cc1C]
319
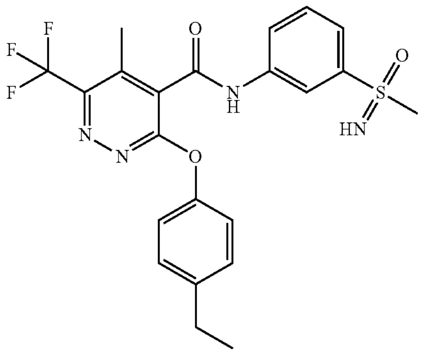 [SMILES: CCc1ccc(Oc2nnc(C(F)(F)F)c(C)c2C(=O)Nc2cccc(S(C)(=N)=O)c2)cc1]
320

TABLE 14-continued
321
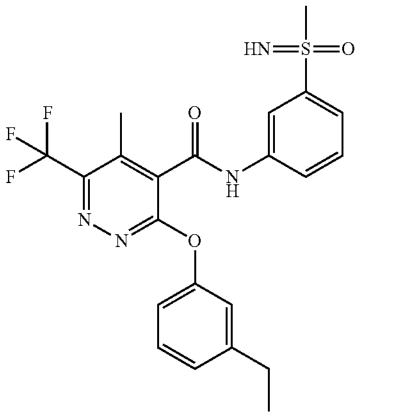 [SMILES: CCc1cccc(Oc2nnc(C(F)(F)F)c(C)c2C(=O)Nc2cccc(S(C)(=N)=O)c2)c1]
321
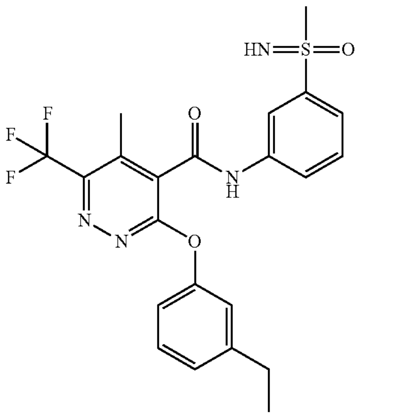 [SMILES: CCc1cccc(Oc2nnc(C(F)(F)F)c(C)c2C(=O)Nc2cccc(S(C)(=N)=O)c2)c1]
322
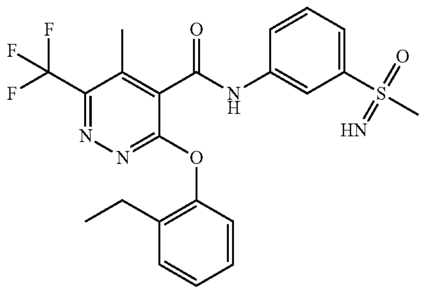 [SMILES: CCc1ccccc1Oc1nnc(C(F)(F)F)c(C)c1C(=O)Nc1cccc(S(C)(=N)=O)c1]
323
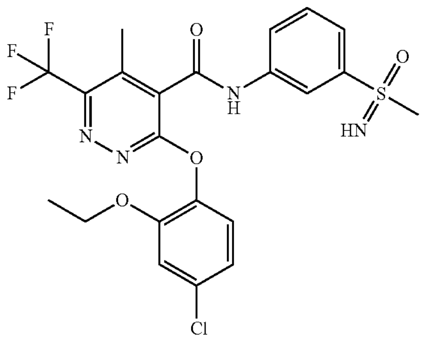 [SMILES: CCOc1cc(Cl)ccc1Oc1nnc(C(F)(F)F)c(C)c1C(=O)Nc1cccc(S(C)(=N)=O)c1]
TABLE 14-continued
324
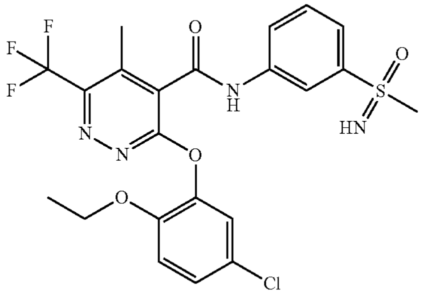 [SMILES: CCOc1ccc(Cl)cc1Oc1nnc(C(F)(F)F)c(C)c1C(=O)Nc1cccc(S(C)(=N)=O)c1]
325
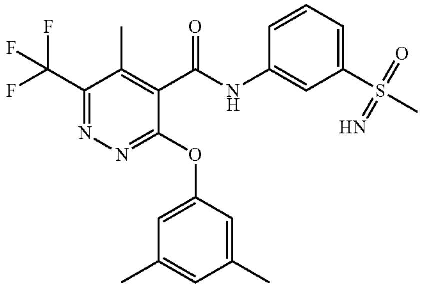 [SMILES: Cc1cc(C)cc(Oc2nnc(C(F)(F)F)c(C)c2C(=O)Nc2cccc(S(C)(=N)=O)c2)c1]
326
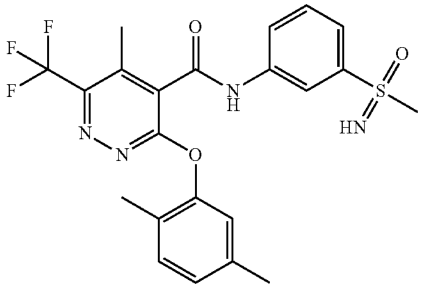 [SMILES: Cc1ccc(C)c(Oc2nnc(C(F)(F)F)c(C)c2C(=O)Nc2cccc(S(C)(=N)=O)c2)c1]
327
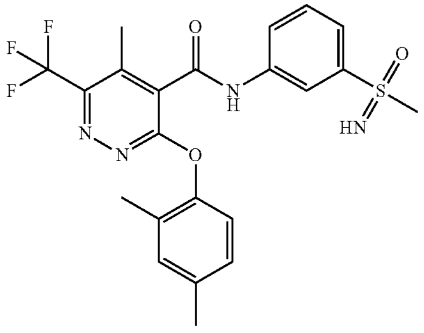 [SMILES: Cc1ccc(Oc2nnc(C(F)(F)F)c(C)c2C(=O)Nc2cccc(S(C)(=N)=O)c2)c(C)c1]
328
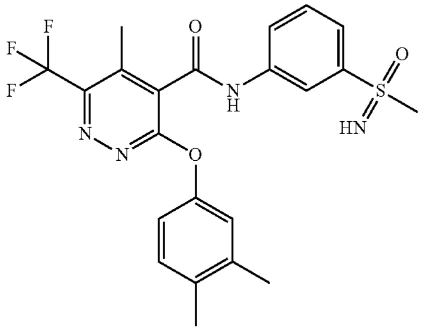

TABLE 14-continued
329
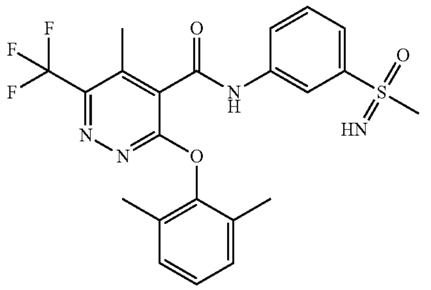 [SMILES: Cc1cccc(C)c1Oc1nnc(C(F)(F)F)c(C)c1C(=O)Nc1cccc(S(C)(=N)=O)c1]
330
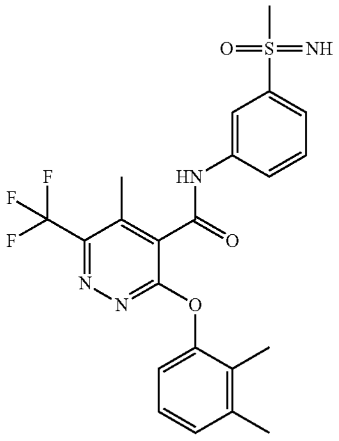 [SMILES: Cc1cccc(Oc2nnc(C(F)(F)F)c(C)c2C(=O)Nc2cccc(S(C)(=N)=O)c2)c1C]
331
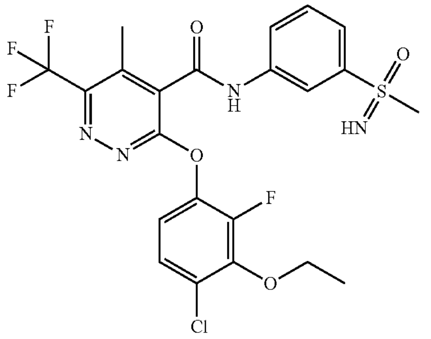 [SMILES: CCOc1c(Cl)ccc(Oc2nnc(C(F)(F)F)c(C)c2C(=O)Nc2cccc(S(C)(=N)=O)c2)c1F]
332
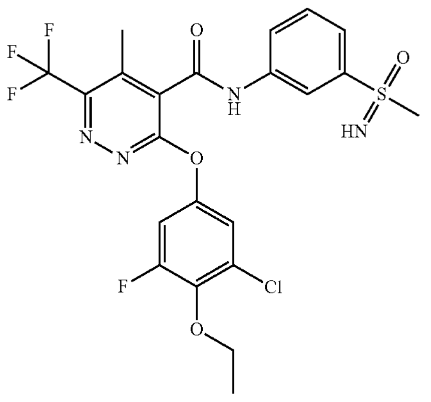 [SMILES: CCOc1c(F)cc(Oc2nnc(C(F)(F)F)c(C)c2C(=O)Nc2cccc(S(C)(=N)=O)c2)cc1Cl]
TABLE 14-continued
333
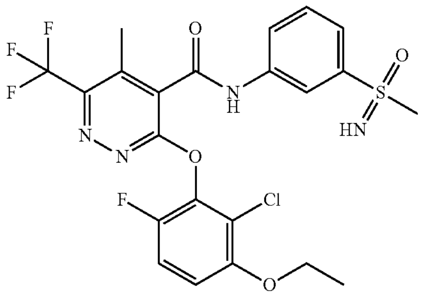 [SMILES: CCOc1ccc(F)c(Oc2nnc(C(F)(F)F)c(C)c2C(=O)Nc2cccc(S(C)(=N)=O)c2)c1Cl]
334
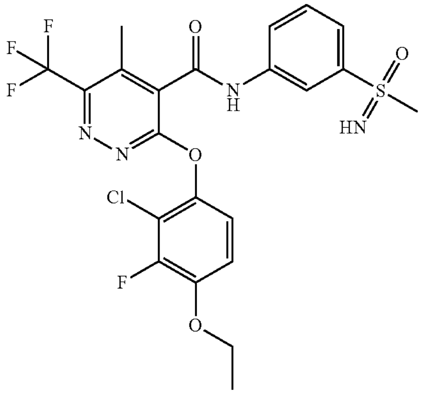 [SMILES: CCOc1ccc(Oc2nnc(C(F)(F)F)c(C)c2C(=O)Nc2cccc(S(C)(=N)=O)c2)c(Cl)c1F]
335
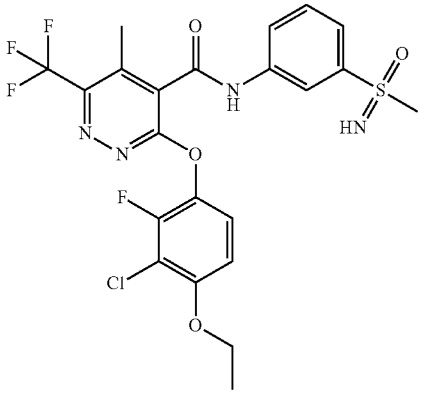 [SMILES: CCOc1ccc(Oc2nnc(C(F)(F)F)c(C)c2C(=O)Nc2cccc(S(C)(=N)=O)c2)c(F)c1Cl]
336
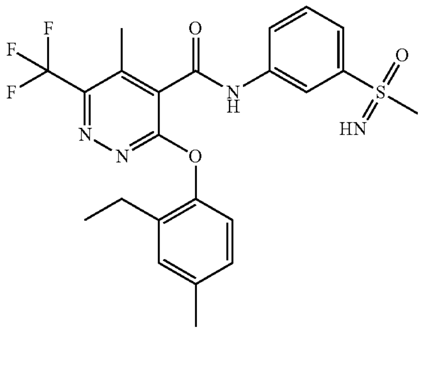 [SMILES: CCc1cc(C)ccc1Oc1nnc(C(F)(F)F)c(C)c1C(=O)Nc1cccc(S(C)(=N)=O)c1]

TABLE 14-continued
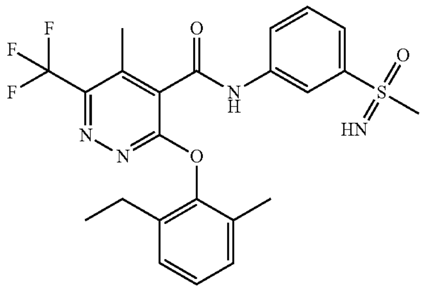 [SMILES: CCc1cccc(C)c1Oc1nnc(C(F)(F)F)c(C)c1C(=O)Nc1cccc(S(C)(=N)=O)c1]
337
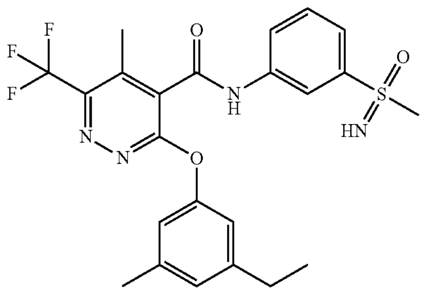 [SMILES: CCc1cc(C)cc(Oc2nnc(C(F)(F)F)c(C)c2C(=O)Nc2cccc(S(C)(=N)=O)c2)c1]
338
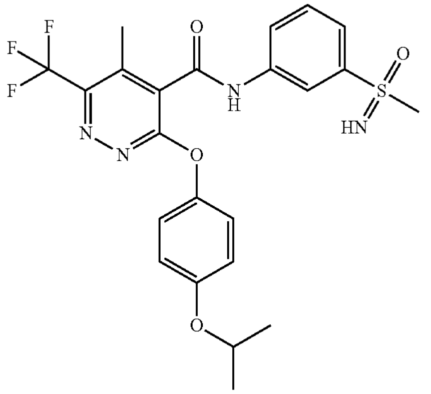 [SMILES: Cc1c(C(F)(F)F)nnc(Oc2ccc(OC(C)C)cc2)c1C(=O)Nc1cccc(S(C)(=N)=O)c1]
339
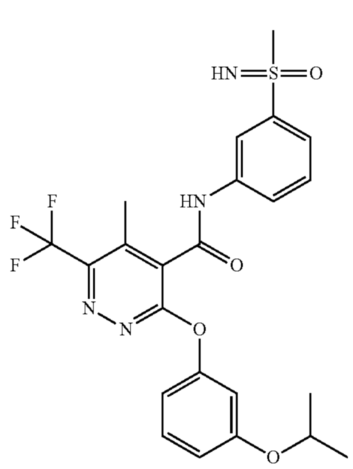 [SMILES: Cc1c(C(F)(F)F)nnc(Oc2cccc(OC(C)C)c2)c1C(=O)Nc1cccc(S(C)(=N)=O)c1]
340
TABLE 14-continued
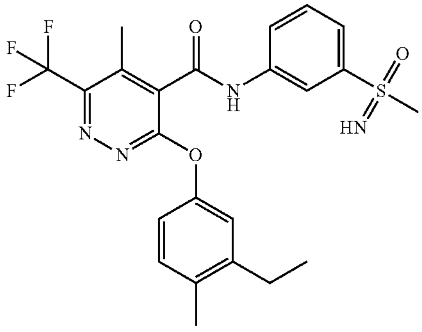 [SMILES: CCc1cc(Oc2nnc(C(F)(F)F)c(C)c2C(=O)Nc2cccc(S(C)(=N)=O)c2)ccc1C]
341
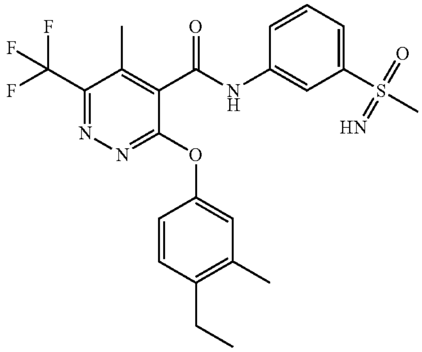 [SMILES: CCc1ccc(Oc2nnc(C(F)(F)F)c(C)c2C(=O)Nc2cccc(S(C)(=N)=O)c2)cc1C]
342
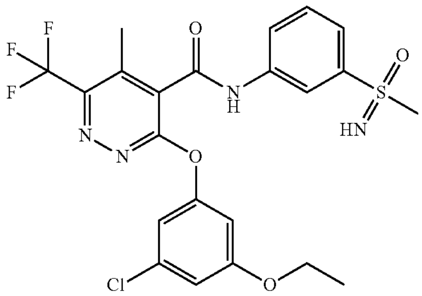 [SMILES: CCOc1cc(Cl)cc(Oc2nnc(C(F)(F)F)c(C)c2C(=O)Nc2cccc(S(C)(=N)=O)c2)c1]
343
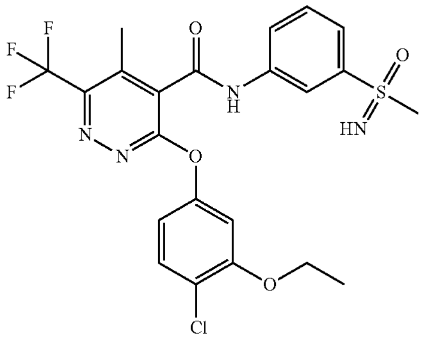 [SMILES: CCOc1cc(Oc2nnc(C(F)(F)F)c(C)c2C(=O)Nc2cccc(S(C)(=N)=O)c2)ccc1Cl]
344
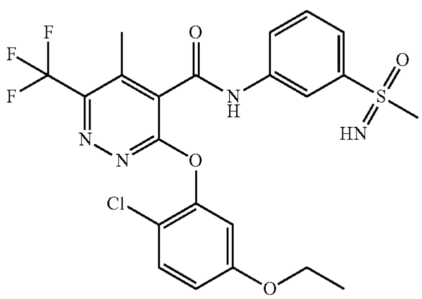 [SMILES: CCOc1ccc(Cl)c(Oc2nnc(C(F)(F)F)c(C)c2C(=O)Nc2cccc(S(C)(=N)=O)c2)c1]
345

TABLE 14-continued
346
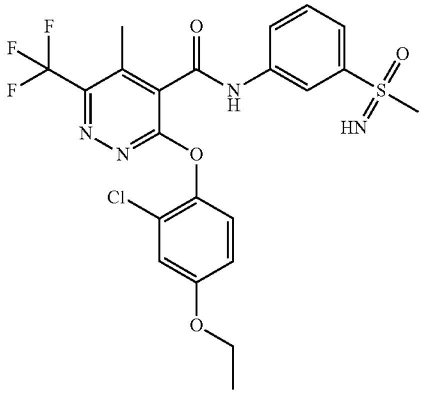 [SMILES: CCOc1ccc(Oc2nnc(C(F)(F)F)c(C)c2C(=O)Nc2cccc(S(C)(=N)=O)c2)c(Cl)c1]
347
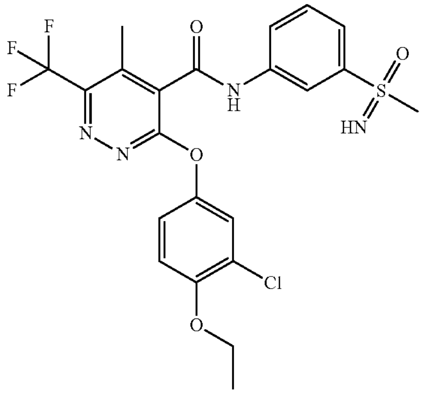 [SMILES: CCOc1ccc(Oc2nnc(C(F)(F)F)c(C)c2C(=O)Nc2cccc(S(C)(=N)=O)c2)cc1Cl]
348
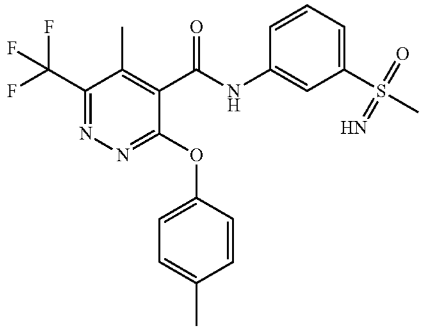 [SMILES: Cc1ccc(Oc2nnc(C(F)(F)F)c(C)c2C(=O)Nc2cccc(S(C)(=N)=O)c2)cc1]
349
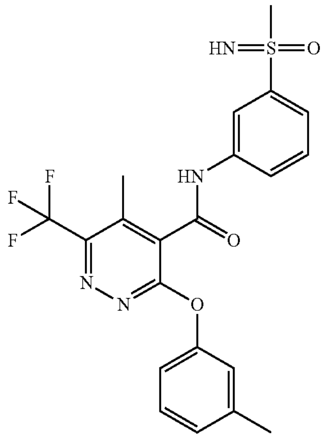 [SMILES: Cc1cccc(Oc2nnc(C(F)(F)F)c(C)c2C(=O)Nc2cccc(S(C)(=N)=O)c2)c1]
TABLE 14-continued
350
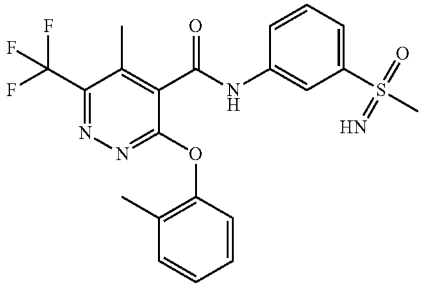 [SMILES: Cc1ccccc1Oc1nnc(C(F)(F)F)c(C)c1C(=O)Nc1cccc(S(C)(=N)=O)c1]
351
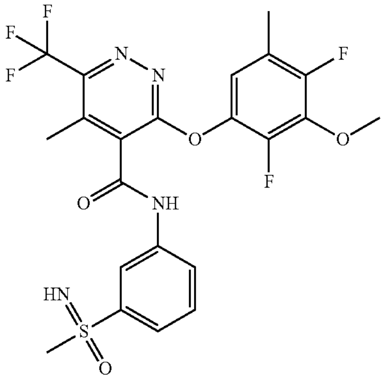 [SMILES: COc1c(F)c(C)cc(Oc2nnc(C(F)(F)F)c(C)c2C(=O)Nc2cccc(S(C)(=N)=O)c2)c1F]
352
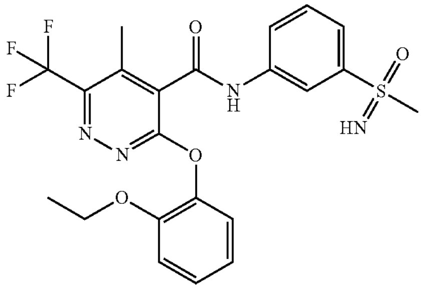 [SMILES: CCOc1ccccc1Oc1nnc(C(F)(F)F)c(C)c1C(=O)Nc1cccc(S(C)(=N)=O)c1]
353
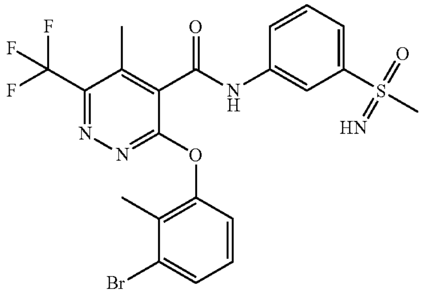 [SMILES: Cc1c(Br)cccc1Oc1nnc(C(F)(F)F)c(C)c1C(=O)Nc1cccc(S(C)(=N)=O)c1]
354
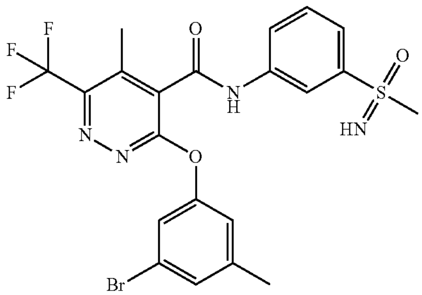

TABLE 14-continued
355
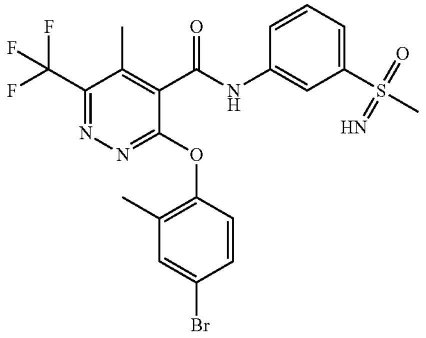 [SMILES: Cc1cc(Br)ccc1Oc1nnc(C(F)(F)F)c(C)c1C(=O)Nc1cccc(S(C)(=N)=O)c1]
356
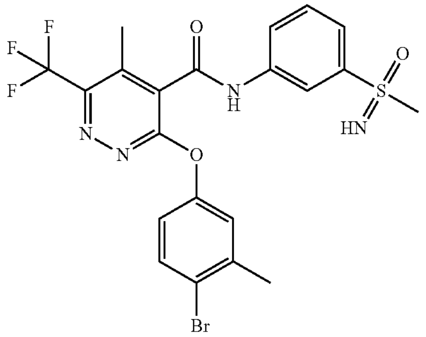 [SMILES: Cc1cc(Oc2nnc(C(F)(F)F)c(C)c2C(=O)Nc2cccc(S(C)(=N)=O)c2)ccc1Br]
357
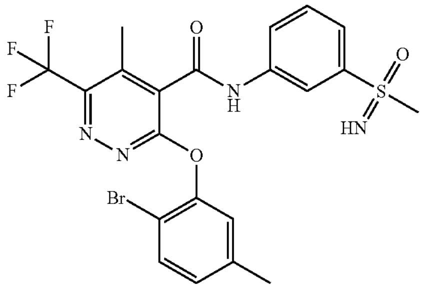 [SMILES: Cc1ccc(Br)c(Oc2nnc(C(F)(F)F)c(C)c2C(=O)Nc2cccc(S(C)(=N)=O)c2)c1]
358
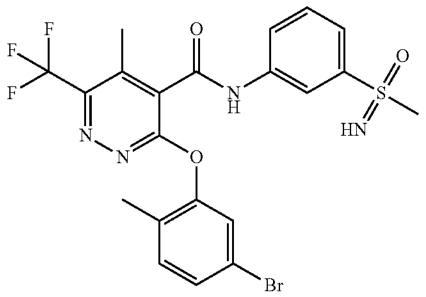 [SMILES: Cc1ccc(Br)cc1Oc1nnc(C(F)(F)F)c(C)c1C(=O)Nc1cccc(S(C)(=N)=O)c1]
359
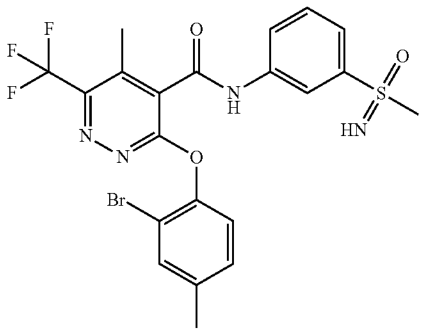 [SMILES: Cc1ccc(Oc2nnc(C(F)(F)F)c(C)c2C(=O)Nc2cccc(S(C)(=N)=O)c2)c(Br)c1]
TABLE 14-continued
360
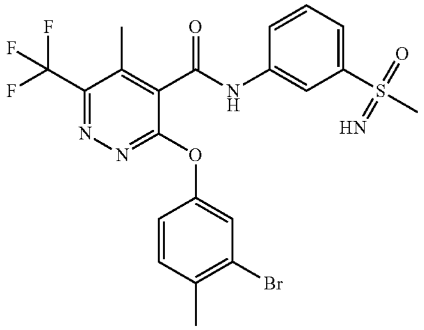 [SMILES: Cc1ccc(Oc2nnc(C(F)(F)F)c(C)c2C(=O)Nc2cccc(S(C)(=N)=O)c2)cc1Br]
361
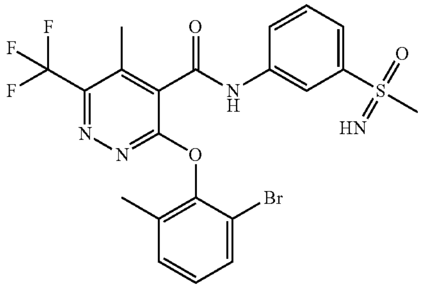 [SMILES: Cc1cccc(Br)c1Oc1nnc(C(F)(F)F)c(C)c1C(=O)Nc1cccc(S(C)(=N)=O)c1]
362
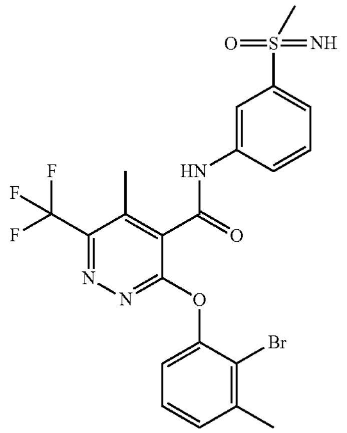 [SMILES: Cc1cccc(Oc2nnc(C(F)(F)F)c(C)c2C(=O)Nc2cccc(S(C)(=N)=O)c2)c1Br]
363
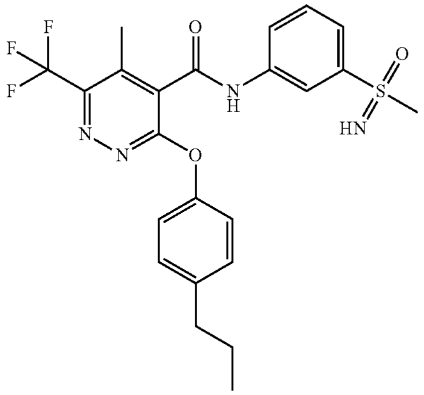 [SMILES: CCCc1ccc(Oc2nnc(C(F)(F)F)c(C)c2C(=O)Nc2cccc(S(C)(=N)=O)c2)cc1]

TABLE 14-continued
364
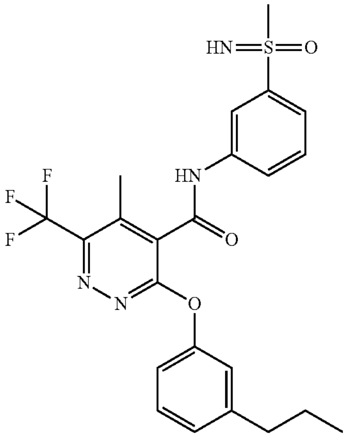 [SMILES: CCCc1cccc(Oc2nnc(C(F)(F)F)c(C)c2C(=O)Nc2cccc(S(C)(=N)=O)c2)c1]
365
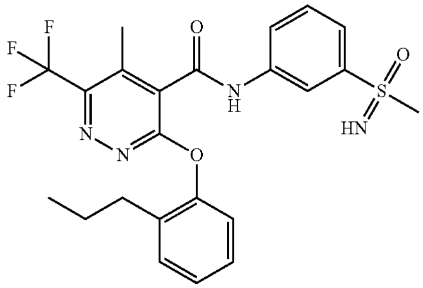 [SMILES: CCCc1ccccc1Oc1nnc(C(F)(F)F)c(C)c1C(=O)Nc1cccc(S(C)(=N)=O)c1]
368
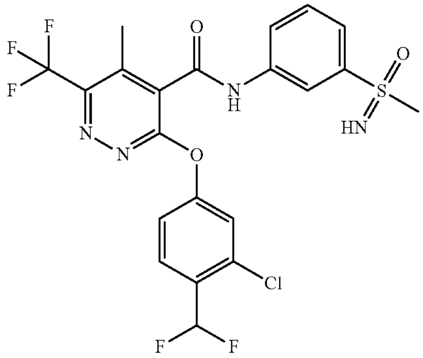
369
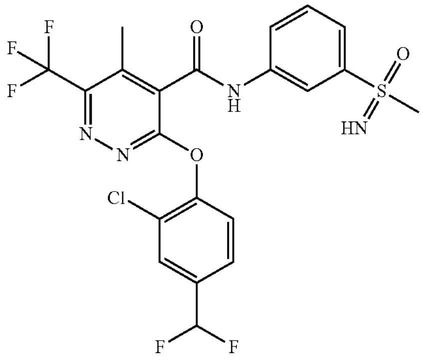 [SMILES: Cc1c(C(F)(F)F)nnc(Oc2ccc(C(F)F)cc2Cl)c1C(=O)Nc1cccc(S(C)(=N)=O)c1]
TABLE 14-continued
371
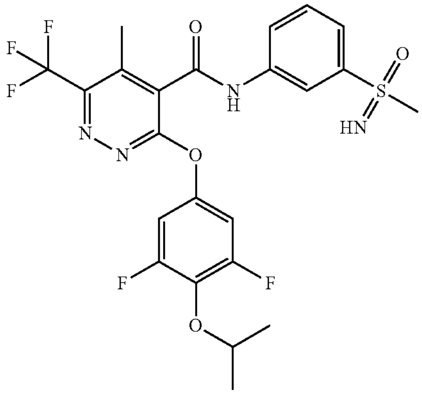 [SMILES: Cc1c(C(F)(F)F)nnc(Oc2cc(F)c(OC(C)C)c(F)c2)c1C(=O)Nc1cccc(S(C)(=N)=O)c1]
372
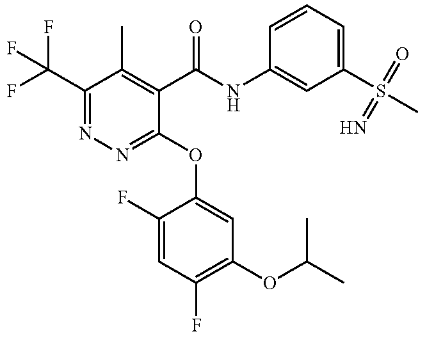 [SMILES: Cc1c(C(F)(F)F)nnc(Oc2cc(OC(C)C)c(F)cc2F)c1C(=O)Nc1cccc(S(C)(=N)=O)c1]
373
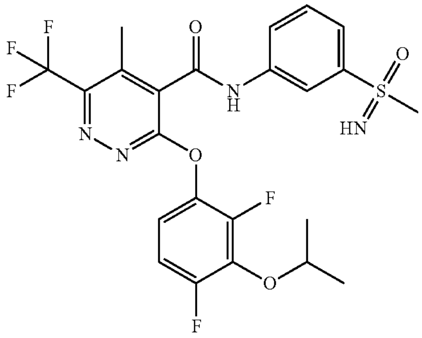 [SMILES: Cc1c(C(F)(F)F)nnc(Oc2ccc(F)c(OC(C)C)c2F)c1C(=O)Nc1cccc(S(C)(=N)=O)c1]
374
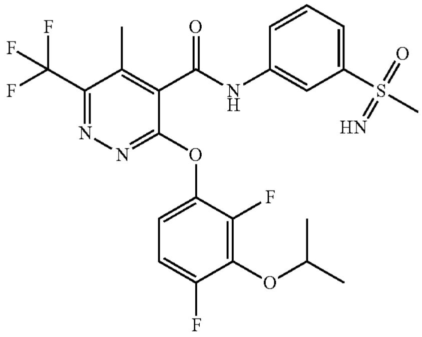 [SMILES: Cc1c(C(F)(F)F)nnc(Oc2ccc(F)c(OC(C)C)c2F)c1C(=O)Nc1cccc(S(C)(=N)=O)c1]

TABLE 14-continued
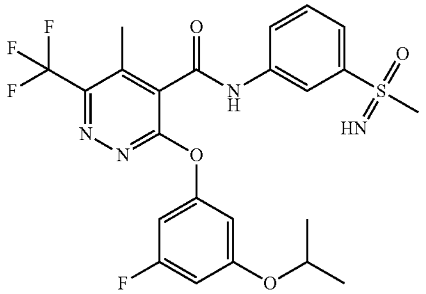 [SMILES: Cc1c(C(F)(F)F)nnc(Oc2cc(F)cc(OC(C)C)c2)c1C(=O)Nc1cccc(S(C)(=N)=O)c1]
375
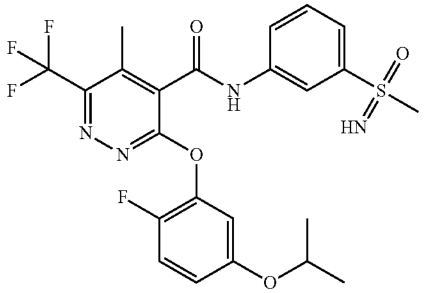 [SMILES: Cc1c(C(F)(F)F)nnc(Oc2cc(OC(C)C)ccc2F)c1C(=O)Nc1cccc(S(C)(=N)=O)c1]
376
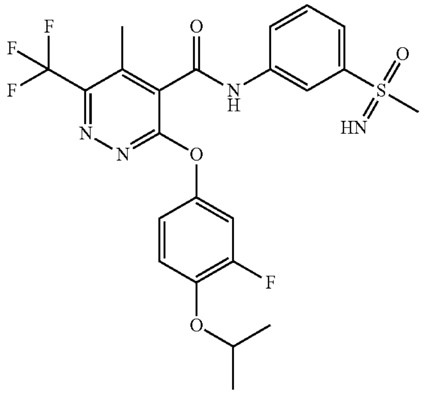 [SMILES: Cc1c(C(F)(F)F)nnc(Oc2ccc(OC(C)C)c(F)c2)c1C(=O)Nc1cccc(S(C)(=N)=O)c1]
377
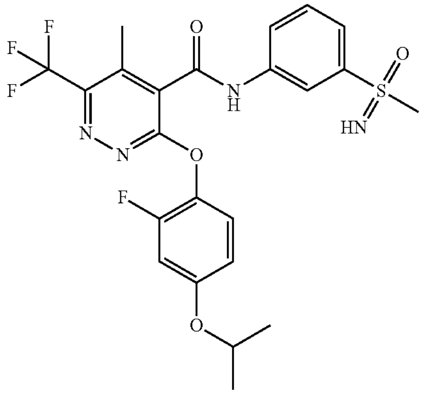 [SMILES: Cc1c(C(F)(F)F)nnc(Oc2ccc(OC(C)C)cc2F)c1C(=O)Nc1cccc(S(C)(=N)=O)c1]
378
TABLE 14-continued
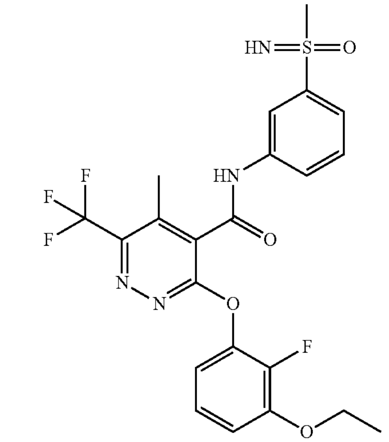 [SMILES: CCOc1cccc(Oc2nnc(C(F)(F)F)c(C)c2C(=O)Nc2cccc(S(C)(=N)=O)c2)c1F]
379
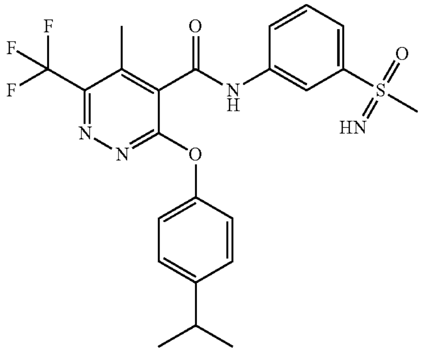 [SMILES: Cc1c(C(F)(F)F)nnc(Oc2ccc(C(C)C)cc2)c1C(=O)Nc1cccc(S(C)(=N)=O)c1]
380
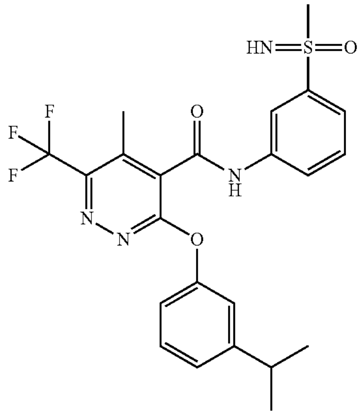 [SMILES: Cc1c(C(F)(F)F)nnc(Oc2cccc(C(C)C)c2)c1C(=O)Nc1cccc(S(C)(=N)=O)c1]
381
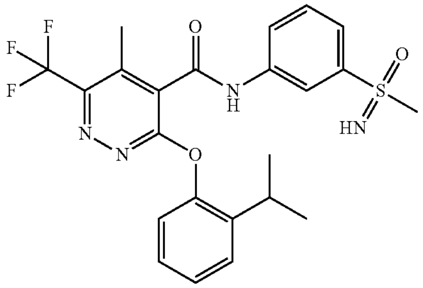 [SMILES: Cc1c(C(F)(F)F)nnc(Oc2ccccc2C(C)C)c1C(=O)Nc1cccc(S(C)(=N)=O)c1]
382

TABLE 14-continued
383
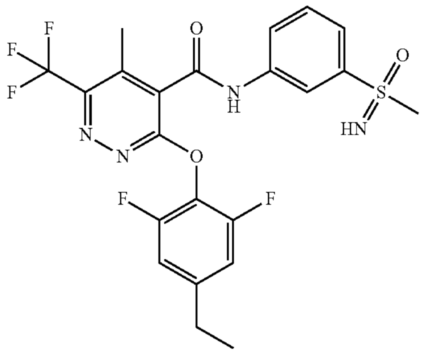 [SMILES: CCc1cc(F)c(Oc2nnc(C(F)(F)F)c(C)c2C(=O)Nc2cccc(S(C)(=N)=O)c2)c(F)c1]
384
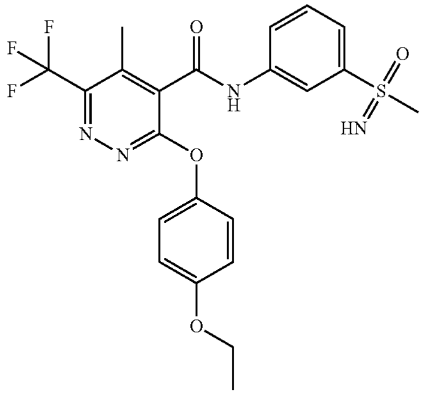 [SMILES: CCOc1ccc(Oc2nnc(C(F)(F)F)c(C)c2C(=O)Nc2cccc(S(C)(=N)=O)c2)cc1]
385
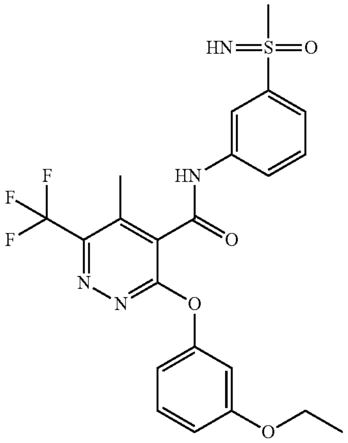 [SMILES: CCOc1cccc(Oc2nnc(C(F)(F)F)c(C)c2C(=O)Nc2cccc(S(C)(=N)=O)c2)c1]
390
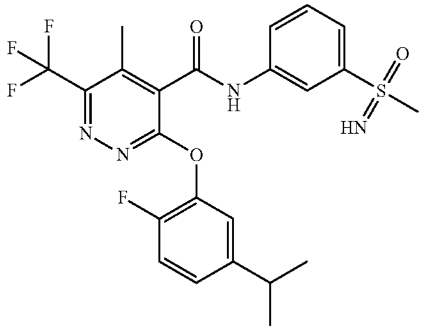 [SMILES: Cc1c(C(F)(F)F)nnc(Oc2cc(C(C)C)ccc2F)c1C(=O)Nc1cccc(S(C)(=N)=O)c1]
391
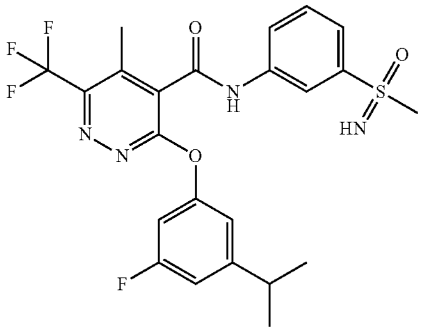 [SMILES: Cc1c(C(F)(F)F)nnc(Oc2cc(F)cc(C(C)C)c2)c1C(=O)Nc1cccc(S(C)(=N)=O)c1]
392
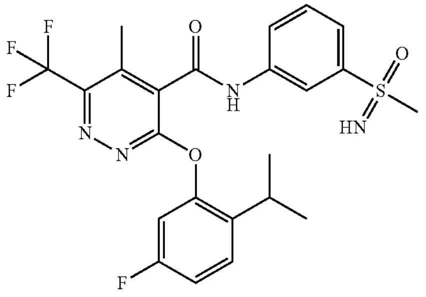 [SMILES: Cc1c(C(F)(F)F)nnc(Oc2cc(F)ccc2C(C)C)c1C(=O)Nc1cccc(S(C)(=N)=O)c1]
393
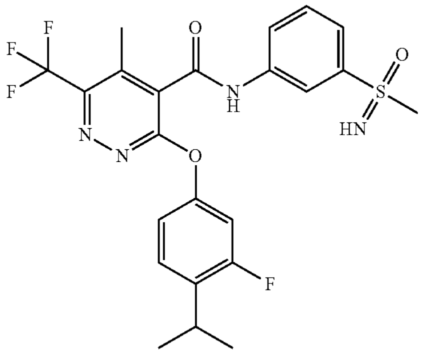 [SMILES: Cc1c(C(F)(F)F)nnc(Oc2ccc(C(C)C)c(F)c2)c1C(=O)Nc1cccc(S(C)(=N)=O)c1]
394
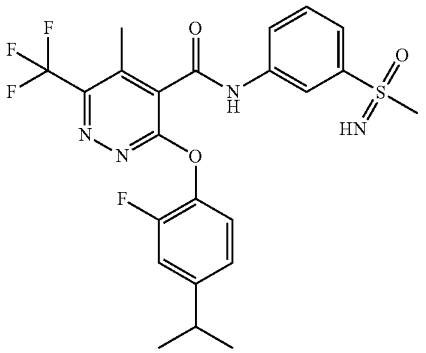 [SMILES: Cc1c(C(F)(F)F)nnc(Oc2ccc(C(C)C)cc2F)c1C(=O)Nc1cccc(S(C)(=N)=O)c1]

TABLE 14-continued
395
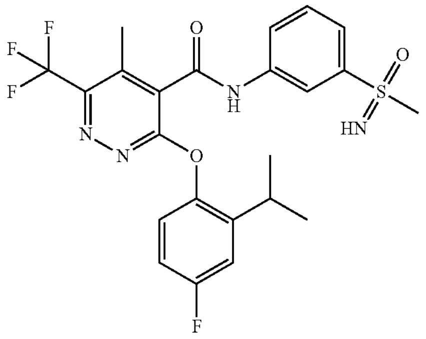 [SMILES: Cc1c(C(F)(F)F)nnc(Oc2ccc(F)cc2C(C)C)c1C(=O)Nc1cccc(S(C)(=N)=O)c1]
396
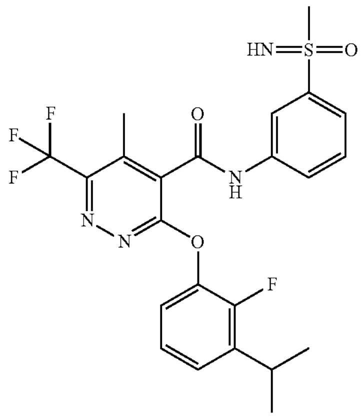 [SMILES: Cc1c(C(F)(F)F)nnc(Oc2cccc(C(C)C)c2F)c1C(=O)Nc1cccc(S(C)(=N)=O)c1]
402
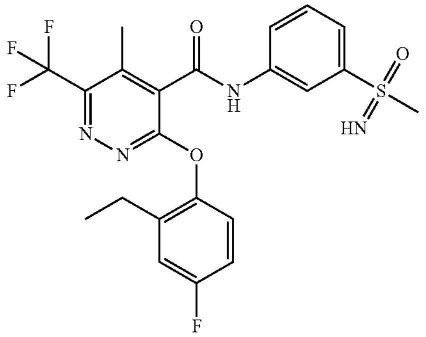 [SMILES: CCc1cc(F)ccc1Oc1nnc(C(F)(F)F)c(C)c1C(=O)Nc1cccc(S(C)(=N)=O)c1]
403
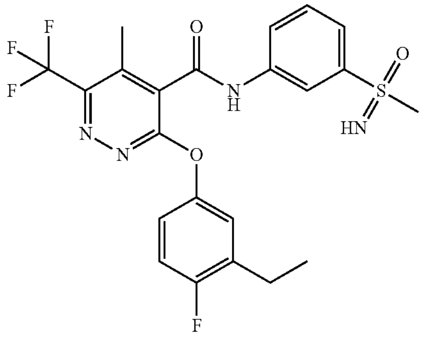 [SMILES: CCc1cc(Oc2nnc(C(F)(F)F)c(C)c2C(=O)Nc2cccc(S(C)(=N)=O)c2)ccc1F]
TABLE 14-continued
404
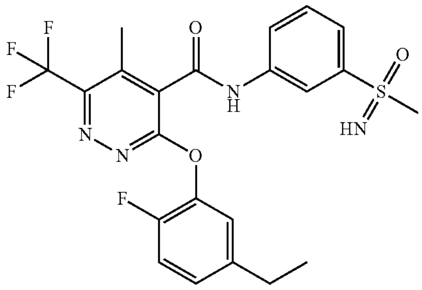 [SMILES: CCc1ccc(F)c(Oc2nnc(C(F)(F)F)c(C)c2C(=O)Nc2cccc(S(C)(=N)=O)c2)c1]
405
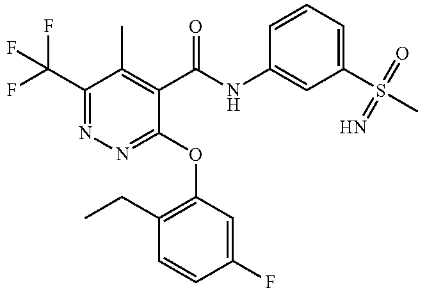 [SMILES: CCc1ccc(F)cc1Oc1nnc(C(F)(F)F)c(C)c1C(=O)Nc1cccc(S(C)(=N)=O)c1]
406
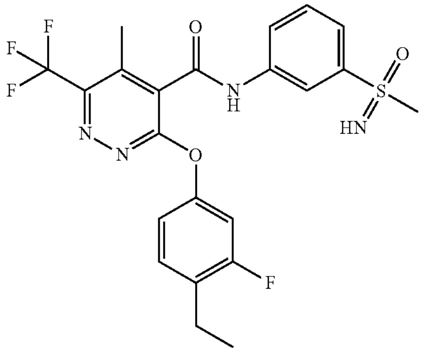
407
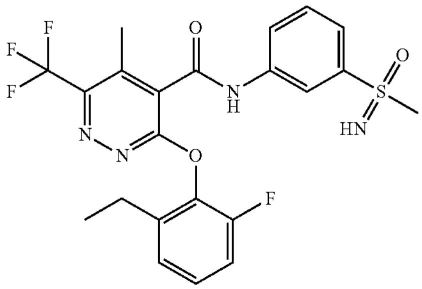 [SMILES: CCc1cccc(F)c1Oc1nnc(C(F)(F)F)c(C)c1C(=O)Nc1cccc(S(C)(=N)=O)c1]

TABLE 14-continued
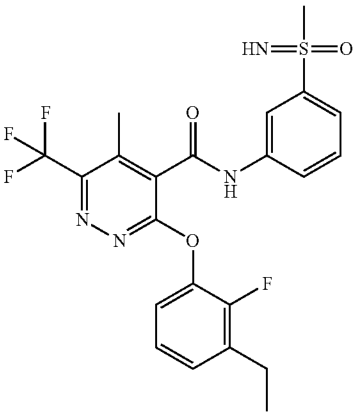 [SMILES: CCc1cccc(Oc2nnc(C(F)(F)F)c(C)c2C(=O)Nc2cccc(S(C)(=N)=O)c2)c1F]
408
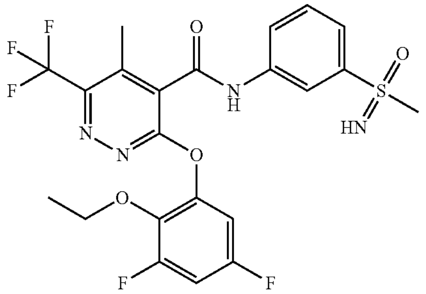 [SMILES: CCOc1c(F)cc(F)cc1Oc1nnc(C(F)(F)F)c(C)c1C(=O)Nc1cccc(S(C)(=N)=O)c1]
416
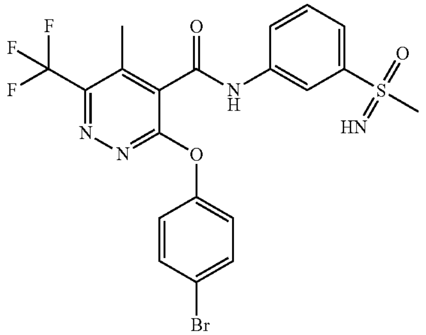 [SMILES: Cc1c(C(F)(F)F)nnc(Oc2ccc(Br)cc2)c1C(=O)Nc1cccc(S(C)(=N)=O)c1]
428
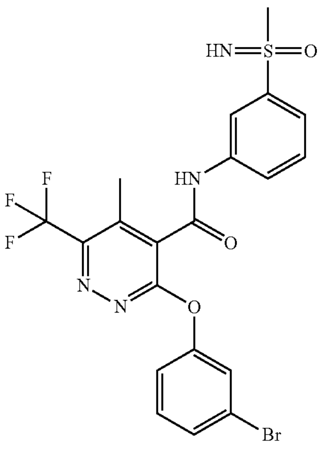 [SMILES: Cc1c(C(F)(F)F)nnc(Oc2cccc(Br)c2)c1C(=O)Nc1cccc(S(C)(=N)=O)c1]
429
TABLE 14-continued
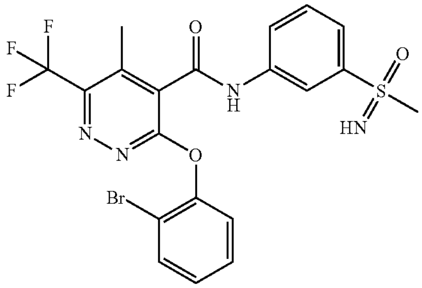 [SMILES: Cc1c(C(F)(F)F)nnc(Oc2ccccc2Br)c1C(=O)Nc1cccc(S(C)(=N)=O)c1]
430
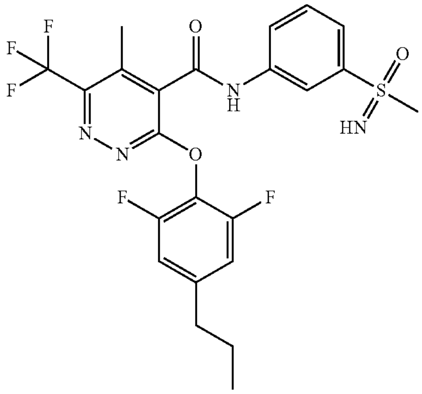 [SMILES: CCCc1cc(F)c(Oc2nnc(C(F)(F)F)c(C)c2C(=O)Nc2cccc(S(C)(=N)=O)c2)c(F)c1]
431
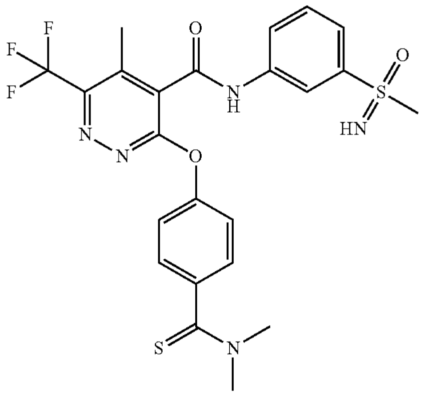 [SMILES: Cc1c(C(F)(F)F)nnc(Oc2ccc(C(=S)N(C)C)cc2)c1C(=O)Nc1cccc(S(C)(=N)=O)c1]
432
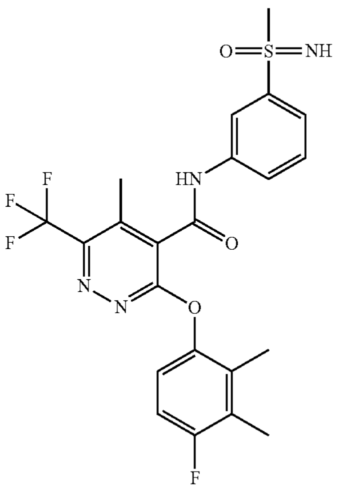 [SMILES: Cc1c(F)ccc(Oc2nnc(C(F)(F)F)c(C)c2C(=O)Nc2cccc(S(C)(=N)=O)c2)c1C]
433

TABLE 14-continued
434
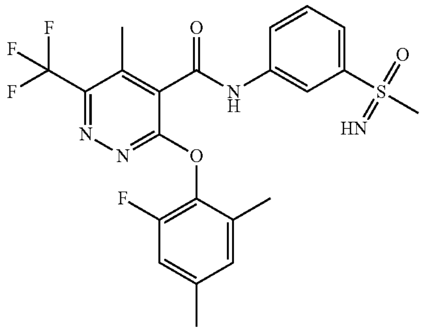 [SMILES: Cc1cc(C)c(Oc2nnc(C(F)(F)F)c(C)c2C(=O)Nc2cccc(S(C)(=N)=O)c2)c(F)c1]
435
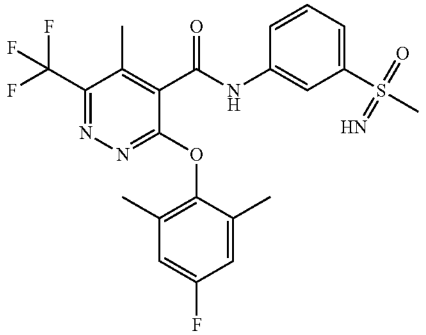 [SMILES: Cc1cc(F)cc(C)c1Oc1nnc(C(F)(F)F)c(C)c1C(=O)Nc1cccc(S(C)(=N)=O)c1]
436
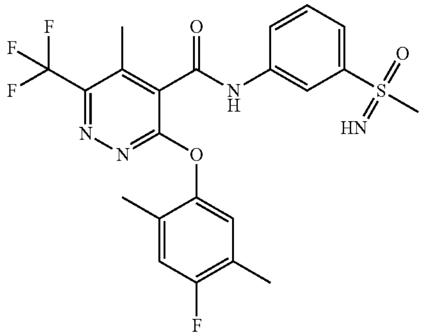 [SMILES: Cc1cc(Oc2nnc(C(F)(F)F)c(C)c2C(=O)Nc2cccc(S(C)(=N)=O)c2)c(C)cc1F]
437
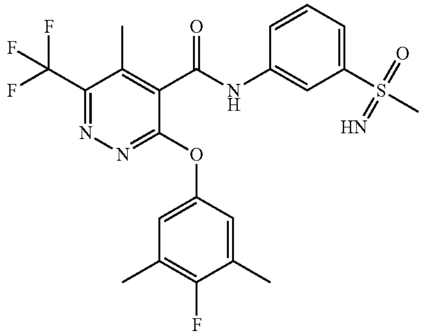 [SMILES: Cc1cc(Oc2nnc(C(F)(F)F)c(C)c2C(=O)Nc2cccc(S(C)(=N)=O)c2)cc(C)c1F]
TABLE 14-continued
438
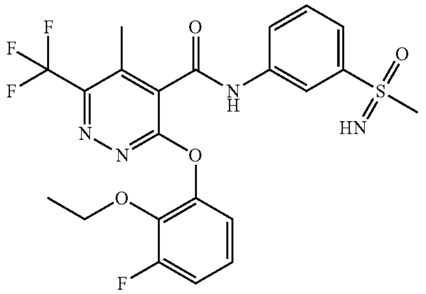 [SMILES: CCOc1c(F)cccc1Oc1nnc(C(F)(F)F)c(C)c1C(=O)Nc1cccc(S(C)(=N)=O)c1]
439
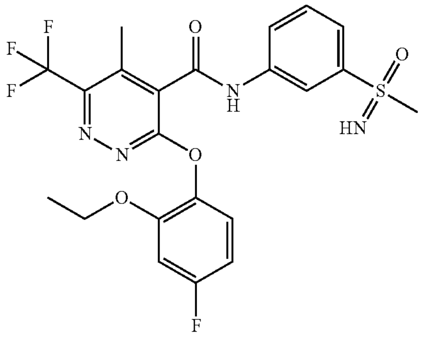 [SMILES: CCOc1cc(F)ccc1Oc1nnc(C(F)(F)F)c(C)c1C(=O)Nc1cccc(S(C)(=N)=O)c1]
440
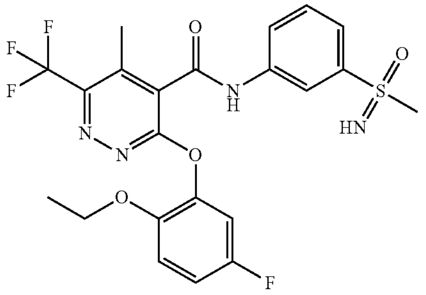 [SMILES: CCOc1ccc(F)cc1Oc1nnc(C(F)(F)F)c(C)c1C(=O)Nc1cccc(S(C)(=N)=O)c1]
441
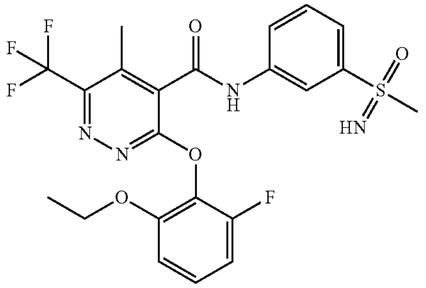 [SMILES: CCOc1cccc(F)c1Oc1nnc(C(F)(F)F)c(C)c1C(=O)Nc1cccc(S(C)(=N)=O)c1]
443
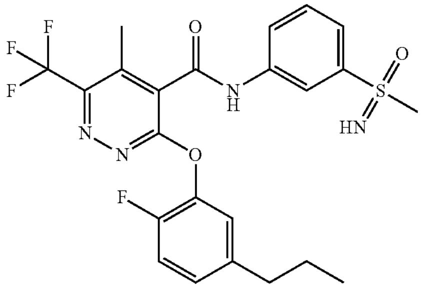 [SMILES: CCCc1ccc(F)c(Oc2nnc(C(F)(F)F)c(C)c2C(=O)Nc2cccc(S(C)(=N)=O)c2)c1]

TABLE 14-continued
444
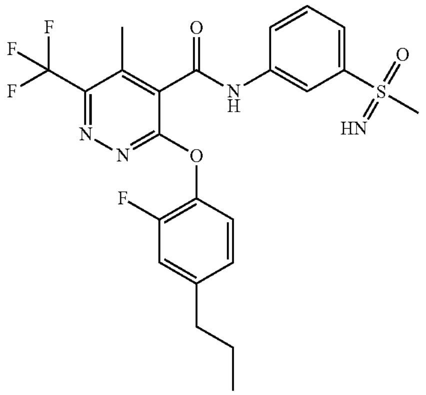 [SMILES: CCCc1ccc(Oc2nnc(C(F)(F)F)c(C)c2C(=O)Nc2cccc(S(C)(=N)=O)c2)c(F)c1]
445
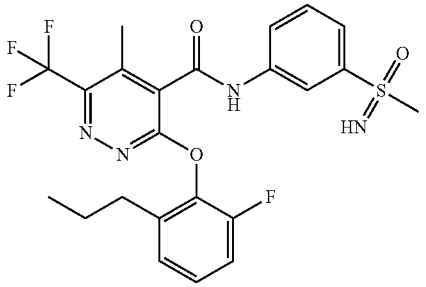 [SMILES: CCCc1cccc(F)c1Oc1nnc(C(F)(F)F)c(C)c1C(=O)Nc1cccc(S(C)(=N)=O)c1]
451
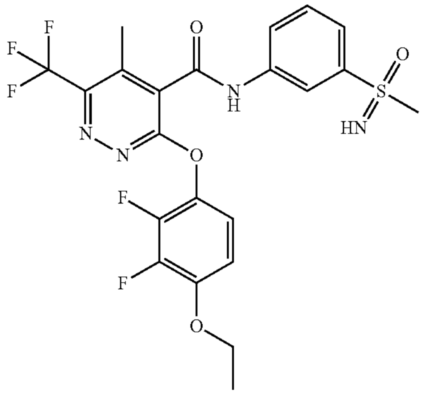 [SMILES: CCOc1ccc(Oc2nnc(C(F)(F)F)c(C)c2C(=O)Nc2cccc(S(C)(=N)=O)c2)c(F)c1F]
452
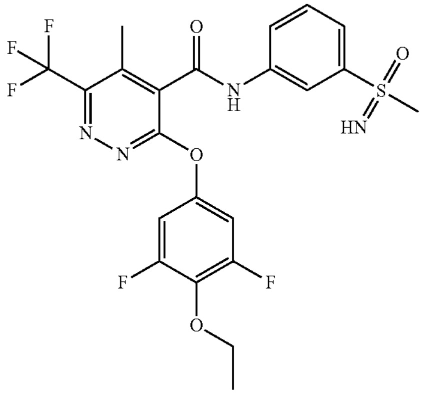 [SMILES: CCOc1c(F)cc(Oc2nnc(C(F)(F)F)c(C)c2C(=O)Nc2cccc(S(C)(=N)=O)c2)cc1F]
TABLE 14-continued
453
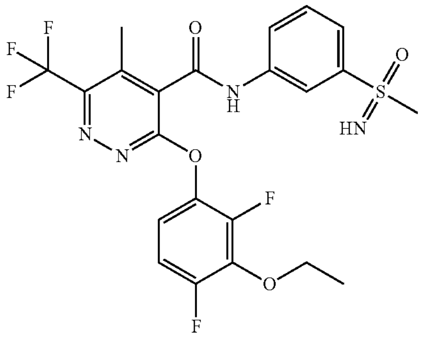 [SMILES: CCOc1c(F)ccc(Oc2nnc(C(F)(F)F)c(C)c2C(=O)Nc2cccc(S(C)(=N)=O)c2)c1F]
454
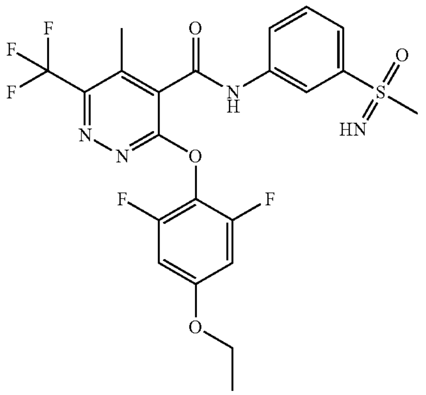 [SMILES: CCOc1cc(F)c(Oc2nnc(C(F)(F)F)c(C)c2C(=O)Nc2cccc(S(C)(=N)=O)c2)c(F)c1]
455
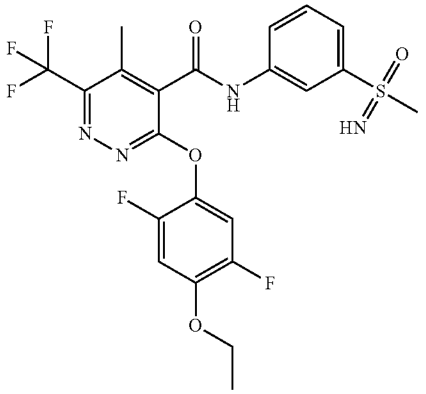 [SMILES: CCOc1cc(F)c(Oc2nnc(C(F)(F)F)c(C)c2C(=O)Nc2cccc(S(C)(=N)=O)c2)cc1F]
456
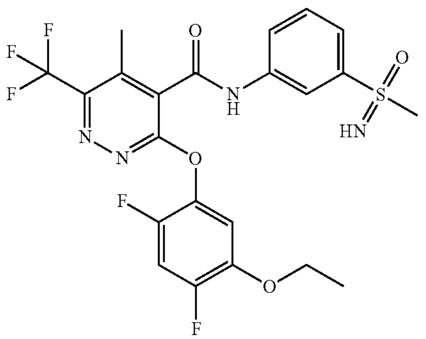 [SMILES: CCOc1cc(Oc2nnc(C(F)(F)F)c(C)c2C(=O)Nc2cccc(S(C)(=N)=O)c2)c(F)cc1F]

TABLE 14-continued
457
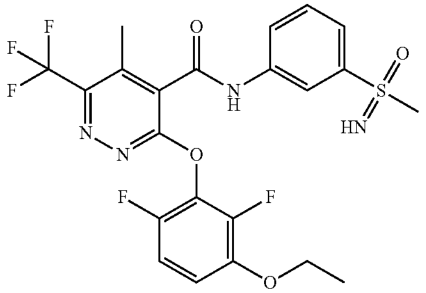 [SMILES: CCOc1ccc(F)c(Oc2nnc(C(F)(F)F)c(C)c2C(=O)Nc2cccc(S(C)(=N)=O)c2)c1F]
458
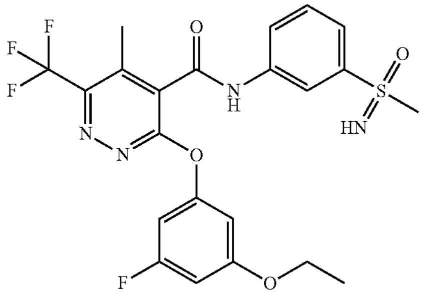 [SMILES: CCOc1cc(F)cc(Oc2nnc(C(F)(F)F)c(C)c2C(=O)Nc2cccc(S(C)(=N)=O)c2)c1]
459
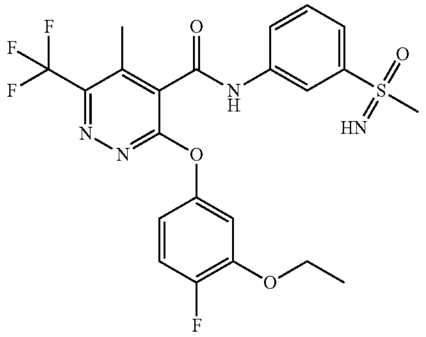 [SMILES: CCOc1cc(Oc2nnc(C(F)(F)F)c(C)c2C(=O)Nc2cccc(S(C)(=N)=O)c2)ccc1F]
460
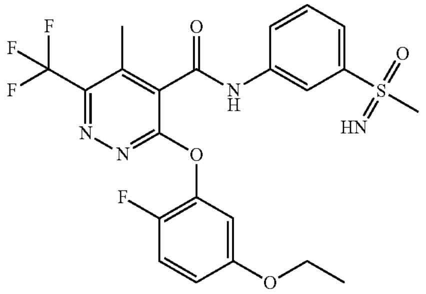 [SMILES: CCOc1ccc(F)c(Oc2nnc(C(F)(F)F)c(C)c2C(=O)Nc2cccc(S(C)(=N)=O)c2)c1]
461
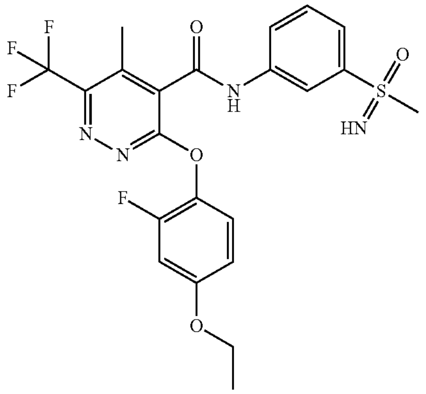 [SMILES: CCOc1ccc(Oc2nnc(C(F)(F)F)c(C)c2C(=O)Nc2cccc(S(C)(=N)=O)c2)c(F)c1]
TABLE 14-continued
462
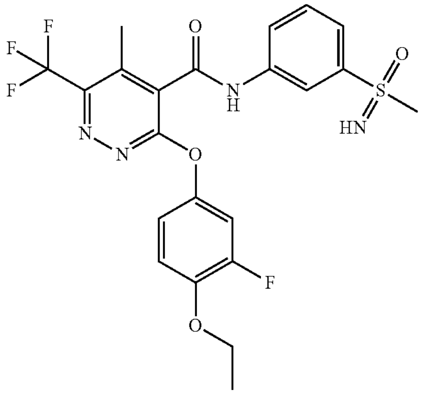 [SMILES: CCOc1ccc(Oc2nnc(C(F)(F)F)c(C)c2C(=O)Nc2cccc(S(C)(=N)=O)c2)cc1F]
463
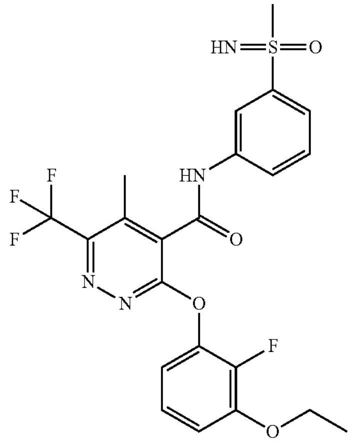 [SMILES: CCOc1cccc(Oc2nnc(C(F)(F)F)c(C)c2C(=O)Nc2cccc(S(C)(=N)=O)c2)c1F]
471
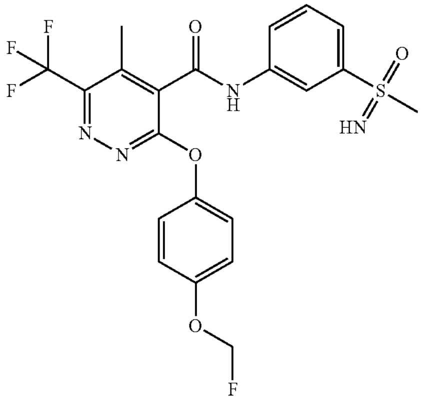 [SMILES: Cc1c(C(F)(F)F)nnc(Oc2ccc(OCF)cc2)c1C(=O)Nc1cccc(S(C)(=N)=O)c1]
472
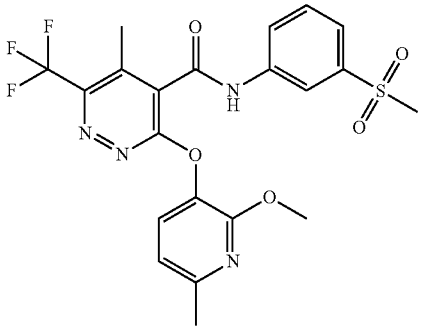 [SMILES: COc1nc(C)ccc1Oc1nnc(C(F)(F)F)c(C)c1C(=O)Nc1cccc(S(C)(=O)=O)c1]

TABLE 14-continued
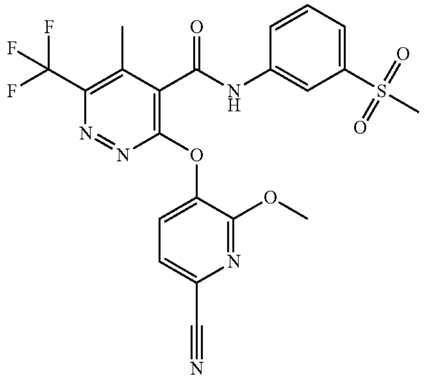 [SMILES: COc1nc(C#N)ccc1Oc1nnc(C(F)(F)F)c(C)c1C(=O)Nc1cccc(S(C)(=O)=O)c1]
473
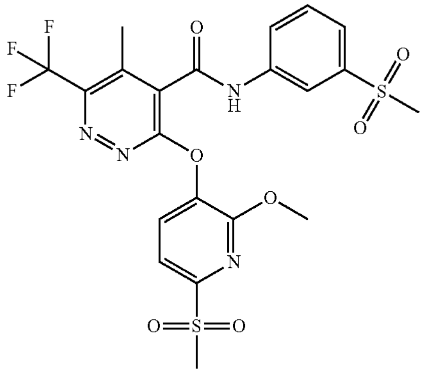 [SMILES: COc1nc(S(C)(=O)=O)ccc1Oc1nnc(C(F)(F)F)c(C)c1C(=O)Nc1cccc(S(C)(=O)=O)c1]
474
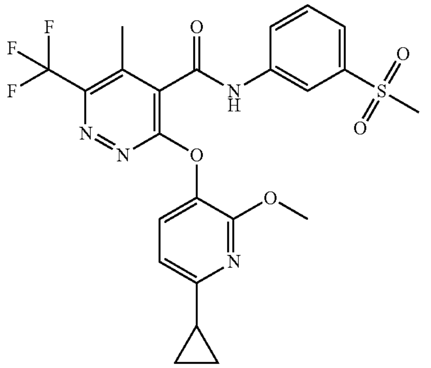 [SMILES: COc1nc(C2CC2)ccc1Oc1nnc(C(F)(F)F)c(C)c1C(=O)Nc1cccc(S(C)(=O)=O)c1]
475
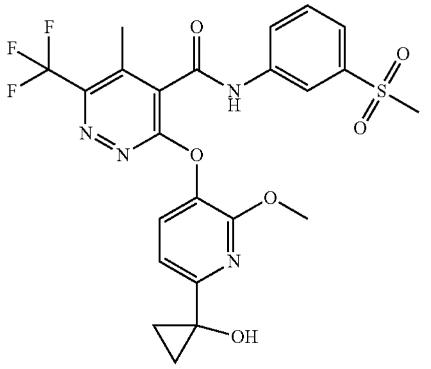 [SMILES: COc1nc(C2(O)CC2)ccc1Oc1nnc(C(F)(F)F)c(C)c1C(=O)Nc1cccc(S(C)(=O)=O)c1]
476
TABLE 14-continued
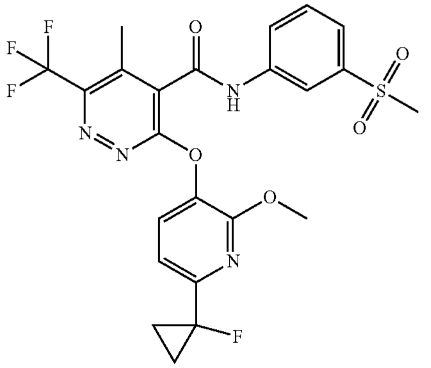 [SMILES: COc1nc(C2(F)CC2)ccc1Oc1nnc(C(F)(F)F)c(C)c1C(=O)Nc1cccc(S(C)(=O)=O)c1]
477
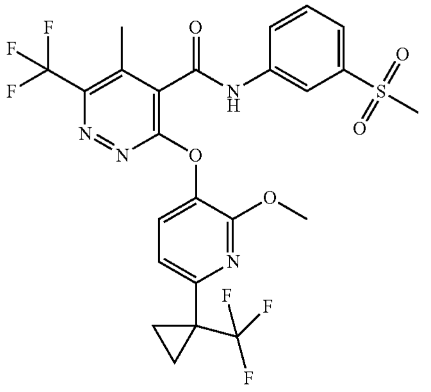 [SMILES: COc1nc(C2(C(F)(F)F)CC2)ccc1Oc1nnc(C(F)(F)F)c(C)c1C(=O)Nc1cccc(S(C)(=O)=O)c1]
478
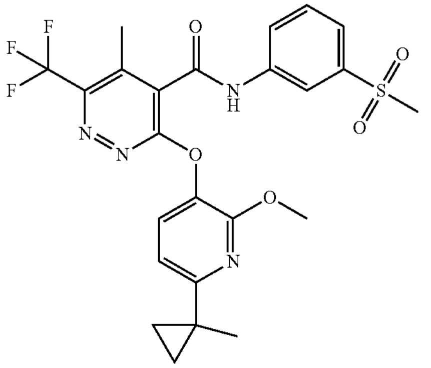 [SMILES: COc1nc(C2(C)CC2)ccc1Oc1nnc(C(F)(F)F)c(C)c1C(=O)Nc1cccc(S(C)(=O)=O)c1]
479
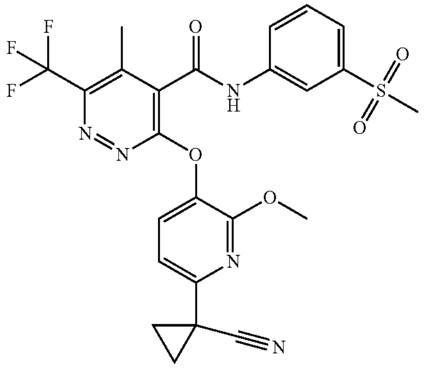 [SMILES: COc1nc(C2(C#N)CC2)ccc1Oc1nnc(C(F)(F)F)c(C)c1C(=O)Nc1cccc(S(C)(=O)=O)c1]
480

TABLE 14-continued
481
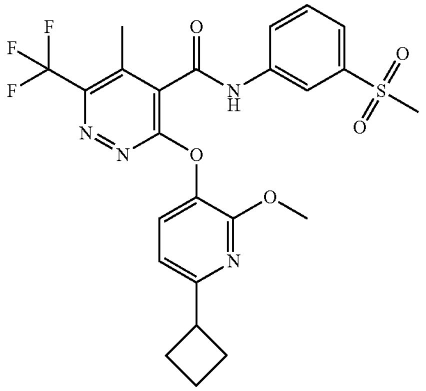 [SMILES: COc1nc(C2CCC2)ccc1Oc1nnc(C(F)(F)F)c(C)c1C(=O)Nc1cccc(S(C)(=O)=O)c1]
482
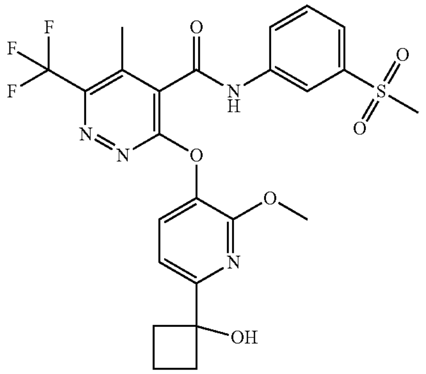 [SMILES: COc1nc(C2(O)CCC2)ccc1Oc1nnc(C(F)(F)F)c(C)c1C(=O)Nc1cccc(S(C)(=O)=O)c1]
483
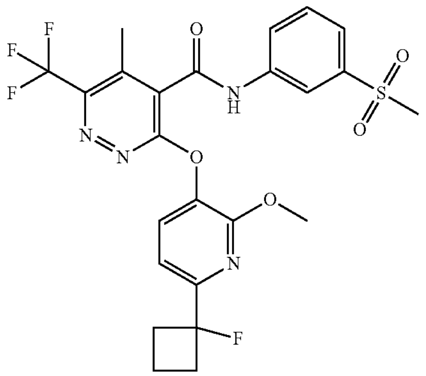 [SMILES: COc1nc(C2(F)CCC2)ccc1Oc1nnc(C(F)(F)F)c(C)c1C(=O)Nc1cccc(S(C)(=O)=O)c1]
484
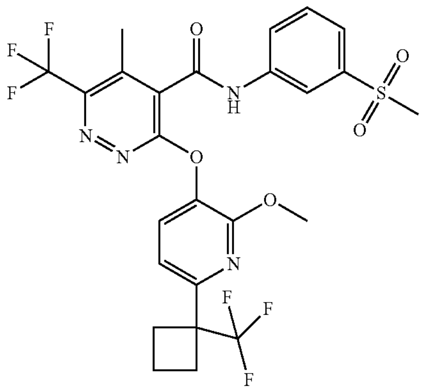 [SMILES: COc1nc(C2(C(F)(F)F)CCC2)ccc1Oc1nnc(C(F)(F)F)c(C)c1C(=O)Nc1cccc(S(C)(=O)=O)c1]
TABLE 14-continued
485
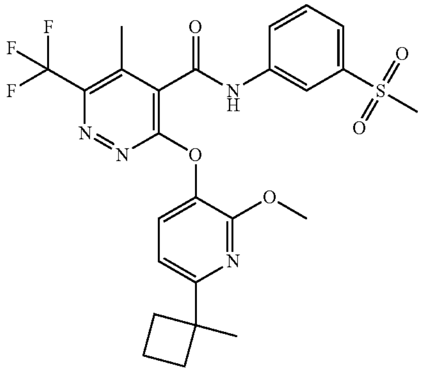 [SMILES: COc1nc(C2(C)CCC2)ccc1Oc1nnc(C(F)(F)F)c(C)c1C(=O)Nc1cccc(S(C)(=O)=O)c1]
486
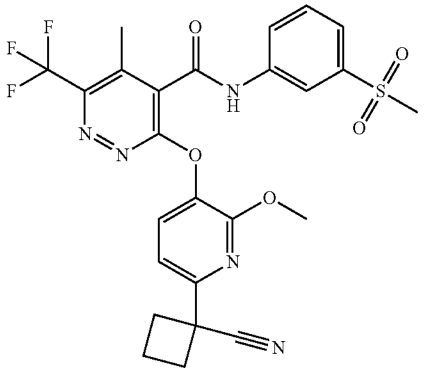 [SMILES: COc1nc(C2(C#N)CCC2)ccc1Oc1nnc(C(F)(F)F)c(C)c1C(=O)Nc1cccc(S(C)(=O)=O)c1]
487
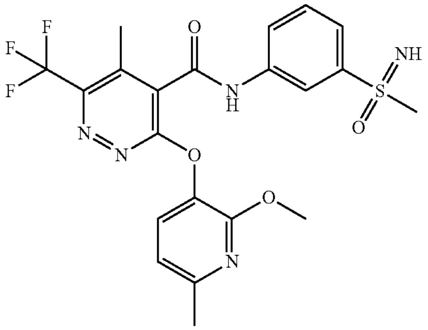 [SMILES: COc1nc(C)ccc1Oc1nnc(C(F)(F)F)c(C)c1C(=O)Nc1cccc(S(C)(=N)=O)c1]
488
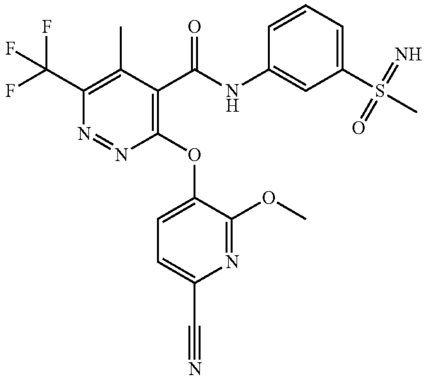 [SMILES: COc1nc(C#N)ccc1Oc1nnc(C(F)(F)F)c(C)c1C(=O)Nc1cccc(S(C)(=N)=O)c1]

TABLE 14-continued
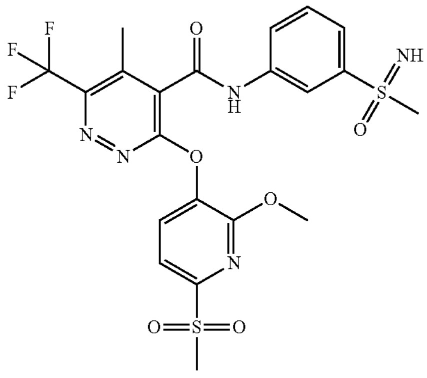 [SMILES: COc1nc(S(C)(=O)=O)ccc1Oc1nnc(C(F)(F)F)c(C)c1C(=O)Nc1cccc(S(C)(=N)=O)c1]
489
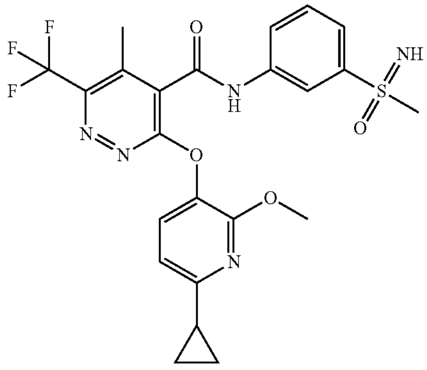 [SMILES: COc1nc(C2CC2)ccc1Oc1nnc(C(F)(F)F)c(C)c1C(=O)Nc1cccc(S(C)(=N)=O)c1]
490
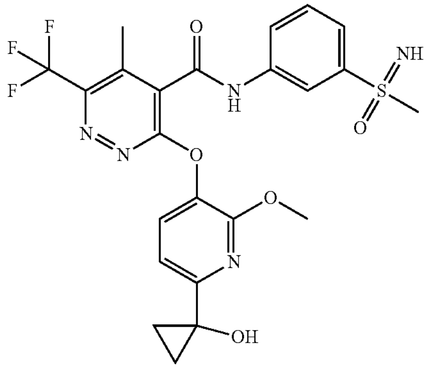 [SMILES: COc1nc(C2(O)CC2)ccc1Oc1nnc(C(F)(F)F)c(C)c1C(=O)Nc1cccc(S(C)(=N)=O)c1]
491
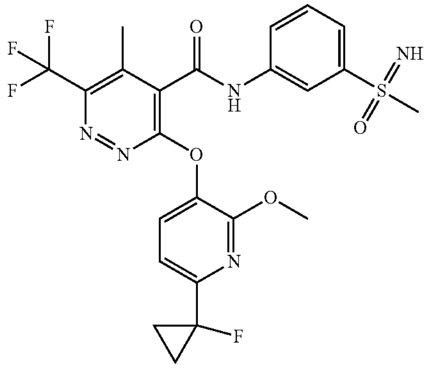 [SMILES: COc1nc(C2(F)CC2)ccc1Oc1nnc(C(F)(F)F)c(C)c1C(=O)Nc1cccc(S(C)(=N)=O)c1]
492
TABLE 14-continued
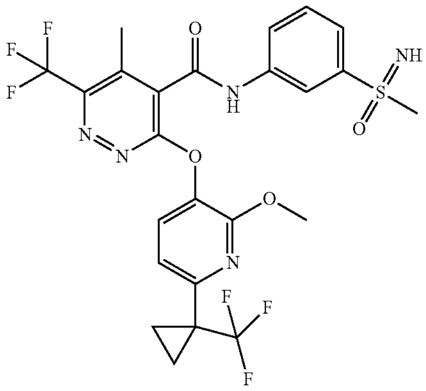 [SMILES: COc1nc(C2(C(F)(F)F)CC2)ccc1Oc1nnc(C(F)(F)F)c(C)c1C(=O)Nc1cccc(S(C)(=N)=O)c1]
493
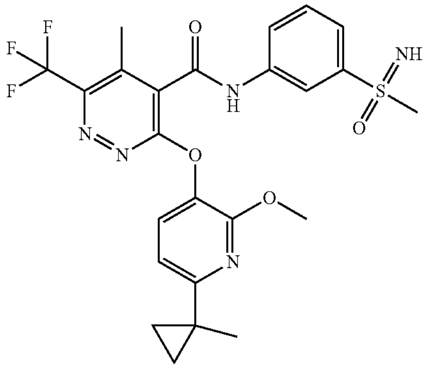 [SMILES: COc1nc(C2(C)CC2)ccc1Oc1nnc(C(F)(F)F)c(C)c1C(=O)Nc1cccc(S(C)(=N)=O)c1]
494
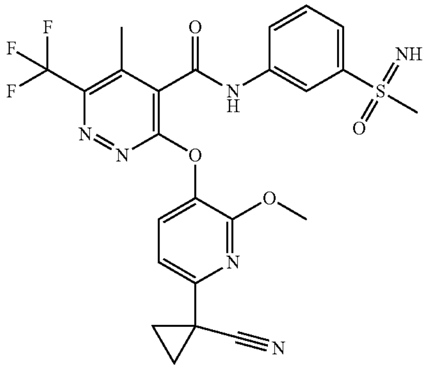 [SMILES: COc1nc(C2(C#N)CC2)ccc1Oc1nnc(C(F)(F)F)c(C)c1C(=O)Nc1cccc(S(C)(=N)=O)c1]
495
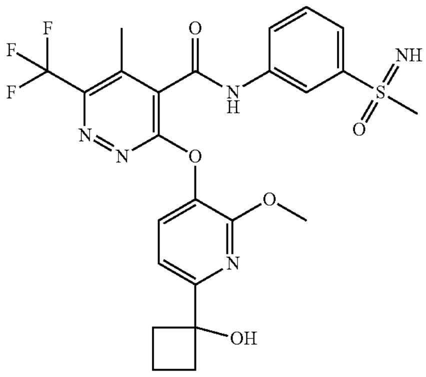 [SMILES: COc1nc(C2(O)CCC2)ccc1Oc1nnc(C(F)(F)F)c(C)c1C(=O)Nc1cccc(S(C)(=N)=O)c1]
496

TABLE 14-continued
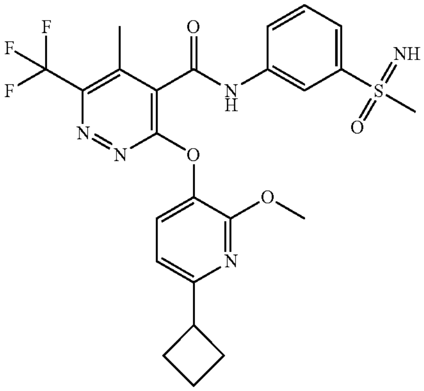 [SMILES: COc1nc(C2CCC2)ccc1Oc1nnc(C(F)(F)F)c(C)c1C(=O)Nc1cccc(S(C)(=N)=O)c1]
497
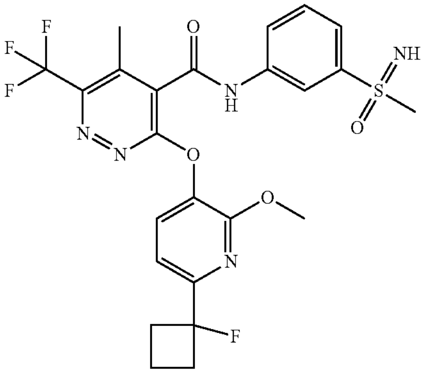 [SMILES: COc1nc(C2(F)CCC2)ccc1Oc1nnc(C(F)(F)F)c(C)c1C(=O)Nc1cccc(S(C)(=N)=O)c1]
498
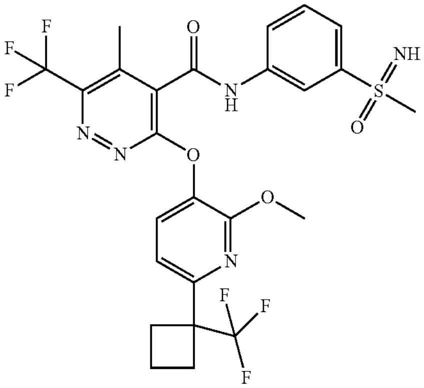
499
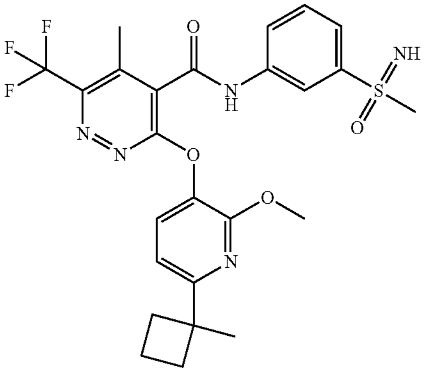 [SMILES: COc1nc(C2(C)CCC2)ccc1Oc1nnc(C(F)(F)F)c(C)c1C(=O)Nc1cccc(S(C)(=N)=O)c1]
500
TABLE 14-continued
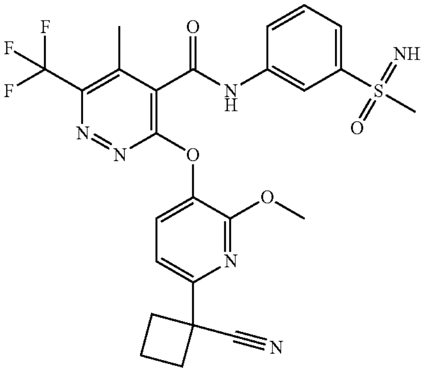 [SMILES: COc1nc(C2(C#N)CCC2)ccc1Oc1nnc(C(F)(F)F)c(C)c1C(=O)Nc1cccc(S(C)(=N)=O)c1]
501
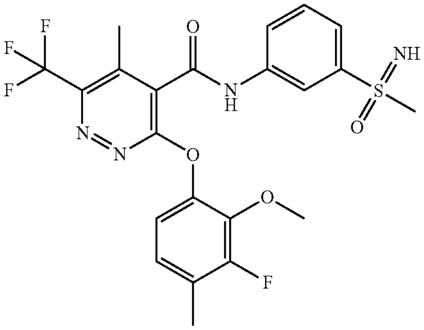 [SMILES: COc1c(Oc2nnc(C(F)(F)F)c(C)c2C(=O)Nc2cccc(S(C)(=N)=O)c2)ccc(C)c1F]
502
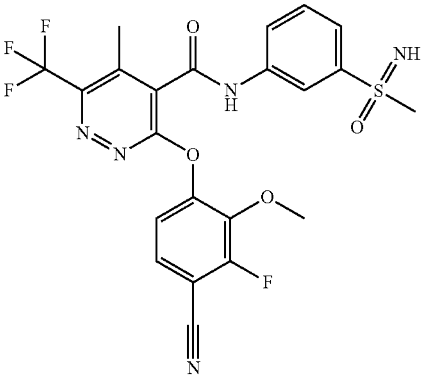
503
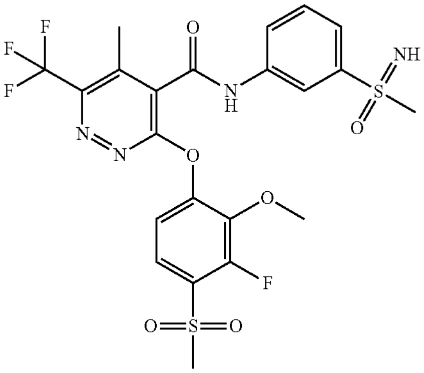 [SMILES: COc1c(Oc2nnc(C(F)(F)F)c(C)c2C(=O)Nc2cccc(S(C)(=N)=O)c2)ccc(S(C)(=O)=O)c1F]
504

TABLE 14-continued
505
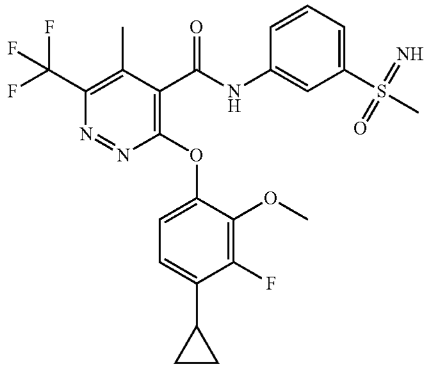 [SMILES: COc1c(Oc2nnc(C(F)(F)F)c(C)c2C(=O)Nc2cccc(S(C)(=N)=O)c2)ccc(C2CC2)c1F]
506
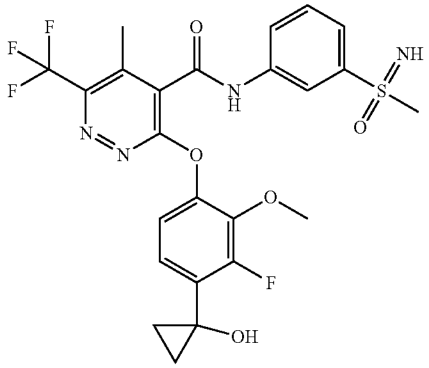
507
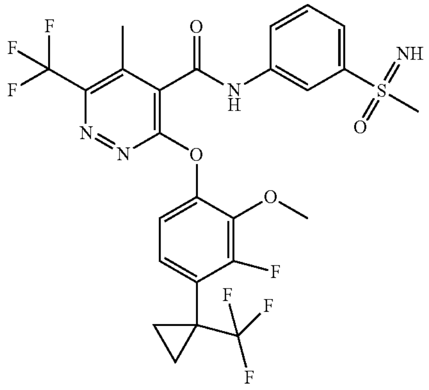 [SMILES: COc1c(Oc2nnc(C(F)(F)F)c(C)c2C(=O)Nc2cccc(S(C)(=N)=O)c2)ccc(C2(C(F)(F)F)CC2)c1F]
508
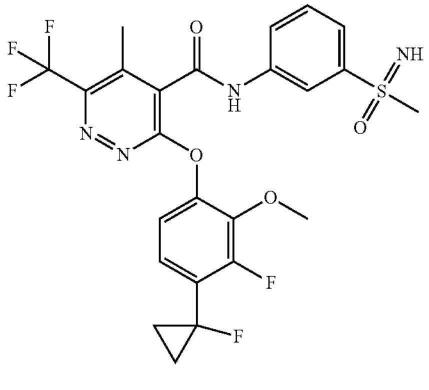
TABLE 14-continued
509
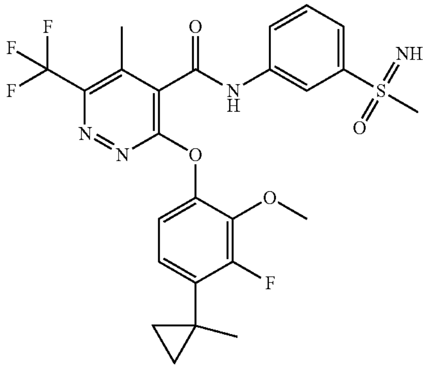
510
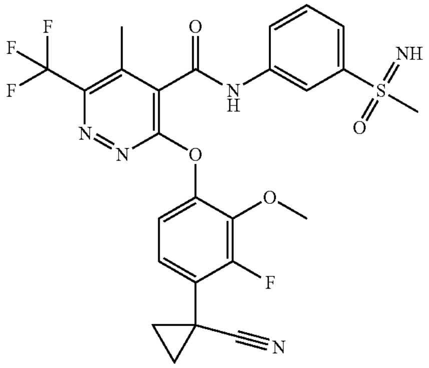
511
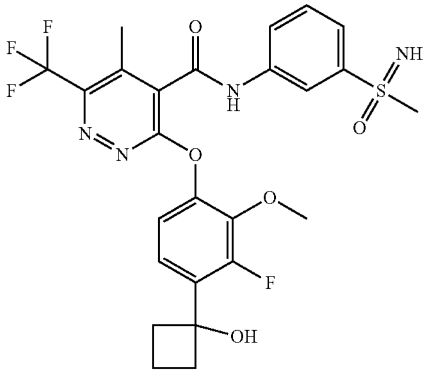 [SMILES: COc1c(Oc2nnc(C(F)(F)F)c(C)c2C(=O)Nc2cccc(S(C)(=N)=O)c2)ccc(C2(O)CCC2)c1F]
512
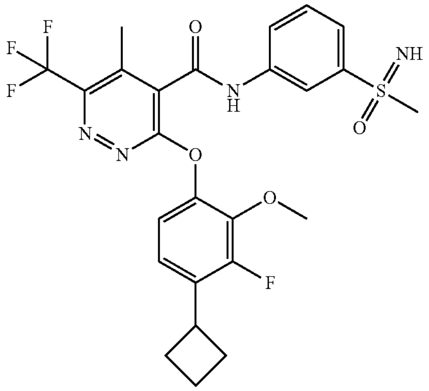 [SMILES: COc1c(Oc2nnc(C(F)(F)F)c(C)c2C(=O)Nc2cccc(S(C)(=N)=O)c2)ccc(C2CCC2)c1F]

513
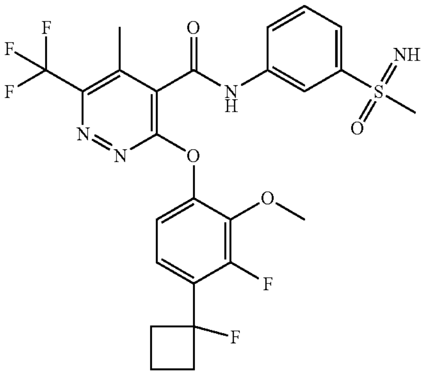
514
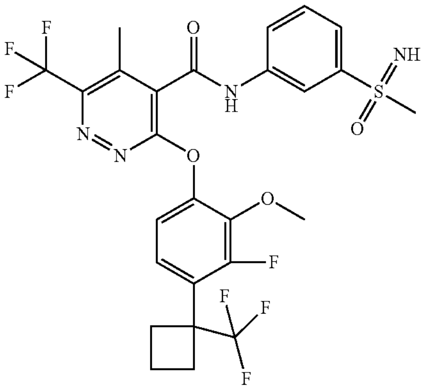
515
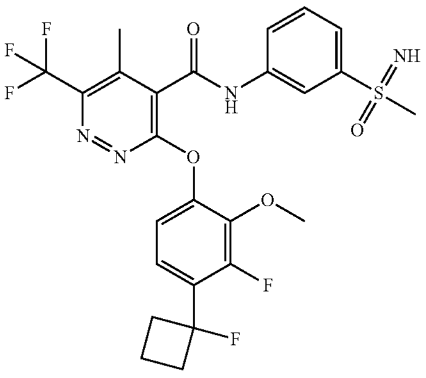
516
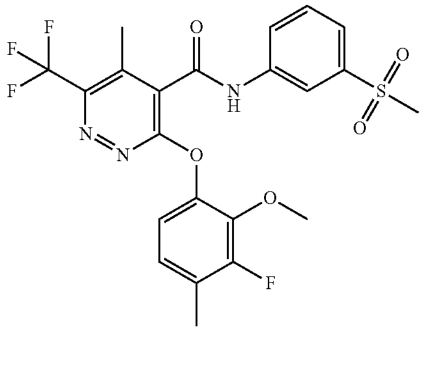 [SMILES: COc1c(Oc2nnc(C(F)(F)F)c(C)c2C(=O)Nc2cccc(S(C)(=O)=O)c2)ccc(C)c1F]
517
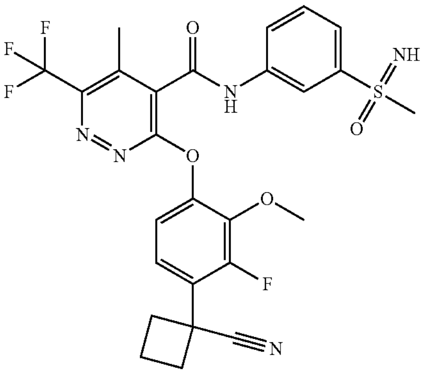 [SMILES: COc1c(Oc2nnc(C(F)(F)F)c(C)c2C(=O)Nc2cccc(S(C)(=N)=O)c2)ccc(C2(C#N)CCC2)c1F]
518
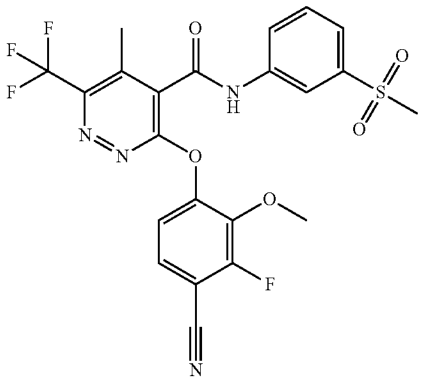 [SMILES: COc1c(Oc2nnc(C(F)(F)F)c(C)c2C(=O)Nc2cccc(S(C)(=O)=O)c2)ccc(C#N)c1F]
519
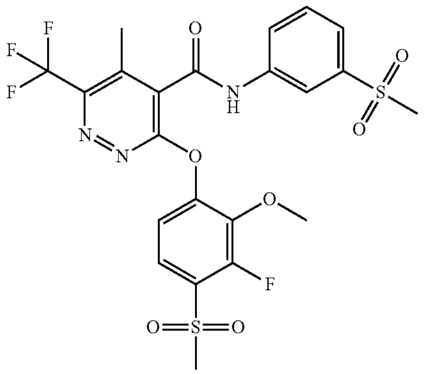 [SMILES: COc1c(Oc2nnc(C(F)(F)F)c(C)c2C(=O)Nc2cccc(S(C)(=O)=O)c2)ccc(S(C)(=O)=O)c1F]
520
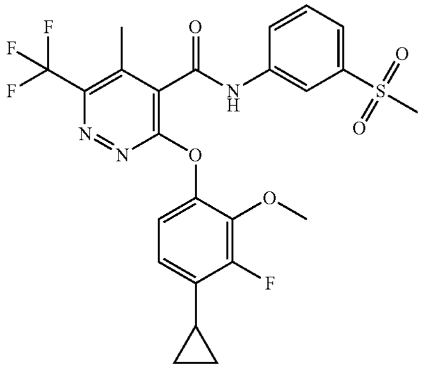 [SMILES: COc1c(Oc2nnc(C(F)(F)F)c(C)c2C(=O)Nc2cccc(S(C)(=O)=O)c2)ccc(C2CC2)c1F]

TABLE 14-continued
521
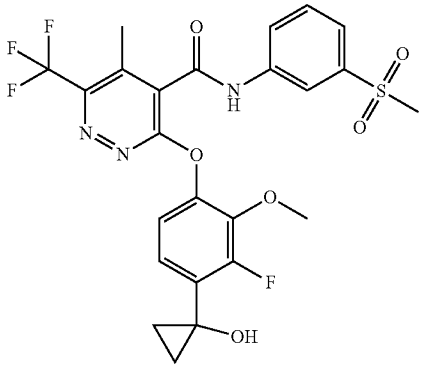
522
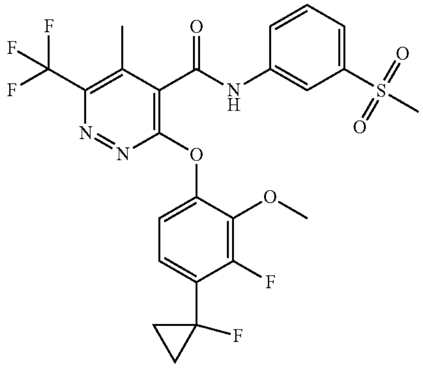 [SMILES: COc1c(Oc2nnc(C(F)(F)F)c(C)c2C(=O)Nc2cccc(S(C)(=O)=O)c2)ccc(C2(F)CC2)c1F]
523
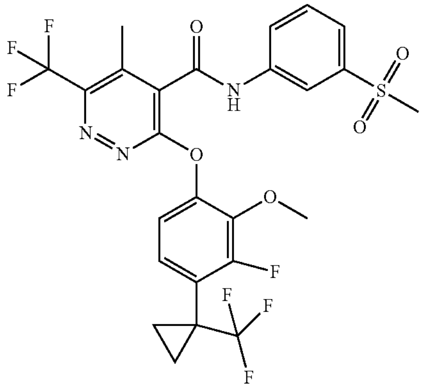 [SMILES: COc1c(Oc2nnc(C(F)(F)F)c(C)c2C(=O)Nc2cccc(S(C)(=O)=O)c2)ccc(C2(C(F)(F)F)CC2)c1F]
524
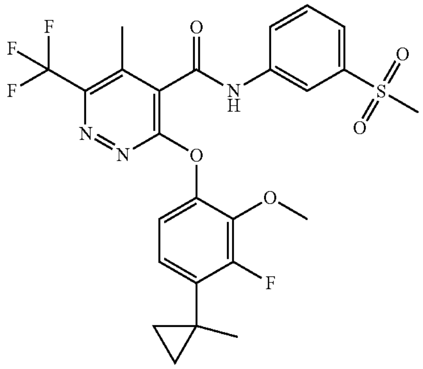
TABLE 14-continued
525
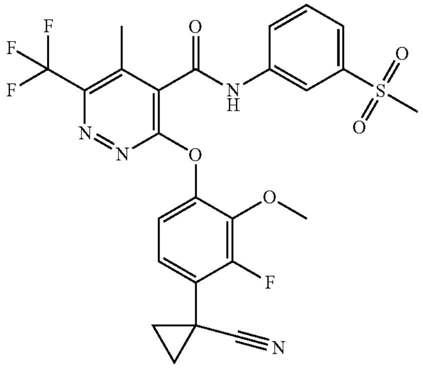 [SMILES: COc1c(Oc2nnc(C(F)(F)F)c(C)c2C(=O)Nc2cccc(S(C)(=O)=O)c2)ccc(C2(C#N)CC2)c1F]
526
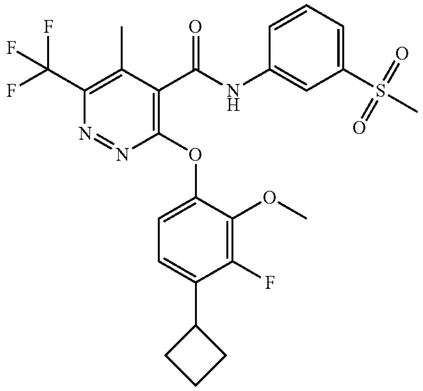 [SMILES: COc1c(Oc2nnc(C(F)(F)F)c(C)c2C(=O)Nc2cccc(S(C)(=O)=O)c2)ccc(C2CCC2)c1F]
527
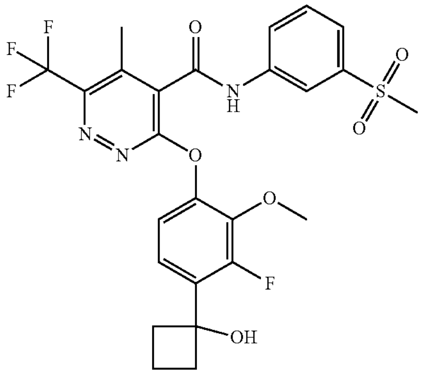 [SMILES: COc1c(Oc2nnc(C(F)(F)F)c(C)c2C(=O)Nc2cccc(S(C)(=O)=O)c2)ccc(C2(O)CCC2)c1F]
528
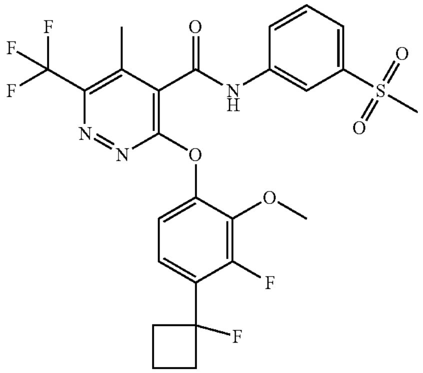 [SMILES: COc1c(Oc2nnc(C(F)(F)F)c(C)c2C(=O)Nc2cccc(S(C)(=O)=O)c2)ccc(C2(F)CCC2)c1F]

TABLE 14-continued
529
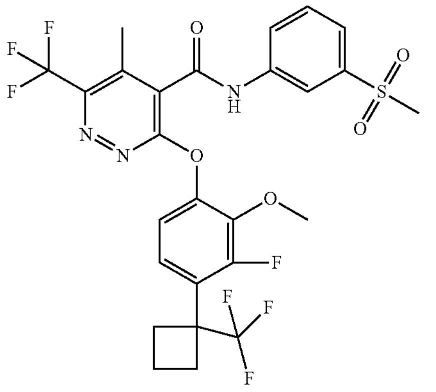 [SMILES: COc1c(Oc2nnc(C(F)(F)F)c(C)c2C(=O)Nc2cccc(S(C)(=O)=O)c2)ccc(C2(C(F)(F)F)CCC2)c1F]
530
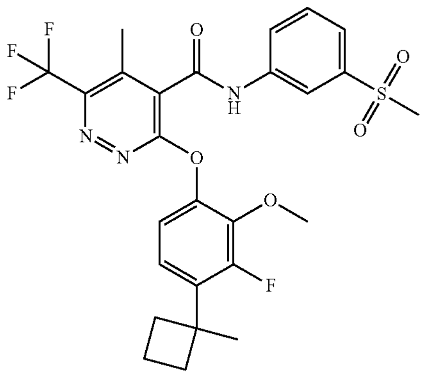 [SMILES: COc1c(Oc2nnc(C(F)(F)F)c(C)c2C(=O)Nc2cccc(S(C)(=O)=O)c2)ccc(C2(C)CCC2)c1F]
531
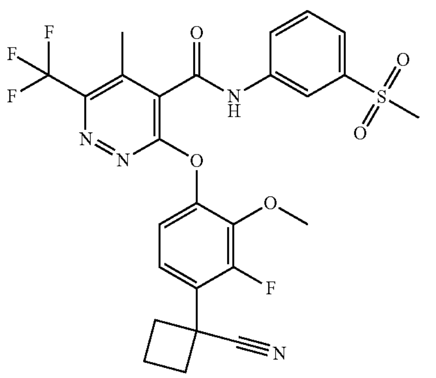 [SMILES: COc1c(Oc2nnc(C(F)(F)F)c(C)c2C(=O)Nc2cccc(S(C)(=O)=O)c2)ccc(C2(C#N)CCC2)c1F]
532
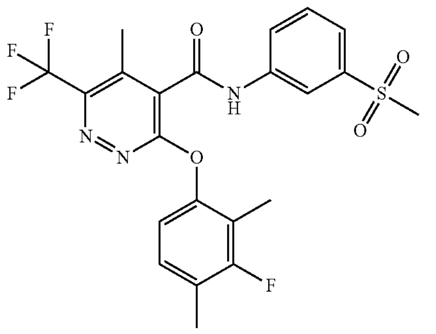 [SMILES: Cc1ccc(Oc2nnc(C(F)(F)F)c(C)c2C(=O)Nc2cccc(S(C)(=O)=O)c2)c(C)c1F]
TABLE 14-continued
533
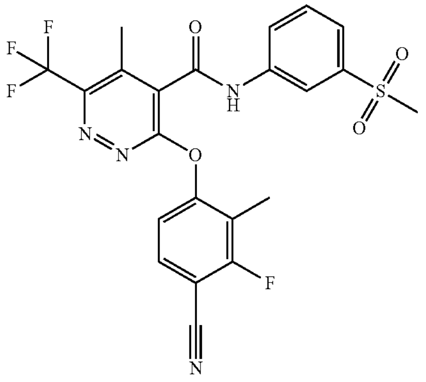
534
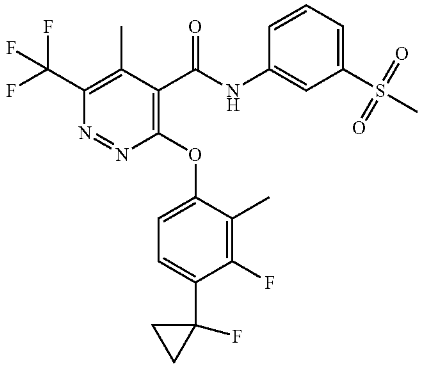 [SMILES: Cc1c(Oc2nnc(C(F)(F)F)c(C)c2C(=O)Nc2cccc(S(C)(=O)=O)c2)ccc(C2(F)CC2)c1F]
535
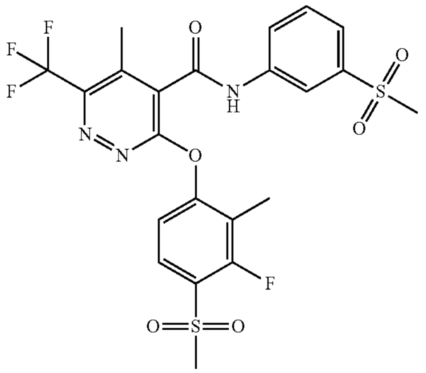 [SMILES: Cc1c(Oc2nnc(C(F)(F)F)c(C)c2C(=O)Nc2cccc(S(C)(=O)=O)c2)ccc(S(C)(=O)=O)c1F]
536
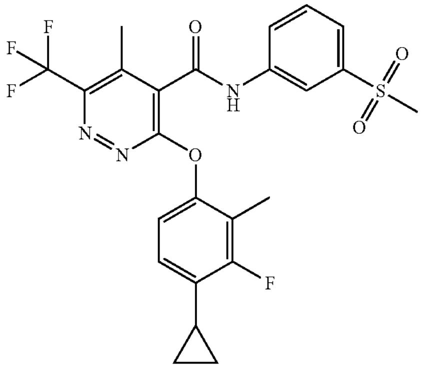 [SMILES: Cc1c(Oc2nnc(C(F)(F)F)c(C)c2C(=O)Nc2cccc(S(C)(=O)=O)c2)ccc(C2CC2)c1F]

TABLE 14-continued
537
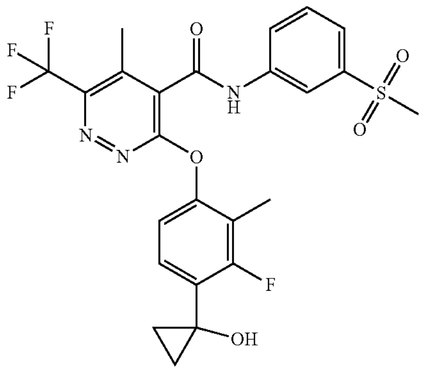
538
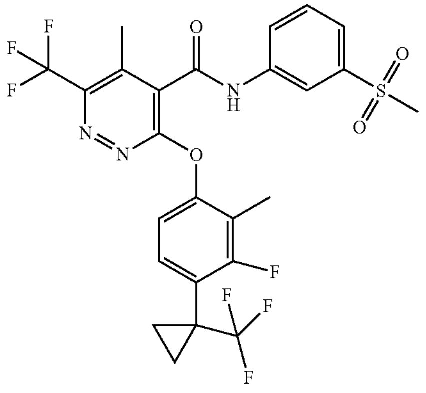 [SMILES: Cc1c(Oc2nnc(C(F)(F)F)c(C)c2C(=O)Nc2cccc(S(C)(=O)=O)c2)ccc(C2(C(F)(F)F)CC2)c1F]
539
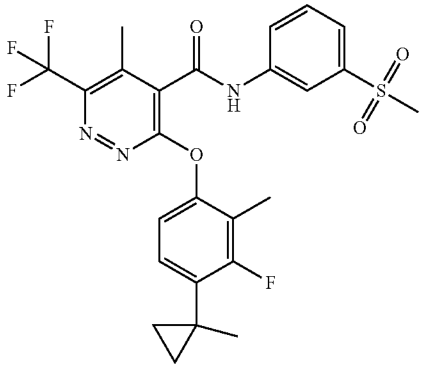
540
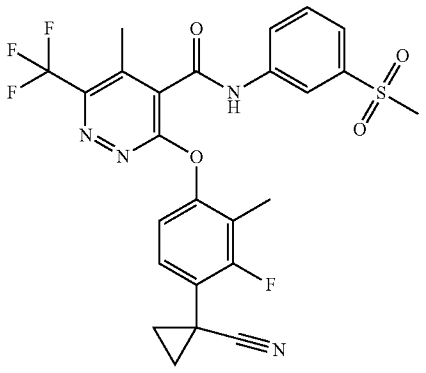 [SMILES: Cc1c(Oc2nnc(C(F)(F)F)c(C)c2C(=O)Nc2cccc(S(C)(=O)=O)c2)ccc(C2(C#N)CC2)c1F]
TABLE 14-continued
541
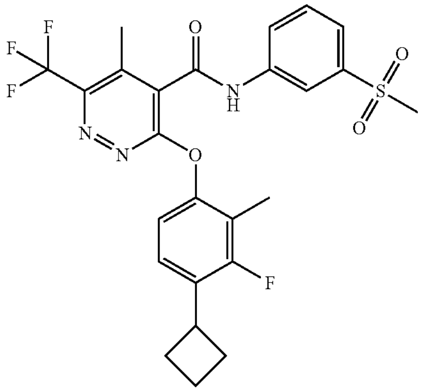
542
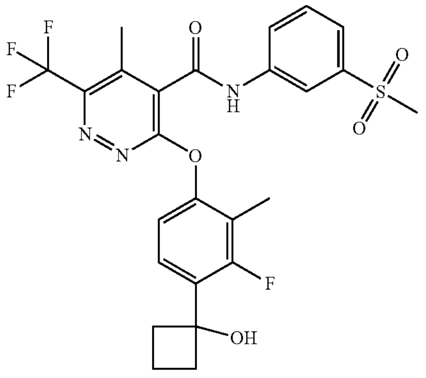 [SMILES: Cc1c(Oc2nnc(C(F)(F)F)c(C)c2C(=O)Nc2cccc(S(C)(=O)=O)c2)ccc(C2(O)CCC2)c1F]
543
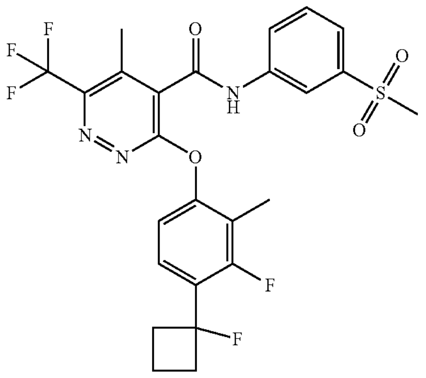
544
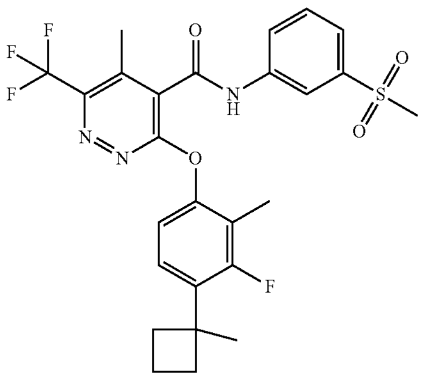

545
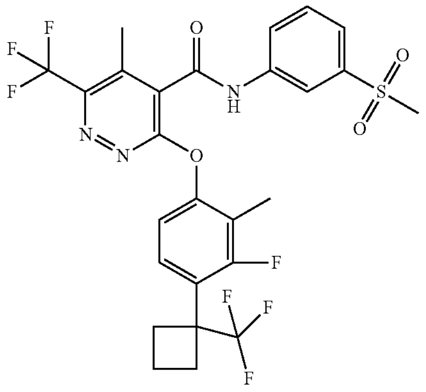
546
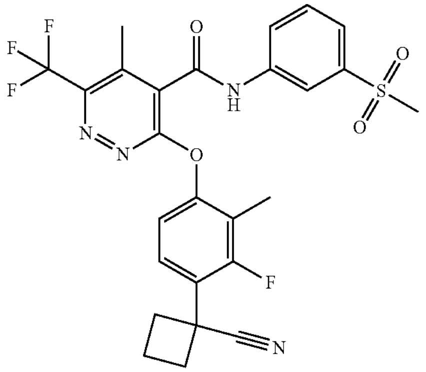 [SMILES: Cc1c(Oc2nnc(C(F)(F)F)c(C)c2C(=O)Nc2cccc(S(C)(=O)=O)c2)ccc(C2(C#N)CCC2)c1F]
547
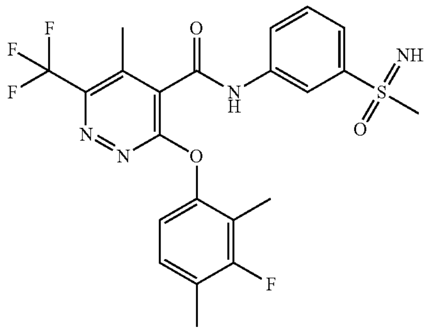
548
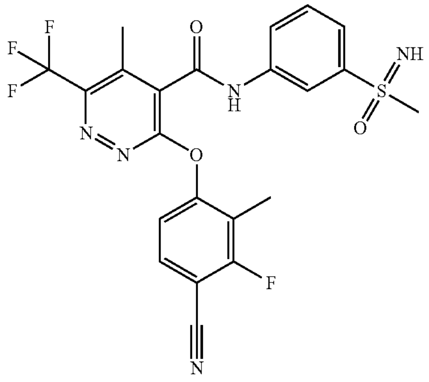
549
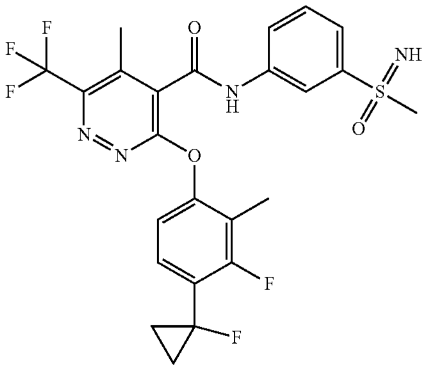 [SMILES: Cc1c(Oc2nnc(C(F)(F)F)c(C)c2C(=O)Nc2cccc(S(C)(=N)=O)c2)ccc(C2(F)CC2)c1F]
550
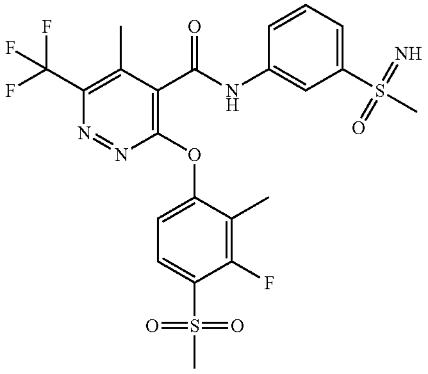
551
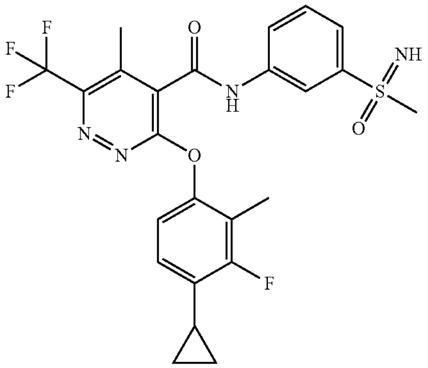 [SMILES: Cc1c(Oc2nnc(C(F)(F)F)c(C)c2C(=O)Nc2cccc(S(C)(=N)=O)c2)ccc(C2CC2)c1F]
552
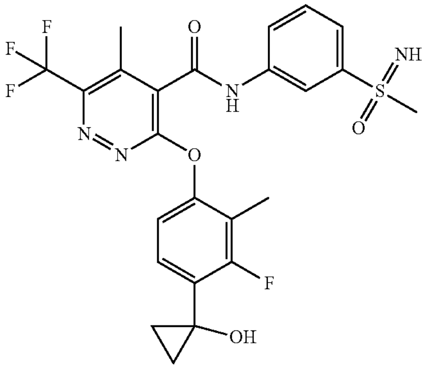 [SMILES: Cc1c(Oc2nnc(C(F)(F)F)c(C)c2C(=O)Nc2cccc(S(C)(=N)=O)c2)ccc(C2(O)CC2)c1F]

TABLE 14-continued
553
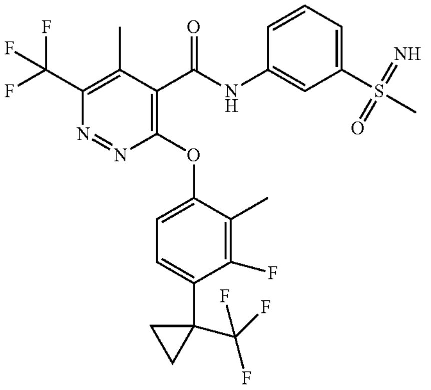 [SMILES: Cc1c(Oc2nnc(C(F)(F)F)c(C)c2C(=O)Nc2cccc(S(C)(=N)=O)c2)ccc(C2(C(F)(F)F)CC2)c1F]
554
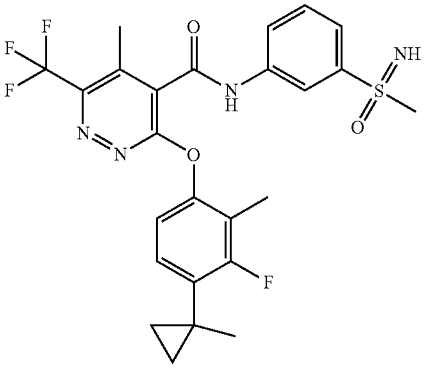
555
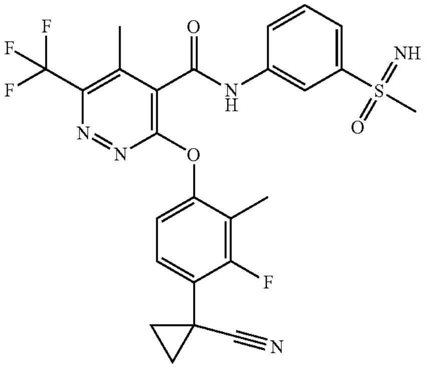
556
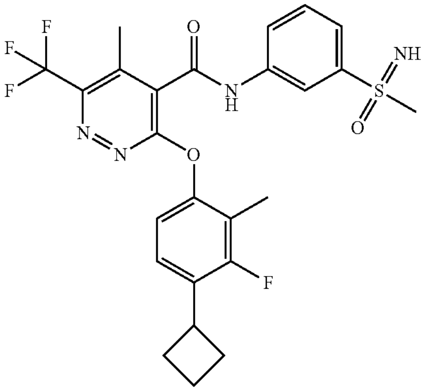 [SMILES: Cc1c(Oc2nnc(C(F)(F)F)c(C)c2C(=O)Nc2cccc(S(C)(=N)=O)c2)ccc(C2CCC2)c1F]
TABLE 14-continued
557
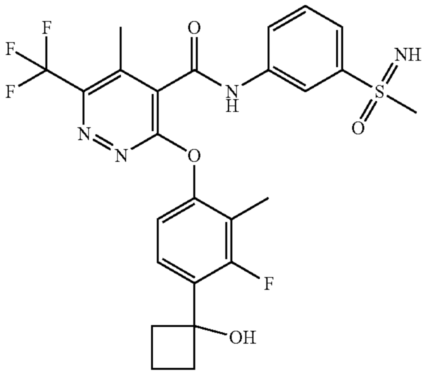 [SMILES: Cc1c(Oc2nnc(C(F)(F)F)c(C)c2C(=O)Nc2cccc(S(C)(=N)=O)c2)ccc(C2(O)CCC2)c1F]
558
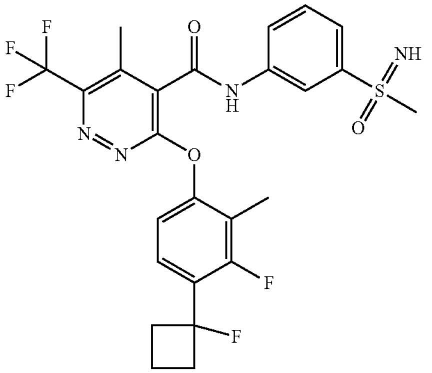 [SMILES: Cc1c(Oc2nnc(C(F)(F)F)c(C)c2C(=O)Nc2cccc(S(C)(=N)=O)c2)ccc(C2(F)CCC2)c1F]
559
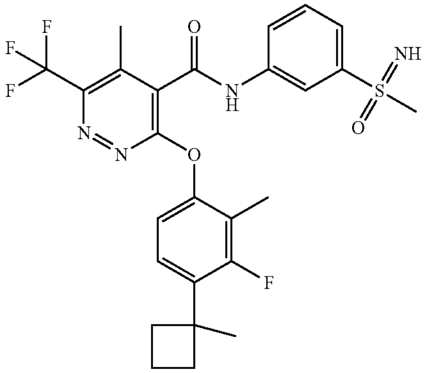 [SMILES: Cc1c(Oc2nnc(C(F)(F)F)c(C)c2C(=O)Nc2cccc(S(C)(=N)=O)c2)ccc(C2(C)CCC2)c1F]
560
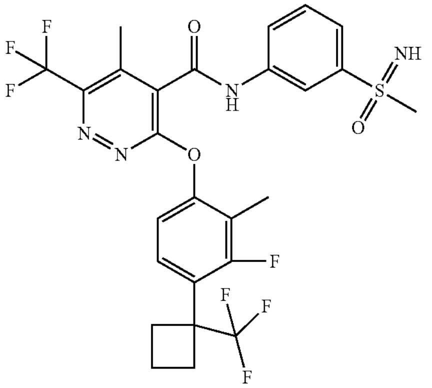 [SMILES: Cc1c(Oc2nnc(C(F)(F)F)c(C)c2C(=O)Nc2cccc(S(C)(=N)=O)c2)ccc(C2(C(F)(F)F)CCC2)c1F]

TABLE 14-continued
561
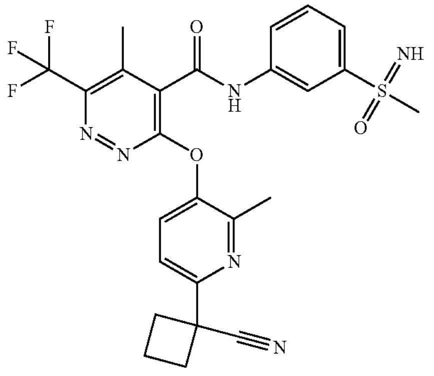 [SMILES: Cc1nc(C2(C#N)CCC2)ccc1Oc1nnc(C(F)(F)F)c(C)c1C(=O)Nc1cccc(S(C)(=N)=O)c1]
562
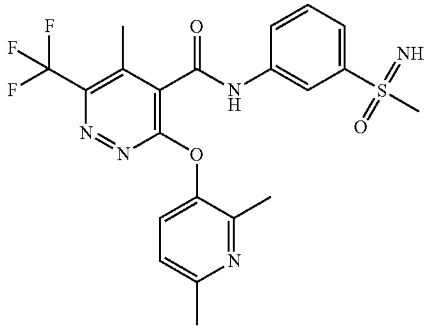
563
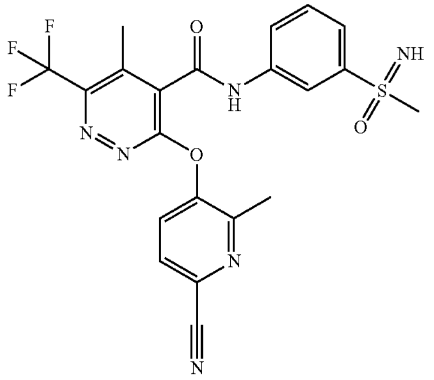
564
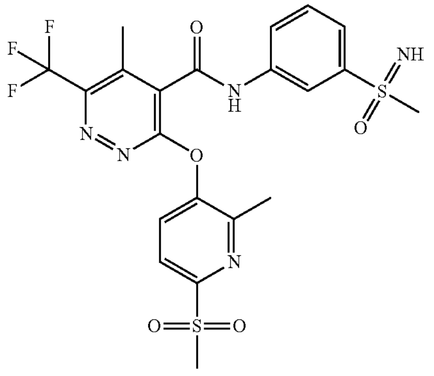
TABLE 14-continued
565
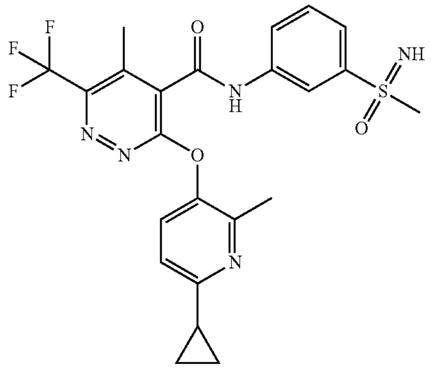 [SMILES: Cc1nc(C2CC2)ccc1Oc1nnc(C(F)(F)F)c(C)c1C(=O)Nc1cccc(S(C)(=N)=O)c1]
566
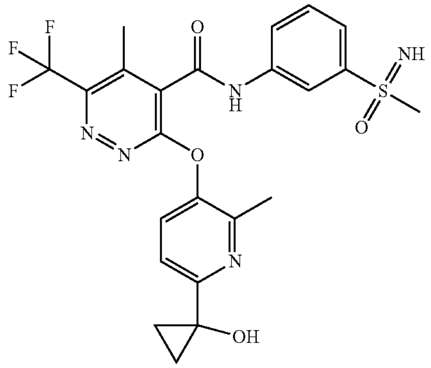
567
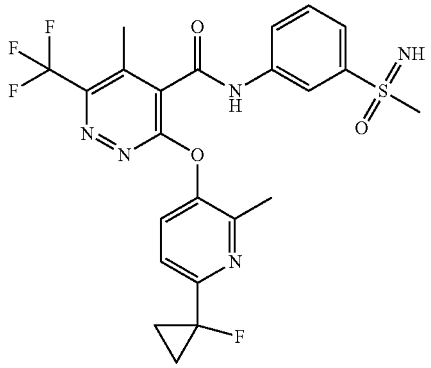 [SMILES: Cc1nc(C2(F)CC2)ccc1Oc1nnc(C(F)(F)F)c(C)c1C(=O)Nc1cccc(S(C)(=N)=O)c1]
568
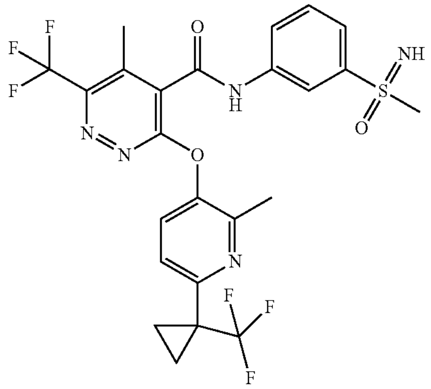 [SMILES: Cc1nc(C2(C(F)(F)F)CC2)ccc1Oc1nnc(C(F)(F)F)c(C)c1C(=O)Nc1cccc(S(C)(=N)=O)c1]

TABLE 14-continued
569
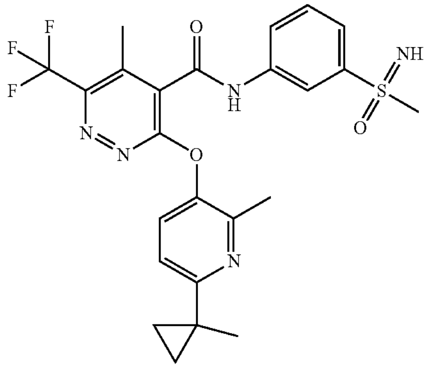 [SMILES: Cc1nc(C2(C)CC2)ccc1Oc1nnc(C(F)(F)F)c(C)c1C(=O)Nc1cccc(S(C)(=N)=O)c1]
570
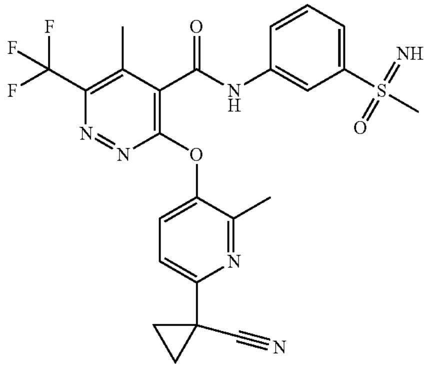 [SMILES: Cc1nc(C2(C#N)CC2)ccc1Oc1nnc(C(F)(F)F)c(C)c1C(=O)Nc1cccc(S(C)(=N)=O)c1]
571
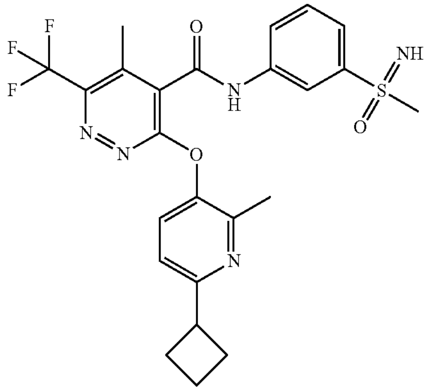
572
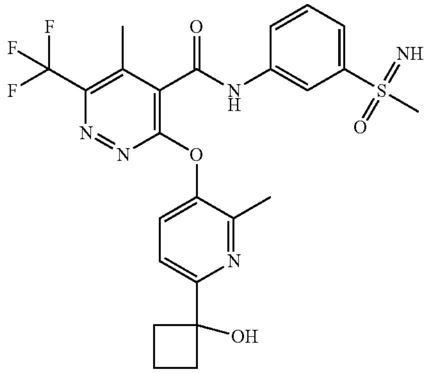 [SMILES: Cc1nc(C2(O)CCC2)ccc1Oc1nnc(C(F)(F)F)c(C)c1C(=O)Nc1cccc(S(C)(=N)=O)c1]
TABLE 14-continued
573
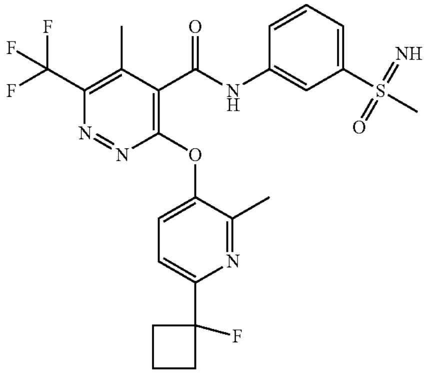 [SMILES: Cc1nc(C2(F)CCC2)ccc1Oc1nnc(C(F)(F)F)c(C)c1C(=O)Nc1cccc(S(C)(=N)=O)c1]
574
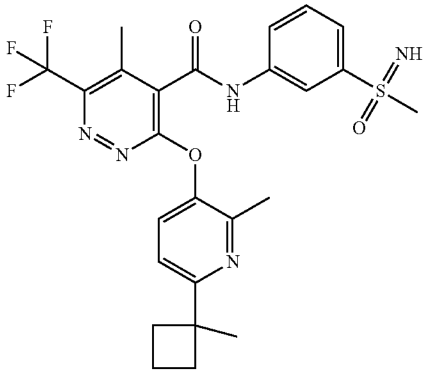 [SMILES: Cc1nc(C2(C)CCC2)ccc1Oc1nnc(C(F)(F)F)c(C)c1C(=O)Nc1cccc(S(C)(=N)=O)c1]
575
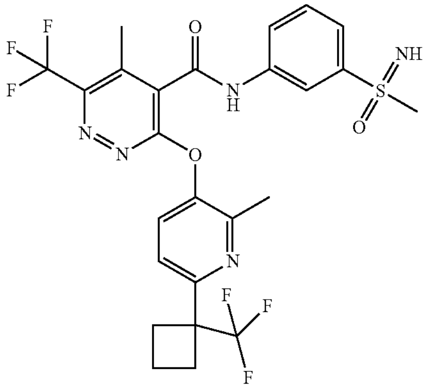 [SMILES: Cc1nc(C2(C(F)(F)F)CCC2)ccc1Oc1nnc(C(F)(F)F)c(C)c1C(=O)Nc1cccc(S(C)(=N)=O)c1]
576
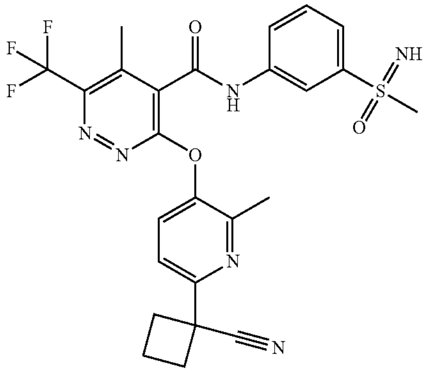 [SMILES: Cc1nc(C2(C#N)CCC2)ccc1Oc1nnc(C(F)(F)F)c(C)c1C(=O)Nc1cccc(S(C)(=N)=O)c1]

TABLE 14-continued
577
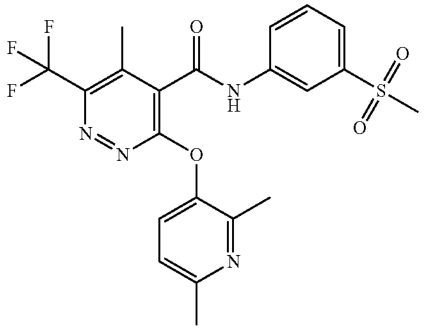 [SMILES: Cc1ccc(Oc2nnc(C(F)(F)F)c(C)c2C(=O)Nc2cccc(S(C)(=O)=O)c2)c(C)n1]
578
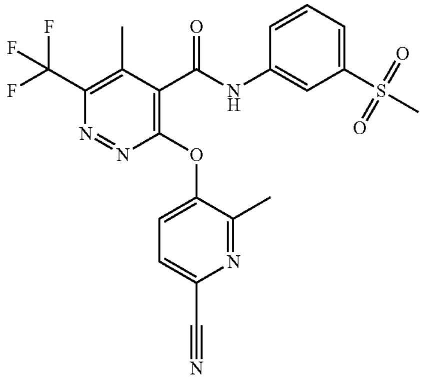 [SMILES: Cc1nc(C#N)ccc1Oc1nnc(C(F)(F)F)c(C)c1C(=O)Nc1cccc(S(C)(=O)=O)c1]
579
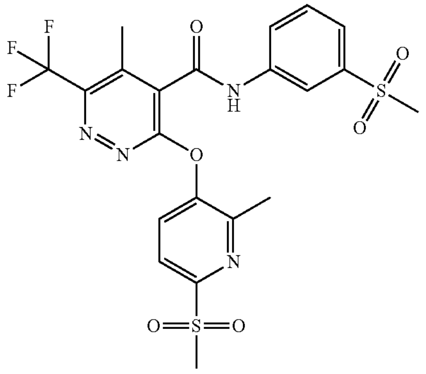 [SMILES: Cc1nc(S(C)(=O)=O)ccc1Oc1nnc(C(F)(F)F)c(C)c1C(=O)Nc1cccc(S(C)(=O)=O)c1]
580
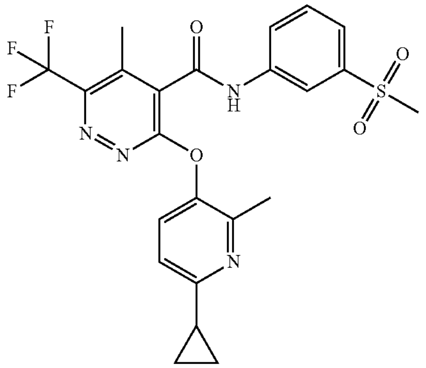 [SMILES: Cc1nc(C2CC2)ccc1Oc1nnc(C(F)(F)F)c(C)c1C(=O)Nc1cccc(S(C)(=O)=O)c1]
TABLE 14-continued
581
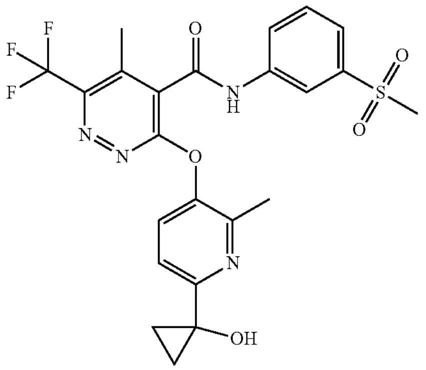 [SMILES: Cc1nc(C2(O)CC2)ccc1Oc1nnc(C(F)(F)F)c(C)c1C(=O)Nc1cccc(S(C)(=O)=O)c1]
582
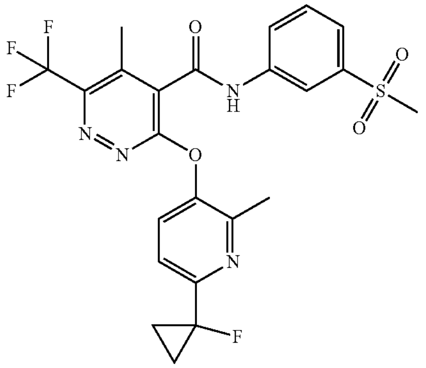 [SMILES: Cc1nc(C2(F)CC2)ccc1Oc1nnc(C(F)(F)F)c(C)c1C(=O)Nc1cccc(S(C)(=O)=O)c1]
583
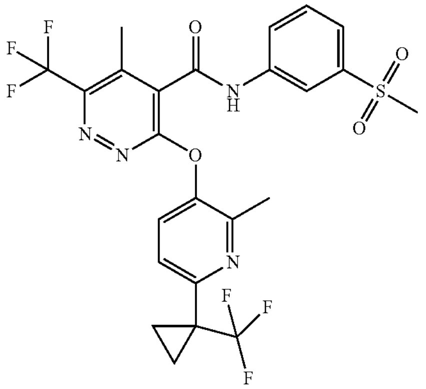 [SMILES: Cc1nc(C2(C(F)(F)F)CC2)ccc1Oc1nnc(C(F)(F)F)c(C)c1C(=O)Nc1cccc(S(C)(=O)=O)c1]
584
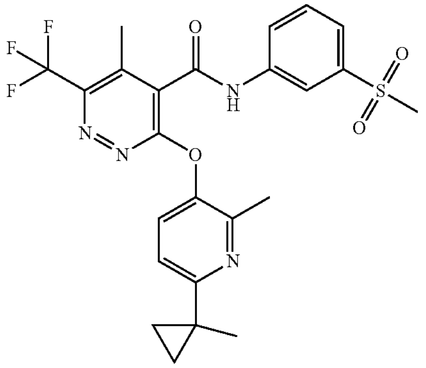 [SMILES: Cc1nc(C2(C)CC2)ccc1Oc1nnc(C(F)(F)F)c(C)c1C(=O)Nc1cccc(S(C)(=O)=O)c1]

TABLE 14-continued
585
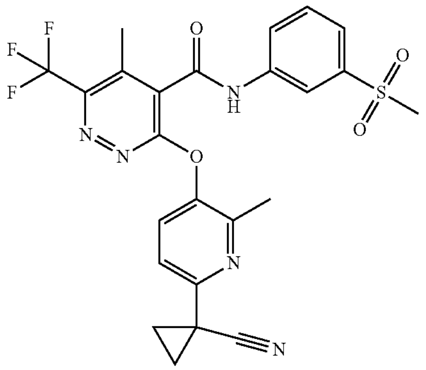 [SMILES: Cc1nc(C2(C#N)CC2)ccc1Oc1nnc(C(F)(F)F)c(C)c1C(=O)Nc1cccc(S(C)(=O)=O)c1]
586
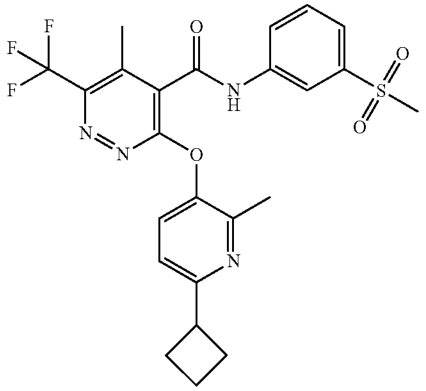 [SMILES: Cc1nc(C2CCC2)ccc1Oc1nnc(C(F)(F)F)c(C)c1C(=O)Nc1cccc(S(C)(=O)=O)c1]
587
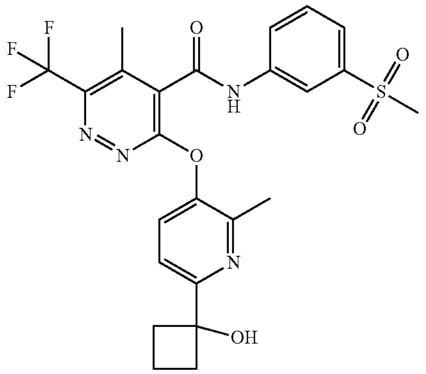 [SMILES: Cc1nc(C2(O)CCC2)ccc1Oc1nnc(C(F)(F)F)c(C)c1C(=O)Nc1cccc(S(C)(=O)=O)c1]
588
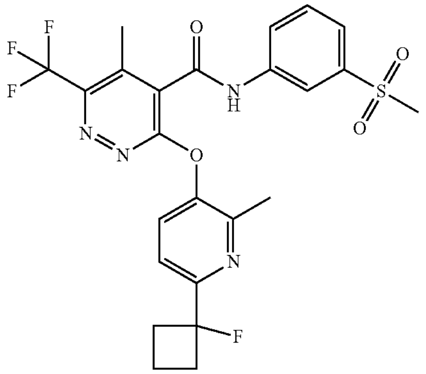 [SMILES: Cc1nc(C2(F)CCC2)ccc1Oc1nnc(C(F)(F)F)c(C)c1C(=O)Nc1cccc(S(C)(=O)=O)c1]
TABLE 14-continued
589
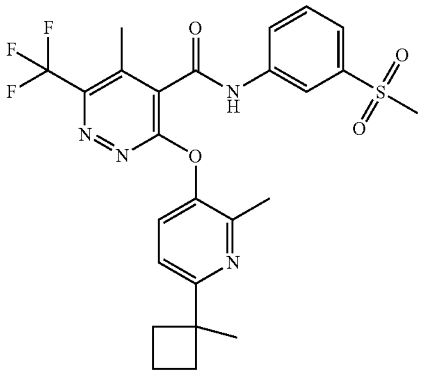 [SMILES: Cc1nc(C2(C)CCC2)ccc1Oc1nnc(C(F)(F)F)c(C)c1C(=O)Nc1cccc(S(C)(=O)=O)c1]
590
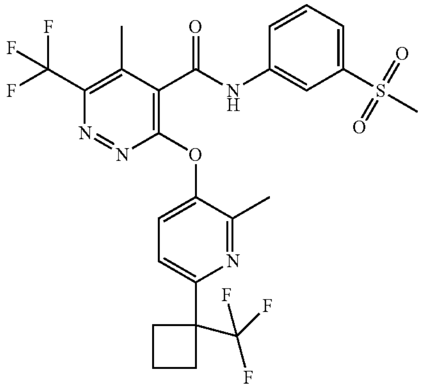
591
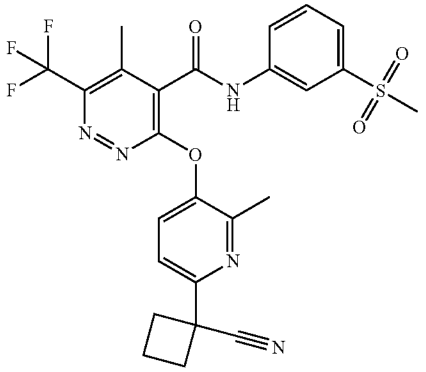 [SMILES: Cc1nc(C2(C#N)CCC2)ccc1Oc1nnc(C(F)(F)F)c(C)c1C(=O)Nc1cccc(S(C)(=O)=O)c1]
592
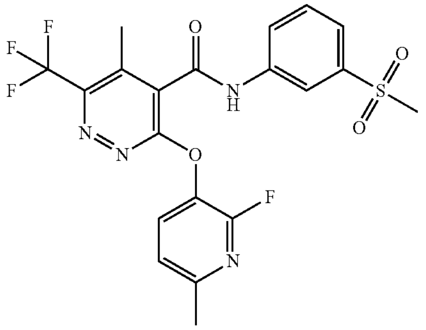

TABLE 14-continued
593
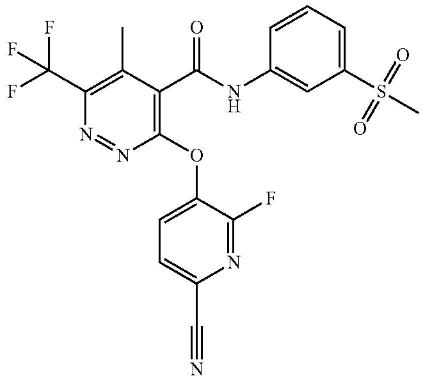
594
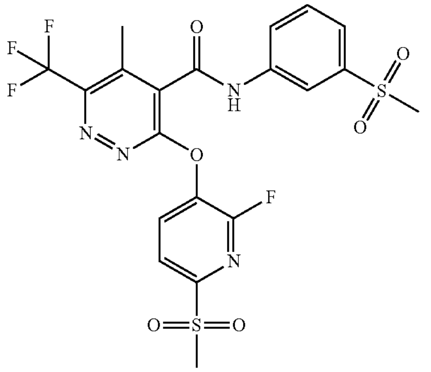 [SMILES: Cc1c(C(F)(F)F)nnc(Oc2ccc(S(C)(=O)=O)nc2F)c1C(=O)Nc1cccc(S(C)(=O)=O)c1]
595
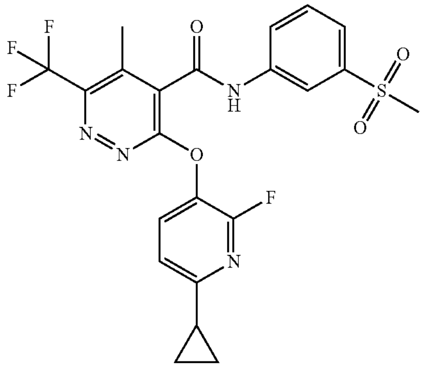 [SMILES: Cc1c(C(F)(F)F)nnc(Oc2ccc(C3CC3)nc2F)c1C(=O)Nc1cccc(S(C)(=O)=O)c1]
596
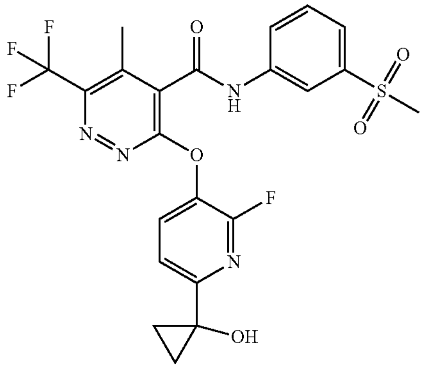 [SMILES: Cc1c(C(F)(F)F)nnc(Oc2ccc(C3(O)CC3)nc2F)c1C(=O)Nc1cccc(S(C)(=O)=O)c1]
TABLE 14-continued
597
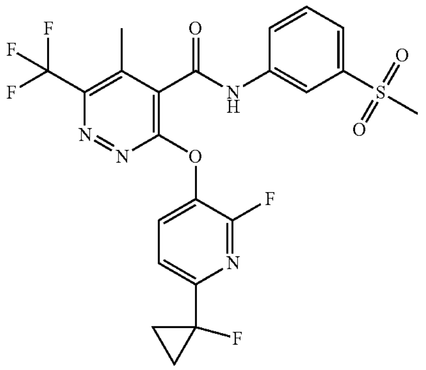
598
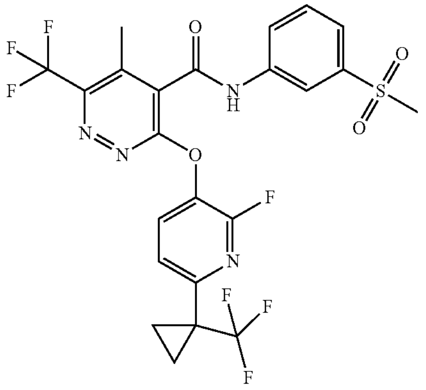 [SMILES: Cc1c(C(F)(F)F)nnc(Oc2ccc(C3(C(F)(F)F)CC3)nc2F)c1C(=O)Nc1cccc(S(C)(=O)=O)c1]
599
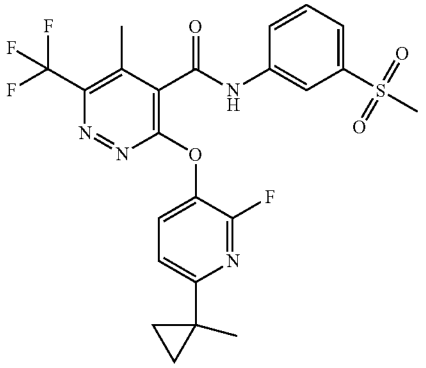
600
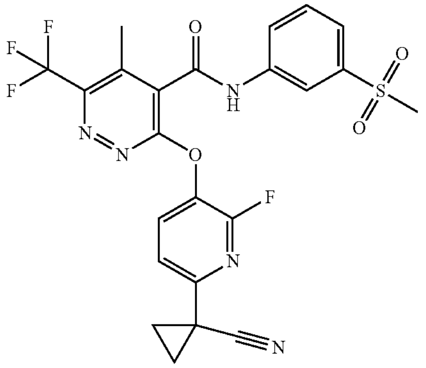

TABLE 14-continued
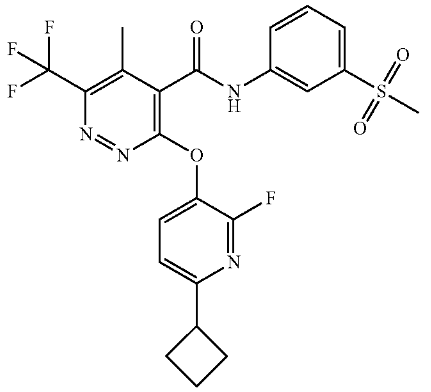
601
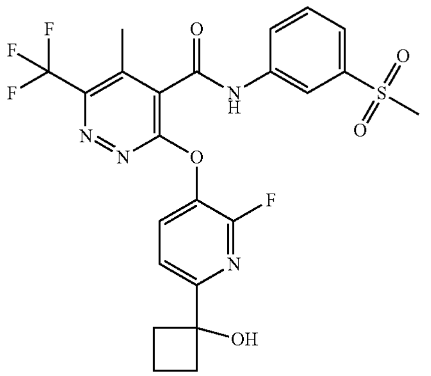 [SMILES: Cc1c(C(F)(F)F)nnc(Oc2ccc(C3(O)CCC3)nc2F)c1C(=O)Nc1cccc(S(C)(=O)=O)c1]
602
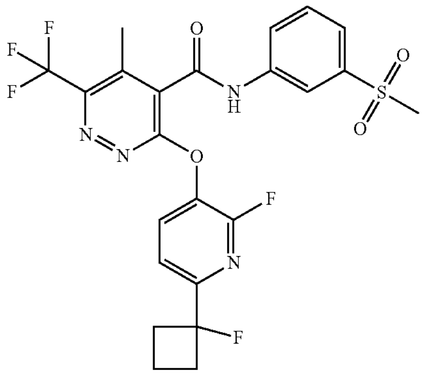 [SMILES: Cc1c(C(F)(F)F)nnc(Oc2ccc(C3(F)CCC3)nc2F)c1C(=O)Nc1cccc(S(C)(=O)=O)c1]
603
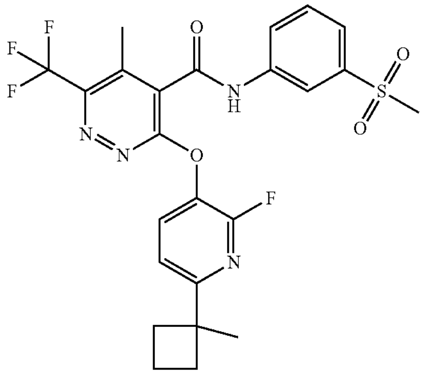 [SMILES: Cc1c(C(F)(F)F)nnc(Oc2ccc(C3(C)CCC3)nc2F)c1C(=O)Nc1cccc(S(C)(=O)=O)c1]
604
TABLE 14-continued
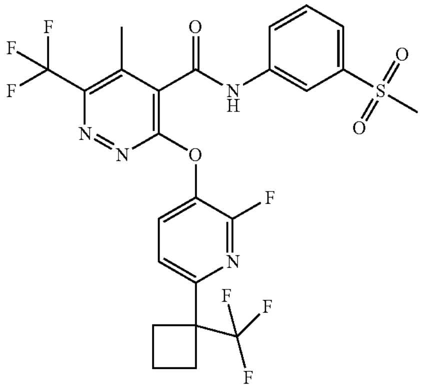 [SMILES: Cc1c(C(F)(F)F)nnc(Oc2ccc(C3(C(F)(F)F)CCC3)nc2F)c1C(=O)Nc1cccc(S(C)(=O)=O)c1]
605
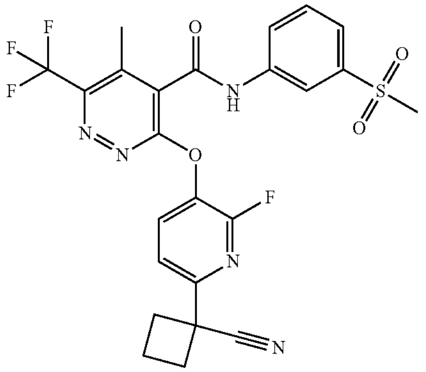 [SMILES: Cc1c(C(F)(F)F)nnc(Oc2ccc(C3(C#N)CCC3)nc2F)c1C(=O)Nc1cccc(S(C)(=O)=O)c1]
606
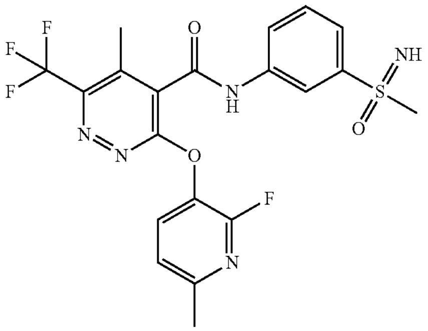
607
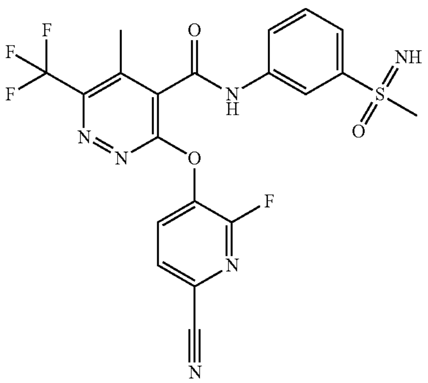 [SMILES: Cc1c(C(F)(F)F)nnc(Oc2ccc(C#N)nc2F)c1C(=O)Nc1cccc(S(C)(=N)=O)c1]
608

TABLE 14-continued
609
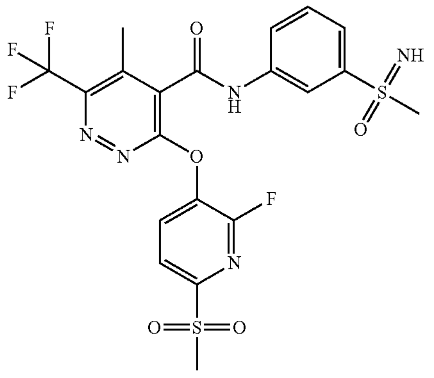
610
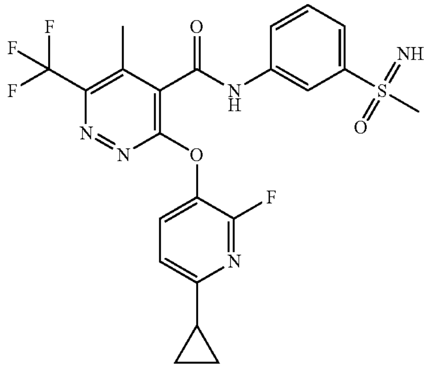
611
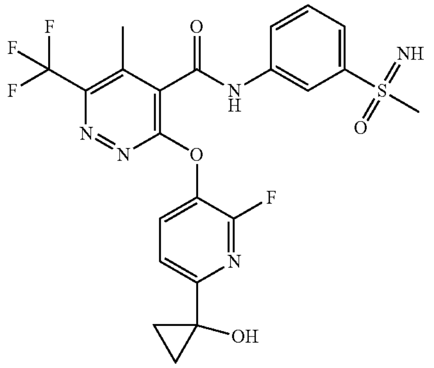
612
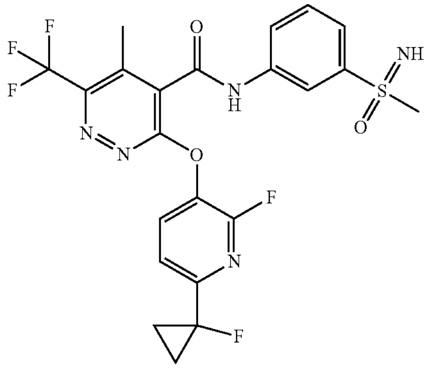 [SMILES: Cc1c(C(F)(F)F)nnc(Oc2ccc(C3(F)CC3)nc2F)c1C(=O)Nc1cccc(S(C)(=N)=O)c1]
TABLE 14-continued
613
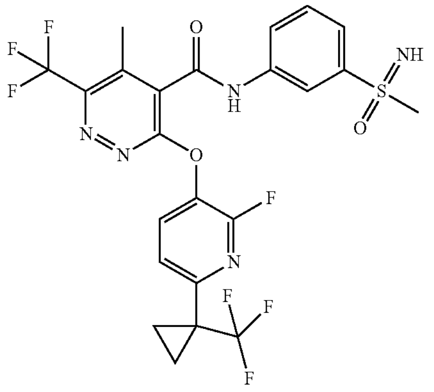
614
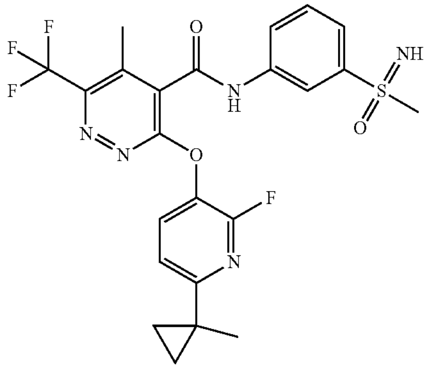
615
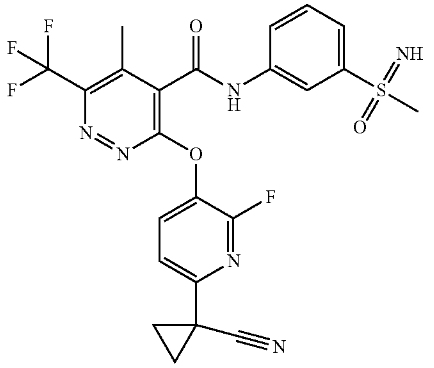
616
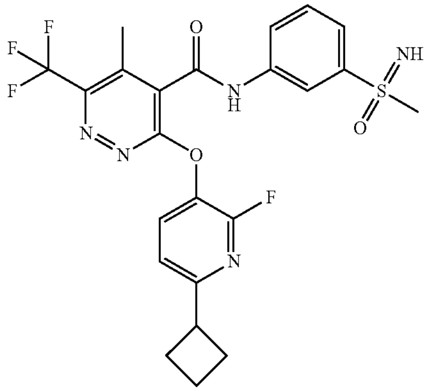

TABLE 14-continued
617
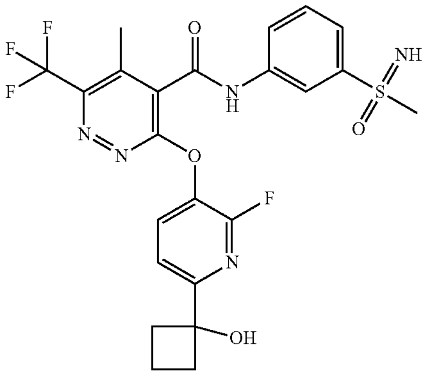
618
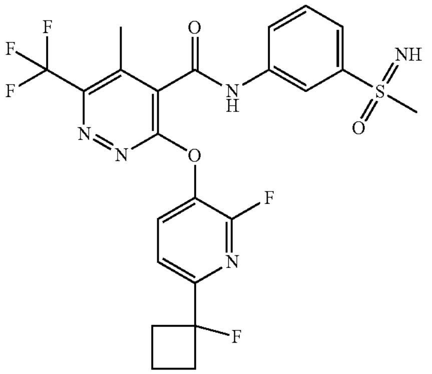
619
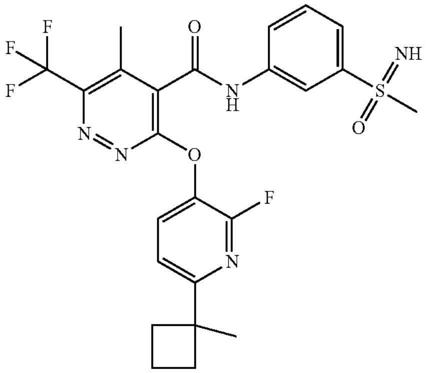 [SMILES: Cc1c(C(F)(F)F)nnc(Oc2ccc(C3(C)CCC3)nc2F)c1C(=O)Nc1cccc(S(C)(=N)=O)c1]
620
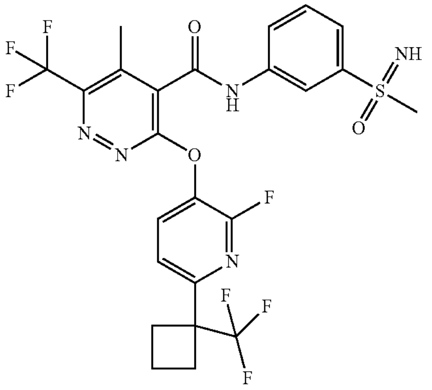
TABLE 14-continued
621
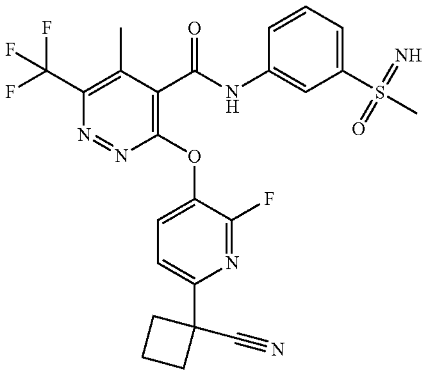
622
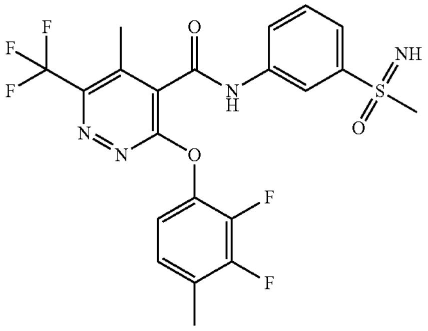 [SMILES: Cc1ccc(Oc2nnc(C(F)(F)F)c(C)c2C(=O)Nc2cccc(S(C)(=N)=O)c2)c(F)c1F]
623
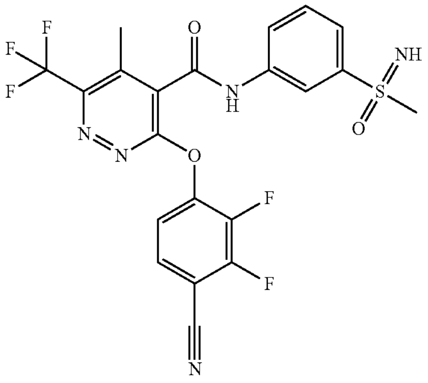 [SMILES: Cc1c(C(F)(F)F)nnc(Oc2ccc(C#N)c(F)c2F)c1C(=O)Nc1cccc(S(C)(=N)=O)c1]
624
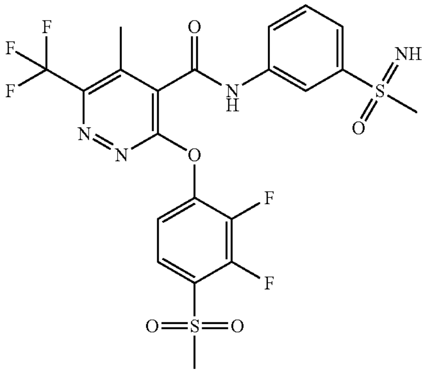 [SMILES: Cc1c(C(F)(F)F)nnc(Oc2ccc(S(C)(=O)=O)c(F)c2F)c1C(=O)Nc1cccc(S(C)(=N)=O)c1]

TABLE 14-continued
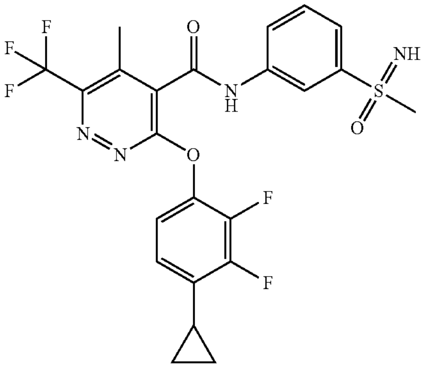
625
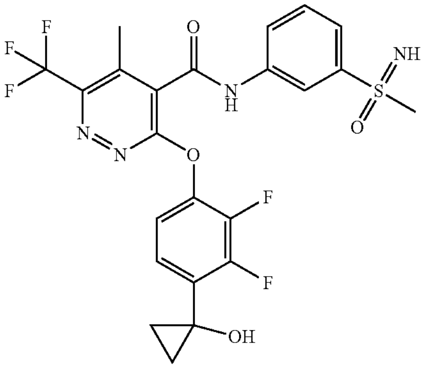
626
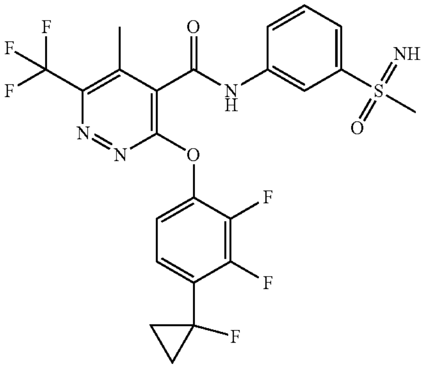
627
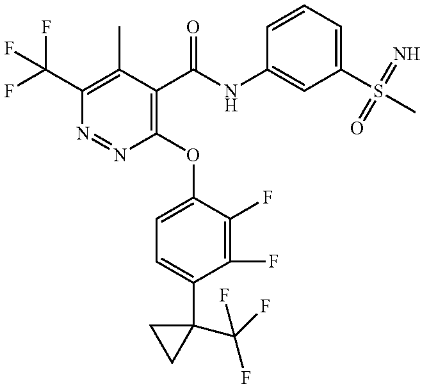 [SMILES: Cc1c(C(F)(F)F)nnc(Oc2ccc(C3(C(F)(F)F)CC3)c(F)c2F)c1C(=O)Nc1cccc(S(C)(=N)=O)c1]
628
TABLE 14-continued
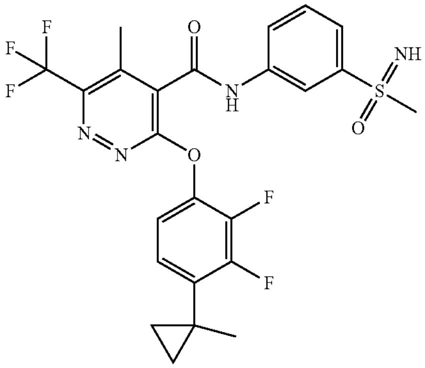
630
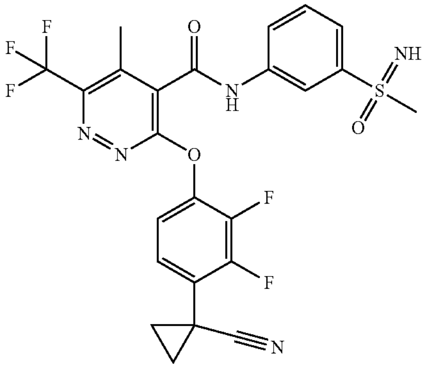
631
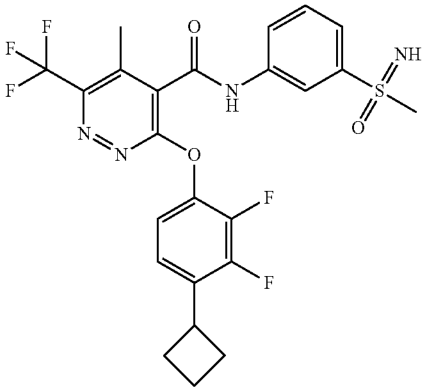 [SMILES: Cc1c(C(F)(F)F)nnc(Oc2ccc(C3CCC3)c(F)c2F)c1C(=O)Nc1cccc(S(C)(=N)=O)c1]
632
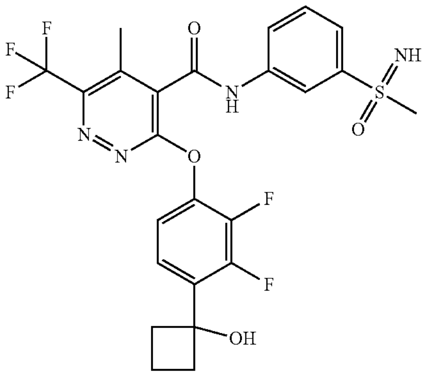 [SMILES: Cc1c(C(F)(F)F)nnc(Oc2ccc(C3(O)CCC3)c(F)c2F)c1C(=O)Nc1cccc(S(C)(=N)=O)c1]
633

TABLE 14-continued
634
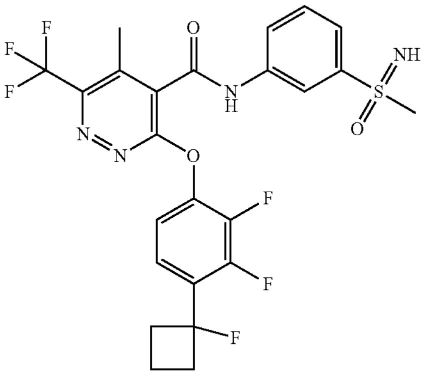
635
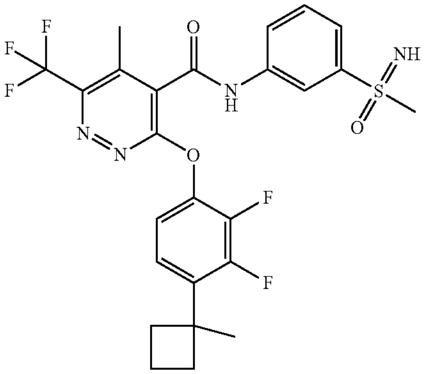
636
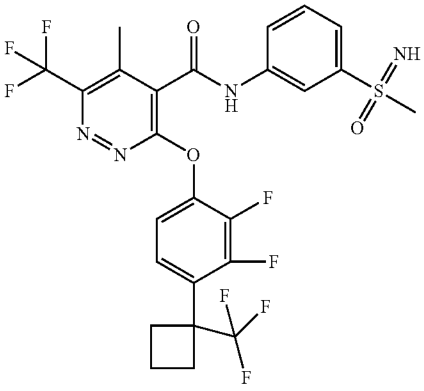
637
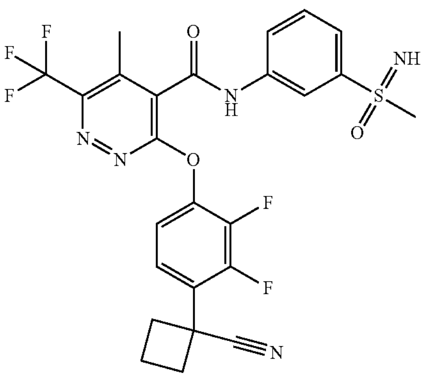 [SMILES: Cc1c(C(F)(F)F)nnc(Oc2ccc(C3(C#N)CCC3)c(F)c2F)c1C(=O)Nc1cccc(S(C)(=N)=O)c1]
TABLE 14-continued
638
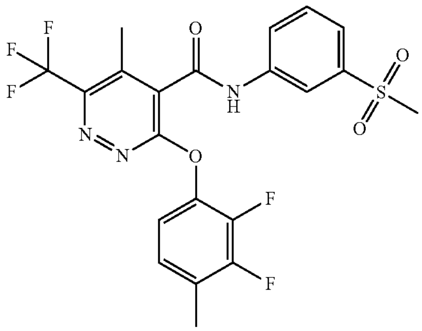
639
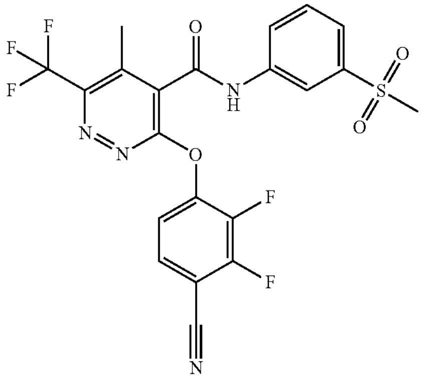 [SMILES: Cc1c(C(F)(F)F)nnc(Oc2ccc(C#N)c(F)c2F)c1C(=O)Nc1cccc(S(C)(=O)=O)c1]
640
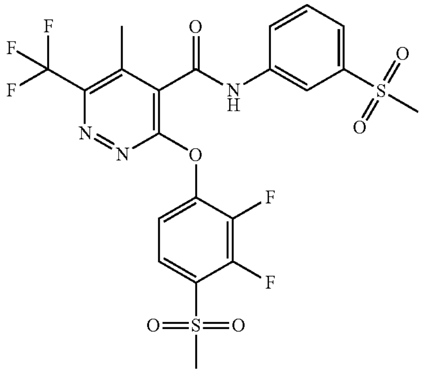 [SMILES: Cc1c(C(F)(F)F)nnc(Oc2ccc(S(C)(=O)=O)c(F)c2F)c1C(=O)Nc1cccc(S(C)(=O)=O)c1]
641
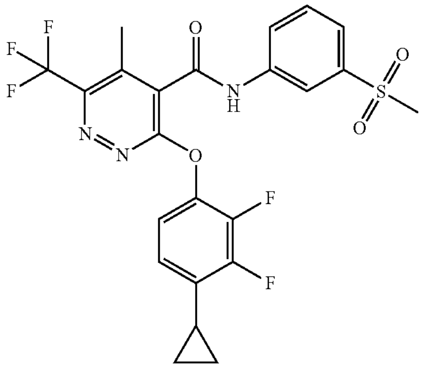 [SMILES: Cc1c(C(F)(F)F)nnc(Oc2ccc(C3CC3)c(F)c2F)c1C(=O)Nc1cccc(S(C)(=O)=O)c1]

TABLE 14-continued
642
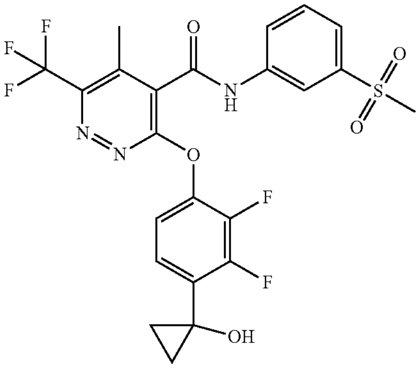 [SMILES: Cc1c(C(F)(F)F)nnc(Oc2ccc(C3(O)CC3)c(F)c2F)c1C(=O)Nc1cccc(S(C)(=O)=O)c1]
643
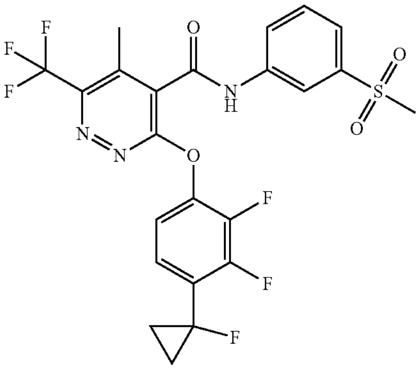 [SMILES: Cc1c(C(F)(F)F)nnc(Oc2ccc(C3(F)CC3)c(F)c2F)c1C(=O)Nc1cccc(S(C)(=O)=O)c1]
644
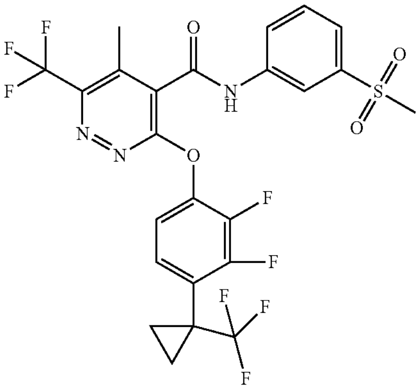 [SMILES: Cc1c(C(F)(F)F)nnc(Oc2ccc(C3(C(F)(F)F)CC3)c(F)c2F)c1C(=O)Nc1cccc(S(C)(=O)=O)c1]
645
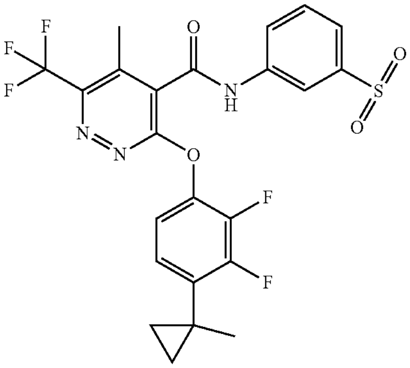
TABLE 14-continued
646
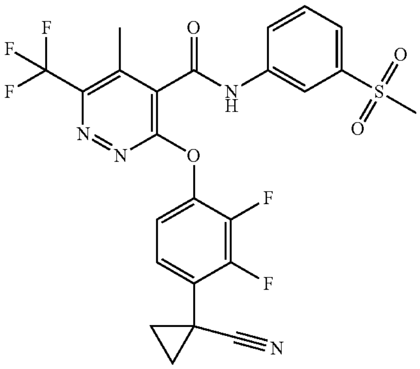
647
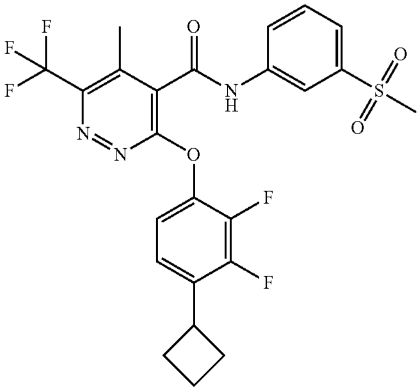 [SMILES: Cc1c(C(F)(F)F)nnc(Oc2ccc(C3CCC3)c(F)c2F)c1C(=O)Nc1cccc(S(C)(=O)=O)c1]
648
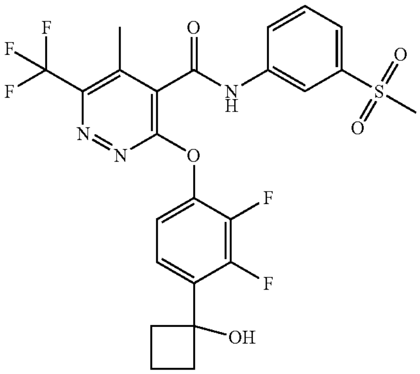 [SMILES: Cc1c(C(F)(F)F)nnc(Oc2ccc(C3(O)CCC3)c(F)c2F)c1C(=O)Nc1cccc(S(C)(=O)=O)c1]
649
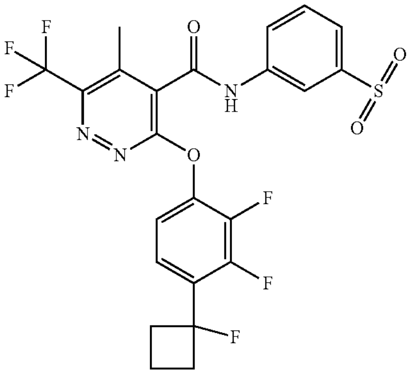

TABLE 14-continued
650
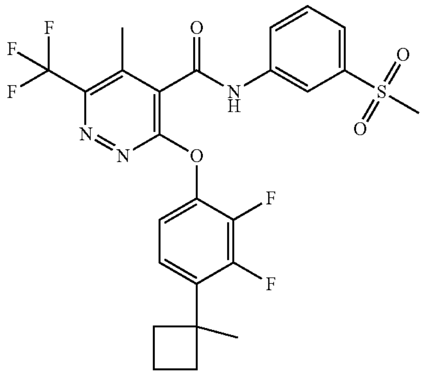 [SMILES: Cc1c(C(F)(F)F)nnc(Oc2ccc(C3(C)CCC3)c(F)c2F)c1C(=O)Nc1cccc(S(C)(=O)=O)c1]
651
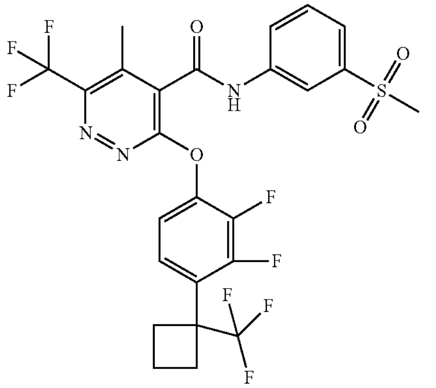 [SMILES: Cc1c(C(F)(F)F)nnc(Oc2ccc(C3(C(F)(F)F)CCC3)c(F)c2F)c1C(=O)Nc1cccc(S(C)(=O)=O)c1]
652
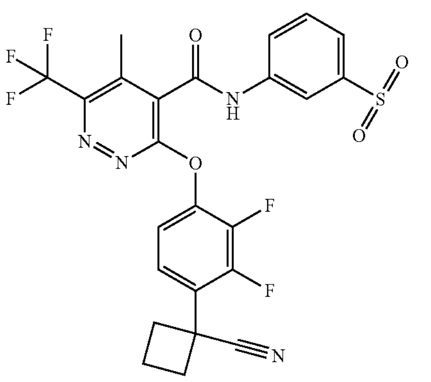
653
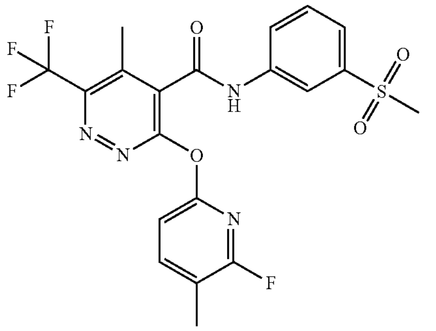 [SMILES: Cc1ccc(Oc2nnc(C(F)(F)F)c(C)c2C(=O)Nc2cccc(S(C)(=O)=O)c2)nc1F]
TABLE 14-continued
654
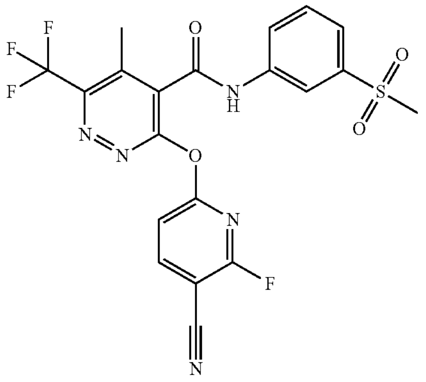 [SMILES: Cc1c(C(F)(F)F)nnc(Oc2ccc(C#N)c(F)n2)c1C(=O)Nc1cccc(S(C)(=O)=O)c1]
655
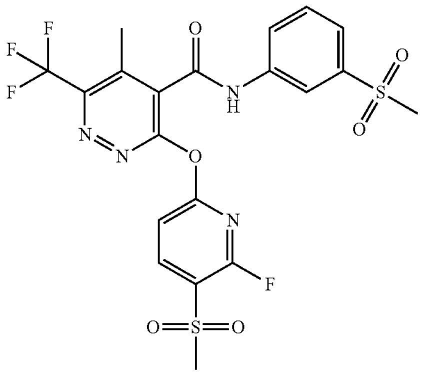
656
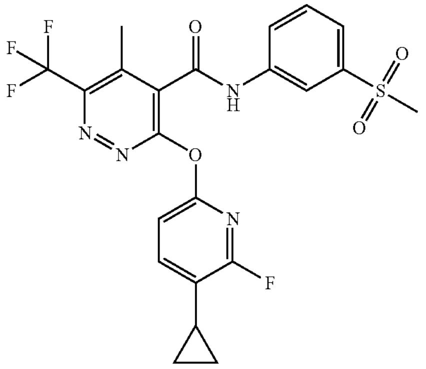 [SMILES: Cc1c(C(F)(F)F)nnc(Oc2ccc(C3CC3)c(F)n2)c1C(=O)Nc1cccc(S(C)(=O)=O)c1]
657
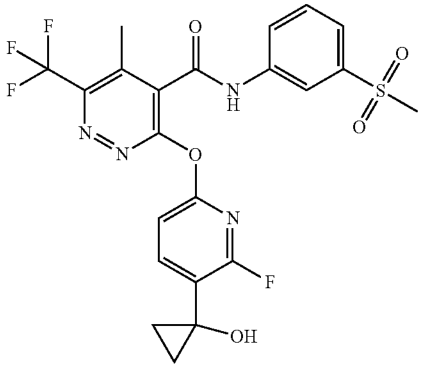 [SMILES: Cc1c(C(F)(F)F)nnc(Oc2ccc(C3(O)CC3)c(F)n2)c1C(=O)Nc1cccc(S(C)(=O)=O)c1]

TABLE 14-continued
658
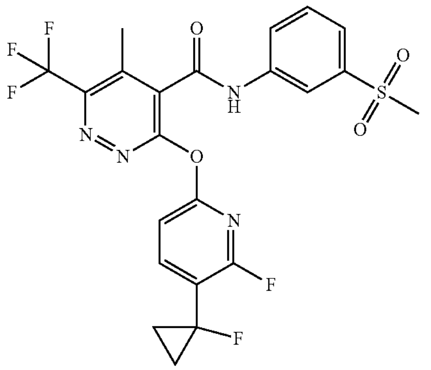
659
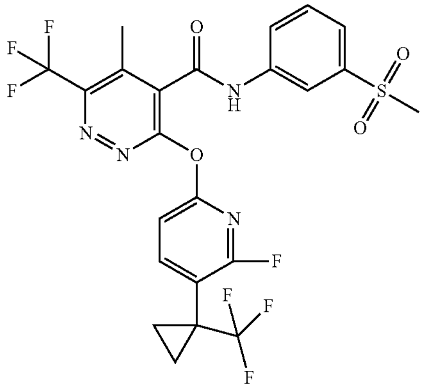
660
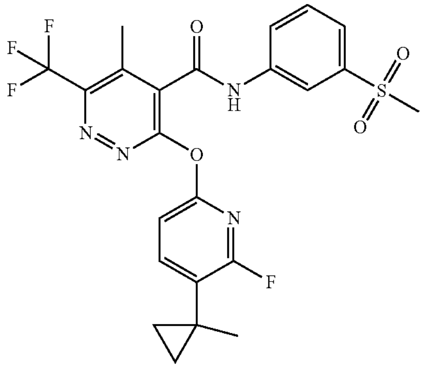 [SMILES: Cc1c(C(F)(F)F)nnc(Oc2ccc(C3(C)CC3)c(F)n2)c1C(=O)Nc1cccc(S(C)(=O)=O)c1]
661
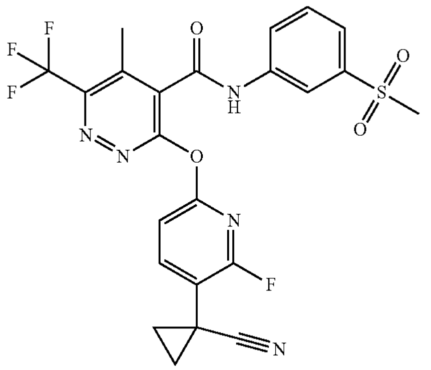 [SMILES: Cc1c(C(F)(F)F)nnc(Oc2ccc(C3(C#N)CC3)c(F)n2)c1C(=O)Nc1cccc(S(C)(=O)=O)c1]
TABLE 14-continued
662
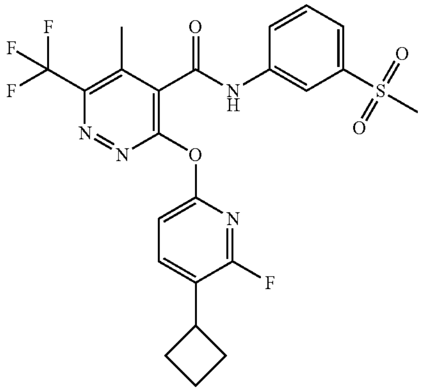 [SMILES: Cc1c(C(F)(F)F)nnc(Oc2ccc(C3CCC3)c(F)n2)c1C(=O)Nc1cccc(S(C)(=O)=O)c1]
663
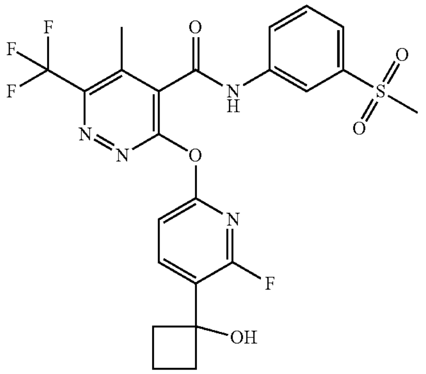
664
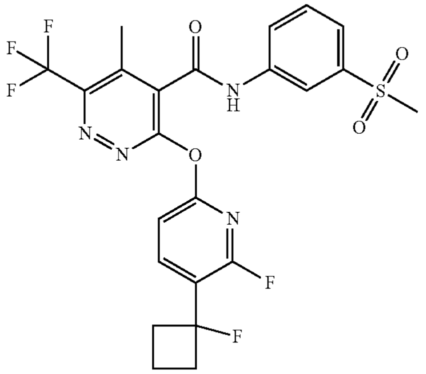 [SMILES: Cc1c(C(F)(F)F)nnc(Oc2ccc(C3(F)CCC3)c(F)n2)c1C(=O)Nc1cccc(S(C)(=O)=O)c1]
665
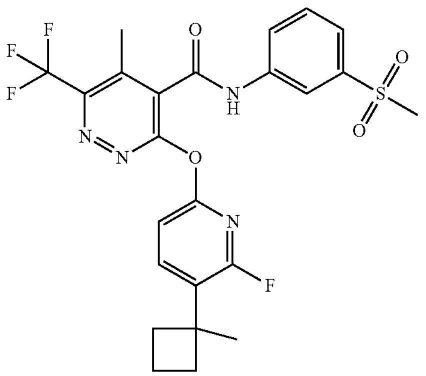

TABLE 14-continued
666
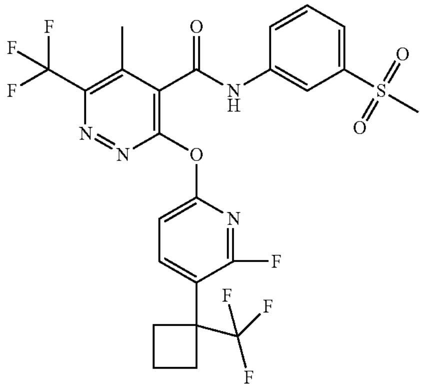 [SMILES: Cc1c(C(F)(F)F)nnc(Oc2ccc(C3(C(F)(F)F)CCC3)c(F)n2)c1C(=O)Nc1cccc(S(C)(=O)=O)c1]
667
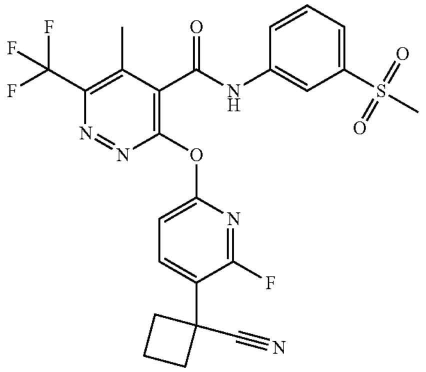 [SMILES: Cc1c(C(F)(F)F)nnc(Oc2ccc(C3(C#N)CCC3)c(F)n2)c1C(=O)Nc1cccc(S(C)(=O)=O)c1]
668
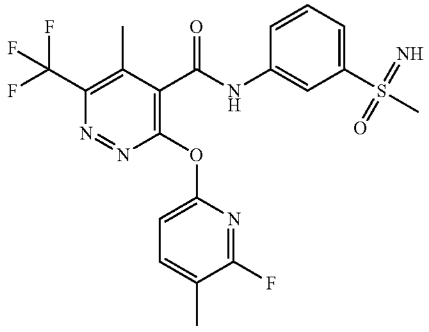
669
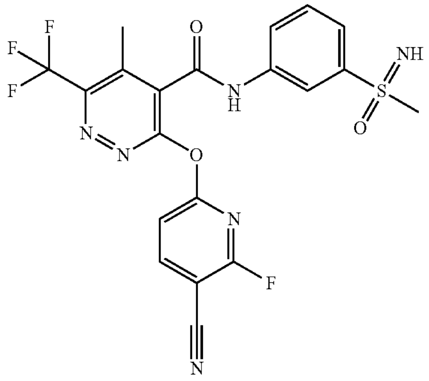
TABLE 14-continued
670
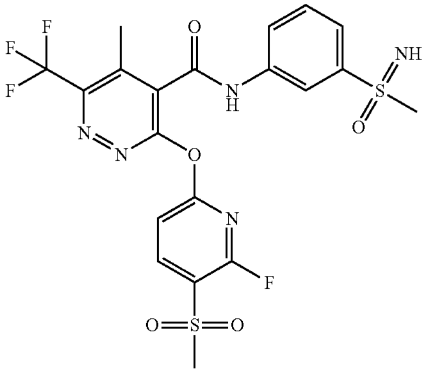
671
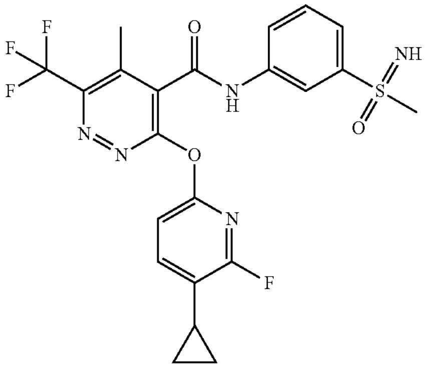 [SMILES: Cc1c(C(F)(F)F)nnc(Oc2ccc(C3CC3)c(F)n2)c1C(=O)Nc1cccc(S(C)(=N)=O)c1]
672
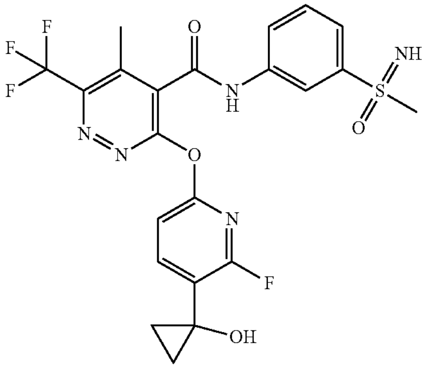 [SMILES: Cc1c(C(F)(F)F)nnc(Oc2ccc(C3(O)CC3)c(F)n2)c1C(=O)Nc1cccc(S(C)(=N)=O)c1]
673
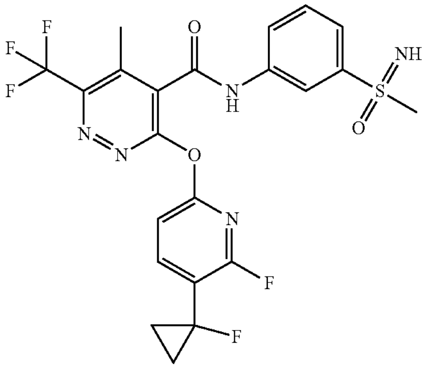 [SMILES: Cc1c(C(F)(F)F)nnc(Oc2ccc(C3(F)CC3)c(F)n2)c1C(=O)Nc1cccc(S(C)(=N)=O)c1]

TABLE 14-continued
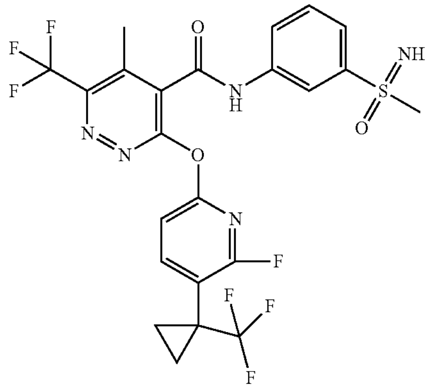 [SMILES: Cc1c(C(F)(F)F)nnc(Oc2ccc(C3(C(F)(F)F)CC3)c(F)n2)c1C(=O)Nc1cccc(S(C)(=N)=O)c1]
674
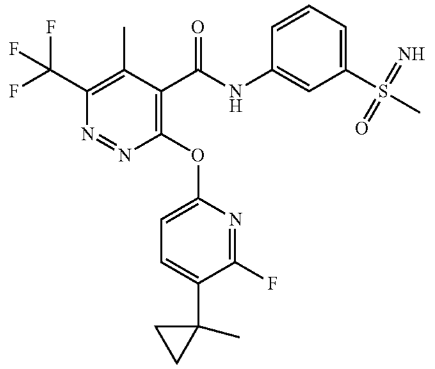 [SMILES: Cc1c(C(F)(F)F)nnc(Oc2ccc(C3(C)CC3)c(F)n2)c1C(=O)Nc1cccc(S(C)(=N)=O)c1]
675
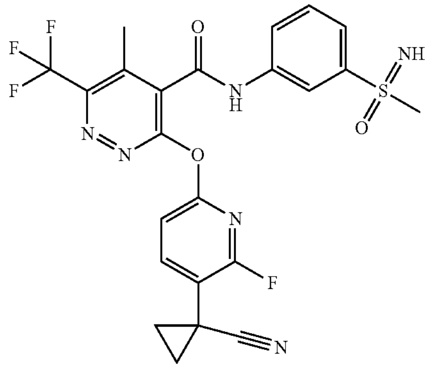 [SMILES: Cc1c(C(F)(F)F)nnc(Oc2ccc(C3(C#N)CC3)c(F)n2)c1C(=O)Nc1cccc(S(C)(=N)=O)c1]
676
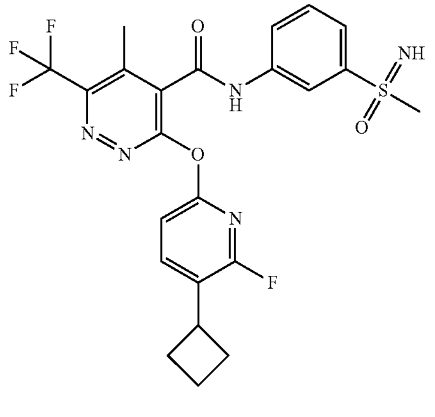
677
TABLE 14-continued
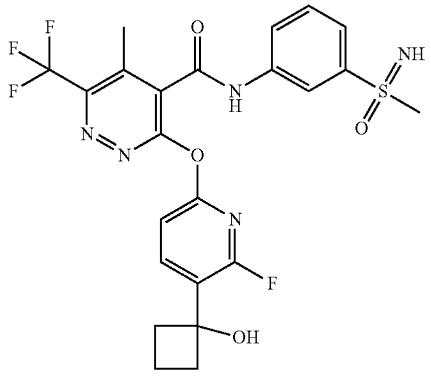 [SMILES: Cc1c(C(F)(F)F)nnc(Oc2ccc(C3(O)CCC3)c(F)n2)c1C(=O)Nc1cccc(S(C)(=N)=O)c1]
678
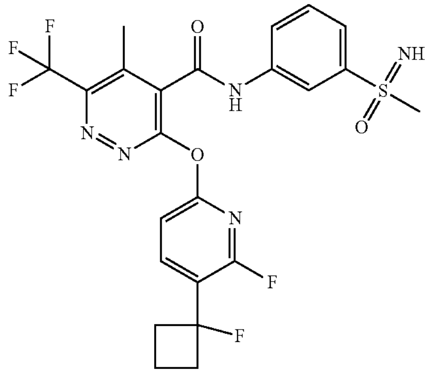 [SMILES: Cc1c(C(F)(F)F)nnc(Oc2ccc(C3(F)CCC3)c(F)n2)c1C(=O)Nc1cccc(S(C)(=N)=O)c1]
679
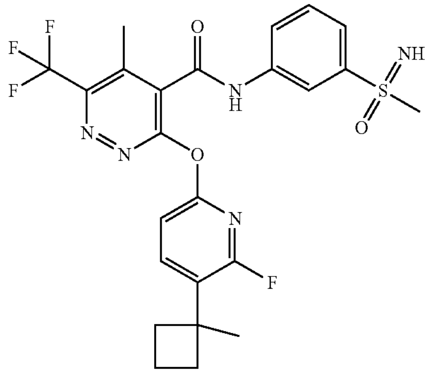 [SMILES: Cc1c(C(F)(F)F)nnc(Oc2ccc(C3(C)CCC3)c(F)n2)c1C(=O)Nc1cccc(S(C)(=N)=O)c1]
680
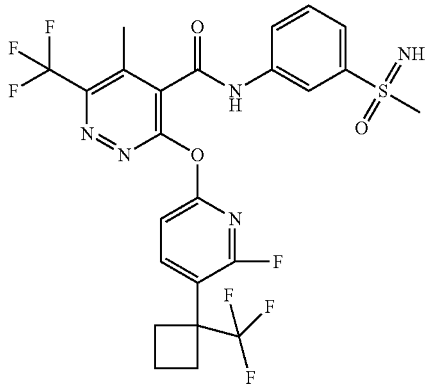 [SMILES: Cc1c(C(F)(F)F)nnc(Oc2ccc(C3(C(F)(F)F)CCC3)c(F)n2)c1C(=O)Nc1cccc(S(C)(=N)=O)c1]
681

682
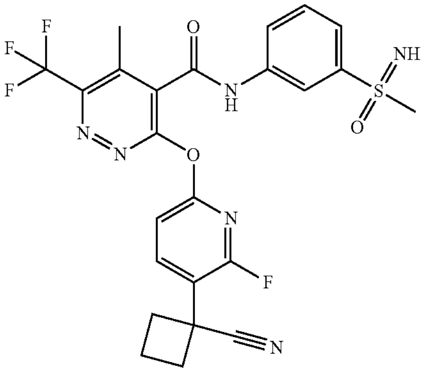 [SMILES: Cc1c(C(F)(F)F)nnc(Oc2ccc(C3(C#N)CCC3)c(F)n2)c1C(=O)Nc1cccc(S(C)(=N)=O)c1]
683
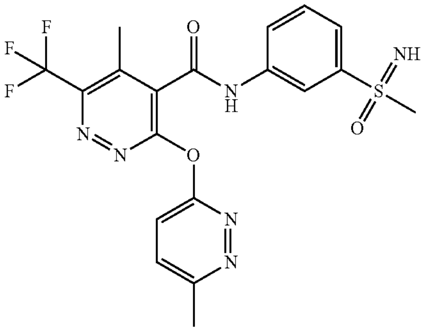 [SMILES: Cc1ccc(Oc2nnc(C(F)(F)F)c(C)c2C(=O)Nc2cccc(S(C)(=N)=O)c2)nn1]
684
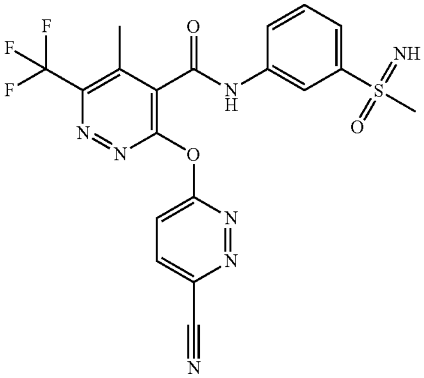 [SMILES: Cc1c(C(F)(F)F)nnc(Oc2ccc(C#N)nn2)c1C(=O)Nc1cccc(S(C)(=N)=O)c1]
685
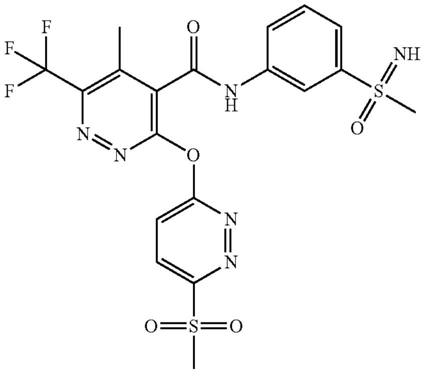 [SMILES: Cc1c(C(F)(F)F)nnc(Oc2ccc(S(C)(=O)=O)nn2)c1C(=O)Nc1cccc(S(C)(=N)=O)c1]
686
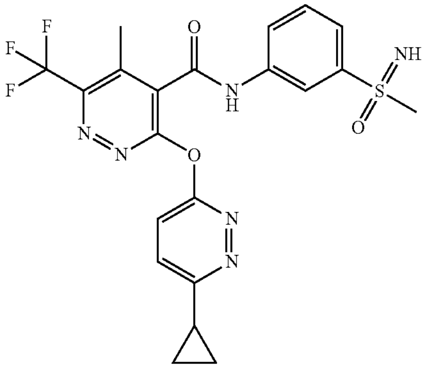 [SMILES: Cc1c(C(F)(F)F)nnc(Oc2ccc(C3CC3)nn2)c1C(=O)Nc1cccc(S(C)(=N)=O)c1]
687
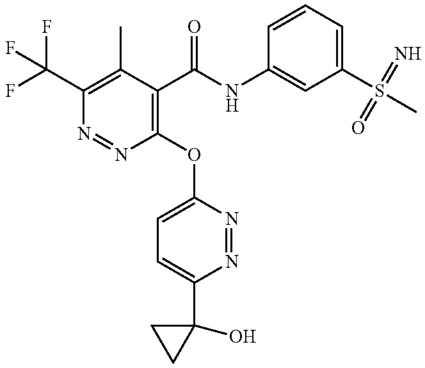 [SMILES: Cc1c(C(F)(F)F)nnc(Oc2ccc(C3(O)CC3)nn2)c1C(=O)Nc1cccc(S(C)(=N)=O)c1]
687
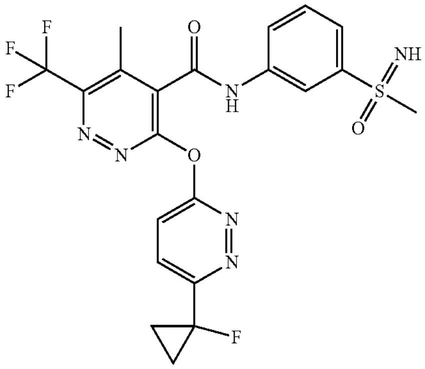 [SMILES: Cc1c(C(F)(F)F)nnc(Oc2ccc(C3(F)CC3)nn2)c1C(=O)Nc1cccc(S(C)(=N)=O)c1]
688
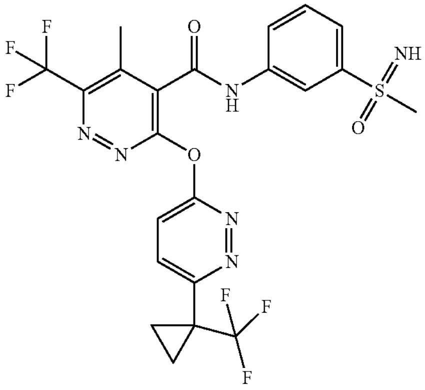 [SMILES: Cc1c(C(F)(F)F)nnc(Oc2ccc(C3(C(F)(F)F)CC3)nn2)c1C(=O)Nc1cccc(S(C)(=N)=O)c1]

TABLE 14-continued
689
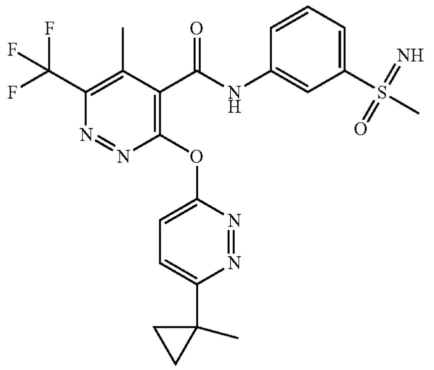 [SMILES: Cc1c(C(F)(F)F)nnc(Oc2ccc(C3(C)CC3)nn2)c1C(=O)Nc1cccc(S(C)(=N)=O)c1]
690
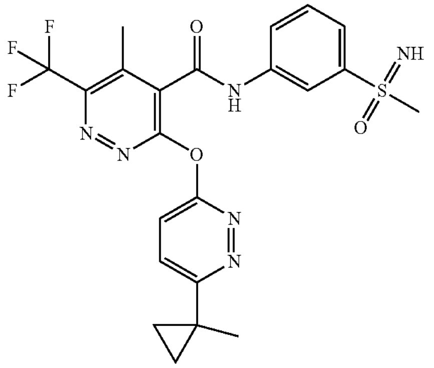
691
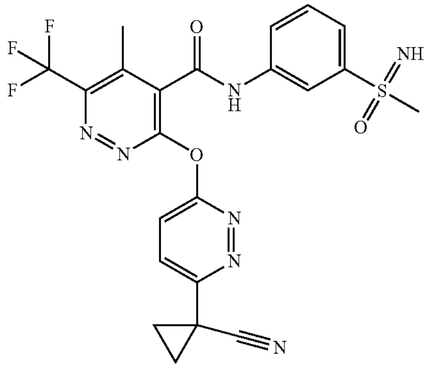 [SMILES: Cc1c(C(F)(F)F)nnc(Oc2ccc(C3(C#N)CC3)nn2)c1C(=O)Nc1cccc(S(C)(=N)=O)c1]
692
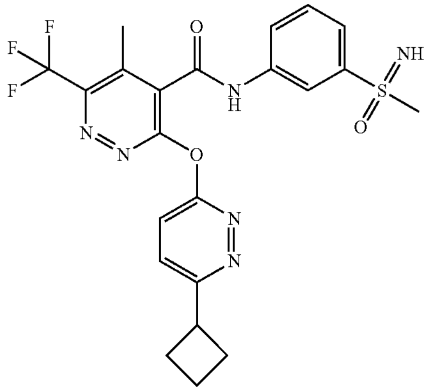 [SMILES: Cc1c(C(F)(F)F)nnc(Oc2ccc(C3CCC3)nn2)c1C(=O)Nc1cccc(S(C)(=N)=O)c1]
TABLE 14-continued
693
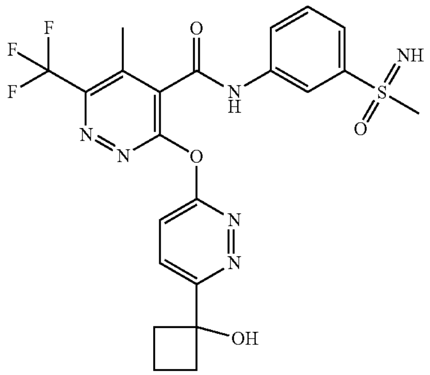 [SMILES: Cc1c(C(F)(F)F)nnc(Oc2ccc(C3(O)CCC3)nn2)c1C(=O)Nc1cccc(S(C)(=N)=O)c1]
694
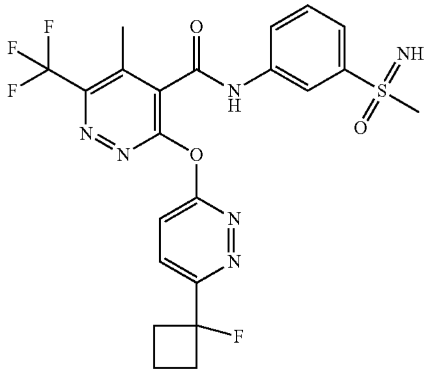
695
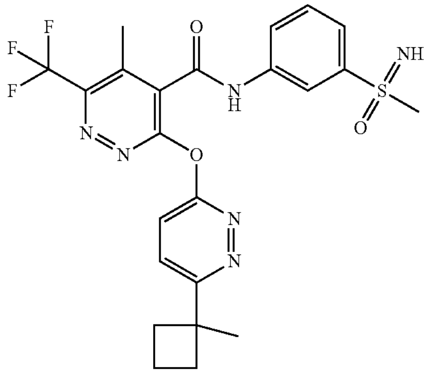 [SMILES: Cc1c(C(F)(F)F)nnc(Oc2ccc(C3(C)CCC3)nn2)c1C(=O)Nc1cccc(S(C)(=N)=O)c1]
696
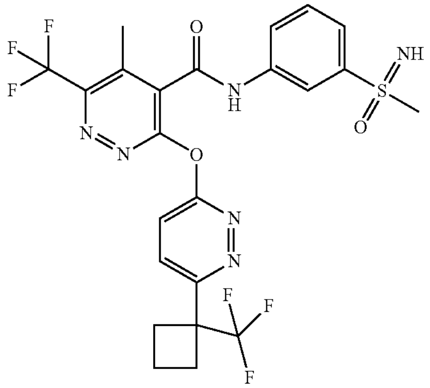 [SMILES: Cc1c(C(F)(F)F)nnc(Oc2ccc(C3(C(F)(F)F)CCC3)nn2)c1C(=O)Nc1cccc(S(C)(=N)=O)c1]

TABLE 14-continued
697
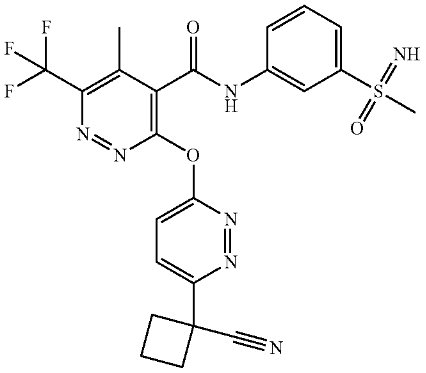 [SMILES: Cc1c(C(F)(F)F)nnc(Oc2ccc(C3(C#N)CCC3)nn2)c1C(=O)Nc1cccc(S(C)(=N)=O)c1]
698
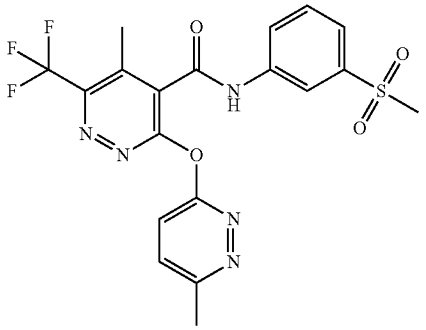 [SMILES: Cc1ccc(Oc2nnc(C(F)(F)F)c(C)c2C(=O)Nc2cccc(S(C)(=O)=O)c2)nn1]
699
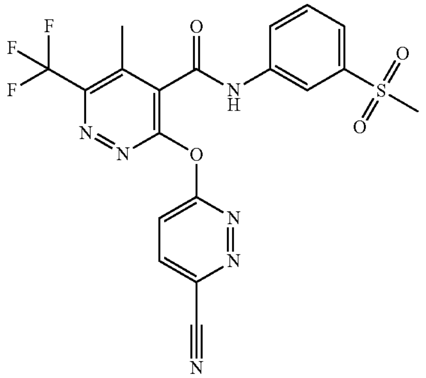 [SMILES: Cc1c(C(F)(F)F)nnc(Oc2ccc(C#N)nn2)c1C(=O)Nc1cccc(S(C)(=O)=O)c1]
700
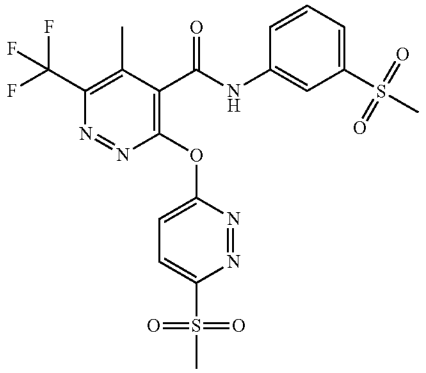 [SMILES: Cc1c(C(F)(F)F)nnc(Oc2ccc(S(C)(=O)=O)nn2)c1C(=O)Nc1cccc(S(C)(=O)=O)c1]
TABLE 14-continued
701
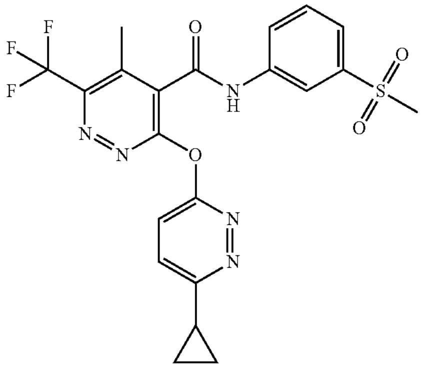 [SMILES: Cc1c(C(F)(F)F)nnc(Oc2ccc(C3CC3)nn2)c1C(=O)Nc1cccc(S(C)(=O)=O)c1]
702
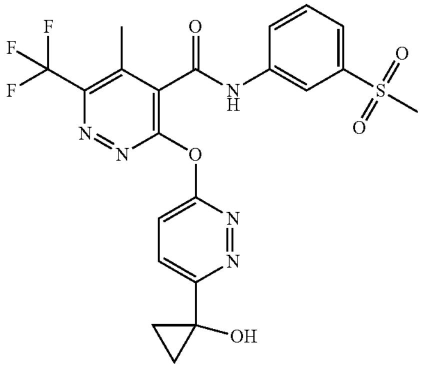 [SMILES: Cc1c(C(F)(F)F)nnc(Oc2ccc(C3(O)CC3)nn2)c1C(=O)Nc1cccc(S(C)(=O)=O)c1]
703
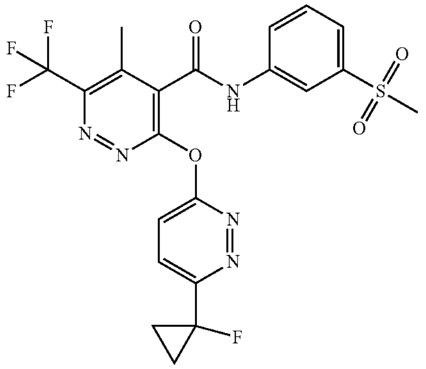 [SMILES: Cc1c(C(F)(F)F)nnc(Oc2ccc(C3(F)CC3)nn2)c1C(=O)Nc1cccc(S(C)(=O)=O)c1]
704
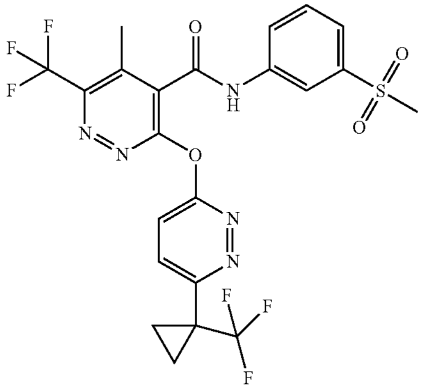 [SMILES: Cc1c(C(F)(F)F)nnc(Oc2ccc(C3(C(F)(F)F)CC3)nn2)c1C(=O)Nc1cccc(S(C)(=O)=O)c1]

TABLE 14-continued
705
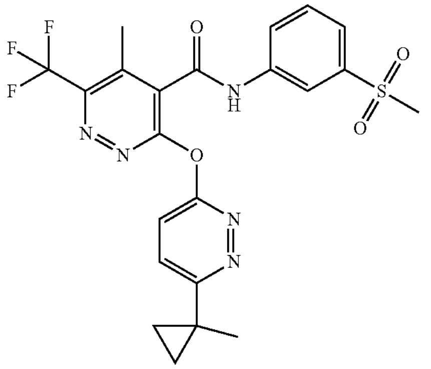
706
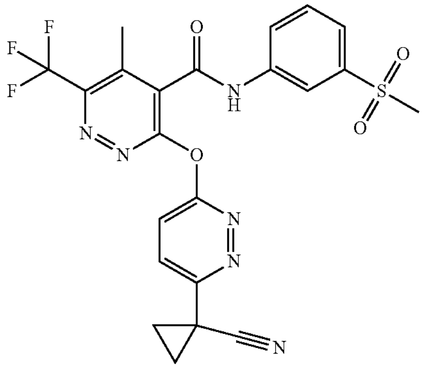 [SMILES: Cc1c(C(F)(F)F)nnc(Oc2ccc(C3(C#N)CC3)nn2)c1C(=O)Nc1cccc(S(C)(=O)=O)c1]
707
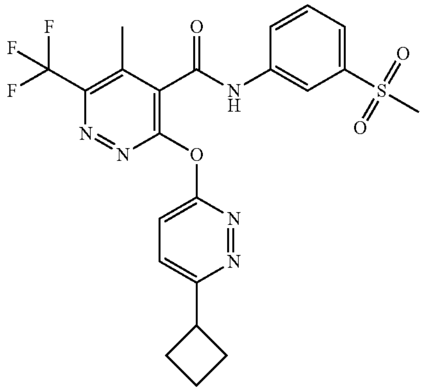 [SMILES: Cc1c(C(F)(F)F)nnc(Oc2ccc(C3CCC3)nn2)c1C(=O)Nc1cccc(S(C)(=O)=O)c1]
708
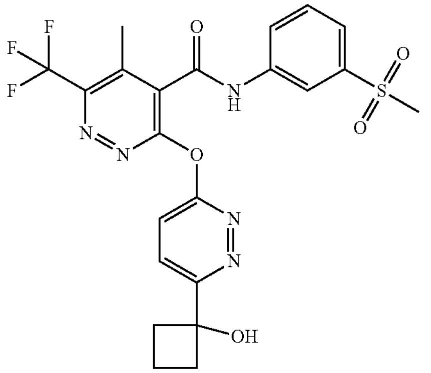 [SMILES: Cc1c(C(F)(F)F)nnc(Oc2ccc(C3(O)CCC3)nn2)c1C(=O)Nc1cccc(S(C)(=O)=O)c1]
TABLE 14-continued
709
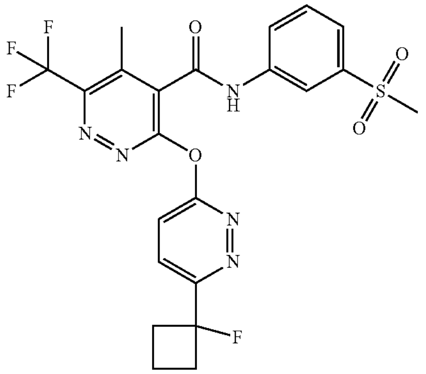
710
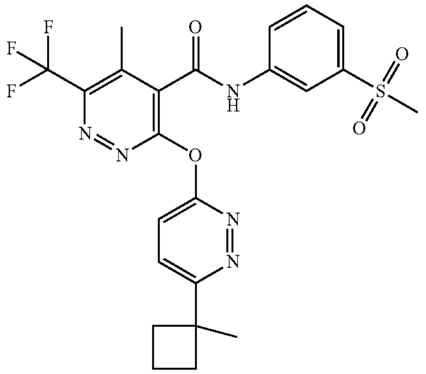 [SMILES: Cc1c(C(F)(F)F)nnc(Oc2ccc(C3(C)CCC3)nn2)c1C(=O)Nc1cccc(S(C)(=O)=O)c1]
711
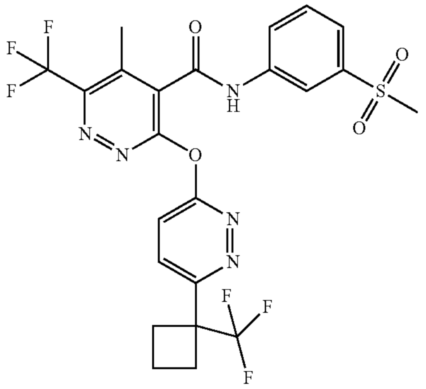 [SMILES: Cc1c(C(F)(F)F)nnc(Oc2ccc(C3(C(F)(F)F)CCC3)nn2)c1C(=O)Nc1cccc(S(C)(=O)=O)c1]
712
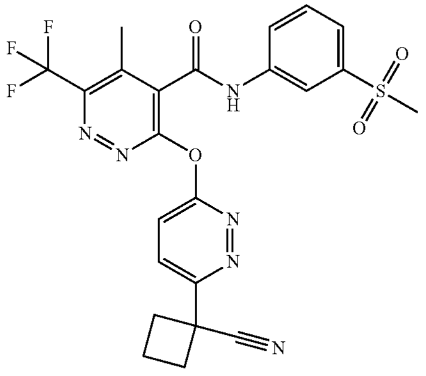 [SMILES: Cc1c(C(F)(F)F)nnc(Oc2ccc(C3(C#N)CCC3)nn2)c1C(=O)Nc1cccc(S(C)(=O)=O)c1]

TABLE 14-continued
713
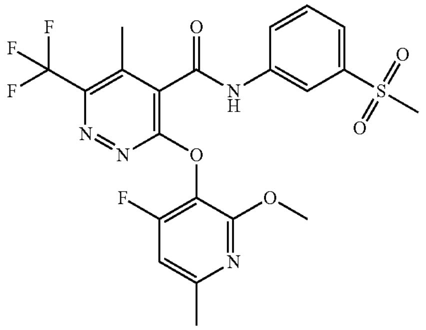
714
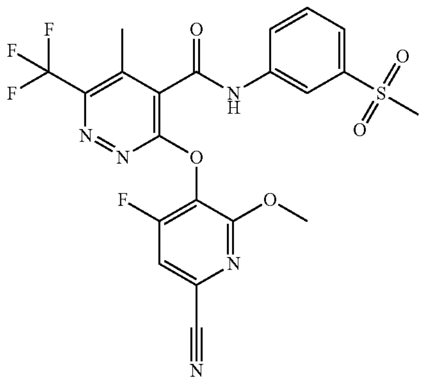 [SMILES: COc1nc(C#N)cc(F)c1Oc1nnc(C(F)(F)F)c(C)c1C(=O)Nc1cccc(S(C)(=O)=O)c1]
715
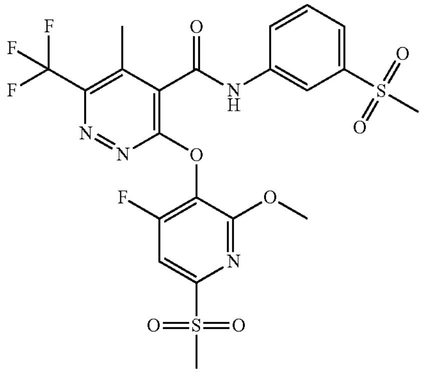
716
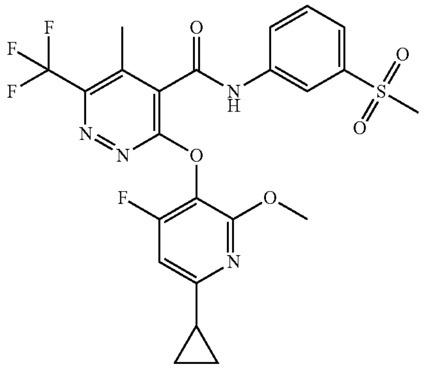
TABLE 14-continued
717
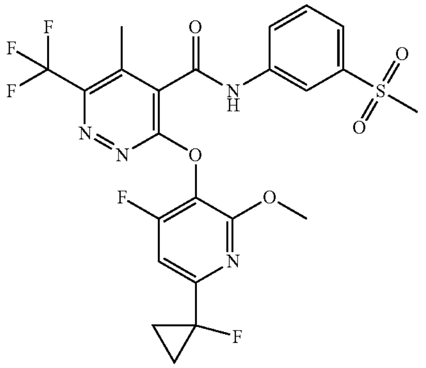
718
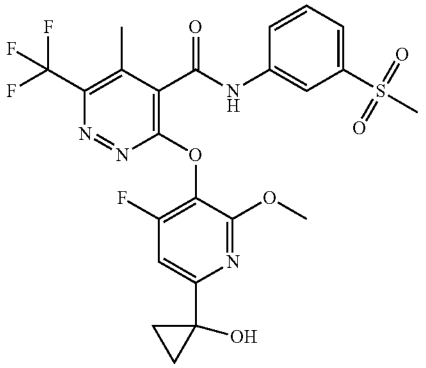
719
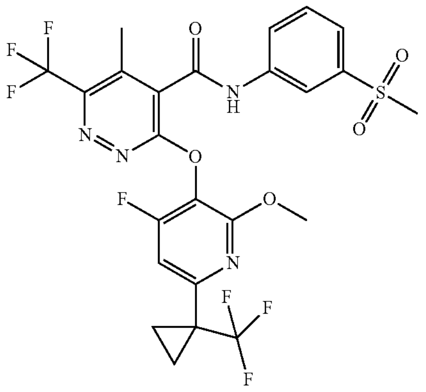 [SMILES: COc1nc(C2(C(F)(F)F)CC2)cc(F)c1Oc1nnc(C(F)(F)F)c(C)c1C(=O)Nc1cccc(S(C)(=O)=O)c1]
720
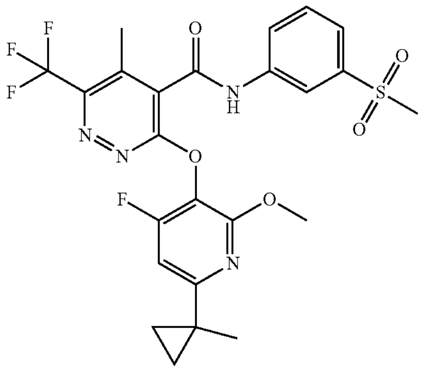 [SMILES: COc1nc(C2(C)CC2)cc(F)c1Oc1nnc(C(F)(F)F)c(C)c1C(=O)Nc1cccc(S(C)(=O)=O)c1]

TABLE 14-continued
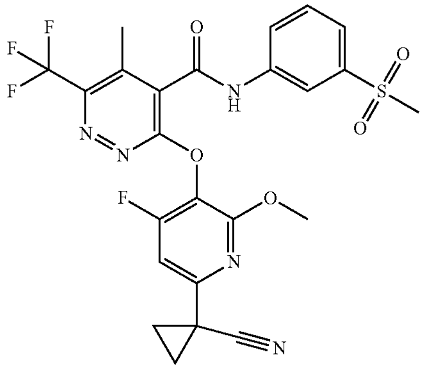 [SMILES: COc1nc(C2(C#N)CC2)cc(F)c1Oc1nnc(C(F)(F)F)c(C)c1C(=O)Nc1cccc(S(C)(=O)=O)c1]
721
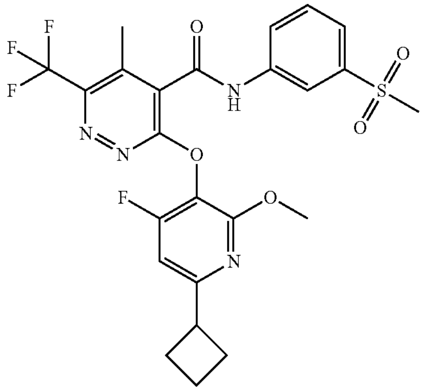 [SMILES: COc1nc(C2CCC2)cc(F)c1Oc1nnc(C(F)(F)F)c(C)c1C(=O)Nc1cccc(S(C)(=O)=O)c1]
722
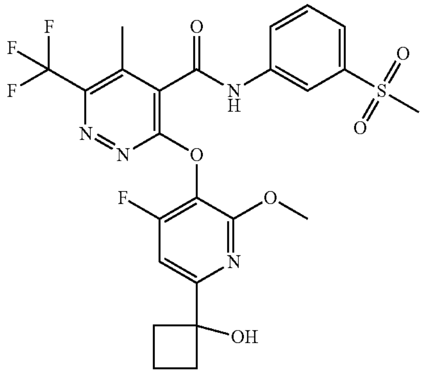 [SMILES: COc1nc(C2(O)CCC2)cc(F)c1Oc1nnc(C(F)(F)F)c(C)c1C(=O)Nc1cccc(S(C)(=O)=O)c1]
723
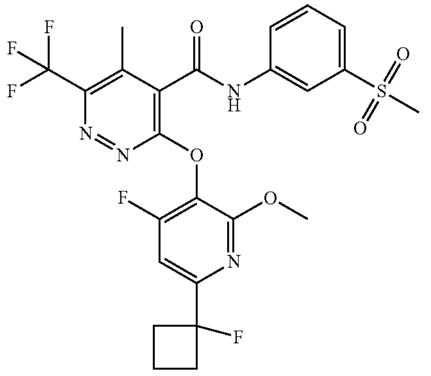 [SMILES: COc1nc(C2(F)CCC2)cc(F)c1Oc1nnc(C(F)(F)F)c(C)c1C(=O)Nc1cccc(S(C)(=O)=O)c1]
724
TABLE 14-continued
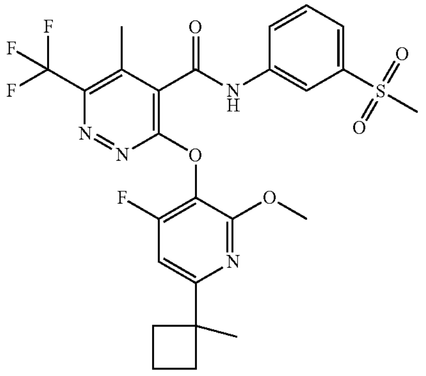 [SMILES: COc1nc(C2(C)CCC2)cc(F)c1Oc1nnc(C(F)(F)F)c(C)c1C(=O)Nc1cccc(S(C)(=O)=O)c1]
725
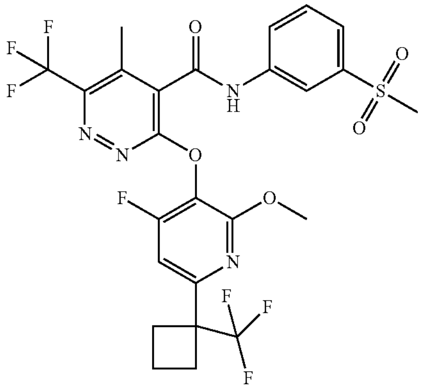 [SMILES: COc1nc(C2(C(F)(F)F)CCC2)cc(F)c1Oc1nnc(C(F)(F)F)c(C)c1C(=O)Nc1cccc(S(C)(=O)=O)c1]
726
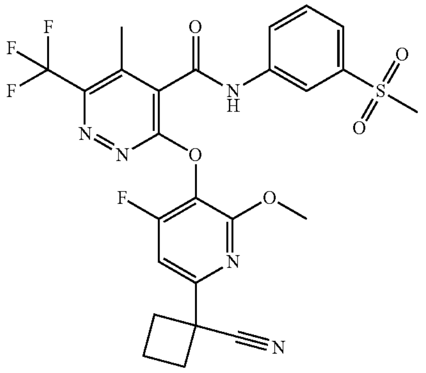 [SMILES: COc1nc(C2(C#N)CCC2)cc(F)c1Oc1nnc(C(F)(F)F)c(C)c1C(=O)Nc1cccc(S(C)(=O)=O)c1]
727
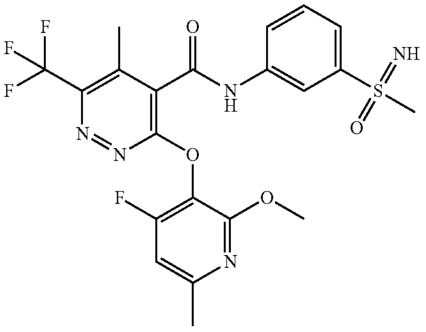 [SMILES: COc1nc(C)cc(F)c1Oc1nnc(C(F)(F)F)c(C)c1C(=O)Nc1cccc(S(C)(=N)=O)c1]
728

TABLE 14-continued
729
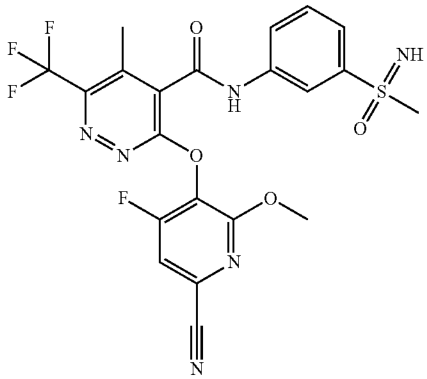 [SMILES: COc1nc(C#N)cc(F)c1Oc1nnc(C(F)(F)F)c(C)c1C(=O)Nc1cccc(S(C)(=N)=O)c1]
730
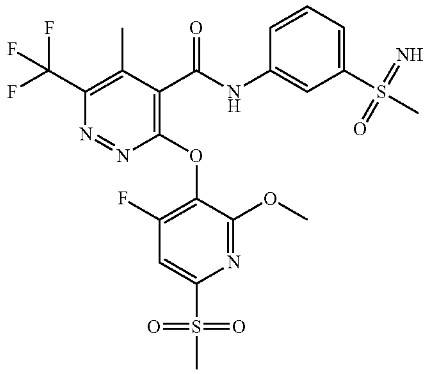 [SMILES: COc1nc(S(C)(=O)=O)cc(F)c1Oc1nnc(C(F)(F)F)c(C)c1C(=O)Nc1cccc(S(C)(=N)=O)c1]
731
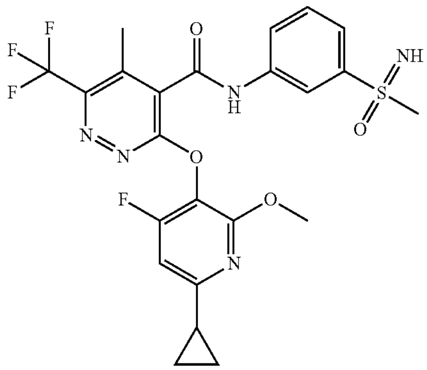 [SMILES: COc1nc(C2CC2)cc(F)c1Oc1nnc(C(F)(F)F)c(C)c1C(=O)Nc1cccc(S(C)(=N)=O)c1]
732
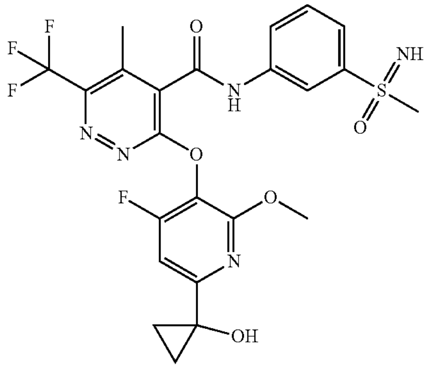 [SMILES: COc1nc(C2(O)CC2)cc(F)c1Oc1nnc(C(F)(F)F)c(C)c1C(=O)Nc1cccc(S(C)(=N)=O)c1]
TABLE 14-continued
733
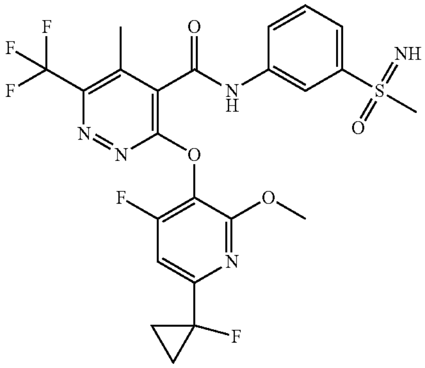 [SMILES: COc1nc(C2(F)CC2)cc(F)c1Oc1nnc(C(F)(F)F)c(C)c1C(=O)Nc1cccc(S(C)(=N)=O)c1]
734
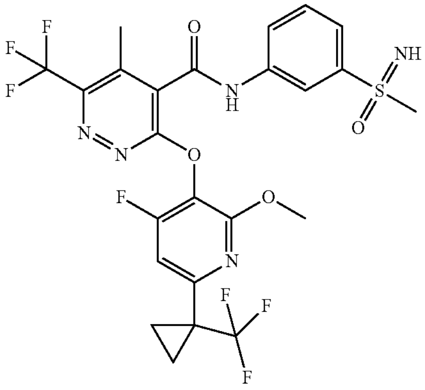 [SMILES: COc1nc(C2(C(F)(F)F)CC2)cc(F)c1Oc1nnc(C(F)(F)F)c(C)c1C(=O)Nc1cccc(S(C)(=N)=O)c1]
735
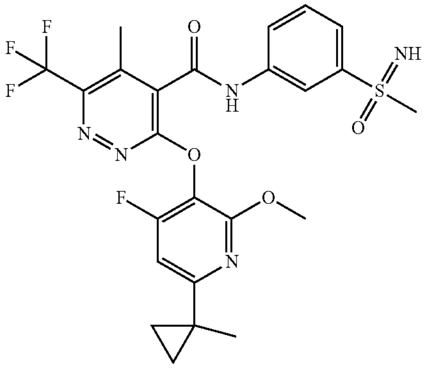
736
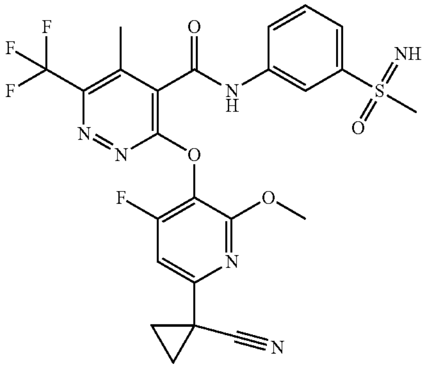 [SMILES: COc1nc(C2(C#N)CC2)cc(F)c1Oc1nnc(C(F)(F)F)c(C)c1C(=O)Nc1cccc(S(C)(=N)=O)c1]

TABLE 14-continued
737
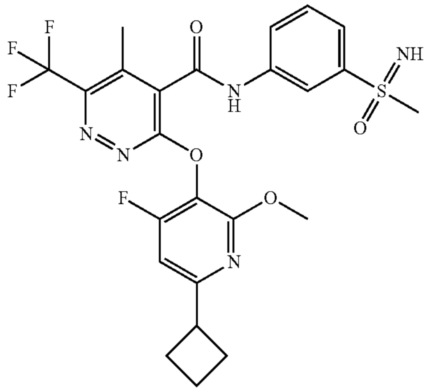 [SMILES: COc1nc(C2CCC2)cc(F)c1Oc1nnc(C(F)(F)F)c(C)c1C(=O)Nc1cccc(S(C)(=N)=O)c1]
738
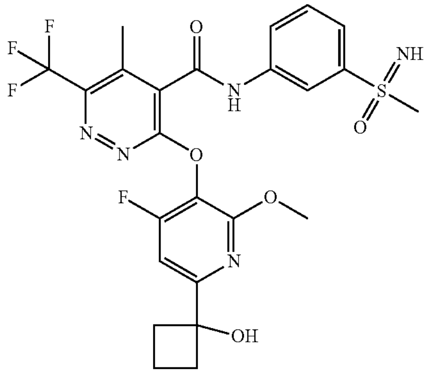 [SMILES: COc1nc(C2(O)CCC2)cc(F)c1Oc1nnc(C(F)(F)F)c(C)c1C(=O)Nc1cccc(S(C)(=N)=O)c1]
739
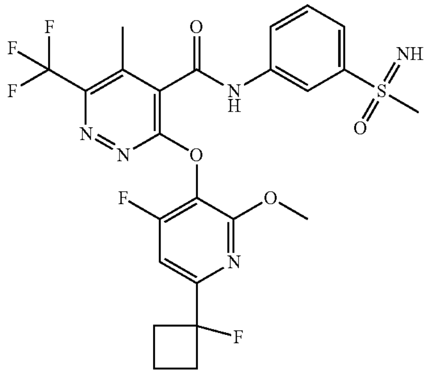 [SMILES: COc1nc(C2(F)CCC2)cc(F)c1Oc1nnc(C(F)(F)F)c(C)c1C(=O)Nc1cccc(S(C)(=N)=O)c1]
740
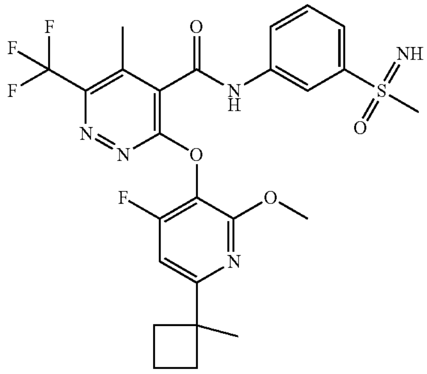
TABLE 14-continued
741
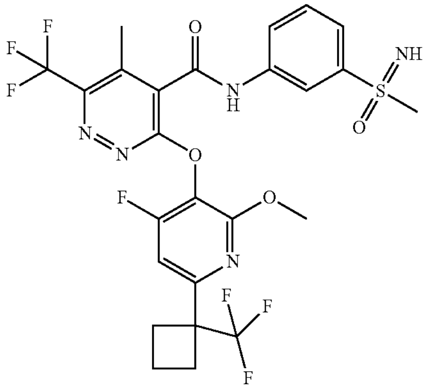 [SMILES: COc1nc(C2(C(F)(F)F)CCC2)cc(F)c1Oc1nnc(C(F)(F)F)c(C)c1C(=O)Nc1cccc(S(C)(=N)=O)c1]
742
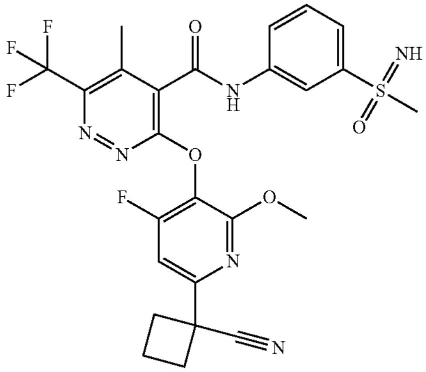 [SMILES: COc1nc(C2(C#N)CCC2)cc(F)c1Oc1nnc(C(F)(F)F)c(C)c1C(=O)Nc1cccc(S(C)(=N)=O)c1]
743
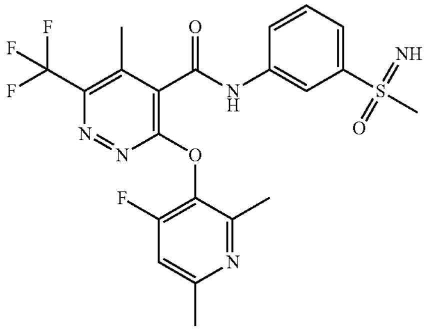
744
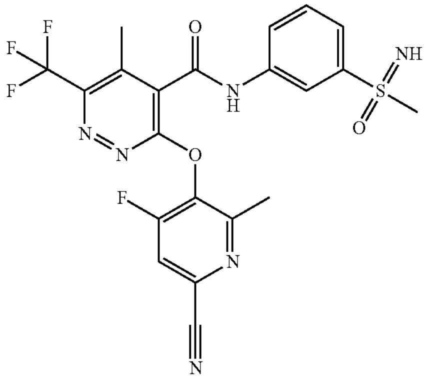

TABLE 14-continued
745
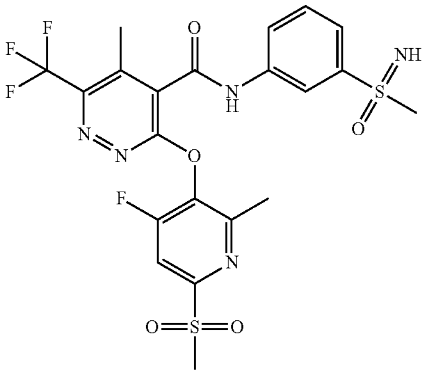 [SMILES: Cc1nc(S(C)(=O)=O)cc(F)c1Oc1nnc(C(F)(F)F)c(C)c1C(=O)Nc1cccc(S(C)(=N)=O)c1]
746
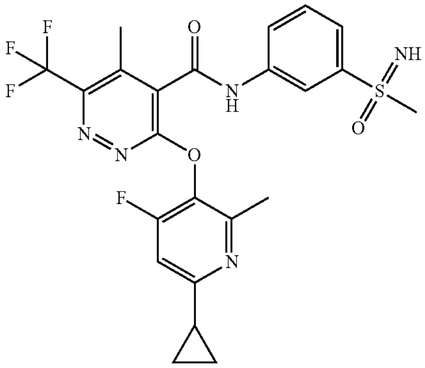 [SMILES: Cc1nc(C2CC2)cc(F)c1Oc1nnc(C(F)(F)F)c(C)c1C(=O)Nc1cccc(S(C)(=N)=O)c1]
747
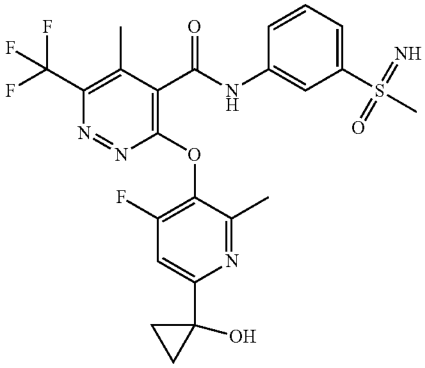 [SMILES: Cc1nc(C2(O)CC2)cc(F)c1Oc1nnc(C(F)(F)F)c(C)c1C(=O)Nc1cccc(S(C)(=N)=O)c1]
748
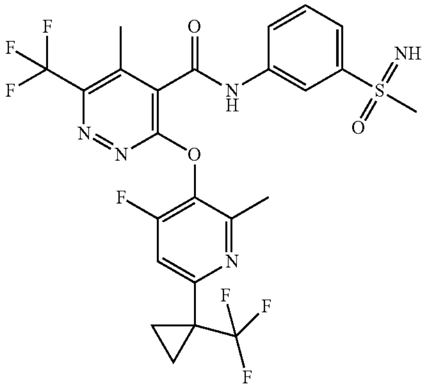 [SMILES: Cc1nc(C2(C(F)(F)F)CC2)cc(F)c1Oc1nnc(C(F)(F)F)c(C)c1C(=O)Nc1cccc(S(C)(=N)=O)c1]
TABLE 14-continued
749
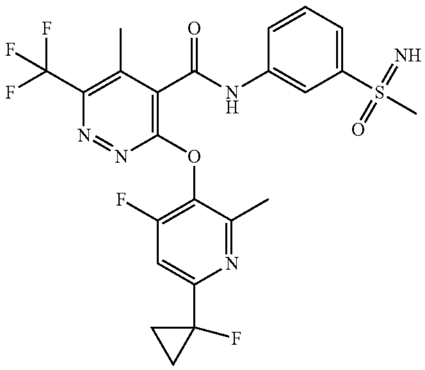 [SMILES: Cc1nc(C2(C)CC2)cc(F)c1Oc1nnc(C(F)(F)F)c(C)c1C(=O)Nc1cccc(S(C)(=N)=O)c1]
750
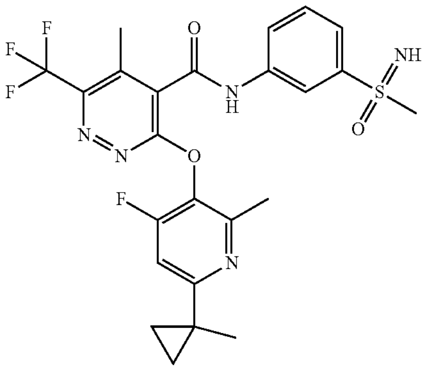
751
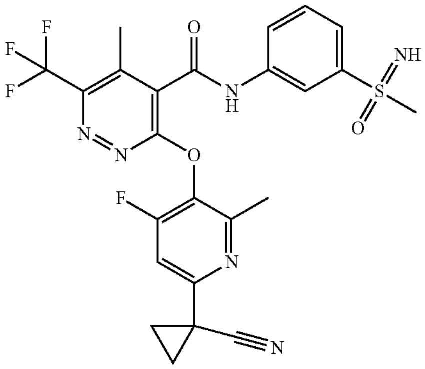 [SMILES: Cc1nc(C2(C#N)CC2)cc(F)c1Oc1nnc(C(F)(F)F)c(C)c1C(=O)Nc1cccc(S(C)(=N)=O)c1]
752
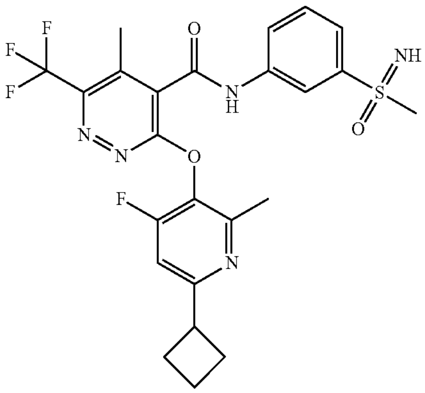 [SMILES: Cc1nc(C2CCC2)cc(F)c1Oc1nnc(C(F)(F)F)c(C)c1C(=O)Nc1cccc(S(C)(=N)=O)c1]

TABLE 14-continued
753
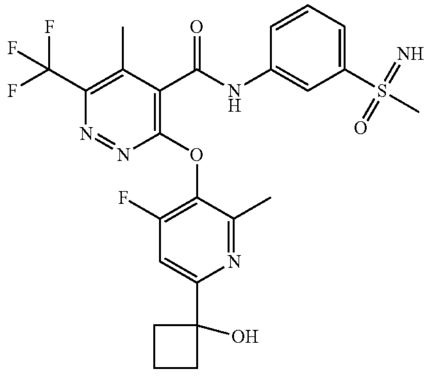 [SMILES: Cc1nc(C2(O)CCC2)cc(F)c1Oc1nnc(C(F)(F)F)c(C)c1C(=O)Nc1cccc(S(C)(=N)=O)c1]
754
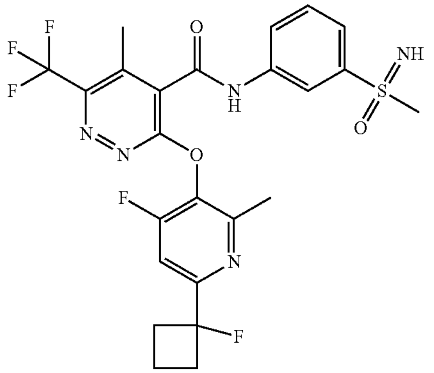
755
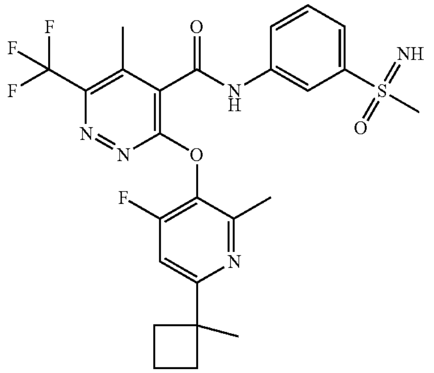 [SMILES: Cc1nc(C2(C)CCC2)cc(F)c1Oc1nnc(C(F)(F)F)c(C)c1C(=O)Nc1cccc(S(C)(=N)=O)c1]
756
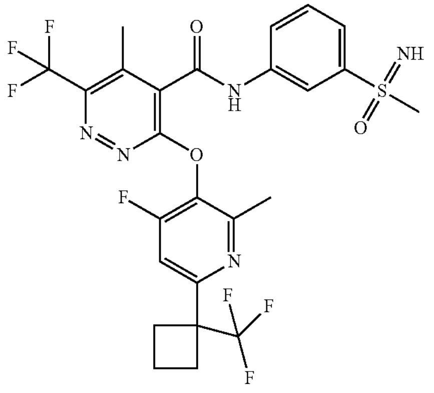 [SMILES: Cc1nc(C2(C(F)(F)F)CCC2)cc(F)c1Oc1nnc(C(F)(F)F)c(C)c1C(=O)Nc1cccc(S(C)(=N)=O)c1]
TABLE 14-continued
757
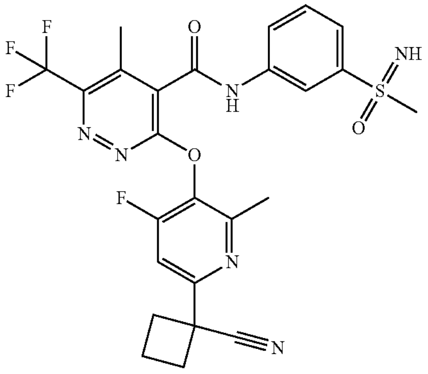 [SMILES: Cc1nc(C2(C#N)CCC2)cc(F)c1Oc1nnc(C(F)(F)F)c(C)c1C(=O)Nc1cccc(S(C)(=N)=O)c1]
758
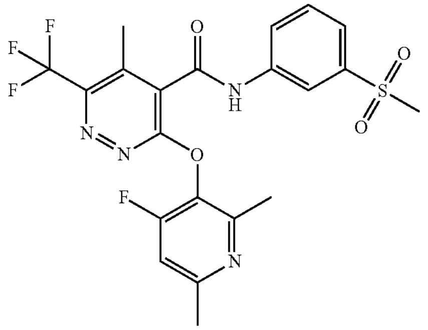
759
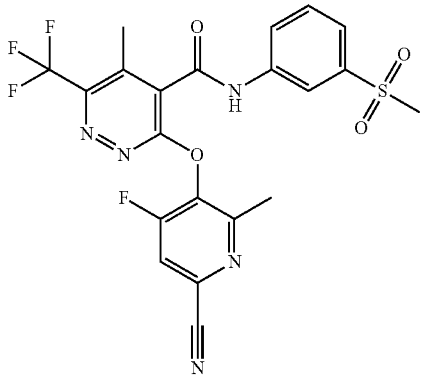 [SMILES: Cc1nc(C#N)cc(F)c1Oc1nnc(C(F)(F)F)c(C)c1C(=O)Nc1cccc(S(C)(=O)=O)c1]
760
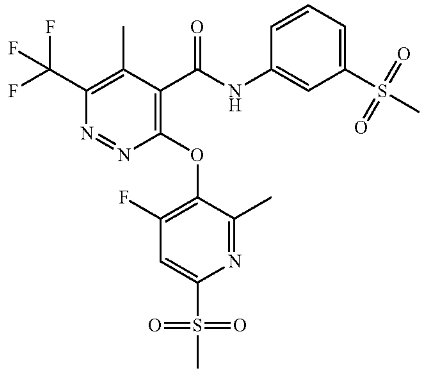 [SMILES: Cc1nc(S(C)(=O)=O)cc(F)c1Oc1nnc(C(F)(F)F)c(C)c1C(=O)Nc1cccc(S(C)(=O)=O)c1]

TABLE 14-continued
761
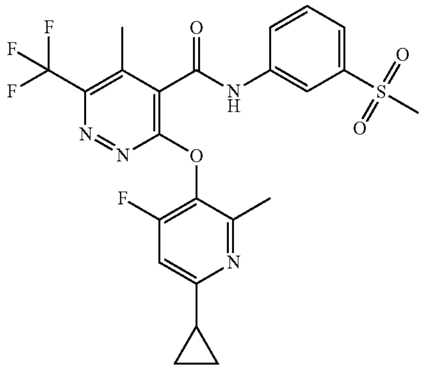
762
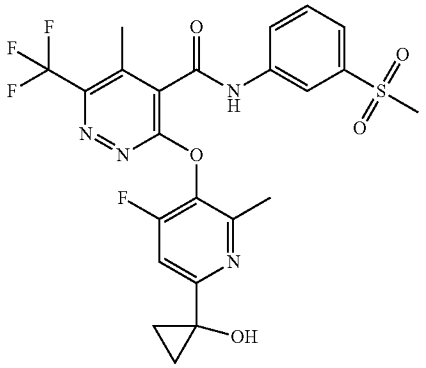 [SMILES: Cc1nc(C2(O)CC2)cc(F)c1Oc1nnc(C(F)(F)F)c(C)c1C(=O)Nc1cccc(S(C)(=O)=O)c1]
763
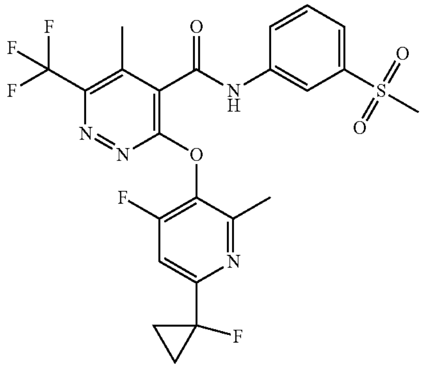
764
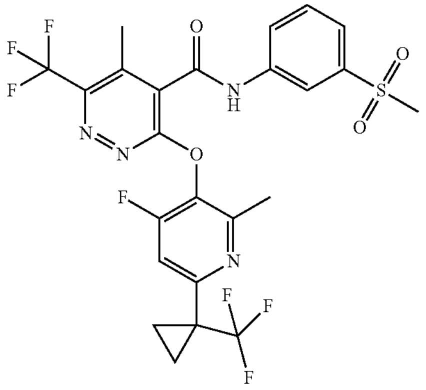 [SMILES: Cc1nc(C2(C(F)(F)F)CC2)cc(F)c1Oc1nnc(C(F)(F)F)c(C)c1C(=O)Nc1cccc(S(C)(=O)=O)c1]
TABLE 14-continued
765
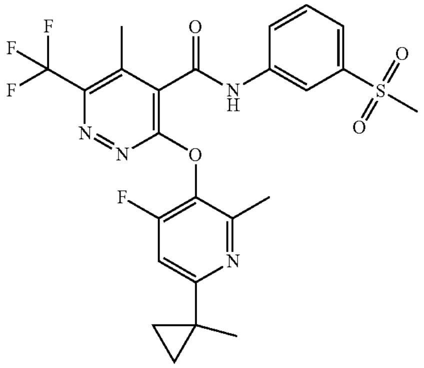 [SMILES: Cc1nc(C2(C)CC2)cc(F)c1Oc1nnc(C(F)(F)F)c(C)c1C(=O)Nc1cccc(S(C)(=O)=O)c1]
766
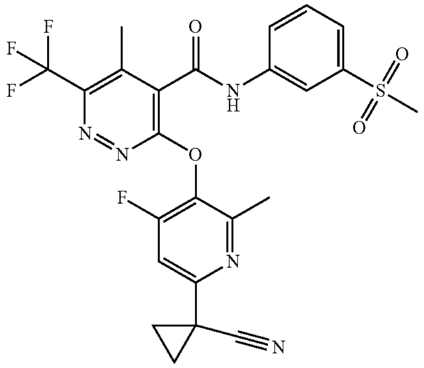 [SMILES: Cc1nc(C2(C#N)CC2)cc(F)c1Oc1nnc(C(F)(F)F)c(C)c1C(=O)Nc1cccc(S(C)(=O)=O)c1]
767
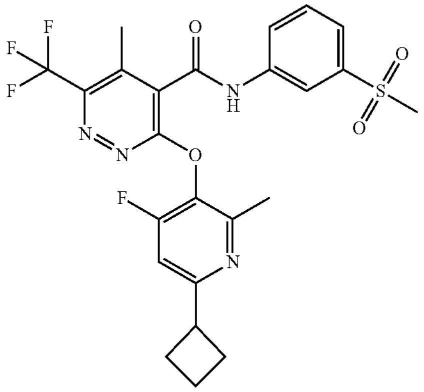
768
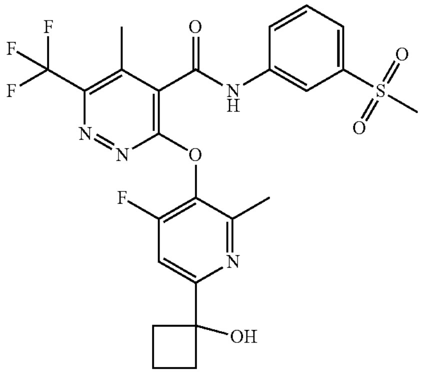 [SMILES: Cc1nc(C2(O)CCC2)cc(F)c1Oc1nnc(C(F)(F)F)c(C)c1C(=O)Nc1cccc(S(C)(=O)=O)c1]

TABLE 14-continued
769
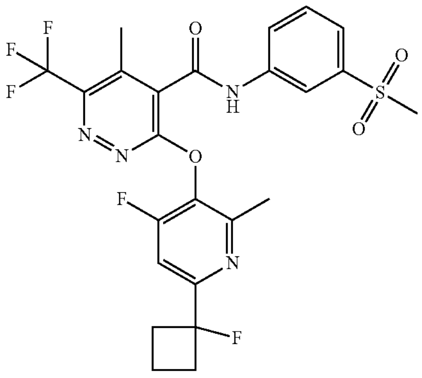 [SMILES: Cc1nc(C2(F)CCC2)cc(F)c1Oc1nnc(C(F)(F)F)c(C)c1C(=O)Nc1cccc(S(C)(=O)=O)c1]
770
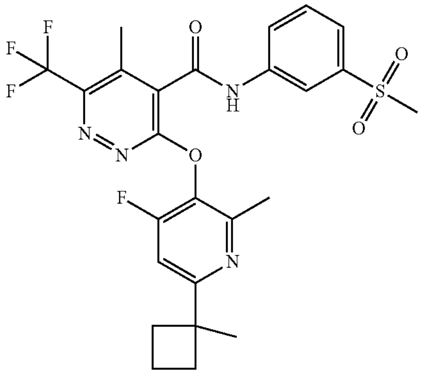 [SMILES: Cc1nc(C2(C)CCC2)cc(F)c1Oc1nnc(C(F)(F)F)c(C)c1C(=O)Nc1cccc(S(C)(=O)=O)c1]
771
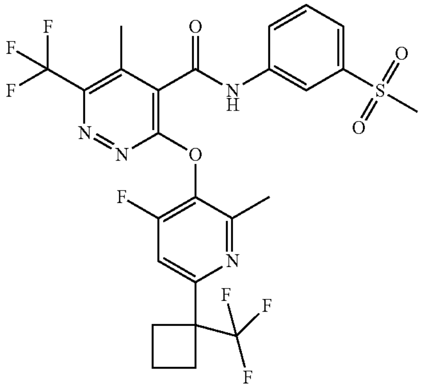
772
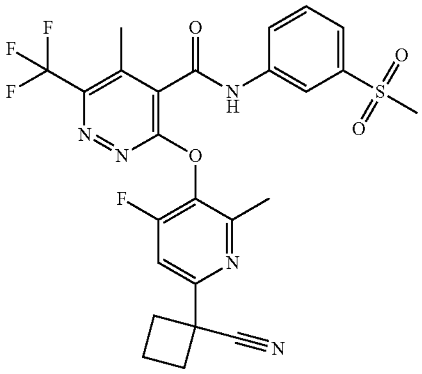 [SMILES: Cc1nc(C2(C#N)CCC2)cc(F)c1Oc1nnc(C(F)(F)F)c(C)c1C(=O)Nc1cccc(S(C)(=O)=O)c1]
TABLE 14-continued
773
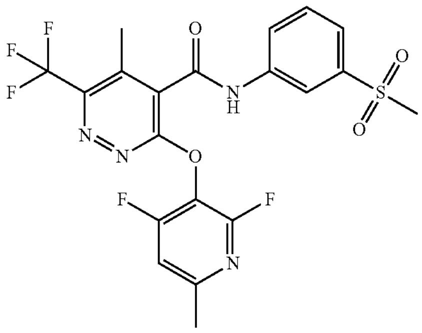 [SMILES: Cc1cc(F)c(Oc2nnc(C(F)(F)F)c(C)c2C(=O)Nc2cccc(S(C)(=O)=O)c2)c(F)n1]
774
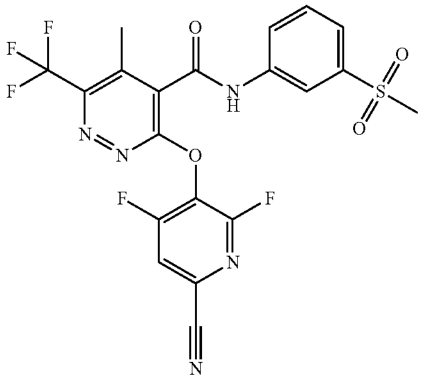 [SMILES: Cc1c(C(F)(F)F)nnc(Oc2c(F)cc(C#N)nc2F)c1C(=O)Nc1cccc(S(C)(=O)=O)c1]
775
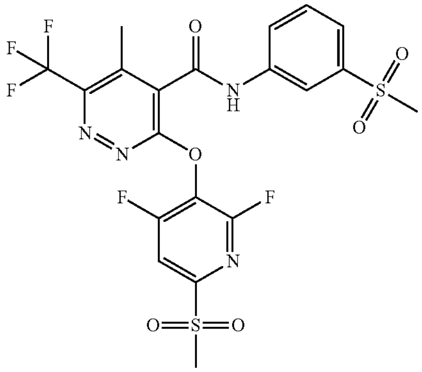
776
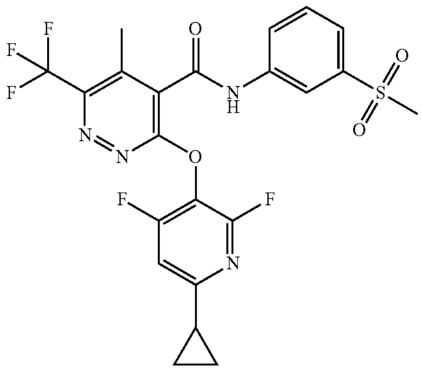 [SMILES: Cc1c(C(F)(F)F)nnc(Oc2c(F)cc(C3CC3)nc2F)c1C(=O)Nc1cccc(S(C)(=O)=O)c1]

TABLE 14-continued
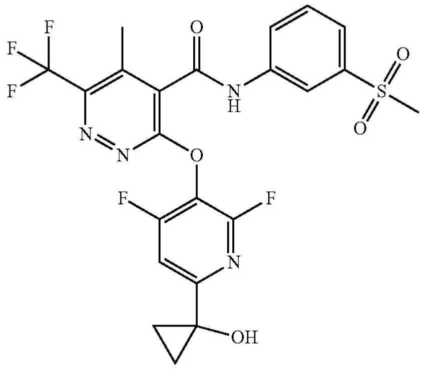
777
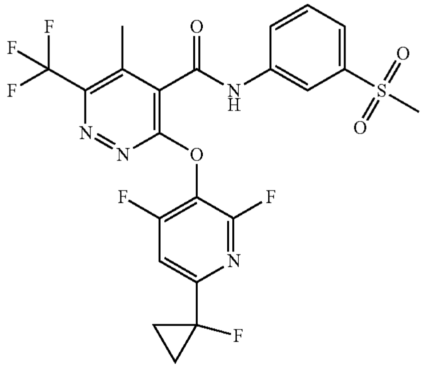
778
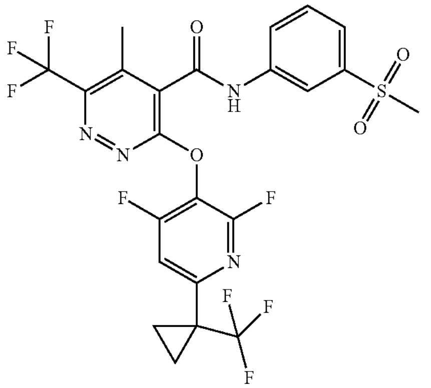
779
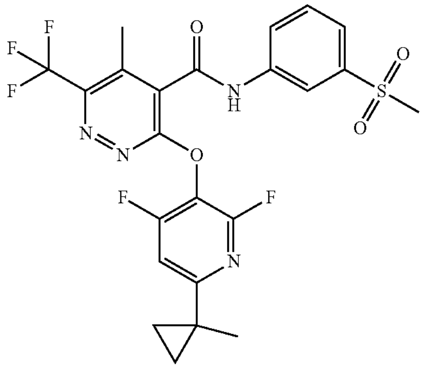
780
TABLE 14-continued
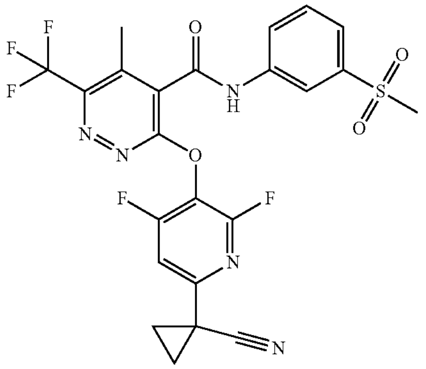
781
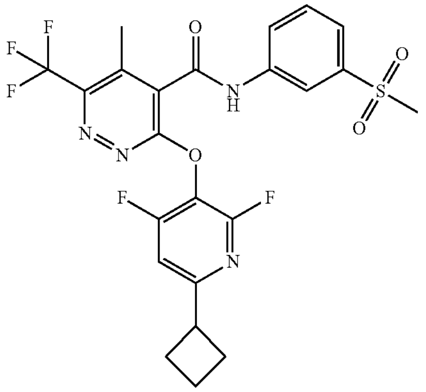 [SMILES: Cc1c(C(F)(F)F)nnc(Oc2c(F)cc(C3CCC3)nc2F)c1C(=O)Nc1cccc(S(C)(=O)=O)c1]
782
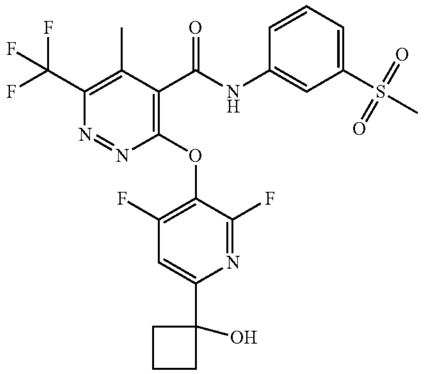 [SMILES: Cc1c(C(F)(F)F)nnc(Oc2c(F)cc(C3(O)CCC3)nc2F)c1C(=O)Nc1cccc(S(C)(=O)=O)c1]
783
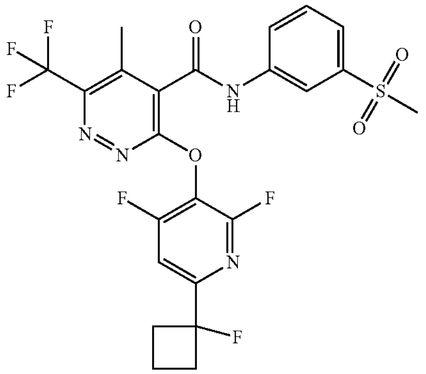 [SMILES: Cc1c(C(F)(F)F)nnc(Oc2c(F)cc(C3(F)CCC3)nc2F)c1C(=O)Nc1cccc(S(C)(=O)=O)c1]
784

TABLE 14-continued
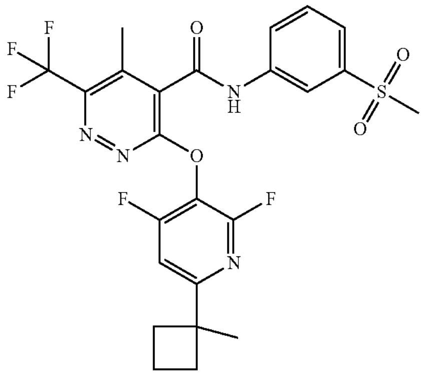
785
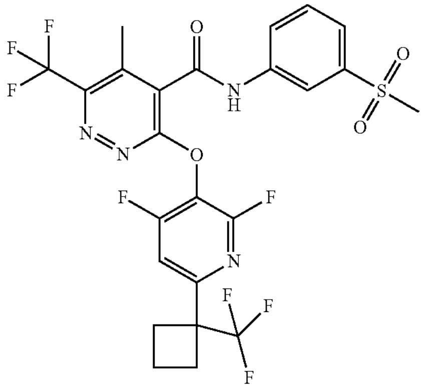
786
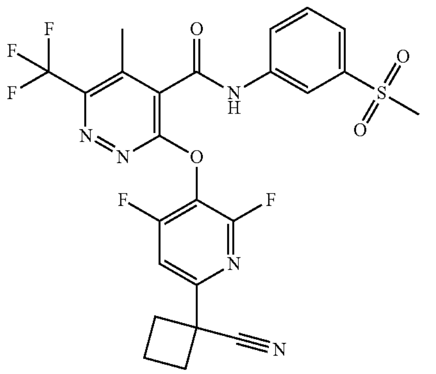 [SMILES: Cc1c(C(F)(F)F)nnc(Oc2c(F)cc(C3(C#N)CCC3)nc2F)c1C(=O)Nc1cccc(S(C)(=O)=O)c1]
787
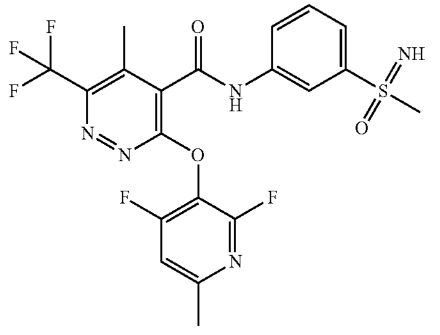
788
TABLE 14-continued
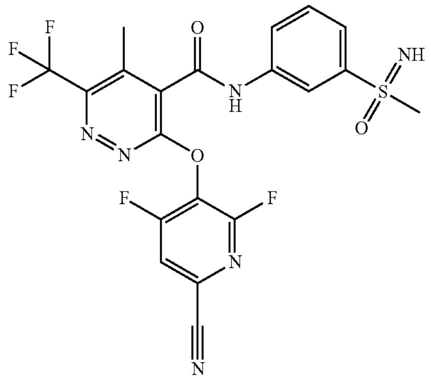
789
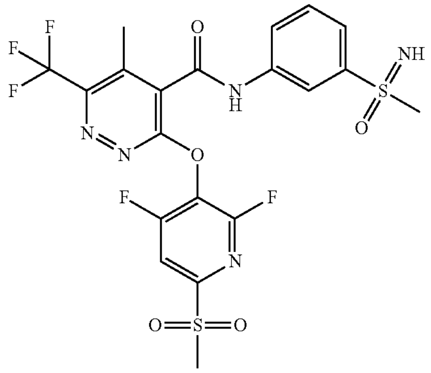
790
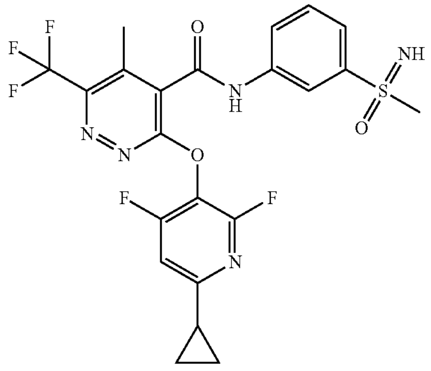 [SMILES: Cc1c(C(F)(F)F)nnc(Oc2c(F)cc(C3CC3)nc2F)c1C(=O)Nc1cccc(S(C)(=N)=O)c1]
791
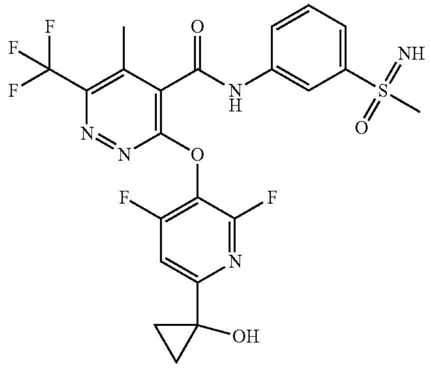
792

TABLE 14-continued
793
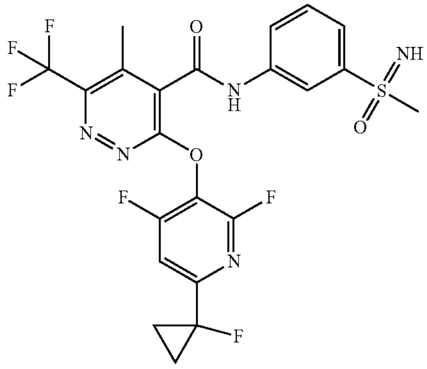
794
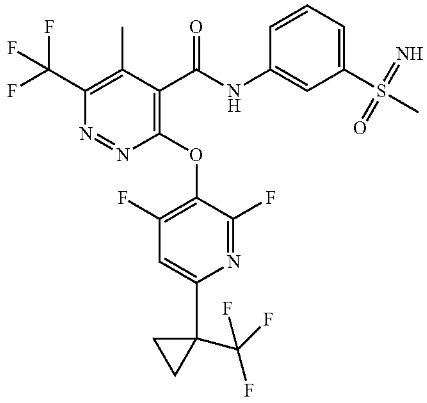 [SMILES: Cc1c(C(F)(F)F)nnc(Oc2c(F)cc(C3(C(F)(F)F)CC3)nc2F)c1C(=O)Nc1cccc(S(C)(=N)=O)c1]
795
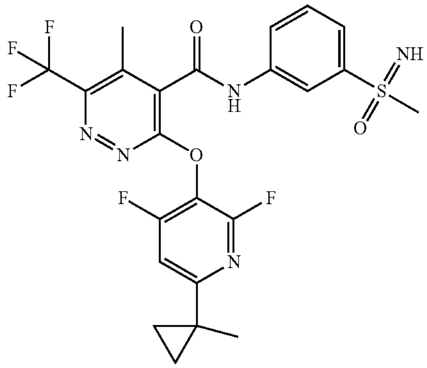
796
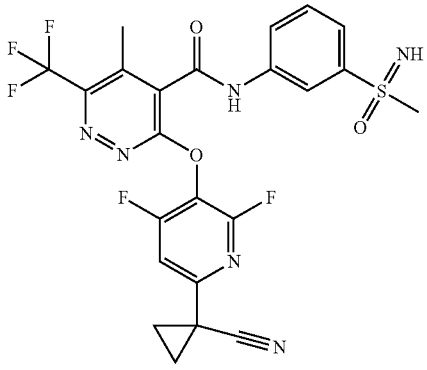
TABLE 14-continued
797
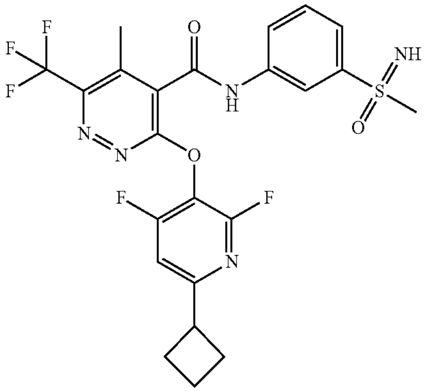
798
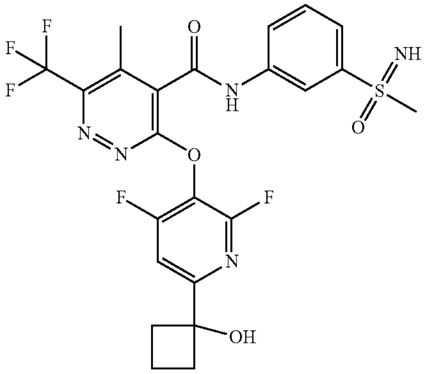
799
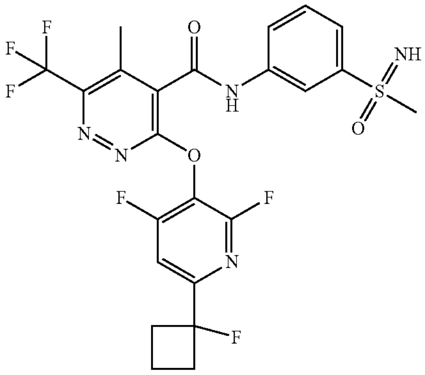 [SMILES: Cc1c(C(F)(F)F)nnc(Oc2c(F)cc(C3(F)CCC3)nc2F)c1C(=O)Nc1cccc(S(C)(=N)=O)c1]
800
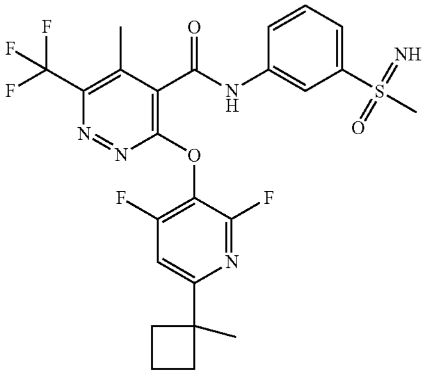 [SMILES: Cc1c(C(F)(F)F)nnc(Oc2c(F)cc(C3(C)CCC3)nc2F)c1C(=O)Nc1cccc(S(C)(=N)=O)c1]

TABLE 14-continued
801
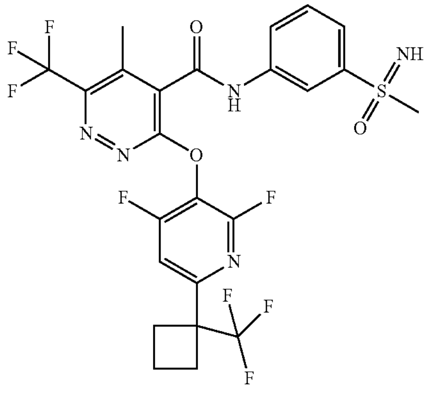
802
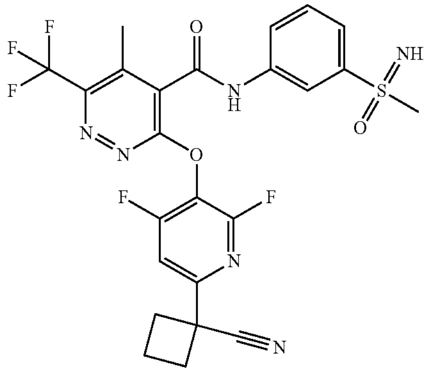
803
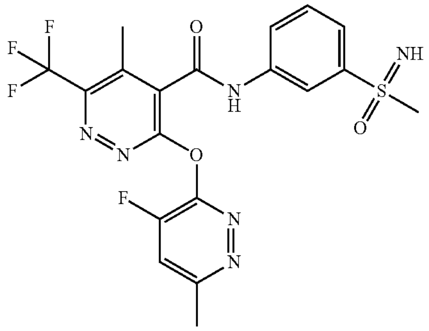 [SMILES: Cc1cc(F)c(Oc2nnc(C(F)(F)F)c(C)c2C(=O)Nc2cccc(S(C)(=N)=O)c2)nn1]
804
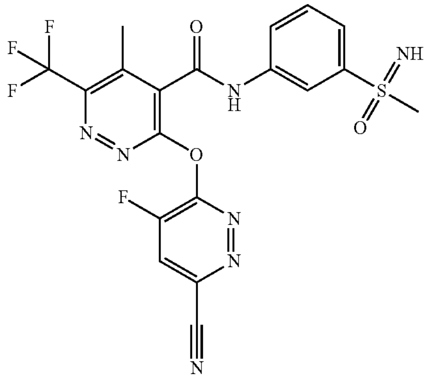 [SMILES: Cc1c(C(F)(F)F)nnc(Oc2nnc(C#N)cc2F)c1C(=O)Nc1cccc(S(C)(=N)=O)c1]
TABLE 14-continued
805
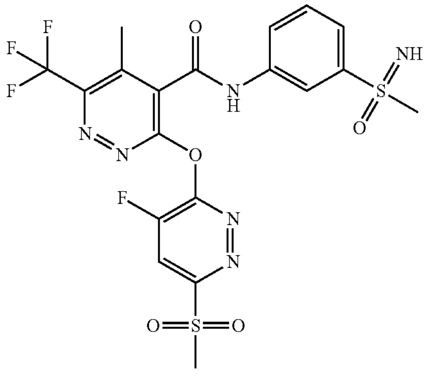 [SMILES: Cc1c(C(F)(F)F)nnc(Oc2nnc(S(C)(=O)=O)cc2F)c1C(=O)Nc1cccc(S(C)(=N)=O)c1]
806
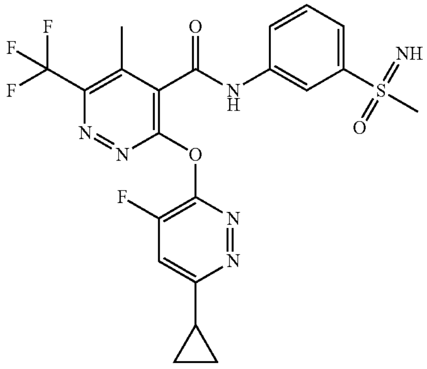 [SMILES: Cc1c(C(F)(F)F)nnc(Oc2nnc(C3CC3)cc2F)c1C(=O)Nc1cccc(S(C)(=N)=O)c1]
807
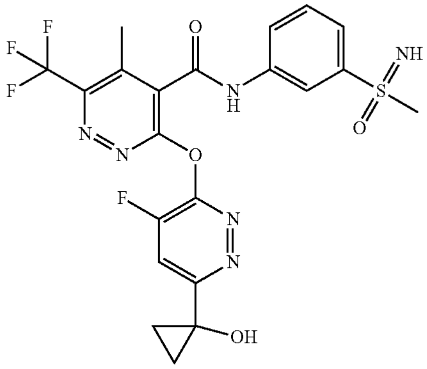 [SMILES: Cc1c(C(F)(F)F)nnc(Oc2nnc(C3(O)CC3)cc2F)c1C(=O)Nc1cccc(S(C)(=N)=O)c1]
808
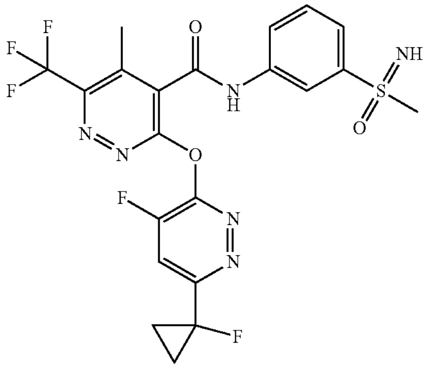 [SMILES: Cc1c(C(F)(F)F)nnc(Oc2nnc(C3(F)CC3)cc2F)c1C(=O)Nc1cccc(S(C)(=N)=O)c1]

809
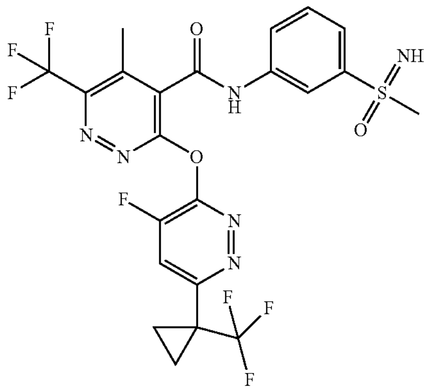
810
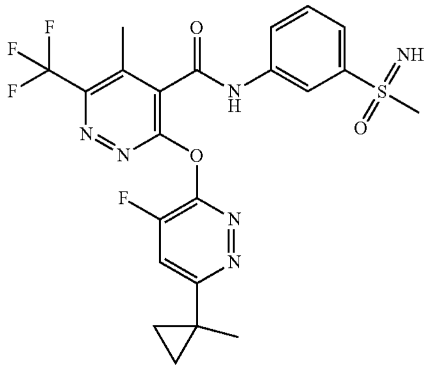
811
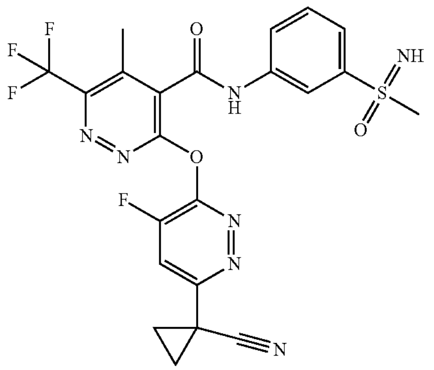 [SMILES: Cc1c(C(F)(F)F)nnc(Oc2nnc(C3(C#N)CC3)cc2F)c1C(=O)Nc1cccc(S(C)(=N)=O)c1]
812
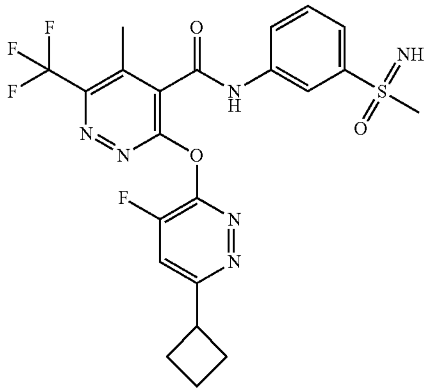 [SMILES: Cc1c(C(F)(F)F)nnc(Oc2nnc(C3CCC3)cc2F)c1C(=O)Nc1cccc(S(C)(=N)=O)c1]
813
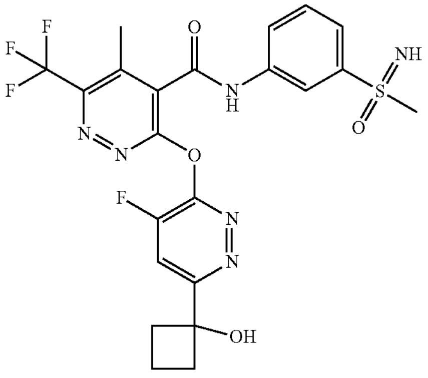 [SMILES: Cc1c(C(F)(F)F)nnc(Oc2nnc(C3(O)CCC3)cc2F)c1C(=O)Nc1cccc(S(C)(=N)=O)c1]
814
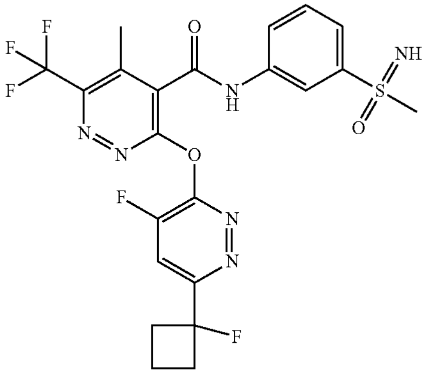 [SMILES: Cc1c(C(F)(F)F)nnc(Oc2nnc(C3(C)CCC3)cc2F)c1C(=O)Nc1cccc(S(C)(=N)=O)c1]
815
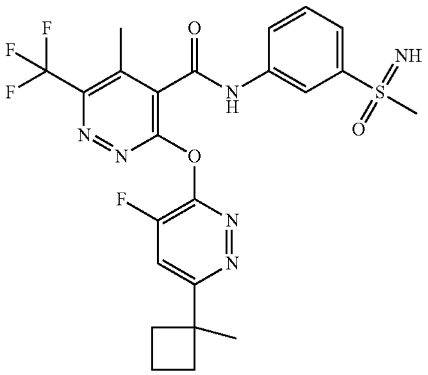
816
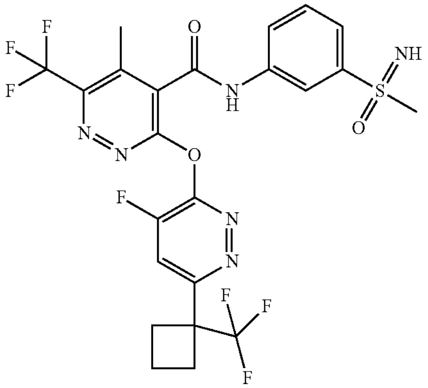 [SMILES: Cc1c(C(F)(F)F)nnc(Oc2nnc(C3(C(F)(F)F)CCC3)cc2F)c1C(=O)Nc1cccc(S(C)(=N)=O)c1]

TABLE 14-continued
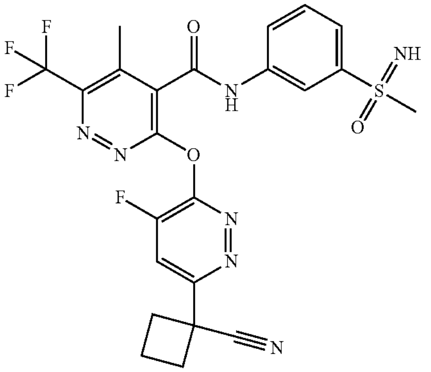 [SMILES: Cc1c(C(F)(F)F)nnc(Oc2nnc(C3(C#N)CCC3)cc2F)c1C(=O)Nc1cccc(S(C)(=N)=O)c1]
817
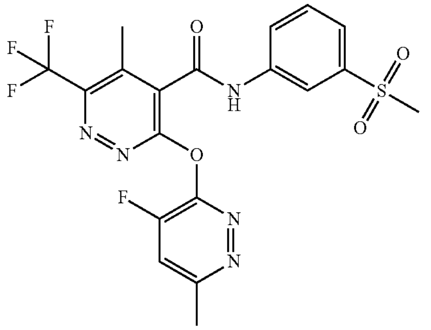 [SMILES: Cc1cc(F)c(Oc2nnc(C(F)(F)F)c(C)c2C(=O)Nc2cccc(S(C)(=O)=O)c2)nn1]
818
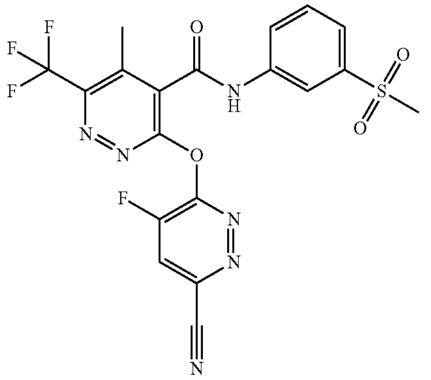 [SMILES: Cc1c(C(F)(F)F)nnc(Oc2nnc(C#N)cc2F)c1C(=O)Nc1cccc(S(C)(=O)=O)c1]
819
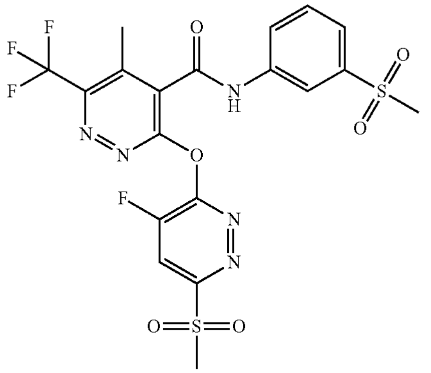 [SMILES: Cc1c(C(F)(F)F)nnc(Oc2nnc(S(C)(=O)=O)cc2F)c1C(=O)Nc1cccc(S(C)(=O)=O)c1]
820
TABLE 14-continued
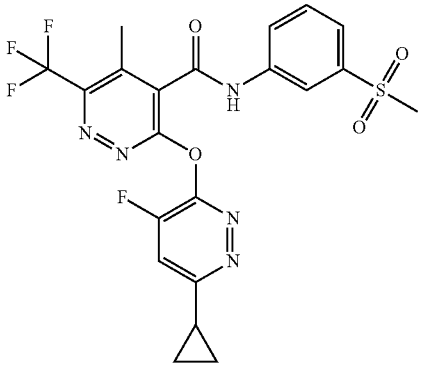 [SMILES: Cc1c(C(F)(F)F)nnc(Oc2nnc(C3CC3)cc2F)c1C(=O)Nc1cccc(S(C)(=O)=O)c1]
821
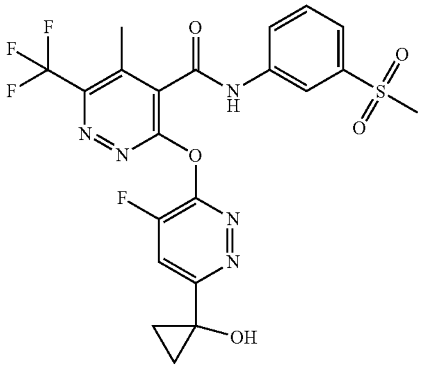 [SMILES: Cc1c(C(F)(F)F)nnc(Oc2nnc(C3(O)CC3)cc2F)c1C(=O)Nc1cccc(S(C)(=O)=O)c1]
822
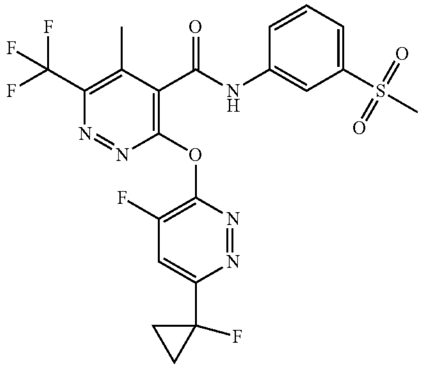 [SMILES: Cc1c(C(F)(F)F)nnc(Oc2nnc(C3(F)CC3)cc2F)c1C(=O)Nc1cccc(S(C)(=O)=O)c1]
823
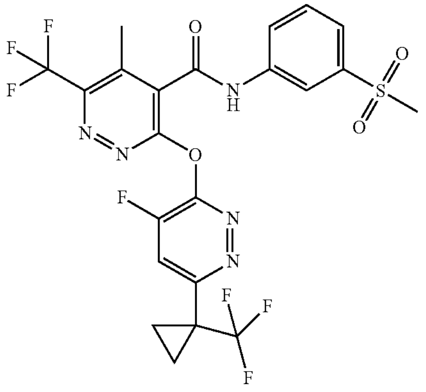 [SMILES: Cc1c(C(F)(F)F)nnc(Oc2nnc(C3(C(F)(F)F)CC3)cc2F)c1C(=O)Nc1cccc(S(C)(=O)=O)c1]
824

TABLE 14-continued
825
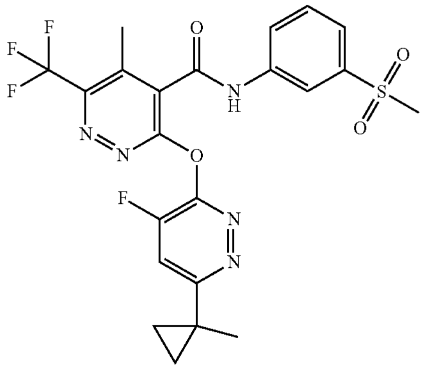
826
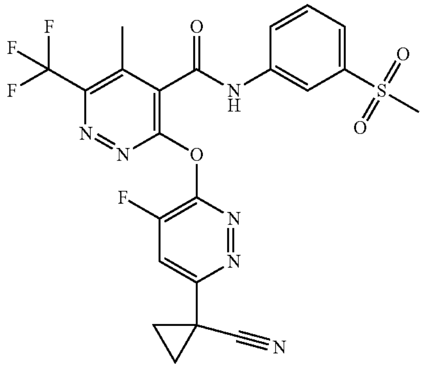 [SMILES: Cc1c(C(F)(F)F)nnc(Oc2nnc(C3(C#N)CC3)cc2F)c1C(=O)Nc1cccc(S(C)(=O)=O)c1]
827
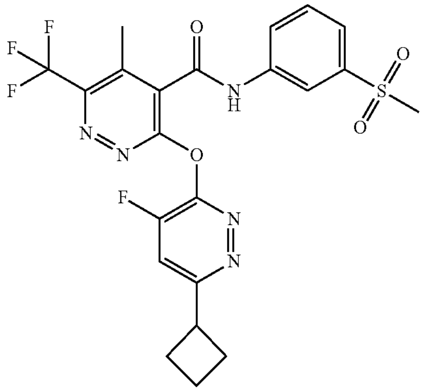 [SMILES: Cc1c(C(F)(F)F)nnc(Oc2nnc(C3CCC3)cc2F)c1C(=O)Nc1cccc(S(C)(=O)=O)c1]
828
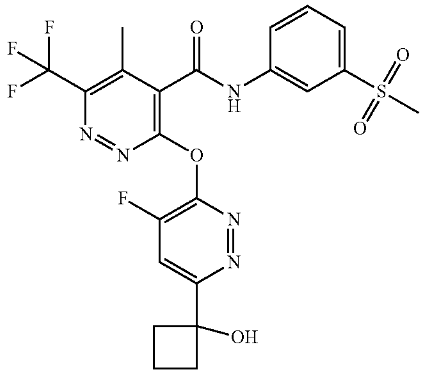 [SMILES: Cc1c(C(F)(F)F)nnc(Oc2nnc(C3(O)CCC3)cc2F)c1C(=O)Nc1cccc(S(C)(=O)=O)c1]
TABLE 14-continued
829
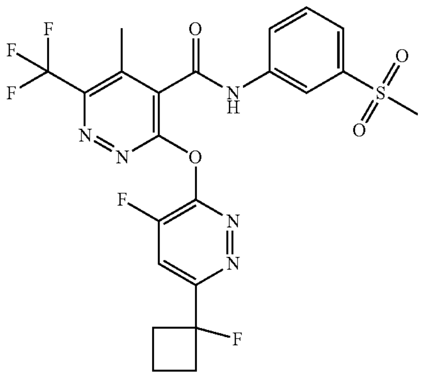 [SMILES: Cc1c(C(F)(F)F)nnc(Oc2nnc(C3(C)CCC3)cc2F)c1C(=O)Nc1cccc(S(C)(=O)=O)c1]
830
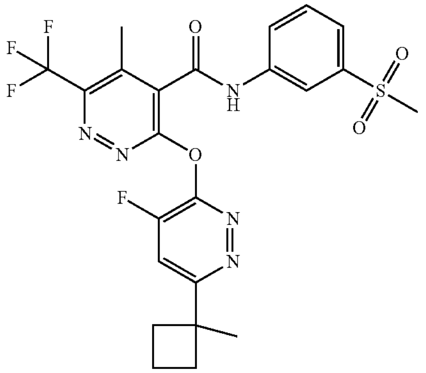
831
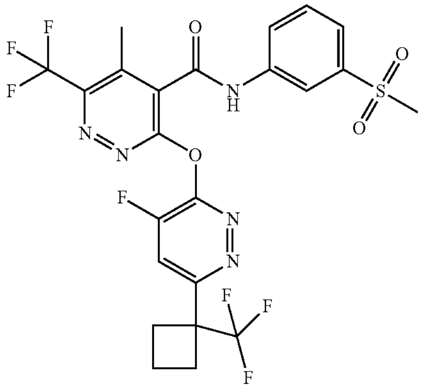 [SMILES: Cc1c(C(F)(F)F)nnc(Oc2nnc(C3(C(F)(F)F)CCC3)cc2F)c1C(=O)Nc1cccc(S(C)(=O)=O)c1]
832
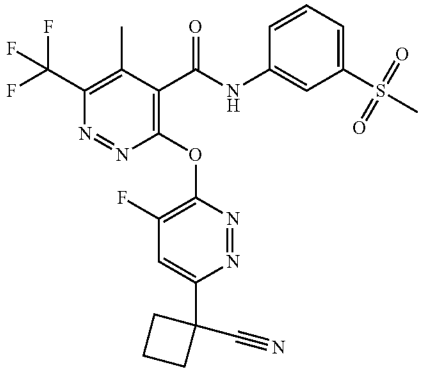 [SMILES: Cc1c(C(F)(F)F)nnc(Oc2nnc(C3(C#N)CCC3)cc2F)c1C(=O)Nc1cccc(S(C)(=O)=O)c1]

TABLE 14-continued
833
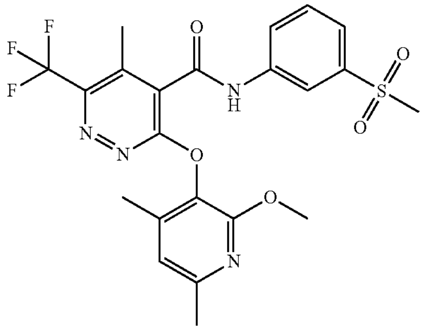 [SMILES: COc1nc(C)cc(C)c1Oc1nnc(C(F)(F)F)c(C)c1C(=O)Nc1cccc(S(C)(=O)=O)c1]
834
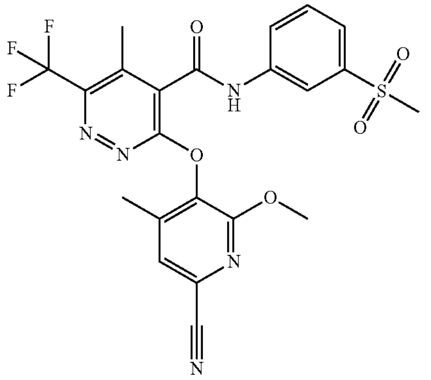
835
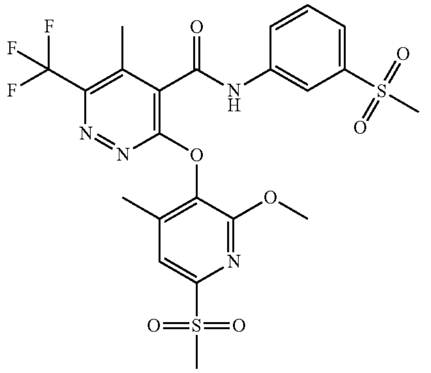 [SMILES: COc1nc(S(C)(=O)=O)cc(C)c1Oc1nnc(C(F)(F)F)c(C)c1C(=O)Nc1cccc(S(C)(=O)=O)c1]
836
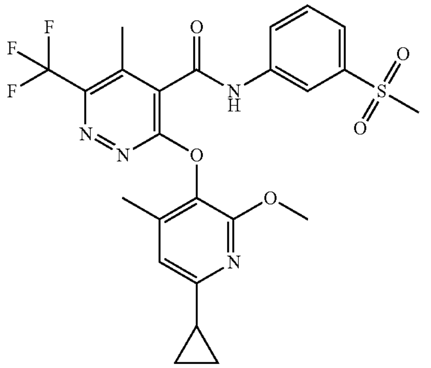 [SMILES: COc1nc(C2CC2)cc(C)c1Oc1nnc(C(F)(F)F)c(C)c1C(=O)Nc1cccc(S(C)(=O)=O)c1]
TABLE 14-continued
837
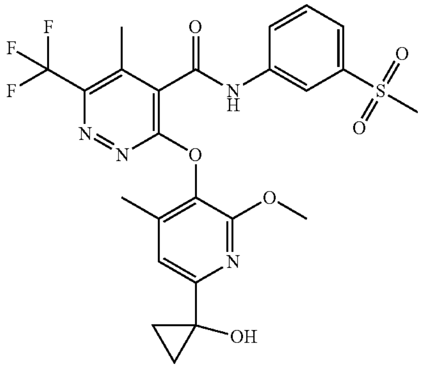 [SMILES: COc1nc(C2(O)CC2)cc(C)c1Oc1nnc(C(F)(F)F)c(C)c1C(=O)Nc1cccc(S(C)(=O)=O)c1]
838
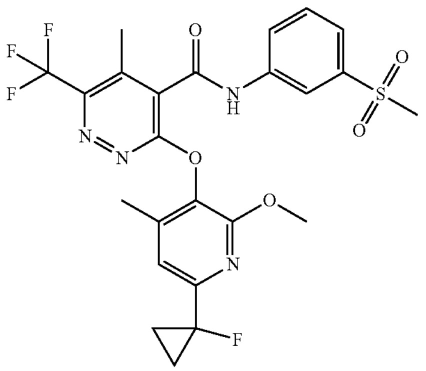
839
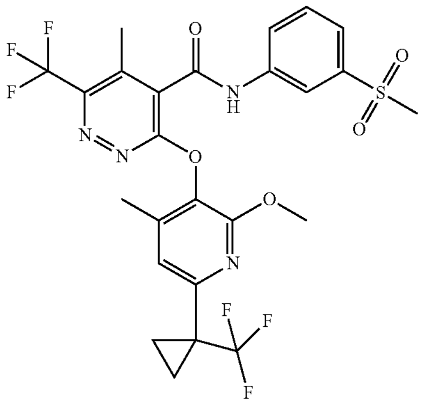 [SMILES: COc1nc(C2(C(F)(F)F)CC2)cc(C)c1Oc1nnc(C(F)(F)F)c(C)c1C(=O)Nc1cccc(S(C)(=O)=O)c1]
840
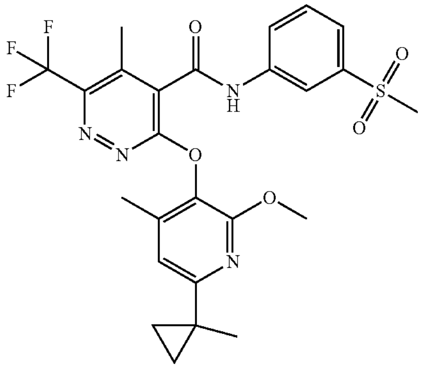 [SMILES: COc1nc(C2(C)CC2)cc(C)c1Oc1nnc(C(F)(F)F)c(C)c1C(=O)Nc1cccc(S(C)(=O)=O)c1]

TABLE 14-continued
841
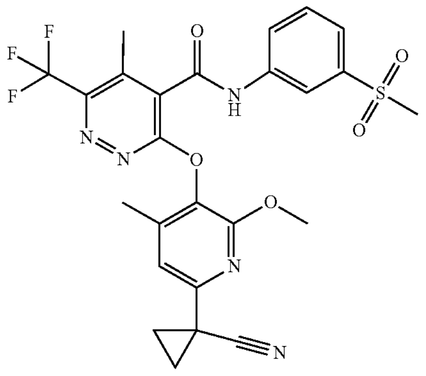 [SMILES: COc1nc(C2(C#N)CC2)cc(C)c1Oc1nnc(C(F)(F)F)c(C)c1C(=O)Nc1cccc(S(C)(=O)=O)c1]
842
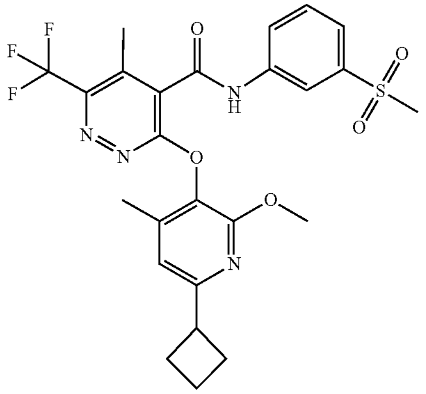 [SMILES: COc1nc(C2CCC2)cc(C)c1Oc1nnc(C(F)(F)F)c(C)c1C(=O)Nc1cccc(S(C)(=O)=O)c1]
843
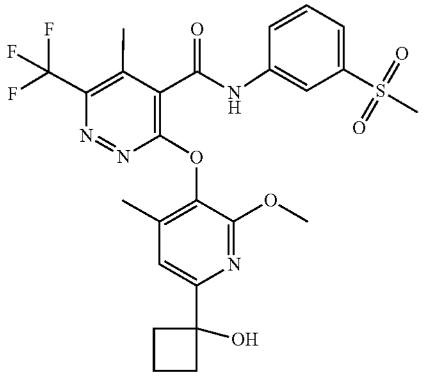 [SMILES: COc1nc(C2(O)CCC2)cc(C)c1Oc1nnc(C(F)(F)F)c(C)c1C(=O)Nc1cccc(S(C)(=O)=O)c1]
844
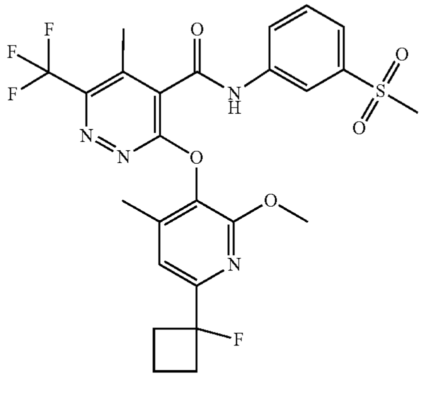 [SMILES: COc1nc(C2(F)CCC2)cc(C)c1Oc1nnc(C(F)(F)F)c(C)c1C(=O)Nc1cccc(S(C)(=O)=O)c1]
TABLE 14-continued
845
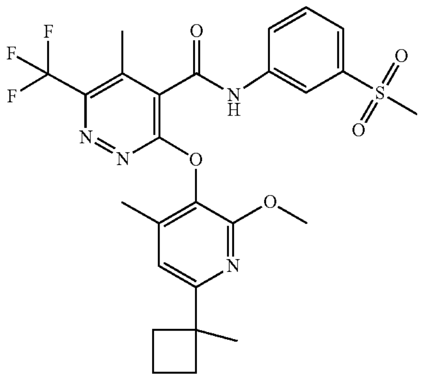 [SMILES: COc1nc(C2(C)CCC2)cc(C)c1Oc1nnc(C(F)(F)F)c(C)c1C(=O)Nc1cccc(S(C)(=O)=O)c1]
846
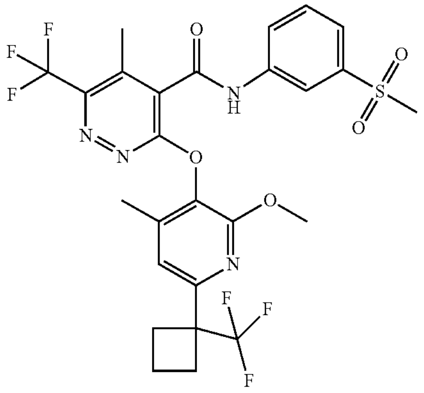 [SMILES: COc1nc(C2(C(F)(F)F)CCC2)cc(C)c1Oc1nnc(C(F)(F)F)c(C)c1C(=O)Nc1cccc(S(C)(=O)=O)c1]
847
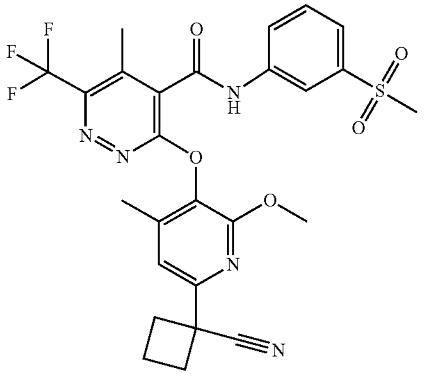 [SMILES: COc1nc(C2(C#N)CCC2)cc(C)c1Oc1nnc(C(F)(F)F)c(C)c1C(=O)Nc1cccc(S(C)(=O)=O)c1]
848
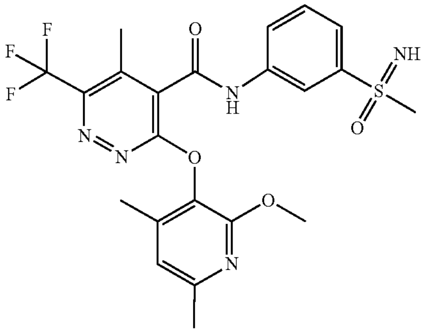 [SMILES: COc1nc(C)cc(C)c1Oc1nnc(C(F)(F)F)c(C)c1C(=O)Nc1cccc(S(C)(=N)=O)c1]

TABLE 14-continued
849
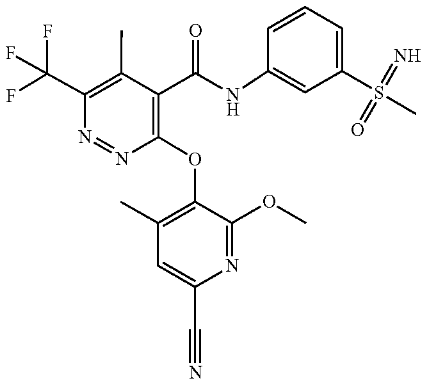 [SMILES: COc1nc(C#N)cc(C)c1Oc1nnc(C(F)(F)F)c(C)c1C(=O)Nc1cccc(S(C)(=N)=O)c1]
850
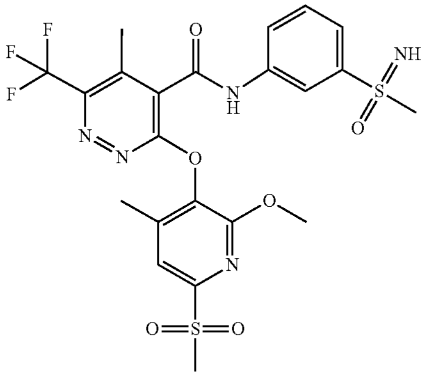 [SMILES: COc1nc(S(C)(=O)=O)cc(C)c1Oc1nnc(C(F)(F)F)c(C)c1C(=O)Nc1cccc(S(C)(=N)=O)c1]
851
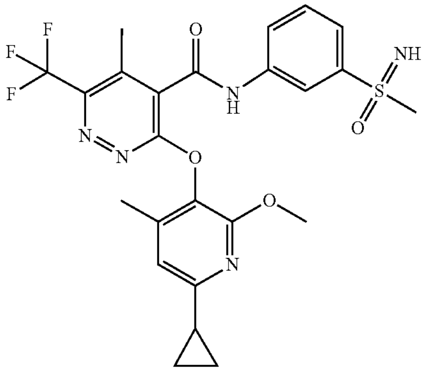
852
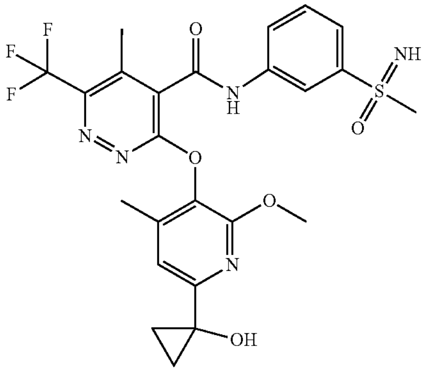 [SMILES: COc1nc(C2(O)CC2)cc(C)c1Oc1nnc(C(F)(F)F)c(C)c1C(=O)Nc1cccc(S(C)(=N)=O)c1]
TABLE 14-continued
853
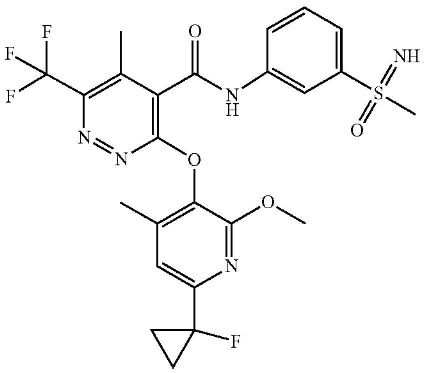 [SMILES: COc1nc(C2(F)CC2)cc(C)c1Oc1nnc(C(F)(F)F)c(C)c1C(=O)Nc1cccc(S(C)(=N)=O)c1]
854
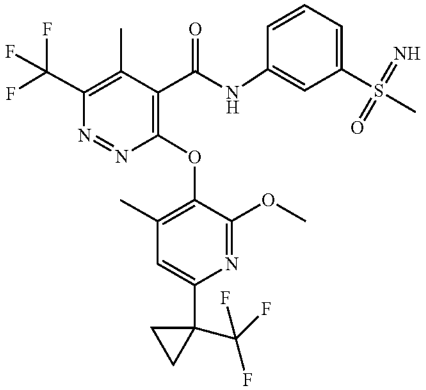 [SMILES: COc1nc(C2(C(F)(F)F)CC2)cc(C)c1Oc1nnc(C(F)(F)F)c(C)c1C(=O)Nc1cccc(S(C)(=N)=O)c1]
855
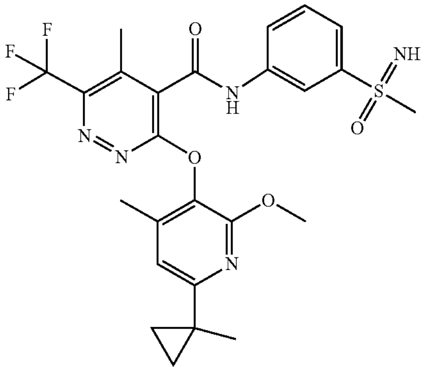 [SMILES: COc1nc(C2(C)CC2)cc(C)c1Oc1nnc(C(F)(F)F)c(C)c1C(=O)Nc1cccc(S(C)(=N)=O)c1]
856
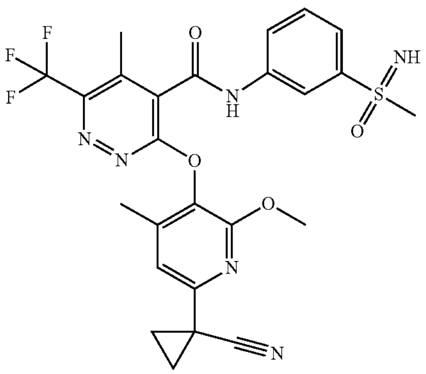 [SMILES: COc1nc(C2(C#N)CC2)cc(C)c1Oc1nnc(C(F)(F)F)c(C)c1C(=O)Nc1cccc(S(C)(=N)=O)c1]

TABLE 14-continued
857
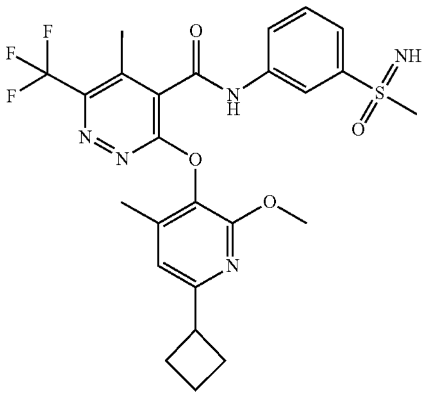 [SMILES: COc1nc(C2CCC2)cc(C)c1Oc1nnc(C(F)(F)F)c(C)c1C(=O)Nc1cccc(S(C)(=N)=O)c1]
858
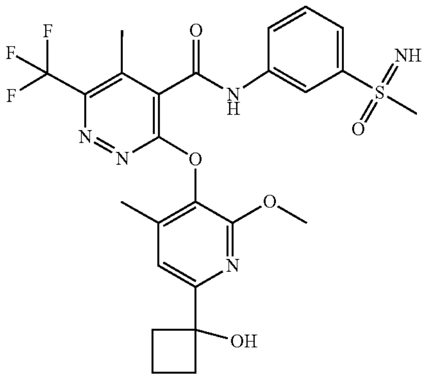 [SMILES: COc1nc(C2(O)CCC2)cc(C)c1Oc1nnc(C(F)(F)F)c(C)c1C(=O)Nc1cccc(S(C)(=N)=O)c1]
859
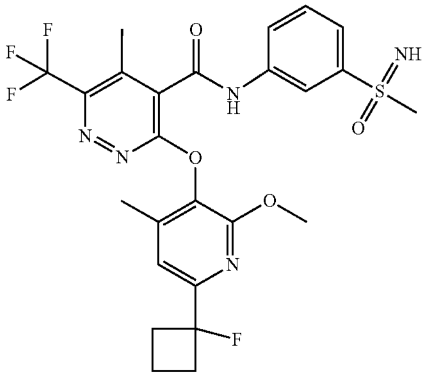 [SMILES: COc1nc(C2(F)CCC2)cc(C)c1Oc1nnc(C(F)(F)F)c(C)c1C(=O)Nc1cccc(S(C)(=N)=O)c1]
860
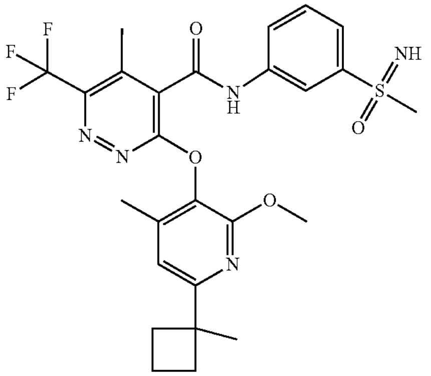 [SMILES: COc1nc(C2(C)CCC2)cc(C)c1Oc1nnc(C(F)(F)F)c(C)c1C(=O)Nc1cccc(S(C)(=N)=O)c1]
TABLE 14-continued
861
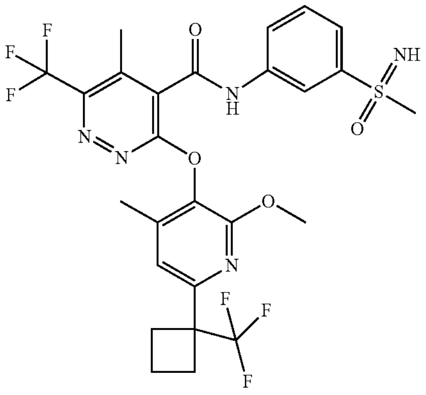 [SMILES: COc1nc(C2(C(F)(F)F)CCC2)cc(C)c1Oc1nnc(C(F)(F)F)c(C)c1C(=O)Nc1cccc(S(C)(=N)=O)c1]
862
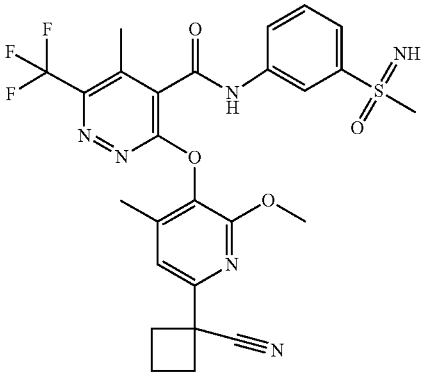 [SMILES: COc1nc(C2(C#N)CCC2)cc(C)c1Oc1nnc(C(F)(F)F)c(C)c1C(=O)Nc1cccc(S(C)(=N)=O)c1]
863
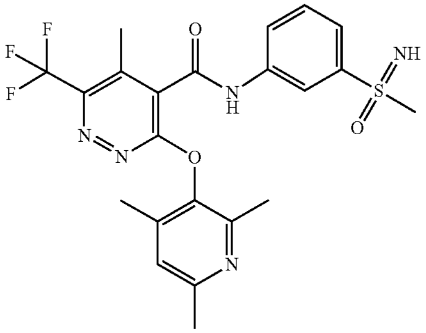
864
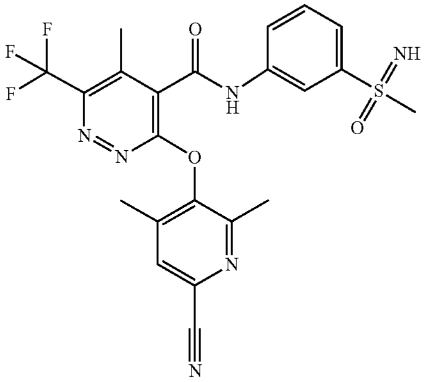

TABLE 14-continued
865
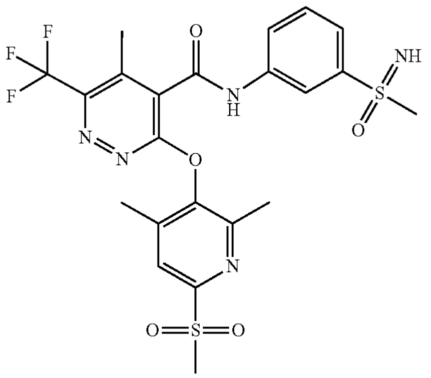 [SMILES: Cc1cc(S(C)(=O)=O)nc(C)c1Oc1nnc(C(F)(F)F)c(C)c1C(=O)Nc1cccc(S(C)(=N)=O)c1]
866
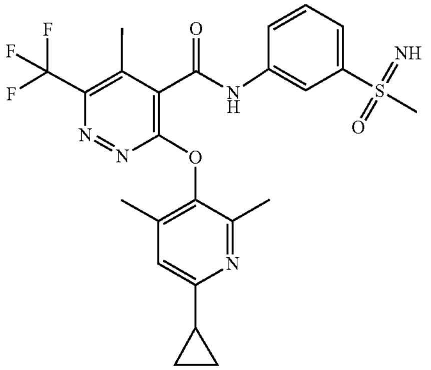
867
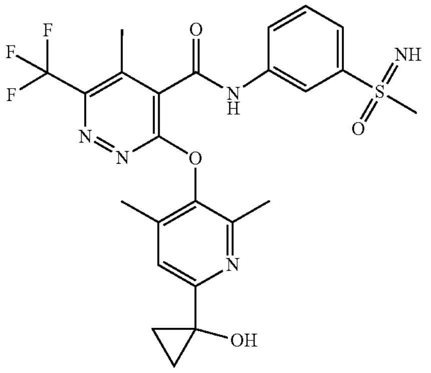
868
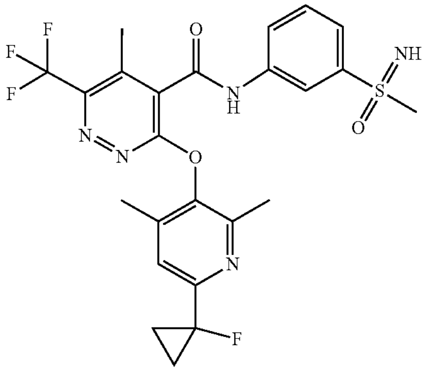
TABLE 14-continued
869
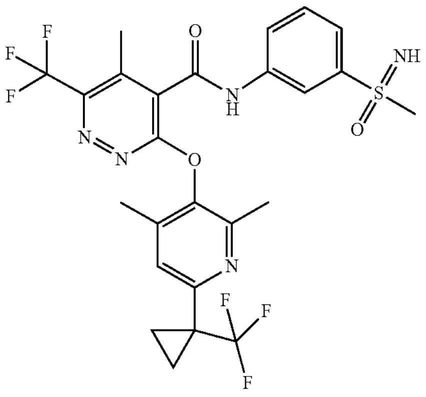 [SMILES: Cc1cc(C2(C(F)(F)F)CC2)nc(C)c1Oc1nnc(C(F)(F)F)c(C)c1C(=O)Nc1cccc(S(C)(=N)=O)c1]
870
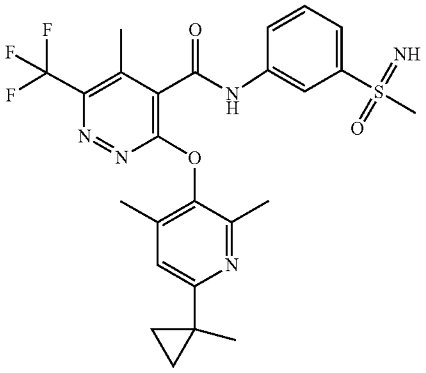
871
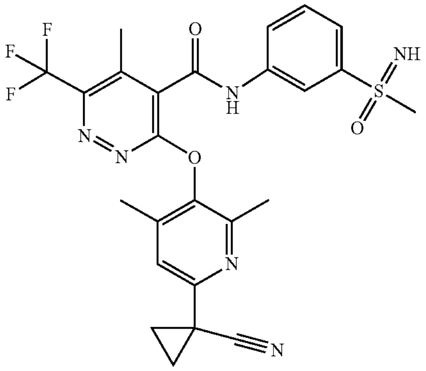 [SMILES: Cc1cc(C2(C#N)CC2)nc(C)c1Oc1nnc(C(F)(F)F)c(C)c1C(=O)Nc1cccc(S(C)(=N)=O)c1]
872
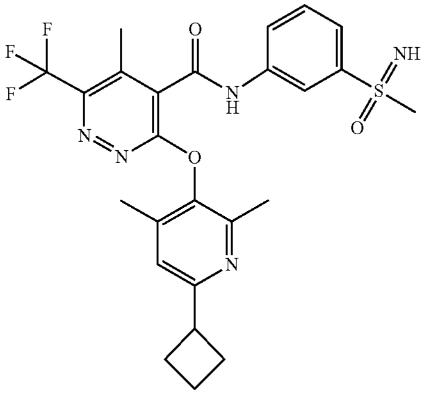 [SMILES: Cc1cc(C2CCC2)nc(C)c1Oc1nnc(C(F)(F)F)c(C)c1C(=O)Nc1cccc(S(C)(=N)=O)c1]

TABLE 14-continued
873
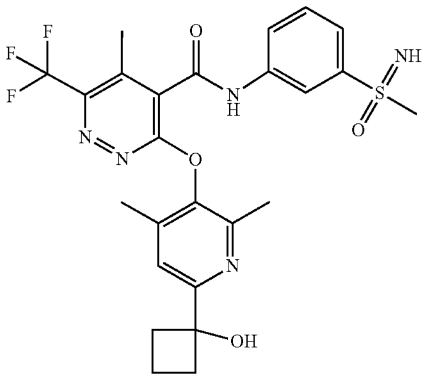 [SMILES: Cc1cc(C2(O)CCC2)nc(C)c1Oc1nnc(C(F)(F)F)c(C)c1C(=O)Nc1cccc(S(C)(=N)=O)c1]
874
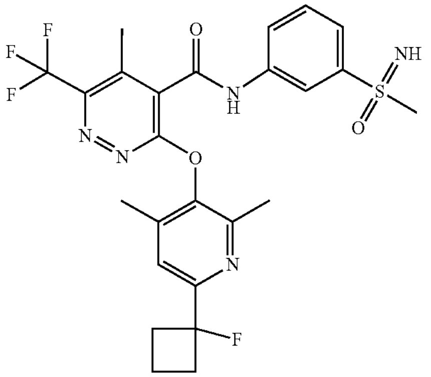
875
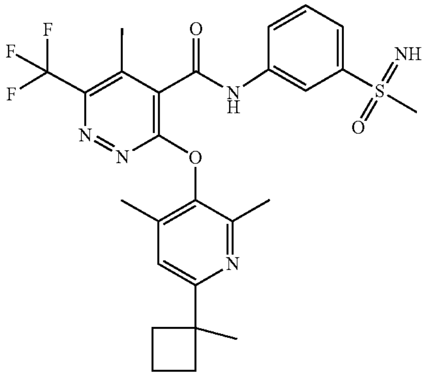 [SMILES: Cc1cc(C2(C)CCC2)nc(C)c1Oc1nnc(C(F)(F)F)c(C)c1C(=O)Nc1cccc(S(C)(=N)=O)c1]
876
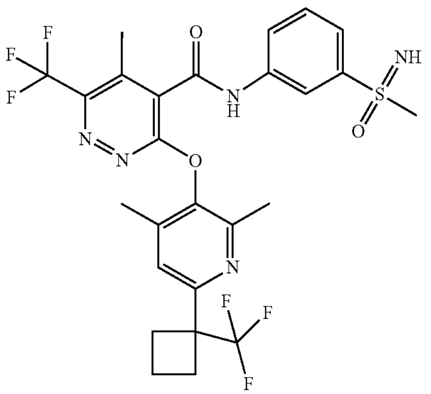 [SMILES: Cc1cc(C2(C(F)(F)F)CCC2)nc(C)c1Oc1nnc(C(F)(F)F)c(C)c1C(=O)Nc1cccc(S(C)(=N)=O)c1]
TABLE 14-continued
877
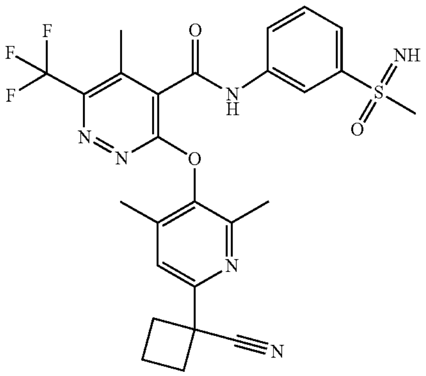 [SMILES: Cc1cc(C2(C#N)CCC2)nc(C)c1Oc1nnc(C(F)(F)F)c(C)c1C(=O)Nc1cccc(S(C)(=N)=O)c1]
878
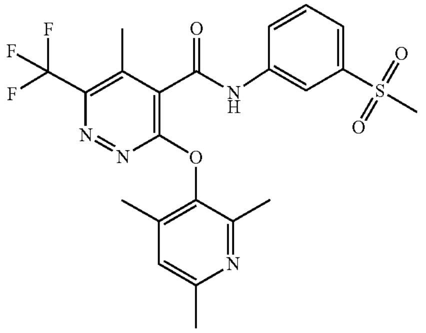 [SMILES: Cc1cc(C)c(Oc2nnc(C(F)(F)F)c(C)c2C(=O)Nc2cccc(S(C)(=O)=O)c2)c(C)n1]
879
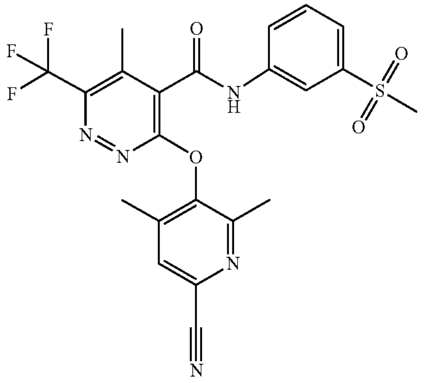 [SMILES: Cc1cc(C#N)nc(C)c1Oc1nnc(C(F)(F)F)c(C)c1C(=O)Nc1cccc(S(C)(=O)=O)c1]
880
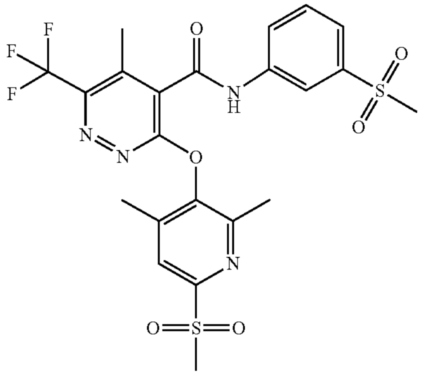 [SMILES: Cc1cc(S(C)(=O)=O)nc(C)c1Oc1nnc(C(F)(F)F)c(C)c1C(=O)Nc1cccc(S(C)(=O)=O)c1]

TABLE 14-continued
881
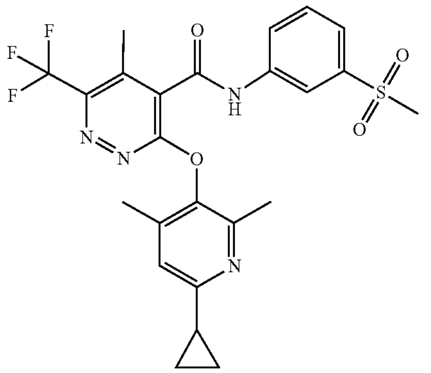 [SMILES: Cc1cc(C2CC2)nc(C)c1Oc1nnc(C(F)(F)F)c(C)c1C(=O)Nc1cccc(S(C)(=O)=O)c1]
882
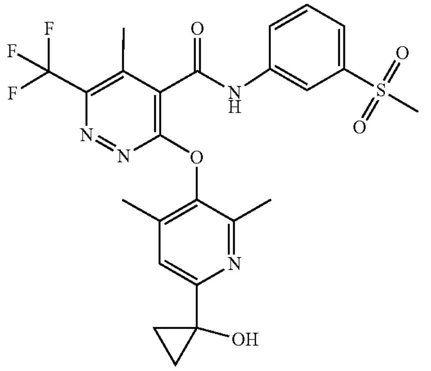 [SMILES: Cc1cc(C2(O)CC2)nc(C)c1Oc1nnc(C(F)(F)F)c(C)c1C(=O)Nc1cccc(S(C)(=O)=O)c1]
883
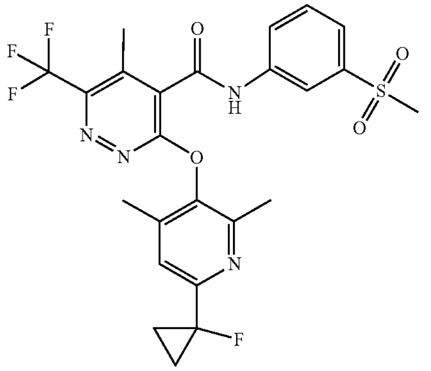 [SMILES: Cc1cc(C2(F)CC2)nc(C)c1Oc1nnc(C(F)(F)F)c(C)c1C(=O)Nc1cccc(S(C)(=O)=O)c1]
884
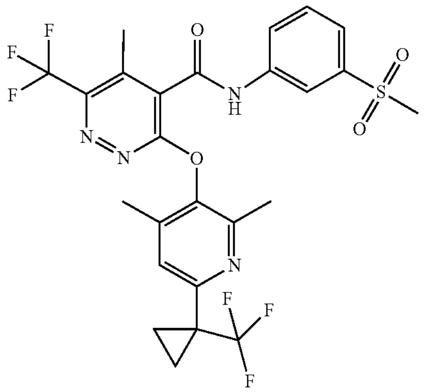 [SMILES: Cc1cc(C2(C(F)(F)F)CC2)nc(C)c1Oc1nnc(C(F)(F)F)c(C)c1C(=O)Nc1cccc(S(C)(=O)=O)c1]
TABLE 14-continued
885
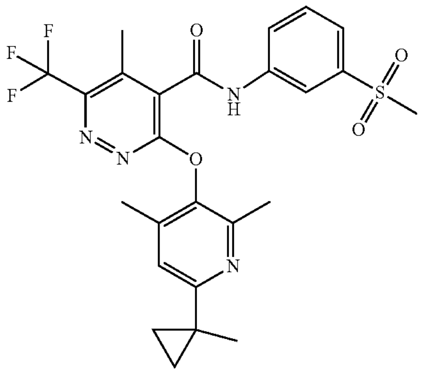 [SMILES: Cc1cc(C2(C)CC2)nc(C)c1Oc1nnc(C(F)(F)F)c(C)c1C(=O)Nc1cccc(S(C)(=O)=O)c1]
886
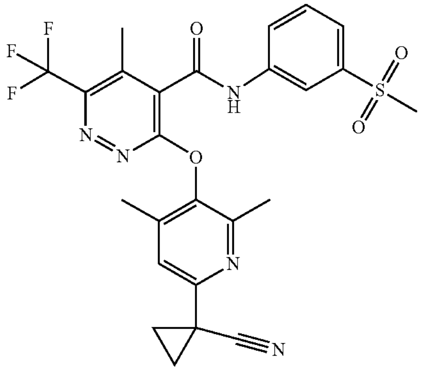 [SMILES: Cc1cc(C2(C#N)CC2)nc(C)c1Oc1nnc(C(F)(F)F)c(C)c1C(=O)Nc1cccc(S(C)(=O)=O)c1]
887
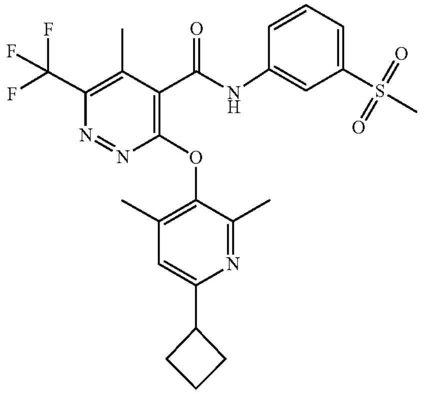 [SMILES: Cc1cc(C2CCC2)nc(C)c1Oc1nnc(C(F)(F)F)c(C)c1C(=O)Nc1cccc(S(C)(=O)=O)c1]
888
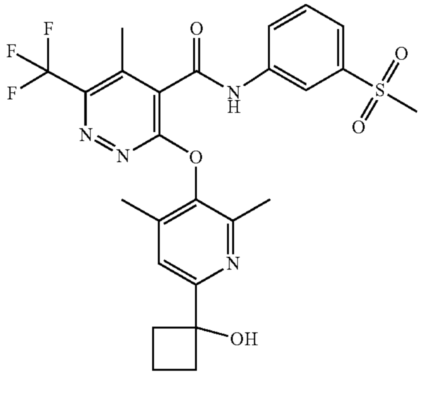 [SMILES: Cc1cc(C2(O)CCC2)nc(C)c1Oc1nnc(C(F)(F)F)c(C)c1C(=O)Nc1cccc(S(C)(=O)=O)c1]

889
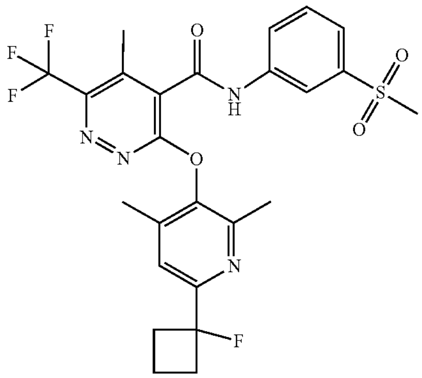 [SMILES: Cc1cc(C2(F)CCC2)nc(C)c1Oc1nnc(C(F)(F)F)c(C)c1C(=O)Nc1cccc(S(C)(=O)=O)c1]
890
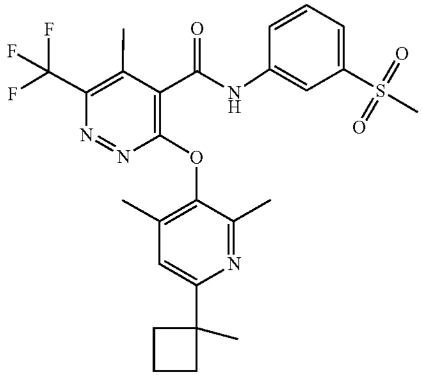 [SMILES: Cc1cc(C2(C)CCC2)nc(C)c1Oc1nnc(C(F)(F)F)c(C)c1C(=O)Nc1cccc(S(C)(=O)=O)c1]
891
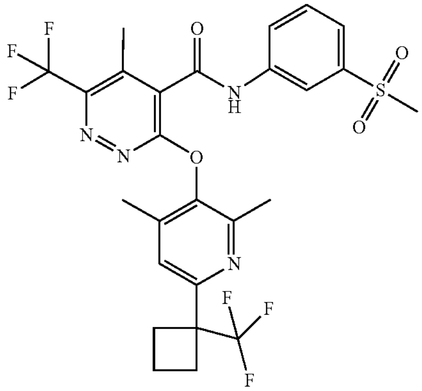 [SMILES: Cc1cc(C2(C(F)(F)F)CCC2)nc(C)c1Oc1nnc(C(F)(F)F)c(C)c1C(=O)Nc1cccc(S(C)(=O)=O)c1]
892
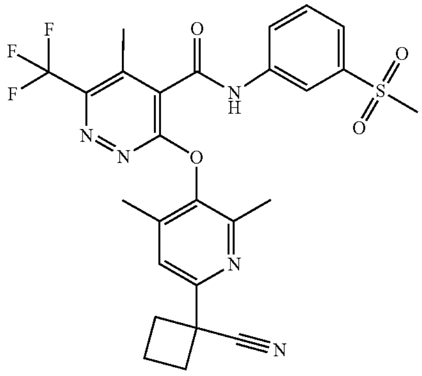 [SMILES: Cc1cc(C2(C#N)CCC2)nc(C)c1Oc1nnc(C(F)(F)F)c(C)c1C(=O)Nc1cccc(S(C)(=O)=O)c1]
893
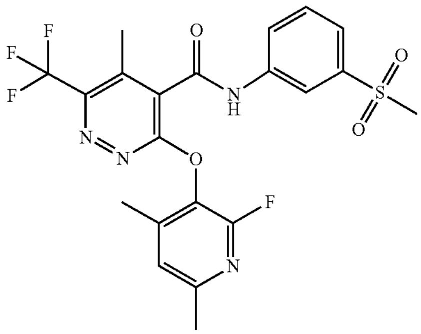 [SMILES: Cc1cc(C)c(Oc2nnc(C(F)(F)F)c(C)c2C(=O)Nc2cccc(S(C)(=O)=O)c2)c(F)n1]
894
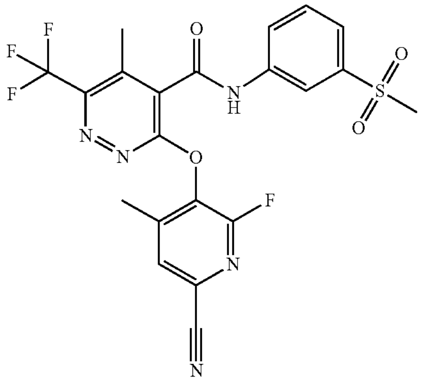 [SMILES: Cc1cc(C#N)nc(F)c1Oc1nnc(C(F)(F)F)c(C)c1C(=O)Nc1cccc(S(C)(=O)=O)c1]
895
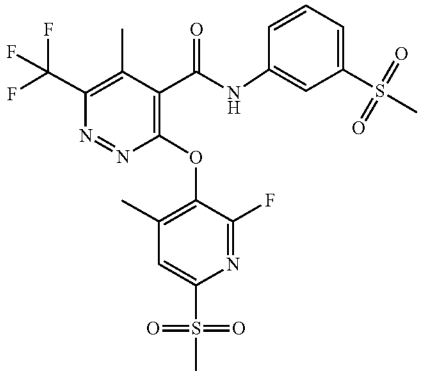 [SMILES: Cc1cc(S(C)(=O)=O)nc(F)c1Oc1nnc(C(F)(F)F)c(C)c1C(=O)Nc1cccc(S(C)(=O)=O)c1]
896
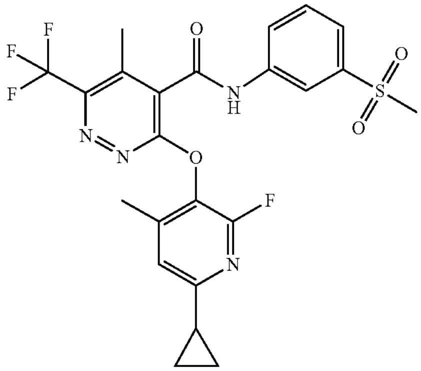 [SMILES: Cc1cc(C2CC2)nc(F)c1Oc1nnc(C(F)(F)F)c(C)c1C(=O)Nc1cccc(S(C)(=O)=O)c1]

TABLE 14-continued
897
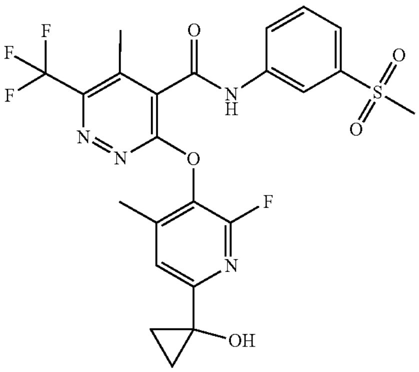 [SMILES: Cc1cc(C2(O)CC2)nc(F)c1Oc1nnc(C(F)(F)F)c(C)c1C(=O)Nc1cccc(S(C)(=O)=O)c1]
898
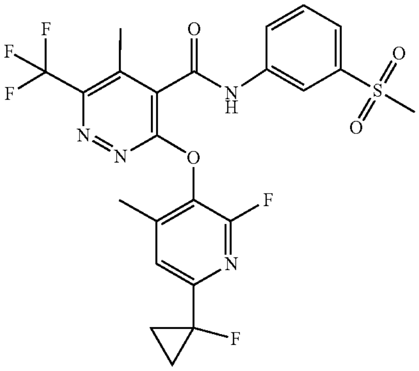 [SMILES: Cc1cc(C2(F)CC2)nc(F)c1Oc1nnc(C(F)(F)F)c(C)c1C(=O)Nc1cccc(S(C)(=O)=O)c1]
899
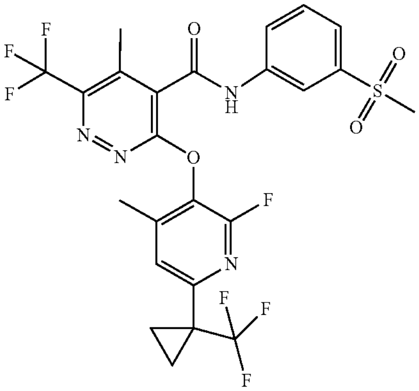 [SMILES: Cc1cc(C2(C(F)(F)F)CC2)nc(F)c1Oc1nnc(C(F)(F)F)c(C)c1C(=O)Nc1cccc(S(C)(=O)=O)c1]
900
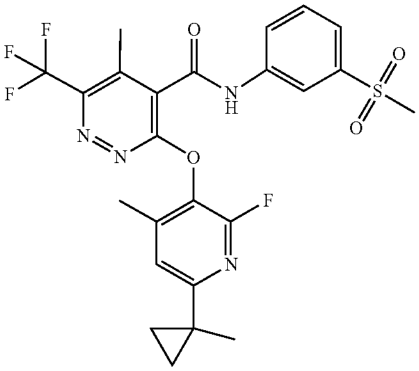 [SMILES: Cc1cc(C2(C)CC2)nc(F)c1Oc1nnc(C(F)(F)F)c(C)c1C(=O)Nc1cccc(S(C)(=O)=O)c1]
TABLE 14-continued
901
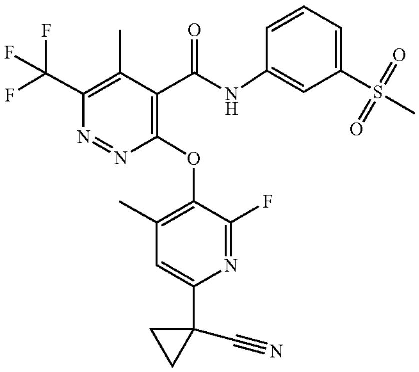 [SMILES: Cc1cc(C2(C#N)CC2)nc(F)c1Oc1nnc(C(F)(F)F)c(C)c1C(=O)Nc1cccc(S(C)(=O)=O)c1]
902
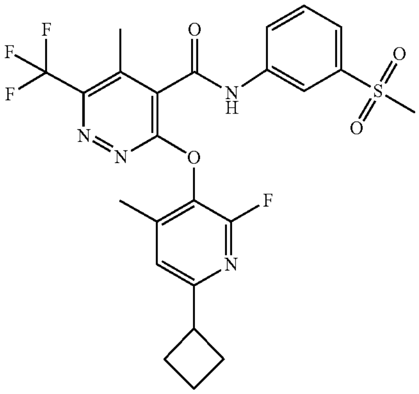 [SMILES: Cc1cc(C2CCC2)nc(F)c1Oc1nnc(C(F)(F)F)c(C)c1C(=O)Nc1cccc(S(C)(=O)=O)c1]
903
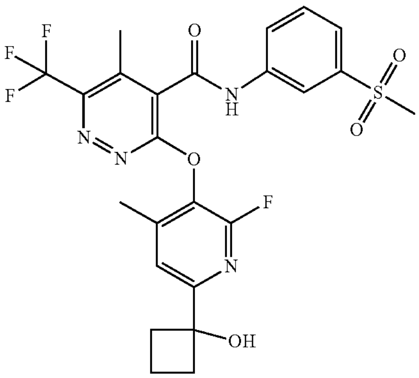 [SMILES: Cc1cc(C2(O)CCC2)nc(F)c1Oc1nnc(C(F)(F)F)c(C)c1C(=O)Nc1cccc(S(C)(=O)=O)c1]
904
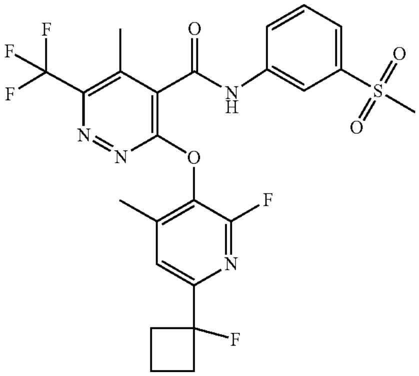 [SMILES: Cc1cc(C2(F)CCC2)nc(F)c1Oc1nnc(C(F)(F)F)c(C)c1C(=O)Nc1cccc(S(C)(=O)=O)c1]

TABLE 14-continued
905
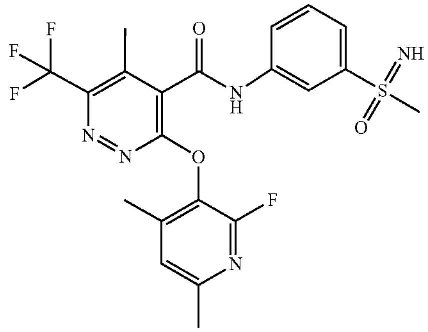 [SMILES: Cc1cc(C)c(Oc2nnc(C(F)(F)F)c(C)c2C(=O)Nc2cccc(S(C)(=N)=O)c2)c(F)n1]
906
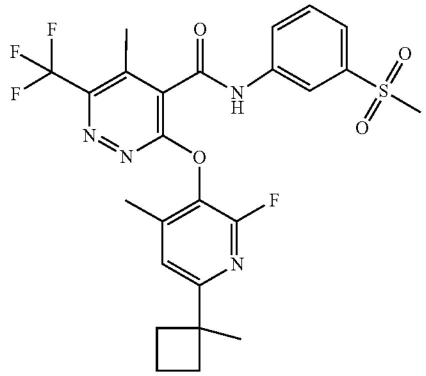 [SMILES: Cc1cc(C2(C)CCC2)nc(F)c1Oc1nnc(C(F)(F)F)c(C)c1C(=O)Nc1cccc(S(C)(=O)=O)c1]
907
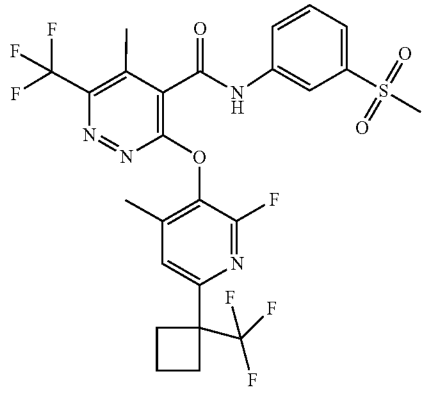 [SMILES: Cc1cc(C2(C(F)(F)F)CCC2)nc(F)c1Oc1nnc(C(F)(F)F)c(C)c1C(=O)Nc1cccc(S(C)(=O)=O)c1]
908
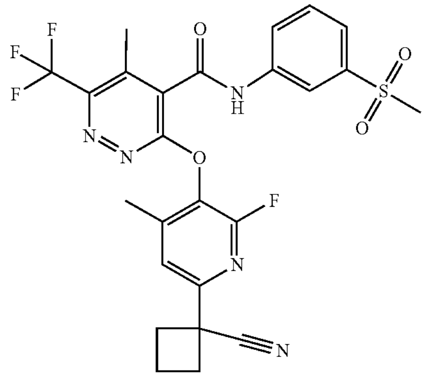 [SMILES: Cc1cc(C2(C#N)CCC2)nc(F)c1Oc1nnc(C(F)(F)F)c(C)c1C(=O)Nc1cccc(S(C)(=O)=O)c1]
TABLE 14-continued
909
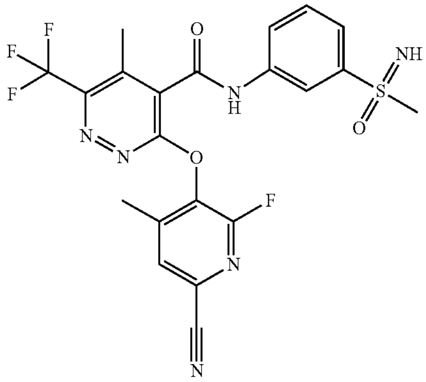 [SMILES: Cc1cc(C#N)nc(F)c1Oc1nnc(C(F)(F)F)c(C)c1C(=O)Nc1cccc(S(C)(=N)=O)c1]
910
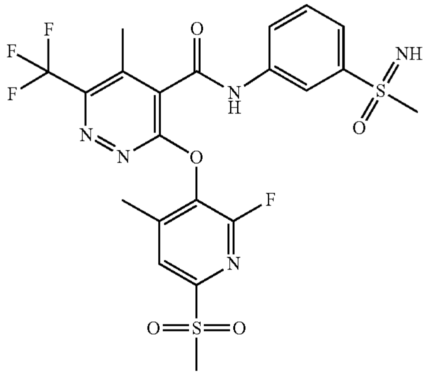 [SMILES: Cc1cc(S(C)(=O)=O)nc(F)c1Oc1nnc(C(F)(F)F)c(C)c1C(=O)Nc1cccc(S(C)(=N)=O)c1]
911
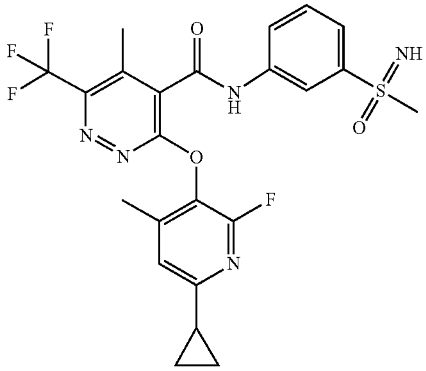 [SMILES: Cc1cc(C2CC2)nc(F)c1Oc1nnc(C(F)(F)F)c(C)c1C(=O)Nc1cccc(S(C)(=N)=O)c1]
912
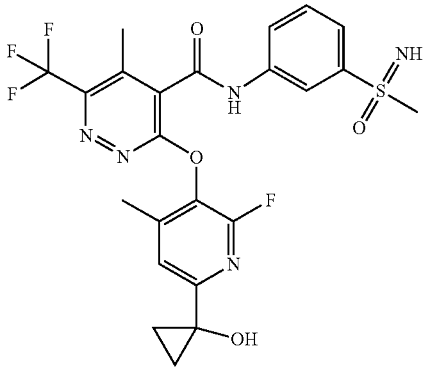 [SMILES: Cc1cc(C2(O)CC2)nc(F)c1Oc1nnc(C(F)(F)F)c(C)c1C(=O)Nc1cccc(S(C)(=N)=O)c1]

TABLE 14-continued
913
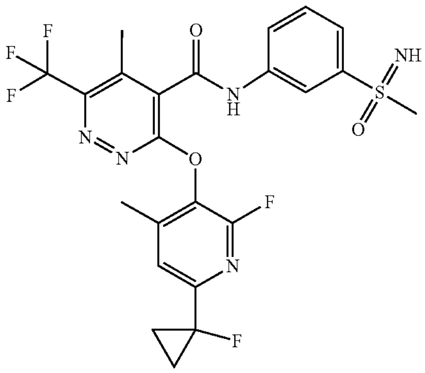 [SMILES: Cc1cc(C2(F)CC2)nc(F)c1Oc1nnc(C(F)(F)F)c(C)c1C(=O)Nc1cccc(S(C)(=N)=O)c1]
914
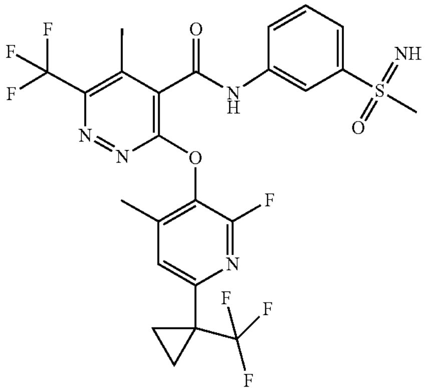 [SMILES: Cc1cc(C2(C(F)(F)F)CC2)nc(F)c1Oc1nnc(C(F)(F)F)c(C)c1C(=O)Nc1cccc(S(C)(=N)=O)c1]
915
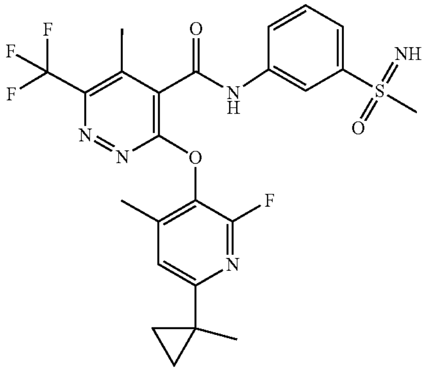 [SMILES: Cc1cc(C2(C)CC2)nc(F)c1Oc1nnc(C(F)(F)F)c(C)c1C(=O)Nc1cccc(S(C)(=N)=O)c1]
916
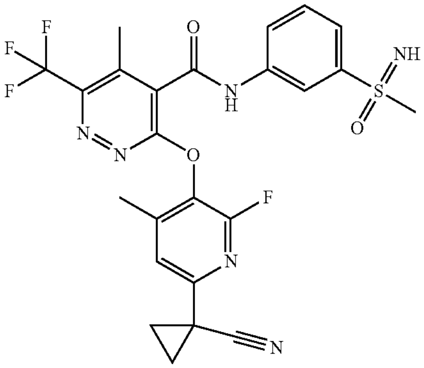 [SMILES: Cc1cc(C2(C#N)CC2)nc(F)c1Oc1nnc(C(F)(F)F)c(C)c1C(=O)Nc1cccc(S(C)(=N)=O)c1]
TABLE 14-continued
917
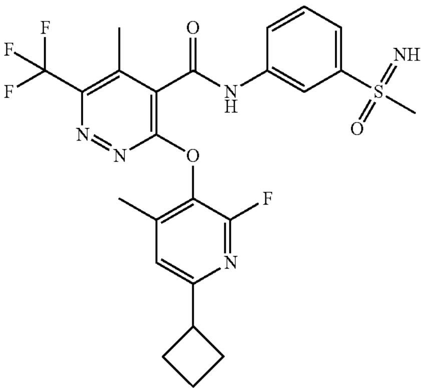 [SMILES: Cc1cc(C2CCC2)nc(F)c1Oc1nnc(C(F)(F)F)c(C)c1C(=O)Nc1cccc(S(C)(=N)=O)c1]
918
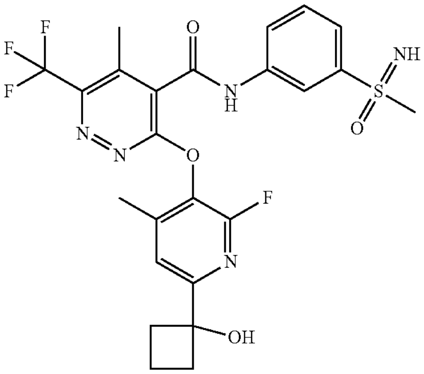 [SMILES: Cc1cc(C2(O)CCC2)nc(F)c1Oc1nnc(C(F)(F)F)c(C)c1C(=O)Nc1cccc(S(C)(=N)=O)c1]
919
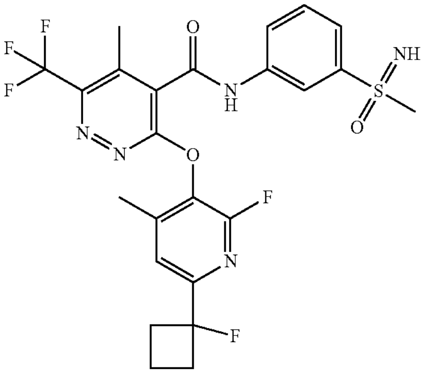
920
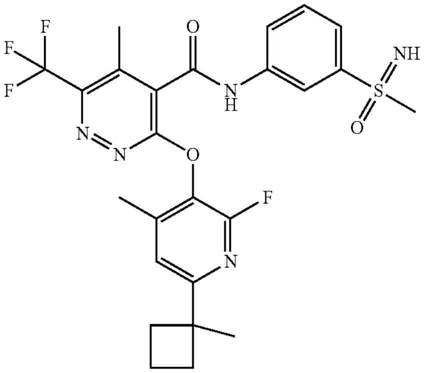

TABLE 14-continued
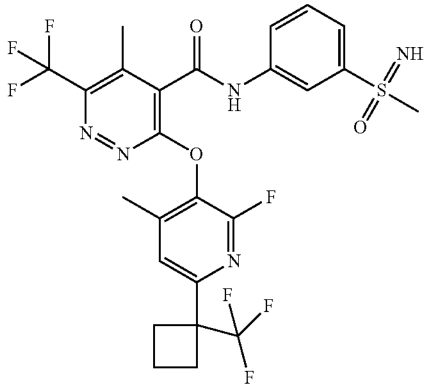 [SMILES: Cc1cc(C2(C(F)(F)F)CCC2)nc(F)c1Oc1nnc(C(F)(F)F)c(C)c1C(=O)Nc1cccc(S(C)(=N)=O)c1]
921
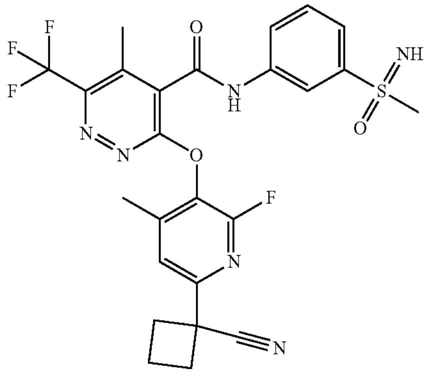 [SMILES: Cc1cc(C2(C#N)CCC2)nc(F)c1Oc1nnc(C(F)(F)F)c(C)c1C(=O)Nc1cccc(S(C)(=N)=O)c1]
922
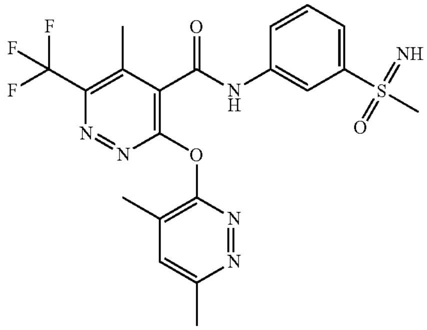 [SMILES: Cc1cc(C)c(Oc2nnc(C(F)(F)F)c(C)c2C(=O)Nc2cccc(S(C)(=N)=O)c2)nn1]
923
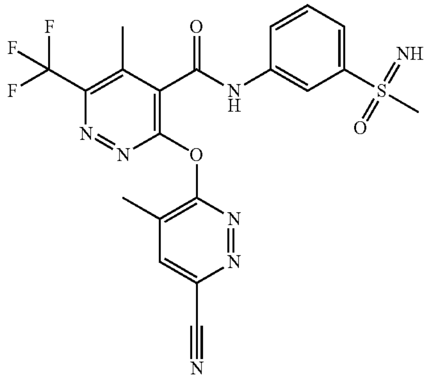 [SMILES: Cc1cc(C#N)nnc1Oc1nnc(C(F)(F)F)c(C)c1C(=O)Nc1cccc(S(C)(=N)=O)c1]
924
TABLE 14-continued
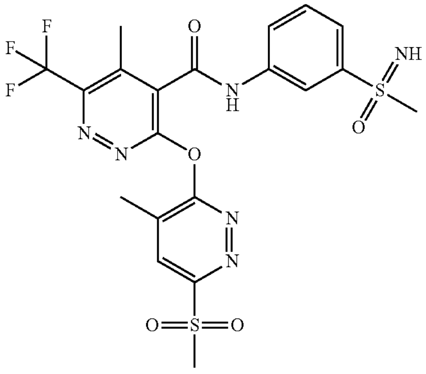
925
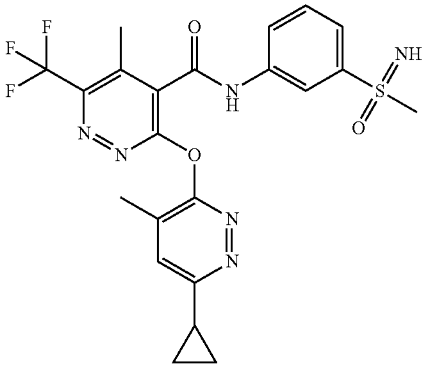 [SMILES: Cc1cc(C2CC2)nnc1Oc1nnc(C(F)(F)F)c(C)c1C(=O)Nc1cccc(S(C)(=N)=O)c1]
926
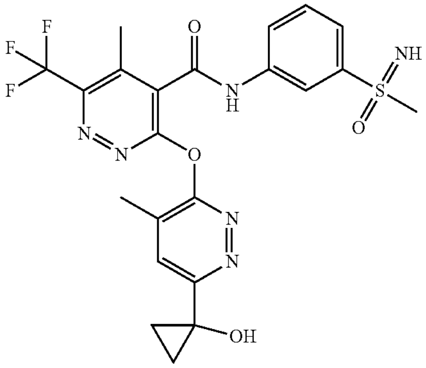
927
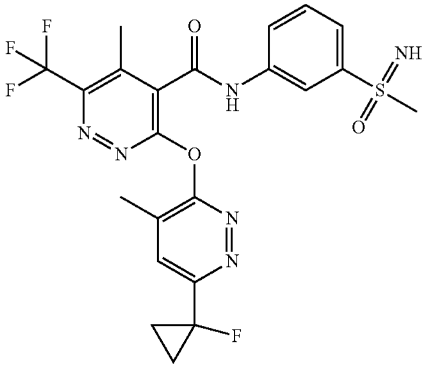 [SMILES: Cc1cc(C2(F)CC2)nnc1Oc1nnc(C(F)(F)F)c(C)c1C(=O)Nc1cccc(S(C)(=N)=O)c1]
928

TABLE 14-continued
929
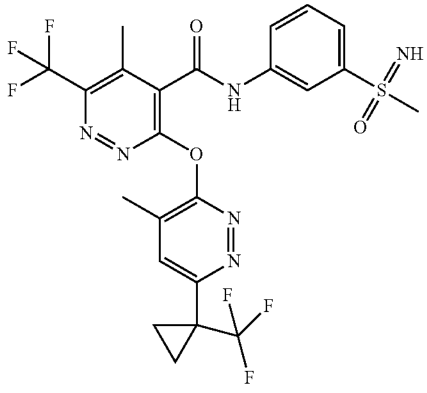 [SMILES: Cc1cc(C2(C(F)(F)F)CC2)nnc1Oc1nnc(C(F)(F)F)c(C)c1C(=O)Nc1cccc(S(C)(=N)=O)c1]
930
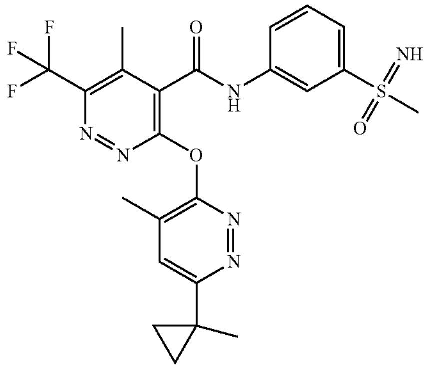 [SMILES: Cc1cc(C2(C)CC2)nnc1Oc1nnc(C(F)(F)F)c(C)c1C(=O)Nc1cccc(S(C)(=N)=O)c1]
931
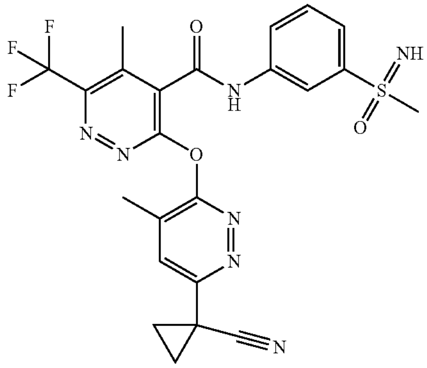 [SMILES: Cc1cc(C2(C#N)CC2)nnc1Oc1nnc(C(F)(F)F)c(C)c1C(=O)Nc1cccc(S(C)(=N)=O)c1]
932
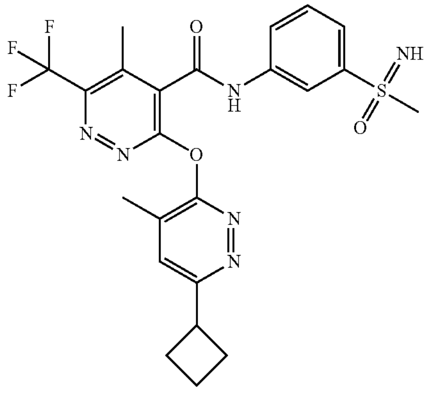
TABLE 14-continued
933
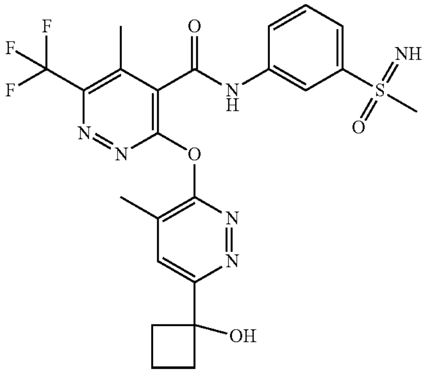
934
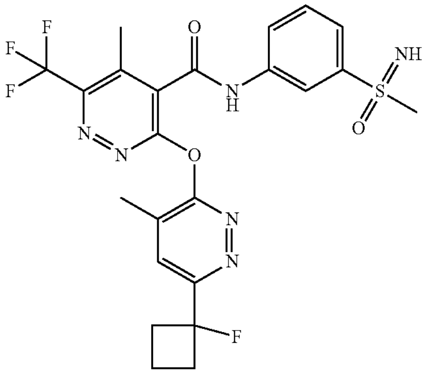
935
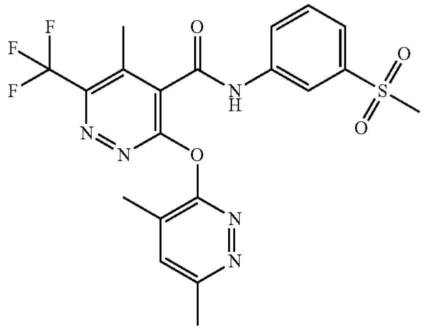
936
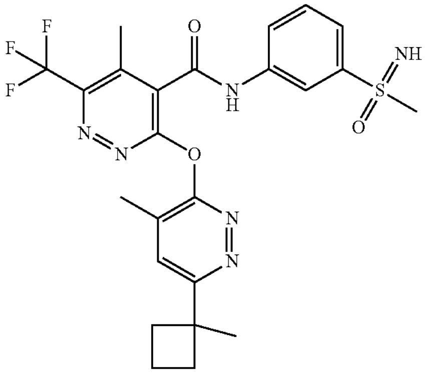

TABLE 14-continued
937
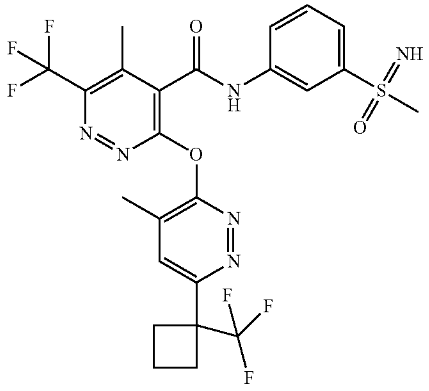 [SMILES: Cc1cc(C2(C(F)(F)F)CCC2)nnc1Oc1nnc(C(F)(F)F)c(C)c1C(=O)Nc1cccc(S(C)(=N)=O)c1]
938
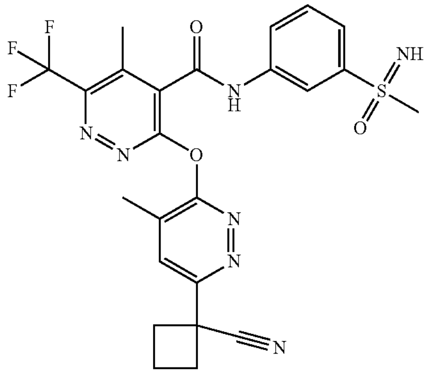 [SMILES: Cc1cc(C2(C#N)CCC2)nnc1Oc1nnc(C(F)(F)F)c(C)c1C(=O)Nc1cccc(S(C)(=N)=O)c1]
939
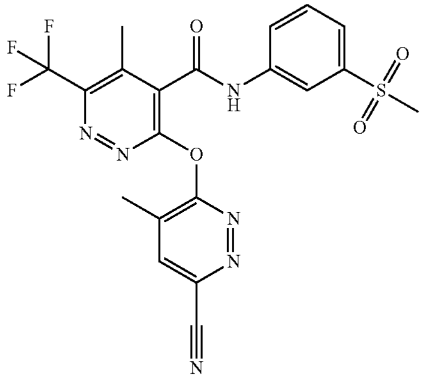
940
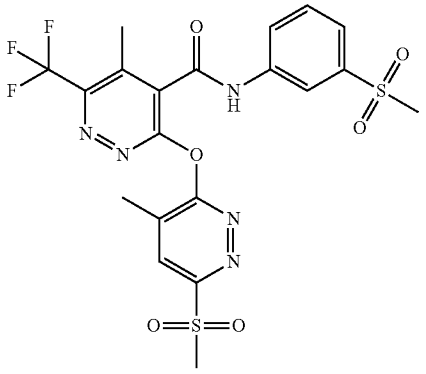
TABLE 14-continued
941
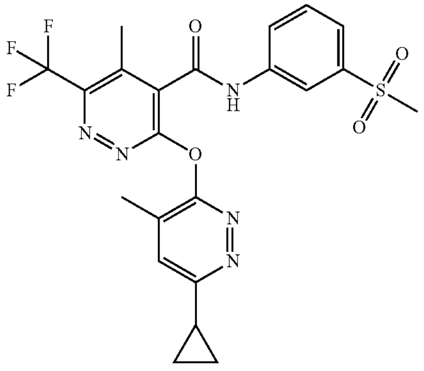 [SMILES: Cc1cc(C2CC2)nnc1Oc1nnc(C(F)(F)F)c(C)c1C(=O)Nc1cccc(S(C)(=O)=O)c1]
942
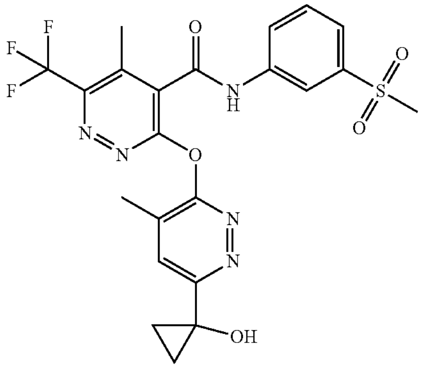
943
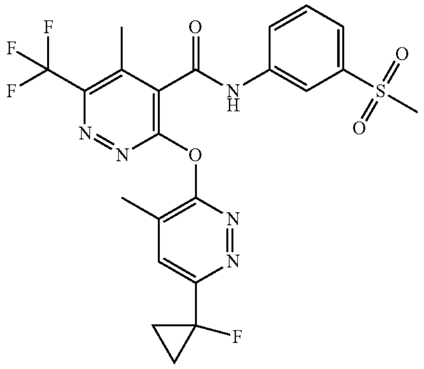
944
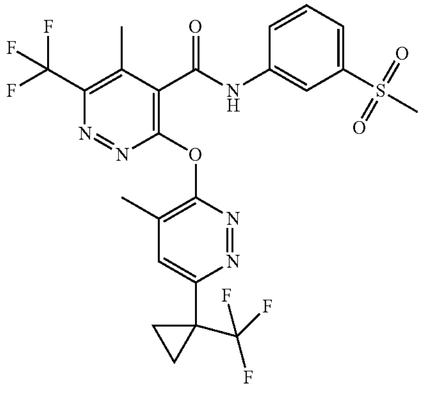

TABLE 14-continued
945
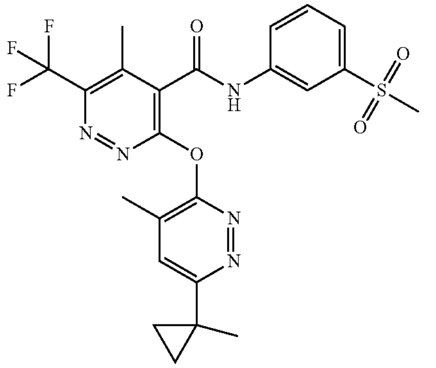 [SMILES: Cc1cc(C2(C)CC2)nnc1Oc1nnc(C(F)(F)F)c(C)c1C(=O)Nc1cccc(S(C)(=O)=O)c1]
946
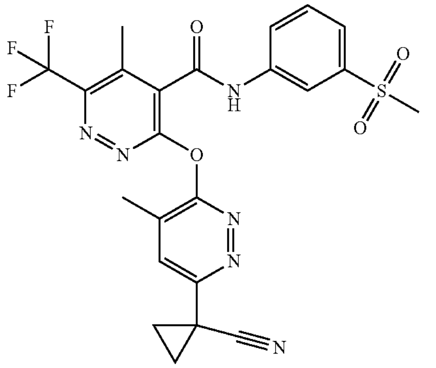 [SMILES: Cc1cc(C2(C#N)CC2)nnc1Oc1nnc(C(F)(F)F)c(C)c1C(=O)Nc1cccc(S(C)(=O)=O)c1]
947
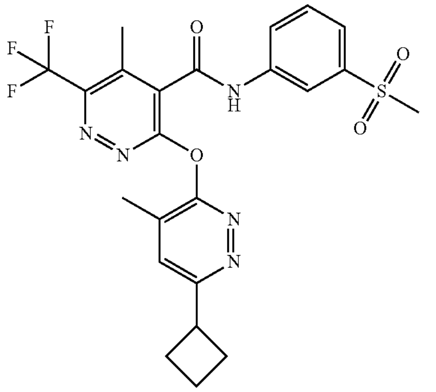 [SMILES: Cc1cc(C2CCC2)nnc1Oc1nnc(C(F)(F)F)c(C)c1C(=O)Nc1cccc(S(C)(=O)=O)c1]
948
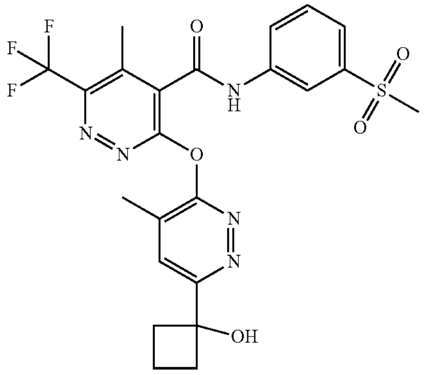 [SMILES: Cc1cc(C2(O)CCC2)nnc1Oc1nnc(C(F)(F)F)c(C)c1C(=O)Nc1cccc(S(C)(=O)=O)c1]
TABLE 14-continued
949
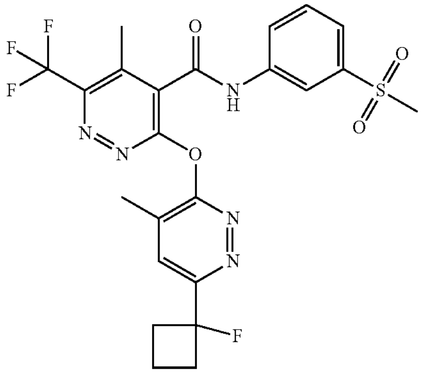 [SMILES: Cc1cc(C2(F)CCC2)nnc1Oc1nnc(C(F)(F)F)c(C)c1C(=O)Nc1cccc(S(C)(=O)=O)c1]
950
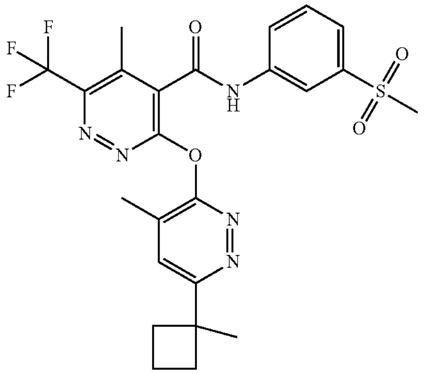
951
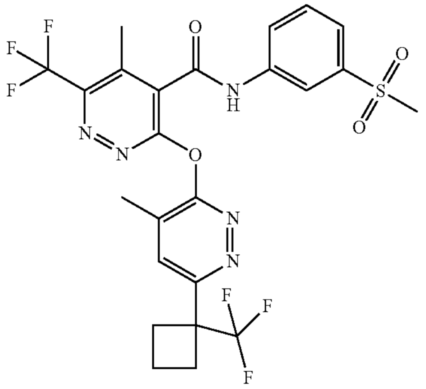 [SMILES: Cc1cc(C2(C(F)(F)F)CCC2)nnc1Oc1nnc(C(F)(F)F)c(C)c1C(=O)Nc1cccc(S(C)(=O)=O)c1]
952
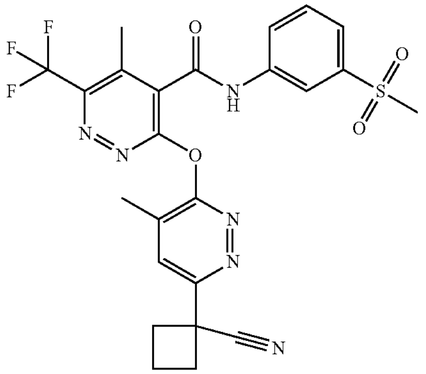 [SMILES: Cc1cc(C2(C#N)CCC2)nnc1Oc1nnc(C(F)(F)F)c(C)c1C(=O)Nc1cccc(S(C)(=O)=O)c1]

TABLE 14-continued
953
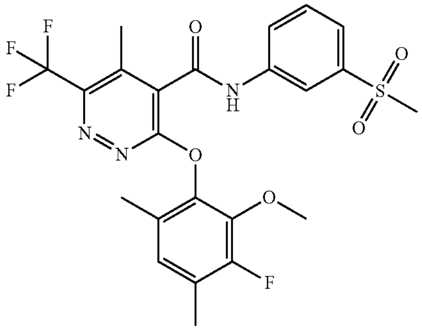 [SMILES: COc1c(F)c(C)cc(C)c1Oc1nnc(C(F)(F)F)c(C)c1C(=O)Nc1cccc(S(C)(=O)=O)c1]
954
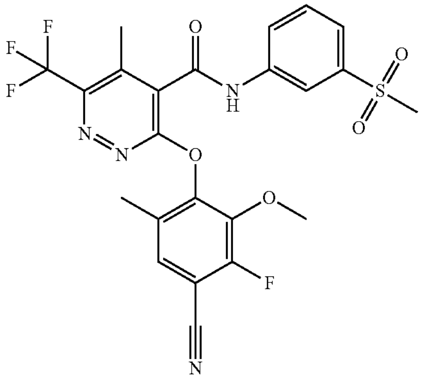
955
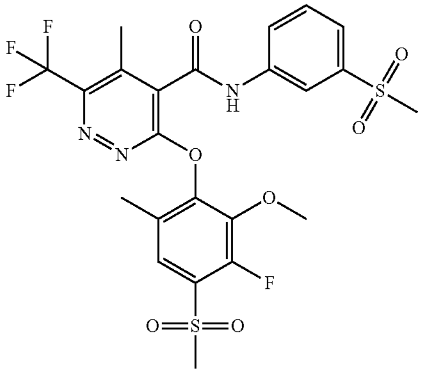 [SMILES: COc1c(F)c(S(C)(=O)=O)cc(C)c1Oc1nnc(C(F)(F)F)c(C)c1C(=O)Nc1cccc(S(C)(=O)=O)c1]
956
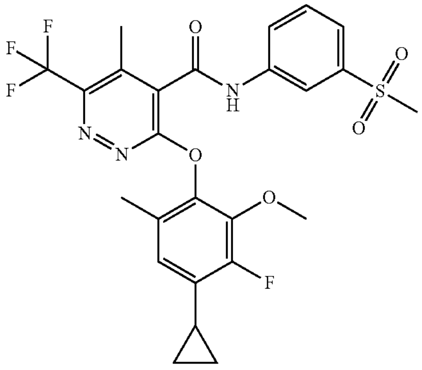 [SMILES: COc1c(F)c(C2CC2)cc(C)c1Oc1nnc(C(F)(F)F)c(C)c1C(=O)Nc1cccc(S(C)(=O)=O)c1]
TABLE 14-continued
957
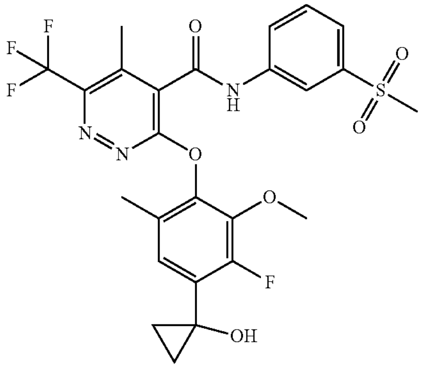 [SMILES: COc1c(F)c(C2(O)CC2)cc(C)c1Oc1nnc(C(F)(F)F)c(C)c1C(=O)Nc1cccc(S(C)(=O)=O)c1]
958
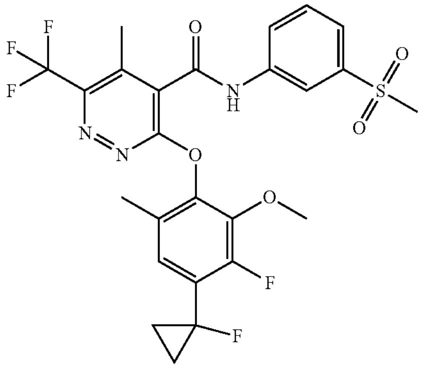 [SMILES: COc1c(F)c(C2(F)CC2)cc(C)c1Oc1nnc(C(F)(F)F)c(C)c1C(=O)Nc1cccc(S(C)(=O)=O)c1]
959
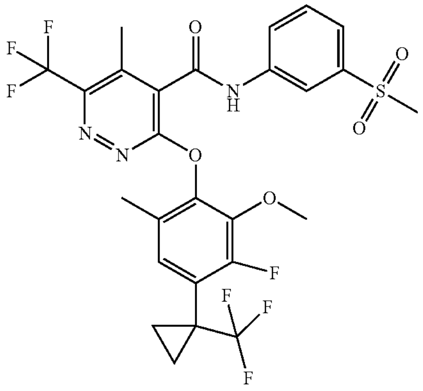 [SMILES: COc1c(F)c(C2(C(F)(F)F)CC2)cc(C)c1Oc1nnc(C(F)(F)F)c(C)c1C(=O)Nc1cccc(S(C)(=O)=O)c1]
960
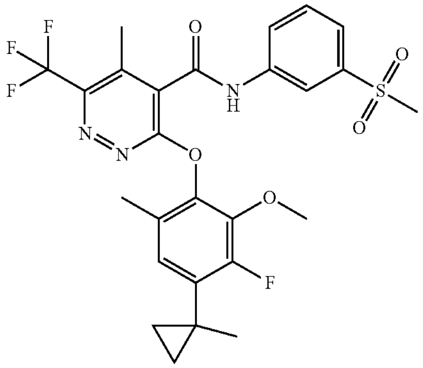 [SMILES: COc1c(F)c(C2(C)CC2)cc(C)c1Oc1nnc(C(F)(F)F)c(C)c1C(=O)Nc1cccc(S(C)(=O)=O)c1]

TABLE 14-continued
961
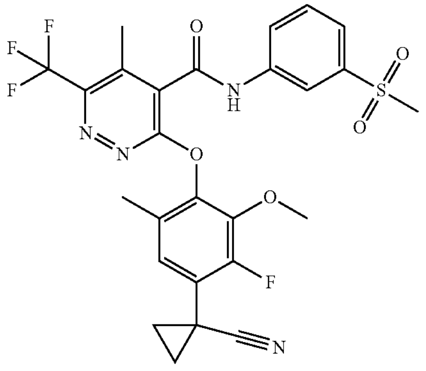 [SMILES: COc1c(F)c(C2(C#N)CC2)cc(C)c1Oc1nnc(C(F)(F)F)c(C)c1C(=O)Nc1cccc(S(C)(=O)=O)c1]
962
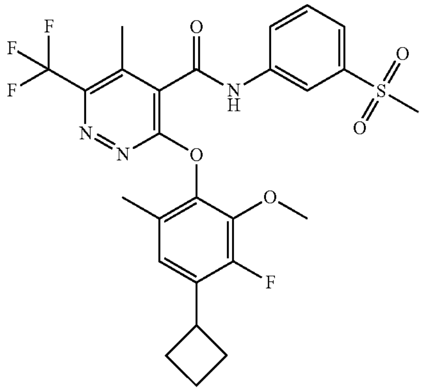 [SMILES: COc1c(F)c(C2CCC2)cc(C)c1Oc1nnc(C(F)(F)F)c(C)c1C(=O)Nc1cccc(S(C)(=O)=O)c1]
964
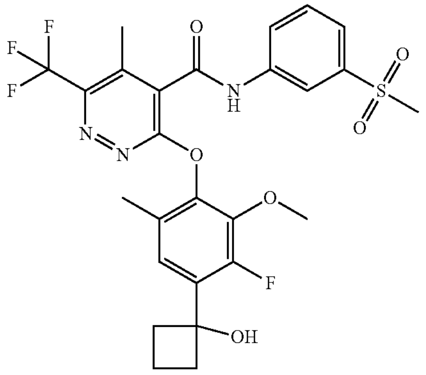 [SMILES: COc1c(F)c(C2(O)CCC2)cc(C)c1Oc1nnc(C(F)(F)F)c(C)c1C(=O)Nc1cccc(S(C)(=O)=O)c1]
965
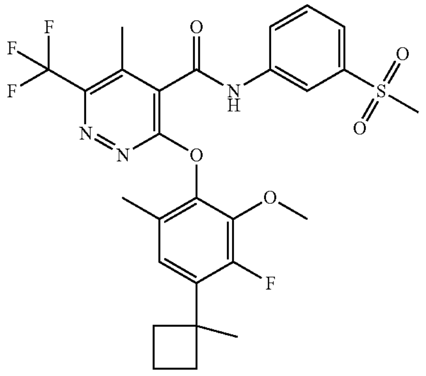 [SMILES: COc1c(F)c(C2(C)CCC2)cc(C)c1Oc1nnc(C(F)(F)F)c(C)c1C(=O)Nc1cccc(S(C)(=O)=O)c1]
TABLE 14-continued
966
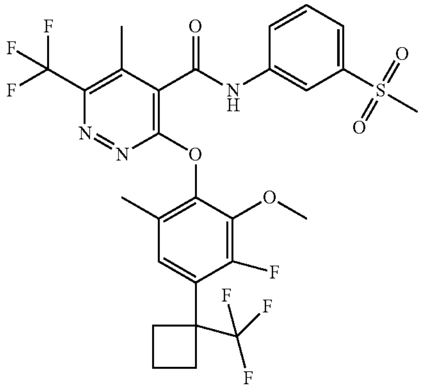 [SMILES: COc1c(F)c(C2(C(F)(F)F)CCC2)cc(C)c1Oc1nnc(C(F)(F)F)c(C)c1C(=O)Nc1cccc(S(C)(=O)=O)c1]
967
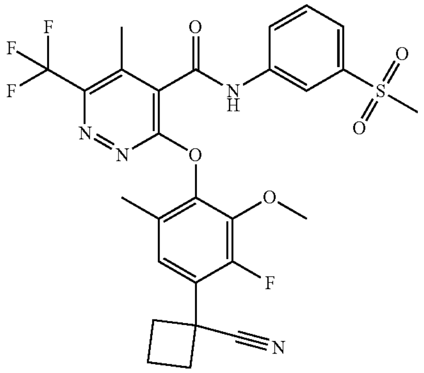 [SMILES: COc1c(F)c(C2(C#N)CCC2)cc(C)c1Oc1nnc(C(F)(F)F)c(C)c1C(=O)Nc1cccc(S(C)(=O)=O)c1]
968
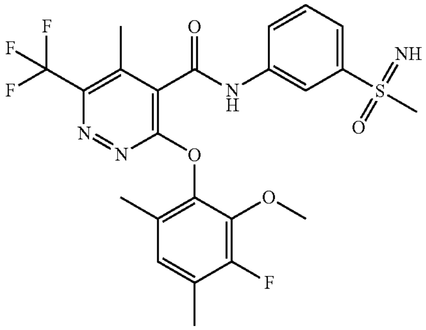 [SMILES: COc1c(F)c(C)cc(C)c1Oc1nnc(C(F)(F)F)c(C)c1C(=O)Nc1cccc(S(C)(=N)=O)c1]
969
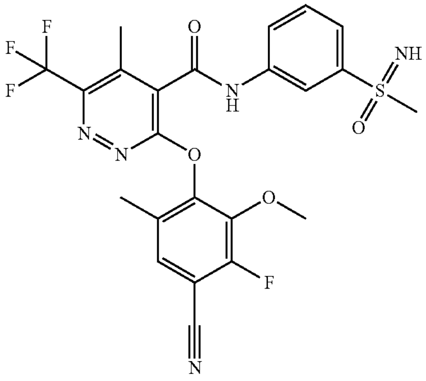 [SMILES: COc1c(F)c(C#N)cc(C)c1Oc1nnc(C(F)(F)F)c(C)c1C(=O)Nc1cccc(S(C)(=N)=O)c1]

TABLE 14-continued
970
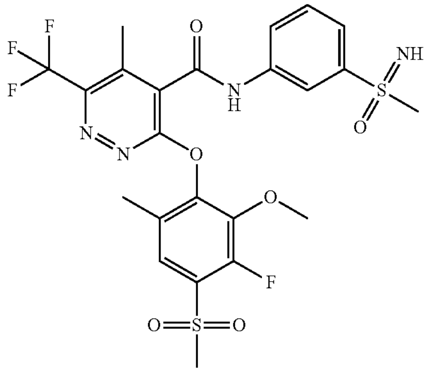 [SMILES: COc1c(F)c(S(C)(=O)=O)cc(C)c1Oc1nnc(C(F)(F)F)c(C)c1C(=O)Nc1cccc(S(C)(=N)=O)c1]
971
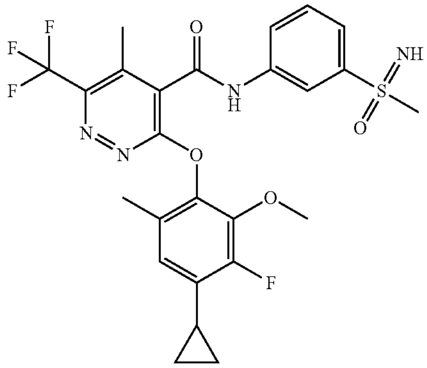 [SMILES: COc1c(F)c(C2CC2)cc(C)c1Oc1nnc(C(F)(F)F)c(C)c1C(=O)Nc1cccc(S(C)(=N)=O)c1]
972
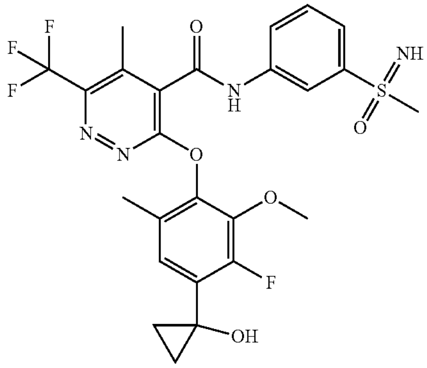 [SMILES: COc1c(F)c(C2(O)CC2)cc(C)c1Oc1nnc(C(F)(F)F)c(C)c1C(=O)Nc1cccc(S(C)(=N)=O)c1]
973
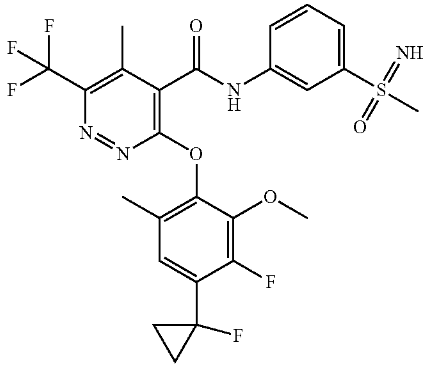 [SMILES: COc1c(F)c(C2(F)CC2)cc(C)c1Oc1nnc(C(F)(F)F)c(C)c1C(=O)Nc1cccc(S(C)(=N)=O)c1]
TABLE 14-continued
974
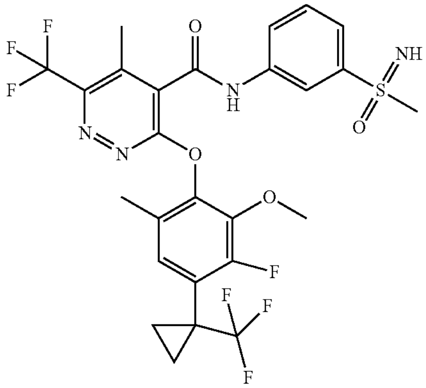 [SMILES: COc1c(F)c(C2(C(F)(F)F)CC2)cc(C)c1Oc1nnc(C(F)(F)F)c(C)c1C(=O)Nc1cccc(S(C)(=N)=O)c1]
975
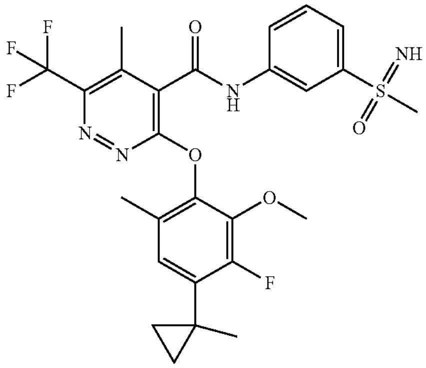 [SMILES: COc1c(F)c(C2(C)CC2)cc(C)c1Oc1nnc(C(F)(F)F)c(C)c1C(=O)Nc1cccc(S(C)(=N)=O)c1]
976
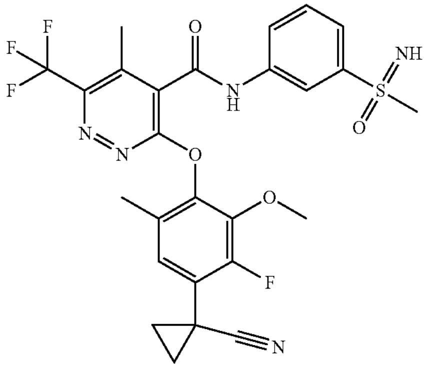 [SMILES: COc1c(F)c(C2(C#N)CC2)cc(C)c1Oc1nnc(C(F)(F)F)c(C)c1C(=O)Nc1cccc(S(C)(=N)=O)c1]
977
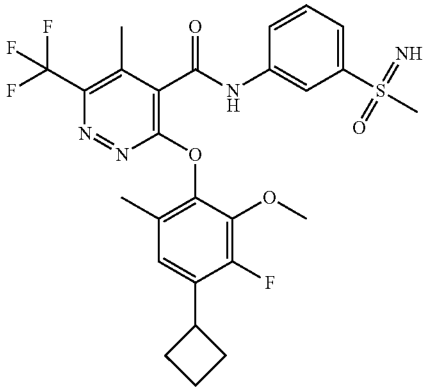 [SMILES: COc1c(F)c(C2CCC2)cc(C)c1Oc1nnc(C(F)(F)F)c(C)c1C(=O)Nc1cccc(S(C)(=N)=O)c1]

TABLE 14-continued
978
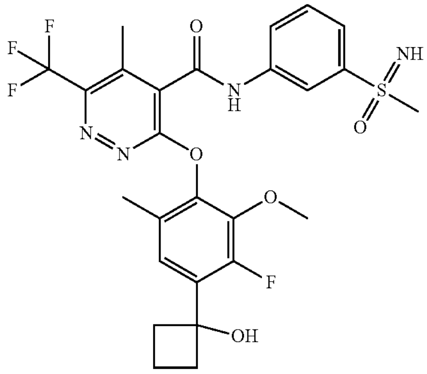 [SMILES: COc1c(F)c(C2(O)CCC2)cc(C)c1Oc1nnc(C(F)(F)F)c(C)c1C(=O)Nc1cccc(S(C)(=N)=O)c1]
979
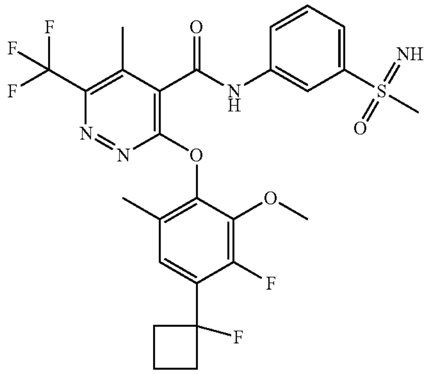 [SMILES: COc1c(F)c(C2(F)CCC2)cc(C)c1Oc1nnc(C(F)(F)F)c(C)c1C(=O)Nc1cccc(S(C)(=N)=O)c1]
980
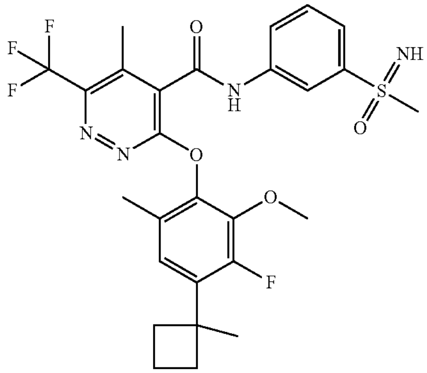 [SMILES: COc1c(F)c(C2(C)CCC2)cc(C)c1Oc1nnc(C(F)(F)F)c(C)c1C(=O)Nc1cccc(S(C)(=N)=O)c1]
981
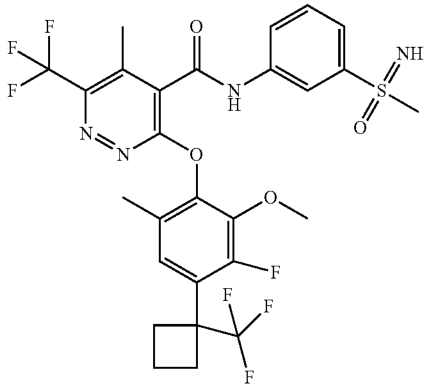 [SMILES: COc1c(F)c(C2(C(F)(F)F)CCC2)cc(C)c1Oc1nnc(C(F)(F)F)c(C)c1C(=O)Nc1cccc(S(C)(=N)=O)c1]
TABLE 14-continued
982
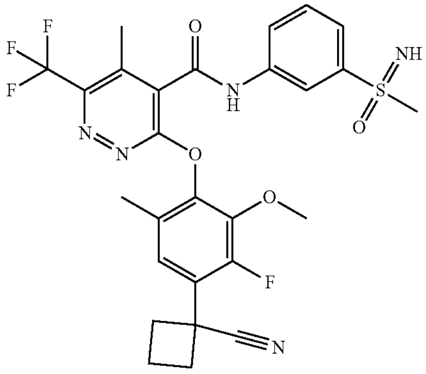 [SMILES: COc1c(F)c(C2(C#N)CCC2)cc(C)c1Oc1nnc(C(F)(F)F)c(C)c1C(=O)Nc1cccc(S(C)(=N)=O)c1]
983
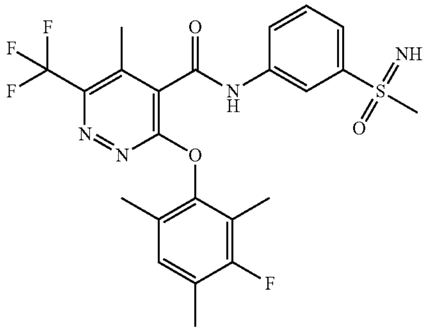 [SMILES: Cc1cc(C)c(Oc2nnc(C(F)(F)F)c(C)c2C(=O)Nc2cccc(S(C)(=N)=O)c2)c(C)c1F]
984
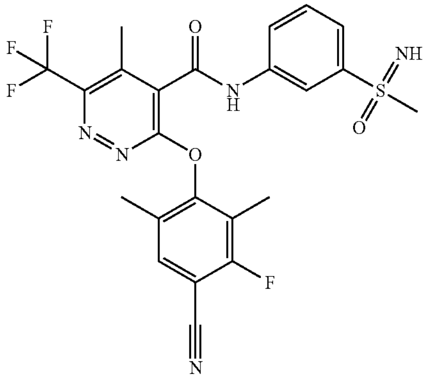 [SMILES: Cc1cc(C#N)c(F)c(C)c1Oc1nnc(C(F)(F)F)c(C)c1C(=O)Nc1cccc(S(C)(=N)=O)c1]
985
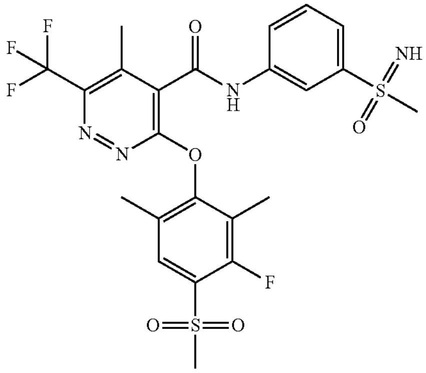 [SMILES: Cc1cc(S(C)(=O)=O)c(F)c(C)c1Oc1nnc(C(F)(F)F)c(C)c1C(=O)Nc1cccc(S(C)(=N)=O)c1]

TABLE 14-continued
986
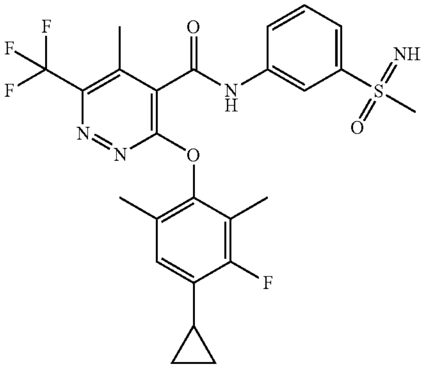 [SMILES: Cc1cc(C2CC2)c(F)c(C)c1Oc1nnc(C(F)(F)F)c(C)c1C(=O)Nc1cccc(S(C)(=N)=O)c1]
987
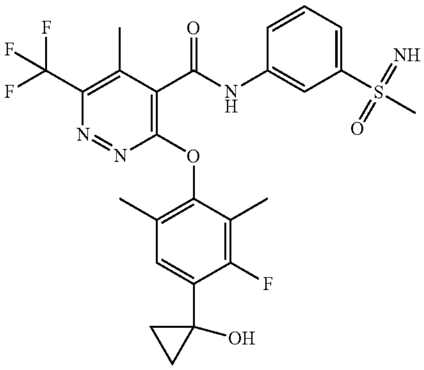 [SMILES: Cc1cc(C2(O)CC2)c(F)c(C)c1Oc1nnc(C(F)(F)F)c(C)c1C(=O)Nc1cccc(S(C)(=N)=O)c1]
988
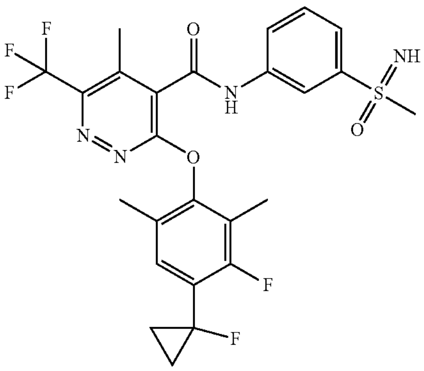 [SMILES: Cc1cc(C2(F)CC2)c(F)c(C)c1Oc1nnc(C(F)(F)F)c(C)c1C(=O)Nc1cccc(S(C)(=N)=O)c1]
989
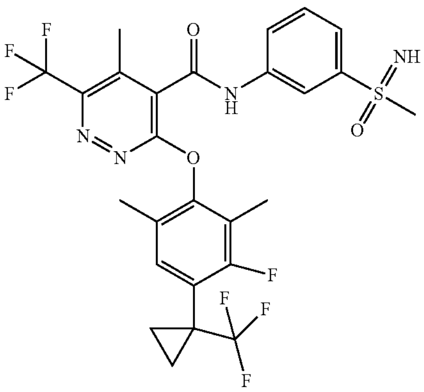 [SMILES: Cc1cc(C2(C(F)(F)F)CC2)c(F)c(C)c1Oc1nnc(C(F)(F)F)c(C)c1C(=O)Nc1cccc(S(C)(=N)=O)c1]
TABLE 14-continued
990
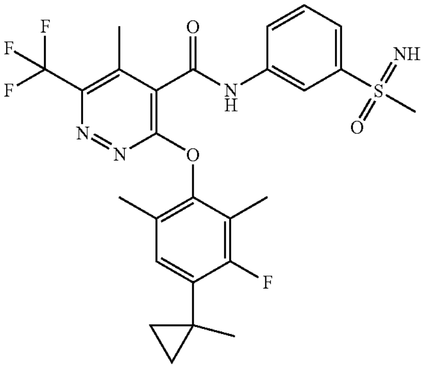 [SMILES: Cc1cc(C2(C)CC2)c(F)c(C)c1Oc1nnc(C(F)(F)F)c(C)c1C(=O)Nc1cccc(S(C)(=N)=O)c1]
991
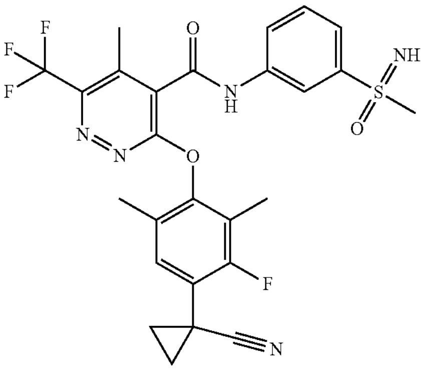 [SMILES: Cc1cc(C2(C#N)CC2)c(F)c(C)c1Oc1nnc(C(F)(F)F)c(C)c1C(=O)Nc1cccc(S(C)(=N)=O)c1]
992
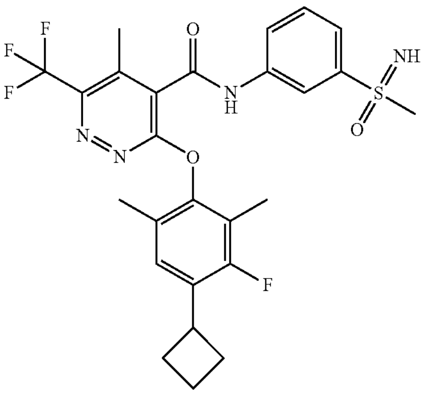 [SMILES: Cc1cc(C2CCC2)c(F)c(C)c1Oc1nnc(C(F)(F)F)c(C)c1C(=O)Nc1cccc(S(C)(=N)=O)c1]
993
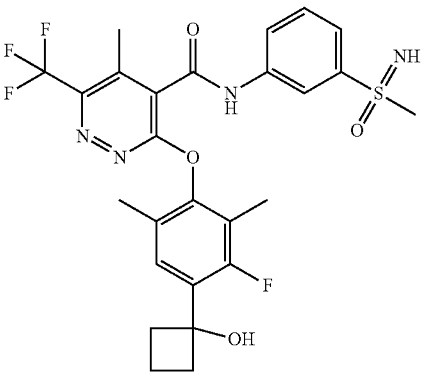 [SMILES: Cc1cc(C2(O)CCC2)c(F)c(C)c1Oc1nnc(C(F)(F)F)c(C)c1C(=O)Nc1cccc(S(C)(=N)=O)c1]

TABLE 14-continued
994
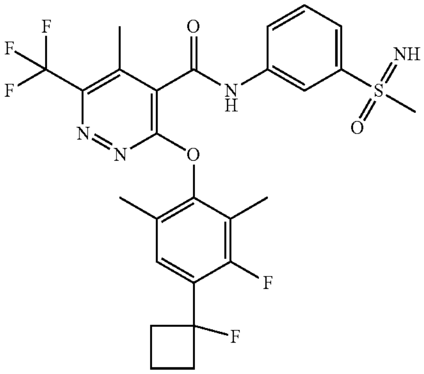 [SMILES: Cc1cc(C2(F)CCC2)c(F)c(C)c1Oc1nnc(C(F)(F)F)c(C)c1C(=O)Nc1cccc(S(C)(=N)=O)c1]
995
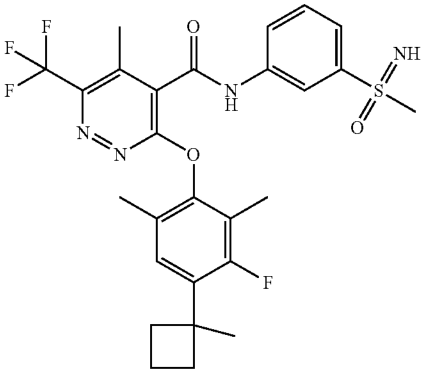 [SMILES: Cc1cc(C2(C)CCC2)c(F)c(C)c1Oc1nnc(C(F)(F)F)c(C)c1C(=O)Nc1cccc(S(C)(=N)=O)c1]
996
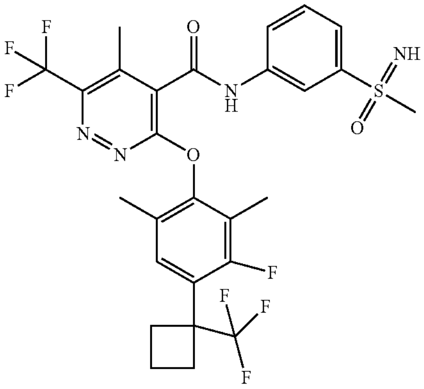 [SMILES: Cc1cc(C2(C(F)(F)F)CCC2)c(F)c(C)c1Oc1nnc(C(F)(F)F)c(C)c1C(=O)Nc1cccc(S(C)(=N)=O)c1]
997
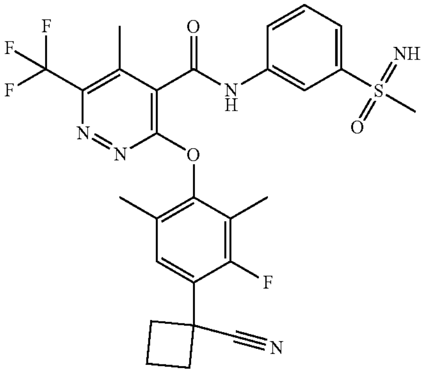 [SMILES: Cc1cc(C2(C#N)CCC2)c(F)c(C)c1Oc1nnc(C(F)(F)F)c(C)c1C(=O)Nc1cccc(S(C)(=N)=O)c1]
TABLE 14-continued
998
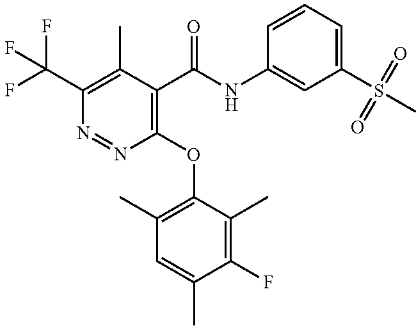 [SMILES: Cc1cc(C)c(Oc2nnc(C(F)(F)F)c(C)c2C(=O)Nc2cccc(S(C)(=O)=O)c2)c(C)c1F]
999
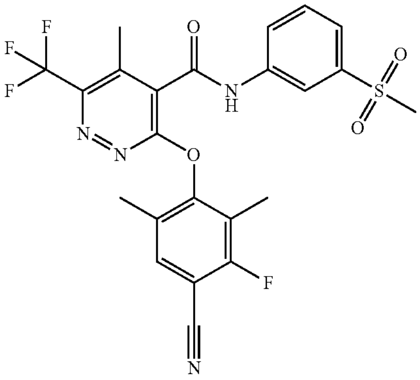 [SMILES: Cc1cc(C#N)c(F)c(C)c1Oc1nnc(C(F)(F)F)c(C)c1C(=O)Nc1cccc(S(C)(=O)=O)c1]
1000
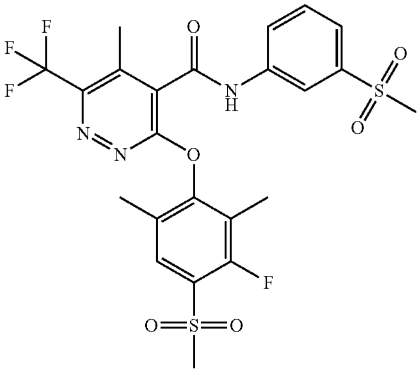
1001
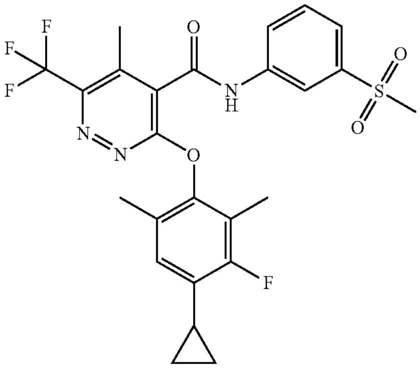 [SMILES: Cc1cc(C2CC2)c(F)c(C)c1Oc1nnc(C(F)(F)F)c(C)c1C(=O)Nc1cccc(S(C)(=O)=O)c1]

TABLE 14-continued
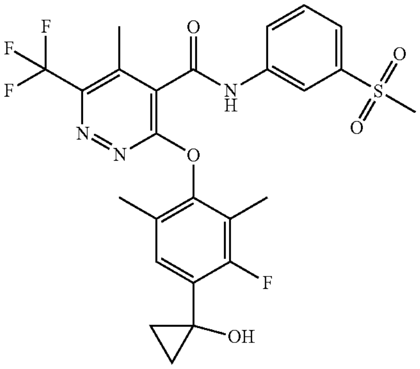 [SMILES: Cc1cc(C2(O)CC2)c(F)c(C)c1Oc1nnc(C(F)(F)F)c(C)c1C(=O)Nc1cccc(S(C)(=O)=O)c1]
1002
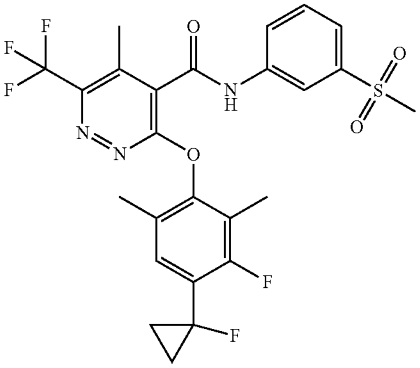 [SMILES: Cc1cc(C2(F)CC2)c(F)c(C)c1Oc1nnc(C(F)(F)F)c(C)c1C(=O)Nc1cccc(S(C)(=O)=O)c1]
1003
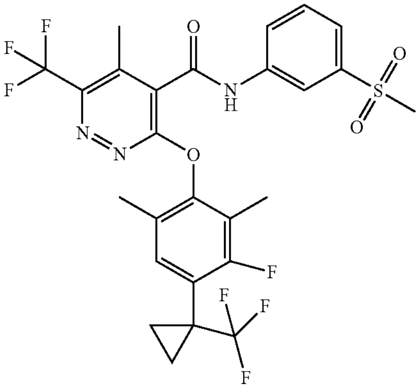 [SMILES: Cc1cc(C2(C(F)(F)F)CC2)c(F)c(C)c1Oc1nnc(C(F)(F)F)c(C)c1C(=O)Nc1cccc(S(C)(=O)=O)c1]
1004
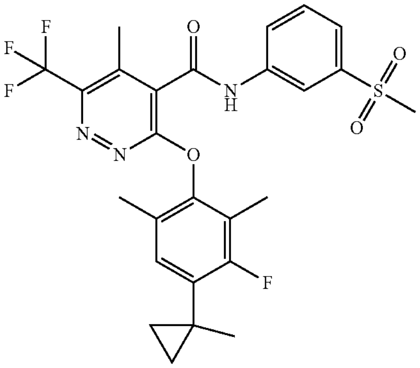 [SMILES: Cc1cc(C2(C)CC2)c(F)c(C)c1Oc1nnc(C(F)(F)F)c(C)c1C(=O)Nc1cccc(S(C)(=O)=O)c1]
1005
TABLE 14-continued
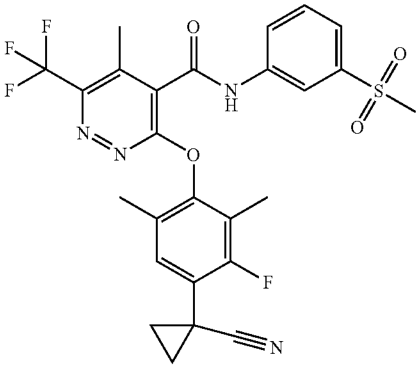 [SMILES: Cc1cc(C2(C#N)CC2)c(F)c(C)c1Oc1nnc(C(F)(F)F)c(C)c1C(=O)Nc1cccc(S(C)(=O)=O)c1]
1006
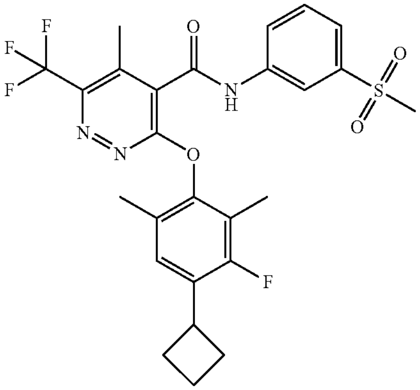 [SMILES: Cc1cc(C2CCC2)c(F)c(C)c1Oc1nnc(C(F)(F)F)c(C)c1C(=O)Nc1cccc(S(C)(=O)=O)c1]
1007
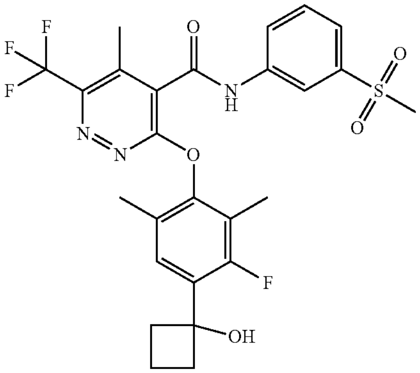 [SMILES: Cc1cc(C2(O)CCC2)c(F)c(C)c1Oc1nnc(C(F)(F)F)c(C)c1C(=O)Nc1cccc(S(C)(=O)=O)c1]
1008
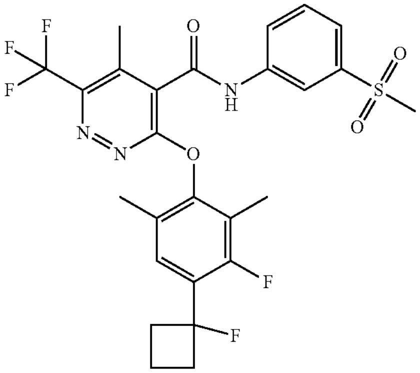 [SMILES: Cc1cc(C2(F)CCC2)c(F)c(C)c1Oc1nnc(C(F)(F)F)c(C)c1C(=O)Nc1cccc(S(C)(=O)=O)c1]
1009

TABLE 14-continued
1010
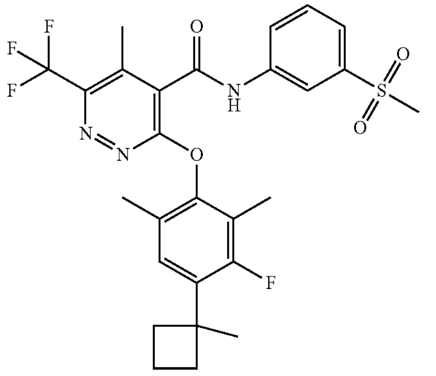 [SMILES: Cc1cc(C2(C)CCC2)c(F)c(C)c1Oc1nnc(C(F)(F)F)c(C)c1C(=O)Nc1cccc(S(C)(=O)=O)c1]
1011
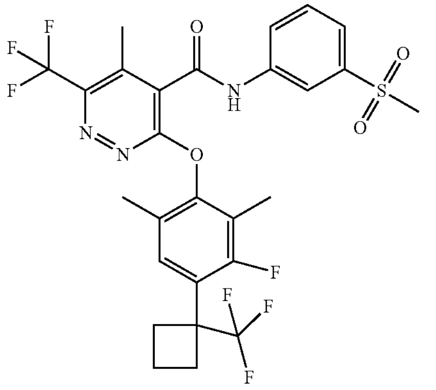 [SMILES: Cc1cc(C2(C(F)(F)F)CCC2)c(F)c(C)c1Oc1nnc(C(F)(F)F)c(C)c1C(=O)Nc1cccc(S(C)(=O)=O)c1]
1012
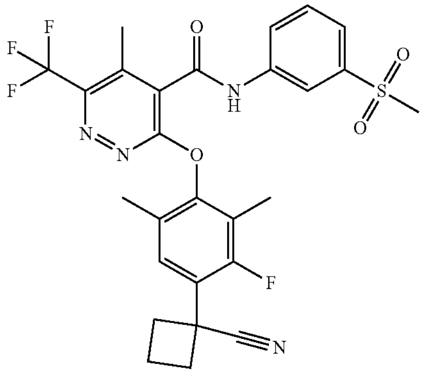 [SMILES: Cc1cc(C2(C#N)CCC2)c(F)c(C)c1Oc1nnc(C(F)(F)F)c(C)c1C(=O)Nc1cccc(S(C)(=O)=O)c1]
1013
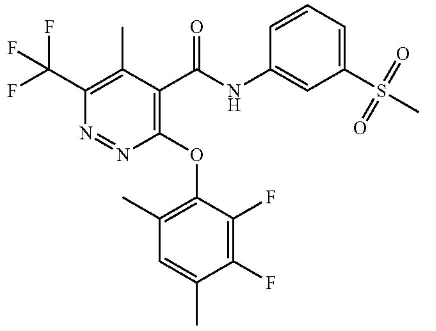 [SMILES: Cc1cc(C)c(Oc2nnc(C(F)(F)F)c(C)c2C(=O)Nc2cccc(S(C)(=O)=O)c2)c(F)c1F]
TABLE 14-continued
1014
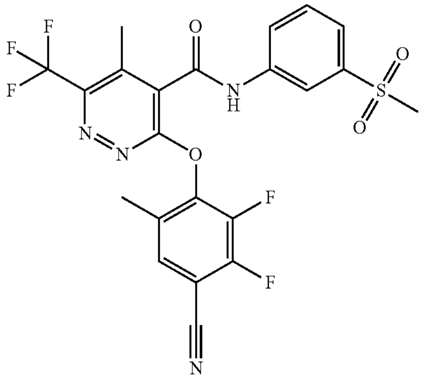 [SMILES: Cc1cc(C#N)c(F)c(F)c1Oc1nnc(C(F)(F)F)c(C)c1C(=O)Nc1cccc(S(C)(=O)=O)c1]
1015
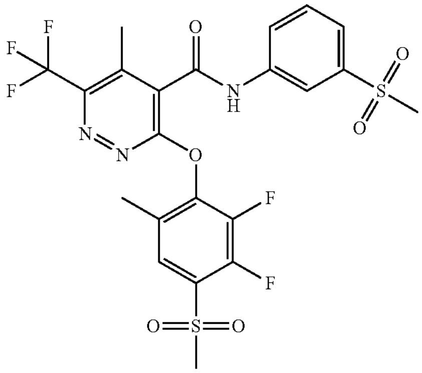
1016
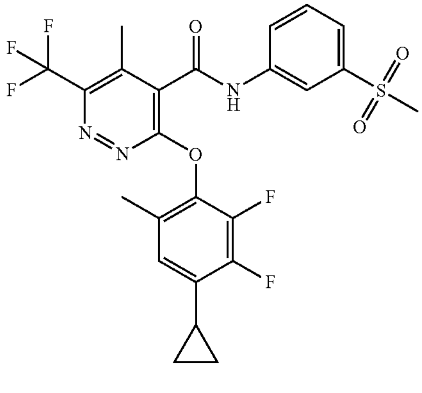
1017
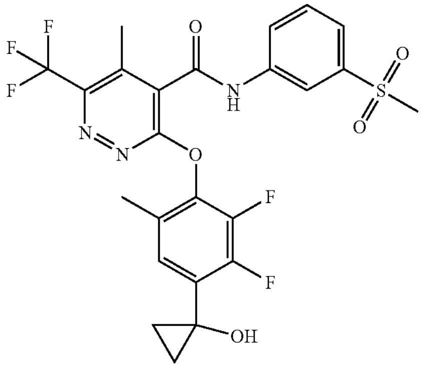 [SMILES: Cc1cc(C2(O)CC2)c(F)c(F)c1Oc1nnc(C(F)(F)F)c(C)c1C(=O)Nc1cccc(S(C)(=O)=O)c1]

TABLE 14-continued
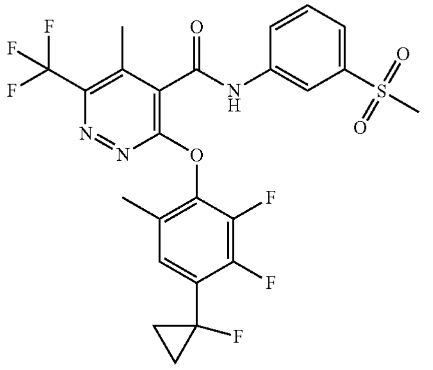 [SMILES: Cc1cc(C2(F)CC2)c(F)c(F)c1Oc1nnc(C(F)(F)F)c(C)c1C(=O)Nc1cccc(S(C)(=O)=O)c1]
1018
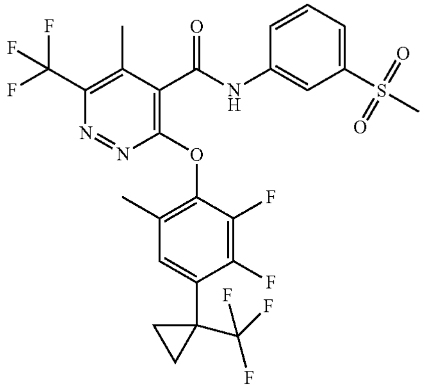 [SMILES: Cc1cc(C2(C(F)(F)F)CC2)c(F)c(F)c1Oc1nnc(C(F)(F)F)c(C)c1C(=O)Nc1cccc(S(C)(=O)=O)c1]
1019
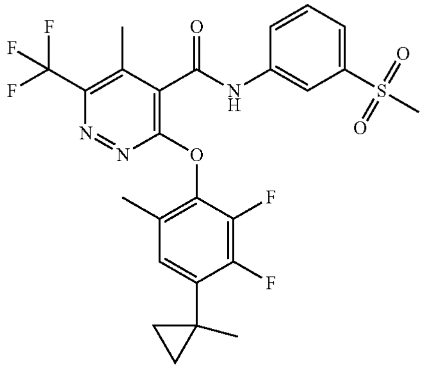 [SMILES: Cc1cc(C2(C)CC2)c(F)c(F)c1Oc1nnc(C(F)(F)F)c(C)c1C(=O)Nc1cccc(S(C)(=O)=O)c1]
1020
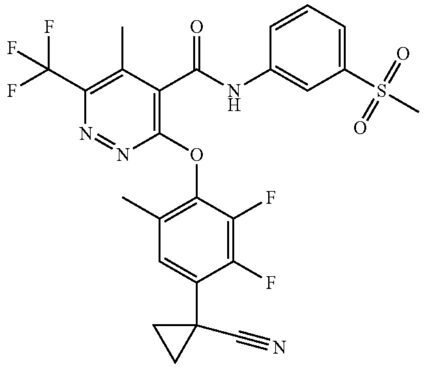 [SMILES: Cc1cc(C2(C#N)CC2)c(F)c(F)c1Oc1nnc(C(F)(F)F)c(C)c1C(=O)Nc1cccc(S(C)(=O)=O)c1]
1021
TABLE 14-continued
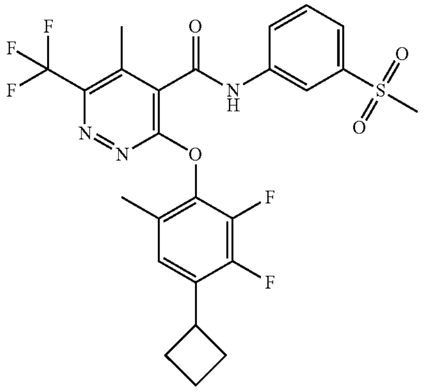
1022
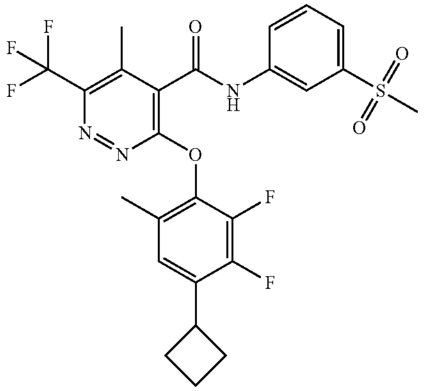
1023
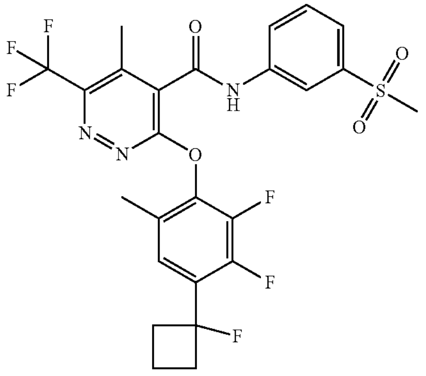 [SMILES: Cc1cc(C2(F)CCC2)c(F)c(F)c1Oc1nnc(C(F)(F)F)c(C)c1C(=O)Nc1cccc(S(C)(=O)=O)c1]
1024
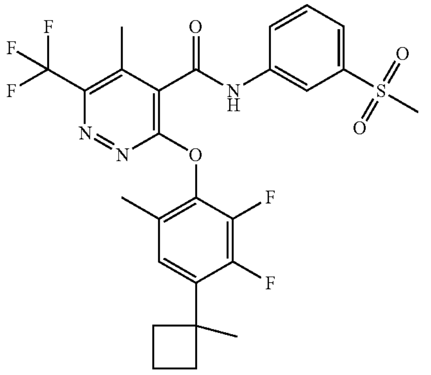 [SMILES: Cc1cc(C2(C)CCC2)c(F)c(F)c1Oc1nnc(C(F)(F)F)c(C)c1C(=O)Nc1cccc(S(C)(=O)=O)c1]
1025

TABLE 14-continued
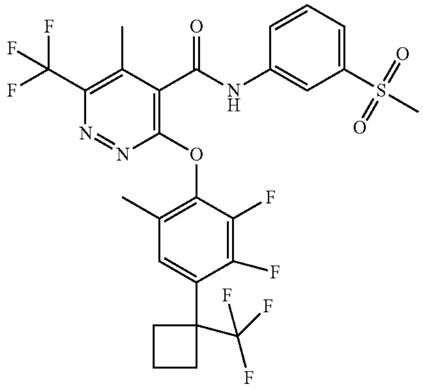 [SMILES: Cc1cc(C2(C(F)(F)F)CCC2)c(F)c(F)c1Oc1nnc(C(F)(F)F)c(C)c1C(=O)Nc1cccc(S(C)(=O)=O)c1]
1026
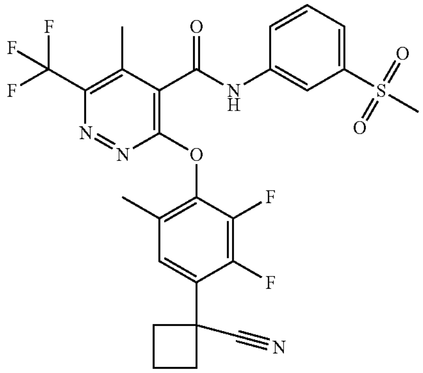 [SMILES: Cc1cc(C2(C#N)CCC2)c(F)c(F)c1Oc1nnc(C(F)(F)F)c(C)c1C(=O)Nc1cccc(S(C)(=O)=O)c1]
1027
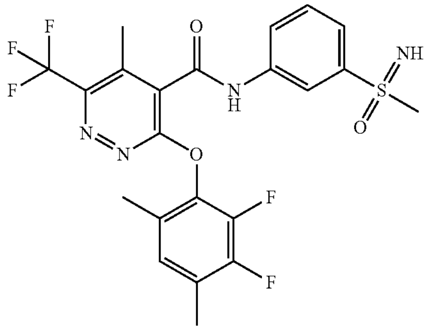 [SMILES: Cc1cc(C)c(Oc2nnc(C(F)(F)F)c(C)c2C(=O)Nc2cccc(S(C)(=N)=O)c2)c(F)c1F]
1028
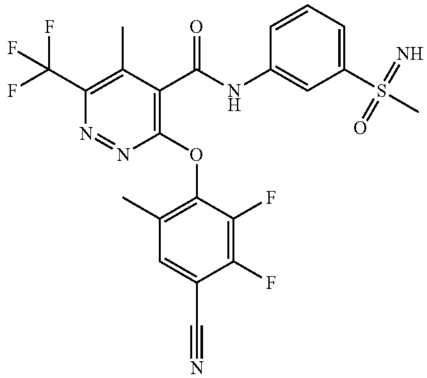 [SMILES: Cc1cc(C#N)c(F)c(F)c1Oc1nnc(C(F)(F)F)c(C)c1C(=O)Nc1cccc(S(C)(=N)=O)c1]
1029
TABLE 14-continued
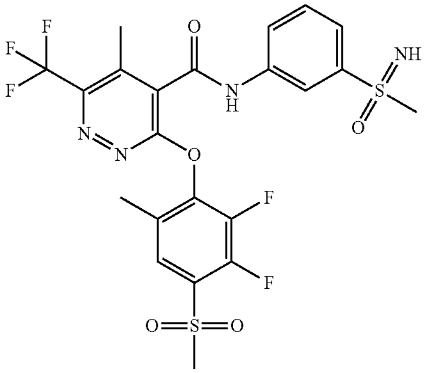 [SMILES: Cc1cc(S(C)(=O)=O)c(F)c(F)c1Oc1nnc(C(F)(F)F)c(C)c1C(=O)Nc1cccc(S(C)(=N)=O)c1]
1030
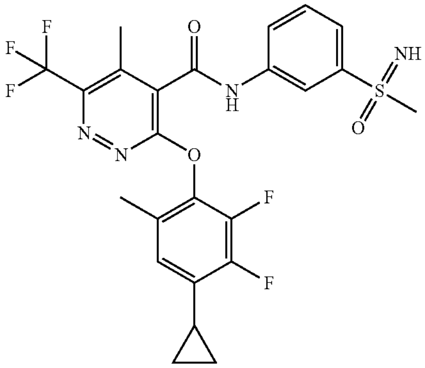 [SMILES: Cc1cc(C2CC2)c(F)c(F)c1Oc1nnc(C(F)(F)F)c(C)c1C(=O)Nc1cccc(S(C)(=N)=O)c1]
1031
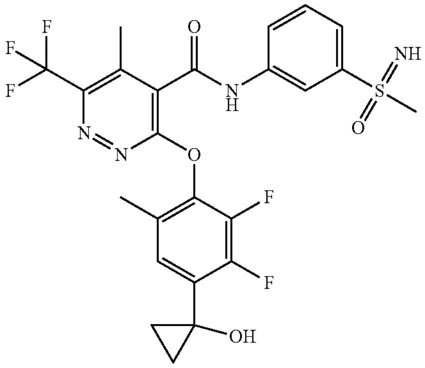 [SMILES: Cc1cc(C2(O)CC2)c(F)c(F)c1Oc1nnc(C(F)(F)F)c(C)c1C(=O)Nc1cccc(S(C)(=N)=O)c1]
1032
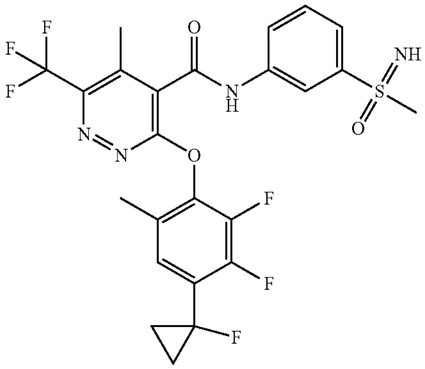 [SMILES: Cc1cc(C2(F)CC2)c(F)c(F)c1Oc1nnc(C(F)(F)F)c(C)c1C(=O)Nc1cccc(S(C)(=N)=O)c1]
1033

TABLE 14-continued
1034
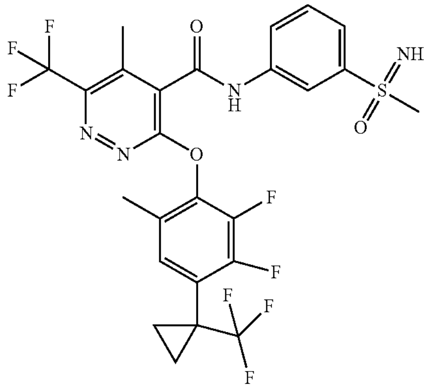 [SMILES: Cc1cc(C2(C(F)(F)F)CC2)c(F)c(F)c1Oc1nnc(C(F)(F)F)c(C)c1C(=O)Nc1cccc(S(C)(=N)=O)c1]
1035
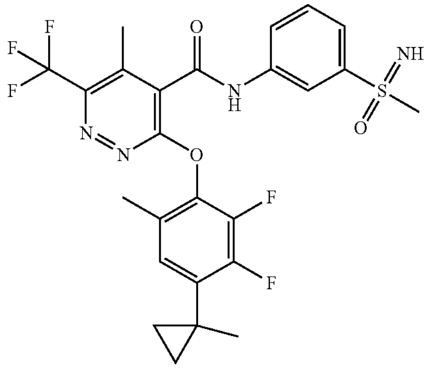 [SMILES: Cc1cc(C2(C)CC2)c(F)c(F)c1Oc1nnc(C(F)(F)F)c(C)c1C(=O)Nc1cccc(S(C)(=N)=O)c1]
1036
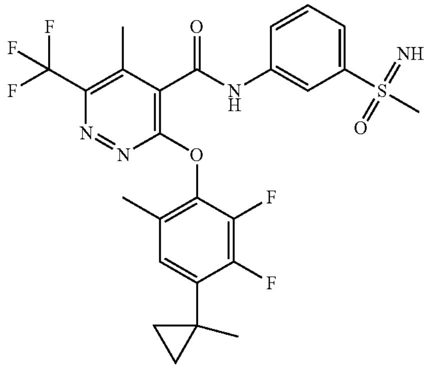 [SMILES: Cc1cc(C2(C)CC2)c(F)c(F)c1Oc1nnc(C(F)(F)F)c(C)c1C(=O)Nc1cccc(S(C)(=N)=O)c1]
1037
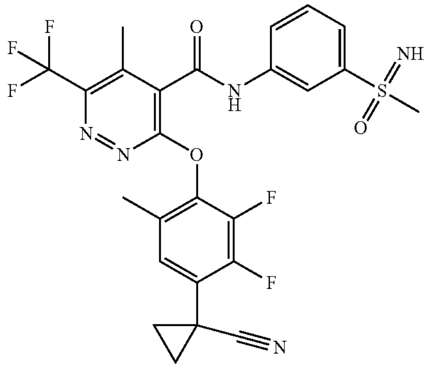 [SMILES: Cc1cc(C2(C#N)CC2)c(F)c(F)c1Oc1nnc(C(F)(F)F)c(C)c1C(=O)Nc1cccc(S(C)(=N)=O)c1]
TABLE 14-continued
1038
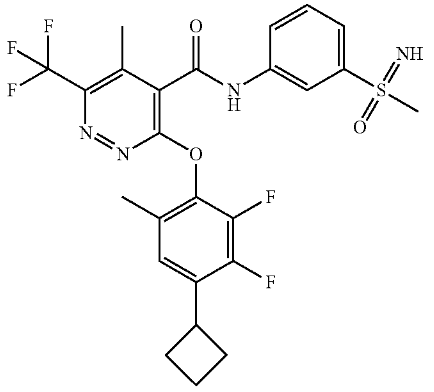 [SMILES: Cc1cc(C2CCC2)c(F)c(F)c1Oc1nnc(C(F)(F)F)c(C)c1C(=O)Nc1cccc(S(C)(=N)=O)c1]
1039
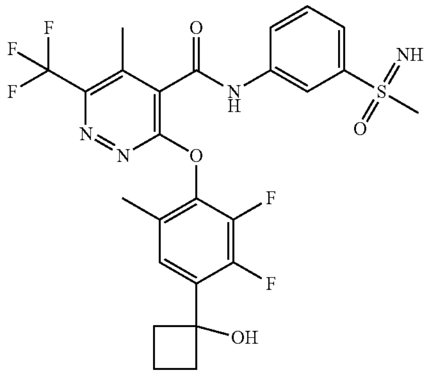 [SMILES: Cc1cc(C2(O)CCC2)c(F)c(F)c1Oc1nnc(C(F)(F)F)c(C)c1C(=O)Nc1cccc(S(C)(=N)=O)c1]
1040
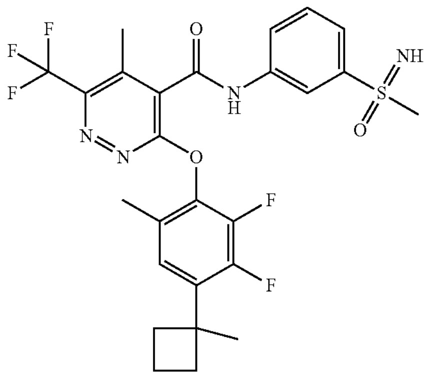 [SMILES: Cc1cc(C2(C)CCC2)c(F)c(F)c1Oc1nnc(C(F)(F)F)c(C)c1C(=O)Nc1cccc(S(C)(=N)=O)c1]
1041
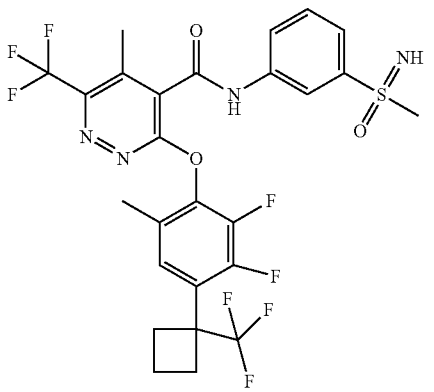 [SMILES: Cc1cc(C2(C(F)(F)F)CCC2)c(F)c(F)c1Oc1nnc(C(F)(F)F)c(C)c1C(=O)Nc1cccc(S(C)(=N)=O)c1]

TABLE 14-continued
1042
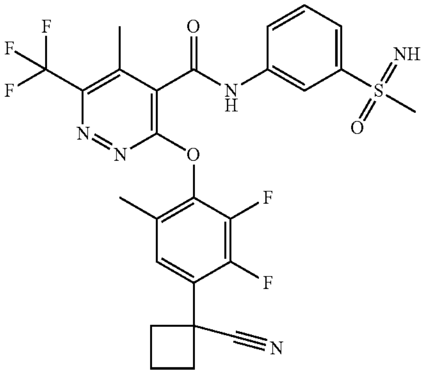 [SMILES: Cc1cc(C2(C#N)CCC2)c(F)c(F)c1Oc1nnc(C(F)(F)F)c(C)c1C(=O)Nc1cccc(S(C)(=N)=O)c1]
1043
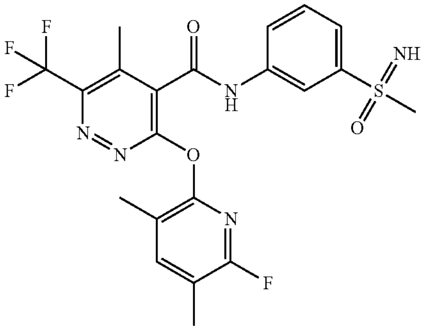 [SMILES: Cc1cc(C)c(Oc2nnc(C(F)(F)F)c(C)c2C(=O)Nc2cccc(S(C)(=N)=O)c2)nc1F]
1044
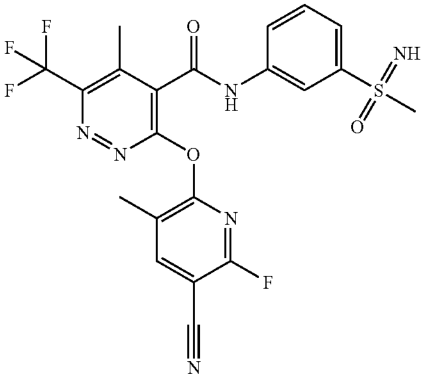 [SMILES: Cc1cc(C#N)c(F)nc1Oc1nnc(C(F)(F)F)c(C)c1C(=O)Nc1cccc(S(C)(=N)=O)c1]
1045
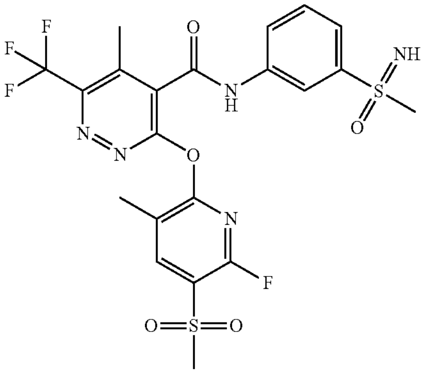 [SMILES: Cc1cc(S(C)(=O)=O)c(F)nc1Oc1nnc(C(F)(F)F)c(C)c1C(=O)Nc1cccc(S(C)(=N)=O)c1]
TABLE 14-continued
1046
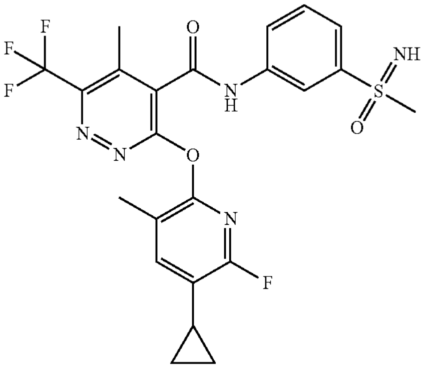 [SMILES: Cc1cc(C2CC2)c(F)nc1Oc1nnc(C(F)(F)F)c(C)c1C(=O)Nc1cccc(S(C)(=N)=O)c1]
1047
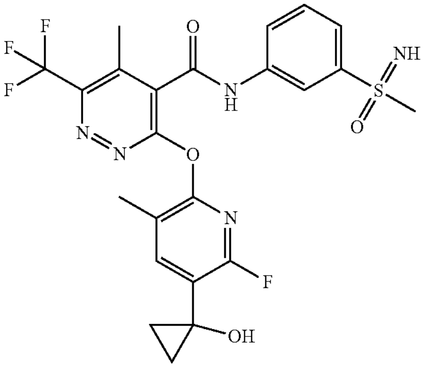 [SMILES: Cc1cc(C2(O)CC2)c(F)nc1Oc1nnc(C(F)(F)F)c(C)c1C(=O)Nc1cccc(S(C)(=N)=O)c1]
1048
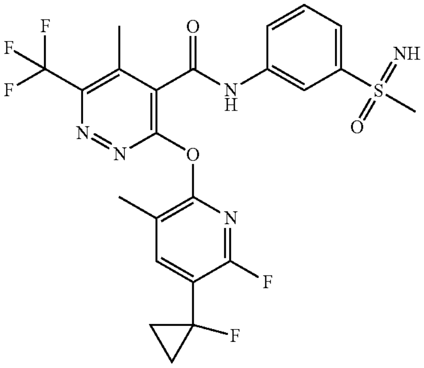 [SMILES: Cc1cc(C2(F)CC2)c(F)nc1Oc1nnc(C(F)(F)F)c(C)c1C(=O)Nc1cccc(S(C)(=N)=O)c1]
1049
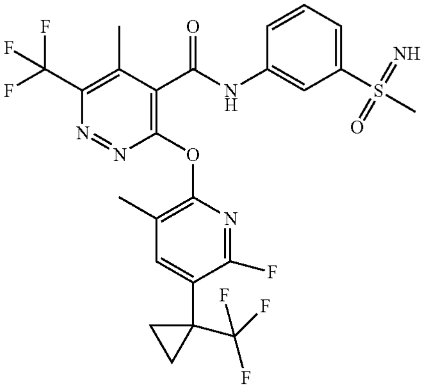 [SMILES: Cc1cc(C2(C(F)(F)F)CC2)c(F)nc1Oc1nnc(C(F)(F)F)c(C)c1C(=O)Nc1cccc(S(C)(=N)=O)c1]

TABLE 14-continued
1050
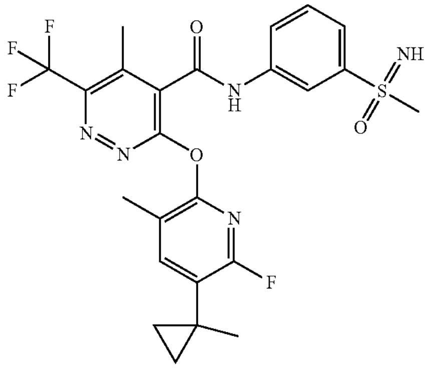 [SMILES: Cc1cc(C2(C)CC2)c(F)nc1Oc1nnc(C(F)(F)F)c(C)c1C(=O)Nc1cccc(S(C)(=N)=O)c1]
1051
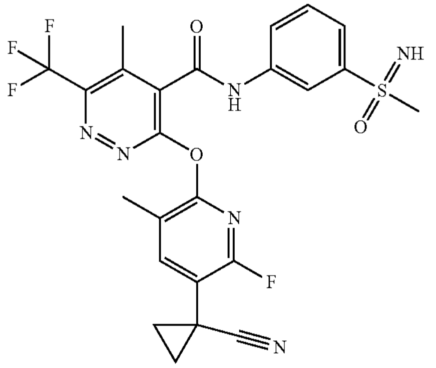 [SMILES: Cc1cc(C2(C#N)CC2)c(F)nc1Oc1nnc(C(F)(F)F)c(C)c1C(=O)Nc1cccc(S(C)(=N)=O)c1]
1052
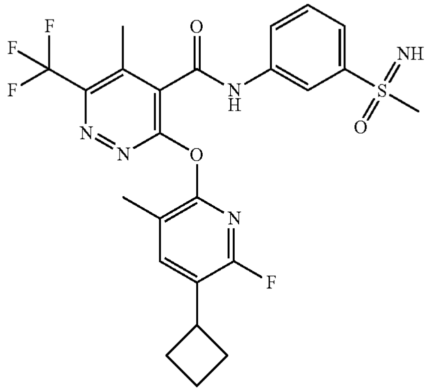 [SMILES: Cc1cc(C2CCC2)c(F)nc1Oc1nnc(C(F)(F)F)c(C)c1C(=O)Nc1cccc(S(C)(=N)=O)c1]
1053
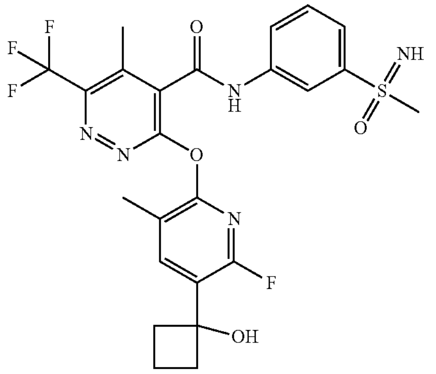 [SMILES: Cc1cc(C2(O)CCC2)c(F)nc1Oc1nnc(C(F)(F)F)c(C)c1C(=O)Nc1cccc(S(C)(=N)=O)c1]
TABLE 14-continued
1054
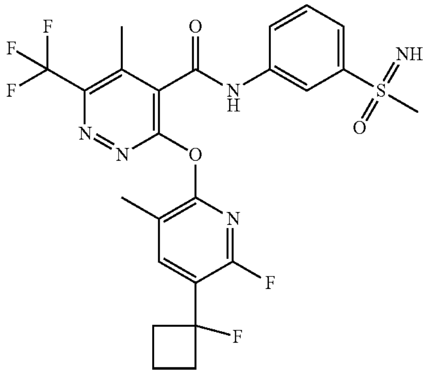 [SMILES: Cc1cc(C2(F)CCC2)c(F)nc1Oc1nnc(C(F)(F)F)c(C)c1C(=O)Nc1cccc(S(C)(=N)=O)c1]
1055
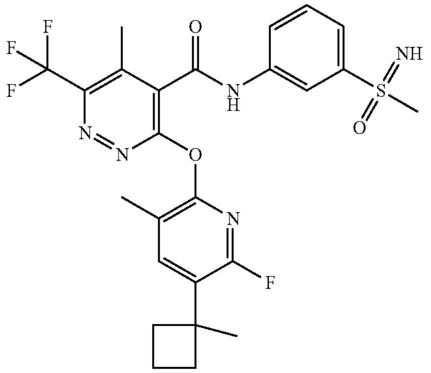 [SMILES: Cc1cc(C2(C)CCC2)c(F)nc1Oc1nnc(C(F)(F)F)c(C)c1C(=O)Nc1cccc(S(C)(=N)=O)c1]
1056
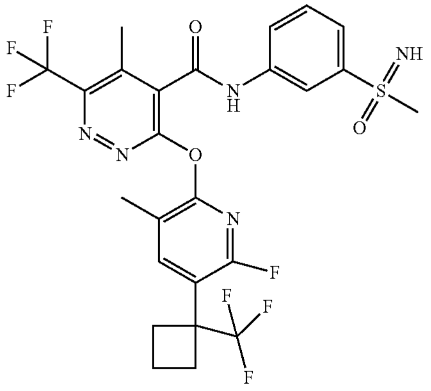 [SMILES: Cc1cc(C2(C(F)(F)F)CCC2)c(F)nc1Oc1nnc(C(F)(F)F)c(C)c1C(=O)Nc1cccc(S(C)(=N)=O)c1]
1057
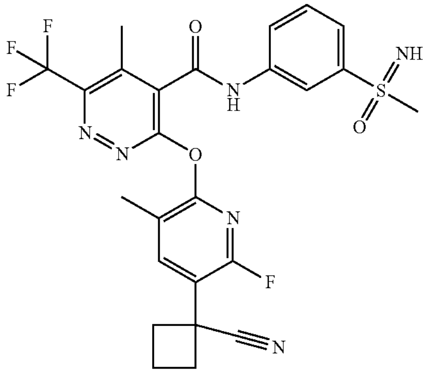 [SMILES: Cc1cc(C2(C#N)CCC2)c(F)nc1Oc1nnc(C(F)(F)F)c(C)c1C(=O)Nc1cccc(S(C)(=N)=O)c1]

TABLE 14-continued
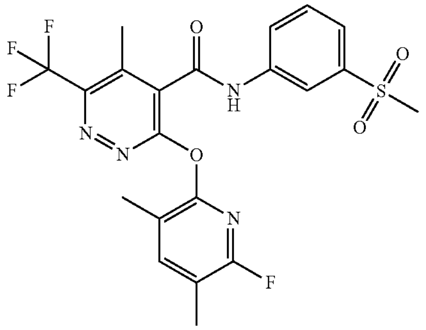 [SMILES: Cc1cc(C)c(Oc2nnc(C(F)(F)F)c(C)c2C(=O)Nc2cccc(S(C)(=O)=O)c2)nc1F]
1058
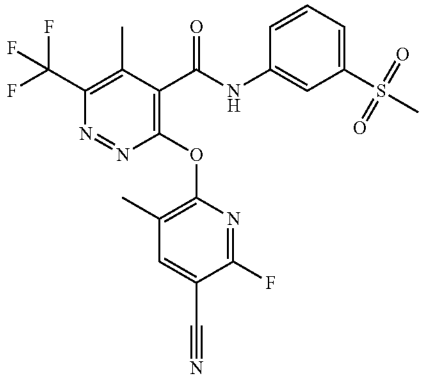 [SMILES: Cc1cc(C#N)c(F)nc1Oc1nnc(C(F)(F)F)c(C)c1C(=O)Nc1cccc(S(C)(=O)=O)c1]
1059
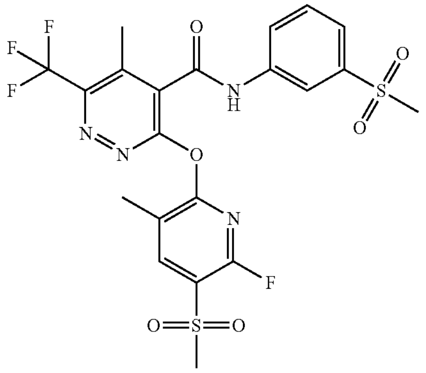
1060
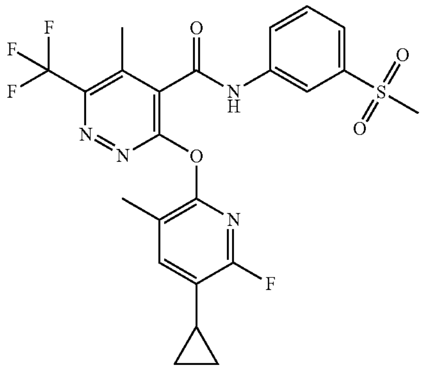 [SMILES: Cc1cc(C2CC2)c(F)nc1Oc1nnc(C(F)(F)F)c(C)c1C(=O)Nc1cccc(S(C)(=O)=O)c1]
1061
TABLE 14-continued
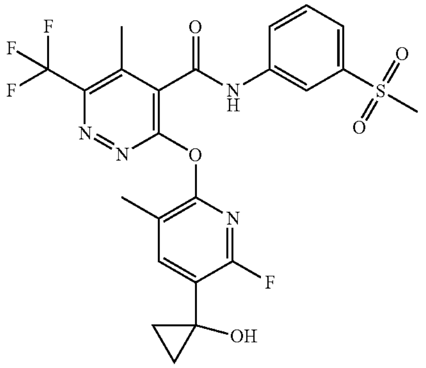 [SMILES: Cc1cc(C2(O)CC2)c(F)nc1Oc1nnc(C(F)(F)F)c(C)c1C(=O)Nc1cccc(S(C)(=O)=O)c1]
1062
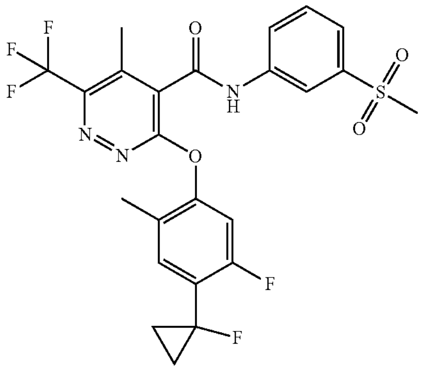 [SMILES: Cc1cc(C2(F)CC2)c(F)cc1Oc1nnc(C(F)(F)F)c(C)c1C(=O)Nc1cccc(S(C)(=O)=O)c1]
1063
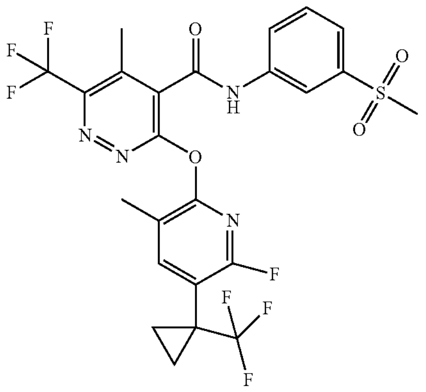 [SMILES: Cc1cc(C2(C(F)(F)F)CC2)c(F)nc1Oc1nnc(C(F)(F)F)c(C)c1C(=O)Nc1cccc(S(C)(=O)=O)c1]
1064
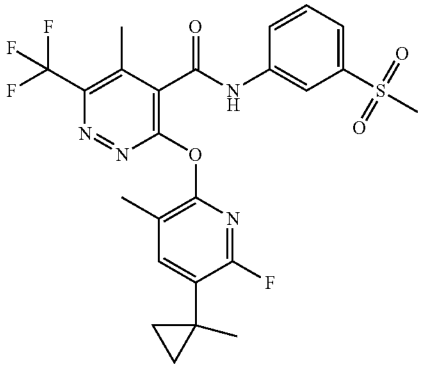 [SMILES: Cc1cc(C2(C)CC2)c(F)nc1Oc1nnc(C(F)(F)F)c(C)c1C(=O)Nc1cccc(S(C)(=O)=O)c1]
1065

TABLE 14-continued
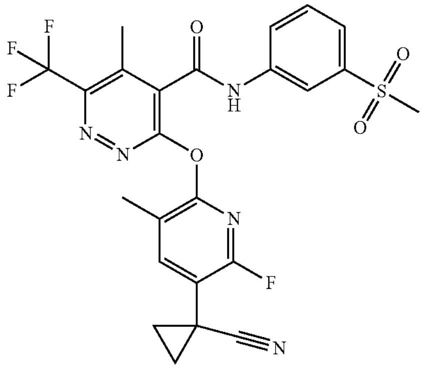 [SMILES: Cc1cc(C2(C#N)CC2)c(F)nc1Oc1nnc(C(F)(F)F)c(C)c1C(=O)Nc1cccc(S(C)(=O)=O)c1]
1066
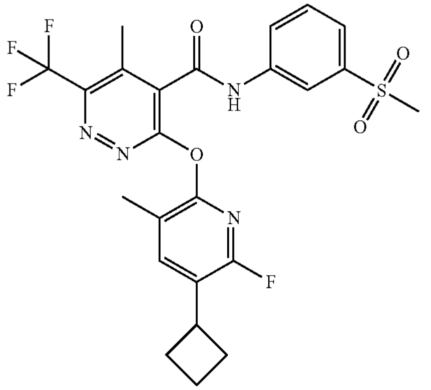 [SMILES: Cc1cc(C2CCC2)c(F)nc1Oc1nnc(C(F)(F)F)c(C)c1C(=O)Nc1cccc(S(C)(=O)=O)c1]
1067
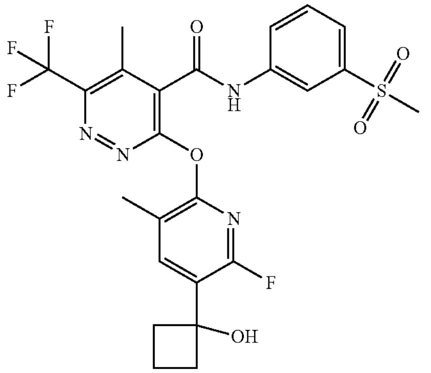 [SMILES: Cc1cc(C2(O)CCC2)c(F)nc1Oc1nnc(C(F)(F)F)c(C)c1C(=O)Nc1cccc(S(C)(=O)=O)c1]
1068
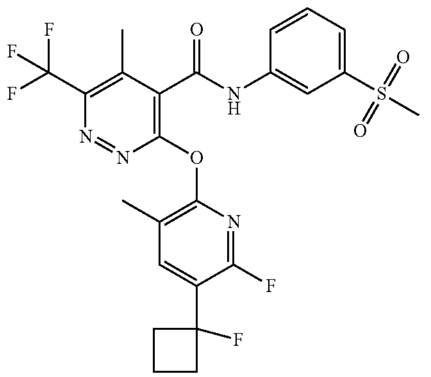 [SMILES: Cc1cc(C2(F)CCC2)c(F)nc1Oc1nnc(C(F)(F)F)c(C)c1C(=O)Nc1cccc(S(C)(=O)=O)c1]
1069
TABLE 14-continued
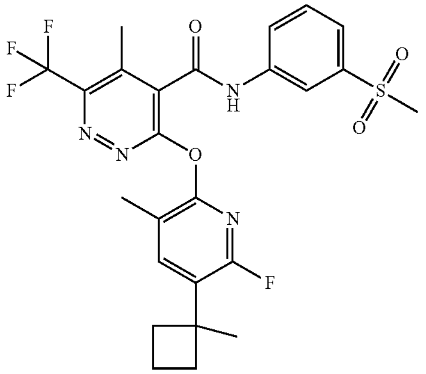 [SMILES: Cc1cc(C2(C)CCC2)c(F)nc1Oc1nnc(C(F)(F)F)c(C)c1C(=O)Nc1cccc(S(C)(=O)=O)c1]
1070
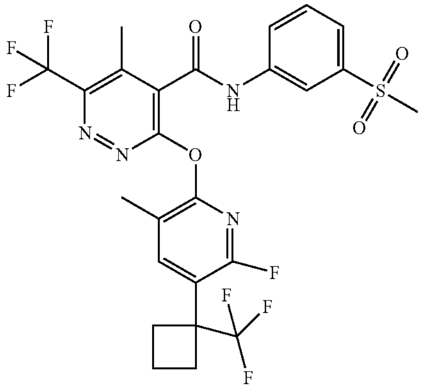 [SMILES: Cc1cc(C2(C(F)(F)F)CCC2)c(F)nc1Oc1nnc(C(F)(F)F)c(C)c1C(=O)Nc1cccc(S(C)(=O)=O)c1]
1071
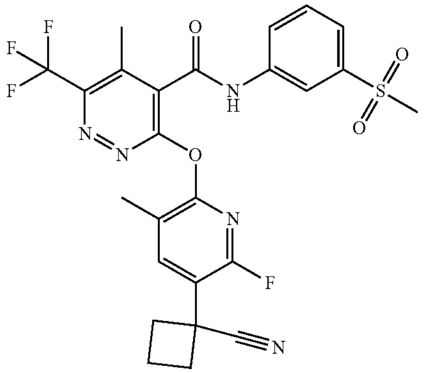 [SMILES: Cc1cc(C2(C#N)CCC2)c(F)nc1Oc1nnc(C(F)(F)F)c(C)c1C(=O)Nc1cccc(S(C)(=O)=O)c1]
1072
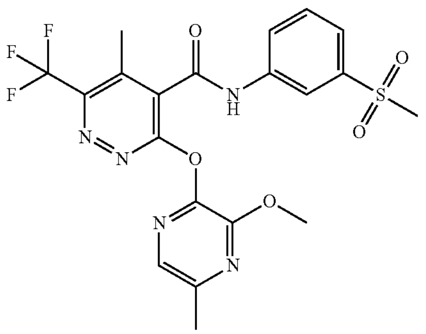 [SMILES: COc1nc(C)cnc1Oc1nnc(C(F)(F)F)c(C)c1C(=O)Nc1cccc(S(C)(=O)=O)c1]
1073

TABLE 14-continued
1074
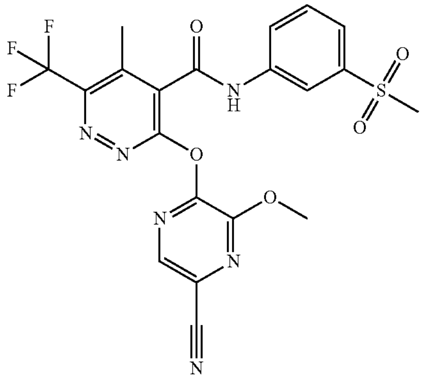 [SMILES: COc1nc(C#N)cnc1Oc1nnc(C(F)(F)F)c(C)c1C(=O)Nc1cccc(S(C)(=O)=O)c1]
1075
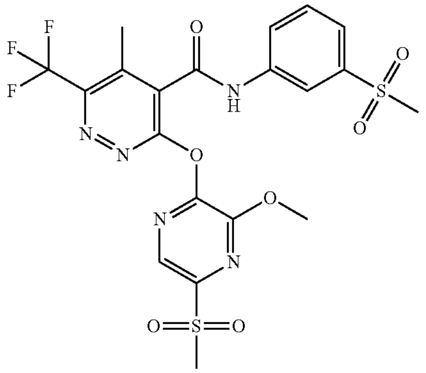
1076
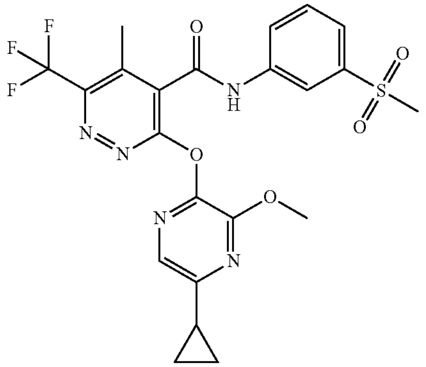 [SMILES: COc1nc(C2CC2)cnc1Oc1nnc(C(F)(F)F)c(C)c1C(=O)Nc1cccc(S(C)(=O)=O)c1]
1077
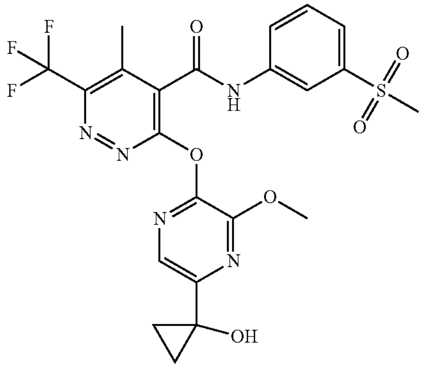 [SMILES: COc1nc(C2(O)CC2)cnc1Oc1nnc(C(F)(F)F)c(C)c1C(=O)Nc1cccc(S(C)(=O)=O)c1]
TABLE 14-continued
1078
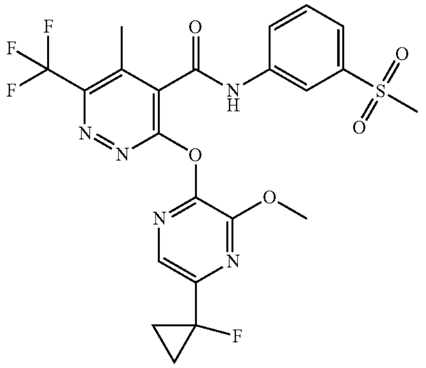 [SMILES: COc1nc(C2(F)CC2)cnc1Oc1nnc(C(F)(F)F)c(C)c1C(=O)Nc1cccc(S(C)(=O)=O)c1]
1079
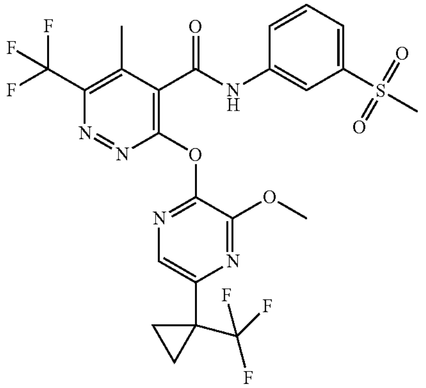 [SMILES: COc1nc(C2(C(F)(F)F)CC2)cnc1Oc1nnc(C(F)(F)F)c(C)c1C(=O)Nc1cccc(S(C)(=O)=O)c1]
1080
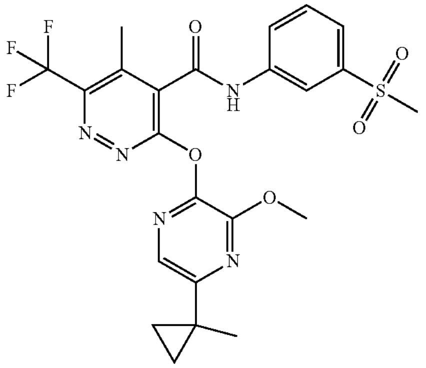 [SMILES: COc1nc(C2(C)CC2)cnc1Oc1nnc(C(F)(F)F)c(C)c1C(=O)Nc1cccc(S(C)(=O)=O)c1]
1081
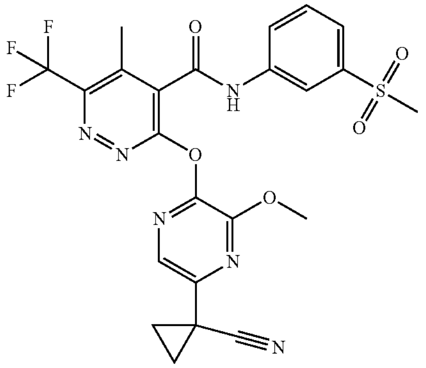 [SMILES: COc1nc(C2(C#N)CC2)cnc1Oc1nnc(C(F)(F)F)c(C)c1C(=O)Nc1cccc(S(C)(=O)=O)c1]

1082
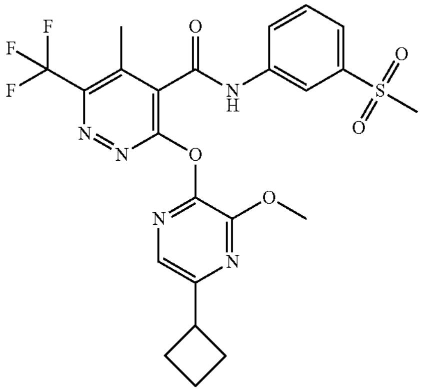 [SMILES: COc1nc(C2CCC2)cnc1Oc1nnc(C(F)(F)F)c(C)c1C(=O)Nc1cccc(S(C)(=O)=O)c1]
1083
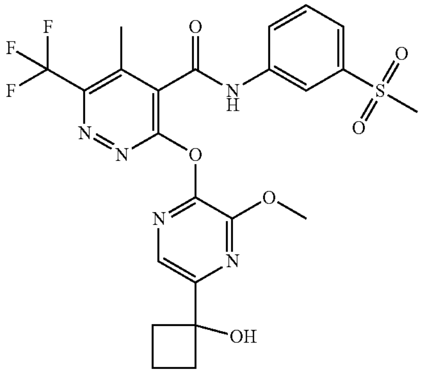 [SMILES: COc1nc(C2(O)CCC2)cnc1Oc1nnc(C(F)(F)F)c(C)c1C(=O)Nc1cccc(S(C)(=O)=O)c1]
1084
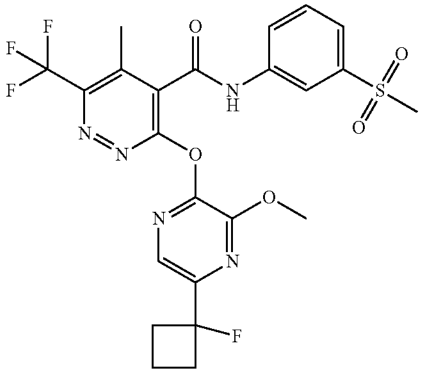 [SMILES: COc1nc(C2(F)CCC2)cnc1Oc1nnc(C(F)(F)F)c(C)c1C(=O)Nc1cccc(S(C)(=O)=O)c1]
1085
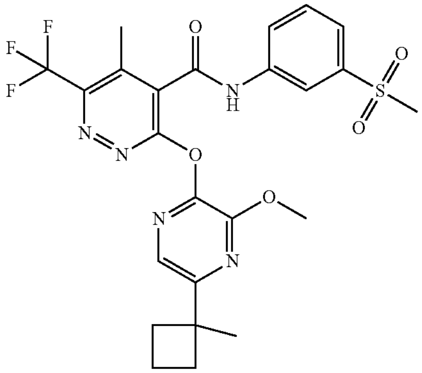 [SMILES: COc1nc(C2(C)CCC2)cnc1Oc1nnc(C(F)(F)F)c(C)c1C(=O)Nc1cccc(S(C)(=O)=O)c1]
1086
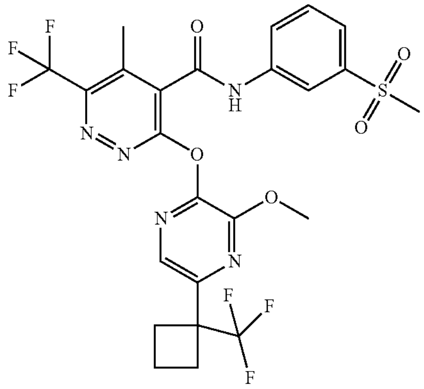 [SMILES: COc1nc(C2(C(F)(F)F)CCC2)cnc1Oc1nnc(C(F)(F)F)c(C)c1C(=O)Nc1cccc(S(C)(=O)=O)c1]
1087
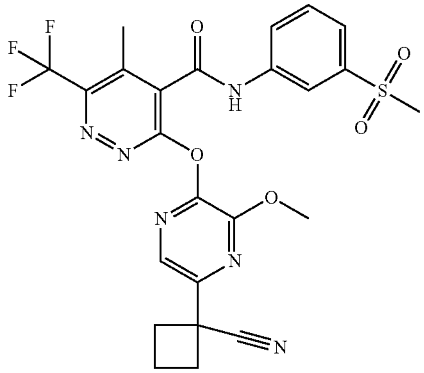 [SMILES: COc1nc(C2(C#N)CCC2)cnc1Oc1nnc(C(F)(F)F)c(C)c1C(=O)Nc1cccc(S(C)(=O)=O)c1]
1088
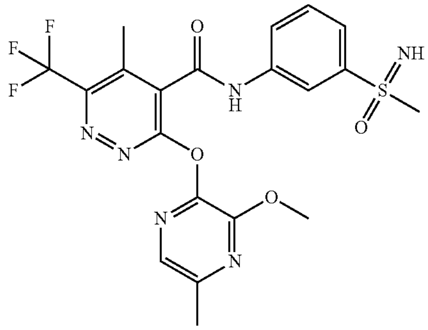 [SMILES: COc1nc(C)cnc1Oc1nnc(C(F)(F)F)c(C)c1C(=O)Nc1cccc(S(C)(=N)=O)c1]
1089
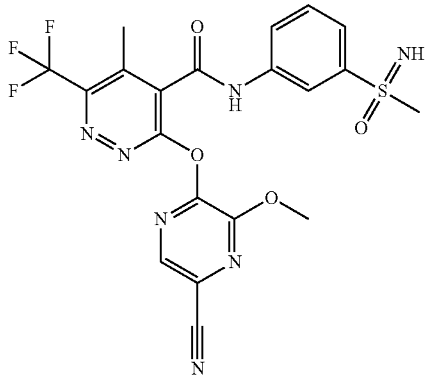

TABLE 14-continued
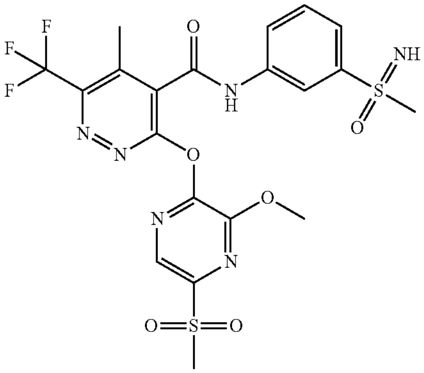 [SMILES: COc1nc(S(C)(=O)=O)cnc1Oc1nnc(C(F)(F)F)c(C)c1C(=O)Nc1cccc(S(C)(=N)=O)c1]
1090
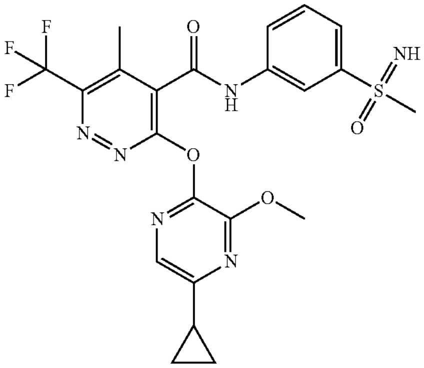 [SMILES: COc1nc(C2CC2)cnc1Oc1nnc(C(F)(F)F)c(C)c1C(=O)Nc1cccc(S(C)(=N)=O)c1]
1091
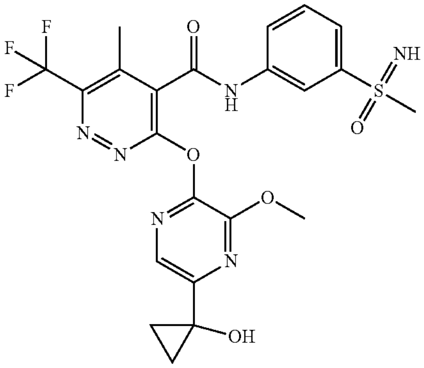 [SMILES: COc1nc(C2(O)CC2)cnc1Oc1nnc(C(F)(F)F)c(C)c1C(=O)Nc1cccc(S(C)(=N)=O)c1]
1092
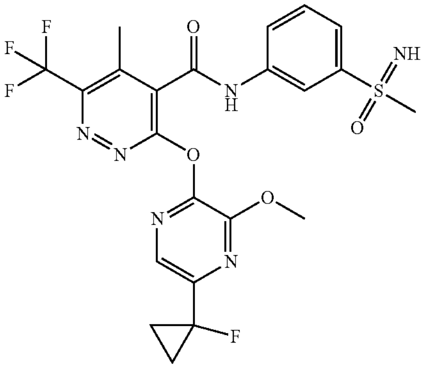 [SMILES: COc1nc(C2(F)CC2)cnc1Oc1nnc(C(F)(F)F)c(C)c1C(=O)Nc1cccc(S(C)(=N)=O)c1]
1093
TABLE 14-continued
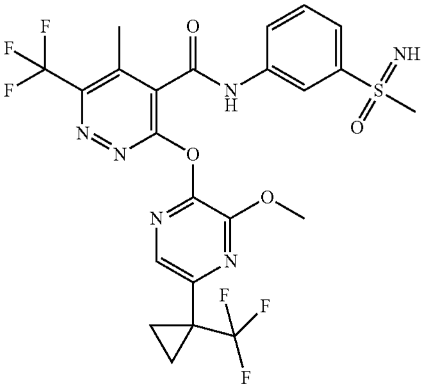 [SMILES: COc1nc(C2(C(F)(F)F)CC2)cnc1Oc1nnc(C(F)(F)F)c(C)c1C(=O)Nc1cccc(S(C)(=N)=O)c1]
1094
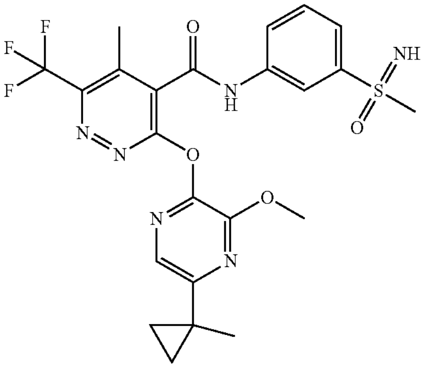 [SMILES: COc1nc(C2(C)CC2)cnc1Oc1nnc(C(F)(F)F)c(C)c1C(=O)Nc1cccc(S(C)(=N)=O)c1]
1095
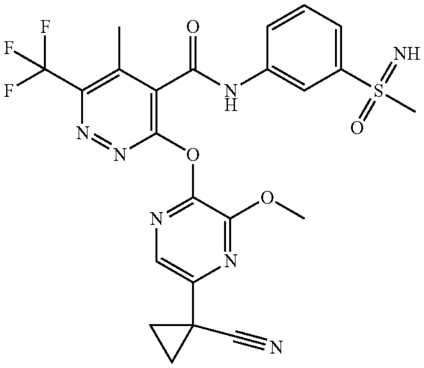 [SMILES: COc1nc(C2(C#N)CC2)cnc1Oc1nnc(C(F)(F)F)c(C)c1C(=O)Nc1cccc(S(C)(=N)=O)c1]
1096
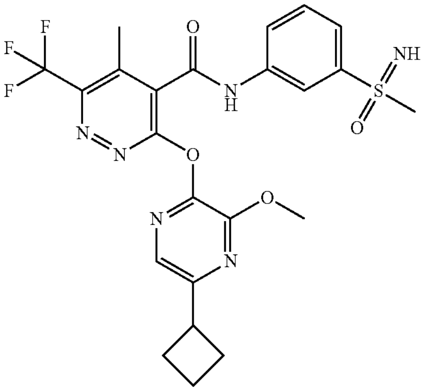 [SMILES: COc1nc(C2CCC2)cnc1Oc1nnc(C(F)(F)F)c(C)c1C(=O)Nc1cccc(S(C)(=N)=O)c1]
1097

TABLE 14-continued
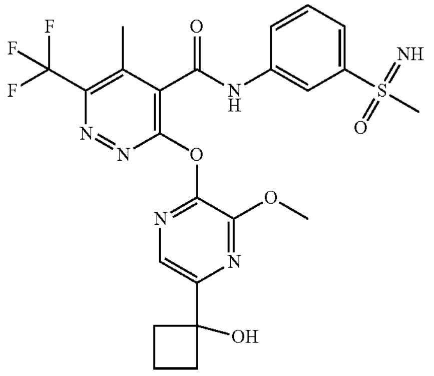 [SMILES: COc1nc(C2(O)CCC2)cnc1Oc1nnc(C(F)(F)F)c(C)c1C(=O)Nc1cccc(S(C)(=N)=O)c1]
1098
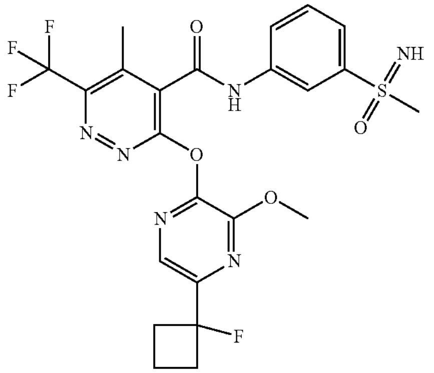 [SMILES: COc1nc(C2(F)CCC2)cnc1Oc1nnc(C(F)(F)F)c(C)c1C(=O)Nc1cccc(S(C)(=N)=O)c1]
1099
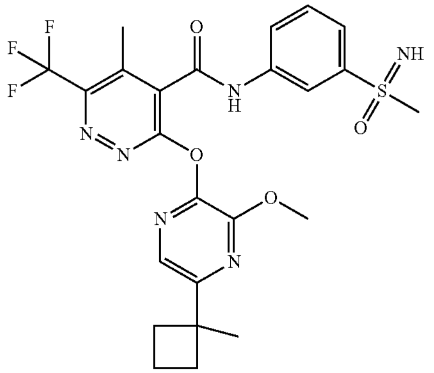 [SMILES: COc1nc(C2(C)CCC2)cnc1Oc1nnc(C(F)(F)F)c(C)c1C(=O)Nc1cccc(S(C)(=N)=O)c1]
1100
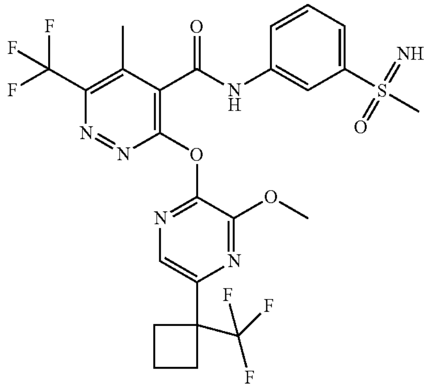 [SMILES: COc1nc(C2(C(F)(F)F)CCC2)cnc1Oc1nnc(C(F)(F)F)c(C)c1C(=O)Nc1cccc(S(C)(=N)=O)c1]
1101
TABLE 14-continued
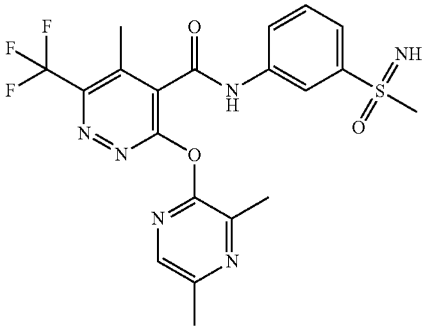 [SMILES: Cc1cnc(Oc2nnc(C(F)(F)F)c(C)c2C(=O)Nc2cccc(S(C)(=N)=O)c2)c(C)n1]
1102
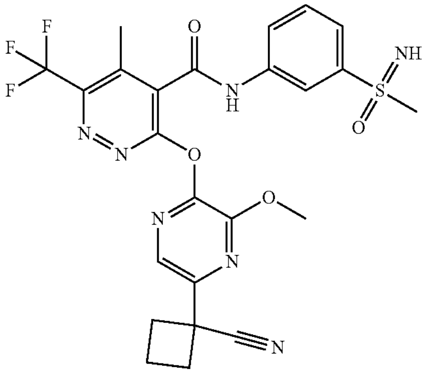 [SMILES: COc1nc(C2(C#N)CCC2)cnc1Oc1nnc(C(F)(F)F)c(C)c1C(=O)Nc1cccc(S(C)(=N)=O)c1]
1103
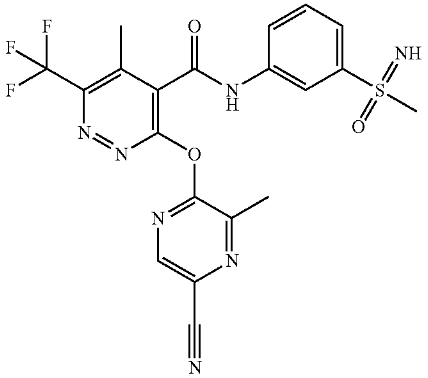 [SMILES: Cc1nc(C#N)cnc1Oc1nnc(C(F)(F)F)c(C)c1C(=O)Nc1cccc(S(C)(=N)=O)c1]
1004
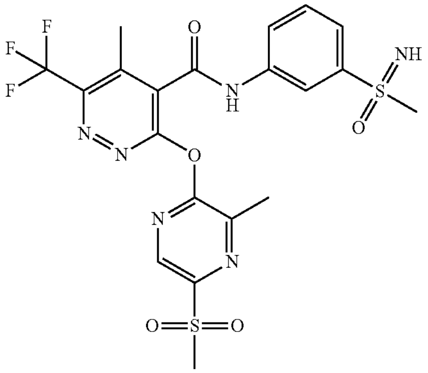
1105

TABLE 14-continued
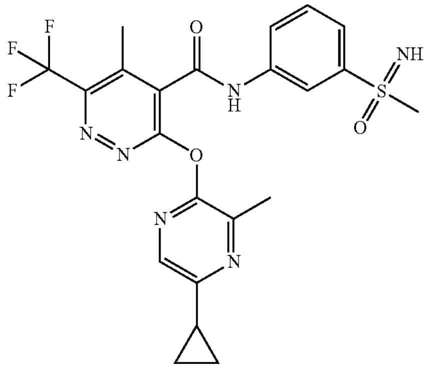 [SMILES: Cc1nc(C2CC2)cnc1Oc1nnc(C(F)(F)F)c(C)c1C(=O)Nc1cccc(S(C)(=N)=O)c1]
1106
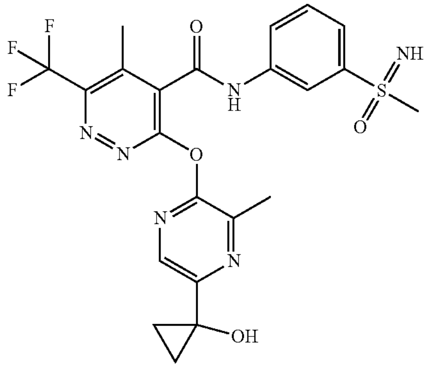 [SMILES: Cc1nc(C2(O)CC2)cnc1Oc1nnc(C(F)(F)F)c(C)c1C(=O)Nc1cccc(S(C)(=N)=O)c1]
1107
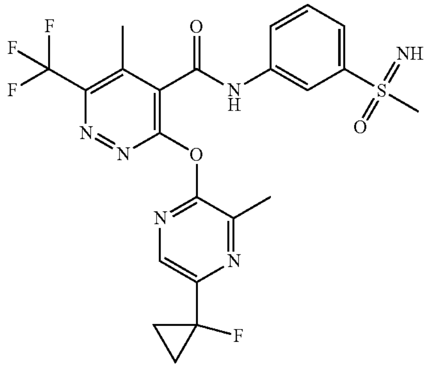 [SMILES: Cc1nc(C2(F)CC2)cnc1Oc1nnc(C(F)(F)F)c(C)c1C(=O)Nc1cccc(S(C)(=N)=O)c1]
1108
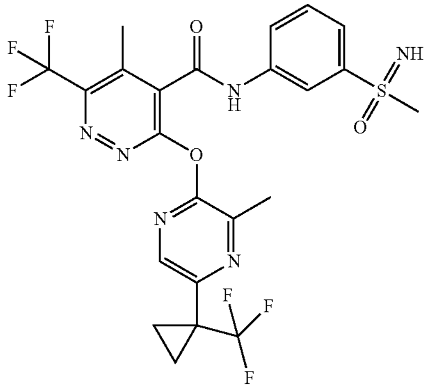 [SMILES: Cc1nc(C2(C(F)(F)F)CC2)cnc1Oc1nnc(C(F)(F)F)c(C)c1C(=O)Nc1cccc(S(C)(=N)=O)c1]
1109
TABLE 14-continued
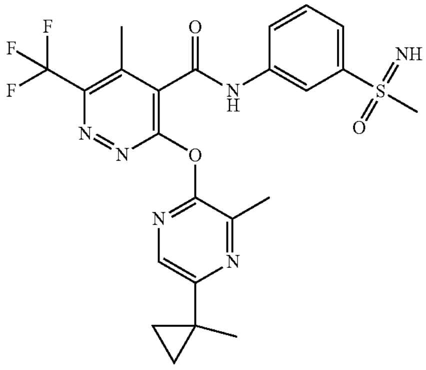 [SMILES: Cc1nc(C2(C)CC2)cnc1Oc1nnc(C(F)(F)F)c(C)c1C(=O)Nc1cccc(S(C)(=N)=O)c1]
1110
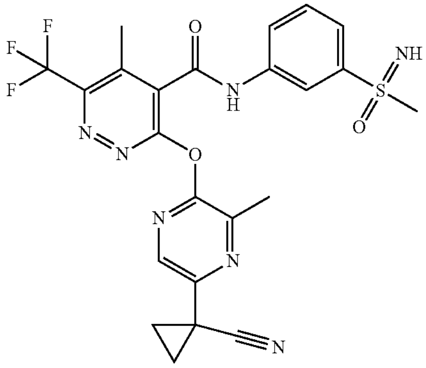 [SMILES: Cc1nc(C2(C#N)CC2)cnc1Oc1nnc(C(F)(F)F)c(C)c1C(=O)Nc1cccc(S(C)(=N)=O)c1]
1111
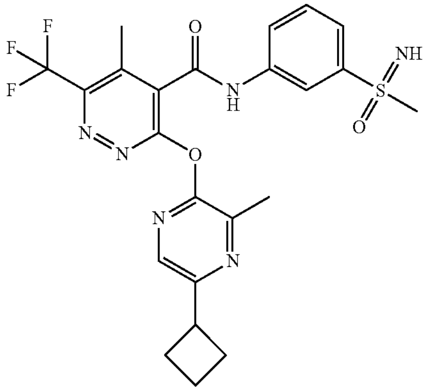 [SMILES: Cc1nc(C2CCC2)cnc1Oc1nnc(C(F)(F)F)c(C)c1C(=O)Nc1cccc(S(C)(=N)=O)c1]
1112
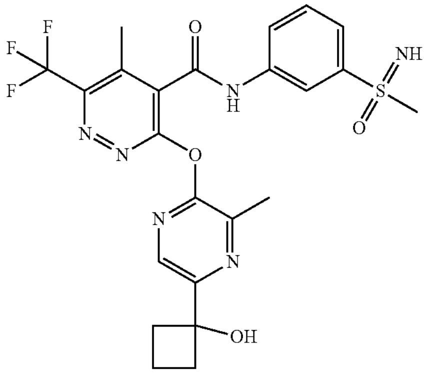 [SMILES: Cc1nc(C2(O)CCC2)cnc1Oc1nnc(C(F)(F)F)c(C)c1C(=O)Nc1cccc(S(C)(=N)=O)c1]
1113

TABLE 14-continued
1114
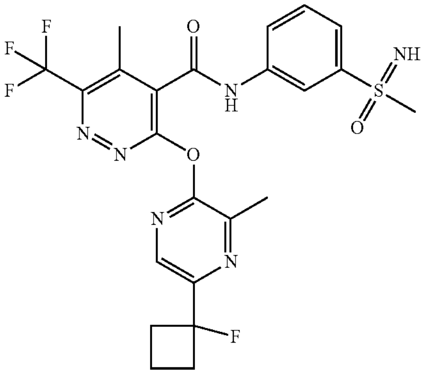 [SMILES: Cc1nc(C2(F)CCC2)cnc1Oc1nnc(C(F)(F)F)c(C)c1C(=O)Nc1cccc(S(C)(=N)=O)c1]
1115
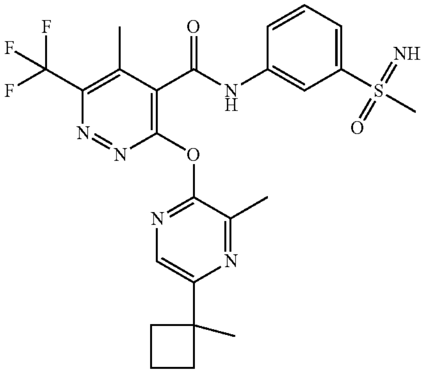 [SMILES: Cc1nc(C2(C)CCC2)cnc1Oc1nnc(C(F)(F)F)c(C)c1C(=O)Nc1cccc(S(C)(=N)=O)c1]
1116
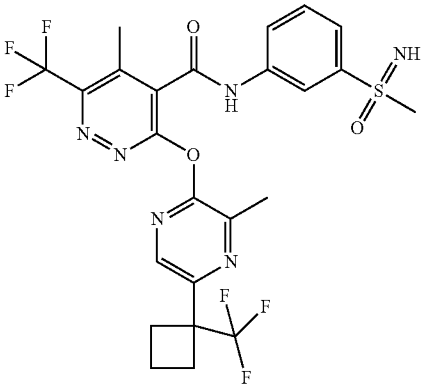 [SMILES: Cc1nc(C2(C(F)(F)F)CCC2)cnc1Oc1nnc(C(F)(F)F)c(C)c1C(=O)Nc1cccc(S(C)(=N)=O)c1]
1117
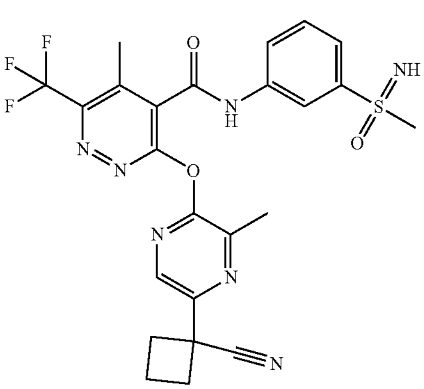 [SMILES: Cc1nc(C2(C#N)CCC2)cnc1Oc1nnc(C(F)(F)F)c(C)c1C(=O)Nc1cccc(S(C)(=N)=O)c1]
TABLE 14-continued
1118
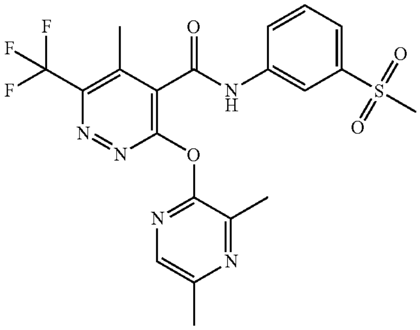 [SMILES: Cc1cnc(Oc2nnc(C(F)(F)F)c(C)c2C(=O)Nc2cccc(S(C)(=O)=O)c2)c(C)n1]
1119
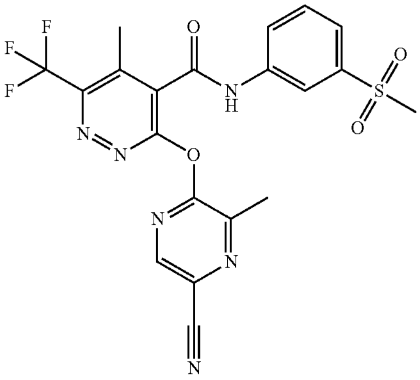
1120
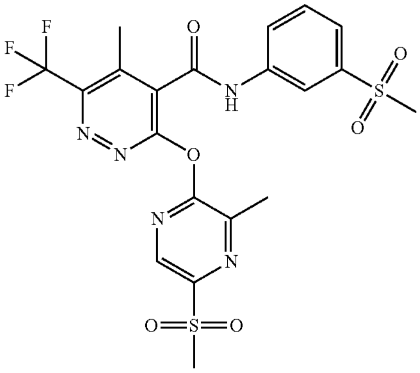
1121
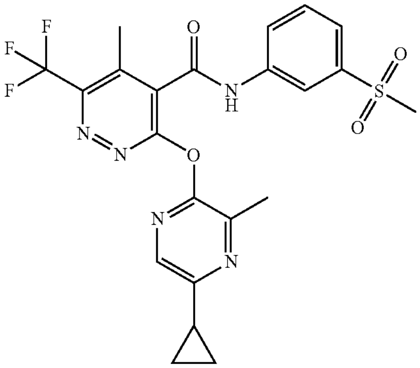 [SMILES: Cc1nc(C2CC2)cnc1Oc1nnc(C(F)(F)F)c(C)c1C(=O)Nc1cccc(S(C)(=O)=O)c1]

TABLE 14-continued
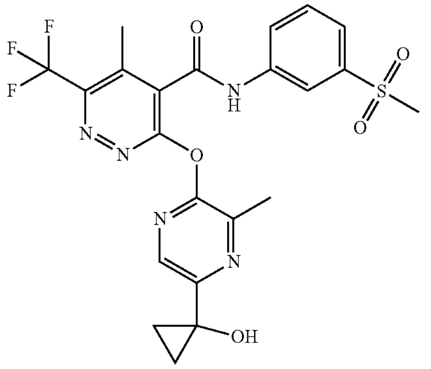 [SMILES: Cc1nc(C2(O)CC2)cnc1Oc1nnc(C(F)(F)F)c(C)c1C(=O)Nc1cccc(S(C)(=O)=O)c1]
1122
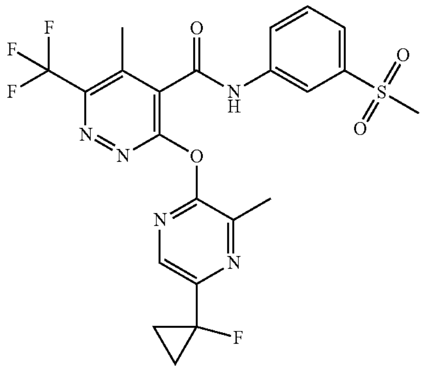 [SMILES: Cc1nc(C2(F)CC2)cnc1Oc1nnc(C(F)(F)F)c(C)c1C(=O)Nc1cccc(S(C)(=O)=O)c1]
1123
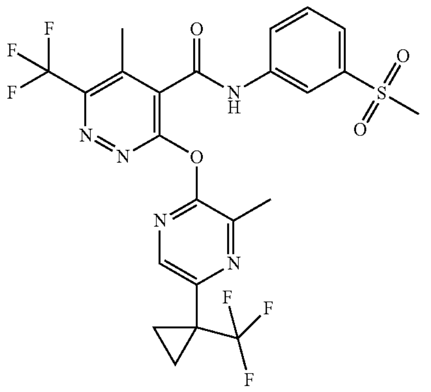 [SMILES: Cc1nc(C2(C(F)(F)F)CC2)cnc1Oc1nnc(C(F)(F)F)c(C)c1C(=O)Nc1cccc(S(C)(=O)=O)c1]
1124
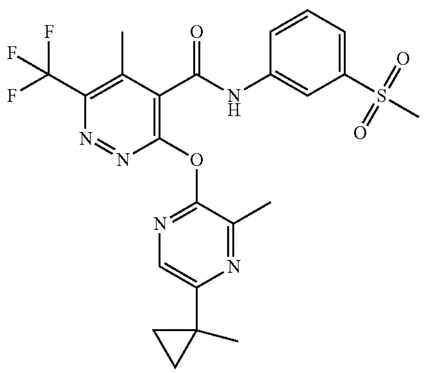 [SMILES: Cc1nc(C2(C)CC2)cnc1Oc1nnc(C(F)(F)F)c(C)c1C(=O)Nc1cccc(S(C)(=O)=O)c1]
1125
TABLE 14-continued
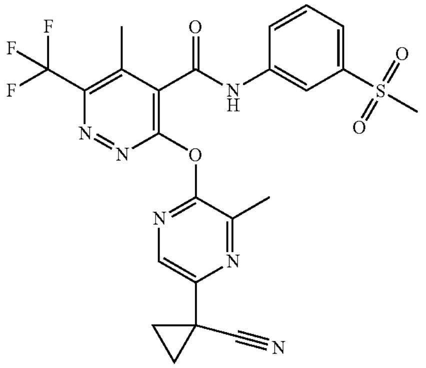 [SMILES: Cc1nc(C2(C#N)CC2)cnc1Oc1nnc(C(F)(F)F)c(C)c1C(=O)Nc1cccc(S(C)(=O)=O)c1]
1126
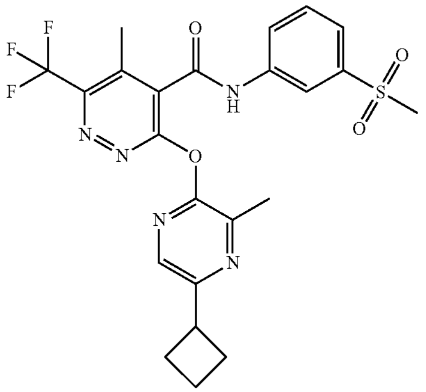 [SMILES: Cc1nc(C2CCC2)cnc1Oc1nnc(C(F)(F)F)c(C)c1C(=O)Nc1cccc(S(C)(=O)=O)c1]
1127
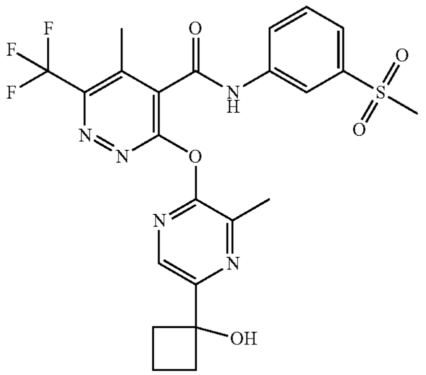
1128
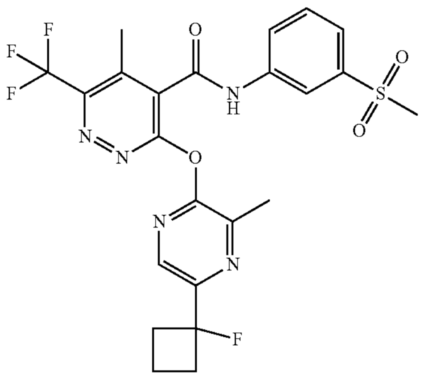 [SMILES: Cc1nc(C2(F)CCC2)cnc1Oc1nnc(C(F)(F)F)c(C)c1C(=O)Nc1cccc(S(C)(=O)=O)c1]
1129

TABLE 14-continued
1130
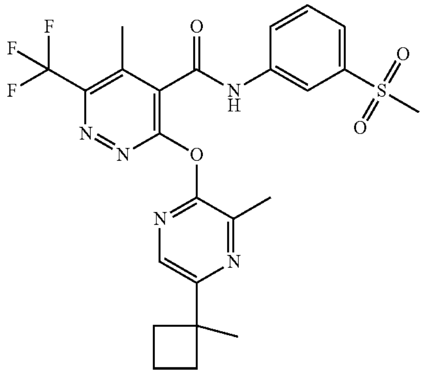 [SMILES: Cc1nc(C2(C)CCC2)cnc1Oc1nnc(C(F)(F)F)c(C)c1C(=O)Nc1cccc(S(C)(=O)=O)c1]
1131
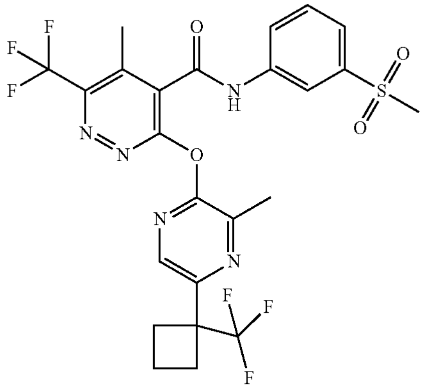 [SMILES: Cc1nc(C2(C(F)(F)F)CCC2)cnc1Oc1nnc(C(F)(F)F)c(C)c1C(=O)Nc1cccc(S(C)(=O)=O)c1]
1132
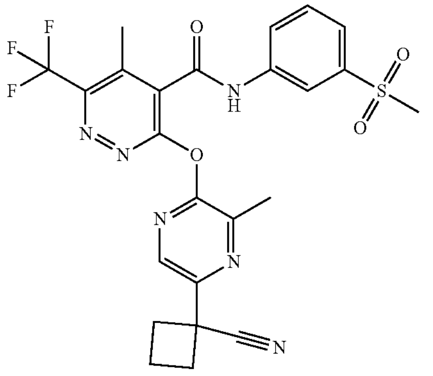 [SMILES: Cc1nc(C2(C#N)CCC2)cnc1Oc1nnc(C(F)(F)F)c(C)c1C(=O)Nc1cccc(S(C)(=O)=O)c1]
1133
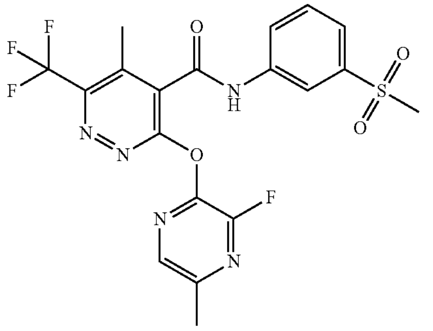 [SMILES: Cc1cnc(Oc2nnc(C(F)(F)F)c(C)c2C(=O)Nc2cccc(S(C)(=O)=O)c2)c(F)n1]
TABLE 14-continued
1134
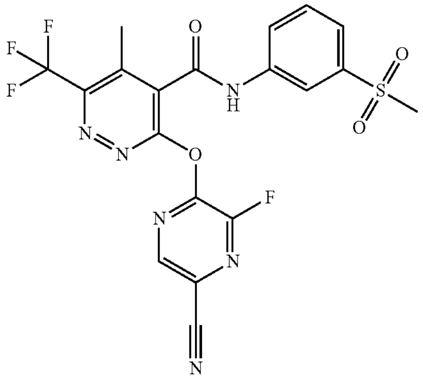 [SMILES: Cc1c(C(F)(F)F)nnc(Oc2ncc(C#N)nc2F)c1C(=O)Nc1cccc(S(C)(=O)=O)c1]
1135
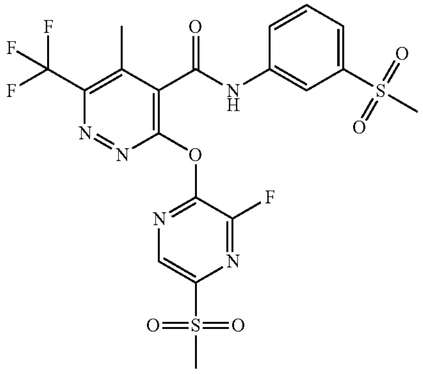 [SMILES: Cc1c(C(F)(F)F)nnc(Oc2ncc(S(C)(=O)=O)nc2F)c1C(=O)Nc1cccc(S(C)(=O)=O)c1]
1136
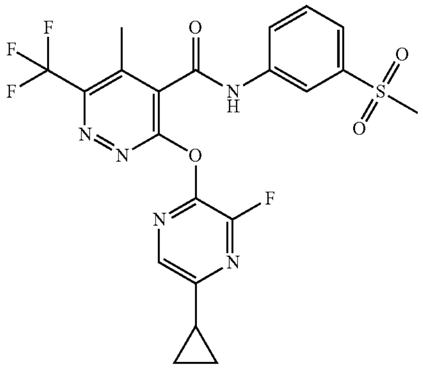 [SMILES: Cc1c(C(F)(F)F)nnc(Oc2ncc(C3CC3)nc2F)c1C(=O)Nc1cccc(S(C)(=O)=O)c1]
1137
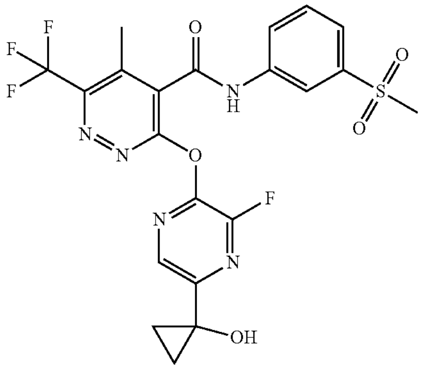

TABLE 14-continued
1138
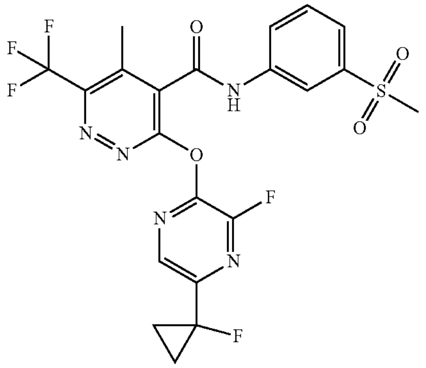
1139
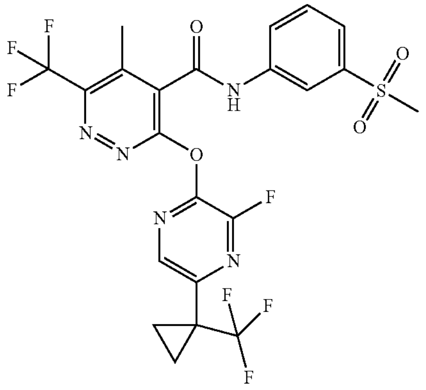
1140
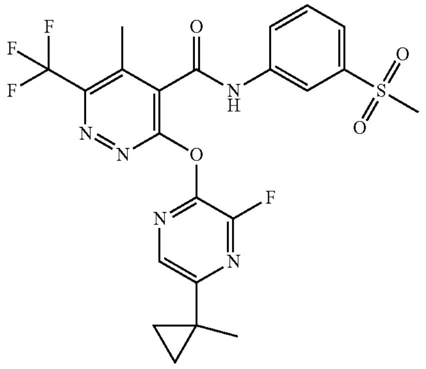
1141
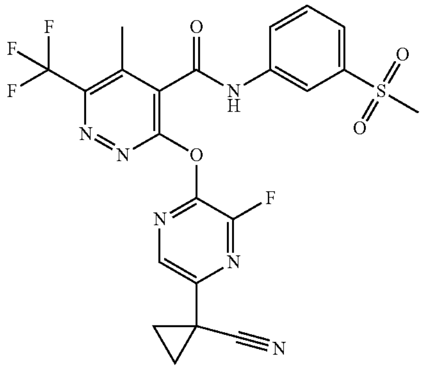
TABLE 14-continued
1142
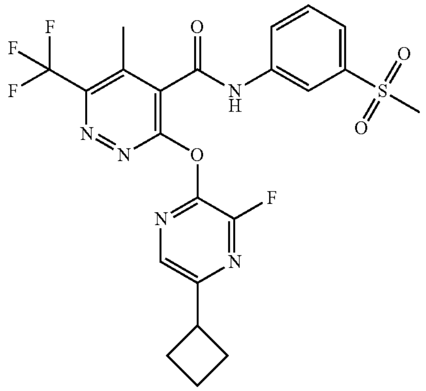
1143
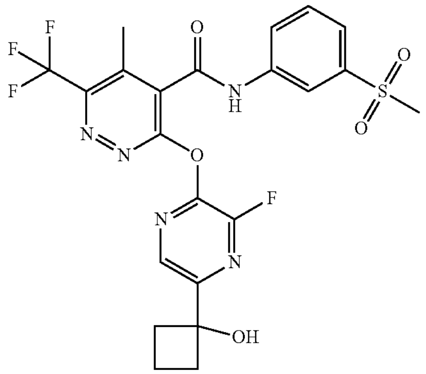
1144
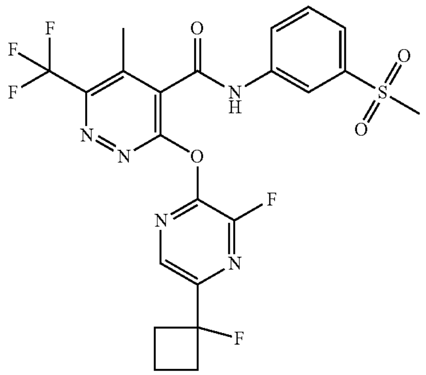
1145
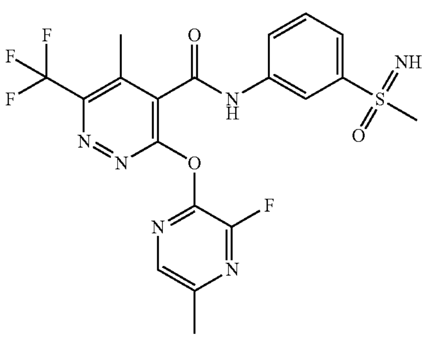 [SMILES: Cc1cnc(Oc2nnc(C(F)(F)F)c(C)c2C(=O)Nc2cccc(S(C)(=N)=O)c2)c(F)n1]

TABLE 14-continued
1146
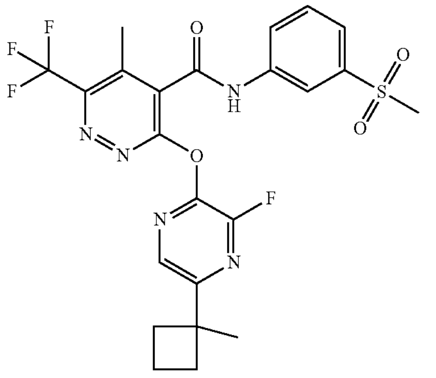 [SMILES: Cc1c(C(F)(F)F)nnc(Oc2ncc(C3(C)CCC3)nc2F)c1C(=O)Nc1cccc(S(C)(=O)=O)c1]
1147
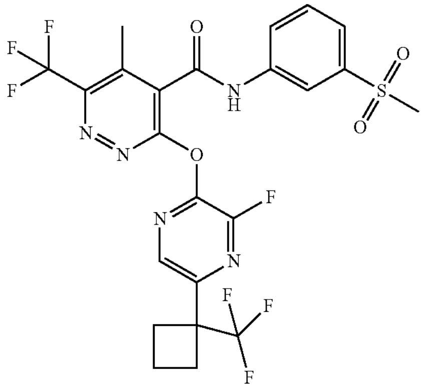
1148
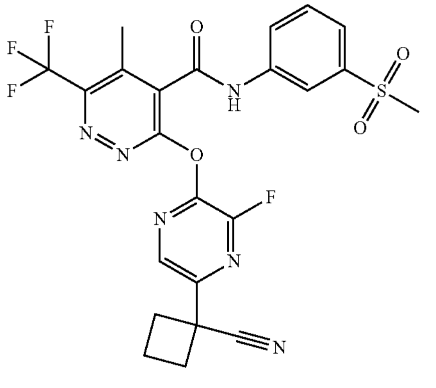 [SMILES: Cc1c(C(F)(F)F)nnc(Oc2ncc(C3(C#N)CCC3)nc2F)c1C(=O)Nc1cccc(S(C)(=O)=O)c1]
1149
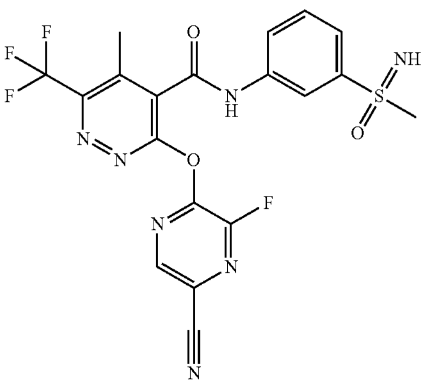 [SMILES: Cc1c(C(F)(F)F)nnc(Oc2ncc(C#N)nc2F)c1C(=O)Nc1cccc(S(C)(=N)=O)c1]
TABLE 14-continued
1150
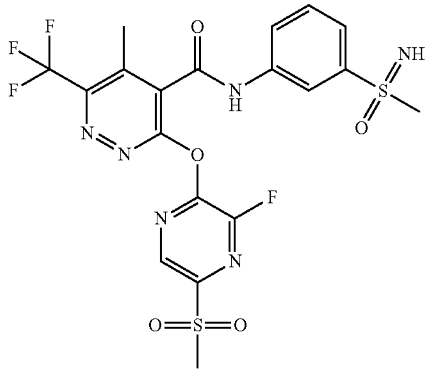 [SMILES: Cc1c(C(F)(F)F)nnc(Oc2ncc(S(C)(=O)=O)nc2F)c1C(=O)Nc1cccc(S(C)(=N)=O)c1]
1151
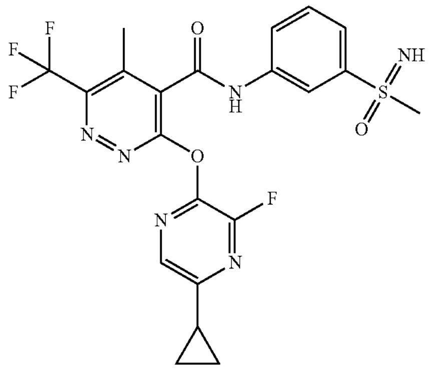 [SMILES: Cc1c(C(F)(F)F)nnc(Oc2ncc(C3CC3)nc2F)c1C(=O)Nc1cccc(S(C)(=N)=O)c1]
1152
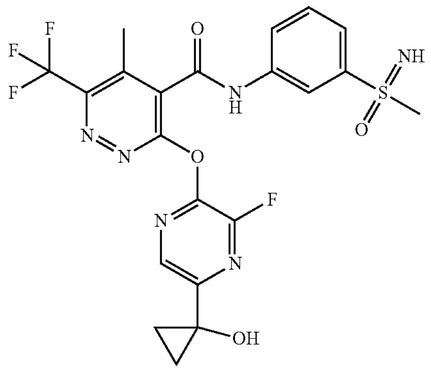 [SMILES: Cc1c(C(F)(F)F)nnc(Oc2ncc(C3(O)CC3)nc2F)c1C(=O)Nc1cccc(S(C)(=N)=O)c1]
1153
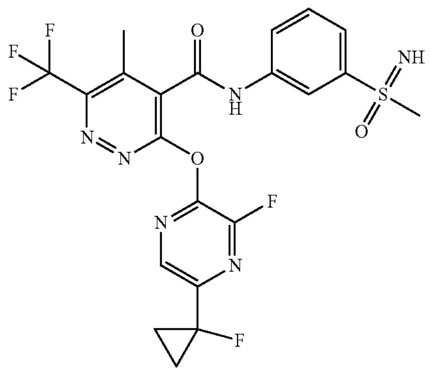 [SMILES: Cc1c(C(F)(F)F)nnc(Oc2ncc(C3(F)CC3)nc2F)c1C(=O)Nc1cccc(S(C)(=N)=O)c1]

TABLE 14-continued
1154
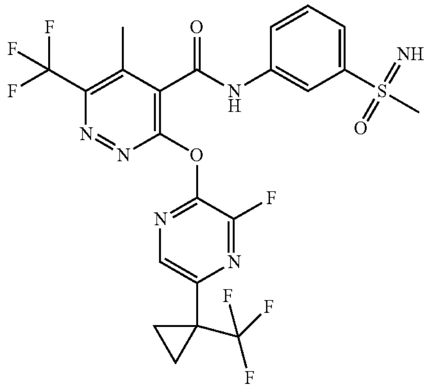 [SMILES: Cc1c(C(F)(F)F)nnc(Oc2ncc(C3(C(F)(F)F)CC3)nc2F)c1C(=O)Nc1cccc(S(C)(=N)=O)c1]
1155
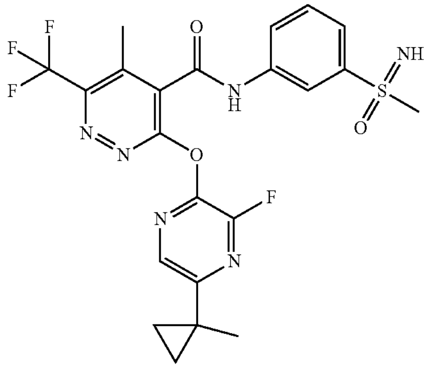 [SMILES: Cc1c(C(F)(F)F)nnc(Oc2ncc(C3(C)CC3)nc2F)c1C(=O)Nc1cccc(S(C)(=N)=O)c1]
1156
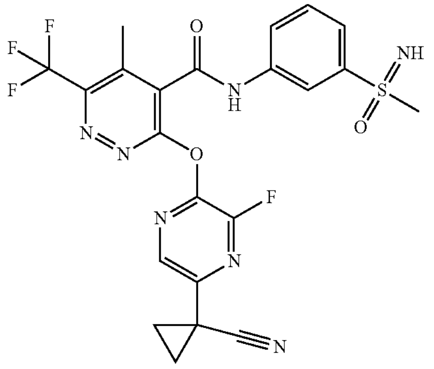 [SMILES: Cc1c(C(F)(F)F)nnc(Oc2ncc(C3(C#N)CC3)nc2F)c1C(=O)Nc1cccc(S(C)(=N)=O)c1]
1157
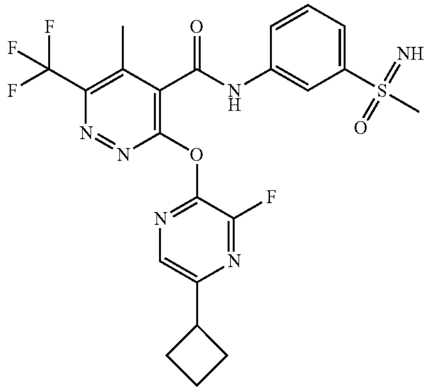 [SMILES: Cc1c(C(F)(F)F)nnc(Oc2ncc(C3CCC3)nc2F)c1C(=O)Nc1cccc(S(C)(=N)=O)c1]
TABLE 14-continued
1158
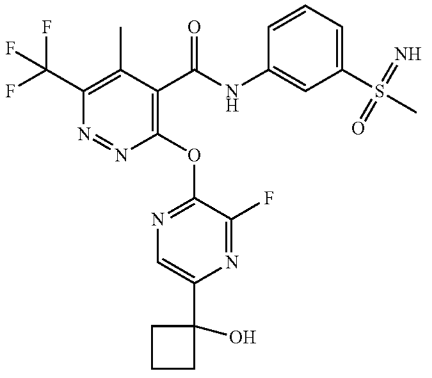 [SMILES: Cc1c(C(F)(F)F)nnc(Oc2ncc(C3(O)CCC3)nc2F)c1C(=O)Nc1cccc(S(C)(=N)=O)c1]
1159
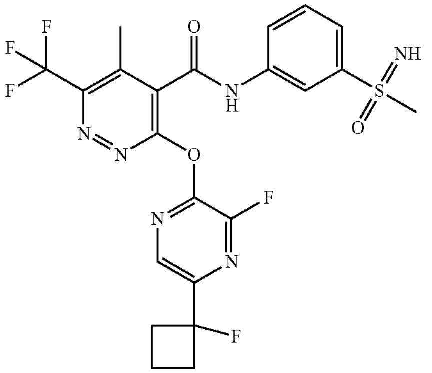 [SMILES: Cc1c(C(F)(F)F)nnc(Oc2ncc(C3(F)CCC3)nc2F)c1C(=O)Nc1cccc(S(C)(=N)=O)c1]
1161
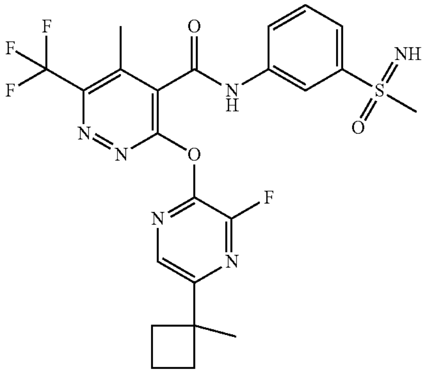 [SMILES: Cc1c(C(F)(F)F)nnc(Oc2ncc(C3(C)CCC3)nc2F)c1C(=O)Nc1cccc(S(C)(=N)=O)c1]
1162
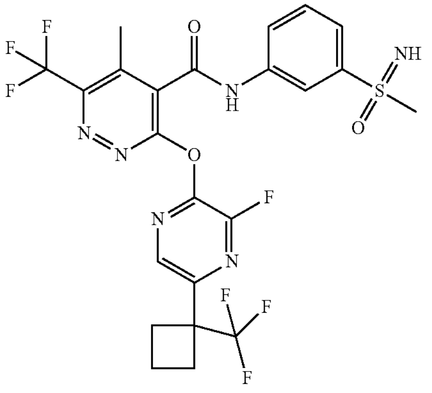 [SMILES: Cc1c(C(F)(F)F)nnc(Oc2ncc(C3(C(F)(F)F)CCC3)nc2F)c1C(=O)Nc1cccc(S(C)(=N)=O)c1]

TABLE 14-continued
1163
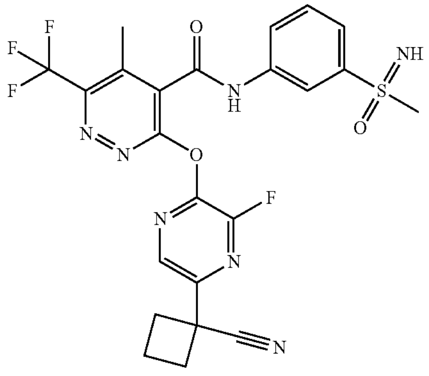 [SMILES: Cc1c(C(F)(F)F)nnc(Oc2ncc(C3(C#N)CCC3)nc2F)c1C(=O)Nc1cccc(S(C)(=N)=O)c1]
1193
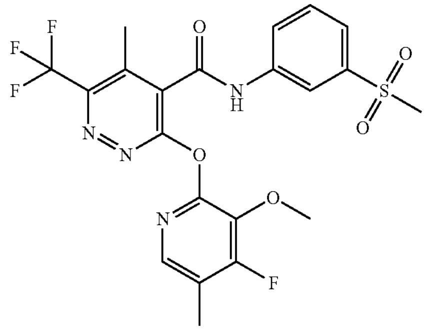 [SMILES: COc1c(Oc2nnc(C(F)(F)F)c(C)c2C(=O)Nc2cccc(S(C)(=O)=O)c2)ncc(C)c1F]
1194
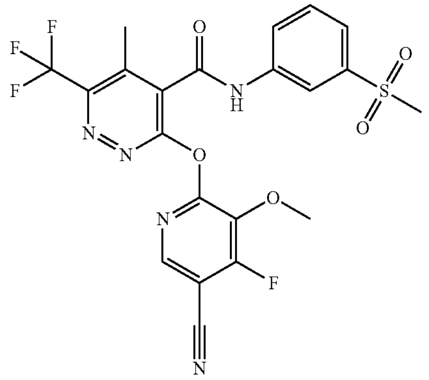 [SMILES: COc1c(Oc2nnc(C(F)(F)F)c(C)c2C(=O)Nc2cccc(S(C)(=O)=O)c2)ncc(C#N)c1F]
1195
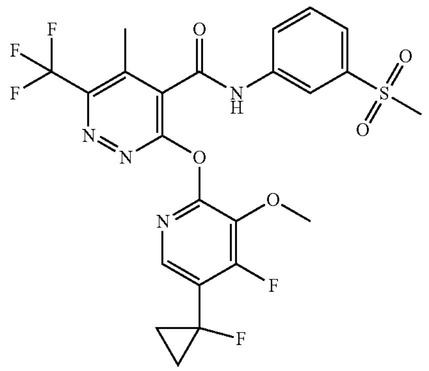
TABLE 14-continued
1196
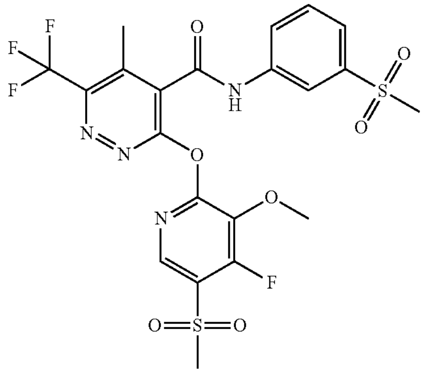 [SMILES: COc1c(Oc2nnc(C(F)(F)F)c(C)c2C(=O)Nc2cccc(S(C)(=O)=O)c2)ncc(S(C)(=O)=O)c1F]
1197
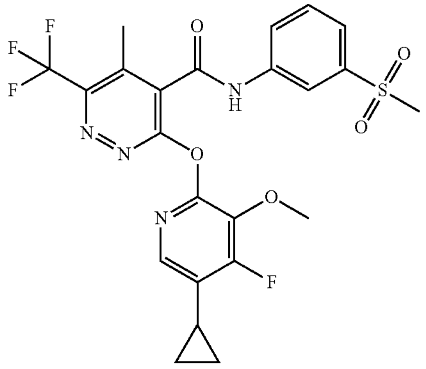 [SMILES: COc1c(Oc2nnc(C(F)(F)F)c(C)c2C(=O)Nc2cccc(S(C)(=O)=O)c2)ncc(C2CC2)c1F]
1198
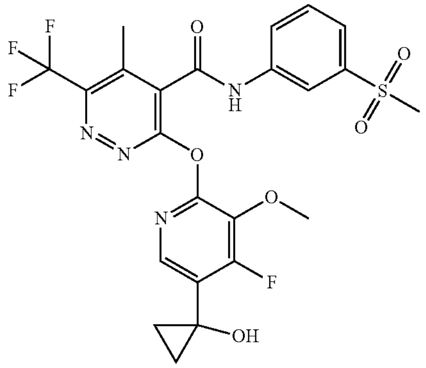 [SMILES: COc1c(Oc2nnc(C(F)(F)F)c(C)c2C(=O)Nc2cccc(S(C)(=O)=O)c2)ncc(C2(O)CC2)c1F]
1199
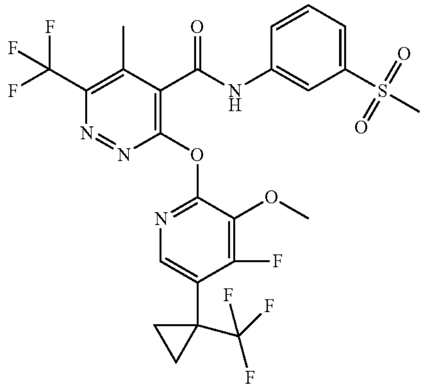 [SMILES: COc1c(Oc2nnc(C(F)(F)F)c(C)c2C(=O)Nc2cccc(S(C)(=O)=O)c2)ncc(C2(C(F)(F)F)CC2)c1F]

TABLE 14-continued
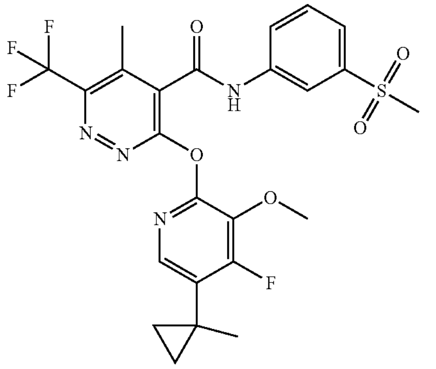 [SMILES: COc1c(Oc2nnc(C(F)(F)F)c(C)c2C(=O)Nc2cccc(S(C)(=O)=O)c2)ncc(C2(C)CC2)c1F]
1200
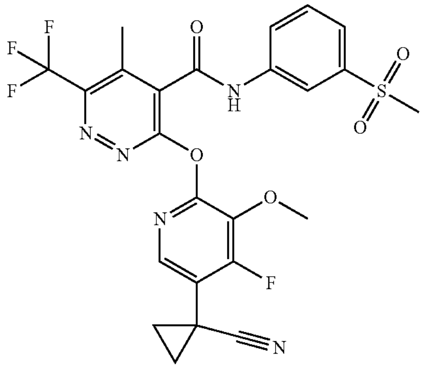
1201
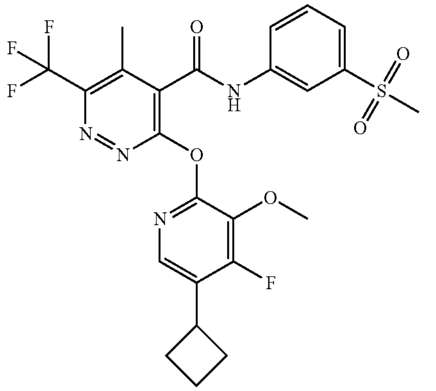 [SMILES: COc1c(Oc2nnc(C(F)(F)F)c(C)c2C(=O)Nc2cccc(S(C)(=O)=O)c2)ncc(C2CCC2)c1F]
1202
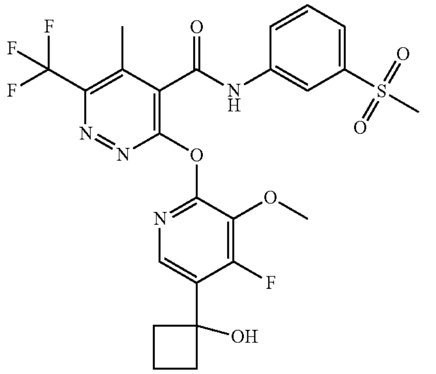 [SMILES: COc1c(Oc2nnc(C(F)(F)F)c(C)c2C(=O)Nc2cccc(S(C)(=O)=O)c2)ncc(C2(O)CCC2)c1F]
1203
TABLE 14-continued
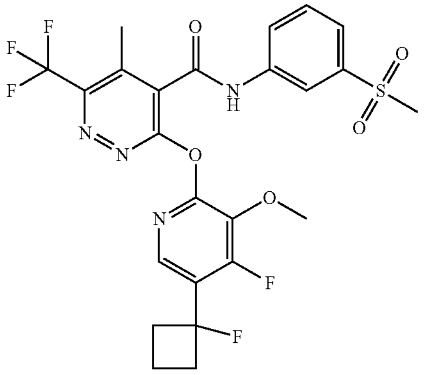
1204
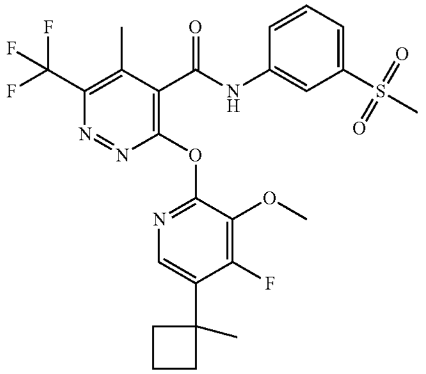 [SMILES: COc1c(Oc2nnc(C(F)(F)F)c(C)c2C(=O)Nc2cccc(S(C)(=O)=O)c2)ncc(C2(C)CCC2)c1F]
1205
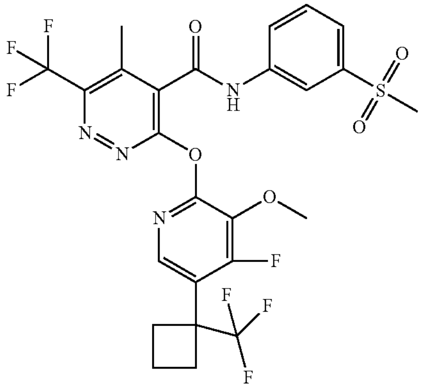 [SMILES: COc1c(Oc2nnc(C(F)(F)F)c(C)c2C(=O)Nc2cccc(S(C)(=O)=O)c2)ncc(C2(C(F)(F)F)CCC2)c1F]
1206
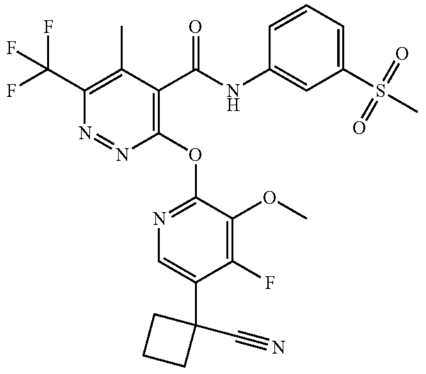
1207

TABLE 14-continued
1208
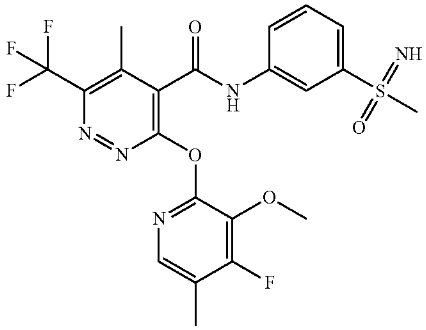 [SMILES: COc1c(Oc2nnc(C(F)(F)F)c(C)c2C(=O)Nc2cccc(S(C)(=N)=O)c2)ncc(C)c1F]
1209
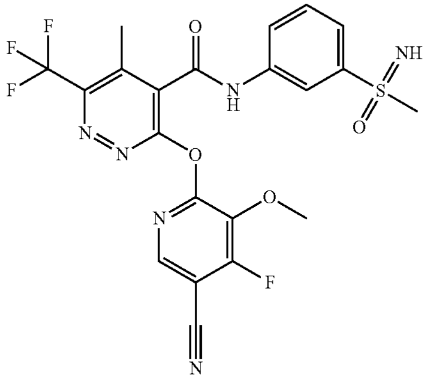 [SMILES: COc1c(Oc2nnc(C(F)(F)F)c(C)c2C(=O)Nc2cccc(S(C)(=N)=O)c2)ncc(C#N)c1F]
1210
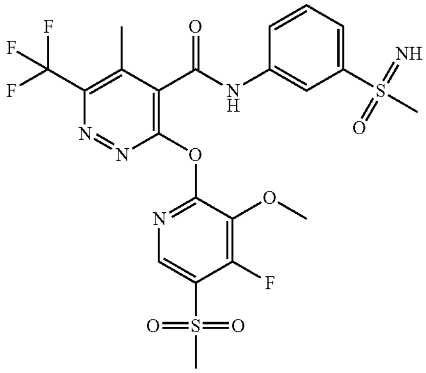 [SMILES: COc1c(Oc2nnc(C(F)(F)F)c(C)c2C(=O)Nc2cccc(S(C)(=N)=O)c2)ncc(S(C)(=O)=O)c1F]
1211
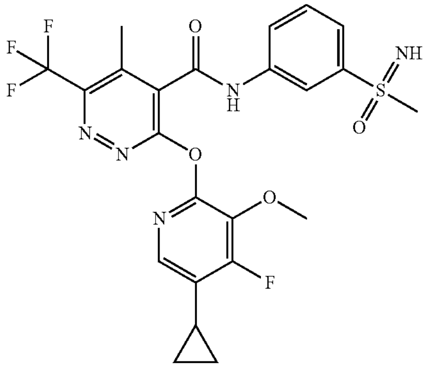 [SMILES: COc1c(Oc2nnc(C(F)(F)F)c(C)c2C(=O)Nc2cccc(S(C)(=N)=O)c2)ncc(C2CC2)c1F]
TABLE 14-continued
1212
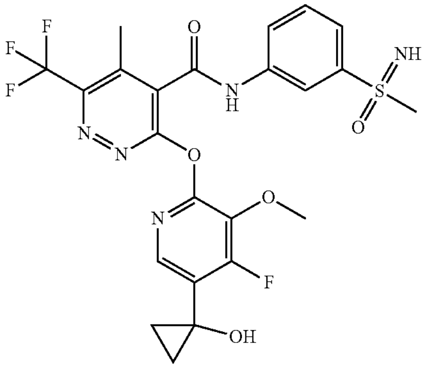 [SMILES: COc1c(Oc2nnc(C(F)(F)F)c(C)c2C(=O)Nc2cccc(S(C)(=N)=O)c2)ncc(C2(O)CC2)c1F]
1213
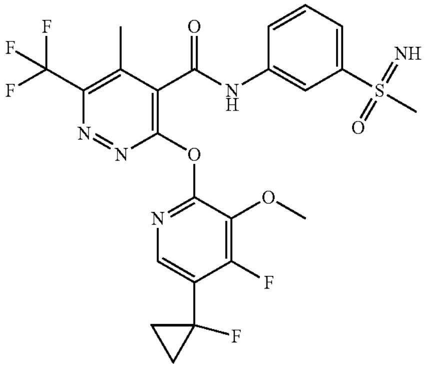
1214
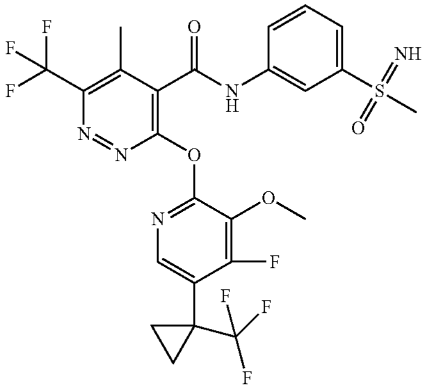 [SMILES: COc1c(Oc2nnc(C(F)(F)F)c(C)c2C(=O)Nc2cccc(S(C)(=N)=O)c2)ncc(C2(C(F)(F)F)CC2)c1F]
1215
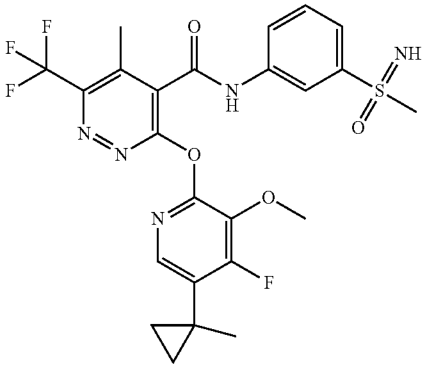 [SMILES: COc1c(Oc2nnc(C(F)(F)F)c(C)c2C(=O)Nc2cccc(S(C)(=N)=O)c2)ncc(C2(C)CC2)c1F]

TABLE 14-continued
1216
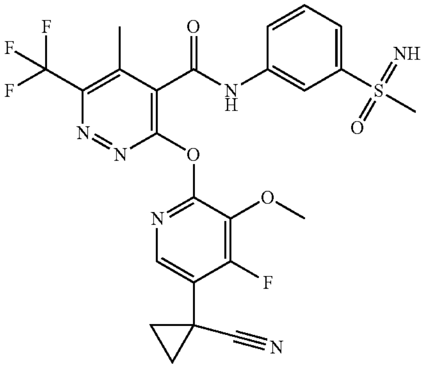 [SMILES: COc1c(Oc2nnc(C(F)(F)F)c(C)c2C(=O)Nc2cccc(S(C)(=N)=O)c2)ncc(C2(C#N)CC2)c1F]
1217
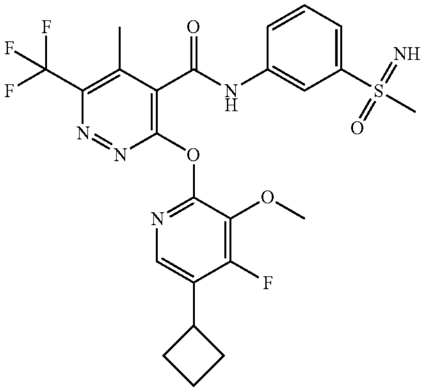 [SMILES: COc1c(Oc2nnc(C(F)(F)F)c(C)c2C(=O)Nc2cccc(S(C)(=N)=O)c2)ncc(C2CCC2)c1F]
1218
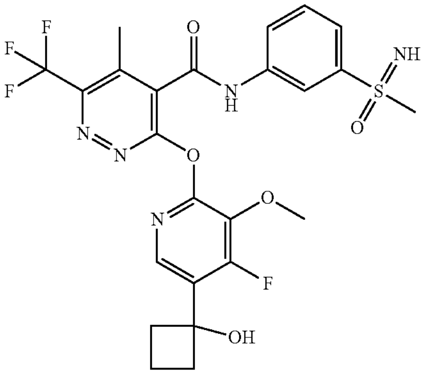 [SMILES: COc1c(Oc2nnc(C(F)(F)F)c(C)c2C(=O)Nc2cccc(S(C)(=N)=O)c2)ncc(C2(O)CCC2)c1F]
1219
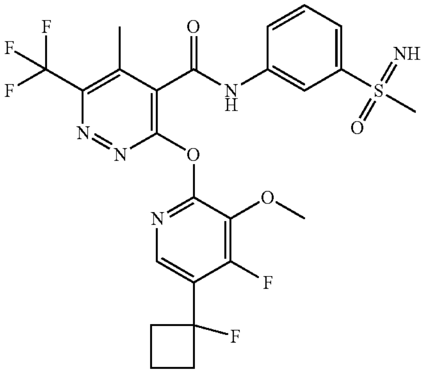
TABLE 14-continued
1220
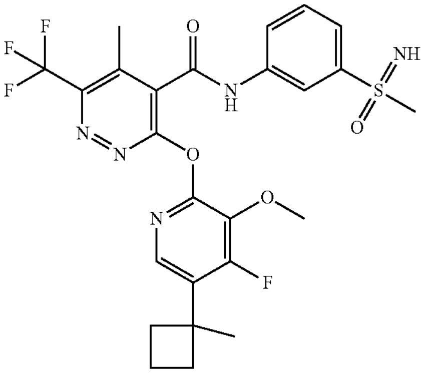 [SMILES: COc1c(Oc2nnc(C(F)(F)F)c(C)c2C(=O)Nc2cccc(S(C)(=N)=O)c2)ncc(C2(C)CCC2)c1F]
1221
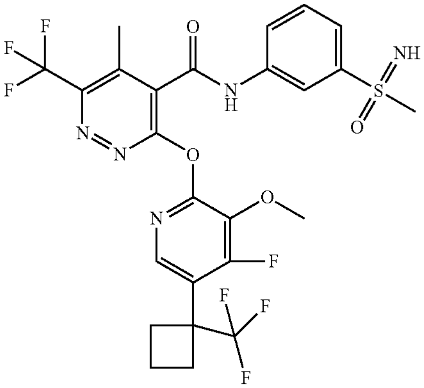 [SMILES: COc1c(Oc2nnc(C(F)(F)F)c(C)c2C(=O)Nc2cccc(S(C)(=N)=O)c2)ncc(C2(C(F)(F)F)CCC2)c1F]
1222
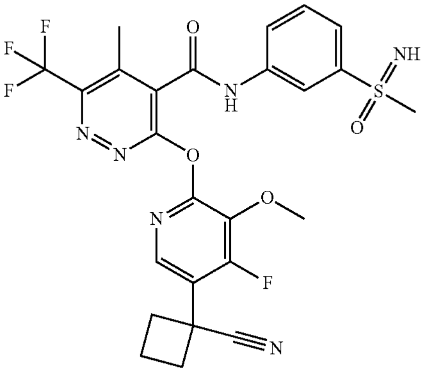 [SMILES: COc1c(Oc2nnc(C(F)(F)F)c(C)c2C(=O)Nc2cccc(S(C)(=N)=O)c2)ncc(C2(C#N)CCC2)c1F]
1223
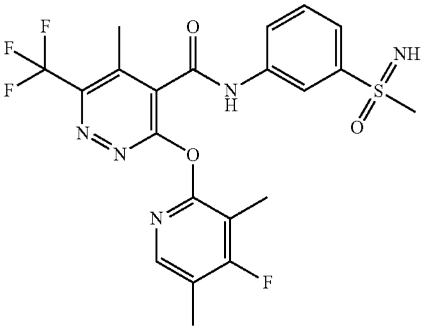 [SMILES: Cc1cnc(Oc2nnc(C(F)(F)F)c(C)c2C(=O)Nc2cccc(S(C)(=N)=O)c2)c(C)c1F]

TABLE 14-continued
1224
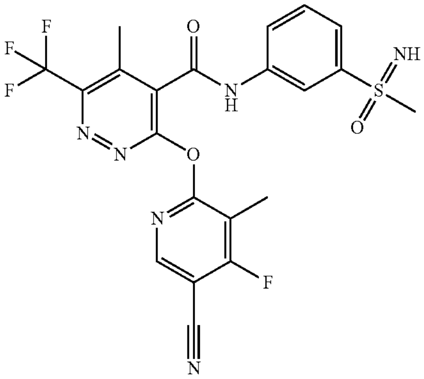 [SMILES: Cc1c(Oc2nnc(C(F)(F)F)c(C)c2C(=O)Nc2cccc(S(C)(=N)=O)c2)ncc(C#N)c1F]
1225
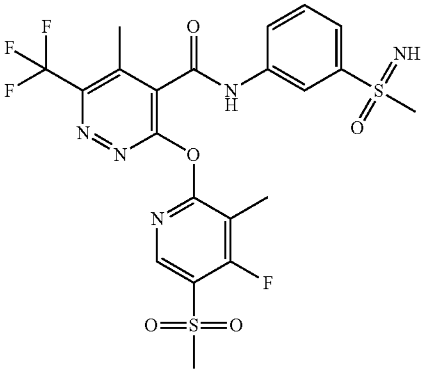
1226
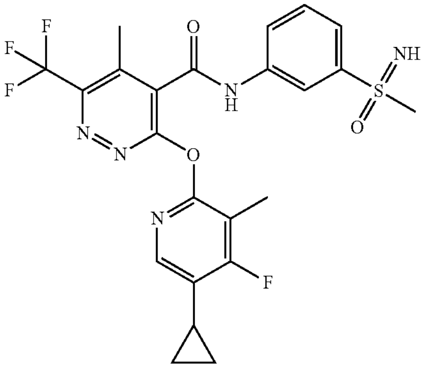 [SMILES: Cc1c(Oc2nnc(C(F)(F)F)c(C)c2C(=O)Nc2cccc(S(C)(=N)=O)c2)ncc(C2CC2)c1F]
1227
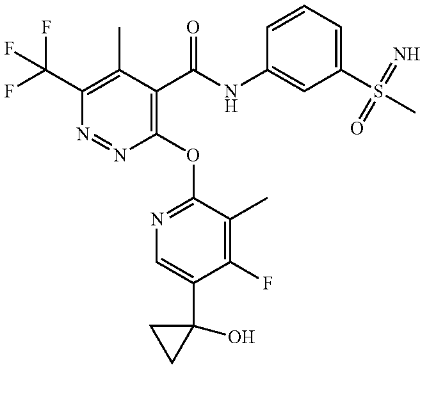
TABLE 14-continued
1228
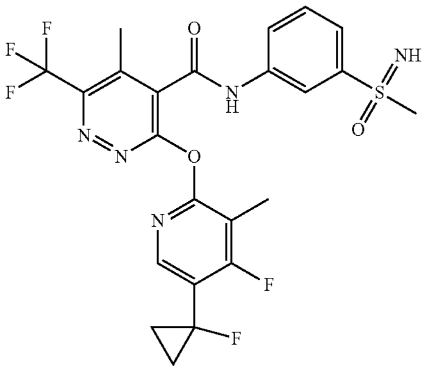
1229
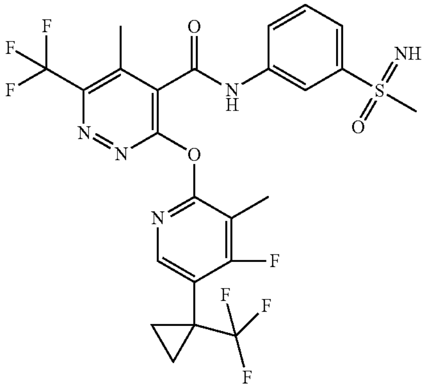 [SMILES: Cc1c(Oc2nnc(C(F)(F)F)c(C)c2C(=O)Nc2cccc(S(C)(=N)=O)c2)ncc(C2(C(F)(F)F)CC2)c1F]
1230
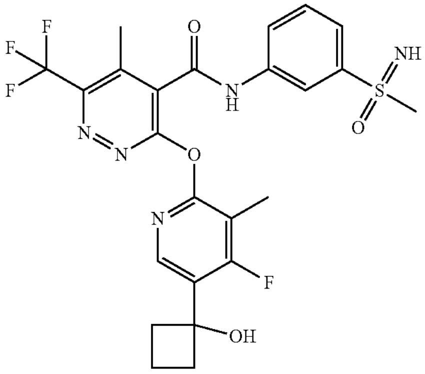 [SMILES: Cc1c(Oc2nnc(C(F)(F)F)c(C)c2C(=O)Nc2cccc(S(C)(=N)=O)c2)ncc(C2(O)CCC2)c1F]
1231
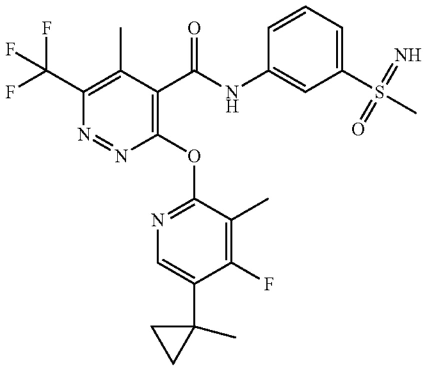 [SMILES: Cc1c(Oc2nnc(C(F)(F)F)c(C)c2C(=O)Nc2cccc(S(C)(=N)=O)c2)ncc(C2(C)CC2)c1F]

TABLE 14-continued
1232
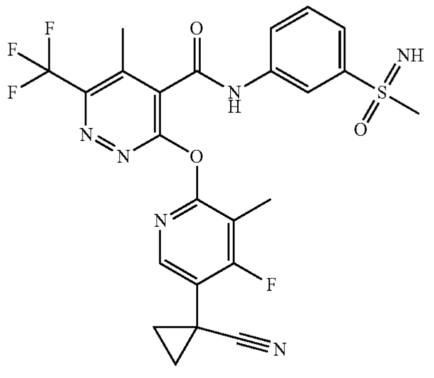 [SMILES: Cc1c(Oc2nnc(C(F)(F)F)c(C)c2C(=O)Nc2cccc(S(C)(=N)=O)c2)ncc(C2(C#N)CC2)c1F]
1233
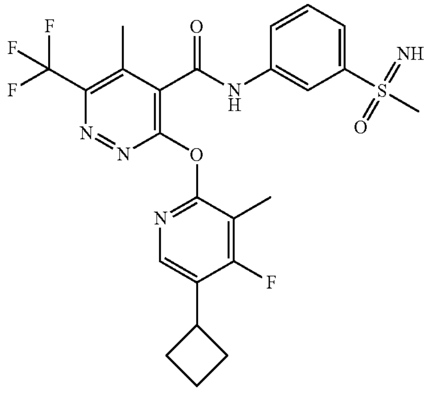 [SMILES: Cc1c(Oc2nnc(C(F)(F)F)c(C)c2C(=O)Nc2cccc(S(C)(=N)=O)c2)ncc(C2CCC2)c1F]
1234
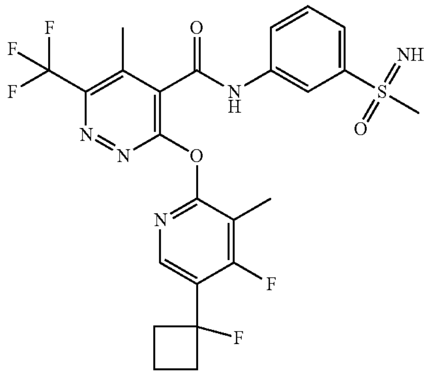
1235
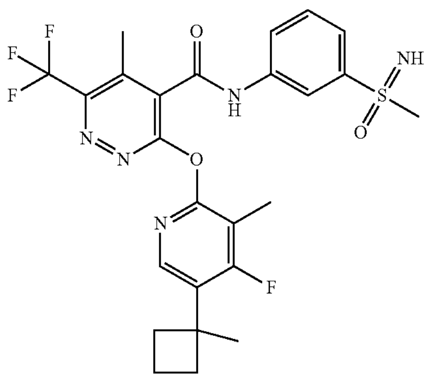 [SMILES: Cc1c(Oc2nnc(C(F)(F)F)c(C)c2C(=O)Nc2cccc(S(C)(=N)=O)c2)ncc(C2(C)CCC2)c1F]
TABLE 14-continued
1236
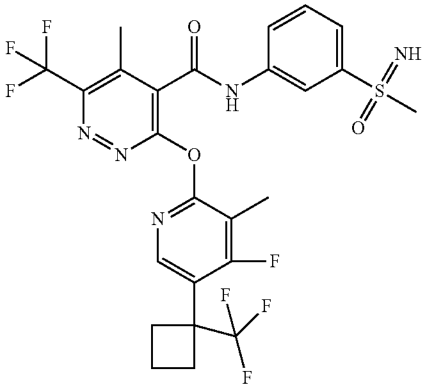
1237
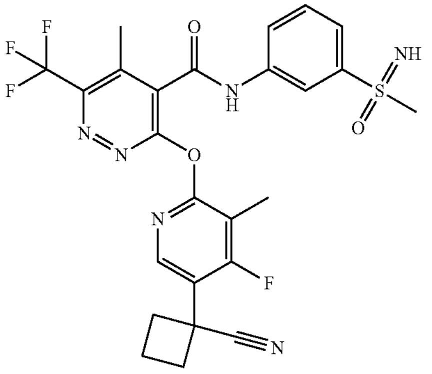 [SMILES: Cc1c(Oc2nnc(C(F)(F)F)c(C)c2C(=O)Nc2cccc(S(C)(=N)=O)c2)ncc(C2(C#N)CCC2)c1F]
1238
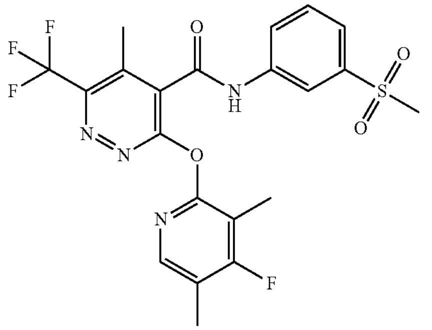
1239
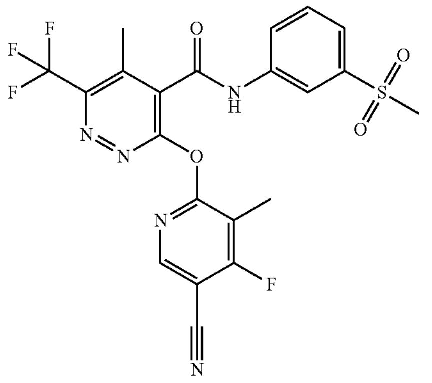 [SMILES: Cc1c(Oc2nnc(C(F)(F)F)c(C)c2C(=O)Nc2cccc(S(C)(=O)=O)c2)ncc(C#N)c1F]

TABLE 14-continued
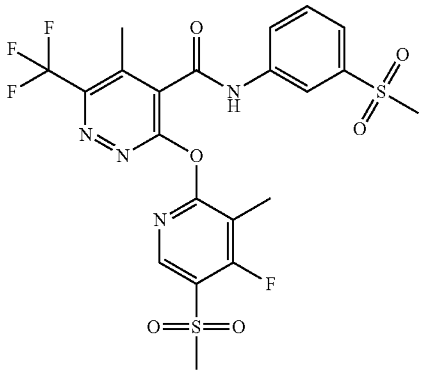
1240
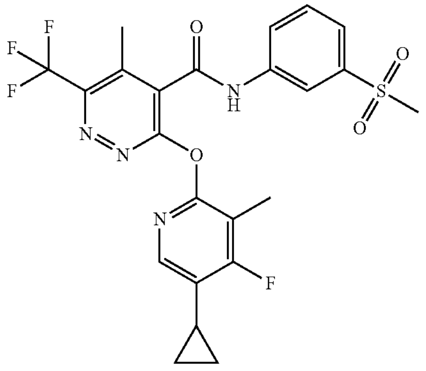
1241
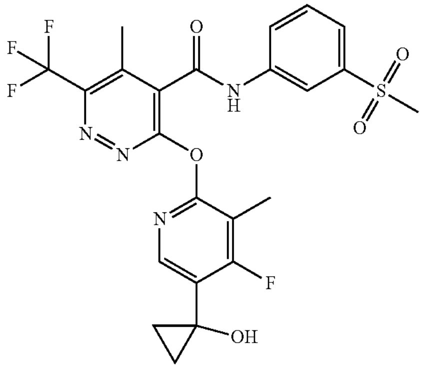
1242
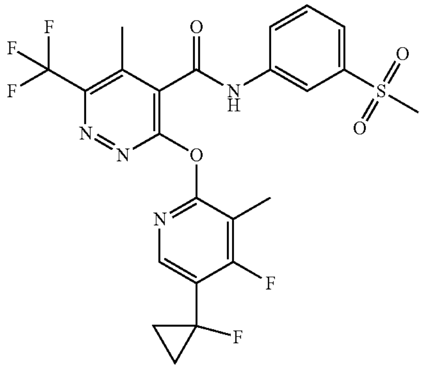
1243
TABLE 14-continued
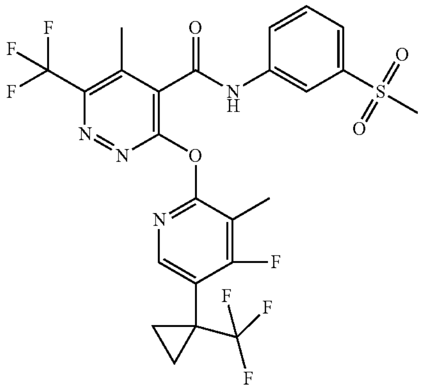 [SMILES: Cc1c(Oc2nnc(C(F)(F)F)c(C)c2C(=O)Nc2cccc(S(C)(=O)=O)c2)ncc(C2(C(F)(F)F)CC2)c1F]
1244
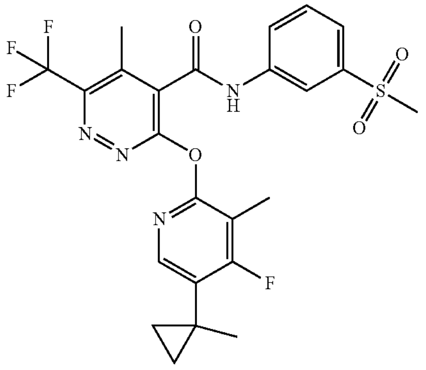 [SMILES: Cc1c(Oc2nnc(C(F)(F)F)c(C)c2C(=O)Nc2cccc(S(C)(=O)=O)c2)ncc(C2(C)CC2)c1F]
1245
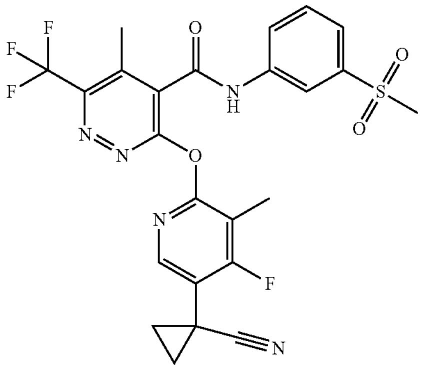 [SMILES: Cc1c(Oc2nnc(C(F)(F)F)c(C)c2C(=O)Nc2cccc(S(C)(=O)=O)c2)ncc(C2(C#N)CC2)c1F]
1246
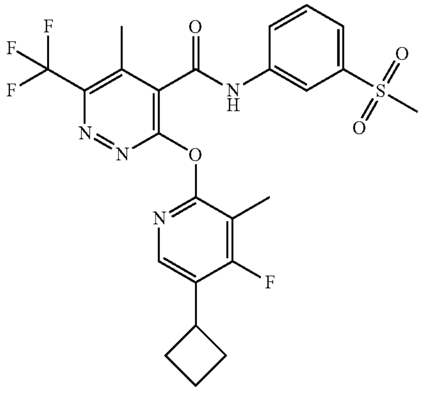 [SMILES: Cc1c(Oc2nnc(C(F)(F)F)c(C)c2C(=O)Nc2cccc(S(C)(=O)=O)c2)ncc(C2CCC2)c1F]
1247

TABLE 14-continued
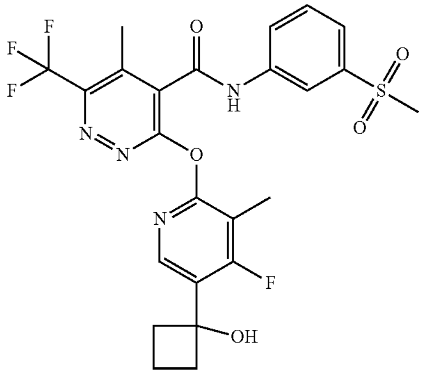
1248
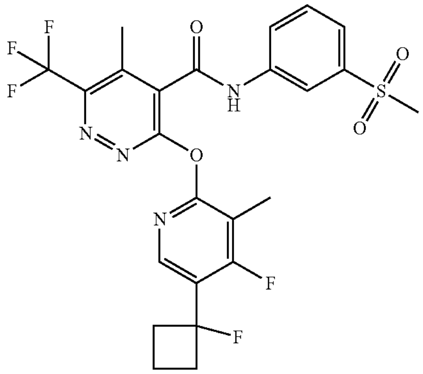
1249
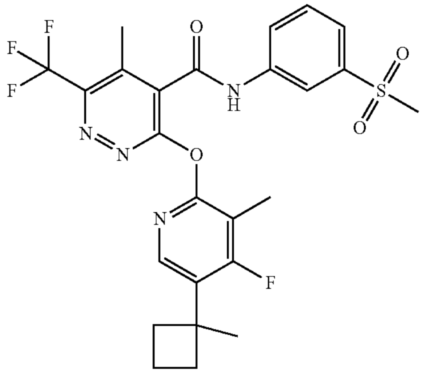 [SMILES: Cc1c(Oc2nnc(C(F)(F)F)c(C)c2C(=O)Nc2cccc(S(C)(=O)=O)c2)ncc(C2(C)CCC2)c1F]
1250
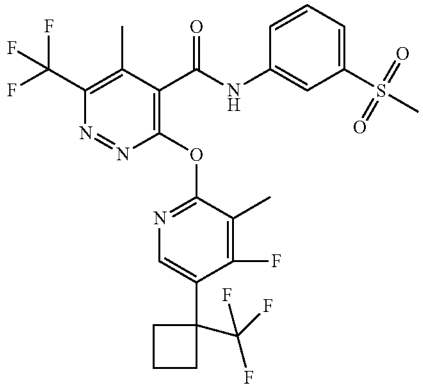
1251
TABLE 14-continued
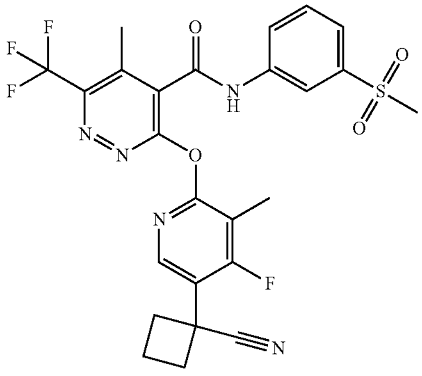
1252
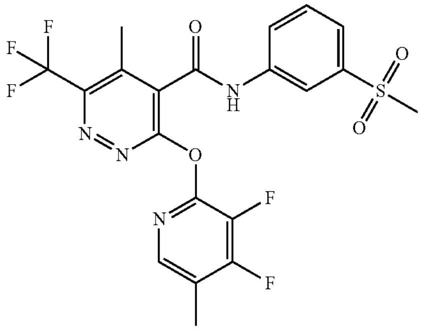 [SMILES: Cc1cnc(Oc2nnc(C(F)(F)F)c(C)c2C(=O)Nc2cccc(S(C)(=O)=O)c2)c(F)c1F]
1253
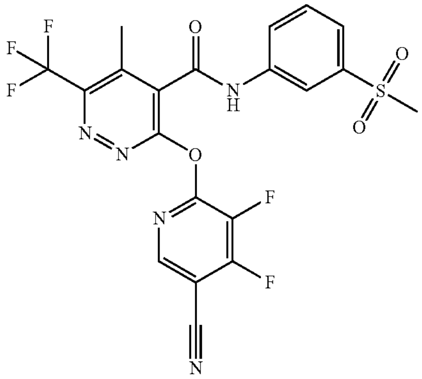
1254
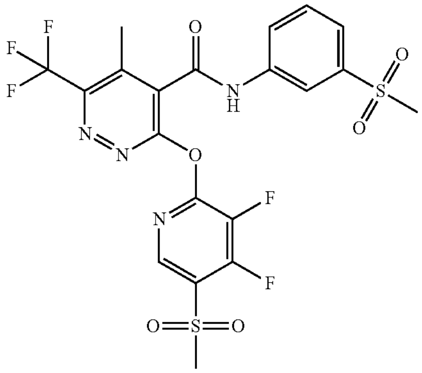
1255

TABLE 14-continued
1256
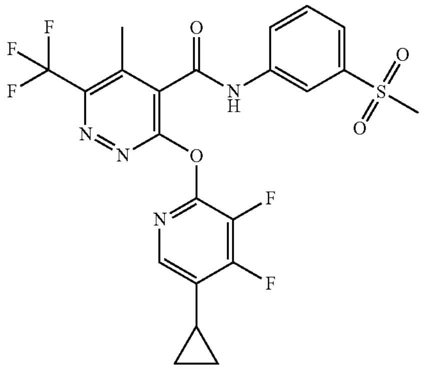
1257
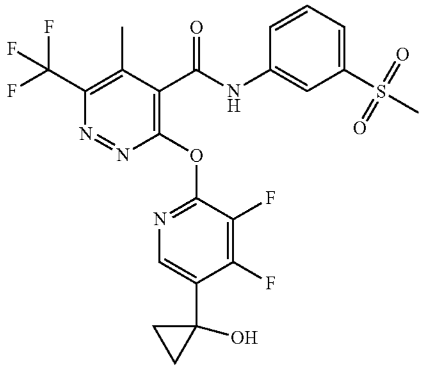
1258
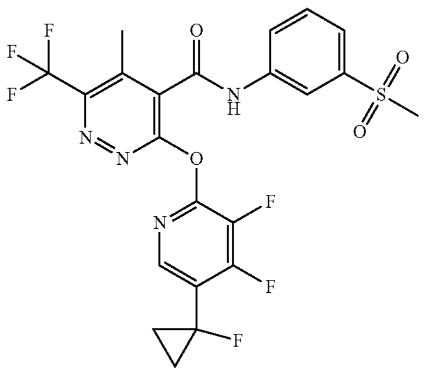
1259
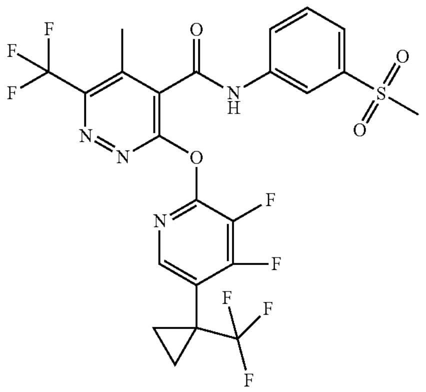
TABLE 14-continued
1260
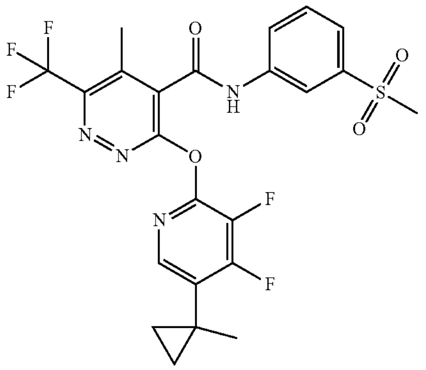
1261
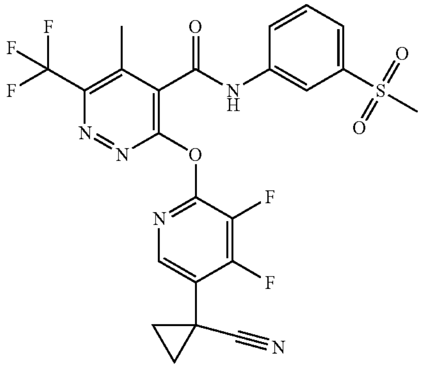
1262
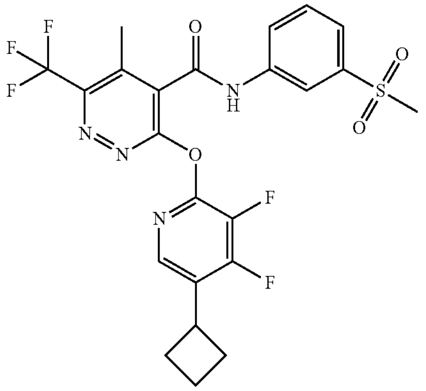
1263
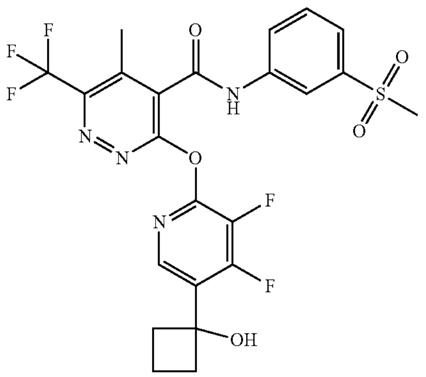 [SMILES: Cc1c(C(F)(F)F)nnc(Oc2ncc(C3(O)CCC3)c(F)c2F)c1C(=O)Nc1cccc(S(C)(=O)=O)c1]

TABLE 14-continued
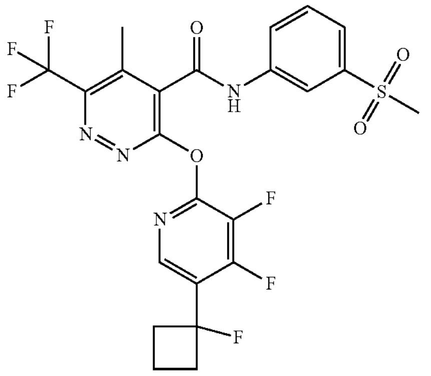 [SMILES: Cc1c(C(F)(F)F)nnc(Oc2ncc(C3(F)CCC3)c(F)c2F)c1C(=O)Nc1cccc(S(C)(=O)=O)c1]
1264
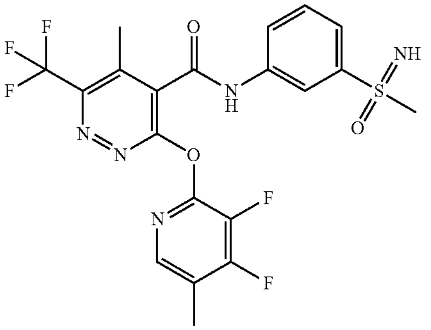
1265
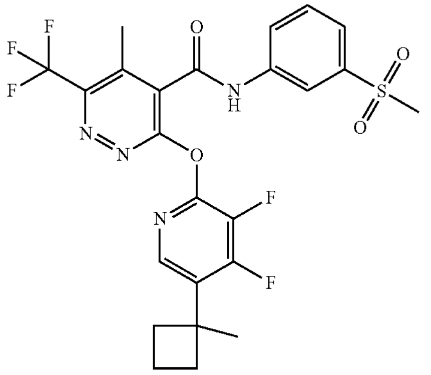
1266
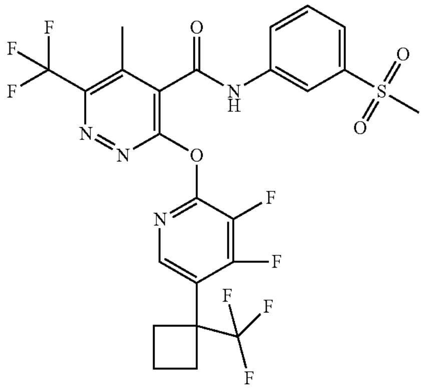 [SMILES: Cc1c(C(F)(F)F)nnc(Oc2ncc(C3(C(F)(F)F)CCC3)c(F)c2F)c1C(=O)Nc1cccc(S(C)(=O)=O)c1]
1267
TABLE 14-continued
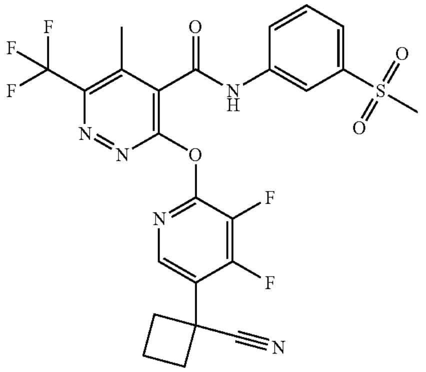 [SMILES: Cc1c(C(F)(F)F)nnc(Oc2ncc(C3(C#N)CCC3)c(F)c2F)c1C(=O)Nc1cccc(S(C)(=O)=O)c1]
1268
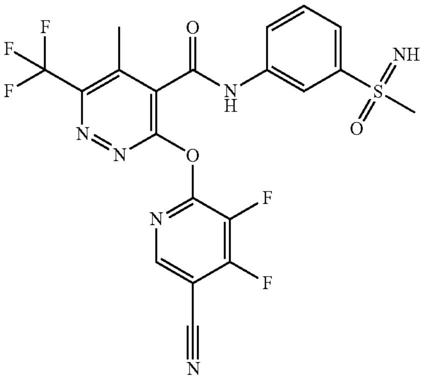 [SMILES: Cc1c(C(F)(F)F)nnc(Oc2ncc(C#N)c(F)c2F)c1C(=O)Nc1cccc(S(C)(=N)=O)c1]
1269
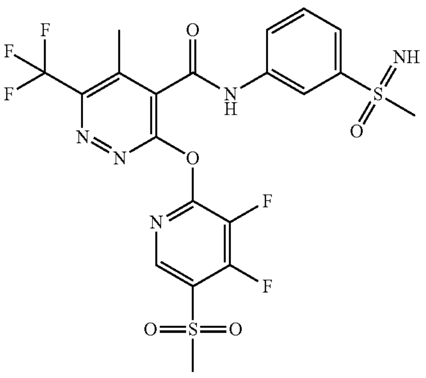 [SMILES: Cc1c(C(F)(F)F)nnc(Oc2ncc(S(C)(=O)=O)c(F)c2F)c1C(=O)Nc1cccc(S(C)(=N)=O)c1]
1270
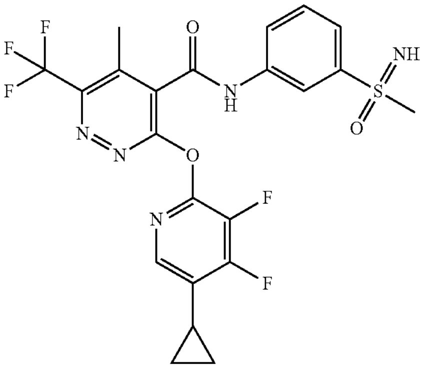 [SMILES: Cc1c(C(F)(F)F)nnc(Oc2ncc(C3CC3)c(F)c2F)c1C(=O)Nc1cccc(S(C)(=N)=O)c1]
1271

TABLE 14-continued
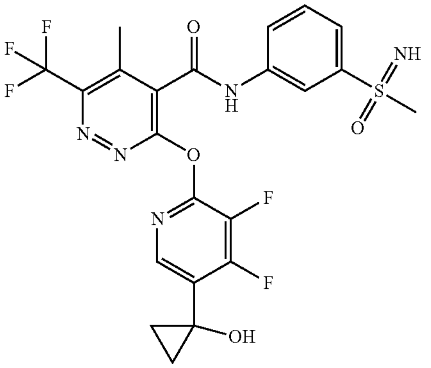 [SMILES: Cc1c(C(F)(F)F)nnc(Oc2ncc(C3(O)CC3)c(F)c2F)c1C(=O)Nc1cccc(S(C)(=N)=O)c1]
1272
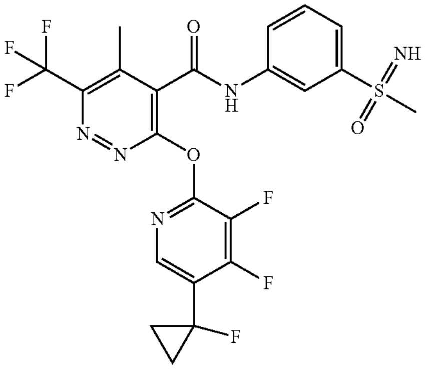 [SMILES: Cc1c(C(F)(F)F)nnc(Oc2ncc(C3(C)CC3)c(F)c2F)c1C(=O)Nc1cccc(S(C)(=N)=O)c1]
1273
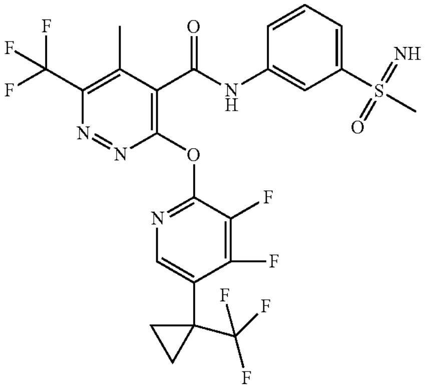
1274
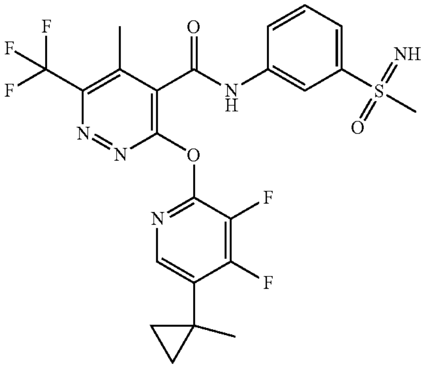
1275
TABLE 14-continued
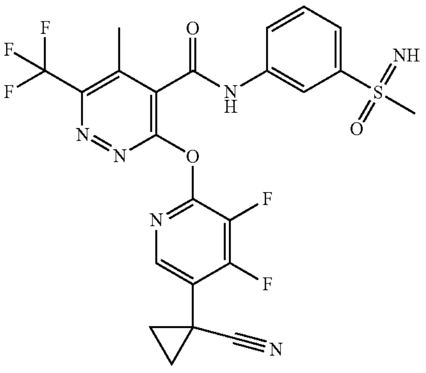
1276
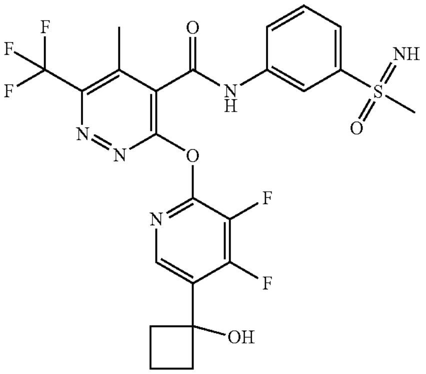 [SMILES: Cc1c(C(F)(F)F)nnc(Oc2ncc(C3(O)CCC3)c(F)c2F)c1C(=O)Nc1cccc(S(C)(=N)=O)c1]
1277
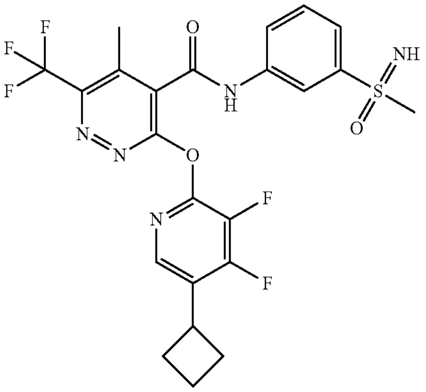 [SMILES: Cc1c(C(F)(F)F)nnc(Oc2ncc(C3CCC3)c(F)c2F)c1C(=O)Nc1cccc(S(C)(=N)=O)c1]
1278
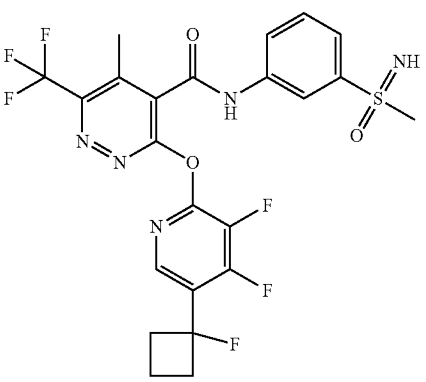 [SMILES: Cc1c(C(F)(F)F)nnc(Oc2ncc(C3(F)CCC3)c(F)c2F)c1C(=O)Nc1cccc(S(C)(=N)=O)c1]
1279

TABLE 14-continued
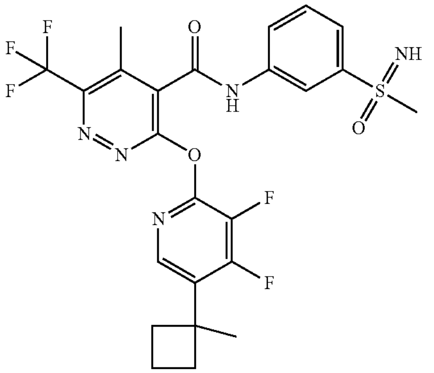
1280
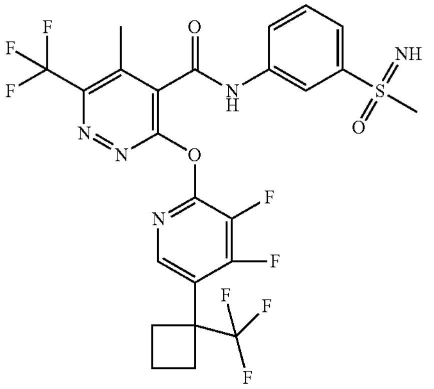 [SMILES: Cc1c(C(F)(F)F)nnc(Oc2ncc(C3(C(F)(F)F)CCC3)c(F)c2F)c1C(=O)Nc1cccc(S(C)(=N)=O)c1]
1281
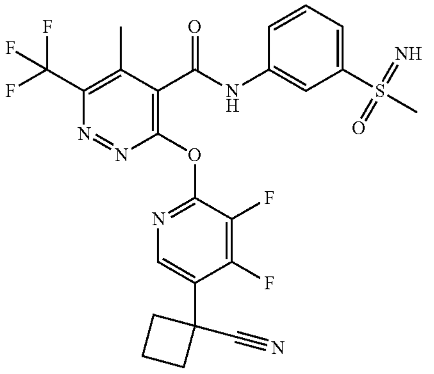 [SMILES: Cc1c(C(F)(F)F)nnc(Oc2ncc(C3(C#N)CCC3)c(F)c2F)c1C(=O)Nc1cccc(S(C)(=N)=O)c1]
1282
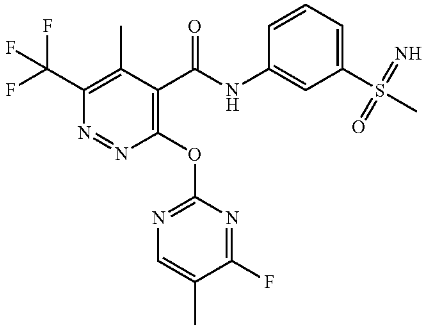 [SMILES: Cc1cnc(Oc2nnc(C(F)(F)F)c(C)c2C(=O)Nc2cccc(S(C)(=N)=O)c2)nc1F]
1283
TABLE 14-continued
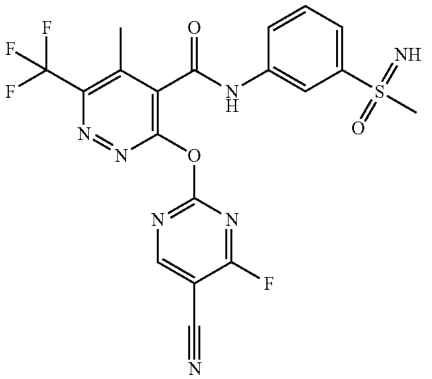 [SMILES: Cc1c(C(F)(F)F)nnc(Oc2ncc(C#N)c(F)n2)c1C(=O)Nc1cccc(S(C)(=N)=O)c1]
1284
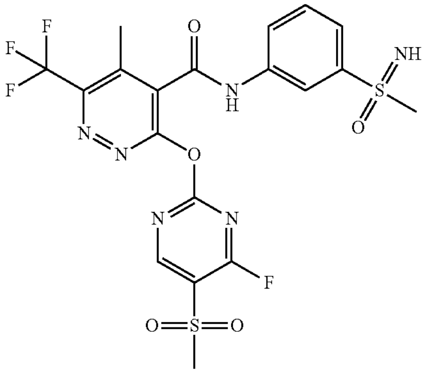 [SMILES: Cc1c(C(F)(F)F)nnc(Oc2ncc(S(C)(=O)=O)c(F)n2)c1C(=O)Nc1cccc(S(C)(=N)=O)c1]
1285
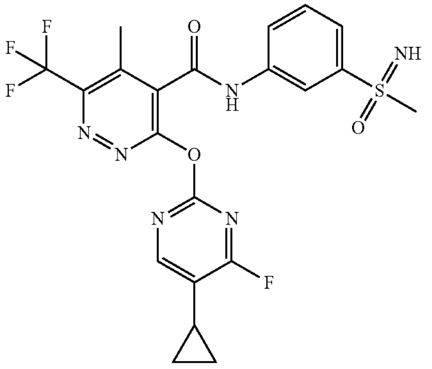 [SMILES: Cc1c(C(F)(F)F)nnc(Oc2ncc(C3CC3)c(F)n2)c1C(=O)Nc1cccc(S(C)(=N)=O)c1]
1286
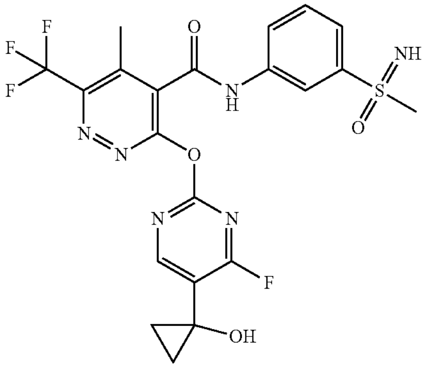 [SMILES: Cc1c(C(F)(F)F)nnc(Oc2ncc(C3(O)CC3)c(F)n2)c1C(=O)Nc1cccc(S(C)(=N)=O)c1]
1287

TABLE 14-continued
1288
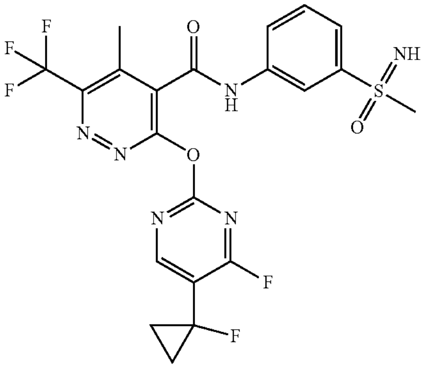
1289
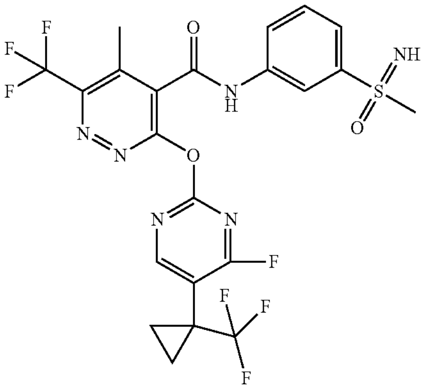 [SMILES: Cc1c(C(F)(F)F)nnc(Oc2ncc(C3(C(F)(F)F)CC3)c(F)n2)c1C(=O)Nc1cccc(S(C)(=N)=O)c1]
1290
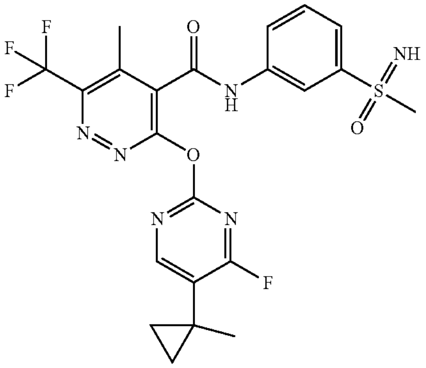 [SMILES: Cc1c(C(F)(F)F)nnc(Oc2ncc(C3(C)CC3)c(F)n2)c1C(=O)Nc1cccc(S(C)(=N)=O)c1]
1291
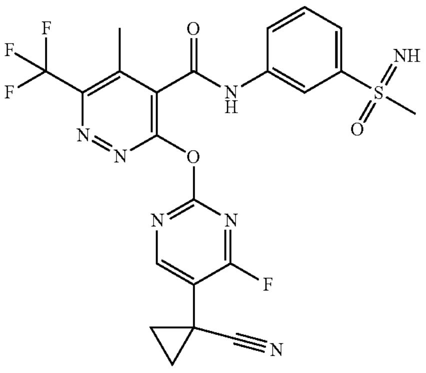 [SMILES: Cc1c(C(F)(F)F)nnc(Oc2ncc(C3(C#N)CC3)c(F)n2)c1C(=O)Nc1cccc(S(C)(=N)=O)c1]
TABLE 14-continued
1292
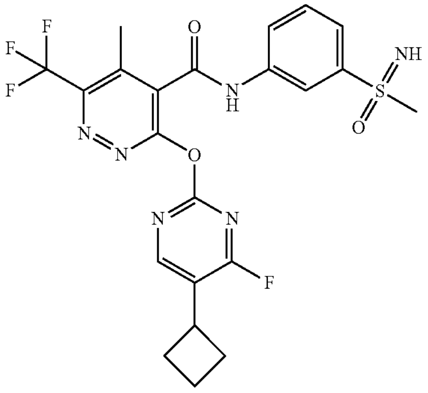 [SMILES: Cc1c(C(F)(F)F)nnc(Oc2ncc(C3CCC3)c(F)n2)c1C(=O)Nc1cccc(S(C)(=N)=O)c1]
1293
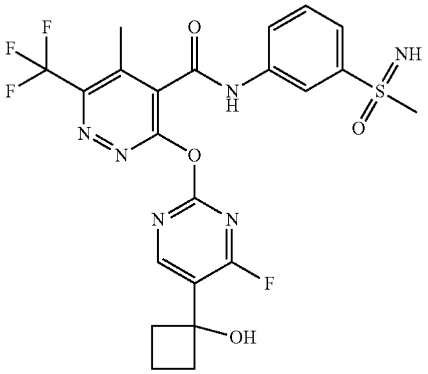 [SMILES: Cc1c(C(F)(F)F)nnc(Oc2ncc(C3(O)CCC3)c(F)n2)c1C(=O)Nc1cccc(S(C)(=N)=O)c1]
1294
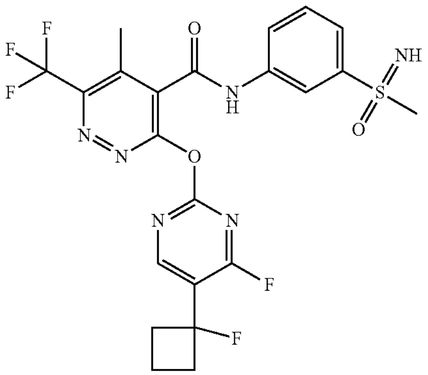 [SMILES: Cc1c(C(F)(F)F)nnc(Oc2ncc(C3(F)CCC3)c(F)n2)c1C(=O)Nc1cccc(S(C)(=N)=O)c1]
1295
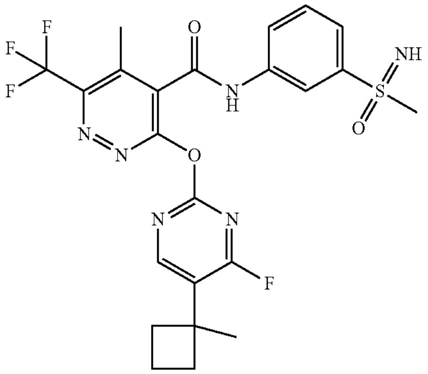 [SMILES: Cc1c(C(F)(F)F)nnc(Oc2ncc(C3(C)CCC3)c(F)n2)c1C(=O)Nc1cccc(S(C)(=N)=O)c1]

TABLE 14-continued
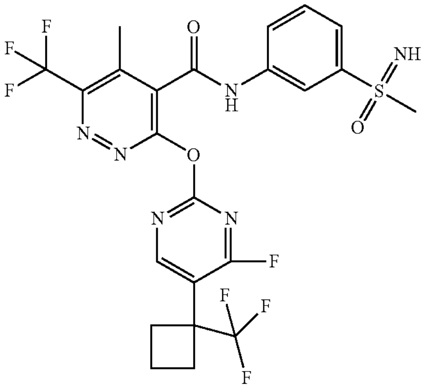 [SMILES: Cc1c(C(F)(F)F)nnc(Oc2ncc(C3(C(F)(F)F)CCC3)c(F)n2)c1C(=O)Nc1cccc(S(C)(=N)=O)c1]
1296
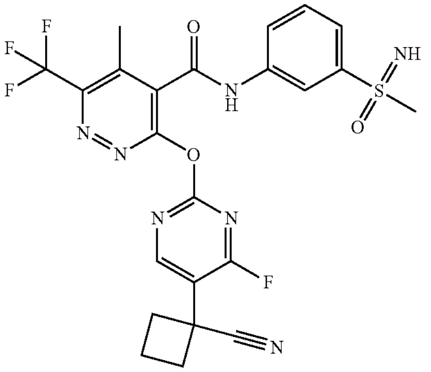
1297
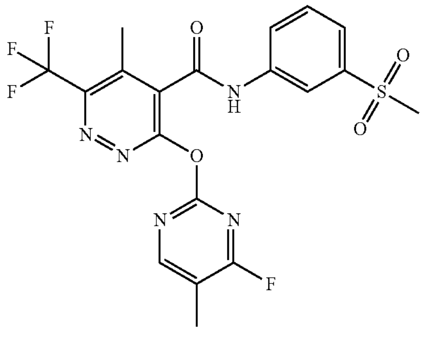 [SMILES: Cc1cnc(Oc2nnc(C(F)(F)F)c(C)c2C(=O)Nc2cccc(S(C)(=O)=O)c2)nc1F]
1298
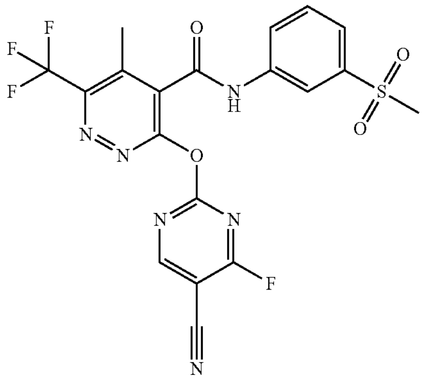 [SMILES: Cc1c(C(F)(F)F)nnc(Oc2ncc(C#N)c(F)n2)c1C(=O)Nc1cccc(S(C)(=O)=O)c1]
1299
TABLE 14-continued
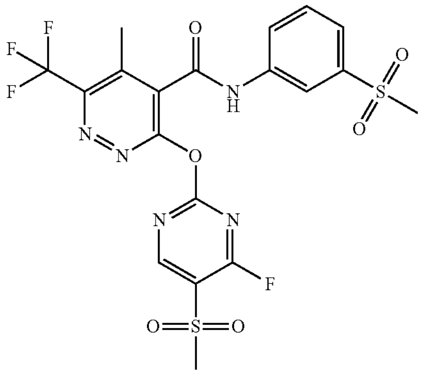 [SMILES: Cc1c(C(F)(F)F)nnc(Oc2ncc(S(C)(=O)=O)c(F)n2)c1C(=O)Nc1cccc(S(C)(=O)=O)c1]
1300
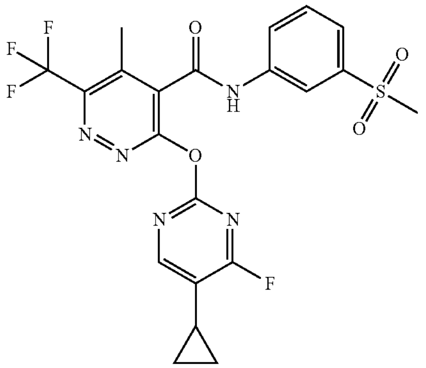 [SMILES: Cc1c(C(F)(F)F)nnc(Oc2ncc(C3CC3)c(F)n2)c1C(=O)Nc1cccc(S(C)(=O)=O)c1]
1301
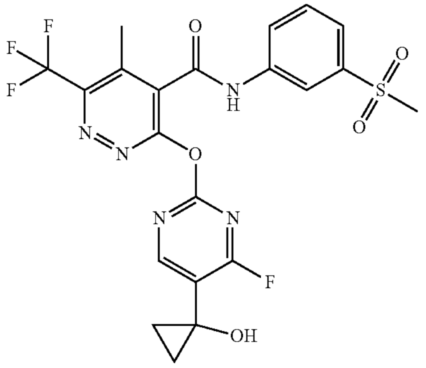 [SMILES: Cc1c(C(F)(F)F)nnc(Oc2ncc(C3(O)CC3)c(F)n2)c1C(=O)Nc1cccc(S(C)(=O)=O)c1]
1302
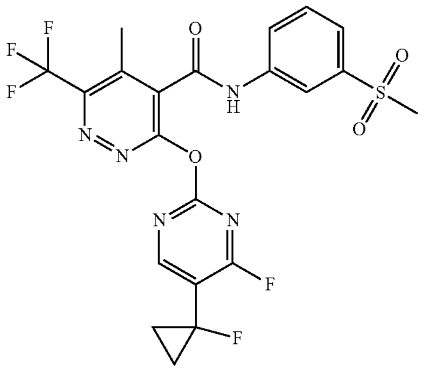 [SMILES: Cc1c(C(F)(F)F)nnc(Oc2ncc(C3(F)CC3)c(F)n2)c1C(=O)Nc1cccc(S(C)(=O)=O)c1]
1303

TABLE 14-continued
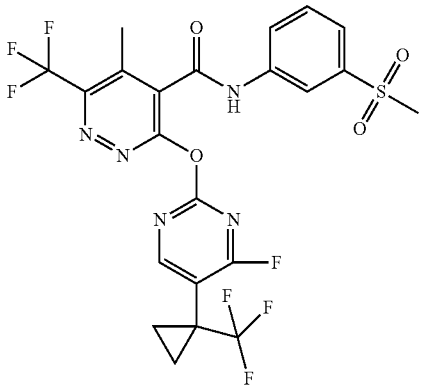 [SMILES: Cc1c(C(F)(F)F)nnc(Oc2ncc(C3(C(F)(F)F)CC3)c(F)n2)c1C(=O)Nc1cccc(S(C)(=O)=O)c1]
1304
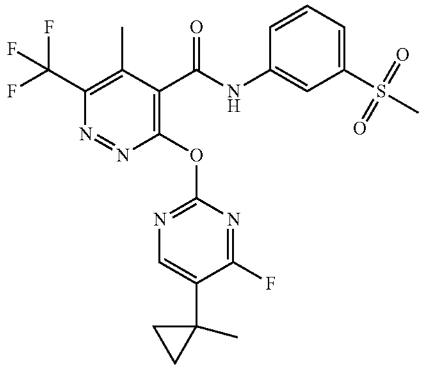 [SMILES: Cc1c(C(F)(F)F)nnc(Oc2ncc(C3(C)CC3)c(F)n2)c1C(=O)Nc1cccc(S(C)(=O)=O)c1]
1305
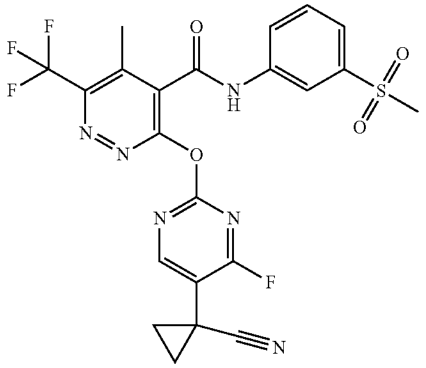 [SMILES: Cc1c(C(F)(F)F)nnc(Oc2ncc(C3(C#N)CC3)c(F)n2)c1C(=O)Nc1cccc(S(C)(=O)=O)c1]
1306
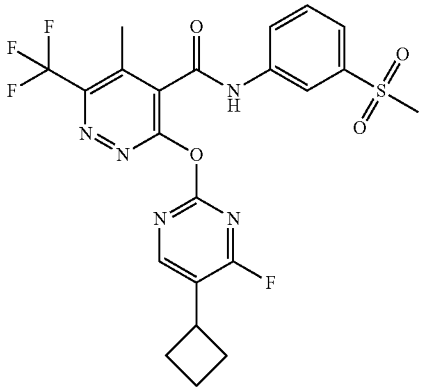 [SMILES: Cc1c(C(F)(F)F)nnc(Oc2ncc(C3CCC3)c(F)n2)c1C(=O)Nc1cccc(S(C)(=O)=O)c1]
1307
TABLE 14-continued
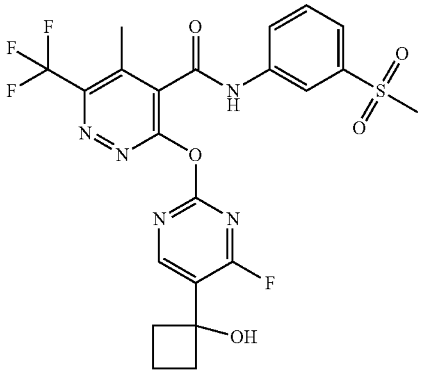 [SMILES: Cc1c(C(F)(F)F)nnc(Oc2ncc(C3(O)CCC3)c(F)n2)c1C(=O)Nc1cccc(S(C)(=O)=O)c1]
1308
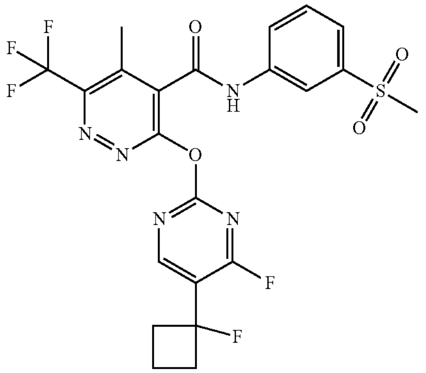 [SMILES: Cc1c(C(F)(F)F)nnc(Oc2ncc(C3(F)CCC3)c(F)n2)c1C(=O)Nc1cccc(S(C)(=O)=O)c1]
1309
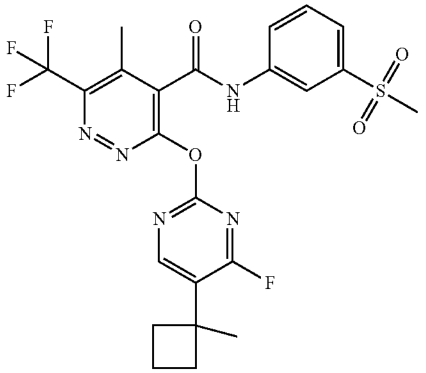
1310
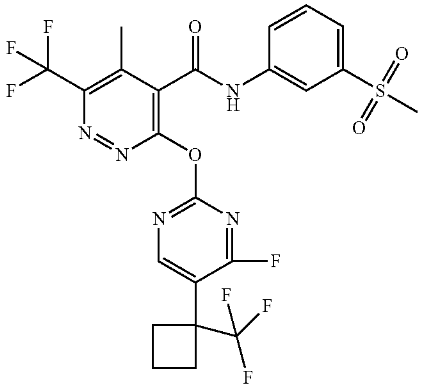 [SMILES: Cc1c(C(F)(F)F)nnc(Oc2ncc(C3(C(F)(F)F)CCC3)c(F)n2)c1C(=O)Nc1cccc(S(C)(=O)=O)c1]
1311

TABLE 14-continued

| | |
|---|---|
| 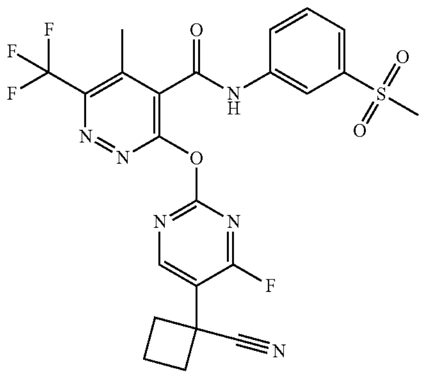 [SMILES: Cc1c(C(F)(F)F)nnc(Oc2ncc(C3(C#N)CCC3)c(F)n2)c1C(=O)Nc1cccc(S(C)(=O)=O)c1] | 1312 |
| 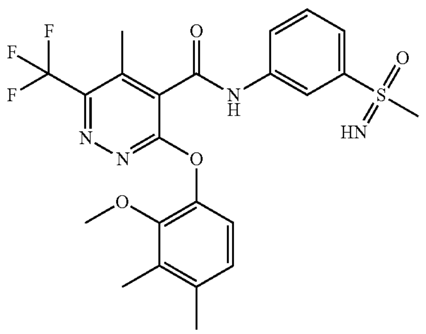 [SMILES: COc1c(Oc2nnc(C(F)(F)F)c(C)c2C(=O)Nc2cccc(S(C)(=N)=O)c2)ccc(C)c1C] | 1313 |

Example 82

General Synthetic Routes for the Synthesis of Substituted Analogs

Compound 1557

Route 1: 2-(4-fluoro-2-methylphenoxy)-4-methyl-N-(3-(S-methylsulfonimidoyl)phenyl)-5-(trifluoromethyl)nicotinamide

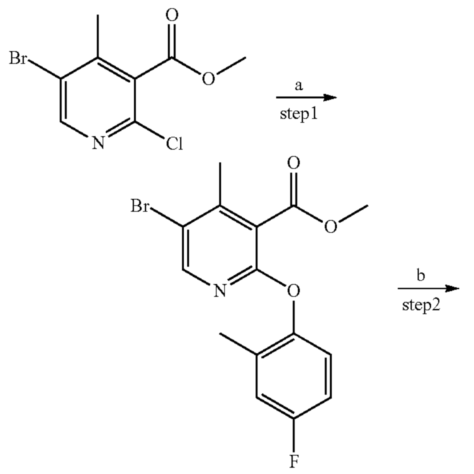

-continued

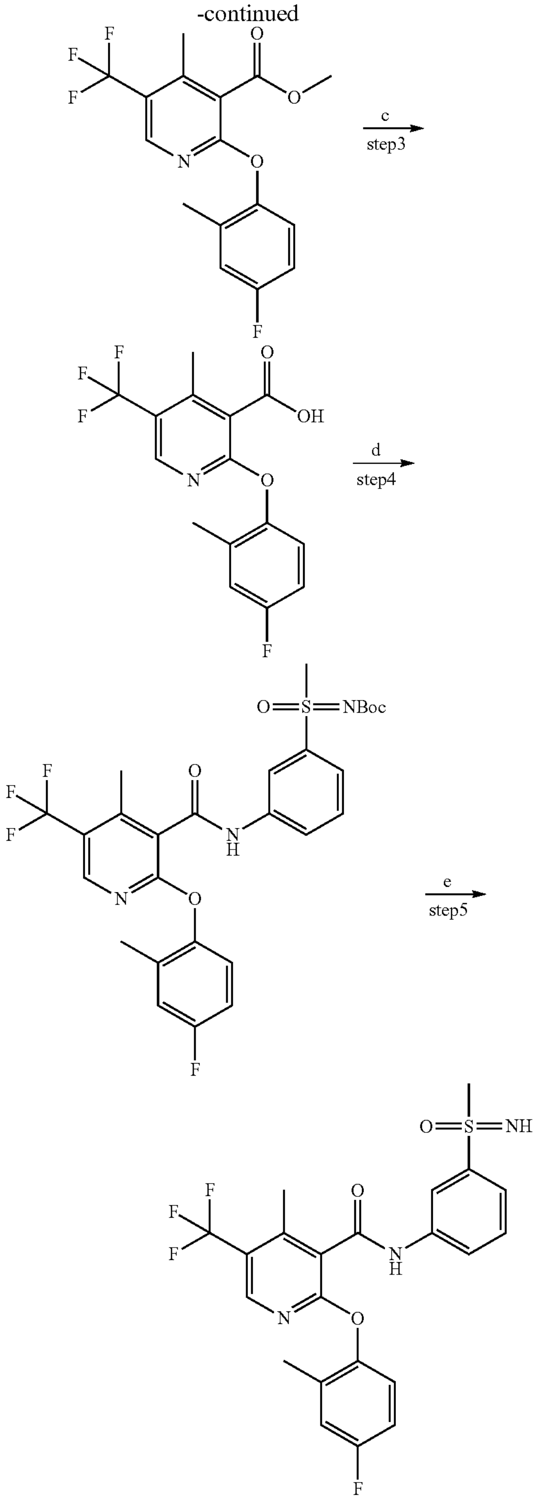

Reagents & conditions:
a) 4-fluoro-2-methylphenol, NaH, DMF;
b) methyl 2,2-difluoro-2-(fluorosulfonyl) acetate, CuI, HMPA, DMF, 160 °C;
c) KOH, MeOH/$H_2O$, 160 °C;
d) tert-butyl ((3-aminophenyl) (methyl)(oxo)-λ6-sulfaneylidene, $POCl_3$, pyr, 0 °C;
e) TFA, DCM Step 1: methyl 5-bromo-2-(4-fluoro-2-methylphenoxy)-4-methylnicotinate: To a solution of 4-fluoro-2-methylphenol (1.08 g, 8.5 mmol) in DMF (7 mL) was added sodium hydride (60%, 0.21 g, 8.5 mmol). The mixture was stirred at room temperature for 0.5 h. Then the mixture was added to a solution of methyl 5-bromo-2-chloro-4-methylpyridine-3-carboxylate (1.5 g, 5.7 mmol) in DMF (8 mL). The mixture was heated at 70 °C for 4 h. LCMS showed the reaction was completed. The resulting solution was quenched with water (80 mL) and extracted with EtOAc (50 mL×3). The combined organic phases were washed with brine, dried over sodium sulfate and concentrated under vacuum. The residue was purified by flash column chromatography on silica gel (PE/EtOAc=2/1) to give methyl 5-bromo-2-(4-fluoro-2-methylphenoxy)-4-methylnicotinate (1.1 g, 49.2% yield). LC-MS: (ESI) calcd. for $C_{15}H_{14}BrFNO_3$ $[M+H]^+$ m/z 356.02, found 355.90.

Step 2: methyl 2-(4-fluoro-2-methylphenoxy)-4-methyl-5-(trifluoromethyl) nicotinate: To a stirred solution of methyl 5-bromo-2-(4-fluoro-2-methylphenoxy)-4-methylpyridine-3-carboxylate (500 mg, 1.41 mmol), HMPA (506 mg, 2.82 mmol) and copper(I) iodide (538 mg, 2.82 mmol) in NMP (10 mL) was added methyl 2,2-difluoro-2-(fluorosulfonyl) acetate (1.36 g, 7.06 mmol) dropwise at 150 °C under an atmosphere of $N_2$. The mixture was heated at 150 °C for 2 h. After the reaction was completed, the resulting solution was diluted with water (60 mL) and extracted with DCM (30 mL×3). The combined organic phases were washed with brine, dried over sodium sulfate, concentrated under vacuum. The residue was purified by flash column chromatography on silica gel (PE/EtOAc=2/1) to give methyl 2-(4-fluoro-2-methylphenoxy)-4-methyl-5-(trifluoromethyl)nicotinate (260 mg, 37.6% yield). LC-MS: (ESI) calcd. for $C_{16}H_{14}F_4NO_3$ $[M+H]^+$ m/z 344.09, found 344.00.

Step 3: 2-(4-fluoro-2-methylphenoxy)-4-methyl-5-(trifluoromethyl)nicotinic acid: To a solution of methyl 2-(4-fluoro-2-methylphenoxy)-4-methyl-5-(trifluoromethyl) nicotinate (250 mg, 0.73 mmol) in MeOH/$H_2O$ (1/1, 4 mL) was added KOH (384 mg, 5.83 mmol) at room temperature. The mixture was heated at 70 °C for 4 hours. After the reaction was completed, the mixture was concentrated to remove most MeOH. The aqueous phase was adjusted to pH=3-4 with 1N HCl then extracted with EtOAc (20 mL×3). The combined organic phases were washed with brine, dried with $Na_2SO_4$, and concentrated under reduced pressure to afford 2-(4-fluoro-2-methylphenoxy)-4-methyl-5-(trifluoromethyl)nicotinic acid (210 mg, 78.8% yield) as a white solid. LC-MS: (ESI) calcd. for $C_{15}H_{12}F_4NO_3$ $[M+H]^+$ m/z 330.08, found 329.95.

Step 4: tert-butyl ((3-(2-(4-fluoro-2-methylphenoxy)-4-methyl-5-(trifluoromethyl) nicotinamido)phenyl)(methyl)(oxo)-$\lambda^6$-sulfaneylidene)carbamate: A mixture of 2-(4-fluoro-2-methylphenoxy)-4-methyl-5-(trifluoromethyl) nicotinic acid (240 mg, 0.73 mmol) and tert-butyl ((3-aminophenyl)(methyl)(oxo)-$\lambda^6$-sulfaneylidene)carbamate (295 mg, 1.09 mmol) in pyridine (5 mL) was added $POCl_3$ (200 μL) dropwise at 0 °C. The reaction solution was stirred at 0 °C for 1 hour. After the reaction was completed, the resulting solution was quenched with water (30 mL) and extracted with EtOAc (30 mL×3). The combined organic phases were washed with brine, dried over sodium sulfate, concentrated under vacuum. The residue was purified by flash column chromatography on silica gel (PE/EtOAc=2/1) to give tert-butyl ((3-(2-(4-fluoro-2-methylphenoxy)-4-methyl-5-(trifluoromethyl)nicotinamido)phenyl)(methyl)(oxo)-$\lambda^6$-sulfaneylidene)carbamate (70 mg, 14.9% yield) as a white solid. LC-MS: (ESI) calcd. for $C_{27}H_{28}F_4N_3O_5S$ $[M+H]^+$ m/z 582.17, found 582.15.

Step 5: 2-(4-fluoro-2-methylphenoxy)-4-methyl-N-(3-(S-methylsulfonimidoyl)phenyl)-5-(trifluoromethyl)nicotinamide: A solution of tert-butyl ((3-(2-(4-fluoro-2-methylphenoxy)-4-methyl-5-(trifluoromethyl) nicotinamido)phenyl)(methyl)(oxo)-λ6-sulfaneylidene)carbamate (70 mg, 0.12 mmol) in DCM (1.5 mL) was added TFA (0.5 mL) at room temperature. The reaction mixture was stirred at room temperature for 2 hours. After the reaction was completed, the mixture was concentrated. The residue was dissolved in THF (2 mL) then adjusted to pH=8-9 with saturated aqueous $NaHCO_3$. The resulting solution was extracted with DCM (10 mL×3). The combined organic phases were washed with brine, dried over sodium sulfate, concentrated under vacuum. The residue was purified by prep-HPLC (Gemini 5 um $C_{18}$ column, 150*21.2 mm, eluting with 40% to 85% MeCN/$H_2O$ containing 0.1% FA) to provide 2-(4-fluoro-2-methylphenoxy)-4-methyl-N-(3-(S-methylsulfonimidoyl)phenyl)-5-(trifluoromethyl)nicotinamide (32.1 mg, 52%) as a white solid. $^1H$ NMR (400 MHz, DMSO-$d_6$, ppm) δ 11.17 (s, 1H), 8.52 (s, 1H), 8.41 (s, 1H), 7.89 (d, J=8.0 Hz, 1H), 7.70 (d, J=7.8 Hz, 1H), 7.61 (t, J=7.9 Hz, 1H), 7.19 (dd, J=8.6, 5.2 Hz, 2H), 7.09 (td, J=8.5, 2.9 Hz, 1H), 4.24 (s, 1H), 3.07 (s, 3H), 2.48 (s, 3H), 2.08 (s, 3H). LC-MS: (ESI) calcd. for $C_{22}H_{20}F_4N_3O_3S$ $[M+H]^+$ m/z 482.12, found 482.00.

Route 2: 2-(4-fluoro-2-methylphenoxy)-4-methyl-N-(3-(S-methylsulfonimidoyl)phenyl)-5-(trifluoromethyl)nicotinamide

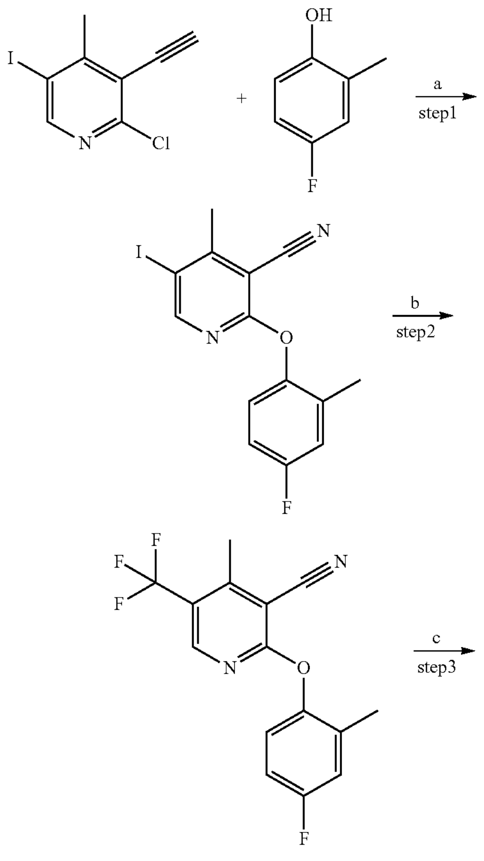

-continued

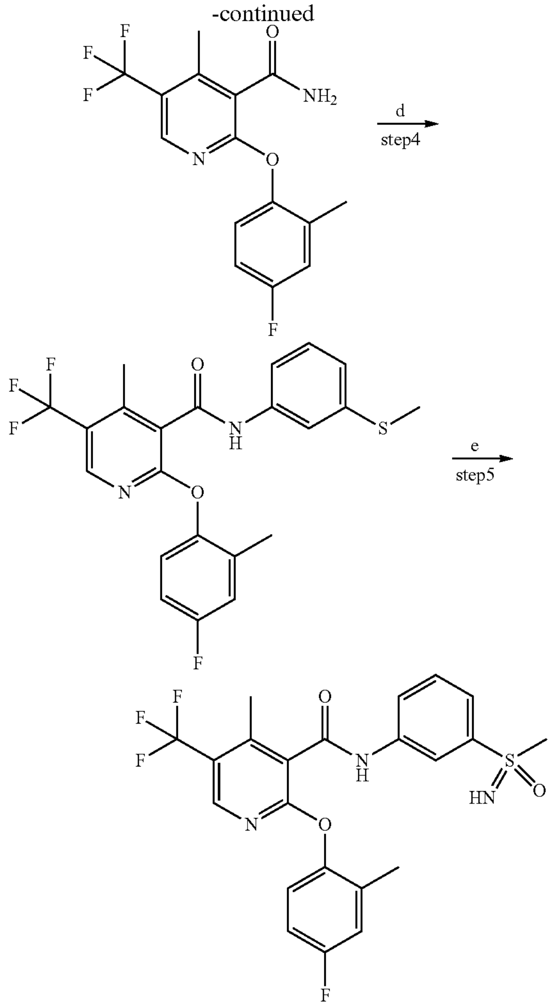

Reagents & conditions:
a) $K_2CO_3$, acetonitrile, 60 °C;
b) methyl difluoro(fluorosulfonyl) acetate, CuI, TBAI, DMF, 70 °C;
c) barium hydroxide, $H_2O$, 90° C.,70 h;
d) 1-bromo-3-(methylsulfanyl)benzene, $Pd_2(dba)_3$, XantPhos, 1,4-dioxane, 100 °C; bis(acetoxy)iodobenzene, $(NH_4)CO_3$, MeOH.

Step 1: 2-(4-fluoro-2-methyl-phenoxy)-5-iodo-4-methyl-pyridine-3-carbonitrile: A mixture of 4-fluoro-2-methyl-phenol (533 mg, 4.22 mmol), 2-chloro-5-iodo-4-methyl-pyridine-3-carbonitrile (980 mg, 3.52 mmol) and $K_2CO_3$ (584 mg, 4.22 mmol) in acetonitrile (5 mL) was stirred at 60 °C for 16 h. The reaction mixture was retreated with 4-fluoro-2-methyl-phenol (533 mg, 4.22 mmol) and stirred at 60 °C for a further 6 h. The reaction was cooled to room temperature, filtered and washed with MeCN (20 mL). Filtrate was concentrated in vacuo to obtain the crude residue. Purification by chromatography on silica (Biotage Isolera, 50 g Sfar Duo column) eluting with a gradient of 0 to 13% EtOAc in heptane afforded 2-(4-fluoro-2-methyl-phenoxy)-5-iodo-4-methyl-pyridine-3-carbonitrile (94.0%) (930 mg, 2.37 mmol, 67%) as a white solid. $^1H$ NMR (400 MHz, DMSO-$d_6$) δ 8.60 (s, 1H), 7.25-7.18 (m, 2H), 7.14-7.05 (m, 1H), 2.62 (s, 3H), 2.08 (s, 3H). m/z: 369.1 $[M+H]^+$, (ESI+), RT=1.04 LCMS Method 2

Step 2: 2-(4-fluoro-2-methyl-phenoxy)-4-methyl-5-(trifluoromethyl)pyridine-3-carbonitrile: To a mixture of 2-(4-fluoro-2-methyl-phenoxy)-5-iodo-4-methyl-pyridine-3-carbonitrile (94%, 930 mg, 2.37 mmol), iodocopper (682 mg, 3.56 mmol), and tetrabutylammonium; iodide (352 mg, 0.950 mmol) in DMF (10 mL), methyl difluoro(fluorosulfonyl)acetate (2281 mg, 11.9 mmol) was added and stirred at 70 °C for 16 h. The reaction was cooled to rt, filtered and washed with EtOAc (2×10 mL). The filtrate was washed with brine (20 mL), dried over $MgSO_4$, filtered and concentrated under reduced pressure to obtain the crude residue. Purification by chromatography on silica (Biotage Isolera, 50 g Sfar Duo column) eluting with a gradient of 0 to 5% EtOAc in heptane afforded 2-(4-fluoro-2-methyl-phenoxy)-4-methyl-5-(trifluoromethyl)pyridine-3-carbonitrile (533 mg, 1.39 mmol, 59% Yield) as a yellow solid. $^1H$ NMR (500 MHz, DMSO-$d_6$) δ 8.66 (s, 1H), 7.29-7.22 (m, 2H), 7.13 (td, J=8.5, 3.2 Hz, 1H), 2.70-2.66 (m, 3H), 2.10 (s, 3H). m/z: 311.3 $[M+H]^+$, (ESI+), RT=1.02 LCMS Method 2

Step 3: 2-(4-fluoro-2-methyl-phenoxy)-4-methyl-5-(trifluoromethyl)pyridine-3-carboxamide: 2-(4-fluoro-2-methyl-phenoxy)-4-methyl-5-(trifluoromethyl)pyridine-3-carbonitrile (533 mg, 1.39 mmol) was suspended in water (4 mL) and barium hydroxide (1.19 g, 6.96 mmol) was added. The resulting mixture was stirred at 90 °C for 16 h. The reaction mixture was diluted with water (4 mL) and retreated with barium hydroxide (1.19 g, 6.96 mmol). Stirring at 90 °C resumed for a total of 70 h. The cooled reaction mixture was diluted with water (50 mL) and acidified to pH 1 using 5M HCl. The aqueous was extracted with EtOAc (3×15 mL) and the combined organics were dried over $MgSO_4$ and concentrated under reduced pressure. The crude product was purified by FCC (Biotage Isolera 4, 10 g Sfar Duo, lambda-all collect) using a 0-50-100% EtOAc/heptane followed by a 0-20% MeOH/EtOAc gradient. Product fractions were combined and concentrated under reduced pressure to afford 2-(4-fluoro-2-methyl-phenoxy)-4-methyl-5-(trifluoromethyl)pyridine-3-carboxamide (98.0%) (220 mg, 47%) as a white powder. $^1H$ NMR (400 MHz, DMSO-$d_6$) δ 8.39 (s, 1H), 8.16 (br.s, 1H), 7.90 (br.s, 1H), 7.21-7.04 (m, 3H), 2.42 (s, 3H), 2.07 (s, 3H). m/z: 329.1 $[M+H]^+$, (ESI+), RT=0.81 LCMS Method 2.

Step 4: 2-(4-fluoro-2-methyl-phenoxy)-4-methyl-N-(3-methylsulfanylphenyl)-5-(trifluoromethyl)pyridine-3-carboxamide: To a degassed solution of 2-(4-fluoro-2-methyl-phenoxy)-4-methyl-5-(trifluoromethyl)pyridine-3-carboxamide (98%, 200 mg, 0.597 mmol), 1-bromo-3-(methylsulfanyl)benzene (97 uL, 0.719 mmol) and caesium carbonate (584 mg, 1.79 mmol) in 1,4-Dioxane-Anhydrous (3 mL) was added (1E,4E)-1,5-diphenylpenta-1,4-dien-3-one-palladium (3:2) $Pd_2(dba)_3$ (27 mg, 0.0295 mmol) and (9,9-dimethyl-9H-xanthene-4,5-diyl)bis(diphenylphosphane [XantPhos] (35 mg, 0.0605 mmol). The reaction was degassed for a further 5 minutes then the vial sealed and stirred at 100 °C for 4 hours. The cooled reaction mixture was diluted with EtOAc (5 mL) and filtered through a pad of Celite. The Celite was washed with EtOAc (2×3 mL) and the combined filtrate washed with sat. aq. sodium bicarbonate solution (10 mL), followed by brine (10 mL). The organic phase was dried using a phase separation cartridge and concentrated under vacuum to give 352 mg as a yellow solid. The crude product was purified by column chromatography (Sfar Duo 10 g, eluting in 0-100% EtOAc in heptanes, lambda-all collection). Product fractions were combined and concentrated under reduced pressure to give the desired product, 2-(4-fluoro-2-methyl-phenoxy)-4-methyl-N-(3-methylsulfanylphenyl)-5-(trifluoromethyl) pyridine-3-carboxamide (72.0%) (240 mg, 0.384 mmol, 64%) as a pale yellow powder. $^1H$ NMR (500 MHz, DMSO-$d_6$) δ 10.83 (s, 1H), 8.50 (s, 1H), 7.70 (t, J=1.9 Hz, 1H), 7.47-7.43 (m, 1H), 7.31 (t, J=8.0 Hz, 1H), 7.21-7.16 (m, 2H), 7.09 (td, J=8.5, 2.9 Hz, 1H), 7.04 (ddd, J=7.9, 1.8, 0.9 Hz, 1H), 2.48-2.44 (m, 6H), 2.08 (s, 3H). m/z: 451.1 $[M+H]^+$, (ESI+), RT=1.09 LCMS Method 2.

Step 5: 2-(4-fluoro-2-methyl-phenoxy)-4-methyl-N-[3-(methylsulfonimidoyl)phenyl]-5-(trifluoromethyl)pyridine-3-carboxamide: To a solution of 2-(4-fluoro-2-methyl-phenoxy)-4-methyl-N-(3-methylsulfanylphenyl)-5-(trifluoromethyl)pyridine-3-carboxamide (72%, 240 mg, 0.384 mmol) in Methanol (7.5 mL), bis(acetoxy)iodobenzene (395 mg, 1.23 mmol) and ammonium carbonate (75 mg, 0.797 mmol) were added and the reaction was stirred at rt for 15 h. The reaction mixture was retreated with bis(acetoxy)iodobenzene (132 mg, 0.410 mmol) and ammonium carbonate (25 mg, 0.266 mmol) and stirred for 2 h then left to stand over the weekend at ambient temperature. Stirring was resumed for 1 h before work-up. The reaction mixture was concentrated under reduced pressure and the resulting residue purified by column chromatography using 0-100% EtOAc in heptane followed by 0-20% MeOH in EtOAc (on a Biotage Sfar Duo 10 g column, lambda-all collection). The resulting residue was dried in a vacuum oven at 40 °C for 2 h to afford 2-(4-fluoro-2-methyl-phenoxy)-4-methyl-N-[3-(methylsulfonimidoyl)phenyl]-5-(trifluoromethyl)pyridine-3-carboxamide (95.0%) (98 mg, 0.193 mmol, 50%) as an off-white powder. $^1H$ NMR (400 MHz, DMSO-$d_6$) δ 11.17 (s, 1H), 8.51 (s, 1H), 8.44-8.37 (m, 1H), 7.92-7.84 (m, 1H), 7.72-7.67 (m, 1H), 7.61 (t, J=7.9 Hz, 1H), 7.22-7.15 (m, 2H), 7.09 (td, J=8.5, 3.0 Hz, 1H), 4.23 (s, 1H), 3.07 (s, 3H), 2.49-2.47 (m, 3H), 2.08 (s, 3H). m/z: 482.2 $[M+H]^+$, (ESI+), RT=3.12 LCMS Method 4.

Example 83

Compound 1558: 5-chloro-2-(4-fluoro-2-methylphenoxy)-4-methyl-N-(3-(S-methylsulfonimidoyl)phenyl)nicotinamide

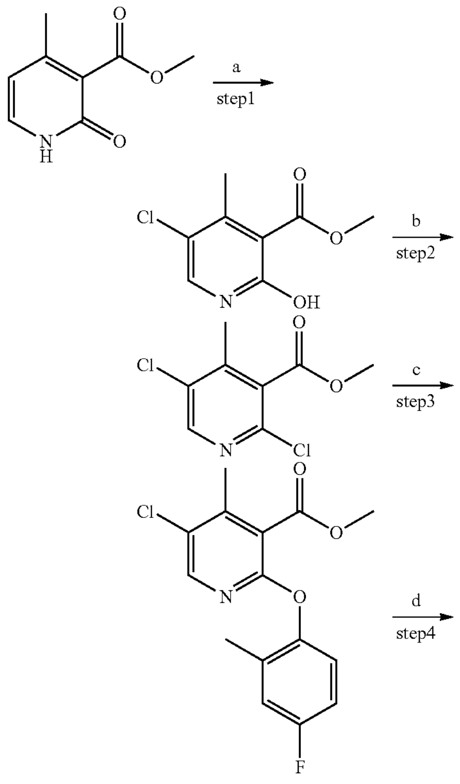

-continued

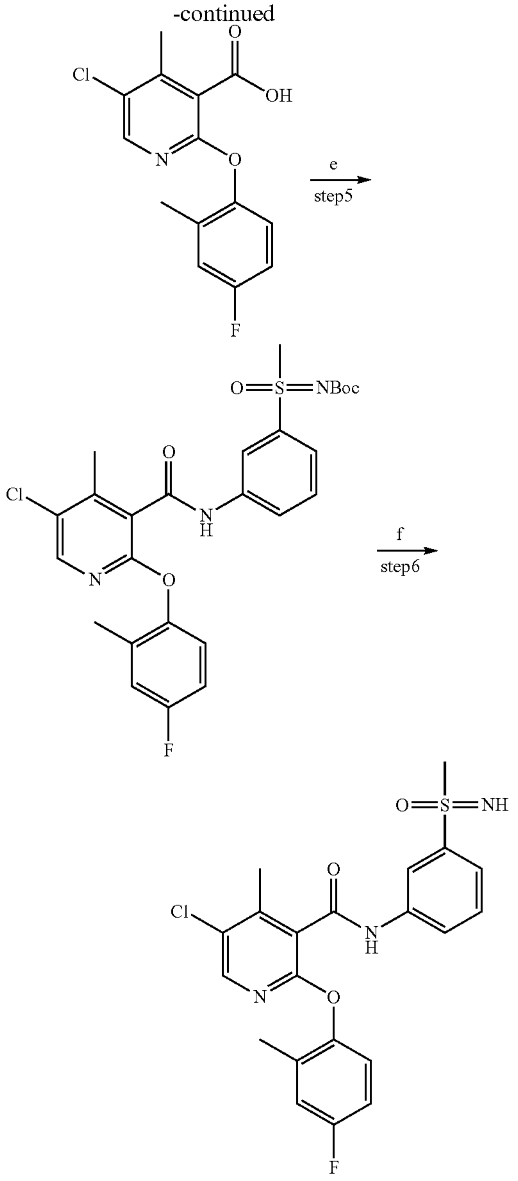

Reagents & conditions:
a) NCS, DCM, 0 °C;
b) $PhOPOCl_2$, 170 °C;
c) 4-fluoro-2-methylphenol, NaH, DMF, 70 °C;
d) KOH, $MeOH/H_2O$, 60 °C;
e) tert-butyl ((3-aminophenyl) (methyl)(oxo)-$\lambda^6$-sulfaneylidene)carbamate, $SOCl_2$, 50 °C; then DIPEA, DCM, 0 °C;
f) TFA, DCM Step 1: methyl 5-chloro-2-hydroxy-4-methylnicotinate: To a solution of methyl 4-methyl-2-oxo-1,2-dihydropyridine-3-carboxylate (5.0 g, 30 mmol) in DCM (50 mL) was added NCS (4.0 g, 30 mmol) at 0 °C. The mixture was stirred at the same temperature for 60 minutes. The mixture was quenched with water (50 mL) and extracted with DCM (50 mL×2). The combine organic phases were washed with brine, dried over sodium sulfate, concentrated under vacuum. The residue was purified by triturate with (PE/EtOAc=3/1) to provide methyl 5-chloro-2-hydroxy-4-methylnicotinate (4 g, 66% yield) as a light brown solid. LC-MS: (ESI) calcd. for $C_8H_9ClNO_3$ $[M+H]^+$ m/z 202.02, found 202.0.

Step 2: methyl 2,5-dichloro-4-methylnicotinate: A solution of methyl 5-chloro-2-hydroxy-4-methylnicotinate (2.0 g, 10 mmol) in phenyl dichlorophosphate (10 mL) was heated to 170 °C for 2 h. The resulting solution was cooled to room temperature, quenched with water (50 mL) and extracted with EtOAc (30 mL×3). The combined organic phases were washed with brine, dried over sodium sulfate, concentrated under vacuum. The residue was purified by flash column chromatography on silica gel (PE/EtOAc=10/1) to provide methyl 2,5-dichloro-4-methylnicotinate (1 g, 45% yield) as a light-yellow oil. LC-MS: (ESI) calcd. for $C_8H_8Cl_2NO_2$ $[M+H]^+$ m/z 219.99, found 220.0.

Step 3: methyl 5-chloro-2-(4-fluoro-2-methylphenoxy)-4-methylnicotinate: To a solution of 4-fluoro-2-methylphenol (286 mg, 2.27 mmol) in DMF (5 mL) was added NaH (60%, 110 mg, 2.72 mmol) at 0 °C. The mixture was stirred at the same temperature for 60 minutes, then 2,5-dichloro-4-methylnicotinate (500 mg, 2.27 mmol) was added. The mixture was heated at 70 °C for 16 hours. The resulting mixture was quenched with water (20 mL) and extracted with DCM (50 mL×2). The combine organic phases were washed with brine, dried over sodium sulfate, concentrated under vacuum. The residue was purified column chromatography on silica gel (PE/EtOAc=3/1) to provide methyl 5-chloro-2-(4-fluoro-2-methylphenoxy)-4-methylnicotinate (250 mg, 35% yield) as a light-yellow oil. $^1H$ NMR (400 MHz, $CDCl_3$, ppm) δ 8.05 (s, 1H), 7.06-6.76 (m, 3H), 3.98 (s, 3H), 2.39 (s, 3H), 2.13 (s, 3H).

Step 4: 5-chloro-2-(4-fluoro-2-methylphenoxy)-4-methylnicotinic acid: To a solution of methyl 5-chloro-2-(4-fluoro-2-methylphenoxy)-4-methylnicotinate (250 mg, 0.81 mmol) in MeOH (5 mL) was added a solution of KOH (453 mg, 8.1 mmol) in water (2 mL). The solution was heated at 60 °C for 16 h. The resulting mixture was adjusted to pH=3-4 with 1N HCl and extracted with EtOAc (30 mL×2). The combine organic phases were washed with brine, dried over sodium sulfate, concentrated under vacuum to provide 5-chloro-2-(4-fluoro-2-methylphenoxy)-4-methylnicotinic acid (150 mg, 63% yield) as a white solid. LC-MS: (ESI) calcd. for $C_{14}H_{12}ClFNO_3$ $[M+H]^+$ m/z 296.04, found 296.0.

Step 5: tert-butyl ((3-(5-chloro-2-(4-fluoro-2-methylphenoxy)-4-methylnicotinamido) phenyl)(methyl)(oxo)-λ6-sulfaneylidene)carbamate: A solution of 5-chloro-2-(4-fluoro-2-methylphenoxy)-4-methylnicotinic acid (100 mg, 0.34 mmol) in $SOC_2$ (1 mL) was heated to 50 °C and stirred for 0.5 hour. The solution was concentrated under vacuum to provide the chloride intermediate. Then the chloride intermediate was added to a stirred solution of tert-butyl ((3-aminophenyl)(methyl)(oxo)-$\lambda^6$-sulfaneylidene) carbamate (92 mg, 0.34 mmol) and DIPEA (88 mg, 0.68 mmol) in DCM (2 mL) at 0 °C. The resulting mixture was stirred at 25 °C for 1 h. Then the mixture was quenched with water (10 mL) and extracted with DCM (10 mL×2). The combined organic phases were washed with brine, dried over sodium sulfate, concentrated under vacuum. The residue was purified by flash column chromatography on silica gel (PE/EtOAc=1/1) to provide tert-butyl ((3-(5-chloro-2-(4-fluoro-2-methylphenoxy)-4-methylnicotinamido)phenyl)(methyl)(oxo)-$\lambda^6$-sulfaneylidene)carbamate (80 mg, 43% yield) as a white oil. LC-MS: (ESI) calcd. for $C_{26}H_{28}ClFN_3O_5S$ $[M+H]^+$ m/z 548.13, found 548.0.

Step 6: Preparation of 5-chloro-2-(4-fluoro-2-methylphenoxy)-4-methyl-N-(3-(S-methylsulfonimidoyl)phenyl)nicotinamide: To a solution of tert-butyl ((3-(5-chloro-2-(4-fluoro-2-methylphenoxy)-4-methylnicotinamido)phenyl) (methyl)(oxo)-sulfaneylidene) carbamate (80 mg, 0.14 mmol) in DCM (5 mL) was added TFA (1 mL) at 0 °C. The mixture was stirred at 25 °C for 1 hour. The resulting mixture was adjusted to pH=8-9 with saturated aqueous $NaHCO_3$ and extracted with DCM (10 mL×2). The combined organic phases were washed with brine, dried over sodium sulfate, concentrated under vacuum and the residue was purified by prep-HPLC (Gemini 5 um $C_{18}$ column, 150*21.2 mm, eluting with 30% to 90% $MeCN/H_2O$ containing 0.1% FA) to afford 5-chloro-2-(4-fluoro-2-methylphenoxy)-4-methyl-N-(3-(S-methylsulfonimidoyl)phenyl)nicotinamide (25 mg, 38%) as a white solid. $^1H$ NMR (400 MHz, DMSO-$d_6$, ppm) δ 11.09 (s, 1H), 8.41 (s, 1H), 8.22 (s, 1H), 7.88 (d, J=8.1 Hz, 1H), 7.69 (d, J=7.9 Hz, 1H), 7.60 (t, J=7.9 Hz, 1H), 7.16 (dd, J=8.8, 4.6 Hz, 2H), 7.10-7.03 (m, 1H), 4.23 (s, 1H), 3.06 (s, 3H), 2.39 (s, 3H), 2.08 (s, 3H). LC-MS: (ESI) calcd. for $C_{21}H_{20}ClFN_3O_3S$ $[M+H]^+$ m/z 448.08, found 448.05.

Example 84

Compound 1559: (R)-2-((6-fluoro-2-methylpyridin-3-yl)oxy)-4-methyl-N-(3-(S-methylsulfonimidoyl) phenyl)-5-(trifluoromethyl)nicotinamide

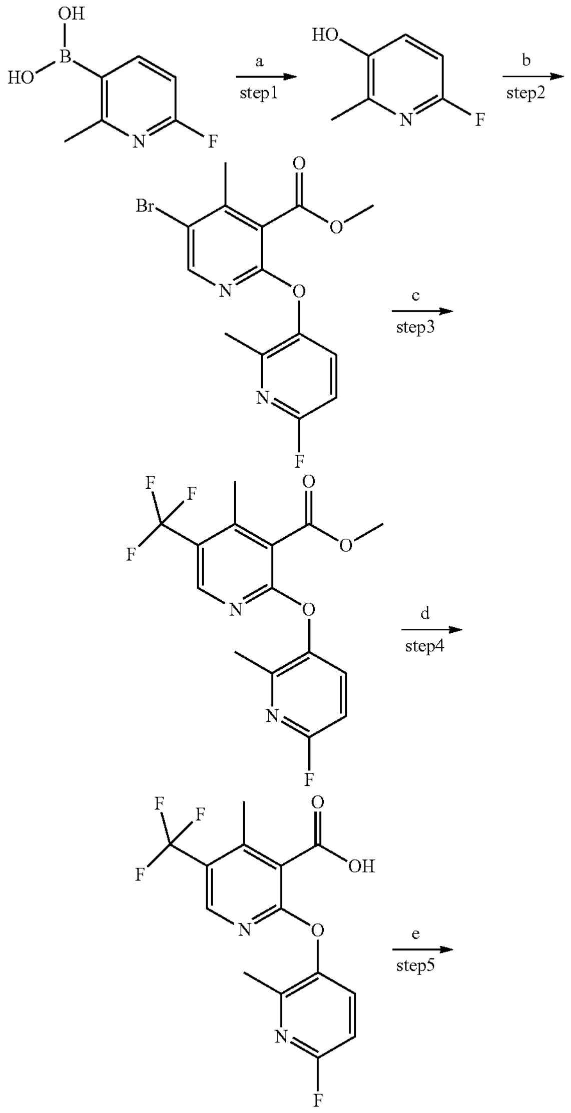

-continued

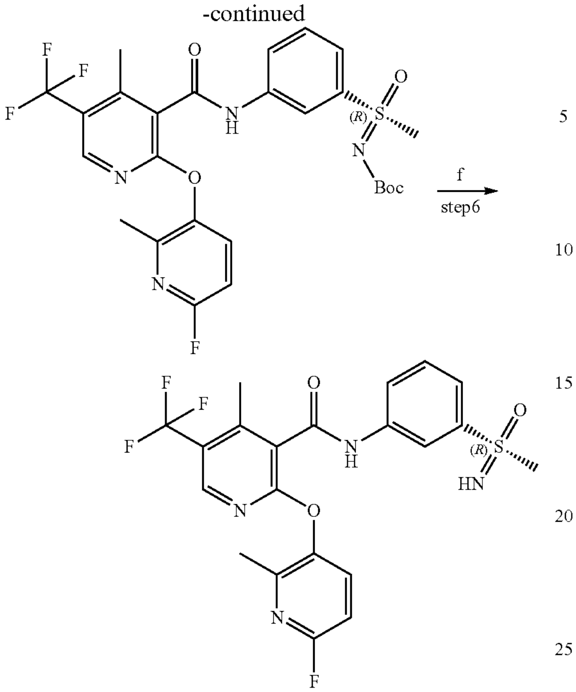

Reagents & conditions:

a) $H_2O_2$, NaOH, THF/$H_2O$;

b) methyl 5-bromo-2-chloro-4-methylnicotinate, NaH, DMF, 70 °C;

c) methyl 2,2-difluoro-2-(fluorosulfonyl) acetate, CuI, HMPA, DMF, 160 °C;

d) KOH, MeOH/$H_2O$, 70 °C;

e) (R)-tert-butyl ((3-aminophenyl)(methyl)(oxo)-λ$^6$-sulfaneylidene)carbamate, $SOCl_2$, DIPEA, DCM;

f) TFA, DCM

Step 1: 6-fluoro-2-methylpyridin-3-ol: To a solution of (6-fluoro-2-methylpyridin-3-yl)boronic acid (2.5 g, 16.12 mmol) in THF (20 mL) was added NaOH (516 mg, 12.89 mmol), $H_2O$ (5 mL) and $H_2O_2$ (1 mL, 30%) at 0 °C. The mixture was stirred at room temperature for 1 h. Then the mixture was adjusted to pH=3-4 with 1N HCl and extracted with EtOAc (20 mL×3). The combined organic phases were washed with brine, dried over sodium sulfate, concentrated under vacuum. The residue was purified by flash column chromatography on silica gel (PE/EtOAc=3/1) to give 6-fluoro-2-methylpyridin-3-ol (1.8 g, 70.59% yield) as a yellow solid. L-CMS: (ESI) calcd. for $C_6H_6FNO$ $[M+H]^+$ m/z 128.05, found 128.15.

Step 2: methyl 5-bromo-2-((6-fluoro-2-methylpyridin-3-yl)oxy)-4-methylnicotinate: To a solution of 6-fluoro-2-methylpyridin-3-ol (1.50 g, 11.81 mmol) in DMF (8 mL) was added sodium hydride (60%, 977 mg, 23.62 mmol) at 0 °C. The mixture was stirred at room temperature for 0.5 h. Then the mixture was added to a stirred solution of methyl 5-bromo-2-chloro-4-methylnicotinate (2.08 g, 7.91 mmol) in DMF (8 mL). The mixture was heated at 70 °C for 4 h. LCMS showed the reaction was completed. The resulting solution was quenched with water (80 mL) and extracted with EtOAc (50 mL×3). The combined organic phases were washed with brine, dried over sodium sulfate, and concentrated under vacuum. The residue was purified by flash column chromatography on silica gel (PE/EtOAc=2/1) to give methyl 5-bromo-2-((6-fluoro-2-methylpyridin-3-yl)oxy)-4-methylnicotinate (0.71 g, 16.9% yield). LC-MS: (ESI) calcd. for $C_{14}H_{13}BrFN_2O_3[M+H]^+$ m/z 355.01, found 354.95.

Step 3: methyl 2-((6-fluoro-2-methylpyridin-3-yl)oxy)-4-methyl-5-(trifluoromethyl)nicotinate: To a stirred solution of methyl 5-bromo-2-((6-fluoro-2-methylpyridin-3-yl)oxy)-4-methylnicotinate (650 mg, 1.84 mmol), HMPA (658 mg, 3.68 mmol) and copper (I) iodide (703 mg, 3.68 mmol) in NMP (10 mL) was added methyl 2,2-difluoro-2-(fluorosulfonyl) acetate (3.53 g, 18.4 mmol) dropwise at 150 °C under an atmosphere of $N_2$. The mixture was heated at 150 °C for 2 h. After the reaction was completed, the resulting solution was diluted with water (60 mL) and extracted with DCM (30 mL×3). The combined organic phases were washed with brine, dried over sodium sulfate, concentrated under vacuum. The residue was purified by flash column chromatography on silica gel (PE/EtOAc=2/1) to afford methyl 2-((6-fluoro-2-methylpyridin-3-yl)oxy)-4-methyl-5-(trifluoromethyl)nicotinate (330 mg, 51.9% yield). LC-MS: (ESI) calcd. for $C_{15}H_{13}F_4N_2O_3[M+H]^+$ m/z 345.09, found 345.05.

Step 4: 2-((6-fluoro-2-methylpyridin-3-yl)oxy)-4-methyl-5-(trifluoromethyl)nicotinic acid: To a solution of methyl 2-((6-fluoro-2-methylpyridin-3-yl)oxy)-4-methyl-5-(trifluoromethyl)nicotinate (300 mg, 0.87 mmol) in THF/$H_2O$ (1/1, 4 mL) was added KOH (487 mg, 8.69 mmol) at room temperature. The mixture was heated at 70 °C for 4 hours. After the reaction was completed, the mixture was concentrated to remove most THF. The aqueous phase was adjusted to pH=3-4 with 1N HCl then extracted with EtOAc (20 mL×3). The combined organic phases were washed with brine, dried with $Na_2SO_4$, and concentrated under reduced pressure to afford 2-((6-fluoro-2-methylpyridin-3-yl)oxy)-4-methyl-5-(trifluoromethyl)nicotinic acid (280 mg, 97.2%) as a white solid. LC-MS: (ESI) calcd. for $C_{14}H_{11}F_4N_2O_3[M+H]^+$ m/z 331.07, found 331.00.

Step 5: tert-butyl (R)-((3-(2-((6-fluoro-2-methylpyridin-3-yl)oxy)-4-methyl-5-(trifluoromethyl) nicotinamido)phenyl)(methyl)(oxo)-λ$^6$-sulfaneylidene)carbamate: A solution of 2-((6-fluoro-2-methylpyridin-3-yl)oxy)-4-methyl-5-(trifluoromethyl)nicotinic acid (120 mg, 0.36 mmol) in $SOCl_2$ (1 mL) was heated to 50 °C and stirred for 0.5 h. The solution was concentrated under vacuum to provide the chloride intermediate. Then the chloride intermediate was added to a stirred solution of tert-butyl (R)-((3-aminophenyl)(methyl)(oxo)-λ$^6$-sulfaneylidene)carbamate (117 mg, 0.43 mmol) and DIEA (88 mg, 0.68 mmol) in DCM (2 mL) at 0 °C. The resulting mixture was stirred at 25 °C for 1 h. Then the mixture was quenched with water (10 mL) and extracted with DCM (10 mL×2). The combined organic phases were washed with brine, dried over sodium sulfate, concentrated under vacuum. The residue was purified by flash column chromatography on silica gel (PE/EtOAc=1/1) to provide tert-butyl (R)-((3-(2-((6-fluoro-2-methylpyridin-3-yl)oxy)-4-methyl-5-(trifluoromethyl)nicotinamido)phenyl)(methyl)(oxo)-λ6-sulfaneylidene)carbamate (100 mg, 47.6%) as a white oil. LC-MS: (ESI) calcd. for $C_{26}H_{27}F_4N_4O_5S$ $[M+H]^+$ m/z 583.17, found 583.10.

Step 6: (R)-2-((6-fluoro-2-methylpyridin-3-yl)oxy)-4-methyl-N-(3-(S-methylsulfonimidoyl)phenyl)-5-(trifluoromethyl)nicotinamide: A solution of tert-butyl (R)-((3-(2-((6-fluoro-2-methylpyridin-3-yl)oxy)-4-methyl-5-(trifluoromethyl)nicotinamido)phenyl)(methyl)(oxo)-λ6-sulfaneylidene)carbamate (100 mg, 0.17 mmol) in DCM (1.5 mL) was added TFA (0.5 mL) at room temperature. The reaction mixture was stirred at room temperature for 2 hours. After the reaction was completed, the mixture was concentrated. The residue was dissolved in THE (2 mL) then adjusted to pH=8-9 with saturated aqueous $NaHCO_3$. The resulting solution was extracted with DCM (10 mL×3). The combined organic phases were washed with brine, dried over sodium sulfate, concentrated under vacuum. The residue was purified by prep-HPLC (Gemini 5 um $C_{18}$ column, 150*21.2 mm, eluting with 40% to 95% $MeCN/H_2O$ containing 0.05% $NH_4OH$) to provide (R)-2-((6-fluoro-2-methylpyridin-3-yl)oxy)-4-methyl-N-(3-(S-methylsulfonimidoyl)phenyl)-5-(trifluoromethyl)nicotinamide (57.2 mg, 69.6%) as a white solid. $^1H$ NMR (400 MHz, DMSO-$d_6$, ppm) δ 11.20 (s, 1H), 8.55 (s, 1H), 8.41 (s, 1H), 7.96-7.78 (m, 2H), 7.74-7.56 (m, 2H), 7.11 (dd, J=8.7, 3.4 Hz, 1H), 4.24 (s, 1H), 3.32 (s, 3H), 3.07 (s, 3H), 2.25 (s, 3H). LC-MS: (ESI) calcd. for $C_{21}H_{19}F_4N_4O_3S$ $[M+H]^+$ m/z 483.11, found 483.00.

Example 85

Compound 1560: (S)-2-((6-fluoro-2-methylpyridin-3-yl)oxy)-4-methyl-N-(3-(S-methylsulfonimidoyl)phenyl)-5-(trifluoromethyl)nicotinamide

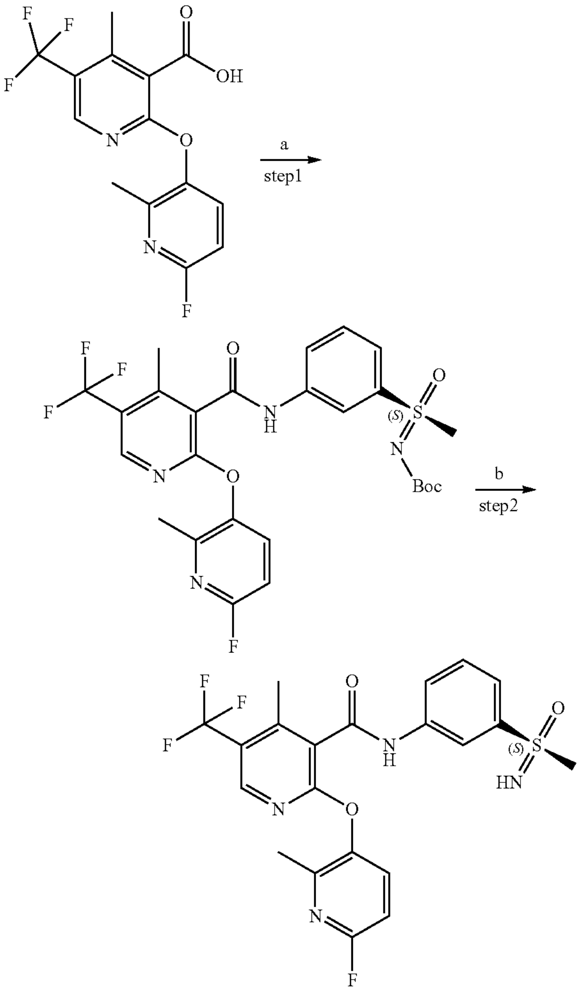

Reagents & conditions:
a) (S)-tert-butyl ((3-aminophenyl) (methyl)(oxo)- -λ$^6$-sulfaneylidene)carbamate, $SOCl_2$, DIPEA, DCM;
b) TFA, DCM Step 1: tert-butyl (S)-((3-(2-((6-fluoro-2-methylpyridin-3-yl)oxy)-4-methyl-5-(trifluoromethyl) nicotinamido)phenyl)(methyl)(oxo)-λ$^6$-sulfaneylidene)carbamate: A solution of 22-((6-fluoro-2-methylpyridin-3-yl)oxy)-4-methyl-5-(trifluoromethyl)nicotinic acid (120 mg, 0.36 mmol) in $SOCl_2$ (1 mL) was heated to 50 °C and stirred for 0.5 h. Then the solution was concentrated under vacuum to provide the chloride intermediate. Then the chloride intermediate was added to a stirred solution of tert-butyl (S)-((3-aminophenyl)(methyl)(oxo)-λ$^6$-sulfaneylidene)carbamate (117 mg, 0.43 mmol) and DIEA (88 mg, 0.68 mmol) in DCM (2 mL) at 0 °C. The resulting mixture was stirred at 25 °C for 1 h. Then the mixture was quenched with water (10 mL) and extracted with DCM (10 mL×2). The combined organic phases were washed with brine, dried over sodium sulfate, concentrated under vacuum. The residue was purified by flash column chromatography on silica gel (PE/EtOAc=1/1) to tert-butyl (S)-((3-(2-((6-fluoro-2-methylpyridin-3-yl)oxy)-4-methyl-5-(trifluoromethyl)nicotinamido)phenyl)(methyl)(oxo)-λ$^6$-sulfaneylidene)carbamate (100 mg, 47.6% yield) as a white oil. LC-MS: (ESI) calcd. for $C_{26}H_{27}F_4N_4O_5S$ $[M+H]^+$ m/z 583.17, found 583.15.

Step 2: (S)-2-((6-fluoro-2-methylpyridin-3-yl)oxy)-4-methyl-N-(3-(S-methylsulfonimidoyl)phenyl)-5-(trifluoromethyl)nicotinamide: A solution of tert-butyl (S)-((3-(2-((6-fluoro-2-methylpyridin-3-yl)oxy)-4-methyl-5-(trifluoromethyl)nicotinamido)phenyl)(methyl)(oxo)-λ$^6$-sulfaneylidene)carbamate (100 mg, 0.17 mmol) in DCM (1.5 mL) was added TFA (0.5 mL) at room temperature. The reaction mixture was stirred at room temperature for 2 hours. After the reaction was completed, the mixture was concentrated. The residue was dissolved in THF (2 mL) then adjusted to pH=8-9 with saturated aqueous $NaHCO_3$. The resulting solution was extracted with DCM (10 mL×3). The combined organic phases were washed with brine, dried over sodium sulfate, concentrated under vacuum. The residue was purified by prep-HPLC (Gemini 5 um $C_{18}$ column, 150*21.2 mm, eluting with 40% to 95% $MeCN/H_2O$ containing 0.05% $NH_4OH$) to give (S)-2-((6-fluoro-2-methylpyridin-3-yl)oxy)-4-methyl-N-(3-(S-methylsulfonimidoyl)phenyl)-5-(trifluoromethyl)nicotinamide (61.3 mg, 74.6% yield) as a white solid. $^1H$ NMR (400 MHz, DMSO-$d_6$, ppm) δ 11.20 (s, 1H), 8.55 (s, 1H), 8.41 (s, 1H), 7.99-7.76 (m, 2H), 7.76-7.52 (m, 2H), 7.11 (dd, J=8.6, 3.4 Hz, 1H), 4.24 (s, 1H), 3.32 (s, 3H), 3.07 (s, 3H), 2.25 (s, 3H). LC-MS: (ESI) calcd. for $C_{21}H_{19}F_4N_4O_3S$ $[M+H]^+$ m/z 483.11, found 482.95.

Example 86

Exemplary compounds of the invention are provided below.

Compound 1561: General route 1: 2-(4-cyano-2-methoxyphenoxy)-N-(3-sulfamoylphenyl)-5-(trifluoromethyl)pyridine-3-carboxamide

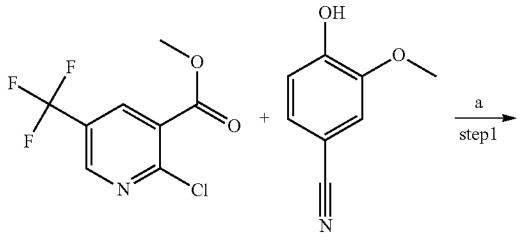

-continued

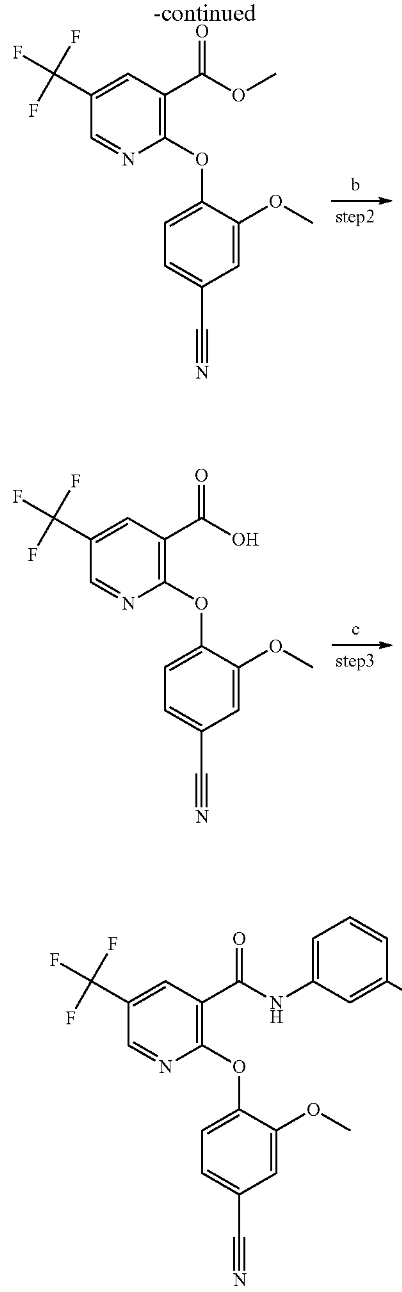

Reagents & conditions:
a) $K_2CO_3$, ACN, 70 °C;
b) LiOH, THF, water, RT;
c) EDC, 3-aminobenzenesulfonamide, pyridine Step 1: methyl 2-(4-cyano-2-methoxy-phenoxy)-5-(trifluoromethyl)pyridine-3-carboxylate: A mixture of 2-chloro-5-trifluoromethyl-nicotinic acid methyl ester (100 mg, 0.417 mmol), 4-hydroxy-3-methoxybenzonitrile (93 mg, 0.624 mmol) and potassium carbonate (87 mg, 0.629 mmol) in acetonitrile-anhydrous (2.5 mL) was stirred at 70 °C in a pressure relief vial for 18 h. The reaction mixture was allowed to cool to rt, diluted with MeCN, filtered through a phase separator and the solids washed with MeCN (2×). The combined filtrate was concentrated under reduced pressure to give the crude material. This crude compound was purified by FCC (Biotage Isolera 4 flash purification system, Sfar Duo 10 g, 0-40% EtOAc in heptanes) to give the desired product, methyl 2-(4-cyano-2-methoxy-phenoxy)-5-(trifluoromethyl)pyridine-3-carboxylate (94.0%) (142 mg, 0.379 mmol, 91%), as a white powder. $^1H$ NMR (500 MHz, DMSO-$d_6$) δ 8.73-8.70 (m, 1H), 8.60-8.58 (m, 1H), 7.69-7.66 (m, 1H), 7.54-7.50 (m, 1H), 7.44-7.41 (m, 1H), 3.90 (s, 3H), 3.74 (s, 3H). LC-MS Method 2. m/z 353.1 $[M+H]^+$, (ESI+), RT=0.96.

Step 2. 2-(4-cyano-2-methoxy-phenoxy)-5-(trifluoromethyl)pyridine-3-carboxylic acid: To a mixture of methyl 2-(4-cyano-2-methoxy-phenoxy)-5-(trifluoromethyl)pyridine-3-carboxylate (142 mg, 0.403 mmol) in THF (2 mL) and water (0.5 mL), lithium hydroxide monohydrate (35 mg, 0.834 mmol) was added and the mixture was stirred at RT for 3 h. The reaction mixture was diluted with water and was adjusted to pH 2 by dropwise addition of 2M HCl. Extraction with EtOAc (3×), drying over $MgSO_4$ and concentration in vacuo afforded the desired product, 2-(4-cyano-2-methoxy-phenoxy)-5-(trifluoromethyl)pyridine-3-carboxylic acid (94.0%) (127 mg, 0.353 mmol, 88% Yield), as a white powder. The product was carried onto the next step crude.

Step 3. 2-(4-cyano-2-methoxy-phenoxy)-N-(3-sulfamoylphenyl)-5-(trifluoromethyl)pyridine-3-carboxamide: To a solution of 2-(4-cyano-2-methoxy-phenoxy)-5-(trifluoromethyl)pyridine-3-carboxylic acid (94%, 63 mg, 0.175 mmol) and N-[3-(dimethylamino)propyl]-N′-ethylcarbodiimide hydrochloride (1:1) (67 mg, 0.350 mmol) in pyridine (1.2 mL) was added 3-aminobenzenesulfonamide (60 mg, 0.348 mmol). The mixture was stirred at room temperature for 2 h. The solvents were removed (co-evaporated with MeCN) and the residue purified by prep HPLC (Prep method 3). Fractions containing the desired product were combined and evaporated to a white powder that was freeze dried overnight to afford the desired product, 2-(4-cyano-2-methoxy-phenoxy)-N-(3-sulfamoylphenyl)-5-(trifluoromethyl)pyridine-3-carboxamide (98.0%) (53 mg, 0.105 mmol, 60% Yield), as an off-white powder. $^1H$ NMR (500 MHz, DMSO-d6) δ 10.91 (s, 1H), 8.68-8.64 (m, 1H), 8.57-8.54 (m, 1H), 8.32-8.29 (m, 1H), 7.87-7.83 (m, 1H), 7.70-7.68 (m, 1H), 7.61-7.49 (m, 4H), 7.44-7.38 (m, 2H), 3.76 (s, 3H). LC-MS Method 4: m/z 493.1 $[M+H]^+$, (ESI+), RT=3.24.

Compound 1562: 2-(4-cyano-2-methoxyphenoxy)-N-{3-[imino(methyl)oxo-λ$^6$-sulfanyl]phenyl}-5-(trifluoromethyl)pyridine-3-carboxamide

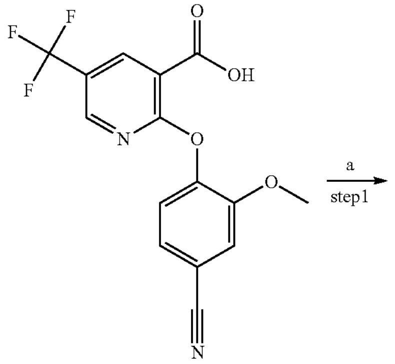

-continued

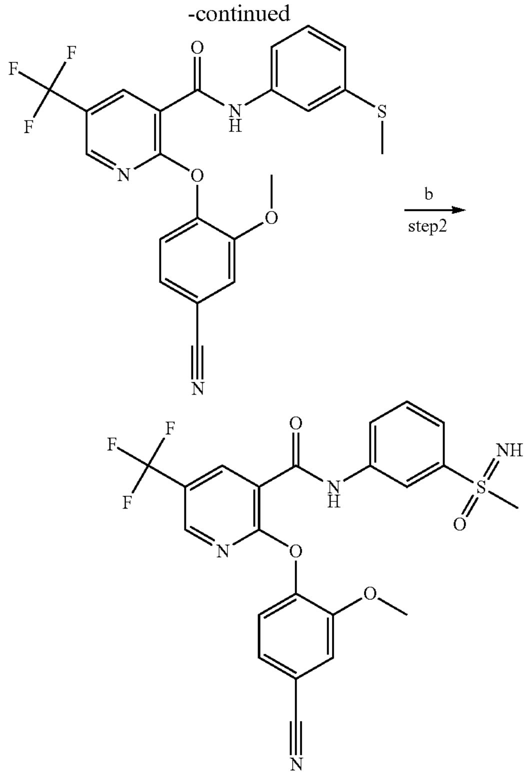

Reagents & conditions:
a) HATU, DIPEA, DMF, 3-(methylthio)aniline;
b) $(NH_4)_2CO_3$, PIDA, MeOH Step 1: 2-(4-cyano-2-methoxy-phenoxy)-N-(3-methylsulfanylphenyl)-5-(trifluoromethyl)pyridine-3-carboxamide: To a mixture of 2-(4-cyano-2-methoxy-phenoxy)-5-(trifluoromethyl)pyridine-3-carboxylic acid (71 mg, 0.210 mmol), DIPEA (0.11 mL, 0.630 mmol) and HATU (96 mg, 0.252 mmol) in DMF (1.2 mL) was added 3-(methylthio)aniline (31 uL, 0.252 mmol). The reaction was stirred at rt for 4 h. The reaction mixture was then poured into water and extracted with EtOAc (2×). The combined organic phases were washed with aq brine (2×), dried over $MgSO_4$, filtered, and concentrated under reduced pressure to give a brown oil. The crude product was purified by FCC (Biotage Isolera 4, 10 g Sfar Duo, lambda-all collection) using a 0-50% EtOAc/heptane gradient to afford 2-(4-cyano-2-methoxy-phenoxy)-N-(3-methylsulfanylphenyl)-5-(trifluoromethyl)pyridine-3-carboxamide (80.0%) (68 mg, 0.118 mmol, 56% Yield) as a brown oil. $^1$H NMR (500 MHz, DMSO-d6) δ 10.62 (s, 1H), 8.66-8.64 (m, 1H), 8.54-8.51 (m, 1H), 7.72-7.66 (m, 2H), 7.57-7.49 (m, 2H), 7.48-7.43 (m, 1H), 7.31 (t, J=8.0 Hz, 1H), 7.05-7.01 (m, 1H), 3.76 (s, 3H), 2.48-2.47 (m, 3H). LC-MS Method 2: m/z 460.1 $[M+H]^+$, (ESI+), RT=1.06.

Step 2: 2-(4-cyano-2-methoxy-phenoxy)-N-[3-(methylsulfonimidoyl)phenyl]-5-(trifluoromethyl)pyridine-3-carboxamide: Diammonium carbonate (20 mg, 0.213 mmol) and bis(acetyloxy)(phenyl)-lambda-3-iodane (PIDA) (107 mg, 0.332 mmol) were added to a solution of 2-(4-cyano-2-methoxy-phenoxy)-N-(3-methylsulfanylphenyl)-5-(trifluoromethyl)pyridine-3-carboxamide (96%, 68 mg, 0.142 mmol) in methanol (0.8 mL) at rt and the reaction was stirred at rt for 17 h. The reaction mixture was concentrated to dryness in vacuo to give crude product which was then purified using FCC (0-100% EtOAc, Sfar Duo 10 g, dry loading onto silica with DCM). Fractions 9-12 were combined, evaporated and freeze dried overnight to the desired product, 2-(4-cyano-2-methoxy-phenoxy)-N-[3-(methylsulfonimidoyl)phenyl]-5-(trifluoromethyl)pyridine-3-carboxamide (99.0%) (49 mg, 0.0989 mmol, 70% Yield), as an off-white powder. $^1$H NMR (500 MHz, DMSO-d6) δ 10.94 (s, 1H), 8.68-8.65 (m, 1H), 8.56 (d, 1H), 8.39-8.35 (m, 1H), 7.97-7.92 (m, 1H), 7.72-7.67 (m, 2H), 7.61 (t, J=7.9 Hz, 1H), 7.56-7.48 (m, 2H), 4.23 (s, 1H), 3.76 (s, 3H), 3.06 (s, 3H). LC-MS Method 4: m/z 491.1 $[M+H]^+$, (ESI+), RT=2.94.

Compound 1563: General Route 2: 2-[4-(difluoromethoxy)phenoxy]-N-(3-methylsulfonylphenyl)-5-(trifluoromethyl)pyridine-3-carboxamide

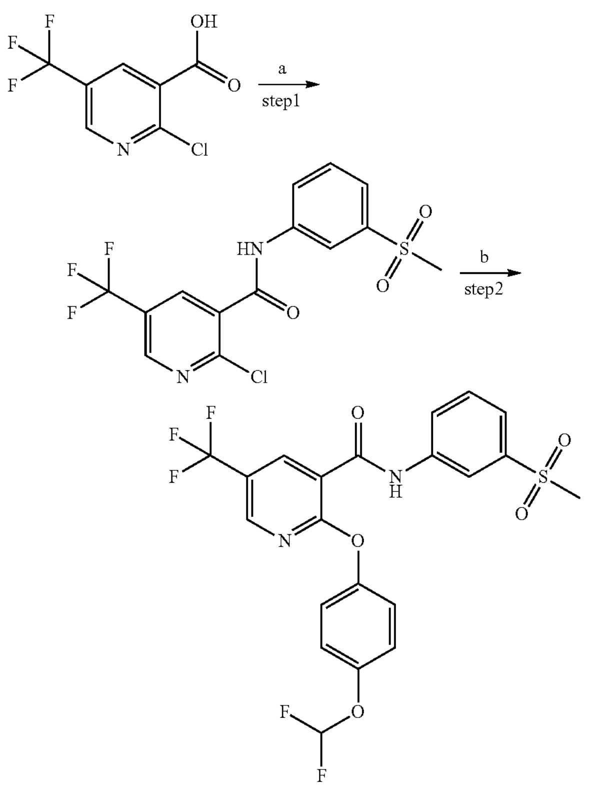

Reagents & conditions:
a) 50% propylphosphonic anhydride, DIPEA, DMAP, 3-(methylsulfonyl)aniline;
b) 4-(difluoromethoxy)phenol, $K_2CO_3$, ACN, 60 °C Step 1. 2-chloro-N-(3-methylsulfonylphenyl)-5-(trifluoromethyl)pyridine-3-carboxamide: A mixture of 2-chloro-5-(trifluoromethyl)pyridine-3-carboxylic acid (2.00 g, 8.87 mmol), 50% propylphosphonic anhydride solution in EtOAc (50%, 6.3 mL, 10.6 mmol), N-ethyl-N-isopropyl-propan-2-amine (3.1 mL, 17.7 mmol) and N,N-dimethylpyridin-4-amine (0.22 g, 1.77 mmol) and were dissolved in DCM (44.336 mL) under nitrogen at rt. After 10 mins 3-(methylsulfonyl)aniline (1.82 g, 10.6 mmol) was added in one portion. The reaction mixture was stirred at rt for 4 h. IPC shows desired product. The reaction mixture was poured into water (20 mL) and brine (10 mL) and extracted with DCM (3×50 mL), dried with sodium sulfate and concentrated. Purification by chromatography on silica eluting with a gradient of 0 to 388% EtOAc in heptane to afford 2-chloro-N-(3-methylsulfonylphenyl)-5-(trifluoromethyl)pyridine-3-carboxamide (99.0%) (1.90 g, 4.97 mmol, 56% Yield) as a yellow solid. $^1$H NMR (500 MHz, DMSO-d6) δ 11.15 (s, 1H), 9.05-9.00 (m, 1H), 8.70 (d, J=2.3 Hz, 1H), 8.34 (t, J=1.8 Hz, 1H), 7.97-7.92 (m, 1H), 7.76-7.66 (m, 2H), 3.24 (s, 3H). LC-MS Method 1: m/z 378.95 $[M+H]^+$, (ESI+), RT=1.09.

Step 2: 2-[4-(difluoromethoxy)phenoxy]-N-(3-methylsulfonylphenyl)-5-(trifluoromethyl)pyridine-3-carboxamide: A mixture of 2-chloro-N-(3-methylsulfonylphenyl)-5-(trifluoromethyl)pyridine-3-carboxamide (99%, 100 mg, 0.261 mmol), 4-(difluoromethoxy)phenol (63 mg, 0.392 mmol) and dipotassium carbonate (54 mg, 0.392 mmol) in acetonitrile (0.5411 mL) was stirred at 60 °C for 1 h. IPC1 showed desired product. The reaction was cooled to room temperature, filtered and washed with MeCN (15 mL). The filtrate was concentrated in vacuo to obtain the crude residue. Purification by chromatography on silica eluting with a gradient of 0 to 70% EtOAc in heptane afforded 2-[4-(difluoromethoxy)phenoxy]-N-(3-methylsulfonylphenyl)-5-(trifluoromethyl)pyridine-3-carboxamide (99.0%) (102 mg, 0.200 mmol, 77% Yield) as an off-white solid. $^1$H NMR (500 MHz, DMSO-d6) δ 11.02 (s, 1H), 8.71-8.66 (m, 1H), 8.55 (d, J=2.3 Hz, 1H), 8.38 (t, J=1.8 Hz, 1H), 7.97 (dt, J=7.6, 1.7 Hz, 1H), 7.73-7.63 (m, 2H), 7.41-7.08 (m, 5H), 3.22 (s, 3H). LC-MS Method 5: m/z 502.9 $[M+H]^+$, (ESI+), RT=4.44.

Compound 1564: General Route 3: N-[3-(methylsulfonimidoyl)phenyl]-5-(trifluoromethyl)-2-[4-(trifluoromethyl)phenoxy]pyridine-3-carboxamide

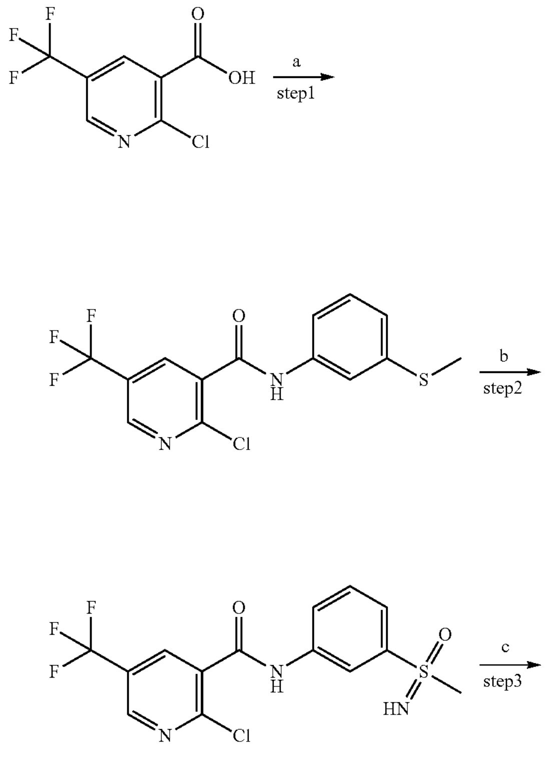

-continued

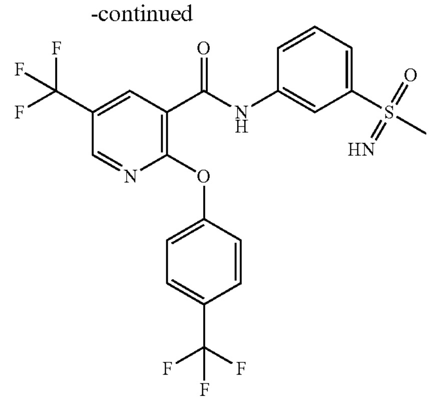

Reagents & conditions:
a) 50% propylphosphonic anhydride, DIPEA, DMAP, 3-(methylsulfonyl)aniline;
b) $(NH_4)_2CO_3$, PIDA, MeOH;
c) 4-(trifluoromethyl)phenol, $K_2CO_3$, 60 °C Step 1: 2-chloro-N-(3-methylsulfanylphenyl)-5-(trifluoromethyl)pyridine-3-carboxamide: A mixture of 2-chloro-5-(trifluoromethyl)pyridine-3-carboxylic acid (4.00 g, 17.7 mmol), dissolved in DCM (80 mL) under air at RT, was treated with 50% propylphosphonic anhydride solution in EtOAc (50%, 13 mL, 21.3 mmol), and N-ethyl-N-isopropyl-propan-2-amine (6.2 mL, 35.5 mmol). Then stirred at RT for 30 minutes. Then added N,N-dimethylpyridin-4-amine (0.43 g, 3.55 mmol) and 3-(methylsulfanyl)aniline (2.2 mL, 17.7 mmol) together in one portion. The reaction mixture was stirred at RT for 2 h. The mixture was poured into water (60 mL) and brine (60 mL) and extracted with DCM (3×40 mL), dried ($MgSO_4$) and concentrated. Purification by column chromatography (50 g, 0 to 10% EA in heptane) afforded 2-chloro-N-(3-methylsulfanylphenyl)-5-(trifluoromethyl) pyridine-3-carboxamide (6.12 g, 17.6 mmol, 100% Yield) as a yellow solid. $^1$H NMR and LC-MS analysis indicated this was the desired product. $^1$H NMR (400 MHz, DMSO-d6) δ 10.79 (s, 1H), 9.04-8.98 (m, 1H), 8.66 (d, J=2.1 Hz, 1H), 7.66 (s, 1H), 7.34 (t, J=7.9 Hz, 1H), 7.06 (d, J=8.3 Hz, 1H), 2.49 (s, 3H). LC-MS Method 1: m/z 347.1 $[M+H]^+$, (ESI+), RT=0.93.

Step 2: 2-chloro-N-[3-(methylsulfonimidoyl)phenyl]-5-(trifluoromethyl)pyridine-3-carboxamide: [acetoxy(phenyl)-$l^{3}-iodanyl] acetate (348 mg, 1.08 mmol) was dissolved in methanol (7.2096 mL) and treated with 2-chloro-N-(3-methylsulfanylphenyl)-5-(trifluoromethyl)pyridine-3-carboxamide (250 mg, 0.721 mmol) and diammonium carbonate (104 mg, 1.08 mmol), each added in one portion. The reaction was stirred at RT for 18 h. The mixture was concentrated in vacuo to obtain the crude residue. Purification by chromatography on silica eluting with a gradient of 0 to 30% EtOAc in heptane afforded 2-chloro-N-[3-(methylsulfonimidoyl)phenyl]-5-(trifluoromethyl)pyridine-3-carboxamide (98.0%) (171 mg, 0.444 mmol, 62% Yield) as a beige solid. [1]H NMR (500 MHz, DMSO-d6) δ 11.08 (s, 1H), 9.02 (dd, J=2.4, 0.8 Hz, 1H), 8.74-8.63 (m, 1H), 8.32 (t, J=1.9 Hz, 1H), 7.92 (ddd, J=8.0, 2.1, 1.0 Hz, 1H), 7.71 (ddd, J=7.8, 1.7, 1.1 Hz, 1H), 7.63 (t, J=7.9 Hz, 1H), 4.25 (s, 1H), 3.07 (d, J=0.9 Hz, 3H). LC-MS Method 1: m/z 378.95 $[M+H]^+$, (ESI+), RT=1.00.

Step 3: N-[3-(methylsulfonimidoyl)phenyl]-5-(trifluoromethyl)-2-[4-(trifluoromethyl)phenoxy]pyridine-3-carboxamide: A suspension of 4-(trifluoromethyl)phenol (63 mg, 0.389 mmol), 2-chloro-N-[3-(methylsulfonimidoyl) phenyl]-5-(trifluoromethyl)pyridine-3-carboxamide (98%, 150 mg, 0.389 mmol) and dipotassium carbonate (81 mg, 0.584 mmol) in acetonitrile (0.8055 mL) under nitrogen was heated to 60 °C for 2 h. The reaction mixture was cooled to rt, filtered and concentrated in vacuo. The filtrate was purified by preparative HPLC (Prep Method 1) afforded N-[3-(methylsulfonimidoyl)phenyl]-5-(trifluoromethyl)-2-[4-(trifluoromethyl)phenoxy]pyridine-3-carboxamide (97.0%) (97 mg, 0.187 mmol, 48% Yield) as a white solid. $^1$H NMR (500 MHz, DMSO-d6) δ 11.01 (s, 1H), 8.75-8.68 (m, 1H), 8.61-8.56 (m, 1H), 8.37 (t, J=1.8 Hz, 1H), 7.99-7.94 (m, 1H), 7.89-7.81 (m, 2H), 7.75-7.66 (m, 1H), 7.61 (t, J=7.9 Hz, 1H), 7.53 (d, J=8.5 Hz, 2H), 4.24 (s, 1H), 3.06 (s, 3H). LC-MS Method 5: m/z 503.9 [M+H]$^+$, (ESI+), RT=4.20.

Compound 1565: General Route 4: N-(3-carbamoylphenyl)-2-[[6-(cyclobutoxy)-2-methyl-3-pyridyl]oxy]-5-(trifluoromethyl)pyridine-3-carboxamide

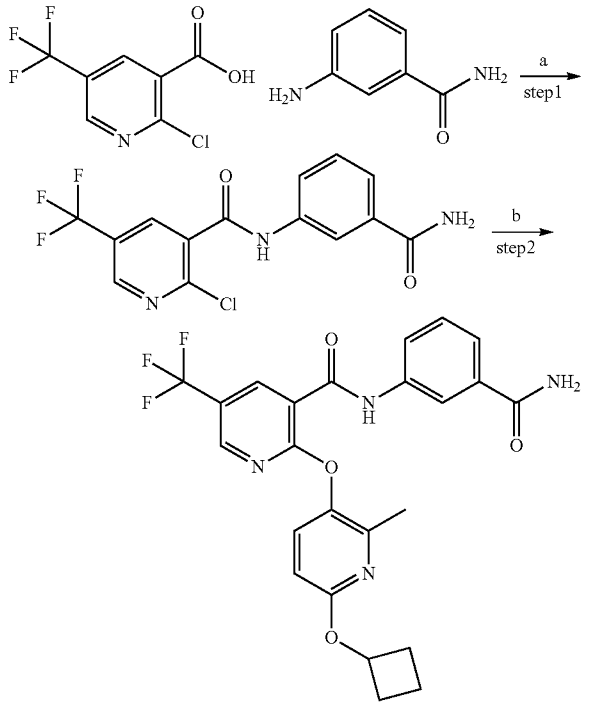

Reagents & conditions:
a) 3-aminobenzamide, EDC, pyr;
b) 6-(cyclobutoxy)-2-methyl-pyridin-3-ol, $K_2CO_3$, ACN, 65 °C Step 1: N-(3-carbamoylphenyl)-2-chloro-5-(trifluoromethyl)pyridine-3-carboxamide: To a solution of 2-chloro-5-(trifluoromethyl)pyridine-3-carboxylic acid (4.00 g, 17.7 mmol) and 3-(ethyliminomethyleneamino)-N,N-dimethyl-propan-1-amine hydrochloride (4.08 g, 21.3 mmol) in pyridine (60 mL) was added 3-aminobenzamide (2.66 g, 19.5 mmol). The mixture was stirred at room temperature for one hour, then concentrated in vacuo. The residue was absorbed onto SiO2 and purified by column chromatography (SiO2, 0 to 100% EA in heptane) to afford N-(3-carbamoylphenyl)-2-chloro-5-(trifluoromethyl)pyridine-3-carboxamide (99%) (EV-TXY001-053-001) (4.51 g, 13.1 mmol, 74% Yield) as a an off-white solid. LC-MS and $^1$H NMR analysis indicated this was the desired product. $^1$H NMR (400 MHz, DMSO-d6) δ 10.87 (s, 1H), 9.01 (d, J=1.6 Hz, 1H), 8.67 (d, J=2.4 Hz, 1H), 8.16 (t, J=1.8 Hz, 1H), 8.00 (s, 1H), 7.85 (dd, J=8.0, 1.3 Hz, 1H), 7.66 (d, J=7.9 Hz, 1H), 7.47 (t, J=7.9 Hz, 1H), 7.40 (s, 1H). LC-MS Method 2: m/z 344.1 [M+H]$^+$, (ESI+), RT=0.65.

Step 2: N-(3-carbamoylphenyl)-2-[[6-(cyclobutoxy)-2-methyl-3-pyridyl]oxy]-5-(trifluoromethyl)pyridine-3-carboxamide: To a mixture of N-(3-carbamoylphenyl)-2-chloro-5-(trifluoromethyl)pyridine-3-carboxamide (50 mg, 0.145 mmol) and 6-(cyclobutoxy)-2-methyl-pyridin-3-ol (34 mg, 0.189 mmol) in acetonitrile-anhydrous (0.5 mL) was added dipotassium carbonate (30 mg, 0.218 mmol). The mixture was heated at 65 °C in a pressure vial for 2 hours. The mixture was filtered and concentrated to afford a pale yellow oil. Purification by prep. HPLC (prep. Method 2). Product containing fractions were combined to afford N-(3-carbamoylphenyl)-2-[[6-(cyclobutoxy)-2-methyl-3-pyridyl]oxy]-5-(trifluoromethyl)pyridine-3-carboxamide (99%) (57 mg, 0.117 mmol, 81% Yield) as a white solid. $^1$H NMR and LC-MS analysis indicated this was the desired compound. $^1$H NMR (500 MHz, $CD_3OD$) δ 8.55 (s, 2H), 8.19 (s, 1H), 7.96 (m, 1H), 7.69 (d, J=7.8 Hz, 1H), 7.55 (d, J=8.7 Hz, 1H), 7.51 (t, J=7.9 Hz, 1H), 6.66 (d, J=8.8 Hz, 1H), 5.13 (m, 1H), 2.54-2.45 (m, 2H), 2.27 (s, 3H), 2.21-2.09 (m, 2H), 1.93-1.82 (m, 1H), 1.80-1.67 (m, 1H). LC-MS Method 4: m/z 487.2 [M+H]$^+$, (ESI+), RT=3.70 LC-MS Method 4.

Compound 1566: General Route 5: N-(4-carbamoylphenyl)-2-[[6-(cyclobutoxy)-2-methyl-3-pyridyl]oxy]-5-(trifluoromethyl)pyridine-3-carboxamide

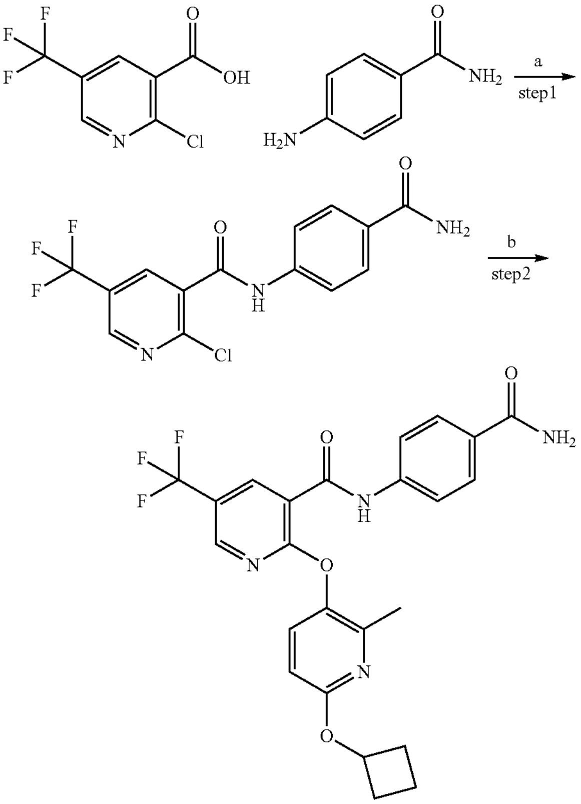

Reagents & conditions:
a) 4-aminobenzamide, EDC, pyridine;
b) 6-(cyclobutoxy)-2-methyl-pyridin-3-ol, $K_2CO_3$, ACN, 65 °C Step 1: N-(4-carbamoylphenyl)-2-chloro-5-(trifluoromethyl)pyridine-3-carboxamide: To a solution of 2-chloro-5-(trifluoromethyl)pyridine-3-carboxylic acid (4.00 g, 17.7 mmol) and 3-(ethyliminomethyleneamino)-N,N-dimethyl-propan-1-amine hydrochloride (4.08 g, 21.3 mmol) in pyridine (60 mL) was added 4-aminobenzamide (2.66 g, 19.5 mmol). The mixture was stirred at room temperature for one hour, then concentrated in vacuo. The residue was absorbed onto SiO2 and purified by column chromatography ($SiO_2$, 0 to 100% EA in heptane) to afford (100%) N-(4-carbamoylphenyl)-2-chloro-5-(trifluoromethyl)pyridine-3-carboxamide (3.33 g, 9.67 mmol, 55% Yield) as an off-white solid. $^1H$ NMR and LC-MS analysis indicated this was the desired product. $^1H$ NMR (500 MHz, $CD_3OD$) δ 8.76 (d, J=1.7 Hz, 2H), 8.32 (d, J=2.3 Hz, 1H), 7.85-7.79 (m, 2H), 7.73-7.67 (m, 2H), 7.57-7.50 (m, 1H), 6.59-6.52 (m, 1H). LC-MS Method 2: m/z 344.0 $[M+H]^+$, (ESI+), RT=0.65.

Step 2: N-(4-carbamoylphenyl)-2-[[6-(cyclobutoxy)-2-methyl-3-pyridyl]oxy]-5-(trifluoromethyl)pyridine-3-carboxamide: To a mixture of N-(4-carbamoylphenyl)-2-chloro-5-(trifluoromethyl)pyridine-3-carboxamide (50 mg, 0.145 mmol) and 6-(cyclobutoxy)-2-methyl-pyridin-3-ol (34 mg, 0.189 mmol) in acetonitrile-anhydrous (0.5 mL) was added dipotassium carbonate (30 mg, 0.218 mmol). The mixture was heated at 65 °C in a pressure vial for 2 h. The mixture was filtered and concentrated to afford an orange oil. Purification by prep. HPLC (prep. Method 2). Product containing fractions were combined to afford (100%) N-(4-carbamoylphenyl)-2-[[6-(cyclobutoxy)-2-methyl-3-pyridyl]oxy]-5-(trifluoromethyl)pyridine-3-carboxamide (49 mg, 0.101 mmol, 69%) as a white solid. $^1H$ NMR and LC-MS analysis indicated this was the desired compound. $^1H$ NMR (500 MHz, $CD_3OD$) δ 8.58-8.51 (m, 2H), 7.94 (d, J=8.8 Hz, 2H), 7.85 (d, J=8.7 Hz, 2H), 7.55 (d, J=8.7 Hz, 1H), 6.66 (d, J=8.8 Hz, 1H), 5.13 (p, J=7.1 Hz, 1H), 2.54-2.44 (m, 2H), 2.27 (s, 3H), 2.21-2.09 (m, 2H), 1.93-1.82 (m, 1H), 1.80-1.67 (m, 1H). LC-MS Method 4: m/z 487.2 $[M+H]^+$, (ESI+), RT=3.68.

Compound 1567: General Route 6: 5-bromo-2-(3,4-difluoro-2-methoxy-phenoxy)-N-[3-(methylsulfonimidoyl)phenyl]pyridine-3-carboxamide

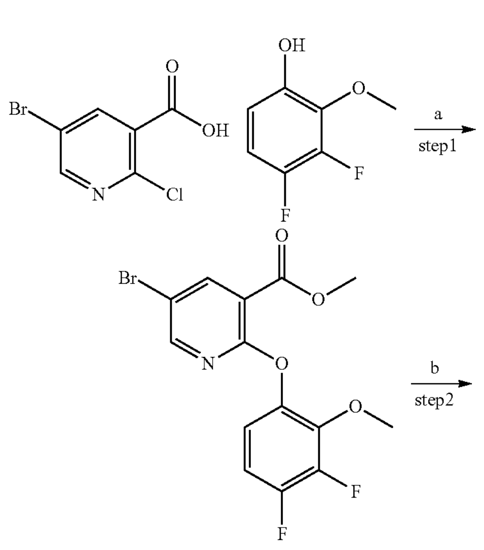

-continued

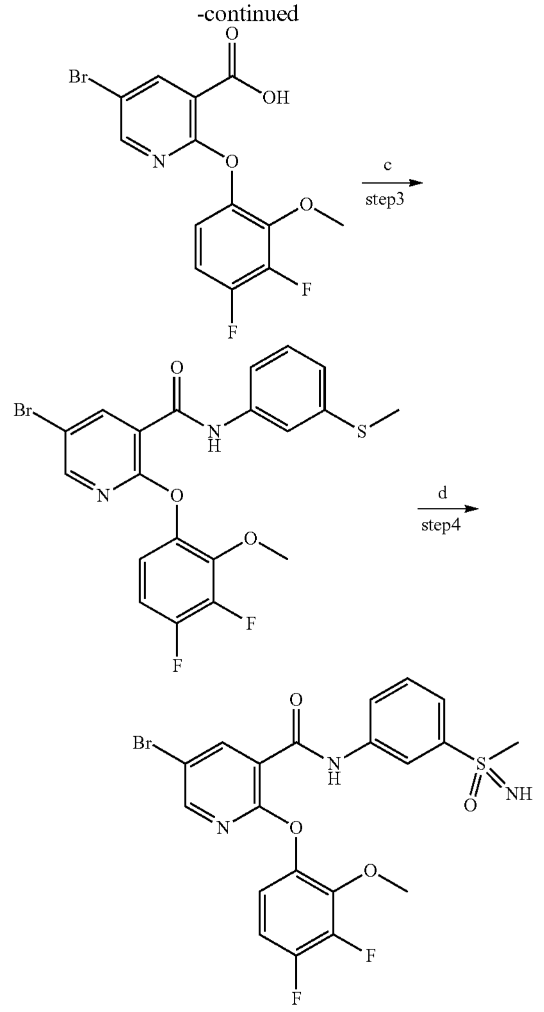

Reagents & conditions:
a) 3,4-difluoro-2-methoxy-phenol, $Cs_2CO_3$, DMF, 80 °C;
b) LiOH, water, THF;
c) 3-(methylsulfanyl)aniline, EDC, pyridine;
d) $(NH_4)_2CO_3$, PIDA, MeOH Step 1: methyl 5-bromo-2-(3,4-difluoro-2-methoxy-phenoxy)pyridine-3-carboxylate: To a mixture of methyl 5-bromo-2-chloropyridine-3-carboxylate (1.00 g, 3.99 mmol) and 3,4-difluoro-2-methoxy-phenol (0.83 g, 5.19 mmol) in DMF-anhydrous (10 mL) was added cesium carbonate (1.95 g, 5.99 mmol). The mixture was heated at 80 °C in a pressure vial for 3 hours. The mixture was diluted with ethyl acetate (30 mL) and washed with water (4×15 mL) and brine (15 mL). The organics were dried (MgSO4), filtered and concentrated to afford an orange oil. Purification by FCC (25 g 20 μm, 0 to 15% EA in heptane) afforded methyl 5-bromo-2-(3,4-difluoro-2-methoxy-phenoxy)pyridine-3-carboxylate (95.0%) (EV-TXY001-100-002) (1.15 g, 2.92 mmol, 73% Yield) as a white solid. LC-MS and $^1H$ NMR analysis indicated this was the desired product. $^1H$ NMR (400 MHz, $CD_3OD$) δ 8.44 (d, J=2.6 Hz, 1H), 8.29 (d, J=2.5 Hz, 1H), 7.08-6.91 (m, 2H), 3.95 (s, 3H), 3.82 (d, J=1.4 Hz, 3H). LC-MS Method 2: m/z 374.1 $[M+H]^+$, (ESI+), RT=1.00.

Step 2:5-bromo-2-(3,4-difluoro-2-methoxy-phenoxy)pyridine-3-carboxylic acid: To a solution of methyl 5-bromo-2-(3,4-difluoro-2-methoxy-phenoxy)pyridine-3-carboxylate (1.15 g, 3.07 mmol) in THF (8 mL):Water (2 mL), lithium hydroxide (0.17 g, 6.76 mmol) was added, and the mixture was stirred at room temperature for 2 hours. The mixture was diluted with water (10 mL) and the pH was adjusted to 1 by dropwise addition of 2M HCl (aq). The aqueous layer was extracted with EtOAc (3×10 mL), dried ($MgSO_4$), filtered and concentrated in vacuo to afford 5-bromo-2-(3,4-difluoro-2-methoxy-phenoxy)pyridine-3-carboxylic acid (97.0%) (1.04 g, 2.79 mmol, 91%) as a white solid. $^1H$ NMR and LC-MS analysis indicated this was the desired product. $^1H$ NMR (500 MHz, $CD_3OD$) δ 8.44 (d, J=2.6 Hz, 1H), 8.27 (d, J=2.6 Hz, 1H), 7.07-6.93 (m, 2H), 3.82 (d, J=1.4 Hz, 3H). LC-MS Method 2: m/z 360.1 [M]+, (ESI+), RT=0.86.

Step 3: 5-bromo-2-(3,4-difluoro-2-methoxy-phenoxy)-N-(3-methylsulfanylphenyl)pyridine-3-carboxamide: To a solution of 5-bromo-2-(3,4-difluoro-2-methoxy-phenoxy) pyridine-3-carboxylic acid (300 mg, 0.833 mmol) and 3-(ethyliminomethyleneamino)-N,N-dimethyl-propan-1-amine hydrochloride (192 mg, 1.00 mmol) in pyridine-anhydrous (3 mL) was added 3-(methylsulfanyl)aniline (139 mg, 1.00 mmol). The mixture was stirred at RT for 0.5 h. LC-MS analysis indicated the reaction was complete. The solvents were removed in vacuo and the residue purified by FCC (10 g, 0 to 30% EA in heptane) to afford 5-bromo-2-(3,4-difluoro-2-methoxy-phenoxy)-N-(3-methylsulfanylphenyl)pyridine-3-carboxamide (92.0%) (402 mg, 0.768 mmol, 92% Yield) as a clear oil. $^1H$ NMR and LC-MS analysis indicated this was the desired compound. $^1H$ NMR (400 MHz, $CD_3OD$) δ 8.38 (d, J=2.5 Hz, 1H), 8.28 (d, J=2.5 Hz, 1H), 7.72 (t, J=2.0 Hz, 1H), 7.39 (m, 1H), 7.28 (t, J=8.0 Hz, 1H), 7.17-7.00 (m, 3H), 3.84 (d, J=1.7 Hz, 3H), 2.49 (s, 3H). LC-MS Method 2: m/z 481.1 [M]+, (ESI+), RT=1.12.

Step 4: 5-bromo-2-(3,4-difluoro-2-methoxy-phenoxy)-N-[3-(methylsulfonimidoyl)phenyl]pyridine-3-carboxamide: Phenyl Iodonium diacetate (PIDA) (803 mg, 2.49 mmol) and diammonium carbonate (235 mg, 2.49 mmol) were added to a solution of 5-bromo-2-(3,4-difluoro-2-methoxy-phenoxy)-N-(3-methylsulfanylphenyl)pyridine-3-carboxamide (400 mg, 0.831 mmol) in methanol (12 mL) at rt and the reaction was stirred at room temperature for 1 hour. The solvents were removed in vacuo, and the residue purified by FCC (10 g, 0 to 100% EA in heptane) to afford 5-bromo-2-(3,4-difluoro-2-methoxy-phenoxy)-N-[3-(methylsulfonimidoyl)phenyl]pyridine-3-carboxamide (88.0%) (328 mg, 0.563 mmol, 68% Yield) as a white solid. $^1H$ NMR and LC-MS analysis indicated this was the desired compound. 30 mg was purified by prep. HPLC (Prep. Method 2). Product fractions were combined, concentrated under reduced pressure and the resulting residue was freeze-dried from MeCN-water (1:1) to afford 5-bromo-2-(3,4-difluoro-2-methoxy-phenoxy)-N-[3-(methylsulfonimidoyl)phenyl] pyridine-3-carboxamide (100.0%) (17 mg, 0.0332 mmol, 4.0%) as a white solid. $^1H$ NMR and LC-MS analysis indicated this was the desired compound. $^1H$ NMR (400 MHz, $CD_3OD$) δ 8.44 (t, J=2.0 Hz, 1H), 8.40 (d, J=2.5 Hz, 1H), 8.31 (d, J=2.5 Hz, 1H), 7.98 (m, 1H), 7.80 (m, 1H), 7.63 (t, J=8.0 Hz, 1H), 7.17-7.00 (m, 2H), 3.84 (d, J=1.7 Hz, 3H), 3.17 (s, 3H). LC-MS Method 7: m/z 512.2 [M]+, (ESI+), RT=3.33.

Compound 1568: General Route 7: 5-bromo-N-(3-carbamoylphenyl)-2-(3,4-difluoro-2-methoxy-phenoxy)pyridine-3-carboxamide

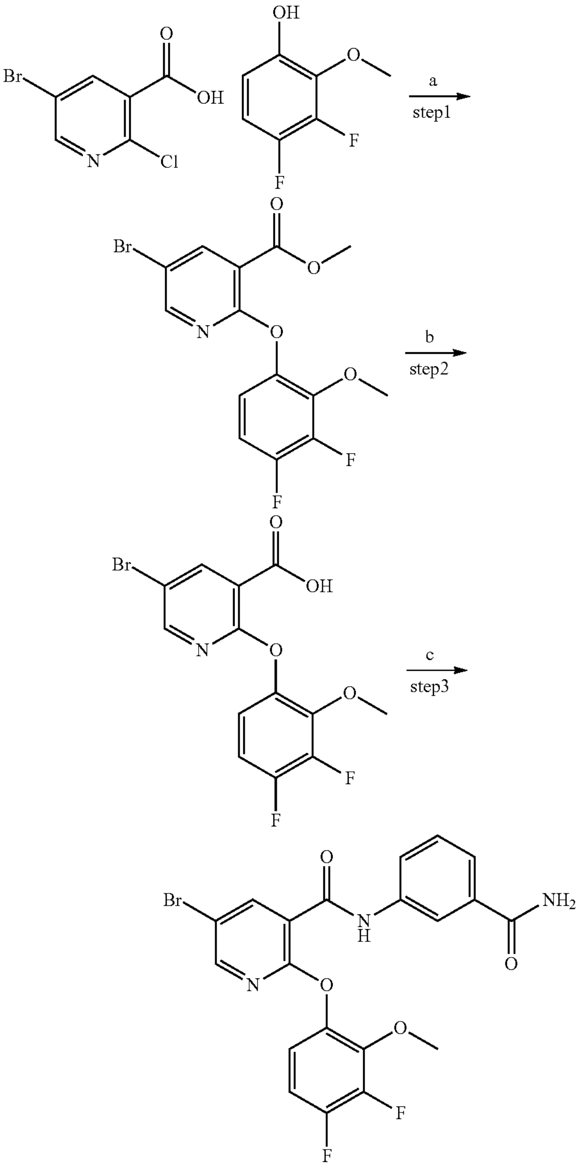

Reagents & conditions:
a) $Cs_2CO_3$, DMF, 80 °C;
b) LiOH, water, THF;
c) 3-aminobenzamide, EDC, pyridine Step 1: methyl 5-bromo-2-(3,4-difluoro-2-methoxy-phenoxy)pyridine-3-carboxylate: To a mixture of methyl 5-bromo-2-chloropyridine-3-carboxylate (1.00 g, 3.99 mmol) and 3,4-difluoro-2-methoxy-phenol (0.83 g, 5.19 mmol) in DMF-anhydrous (10 mL) was added cesium carbonate (1.95 g, 5.99 mmol). The mixture was heated at 80 °C in a pressure vial for 3 hours. The mixture was diluted with ethyl acetate (30 mL) and washed with water (4×15 mL) and brine (15 mL). The organics were dried ($MgSO_4$), filtered and concentrated to afford an orange oil. Purification by FCC (25 g 20 μm, 0 to 15% EA in heptane) afforded methyl 5-bromo-2-(3,4-difluoro-2-methoxy-phenoxy)pyridine-3-carboxylate (95.0%) (1.15 g, 2.92 mmol, 73%) as a white solid. LC-MS and $^1H$ NMR analysis indicated this was the desired product. $^1H$ NMR (400 MHz, $CD_3OD$) δ 8.44 (d, J=2.6 Hz, 1H), 8.29 (d, J=2.5 Hz, 1H), 7.08-6.91 (m, 2H), 3.95 (s, 3H), 3.82 (d, J=1.4 Hz, 3H). LC-MS Method 2: m/z 374.1 $[M+H]^+$, (ESI+), RT=1.00.

Step 2: 5-bromo-2-(3,4-difluoro-2-methoxy-phenoxy) pyridine-3-carboxylic acid: To a solution of methyl 5-bromo-2-(3,4-difluoro-2-methoxy-phenoxy)pyridine-3-carboxylate (1.15 g, 3.07 mmol) in THF (8 mL):Water (2 mL), lithium hydroxide (0.17 g, 6.76 mmol) was added, and the mixture was stirred at room temperature for 2 hours. The mixture was diluted with water (10 mL) and the pH was adjusted to 1 by dropwise addition of 2M HCl (aq). The aqueous layer was extracted with EtOAc (3×10 mL), dried ($MgSO_4$), filtered and concentrated in vacuo to afford 5-bromo-2-(3,4-difluoro-2-methoxy-phenoxy)pyridine-3-carboxylic acid (97.0%)(1.04 g, 2.79 mmol, 91%) as a white solid. $^1H$ NMR and LC-MS analysis indicated this was the desired product. $^1H$ NMR (500 MHz, $CD_3OD$) δ 8.44 (d, J=2.6 Hz, 1H), 8.27 (d, J=2.6 Hz, 1H), 7.07-6.93 (m, 2H), 3.82 (d, J=1.4 Hz, 3H). LC-MS Method 2: m/z 360.1 $[M]^+$, (ESI+), RT=0.86.

Step 3: 5-bromo-N-(3-carbamoylphenyl)-2-(3,4-difluoro-2-methoxy-phenoxy)pyridine-3-carboxamide: To a solution of 5-bromo-2-(3,4-difluoro-2-methoxy-phenoxy)pyridine-3-carboxylic acid (300 mg, 0.833 mmol) and 3-(ethyliminomethyleneamino)-N,N-dimethyl-propan-1-amine hydrochloride (192 mg, 1.00 mmol) in pyridine-anhydrous (3 mL) was added 3-aminobenzamide (139 mg, 1.00 mmol). The mixture was stirred at rt for 0.5 hours. The solvents were removed and the residue purified by FCC (10 g, 0 to 100% EA in heptane) to afford 5-bromo-N-(3-carbamoylphenyl)-2-(3,4-difluoro-2-methoxy-phenoxy)pyridine-3-carboxamide (92.0%) (385 mg, 0.741 mmol, 89%) as a white solid. $^1H$ NMR and LC-MS analysis indicated this was the desired product. 30 mg was further purified by purified by prep. HPLC (Prep. Method 2). Product fractions were combined, concentrated under reduced pressure and the resulting residue was freeze-dried from MeCN-water (1:1) to afford 5-bromo-N-(3-carbamoylphenyl)-2-(3,4-difluoro-2-methoxy-phenoxy)pyridine-3-carboxamide (100.0%) (23 mg, 0.0481 mmol, 5.8%) as a white solid. $^1H$ NMR and LC-MS analysis indicated this was the desired product. $^1H$ NMR (400 MHz, $CD_3OD$) δ 8.42 (d, J=2.5 Hz, 1H), 8.30 (d, J=2.5 Hz, 1H), 8.16 (t, J=2.0 Hz, 1H), 7.92 (m, 1H), 7.70-7.63 (m, 1H), 7.48 (t, J=7.9 Hz, 1H), 7.13 (m, 1H), 7.10-7.02 (m, 1H), 3.84 (d, J=1.7 Hz, 3H). LC-MS Method 4: m/z 478.1 [M]+, (ESI+), RT=3.36.

Compound 1569: General Route 8: 5-bromo-N-(4-carbamoylphenyl)-2-(3,4-difluoro-2-methoxy-phenoxy)pyridine-3-carboxamide

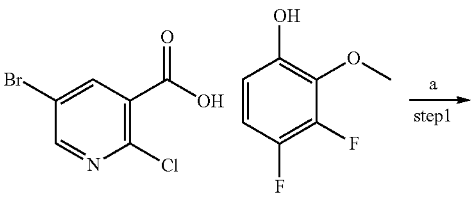

-continued

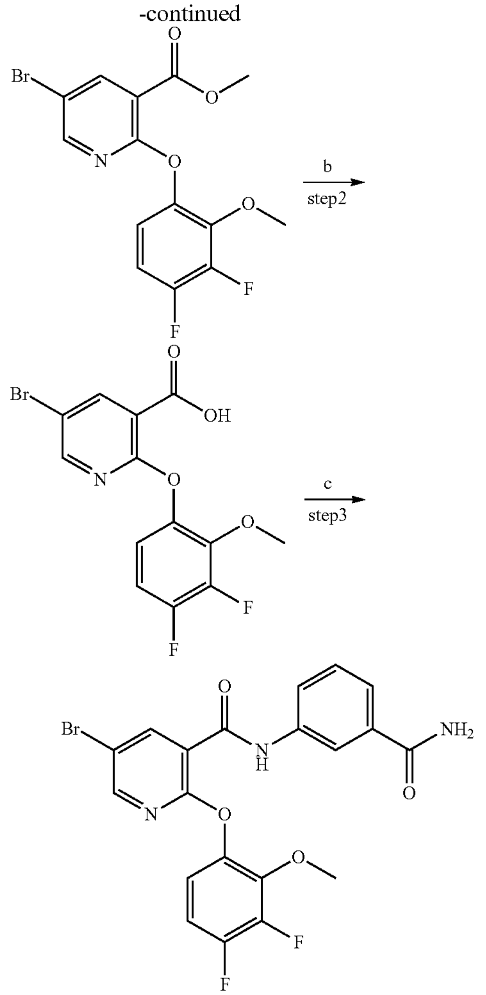

Reagents & conditions:
a) $Cs_2CO_3$, DMF, 80 °C;
b) LiOH, water, THF;
c) 4-aminobenzamide, EDC, pyridine Step 1: methyl 5-bromo-2-(3,4-difluoro-2-methoxy-phenoxy)pyridine-3-carboxylate: To a mixture of methyl 5-bromo-2-chloropyridine-3-carboxylate (1.00 g, 3.99 mmol) and 3,4-difluoro-2-methoxy-phenol (0.83 g, 5.19 mmol) in DMF-anhydrous (10 mL) was added cesium carbonate (1.95 g, 5.99 mmol). The mixture was heated at 80 °C in a pressure vial for 3 hours. The mixture was diluted with ethyl acetate (30 mL) and washed with water (4×15 mL) and brine (15 mL). The organics were dried ($MgSO_4$), filtered and concentrated to afford an orange oil. Purification by FCC (25 g 20 μm, 0 to 15% EA in heptane) afforded methyl 5-bromo-2-(3,4-difluoro-2-methoxy-phenoxy)pyridine-3-carboxylate (95.0%) (1.15 g, 2.92 mmol, 73% Yield) as a white solid. LC-MS and $^1H$ NMR analysis indicated this was the desired product. $^1H$ NMR (400 MHz, $CD_3OD$) δ 8.44 (d, J=2.6 Hz, 1H), 8.29 (d, J=2.5 Hz, 1H), 7.08-6.91 (m, 2H), 3.95 (s, 3H), 3.82 (d, J=1.4 Hz, 3H). LC-MS Method 2: m/z 374.1 $[M+H]^+$, (ESI+), RT=1.00.

Step 2: 5-bromo-2-(3,4-difluoro-2-methoxy-phenoxy) pyridine-3-carboxylic acid: To a solution of methyl 5-bromo-2-(3,4-difluoro-2-methoxy-phenoxy)pyridine-3-carboxylate (1.15 g, 3.07 mmol) in THF (8 mL):water (2 mL), lithium hydroxide (0.17 g, 6.76 mmol) was added, and the mixture was stirred at room temperature for 2 hours. The mixture was diluted with water (10 mL) and the pH was adjusted to 1 by dropwise addition of 2M HCl (aq). The aqueous layer was extracted with EtOAc (3×10 mL), dried ($MgSO_4$), filtered and concentrated in vacuo to afford 5-bromo-2-(3,4-difluoro-2-methoxy-phenoxy)pyridine-3-carboxylic acid (97.0%) (1.04 g, 2.79 mmol, 91%) as a white solid. $^1H$ NMR and LC-MS analysis indicated this was the desired product. $^1H$ NMR (500 MHz, $CD_3OD$) δ 8.44 (d, J=2.6 Hz, 1H), 8.27 (d, J=2.6 Hz, 1H), 7.07-6.93 (m, 2H), 3.82 (d, J=1.4 Hz, 3H). LC-MS Method 2: m/z 360.1 [M]+, (ESI+), RT=0.86.

Step 3: 5-bromo-N-(4-carbamoylphenyl)-2-(3,4-difluoro-2-methoxy-phenoxy)pyridine-3-carboxamide: To a solution of 5-bromo-2-(3,4-difluoro-2-methoxy-phenoxy)pyridine-3-carboxylic acid (300 mg, 0.833 mmol) and 3-(ethyliminomethyleneamino)-N,N-dimethyl-propan-1-amine hydrochloride (192 mg, 1.00 mmol) in pyridine-anhydrous (3 mL) was added 4-aminobenzamide (139 mg, 1.00 mmol). The mixture was stirred at RT for 0.5 h. LC-MS analysis indicated the reaction was complete. The solvents were removed and the residue purified by FCC (10 g, 0 to 100% EA in heptane, then 0 to 5% MeOH in EA) to afford 5-bromo-N-(4-carbamoylphenyl)-2-(3,4-difluoro-2-methoxy-phenoxy) pyridine-3-carboxamide (95.0%) (298 mg, 0.592 mmol, 71%) as a white solid. 1H-19F-NMR and LC-MS analysis indicated this was the desired product. 30 mg was further purified by prep. HPLC (Prep. Method 2) to afford 5-bromo-N-(4-carbamoylphenyl)-2-(3,4-difluoro-2-methoxy-phenoxy)pyridine-3-carboxamide (100.0%) (21 mg, 0.0439 mmol, 5.3%) as a white solid after freeze drying. $^1H$ NMR and LC-MS analysis indicated this was the desired product. $^1H$ NMR (400 MHz, $CD_3OD$) δ 8.39 (d, J=2.5 Hz, 1H), 8.30 (d, J=2.5 Hz, 1H), 7.95-7.87 (m, 2H), 7.85-7.78 (m, 2H), 7.13 (m, 1H), 7.05 (m, 1H), 3.84 (d, J=1.7 Hz, 3H). LC-MS Method 3: m/z 478.2 [M]+, (ESI+), RT=3.36

Compound 1570: General Route 9: 5-bromo-2-(3,4-difluoro-2-methoxy-phenoxy)-N-pyridazin-4-yl-pyridine-3-carboxamide

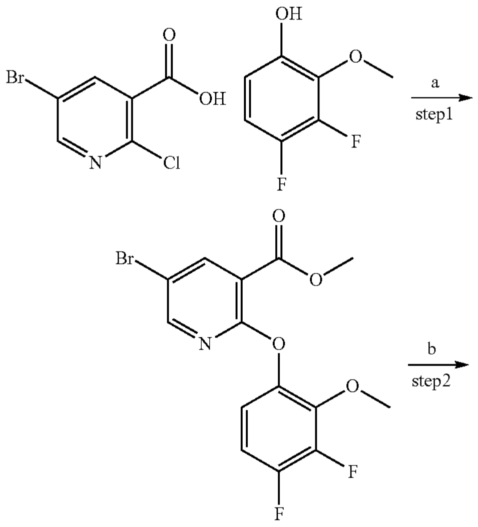

-continued

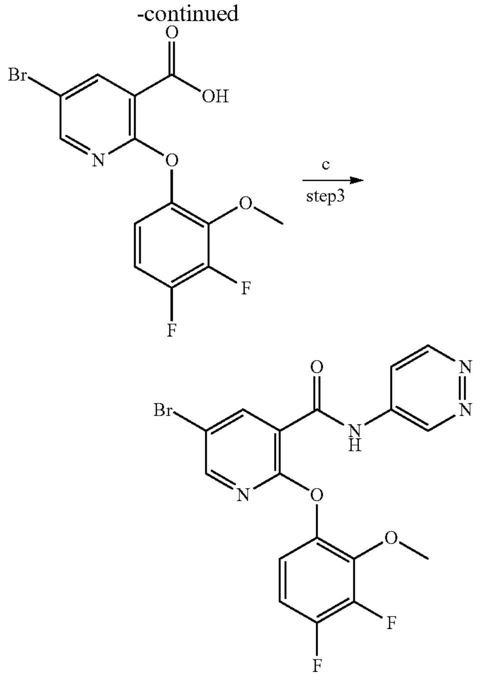

Reagents & conditions:
a) $Cs_2CO_3$, DMF, 80 °C;
b) LiOH, water, THF;
c) pyridazin-4-amine, EDC, pyridine Step 1: methyl 5-bromo-2-(3,4-difluoro-2-methoxy-phenoxy)pyridine-3-carboxylate: To a mixture of methyl 5-bromo-2-chloropyridine-3-carboxylate (1.00 g, 3.99 mmol) and 3,4-difluoro-2-methoxy-phenol (0.83 g, 5.19 mmol) in DMF-anhydrous (10 mL) was added cesium carbonate (1.95 g, 5.99 mmol). The mixture was heated at 80 °C in a pressure vial for 3 hours. The mixture was diluted with ethyl acetate (30 mL) and washed with water (4×15 mL) and brine (15 mL). The organics were dried ($MgSO_4$), filtered and concentrated to afford an orange oil. Purification by FCC (25 g 20 μm, 0 to 15% EA in heptane) afforded methyl 5-bromo-2-(3,4-difluoro-2-methoxy-phenoxy)pyridine-3-carboxylate (95.0%) (1.15 g, 2.92 mmol, 73% Yield) as a white solid. LC-MS and $^1H$ NMR analysis indicated this was the desired product. $^1H$ NMR (400 MHz, $CD_3OD$) δ 8.44 (d, J=2.6 Hz, 1H), 8.29 (d, J=2.5 Hz, 1H), 7.08-6.91 (m, 2H), 3.95 (s, 3H), 3.82 (d, J=1.4 Hz, 3H). LC-MS Method 2: m/z 374.1 $[M+H]^+$, (ESI+), RT=1.00.

Step 2: 5-bromo-2-(3,4-difluoro-2-methoxy-phenoxy) pyridine-3-carboxylic acid: To a solution of methyl 5-bromo-2-(3,4-difluoro-2-methoxy-phenoxy)pyridine-3-carboxylate (1.15 g, 3.07 mmol) in THF (8 mL):water (2 mL), lithium hydroxide (0.17 g, 6.76 mmol) was added, and the mixture was stirred at room temperature for 2 hours. The mixture was diluted with water (10 mL) and the pH was adjusted to 1 by dropwise addition of 2M HCl (aq). The aqueous layer was extracted with EtOAc (3×10 mL), dried ($MgSO_4$), filtered and concentrated in vacuo to afford 5-bromo-2-(3,4-difluoro-2-methoxy-phenoxy)pyridine-3-carboxylic acid (97.0%) (1.04 g 2.79 mmol, 91%) as a white solid. $^1H$ NMR and LC-MS analysis indicated this was the desired product. $^1H$ NMR (500 MHz, $CD_3OD$) δ 8.44 (d, J=2.6 Hz, 1H), 8.27 (d, J=2.6 Hz, 1H), 7.07-6.93 (m, 2H), 3.82 (d, J=1.4 Hz, 3H). LC-MS Method 2: m/z 360.1 [M]+, (ESI+), RT=0.86.

Step 3: 5-bromo-2-(3,4-difluoro-2-methoxy-phenoxy)-N-pyridazin-4-yl-pyridine-3-carboxamid To a solution of 5-bromo-2-(3,4-difluoro-2-methoxy-phenoxy)pyridine-3-carboxylic acid (165 mg, 0.458 mmol) and 3-(ethyliminomethyleneamino)-N,N-dimethyl-propan-1-amine hydrochloride (105 mg, 0.550 mmol) in pyridine-anhydrous (1.65 mL) was added pyridazin-4-amine (52 mg, 0.550 mmol). The mixture was stirred at RT for 1 h. LC-MS analysis (EV-TXY001-107-IPC1) indicated the reaction was complete. The solvents were removed and the residue purified by FCC (10 g, 0 to 100% EA in heptane) to afford 5-bromo-2-(3,4-difluoro-2-methoxy-phenoxy)-N-pyridazin-4-yl-pyridine-3-carboxamide (146 mg, 0.334 mmol, 73% Yield) as a white solid. $^1$H NMR and LC-MS analysis indicated this was the desired compound. $^1$H NMR (400 MHz, $CD_3OD$) δ 9.41 (dd, J=2.7, 1.0 Hz, 1H), 9.07 (dd, J=6.0, 1.0 Hz, 1H), 8.43 (d, J=2.5 Hz, 1H), 8.34 (d, J=2.5 Hz, 1H), 8.23 (dd, J=6.0, 2.7 Hz, 1H), 7.16-7.00 (m, 2H), 3.83 (d, J=1.7 Hz, 3H). LC-MS Method 3: m/z 437.1 $[M]^+$, (ESI+), RT=3.24.

Compound 1571: General Route 10: methyl 3-[[2-(3,4-difluoro-2-methoxy-phenoxy)-5-(trifluoromethyl)pyridine-3-carbonyl]amino]bicyclo[1.1.1]pentane-1-carboxylate

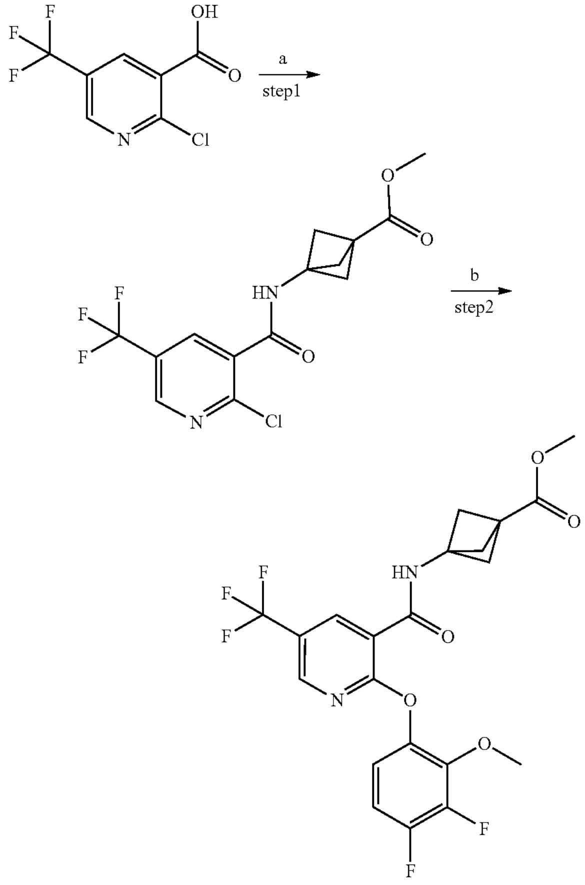

Reagents & conditions:
a) 3-aminobicyclol[1.1.1]pentane-1-carboxylate hydrochloride, EDC, pyr;
b) difluoro-2-methoxy-phenol, $K_2CO_3$, ACN, 65 °C Step 1: methyl 3-[2-chloro-5-(trifluoromethyl)pyridine-3-carbonyl]bicyclo[1.1.1]pentane-1-carboxylate: To a solution of 2-chloro-5-(trifluoromethyl)pyridine-3-carboxylic acid (100 mg, 0.443 mmol) and 3-(ethyliminomethyleneamino)-N,N-dimethyl-propan-1-amine hydrochloride (102 mg, 0.532 mmol) in pyridine (1.5 mL) was added methyl 3-aminobicyclo[1.1.1]pentane-1-carboxylate hydrochloride (79 mg, 0.443 mmol) The mixture was stirred at room temperature for 1 h. LC-MS analysis indicated the reaction was mostly complete. The solvents were removed and the residue purified by FCC (10 g, 0 to 40% EA in heptane) to afford methyl 3-[[2-chloro-5-(trifluoromethyl)pyridine-3-carbonyl]amino]bicyclo[1.1.1]pentane-1-carboxylate (100%) (126 mg, 0.361 mmol, 82%) as a white solid. $^1$H NMR and LC-MS analysis indicated this was the desired product. $^1$H NMR (400 MHz, $CD_3OD$) δ 8.82 (d, J=1.6 Hz, 1H), 8.25 (d, J=2.3 Hz, 1H), 3.72 (s, 3H), 2.46 (s, 6H). LC-MS Method 2: m/z 349.0 $[M+H]^+$, (ESI+), RT=0.76.

Step 2: methyl 3-[[2-(4-cyano-2-methoxy-phenoxy)-5-(trifluoromethyl)pyridine-3-carbonyl]amino]bicyclo[1.1.1]pentane-1-carboxylate: To a mixture of methyl 3-[[2-chloro-5-(trifluoromethyl)pyridine-3-carbonyl]amino]bicyclo[1.1.1]pentane-1-carboxylate (50 mg, 0.143 mmol) and 3,4-difluoro-2-methoxy-phenol (30 mg, 0.186 mmol) in acetonitrile-anhydrous (0.5 mL) was added dipotassium carbonate (30 mg, 0.215 mmol). The mixture was heated at 65 °C in a pressure vial for 3 h. LC-MS analysis indicated the reaction was complete. The mixture was filtered and concentrated to afford a clear oil. Purification by FCC (10 g, 0 to 20% EA in Heptane) afforded methyl 3-[[2-(3,4-difluoro-2-methoxy-phenoxy)-5-(trifluoromethyl)pyridine-3-carbonyl]amino]bicyclo[1.1.1]pentane-1-carboxylate (99.0%) (55 mg, 0.115 mmol, 80% Yield) as a white solid. $^1$H NMR and LC-MS analysis indicated this was the desired product. $^1$H NMR (400 MHz, $CD_3OD$) δ 8.51 (dd, J=2.4, 0.9 Hz, 1H), 8.44 (d, J=2.4 Hz, 1H), 7.14-7.03 (m, 2H), 3.85 (d, J=1.8 Hz, 3H), 3.71 (s, 3H), 2.47 (s, 6H). LC-MS Method 6: m/z 473.3 $[M+H]^+$, (ESI+), RT=3.98.

Compound 1572: General Route 11: 2-(4-cyano-2-methoxy-phenoxy)-N-(1-oxidopyridin-1-ium-3-yl)-5-(trifluoromethyl)pyridine-3-carboxamide

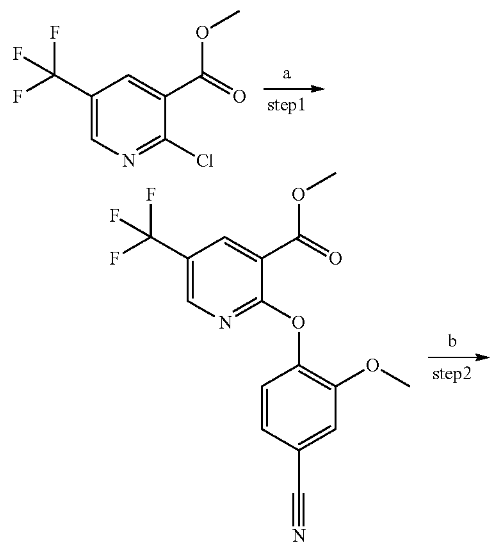

-continued

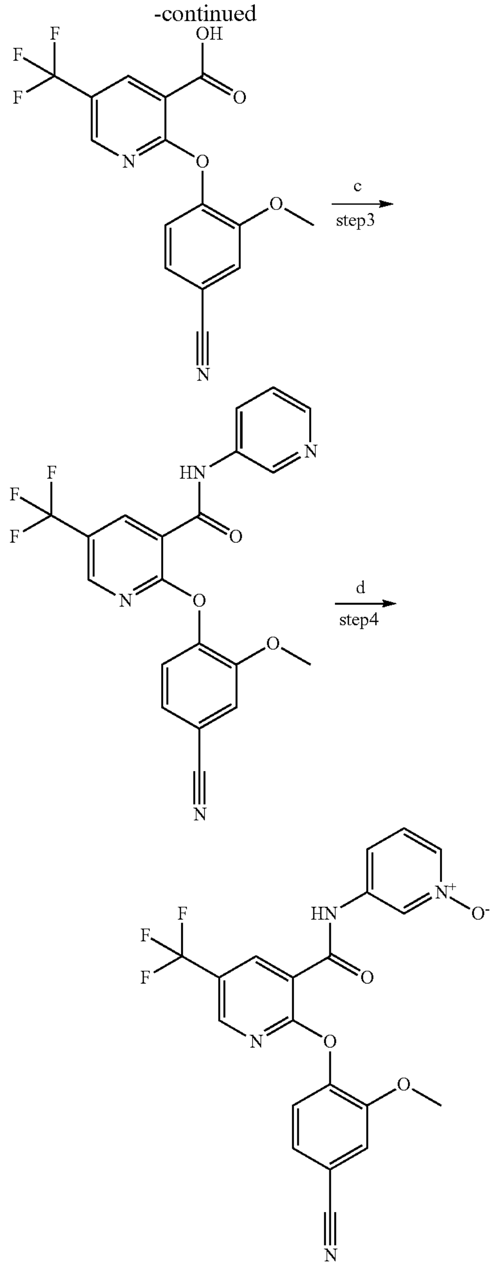

Reagents & conditions:
a) 4-hydroxy-3-methoxybenzonitrile, $K_2CO_3$, ACN, 80 °C;
b) LiOH, water, THF;
c) pyridine-3-amine, EDC, pyridine
d) MCPBA, DCM Step 1: methyl 2-(4-cyano-2-methoxy-phenoxy)-5-(trifluoromethyl)pyridine-3-carboxylate: A mixture of 2-chloro-5-trifluoromethyl-nicotinic acid methyl ester (100 mg, 0.417 mmol), 4-hydroxy-3-methoxybenzonitrile (93 mg, 0.624 mmol) and potassium carbonate (87 mg, 0.629 mmol) in acetonitrile-anhydrous (2.5 mL) was stirred at 80 °C in a pressure relief vial for 1 h. LC-MS analysis indicated the reaction was mostly complete. The mixture was filtered and concentrated to afford a clear oil. Purification by FCC (5 g, 0 to 40% EA in heptane) afforded methyl 2-(4-cyano-2-methoxy-phenoxy)-5-(trifluoromethyl)pyridine-3-carboxylate (100.0%) (142 mg, 0.403 mmol, 97%) as a white semi-solid. $^1$H NMR and LC-MS analysis indicated this was the desired product. $^1$H NMR (400 MHz, DMSO-d6) δ 8.73 (m, 1H), 8.60 (d, J=2.5 Hz, 1H), 7.69 (d, J=1.8 Hz, 1H), 7.53 (dd, J=8.2, 1.8 Hz, 1H), 7.43 (d, J=8.2 Hz, 1H), 3.91 (s, 3H), 3.74 (s, 3H). LC-MS Method 2: m/z 353.1 $[M+H]^+$, (ESI+), RT=0.94.

Step 2: 2-(4-cyano-2-methoxy-phenoxy)-5-(trifluoromethyl)pyridine-3-carboxylic acid: To a solution of methyl 2-(4-cyano-2-methoxy-phenoxy)-5-(trifluoromethyl)pyridine-3-carboxylate (142 mg, 0.403 mmol) in THF (1.8 mL):water (0.4 mL), lithium hydroxide (10 mg, 0.403 mmol) was added, and the mixture was stirred at rt for 1 h. LC-MS analysis indicated the reaction was complete. The mixture was diluted with water (5 mL) and the pH was adjusted to 1 by dropwise addition of 2M HCl (aq). The aqueous layer was extracted with EtOAc (3×5 mL), dried ($MgSO_4$), filtered and concentrated in vacuo to afford 2-(4-cyano-2-methoxy-phenoxy)-5-(trifluoromethyl)pyridine-3-carboxylic acid (100.0%)(134 mg, 0.396 mmol, 98% Yield) as a white solid. $^1$H NMR and LC-MS analysis indicated this was the desired product. $^1$H NMR (400 MHz, DMSO-d6) δ 8.68 (m, 1H), 8.55 (d, J=2.5 Hz, 1H), 7.69 (d, J=1.8 Hz, 1H), 7.53 (dd, J=8.2, 1.8 Hz, 1H), 7.42 (d, J=8.2 Hz, 1H), 3.75 (s, 3H). LC-MS Method 2: m/z 339.1 $[M+H]^+$, (ESI+), RT=0.79.

Step 3: 2-(4-cyano-2-methoxy-phenoxy)-N-(3-pyridyl)-5-(trifluoromethyl)pyridine-3-carboxamide: To a solution of 2-(4-cyano-2-methoxy-phenoxy)-5-(trifluoromethyl)pyridine-3-carboxylic acid (70 mg, 0.207 mmol) and 3-(ethyliminomethyleneamino)-N,N-dimethyl-propan-1-amine hydrochloride (48 mg, 0.248 mmol) in pyridine (0.8 mL) was added pyridin-3-amine (21 mg, 0.228 mmol). The mixture was stirred at room temperature for 1 h. LC-MS analysis indicated the reaction was complete. The solvents were removed and the residue purified by FCC (5 g, 0 to 70% EA in heptane) to afford 2-(4-cyano-2-methoxy-phenoxy)-N-(3-pyridyl)-5-(trifluoromethyl)pyridine-3-carboxamide (98.0%) (75 mg, 0.177 mmol, 86% Yield) as a white solid. 1H-19F-NMR and LC-MS analysis indicated this was the desired product. $^1$H NMR (400 MHz, DMSO-d6) δ 10.83 (s, 1H), 8.86 (d, J=2.5 Hz, 1H), 8.67 (m, 1H), 8.58 (d, J=2.5 Hz, 1H), 8.35 (dd, J=4.7, 1.5 Hz, 1H), 8.17 (dt, J=8.5, 1.8 Hz, 1H), 7.69 (m, 1H), 7.58-7.48 (m, 2H), 7.43 (dd, J=8.3, 4.7 Hz, 1H), 3.76 (s, 3H). LC-MS Method 2: m/z 415.2 $[M+H]^+$, (ESI+), RT=0.78.

Step 4: 2-(4-cyano-2-methoxy-phenoxy)-N-(1-oxidopyridin-1-ium-3-yl)-5-(trifluoromethyl)pyridine-3-carboxamide: A solution of 2-(4-cyano-2-methoxy-phenoxy)-N-(3-pyridyl)-5-(trifluoromethyl)pyridine-3-carboxamide (75 mg, 0.181 mmol) in DCM (3 mL) at 0 °C was treated with 3-chloroperoxybenzoic acid (73%, 45 mg, 0.190 mmol) then allowed to warm to room temperature and stirred for 0.5 h. LC-MS analysis indicated the reaction was mostly complete. The mixture was concentrated under reduced pressure and the residue purified by prep. HPLC (Prep. Method 2) to afforded a white solid (about 80 mg, containing mCBA). Further purification (Prep. Method 1) afforded 2-(4-cyano-2-methoxy-phenoxy)-N-(1-oxidopyridin-1-ium-3-yl)-5-(trifluoromethyl)pyridine-3-carboxamide (100.0%) (13 mg, 0.0302 mmol, 17% Yield) as a white solid. $^1$H NMR and LC-MS analysis indicated this was the desired product. $^1$H NMR (400 MHz, $CD_3OD$) δ 9.10 (m, 1H), 8.58 (m, 1H), 8.54 (m, 1H), 8.19-8.13 (1H), 7.81 (n, NH), 7.58-7.41 (m, 4H), 3.80 (s, 3H). LC-MS Method 4: m/z 431.2 $[M+H]^+$, (ESI+), RT=2.63.

Example 87

Exemplary compounds of the invention are listed in Table 15 were prepared using one of the general routes described above.

TABLE 15

| Compound | Route | Structure and name | Analytical data |
|---|---|---|---|
| 1573 | 2 | 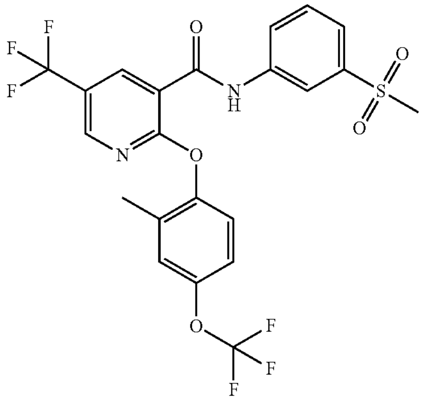 N-(3-methylsulfonylphenyl)-2-[2-methyl-4-(trifluoromethoxy)phenoxy]-5-(trifluoromethyl)pyridine-3-carboxamide | $^1$H NMR (500 MHz, DMSO-d6) δ 11.04 (s, 1H), 8.69 (dd, J = 2.3, 0.9 Hz, 1H), 8.62 – 8.53 (m, 1H), 8.40 (t, J = 1.9 Hz, 1H), 7.97 (dt, J = 7.6, 1.6 Hz, 1H), 7.73 7.65 (m, 2H), 7.40 – 7.36 (m, 2H), 7.32 – 7.27 (m, 1H), 3.22 (s, 3H), 2.13 (s, 3H). m/z 534.9 [M + H]$^+$, (ESI+), RT = 4.82 LC-MS Method 5 |
| 1574 | 2 | 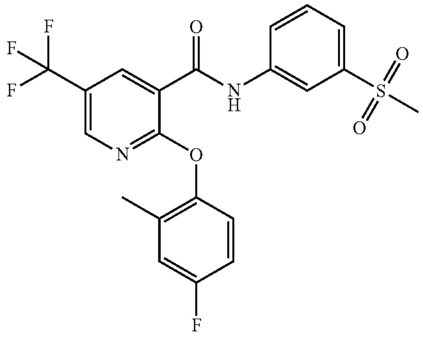 2-(4-fluoro-2-methyl-phenoxy)-N-(3-methylsulfonylphenyl)-5-(trifluoromethyl)pyridine-3-carboxamide | $^1$H NMR (500 MHz, DMSO-d6) δ 11.03 (s, 1H), 8.71 – 8.65 (m, 1H), 8.62 – 8.52 (m, 1H), 8.43 – 8.35 (m, 1H), 7.97 (dt, J = 7.6, 1.7 Hz, 1H), 7.72 – 7.63 (m, 2H), 7.27 (dd, J = 8.9, 5.1 Hz, 1H), 7.20 (dd, J = 9.4, 3.0 Hz, 1H), 7.11 (td, J = 8.5, 3.1 Hz, 1H), 3.22 (s, 3H), 2.09 (s, 3H). m/z 468.9 [M + H]$^+$, (ESI+), RT = 4.49 LC-MS Method 5 |
| 1575 | 2 | 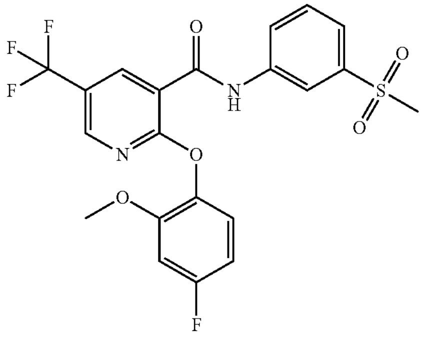 2-(4-fluoro-2-methoxy-phenoxy)-N-(3-methylsulfonylphenyl)-5-(trifluoromethyl)pyridine-3-carboxamide | $^1$H NMR (500 MHz, DMSO-d6) δ 10.98 (s, 1H), 8.69 – 8.62 (m, 1H), 8.52 (d, J = 2.4 Hz, 1H), 8.46 – 8.35 (m, 1H), 7.98 (dt, J = 7.5, 1.7 Hz, 1H), 7.72 – 7.65 (m, 2H), 7.32 (dd, J = 8.8, 5.9 Hz, 1H), 7.10 (dd, J = 10.7, 2.9 Hz, 1H), 6.84 (td, J = 8.5, 2.9 Hz, 1H), 3.71 (s, 3H), 3.22 (s, 3H). m/z 484.9 [M + H]$^+$, (ESI+), RT = 4.43 LC-MS Method 8 |

TABLE 15-continued

| Compound | Route | Structure and name | Analytical data |
|---|---|---|---|
| 1576 | | 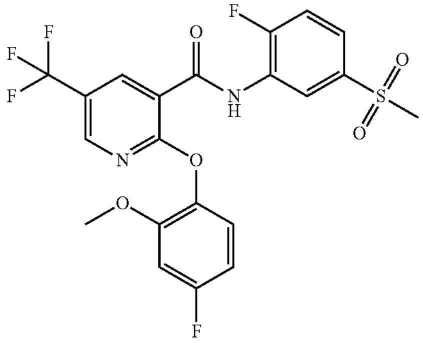 2-(4-fluoro-2-methoxy-phenoxy)-N-(2-fluoro-5-methylsulfonyl-phenyl)-5-(trifluoromethyl)pyridine-3-carboxamide | $^1$H NMR (500 MHz, DMSO-d6) δ 10.66 (s, 1H), 8.74 (d, J = 5.3 Hz, 1H), 8.69 (s, 1H), 8.56 (d, J = 2.4 Hz, 1H), 7.82 (ddd, J = 8.4, 4.4, 2.4 Hz, 1H), 7.67 − 7.59 (m, 1H), 7.35 (dd, J = 8.6, 6.0 Hz, 1H), 7.12 (dd, J = 10.7, 2.8 Hz, 1H), 6.86 (td, J = 8.5, 2.8 Hz, 1H), 3.72 (s, 3H), 3.26 (s, 3H). m/z 503.0 [M + H]$^+$, (ESI+), RT = 4.57 LC-MS Method 5 |
| 1577 | | 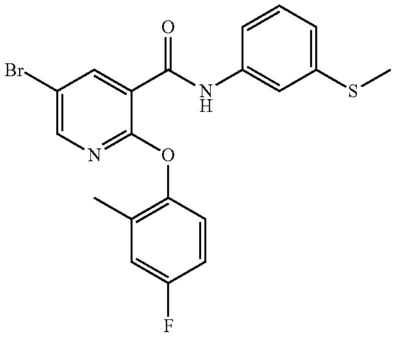 5-bromo-2-(4-fluoro-2-methyl-phenoxy)-N-(3-methylsulfanylphenyl) pyridine-3-carboxamide | $^1$H NMR (400 MHz, DMSO-d6) δ 10.57 (s, 1H), 8.34 (q, J = 2.5 Hz, 2H), 7.71 (t, J = 1.8 Hz, 1H), 7.48 − 7.43 (m, 1H), 7.30 (t, J = 8.0 Hz, 1H), 7.21 (dd, J = 8.8, 5.1 Hz, 1H), 7.16 (dd, J = 9.4, 3.0 Hz, 1H), 7.08 (td, J = 8.5, 3.1 Hz, 1H), 7.02 (ddd, J =7.8, 1.8, 0.9 Hz, 1H), 2.47 (s, 3H), 2.08 (s, 3H). m/z 446.95,448.95 [M + H]$^+$, (ESI+), RT = 1.47 LC-MS Method 1 |
| 1578 | | 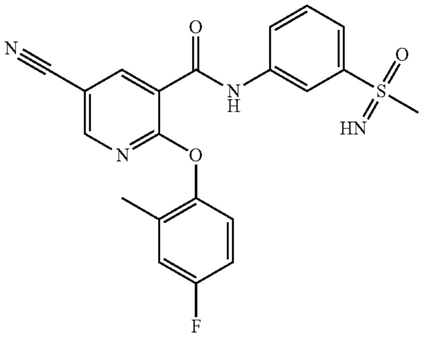 5-cyano-2-(4-fluoro-2-methyl-phenoxy)-N-[3-(methylsulfonimidoyl)phenyl] pyridine-3-carboxamide | $^1$H NMR (400 MHz, DMSO-d6) δ 10.99 (s, 1H), 8.72 (d, J = 2.2 Hz, 1H), 8.66 (d, J = 2.2 Hz, 1H), 8.38 (s, 1H), 7.93 (d, J = 8.1 Hz, 1H), 7.70 (d, J = 8.0 Hz, 1H), 7.61 (t, J = 7.9 Hz, 1H), 7.27 (dd, J = 8.9, 5.1 Hz, 1H), 7.20 (dd, J = 9.4, 2.9 Hz, 1H), 7.10 (dt, J = 8.5, 4.2 Hz, 1H), 4.23 (s, 1H), 3.06 (s, 3H), 2.08 (s, 3H). m/z 424.9 [M + H]$^+$, (ESI+), RT = 3.65 LC-MS Method 5 |

TABLE 15-continued

| Compound | Route | Structure and name | Analytical data |
| --- | --- | --- | --- |
| 1579 | | 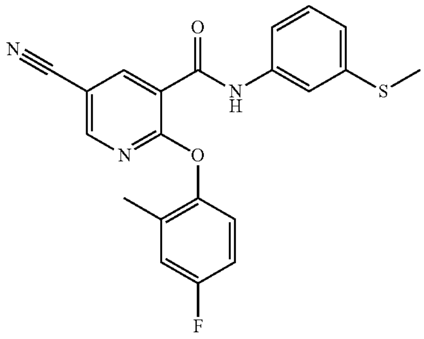 5-cyano-2-(4-fluoro-2-methyl-phenoxy)-N-[3-(methylsulfanylphenyl) pyridine-3-3-carboxamide | $^1$H NMR (500 MHz, DMSO-d6) δ 10.65 (s, 1H), 8.71 (d, J = 2.2 Hz, 1H), 8.63 (d, J = 2.2 Hz, 1H), 7.70 (t, J = 1.8 Hz, 1H), 7.48 - 7.41 (m, 1H), 7.32 (t, J = 8.0 Hz, 1H), 7.26 (dd, J = 8.9, 5.1 Hz, 1H), 7.20 (dd, J = 9.4, 3.0 Hz, 1H), 7.11 (td, J = 8.5, 3.1 Hz, 1H), 7.07 - 6.98 (m, 1H), 2.47 (s, 3H), 2.07 (s, 3H). m/z 393.9 [M + H]$^+$, (ESI+), RT = 4.76 LC-MS Method 5 |
| 1581 | 2 | 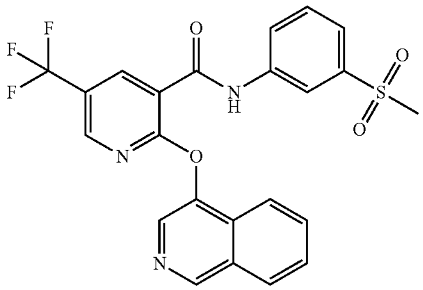 2-(4-isoquinolyloxy)-N-(3-methylsulfonylphenyl)-5-(trifluoromethyl)pyridine-3-carboxamide | $^1$H NMR (400 MHz, DMSO-d6) δ 11.20 (s, 1H), 9.31 (s, 1H), 8.68 - 8.65 (m, 1H), 8.63 - 8.59 (m, 1H), 8.55 (s, 1H), 8.47 - 8.42 (m, 1H), 8.29 - 8.22 (m, 1H), 8.02 (dt, J = 7.1, 2.0 Hz, 1H), 7.99 - 7.94 (m, 1H), 7.85 - 7.74 (m, 2H), 7.73 - 7.66 (m, 2H), 3.22 (s, 3H). m/z 488.5 [M + H]$^+$, (ESI+), RT = 3.96 LC-MS Method 5 |
| 1582 | 2 | 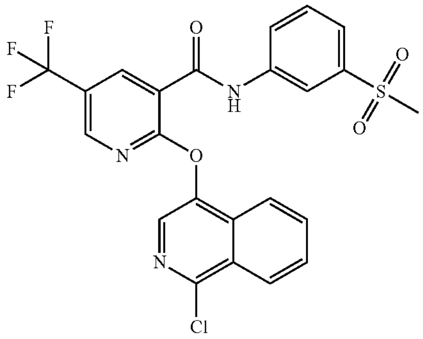 2-[(1-chloro-4-isoquinolyl)oxy]-N-(3-methylsulfonylphenyl)-5-(trifluoromethyl)pyridine-3-carboxamide | $^1$H NMR (500 MHz, DMSO-d6) δ 11.21 (s, 1H), 8.72 - 8.66 (m, 1H), 8.66 - 8.60 (m, 1H), 8.47 - 8.41 (m, 2H), 8.40 - 8.33 (m, 1H), 8.10 - 8.05 (m, 1H), 8.02 (dt, J = 7.5, 1.8 Hz, 1H), 7.98 - 7.87 (m, 2H), 7.74 - 7.66 (m, 2H), 3.23 (s, 3H). m/z 522.5 [M + H]$^+$, (ESI+), RT = 4.49 LC-MS Method 5 |

TABLE 15-continued

| Compound | Route | Structure and name | Analytical data |
| --- | --- | --- | --- |
| 1583 | 2 | 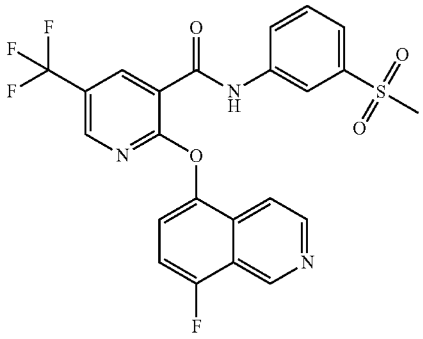 2-[(8-fluoro-5-isoquinolyl)oxy]-N-(3-methylsulfonylphenyl)-5-(trifluoromethyl)pyridine-3-carboxamide | $^1H$ NMR (500 MHz, DMSO-d6) δ 11.20 (s, 1H), 9.45 (s, 1H), 8.70 (d, J = 5.9 Hz, 1H), 8.68 - 8.65 (m, 1H), 8.65 - 8.62 (m, 1H), 8.44 - 8.42 (m, 1H), 8.01 (dt, J = 7.3, 1.8 Hz, 1H), 7.99 (dd, J = 5.9, 0.9 Hz, 1H), 7.76 - 7.66 (m, 3H), 7.63 (dd, J = 8.5, 4.2 Hz, 1H), 3.22 (s, 3H). m/z 506.5 [M + H]$^+$, (ESI+), RT = 4.04 LC-MS Method 5 |
| 1584 | 2 | 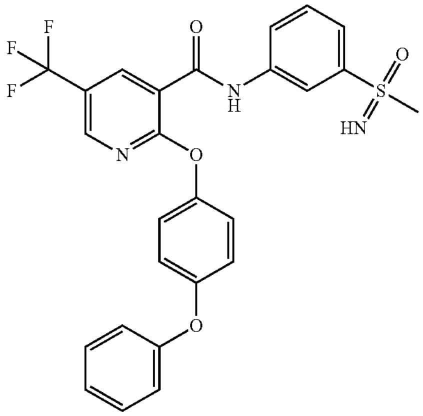 N-[3-(methylsulfonimidoyl)phenyl]-2-(4-phenoxyphenoxy)-5-(trifluoromethyl)pyridine-3-carboxamide | $^1H$ NMR (400 MHz, DMSO-d6) δ 10.95 (s, 1H), 8.73 - 8.67 (m, 1H), 8.52 (d, J = 2.2 Hz, 1H), 8.37 (t, J = 1.8 Hz, 1H), 7.98 - 7.92 (m, 1H), 7.72 - 7.66 (m, 1H), 7.64 - 7.57 (m, 1H), 7.45 - 7.36 (m, 2H), 7.35 - 7.25 (m, 2H), 7.20 - 7.12 (m, 1H), 7.12 - 6.98 (m, 4H), 4.22 (s, 1H), 3.06 (s, 3H). m/z 528.0 [M + H]$^+$, (ESI+), RT = 4.45 LC-MS Method 5 |
| 1585 | 2 | 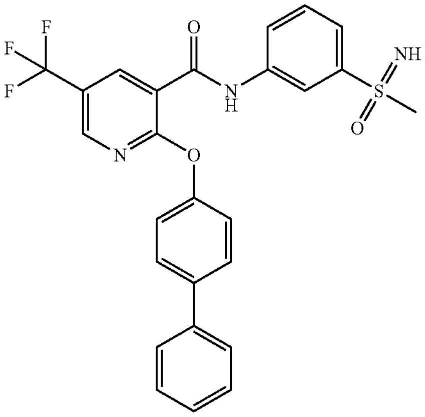 N-[3-(methylsulfonimidoyl)phenyl]-2-(4-phenylphenoxy)-5-(trifluoromethyl)pyridine-3-carboxamide | $^1H$ NMR (400 MHz, DMSO-d6) δ 10.97 (s, 1H), 8.74 - 8.68 (m, 1H), 8.55 (d, J = 2.4 Hz, 1H), 8.38 (t, J = 1.9 Hz, 1H), 7.99 - 7.93 (m, 1H), 7.77 - 7.72 (m, 2H), 7.71 - 7.66 (m, 3H), 7.65 - 7.59 (m, 1H), 7.51 - 7.45 (m, 2H), 7.40 - 7.34 (m, 3H), 4.23 (s, 1H), 3.06 (s, 3H). m/z 512.0 [M + H]$^+$, (ESI+), RT = 4.47 LC-MS Method 1 |

TABLE 15-continued

| Compound | Route | Structure and name | Analytical data |
|---|---|---|---|
| 1586 | 2 | 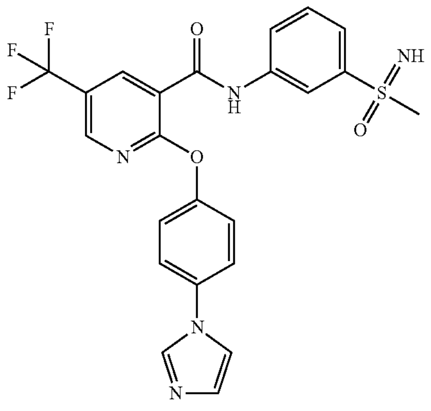 2-(4-imidazol-1-ylphenoxy)-N-[3-(methylsulfonimidoyl)phenyl]-5-(trifluoromethyl)pyridine-3-carboxamide | $^1$H NMR (400 MHz, DMSO-d6) δ 10.96 (s, 1H), 8.74 – 8.68 (m, 1H), 8.58 – 8.53 (m, 1H), 8.37 (t, J = 1.8 Hz, 1H), 8.27 – 8.21 (m, 1H), 8.13 (s, 1H), 8.01 – 7.91 (m, 1H), 7.77 – 7.68 (m, 3H), 7.67 – 7.58 (m, 1H), 7.47 – 7.39 (m, 2H), 7.17 – 7.08 (m, 1H), 4.23 (s, 1H), 3.06 (s, 3H). m/z 501.9 [M + H]$^+$, (ESI+), RT = 2.86 LC-MS Method 5 |
| 1587 | 2 | 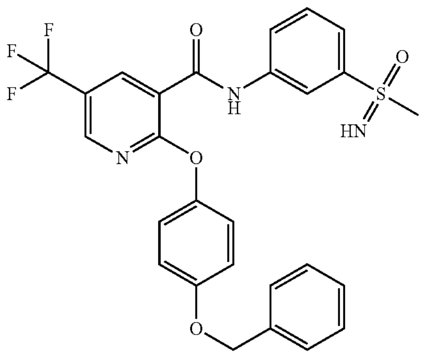 2-(4-benzyloxyphenoxy)-N-[3-(methylsulfonimidoyl)phenyl]-5-(trifluoromethyl)pyridine-3-carboxamide | $^1$H NMR (400 MHz, DMSO-d6) δ 10.92 (s, 1H), 8.69 – 8.63 (m, 1H), 8.49 (d, J = 2.3 Hz, 1H), 8.37 (t, J = 1.8 Hz, 1H), 7.99 – 7.91 (m, 1H), 7.73 – 7.66 (m, 1H), 7.66 – 7.55 (m, 1H), 7.49 – 7.44 (m, 2H), 7.43 – 7.37 (m, 2H), 7.36 – 7.31 (m, 1H), 7.21 – 7.16 (m, 2H), 7.10 – 7.04 (m, 2H), 5.12 (s, 2H), 4.22 (s, 1H), 3.08 – 3.03 (m, 3H). m/z 541.9 [M + H]$^+$, (ESI+), RT = 4. 6 LC-MS Method 5 |
| 1588 | 2 | 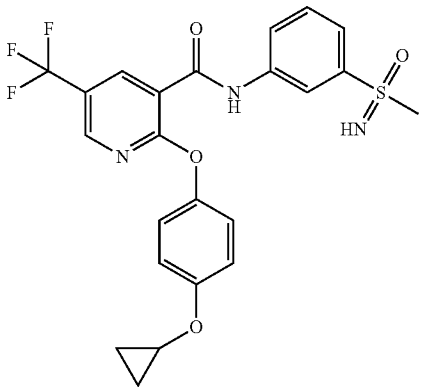 2-[4-(cyclopropoxy)phenoxy]-N-[3-(methylsulfonimidoyl)phenyl]-5-(trifluoromethyl)pyridine-3-carboxamide | $^1$H NMR (400 MHz, DMSO-d6) δ 10.93 (s, 1H), 8.70 – 8.63 (m, 1H), 8.50 (d, J = 2.4 Hz, 1H), 8.41 – 8.33 (m, 1H), 7.99 – 7.91 (m, 1H), 7.72 – 7.66 (m, 1H), 7.66 – 7.57 (m, 1H), 7.26 – 7.15 (m, 2H), 7.15 – 7.08 (m, 2H), 4.22 (s, 1H), 3.89 – 3.80 (m, 1H), 3.06 (s, 3H), 0.82 – 0.75 (m, 2H), 0.71 – 0.61 (m, 2H). m/z 492.5 [M + H]$^+$, (ESI+), RT = 4.16 LC-MS Method 5 |

TABLE 15-continued

| Compound | Route | Structure and name | Analytical data |
|---|---|---|---|
| 1589 | 3 | 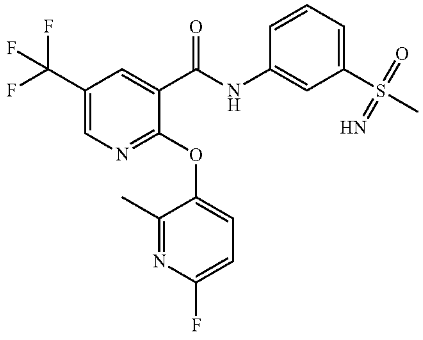 2-[(6-fluoro-2-methyl-3-pyridyl)oxy]-N-[3-(methylsulfonimidoyl)phenyl]-5-(trifluoromethyl)pyridine-3-carboxamide | $^1H$ NMR (400 MHz, $CD_3OD$) δ 8.55 (s, 2H), 8.46 (s, 1H), 8.01 (d, J = 8.1 Hz, 1H), 7.86 - 7.78 (m, 2H), 7.65 (t, J = 8.0 Hz, 1H), 7.00 (d, J = 8.9 Hz, 1H), 3.17 (s, 3H), 2.32 (s, 3H). 2 NH not seen. m/z 469.0 $[M + H]^+$, (ESI+), RT = 3.01 LC-MS Method 4 |
| 1590 | 3 | 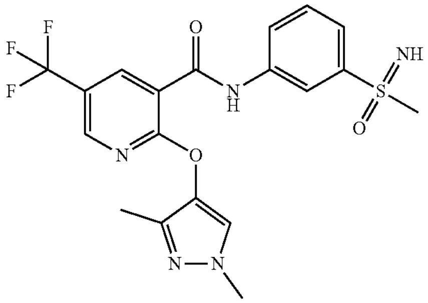 2-(1,3-dimethylpyrazol-4-yl)oxy-N-[3-(methylsulfonimidoyl)phenyl]-5-(trifluoromethyl)pyridine-3-carboxamide | $^1H$ NMR (400 MHz, $CD_3OD$) δ 8.69 - 8.61 (m, 1H), 8.55 - 8.37 (m, 2H), 8.05 - 7.98 (m, 1H), 7.89 - 7.75 (m, 2H), 7.65 (t, J = 8.0 Hz, 1H), 3.83 (s, 3H), 3.18 (s, 3H), 2.12 (s, 3H) 2NH not seen. m/z 454.2 $[M + H]^+$, (ESI+), RT = 2.39 LC-MS Method 4 |
| 1591 | 3 | 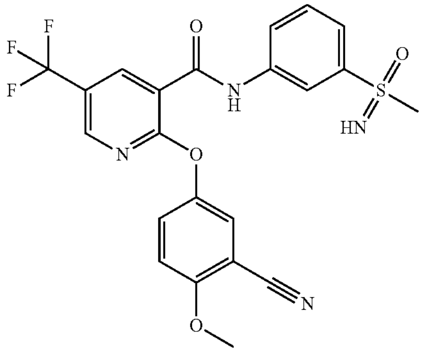 2-(3-cyano-4-methoxy-phenoxy)-N-[3-(methylsulfonimidoyl)pheny]-5-(trifluoromethyl) pyridine-3-carboxamide | $^1H$ NMR (400 MHz, $CD_3OD$) δ 8.60 - 8.54 (m, 1H), 8.54 - 8.48 (m, 1H), 8.47 - 8.40 (m, 1H), 8.04 - 7.97 (m, 1H), 7.86 - 7.77 (m, 1H), 7.73 - 7.58 (m, 2H), 7.55 (dd, J = 9.1, 2.9 Hz, 1H), 7.26 (d, J = 9.2 Hz, 1H), 3.99 (s, 3H), 3.17 (s, 3H). 2 NH not seen. m/z 491.2 $[M + H]^+$, (ESI+), RT = 2.99 LC-MS Method 4 |

TABLE 15-continued

| Compound | Route | Structure and name | Analytical data |
|---|---|---|---|
| 1592 | 3 | 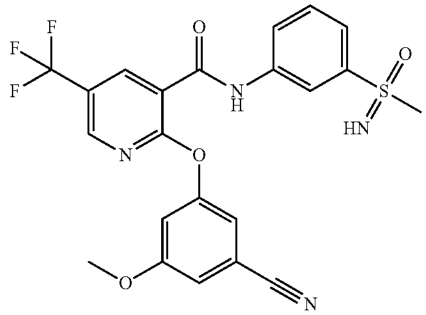 2-(3-cyano-5-methoxy-phenoxy)-N-[3-(methylsulfonimidoyl)phenyl]-5-(trifluoromethyl)pyridine-3-carboxamide | $^1$H NMR (400 MHz, $CD_3OD$) δ 8.59 (s, 1H), 8.54 (d, J = 2.3 Hz, 1H), 8.43 (t, J = 1.8 Hz, 1H), 8.03 - 7.97 (m, 1H), 7.84 - 7.78 (m, 1H), 7.64 (t, J = 8.0 Hz, 1H), 7.30 - 7.18 (m, 3H), 3.86 (s, 3H), 3.17 (s, 3H). 2NH not seen. m/z 491.2 $[M + H]^+$, (ESI+), RT = 3.17 LC-MS Method 6 |
| 1593 | 3 | 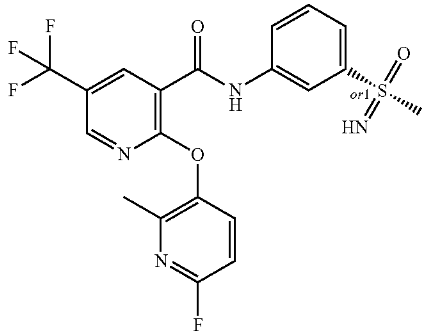 2-[(6-fluoro-2-methyl-3-pyridyl)oxy]-N-[3-(methylsulfonimidoyl)phenyl]-5-(trifluoromethyl)pyridine-3-carboxamide | $^1$H NMR (400 MHz, $CD_3OD$) δ 8.76 - 8.51 (m, 2H), 8.46 (t, J = 1.8 Hz, 1H), 8.08 - 7.96 (m, 1H), 7.93 - 7.73 (m, 2H), 7.65 (t, J = 8.0 Hz, 1H), 7.00 (dd, J = 8.7, 3.2 Hz, 1H), 3.17 (s, 3H), 2.32 (s, 3H). 2 exchangeable Hs not seen. m/z 469.7 $[M + H]^+$, (ESI+), RT = 2.88 LC-MS Method 6. Chiral Analysis Conditions Chiralpak IG (4.6 mm × 250 mm, 5um) Column Temperature 40° C. Flow Rate 4 mL/min Injection Volume 1.0 uL BPR 125 BarG Isocratic Conditions 50:50 MeOH:CO2 (0.1%% v/v NH3). Chiral LC m/z 469.2 $[M + H]^+$, (ESI+), RT = 2.06 |
| 1594 | 3 | 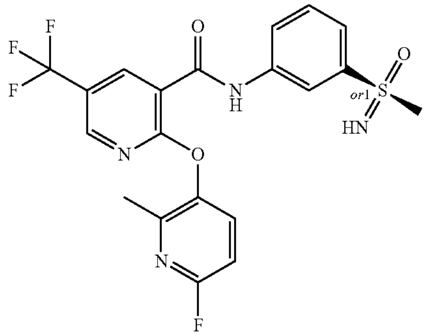 2-[(6-fluoro-2-methyl-3-pyridyl)oxy]-N-[3-(methylsulfonimidoyl)phenyl]-5-(trifluoromethyl)pyridine-3-carboxamide | $^1$H NMR (400 MHz, $CD_3OD$) δ 8.63 - 8.51 (m, 2H), 8.46 (t, J = 1.9 Hz, 1H), 8.05 - 7.97 (m, 1H), 7.86 - 7.76 (m, 2H), 7.65 (t, J = 8.0 Hz, 1H), 7.00 (dd, J = 8.7, 3.1 Hz, 1H), 3.17 (s, 3H), 2.32 (s, 3H). 2 exchangeable Hs not seen. m/z 469.7 $[M + H]^+$, (ESI+), RT = 2.88 LC-MS Method 6. Chiralpak IG (4.6mm x 250mm, 5um) Column Temperature 40°° C. Flow Rate 4 mL/min Injection Volume 1.0 uL BPR 125 BarG Isocratic Conditions 50:50 MeOH:CO2 (0.1%% v/v NH3). Chiral LC m/z 469.2 $[M + H]^+$, (ESI+), RT = 3.23 |

TABLE 15-continued

| Compound | Route | Structure and name | Analytical data |
|---|---|---|---|
| 1595 | 2 | 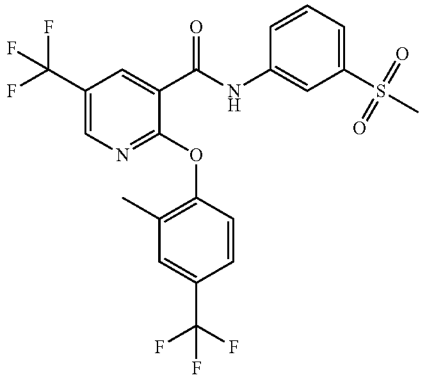 N-(3-methylsulfonylphenyl)-2-[2-methyl-4-(trifluoromethyl)phenoxy]-5-(trifluoromethyl)pyridine-3-carboxamide | $^1$H NMR (400 MHz, DMSO-d6) δ 11.05 (s, 1H), 8.72 – 8.63 (m, 1H), 8.59 (d, J = 2.2 Hz, 1H), 8.41 – 8.32 (m, 1H), 7.99 – 7.91 (m, 1H), 7.76 – 7.72 (m, 1H), 7.72 – 7.61 (m, 3H), 7.45 (d, J = 8.4 Hz, 1H), 3.21 (s, 3H), 2.17 (s, 3H). m/z 519.1 $[M + H]^+$, (ESI+), RT = 4.04 LC-MS Method 4 |
| 1596 | 2 | 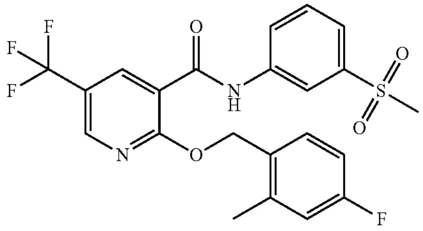 2-[(4-fluoro-2-methyl-phenyl)methoxy]-N-(3-methylsulfonylphenyl)-5-(trifluoromethyl)pyridine-3-carboxamide | $^1$H NMR (400 MHz, DMSO-d6) δ 10.83 (s, 1H), 8.77 (dd, J = 2.4, 1.0 Hz, 1H), 8.39 (d, J = 2.4 Hz, 1H), 8.28 (t, J = 1.8 Hz, 1H), 7.87 (dt, J = 7.5, 1.8 Hz, 1H), 7.69 – 7.60 (m, 2H), 7.48 (dd, J = 8.4, 6.1 Hz, 1H), 7.06 (dd, J = 10.0, 2.6 Hz, 1H), 6.97 (td, J = 8.6, 2.7 Hz, 1H), 5.50 (s, 2H), 3.19 (s, 3H), 2.33 (s, 3H). m/z 483.1 $[M + H]^+$, (ESI+), RT = 4.08 LC-MS Method 4 |
| 1597 | 2 | 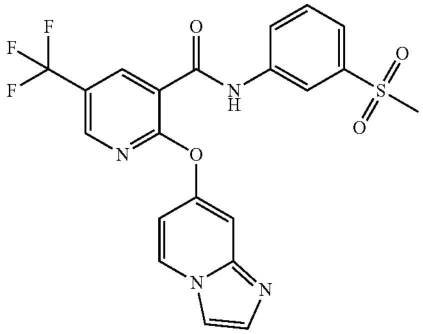 2-imidazo[1,2-a]433yridine-7-yloxy-N-(3-methylsulfonylphenyl)-5-(trifluoromethyl)pyridine-3-carboxamide | $^1$H NMR (500 MHz, DMSO-d6) δ 11.03 (s, 1H), 8.74 – 8.71 (m, 1H), 8.62 (d, J = 7.3 Hz, 1H), 8.59 (d, J = 2.5 Hz, 1H), 8.40 (t, J = 1.9 Hz, 1H), 8.17 (s, 1H), 7.99 (dt, J = 7.6, 1.8 Hz, 1H), 7.96 (s, 1H), 7.74 – 7.64 (m, 2H), 7.57 (d, J = 1.0 Hz, 1H), 7.49 (d, J = 2.3 Hz, 1H), 6.93 (dd, J = 7.4, 2.3 Hz, 1H), 3.23 (s, 3H). m/z 477.2 $[M + H]^+$, (ESI+), RT = 1.67 LC-MS Method 4 |

TABLE 15-continued

| Compound | Route | Structure and name | Analytical data |
|---|---|---|---|
| 1598 | 2 | 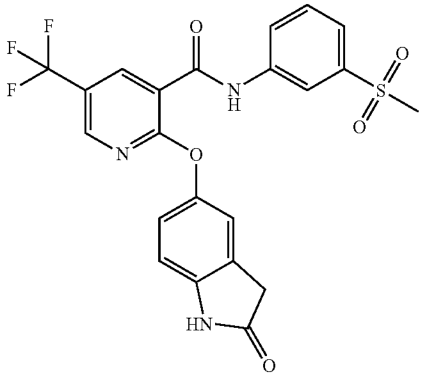 N-(3-methylsulfonylphenyl)-2-(2-oxoindolin-5-yl)oxy-5-(trifluoromethyl)pyridine-3-carboxamide | $^1$H NMR (400 MHz, DMSO-d6) δ 10.98 (s, 1H), 10.41 (s, 1H), 8.69 − 8.63 (m, 1H), 8.50 (d, J = 2.5 Hz, 1H), 8.42 − 8.35 (m, 1H), 7.97 (dt, J = 7.2, 1.9 Hz, 1H), 7.74 − 7.61 (m, 2H), 7.15 (s, 1H), 7.06 (dd, J = 8.3, 2.3 Hz, 1H), 6.85 (d, J = 8.3 Hz, 1H), 3.52 (s, 2H), 3.22 (s, 3H). m/z 492.5 [M + H]$^+$, (ESI+), RT = 3.66 LC-MS Method 5 |
| 1599 | 2 | 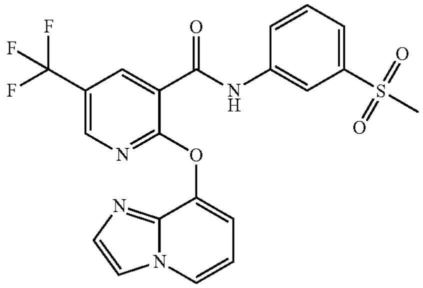 2-imidazo[1,2-a]pyridine-8-yloxy-N-(3-methylsulfonylphenyl)-5-(trifluoromethyl)pyridine-3-carboxamide | $^1$H NMR (400 MHz, DMSO-d6) δ 11.39 (s, 1H), 8.66 (d, J = 1.4 Hz, 1H), 8.60 (d, J = 2.3 Hz, 1H), 8.53 (dd, J =6.8, 0.9 Hz, 1H), 8.44 (t, J = 1.8 Hz, 1H), 8.05 (d, J = 1.2 Hz, 1H), 8.01 (dt, J = 7.4, 1.8 Hz, 1H), 7.73 − 7.63 (m, 2H), 7.54 (d, J = 1.1 Hz, 1H), 7.36 − 7.31 (m, 1H), 6.99 (t, J = 7.1 Hz, 1H), 3.32 (s, 3H). m/z 476.8 [M + H]$^+$, (ESI+), RT = 3.13 LC-MS Method 5 |
| 1600 | 2 | 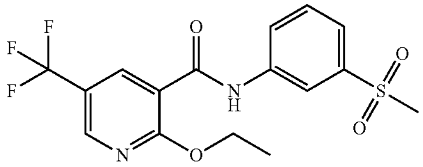 2-ethoxy-N-(3-methylsulfonylphenyl)-5-(trifluoromethyl)pyridine-3-carboxamide | $^1$H NMR (400 MHz, DMSO-d6) δ 10.72 (s, 1H), 8.75 (dd, J = 2.4, 1.0 Hz, 1H), 8.40 − 8.34 (m, 2H), 7.94 (dt, J = 7.3, 1.8 Hz, 1H), 7.73 − 7.62 (m, 2H), 4.52 (q, J = 7.0 Hz, 2H), 3.22 (s, 3H), 1.37 (t, J = 7.0 Hz, 3H). m/z 388.9 [M + H]$^+$, (ESI+), RT = 4.24 LC-MS Method 5 |

TABLE 15-continued

| Compound | Route | Structure and name | Analytical data |
|---|---|---|---|
| 1601 | 2 | 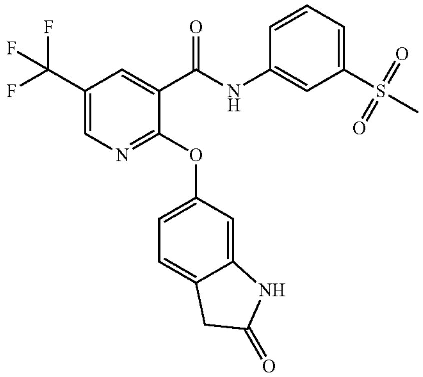 N-(3-methylsulfonylphenyl)-2-(2-oxoindolin-6-yl)oxy-5-(trifluoromethyl)pyridine-3-carboxamide | $^1$H NMR (400 MHz, DMSO-d6) δ 11.01 (s, 1H), 10.50 (s, 1H), 8.69 (dd, J = 2.4, 0.9 Hz, 1H), 8.55 - 8.50 (m, 1H), 8.38 (t, J = 1.8 Hz, 1H), 7.97 (dt, J = 7.3, 1.9 Hz, 1H), 7.74 - 7.58 (m, 2H), 7.25 (d, J = 8.0 Hz, 1H), 6.79 (dd, J = 8.0, 2.2 Hz, 1H), 6.74 (d, J = 2.1 Hz, 1H), 3.49 (s, 2H), 3.22 (s, 3H). m/z 491.9 $[M + H]^+$, (ESI+), RT = 3.72 LC-MS Method 5 |
| 1602 | 2 | 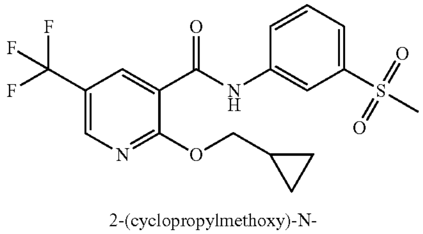 2-(cyclopropylmethoxy)-N-(3-methylsulfonylphenyl)-5-(trifluoromethyl)pyridine-3-carboxamide | $^1$H NMR (400 MHz, DMSO-d6) δ 10.72 (s, 1H), 8.74 (dd, J = 2.4, 0.9 Hz, 1H), 8.38 (d, J = 2.1 Hz, 2H), 7.95 (dt, J = 7.0, 2.0 Hz, 1H), 7.73 - 7.63 (m, 2H), 4.33 (d, J = 7.1 Hz, 2H), 3.23 (s, 3H), 1.37 - 1.24 (m, 1H), 0.62 - 0.51 (m, 2H), 0.45 - 0.36 (m, 2H). m/z 415.5 $[M + H]^+$, (ESI+), RT = 4.51 LC-MS Method 5 |
| 1603 | 2 | 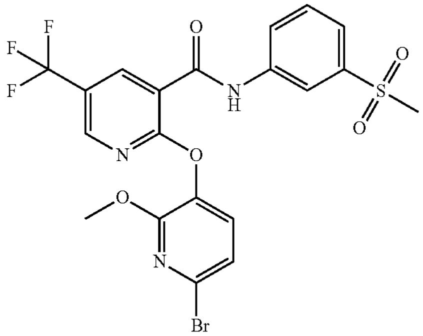 2-[(6-bromo-2-methoxy-3-pyridyl)oxy]-N-(3-methylsulfonylphenyl)-5-(trifluoromethyl)pyridine-3-carboxamide | $^1$H NMR (400 MHz, DMSO-d6) δ 11.00 (s, 1H), 8.69 (d, J = 1.4 Hz, 1H), 8.58 (d, J = 2.3 Hz, 1H), 8.39 (s, 1H), 7.98 (d, J = 7.5 Hz, 1H), 7.78 - 7.60 (m, 3H), 7.34 (d, J = 8.0 Hz, 1H), 3.81 (s, 3H), 3.22 (s, 3H). m/z 546.5, 548.4 $[M + H]^+$, (ESI+), RT = 4.56 LC-MS Method 5 |
| 1604 | 2 | 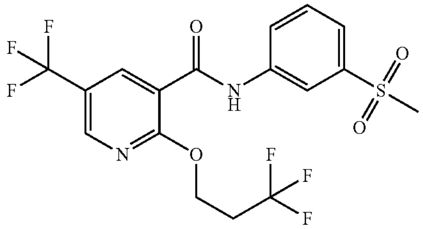 N-(3-methylsulfonylphenyl)-5-(trifluoromethyl)-2-(3,3,3-trifluoropropoxy)pyridine-3-carboxamide | $^1$H NMR (400 MHz, DMSO-d6) δ 10.66 (s, 1H), 8.79 (dd, J = 2.4, 1.0 Hz, 1H), 8.41 (d, J = 2.3 Hz, 1H), 8.39 - 8.35 (m, 1H), 7.91 (dt, J = 7.2, 1.9 Hz, 1H), 7.73 - 7.61 (m, 2H), 4.69 (t, J = 6.0 Hz, 2H), 3.22 (s, 3H), 2.87 (m, 2H). m/z 457.5 $[M + H]^+$, (ESI+), RT = 4.32 LC-MS Method 5 |

TABLE 15-continued

| Compound | Route | Structure and name | Analytical data |
|---|---|---|---|
| 1605 | | 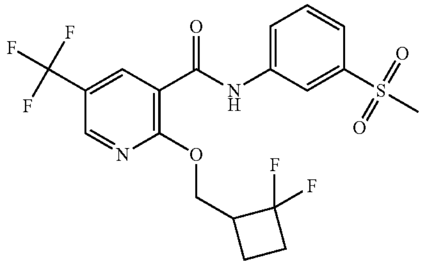 2-[(2,2-difluorocyclobutyl)methoxy]-N-(3-methylsulfonylphenyl)-5-(trifluoromethyl)pyridine-3-carboxamide | $^1$H NMR (400 MHz, DMSO-d6) δ 10.66 (s, 1H), 8.78 (dd, J =2.4, 1.0 Hz, 1H), 8.43 - 8.38 (m, 1H), 8.38 - 8.33 (m, 1H), 7.91 (dt, J = 7.2, 1.9 Hz, 1H), 7.72 - 7.63 (m, 2H), 4.62 - 4.55 (m, 2H), 3.34 (m, 1H), 3.21 (s, 3H), 2.48 - 2.41 (m, 2H), 1.98 - 1.83 (m, 1H), 1.73 - 1.59 (m, 1H). m/z 465.5 [M + H]$^+$, (ESI+), RT = 4.44 LC-MS Method 5 |
| 1606 | | 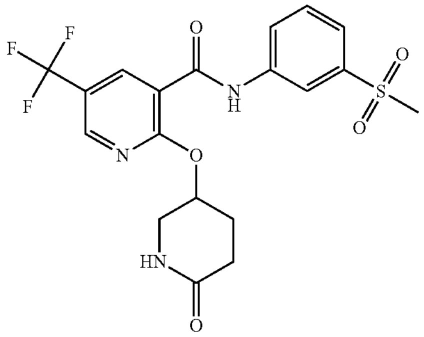 N-(3-methylsulfonylphenyl)-2-[(6-oxo-3-piperidyl)oxy]-5-(trifluoromethyl)pyridine-3-carboxamide | $^1$H NMR (400 MHz, DMSO-d6) δ 10.63 (s, 1H), 8.78 (dd, J = 2.5, 1.0 Hz, 1H), 8.44 - 8.38 (m, 1H), 8.37 - 8.32 (m, 1H), 7.88 (dt, J = 7.7, 1.8 Hz, 1H), 7.71 - 7.62 (m, 2H), 7.46 - 7.40 (m, 1H), 5.61 - 5.52 (m, 1H), 3.62 - 3.51 (m, 1H), 3.45 - 3.37 (m, 1H), 3.23 (s, 3H), 2.35 - 2.24 (m, 1H), 2.23 - 2.05 (m, 3H). m/z 458.5 [M + H]$^+$, (ESI+), RT = 3.53 LC-MS Method 5 |
| 1607 | 3 | 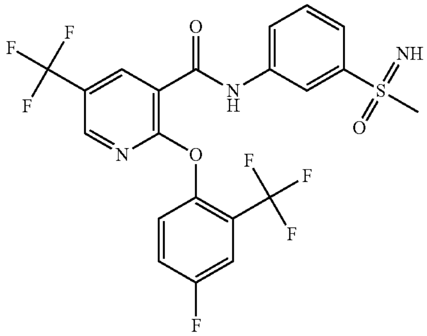 2-[4-fluoro-2-(trifluoromethyl)phenoxy]-N-[3-(methylsulfonimidoyl)phenyl]-5-(trifluoromethyl)pyridine-3-carboxamide | $^1$H NMR (400 MHz, DMSO-d6) δ 10.93 (s, 1H), 8.73 - 8.70 (m, 1H), 8.62 - 8.58 (m, 1H), 8.33 (t, J = 1.9 Hz, 1H), 7.96 - 7.91 (m, 1H), 7.76 (dd, J = 8.5, 3.0 Hz, 1H), 7.73 - 7.58 (m, 4H), 4.23 (s, 1H), 3.10 - 3.02 (m, 3H). m/z 521.8 [M + H]$^+$, (ESI+), RT = 4.16 LC-MS Method 5 |

TABLE 15-continued

| Compound | Route | Structure and name | Analytical data |
|---|---|---|---|
| 1608 | 2 | 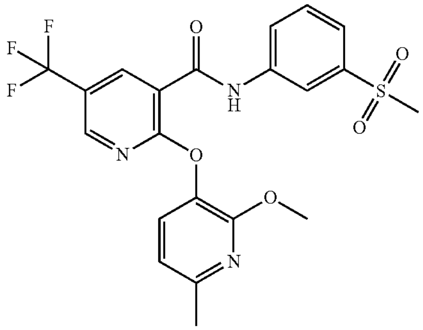 2-[(2-methoxy-6-methyl-3-pyridyl)oxy]-N-(3-methylsulfonylphenyl)-5-(trifluoromethyl)pyridine-3-carboxamide | $^1$H NMR (400 MHz, DMSO-d6) δ 10.99 (s, 1H), 8.67 (dd, J = 2.4, 1.0 Hz, 1H), 8.54 (d, J = 2.3 Hz, 1H), 8.44 - 8.35 (m, 1H), 7.98 (dt, J = 7.3, 1.9 Hz, 1H), 7.74 - 7.63 (m, 2H), 7.58 (d, J = 7.8 Hz, 1H), 6.93 (d, J = 8.0 Hz, 1H), 3.78 (s, 3H), 3.22 (s, 3H), 2.42 (s, 3H). m/z 482.5 [M + H]$^+$, (ESI+), RT = 4.41 LC-MS Method 5 |
| 1609 | 3 | 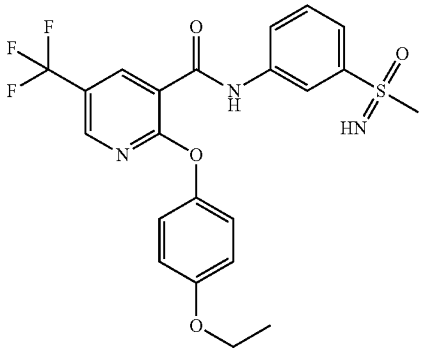 2-(4-ethoxyphenoxy)-N-[3-(methylsulfonimidoyl)phenyl]-5-(trifluoromethyl)pyridine-3-carboxamide | $^1$H NMR (400 MHz, DMSO-d6) δ 10.92 (s, 1H), 8.69 - 8.63 (m, 1H), 8.49 (d, J = 2.3 Hz, 1H), 8.39 - 8.34 (m, 1H), 7.94 (d, J = 8.2 Hz, 1H), 7.72 - 7.65 (m, 1H), 7.60 (t, J = 7.9 Hz, 1H), 7.21 - 7.10 (m, 2H), 7.03 - 6.91 (m, 2H), 4.21 (s, 1H), 4.03 (q, J = 7.0 Hz, 2H), 3.06 (s, 3H), 1.33 (t, J = 7.0 Hz, 3H). m/z 480.5 [M + H]$^+$, (ESI+), RT = 4.09 LC-MS Method 5 |
| 1610 | 2 | 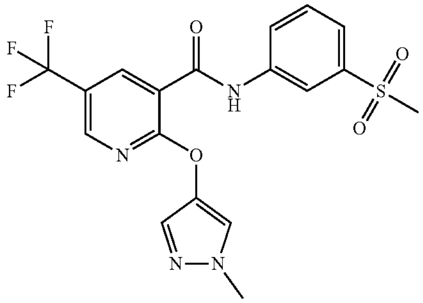 2-(1-methylpyrazol-4-yl)oxy-N-(3-methylsulfonylphenyl)-5-(trifluoromethyl)pyridine-3-carboxamide | $^1$H NMR (400 MHz, DMSO-d6) δ 11.00 (s, 1H), 8.74 (dd, J = 2.4, 0.9 Hz, 1H), 8.50 (d, J = 2.2 Hz, 1H), 8.40 - 8.35 (m, 1H), 7.97 (dt, J = 7.3, 1.9 Hz, 1H), 7.89 (s, 1H), 7.73 - 7.62 (m, 2H), 7.48 (s, 1H), 3.83 (s, 3H), 3.22 (s, 3H). m/z 441.5 [M + H]$^+$, (ESI+), RT = 3.72 LC-MS Method 5 |

TABLE 15-continued

| Compound | Route | Structure and name | Analytical data |
| --- | --- | --- | --- |
| 1611 | 2 | 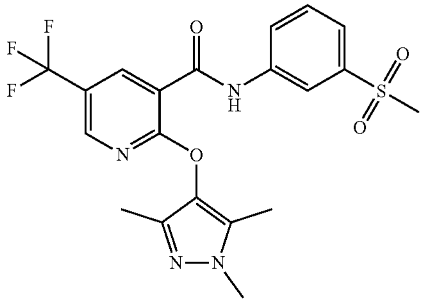 N-(3-methylsulfonylphenyl)-5-(trifluoromethyl)-2-(1,3,5-trimethylpyrazol-4-yl)oxy-pyridine-3-carboxamide | $^1$H NMR (400 MHz, DMSO-d6) δ 11.01 (s, 1H), 8.68 (dd, J = 2.4, 1.0 Hz, 1H), 8.52 (d, J = 2.2 Hz, 1H), 8.43 - 8.35 (m, 1H), 7.95 (dt, J = 7.3, 1.9 Hz, 1H), 7.73 - 7.62 (m, 2H), 3.65 (s, 3H), 3.22 (s, 3H), 2.07 (s, 3H), 1.94 (s, 3H). m/z 469.5 [M + H]$^+$, (ESI+), RT = 3.84 LC-MS Method 5 |
| 1612 | 2 | 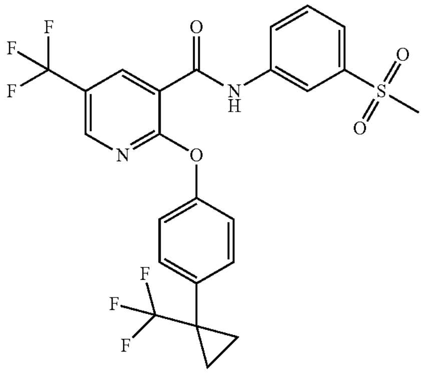 N-(3-methylsulfonylphenyl)-5-(trifluoromethyl)-2-[4-[1-(trifluoromethyl)cyclopropyl] phenoxy]pyridine-3-carboxamide | $^1$H NMR (400 MHz, DMSO-d6) δ 11.01 (s, 1H), 8.73 - 8.67 (m, 1H), 8.58 - 8.52 (m, 1H), 8.39 - 8.31 (m, 1H), 7.97 (dt, J = 7.4, 1.9 Hz, 1H), 7.74 - 7.61 (m, 2H), 7.58 - 7.50 (m, 2H), 7.35 - 7.24 (m, 2H), 3.22 (s, 3H), 1.38 - 1.31 (m, 2H), 1.20 - 1.11 (m, 2H). m/z 544.9 [M + H]$^+$, (ESI+), RT = 4.74 LC-MS Method 5 |
| 1613 | 2 | 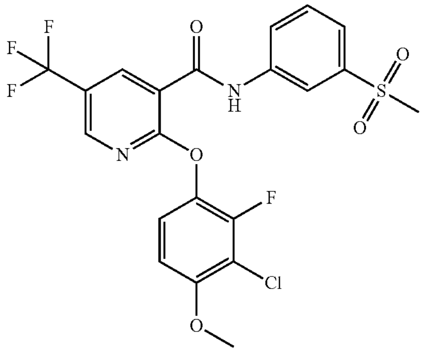 2-(3-chloro-2-fluoro-4-methoxy-phenoxy)-N-(3-methylsulfonylphenyl)-5-(trifluoromethyl)pyridine-3-carboxamide | $^1$H NMR (400 MHz, DMSO-d6) δ 11.05 (s, 1H), 8.72 (d, J = 1.4 Hz, 1H), 8.62 - 8.58 (m, 1H), 8.41 - 8.37 (m, 1H), 7.99 (dt, J = 7.4, 1.9 Hz, 1H), 7.75 - 7.63 (m, 2H), 7.45 (t, J = 9.0 Hz, 1H), 7.10 (dd, J = 9.4, 1.8 Hz, 1H), 3.92 (s, 3H), 3.22 (s, 3H). m/z 518.8 [M + H]$^+$, (ESI+), RT = 4.49 LC-MS Method 5 |

TABLE 15-continued

| Compound | Route | Structure and name | Analytical data |
| --- | --- | --- | --- |
| 1614 | 2 | 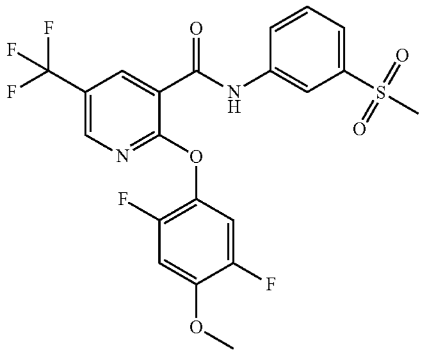 2-(2,5-difluoro-4-methoxy-phenoxy)-N-(3-methylsulfonylphenyl)-5-(trifluoromethyl)pyridine-3-carboxamide | $^1$H NMR (400 MHz, DMSO-d6) δ 11.02 (s, 1H), 8.75 - 8.68 (m, 1H), 8.59 (d, J = 2.3 Hz, 1H), 8.43 - 8.35 (m, 1H), 7.98 (dt, J = 7.4, 1.9 Hz, 1H), 7.74 - 7.62 (m, 2H), 7.49 (dd, J = 11.3, 7.4 Hz, 1H), 7.37 (dd, J = 11.9, 8.0 Hz, 1H), 3.88 (s, 3H), 3.22 (s, 3H). m/z 502.9 $[M + H]^+$, (ESI+), RT = 4.33 LC-MS Method 5 |
| 1615 | 2 | 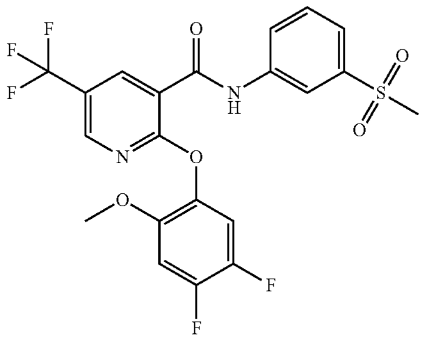 2-(4,5-difluoro-2-methoxy-phenoxy)-N-(3-methylsulfonylphenyl)-5-(trifluoromethyl)pyridine-3-carboxamide | $^1$H NMR (500 MHz, DMSO-d6) δ 10.96 (s, 1H), 8.71 - 8.66 (m, 1H), 8.55 (d, J = 2.4 Hz, 1H), 8.40 (t, J = 2.0 Hz, 1H), 7.97 (dt, J = 7.8, 1.9 Hz, 1H), 7.73 - 7.64 (m, 2H), 7.55 (dd, J = 10.7, 8.3 Hz, 1H), 7.38 (dd, J = 12.5, 7.7 Hz, 1H), 3.70 (s, 3H), 3.22 (s, 3H). m/z 503.0 $[M + H]^+$, (ESI+), RT = 3.86 LC-MS Method 4 |
| 1616 | 2 | 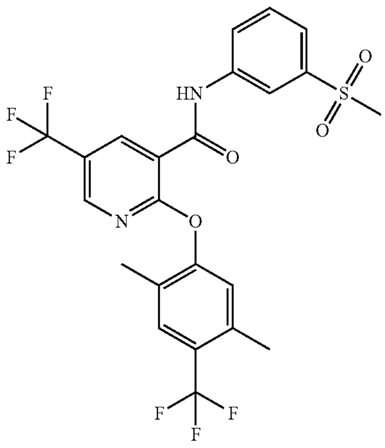 2-[2,5-dimethyl-4-(trifluoromethyl)phenoxy]-N-(3-methylsulfonylphenyl)-5-(trifluoromethyl)pyridine-3-carboxamide | $^1$H NMR (400 MHz, DMSO-d6) δ 11.05 (s, 1H), 8.69 (dd, J = 2.4, 1.1 Hz, 1H), 8.60 (d, J = 2.5 Hz, 1H), 8.40 (t, J = 1.9 Hz, 1H), 7.97 (dt, J = 7.5, 1.9 Hz, 1H), 7.75 - 7.61 (m, 3H), 7.32 (s, 1H), 3.22 (s, 3H), 2.41 (s, 3H), 2.13 (s, 3H). m/z 533.1 $[M + H]^+$, (ESI+), RT = 4.21 LC-MS Method 4 |

TABLE 15-continued

| Compound | Route | Structure and name | Analytical data |
|---|---|---|---|
| 1617 | 3 | 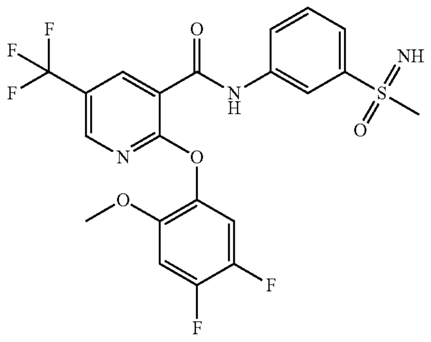 2-(4,5-difluoro-2-methoxy-phenoxy)-N-(3-(methylsulfonimidoyl)phenyl]-5-(trifluoromethyl)pyridine-3-carboxamide | $^1$H NMR (400 MHz, DMSO-d6) δ 10.88 (s, 1H), 8.68 (dd, J =2.4, 1.1 Hz, 1H), 8.53 (d, J = 2.5 Hz, 1H), 8.38 (t, J = 2.0 Hz, 1H), 7.94 (ddd, J = 8.1, 2.2, 1.1 Hz, 1H), 7.69 (dt, J = 7.9, 1.4 Hz, 1H), 7.65 – 7.48 (m, 2H), 7.38 (dd, J = 12.6, 7.7 Hz, 1H), 4.23 (s, 1H), 3.70 (s, 3H), 3.06 (s, 3H). m/z 502.1 [M + H]$^+$, (ESI+), RT = 3.24 LC-MS Method 4 |
| 1618 | 3 | 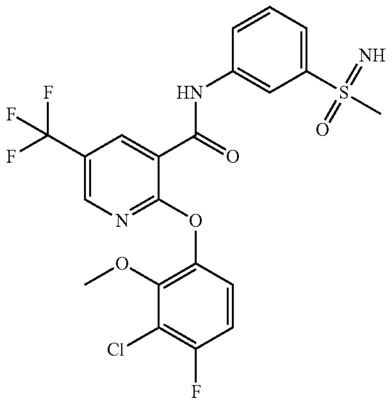 2-(3-chloro-4-fluoro-2-methoxyphenoxy)-N-(3-(S-methylsulfonimidoyl)phenyl)-5-(trifluoromethyl)nicotinamide | $^1$H NMR (400 MHz, DMSO-d6) δ 11.02 (s, 1H), 8.69 (s, 1H), 8.59 (s, 1H), 8.38 (s, 1H), 7.95 (d, J = 8.0 Hz, 1H), 7.69 (d, J = 7.8 Hz, 1H), 7.61 (t, J = 8.1 Hz, 1H), 7.41 (dd, J = 9.1, 5.7 Hz, 1H), 7.31 (t, J = 9.0 Hz, 1H), 4.24 (s, 1H), 3.75 (s, 3H), 3.06 (s, 3H). m/z 518.1, 520.1 [M + H]$^+$, (ESI+), RT = 3.36 LC-MS Method 4 |
| 1619 | 5 | 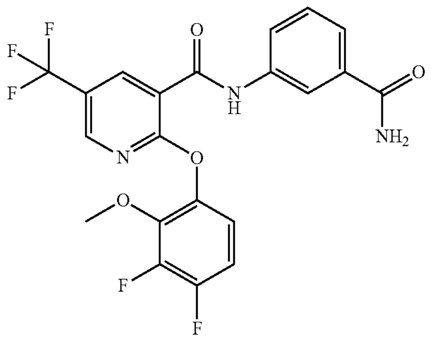 N-(3-carbamoylphenyl)-2-(3,4-difluoro-2-methoxy-phenoxy)-5-(trifluoromethyl)pyridine-3-carboxamide | $^1$H NMR (500 MHz, DMSO-d6) δ 10.76 (s, 1H), 8.70 – 8.65 (m, 1H), 8.55 (d, J = 2.5 Hz, 1H), 8.19 (t, J = 1.9 Hz, 1H), 7.98 (s, 1H), 7.92 – 7.83 (m, 1H), 7.65 – 7.59 (m, 1H), 7.45 (t, J = 7.9 Hz, 1H), 7.38 (s, 1H), 7.31 – 7.18 (m, 2H), 3.80 (d, J = 1.2 Hz, 3H). m/z 468.2 [M + H]$^+$, (ESI+), RT = 3.32 LC-MS Method 4 |

TABLE 15-continued

| Compound | Route | Structure and name | Analytical data |
|---|---|---|---|
| 1620 | 3 | 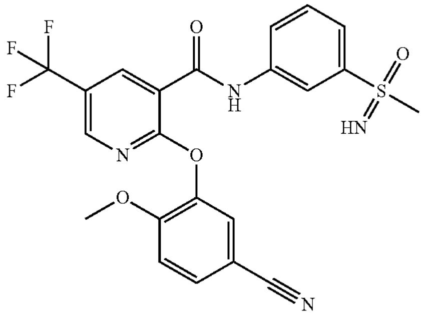 2-(5-cyano-2-methoxy-phenoxy)-N-[3-(methylsulfonimidoyl)phenyl]-5-(trifluoromethyl)pyridine-3-carboxamide | $^1$H NMR (400 MHz, DMSO-d6) δ 10.90 (s, 1H), 8.70 - 8.63 (m, 1H), 8.55 (d, J = 2.5 Hz, 1H), 8.39 (t, J = 2.0 Hz, 1H), 7.99 - 7.90 (m, 1H), 7.84 (d, J = 2.1 Hz, 1H), 7.81 (dd, J = 8.6, 2.1 Hz, 1H), 7.72 - 7.66 (m, 1H), 7.61 (t, J = 7.9 Hz, 1H), 7.36 (d, J = 8.6 Hz, 1H), 4.26 - 4.20 (m, 1H), 3.80 (s, 3H), 3.09 - 3.03 (m, 3H). m/z 491.2 [M + H]$^+$, (ESI+), RT = 2.96 LC-MS Method 4 |
| 1621 | 3 | 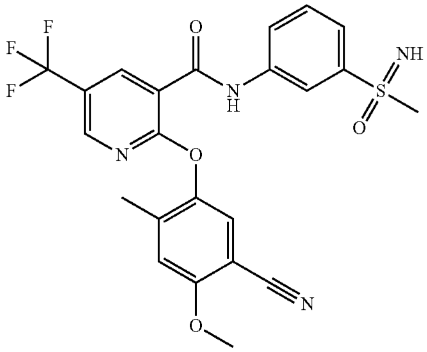 2-(5-cyano-4-methoxy-2-methyl-phenoxy)-N-[3-(methylsulfonimidoyl)phenyl]-5-(trifluoromethyl)pyridine-3-carboxamide | $^1$H NMR (400 MHz, DMSO-d6) δ 10.93 (s, 1H), 8.67 (dd, J = 2.4, 1.1 Hz, 1H), 8.56 (d, J = 2.5 Hz, 1H), 8.39 (t, J = 2.0 Hz, 1H), 7.97 - 7.88 (m, 1H), 7.75 - 7.66 (m, 2H), 7.62 (t, J = 7.9 Hz, 1H), 7.25 (s, 1H), 4.27 - 4.21 (m, 1H), 3.93 (s, 3H), 3.11 - 3.02 (m, 3H), 2.18 (s, 3H). m/z 505.0 [M + H]$^+$, (ESI+), RT = 3.20 LC-MS Method 4 |
| 1622 | 3 | 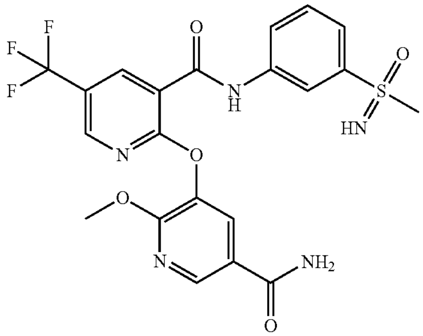 6-methoxy-5-[[3-[[3-(methylsulfonimidoyl)phenyl] carbamoyl]-5-(trifluoromethyl)-2-pyridyl]oxy]pyridine-3-carboxamide | $^1$H NMR (500 MHz, $CD_3OD$) δ 8.64 (d, J = 2.1 Hz, 1H), 8.58 (d, J = 2.5 Hz, 1H), 8.57 - 8.54 (m, 1H), 8.44 (t, J = 2.0 Hz, 1H), 8.17 (d, J = 2.2 Hz, 1H), 8.04 (ddd, J = 8.2, 2.2, 1.0 Hz, 1H), 7.82 (ddd, J = 7.9, 1.9, 1.0 Hz, 1H), 7.64 (t, J = 8.0 Hz, 1H), 3.96 (s, 3H), 3.17 (s, 3H). m/z 510.5 [M + H]$^+$, (ESI+), RT = 2.33 LC-MS Method 4 |

TABLE 15-continued

| Compound | Route | Structure and name | Analytical data |
|---|---|---|---|
| 1623 | 3 | 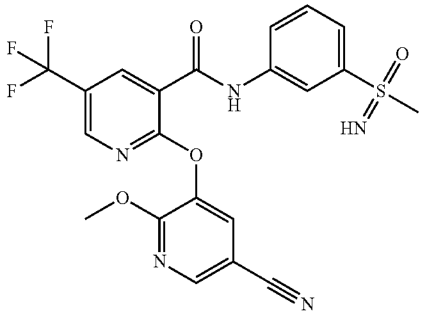 2-[(5-cyano-2-methoxy-3-pyridyl)oxy]-N-[3-(methylsulfonimidoyl)phenyl]-5-(trifluoromethyl)pyridine-3-carboxamide | $^1$H NMR (500 MHz, $CD_3OD$) δ 8.60 – 8.55 (m, 2H), 8.51 (d, J = 2.0 Hz, 1H), 8.43 (t, J = 2.0 Hz, 1H), 8.10 (d, J = 2.0 Hz, 1H), 8.03 (ddd, J = 8.2, 2.2, 1.1 Hz, 1H), 7.82 (ddd, J = 7.9, 1.9, 1.1 Hz, 1H), 7.65 (t, J = 8.0 Hz, 1H), 3.97 (s, 3H), 3.17 (s, 3H). m/z 492.4 $[M + H]^+$, (ESI+), RT = 3.00 LC-MS Method 4 |
| 1624 | 2 | 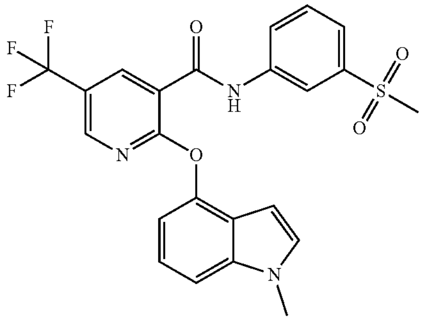 2-(1-methylindol-4-yl)oxy-N-(3-methylsulfonylphenyl)-5-(trifluoromethyl)pyridine-3-carboxamide | $^1$H NMR (500 MHz, DMSO-d6) δ 11.10 (s, 1H), 8.62 – 8.58 (m, 1H), 8.56 (d, J = 2.6 Hz, 1H), 8.44 – 8.40 (m, 1H), 7.99 (dt, J = 7.3, 1.9 Hz, 1H), 7.72 – 7.65 (m, 2H), 7.39 – 7.34 (m, 1H), 7.29 (d, J = 3.1 Hz, 1H), 7.19 (t, J = 7.9 Hz, 1H), 6.94 (d, J = 7.3 Hz, 1H), 6.23 – 6.17 (m, 1H), 3.81 (s, 3H), 3.21 (s, 3H). m/z 489.9 $[M + H]^+$, (ESI+), RT = 4.35 LC-MS Method 5 |
| 1625 | 2 | 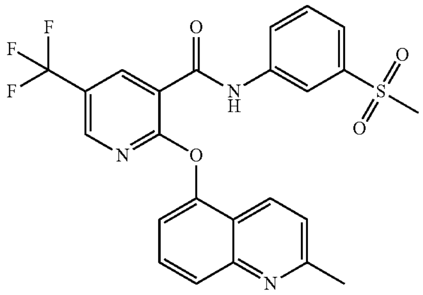 2-[(2-methyl-5-quinolyl)oxy]-N-(3-methylsulfonylphenyl)-5-(trifluoromethyl)pyridine-3-carboxamide | $^1$H NMR (500 MHz, DMSO-d6) δ 11.18 (s, 1H), 8.64 (d, J = 2.3 Hz, 1H), 8.62 – 8.56 (m, 1H), 8.43 (t, J = 1.8 Hz, 1H), 8.24 (d, J = 8.7 Hz, 1H), 8.00 (dt, J = 7.6, 1.8 Hz, 1H), 7.91 – 7.84 (m, 1H), 7.81 – 7.74 (m, 1H), 7.74 – 7.65 (m, 2H), 7.50 – 7.45 (m, 1H), 7.44 (d, J = 8.5 Hz, 1H), 3.22 (s, 3H), 2.66 (s, 3H). m/z 501.9 $[M + H]^+$, (ESI+), RT = 3.45 LC-MS Method 5 |

TABLE 15-continued

| Compound | Route | Structure and name | Analytical data |
|---|---|---|---|
| 1626 | 2 | 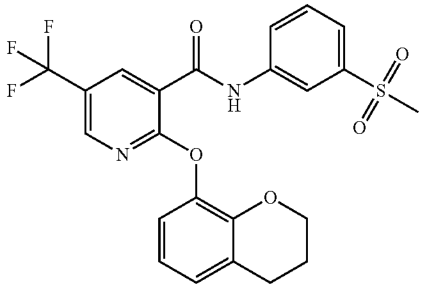 2-chroman-8-yloxy-N-(3-methylsulfonylphenyl)-5-(trifluoromethyl)pyridine-3-carboxamide | $^1H$ NMR (500 MHz, DMSO-d6) δ 10.96 (s, 1H), 8.68 - 8.64 (m, 1H), 8.50 (d, J = 2.4 Hz, 1H), 8.40 (t, J = 1.7 Hz, 1H), 7.99 (dt, J = 7.5, 1.7 Hz, 1H), 7.72 - 7.65 (m, 2H), 7.08 (dd, J = 7.9, 1.3 Hz, 1H), 7.01 - 6.95 (m, 1H), 6.87 (t, J = 7.8 Hz, 1H), 4.07 - 3.98 (m, 2H), 3.22 (s, 3H), 2.78 (t, J = 6.4 Hz, 2H), 1.88 (p, J = 6.3 Hz, 2H). m/z 492.9 $[M + H]^+$, (ESI+), RT = 4.55 LC-MS Method 5 |
| 1627 | 2 | 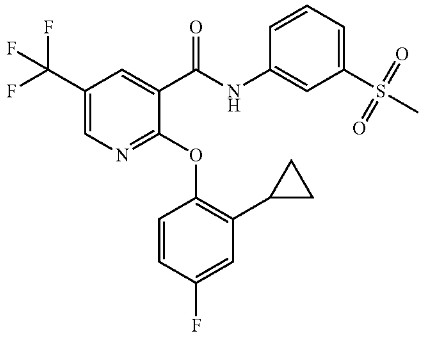 2-(2-cyclopropyl-4-fluoro-phenoxy)-N-(3-methylsulfonylphenyl)-5-(trifluoromethyl)pyridine-3-carboxamide | $^1H$ NMR (400 MHz, DMSO-d6) δ 11.03 (s, 1H), 8.72 - 8.66 (m, 1H), 8.58 - 8.52 (m, 1H), 8.41 - 8.37 (m, 1H), 7.97 (dt, J = 7.4, 1.8 Hz, 1H), 7.73 - 7.65 (m, 2H), 7.25 (dd, J = 8.9, 5.2 Hz, 1H), 7.06 (td, J = 8.5, 3.1 Hz, 1H), 6.83 (dd, J = 10.1, 3.0 Hz, 1H), 3.22 (s, 3H), 1.94 - 1.82 (m, 1H), 0.86 - 0.74 (m, 2H), 0.70 - 0.57 (m, 2H). m/z 495.5 $[M + H]^+$, (ESI+), RT = 4.57 LC-MS Method 5 |
| 1628 | 2 | 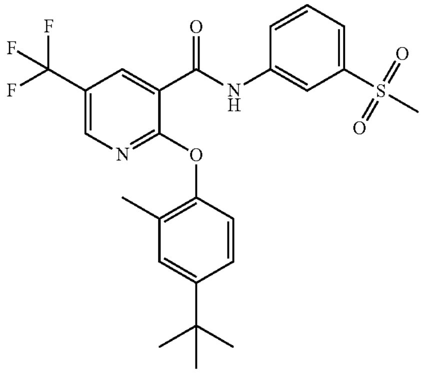 2-(4-tert-butyl-2-methyl-phenoxy)-N-(3-methylsulfonylphenyl)-5-(trifluoromethyl)pyridine-3-carboxamide | $^1H$ NMR (400 MHz, DMSO-d6) δ 11.00 (s, 1H), 8.69 - 8.60 (m, 1H), 8.57 - 8.49 (m, 1H), 8.41 - 8.36 (m, 1H), 7.98 (dt, J = 7.4, 1.9 Hz, 1H), 7.73 - 7.64 (m, 2H), 7.32 (d, J = 2.2 Hz, 1H), 7.28 (dd, J = 8.4, 2.3 Hz, 1H), 7.13 (d, J = 8.4 Hz, 1H), 3.22 (s, 3H), 2.09 (s, 3H), 1.29 (s, 9H). m/z 507.6 $[M + H]^+$, (ESI+), RT = 5.01 LC-MS Method 5 |

TABLE 15-continued

| Compound | Route | Structure and name | Analytical data |
|---|---|---|---|
| 1629 | | 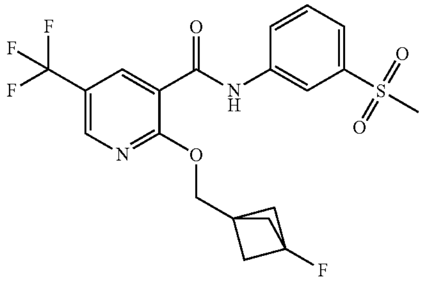 2-[(3-fluoro-1-bicyclo[1.1.1]pentanyl) methoxy]-N-(3-methylsulfonylphenyl)-5-(trifluoromethyl)pyridine-3-carboxamide | $^1$H NMR (500 MHz, DMSO-d6) δ 10.75 (s, 1H), 8.76 - 8.72 (m, 1H), 8.40 - 8.35 (m, 2H), 7.94 (dt, J = 6.7, 2.2 Hz, 1H), 7.72 - 7.65 (m, 2H), 4.73 (s, 2H), 3.22 (s, 3H), 2.02 (d, J = 2.7 Hz, 6H). m/z 458.9 [M + H]$^+$, (ESI+), RT = 4.46 LC-MS Method 5 |
| 1630 | 3 | 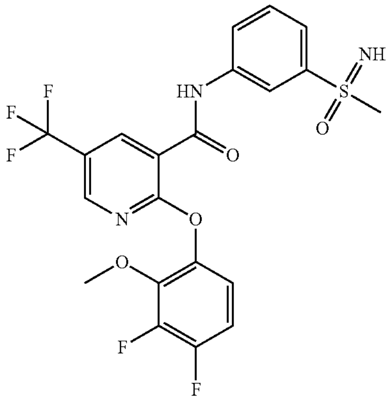 2-(3,4-difluoro-2-methoxy-phenoxy)-N-[3-(methylsulfonimidoyl)phenyl]-5-(trifluoromethyl)pyridine-3-carboxamide | $^1$H NMR (500 MHz, DMSO-d6) δ 10.99 (s, 1H), 8.72 - 8.67 (m, 1H), 8.58 (d, J = 2.3 Hz, 1H), 8.38 (t, J = 1.9 Hz, 1H), 7.98 - 7.92 (m, 1H), 7.72 - 7.68 (m, 1H), 7.61 (t, J = 7.9 Hz, 1H), 7.31 - 7.19 (m, 2H), 4.23 (s, 1H), 3.80 (d, J = 0.9 Hz, 3H), 3.06 (s, 3H). m/z 501.9 [M + H]$^+$, (ESI+), RT = 4.06 LC-MS Method 5 |
| 1631 | 3 | 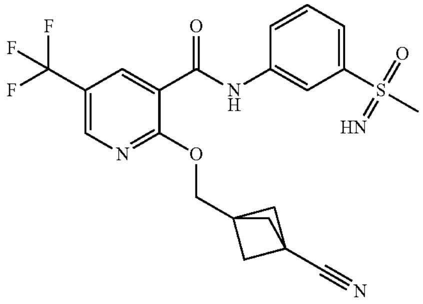 2-[(3-cyano-1-bicyclo[1.1.1]pentanyl) methoxy]-N-[3-(methylsulfonimidoyl)phenyl]-5-(trifluoromethyl)pyridine-3-carboxamide | $^1$H NMR (500 MHz, DMSO-d6) δ 10.66 (s, 1H), 8.73 - 8.67 (m, 1H), 8.39 - 8.31 (m, 2H), 7.93 - 7.87 (m, 1H), 7.71 - 7.65 (m, 1H), 7.61 (t, J = 7.9 Hz, 1H), 4.47 (s, 2H), 4.23 (s, 1H), 3.05 (s, 3H), 2.20 (s, 6H). m/z 465.0 [M + H]$^+$, (ESI+), RT = 3.16 LC-MS Method 4 |

TABLE 15-continued

| Compound | Route | Structure and name | Analytical data |
|---|---|---|---|
| 1632 | 3 | 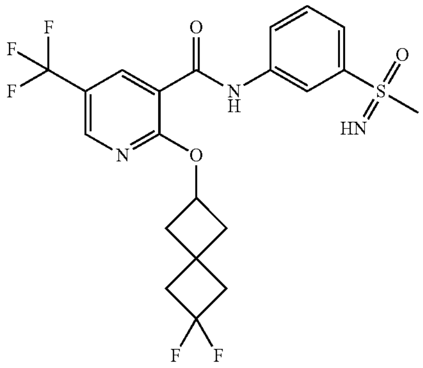 2-(2,2-difluorospiro[3.3]heptan-6-yl)oxy-N-[3-(methylsulfonimidoyl)phenyl]-5-(trifluoromethyl)pyridine-3-carboxamide | $^1$H NMR (400 MHz, DMSO-d6) δ 10.65 (s, 1H), 8.73 - 8.66 (m, 1H), 8.39 - 8.31 (m, 2H), 7.91 - 7.82 (m, 1H), 7.70 - 7.63 (m, 1H), 7.59 (t, J = 7.9 Hz, 1H), 5.27 (p, J = 7.1 Hz, 1H), 4.22 (s, 1H), 3.05 (s, 3H), 2.73 - 2.57 (m, 6H), 2.37 - 2.26 (m, 2H). m/z 490.3 [M + H]$^+$, (ESI+), RT = 3.67 LC-MS Method 6 |
| 1633 | 3 | 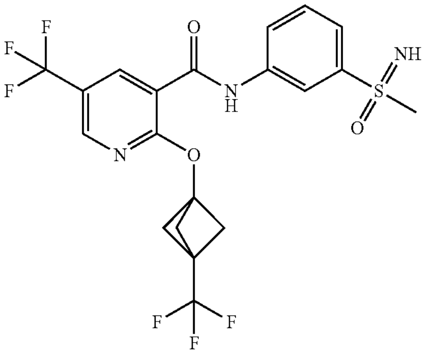 N-[3-(methylsulfonimidoyl)phenyl]-5-(trifluoromethyl)-2-[[3-(trifluoromethyl)-1-bicyclo[1.1.1]pentanyl]oxy] pyridine-3-carboxamide | $^1$H NMR (400 MHz, DMSO-d6) δ 10.79 (s, 1H), 8.78 - 8.71 (m, 1H), 8.40 (d, J = 2.5 Hz, 1H), 8.33 (t, J = 1.9 Hz, 1H), 7.91 - 7.84 (m, 1H), 7.70 - 7.64 (m, 1H), 7.58 (t, J = 7.9 Hz, 1H), 4.22 (s, 1H), 3.04 (s, 3H), 2.58 (s, 6H). m/z 494.2 [M + H]$^+$, (ESI+), RT = 3.86 LC-MS Method 6 |
| 1634 | 5 | 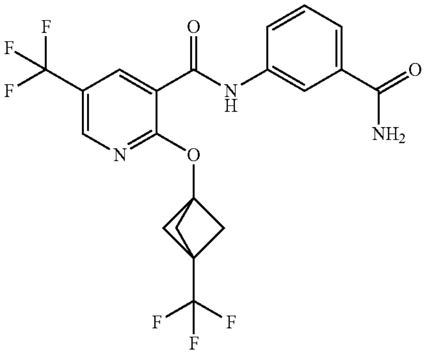 N-(3-carbamoylphenyl)-5-(trifluoromethyl)-2-[[3-(trifluoromethyl)-1-bicyclo[1.1.1]pentanyl]oxy] pyridine-3-carboxamide | $^1$H NMR (400 MHz, DMSO-d6) δ 10.57 (s, 1H), 8.80 - 8.72 (m, 1H), 8.38 (d, J = 2.5 Hz, 1H), 8.14 (t, J = 1.9 Hz, 1H), 7.96 (s, 1H), 7.86 - 7.76 (m, 1H), 7.65 - 7.56 (m, 1H), 7.42 (t, J = 7.9 Hz, 1H), 7.37 (s, 1H), 2.58 (s, 6H). m/z 458.2 [M - H]- , (ESI-), RT = 3.93 LC-MS Method 6 |

TABLE 15-continued

| Compound | Route | Structure and name | Analytical data |
|---|---|---|---|
| 1635 | 5 | 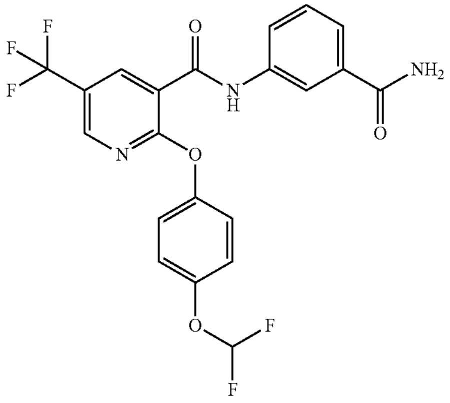 N-(3-carbamoylphenyl)-2-[4-(difluoromethyl)phenoxy]-5-(trifluoromethyl)pyridine-3-carboxamide | $^1$H NMR (400 MHz, DMSO-d6) δ 10.74 (s, 1H), 8.70 – 8.64 (m, 1H), 8.51 (d, J = 2.5 Hz, 1H), 8.17 (t, J = 1.9 Hz, 1H), 7.99 (s, 1H), 7.93 – 7.86 (m, 1H), 7.66 – 7.59 (m, 1H), 7.48 – 7.03 (m, 7H). m/z 468.0 [M + H]$^+$, (ESI+), RT = 3.38 LC-MS Method 4 |
| 1636 | 3 | 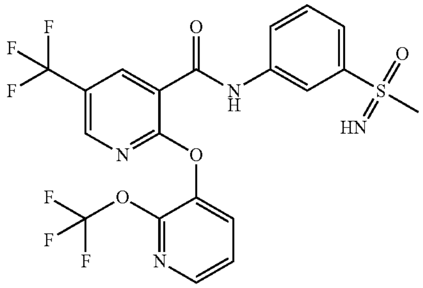 N-[3-(methylsulfonimidoyl)phenyl]-2-[[2-(trifluoromethoxy)-3-pyridyl]oxy]-5-(trifluoromethyl)pyridine-3-carboxamide | $^1$H NMR (400 MHz, DMSO-d6) δ 11.02 (s, 1H), 8.75 – 8.69 (m, 1H), 8.66 – 8.60 (m, 1H), 8.39 – 8.34 (m, 1H), 8.30 (dd, 1H), 8.09 (dd, 1H), 7.99 – 7.92 (m, 1H), 7.74 – 7.66 (m, 1H), 7.66 – 7.55 (m, 2H), 4.24 (s, 1H), 3.06 (s, 3H). m/z 521.1 [M + H]$^+$, (ESI+), RT = 3.13 LC-MS Method 4 |
| 1637 | 3 | 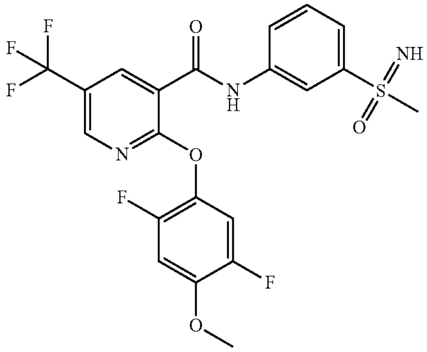 2-(2,5-difluoro-4-methoxy-phenoxy)-N-[3-(methylsulfonimidoyl)phenyl]-5-(trifluoromethyl)pyridine-3-carboxamide | $^1$H NMR (500 MHz, DMSO-d6) δ 10.97 (s, 1H), 8.73 – 8.68 (m, 1H), 8.60 – 8.55 (m, 1H), 8.40 – 8.36 (m, 1H), 7.97 – 7.92 (m, 1H), 7.72 – 7.67 (m, 1H), 7.64 – 7.58 (m, 1H), 7.53 – 7.45 (m, 1H), 7.40 – 7.33 (m, 1H), 4.23 (s, 1H), 3.88 (s, 3H), 3.08 – 3.04 (m, 3H). m/z 502.1 [M + H]$^+$, (ESI+), RT = 3.19 LC-MS Method 4 |

TABLE 15-continued

| Compound | Route | Structure and name | Analytical data |
|---|---|---|---|
| 1638 | 5 | 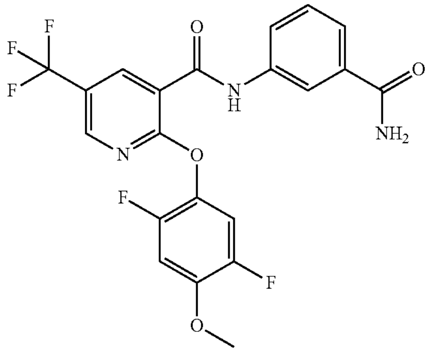 N-(3-carbamoylphenyl)-2-(2,5-difluoro-4-methoxy-phenoxy)-5-(trifluoromethyl)pyridine-3-carboxamide | $^{1}H$ NMR (500 MHz, DMSO-d6) δ 10.74 (s, 1H), 8.73 - 8.68 (m, 1H), 8.57 - 8.53 (m, 1H), 8.21 - 8.16 (m, 1H), 8.03 - 7.94 (m, 1H), 7.92 - 7.86 (m, 1H), 7.66 - 7.60 (m, 1H), 7.53 - 7.48 (m, 1H), 7.48 - 7.43 (m, 1H), 7.40 - 7.34 (m, 2H), 3.88 (s, 3H). m/z 485.3 $[M + NH4]^{+}$, (ESI+), RT = 3.33 LC-MS Method 6 |
| 1639 | 3 | 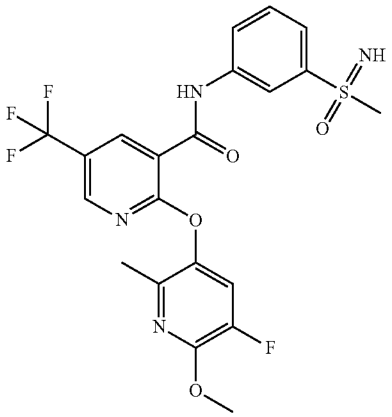 2-[(5-fluoro-6-methoxy-2-methyl-3-pyridyl)oxy]-N-[3-(methylsulfonimidoyl)phenyl]-5-(trifluoromethyl)pyridine-3-carboxamide | $^{1}H$ NMR (400 MHz, DMSO-d6) δ 10.97 (s, 1H), 8.71 - 8.68 (m, 1H), 8.59 - 8.56 (m, 1H), 8.40 - 8.37 (m, 1H), 7.96 - 7.91 (m, 1H), 7.80 (d, J = 10.4 Hz, 1H), 7.72 - 7.67 (m, 1H), 7.62 (t, J = 7.9 Hz, 1H), 4.24 (s, 1H), 3.95 (s, 3H), 3.06 (s, 3H), 2.22 (s, 3H). m/z 499.3 $[M + H]^{+}$, (ESI+), RT = 3.44 LC-MS Method 6 |
| 1640 | 3 | 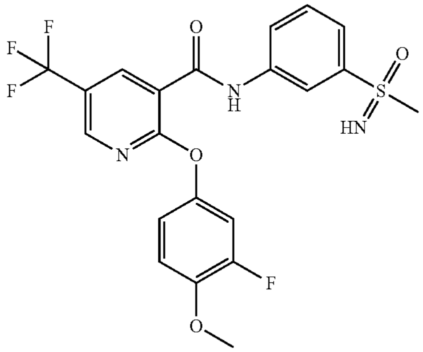 2-(3-fluoro-4-methoxy-phenoxy)-N-[3-(methylsulfonimidoyl)phenyl]-5-(trifluoromethyl)pyridine-3-carboxamide | $^{1}H$ NMR (400 MHz, DMSO-d6) δ 10.93 (s, 1H), 8.71 - 8.67 (m, 1H), 8.54 - 8.50 (m, 1H), 8.38 - 8.35 (m, 1H), 7.97 - 7.91 (m, 1H), 7.72 - 7.66 (m, 1H), 7.64 - 7.58 (m, 1H), 7.30 - 7.20 (m, 2H), 7.11 - 7.06 (m, 1H), 4.23 (s, 1H), 3.86 (s, 3H), 3.06 (s, 3H). m/z 484.3 [M + H]*, (ESI+), RT = 3.20 LC-MS Method 6 |

TABLE 15-continued

| Compound | Route | Structure and name | Analytical data |
|---|---|---|---|
| 1642 | 3 | 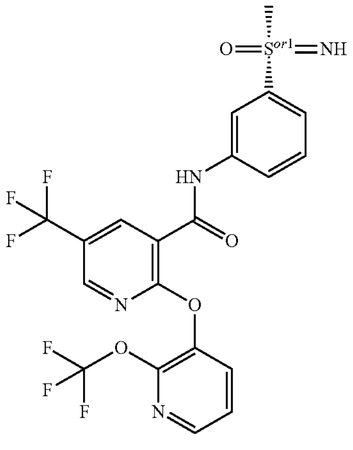 N-[3-(methylsulfonimidoyl)phenyl]-2-[[2-(trifluoromethoxy)-3-pyridyl]oxy]-5-(trifluoromethyl)pyridine-3-carboxamide | $^1$H NMR (500 MHz, DMSO-d6) δ 11.01 (s, 1H), 8.74 – 8.71 (m, 1H), 8.65 – 8.62 (m, 1H), 8.39 – 8.36 (m, 1H), 8.30 (dd, J = 4.8, 1.6 Hz, 1H), 8.09 (dd, J = 8.0, 1.6 Hz, 1H), 7.98 – 7.94 (m, 1H), 7.72 – 7.68 (m, 1H), 7.64 – 7.57 (m, 2H), 4.24 (s, 1H), 3.07 – 3.05 (m, 3H). m/z 521.2 [M + H]$^+$, (ESI+), RT = 3.26 |
| 1643 | 3 | 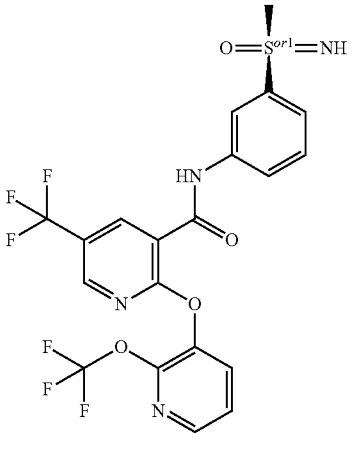 N-[3-(methylsulfonimidoyl)phenyl]-2-[[2-(trifluoromethoxy)-3-pyridyl]oxy]-5-(trifluoromethyl)pyridine-3-carboxamide | $^1$H NMR (500 MHz, DMSO-d6) δ 11.01 (s, 1H), 8.74 – 8.71 (m, 1H), 8.65 – 8.62 (m, 1H), 8.39 – 8.36 (m, 1H), 8.30 (dd, J = 4.8, 1.6 Hz, 1H), 8.09 (dd, J = 8.0, 1.6 Hz, 1H), 7.98 – 7.94 (m, 1H), 7.72 – 7.68 (m, 1H), 7.64 – 7.58 (m, 2H), 4.24 (s, 1H), 3.07 – 3.05 (m, 3H). m/z 521.2 [M + H]$^+$, (ESI+), RT = 4.03 |

TABLE 15-continued

| Compound | Route | Structure and name | Analytical data |
|---|---|---|---|
| 1644 | 3 | 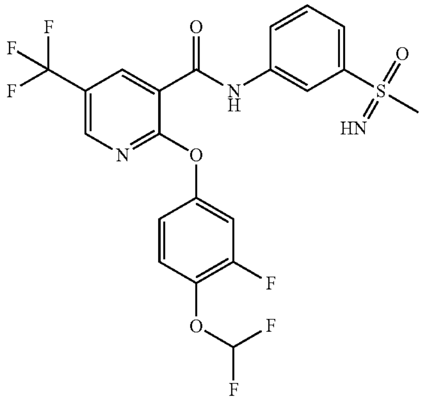 2-[4-(difluoromethoxy)-3-fluoro-phenoxy]-N-[3-(methylsulfonimidoyl)phenyl]-5-(trifluoromethyl)pyridine-3-carboxamide | $^1$H NMR (500 MHz, DMSO-d6) δ 10.94 (s, 1H), 8.73 - 8.71 (m, 1H), 8.57 - 8.55 (m, 1H), 8.37 - 8.35 (m, 1H), 7.96 - 7.92 (m, 1H), 7.71 - 7.67 (m, 1H), 7.61 (t, J = 7.9 Hz, 1H), 7.51 - 7.45 (m, 2H), 7.42 - 7.10 (m, 2H), 4.23 (s, 1H), 3.07 - 3.05 (m, 3H). m/z 520.1 $[M + H]^+$, (ESI+), RT = 3.28 LC-MS Method 4 |
| 1645 | 1 | 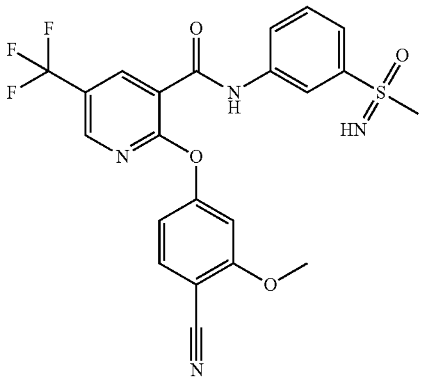 2-(4-cyano-3-methoxy-phenoxy)-N-[3-(methylsulfonimidoyl)phenyl]-5-(trifluoromethyl)pyridine-3-carboxamide | $^1$H NMR (500 MHz, DMSO-d6) δ 10.97 (s, 1H), 8.77 - 8.71 (m, 1H), 8.61 - 8.57 (m, 1H), 8.38 - 8.34 (m, 1H), 7.95 - 7.91 (m, 1H), 7.83 (d, J = 8.5 Hz, 1H), 7.71 - 7.67 (m, 1H), 7.61 (t, J = 7.9 Hz, 1H), 7.24 - 7.21 (m, 1H), 7.02 (dd, J = 8.5, 2.1 Hz, 1H), 4.24 (s, 1H), 3.89 (s, 3H), 3.06 (s, 3H). m/z 491.1 $[M + H]^+$, (ESI+), RT = 2.89 LC-MS Method 4 |
| 1646 | | 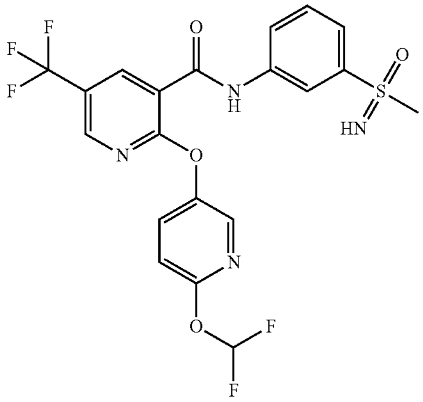 2-[[6-(difluoromethoxy)-3-pyridyl]oxy]-N-[3-(methylsulfonimidoyl)phenyl]-5-(trifluoromethyl)pyridine-3-carboxamide | $^1$H NMR (500 MHz, DMSO-d6) δ 10.99 (s, 1H), 8.73 - 8.69 (m, 1H), 8.58 (d, J = 2.4 Hz, 1H), 8.40 - 8.35 (m, 1H), 8.30 (d, J = 2.8 Hz, 1H), 8.00 - 7.92 (m, 2H), 7.71 (t, J = 72.8 Hz, 1H), 7.72 - 7.69 (m, 1H), 7.63 (t, J = 7.9 Hz, 1H), 7.24 (d, J = 8.9 Hz, 1H), 4.24 (s, 1H), 3.07 (s, 3H). m/z 501.3 [M - H]-, (ESI+), RT = 3.12 LC-MS Method 4 |

TABLE 15-continued

| Compound | Route | Structure and name | Analytical data |
|---|---|---|---|
| 1647 | | 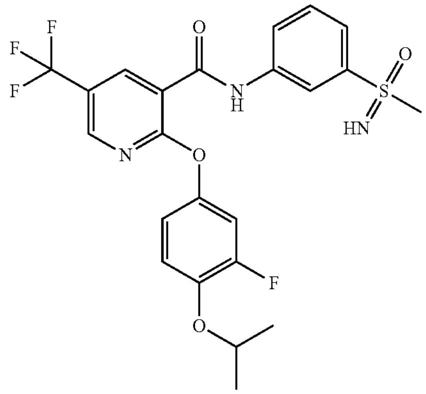 2-(3-fluoro-4-isopropoxy-phenoxy)-N-[3-(methylsulfonimidoyl)phenyl]-5-(trifluoromethyl)pyridine-3-carboxamide | $^{1}H$ NMR (400 MHz, DMSO-d6) δ 10.92 (s, 1H), 8.71 (d, J = 1.5 Hz, 1H), 8.55 - 8.50 (m, 1H), 8.40 - 8.34 (m, 1H), 7.98 - 7.91 (m, 1H), 7.73 - 7.66 (m, 1H), 7.66 - 7.58 (m, 1H), 7.31 - 7.20 (m, 2H), 7.10 - 7.02 (m, 1H), 4.61 (hept, J = 6.0 Hz, 1H), 4.27 - 4.22 (m, 1H), 3.07 (s, 3H), 1.30 (d, J = 6.0 Hz, 6H). m/z 512.2 $[M + H]^{+}$, (ESI+), RT = 3.59 LC-MS Method 6 |
| 1648 | | 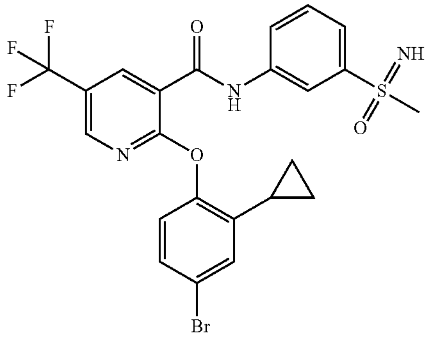 2-(4-bromo-2-cyclopropyl-phenoxy)-N-[3-(methylsulfonimidoyl)phenyl]-5-(trifluoromethyl)pyridine-3-carboxamide | $^{1}H$ NMR (400 MHz, DMSO-d6) δ 10.97 (s, 1H), 8.71 - 8.66 (m, 1H), 8.56 (d, J = 2.4 Hz, 1H), 8.38 (s, 1H), 7.94 (d, J = 8.1 Hz, 1H), 7.70 (d, J = 7.9 Hz, 1H), 7.62 (t, J = 7.9 Hz, 1H), 7.43 (dd, J = 8.6, 2.4 Hz, 1H), 7.20 (d, J = 8.6 Hz, 1H), 7.16 (d, J = 2.4 Hz, 1H), 4.24 (s, 1H), 3.07 (s, 3H), 1.93 - 1.82 (m, 1H), 0.82 - 0.74 (m, 2H), 0.71 - 0.62 (m, 2H). m/z 554.8, 556.7 $[M + H]^{+}$, (ESI+), RT = 3.82 LC-MS Method 6 |
| 1649 | | 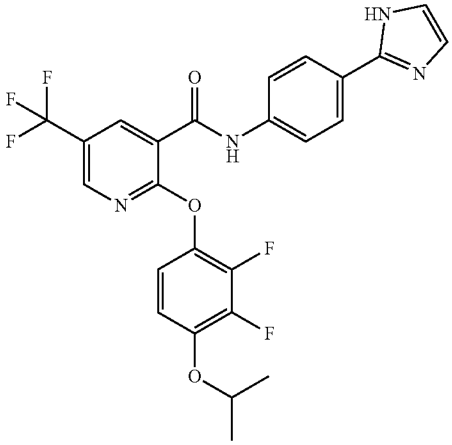 2-(2,3-difluoro-4-isopropoxy-phenoxy)-N-[4-(1H-imidazol-2-yl)phenyl]-5-(trifluoromethyl)pyridine-3-carboxamide | $^{1}H$ NMR (500 MHz, DMSO-d6) δ 10.79 (s, 1H), 8.75 - 8.69 (m, 1H), 8.58 (d, J = 2.3 Hz, 1H), 8.15 (s, 1H), 7.94 (d, J = 8.7 Hz, 2H), 7.81 (d, J = 8.8 Hz, 2H), 7.30 - 7.20 (m, 1H), 7.17 - 7.07 (m, 3H), 4.70 (hept, J = 6.1 Hz, 1H), 1.33 (d, J = 6.0 Hz, 6H). m/z 519.1 $[M + H]^{+}$, (ESI+), RT = 3.81 LC-MS Method 6 |

TABLE 15-continued

| Compound | Route | Structure and name | Analytical data |
| --- | --- | --- | --- |
| 1650 | | 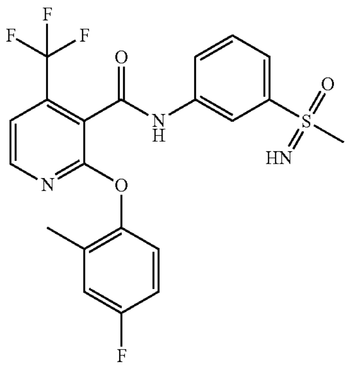 2-(4-fluoro-2-methyl-phenoxy)-N-[3-(methylsulfonimidoyl)phenyl]-4-(trifluoromethyl)pyridine-3-carboxamide | $^1$H NMR (400 MHz, DMSO-d6) δ 11.23 (s, 1H), 8.46 (d, J = 4.9 Hz, 1H), 8.34 (s, 1H), 7.87 (d, J = 8.0 Hz, 1H), 7.74 - 7.67 (m, 1H), 7.64 - 7.58 (m, 2H), 7.20 (dt, J = 9.9, 5.1 Hz, 2H), 7.10 (td, J = 8.5, 3.3 Hz, 1H), 4.25 (s, 1H), 3.07 (s, 3H), 2.10 (s, 3H). m/z 468.1 [M + H]$^+$, (ESI+), RT = 2.87 LC-MS Method 6 |
| 1651 | | 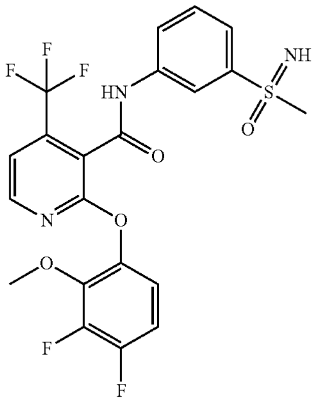 2-(3,4-difluoro-2-methoxy-phenoxy)-N-[3-(methylsulfonimidoyl)phenyl]-4-(trifluoromethyl)pyridine-3-carboxamide | $^1$H NMR (500 MHz, DMSO-d6) δ 11.24 (s, 1H), 8.52 - 8.47 (m, 1H), 8.34 (t, J = 1.9 Hz, 1H), 7.88 (ddd, J = 8.1, 2.1, 1.0 Hz, 1H), 7.71 (ddd, J = 7.8, 1.7, 1.1 Hz, 1H), 7.67 (d, J = 5.4 Hz, 1H), 7.62 (t, J = 7.9 Hz, 1H), 7.26 (q, J = 9.6 Hz, 1H), 7.14 (ddd, J = 9.3, 5.2, 2.2 Hz, 1H), 4.26 (s, 1H), 3.81 (d, J = 0.9 Hz, 3H), 3.10 - 3.06 (m, 3H). m/z 502.1 [M + H]$^+$, (ESI+), RT = 2.88 LC-MS Method 6 |
| 1652 | | 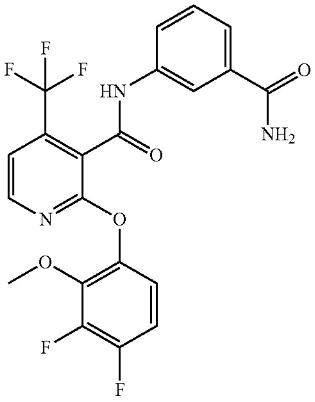 N-(3-carbamoylphenyl)-2-(3,4-difluoro-2-methoxy-phenoxy)-4-(trifluoromethyl)pyridine-3-carboxamide | $^1$H NMR (500 MHz, DMSO-d6) δ 11.00 (s, 1H), 8.48 (d, J = 5.2 Hz, 1H), 8.16 (t, J = 1.8 Hz, 1H), 8.00 (s, 1H), 7.82 - 7.77 (m, 1H), 7.64 (dd, J = 8.9, 6.7 Hz, 2H), 7.45 (t, J = 7.9 Hz, 1H), 7.40 (d, J = 7.2 Hz, 1H), 7.25 (q, J = 9.5 Hz, 1H), 7.14 (ddd, J = 9.2, 5.1, 2.1 Hz, 1H), 3.83 - 3.79 (m, 3H). m/z 485.1 [M + NH4]$^+$, (ESI+), RT = 2.89 LC-MS Method 6 |

TABLE 15-continued

| Compound | Route | Structure and name | Analytical data |
| --- | --- | --- | --- |
| 1653 | | 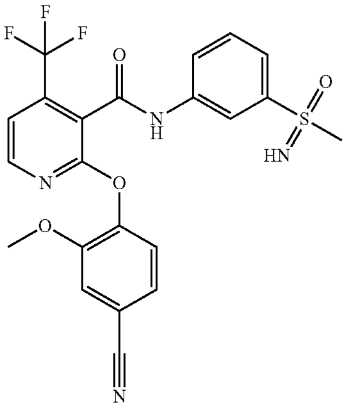 2-(4-cyano-2-methoxy-phenoxy)-N-[3-(methylsulfonimidoyl)phenyl]-4-(trifluoromethyl)pyridine-3-carboxamide | $^{1}$H NMR (400 MHz, DMSO-d6) δ 11.21 (s, 1H), 8.46 (d, J = 5.1 Hz, 1H), 8.33 (t, J = 1.8 Hz, 1H), 7.89 - 7.83 (m, 1H), 7.74 - 7.67 (m, 2H), 7.66 - 7.57 (m, 2H), 7.52 (dd, J = 8.2, 1.8 Hz, 1H), 7.41 (d, J = 8.2 Hz, 1H), 4.25 (s, 1H), 3.78 (s, 3H), 3.11 - 3.00 (m, 3H). m/z 491 [M + H]$^{+}$, (ESI+), RT = 2.56 LC-MS Method 6 |
| 1655 | | 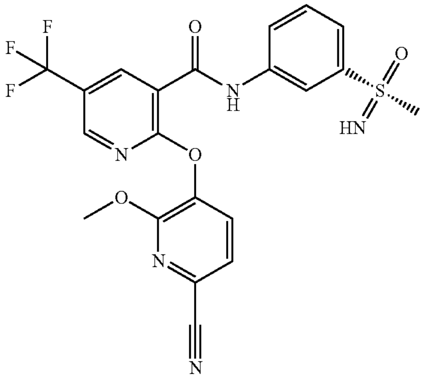 (R)-2-((6-cyano-2-methoxypyridin-3-yl)oxy)-N-(3-(S-methylsulfonimidoyl)phenyl)-5-(trifluoromethyl)nicotinamide | $^{1}$H NMR (400 MHz, DMSO-d6) δ 10.99 (s, 1H), 8.77 - 8.69 (m, 1H), 8.62 (d, J = 2.3 Hz, 1H), 8.37 (s, 1H), 7.99 (d, J = 7.9 Hz, 1H), 7.96 (d, J = 8.9 Hz, 1H), 7.83 (d, J = 7.9 Hz, 1H), 7.71 (d, J = 8.0 Hz, 1H), 7.62 (t, J = 7.9 Hz, 1H), 4.24 (s, 1H), 3.86 (s, 3H), 3.07 (s, 3H). m/z 492.2 [M + H]$^{+}$, (ESI+), RT = 3.01 LC-MS Method 4 |
| 1656 | 2 | 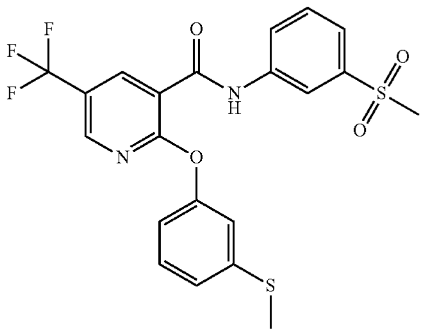 2-(3-methylsulfanylphenoxy)-N-(3-methylsulfonylphenyl)-5-(trifluoromethyl)pyridine-3-carboxamide | $^{1}$H NMR (400 MHz, DMSO-d6) δ 10.98 (s, 1H), 8.73 - 8.67 (m, 1H), 8.56 - 8.51 (m, 1H), 8.41 - 8.36 (m, 1H), 7.97 (dt, J = 7.2, 1.8 Hz, 1H), 7.72 - 7.64 (m, 2H), 7.43 - 7.34 (m, 1H), 7.19 - 7.15 (m, 2H), 7.07 - 7.00 (m, 1H), 4.05 (d, J = 7.2 Hz, OH), 3.22 (s, 3H), 2.48 (s, 3H). m/z 483.0 [M + H]$^{+}$, (ESI+), RT = 4.52 LC-MS Method 5 |

TABLE 15-continued

| Compound | Route | Structure and name | Analytical data |
|---|---|---|---|
| 1657 | 2 | 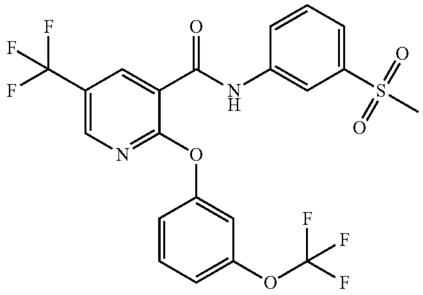 N-(3-methylsulfonylphenyl)-2-[3-(trifluoromethoxy)phenoxy]-5-(trifluoromethyl)pyridine-3-carboxamide | $^1$H NMR (400 MHz, DMSO-d6) δ 11.00 (s, 1H), 8.75 – 8.71 (m, 1H)), 8.60 – 8.55 (m, 1H), 8.41 – 8.36 (m, 1H), 7.98 – 7.94 (m, 1H), 7.73 – 7.64 (m, 2H), 7.61 (t, J = 8.3 Hz, 1H), 7.40 (s, 1H), 7.38 – 7.33 (m, 1H), 7.33 – 7.29 (m, 1H), 3.22 (s, 3H). m/z 521.0 [M + H]$^+$, (ESI+), RT = 4.67 LC-MS Method 5 |
| 1658 | 2 | 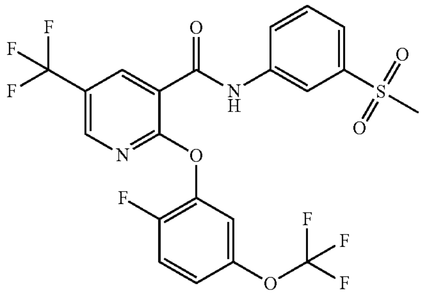 2-[2-fluoro-5-(trifluoromethoxy)phenoxy]-N-(3-methylsulfonylphenyl)-5-(trifluoromethyl)pyridine-3-carboxamide | $^1$H NMR (400 MHz, DMSO-d6) δ 11.04 (s, 1H), 8.76 – 8.74 (m, 1H), 8.65 – 8.61 (m, 1H), 8.41 – 8.38 (m, 1H), 7.98 (dt, J = 7.3, 1.8 Hz, 1H), 7.73 – 7.64 (m, 3H), 7.59 (t, J = 9.5 Hz, 1H), 7.46 – 7.38 (m, 1H), 3.22 (s, 3H). m/z 539.0 [M + H]$^+$, (ESI+), RT = 4.68 LC-MS Method 5 |
| 1659 | 2 | 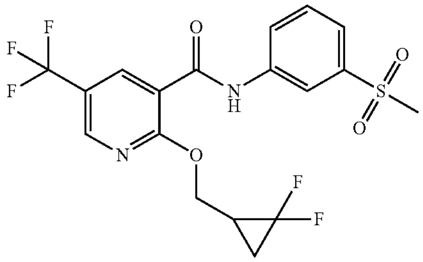 2-[(2,2-difluorocyclopropyl)methoxy]-N-(3-methylsulfonylphenyl)-5-(trifluoromethyl)pyridine-3-carboxamide | $^1$H NMR (400 MHz, DMSO-d6) δ 10.73 (s, 1H), 8.77 (dd, J = 2.3, 0.9 Hz, 1H), 8.43 – 8.40 (m, 1H), 8.38 – 8.36 (m, 1H), 7.93 (dt, J = 7.2, 1.9 Hz, 1H), 7.72 – 7.69 (m, 1H), 7.69 – 7.64 (m, 1H), 4.64 – 4.57 (m, 1H), 4.53 – 4.46 (m, 1H), 3.22 (s, 3H), 2.36 – 2.25 (m, 1H), 1.79 – 1.65 (m, 1H), 1.67 – 1.53 (m, 1H). m/z 449.3 [M – H]–, (ESI–), RT = 3.79 LC-MS Method 7 |

TABLE 15-continued

| Compound | Route | Structure and name | Analytical data |
|---|---|---|---|
| 1660 | 2 | 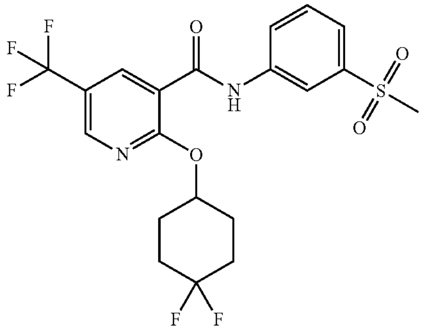 2-(4,4-difluorocyclohexoxy-N-(3-methylsulfonylphenyl)-5-(trifluoromethyl)pyridine-3-carboxamide | $^1$H NMR (400 MHz, DMSO-d6) δ 10.75 (s, 1H), 8.75 (dd, J = 2.4, 1.0 Hz, 1H), 8.42 – 8.37 (m, 1H), 8.38 – 8.33 (m, 1H), 7.90 (dt, J = 7.1, 1.9 Hz, 1H), 7.73 – 7.62 (m, 2H), 5.45 – 5.37 (m, 1H), 3.21 (s, 3H), 2.06 – 1.91 (m, 8H). m/z 477.3 [M – H]–, (ESI–), RT = 3.92 LC-MS Method 7 |
| 1661 | 2 | 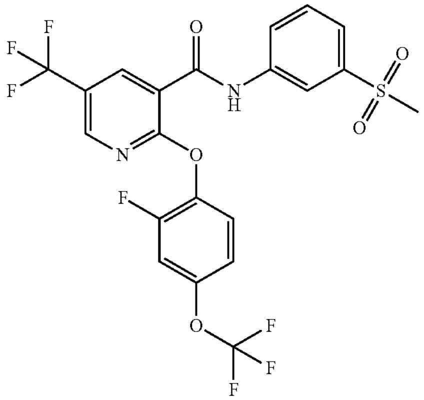 [SMILES: Cc1cc(OC(F)(F)F)ccc1Oc1ncc(C(F)(F)F)cc1C(=O)Nc1cccc(S(C)(=O)=O)c1] 2-[2-fluoro-4-(trifluoromethoxy)phenoxy]-N-(3-methylsulfonylphenyl)-5-(trifluoromethyl)pyridine-3-carboxamide | $^1$H NMR (400 MHz, DMSO-d6) δ 11.07 (s, 1H), 8.76 – 8.70 (m, 1H), 8.62 (d, J = 2.4 Hz, 1H), 8.38 (s, 1H), 8.03 – 7.96 (m, 1H), 7.74 – 7.59 (m, 4H), 7.41 – 7.32 (m, 1H), 3.22 (s, 3H). m/z 537.2 [M]–, (ESI–), RT = 4.12 LC-MS Method 7 |
| 1662 | 2 | 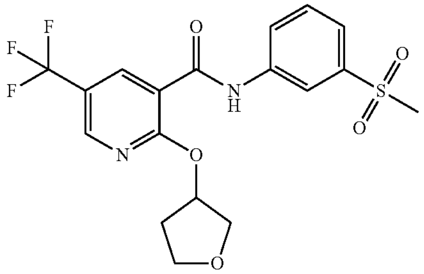 N-(3-methylsulfonylphenyl)-2-tetrahydrofuran-3-yloxy-5-(trifluoromethyl)pyridine-3-carboxamide | $^1$H NMR (400 MHz, DMSO-d6) δ 10.68 (s, 1H), 8.78 – 8.73 (m, 1H), 8.41 – 8.36 (m, 2H), 7.95 – 7.87 (m, 1H), 7.73 – 7.61 (m, 2H), 5.72 – 5.66 (m, 1H), 3.95 (dd, J = 10.5, 4.6 Hz, 1H), 3.90 – 3.84 (m, 1H), 3.84 – 3.78 (m, 1H), 3.78 – 3.73 (m, 1H), 3.22 (s, 3H), 2.31 – 2.20 (m, 1H), 2.13 – 2.03 (m, 1H). m/z 429.2 |

TABLE 15-continued

| Compound | Route | Structure and name | Analytical data |
|---|---|---|---|
| 1663 | 2 | 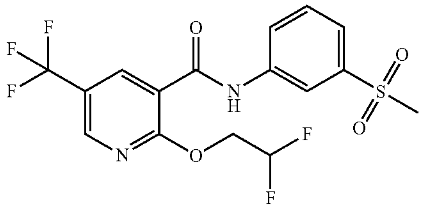 2-(2,2-difluoroethoxy)-N-(3-methylsulfonylphenyl)-5-(trifluoromethyl)pyridine-3-carboxamide | [M]−, (ESI−), RT = 3.30 LC-MS Method 7 $^1$H NMR (500 MHz, DMSO-d6) δ 10.77 (s, 1H), 8.82 − 8.78 (m, 1H), 8.46 (d, J = 2.3 Hz, 1H), 8.38 − 8.35 (m, 1H), 7.94 − 7.89 (m, 1H), 7.72 − 7.69 (m, 1H), 7.69 − 7.65 (m, 1H), 6.57 − 6.32 (m, 1H), 4.77 (td, J = 14.8, 3.5 Hz, 2H), 3.22 (s, 3H). m/z 423.2 [M] −, (ESI −), RT = 3.40 LC-MS Method 7 |
| 1664 | 2 | 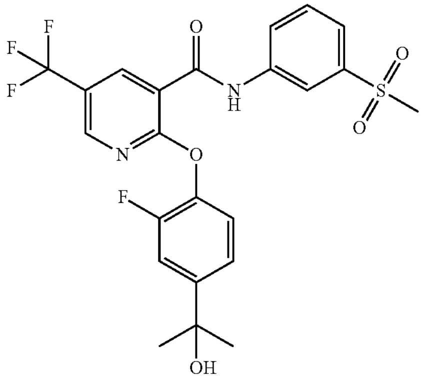 2-[2-fluoro-4-(1-hydroxy-1-methyl-ethyl)phenoxy]-N-(3-methylsulfonylphenyl)-5-(trifluoromethyl)pyridine-3-carboxamide | $^1$H NMR (400 MHz, DMSO-d6) δ 11.05 (s, 1H), 8.71 − 8.68 (m, 1H), 8.61 − 8.54 (m, 1H), 8.41 − 8.34 (m, 1H), 8.00 − 7.95 (m, 1H), 7.73 − 7.61 (m, 2H), 7.45 − 7.38 (m, 1H), 7.39 − 7.29 (m, 2H), 5.18 (s, 1H), 3.21 (s, 3H), 1.43 (s, 6H). m/z 535.1 [M + Na]$^+$, (ESI+), RT = 3.32 LC-MS Method 4 |
| 1665 | 3 | 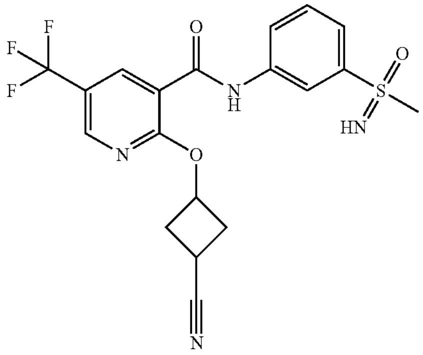 2-(3-cyanocyclobutoxy)-N-[3-(methylsulfonimidoyl)phenyl]-5-(trifluoromethyl)pyridine-3-carboxamide | $^1$H NMR (400 MHz, $CD_3OD$) δ 8.68 (d, J = 10.5 Hz, 2H), 8.48 (s, 1H), 8.04 (d, J = 8.8 Hz, 1H), 7.92 (d, J = 7.6 Hz, 1H), 7.78 (t, J = 7.9 Hz, 1H), 5.47 − 5.39 (m, 1H), 3.59 (s, 3H), 3.16 − 3.04 (m, 3H), 2.65 (m, 2H). m/z 439.2 [M + H]$^+$, (ESI+), RT = 2.74 LC-MS Method 4 |

TABLE 15-continued

| Compound | Route | Structure and name | Analytical data |
|---|---|---|---|
| 1666 | 4 | 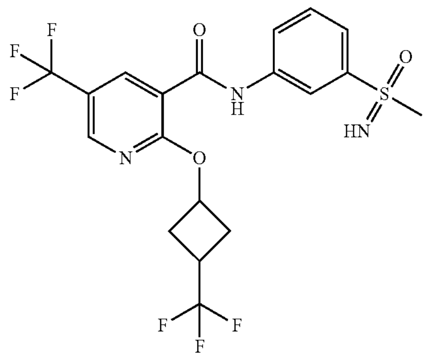 N-[3-(methylsulfonimidoyl)phenyl]-5-(trifluoromethyl)-2-[3-(trifluoromethyl)cyclobutoxy] pyridine-3-carboxamide | $^1H$ NMR (400 MHz, $CD_3OD$) δ 8.66 (s, 1H), 8.52 - 8.43 (m, 2H), 7.98 (dd, J = 19.1, 7.9 Hz, 1H), 7.83 (d, J = 7.8 Hz, 1H), 7.67 (t, J = 8.0 Hz, 1H), 5.50 - 5.38 (m, 1H), 3.20 (s, 3H), 3.01 - 2.76 (m, 3H), 2.45 - 2.35 (m, 2H). m/z 482.2 $[M + H]^+$, (ESI+), RT = 3.38 and 3.50 LC-MS Method 4. Data supports product obtained as a mixture of diastereomers. |
| 1667 | | 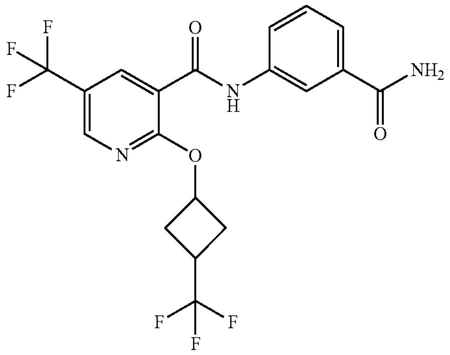 N-(3-carbamoylphenyl)-5-trifluoromethyl)-2-[3-(trifluoromethyl)cyclobutoxy] pyridine-3-carboxamide | $^1H$ NMR (500 MHz, $CD_3OD$) δ 8.65 (d, J = 1.5 Hz, 1H), 8.47 (d, J = 2.4 Hz, 1H), 8.22 (t, J = 1.8 Hz, 1H), 7.88 (dd, J = 8.1, 1.2 Hz, 1H), 7.69 (m, 1H), 7.51 (t, J = 7.9 Hz, 1H), 5.44 (p, J = 7.1 Hz, 1H), 2.99 - 2.75 (m, 3H), 2.43 (m, 2H). m/z 465.3 $[M + NH4]^+$, (ESI+), RT = 3.54 and 3.69 LC-MS Method 6 Data supports product obtained as a mixture of diastereomers. |
| 1668 | 4 | 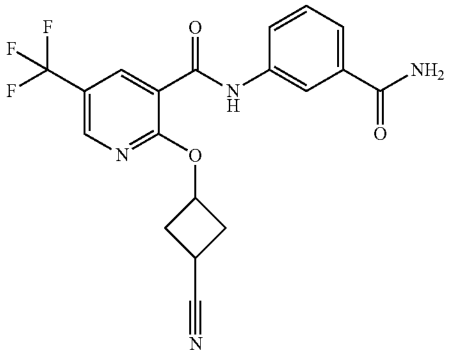 N-(3-carbamoylphenyl)-2-(3-cyanocyclobutoxy)-5-(trifluoromethyl)pyridine-3-carboxamide | $^1H$ NMR (400 MHz, $CD_3OD$) δ 8.65 (m, 1H), 8.48 (m, 1H), 8.21 (t, 1H), 7.93 (m, 1H), 7.69 (dd, J = 8.0, 1.4 Hz, 1H), 7.51 (m, 1H), 5.47 - 5.36 (m, 1H), 3.15 - 3.01 (m, 3H), 2.67 (m, 1H). m/z 405.2 $[M + H]^+$, (ESI+), RT = 2.83 and 2.87 LC-MS Method 4. Data supports product obtained as a mixture of diastereomers. |

TABLE 15-continued

| Compound | Route | Structure and name | Analytical data |
|---|---|---|---|
| 1669 | 3 | 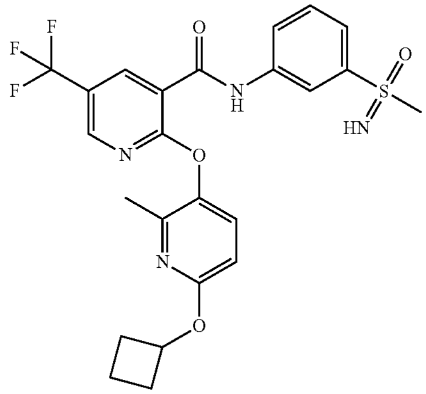 2-[[6-(cyclobutoxy)-2-methyl-3-pyridyl]oxy]-N-[3-methylsulfonimidoyl)phenyl]-5-(trifluoromethyl)pyridine-3-carboxamide | $^1$H NMR (500 MHz, $CD_3OD$) δ 8.58 – 8.52 (m, 2H), 8.46 (t, J = 1.8 Hz, 1H), 8.05 – 7.99 (m, 1H), 7.86 – 7.80 (m, 1H), 7.66 (t, J = 8.0 Hz, 1H), 7.55 (d, J = 8.7 Hz, 1H), 6.66 (d, J = 8.7 Hz, 1H), 5.13 (p, J = 7.3 Hz, 1H), 3.19 (s, 3H), 2.54 – 2.44 (m, 2H), 2.26 (s, 3H), 1.87 (m, 1H), 1.73 (m, 1H). m/z 521.2 $[M + H]^+$, (ESI+), RT = 3.62 LC-MS Method 4 |
| 1670 | 5 | 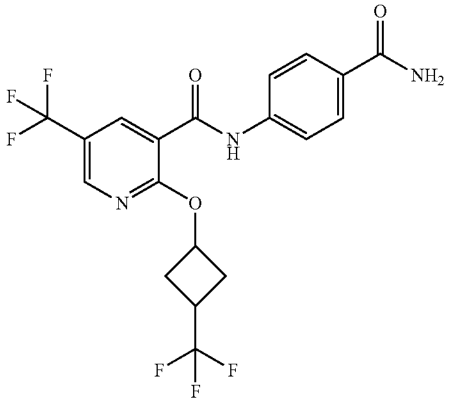 N-(4-carbamoylphenyl)-5-trifluoromethyl)-2-[3-(trifluoromethyl)cyclobutoxy]pyridine-3-carboxamide | $^1$H NMR (500 MHz, $CD_3OD$) δ 8.65 (s, 1H), 8.47 (m, 1H), 7.94 (d, J = 8.6 Hz, 2H), 7.83 (d, J = 8.6 Hz, 2H), 5.45 (p, J = 7.2 Hz, 1H), 3.00 – 2.75 (m, 3H), 2.42 (m, 2H). m/z 448.2 $[M + H]^+$, (ESI+), RT = 3.46 and 3.60 LC-MS Method 4. Data supports product obtained as a mixture of diastereomers. |
| 1671 | 5 | 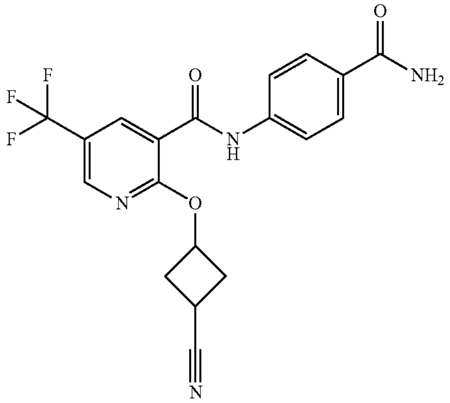 N-(4-carbamoylphenyl)-2-(3-cyanocyclobuyoxy)-5-(trifluoromethyl)pyridine-3-carboxamide | $^1$H NMR (500 MHz, $CD_3OD$) δ 8.64 (m, 1H), 8.48 (m, 1H), 7.98 – 7.91 (m, 2H), 7.88 – 7.81 (m, 2H), 5.46 – 5.38 (m, 1H), 3.14 – 3.09 (m, 3H), 2.72 – 2.62 (m, 2H). m/z 405.2 $[M + H]^+$, (ESI+), RT = 2.84 and 2.88 LC-MS Method 4 Data supports product obtained as a mixture of diastereomers. |

TABLE 15-continued

| Compound | Route | Structure and name | Analytical data |
|---|---|---|---|
| 1672 | 1 | 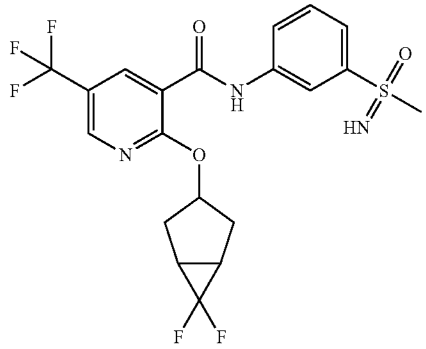 2-[(6,6-difluoro-3-bicyclo[3.1.0]hexanyl)oxy]-N-[3-(methylsulfonimidoyl)phenyl]-5-(trifluoromethyl)pyridine-3-carboxamide | $^1$H NMR (400 MHz, $CD_3OD$) δ 8.69 – 8.63 (m, 1H), 8.55 (m, 1H), 8.49 (t, J = 2.0 Hz, 1H), 7.96 – 7.88 (m, 1H), 7.82 (m, 1H), 7.65 (t, J = 8.0 Hz, 1H), 5.97 (m, 1H), 3.18 (s, 3H), 2.89 – 2.81 (m, 2H), 2.23 – 2.14 (m, 4H). m/z 476.3 $[M + H]^+$, (ESI+), RT = 3.44 LC-MS Method 6 |
| 1673 | 5 | 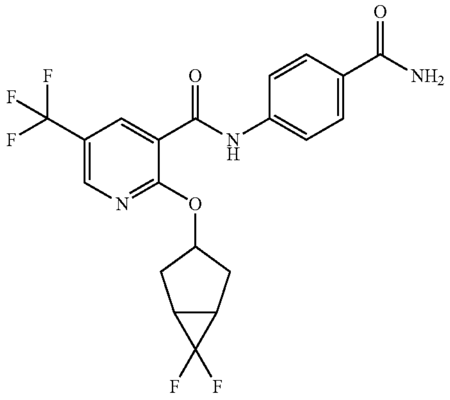 N-(4-carbamoylphenyl)-2-[(6,6-difluoro-3-bicyclo[3.1.0]hexanyl)oxy]-5-(trifluoromethyl)pyridine-3-carboxamide | $^1$H NMR (400 MHz, $CD_3OD$) δ 8.67 (d, J = 1.6 Hz, 1H), 8.59 (d, J = 2.4 Hz, 1H), 7.99 – 7.91 (m, 2H), 7.83 (d, J = 8.7 Hz, 2H), 5.98 (m, 1H), 2.92 – 2.84 (m, 2H), 2.21 (m, 4H). m/z 442.2 $[M + H]^+$, (ESI+), RT = 3.38 LC-MS Method 4 |
| 1674 | 3 | 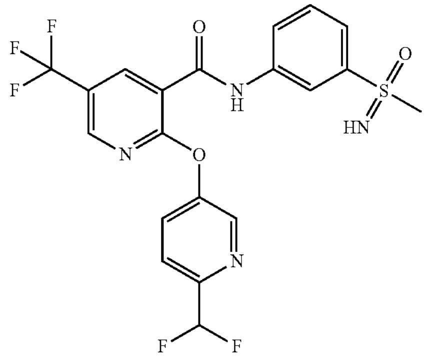 2-[[6-difluoromethyl)-3-pyridyl]oxy]-N-[3-(methylsulfonimidoyl)phenyl]-5-(trifluoromethyl)pyridine-3-carboxamide | $^1$H NMR (500 MHz, $CD_3OD$) δ 8.68 – 8.55 (m, 3H), 8.47 (m, 1H), 8.04 (d, J = 8.1 Hz, 1H), 7.96 (dd, J = 8.6, 2.6 Hz, 1H), 7.84 (m, 2H), 7.66 (t, J = 8.0 Hz, 1H), 6.79 (t, J = 55.2 Hz, 1H), 3.19 (s, 3H). m/z 487.1 $[M + H]^+$, (ESI+), RT = 2.83 LC-MS Method 4 |

TABLE 15-continued

| Compound | Route | Structure and name | Analytical data |
|---|---|---|---|
| 1675 | 4 | 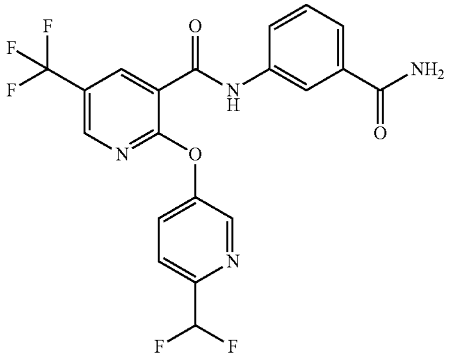 N-(3-carbamoylphenyl)-2-[[6-(difluoromethyl)-3-pyridyl]oxy]-5-(trifluoromethyl)pyridine-3-carboxamide | $^1$H NMR (500 MHz, $CD_3OD$) δ 8.67 (d, J = 2.5 Hz, 1H), 8.63 – 8.55 (m, 2H), 8.20 (t, J = 1.8 Hz, 1H), 7.96 (m, 2H), 7.84 (d, J = 8.6 Hz, 1H), 7.69 (dt, J = 7.8, 1.1 Hz, 1H), 7.51 (t, J = 7.9 Hz, 1H), 6.79 (t, J = 55.2 Hz, 1H). m/z 453.3 $[M + H]^+$, (ESI+), RT = 3.11 LC-MS Method 6 |
| 1676 | 5 | 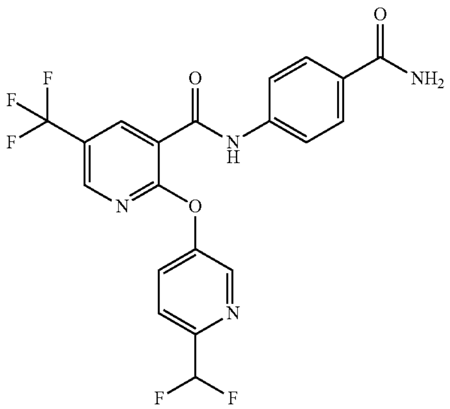 N-(4-carbamoylphenyl)-2-[[6-(difluoromethyl)-3-pyridyl]oxy]-5-(trifluoromethyl)pyridine-3-carboxamide | $^1$H NMR (500 MHz, $CD_3OD$) δ 8.69 – 8.54 (m, 3H), 7.95 (m, 3H), 7.85 (m, 3H), 6.79 (t, J = 55.2 Hz, 1H). m/z 453.3 $[M + H]^+$, (ESI+), RT = 3.08 LC-MS Method 6 |
| 1677 | 4 | 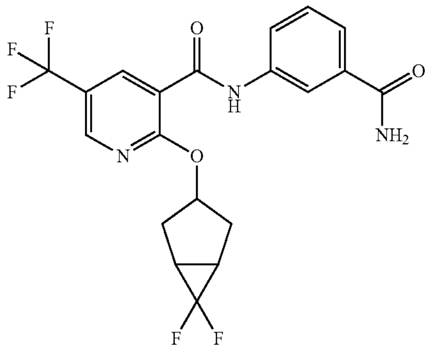 N-(3-carbamoylphenyl)-2-[(6,6-difluoro-3-bicyclo[3.1.0]hexanyl)oxy]-5-(trifluoromethyl)pyridine-3-carboxamide | $^1$H NMR (400 MHz, $CD_3OD$) δ 8.67 (m, 1H), 8.59 (d, J = 2.3 Hz, 1H), 8.27 (m, 1H), 7.84 (d, J = 8.2 Hz, 1H), 7.69 (m, 1H), 7.52 (t, J = 7.9 Hz, 1H), 5.98 (m, 1H), 2.87 (m, 2H), 2.21 (m, 4H). m/z 459.3 $[M + NH4]^+$, (ESI+), RT = 3.52 LC-MS Method 6 |

TABLE 15-continued

| Compound | Route | Structure and name | Analytical data |
|---|---|---|---|
| 1678 | 10 | 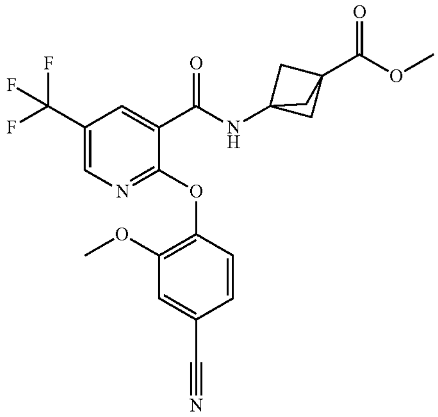 methyl 3-[[2-(4-cyano-2-methoxy-phenoxy)-5-(trifluoromethyl)pyridine-3-carbonyl]amino]bicycl[1.1 1]pentane-1-carboxylate | $^1H$ NMR (400 MHz, $CD_3OD$) δ 8.47 (s, 2H), 7.53 (s, 1H), 7.46 (m, 2H), 3.80 (s, 3H), 3.71 (s, 3H), 2.47 (s, 6H). m/z 462.3 $[M + H]^+$, (ESI+), RT = 3.69 LC-MS Method 6 |
| 1679 | 10 | 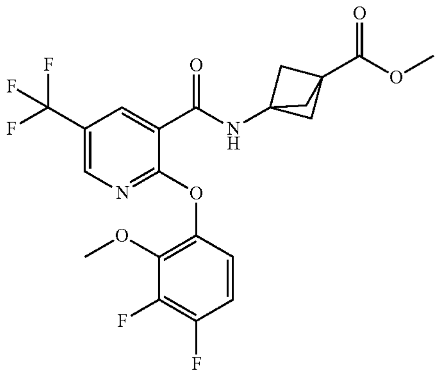 methyl 3-[[2-(3,4-difluoro-2-methoxy-phenoxy)-5-(trifluoromethyl)pyridine-3-carbonyl]amino]bicyclo[1.1.1]pentane-1-carboxylate | $^1H$ NMR (400 MHz, $CD_3OD$) 88.51 (dd, J = 2.4, 0.9 Hz, 1H), 8.44 (d, J = 2.4 Hz, 1H), 7.14 - 7.03 (m, 2H), 3.85 (d, J = 1.8 Hz, 3H), 3.71 (s, 3H), 2.47 (s, 6H). m/z 473.3 $[M + H]^+$, (ESI+), RT = 3.98 LC-MS Method 6 |
| 1680 | 9 | 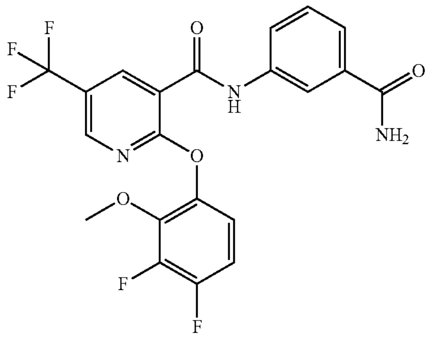 5-bromo-N-(3-carbamoylphenyl)-2-(3,4-difluoro-2-methoxy-phenoxy)pyridine-3-carboxamide | $^1H$ NMR (400 MHz, $CD_3OD$) δ 8.42 (d, J = 2.5 Hz, 1H), 8.30 (d, J = 2.5 Hz, 1H), 8.16 (t, J = 2.0 Hz, 1H), 7.92 (m, 1H), 7.70 - 7.63 (m, 1H), 7.48 (t, J = 7.9 Hz, 1H), 7.13 (m, 1H), 7.10 - 7.02 (m, 1H), 3.84 (d, J = 1.7 Hz, 3H). m/z 478.1 $[M]^+$, (ESI+), RT = 3.36 LC-MS Method 4 |

TABLE 15-continued

| Compound | Route | Structure and name | Analytical data |
|---|---|---|---|
| 1681 | 8 | 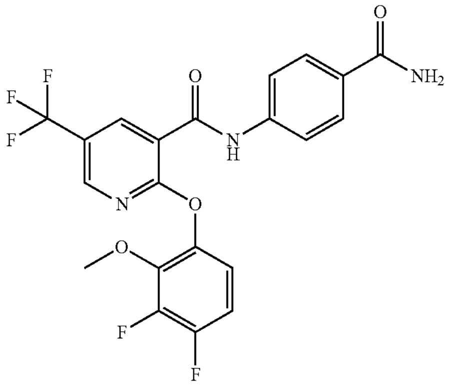 5-bromo-N-(4-carbamoylphenyl)-2-(3,4-difluoro-2-methoxy-phenoxy)pyridine-3-carboxamide | $^1H$ NMR (400 MHz, $CD_3OD$) δ 8.39 (d, J = 2.5 Hz, 1H), 8.30 (d, J = 2.5 Hz, 1H), 7.95 - 7.87 (m, 2H), 7.85 - 7.78 (m, 2H), 7.13 (m, 1H), 7.05 (m, 1H), 3.84 (d, J = 1.7 Hz, 3H). m/z 478.2 $[M]^+$, (ESI+), RT = 3.36 LC-MS Method 6 |
| 1683 | 9 | 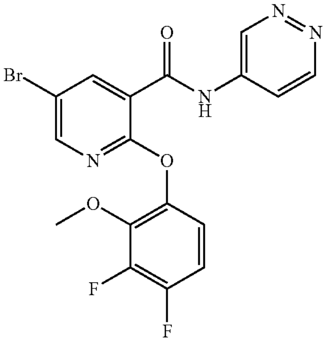 5-bromo-2-(3,4-difluoro-2-methoxy-phenoxy)-N-pyridazin-4-yl-pyridine-3-carboxamide | $^1H$ NMR (400 MHz, $CD_3OD$) 89.41 (dd, J = 2.7, 1.0 Hz, 1H), 9.07 (dd, J = 6.0, 1.0 Hz, 1H), 8.43 (d, J = 2.5 Hz, 1H), 8.34 (d, J = 2.5 Hz, 1H), 8.23 (dd, J = 6.0, 2.7 Hz, 1H), 7.16 - 7.00 (m, 2H), 3.83 (d, J = 1.7 Hz, 3H). m/z 437.1 $[M]^+$, (ESI+), RT = 3.24 LC-MS Method 6 |
| 1684 | 3 | 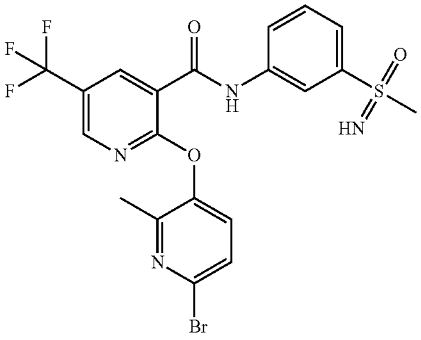 2-[(6-bromo-2-methyl-3-pyridyl)oxy]-N-[3-(methylsulfonimidoyl)phenyl]-5-(trifluoromethyl)pyridine-3-carboxamide | $^1H$ NMR (400 MHz, $CD_3OD$) δ 8.60 - 8.52 (m, 2H), 8.45 (t, J = 2.0 Hz, 1H), 8.00 (m, 1H), 7.82 (m, 1H), 7.64 (t, J = 8.0 Hz, 1H), 7.61 (d, J = 8.5 Hz, 1H), 7.53 (d, J = 8.4 Hz, 1H), 3.17 (s, 3H), 2.36 (s, 3H). m/z 529.2 $[M]^+$, (ESI+), RT = 3.24 LC-MS Method 6 |

TABLE 15-continued

| Compound | Route | Structure and name | Analytical data |
|---|---|---|---|
| 1685 | 3 | 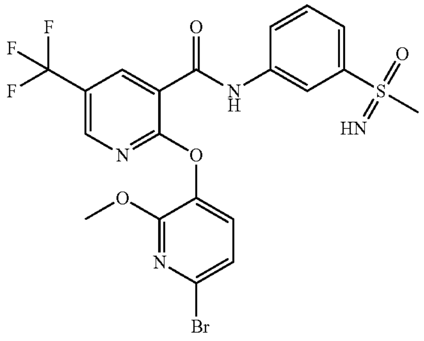 2-[(6-bromo-2-methoxy-3-pyridyl)oxy]-N-[3-(methylsulfonimidoyl)phenyl]-5-(trifluoromethyl)pyridine-3-carboxamide | $^1H$ NMR (400 MHz, $CD_3OD$) δ 8.56 (s, 2H), 8.43 (t, J = 2.0 Hz, 1H), 8.06 – 7.99 (m, 1H), 7.82 (m, 1H), 7.69 – 7.59 (m, 2H), 7.25 (d, J = 8.0 Hz, 1H), 3.89 (s, 3H), 3.17 (s, 3H). m/z 545.1 $[M]^+$, (ESI+), RT = 3.57 LC-MS Method 6 |
| 1686 | 6 | 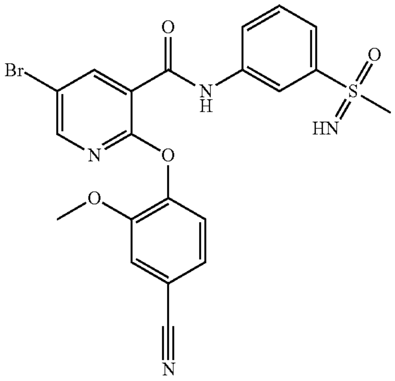 5-bromo-2-(4-cyano-2-methoxy-phenoxy)-N-[3-(methylsulfonimidoyl)phenyl] pyridine-3-carboxamide | $^1H$ NMR (400 MHz, DMSO-d6) δ 10.85 (s, 1H), 8.41 – 8.34 (m, 3H), 7.96 – 7.89 (m, 1H), 7.70 – 7.66 (m, 1H), 7.66 (d, J = 1.8 Hz, 1H), 7.60 (t, J = 7.9 Hz, 1H), 7.51 (dd, J = 8.2, 1.8 Hz, 1H), 7.45 (d, J = 8.2 Hz, 1H), 4.22 (s, 1H), 3.75 (s, 3H), 3.05 (d, J = 1.1 Hz, 3H). m/z 501.1, 503.1 $[M]^+$, (ESI+), RT = 3.13 LC-MS Method 4 |
| 1687 | 4 | 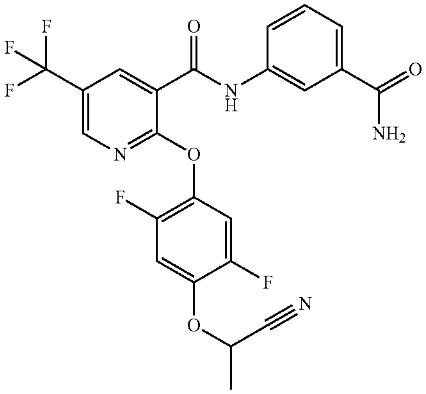 N-(3-carbamoylphenyl)-2-[4-(1-cyanoethoxy)-2,5-difluoro-phenoxy]-5-(trifluoromethyl)pyridine-3-carboxamide | $^1H$ NMR (500 MHz, DMSO-d6) δ 10.75 (s, 1H), 8.74 (m, 1H), 8.58 (d, J = 2.5 Hz, 1H), 8.18 (t, J = 2.0 Hz, 1H), 7.98 (s, 1H), 7.89 (m, 1H), 7.69 – 7.60 (m, 3H), 7.46 (t, J = 7.9 Hz, 1H), 7.38 (s, 1H), 5.54 (q, J = 6.7 Hz, 1H), 1.74 (d, J = 6.6 Hz, 3H). m/z 507.1 $[M + H]^+$, (ESI+), RT = 3.32 LC-MS Method 4 |

TABLE 15-continued

| Compound | Route | Structure and name | Analytical data |
| --- | --- | --- | --- |
| 1688 | 5 | 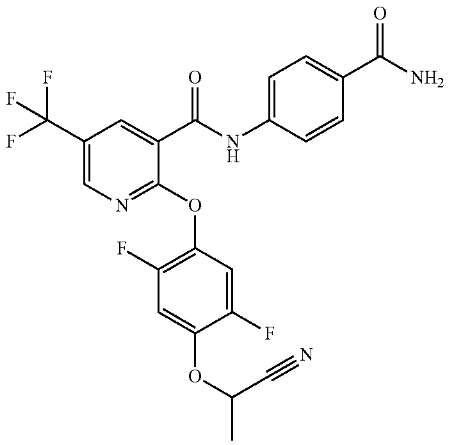 N-(4-carbamoylphenyl)-2-[4-(1-cyanoethoxy)-2,5-difluoro-phenoxy]-5-(trifluoromethyl)pyridine-3-carboxamide | $^1$H NMR (400 MHz, DMSO-d6) δ 10.85 (s, 1H), 8.74 (dd, J = 2.4, 1.1 Hz, 1H), 8.59 (d, J = 2.5 Hz, 1H), 7.94 - 7.86 (m, 3H), 7.79 (d, J = 8.6 Hz, 2H), 7.64 (m, 2H), 7.29 (s, 1H), 5.54 (q, J = 6.6 Hz, 1H), 1.74 (d, J = 6.7 Hz, 3H). m/z 507.1 [M + H]$^+$, (ESI+), RT = 3.36 LC-MS Method 4 |
| 1689 | 3 | 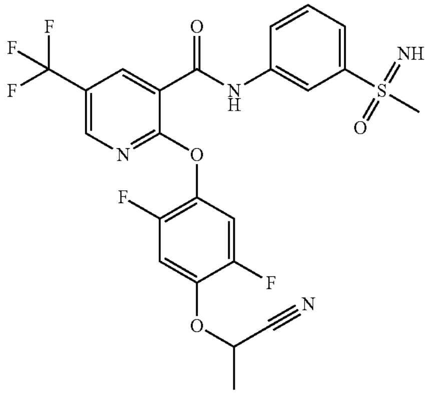 2-[4-(1-cyanoethoxy)-2,5-difluoro-phenoxy]-N-[3-(methylsufonimidoyl)phenyl]-5-(trifluoromethyl)pyridine-3-carboxamide | $^1$H NMR (400 MHz, DMSO-d6) δ 10.97 (s, 1H), 8.74 (d, J = 2.2 Hz, 1H), 8.60 (d, J = 2.4 Hz, 1H), 8.38 (m, 1H), 7.95 (d, J = 8.1 Hz, 1H), 7.73 - 7.58 (m, 4H), 5.54 (q, J = 6.7 Hz, 1H), 4.24 (s, 1H), 3.06 (d, J = 1.1 Hz, 3H), 1.74 (d, J = 6.7 Hz, 3H). m/z 541.1 [M + H]$^+$, (ESI+), RT = 3.31 LC-MS Method 4 |
| 1690 | 3 | 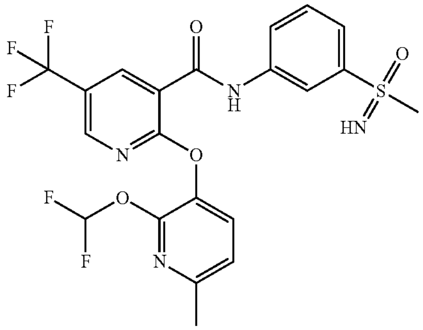 2-[[2-(difluoromethoxy)-6-methyl-3-pyridyl]oxy]-N-[3-(methylsulfonimidoyl)phenyl]-5-(trifluoromethyl)pyridine-3-carboxamide | $^1$H NMR (400 MHz, DMSO-d6) δ 10.99 (s, 1H), 8.68 (m, 1H), 8.58 (d, J = 2.5 Hz, 1H), 8.39 (t, J = 1.9 Hz, 1H), 7.84 - 7.39 (m, 4H), 7.24 (d, J = 8.1 Hz, 1H), 4.23 (s, 1H), 3.06 (d, J = 1.0 Hz, 3H), 2.46 (s, 3H). m/z 517.2 [M + H]$^+$, (ESI+), RT = 3.26 LC-MS Method 4 |

TABLE 15-continued

| Compound | Route | Structure and name | Analytical data |
|---|---|---|---|
| 1691 | 4 | 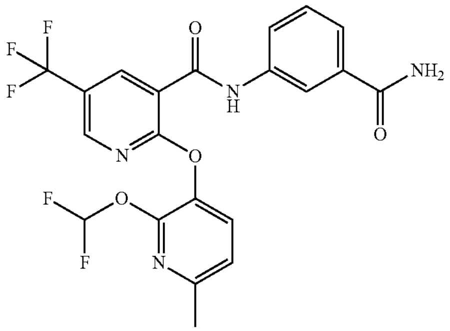 N-(3-carbamoylphenyl)-2-[[2-(difluoromethoxy)-6-methyl-3-pyridyl]oxy]-5-(trifluoromethyl)pyridine-3-carboxamide | $^1$H NMR (400 MHz, DMSO-d6) δ 10.77 (s, 1H), 8.68 (m, 1H), 8.57 (d, J = 2.7 Hz, 1H), 8.20 (t, J = 1.9 Hz, 1H), 7.98 (s, 1H), 7.90 (m, 1H), 7.86 - 7.42 (m, 4H), 7.38 (s, 1H), 7.25 (d, J = 8.1 Hz, 1H), 2.47 (s, 3H). m/z 483.2 [M + H]$^+$, (ESI+), RT = 3.33 LC-MS Method 4 |
| 1692 | 1 | 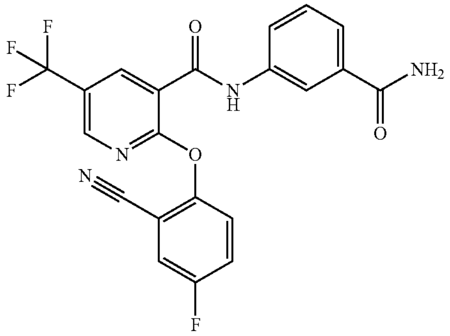 N-(3-carbamoylphenyl)-2-(2-cyano-4-fluoro-phenoxy)-5-(trifluoromethyl)pyridine-3-carboxamide | $^1$H NMR (400 MHz, DMSO-d6) δ 10.79 (s, 1H), 8.74 (m, 1H), 8.63 (d, J = 2.5 Hz, 1H), 8.19 (t, J = 2.0 Hz, 1H), 8.01 (dd, J = 8.1, 3.1 Hz, 1H), 7.98 (s, 1H), 7.92 - 7.85 (m, 1H), 7.75 (m, 1H), 7.70 - 7.60 (m, 2H), 7.46 (t, J = 7.9 Hz, 1H), 7.38 (s, 1H). m/z 445.2 [M + H]$^+$, (ESI+), RT = 3.00 LC-MS Method 4 |
| 1693 | 1 | 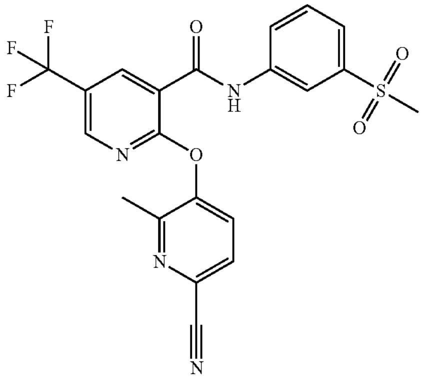 2-[(6-cyano-2-methyl-3-pyridyl)oxy]-N-(3-methylsulfonylphenyl)-5-(trifluoromethyl)pyridine-3-carboxamide | $^1$H NMR (400 MHz, DMSO-d6) δ 11.07 (s, 1H), 8.73 (m, 1H), 8.69 - 8.64 (m, 1H), 8.39 (t, J = 1.9 Hz, 1H), 8.05 (d, J = 8.3 Hz, 1H), 8.00 (d, J = 8.4 Hz, 1H), 7.97 (dt, J = 7.6, 1.9 Hz, 1H), 7.75 - 7.64 (m, 2H), 3.23 (s, 3H), 2.39 (s, 3H). m/z 477.2 [M + H]$^+$, (ESI+), RT = 3.26 LC-MS Method 4 |

TABLE 15-continued

| Compound | Route | Structure and name | Analytical data |
|---|---|---|---|
| 1694 | 1 | 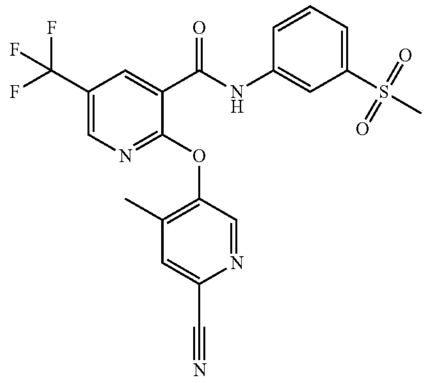 2-[(6-cyano-4-methyl-3-pyridyl)oxy]-N-(3-methylsulfonylphenyl)-5-(trifluoromethyl)pyridine-3-carboxamide | $^1H$ NMR (400 MHz, DMSO-d6) δ 11.07 (s, 1H), 8.71 (m, 2H), 8.66 (d, J = 2.4 Hz, 1H), 8.39 (m, 1H), 8.15 (s, 1H), 7.97 (m, 1H), 7.75 − 7.64 (m, 2H), 3.23 (s, 3H), 2.22 (s, 3H). m/z 477.1 $[M + H]^+$, (ESI+), RT = 3.26 LC-MS Method 4 |
| 1695 | 1 | 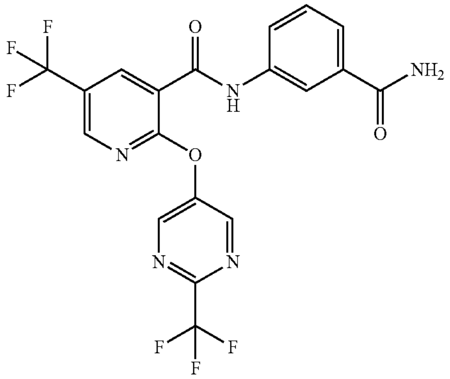 N-(3-carbamoylphenyl)-5-(trifluoromethyl)-2-[2-(trifluoromethyl)pyrimidin-5-yl]oxy-pyridine-3-carboxamide | $^1H$ NMR (400 MHz, DMSO-d6) δ 10.80 (s, 1H), 9.20 (s, 2H), 8.76 (m, 1H), 8.65 (d, J = 2.5 Hz, 1H), 8.17 (t, J = 1.9 Hz, 1H), 7.98 (s, 1H), 7.95 − 7.90 (m, 1H), 7.64 (m, 1H), 7.46 (t, J = 7.9 Hz, 1H), 7.39 (s, 1H). m/z 472.1 $[M + H]^+$, (ESI+), RT =3.13 LC-MS Method 4 |
| 1696 | 1 | 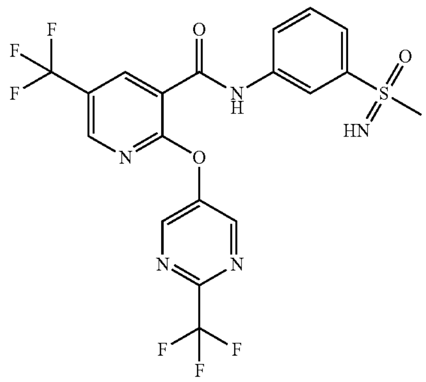 N-(3-(methylsulfonimidoyl)phenyl]-5-(trifluoromethyl)-2-[2-(trifluoromethyl)pyrimidin-5-yl]oxy-pyridine-3-carboxamide | $^1H$ NMR (400 MHz, DMSO-d6) δ 11.03 (s, 1H), 9.19 (s, 2H), 8.77 (m, 1H), 8.67 (d, J = 2.5 Hz, 1H), 8.37 (t, J = 2.0 Hz, 1H), 8.03 − 7.93 (m, 1H), 7.71 (m, 1H), 7.63 (t, J = 7.9 Hz, 1H), 4.25 (s, 1H), 3.07 (s, 3H). m/z 506.1 $[M + H]^+$, (ESI+), RT = 3.05 LC-MS Method 4 |

TABLE 15-continued

| Compound | Route | Structure and name | Analytical data |
|---|---|---|---|
| 1697 | 1 | 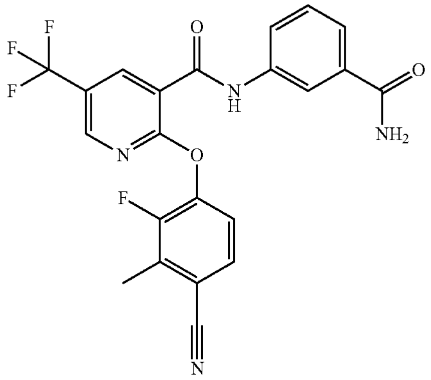 N-(3-carbamoylphenyl)-2-(4-cyano-2-fluoro-3-methyl-phenoxy)-5-(trifluoromethyl)pyridine-3-carboxamide | $^1H$ NMR (400 MHz, DMSO-d6) δ 10.80 (s, 1H), 8.72 (m, 1H), 8.62 (m, 1H), 8.17 (t, J = 2.0 Hz, 1H), 7.98 (s, 1H), 7.92 – 7.85 (m, 1H), 7.79 (m, 1H), 7.63 (m, 1H), 7.54 (t, J = 8.0 Hz, 1H), 7.45 (t, J = 7.9 Hz, 1H), 7.38 (s, 1H), 2.44 (d, J = 2.1 Hz, 3H). m/z 459.2 $[M + H]^+$, (ESI+), RT = 3.19 LC-MS Method 4 |
| 1698 | 4 | 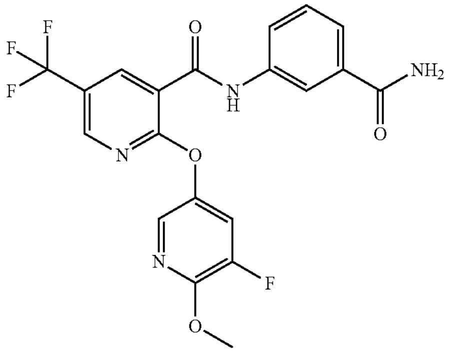 N-(3-carbamoylphenyl)-2-[(5-fluoro-6-methoxy-3-pyridyl)oxy]-5-(trifluoromethyl)pyridine-3-carboxamide | $^1H$ NMR (400 MHz, DMSO-d6) δ 10.71 (s, 1H), 8.70 (m, 1H), 8.54 (d, J = 2.5 Hz, 1H), 8.17 (t, J = 1.9 Hz, 1H), 8.05 (d, J = 2.3 Hz, 1H), 7.98 (s, 1H), 7.94 – 7.85 (m, 2H), 7.63 (m, 1H), 7.46 (t, J = 7.9 Hz, 1H), 7.39 (s, 1H), 3.97 (s, 3H). m/z 451.1 $[M + H]^+$, (ESI+), RT = 3.09 LC-MS Method 4 |
| 1699 | 3 | 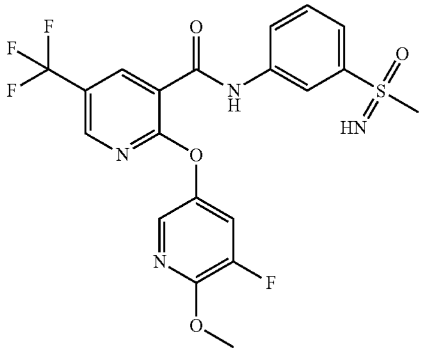 2-[(5-fluoro-6-methoxy-3-pyridyl)oxy]-N-[3-(methylsulfonimidoyl)phenyl]-5-(trifluoromethyl)pyridine-3-carboxamide | $^1H$ NMR (400 MHz, DMSO-d6) δ 10.94 (s, 1H), 8.72 (m, 1H), 8.56 (d, J = 2.5 Hz, 1H), 8.37 (t, J = 2.0 Hz, 1H), 8.05 (d, J = 2.4 Hz, 1H), 7.95 (m, 1H), 7.88 (dd, J = 10.8, 2.4 Hz, 1H), 7.70 (m, 1H), 7.62 (t, J = 7.9 Hz, 1H), 4.24 (s, 1H), 3.97 (s, 3H), 3.06 (s, 3H). m/z 485.2 $[M + H]^+$, (ESI+), RT = 3.00 LC-MS Method 4 |

TABLE 15-continued

| Compound | Route | Structure and name | Analytical data |
|---|---|---|---|
| 1700 | 1 | 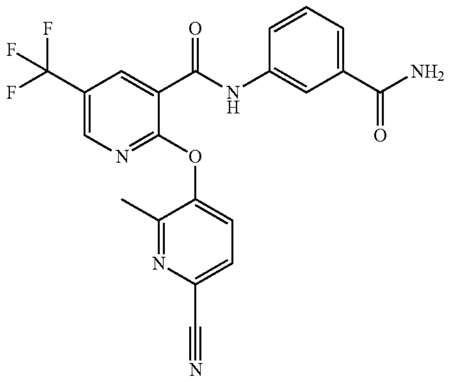 N-(3-carbamoylphenyl)-2-[(6-cyano-2-methyl-3-pyridyl)oxy]-5-(trifluoromethyl)pyridine-3-carboxamide | $^1$H NMR (400 MHz, $CD_3OD$) δ 8.57 (m, 1H), 8.18 (m, 1H), 7.95 – 7.88 (m, 2H), 7.84 (d, J = 8.3 Hz, 1H), 7.67 (m, 1H), 7.49 (t, J = 7.9 Hz, 1H), 2.46 (s, 3H). m/z 442.2 $[M + H]^+$, (ESI+), RT = 2.84 LC-MS Method 4 |
| 1701 | 1 | 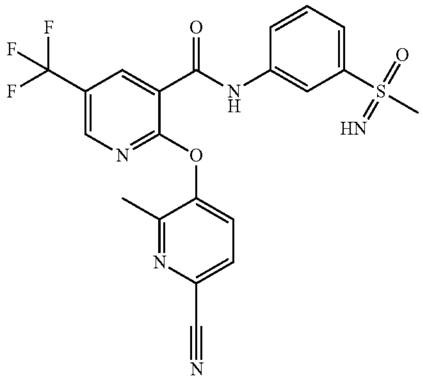 2-[(6-cyano-2-methyl-3-pyridyl)oxy]-N-[3-(methylsulfonimidoyl)phenyl]-5-(trifluoromethyl)pyridine-3-carboxamide | $^1$H NMR (400 MHz, $CD_3OD$) δ 8.62 – 8.55 (m, 2H), 8.45 (m, 1H), 8.00 (m, 1H), 7.90 (d, J = 8.4 Hz, 1H), 7.87 – 7.78 (m, 2H), 7.64 (t, J = 8.0 Hz, 1H), 3.17 (s, 3H), 2.45 (s, 3H). m/z 476.2 $[M + H]^+$, (ESI+), RT = 2.76 LC-MS Method 4 |
| 1702 | 11 | 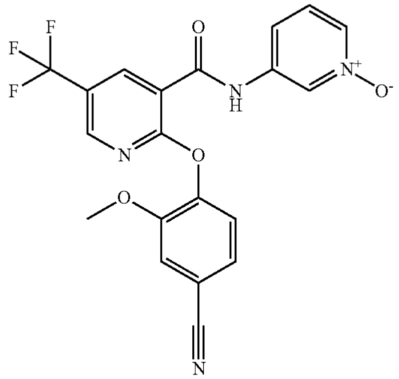 2-(4-cyano-2-methoxy-phenoxy)-N-(1-oxidopyridin-1-ium-3-yl)-5-(trifluoromethyl)pyridine-3-carboxamide | $^1$H NMR (400 MHz, $CD_3OD$) 89.10 (m, 1H), 8.58 (m, 1H), 8.54 (m, 1H), 8.19 – 8.13 (m, 1H), 7.81 (m, 1H), 7.58 – 7.41 (m, 4H), 3.80 (s, 3H). m/z 431.2 $[M + H]^+$, (ESI+), RT = 2.63 LC-MS Method 4 |

TABLE 15-continued

| Compound | Route | Structure and name | Analytical data |
| --- | --- | --- | --- |
| 1703 | | 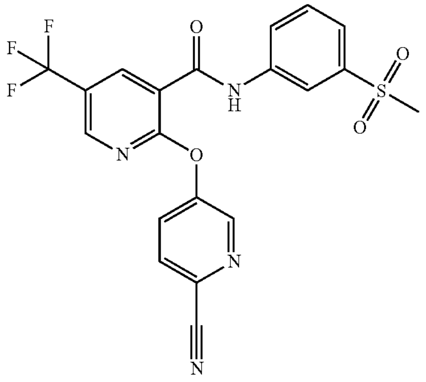 2-[(6-cyano-3-pyridyl)oxy]-N-(3-methylsulfonylphenyl)-5-(trifluoromethyl)pyridine-3-carboxamide | $^1H$ NMR (500 MHz, DMSO-d6) δ 12.60 (br.s, 1H), 8.74 (d, J = 2.2 Hz, 1H), 8.17 - 7.83 (m, 6H), 7.72 - 7.65 (m, 2H), 3.18 (s, 3H). m/z 463.1 $[M + H]^+$, (ESI+), RT = 2.33 LC-MS Method 4 |
| 1704 | | 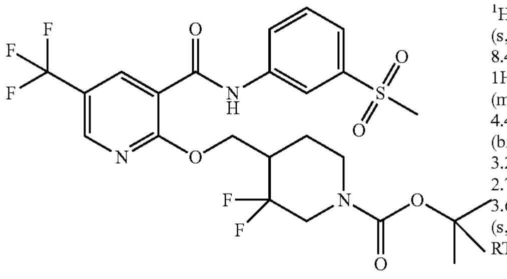 tert-butyl 3,3-difluoro-4-[[3-[(3-methylsulfonylphenyl) carbamoyl]-5-(trifluoromethyl)-2-pyridyl]oxymethyl]piperidine-1-carboxylate | $^1H$ NMR (400 MHz, DMSO-d6) δ 10.69 (s, 1H), 8.78 (dd, J = 2.4, 0.9 Hz, 1H), 8.41 (d, J = 2.5 Hz, 1H), 8.38 - 8.32 (m, 1H), 7.97 - 7.89 (m, 1H), 7.72 - 7.63 (m, 2H), 4.77 (dd, J = 11.0, 5.4 Hz, 1H), 4.44 (dd, J = 10.9, 7.3 Hz, 1H), 4.08 (br.s, 1H), 3.89 (d, J = 12.3 Hz, 1H), 3.29 - 3.08 (m, 4H), 2.91 (br.s, 1H), 2.76 - 2.58 (m, 1H), 1.89 (dt, J = 13.9, 3.6 Hz, 1H), 1.57 - 1.42 (m, 1H), 1.37 (s, 9H). m/z 616.0 $[M + Na]^+$, (ESI+), RT = 4.17 LC-MS Method 4 |
| 1705 | | 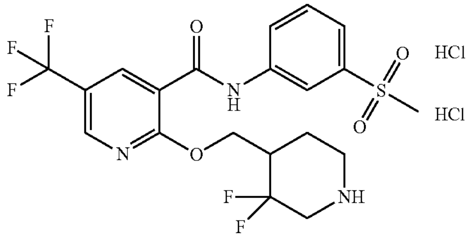 2-[(3,3-difluoro-4-piperidyl)methoxy]-N-(3-methylsulfonylphenyl)-5-(trifluoromethyl)pyridine-3-carboxamide dihydrochloride | $^1H$ NMR (400 MHz, DMSO-d6) δ 10.82 (s, 1H), 9.69 (br.s, 2H), 8.78 (dd, J = 2.3, 0.9 Hz, 1H), 8.41 (d, J = 2.3 Hz, 1H), 8.39 - 8.36 (m, 1H), 7.95 (dt, J = 7.4, 1.7 Hz, 1H), 7.72 - 7.64 (m, 2H), 4.80 (dd, J = 11.1, 5.5 Hz, 1H), 4.49 (dd, J = 11.1, 7.3 Hz, 1H), 3.73 - 3.64 (m, 1H), 3.52 - 3.38 (m, 2H), 3.28 - 3.20 (m, 4H), 3.00 (td, J = 12.5, 2.8 Hz, 1H), 2.93 - 2.77 (m, 1H), 2.18 - 2.08 (m, 1H), 1.82 - 1.69 (m, 1H). m/z 494.0 $[M + H]^+$, (ESI+), RT = 1.93 LC-MS Method 4 |

TABLE 15-continued

| Compound | Route | Structure and name | Analytical data |
|---|---|---|---|
| 1706 | | 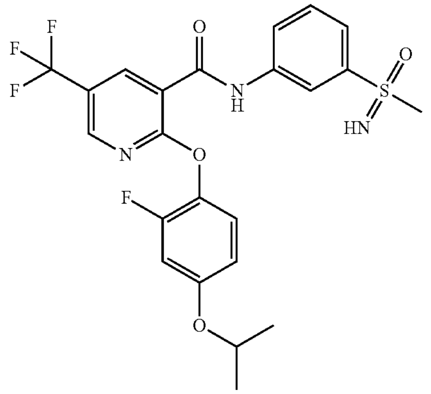<br>2-(2-fluoro-4-isopropoxy-phenoxy)-N-[3-(methylsulfonimidoyl)phenyl]-5-(trifluoromethyl)pyridine-3-carboxamide | $^1$H NMR (400 MHz, DMSO-d6) δ 10.91 (s, 1H), 8.68 (s, 1H), 8.57 (s, 1H), 8.38 (s, 1H), 7.96 (d, J = 7.9 Hz, 1H), 7.69 (d, J = 7.7 Hz, 1H), 7.61 (t, J = 7.8 Hz, 1H), 7.24 (q, J - 7.6 Hz, 1H), 7.05 - 6.92 (m, 2H), 4.55 (hept, J = 5.9 Hz, 1H), 4.23 (s, 1H), 3.06 (s, 3H), 1.07 (d, J = 5.9 Hz, 6H). m/z 512.2 [M + H]$^+$, (ESI+), RT = 3.44 LC-MS Method 4 |
| 1707 | | 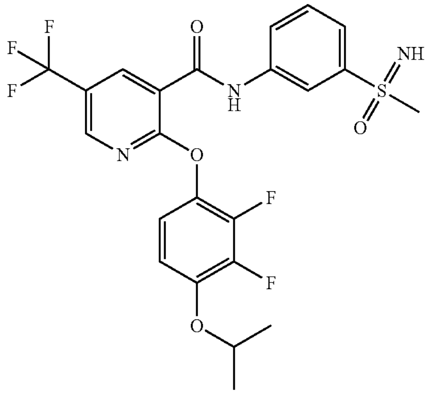<br>2-(2,3-difluoro-4-isopropoxy-phenoxy)-N-[3-(methylsulfonimidoyl)phenyl]-5-(trifluoromethyl)pyridine-3-carboxamide | $^1$H NMR (400 MHz, DMSO-d6) δ 11.01 (s, 1H), 8.73 (s, 1H), 8.59 (s, 1H), 8.38 (s, 1H), 7.96 (d, J = 8.0 Hz, 1H), 7.70 (d, J = 7.8 Hz, 1H), 7.62 (t, J = 7.9 Hz, 1H), 7.23 (t, J = 8.8 Hz, 1H), 7.11 (t, J = 8.9 Hz, 1H), 4.69 (hept, J = 5.9 Hz, 1H), 4.24 (s, 1H), 3.06 (s, 3H), 1.32 (d, J = 6.0 Hz, 6H). m/z 530.1 [M + H]$^+$, (ESI+), RT = 3.59 LC-MS Method 4 |
| 1708 | | 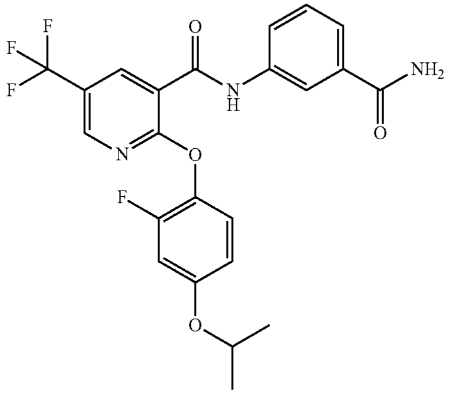<br>N-(3-carbamoylphenyl)-2-(2-fluoro-4-isopropoxy-phenoxy)-5-(trifluoromethyl)pyridine-3-carboxamide | $^1$H NMR (500 MHz, DMSO-d6) δ 10.67 (s, 1H), 8.69 - 8.64 (m, 1H), 8.55 (d, J = 2.3 Hz, 1H), 8.20 (t, J = 1.7 Hz, 1H), 7.98 (s, 1H), 7.92 - 7.86 (m, 1H), 7.66 - 7.61 (m, 1H), 7.45 (t, J = 7.9 Hz, 1H), 7.37 (s, 1H), 7.24 (td, J = 8.5, 6.5 Hz, 1H), 7.04 - 6.94 (m, 2H), 4.55 (hept, J = 6.1 Hz, 1H), 1.07 (d, J = 6.0 Hz, 6H). m/z 495.3 [M + NH4]$^+$, (ESI+), RT = 3.61 LC-MS Method 6 |

TABLE 15-continued

| Compound | Route | Structure and name | Analytical data |
|---|---|---|---|
| 1709 | | 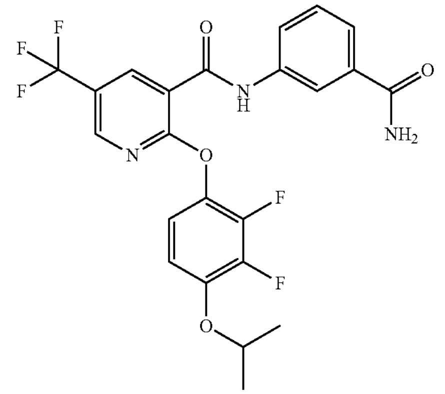 N-(3-carbamoylphenyl)-2-(2,3-difluoro-4-isopropoxy-phenoxy)-5-(trifluoromethyl)pyridine-3-carboxamide | $^1$H NMR (500 MHz, DMSO-d6) δ 10.79 (s, 1H), 8.73 – 8.69 (m, 1H), 8.57 (d, J = 2.3 Hz, 1H), 8.19 (t, J = 1.7 Hz, 1H), 7.98 (s, 1H), 7.92 – 7.87 (m, 1H), 7.66 – 7.61 (m, 1H), 7.45 (t, J = 7.9 Hz, 1H), 7.38 (s, 1H), 7.27 – 7.21 (m, 1H), 7.15 – 7.08 (m, 1H), 4.69 (hept, J = 6.0 Hz, 1H), 1.32 (d, J = 6.0 Hz, 6H). m/z 513.3 $[M + NH4]^+$, (ESI+), RT = 3.75 LC-MS Method 6 |
| 1710 | | 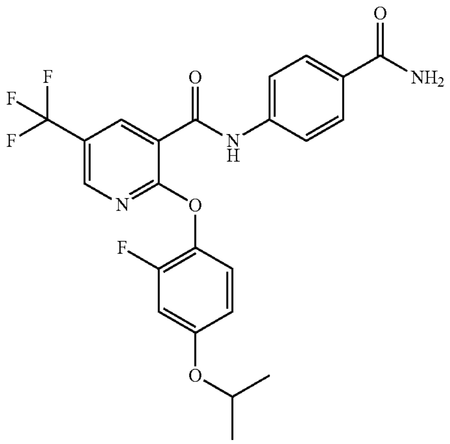 N-(4-carbamoylphenyl)-2-(2-fluoro-4-isopropoxy-phenoxy)-5-(trifluoromethyl)pyridine-3-carboxamide | $^1$H NMR (500 MHz, DMSO-d6) δ 10.78 (s, 1H), 8.70 – 8.65 (m, 1H), 8.57 (d, J = 2.3 Hz, 1H), 7.96 – 7.85 (m, 3H), 7.83 – 7.75 (m, 2H), 7.29 (br.s, 1H), 7.24 (td, J = 8.5, 6.5 Hz, 1H), 7.02 (d, J = 8.6 Hz, 1H), 7.01 – 6.93 (m, 1H), 4.55 (hept, J = 6.0 Hz, 1H), 1.07 (d, J = 6.0 Hz, 6H). m/z 478.3 $[M + H]^+$, (ESI+), RT = 3.61 LC-MS Method 6 |

TABLE 15-continued

| Compound | Route | Structure and name | Analytical data |
|---|---|---|---|
| 1711 | | 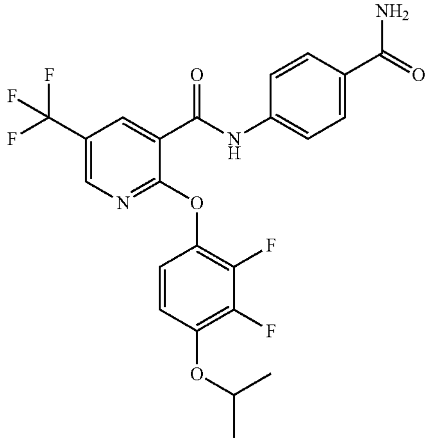<br>N-(4-carbamoylphenyl)-2-(2,3-difluoro-4-isopropoxy-phenoxy)-5-(trifluoromethyl)pyridine-3-carboxamide | $^1$H NMR (500 MHz, DMSO-d6) δ 10.89 (s, 1H), 8.75 – 8.70 (m, 1H), 8.58 (d, J = 2.4 Hz, 1H), 7.98 – 7.85 (m, 3H), 7.82 – 7.76 (m, 2H), 7.30 (br.s, 1H), 7.27 – 7.21 (m, 1H), 7.15 – 7.07 (m, 1H), 4.69 (hept, J = 6.0 Hz, 1H), 1.32 (d, J = 6.0 Hz, 6H). m/z 496.3 $[M + H]^+$, (ESI+), RT = 3.75 LC-MS Method 6 |
| 1712 | | 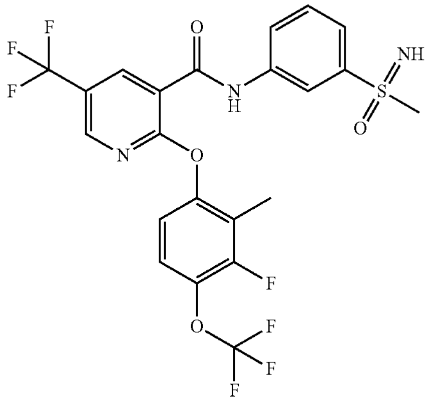<br>2-[3-fluoro-2-methyl-4-(trifluoromethoxy)phenoxy]-N-[3-(methylsulfonimidoyl)phenyl]-5-(trifluoromethyl)pyridine-3-carboxamide | $^1$H NMR (500 MHz, DMSO-d6) δ 11.02 (s, 1H), 8.73 – 8.68 (m, 1H), 8.60 (d, J = 2.4 Hz, 1H), 8.38 (t, J = 1.8 Hz, 1H), 7.98 – 7.91 (m, 1H), 7.70 (dt, J = 7.8, 1.1 Hz, 1H), 7.62 (t, J – 7.9 Hz, 1H), 7.53 (t, J = 8.8 Hz, 1H), 7.31 – 7.24 (m, 1H), 4.24 (s, 1H), 3.06 (s, 3H), 2.13 – 2.07 (m, 3H). m/z 552.1 $[M + H]^+$, (ESI+), RT = 3.73 LC-MS Method 4 |
| 1714 | | 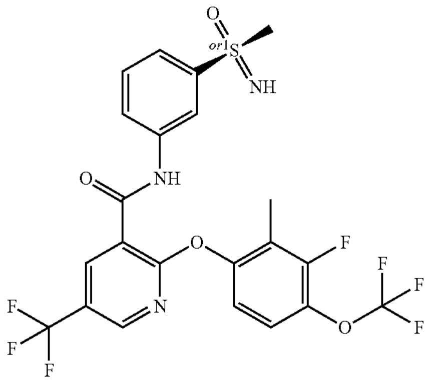<br>2-[3-fluoro-2-methyl-4-(trifluoromethoxy)phenoxy]-N-[3-(methylsulfonimidoyl)phenyl]-5-(trifluoromethyl)pyridine-3-carboxamide | $^1$H NMR (500 MHz, DMSO-d6) δ 11.01 (s, 1H), 8.72 – 8.68 (m, 1H), 8.60 (d, J = 2.2 Hz, 1H), 8.37 (t, J = 1.8 Hz, 1H), 7.97 – 7.91 (m, 1H), 7.70 (ddd, J = 7.8, 1.6, 1.1 Hz, 1H), 7.61 (t, J = 7.9 Hz, 1H), 7.53 (t, J = 8.8 Hz, 1H), 7.27 (dd, J = 9.1, 1.4 Hz, 1H), 4.23 (s, 1H), 3.06 (s, 3H), 2.12 – 2.07 (m, 3H). m/z 552.2 $[M + H]^+$, (ESI+), RT = 6.98 Chiral LC |

TABLE 15-continued

| Compound | Route | Structure and name | Analytical data |
|---|---|---|---|
| 1715 | | 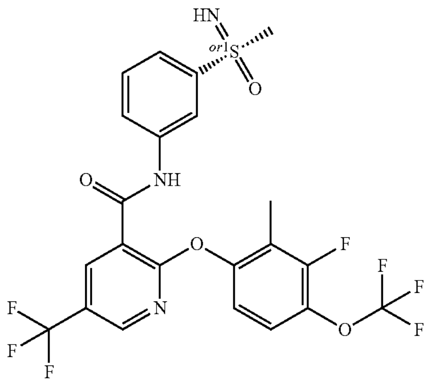 2-[3-fluoro-2-methyl-4-(trifluoromethoxy)phenoxy]-N-[3-(methylsulfonimidoyl)phenyl]-5-(trifluoromethyl)pyridine-3-carboxamide | $^1$H NMR (500 MHz, DMSO-d6) δ 11.01 (s, 1H), 8.72 - 8.68 (m, 1H), 8.60 (d, J = 2.4 Hz, 1H), 8.37 (t, J = 1.7 Hz, 1H), 7.97 - 7.91 (m, 1H), 7.73 - 7.67 (m, 1H), 7.61 (t, J = 7.9 Hz, 1H), 7.53 (t, J = 8.8 Hz, 1H), 7.27 (dd, J = 9.1, 1.2 Hz, 1H), 4.24 (s, 1H), 3.06 (s, 3H), 2.13 - 2.06 (m, 3H). m/z 552.2 [M + H]$^+$, (ESI+), RT = 5.61 Chiral LC |

Example 88

Compound 1716: N-[3-(N-acetyl-S-methyl-sulfonimidoyl)phenyl]-2-(4-fluoro-2-methyl-phenoxy)-5-(trifluoromethyl)pyridine-3-carboxamide

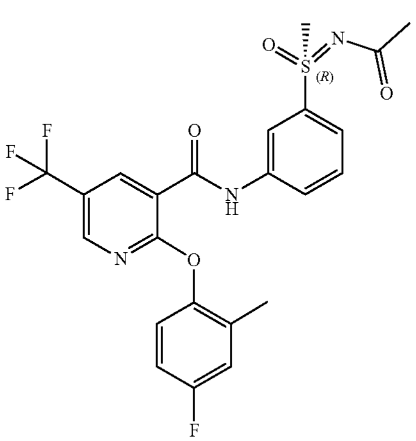

To a solution of (R)-2-(4-fluoro-2-methyl-phenoxy)-N-[3-(methylsulfonimidoyl)phenyl]-5-(trifluoromethyl)pyridine-3-carboxamide (50 mg, 0.107 mmol) in DCM (1.0697 mL) at rt was added pyridine (0.017 mL, 0.214 mmol) and acetic anhydride (0.012 mL, 0.128 mmol). The mixture was stirred at rt overnight under an atmosphere of nitrogen. Reaction was concentrated under a stream of nitrogen. Loaded on to 10 g Sfar Duo cartridge in DCM (3×0.5 mL), then eluted with 0-50% EtOAc/Hept. Relevant fractions concentrated to yield N-[3-(N-acetyl-S-methyl-sulfonimidoyl)phenyl]-2-(4-fluoro-2-methyl-phenoxy)-5-(trifluoromethyl)pyridine-3-carboxamide (98.0%) (45 mg, 0.0873 mmol, 82%). $^1$H NMR (400 MHz, DMSO-d6) δ 11.05 (s, 1H), 8.67-8.63 (m, 1H), 8.57-8.53 (m, 1H), 8.41-8.36 (m, 1H), 8.00-7.94 (m, 1H), 7.70-7.63 (m, 2H), 7.28-7.22 (m, 1H), 7.22-7.15 (m, 1H), 7.13-7.05 (m, 1H), 3.40 (s, 3H), 2.08 (s, 3H), 1.96 (s, 3H). LC-MS Method 4: m/z 510.1 [M+H]$^+$, (ESI+), RT=3.51.

Example 89

Compound 1717: N-[3-(N,S-dimethylsulfonimidoyl)phenyl]-2-(4-fluoro-2-methyl-phenoxy)-5-(trifluoromethyl)pyridine-3-carboxamide

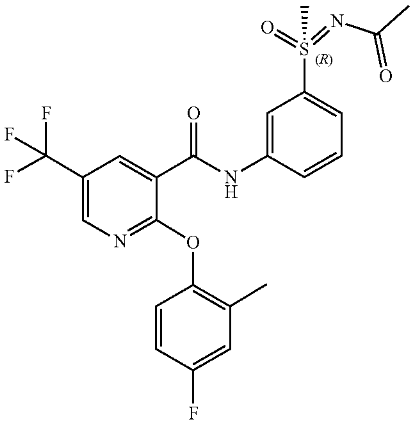

(R)-2-(4-fluoro-2-methyl-phenoxy)-N-[3-(methylsulfonimidoyl)phenyl]-5-(trifluoromethyl)pyridine-3-carboxamide (50 mg, 0.107 mmol), copper(2+) diacetate (29 mg, 0.160 mmol) and methylboronic acid (13 mg, 0.214 mmol), were suspended in 1,4-Dioxane-Anhydrous (0.8557 mL) was stirred at RT under air for 5 minutes. Then pyridine (0.017 mL, 0.214 mmol) was added, the vessel sealed and heated to 100 °C for 40 minutes. Reaction mixture diluted with water (~1.5 mL) and DCM (3 mL), shaken vigorously then the mixture filtered through a PTFE phase separator. Aqueous re-extracted with DCM (2 mL) and layers separated. Combined organics were concentrated under a gentle stream of nitrogen. Crude material was purified by preparatory HPLC (Prep Method 2) to yield N-[3-(N,S-dimethylsulfonimidoyl)phenyl]-2-(4-fluoro-2-methyl-phenoxy)-5-(trifluoromethyl)pyridine-3-carboxamide, as a white powder (43 mg, 51%). $^1$H NMR (500 MHz, DMSO-d6) δ 10.97 (s, 1H), 8.66 (dd, J=2.5, 1.1 Hz, 1H), 8.57-8.53 (m, 1H), 8.30 (t, J=1.9 Hz, 1H), 7.95 (ddd, J=8.0, 2.2, 1.2 Hz, 1H), 7.65 (t, J=7.9 Hz, 1H), 7.60-7.56 (m, 1H), 7.26 (dd, J=8.9, 5.1 Hz, 1H), 7.20 (dd, J=9.7, 3.2 Hz, 1H), 7.11 (td, J=8.5, 3.2 Hz, 1H), 3.11 (s, 3H), 2.49 (s, 3H), 2.09 (s, 3H). LC-MS Method 6: m/z 482.3 [M+H]$^+$, (ESI+), RT=3.62.

Example 90

Compound 1718: 2-(3-methylsulfonylphenoxy)-N-(3-methylsulfonylphenyl)-5-(trifluoromethyl)pyridine-3-carboxamide

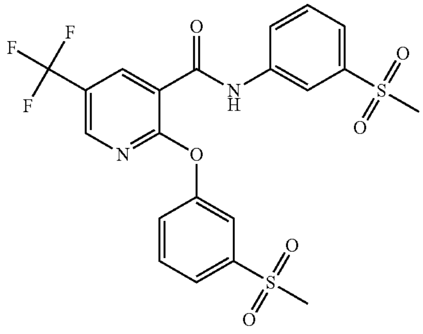 [SMILES: CS(=O)(=O)c1cccc(NC(=O)c2cc(C(F)(F)F)cnc2Oc2cccc(S(C)(=O)=O)c2)c1]

2-(3-methylsulfanylphenoxy)-N-(3-methylsulfonylphenyl)-5-(trifluoromethyl)pyridine-3-carboxamide (48 mg, 0.0997 mmol) was dissolved in Methanol (1.0 mL) and treated with potassium; oxido hydrogen sulfate (33 mg, 0.219 mmol) and the resultant mixture stirred at RT. After 24 hrs more potassium; oxido hydrogen sulfate (40 mg, 0.267 mmol) was added and the reaction stirred at RT for a further 24 hrs. Diluted reaction with DCM (25 mL) and $NaHCO_3$ (sat. aq. soln, 25 mL). Stirred vigorously for 5 minutes and filtered through a phase separator. Aqueous re-extracted with DCM (×1) and filtered. Combined organics concentrated in vacuo to a white solid. Columned in 0-100% EtOAc/Hep on 10 g Sfar Duo cartridge yielding 2-(3-methylsulfonylphenoxy)-N-(3-methylsulfonylphenyl)-5-(trifluoromethyl)pyridine-3-carboxamide (98.0%) (33 mg, 0.0629 mmol, 63%). $^1$H NMR (400 MHz, DMSO-d6) δ 11.04 (s, 1H), 8.74-8.71 (m, 1H), 8.59 (d, J=2.1 Hz, 1H), 8.41-8.38 (m, 1H), 7.97 (dt, J=7.3, 1.8 Hz, 1H), 7.91-7.84 (m, 2H), 7.76 (t, J=7.9 Hz, 1H), 7.73-7.64 (m, 3H), 3.27 (s, 3H), 3.22 (s, 3H). LC-MS Method 4: m/z 515.1 [M+H]$^+$, (ESI+), RT=3.06.

Example 91

Compound 1719: tert-butyl (R)-(2-(((3-(2-(4-fluoro-2-methylphenoxy)-5-(trifluoromethyl)nicotinamido)phenyl)(methyl)(oxo)-λ$^6$-sulfaneylidene)amino)-2-oxoethyl)(methyl)carbamate

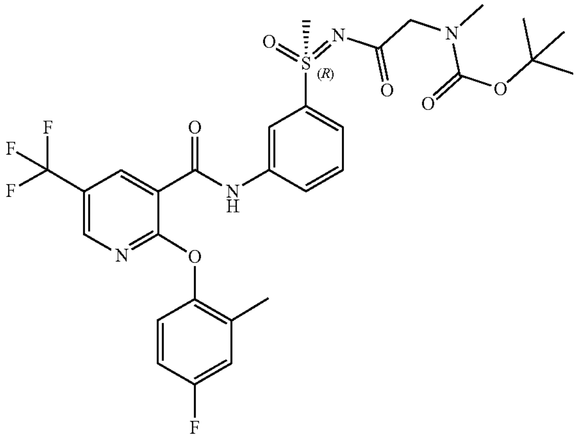

To N-(tert-butoxycarbonyl)-N-methylglycine (18 mg, 0.0941 mmol) and N-(tert-butoxycarbonyl)-N-methylglycine (18 mg, 0.0941 mmol) was added DCM (0.4279 mL) at rt and then N-ethyl-N-(propan-2-yl)propan-2-amine (0.036 mL, 0.205 mmol). The suspension was stirred at rt for 5-10 minutes, then added (R)-2-(4-fluoro-2-methylphenoxy)-N-(3-(S-methylsulfonimidoyl)phenyl)-5-(trifluoromethyl)nicotinamide (100%, 40 mg, 0.0856 mmol) in one portion. The resulting suspension was stirred at rt. Reaction was concentrated under a stream of nitrogen. Loaded onto 10 g Sfar Duo cartridge in DCM (3×0.5 mL), then eluted with 0-50% EtOAc/Hept. Relevant fractions concentrated to yield colorless glass (54 mg, 99%). $^1$H NMR (400 MHz, DMSO-d6) δ 11.07 (s, 1H), 8.68-8.64 (m, 1H), 8.57-8.51 (m, 1H), 8.50-8.43 (m, 1H), 8.01-7.92 (m, 1H), 7.71-7.63 (m, 2H), 7.26 (dd, J=8.9, 5.0 Hz, 1H), 7.20 (dd, J=9.3, 3.1 Hz, 1H), 7.11 (td, J=8.5, 3.1 Hz, 1H), 3.97-3.77 (m, 2H), 3.47 (s, 3H), 2.80-2.72 (m, 3H), 2.09 (s, 3H), 1.36 (s, 4H), 1.28 (s, 5H). LC-MS Method 6: m/z 639.3 [M+H]$^+$, (ESI+), RT=4.15.

Example 92

Compound 1720: (R)-2-(4-fluoro-2-methylphenoxy)-N-(3-(S-methyl-N-(methylglycyl)sulfonimidoyl)phenyl)-5-(trifluoromethyl)nicotinamide

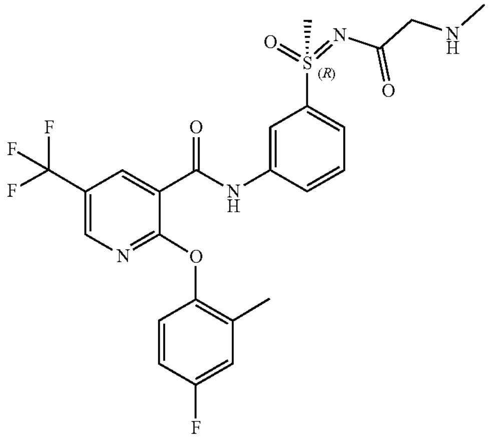

To a solution of tert-butyl (R)-(2-(((3-(2-(4-fluoro-2-methylphenoxy)-5-(trifluoromethyl)nicotinamido)phenyl)(methyl)(oxo)-$\lambda^6$-sulfaneylidene)amino)-2-oxoethyl)(methyl)carbamate (61 mg, 0.0955 mmol) in DCM (1.0 mL) was added phosphoric acid (85% wt) in water (85%, 0.044 mL, 0.382 mmol) (added 12 μL) at rt. The mixture was stirred vigorously for 2-3 hrs at rt. Reaction mixture diluted with NaOH (2N, 5 mL) and extracted twice with DCM (2×5 mL). Each extraction filtered through a phase separator cartridge and concentrated to a brown gum. Crude material loaded on to 10 g Sfar Duo cartridge and eluted with 0-100% EtOAc/Hep then 0-50% MeOH/EtOAc to yield (R)-2-(4-fluoro-2-methylphenoxy)-N-(3-(S-methyl-N-(methylglycyl)sulfonimidoyl)phenyl)-5-(trifluoromethyl)nicotinamide (93.5%) (36 mg, 0.0625 mmol, 65% Yield) as a pale brown powder. $^1$H NMR (400 MHz, DMSO-d6) δ 11.07 (s, 1H), 8.70-8.65 (m, 1H), 8.58-8.54 (m, 1H), 8.47-8.41 (m, 1H), 8.02-7.96 (m, 1H), 7.74-7.65 (m, 2H), 7.27 (dd, J=8.9, 5.0 Hz, 1H), 7.21 (dd, J=9.3, 3.1 Hz, 1H), 7.12 (td, J=8.5, 3.3 Hz, 1H), 3.46 (s, 3H), 3.20 (s, 2H), 2.24 (s, 3H), 2.10 (s, 3H). LC-MS Method 6: m/z 539.2 $[M+H]^+$, (ESI+), RT=3.42.

Example 93

Compound 1721: N-(3-carbamoyl-1-bicyclo[1.1.1]pentanyl)-2-(3,4-difluoro-2-methoxy-phenoxy)-5-(trifluoromethyl)pyridine-3-carboxamide

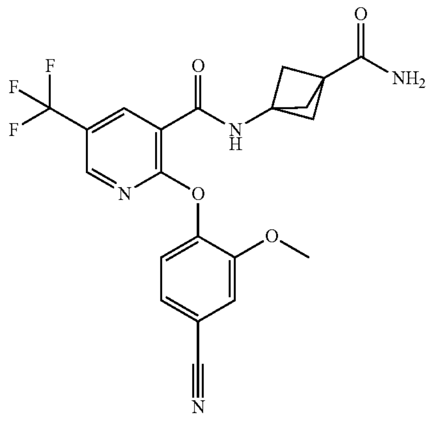 [SMILES: COc1cc(C#N)ccc1Oc1ncc(C(F)(F)F)cc1C(=O)NC12CC(C(N)=O)(C1)C2]

Methyl 3-[[2-(4-cyano-2-methoxy-phenoxy)-5-(trifluoromethyl)pyridine-3-carbonyl]amino]bicyclo[1.1.1]pentane-1-carboxylate (34 mg, 0.0737 mmol) was dissolved in IPA (0.257 mL) and diluted with 14.5 M ammonium hydroxide (1.0 mL, 14.5 mmol). The solution was stirred at 40 °C in a pressure vial for 2 h. LC-MS analysis indicated the reaction was mostly complete. The solvents were removed and the residue purified by prep. HPLC (Prep. Method 2) to afford N-(3-carbamoyl-1-bicyclo[1.1.1]pentanyl)-2-(4-cyano-2-methoxy-phenoxy)-5-(trifluoromethyl)pyridine-3-carboxamide (100.0%) (13 mg, 0.0291 mmol, 40% Yield) as a white solid. $^1$H NMR and LC-MS analysis indicated this was the desired product. $^1$H NMR (400 MHz, $CD_3OD$) δ 8.47 (s, 2H), 7.54 (d, J=1.3 Hz, 1H), 7.51-7.41 (m, 2H), 3.81 (s, 3H), 2.45 (s, 6H). LC-MS Method 6: m/z 447.3 $[M+H]^+$, (ESI+), RT=2.96.

Example 94

Compound 1722: N-(3-carbamoyl-1-bicyclo[1.1.1]pentanyl)-2-(3,4-difluoro-2-methoxy-phenoxy)-5-(trifluoromethyl)pyridine-3-carboxamide

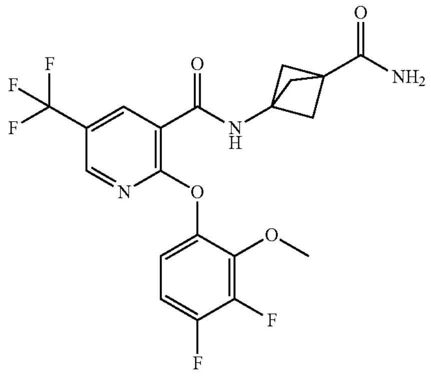 [SMILES: COc1c(Oc2ncc(C(F)(F)F)cc2C(=O)NC23CC(C(N)=O)(C2)C3)ccc(F)c1F]

methyl 3-[[2-(3,4-difluoro-2-methoxy-phenoxy)-5-(trifluoromethyl)pyridine-3-carbonyl]amino]bicyclo[1.1.1]pentane-1-carboxylate (35 mg, 0.0741 mmol) was dissolved in IPA (0.2584 mL) and diluted with 14.5 M ammonium hydroxide (0.50 mL, 7.3 mmol). The solution was stirred at 40 °C in a pressure vial for 1 h. LC-MS analysis indicated the reaction was mostly complete. Purification by prep. HPLC (Prep. Method 2) afforded N-(3-carbamoyl-1-bicyclo[1.1.1]pentanyl)-2-(3,4-difluoro-2-methoxy-phenoxy)-5-(trifluoromethyl)pyridine-3-carboxamide (100.0%) (16 mg, 0.0350 mmol, 47% Yield) as a white solid. $^1$H NMR and LC-MS analysis indicated this was the desired compound. $^1$H NMR (400 MHz, $CD_3OD$) δ 8.51 (m, 1H), 8.44 (m, 1H), 7.19-7.03 (m, 2H), 3.85 (d, J=1.8 Hz, 3H), 2.45 (s, 6H). LC-MS Method 6: m/z 458.2 $[M+H]^+$, (ESI+), RT=3.23.

Example 95

Compound 1723: 5-cyano-2-(3,4-difluoro-2-methoxy-phenoxy)-N-[3 (methylsulfonimidoyl)phenyl]pyridine-3-carboxamide

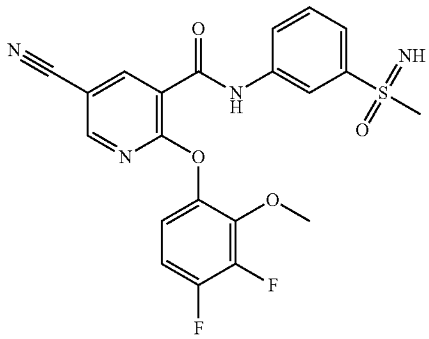 [SMILES: COc1c(Oc2ncc(C#N)cc2C(=O)Nc2cccc(S(C)(=N)=O)c2)ccc(F)c1F]

Palladium acetate (8.8 mg, 0.0390 mmol) was added to a stirred, degassed solution of (LTGO 0001070) 5-bromo-2-(3,4-difluoro-2-methoxy-phenoxy)-N-[3-(methylsulfonimidoyl)phenyl]pyridine-3-carboxamide (200 mg, 0.390 mmol), potassium hexakis(cyano-kappaC)ferrate(4-)

hydrate (4:1:3) (82 mg, 0.195 mmol), sodium carbonate (41 mg, 0.390 mmol) and [2-(2-diphenylphosphanylphenoxy) phenyl]-diphenyl-phosphane (42 mg, 0.0781 mmol) in DMF (2 mL) and Water (2 mL). The reaction mixture was heated at 70 °C for 3 h. LC-MS analysis indicated the reaction was complete. Diluted with water (10 mL) and extracted with ethyl acetate (3×8 mL). Organics were dried (MgSO4), filtered and concentrated to afford an orange oil. Purification by prep. HPLC (Prep. Method 2) afforded 5-cyano-2-(3,4-difluoro-2-methoxy-phenoxy)-N-[3-(methylsulfonimidoyl) phenyl]pyridine-3-carboxamide (100.0%) (59 mg, 0.129 mmol, 33% Yield) as a white solid. $^1$H and $^{19}$F NMR and LC-MS analysis indicated this was the desired product. $^1$H NMR (400 MHz, $CD_3OD$) δ 8.60 (d, J=2.3 Hz, 1H), 8.58 (d, J=2.3 Hz, 1H), 8.45 (t, J=2.0 Hz, 1H), 8.03-7.95 (m, 1H), 7.81 (m, 1H), 7.64 (t, J=8.0 Hz, 1H), 7.17-7.10 (m, 1H), 7.10-7.03 (m, 1H), 3.85 (d, J=1.8 Hz, 3H), 3.17 (s, 3H). LC-MS Method 7: m/z 459.2 $[M+H]^+$, (ESI+), RT=2.87.

Example 96

Compound 1724: N-(3-carbamoylphenyl)-5-cyano-2-(3,4-difluoro-2-methoxy-phenoxy)pyridine-3-carboxamide

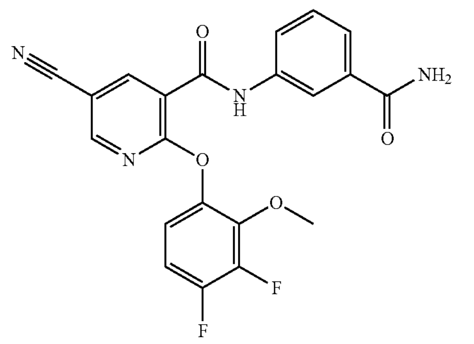 [SMILES: COc1c(Oc2ncc(C#N)cc2C(=O)Nc2cccc(C(N)=O)c2)ccc(F)c1F]

Palladium acetate (4.7 mg, 0.0209 mmol) was added to a stirred, degassed solution of 5-bromo-N-(3-carbamoylphenyl)-2-(3,4-difluoro-2-methoxy-phenoxy)pyridine-3-carboxamide (100 mg, 0.209 mmol), potassium hexakis(cyano-kappaC)ferrate(4-) hydrate (4:1:3) (44 mg, 0.105 mmol), sodium carbonate (22 mg, 0.209 mmol) and [2-(2-diphenylphosphanylphenoxy)phenyl]-diphenyl-phosphane (23 mg, 0.0418 mmol) in DMF (1.5 mL) and Water (1.5 mL). The reaction mixture was heated at 75 °C for 4 h. LC-MS analysis indicated starting material remaining, but reaction profile becoming more messy, so reaction stopped. Diluted with water (10 mL) and extracted with ethyl acetate (3×8 mL). Organics were dried ($MgSO_4$), filtered and concentrated to afford an orange oil. Purification by prep. HPLC (Prep. Method 2) afforded 15 mg as a white solid. LC-MS analysis indicated this was the desired compound, but not clean (84% at 215 nm). Further purification by prep. HPLC (Prep. Method 1) afforded 10.2 mg as a white solid. LC-MS analysis indicated only 82% at 215 nm. Further purification by prep. HPLC (Waters Sunfire C18 column (19 mm×100 mm, 5 μm; temperature: room temperature), with an injection volume of 1500 μL at flow rate of 20 mL/min at 5% B (A=0.10% formic acid in water; B=0.10% formic acid in acetonitrile for 1.9. min then a gradient of 35-95% B over 16 min then held for 2 min. UV spectra were recorded at 215 nm using a Gilson detector) afforded N-(3-carbamoylphenyl)-5-cyano-2-(3,4-difluoro-2-methoxy-phenoxy)pyridine-3-carboxamide (100.0%) (6.8 mg, 0.016 mmol, 7.7% Yield) as a white solid. $^1$H NMR and LC-MS analysis indicated this was the desired product. $^1$H NMR (400 MHz, $CDCl_3$) δ 9.62 (s, 1H), 8.92 (d, J=2.3 Hz, 1H), 8.51 (d, J=2.3 Hz, 1H), 8.08 (t, J=1.9 Hz, 1H), 8.02-7.96 (m, 1H), 7.60 (m, 1H), 7.49 (t, J=7.9 Hz, 1H), 7.10-6.94 (m, 2H), 6.14 (s, 1H), 5.58 (s, 1H), 3.93 (d, J=2.8 Hz, 3H). LC-MS Method 4: m/z 425.5 $[M+H]^+$, (ESI+), RT=2.93.

Example 97

Compound 1725: 2-(4-cyano-2-methoxy-phenoxy)-N-[3-(methylsulfonimidoyl)phenyl]-5-(3-oxabicyclo[4.1.0]heptan-6-yl)pyridine-3-carboxamide

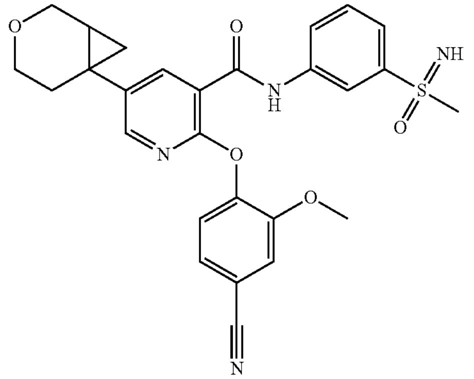 [SMILES: COc1cc(C#N)ccc1Oc1ncc(C23CCOCC2C3)cc1C(=O)Nc1cccc(S(C)(=N)=O)c1]

A mixture of 5-bromo-2-(4-cyano-2-methoxy-phenoxy)-N-[3-(methylsulfonimidoyl)phenyl]pyridine-3-carboxamide (40 mg, 0.0798 mmol), potassium; trifluoro(3-oxabicyclo[4.1.0]heptan-6-yl)boranuide (20 mg, 0.0957 mmol), cyclopentyl(diphenyl)phosphane; dichloropalladium; iron (5.9 mg, 7.98 μmol) and cesium carbonate (52 mg, 0.160 mmol) was suspended in Toluene (0.8 mL) and Water (0.2 mL) then degassed for 5 minutes. The mixture was heated to 80 °C for 2 h. LC-MS analysis indicated the starting material had been consumed. The mixture was diluted with ethyl acetate (5 mL), filtered and concentrated to afford a brown oil. Purification by prep. HPLC (standard method) afforded 2-(4-cyano-2-methoxy-phenoxy)-N-[3-(methylsulfonimidoyl) phenyl]-5-(3-oxabicyclo[4.1.0]heptan-6-yl)pyridine-3-carboxamide (100.0%) (20 mg, 0.0386 mmol, 48% Yield) as an off-white solid. $^1$H NMR and LC-MS analysis indicated this was the desired product. $^1$H NMR (400 MHz, $CD_3OD$) δ 8.39 (m, 1H), 8.23 (d, J=2.5 Hz, 1H), 8.14 (d, J=2.5 Hz, 1H), 8.01 (m, 1H), 7.83-7.76 (m, 1H), 7.63 (t, J=8.0 Hz, 1H), 7.53-7.39 (m, 3H), 4.10 (dd, J=11.4, 4.5 Hz, 1H), 3.92 (m, 1H), 3.81 (s, 3H), 3.58 (m, 1H), 3.54-3.41 (m, 1H), 3.17 (s, 3H), 2.18 (m, 1H), 2.01 (m, 1H), 1.42 (m, 1H), 1.12 (m, 1H), 1.00 (t, J=5.4 Hz, 1H). LC-MS Method 4: m/z 519.2 $[M+H]^+$, (ESI+), RT=2.69.

Example 98

Compound 1726: 2-(4-cyano-2-methoxy-phenoxy)-5-(3,6-dihydro-2H-pyran-4-yl)-N-(3-methylsulfanylphenyl)pyridine-3-carboxamide

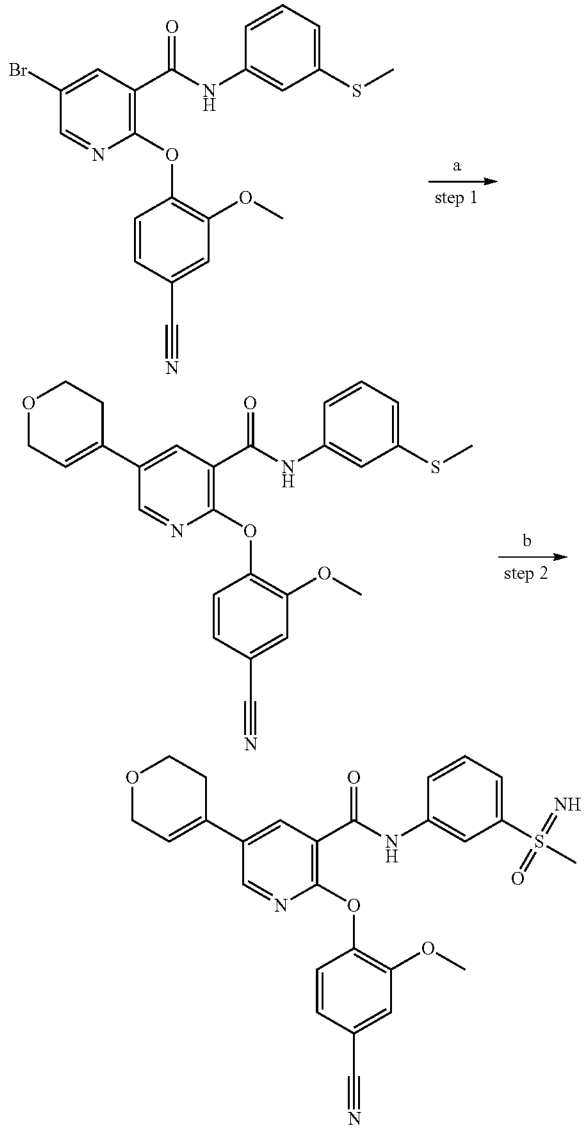

Reagents & conditions: a) 4-(4,4,5,5-tetramethyl-1,3,2-dioxaborolan-2-yl)-3,6-dihydro-2H-pyran, $Pd(OAc)_2$, dicyclohexyl-[2-(2,4,6-triisopropylphenyl)phenyl]phosphane, $Na_3PO_4$, dioxane, 80 °C; b) PIDA, $(NH_4)_2CO_3$, MeOH Step 1: 2-(4-cyano-2-methoxy-phenoxy)-5-(3,6-dihydro-2H-pyran-4-yl)-N-(3-methylsulfanylphenyl)pyridine-3-carboxamide: A mixture of 5-bromo-2-(4-cyano-2-methoxy-phenoxy)-N-(3-methylsulfanylphenyl)pyridine-3-carboxamide (50 mg, 0.106 mmol), dicyclohexyl-[2-(2,4,6-triisopropylphenyl)phenyl]phosphane (5.1 mg, 0.0106 mmol), 4-(4,4,5,5-tetramethyl-1,3,2-dioxaborolan-2-yl)-3,6-dihydro-2H-pyran (25 mg, 0.117 mmol) and tripotassium phosphate (68 mg, 0.319 mmol) in 1,4-dioxane (0.8 mL) and Water (0.2 mL) was degassed with nitrogen for 5 minutes, before the addition of palladium(2+) diacetate (2.4 mg, 0.0106 mmol). The mixture was heated to 80 °C for 8 h in a pressure vial. LC-MS analysis indicated the reaction was complete. Diluted with ethyl acetate (8 mL) and washed with water (5 mL) and brine (5 mL). Organics dried ($MgSO_4$), filtered and concentrated to afford a brown oil. Purification by FCC (5 g, 0 to 30% EA in Heptane) afforded 2-(4-cyano-2-methoxy-phenoxy)-5-(3,6-dihydro-2H-pyran-4-yl)-N-(3-methylsulfanylphenyl)pyridine-3-carboxamide (37.0%) (34 mg, 0.0266 mmol, 25% Yield) an off-white solid, 34 mg. LC-MS analysis indicated this was a ca. 5:4 mixture of hydrodehalogenated by-product (1.06 min) and desired product (1.11 min). Used without further purification in oxidation. LC-MS Method 2: m/z 474.2 $[M+H]^+$, (ESI+), RT=1.11.

Step 2: 2-(4-cyano-2-methoxy-phenoxy)-5-(3,6-dihydro-2H-pyran-4-yl)-N-[3-(methylsulfonimidoyl)phenyl]pyridine-3-carboxamide: Phenyl iodonium diacetate (PIDA) (29 mg, 0.0912 mmol) and diammonium carbonate (8.6 mg, 0.0912 mmol) were added to a solution of 2-(4-cyano-2-methoxy-phenoxy)-5-(3,6-dihydro-2H-pyran-4-yl)-N-(3-methylsulfanylphenyl)pyridine-3-carboxamide (40%, 36 mg, 0.0304 mmol) in methanol (0.4 mL) and the reaction was stirred at room temperature for 1 h. LC-MS analysis indicated the reaction was complete. The solvents were removed, and the residue purified by prep. HPLC (Prep. Method 1) to afford 2-(4-cyano-2-methoxy-phenoxy)-5-(3,6-dihydro-2H-pyran-4-yl)-N-[3-(methylsulfonimidoyl)phenyl]pyridine-3-carboxamide (100.0%) (8.0 mg, 0.0159 mmol, 52% Yield) as a white solid after freeze drying. $^1H$ NMR and LC-MS analysis indicated this was the desired product. $^1H$ NMR (500 MHz, DMSO-d6) δ 10.78 (s, 1H), 8.39 (m, 1H), 8.29 (d, J=2.5 Hz, 1H), 8.20 (d, J=2.5 Hz, 1H), 7.94 (m, 1H), 7.69-7.66 (m, 1H), 7.65 (d, J=1.9 Hz, 1H), 7.59 (t, J=7.9 Hz, 1H), 7.51 (dd, J=8.2, 1.9 Hz, 1H), 7.45 (d, J=8.2 Hz, 1H), 6.38 (s, 1H), 4.23 (d, J=2.8 Hz, 2H), 4.21 (s, 1H), 3.82 (t, J=5.4 Hz, 2H), 3.75 (s, 3H), 3.05 (d, J=1.0 Hz, 3H). LC-MS Method 6: m/z 505.3 $[M+H]^+$, (ESI+), RT=1.11.

Example 99

Compound 1727: 2-(4-cyano-2-methoxy-phenoxy)-N-[3-(methylsulfonimidoyl)phenyl]-5-tetrahydropyran-4-yl-pyridine-3-carboxamide

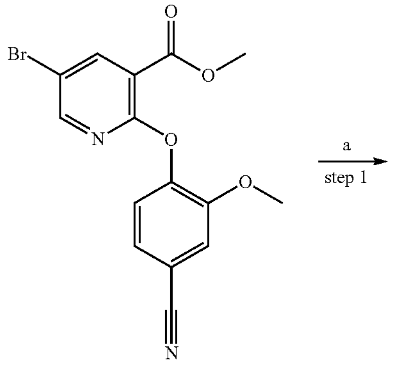

-continued

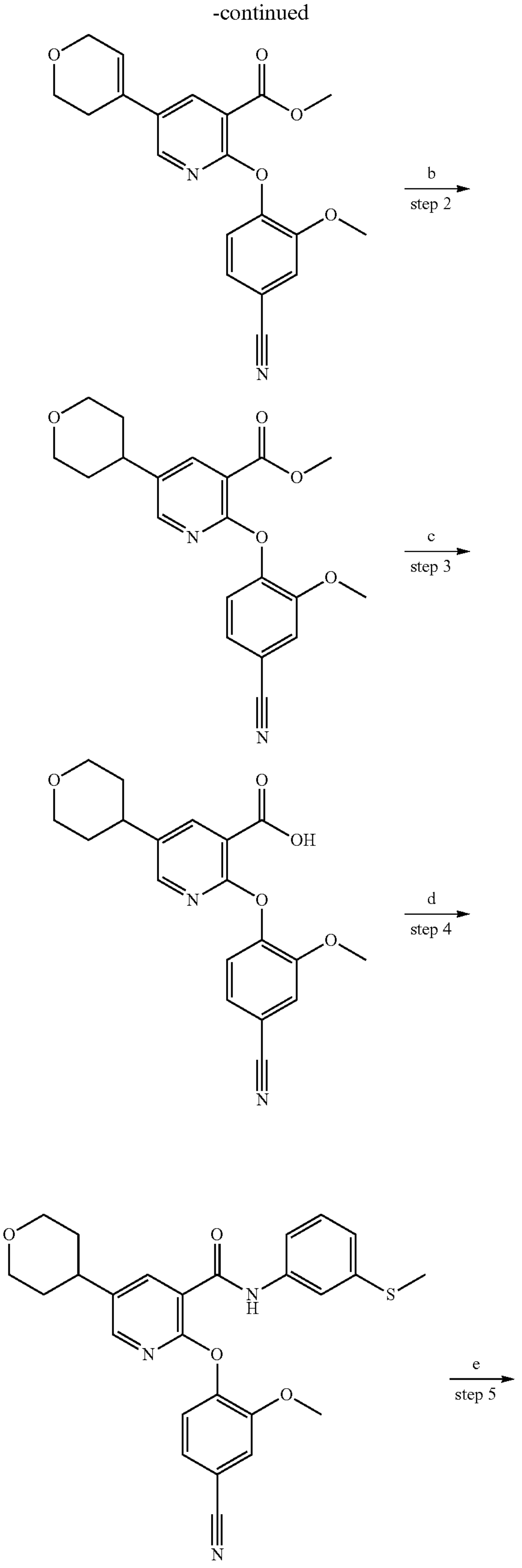

-continued

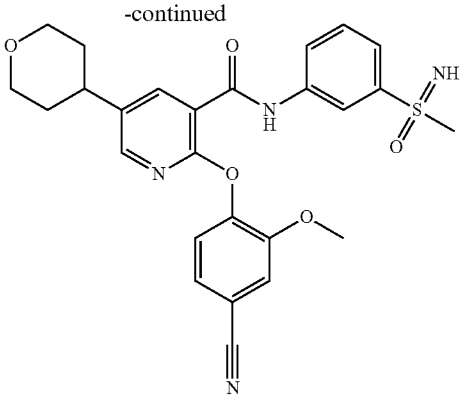

Reagents & conditions: a) 4-(4,4,5,5-tetramethyl-1,3,2-dioxaborolan-2-yl)-3,6-dihydro-2H-pyran, $Pd(OAc)_2$, dicyclohexyl-[2-(2,4,6-triisopropylphenyl)phenyl]phosphane, $Na_3PO_4$, dioxane, 80 °C;
b) $H_2$, Pd (10%), EtOH; c) LiOH, water, THF;
d) 3-(methylsulfanyl)aniline, EDC, pyr; e) PIDA, $(NH_4)_2CO_3$, MeOH Step 1: methyl 2-(4-cyano-2-methoxy-phenoxy)-5-(3,6-dihydro-2H-pyran-4-yl)pyridine-3-carboxylate: A mixture of methyl 5-bromo-2-(4-cyano-2-methoxy-phenoxy)pyridine-3-carboxylate (250 mg, 0.688 mmol), dicyclohexyl-[2-(2,4,6-triisopropylphenyl)phenyl]phosphane (33 mg, 0.0688 mmol), 4-(4,4,5,5-tetramethyl-1,3,2-dioxaborolan-2-yl)-3,6-dihydro-2H-pyran (217 mg, 1.03 mmol) and tripotassium phosphate (438 mg, 2.07 mmol) in 1,4-dioxane (5 mL) and water (1.5 mL) was degassed with nitrogen for 5 minutes, before the addition of palladium(2+) diacetate (15 mg, 0.0688 mmol). The mixture was heated to 80 °C for 2 h in a pressure vial. LC-MS analysis indicated the reaction was complete. Diluted with ethyl acetate (20 mL) and washed with water (8 mL) and brine (8 mL). Organics dried (MgSO4), filtered and concentrated. Purification by FCC (5 g, 0 to 30% EA in Heptane) afforded methyl 2-(4-cyano-2-methoxy-phenoxy)-5-(3,6-dihydro-2H-pyran-4-yl)pyridine-3-carboxylate (99.0%) (249 mg, 0.673 mmol, 98% Yield) as a beige foam. $^1H$ NMR and LC-MS analysis indicated this was the desired product. $^1H$ NMR (400 MHz, $CDCl_3$) δ 8.30 (d, J=2.3 Hz, 1H), 8.22 (d, J=2.6 Hz, 1H), 7.34 (dd, J=8.2, 1.8 Hz, 1H), 7.25-7.21 (m, 2H), 6.17 (m, 1H), 4.32 (q, J=2.8 Hz, 2H), 3.96 (s, 3H), 3.94 (t, J=5.5 Hz, 2H), 3.76 (s, 3H), 2.52-2.45 (m, 2H). LC-MS Method 2: m/z 367.2 $[M+H]^+$, (ESI+), RT=0.86.

Step 2: methyl 2-(4-cyano-2-methoxy-phenoxy)-5-tetrahydropyran-4-yl-pyridine-3-carboxylate: Three vacuum/nitrogen cycles were applied to a solution of methyl 2-(4-cyano-2-methoxy-phenoxy)-5-(3,6-dihydro-2H-pyran-4-yl)pyridine-3-carboxylate (100 mg, 0.273 mmol) in ethanol (2 mL). Palladium (10%, 29 mg, 0.0273 mmol) was added, and three vacuum/hydrogen cycles were applied. The mixture was stirred at rt for 4 h. LC-MS analysis indicated the starting material had been consumed. Filtered through celite and concentrated to afford a clear oil. Purification by FCC (10 g, 0 to 100% EA in heptane) afforded methyl 2-(4-cyano-2-methoxy-phenoxy)-5-tetrahydropyran-4-yl-pyridine-3-carboxylate (87.0%) (28 mg, 0.0661 mmol, 24% Yield) as a white semi-solid. $^1H$ NMR and LC-MS analysis indicated this was the desired product. $^1H$ NMR (400 MHz, $CDCl_3$) δ 8.17 (d, J=2.5 Hz, 1H), 8.07 (d, J=2.5 Hz, 1H), 7.33 (dd, J=8.2, 1.9 Hz, 1H), 7.25-7.18 (m, 2H), 4.15-4.04 (m, 2H), 3.95 (s, 3H), 3.77 (s, 3H), 3.52 (m, 2H), 2.79 (m, 1H), 1.81-1.73 (m, 4H). LC-MS Method 2: m/z 369.2 $[M+H]^+$, (ESI+), RT=0.83.

Step 3: 2-(4-cyano-2-methoxy-phenoxy)-5-tetrahydropyran-4-yl-pyridine-3-carboxylic acid: To a solution of methyl 2-(4-cyano-2-methoxy-phenoxy)-5-tetrahydropyran-4-yl-pyridine-3-carboxylate (28 mg, 0.0760 mmol) in THF (0.2 mL):water (0.1 mL), lithium hydroxide (4.2 mg, 0.167 mmol) was added, and the mixture was stirred at RT for 2 h. LC-MS analysis indicated the reaction was complete. The mixture was diluted with water (5 mL) and the pH was adjusted to 1 by dropwise addition of 2M HCl (aq). The aqueous layer was extracted with EtOAc (3×5 mL), dried ($MgSO_4$), filtered and concentrated in vacuo to afford 2-(4-cyano-2-methoxy-phenoxy)-5-tetrahydropyran-4-yl-pyridine-3-carboxylic acid (90.0%) (25 mg, 0.0635 mmol, 84% Yield) as a clear oil. $^{1}$H NMR and LC-MS analysis indicated this was the desired product. $^{1}$H NMR (400 MHz, $CDCl_3$) δ 8.37 (d, J=2.2 Hz, 1H), 8.13 (d, J=2.5 Hz, 1H), 7.46-7.32 (m, 2H), 4.10 (m, 2H), 3.81 (s, 3H), 3.53 (m, 2H), 2.83 (m, 1H), 1.89-1.75 (m, 4H). LC-MS Method 2: m/z 355.2 $[M+H]^+$, (ESI+), RT=0.69.

Step 4: 2-(4-cyano-2-methoxy-phenoxy)-N-(3-methylsulfanylphenyl)-5-tetrahydropyran-4-yl-pyridine-3-carboxamide: To a solution of 2-(4-cyano-2-methoxy-phenoxy)-5-tetrahydropyran-4-yl-pyridine-3-carboxylic acid (25 mg, 0.0705 mmol) and 3-(ethyliminomethyleneamino)-N,N-dimethyl-propan-1-amine hydrochloride (16 mg, 0.0847 mmol) in pyridine-anhydrous (0.4 mL) was added 3-(methylsulfanyl)aniline (12 mg, 0.0847 mmol). The mixture was stirred at RT for 1 h. LC-MS analysis indicated the reaction was complete. The solvents were removed and the residue purified by FCC (5 g, 0 to 60% EA in heptane) to afford 2-(4-cyano-2-methoxy-phenoxy)-N-(3-methylsulfanylphenyl)-5-tetrahydropyran-4-yl-pyridine-3-carboxamide (87.0%) (17 mg, 0.0311 mmol, 44%) as an off-white solid. $^{1}$H NMR and LC-MS analysis indicated this was the desired product. $^{1}$H NMR (400 MHz, $CDCl_3$) δ 9.92 (s, 1H), 8.51 (d, J=2.5 Hz, 1H), 8.08 (d, J=2.6 Hz, 1H), 7.98-7.92 (m, 2H), 7.53 (m, 2H), 7.41 (dd, J=8.3, 1.8 Hz, 1H), 7.39-7.36 (m, 1H), 7.31 (d, J=1.8 Hz, 1H), 4.10 (m, 2H), 3.89 (s, 3H), 3.60-3.49 (m, 2H), 2.91-2.81 (m, 1H), 2.76 (s, 3H), 1.89-1.79 (m, 4H). m/z 476.2 $[M+H]^+$, (ESI+), RT=1.01.

Step 5: 2-(4-cyano-2-methoxy-phenoxy)-N-[3-(methylsulfonimidoyl)phenyl]-5-tetrahydropyran-4-yl-pyridine-3-carboxamide: Phenyl iodonium diacetate (PIDA) (35 mg, 0.107 mmol) and diammonium carbonate (10 mg, 0.107 mmol) were added to a solution of 2-(4-cyano-2-methoxy-phenoxy)-N-(3-methylsulfanylphenyl)-5-tetrahy dropyran-4-yl-pyridine-3-carboxamide (17 mg, 0.0357 mmol) in methanol (0.5 mL) and the reaction was stirred at room temperature for 2 h. LC-MS analysis indicated the reaction was complete. The solvents were removed, and the residue purified by prep. HPLC (standard method) to afford 2-(4-cyano-2-methoxy-phenoxy)-N-[3-(methylsulfonimidoyl)phenyl]-5-tetrahydropyran-4-yl-pyridine-3-carboxamide (98.0%) (10 mg, 0.0193 mmol, 54% Yield) as a white solid after freeze drying. $^{1}$H NMR and LC-MS analysis indicated this was the desired product. $^{1}$H NMR (400 MHz, DMSO-d6) δ 10.73 (s, 1H), 8.39 (m, 1H), 8.13 (d, J=2.4 Hz, 1H), 8.04 (d, J=2.4 Hz, 1H), 7.94 (m, 1H), 7.70-7.66 (m, 1H), 7.64 (d, J=1.8 Hz, 1H), 7.60 (t, J=7.9 Hz, 1H), 7.51 (dd, J=8.2, 1.8 Hz, 1H), 7.45 (d, J=8.2 Hz, 1H), 4.22 (s, 1H), 3.96 (m, 2H), 3.76 (s, 3H), 3.49-3.38 (m, 2H), 3.06 (s, 3H), 2.87 (m, 1H), 1.76-1.67 (m, 4H). LC-MS Method 4: m/z 507.2 $[M+H]^+$, (ESI+), RT=2.53.

Example 100

Compound 1728: 5-bromo-2-(4-fluoro-2-methylphenoxy)-N-{3-[(S)-imino(methyl)oxo-$\lambda^6$-sulfanyl]phenyl}-4-methylpyridine-3-carboxamide

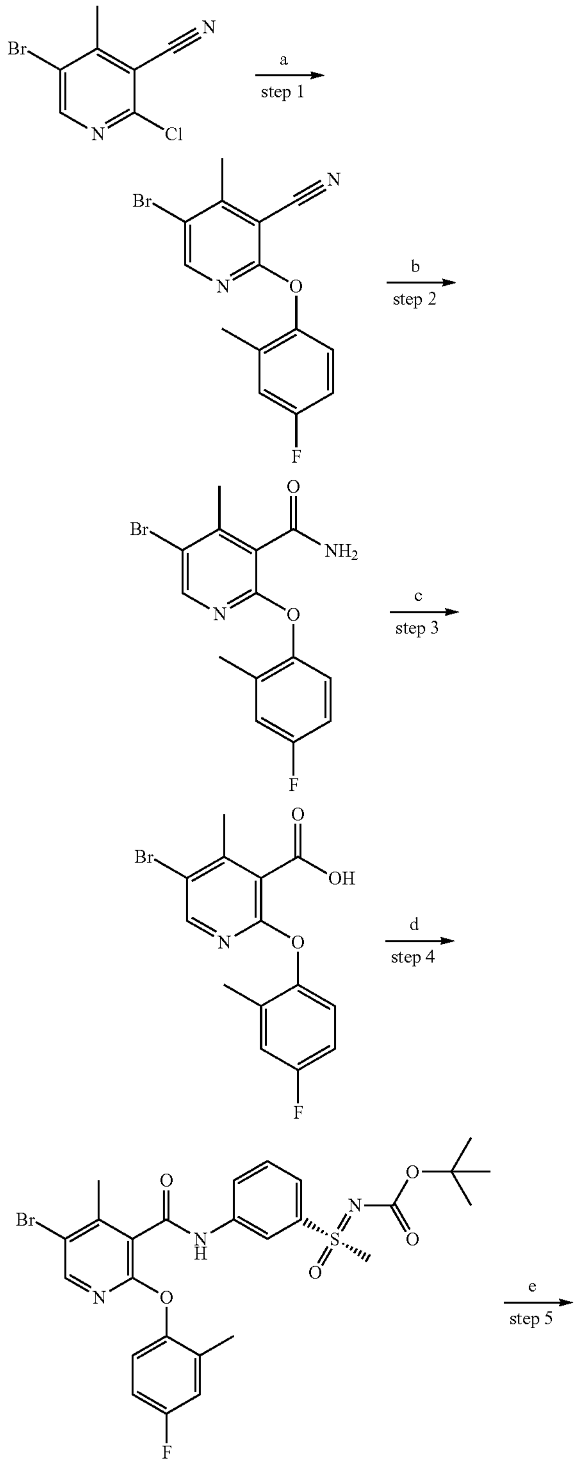

-continued

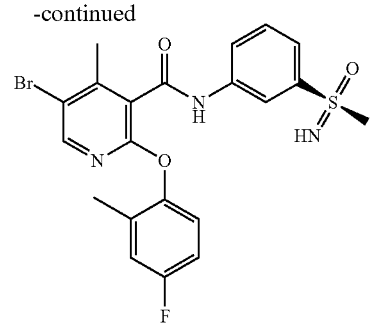

Reagents & conditions: a) $K_2CO_3$, DMF, 100 °C;
b) $K_2CO_3$, $H_2O_2$(50%, v/v), DMSO; c) tert-butyl nitrite, AcOH, NaOH, 70 °C;
d) (S)-tert-butyl N-[(3-aminophenyl)-methyl-oxo-$\lambda^6$-sulfanylidene]carbamate.
HATU, DIEA, DMF; e) 2-propanol, 4M HCl in dioxane, 1,4-dioxane Step 1: 5-bromo-2-(4-fluoro-2-methyl-phenoxy)-4-methyl-pyridine-3-carbonitrile 5-bromo-2-chloro-4-methyl-pyridine-3-carbonitrile was made as described in WO2016021742A. A mixture of 4-fluoro-2-methyl-phenol (1.61 g, 12.8 mmol), 5-bromo-2-chloro-4-methyl-pyridine-3-carbonitrile (1.98 g, 8.53 mmol) and $K_2CO_3$ (2.36 g, 17.1 mmol) in DMF-Anhydrous (20 mL) was stirred at 100 °C for 16 hours. The reaction was cooled to room temperature, poured into ice cold water, and the mixture extracted with EtOAc (25×3 mL). The combined layers were dried to obtain the crude residue. Purification by chromatography on silica eluting with a gradient of 0 to 20% EtOAc in heptane afforded 5-bromo-2-(4-fluoro-2-methyl-phenoxy)-4-methyl-pyridine-3-carbonitrile (100.0%) (1.00 g, 36%) as a white solid. 1H NMR (500 MHz, DMSO-$d_6$) δ 8.47 (s, 1H), 7.29-7.18 (m, 2H), 7.16-7.05 (m, 1H), 2.60 (s, 3H), 2.09 (s, 3H). m/z: 321.0 (Br isotope pattern) $[M+H]^+$, (ESI+), RT=4.21 LCMS Method 4.

Step 2: 5-bromo-2-(4-fluoro-2-methyl-phenoxy)-4-methyl-pyridine-3-carboxamide 5-bromo-2-(4-fluoro-2-methyl-phenoxy)-4-methyl-pyridine-3-carbonitrile (1.00 g, 3.11 mmol) was dissolved in DMSO (17.2 mL), then potassiooxycarbonyloxypotassium (1.90 g, 13.7 mmol) was added. The reaction mixture was cooled slightly in a water bath. To the reaction mixture was added hydrogen peroxide 50% wt aq (50%, 1.9 mL, 34.2 mmol) dropwise over 5 min (slight exotherm), and the reaction mixture was stirred at room temperature overnight. The reaction mixture was diluted with EtOAc (80 mL) and dilute HCl (1N) (25 mL). Organic phase was separated, washed with sat. $NaHCO_3$ (2×25 mL) and brine (1×25 mL), dried and filtered. Solvent was removed under reduced pressure delivering 5-bromo-2-(4-fluoro-2-methyl-phenoxy)-4-methyl-pyridine-3-carboxamide (99.0%) (950 mg, 2.77 mmol, 89%) as a white solid. $^1$H NMR (400 MHz, DMSO-$d_6$) δ 8.19 (s, 1H), 8.08-8.07 (m, 1H), 7.82 (d, J=2.3 Hz, 1H), 7.15 (dd, J=9.4, 3.0 Hz, 1H), 7.12-7.02 (m, 2H), 2.36 (s, 3H), 2.08 (s, 3H). m/z: 339.4 (Br isotope pattern) $[M+H]^+$, (ESI+), RT=2.85 LCMS Method 4.

Step 3: 5-bromo-2-(4-fluoro-2-methylphenoxy)-4-methylpyridine-3-carboxylic acid: To a stirred solution of 5-bromo-2-(4-fluoro-2-methyl-phenoxy)-4-methyl-pyridine-3-carboxamide (170 mg, 0.501 mmol) in Acetic acid (1.5 mL), tert-butyl nitrite (0.18 mL, 1.51 mmol) was added slowly under $N_2$ atmosphere. Then the reaction mixture was allowed to stir for 2 hours min at 70 °C. After completion, the reaction mixture was evaporated to dryness and NaOH (2 M) added. The aqueous phase was washed with EtOAc (3×10 mL) and then the pH adjusted to 1. The aqueous layer has then been extracted with EtOAc (3×15 mL), the organic layers collected and dried to obtain 5-bromo-2-(4-fluoro-2-methyl-phenoxy)-4-methyl-pyridine-3-carboxylic acid (89.0%) (154 mg, 0.403 mmol, 80%) as an orange solid. $^1$H NMR (500 MHz, DMSO-$d_6$) δ 8.25 (s, 1H), 7.17 (dd, J=9.5, 3.0 Hz, 1H), 7.10 (dd, J=8.9, 5.2 Hz, 1H), 7.05 (td, J=8.5, 3.1 Hz, 1H), 2.38 (s, 3H), 2.05 (s, 3H). m/z: 340.0 (Br isotope pattern) $[M+H]^+$, (ESI+), RT=3.25 LCMS Method 4.

Step 4: tert-butyl N—[(S)-{3-[5-bromo-2-(4-fluoro-2-methylphenoxy)-4-methylpyridine-3-amido]phenyl}(methyl)oxo-$\lambda^6$-sulfanylidene]carbamate; A mixture of N-ethyl-N-(propan-2-yl)propan-2-amine (195 μL, 1.12 mmol), (S)-tert-butyl N-[(3-aminophenyl)-methyl-oxo-$\lambda^6$-sulfanylidene]carbamate (83 mg, 0.307 mmol), 5-bromo-2-(4-fluoro-2-methyl-phenoxy)-4-methyl-pyridine-3-carboxylic acid (89%, 107 mg, 0.280 mmol) in DMF-Anhydrous (0.56 mL) was stirred for 10 minutes. Next HATU (160 mg, 0.421 mmol) was added. The reaction mixture was stirred at 55 °C for 26 hours. The reaction mixture was concentrated in vacuo then purified via flash chromatography. Fractions containing desired compound were combined and concentrated to afford tert-butyl N—[(S)-{3-[5-bromo-2-(4-fluoro-2-methylphenoxy)-4-methylpyridine-3-amido]phenyl}(methyl)oxo-$\lambda^6$-sulfanylidene]carbamate (139 mg, 0.235 mmol, 84% Yield) as a white solid. $^1$H NMR (500 MHz, DMSO-$d_6$) δ 11.18 (s, 1H), 8.46-8.37 (m, 1H), 8.32 (s, 1H), 7.98-7.90 (m, 1H), 7.70-7.65 (m, 2H), 7.19-7.11 (m, 2H), 7.06 (td, J=8.6, 3.1 Hz, 1H), 3.38 (s, 3H), 2.40 (s, 3H), 2.07 (s, 3H), 1.22 (s, 9H). m/z: 492.0 (Br isotope pattern) $[M-BOC+H]^+$, (ESI+), RT=0.98 LCMS Method 2.

Step 5: 5-bromo-2-(4-fluoro-2-methylphenoxy)-N-{3-[(S)-imino(methyl)oxo-$\lambda^6$-sulfanyl]phenyl}-4-methylpyridine-3-carboxamide. To a solution of tert-butyl N—[(S)-{3-[5-bromo-2-(4-fluoro-2-methylphenoxy)-4-methylpyridine-3-amido]phenyl}(methyl)oxo-$\lambda^6$-sulfanylidene]carbamate (115 mg, 0.194 mmol) in 1,4-Dioxane-Anhydrous (1 mL) and 2-Propanol (1 mL) was added 4 M hydrogen chloride 4m in dioxane (2.4 mL, 9.72 mmol). The mixture was stirred at rt overnight. The mixture was then cooled to 0 °C, diluted with ethyl acetate (20 mL) and the pH adjusted to ~9 with sat. $NaHCO_3$. Extracted with ethyl acetate (3×30 mL), and the organics dried ($MgSO_4$), filtered and concentrated. Purification by flash chromatography afforded (100.0%) ((31 mg, 33%) as a white solid. $^1$H NMR (400 MHz, DMSO-$d_6$) δ 11.09 (s, 1H), 8.41-8.39 (m, 1H), 8.31 (s, 1H), 7.87 (d, J=8.0 Hz, 1H), 7.68 (d, J=7.9 Hz, 1H), 7.60 (t, J=7.9 Hz, 1H), 7.16 (d, J=4.4 Hz, 1H), 7.14 (d, J=4.5 Hz, 1H), 7.06 (td, J=8.6, 3.0 Hz, 1H), 4.22 (s, 1H), 3.06 (s, 3H), 2.41 (s, 3H), 2.08 (s, 3H). m/z: 492.0 (Br isotope pattern) $[M+H]^+$, (ESI+), RT=2.98 LCMS Method 4.

Example 101

Compound 1729: 2-(3,4-difluoro-2-methoxy-phenoxy)-N-[3-(methylsulfonimidoyl)phenyl]-6-(trifluoromethyl)pyridine-3-carboxamide

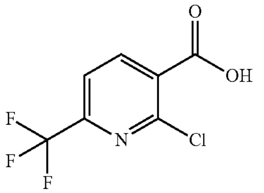

+

-continued

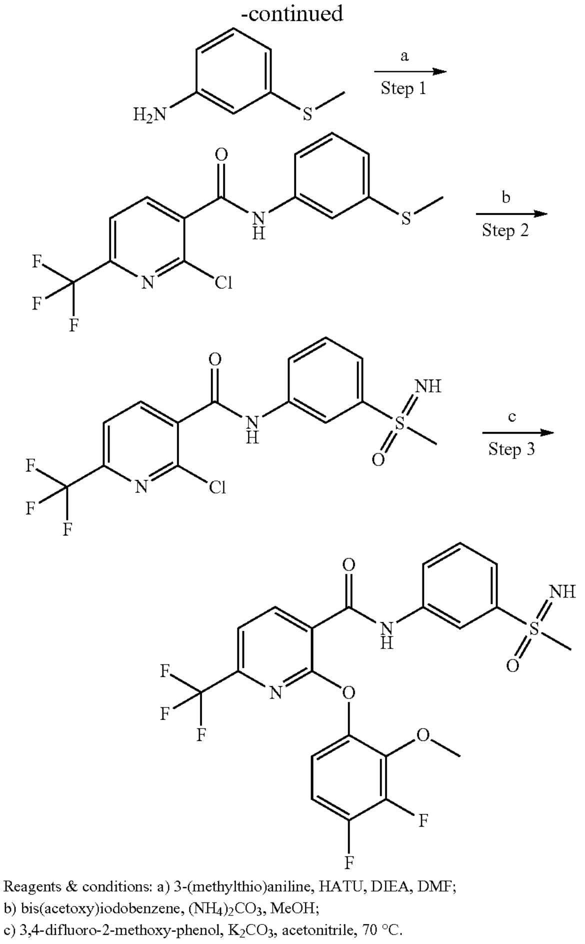

Step 1: 2-chloro-N-(3-methylsulfanylphenyl)-6-(trifluoromethyl)pyridine-3-carboxamide To a mixture of 2-chloro-6-(trifluoromethyl)pyridine-3-carboxylic acid (300 mg, 1.33 mmol), HATU (607 mg, 1.60 mmol) and DIPEA (465 uL, 2.66 mmol) in DMF (3.6 mL) was added 3-(methylthio) aniline (197 uL, 1.60 mmol). The reaction mixture was stirred at rt for 17 h then poured into water (20 mL) and extracted with EtOAc (3×15 mL). The combined organic phases were washed with 5% aq LiCl (2×10 mL), dried over MgSO4 and concentrated under reduced pressure to give 737 mg, as a brown gum. The crude product was purified by FCC (Biotage Isolera 4, 25 g Sfar Duo, lambda-all collection) using a 0-100% EtOAc/heptane gradient to afford 2-chloro-N-(3-methylsulfanylphenyl)-6-(trifluoromethyl) pyridine-3-carboxamide (97.0%) (277 mg, 58%) as a pale yellow solid. $^1$H NMR (400 MHz, DMSO-$d_6$) δ 10.79 (br.s, 1H), 8.42 (d, J=7.5 Hz, 1H), 8.13 (d, J=7.8 Hz, 1H), 7.66 (t, J=1.9 Hz, 1H), 7.42 (ddd, J=8.1, 1.9, 0.9 Hz, 1H), 7.33 (t, J=7.9 Hz, 1H), 7.05 (ddd, J=7.8, 1.7, 0.9 Hz, 1H), 2.48 (s, 3H). m/z: 347.0, 349.0 $[M+H]^+$, (ESI+), RT=0.93 LCMS Method 2.

Step 2: 2-chloro-N-[3-(methylsulfonimidoyl)phenyl]-6-(trifluoromethyl)pyridine-3-carboxamide: To a solution of 2-chloro-N-(3-methylsulfanylphenyl)-6-(trifluoromethyl) pyridine-3-carboxamide (97%, 277 mg, 0.775 mmol) in Methanol (11 mL), bis(acetoxy)iodobenzene (574 mg, 1.78 mmol) and ammonium carbonate (109 mg, 1.16 mmol) were added and the reaction was stirred at rt for 16 h. The reaction mixture was then diluted with DCM, dry-loaded onto silica and purified by column chromatography using 0-100% EtOAc in heptane followed by 0-20% MeOH in EtOAc (on a Biotage Sfar Duo 10 g column, lambda-all collection) to afford 2-chloro-N-[3-(methylsulfonimidoyl)phenyl]-6-(trifluoromethyl)pyridine-3-carboxamide (95.0%) (272 mg, 88%) as a beige powder. $^1$H NMR (400 MHz, DMSO-$d_6$) δ 11.11 (s, 1H), 8.45 (d, J=7.5 Hz, 1H), 8.34 (t, J=1.9 Hz, 1H), 8.15 (d, J=7.8 Hz, 1H), 7.89 (ddd, J=8.0, 2.0, 1.0 Hz, 1H), 7.72 (dt, J=7.8, 1.1 Hz, 1H), 7.63 (t, J=7.9 Hz, 1H), 4.25 (s, 1H), 3.07 (s, 3H). m/z: 378.1, 380.0 $[M+H]^+$(ESI+), RT=0.68 LCMS Method 2.

Step 3: 2-(3,4-difluoro-2-methoxy-phenoxy)-N-[3-(methylsulfonimidoyl)phenyl]-6-(trifluoromethyl)pyridine-3-carboxamide: A mixture of 2-chloro-N-[3-(methylsulfonimidoyl)phenyl]-6-(trifluoromethyl)pyridine-3-carboxamide (120 mg, 0.318 mmol), 3,4-difluoro-2-methoxy-phenol (56 mg, 0.349 mmol) and potassium carbonate (66 mg, 0.476 mmol) in Acetonitrile-Anhydrous (2.4 mL) was stirred at 60 °C for 17 h. The reaction mixture was allowed to cool, diluted with MeCN (2 mL), filtered through a phase separator and the solids washed with MeCN (2×2 mL). The combined filtrate was concentrated under reduced pressure to give 183 mg as a yellow gum. The crude compound was purified by prep. HPLC (Prep. Method 1). Product fractions were combined and concentrated under reduced pressure. The resulting residue was freeze-dried from MeCN-water (1:1) to afford 2-(3,4-difluoro-2-methoxy-phenoxy)-N-[3-(methylsulfonimidoyl)phenyl]-6-(trifluoromethyl)pyridine-3-carboxamide (99.0%) (129 mg, 80%) as a white powder. $^1$H NMR (400 MHz, DMSO-$d_6$) δ 11.01 (s, 1H), 8.45-8.36 (m, 2H), 7.96-7.89 (m, 1H), 7.82 (d, J=7.6 Hz, 1H), 7.69 (dt, J=7.9, 1.2 Hz, 1H), 7.61 (t, J=7.9 Hz, 1H), 7.32-7.18 (m, 2H), 4.24 (s, 1H), 3.81-3.73 (m, 3H), 3.06 (s, 3H). m/z: 502.0 $[M+H]^+$, (ESI+), RT=3.40 LCMS Method 4.

Compound 1730: (R)-2-(4-cyano-2-methoxyphenoxy)-4-methyl-N-(3-(S-methylsulfonimidoyl)phenyl)-6-(trifluoromethyl)nicotinamide

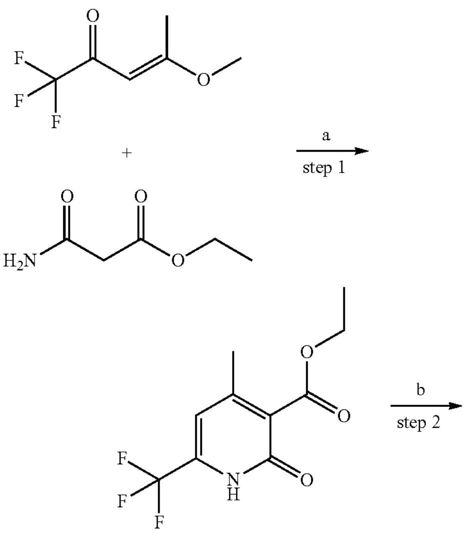

-continued

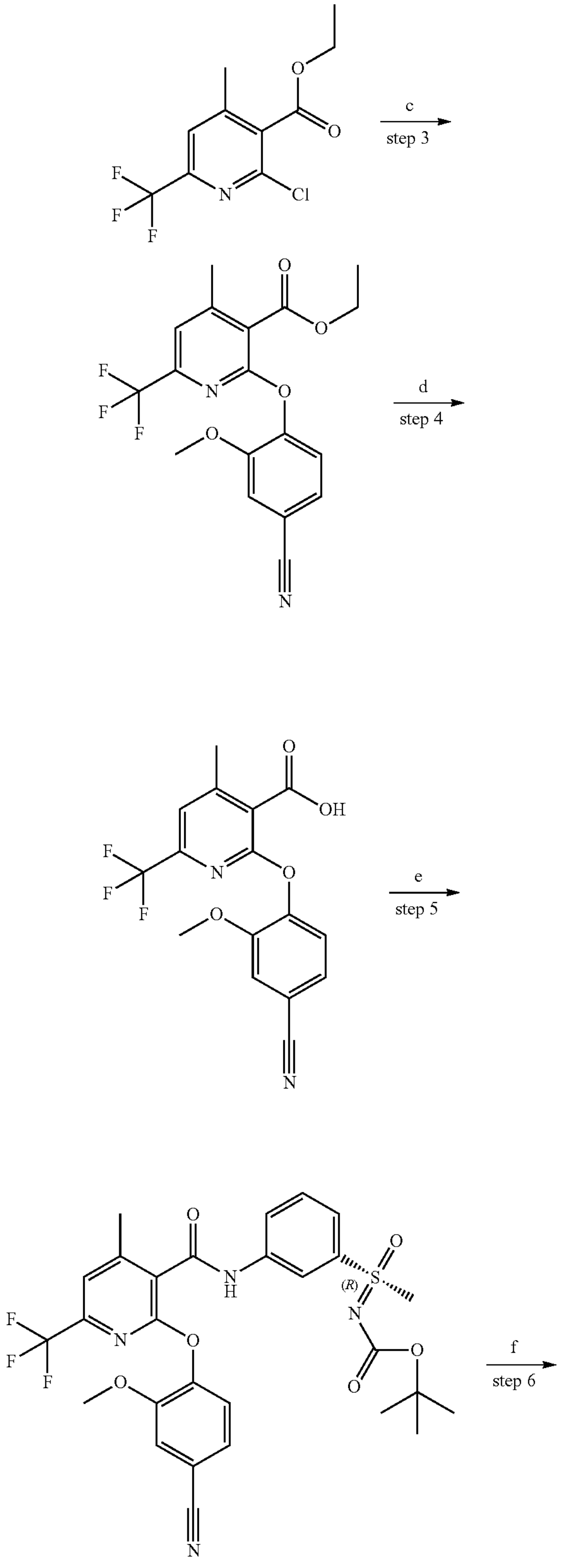

-continued

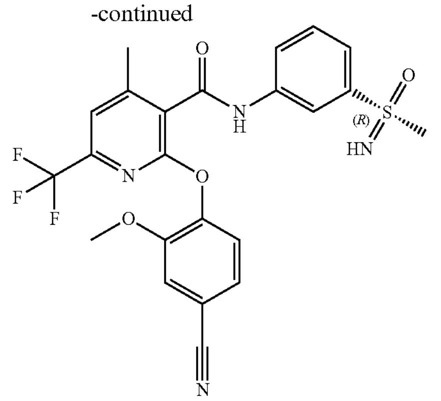

Reagents & conditions: a) NaOEt in EtOH, 85 °C; b) $POCl_3$, $Et^3N$•HCl, 105 °C; c) 4-hydroxy-3-methoxybenzonitrile, $K_2CO_3$, NMP, 100 °C; d) LiOH, THF/$H_2O$; e) tert-butyl (R)-((3-aminophenyl)(methyl)(oxo)-$\lambda^6$- sulfaneylidene)carbamate, Oxalyl chloride, DCM, DMF, DIEA; f) 4M HCl in dioxane, 1,4-dioxane, 2-propanol, rt.

Step 1: ethyl 4-methyl-2-oxo-6-(trifluoromethyl)-1H-pyridine-3-carboxylate: To a solution of ethyl malonate monoamide (1.56 g, 11.9 mmol) and (E)-1,1,1-trifluoro-4-methoxy-pent-3-en-2-one (2.00 g, 11.9 mmol) in Ethanol (20 mL) was added sodium ethoxide in ethanol (21%, 23 mL, 61.8 mmol) and the mixture was heated at 85 °C for 17 h. Aqueous 2M HCl was added to the reaction mixture at room temp until pH 5 and the volatiles removed under reduced pressure. The remaining aqueous was extracted with EtOAc (3×30 mL) and the combined organics washed with brine (30 mL), dried over $MgSO_4$ and concentrated under reduced pressure to afford ethyl 4-methyl-2-oxo-6-(trifluoromethyl)-1H-pyridine-3-carboxylate (86.0%) (1.49 g, 5.14 mmol, 430%) as a brown free-flowing oil. $^1H$ NMR (400 MHz, DMSO-$d_6$) δ 12.36 (br.s, 1H), 7.31 (s, 1H), 4.32 (q, J=7.1 Hz, 2H), 2.30 (s, 3H), 1.28 (t, J=7.1 Hz, 3H). m/z: 250.1 $[M+H]^+$, (ESI+), RT=0.75 LCMS Method 2

Step 2: ethyl 2-chloro-4-methyl-6-(trifluoromethyl)pyridine-3-carboxylate: A mixture of ethyl 4-methyl-2-oxo-6-(trifluoromethyl)-1H-pyridine-3-carboxylate (86%, 750 mg, 2.59 mmol), trimethylamine hydrochloride (1:1) (371 mg, 3.88 mmol) and phosphorus oxychloride (6.0 mL, 64.2 mmol) was stirred at 105 °C in a pressure-relief vial for 17 h. The reaction mixture was allowed to cool then retreated with phosphorus oxychloride (2.0 mL, 21.4 mmol) and trimethylamine hydrochloride (1:1) (124 mg, 1.29 mmol). Heating at 105 °C was resumed for 18 h. The reaction mixture was retreated again with phosphorus oxychloride (2.0 mL, 21.4 mmol) and trimethylamine hydrochloride (1:1) (124 mg, 1.29 mmol) at room temp. Heating at 105 °C was resumed for 18 h. The cooled reaction mixture was added dropwise to a stirring solution of water and sat. aq. $Na_2CO_3$ (1:1, 50 mL). The mixture was neutralised by the cautious addition of solid $Na_2CO_3$ before the product was extracted with DCM (3×50 mL). The combined organics were dried using a phase separation cartridge and concentrated under reduced pressure to give ethyl 2-chloro-4-methyl-6-(trifluoromethyl)pyridine-3-carboxylate (87.0%) (425 mg, 1.38 mmol, 53%) as a dark brown free-flowing oil. $^1H$ NMR (400 MHz, DMSO-$d_6$) δ 8.04 (s, 1H), 4.45 (q, J=7.1 Hz, 2H), 2.44 (s, 3H), 1.34 (t, J=7.1 Hz, 3H). m/z: 268.0, 270.0 $[M+H]^+$, (ESI+), RT=0.97 LCMS Method 2.

Step 3: ethyl 2-(4-cyano-2-methoxy-phenoxy)-4-methyl-6-(trifluoromethyl)pyridine-3-carboxylate: A mixture of ethyl 2-chloro-4-methyl-6-(trifluoromethyl)pyridine-3-carboxylate (79%, 208 mg, 0.614 mmol), 4-hydroxy-3-methoxybenzonitrile (137 mg, 0.921 mmol) and potassium carbonate (255 mg, 1.84 mmol) in NMP-Anhydrous (2.5 mL) was stirred at 100 °C for 22 h in an Ace pressure tube. The reaction mixture was allowed to cool to RT then diluted with DCM (15 mL) and water (20 mL). The layers were separated and the aqueous phase extracted with DCM (2×15 mL). The combined organics were dried using a phase separator and concentrated under reduced pressure to give a brown free-flowing oil. The crude product was purified by FCC (Biotage Isolera, 10 g Sfar Duo cartridge, lambda-all collection) using a 0-25% EtOAc/heptane gradient. Product fractions were combined and concentrated under reduced pressure to give ethyl 2-(4-cyano-2-methoxy-phenoxy)-4-methyl-6-(trifluoromethyl)pyridine-3-carboxylate (35.0%) (571 mg, 0.525 mmol, 86%) as a yellow free-flowing oil. 65% NMP w/w $^1$H NMR (400 MHz, DMSO-$d_6$) δ 7.71-7.67 (m, 2H), 7.50 (dd, J=8.2, 1.8 Hz, 1H), 7.38 (d, J=8.2 Hz, 1H), 4.40 (q, J=7.1 Hz, 2H), 3.73 (s, 3H), 2.45 (s, 3H), 1.30 (t, J=7.1 Hz, 3H). m/z: 381.1 [M+H]$^+$, (ESI+), RT=1.01 LCMS Method 2

Step 4: 2-(4-cyano-2-methoxy-phenoxy)-4-methyl-6-(trifluoromethyl)pyridine-3-carboxylic acid: To a mixture of ethyl 2-(4-cyano-2-methoxy-phenoxy)-4-methyl-6-(trifluoromethyl)pyridine-3-carboxylate (42%, 571 mg, 0.631 mmol) in THF (3 mL)-Water (1.5 mL), lithium hydroxide (45 mg, 1.89 mmol) was added and the mixture stirred at rt for 16 h. The reaction mixture was retreated with lithium hydroxide (45 mg, 1.89 mmol) and stirring at rt continued for 5 h. Methanol (0.2 mL) was added to the reaction mixture and stirring at rt continued for 17 h. The reaction mixture was retreated with lithium hydroxide (45 mg, 1.89 mmol) and stirred for a further 22 h. The reaction mixture was diluted with water (15 mL) and the pH adjusted to 1 by dropwise addition of 2M HCl then extracted with EtOAc (3×10 mL), dried using a phase separator and concentrated in vacuo to give 256 mg, as a pale yellow gum. The crude product was purified by FCC (Biotage Isolera 4, 10 g Sfar Duo, lambda-all collect) using a 0-100% EtOAc/heptane gradient and flushed with 0-60% MeOH/EtOAC. Product fractions were combined and concentrated under reduced pressure to afford 2-(4-cyano-2-methoxy-phenoxy)-4-methyl-6-(trifluoromethyl)pyridine-3-carboxylic acid (99.0%) (108 mg, 0.304 mmol, 48%) as a white powder. $^1$H NMR (500 MHz, DMSO-$d_6$) δ 7.68 (d, J=1.8 Hz, 1H), 7.64 (s, 1H), 7.50 (dd, J=8.2, 1.9 Hz, 1H), 7.36 (d, J=8.2 Hz, 1H), 3.73 (s, 3H), 2.45 (s, 3H). Acid proton not observed m/z: 353.1 [M+H]$^+$, (ESI+), RT=0.81 LCMS Method 2.

Step 5: tert-butyl (R)-((3-(2-(4-cyano-2-methoxyphenoxy)-4-methyl-6-(trifluoromethyl)nicotinamido)phenyl)(methyl)(oxo)-λ$^6$-sulfaneylidene)carbamate To a stirring solution of 2-(4-cyano-2-methoxy-phenoxy)-4-methyl-6-(trifluoromethyl)pyridine-3-carboxylic acid (99%, 105 mg, 0.295 mmol) in DCM-Anhydrous (1.3 mL), anhydrous DMF (4.6 uL, 0.0590 mmol) was added followed by oxalyl chloride (28 uL, 0.325 mmol) under nitrogen and at rt. The reaction was stirred for 50 mins. Subsequently tert-butyl (R)-((3-aminophenyl)(methyl)(oxo)-λ$^6$-sulfaneylidene)carbamate (86%, 111 mg, 0.354 mmol) in DCM-Anhydrous (0.5 mL) was added followed by DIPEA (103 uL, 0.590 mmol) and the reaction was stirred at rt for 1 h. Water (2 mL) was added to the reaction and the mixture passed through a phase separator and rinsed with DCM (3×3 mL). The combined organic phases were concentrated in vacuo to give 227 mg as a light yellow foam. The crude product was purified by FCC using 0-100% EtOAc in Heptane over silica and flushed with 0-20% MeOH in EtOAc (on a Biotage Sfar Duo 10 g column) and concentrated in vacuo to afford tert-butyl (R)-((3-(2-(4-cyano-2-methoxyphenoxy)-4-methyl-6-(trifluoromethyl)nicotinamido)phenyl)(methyl)(oxo)-λ$^6$-sulfaneylidene)carbamate (89.0%)(171 mg, 0.252 mmol, 85%) as an off-white solid. m/z: 505.1 [M-BOC+H]$^+$, (ESI+), RT=0.94 LCMS Method 2

Step 6: (R)-2-(4-cyano-2-methoxyphenoxy)-4-methyl-N-(3-(S-methylsulfonimidoyl)phenyl)-6-(trifluoromethyl)nicotinamide: To a solution of tert-butyl (R)-((3-(2-(4-cyano-2-methoxyphenoxy)-4-methyl-6-(trifluoromethyl)nicotinamido)phenyl)(methyl)(oxo)-λ$^6$-sulfaneylidene)carbamate (89%, 168 mg 0.247 mmol) in 1,4-Dioxane-Anhydrous (1.4 mL) and 2-Propanol (1.4 mL) was added 4 M HCl in dioxane (3.1 mL, 12.4 mmol) and the mixture stirred at rt for 1 h 15 mins. The reaction mixture was then cooled to 0 °C, diluted with EtOAc (20 mL) and basified to pH 9 with sat. aq. $NaHCO_3$. The layers were separated and the aqueous phase extracted with EtOAc (2×15 mL). The combined organics were dried over $MgSO_4$ and concentrated to dryness under vacuum to give 206 mg crude as a pale yellow residue. The crude was purified by acidic (0.1% Formic acid) reverse phase chromatography (Sfar C18 6 g D Duo, 10-100% MeCN in water). Pure product fractions were concentrated under reduced pressure and the resulting residue freeze-dried from MeCN-water (1:1) to afford (R)-2-(4-cyano-2-methoxyphenoxy)-4-methyl-N-(3-(S-methylsulfonimidoyl)phenyl)-6-(trifluoromethyl)nicotinamide (97.0%) (88 mg, 0.169 mmol, 68%) as a white powder. $^1$H NMR (500 MHz, DMSO-$d_6$) δ 11.09 (s, 1H), 8.40 (t, J=1.9 Hz, 1H), 7.88 (ddd, J=8.1, 2.0, 1.0 Hz, 1H), 7.72 (s, 1H), 7.71-7.67 (m, 2H), 7.60 (t, J=7.9 Hz, 1H), 7.51 (dd, J=8.2, 1.9 Hz, 1H), 7.41 (d, J=8.2 Hz, 1H), 4.22 (s, 1H), 3.75 (s, 3H), 3.09-3.04 (m, 3H), 2.48 (s, 3H). m/z: 505.1 [M+H]$^+$, (ESI+), RT=2.89 LCMS Method 4.

Compound 1731: (R)-5-bromo-2-(4-fluoro-2-methylphenoxy)-4-methyl-N-(3-(S-methylsulfonimidoyl)phenyl)nicotinamide

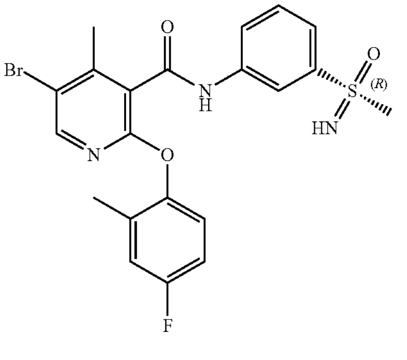

The title compound was prepared by a similar procedure described for compound 1728 using appropriate starting materials. $^1$H NMR (400 MHz, DMSO-$d_6$) δ 11.10 (s, 1H), 8.41 (t, J=1.9 Hz, 1H), 8.31 (s, 1H), 7.91-7.84 (m, 1H), 7.75-7.66 (m, 1H), 7.60 (t, J=7.9 Hz, 1H), 7.19-7.12 (m, 2H), 7.06 (td, J=8.4, 3.1 Hz, 1H), 4.23 (s, 1H), 3.07-3.04 (m, 3H), 2.41 (s, 3H), 2.08 (s, 3H). m/z: 492.0-494.0 [M+H]$^+$, (ESI+), RT=2.98 LCMS Method 4.

Compound 1732: (S)-3-(4-fluoro-2-methylphenoxy)-N-(3-(S-methylsulfonimidoyl)phenyl)-5-(piperidin-1-yl)-6-(trifluoromethyl)pyridazine-4-carboxamide

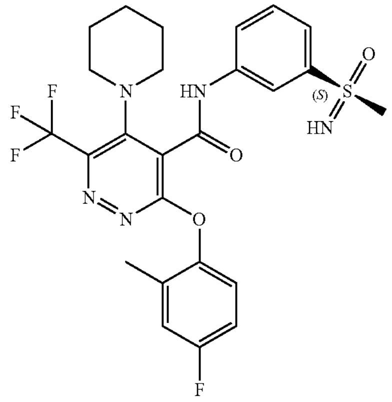

The title compound was prepared by a similar procedure described for compound 1522 using appropriate starting materials. $^1$H NMR (400 MHz, DMSO-$d_6$) δ 11.24 (s, 1H), 8.31 (t, J=1.9 Hz, 1H), 7.87 (ddd, J=8.1, 2.2, 1.1 Hz, 1H), 7.72 (dt, J=8.0, 1.3 Hz, 1H), 7.64 (t, J=7.9 Hz, 1H), 7.29-7.16 (m, 2H), 7.11 (td, J=8.7, 3.3 Hz, 1H), 4.27 (d, J=1.3 Hz, 1H), 3.25-3.17 (m, 4H), 3.07 (d, J=1.1 Hz, 3H), 2.12 (s, 3H), 1.64-1.43 (m, 6H). m/z: 552.1 [M+H]$^+$, (ESI+), RT=3.48 LCMS Method 4.

Compound 1733: (R)-3-(4-cyano-2-methoxyphenoxy)-6-(6-methoxypyridin-3-yl)-5-methyl-N-(3-(S-methylsulfonimidoyl)phenyl)pyridazine-4-carboxamide

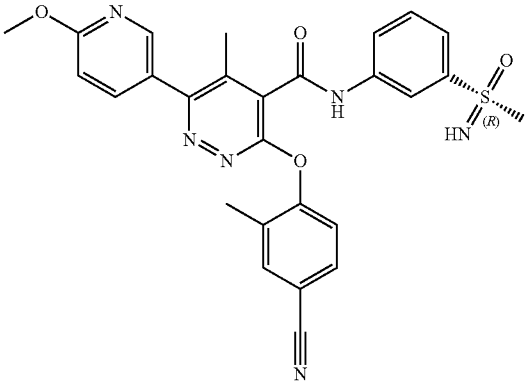

The title compound was prepared by a similar procedure described for compound 1531 using appropriate starting materials. $^1$H NMR (400 MHz, MeOD) δ 6.92 (t, J=2.0 Hz, 1H), 6.81 (m, 1H), 6.43 (m, 1H), 6.36 (dd, J=8.6, 2.5 Hz, 1H), 6.29 (m, 1H), 6.11 (t, J=8.0 Hz, 1H), 5.98 (d, J=1.5 Hz, 1H), 5.93-5.85 (m, 2H), 5.42 (m, 1H), 2.45 (s, 3H), 2.28 (s, 3H), 1.63 (s, 3H), 0.91 (s, 3H). m/z: 545.1 [M+H]$^+$, (ESI+), RT=2.46 LCMS Method 4.

Compound 1734: (R)N-[3-(N-acetyl-S-methylsulfonimidoyl)phenyl]-3-(4-cyano-2-methoxy-phenoxy)-5-methyl-6-(p-tolyl)pyridazine-4-carboxamide

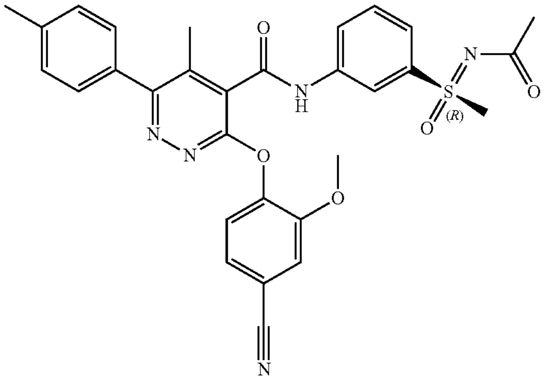

The title compound was prepared (R)-3-(4-cyano-2-methoxyphenoxy)-5-methyl-N-(3-(S-methylsulfonimidoyl)phenyl)-6-(p-tolyl)pyridazine-4-carboxamide. $^1$H NMR (400 MHz, DMSO-$d_6$) δ 11.38 (s, 1H), 8.43-8.39 (m, 1H), 7.95 (dt, J=6.8, 2.1 Hz, 1H), 7.73-7.66 (m, 3H), 7.55 (dd, J=8.2, 1.8 Hz, 1H), 7.52-7.43 (m, 3H), 7.36 (d, J=7.9 Hz, 2H), 3.81 (s, 3H), 3.43 (s, 3H), 2.40 (s, 3H), 2.35 (s, 3H), 1.98 (s, 3H). m/z: 570.1 [M+H]$^+$, (ESI+), RT=3.14 LCMS Method 4.

Compound 1735: (R)-3-(4-cyano-2-methoxyphenoxy)-5-methyl-N-(3-(S-methylsulfonimidoyl)phenyl)-6-(o-tolyl)pyridazine-4-carboxamide

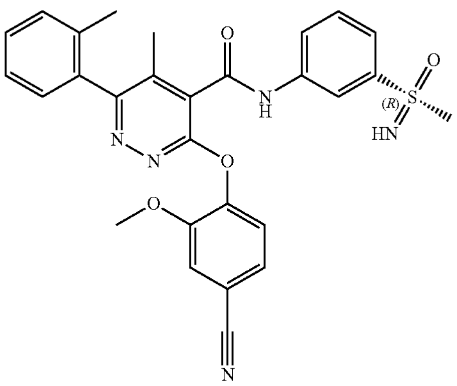

$^1$H NMR (400 MHz, $CD_3OD$) δ 8.46 (t, J=2.0 Hz, 1H), 7.98 (m, 1H), 7.83 (m, 1H), 7.66 (t, J=8.0 Hz, 1H), 7.52 (d, J=1.8 Hz, 1H), 7.49-7.31 (m, 5H), 7.24 (m, 1H), 3.83 (s, 3H), 3.17 (s, 3H), 2.21 (s, 3H), 2.13 (s, 3H). m/z: 528.2 [M+H]$^+$, (ESI+), RT=2.79 LCMS Method 4

Compound 1736: (R)-3-((6-cyano-2-methoxypyridin-3-yl)oxy)-5-methyl-N-(3-(S-methylsulfonimidoyl)phenyl)-6-(trifluoromethyl)pyridazine-4-carboxamide

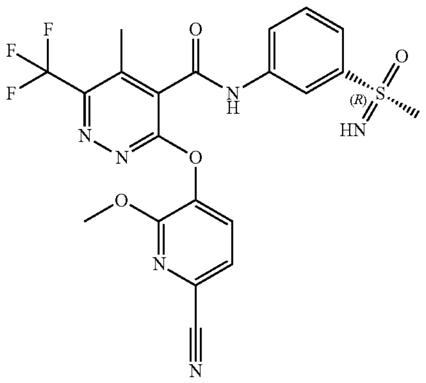

$^1$H NMR (400 MHz, DMSO-$d_6$) δ 11.32 (s, 1H), 8.34 (t, J=1.9 Hz, 1H), 8.01 (d, J=7.9 Hz, 1H), 7.90-7.86 (m, 1H), 7.84 (d, J=7.9 Hz, 1H), 7.76-7.71 (m, 1H), 7.65 (d, J=7.9 Hz, 1H), 4.27 (d, J=1.2 Hz, 1H), 3.88 (s, 3H), 3.08 (d, J=1.1 Hz, 3H), 2.54-2.52 (m, 3H). m/z: 507.3 $[M+H]^+$, (ESI+), RT=2.95 LCMS Method 4.

Compound 1737: (R)-3-((6-cyano-2-methylpyridin-3-yl)oxy)-5-methyl-N-(3-(S-methylsulfonimidoyl)phenyl)-6-(trifluoromethyl)pyridazine-4-carboxamide

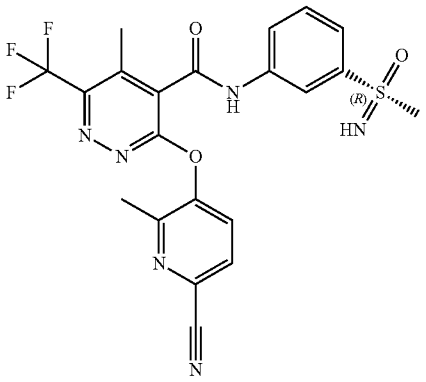

$^1$H NMR (400 MHz, DMSO-$d_6$) δ 11.39 (s, 1H), 8.35 (t, J=1.9 Hz, 1H), 8.10-8.03 (m, 2H), 7.87 (ddd, J=8.0, 2.2, 1.1 Hz, 1H), 7.77-7.71 (m, 1H), 7.64 (t, J=7.9 Hz, 1H), 4.27 (s, 1H), 3.11-3.02 (m, 3H), 2.57-2.54 (m, 3H), 2.41 (s, 3H). m/z: 491.4 $[M+H]^+$, (ESI+), RT=2.73 LCMS Method 4.

Compound 1738: (R)-3-(4-cyano-2-methoxyphenoxy)-N-(3-(S-methylsulfonimidoyl)phenyl)-6-(trifluoromethyl)pyridazine-4-carboxamide

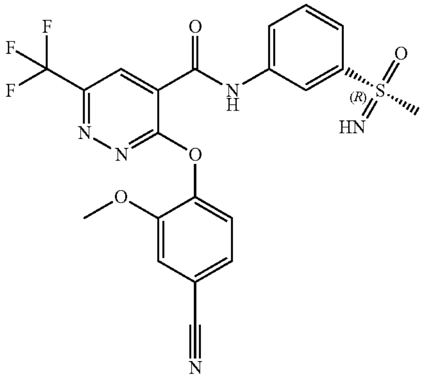

$^1$H NMR (400 MHz, DMSO-$d_6$) δ 11.21 (s, 1H), 8.69 (s, 1H), 8.34 (t, J=1.9 Hz, 1H), 7.93 (ddd, J=8.0, 2.2, 1.1 Hz, 1H), 7.78-7.69 (m, 2H), 7.64 (t, J=7.9 Hz, 1H), 7.58 (d, J=1.0 Hz, 2H), 4.26 (s, 1H), 3.78 (s, 3H), 3.07 (s, 3H). m/z: 492.4 $[M+H]^+$, (ESI+), RT=2.84 LCMS Method 4.

Compound 1739: (R)-3-(4-cyano-2-methoxyphenoxy)-5-methyl-N-(3-(S-methyl-N-(methylglycyl)sulfonimidoyl)phenyl)-6-(p-tolyl)pyridazine-4-carboxamide

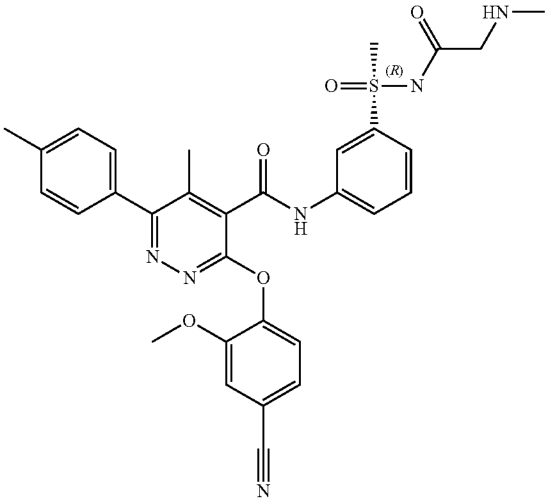

$^1$H NMR (400 MHz, DMSO-$d_6$) δ 11.42 (s, 1H), 8.44 (s, 1H), 7.93 (d, J=7.4 Hz, 1H), 7.80-7.60 (m, 3H), 7.54 (dd, J=8.2, 1.7 Hz, 1H), 7.51-7.40 (m, 3H), 7.35 (d, J=8.0 Hz, 2H), 3.80 (s, 3H), 3.71-3.66 (m, 1H), 3.45 (s, 3H), 3.18 (s, 2H), 2.39 (s, 3H), 2.34 (s, 3H), 2.21 (s, 3H). m/z: 599.1 $[M+H]^+$, (ESI+), RT=2.16 LCMS Method 2.

Compound 1740: (R)-5-(4-cyanophenyl)-2-(4-fluoro-2-methylphenoxy)-4-methyl-N-(3-(S-methyl-sulfonimidoyl)phenyl)nicotinamide

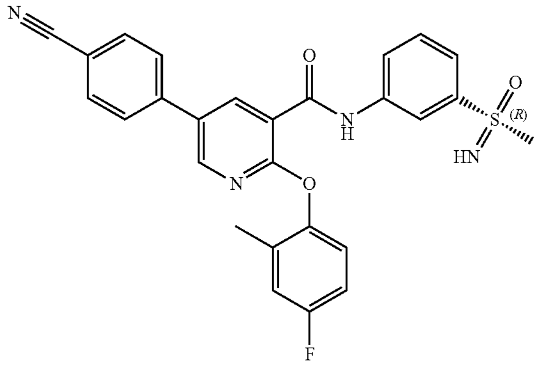

$^1$H NMR (400 MHz, DMSO-$d_6$) δ 11.13 (s, 1H), 8.46 (t, J=2.0 Hz, 1H), 8.05 (s, 1H), 8.01-7.94 (m, 2H), 7.91-7.86 (m, 1H), 7.71-7.65 (m, 1H), 7.64-7.56 (m, 3H), 7.27-7.14 (m, 2H), 7.08 (td, J=8.5, 3.1 Hz, 1H), 4.23-4.21 (m, 1H), 3.09-2.98 (m, 3H), 2.28 (s, 3H), 2.13 (s, 3H). m/z: 515.2 $[M+H]^+$, (ESI+), RT=3.06 LCMS Method 4.

Compound 1741: (S)-5-(4-cyanophenyl)-2-(4-fluoro-2-methylphenoxy)-4-methyl-N-(3-(S-methyl-sulfonimidoyl)phenyl)nicotinamide

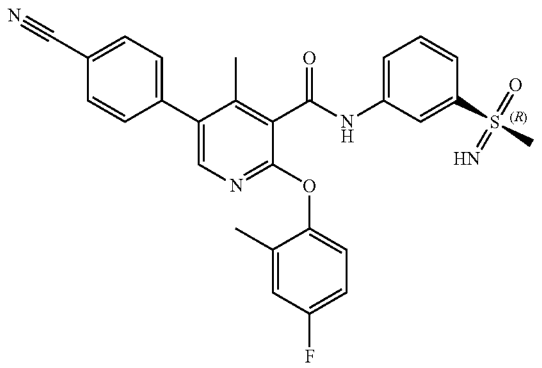

1H NMR (400 MHz, DMSO-$d_6$) δ 11.13 (s, 1H), 8.45 (t, J=1.9 Hz, 1H), 8.05 (s, 1H), 7.99-7.94 (m, 2H), 7.91-7.87 (m, 1H), 7.70-7.66 (m, 1H), 7.64-7.57 (m, 3H), 7.22-7.14 (m, 2H), 7.07 (td, J=8.6, 3.2 Hz, 1H), 4.23-4.21 (m, 1H), 3.12-3.02 (m, 3H), 2.28 (s, 3H), 2.12 (s, 3H). m/z: 515.2 $[M+H]^+$, (ESI+), RT=3.06 LCMS Method 4.

Compound 1742: N-(3-carbamoylphenyl)-4-(4-cyano-2-methoxy-phenoxy)-6-methyl-2-(trifluoromethyl)pyrimidine-5-carboxamide

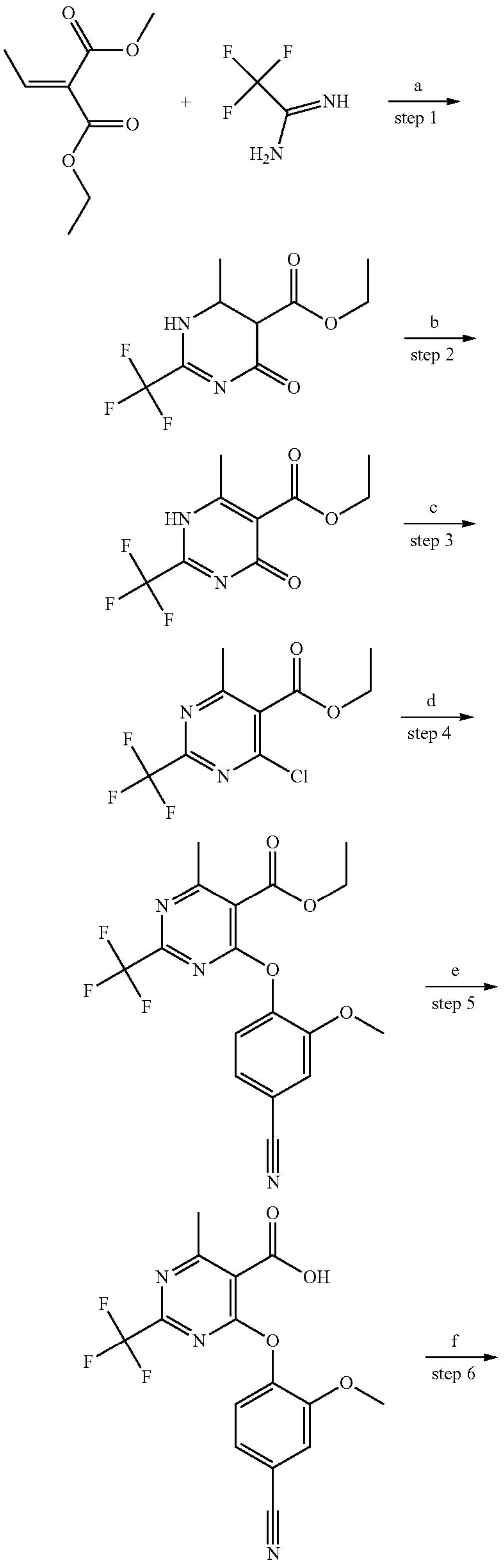

-continued

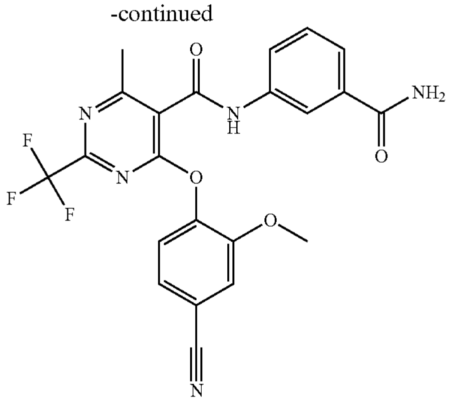

Reagents & conditions: a) EtOH, 90 °C; b) 1-bromopyrrolidine-2,5-dione, α,α,α-trifluorotoluene, $K_2CO_3$, 70 °C; c) 2,2,2-trichloroacetonitrile, triphenylphosphine, toluene, 100 °C; d) 4-hydroxy-3-methoxybenzonitrile, $K_2CO_3$, acetonitrile, 60 °C; e) LiOH, THF/$H_2O$; e) 3-aminobenzamide, HATU, DIEA, DMF.

Step 1: ethyl 6-methyl-4-oxo-2-(trifluoromethyl)-5,6-dihydro-1H-pyrimidine-5-carboxylate: 2,2,2-trifluoroethanimidamide (0.40 mL, 4.46 mmol) and diethyl ethylidenepropanedioate (0.90 mL, 4.91 mmol) were dissolved in Ethanol (5 mL) and heated at 90 °C in a pressure tube for 2 h. The mixture was concentrated, and the residue dissolved in water (10 mL). The pH was adjusted to pH 4 with 1M HCl, then extracted with ethyl acetate (3×10 mL). The organics were dried, filtered and concentrated to afford a yellow oil. Purification by FCC (EtOAc in DCM) afforded ethyl 6-methyl-4-oxo-2-(trifluoromethyl)-5,6-dihydro-1H-pyrimidine-5-carboxylate (90.0%) (285 mg, 1.02 mmol, 21% Yield) as a yellow oil. 1H-19F-NMR and LCMS analysis indicated this was the desired product as a ca. 8:1 mixture of isomers. $^1$H NMR (400 MHz, $CDCl_3$) δ 8.57 (s, 1H), 4.36-4.14 (m, 3H), 3.28 (d, J=8.8 Hz, 1H), 1.39 (d, J=6.9 Hz, 3H), 1.29 (t, J=7.1 Hz, 3H). m/z: 253.1 $[M+H]^+$, (ESI+), RT=0.63 LCMS Method 2.

Step 2: ethyl 6-methyl-4-oxo-2-(trifluoromethyl)-1H-pyrimidine-5-carboxylate: A mixture of ethyl 6-methyl-4-oxo-2-(trifluoromethyl)-5,6-dihydro-1H-pyrimidine-5-carboxylate (1.33 g, 5.29 mmol), 2,2⌧( (E)-diazene-1,2-diylbis(2-methylpropanenitrile) (0.043 g, 0.264 mmol), 1-bromopyrrolidine-2,5-dione (1.32 g, 7.41 mmol) and $K_2CO_3$ (7.31 g, 52.9 mmol) in α,α,α-Trifluorotoluene (40 mL) in a pressure vial was heated at 70 °C for 1 h. LCMS analysis indicated the reaction was complete. The mixture was filtered through cotton wool, eluted further with MeCN, and concentrated to afford an orange oil. Purification by FCC (25 g, 0 to 100% EA in DCM, then 0 to 15% MeOH in EA) afforded ethyl 6-methyl-4-oxo-2-(trifluoromethyl)-1H-pyrimidine-5-carboxylate (91.0%) (0.60 g, 2.19 mmol, 41% Yield) as a yellow oil. $^1$H NMR (400 MHz, $CDCl_3$) δ 4.49 (m, 2H), 2.78 (s, 3H), 1.45 (t, J=7.2 Hz, 3H). m/z: 251.1 $[M+H]^+$, (ESI+), RT=0.68 LCMS Method 2.

Step 3: ethyl 4-chloro-6-methyl-2-(trifluoromethyl)pyrimidine-5-carboxylate: To solution of ethyl 6-methyl-4-oxo-2-(trifluoromethyl)-1H-pyrimidine-5-carboxylate (412 mg, 1.65 mmol) and triphenylphosphine (1296 mg, 4.94 mmol) in Toluene Anhydrous (10 mL) was added 2,2,2-trichloroacetonitrile (0.25 mL, 2.47 mmol). The mixture was heated at 100 °C for 0.5 h. Filtered and concentrated to afford ethyl 4-chloro-6-methyl-2-(trifluoromethyl)pyrimidine-5-carboxylate (11.0%)(2402 mg, 0.984 mmol, 60% Yield) as a brown oil. Used directly in the next step. m/z: 538.3 $[2M+H]^+$, (ESI+), RT=1.00 LCMS Method 2.

Step 4: ethyl 4-(4-cyano-2-methoxy-phenoxy)-6-methyl-2-(trifluoromethyl)pyrimidine-5-carboxylate: To a solution of ethyl 4-chloro-6-methyl-2-(trifluoromethyl)pyrimidine-5-carboxylate (442 mg, 1.65 mmol) and 4-hydroxy-3-methoxybenzonitrile (295 mg, 1.97 mmol) in Acetonitrile (10 mL) was added $K_2CO_3$ (455 mg, 3.29 mmol). the mixture was stirred at 60 °C for 3 h. The mixture was diluted with water (20 mL) extracted with ethyl acetate (3×20 mL). The combined organics were dried ($MgSO_4$), filtered and concentrated to afford a brown oil. Purification by FCC (25 g, 0 to 100% EA in Heptane) afforded ethyl 4-(4-cyano-2-methoxy-phenoxy)-6-methyl-2-(trifluoromethyl)pyrimidine-5-carboxylate (84.0%) (323 mg, 0.712 mmol, 43% Yield) as a pale yellow solid. $^1$H NMR (400 MHz, $CDCl_3$) δ 7.34 (dd, J=8.2, 1.8 Hz, 1H), 7.24 (d, J=1.9 Hz, 2H), 4.49 (q, J=7.1 Hz, 2H), 3.77 (s, 3H), 2.67 (s, 3H), 1.42 (t, J=7.1 Hz, 3H). m/z: 382.2 $[M+H]^+$, (ESI+), RT=1.04 LCMS Method 2.

Step 5: 4-(4-cyano-2-methoxy-phenoxy)-6-methyl-2-(trifluoromethyl)pyrimidine-5-carboxylic acid: To a solution of ethyl 4-(4-cyano-2-methoxy-phenoxy)-6-methyl-2-(trifluoromethyl)pyrimidine-5-carboxylate (323 mg, 0.847 mmol) in THF (2.5 mL):Water (0.5 mL), lithium hydroxide (47 mg, 1.86 mmol) was added, and the mixture stirred at 40 °C for 2 h then overnight at rt. The mixture was diluted with water (10 mL) and the pH was adjusted to 1 by dropwise addition of 1M HCl (aq). The aqueous layer was extracted with EtOAc (3×8 mL), dried ($MgSO_4$), filtered and concentrated in vacuo to afford a yellow oil. Purification by FCC (10 g, 0 to 20% MeOH in EA) afforded 4-(4-cyano-2-methoxy-phenoxy)-6-methyl-2-(trifluoromethyl)pyrimidine-5-carboxylic acid (323 mg, 0.847 mmol) as a pale yellow foam. $^1$H NMR (400 MHz, $CDCl_3$) δ 7.36 (dd, J=8.2, 1.8 Hz, 1H), 7.28 (d, J=8.3 Hz, 1H), 7.25 (m, 1H), 3.78 (s, 3H), 2.79 (s, 3H). m/z: 354.2 $[M+H]^+$, (ESI+), RT=0.76 LCMS Method 2

Step 6: N-(3-carbamoylphenyl)-4-(4-cyano-2-methoxy-phenoxy)-6-methyl-2-(trifluoromethyl)pyrimidine-5-carboxamide: N-[(dimethylamino)(3H-[1,2,3]triazolo[4,5-b]pyridin-3-yloxy)methylidene]-N-methylmethanaminium hexafluorophosphate (77 mg, 0.204 mmol) was added to a solution of 4-(4-cyano-2-methoxy-phenoxy)-6-methyl-2-(trifluoromethyl)pyrimidine-5-carboxylic acid (60 mg, 0.170 mmol) and N-ethyl-N-isopropyl-propan-2-amine (0.059 mL, 0.340 mmol) in DMF-Anhydrous (1.2 mL). The mixture was stirred at rt for 5 minutes, before the addition of 3-aminobenzamide (98%, 31 mg, 0.221 mmol). The mixture was stirred at rt for 1 h. LCMS analysis indicated the reaction was complete. The mixture was diluted with ethyl acetate (8 mL) and washed with water (3×4 mL) and brine (4 mL). Organics were dried ($MgSO_4$), filtered and concentrated to afford an orange oil. Purification by Prep Method 2 afforded N-(3-carbamoylphenyl)-4-(4-cyano-2-methoxy-phenoxy)-6-methyl-2-(trifluoromethyl)pyrimidine-5-carboxamide (100.0%) (44 mg, 0.0933 mmol, 55% Yield) as a white solid. $^1$H NMR (400 MHz, $CD_3OD$) δ 8.18 (t, J=1.9 Hz, 1H), 7.91 (m, 1H), 7.68 (m, 1H), 7.54 (d, J=1.6 Hz, 1H), 7.50 (t, J=7.9 Hz, 1H), 7.46-7.39 (m, 2H), 3.81 (s, 3H), 2.69 (s, 3H). m/z: 472.5 $[M+H]^+$, (ESI+), RT=2.94 LCMS Method 4.

Compound 1743: 4-(4-cyano-2-methoxy-phenoxy)-6-methyl-N-[3-(methylsulfonimidoyl)phenyl]-2-(trifluoromethyl)pyrimidine-5-carboxamide

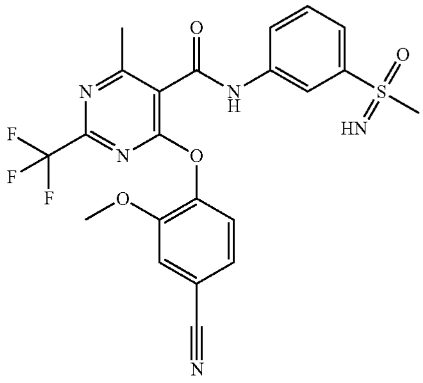 [SMILES: COc1cc(C#N)ccc1Oc1nc(C(F)(F)F)nc(C)c1C(=O)Nc1cccc(S(C)(=N)=O)c1]

The title compound was prepared using 4-(4-cyano-2-methoxy-phenoxy)-6-methyl-2-(trifluoromethyl)pyrimidine-5-carboxylic acid an appropriate substituted aniline. $^1$H NMR (400 MHz, $CD_3OD$) δ 8.45 (t, J=2.0 Hz, 1H), 7.98 (m, 1H), 7.83 (m, 1H), 7.66 (t, J=8.0 Hz, 1H), 7.54 (d, J=1.7 Hz, 1H), 7.47-7.37 (m, 2H), 3.81 (s, 3H), 3.17 (s, 3H), 2.69 (s, 3H). m/z: 506.5 $[M+H]^+$, (ESI+), RT=2.93 LCMS Method 4.

Compound 1744: N-(4-carbamoylphenyl)-4-(4-cyano-2-methoxy-phenoxy)-6-methyl-2-(trifluoromethyl)pyrimidine-5-carboxamide

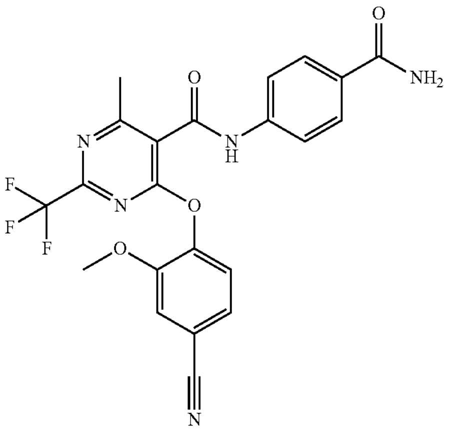 [SMILES: COc1cc(C#N)ccc1Oc1nc(C(F)(F)F)nc(C)c1C(=O)Nc1ccc(C(N)=O)cc1]

The title compound was prepared using 4-(4-cyano-2-methoxy-phenoxy)-6-methyl-2-(trifluoromethyl)pyrimidine-5-carboxylic acid and 4-aminobenzamide using coupling conditions described above. $^1$H NMR (400 MHz, DMSO-$d_6$) δ 11.05 (s, 1H), 7.95-7.87 (m, 3H), 7.78-7.71 (m, 3H), 7.56 (dd, J=8.2, 1.8 Hz, 1H), 7.50 (d, J=8.2 Hz, 1H), 7.31 (s, 1H), 3.78 (s, 3H), 2.63 (s, 3H). m/z: 472.2 $[M+H]^+$, (ESI+), RT=2.86 MET-uPLC-AB-101 (7 min, low pH).

Example 102

Compound Profiling on $Na_V1.8$—Human $Na_V1.8$ Cell Line—SyncroPatch384PE Assay Compounds were tested on recombinant human $Na_V1.8$ stably transfected HEK cells using the SyncroPatch384PE system, an automated patch clamp device. Cells were cultured at 37 °C/5% $CO_2$ in DMEM medium supplemented with GlutaMAX I, NEAA 1%, FBS 10% and seeded in T175 flasks. Cells were cultured at 30 °C one day prior to recording sodium currents. On the day of the recordings, cells were detached with 0.05% Trypsin-EDTA, resuspended in serum free DMEM medium and placed into the SyncroPatch384PE 6 °C pre-cooled cell hotel and shaken at 200 rpm. Intracellular solution (IC) contained, in mM: 10, CsCl; 110, CsF; 20, EGTA; 10, HEPES. Extracellular solution (EC) contained, in mM: 140, NaCl; 4, KCl; 5, Glucose; 10, HEPES; 2, $CaCl_2$; 1, $MgCl_2$. Washing solution contained, in mM: 40, NMDG; 100, NaCl; 4, KCl; 10, Glucose; 10, HEPES; 5, $CaCl_2$; 1, $MgCl_2$.

Compounds were tested in triplicate in 0.1% DMSO and 0.030% Pluronic Acid. Compounds were diluted 1:3 in EC solution to create a 10-point concentration response curve, spanning a final concentration range from 20-0.001 μM in the assay plate. Each plate contained tetracaine and another tool compound as positive controls. Up to 8 compounds were tested on one plate. 250 μM tetracaine and 0.1% DMSO were used as high and low controls, respectively. Whole cell patch clamp recordings were conducted according to Nanion's standard procedure for SyncroPatch384PE®. Cells were held at a holding potential of −120 mV. A depolarization step to 10 mV for 30 ms was applied (P1 measurement), followed by a hyperpolarization step to −100 mV for 100 ms. An inactivation step at −40 mV for 10 sec was applied before stepping to −100 mV for 20 ms, followed by a step to 10 mV for 30 ms (P2 measurement) and then back to −100 mV for 30 ms. Sweep interval was 15 sec with a sampling rate of 10 kHz. Following establishment of the whole-cell configuration in EC, two washing steps with reference buffer were performed to stabilize the baseline. Compounds were then applied by the SynchroPatch into each well and the current was recorded for five minutes in EC, followed by application of tetracaine to achieve full block at the end of the experiment. The potency of the compounds was assessed on two read-outs, resting state block (P1 measurement) or inactivated state block (P2 measurement) to obtain IC50 values. Values were normalized to high (tetracaine) and low (DMSO) controls. The IC50 values are listed in Table 16 as follows: "A" represents an IC50 less than or equal to 20 nM, "B" represents an IC50 greater than 20 nM to less than or equal to 40 nM, "C" represents an IC50 greater than 40 nM to less than or equal to 200 nM, "D" represents an IC50 greater than 200 nM to less than or equal to 500 nM.

TABLE 16

| Compound | P1IC50 | P2IC50 | Compound | P1IC50 | P2IC50 |
|---|---|---|---|---|---|
| 1 | A | A | 2 | A | A |
| 4 | A | A | 14 | D | D |
| 20 | A | B | 21 | B | C |
| 22 | B | C | 23 | A | B |
| 24 | B | C | 25 | A | A |
| 30 | C | C | 31 | C | B |
| 1401 | D | D | 1402 | B | B |
| 1403 | B | B | 1404 | C | C |

TABLE 16-continued

| Compound | P1IC50 | P2IC50 | Compound | P1IC50 | P2IC50 |
|---|---|---|---|---|---|
| 1405 | A | A | 1406 | C | C |
| 1407 | D | D | 1408 | C | C |
| 1409 | A | A | 1412 | A | A |
| 1415 | A | A | 1416 | C | C |
| 1417 | D | D | 1418 | A | A |
| 1419 | A | A | 1420 | D | D |
| 1421 | A | A | 1422 | A | A |
| 1423 | D | D | 1424 | A | A |
| 1425 | A | A | 1426 | A | A |
| 1427 | A | A | 1428 | C | C |
| 1429 | D | D | 1431 | D | D |
| 1432 | D | D | 1433 | C | C |
| 1434 | D | D | 1435 | D | D |
| 1436 | B | C | 1437 | C | C |
| 1438 | C | C | 1439 | C | C |
| 1440 | D | D | 1441 | D | D |
| 1442 | D | D | 1443 | D | D |
| 1444 | D | D | 1445 | D | D |
| 1446 | B | B | 1447 | B | B |
| 1448 | D | D | 1449 | D | D |
| 1450 | A | A | 1451 | D | D |
| 1452 | C | C | 1453 | A | A |
| 1454 | A | A | 1455 | D | D |
| 1456 | D | D | 1457 | D | D |
| 1458 | D | D | 1459 | A | A |
| 1460 | D | D | 1461 | D | C |
| 1462 | D | D | 1463 | A | A |
| 1464 | D | D | 1465 | A | A |
| 1466 | A | A | 1467 | A | A |
| 1468 | A | A | 1469 | A | A |
| 1470 | D | D | 1471 | A | A |
| 1472 | A | A | 1473 | A | A |
| 1474 | A | A | 1475 | A | A |
| 1476 | A | A | 1477 | A | A |
| 1478 | A | A | 1479 | A | A |
| 1480 | A | A | 1481 | A | A |
| 1482 | A | A | 1484 | D | D |
| 1485 | D | D | 1486 | A | A |
| 1487 | A | A | 1488 | A | A |
| 1489 | A | A | 1490 | A | A |
| 1491 | A | A | 1492 | A | A |
| 1493 | A | A | 1494 | A | B |
| 1495 | A | A | 1496 | A | A |
| 1497 | A | A | 1498 | C | C |
| 1499 | C | C | 1500 | C | C |
| 1501 | A | A | 1502 | A | A |
| 1503 | A | A | 1504 | A | A |
| 1505 | A | A | 1506 | A | A |
| 1507 | C | C | 1508 | C | C |
| 1509 | C | C | 1510 | A | A |
| 1511 | A | A | 1512 | A | A |
| 1513 | D | D | 1514 | C | C |
| 1515 | A | A | 1516 | D | D |
| 1517 | A | B | 1518 | A | A |
| 1519 | B | B | 1520 | D | D |
| 1521 | D | D | 1522 | D | D |
| 1523 | D | D | 1524 | D | D |
| 1525 | A | A | 1526 | A | A |
| 1527 | B | B | 1528 | C | C |
| 1529 | A | A | 1530 | C | C |
| 1531 | C | C | 1532 | C | C |
| 1533 | B | B | 1534 | B | B |
| 1535 | B | B | 1536 | C | C |
| 1537 | B | B | 1538 | C | C |
| 1539 | C | B | 1540 | C | C |
| 1541 | D | D | 1542 | D | D |
| 1543 | C | C | 1544 | C | B |
| 1545 | D | D | 1546 | C | C |
| 1547 | D | D | 1548 | B | B |
| 1549 | A | A | 1550 | A | A |
| 1551 | A | A | 1552 | A | A |
| 1553 | D | D | 1554 | D | D |
| 1555 | D | D | 1556 | C | C |
| 1557 | A | A | 1558 | A | A |
| 1559 | A | A | 1560 | A | A |
| 1561 | A | A | 1562 | A | A |
| 1563 | B | B | 1564 | B | C |
| 1565 | D | D | 1566 | D | D |

TABLE 16-continued

| Compound | P1IC50 | P2IC50 | Compound | P1IC50 | P2IC50 |
|---|---|---|---|---|---|
| 1567 | A | A | 1568 | B | B |
| 1569 | A | A | 1570 | B | A |
| 1571 | D | D | 1572 | C | C |
| 1573 | A | A | 1574 | A | A |
| 1575 | A | A | 1576 | C | C |
| 1577 | D | D | 1578 | D | D |
| 1579 | D | D | 1581 | D | D |
| 1582 | D | D | 1583 | B | B |
| 1584 | ND | ND | 1585 | D | D |
| 1586 | D | D | 1587 | C | C |
| 1588 | C | C | 1589 | C | C |
| 1590 | D | D | 1591 | D | D |
| 1592 | D | D | 1593 | A | A |
| 1594 | C | C | 1595 | B | A |
| 1596 | D | D | 1597 | D | D |
| 1598 | D | D | 1599 | D | D |
| 1600 | D | D | 1601 | D | D |
| 1602 | D | D | 1603 | A | A |
| 1604 | C | D | 1605 | D | D |
| 1606 | D | D | 1607 | nd | nd |
| 1608 | A | A | 1609 | C | C |
| 1610 | D | D | 1611 | D | D |
| 1612 | ND | ND | 1613 | ND | ND |
| 1614 | ND | ND | 1615 | A | A |
| 1616 | D | D | 1617 | B | B |
| 1618 | A | A | 1619 | A | A |
| 1620 | D | D | 1621 | D | D |
| 1622 | D | D | 1623 | D | D |
| 1624 | D | D | 1625 | D | D |
| 1626 | D | D | 1627 | ND | ND |
| 1628 | ND | ND | 1629 | C | C |
| 1630 | A | A | 1631 | D | D |
| 1632 | D | D | 1633 | C | D |
| 1634 | D | D | 1635 | C | C |
| 1636 | A | A | 1637 | D | D |
| 1638 | D | D | 1639 | D | D |
| 1640 | D | D | 1642 | A | A |
| 1643 | A | A | 1644 | A | A |
| 1645 | D | D | 1646 | C | C |
| 1647 | A | A | 1648 | A | A |
| 1649 | D | D | 1650 | C | C |
| 1651 | A | A | 1652 | B | B |
| 1653 | C | C | 1655 | A | A |
| 1656 | C | C | 1657 | D | D |
| 1658 | D | C | 1659 | C | C |
| 1660 | C | C | 1661 | A | A |
| 1662 | D | D | 1663 | D | D |
| 1664 | D | D | 1665 | D | D |
| 1666 | C | C | 1667 | D | D |
| 1668 | D | D | 1669 | C | C |
| 1670 | D | D | 1671 | D | D |
| 1672 | D | D | 1673 | D | D |
| 1674 | D | D | 1675 | D | D |
| 1676 | D | D | 1677 | D | D |
| 1678 | D | D | 1679 | D | D |
| 1680 | B | B | 1681 | A | A |
| 1683 | B | A | 1684 | A | A |
| 1685 | A | A | 1686 | A | A |
| 1687 | D | D | 1688 | D | D |
| 1689 | C | C | 1690 | A | A |
| 1691 | C | C | 1692 | C | C |
| 1693 | A | A | 1694 | D | D |
| 1695 | D | D | 1696 | D | D |
| 1697 | B | B | 1698 | D | D |
| 1699 | D | D | 1700 | D | D |
| 1701 | B | B | 1702 | C | C |
| 1703 | D | D | 1704 | ND | ND |
| 1705 | ND | ND | 1706 | D | D |
| 1707 | A | A | 1708 | D | D |
| 1709 | A | B | 1710 | D | D |
| 1711 | B | B | 1712 | A | A |
| 1714 | A | A | 1715 | A | A |
| 1716 | A | A | 1717 | A | A |
| 1718 | D | D | 1719 | A | A |
| 1720 | A | A | 1721 | D | D |
| 1722 | D | D | 1723 | B | B |
| 1724 | C | C | 1725 | D | D |
| 1726 | D | D | 1727 | D | D |

TABLE 16-continued

| Compound | P1IC50 | P2IC50 | Compound | P1IC50 | P2IC50 |
|---|---|---|---|---|---|
| 1728 | A | A | 1729 | A | A |
| 1730 | A | A | 1731 | A | A |
| 1732 | D | D | 1733 | D | C |
| 1742 | C | B | 1743 | A | A |
| 1744 | C | C | | | |

ND—Not Determined

B. Examples for Second Set of Compounds

Example 103

Compound 1: 2-(4-fluoro-2-methylphenoxy)-N-{3-[imino(($^2H_3$)methyl)oxo-$\lambda^6$-sulfanyl]phenyl}-5-(trifluoromethyl)pyridine-3-carboxamide

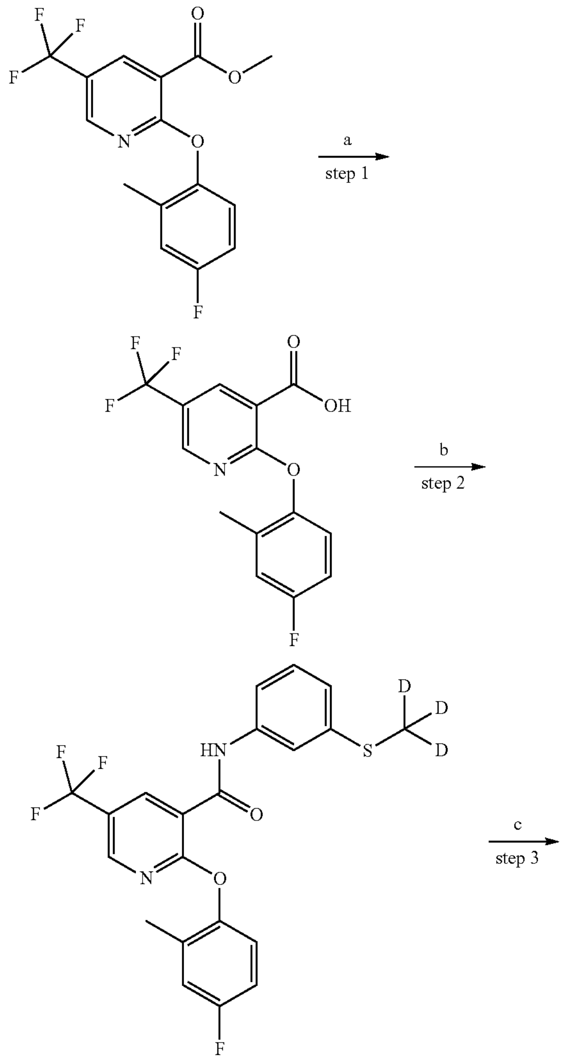

-continued

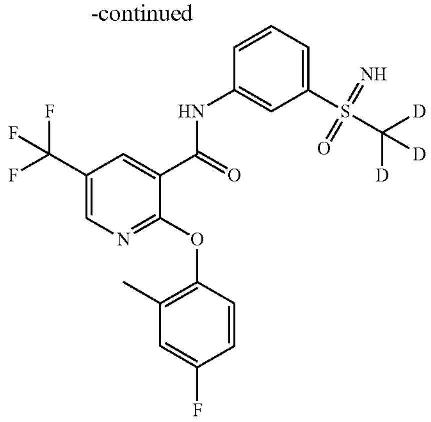

Reagents and conditions: LiOH•$H_2O$, THF/H2O, rt; b) 3-[($^2H_3$)methylsulfanyl]aniline, HATU, DIEA, DMF; c) PIDA, $(NH_4)_2CO_3$, MeOH, rt.

Step 1: 2-(4-fluoro-2-methylphenoxy)-5-(trifluoromethyl)pyridine-3-carboxylic acid: To a solution of methyl 2-(4-fluoro-2-methylphenoxy)-5-(trifluoromethyl)pyridine-3-carboxylate (8.80 g, 26.1 mmol) in THF: water (33.4 mL; 5:1 v/v) was added LiOH·$H_2O$ (5.61 g, 134 mmol) at rt. The resulting mixture was stirred at rt for further 3 h. AT the end of the tis period solvent was evaporated, to the residue water (20 mL) was added and acidified with 1N HCl. The solid separated was filtered and washed with water (2×20 mL) to provide 2-(4-fluoro-2-methylphenoxy)-5-(trifluoromethyl) pyridine-3-carboxylic acid (7.6 g, 90%). $^1H$ NMR (300 MHz, $CDCl_3$) δ 8.63 (dd, J=2.6, 0.7 Hz, 1H), 8.47 (dq, J=2.7, 0.9 Hz, 1H), 7.03-6.84 (m, 3H), 2.09 (s, 3H).

Step 2: 2-(4-fluoro-2-methylphenoxy)-N-{3-[($^2H_3$)methylsulfanyl]phenyl}-5-(trifluoromethyl)pyridine-3-carboxamide: To a mixture of 2-(4-fluoro-2-methylphenoxy)-5-(trifluoromethyl)pyridine-3-carboxylic acid (6.0 g, 19.0 mmol), 3-[($^2H_3$)methylsulfanyl]aniline (2.98 g, 20.9 mmol) in DMF (30 mL) was added HATU (10.9 g, 28.6 mmol) followed by DIEA (7.38 g, 57.1 mmol) at rt. The resulting mixture was stirred at rt for 16 h. At the end of this period water (30 mL) was added and extracted with EtOAc (2×40 mL). The EtOAc layer was washed with water (30 mL) and brine (30 mL), the organic layer was dried over $Na_2SO_4$, filtered and the solvent evaporated. The crude was chromatographed over $SiO_2$ with a gradient of 0-30 EtOAc % in hexane to provide 2-(4-fluoro-2-methylphenoxy)-N-{3-[($^2H_3$)methylsulfanyl]phenyl}-5-(trifluoromethyl)pyridine-3-carboxamide (7.80 g, 93%). $^1H$ NMR (300 MHz, $CDCl_3$) δ 9.63 (s, 1H), 8.92-8.87 (m, 1H), 8.41 (dq, J=1.8, 0.9 Hz, 1H), 7.65 (t, J=1.9 Hz, 1H), 7.29-7.16 (m, 2H), 7.09-6.92 (m, 4H), 2.13 (s, 3H).

Step 3: 2-(4-fluoro-2-methylphenoxy)-N-{3-[imino(($^2H_3$)methyl)oxo-$\lambda^6$-sulfanyl]phenyl}-5-(trifluoromethyl)pyridine-3-carboxamide: To a solution of 2-(4-fluoro-2-methylphenoxy)-N-{3-[($^2H_3$)methylsulfanyl]phenyl}-5-(trifluoromethyl)pyridine-3-carboxamide (7.80 g, 17.7 mmol) in MeOH (150 mL) was added ammonium carbobane (2.56 g, 26.6 mmol) and PIDA (13.1 g, 40.8 mmol) at rt. The mixture was stirred for 16 h at rt. At the end of this period solvent was evaporated, crude was dissolved in EtOAc (150 mL) and washed with saturated NaHCO3 solution, The EtOAc layer was dried over $Na_2SO_4$, filtered and the solvent evaporated. The crude mixture was chromatographed over $SiO_2$ with a gradient of 0-10% MeOH in DCM to provide 2-(4-fluoro-2-methylphenoxy)-N-{3-[imino(($^2H_3$)methyl) oxo-$\lambda^6$-sulfanyl]phenyl}-5-(trifluoromethyl)pyridine-3-carboxamide (6.02 g, 72%). $^1$H NMR (300 MHz, DMSO-$d_6$) δ 10.98 (s, 1H), 8.67 (dt, J=2.5, 1.1 Hz, 1H), 8.61-8.52 (m, 1H), 8.39 (t, J=1.9 Hz, 1H), 7.95 (dt, J=8.2, 1.4 Hz, 1H), 7.75-7.56 (m, 2H), 7.34-7.06 (m, 3H), 4.25 (s, 1H), 2.10 (s, 3H).

Example 104

Compounds 2 and 3: (S)-2-(4-fluoro-2-methylphenoxy)-N-{3-[imino(($^2H_3$)methyl)oxo-λ$^6$-sulfanyl]phenyl}-5-(trifluoromethyl)pyridine-3-carboxamide and (R)-2-(4-fluoro-2-methylphenoxy)-N-{3-[imino(($^2H_3$)methyl)oxo-λ$^6$-sulfanyl]phenyl}-5-(trifluoromethyl)pyridine-3-carboxamide

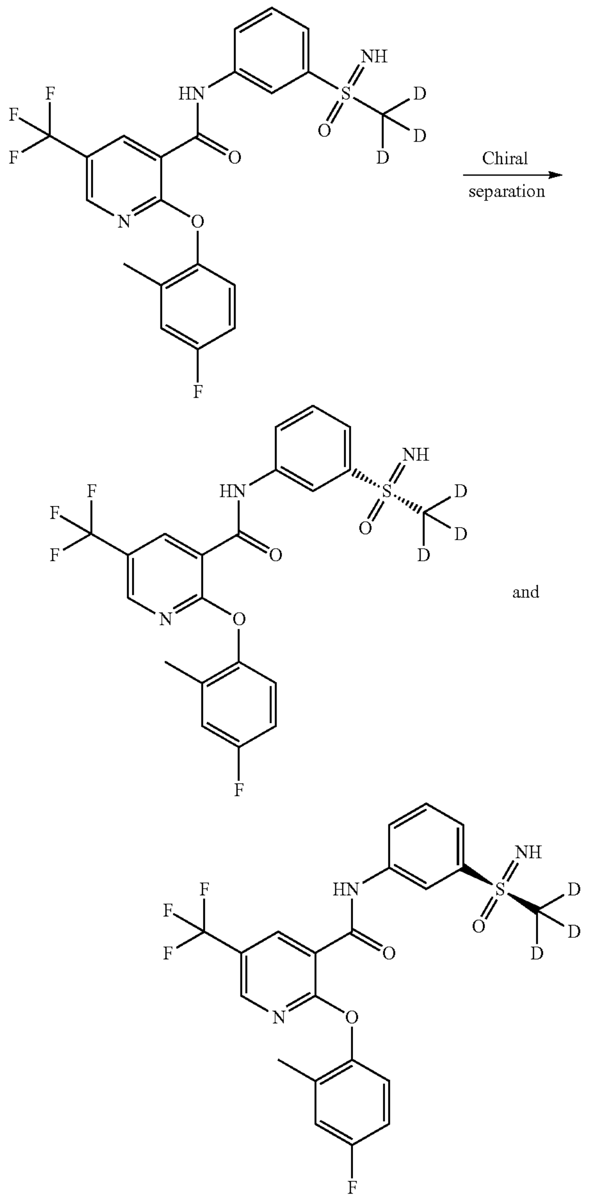

and

Racemic mixture of 2-(4-fluoro-2-methylphenoxy)-N-{3-[imino((2$H_3$)methyl)oxo-6-sulfanyl]phenyl}-5-(trifluoromethyl)pyridine-3-carboxamide was separated using following Chiral Purification Method: Mobile phase: 20% Methanol: 80% $CO_2$; Column: Chiralpak AD-H, 10×250 mm, 5 μm. Flow rate: 15 ml/min. First eluting isomer (S)-2-(4-fluoro-2-methylphenoxy)-N-{3-[imino(($^2H_3$)methyl)oxo-λ$^6$-sulfanyl]phenyl}-5-(trifluoromethyl)pyridine-3-carboxamide (S)-2-(4-fluoro-2-methylphenoxy)-N-{3-[imino(($^2H_3$)methyl)oxo-λ$^6$-sulfanyl]phenyl}-5-(trifluoromethyl)pyridine-3-carboxamide. $^1$H NMR (400 MHz, DMSO-d6) δ 10.96 (s, 1H), 8.66 (dd, J=2.4, 1.0 Hz, 1H), 8.57-8.51 (m, 1H), 8.38 (t, J=1.8 Hz, 1H), 7.96-7.90 (m, 1H), 7.71-7.65 (m, 1H), 7.61 (t, J=7.9 Hz, 1H), 7.27 (dd, J=8.9, 5.1 Hz, 1H), 7.20 (dd, J=9.5, 3.0 Hz, 1H), 7.11 (td, J=8.5, 3.1 Hz, 1H), 4.21 (s, 1H), 2.09 (s, 3H). m/z 471.5 $[M+H]^+$, (ESI+), RT=4.04 LC-MS Method 5 and the second eluting isomer(R)-2-(4-fluoro-2-methylphenoxy)-N-{3-[imino(($^2H_3$)methyl)oxo-λ$^6$-sulfanyl]phenyl}-5-(trifluoromethyl)pyridine-3-carboxamide. $^1$H NMR (400 MHz, DMSO-d6) δ 10.96 (s, 1H), 8.66 (dd, J=2.4, 1.0 Hz, 1H), 8.57-8.51 (m, 1H), 8.38 (t, J=1.9 Hz, 1H), 7.98-7.90 (m, 1H), 7.72-7.67 (m, 1H), 7.61 (t, J=7.9 Hz, 1H), 7.27 (dd, J=8.8, 5.1 Hz, 1H), 7.20 (dd, J=9.5, 3.0 Hz, 1H), 7.11 (td, J=8.5, 3.0 Hz, 1H), 4.22 (s, 1H), 2.09 (s, 3H). m/z 471.5 $[M+H]^+$, (ESI+), RT=4.05 LC-MS Method 5.

Example 105

Compound Profiling on $Na_V1.8$—Human $Na_V1.8$ Cell Line—SyncroPatch384PE Assay Compounds were tested on recombinant human $Na_V1.8$ stably transfected HEK cells using the SyncroPatch384PE system, an automated patch clamp device. Cells were cultured at 37 °C/5% $CO_2$ in DMEM medium supplemented with GlutaMAX I, NEAA 1%, FBS 10% and seeded in T175 flasks. Cells were cultured at 30 °C one day prior to recording sodium currents. On the day of the recordings, cells were detached with 0.05% Trypsin-EDTA, resuspended in serum free DMEM medium and placed into the SyncroPatch384PE 6 °C pre-cooled cell hotel and shaken at 200 rpm. Intracellular solution (IC) contained, in mM: 10, CsCl; 110, CsF; 20, EGTA; 10, HEPES. Extracellular solution (EC) contained, in mM: 140, NaCl; 4, KCl; 5, Glucose; 10, HEPES; 2, $CaCl_2$; 1, $MgCl_2$. Washing solution contained, in mM: 40, NMDG; 100, NaCl; 4, KCl; 10, Glucose; 10, HEPES; 5, $CaCl_2$; 1, $MgCl_2$.

Compounds were tested in triplicate in 0.1% DMSO and 0.030% Pluronic Acid. Compounds were diluted 1:3 in EC solution to create a 10-point concentration response curve, spanning a final concentration range from 20-0.001 μM in the assay plate. Each plate contained tetracaine and another tool compound as positive controls. Up to 8 compounds were tested on one plate. 250 μM tetracaine and 0.1% DMSO were used as high and low controls, respectively. Whole cell patch clamp recordings were conducted according to Nanion's standard procedure for SyncroPatch384PE®. Cells were held at a holding potential of −120 mV. A depolarization step to 10 mV for 30 ms was applied (P1 measurement), followed by a hyperpolarization step to −100 mV for 100 ms. An inactivation step at −40 mV for 10 sec was applied before stepping to −100 mV for 20 ms, followed by a step to 10 mV for 30 ms (P2 measurement) and then back to −100 mV for 30 ms. Sweep interval was 15 sec with a sampling rate of 10 kHz. Following establishment of the whole-cell configuration in EC, two washing steps with reference buffer were performed to stabilize the baseline. Compounds were then applied by the SynchroPatch into each well and the current was recorded for five minutes in EC, followed by application of tetracaine to achieve full block at the end of the experiment. The potency of the compounds was assessed on two read-outs, resting state block (P1 measurement) or inactivated state block (P2 measurement) to obtain IC50 values. Values were normalized to high (tetracaine) and low (DMSO) controls. The IC50 values are listed in Table 17 as follows: "A" represents an IC50 less than or equal to 20 nM, "B" represents an IC50 greater than 20 nM to less than or equal to 40 nM, "C" represents an IC50 greater than 40 nM to less than or equal to 200 nM, "D" represents an IC50 greater than 200 nM to less than or equal to 500 nM.

TABLE 17

| Compound | P1IC50 | P2IC50 |
|---|---|---|
| 1 | B | B |
| 2 | A | A |
| 3 | A | A |

C. Examples for Third Set of Compounds

Example 106

Methods of making the compounds of the present invention, and intermediates used in their synthesis, are provided in the General Synthetic Schemes and Specific Syntheses Procedures below. Chemicals were purchased from standard commercial vendors and used as received unless otherwise noted. Otherwise, their preparation is facile and known to one of ordinary skill in the art, or it is referenced or described herein. Abbreviations are consistent with those in the ACS Style Guide. "Dry" glassware means oven/desiccator dried. Solvents were ACS grade unless otherwise noted.

All reactions were performed in flame-dried or oven-dried glassware under a positive pressure of dry nitrogen or dry argon and were stirred magnetically unless otherwise indicated. Chemicals were purchased from standard commercial vendors and used as received unless otherwise noted. Yields are not optimized. The chemical names were generated using the ChemDraw Professional 19.1, available from PerkinElmer or chem Axon.

Reactions were monitored by thin layer chromatography (TLC) using 0.25 mm silica gel 60 F254 plates purchased from EMD MILLIPORE™. Purification was performed with CombiFlash NextGen 300 Automated Flash Chromatography System or purified using one of the preparative HPLC methods mentioned below.

Prep Method 1 (P1): Acidic Early Method

Purification (METCR/Prep004) (P1) LC were performed using a Waters Sunfire C18 column (30 mm×100 mm, 5 μm; temperature: room temperature), with an injection volume of 1500 μL at flow rate of 40 mL/min at 100% B (A=0.1% formic acid in water; B=0.1% formic acid in acetonitrile) for 0.55 min then a gradient of 10-95% B over 13.89 min and held for 2.11 min. A second gradient of 95-10% B was then applied over 0.2 min. UV spectra were recorded at 215 nm using a Gilson detector.

Prep Method 2 (P2): Acidic Standard Method

Purification (METCR/Prep001) (P2) LC were performed using a Waters Sunfire C18 column (30 mm×100 mm, 5 μm; temperature: room temperature), with an injection volume of 1500 μL at flow rate of 40 mL/min at 30% B (A=0.10% formic acid in water; B=0.1% formic acid in acetonitrile) for 0.55 min then a gradient of 30-95% B over 10.45 min and held for 2.10 min. A second gradient of 95-30% B was then applied over 0.21 min. UV spectra were recorded at 215 nm using a Gilson detector.

Prep Method 3 (P3): Basic Early Method

Purification (METCR/Prep002) (P3) LC were performed using a Waters X-Bridge C18 column (30 mm×100 mm, 5 μm; temperature: room temperature), with an injection volume of 1500 μL at flow rate of 40 mL/min at 10% B (A=0.2% ammonium hydroxide in water; B=0.2% ammonium hydroxide in acetonitrile) for 0.55 min then a gradient of 10-95% B over 13.89 min and held for 2.11 min. A second gradient of 95-10% B was then applied over 0.2 min. UV spectra were recorded at 215 nm using a Gilson detector.

Prep Method 4 (P4): Basic Standard Method

Purification (METCR/Prep003) (P4) LC were performed using a Waters X-Bridge C18 column (30 mm×100 mm, 5 μm; temperature: room temperature), with an injection volume of 1500 μL at flow rate of 40 mL/min at 300% B (A=0.2% ammonium hydroxide in water; B=0.2% ammonium hydroxide in acetonitrile) for 0.55 min then a gradient of 30-95% B over 10.45 min and held for 2.10 min. A second gradient of 95-30% B was then applied over 0.21 min. UV spectra were recorded at 215 nm using a Gilson detector.

Analytical LCMC were collected using one of following methods.

Method 1 (M1): Acidic IPC Method (METCR1410—MS17, MS18, MS19)

Analytical (MET/CR/1410) (M1) HPLC-MS were performed using a Kinetex Core shell C18 column (2.1 mm×50 mm, 5 μm; temperature: 40 °C), with an injection volume of 3 μL at a flow rate of 1.2 mL/min and a gradient of 5-100% B (A=0.1% formic acid in water; B=0.10% formic acid in acetonitrile) over 1.2 min, then 100% B for 0.1 min. A second gradient of 100-5% B was then applied over 0.01 min and held for 0.39 min. UV spectra were recorded at 215 nm using a SPD-M20A PDA detector, spectrum range: 210-400 nm. Mass spectra were obtained using a 2010EV detector. Data were integrated and reported using Shimadzu LCMS-Solutions and PsiPort software.

Method 2(M2):

Mass spectrometry data were collected using a Waters Acquity H-class ultra-high pressure liquid chromatograph coupled to a Waters Acquity TQD mass spectrometer. An Acquity UPLC BEH C18 column (2.1×50 mm) was used for separation and resolving samples. The compounds were eluted from the column using a 10-minute linear solvent gradient: 0-0.5 min, 5% B; 0.5-6.5 min, 100% B, 6.5-7.5 min; 100% B, 7.5-8.1 min; 5% B, 8.1-10 min; 5% B. The solvent flow rate is 0.45 mL per minute. Solvent A was water and solvent B was acetonitrile. Mass spectra were collected in positive or negative ion mode, with following parameters: 2.5 kV capillary voltage; 25 V sampling cone voltage; 140 C source temperature; 400 C desolvation temperature; nitrogen desolvation at 800 L/hr.

Method 3 (M3): Basic IPC Method (MET-uPLC-AB-2005—MS16, MSQ5)

Analytical (MET/uPLC/AB2005) (M14) uHPLC-MS were performed using a Waters uPLC® BEHTM C18 column (2.1 mm×30 mm, 1.7 μm; temperature 40 °C), with an injection volume of 1 μL at a flow rate of 1.0 mL/min and a gradient of 1-100% B (A=2 mM ammonium bicarbonate in water, buffered to pH 10; B=acetonitrile) over 1.1 min, then 100% B for 0.25 min. A second gradient of 100-1% B was then applied over 0.05 min and held for 0.4 min. UV spectra were recorded at 215 nm using a Waters ACQUITY PDA detector, spectrum range: 200-400 nm. Mass spectra were obtained using a Waters Quattro Premier XE mass detector or a Waters SQD2. Data were integrated and reported using Waters MassLynx and OpenLynx software.

Method 4 (M4): Acidic Final Analysis Method (METCR-uPLC-AB101—MSQ1, MSQ2, MSQ4)

Analytical (MET/uPLC/AB101) (M4) uHPLC-MS were performed using a Phenomenex Kinetex-XB C18 column (2.1 mm×100 mm, 1.7 μm; temperature: 40 °C), with an injection volume of 1 μL at flow rate of 0.6 mL/min and a gradient of 5-100% B (A=0.1% formic acid in water; B=0.1% formic acid in acetonitrile) over 5.3 min, then 100% B for 0.5 min. A second gradient of 100-5% B was then applied over 0.02 min and held for 1.18 min. UV spectra were recorded at 215 nm using a Waters ACQUITY PDA detector, spectrum range: 200-400 nm, ELS data was collected on a Waters ACQUITY ELS detector when reported. Mass spectra were obtained using a Waters SQD or Waters ACQUITY QDA. Data were integrated and reported using Waters MassLynx and OpenLynx software.

Method 5 (M5): Acidic Final Analysis Method (METCR1416—MS18, MS19)

Analytical (MET/CR/1416) (M5) HPLC-MS were performed using a Waters Atlantis dC18 column (2.1 mm×100 mm, 3 μm; temperature: 40 °C), with an injection volume of 3 μL at flow rate of 0.6 mL/min and a gradient of 5-100% B (A=0.1% formic acid in water; B=0.1% formic acid in acetonitrile) over 5 min, then 100% B for 0.4 min. A second gradient of 100-5% B was then applied over 0.02 min and held for 1.58 min. UV spectra were recorded at 215 nm using a SPD-M20A PDA detector, spectrum range: 210-400 nm. Mass spectra were obtained using a 2010EV detector. Data were integrated and reported using Shimadzu LCMS-Solutions and PsiPort software.

Method 6 (M6): Basic Final Analysis Method (MET-uPLC-ABI05—MS16, MSQ5)

Analytical (MET/uHPLC/AB105) (M8) uHPLC-MS were performed using a Waters uPLC® BEHTM C18 column (2.1 mm×100 mm, 1.7 μm column; temperature: 40 °C), with an injection volume of 1 μL and at flow rate of 0.6 mL/min and a gradient of 5-100% B (A=2 mM ammonium bicarbonate in water, buffered to pH 10; B=acetonitrile) over 5.3 min, then 100% B for 0.5 min. A second gradient of 100-5% B was then applied over 0.02 min and held for 1.18 min. UV spectra were recorded at 215 nm using a Waters ACQUITY PDA detector, spectrum range: 200-400 nm. Mass spectra were obtained using a Waters Quattro Premier XE mass detector or a Waters SQD2. Data were integrated and reported using Waters MassLynx and OpenLynx software.

SFC chiral resolution was performed using following method: Column: Daicel CHIRALPAK IG, 250 mm×20 mm I.D., 5 μm; Mobile Phase A: $CO_2$/MeOH [0.2% $NH_3$ (7M Solution in MeOH)]=70/30; Flow rate: 60 g/min; 214 nm. Temperature: 35 °C.

Unless otherwise stated, $^1$H nuclear magnetic resonance spectroscopy (NMR) spectra were recorded on a Bruker™ 300 MHz, or 500 MHz, 400 MHz or 250 MHz on either a Bruker Avance III HD 500 MHz spectrometer Bruker Avance III HD 400 MHz spectrometer. Chemical shifts, 6, are quoted in parts per million (ppm) relative to TMS and calibrated using residual un-deuterated solvent as an internal reference. The following abbreviations are used to denote the multiplicities and general assignments: s (singlet), d (doublet), t (triplet), q (quartet), dd (doublet of doublets), ddd (doublet of doublet of doublets), dt (doublet of triplets), dq (doublet of quartets), hep (heptet), m (multiplet), pent (pentet), td (triplet of doublets), qd (quartet of doublets), app. (apparent) and br. (broad). Coupling constants, J, are quoted to the nearest 0.1 Hz.

Example 107

General Synthetic Schemes

Several methods for preparing the compounds of this invention are illustrated in the following Schemes and Examples. The present invention further provides processes for the preparation of compounds of structural Formula I as defined above. In some cases, the order of carrying out the foregoing reaction schemes may be varied to facilitate the reaction or to avoid unwanted reaction products. The following examples are provided for the purpose of illustration only and are not to be construed as limitations on the disclosed invention.

Scheme 1

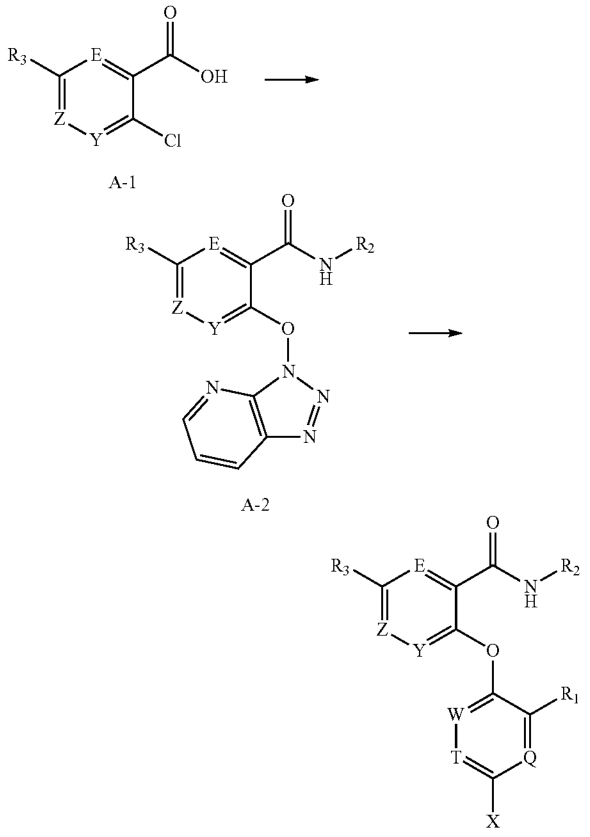

A-1

A-2

A-3

Scheme 1 represents a general method for the preparation of carboxamide derivatives of the present invention by treating carboxylic acid A-1 with $R_2NH_2$ using amide coupling agent HATU and DIEA as the base to provide intermediates of type A-2. The compounds of type A-3 can be obtained by reacting intermediates of type A-2 in organic solvents with various phenols in the presence of base, such as $K_2CO_3$, $Cs_2CO_3$, DIEA or $Et_3N$.

Scheme 2

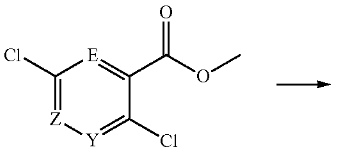

B-1

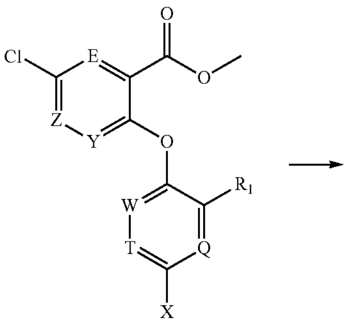

B-2

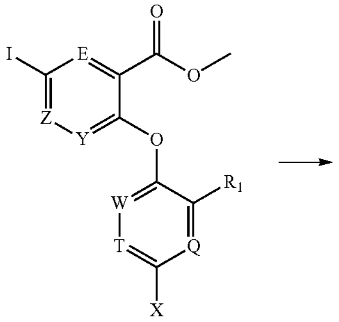

B-3

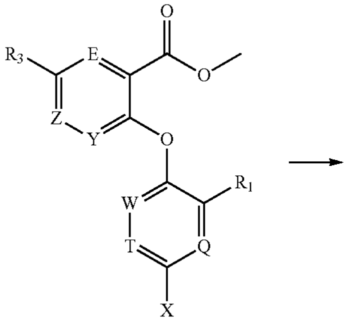

B-4

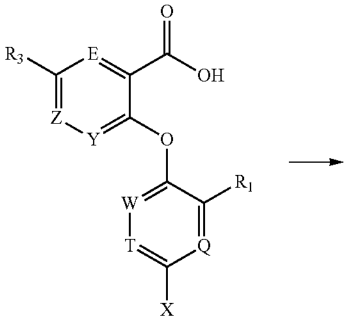

B-5

-continued

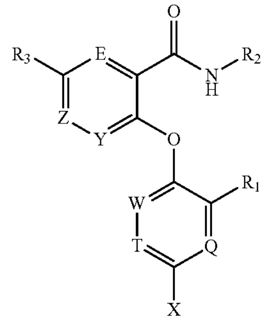

A-3

Alternatively, compounds of the formula A-3 may be synthesized in five step linear synthesis starting from dichlorocarboxylic acid ester B-1 by nucleophilic displacement of Cl adjacent to the carboxylic acid ester using various substituted phenols in the presence of base, such as $K_2CO_3$, $Cs_2CO_3$, NaH, KH or other organic bases to provide intermediates of type B-2. Intermediates of type B-2 was further treated with HI (50%), HI (57%) or HI (40%) to furnish intermediates of type B-3. Variously substituted $R_3$ groups can be introduced either by Pd mediated or Cu mediated coupling with intermediates of type B-3 to furnish B4. The carboxylic acid of intermediates type B-5 can be prepared by hydrolyzing ester intermediates of type B-4 using a base, such as aqueous NaOH, KOH, or LiOH. Alternatively, intermediates of type B-5 can be prepared by treating intermediates B-4 using aqueous 1 to 6N HCl. The carboxylic acids (B-5) can be activated to the acid chloride and coupled with $R_2NH_2$ or carboxylic acids (B-5) can be coupled with $R_2NH_2$ using standard amide coupling agents, not limited to HATU, TBTU, EDC or $T_3P$ in organic solvents and base, such as DIEA, $Et_3N$, DMAP or pyridine to furnish A-3.

Scheme 3

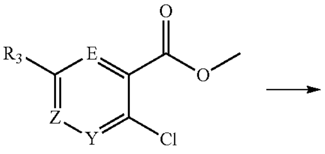

C-1

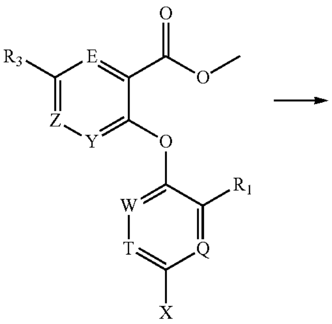

C-2

-continued

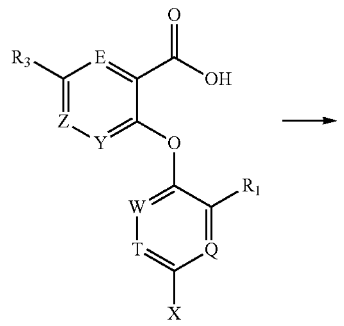

C-3

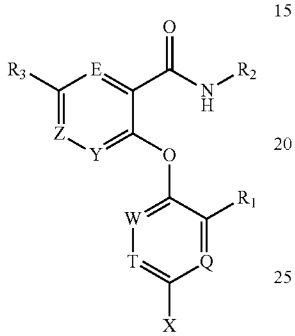

A-3

Alternatively, compounds of the formula A-3 can be prepared nucleophilic displacement of Cl intermediates of type C-1 using various substituted phenols in the presence of base, such as $K_2CO_3$, $Cs_2CO_3$, NaH, KH or other organic bases to provide intermediates of type C-2. The carboxylic acid of intermediates type C-3 can be prepared by hydrolyzing ester intermediates of type C-2 using a base, such as aqueous NaOH, KOH, or LiOH. Alternatively, intermediates of type C-3 can also be prepared by treating intermediates C-2 using aqueous 1 to 6N HCl. The carboxylic acids (C-3) can be activated to the acid chloride and coupled with $R_2NH_2$ or carboxylic acids (C-3) can coupled with $R_2NH_2$ using standard amide coupling agents, not limited to HATU, TBTU, EDC or $T_3P$ in organic solvents and base, such as DIEA, $Et_3N$, DMAP or pyridine to furnish A-3.

Scheme 4

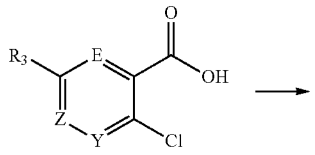

A-1

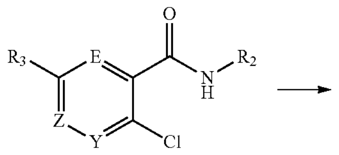

D-1

-continued

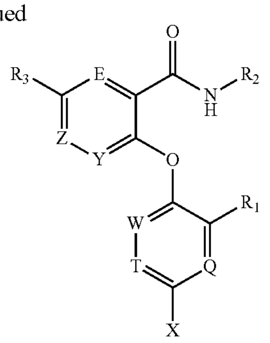

A-3

Alternatively, compounds of type A-3 can also be prepared by activating carboxylic acids (A-1) to the acid chloride and coupled with $R_2NH_2$ or carboxylic acids (A-1) can be coupled with $R_2NH_2$ using standard amide coupling agents, not limited to TBTU, EDC or $T_3P$ in organic solvents and base, such as DIEA, $Et_3N$, DMAP or pyridine to furnish D-1. The compounds of type A-3 can be obtained by treating intermediates of type D-1 with various phenols in the presence of base, such as NaH (60%), $K_2CO_3$, $Cs_2CO_3$, DIEA or $Et_3N$ in organic solvents.

Example 108

Specific Synthesis

Intermediate 1: 3-(4-Fluoro-2-methyl-phenoxy)-6-(trifluoromethyl)pyridazine-4-carboxylic Acid

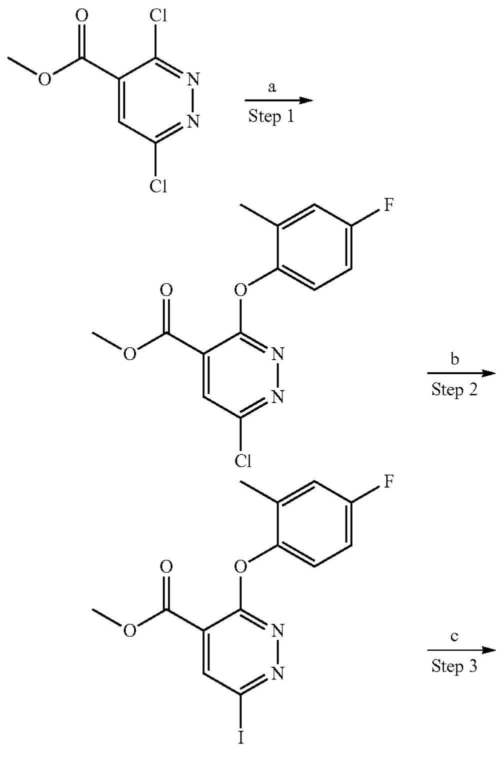

-continued

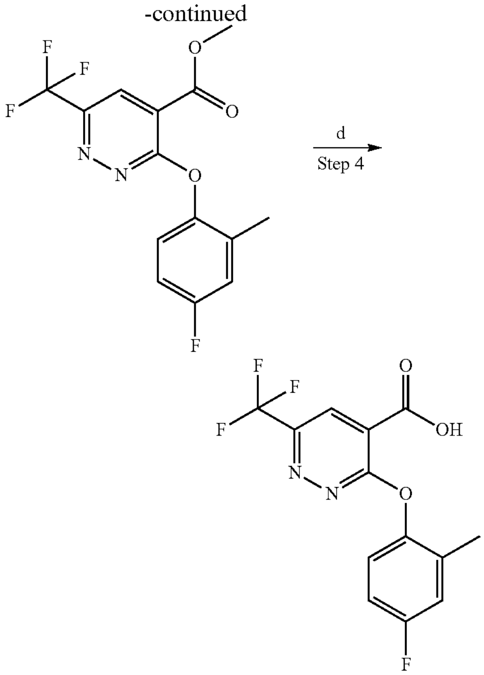

Reagents & conditions: a) 4-fluoro-2-methylphenol, $K_2CO_3$, $CH_3CN$, 90 °C, 16 h; b) HI, 40 °C, 5 h; c) methyl 2,2-difluoro-2-(fluorosulfonyl) acetate, TBAI, CuI, DMF, 120 °C, 2 h; d) LiOH, THF, $H_2O$, rt.

Step 1: methyl 6-chloro-3-(4-fluoro-2-methyl-phenoxy)pyridazine-4-carboxylate

A mixture of 4-fluoro-2-methyl-phenol (3.01 g, 23.8 mmol), methyl 3,6-dichloropyridazine-4-carboxylate (4.70 g, 22.7 mmol) and potassium carbonate (4.71 g, 34.1 mmol) in acetonitrile (47 mL) was stirred at 80 °C for 3 h. The reaction was cooled to room temperature, filtered, and washed with MeCN (20 mL). Filtrate was concentrated in vacuo to obtain the crude residue. Purification by chromatography on silica eluting with a gradient of 0 to 15% EtOAc in heptane afforded methyl 6-chloro-3-(4-fluoro-2-methyl-phenoxy)pyridazine-4-carboxylate (95.0%) (4.10 g, 58%) as a pale yellow oil. $^1H$ NMR (500 MHz, DMSO-$d_6$) δ 8.26 (s, 1H), 7.29-7.20 (m, 2H), 7.16-7.06 (m, 1H), 3.94 (s, 3H), 2.11 (s, 3H). LC-MS (Method 5): m/z: 297/299 $[M+H]^+$, (ESI+), RT=4.26.

Step 2: methyl 3-(4-fluoro-2-methyl-phenoxy)-6-iodo-pyridazine-4-carboxylate: A mixture of methyl 6-chloro-3-(4-fluoro-2-methyl-phenoxy)pyridazine-4-carboxylate (4.10 g, 13.1 mmol) in hydroiodic acid (55%) (50 mL, 0.197 mol) was stirred at 40 °C for 3 h. The mixture was left overnight at rt. The reaction mixture was filtered. The filter cake was washed with water. The solid was re-dissolved in 55% aqueous hydrogen iodide (50 mL, 0.197 mol) and stirred at 40 °C for 24 h. The mixture was cooled to RT and filtered, the solid was washed with water and dried in high vacuum oven at 40 °C overnight to afford methyl 3-(4-fluoro-2-methyl-phenoxy)-6-iodo-pyridazine-4-carboxylate (79.0%) (2.70 g, 5.50 mmol, 42% Yield) as a yellow solid. $^1H$ NMR (400 MHz, DMSO-$d_6$) δ 8.37 (s, 1H), 7.26-7.17 (m, 2H), 7.15-7.05 (m, 1H), 3.91 (s, 3H), 2.09 (s, 3H). LC-MS (Method 1): m/z: 388.9 $[M+H]^+$, (ESI+), RT=1.24.

Step 3: methyl 3-(4-fluoro-2-methyl-phenoxy)-6-(trifluoromethyl)pyridazine-4-carboxylate: To a mixture of methyl 3-(4-fluoro-2-methyl-phenoxy)-6-iodo-pyridazine-4-carboxylate (80%, 2.70 g, 5.57 mmol), copperiodide (1.598 g, 8.35 mmol), tetrabutylammonium iodide (0.824 g, 2.23 mmol) in DMF (10 mL). The mixture was degassed with nitrogen for 5 minutes and methyl difluoro(fluorosulfonyl) acetate (5.346 g, 27.8 mmol) was added and stirred at 90 °C for 2 h. The reaction was cooled to rt, filtered and the cake was washed with EtOAc (2×10 mL). The filtrate was washed with brine (50 mL) and dried over $MgSO_4$, filtered, concentrated under reduced pressure to obtain the crude residue. Purification by chromatography on silica eluting with a gradient of 0 to 50% EtOAc in heptane afforded the title compound methyl 3-(4-fluoro-2-methyl-phenoxy)-6-(trifluoromethyl)pyridazine-4-carboxylate (0.770 g, 41%) as a pale yellow solid. $^1H$ NMR (400 MHz, DMSO-$d_6$) δ 8.54 (s, 1H), 7.32-7.20 (m, 2H), 7.14 (td, J=8.5, 3.2 Hz, 1H), 3.97 (s, 3H), 2.13 (s, 3H). LC-MS (Method 1): m/z: 316.95 $[M+H]^+$, (ESI+), RT=1.06 and unreacted starting material methyl 6-chloro-3-(4-fluoro-2-methyl-phenoxy)pyridazine-4-carboxylate (0.220 g, 13%) as a pale yellow oil.

Step 4: 3-(4-fluoro-2-methyl-phenoxy)-6-(trifluoromethyl)pyridazine-4-carboxylic acid: To a mixture of methyl 3-(4-fluoro-2-methyl-phenoxy)-6-(trifluoromethyl) pyridazine-4-carboxylate (0.770 g, 2.31 mmol) in THF: $H_2O$ (10 mL, 4:1; v/v), lithium hydroxide (0.288 g, 11.5 mmol) was added and the mixture was stirred at rt overnight. The reaction was diluted with water (10 mL) and the pH was adjusted to 1 by dropwise addition of 1M HCl. The solids were filtered, washed with water (2×10 mL), dissolved in EtOAc (20 mL), dried over sodium sulphate and concentrated under reduced pressure to obtain the title compound 3-(4-fluoro-2-methyl-phenoxy)-6-(trifluoromethyl) pyridazine-4-carboxylic acid (0.640 g, 87%) as an off white solid. $^1H$ NMR (400 MHz, DMSO-$d_6$) δ 8.49 (s, 1H), 7.31-7.22 (m, 2H), 7.18-7.09 (m, 1H), 2.12 (s, 3H). LC-MS (Method 1): m/z: 316.95 $[M+H]^+$, (ESI+), RT=1.06.

The intermediates listed in Table 18 were synthesized by a similar method as described for step 1 of Intermediate 1 synthesis using appropriate starting materials.

TABLE 18

| Intermediate | Structure and name | Analytical data |
|---|---|---|
| 2 | 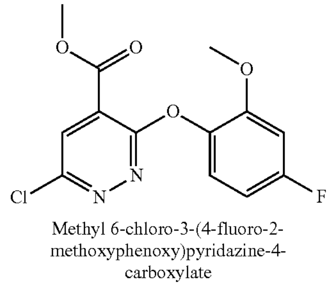 [SMILES: COC(=O)c1cc(Cl)nnc1Oc1ccc(F)cc1OC] Methyl 6-chloro-3-(4-fluoro-2-methoxyphenoxy)pyridazine-4-carboxylate | $^1H$ NMR (400 MHz, DMSO-$d_6$) δ 8.24 (s, 1H), 7.28 (dd, J = 8.8, 5.8 Hz, 1H), 7.12 (dd, J = 10.7, 2.9 Hz, 1H), 6.88-6.79 (m, 1H), 3.93 (s, 3H), 3.71 (s, 3H). LC-MS (Method 1) m/z: 313.3/315.3 $[M + H]^+$, (ESI+), RT = 1.20 |

TABLE 18-continued

| Intermediate | Structure and name | Analytical data |
|---|---|---|
| 3 | 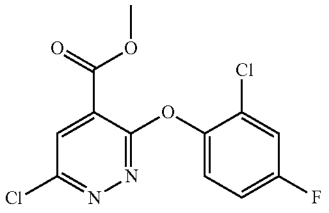 Methyl 6-chloro-3-(2,4-difluorophenoxy)pyridazine-4-carboxylate | LC-MS: m (Method 2): m/z 301.0, 302.9 $[M + H]^+$ |
| 4 | 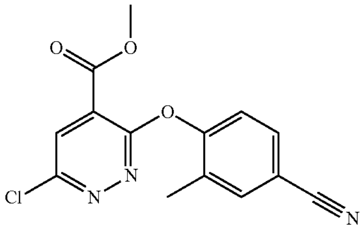 Methyl 6-chloro-3-(4-cyano-2-methylphenoxy)pyridazine-4-carboxylate | $^1H$ NMR (300 MHz, $CDCl_3$) δ 7.96 (s, 1H), 7.65-7.49 (m, 3H), 7.23 (dd, J = 8.3, 2.7 Hz, 1H), 4.04 (s, 1H), 4.03 (s, 3H), 2.24 (d, J = 1.6 Hz, 3H) |
| 5 | 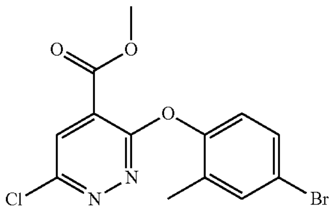 Methyl 3-(4-bromo-2-methylphenoxy)-6-chloropyridazine-4-carboxylate | $^1H$ NMR (300 MHz, $CDCl_3$) δ 7.90 (s, 1H), 7.43 (td, J = 2.9, 2.4, 1.6 Hz, 1H), 7.36 (ddd, J = 8.5, 2.5, 0.7 Hz, 1H), 6.99 (dd, J = 8.5, 6.4 Hz, 1H), 4.02(d, J = 1.5 Hz, 3H), 2.17 (s, 3H). |
| 6 | 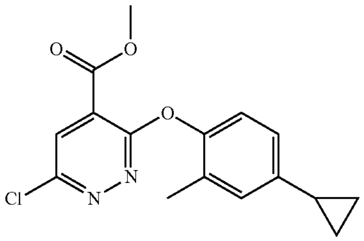 Methyl 6-chloro-3-(4-cyclopropyl-2-methylphenoxy)pyridazine-4-carboxylate | $^1H$ NMR (300 MHz, $CDCl_3$) δ 7.87 (s, 1H), 7.04-6.88 (m, 3H), 4.00 (s, 3H), 2.14 (s, 3H), 1.88 (tt, J = 8.4, 5.0 Hz, 1H), 1.02-0.86 (m, 2H), 0.76-0.62 (m, 2H). |
| 7 | 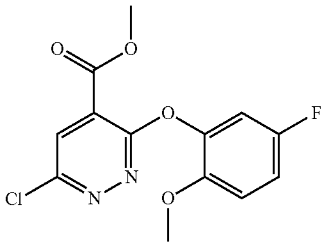 Methyl 6-chloro-3-(5-fluoro-2-methoxyphenoxy)pyridazine-4-carboxylate | $^1H$ NMR (300 MHz, DMSO-$d_6$) δ 8.29 (s, 1H), 7.38-7.07 (m, 3H), 3.94 (s, 3H), 3.68 (s, 3H). |

TABLE 18-continued

| Intermediate | Structure and name | Analytical data |
| --- | --- | --- |
| 8 | 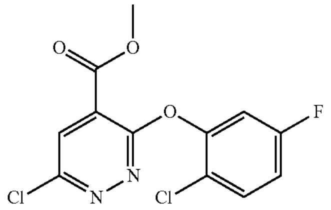 Methyl 6-chloro-3-(2-chloro-5-fluorophenoxy)pyridazine-4-carboxylate | $^1$H NMR (300 MHz, $CDCl_3$) δ 7.97 (s, 1H), 7.45 (ddd, J = 9.0, 5.6, 3.7 Hz, 1H), 7.08 (dt, J = 8.5, 3.2 Hz, 1H), 7.04-6.94 (m, 1H), 4.03 (d, J = 1.1 Hz,3H). |
| 9 | 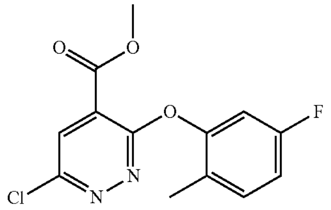 Methyl 6-chloro-3-(5-fluoro-2-methylphenoxy)pyridazine-4-carboxylate | $^1$H NMR (300 MHz, $CDCl_3$) δ 7.92 (s, 1H), 7.25-7.19 (m, 1H), 6.98-6.77 (m, 2H), 4.02 (d, J = 1.8 Hz, 3H), 2.14 (d, J = 1.0 Hz, 3H). |
| 10 | 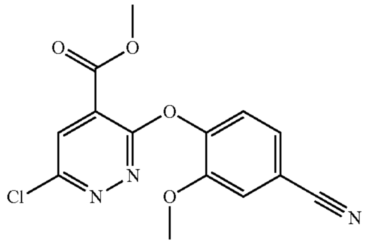 Methyl 6-chloro-3-(4-cyano-2-methoxyphenoxy)pyridazine-4-carboxylate | $^1$H NMR (300 MHz, $CDCl_3$) δ 7.96 (s, 1H), 7.42-7.17 (m, 3H), 4.03 (d, J = 3.2 Hz, 3H), 3.77 (d, J = 6.0 Hz, 3H) |
| 11 | 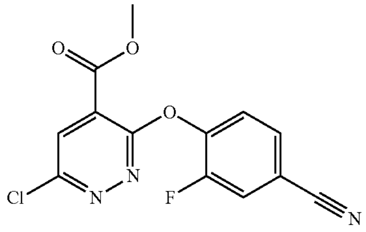 Methyl 6-chloro-3-(4-cyano-2-fluorophenoxy)pyridazine-4-carboxylate | $^1$H NMR (300 MHz, $CDCl_3$) δ 8.01 (s, 1H), 7.60-7.31 (m, 3H), 4.03 (d, J = 2.0 Hz, 3H) |
| 12 | 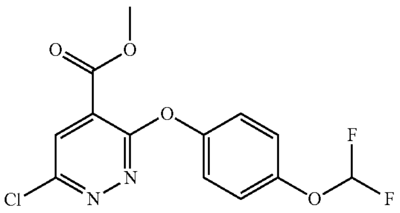 Methyl 6-chloro-3-(4-(difluoromethoxy)phenoxy)pyridazine-4-carboxylate | $^1$H NMR (400 MHz, DMSO-$d_6$) δ 8.27 (s, 1H), 7.46-7.05 (m, 5H), 3.92 (s, 3H). LC-MS (Method 1): m/z 330.95 $[M + H]^+$, (ESI+), RT = 1.20 |

TABLE 18-continued

| Intermediate | Structure and name | Analytical data |
|---|---|---|
| 13 | 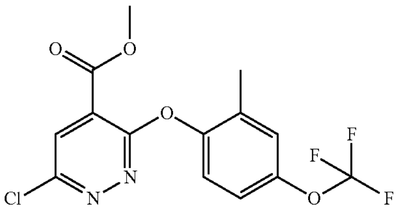 Methyl 6-chloro-3-(2-methyl-4-(trifluoromethoxy)phenoxy)pyridazine-4-carboxylate | $^1$H NMR (400 MHz, DMSO-$d_6$) δ 8.29 (s, 1H), 7.44-7.40 (m, 1H), 7.39-7.26 (m, 2H), 3.94 (s, 3H), 2.16 (s, 3H). LC-MS (Method 1): m/z 363.0 $[M + H]^+$, (ESI+), RT = 1.32 |
| 14 | 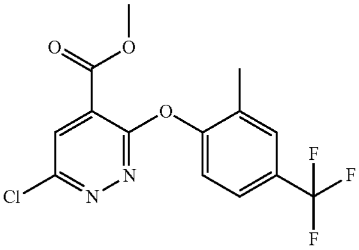 Methyl 6-chloro-3-(2-methyl-4-(trifluoromethyl)phenoxy)pyridazine-4-carboxylate | $^1$H NMR (400 MHz, DMSO-$d_6$) δ 8.29 (s, 1H), 7.78-7.74 (m, 1H), 7.67-7.61 (m, 1H), 7.47-7.38 (m, 1H), 3.92 (s, 3H), 2.20 (s, 3H). LC-MS(Method 1): m/z 347.1 $[M + H]^+$, (ESI+), RT = 0.98 |
| 15 | 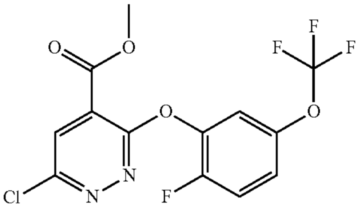 Methyl 6-chloro-3-(2-methyl-4-(trifluoromethyl)phenoxy)pyridazine-4-carboxylate | $^1$H NMR (400 MHz, DMSO-$d_6$) δ 8.35 (s, 1H), 7.68-7.57 (m, 2H), 7.48-7.40 (m, 1H), 3.94 (s, 3H). LC-MS (Method 1): m/z 367.3 $[M + H]^+$, (ESI+), RT = 1.30 |
| 16 | 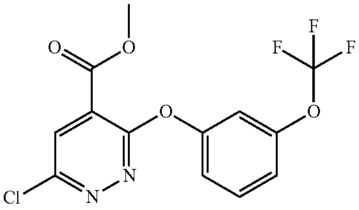 Methyl 6-chloro-3-(3-(trifluoromethoxy)phenoxy)pyridazine-4-carboxylate | $^1$H NMR (400 MHz, DMSO-$d_6$) δ 8.30 (s, 1H), 7.64-7.58 (m, 1H), 7.41-7.28 (m, 3H), 3.92 (s, 3H). LC-MS (Method1): m/z 348.95 $[M + H]^+$, (ESI+), RT = 1.29 |
| 17 | 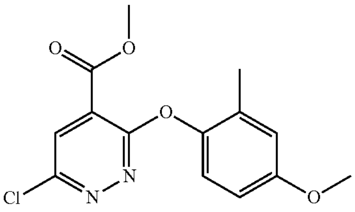 Methyl 6-chloro-3-(4-methoxy-2-methylphenoxy)pyridazine-4-carboxylate | $^1$H NMR (400 MHz, DMSO-$d_6$) δ 8.21 (s, 1H), 7.07 (d, J = 8.8 Hz, 1H), 6.90-6.88 (m, 1H), 6.84-6.77 (m, 1H), 3.92 (s, 3H), 3.75 (s, 3H), 2.05 (s, 3H) LC-MS (Method 1): m/z 309.0 $[M + H]^+$, (ESI+), RT = 1.22 |

TABLE 18-continued

| Intermediate | Structure and name | Analytical data |
|---|---|---|
| 18 | 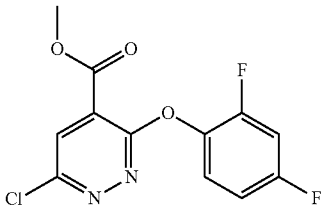 Methyl 6-chloro-3-(2,4-difluorophenoxy)pyridazine-4-carboxylate | LC-MS (ESI): m/z 301.0, 302.9[M + H]$^+$ |

The intermediates listed in Table 19 were synthesized by a similar method as described for step 2 of Intermediate 1 synthesis using appropriate starting material.

TABLE 19

| Intermediate | Structure and name | Analytical data |
|---|---|---|
| 19 | 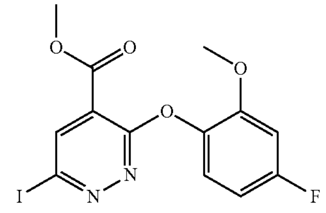 Methyl 3-(4-fluoro-2-methoxyphenoxy)-6-iodopyridazine-4-carboxylate | $^1$H NMR (400 MHz, DMSO-$d_6$) δ 8.35 (s, 1H), 7.25 (m, 1H), 7.13-7.09 (m, 1H), 6.84-6.79 (m, 1H), 3.90 (s, 3H), 3.70 (s, 3H). LC-MS (Method 1): m/z: 404.9 [M + H]$^+$, (ESI+), RT = 1.19 |
| 20 | 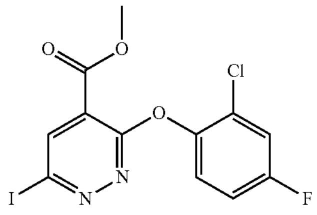 Methyl 3-(2,4-difluorophenoxy-6-iodopyridazine-4-carboxylate | MS (ESI+): m/z 392.9 [M + H]$^+$. |
| 21 | 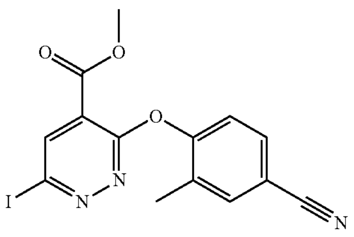 Methyl 3-(4-cyano-2-methylphenoxy)-6-iodopyridazine-4-carboxylate | MS (ESI+): m/z 396.1 [M + H]$^+$ |

TABLE 19-continued

| Intermediate | Structure and name | Analytical data |
| --- | --- | --- |
| 22 | 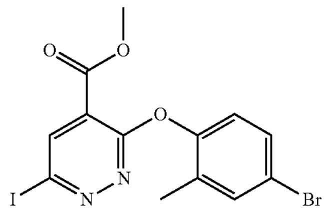 Methyl 3-(4-bromo-2-methylphenoxy)-6-iodopyridazine-4-carboxylate | MS (ESI+): m/z 449.0, 451.0[M + H]+ |
| 23 | 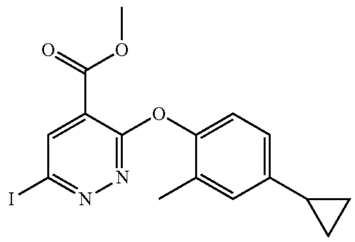 Methyl 3-(4-cyclopropyl)-2-methylphenoxy)-6-iodopyridazine-4-carboxylate | MS(ESI+): m/z 411.1,413.1[M + H]+ |
| 24 | 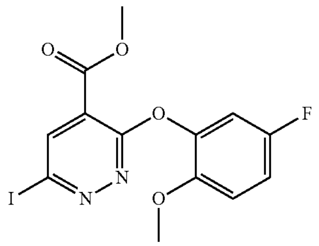 Methyl 3-(5-fluoro-2-methoxyphenoxy)-6-iodopyridazine-4-carboxylate | MS(ESI+): m/z 405.1[M + H]+ |
| 25 | 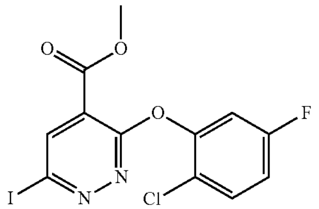 Methyl 3-(2-chloro-5-fluorophenoxy)-6-iodopyridazine-4-carboxylate | |
| 26 | 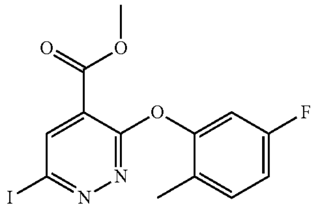 Methyl 3-(5-fluoro-2-methylphenoxy)-6-iodopyridazine-4-carboxylate | MS(ESI+): m/z 389.0[M + H]+ |

TABLE 19-continued

| Intermediate | Structure and name | Analytical data |
| --- | --- | --- |
| 27 | 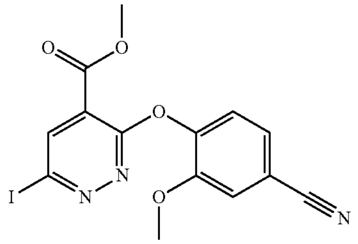 methyl 3-(4-cyano-2-methoxyphenoxy)-6-iodopyridazine-4-carboxylate | MS(ESI+): m/z 412.1 [M + H]$^+$ |
| 28 | 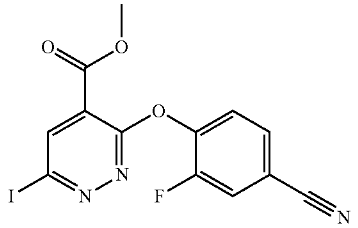 Methyl 3-(4-cyano-2-fluorophenoxy)-6-iodopyridazine-4-carboxylate | MS(ESI+): m/z 400.0 [M + H]$^+$ |
| 29 | 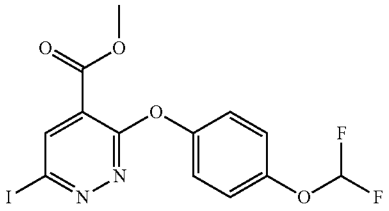 Methyl 3-(4-(difluoromethoxy)phenoxy)-6-iodopyridazine-4-carboxylate | $^1$H NMR (500 MHz, DMSO-$d_6$) δ 8.38 (s, 1H), 7.41-7.10 (m, 5H), 3.90 (s, 3H). LC-MS (Method 1): m/z 422.95 [M + H]$^+$, (ESI+), RT = 1.23 |
| 30 | 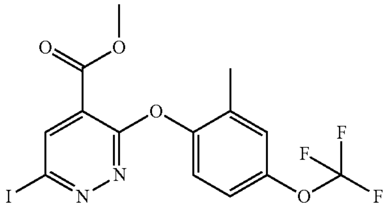 Methyl 6-iodo-3-(2-methyl-4-(trifluoromethoxy)phenoxy)pyridazine-4-carboxylate | $^1$H NMR (500 MHz, DMSO-$d_6$) δ 8.40 (s, 1H), 7.43-7.39 (m, 1H), 7.34-7.24 (m, 2H), 3.91 (s, 3H), 2.14 (s, 3H). LC-MS (Method 1): m/z 454.95 [M + H]$^+$, (ESI+), RT = 1.35 |
| 31 | 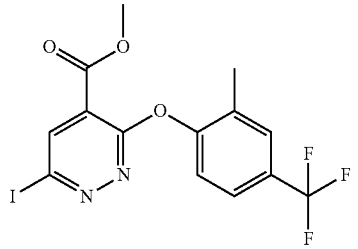 Methyl 6-iodo-3-(2-methyl-4-(trifluoromethyl)phenoxy)pyridazine-4-carboxylate | LC-MS (Method 1): m/z 438.9 [M + H]$^+$, (ESI+), RT = 1.35 |

TABLE 19-continued

| Intermediate | Structure and name | Analytical data |
| --- | --- | --- |
| 32 | 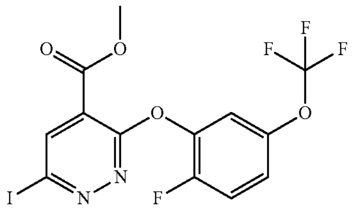<br>Methyl 3-(2-fluoro-5-(trifluoromethoxy)phenoxy)-6-iodopyridazine-4-carboxylate | $^1$H NMR (400 MHz, DMSO-$d_6$) δ 8.35 (s, 1H), 7.68-7.57 (m, 2H), 7.47-7.41 (m, 1H), 3.94 (s, 3H). LC-MS (Method 1): m/z 458.9 $[M + H]^+$, (ESI+), RT = 1.31 |
| 33 | 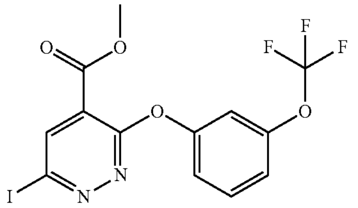<br>Methyl 6-iodo-3-(3-(trifluoromethoxy)phenoxy)pyridazine-4-carboxylate | $^1$H NMR (400 MHz, DMSO-$d_6$) δ 8.41 (s, 1H), 7.65-7.57 (m, 1H), 7.37-7.25 (m, 3H), 3.90 (s, 3H). LC-MS (Method 3): m/z 441.1 $[M + H]^+$, (ESI+), RT = 0.87 |
| 34 | 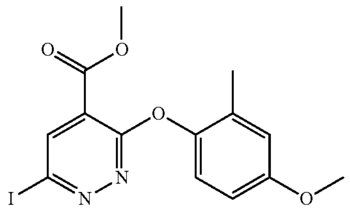<br>Methyl 6-iodo-3-(4-methoxy-2-methylphenoxy)pyridazine-4-carboxylate | LC-MS (Method 1): m/z 401.0 [M + H]+, (ESI+), RT = 1.24 |
| 35 | 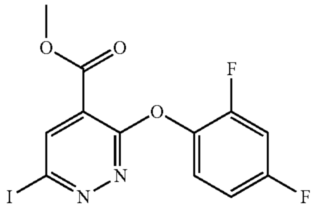<br>Methyl 3-(2,4-difluorophenoxy)-6-iodopyridazine-4-carboxylate | LC-MS (ESI): m/z 392.9 $[M + H]^+$ |

The intermediates listed in Table 20 were synthesized by a similar method as described for step 3 of Intermediate 1 synthesis using appropriate starting material.

TABLE 20

| Intermediate | Structure and name | Analytical data |
| --- | --- | --- |
| 36 | 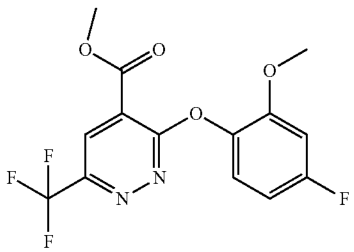 [SMILES: COC(=O)c1cc(C(F)(F)F)nnc1Oc1ccc(F)cc1OC] | $^1$H NMR (500 MHz, DMSO-$d_6$) δ 8.53 (s, 1H), 7.32 (dd, J = 8.8, 5.8 Hz, 1H), 7.16 (dd, J = 10.7, 2.9 Hz, 1H), 6.87 (td, J = 8.5, 2.9 Hz, 1H), 3.96 (s, 3H), 3.72 (s, 3H). LC-MS(Method 3): m/z: 347.3 $[M + H]^+$, (ESI+), RT = 3.57 |

TABLE 20-continued

| Intermediate | Structure and name | Analytical data |
|---|---|---|
| | Methyl 3-(4-fluoro-2-methoxyphenoxy)-6-(trifluoromethyl)pyridazine-4-carboxylate | |
| 37 | 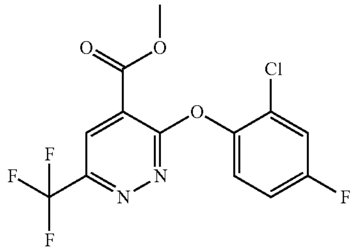 Methyl 3-(2,4-difluorophenoxy)-6-(trifluoromethyl)pyridazine-4-carboxylate | MS(ESI+): m/z 335.0 $[M + H]^+$. |
| 38 | 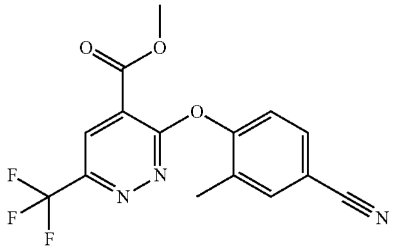 [SMILES: COC(=O)c1cc(C(F)(F)F)nnc1Oc1ccc(C#N)cc1C] Methyl 3-(4-cyano-2-methylphenoxy)-6-(trifluoromethyl)pyridazine-4-carboxylate | $^1H$ NMR (300 MHz, $CDCl_3$) δ 8.28 (s, 1H), 7.68-7.55 (m, 2H), 7.27 (d, J = 8.5 Hz, 2H), 4.06 (s, 3H), 2.25 (s, 3H). |
| 39 | 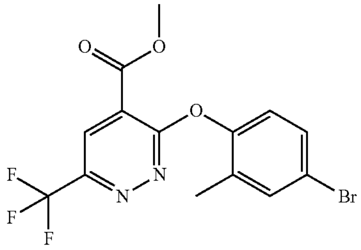 [SMILES: COC(=O)c1cc(C(F)(F)F)nnc1Oc1ccc(Br)cc1C] Methyl 3-(4-bromo-2-methylphenoxy)-6-(trifluoromethyl)pyridazine-4-carboxylate | $^1H$ NMR (300 MHz, DMSO-$d_6$) δ 8.62 (s, 1H), 7.70 (dd, J = 2.5, 0.8 Hz, 1H), 7.57 (ddd, J = 8.6, 2.5, 0.7 Hz, 1H), 7.29 (d, J = 8.6 Hz, 1H), 4.03 (s, 3H), 2.19 (s, 3H) |
| 40 | 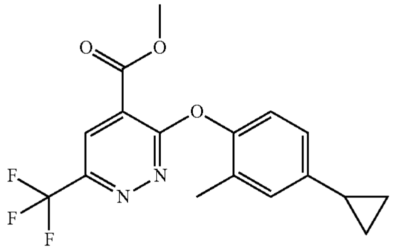 [SMILES: COC(=O)c1cc(C(F)(F)F)nnc1Oc1ccc(C2CC2)cc1C] Methyl 3-(4-cyclopropyl-2-methylphenoxy)-6-(trifluoromethyl)pyridazine-4-carboxylate | $^1H$ NMR (300 MHz, $CDCl_3$) δ 8.20 (d, J = 3.1 Hz, 1H), 7.11-6.85 (m, 3H), 4.08-3.99 (m, 5H), 2.21 (dd, J = 9.1, 3.7 Hz, 1H), 2.16 (d, J = 7.0 Hz,4H), 1.06-0.84 (m, 2H), 0.78-0.52 (m, 2H). |

TABLE 20-continued

| Intermediate | Structure and name | Analytical data |
|---|---|---|
| 41 | 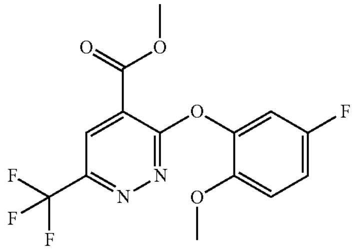 [SMILES: COC(=O)c1cc(C(F)(F)F)nnc1Oc1cc(F)ccc1OC] Methyl 3-(5-fluoro-2-methoxyphenoxy)-6-(trifluoromethyl)pyridazine-4-carboxylate | $^1H$ NMR (300 MHz, $CDCl_3$) δ 8.25 (s, 1H), 7.07-6.88 (m, 3H), 4.05 (s, 3H), 3.70 (s, 3H). |
| 42 | 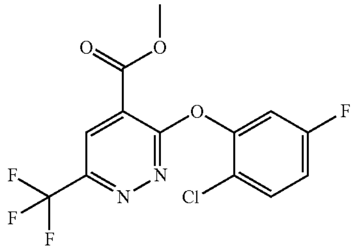 [SMILES: COC(=O)c1cc(C(F)(F)F)nnc1Oc1cc(F)ccc1Cl] Methyl 3-(2-chloro-5-fluorophenoxy)-6-(trifluoromethyl)pyridazine-4-carboxylate | $^1H$ NMR (300 MHz, $CDCl_3$) δ 8.29 (s, 1H), 7.47 (dd, J = 8.9, 5.6 Hz, 1H), 7.17-6.97 (m, 2H), 4.07 (s, 3H). |
| 43 | 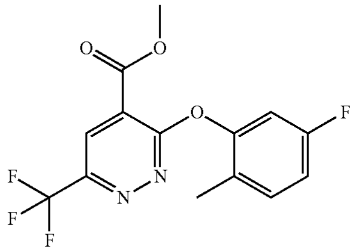 [SMILES: COC(=O)c1cc(C(F)(F)F)nnc1Oc1cc(F)ccc1C] Methyl 3-(5-fluoro-2-methylphenoxy)-6-(trifluoromethyl)pyridazine-4-carboxylate | MS(ESI+): m/z 331.1[M + H]$^+$ |
| 44 | 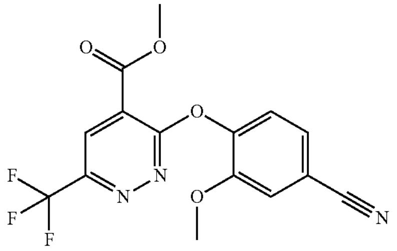 [SMILES: COC(=O)c1cc(C(F)(F)F)nnc1Oc1ccc(C#N)cc1OC] Methyl 3-(4-cyano-2-methoxyphenoxy)-6-(trifluoromethyl)pyridazine-4-carboxylate | $^1H$ NMR (300 MHz, $CDCl_3$) δ 8.28 (s, 1H), 7.43-7.30 (m, 2H), 7.30-7.23 (m, 2H), 4.06 (s, 3H), 3.76 (s, 3H). |

TABLE 20-continued

| Intermediate | Structure and name | Analytical data |
|---|---|---|
| 45 | 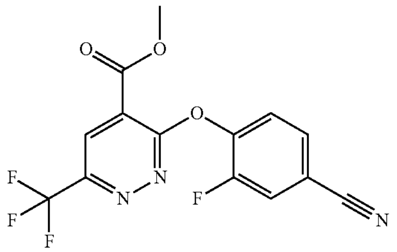 [SMILES: COC(=O)c1cc(C(F)(F)F)nnc1Oc1ccc(C#N)cc1F] Methyl 3-(4-cyano-2-fluorophenoxy)-6-(trifluoromethyl)pyridazine-4-carboxylate | $^1H$ NMR (300 MHz, $CDCl_3$) δ 8.32 (s, 1H), 7.62-7.53 (m, 2H), 7.51-7.44 (m, 1H), 4.07 (s, 3H). |
| 46 | 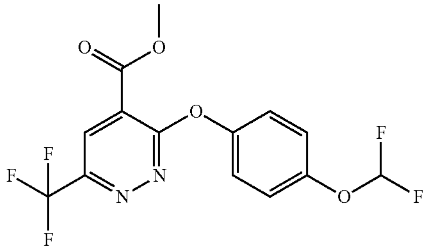 [SMILES: COC(=O)c1cc(C(F)(F)F)nnc1Oc1ccc(OC(F)F)cc1] Methyl 3-(4-(difluoromethoxy)phenoxy)-6-(trifluoromethyl)pyridazine-4-carboxylate | $^1H$ NMR (500 MHz, DMSO-$d_6$) δ 8.54 (s, 1H), 7.44-7.12 (m, 5H), 3.96 (s, 3H). LC-MS (Method 1): m/z 365.0 $[M + H]^+$, (ESI+), RT = 1.26 |
| 47 | 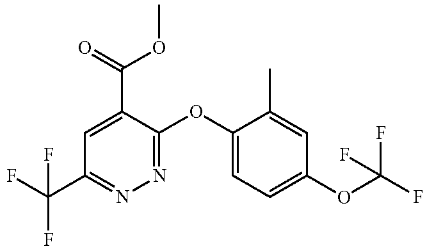 [SMILES: COC(=O)c1cc(C(F)(F)F)nnc1Oc1ccc(OC(F)(F)F)cc1C] Methyl 3-(2-methyl-4-(trifluoromethoxy)phenoxy)-6-(trifluoromethyl)pyridazine-4-carboxylate | $^1H$ NMR (500 MHz, DMSO-$d_6$) δ 8.56 (s, 1H), 7.45 (d, J = 2.7 Hz, 1H), 7.40 (d, J = 8.7 Hz, 1H), 7.33 (dd, J = 8.9, 2.7 Hz, 1H), 3.97 (s, 3H), 2.17 (s, 3H). LC-MS (Method 1): m/z 397.0 $[M + H]^+$, (ESI+), RT = 1.38 |
| 48 | 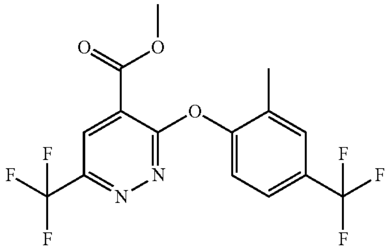 [SMILES: COC(=O)c1cc(C(F)(F)F)nnc1Oc1ccc(C(F)(F)F)cc1C] Methyl 3-(2-methyl-4-(trifluoromethyl)phenoxy)-6-(trifluoromethyl)pyridazine-4-carboxylate | $^1H$ NMR (400 MHz, DMSO-$d_6$) δ 8.57 (s, 1H), 7.80 (d, J = 1.8 Hz, 1H), 7.68 (dd, J = 8.5, 2.2 Hz, 1H), 7.48 (d, J = 8.4 Hz, 1H), 3.96 (s, 3H), 2.22 (s, 3H). LC-MS (Method 1): m/z 381.0 $[M + H]^+$, (ESI+), RT = 1.36 |

TABLE 20-continued

| Intermediate | Structure and name | Analytical data |
|---|---|---|
| 49 | 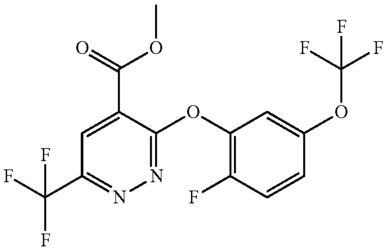 [SMILES: COC(=O)c1cc(C(F)(F)F)nnc1Oc1cc(OC(F)(F)F)ccc1F] Methyl 3-(2-fluoro-5-(trifluoromethoxy)phenoxy)-6-(trifluoromethyl)pyridazine-4-carboxylate | $^1$H NMR (500 MHz, DMSO-$d_6$) δ 8.62 (s, 1H), 7.72 (dd, J = 6.1, 2.7 Hz, 1H), 7.65 (t, J = 9.5 Hz, 1H), 7.51-7.46 (m, 1H), 3.97 (s, 3H). LC-MS (Method 1): m/z 400.95 [M + H]+, (ESI+), RT = 1.36 |
| 50 | 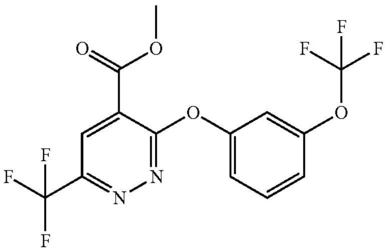 [SMILES: COC(=O)c1cc(C(F)(F)F)nnc1Oc1cccc(OC(F)(F)F)c1] Methyl 3-(3-(trifluoromethoxy)phenoxy)-6-(trifluoromethyl)pyridazine-4-carboxylate | $^1$H NMR (400 MHz, DMSO-$d_6$) δ 8.57 (s, 1H), 7.68-7.60 (m, 1H), 7.49-7.44 (m, 1H), 7.43-7.33 (m, 2H), 3.96 (s, 3H). LC-MS (Method 1): m/z 382.95 $[M + H]^+$, (ESI+), RT = 1.38 |
| 51 | 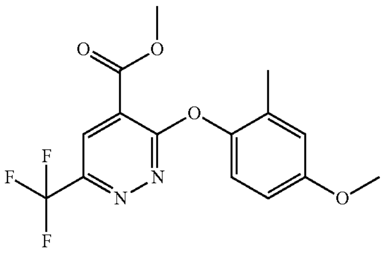 [SMILES: COC(=O)c1cc(C(F)(F)F)nnc1Oc1ccc(OC)cc1C] methyl 3-(4-methoxy-2-methylphenoxy)-6-(trifluoromethyl)pyridazine-4-carboxylate | $^1$H NMR (400 MHz, DMSO-$d_6$) δ 8.50 (s, 1H), 7.13 (d, J = 8.8 Hz, 1H), 6.92 (d, J = 3.0 Hz, 1H), 6.83 (dd, J = 8.8, 3.1 Hz, 1H), 3.95 (s, 3H), 3.76 (s, 3H), 2.07 (s, 3H).LC-MS (Method 4): m/z 343.0 $[M + H]^+$, (ESI+), RT = 1.29 |
| 52 | 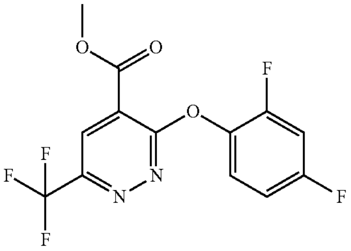 [SMILES: COC(=O)c1cc(C(F)(F)F)nnc1Oc1ccc(F)cc1F] Methyl 3-(2,4-difluorophenoxy)-6-(trifluoromethyl)pyridazine-4-carboxylate | LC-MS (ESI): m/z 335.0 $[M + H]^+$ |

The intermediates listed in Table 21 were synthesized by a similar method as described for step 4 of Intermediate 1 synthesis using appropriate starting materials.

TABLE 21

| Intermediate | Structure and name | Analytical data |
|---|---|---|
| 53 | 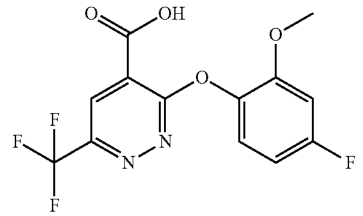 [SMILES: COc1cc(F)ccc1Oc1nnc(C(F)(F)F)cc1C(=O)O] 3-(4-Fluoro-2-methoxyphenoxy)-6-(trifluoromethyl)pyridazine-4-carboxylic acid | $^{1}H$ NMR (500 MHz, DMSO-$d_6$) δ 8.11 (s, 1H), 7.24 (dd, J = 8.8, 5.9 Hz, 1H), 7.12 (dd, J = 10.7, 2.8 Hz, 1H), 6.84 (dt, J = 8.5, 4.2 Hz, 1H), 3.71 (s, 4H). LC-MS(Method 1): m/z: 332.95 $[M + H]^+$, (ESI+), RT = 1.03 |
| 54 | 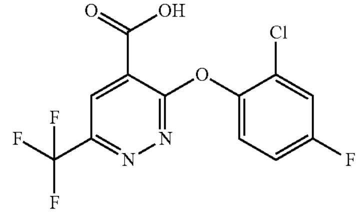 [SMILES: O=C(O)c1cc(C(F)(F)F)nnc1Oc1ccc(F)cc1Cl] 3-(2,4-Difluorophenoxy)-6-(trifluoromethyl)pyridazine-4-carboxylic acid | LC-MS (Method 2): m/z 321.0 $[M + H]^+$. |
| 55 | 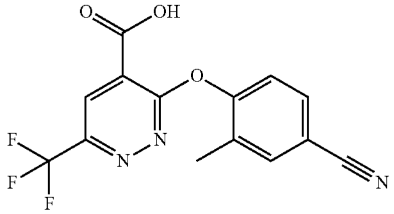 [SMILES: Cc1cc(C#N)ccc1Oc1nnc(C(F)(F)F)cc1C(=O)O] 3-(4-Cyano-2-methylphenoxy)-6-(trifluoromethyl)pyridazine-4-carboxylic acid | $^{1}H$ NMR (300 MHz, DMSO-$d_6$) δ 8.55 (s, 1H), 7.95 (d, J = 2.1 Hz, 1H), 7.82 (dd, J = 8.4, 2.1 Hz, 1H), 7.48 (d, J = 8.4 Hz, 1H), 2.20 (s, 3H). |
| 56 | 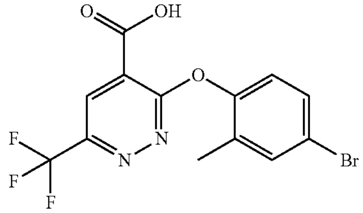 [SMILES: Cc1cc(Br)ccc1Oc1nnc(C(F)(F)F)cc1C(=O)O] 3-(4-Bromo-2-methylphenoxy)-6-(trifluoromethyl)pyridazine-4-carboxylic acid | $^{1}H$ NMR (300 MHz, DMSO-$d_6$) δ 8.56 (s, 1H), 7.69 (dd, J = 2.4, 0.9 Hz, 1H), 7.56 (dd, J = 8.6, 2.5 Hz, 1H), 7.29 (d, J = 8.6 Hz, 1H), 2.18 (s, 3H). |
| 57 | 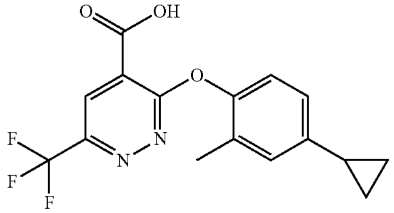 [SMILES: Cc1cc(C2CC2)ccc1Oc1nnc(C(F)(F)F)cc1C(=O)O] 3-(4-Cyclopropyl-2-methylphenoxy)-6-(trifluoromethyl)pyridazine-4-carboxylic acid | MS(ESI+): m/z 337.0 $[M - H]^+$ |

TABLE 21-continued

| Intermediate | Structure and name | Analytical data |
|---|---|---|
| 58 | 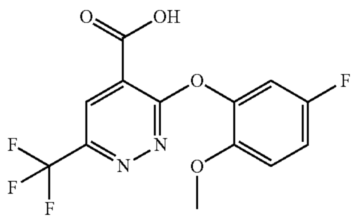 [SMILES: COc1ccc(F)cc1Oc1nnc(C(F)(F)F)cc1C(=O)O] 3-(5-Fluoro-2-methoxyphenoxy)-6-(trifluoromethyl)pyridazine-4-carboxylic acid | $^1H$ NMR (300 MHz, DMSO-$d_6$) δ 8.51 (s, 1H), 7.38-7.29 (m, 1H), 7.29-7.12 (m, 2H), 3.69 (s, 3H) |
| 59 | 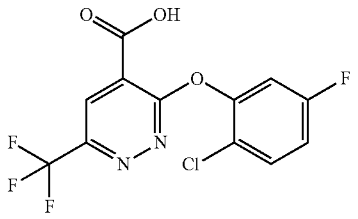 [SMILES: O=C(O)c1cc(C(F)(F)F)nnc1Oc1cc(F)ccc1Cl] 3-(2-Chloro-5-fluorophenoxy)-6-(trifluoromethyl)pyridazine-4-carboxylic acid | $^1H$ NMR (300 MHz, DMSO-$d_6$) δ 8.62 (s, 1H), 7.79 (dd, J = 9.0, 5.7 Hz, 1H), 7.62 (dd, J = 9.1, 3.0 Hz, 1H), 7.47-7.26 (m, 1H). |
| 60 | 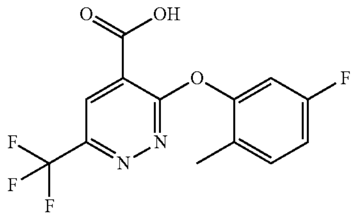 [SMILES: Cc1ccc(F)cc1Oc1nnc(C(F)(F)F)cc1C(=O)O] 3-(5-Fluoro-2-methylphenoxy)-6-(trifluoromethyl)pyridazine-4-carboxylic acid | $^1H$ NMR (300 MHz, DMSO-$d_6$) δ 8.27 (s, 1H), 7.40 (dd, J = 8.5, 6.6 Hz, 1H), 7.21-7.03 (m, 2H), 2.07 (d, J = 2.9 Hz, 3H). |
| 61 | 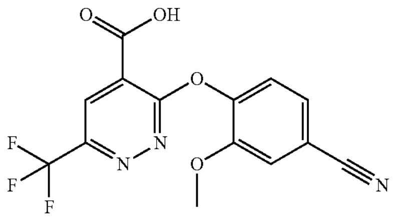 [SMILES: COc1cc(C#N)ccc1Oc1nnc(C(F)(F)F)cc1C(=O)O] 3-(4-Cyano-2-methoxyphenoxy)-6-(trifluoromethyl)pyridazine-4-carboxylic acid | $^1H$ NMR (300 MHz, DMSO-$d_6$) δ 8.53 (s, 1H), 7.76 (d, J = 1.8 Hz, 1H), 7.63-7.49 (m, 2H), 3.77 (s, 3H) |
| 62 | 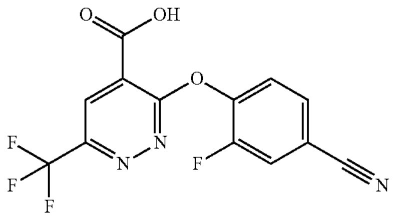 [SMILES: N#Cc1ccc(Oc2nnc(C(F)(F)F)cc2C(=O)O)c(F)c1] 3-(4-Cyano-2-fluorophenoxy)-6-(trifluoromethyl)pyridazine-4-carboxylic acid | $^1H$ NMR (300 MHz, DMSO-$d_6$) δ 8.56 (s, 1H), 8.26-8.10 (m, 1H), 7.96-7.80 (m, 1H), 7.83-7.71 (m, 1H). |

TABLE 21-continued

| Intermediate | Structure and name | Analytical data |
|---|---|---|
| 63 | 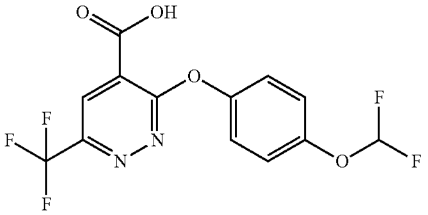 [SMILES: O=C(O)c1cc(C(F)(F)F)nnc1Oc1ccc(OC(F)F)cc1] 3-(4-(Difluoromethoxy)phenoxy)-6-(trifluoromethyl)pyridazine-4-carboxylic acid | $^1$H NMR (400 MHz, DMSO-$d_6$) δ 8.48 (s, 1H), 7.47-7.06 (m, 5H).LC-MS (Method 1): m/z 350.95 [M + H]$^+$, (ESI+), RT = 1.07 |
| 64 | 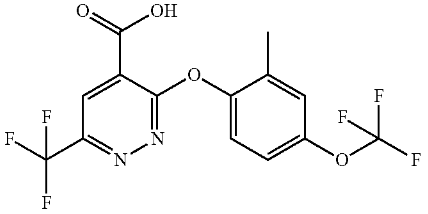 [SMILES: Cc1cc(OC(F)(F)F)ccc1Oc1nnc(C(F)(F)F)cc1C(=O)O] 3-(2-Methyl-4-(trifluoromethoxy)phenoxy)-6-(trifluoromethyl)pyridazine-4-carboxylic acid | $^1$H NMR (400 MHz, DMSO-$d_6$) δ 8.50 (s, 1H), 7.46-7.29 (m, 3H), 2.16 (s, 3H). LC-MS (Method 1): m/z 382.95 [M + H]$^+$, (ESI+), RT = 1.19 |
| 65 | 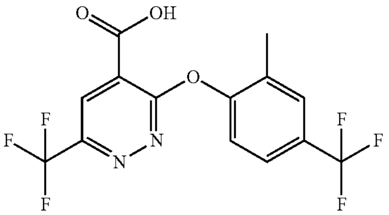 [SMILES: Cc1cc(C(F)(F)F)ccc1Oc1nnc(C(F)(F)F)cc1C(=O)O] 3-(2-Methyl-4-(trifluoromethyl)phenoxy)-6-(trifluoromethyl)pyridazine-4-carboxylic acid | $^1$H NMR (500 MHz, DMSO-$d_6$) δ 10.16 (s, 1H), 8.51 (s, 1H), 7.82-7.78 (m, 1H), 7.67 (dd, J = 8.5, 2.0 Hz, 1H), 7.46 (d, J = 8.5 Hz, 1H), 2.21 (s, 3H). LC-MS (Method 1): m/z 367.0 [M + H]$^+$, (ESI+), RT = 1.18 |
| 66 | 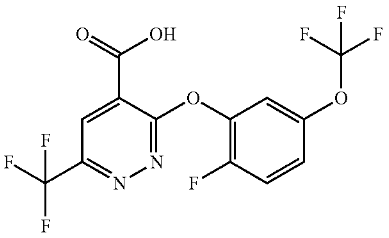 [SMILES: O=C(O)c1cc(C(F)(F)F)nnc1Oc1cc(OC(F)(F)F)ccc1F] 3-(2-Fluoro-5-(trifluoromethoxy)phenoxy)-6-(trifluoromethyl)pyridazine-4-carboxylic acid | $^1$H NMR (400 MHz, DMSO-$d_6$) δ 8.53 (s, 1H), 7.71 (dd, J = 6.3, 2.7 Hz, 1H), 7.67-7.59 (m, 1H), 7.46 (d, J = 9.2 Hz, 1H). LC-MS (Method 1): m/z 386.85 [M + H]$^+$, (ESI+), RT = 1.15 |
| 67 | 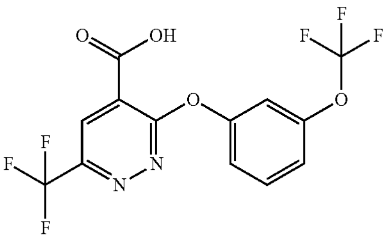 [SMILES: O=C(O)c1cc(C(F)(F)F)nnc1Oc1cccc(OC(F)(F)F)c1] 3-(3-(Trifluoromethoxy)phenoxy)-6-(trifluoromethyl)pyridazine-4-carboxylic acid | LC-MS (Method 1): m/z 368.9 [M + H]$^+$, (ESI+), RT = 1.14 |

TABLE 21-continued

| Intermediate | Structure and name | Analytical data |
|---|---|---|
| 68 | 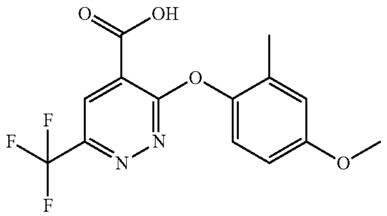 [SMILES: COc1ccc(Oc2nnc(C(F)(F)F)cc2C(=O)O)c(C)c1] 3-(4-Methoxy-2-methylphenoxy)-6-(trifluoromethyl)pyridazine-4-carboxylic acid | $^1H$ NMR (400 MHz, DMSO-$d_6$) δ 8.43 (s, 1H), 7.12 (d, J = 8.8 Hz, 1H), 6.92 (d, J = 3.0 Hz, 1H), 6.83 (dd, J = 8.8, 3.0 Hz, 1H), 3.76 (s, 3H), 2.06 (s, 3H). LC-MS (Method 1): m/z 328.95 $[M + H]^+$, (ESI+), RT = 1.06 |
| 69 | 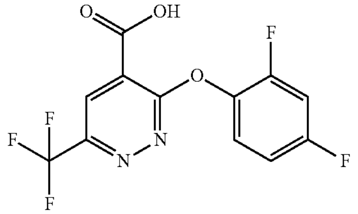 [SMILES: O=C(O)c1cc(C(F)(F)F)nnc1Oc1ccc(F)cc1F] 3-(2,4-Difluorophenoxy)-6-(trifluoromethyl)pyridazine-4-carboxylic acid | LC-MS (ESI): m/z found 321.0 $[M + H]^+$ |

Example 109

Intermediate 70: 2-ethoxy-4-fluoro-phenol

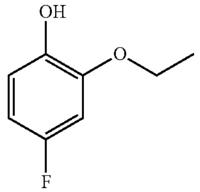

(2-Ethoxy-4-fluoro-phenyl)boronic acid (0.725 g, 3.94 mmol) was dissolved in THE (15.7 mL) and cooled to 0 °C. Then 14.7 M hydrogen peroxide (50% aqueous solution) (50%, 1.2 mL, 17.3 mmol) and 2 M sodium hydroxide (3.9 mL, 7.88 mmol) were added. The reaction mixture was slowly warmed to rt. Stirred at rt for 90 minutes. The reaction was diluted with HCl (2N, 20 mL) and water (10 mL) and extracted with EtOAc (×2). Combined organics dried ($Na_2SO_4$), filtered and concentrated in vacuo to a dark brown gum. Purified by column chromatography in a gradient of (0-50%) ethyl acetate and heptane to yield the title compound 2-ethoxy-4-fluoro-phenol (0.503 g, 690%) as a pale brown oil. $^1H$ NMR (400 MHz, $CDCl_3$) δ 6.83 (dd, J=8.7, 5.5 Hz, 1H), 6.60 (dd, J=9.8, 2.8 Hz, 1H), 6.55 (td, J=8.6, 2.8 Hz, 1H), 5.38 (s, 1H), 4.09 (q, J=7.0 Hz, 2H), 1.46 (t, J=7.0 Hz, 3H). LC-MS (Method 3): m/z: 155.1 $[M-H]^-$, (ESI−), RT=0.61.

Intermediate 71 and 72

Synthesis of tert-butyl (S)-((3-aminophenyl)(methyl)(oxo)-λ$^6$-sulfaneylidene) carbamate [Intermediate 71] and tert-butyl (R)-((3-aminophenyl)(methyl)(oxo)-λ$^6$-sulfaneylidene) carbamate [Intermediate 72]

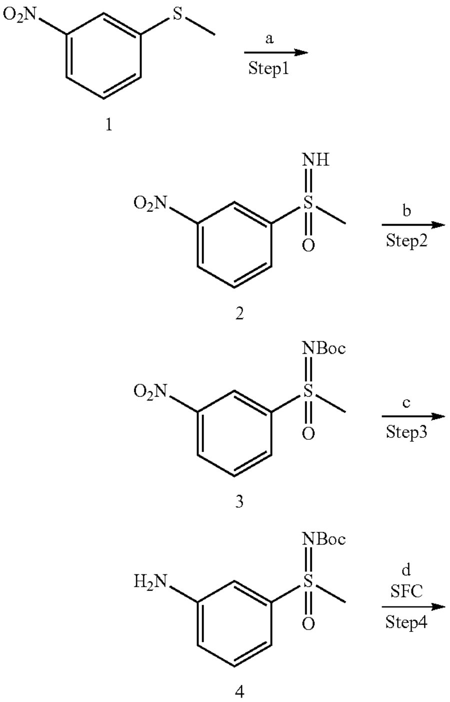

-continued

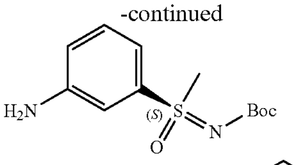

and

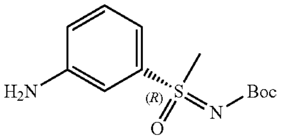

Reagents & conditions: $NH_4(OAc)$, PhI(OAc)2, EtOH, rt, 16 h; b) t-BuOK, $(Boc)_2O$, t-BuOH, reflux, 10 h; c) $Pd(OH)^2$, $H_2$, MeOH, rt, 2 h; d) SFC purification Step 1: imino(methyl)(3-nitrophenyl)-$\lambda^6$-sulfanone To a mixture of methyl(3-nitrophenyl) sulfane (8.2 g, 48.5 mmol) and ammonium acetate (5.6 g, 72.7 mmol) in EtOH (120 mL) was added $PhI(OAc)_2$ (31.2 g, 97 mmol) in one portion. The reaction mixture was stirred at room temperature under atmosphere for 16 h. The mixture was concentrated directly to give a residue which was purified by silica gel chromatography column (PE:EA=5:1 to 1:3) to afford imino(methyl)(3-nitrophenyl)-$\lambda^6$-sulfanone as a white solid (7.0 g, 72%). MS (ESI+): m/z found 201.03 $[M+H]^+$.

Step 2: tert-butyl (methyl(3-nitrophenyl)(oxo)-$\lambda^6$-sulfaneylidene)carbamate To a solution of imino(methyl)(3-nitrophenyl)-16-sulfanone (3.5 g, 17.5 mmol) in t-BuOH (200 mL) cooled with ice water bath was added t-BuOK (3.9 g, 35.0 mmol) under $N_2$ protection. Subsequently, $(Boc)_2O$ (7.6 g, 35.0 mmol) was added slowly and the reaction mixture was then refluxed for 10 h. The reaction mixture was quenched with saturated $NH_4Cl$ solution (200 mL) and extracted with EA (200 mL×2). The combined organic layer was washed with brine, dried over $Na_2SO_4$ and concentrated to give a residue which was purified with silica gel chromatography column (PE: EA=5:1 to 1:1) to afford tert-butyl (methyl(3-nitrophenyl)(oxo)-$\lambda^6$-sulfaneylidene)carbamate as yellow solid (1.8 g, 34%). LC-MS(ESI+): m/z 301.09 $[M+H]^+$.

Step 3: (3-aminophenyl)(imino)(methyl)-$\lambda^6$-sulfanone

To a solution of tert-butyl (methyl(3-nitrophenyl)(oxo)-$\lambda^6$-sulfaneylidene)carbamate (1.8 g, 6 mmol) in MeOH (30 mL) was added $Pd(OH)_2$ (300 mg) and the reaction mixture was stirred at room temperature for 2 h. The reaction mixture was filtered through celite and washed with MeOH (100 mL). The filtrate was concentrated to give a residue which was re-dissolved in EA (30 mL) and the resulting solution was filtered through celite again and washed with EA (100 mL). The filtrate was concentrated to give tert-butyl ((3-aminophenyl)(methyl)(oxo)-$\lambda^6$-sulfaneylidene) carbamate (1.4 g, 86%) as off-white solid. MS (ESI+): m/z found 271.10 $[M+H]^+$.

Step 4: SFC Separation

The racemic product was separated by chiral HPLC with the Chiral separation condition: Column: Daicel CHIRALPAK IG, 250 mm×20 mm I.D., 5 μm; Mobile Phase A: $CO_2$/MeOH [0.2% $NH_3$ (7M Solution in MeOH)]=70/30; Flow rate: 60 g/min; 214 nm. Temperature: 35 °C. The first eluting isomer tert-butyl (S)-((3-aminophenyl)(methyl)(oxo)-$\lambda^6$-sulfaneylidene) carbamate [Intermediate 71]. $^1$H NMR (DMSO-$d_6$) δ7.26 (t, 1H), 7.08 (s, 1H), 6.97 (d, 1H), 6.83 (d, 1H), 5.71 (s, 2H), 3.28 (s, 3H), 1.27 (s. 9H) and the second eluting isomer tert-butyl (R)-((3-aminophenyl)(methyl)(oxo)-$\lambda^6$-sulfaneylidene) carbamate [Intermediate 72]. $^1$H NMR (DMSO-$d_6$) δ7.26 (t, 1H), 7.08 (s, 1H), 6.97 (d, 1H), 6.83 (d, 1H), 5.71 (s, 2H), 3.28 (s, 3H), 1.27 (s. 9H).

Example 110

Compound 1: 3-(4-fluoro-2-methoxyphenoxy)-N-(2-(methylsulfonyl)pyridin-4-yl)-6-(trifluoromethyl) pyridazine-4-carboxamide

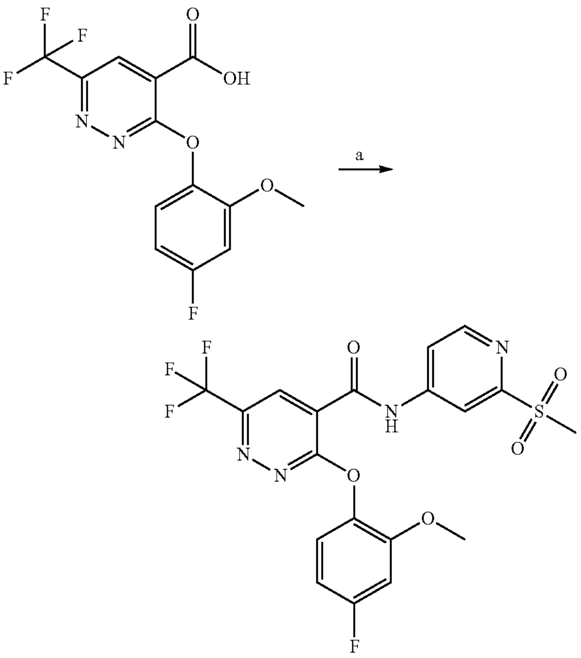

Reagents & conditions: 2-methylsulfonylpyridin-4-amine, 50% propylphosphonic anhydride solution in EtOAc, DIEA, DMAP, DCM, rt.

A mixture of 50% propylphosphonic anhydride solution in EtOAc (0.098 g, 0.309 mmol) 3-(4-fluoro-2-methoxyphenoxy)-6-(trifluoromethyl)pyridazine-4-carboxylic acid (0.090 g, 0.257 mmol), N,N-dimethylpyridin-4-amine (6.3 mg, 0.0515 mmol) and N-ethyl-N-isopropyl-propan-2-amine (DIEA) (0.090 mL, 0.515 mmol) were dissolved in DCM (1.28 mL) under nitrogen at rt. After 15 min 2-methylsulfonylpyridin-4-amine (0.053 g, 0.309 mmol) was added in one portion. The reaction mixture was stirred at rt for 3 h. The reaction mixture was poured into water (10 mL) and brine (5 mL) and extracted with DCM (3×10 mL), dried over $Na_2SO_4$ and concentrated. Purification by Method 2 afforded the title compound 3-(4-fluoro-2-methoxy-phenoxy)-N-(2-methylsulfonyl-4-pyridyl)-6-(trifluoromethyl)pyridazine-4-carboxamide (0.087 g, 69%) as a white solid. $^1$H NMR (400 MHz, DMSO-$d_6$) δ 11.67 (s, 1H), 8.74 (d, J=5.4 Hz, 1H), 8.68 (s, 1H), 8.40 (d, J=1.9 Hz, 1H), 7.91 (dd, J=5.4, 2.0 Hz, 1H), 7.39 (dd, J=8.8, 5.8 Hz, 1H), 7.16 (dd, J=10.7, 2.9 Hz, 1H), 6.88 (td, J=8.5, 2.9 Hz, 1H), 3.73 (s, 3H), 3.29 (s, 3H). LC-MS (Method 1): m/z: 487.3 $[M+H]^+$, (ESI+), RT=3.15.

The compounds listed in Table 22 were synthesized by a similar method as described for Compound 1 using appropriate acids and substituted anilines.

TABLE 22

| Compound | Structure & name | Analytical data |
| --- | --- | --- |
| 2 | 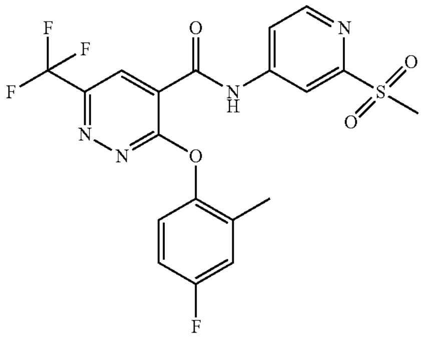 [SMILES: Cc1cc(F)ccc1Oc1nnc(C(F)(F)F)cc1C(=O)Nc1ccnc(S(C)(=O)=O)c1] 3-(4-Fluoro-2-methylphenoxy)-N-(2-(methylsulfonyl)pyridin-4-yl)-6-(trifluoromethyl)pyridazine-4-carboxamide | $^1$H NMR (500 MHz, DMSO-$d_6$) δ 11.68 (s, 1H), 8.75 (d, J = 5.3 Hz, 1H), 8.70 (s, 1H), 8.41 (d, J = 1.8 Hz, 1H), 7.92-7.85 (m, 1H), 7.35 (dd, J = 9.0, 5.0 Hz, 1H), 7.26 (dd, J = 9.5, 2.9 Hz, 1H), 7.19-7.12 (m, 1H), 3.29 (s, 3H), 2.13 (s, 3H). LC-MS(Method 6): m/z: 470.9 [M + H]$^+$, (ESI+), RT = 4.22 |
| 3 | 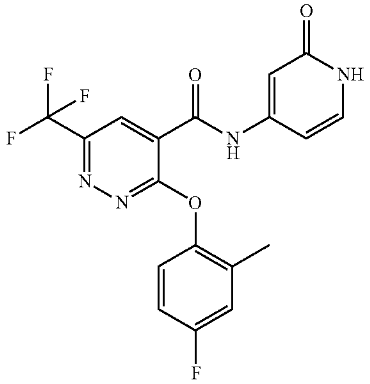 [SMILES: Cc1cc(F)ccc1Oc1nnc(C(F)(F)F)cc1C(=O)Nc1cc[nH]c(=O)c1] 3-(4-Fluoro-2-methylphenoxy)-N-(2-oxo-1,2-dihydropyridin-4-yl)-6-(trifluoromethyl)pyridazine-4-carboxamide | $^1$H NMR (400 MHz, DMSO-$d_6$) δ 11.36 (s, 1H), 10.94 (s, 1H), 8.63 (s, 1H), 7.40-7.30 (m, 2H), 7.25 (dd, J = 9.4, 3.1 Hz, 1H), 7.15 (td, J = 8.5, 3.1 Hz, 1H), 6.76 (d, J = 1.4 Hz, 1H), 6.38 (dd, J = 7.2, 2.0 Hz, 1H), 2.12 (s, 3H). LC-MS(Method 4): m/z 408.9 [M + H]$^+$, (ESI+), RT = 3.72 |
| 4 | 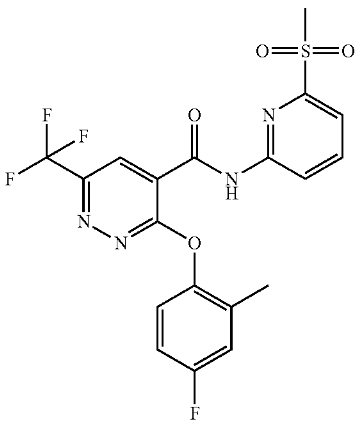 [SMILES: Cc1cc(F)ccc1Oc1nnc(C(F)(F)F)cc1C(=O)Nc1cccc(S(C)(=O)=O)n1] 3-(4-Fluoro-2-methylphenoxy)-N-(6-(methylsulfonyl)pyridin-2-yl)-6-(trifluoromethyl)pyridazine-4-carboxamide | $^1$H NMR (500 MHz, DMSO-$d_6$) δ 11.90 (s, 1H), 8.65 (s, 1H), 8.47 (s, 1H), 8.24 (t, J = 8.0 Hz, 1H), 7.85 (d, J = 7.5 Hz, 1H), 7.32 (s, 1H), 7.24 (dd, J = 9.3, 2.9 Hz, 1H), 7.14 (td, J = 8.6, 3.0 Hz, 1H), 3.25 (s, 3H), 2.11 (s, 3H). LC-MS (method 4): m/z 470.9 [M + H]$^+$, (ESI+), RT = 4.3 |

TABLE 22-continued

| Compound | Structure & name | Analytical data |
| --- | --- | --- |
| 5 | 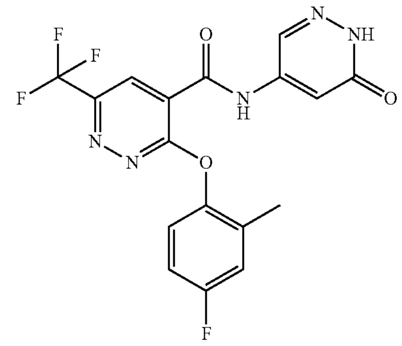 [SMILES: Cc1cc(F)ccc1Oc1nnc(C(F)(F)F)cc1C(=O)Nc1cn[nH]c(=O)c1] 3-(4-Fluoro-2-methylphenoxy)-N-(6-oxo-1,6-dihydropyridazin-4-yl)-6-(trifluoromethyl)pyridazine-4-carboxamide | $^1$H NMR (500 MHz, DMSO-$d_6$) δ 12.96 (s, 1H), 11.34 (s, 1H), 8.67 (s, 1H), 7.93 (d, J = 2.3 Hz, 1H), 7.34 (dd, J = 9.0, 5.0 Hz, 1H), 7.29-7.23 (m, 2H), 7.16 (td, J = 8.5, 3.1 Hz, 1H), 2.13 (s, 3H). LC-MS (Method 4): m/z 409.9 [M + H]$^+$, (ESI+), RT = 3.75 |
| 6 | 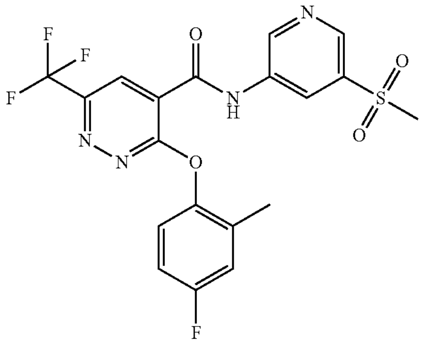 [SMILES: Cc1cc(F)ccc1Oc1nnc(C(F)(F)F)cc1C(=O)Nc1cncc(S(C)(=O)=O)c1] 3-(4-Fluoro-2-methylphenoxy)-N-(5-(methylsulfonyl)pyridin-3-yl)-6-(trifluoromethyl)pyridazine-4-carboxamide | $^1$H NMR (500 MHz, DMSO-$d_6$) δ 11.53 (s, 1H), 9.05 (d, J = 2.4 Hz, 1H), 8.91 (d, J = 2.0 Hz, 1H), 8.73 (t, J = 2.2 Hz, 1H), 8.69 (s, 1H), 7.35 (dd, J = 8.9, 5.0 Hz, 1H), 7.26 (dd, J = 9.4, 3.0 Hz, 1H), 7.16 (td, J = 8.5, 3.1 Hz, 1H), 3.37 (s, 3H), 2.14 (s, 3H). LC-MS (Method 4): m/z 470.9 [M + H]$^+$, (ESI+), RT = 4.09 |
| 7 | 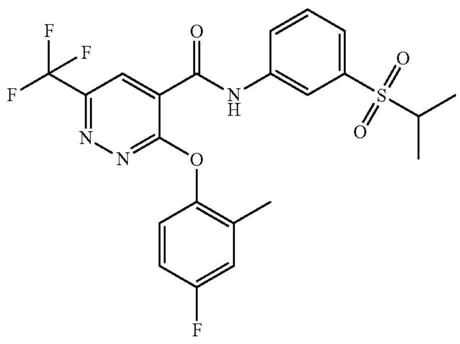 [SMILES: Cc1cc(F)ccc1Oc1nnc(C(F)(F)F)cc1C(=O)Nc1cccc(S(=O)(=O)C(C)C)c1] 3-(4-Fluoro-2-methylphenoxy)-N-(3-(isopropylsulfonyl)phenyl)-6-(trifluoromethyl)pyridazine-4-carboxamide | $^1$H NMR (500 MHz, DMSO-$d_6$) δ 11.27 (s, 1H), 8.68 (s, 1H), 8.30 (t, J = 1.8 Hz, 1H), 8.00-7.93 (m, 1H), 7.72 (t, J = 7.9 Hz, 1H), 7.68-7.64 (m, 1H), 7.34 (dd, J = 8.9, 5.0 Hz, 1H), 7.25 (dd, J = 9.4, 3.0 Hz, 1H), 7.15 (td, J = 8.5, 3.1 Hz, 1H), 3.42 (hept, J = 6.7 Hz, 1H), 2.13 (s, 3H), 1.18 (d, J = 6.7 Hz, 6H). LC-MS (Method 5): m/z 498.0 [M + H]$^+$, RT = 4.53 |

TABLE 22-continued

| Compound | Structure & name | Analytical data |
| --- | --- | --- |
| 8 | 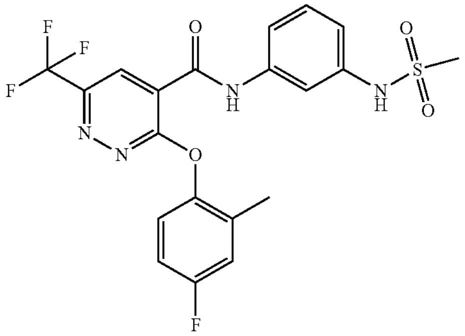 [SMILES: Cc1cc(F)ccc1Oc1nnc(C(F)(F)F)cc1C(=O)Nc1cccc(NS(C)(=O)=O)c1] 3-(4-Fluoro-2-methylphenoxy)-N-(3-(methylsulfonamido)phenyl)-6-(trifluoromethyl)pyridazine-4-carboxamide | $^1$H NMR (400 MHz, DMSO-$d_6$) δ 10.91 (s, 1H), 9.86 (s, 1H), 8.63 (s, 1H), 7.64 (t, J = 2.0 Hz, 1H), 7.50-7.43 (m, 1H), 7.38-7.30 (m, 2H), 7.25 (dd, J = 9.4, 3.0 Hz, 1H), 7.15 (td, J = 8.5, 3.1 Hz, 1H), 7.04-6.97 (m, 1H), 3.00 (s, 3H), 2.13 (s, 3H). LC-MS (Method 5): m/z 484.9 $[M + H]^+$, RT = 4.24 |
| 9 | 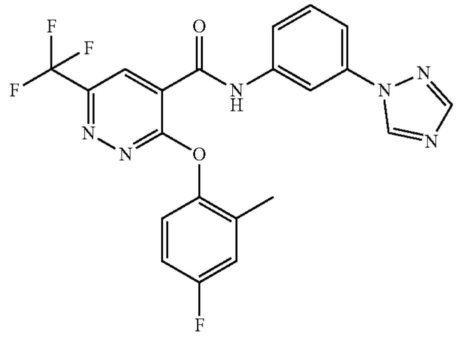 [SMILES: Cc1cc(F)ccc1Oc1nnc(C(F)(F)F)cc1C(=O)Nc1cccc(-n2cncn2)c1] N-(3-(1H-1,2,4-Triazol-1-yl)phenyl)-3-(4-fluoro-2-methylphenoxy)-6-(trifluoromethyl)pyridazine-4-carboxamide | $^1$H NMR (400 MHz, DMSO-$d_6$) δ 10.87 (s, 1H), 9.17 (s, 1H), 8.55 (s, 1H), 8.25 (t, J = 2.0 Hz, 1H), 8.19 (s, 1H), 7.72-7.68 (m, 1H), 7.66 (ddd, J = 8.2, 2.1, 1.1 Hz, 1H), 7.58 (t, J = 8.1 Hz, 1H), 7.34 (dd, J = 8.9, 5.1 Hz, 1H), 7.20 (dd, J = 9.3, 3.1 Hz, 1H), 7.11 (td, J = 8.5, 3.1 Hz, 1H), 2.17 (s, 3H). LC-MS (Method 5): m/z 458.9 $[M + H]^+$, (ESI+), RT = 4.33 |
| 10 | 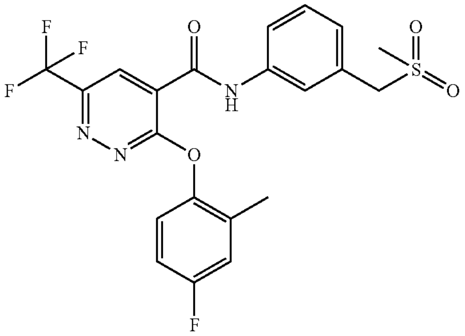 [SMILES: Cc1cc(F)ccc1Oc1nnc(C(F)(F)F)cc1C(=O)Nc1cccc(CS(C)(=O)=O)c1] 3-(4-Fluoro-2-methylphenoxy)-N-(3-((methylsulfonyl)methyl)phenyl)-6-(trifluoromethyl)pyridazine-4-carboxamide | $^1$H NMR (500 MHz, DMSO-$d_6$) δ 10.97 (s, 1H), 8.65 (s, 1H), 7.77 (t, J = 1.9 Hz, 1H), 7.74-7.70 (m, 1H), 7.44 (t, J = 7.9 Hz, 1H), 7.34 (dd, J = 9.0, 5.0 Hz, 1H), 7.25 (dd, J = 9.4, 3.0 Hz, 1H), 7.23-7.19 (m, 1H), 7.15 (td, J = 8.5, 3.1 Hz, 1H), 4.53 (s, 2H), 2.94 (s, 3H), 2.13 (s, 3H). LC-MS (Method 5): m/z 483.9 $[M + H]^+$, (ESI+), RT = 4.21 |

TABLE 22-continued

| Compound | Structure & name | Analytical data |
|---|---|---|
| 11 | 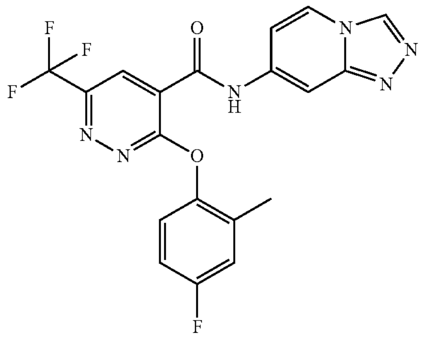 [SMILES: Cc1cc(F)ccc1Oc1nnc(C(F)(F)F)cc1C(=O)Nc1ccn2cnnc2c1] N-([1,2,4]Triazolo[4,3-a]pyridin-7-yl)-3-(4-fluoro-2-methylphenoxy)-6-(trifluoromethyl)pyridazine-4-carboxamide | $^1H$ NMR (500 MHz, DMSO-$d_6$) δ 11.35 (s, 1H), 9.20 (s, 1H), 8.70 (s, 1H), 8.57 (d, J = 7.3 Hz, 1H), 8.25 (s, 1H), 7.36 (dd, J = 8.9, 5.0 Hz, 1H), 7.25 (dd, J = 9.3, 3.1 Hz, 1H), 7.16 (td, J = 8.5, 3.1 Hz, 1H), 7.06 (dd, J = 7.4, 1.8 Hz, 1H), 2.14 (s, 3H). LC-MS(Method 5): m/z: 433.0 [M + H]+, (ESI+), RT = 3.68 |
| 12 | 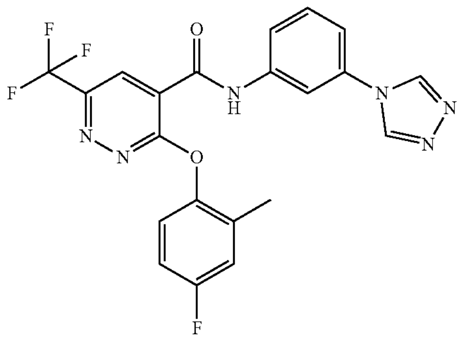 [SMILES: Cc1cc(F)ccc1Oc1nnc(C(F)(F)F)cc1C(=O)Nc1cccc(-n2cnnc2)c1] N-(3-(4H-1,2,4-Triazol-4-yl)phenyl)-3-(4-fluoro-2-methylphenoxy)-6-(trifluoromethyl)pyridazine-4-carboxamide | $^1H$ NMR (400 MHz, DMSO-$d_6$) δ 11.15 (s, 1H), 9.07 (s, 2H), 8.64 (s, 1H), 8.01-7.94 (m, 1H), 7.71 (d, J = 8.3 Hz, 1H), 7.61 (t, J = 8.1 Hz, 1H), 7.52-7.45 (m, 1H), 7.34 (dd, J = 8.8, 5.1 Hz, 1H), 7.25 (dd, J = 9.4, 3.0 Hz, 1H), 7.15 (td, J = 8.5, 3.1 Hz, 1H), 2.14 (s, 3H). LC-MS (Method 5): m/z: 458.9 [M + H]+, (ESI+), RT = 4.01 |
| 13 | 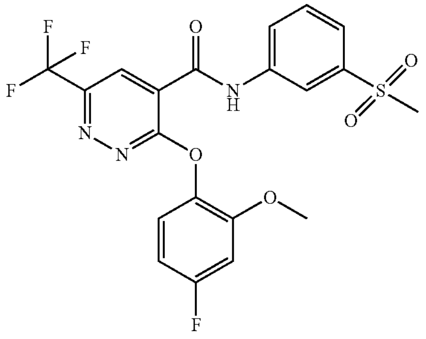 [SMILES: COc1cc(F)ccc1Oc1nnc(C(F)(F)F)cc1C(=O)Nc1cccc(S(C)(=O)=O)c1] 3-(4-Fluoro-2-methoxyphenoxy)-N-(3-(methylsulfonyl)phenyl)-6-(trifluoromethyl)pyridazine-4-carboxamide | $^1H$ NMR (400 MHz, DMSO-$d_6$) δ 11.54 (s, 1H), 9.39 (m, 1H), 9.18 (m, 1H), 8.69 (s, 1H), 8.06 (dd, J = 5.9, 2.7 Hz, 1H), 7.39 (dd, J = 8.8, 5.8 Hz, 1H), 7.16 (dd, J = 10.7, 2.9 Hz, 1H), 6.89 (td, J = 8.5, 2.9 Hz, 1H), 3.73 (s, 3H). LC-MS (Method 6): m/z: 486.3 $[M + H]^+$, (ESI+), RT = 3.48 |

TABLE 22-continued

| Compound | Structure & name | Analytical data |
|---|---|---|
| 14 | 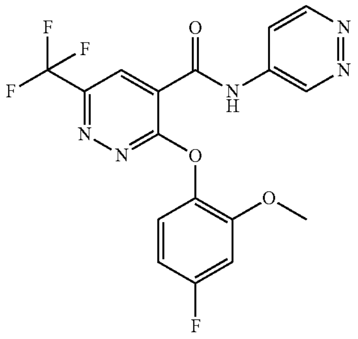 [SMILES: COc1cc(F)ccc1Oc1nnc(C(F)(F)F)cc1C(=O)Nc1ccnnc1] 3-(4-Fluoro-2-methoxyphenoxy)-N-(pyridazin-4-yl)-6-(trifluoromethyl)pyridazine-4-carboxamide | $^1$H NMR (400 MHz, DMSO-$d_6$) δ 11.54 (s, 1H), 9.39 (m, 1H), 9.18 (m, 1H), 8.69 (s, 1H), 8.06 (dd, J = 5.9, 2.7 Hz, 1H), 7.39 (dd, J = 8.8, 5.8 Hz, 1H), 7.16 (dd, J = 10.7, 2.9 Hz, 1H), 6.89 (td, J = 8.5, 2.9 Hz, 1H), 3.73 (s, 3H). LC-MS (Method 6): m/z: 410.4 [M + H]+, (ESI+), RT = 2.52 |
| 15 | 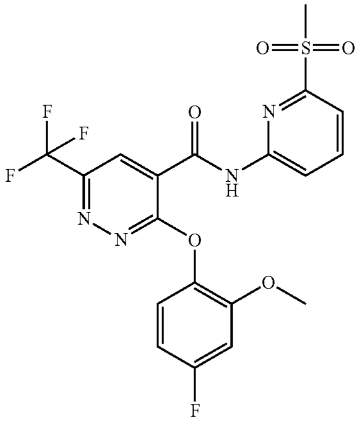 [SMILES: COc1cc(F)ccc1Oc1nnc(C(F)(F)F)cc1C(=O)Nc1cccc(S(C)(=O)=O)n1] 3-(4-Fluoro-2-methoxyphenoxy)-N-(6-(methylsulfonyl)pyridin-2-yl)-6-(trifluoromethyl)pyridazine-4-carboxamide | $^1$H NMR (400 MHz, DMSO-$d_6$) δ 11.86 (s, 1H), 8.62 (s, 1H), 8.48 (m, 1H), 8.25 (t, J = 8.0 Hz, 1H), 7.85 (d, J = 7.5 Hz, 1H), 7.36 (m, 1H), 7.14 (dd, J = 10.6, 2.6 Hz, 1H), 6.86 (m, 1H), 3.72 (s, 3H), 3.30-3.18 (m, 3H). LC-MS (Method 6): m/z 487.3 $[M + H]^+$, (ESI+), RT = 3.4 |
| 16 | 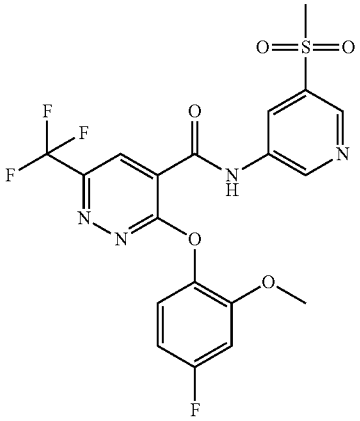 [SMILES: COc1cc(F)ccc1Oc1nnc(C(F)(F)F)cc1C(=O)Nc1cncc(S(C)(=O)=O)c1] 3-(4-Fluoro-2-methoxyphenoxy)-N-(5-(methylsulfonyl)pyridin-3-yl)-6-(trifluoromethyl)pyridazine-4-carboxamide | $^1$H NMR (500 MHz, DMSO-$d_6$) δ 11.50 (s, 1H), 9.07 (d, J = 2.4 Hz, 1H), 8.91 (d, J = 2.0 Hz, 1H), 8.73 (t, J = 2.2 Hz, 1H), 8.67 (s, 1H), 7.38 (dd, J = 8.8, 5.8 Hz, 1H), 7.16 (dd, J = 10.7, 2.9 Hz, 1H), 6.88 (td, J = 8.5, 2.9 Hz, 1H), 3.73 (s, 3H), 3.37 (s, 3H). LC-MS (Method 6): m/z 487.3 [M + H]+, RT = 3.07 |

TABLE 22-continued

| Compound | Structure & name | Analytical data |
| --- | --- | --- |
| 17 | 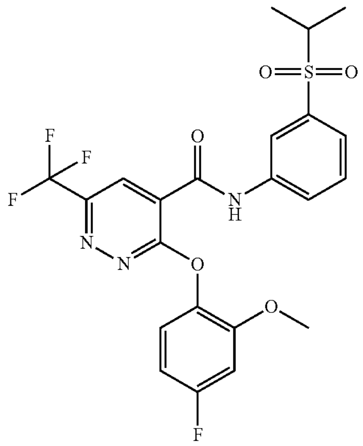 [SMILES: COc1cc(F)ccc1Oc1nnc(C(F)(F)F)cc1C(=O)Nc1cccc(S(=O)(=O)C(C)C)c1] 3-(4-Fluoro-2-methoxyphenoxy)-N-(3-(isopropylsulfonyl)phenyl)-6-(trifluoromethyl)pyridazine-4-carboxamide | $^1$H NMR (500 MHz, DMSO-$d_6$) δ 11.27 (s, 1H), 8.66 (s, 1H), 8.32 (t, J = 1.8 Hz, 1H), 7.97 (ddd, J = 8.1, 2.0, 1.0 Hz, 1H), 7.71 (t, J = 7.9 Hz, 1H), 7.65 (dt, J = 7.8, 1.2 Hz, 1H), 7.38 (dd, J = 8.8, 5.8 Hz, 1H), 7.16 (dd, J = 10.7, 2.9 Hz, 1H), 6.88 (td, J = 8.5, 2.9 Hz, 1H), 3.73 (s, 3H), 3.42 (hept, J = 6.8 Hz, 1H), 1.18 (d, J = 6.8 Hz, 6H). LC-MS (Method 5): m/z 514.0 $[M + H]^+$, RT = 4.47 |
| 18 | 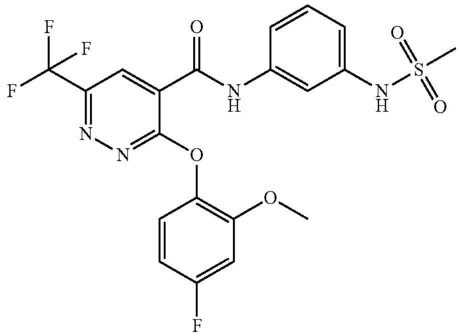 [SMILES: COc1cc(F)ccc1Oc1nnc(C(F)(F)F)cc1C(=O)Nc1cccc(NS(C)(=O)=O)c1] 3-(4-Fluoro-2-methoxyphenoxy)-N-(3-(methylsulfonamido)phenyl)-6-(trifluoromethyl)pyridazine-4-carboxamide | $^1$H NMR (500 MHz, DMSO-$d_6$) δ 10.91 (s, 1H), 9.87 (s, 1H), 8.59 (s, 1H), 7.66 (t, J = 2.0 Hz, 1H), 7.49-7.43 (m, 1H), 7.41-7.29 (m, 2H), 7.15 (dd, J = 10.7, 2.9 Hz, 1H), 7.00 (ddd, J = 8.1, 2.0, 0.8 Hz, 1H), 6.88 (td, J = 8.5, 2.9 Hz, 1H), 3.73 (s, 3H), 3.00 (s, 3H). LC-MS (Method 5): m/z 500.9 $[M + H]^+$, RT = 4.18 |
| 19 | 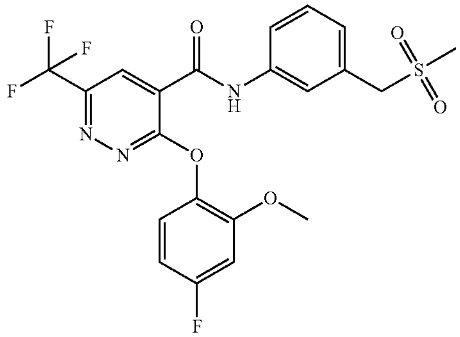 [SMILES: COc1cc(F)ccc1Oc1nnc(C(F)(F)F)cc1C(=O)Nc1cccc(CS(C)(=O)=O)c1] 3-(4-Fluoro-2-methoxyphenoxy)-N-(3-((methylsulfonyl)methyl)phenyl)-6-(trifluoromethyl)pyridazine-4-carboxamide | $^1$H NMR (400 MHz, DMSO-$d_6$) δ 10.96 (s, 1H), 8.61 (s, 1H), 7.83-7.76 (m, 1H), 7.76-7.69 (m, 1H), 7.43 (t, J = 7.9 Hz, 1H), 7.38 (dd, J = 8.8, 5.8 Hz, 1H), 7.25-7.18 (m, 1H), 7.15 (dd, J = 10.7, 2.9 Hz, 1H), 6.88 (td, J = 8.5, 2.9 Hz, 1H), 4.53 (s, 2H), 3.73 (s, 3H), 2.94 (s, 3H). LC-MS (Method 5): m/z 499.9 $[M + H]^+$, RT = 4.14 |

TABLE 22-continued

| Compound | Structure & name | Analytical data |
| --- | --- | --- |
| 20 | 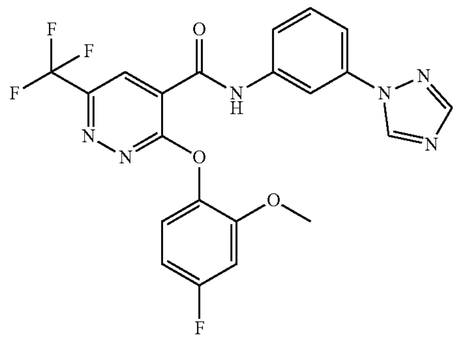 [SMILES: COc1cc(F)ccc1Oc1nnc(C(F)(F)F)cc1C(=O)Nc1cccc(-n2cncn2)c1] N-(3-(1H-1,2,4-Triazol-1-yl)phenyl)-3-(4-fluoro-2-methoxyphenoxy)-6-(trifluoromethyl)pyridazine-4-carboxamide | $^1H$ NMR (400 MHz, DMSO-$d_6$) δ 11.13 (s, 1H), 9.30 (s, 1H), 8.63 (s, 1H), 8.31 (t, J = 2.0 Hz, 1H), 8.26 (s, 1H), 7.71-7.68 (m, 1H), 7.68 (d, J = 1.9 Hz, 1H), 7.58 (dd, J = 8.7, 7.4 Hz, 1H), 7.38 (dd, J = 8.8, 5.8 Hz, 1H), 7.15 (dd, J = 10.7, 2.9 Hz, 1H), 6.88 (td, J = 8.5, 2.9 Hz, 1H), 3.73 (s, 3H). LC-MS (Method 6): m/z: 475.5 $[M + H]^+$, RT = 3.43 |
| 21 | 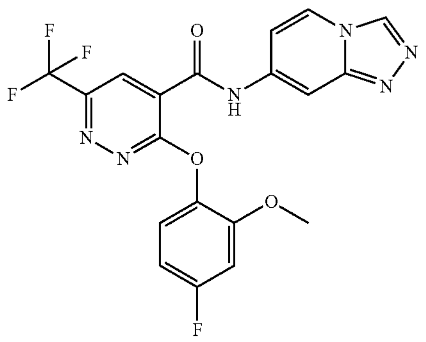 [SMILES: COc1cc(F)ccc1Oc1nnc(C(F)(F)F)cc1C(=O)Nc1ccn2cnnc2c1] N-([1,2,4]Triazolo[4,3-a]pyridin-7-yl)-3-(4-fluoro-2-methoxyphenoxy)-6-(trifluoromethyl)pyridazine-4-carboxamide | $^1H$ NMR (400 MHz, DMSO-$d_6$) δ 11.29 (s, 1H), 9.20-9.20 (m, 1H), 8.68 (s, 1H), 8.57 (d, J = 7.2 Hz, 1H), 8.25 (s, 1H), 7.40 (dd, J = 8.8, 5.8 Hz, 1H), 7.16 (dd, J = 10.7, 2.8 Hz, 1H), 7.06 (dd, J = 7.4, 1.7 Hz, 1H), 6.88 (td, J = 8.5, 2.9 Hz, 1H), 3.73 (s, 3H). LC-MS (Method 5): m/z: 449.0 $[M + H]^+$, RT = 3.58 |
| 22 | 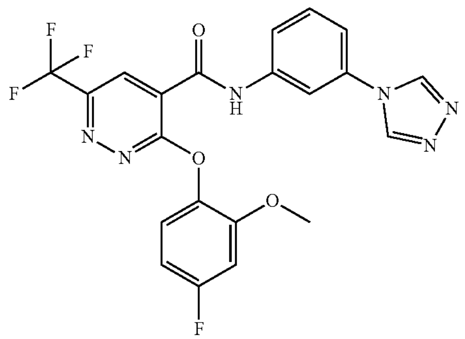 [SMILES: COc1cc(F)ccc1Oc1nnc(C(F)(F)F)cc1C(=O)Nc1cccc(-n2cnnc2)c1] N-(3-(4H-1,2,4-Triazol-4-yl)phenyl)-3-(4-fluoro-2-methoxyphenoxy)-6-(trifluoromethyl)pyridazine-4-carboxamide | $^1H$ NMR (500 MHz, DMSO-$d_6$) δ 11.15 (s, 1H), 9.08 (s, 2H), 8.62 (s, 1H), 8.00 (t, J = 2.0 Hz, 1H), 7.71 (ddd, J = 8.3, 2.0, 1.0 Hz, 1H), 7.61 (t, J = 8.1 Hz, 1H), 7.49 (ddd, J = 8.0, 2.1, 0.9 Hz, 1H), 7.38 (dd, J = 8.8, 5.8 Hz, 1H), 7.16 (dd, J = 10.7, 2.9 Hz, 1H), 6.88 (td, J = 8.5, 2.9 Hz, 1H), 3.73 (s, 3H). LC-MS (Method 5): m/z 474.9 $[M + H]^+$,RT = 3.93 |

TABLE 22-continued

| Compound | Structure & name | Analytical data |
|---|---|---|
| 23 | 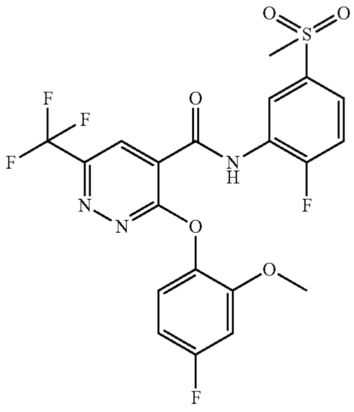 [SMILES: COc1cc(F)ccc1Oc1nnc(C(F)(F)F)cc1C(=O)Nc1cc(S(C)(=O)=O)ccc1F] 3-(4-Fluoro-2-methoxyphenoxy)-N-(2-fluoro-5-(methylsulfonyl)phenyl)-6-(trifluoromethyl)pyridazine-4-carboxamide | $^1$H NMR (400 MHz, DMSO-$d_6$) δ 11.01 (s, 1H), 8.73 (dd, J = 7.1, 2.3 Hz, 1H), 8.61 (s, 1H), 7.85 (ddd, J = 8.6, 4.5, 2.4 Hz, 1H), 7.66 (dd, J = 10.4, 8.7 Hz, 1H), 7.38 (dd, J = 8.8, 5.8 Hz, 1H), 7.16 (dd, J = 10.7, 2.9 Hz, 1H), 6.88 (td, J = 8.5, 2.9 Hz, 1H), 3.74 (s, 3H), 3.26 (s, 3H). LC_MS (Method 5): m/z 503.9 $[M + H]^+$, RT = 4.30 |
| 24 | 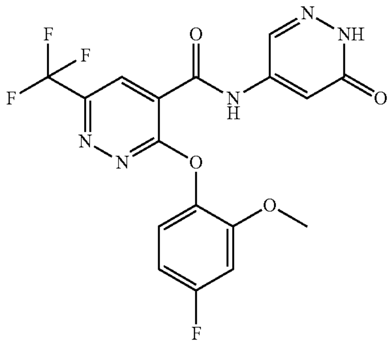 [SMILES: COc1cc(F)ccc1Oc1nnc(C(F)(F)F)cc1C(=O)Nc1cn[nH]c(=O)c1] 3-(4-Fluoro-2-methoxyphenoxy)-N-(6-oxo-1,6-dihydropyridazin-4-yl)-6-(trifluoromethyl)pyridazine-4-carboxamide | $^1$H NMR (400 MHz, DMSO-$d_6$) δ 12.94 (s, 1H), 11.32 (s, 1H), 8.65 (s, 1H), 7.93 (d, J = 2.3 Hz, 1H), 7.38 (dd, J = 8.9, 5.8 Hz, 1H), 7.27 (s, 1H), 7.16 (dd, J = 10.8, 2.8 Hz, 1H), 6.88 (td, J = 8.5, 2.9 Hz, 1H), 3.72 (s, 3H). LC-MS (Method 5): m/z 425.9 $[M + H]^+$, RT = 3.64 |
| 25 | 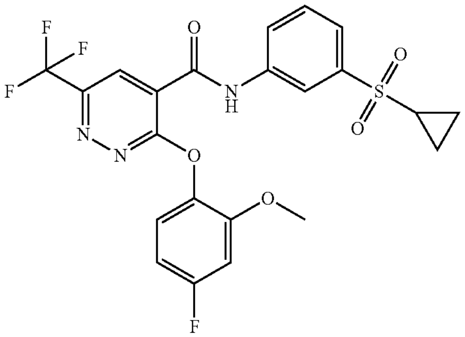 [SMILES: COc1cc(F)ccc1Oc1nnc(C(F)(F)F)cc1C(=O)Nc1cccc(S(=O)(=O)C2CC2)c1] N-(3-(Cyclopropylsulfonyl)phenyl)-3-(4-fluoro-2-methoxyphenoxy)-6-(trifluoromethyl)pyridazine-4-carboxamide | $^1$H NMR (500 MHz, DMSO-$d_6$) δ 11.25 (s, 1H), 8.66 (s, 1H), 8.37-8.31 (m, 1H), 7.99-7.92 (m, 1H), 7.73-7.66 (m, 2H), 7.38 (dd, J = 8.9, 5.9 Hz, 1H), 7.16 (dd, J = 10.7, 2.9 Hz, 1H), 6.88 (td, J = 8.5, 2.9 Hz, 1H), 3.73 (s, 3H), 2.91-2.84 (m, 1H), 1.15-1.10 (m, 2H), 1.10-1.04 (m, 2H). LC-MS (Method 5): m/z 511.9 $[M + H]^+$, RT = 4.39 |

TABLE 22-continued

| Compound | Structure & name | Analytical data |
| --- | --- | --- |
| 26 | 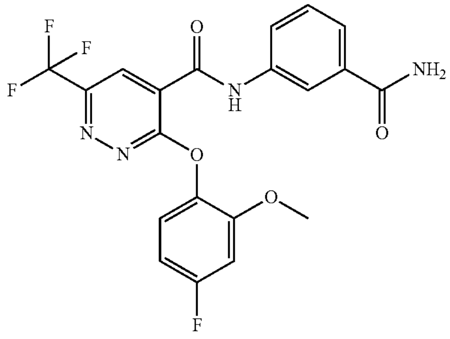 [SMILES: COc1cc(F)ccc1Oc1nnc(C(F)(F)F)cc1C(=O)Nc1cccc(C(N)=O)c1] N-(3-Carbamoylphenyl)-3-(4-fluoro-2-methoxyphenoxy)-6-(trifluoromethyl)pyridazine-4-carboxamide | $^1$H NMR (400 MHz, DMSO-$d_6$) δ 10.95 (s, 1H), 8.61 (s, 1H), 8.17 (t, J = 1.8 Hz, 1H), 8.00 (s, 1H), 7.89-7.82 (m, 1H), 7.69-7.62 (m, 1H), 7.47 (t, J = 7.9 Hz, 1H), 7.42-7.34 (m, 2H), 7.15 (dd, J = 10.7, 2.9 Hz, 1H), 6.88 (td, J = 8.5, 2.9 Hz, 1H), 3.73 (s, 3H). LC_MS (Method 5): m/z 450.9 $[M + H]^+$, RT = 3.88 |
| 27 | 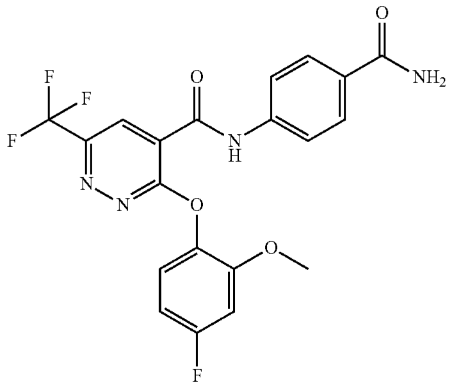 [SMILES: COc1cc(F)ccc1Oc1nnc(C(F)(F)F)cc1C(=O)Nc1ccc(C(N)=O)cc1] N-(4-Carbamoylphenyl)-3-(4-fluoro-2-methoxyphenoxy)-6-(trifluoromethyl)pyridazine-4-carboxamide | $^1$H NMR (400 MHz, DMSO-$d_6$) δ 11.05 (s, 1H), 8.63 (s, 1H), 7.92 (d, J = 8.8 Hz, 2H), 7.76 (d, J = 8.7 Hz, 2H), 7.38 (dd, J = 8.8, 5.9 Hz, 1H), 7.31 (s, 2H), 7.15 (dd, J = 10.7, 2.9 Hz, 1H), 6.88 (td, J = 8.5, 2.8 Hz, 1H), 3.73 (s, 3H). LC-MS (Method 5): m/z 450.9 $[M + H]^+$, RT = 3.88 |
| 28 | 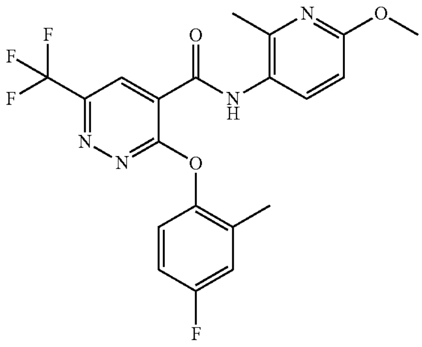 [SMILES: COc1ccc(NC(=O)c2cc(C(F)(F)F)nnc2Oc2ccc(F)cc2C)c(C)n1] 3-(4-Fluoro-2-methylphenoxy)-N-(6-methoxy-2-methylpyridin-3-yl)-6-(trifluoromethyl)pyridazine-4-carboxamide | $^1$H NMR (400 MHz, DMSO-$d_6$) δ 10.32 (s, 1H), 8.63 (s, 1H), 7.80 (d, J = 8.7 Hz, 1H), 7.35 (dd, J = 8.9, 5.0 Hz, 1H), 7.27 (dd, J = 9.4, 3.1 Hz, 1H), 7.17 (td, J = 8.7, 3.3 Hz, 1H), 6.73 (d, J = 8.8 Hz, 1H), 3.84 (s, 3H), 2.39 (s, 3H), 2.15 (s, 3H). LC-MS (Method 6): m/z 437.4 $[M + H]^+$, RT = 3.92 |

TABLE 22-continued

| Compound | Structure & name | Analytical data |
| --- | --- | --- |
| 29 | 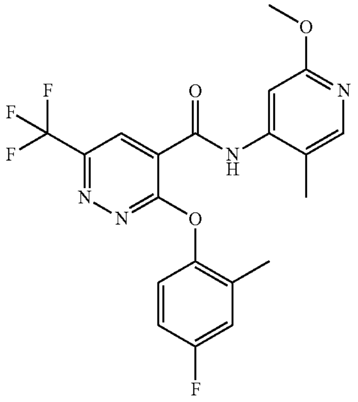 [SMILES: COc1cc(NC(=O)c2cc(C(F)(F)F)nnc2Oc2ccc(F)cc2C)c(C)cn1] 3-(4-Fluoro-2-methylphenoxy)-N-(2-methoxy-5-methylpyridin-4-yl)-6-(trifluoromethyl)pyridazine-4-carboxamide | $^1H$ NMR (500 MHz, DMSO-$d_6$) δ 10.24 (s, 1H), 8.65 (s, 1H), 8.01 (s, 1H), 7.49 (s, 1H), 7.37 (dd, J = 8.8, 5.1 Hz, 1H), 7.27 (dd, J = 9.3, 3.0 Hz, 1H), 7.17 (td, J = 8.6, 3.1 Hz, 1H), 3.83 (s, 3H), 2.18 (s, 3H), 2.15 (s, 3H). LC-MS (Method 6): m/z 437.4 $[M + H]^+$, RT = 4.0 |
| 30 | 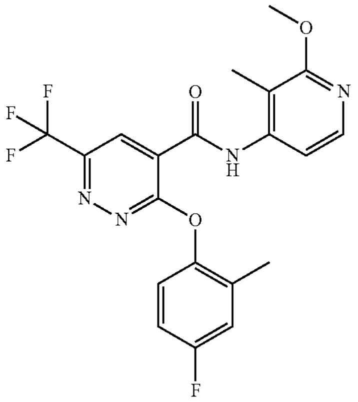 3-(4-Fluoro-2-methylphenoxy)-N-(2-methoxy-3-methylpyridin-4-yl)-6-(trifluoromethyl)pyridazine-4-carboxamide | $^1H$ NMR (400 MHz, DMSO-$d_6$) δ 10.55 (s, 1H), 8.64 (s, 1H), 8.19 (d, J = 5.6 Hz, 1H), 7.88 (d, J = 5.5 Hz, 1H), 7.39 (dd, J = 9.0, 5.1 Hz, 1H), 7.27 (dd, J = 9.3, 2.9 Hz, 1H), 7.17 (td, J = 8.5, 3.2 Hz, 1H), 3.94 (s, 3H), 2.18 (s, 3H). LC-MS (Method 5): m/z 500.9, 502.9 $[M + H]^+$, RT = 5.09 |
| 31 | 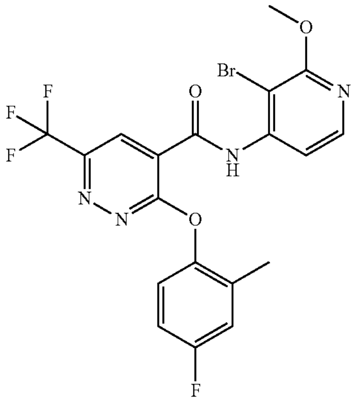 [SMILES: COc1nccc(NC(=O)c2cc(C(F)(F)F)nnc2Oc2ccc(F)cc2C)c1Br] N-(3-Bromo-2-methoxypyridin-4-yl)-3-(4-fluoro-2-methylphenoxy)-6-(trifluoromethyl)pyridazine-4-carboxamide | $^1H$ NMR (400 MHz, DMSO-$d_6$) δ 10.55 (s, 1H), 8.64 (s, 1H), 8.19 (d, J = 5.6 Hz, 1H), 7.88 (d, J = 5.5 Hz, 1H), 7.39 (dd, J = 9.0, 5.1 Hz, 1H), 7.27 (dd, J = 9.3, 2.9 Hz, 1H), 7.17 (td, J = 8.5, 3.2 Hz, 1H), 3.94 (s, 3H), 2.18 (s, 3H). LC-MS (Method 5) m/z 500.9, 502.9 $[M + H]^+$, RT = 5.09 |

TABLE 22-continued

| Compound | Structure & name | Analytical data |
|---|---|---|
| 32 | 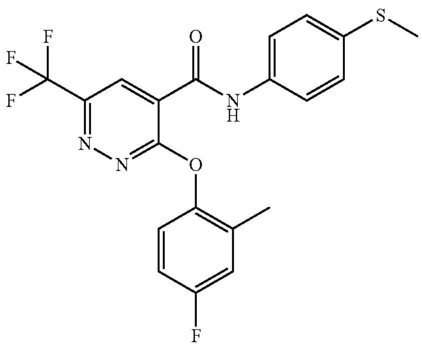 [SMILES: CSc1ccc(NC(=O)c2cc(C(F)(F)F)nnc2Oc2ccc(F)cc2C)cc1] 3-(4-Fluoro-2-methylphenoxy)-N-(4-(methylthio)phenyl)-6-(trifluoromethyl)pyridazine-4-carboxamide | $^1$H NMR (400 MHz, DMSO-$d_6$) δ 10.84 (s, 1H), 8.63 (s, 1H), 7.70-7.63 (m, 2H), 7.37-7.29 (m, 3H), 7.25 (dd, J = 9.4, 3.0 Hz, 1H), 7.15 (td, J = 8.6, 3.2 Hz, 1H), 2.47 (s, 3H), 2.13 (s, 3H). |
| 33 | 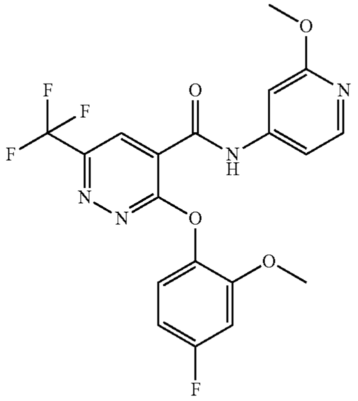 [SMILES: COc1cc(NC(=O)c2cc(C(F)(F)F)nnc2Oc2ccc(F)cc2OC)ccn1] 3-(4-Fluoro-2-methoxyphenoxy)-N-(2-methoxypyridin-4-yl)-6-(trifluoromethyl)pyridazine-4-carboxamide | $^1$H NMR (500 MHz, DMSO-$d_6$) δ 11.17 (s, 1H), 8.64 (s, 1H), 8.16-8.10 (m, 1H), 7.37 (dd, J = 8.8, 5.9 Hz, 1H), 7.22-7.11 (m, 3H), 6.88 (td, J = 8.5, 2.9 Hz, 1H), 3.85 (s, 3H), 3.72 (s, 3H). LC_MS (Method 5): m/z 439.1 [M + H]$^+$, RT = 4.35 |
| 34 | 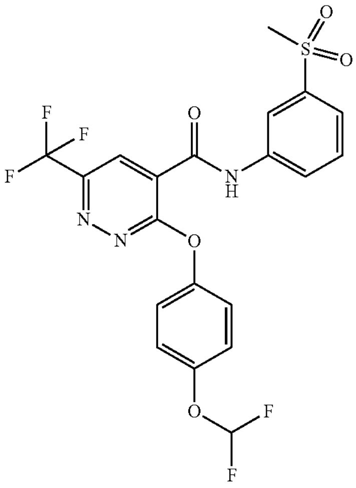 [SMILES: CS(=O)(=O)c1cccc(NC(=O)c2cc(C(F)(F)F)nnc2Oc2ccc(OC(F)F)cc2)c1] 3-(4-(Difluoromethoxy)phenoxy)-N-(3-(methylsulfonyl)phenyl)-6-(trifluoromethyl)pyridazine-4-carboxamide | $^1$H NMR (500 MHz, DMSO-$d_6$) δ 11.24 (s, 1H), 8.64 (s, 1H), 8.35 (t, J = 1.8 Hz, 1H), 7.98-7.93 (m, 1H), 7.74 (dt, J = 7.9, 1.5 Hz, 1H), 7.70 (t, J = 7.9 Hz, 1H), 7.45-7.11 (m, 5H), 3.23 (s, 3H). LCMS (Method 5): m/z 504.0 [M + H]$^+$, RT = 4.23 |

TABLE 22-continued

| Compound | Structure & name | Analytical data |
|---|---|---|
| 35 | 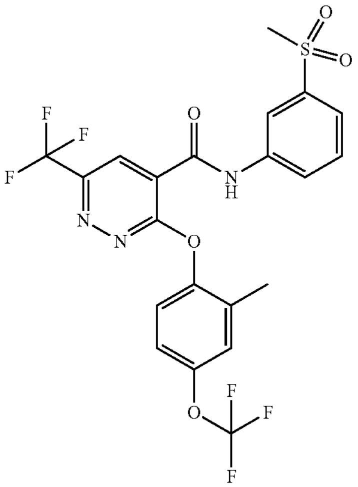 [SMILES: Cc1cc(OC(F)(F)F)ccc1Oc1nnc(C(F)(F)F)cc1C(=O)Nc1cccc(S(C)(=O)=O)c1] 3-(2-Methyl-4-(trifluoromethoxy)phenoxy)-N-(3-(methylsulfonyl)phenyl)-6-(trifluoromethyl)pyridazine-4-carboxamide | $^1$H NMR (500 MHz, DMSO-$d_6$) δ 11.26 (s, 1H), 8.69 (s, 1H), 8.36 (t, J = 1.8 Hz, 1H), 7.97-7.92 (m, 1H), 7.75 (dt, J = 7.8, 1.4 Hz, 1H), 7.70 (t, J = 7.9 Hz, 1H), 7.48-7.41 (m, 2H), 7.34 (dd, J = 8.8, 2.8 Hz, 1H), 3.23 (s, 3H), 2.18 (s, 3H). LCMS (Method 5): m/z 536.0 [M + H]$^+$, RT = 4.59 |
| 36 | 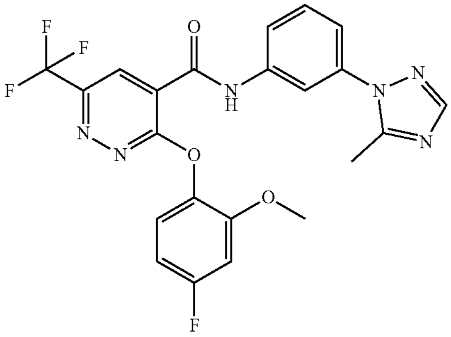 [SMILES: COc1cc(F)ccc1Oc1nnc(C(F)(F)F)cc1C(=O)Nc1cccc(-n2ncnc2C)c1] 3-(4-Fluoro-2-methoxyphenoxy)-N-(3-(5-methyl-1H-1,2,4-triazol-1-yl)phenyl)-6-(trifluoromethyl)pyridazine-4-carboxamide | $^1$H NMR (400 MHz, DMSO-$d_6$) δ 11.13 (s, 1H), 8.64 (s, 1H), 8.05 (s, 1H), 8.02 (t, J = 2.0 Hz, 1H), 7.78-7.71 (m, 1H), 7.60 (t, J = 8.1 Hz, 1H), 7.42 (ddd, J = 8.0, 2.1, 0.9 Hz, 1H), 7.38 (dd, J = 8.8, 5.9 Hz, 1H), 7.15 (dd, J = 10.7, 2.9 Hz, 1H), 6.88 (td, J = 8.6, 2.9 Hz, 1H), 3.73 (s, 3H), 2.51 (s, 3H). LC-MS (Method 6): m/z 489.3 [M + H]$^+$, RT = 3.39 |
| 37 | 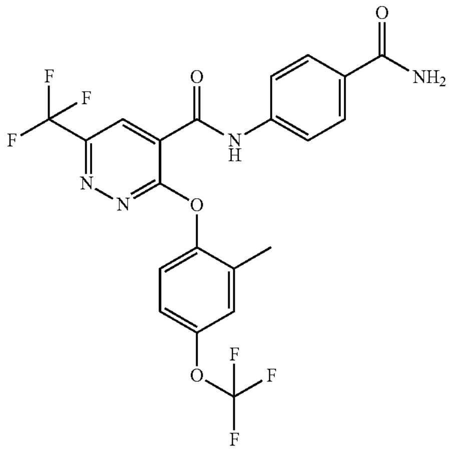 [SMILES: Cc1cc(OC(F)(F)F)ccc1Oc1nnc(C(F)(F)F)cc1C(=O)Nc1ccc(C(N)=O)cc1] N-(4-Carbamoylphenyl)-3-(2-methyl-4-(trifluoromethoxy)phenoxy)-6-(trifluoromethyl)pyridazine-4-carboxamide | $^1$H NMR (500 MHz, DMSO-$d_6$) δ 11.06 (s, 1H), 8.67 (s, 1H), 7.91 (d, J = 8.7 Hz, 3H), 7.74 (d, J = 8.7 Hz, 2H), 7.48-7.39 (m, 2H), 7.36-7.28 (m, 2H), 2.16 (s, 3H). LC-MS (Method 4): m/z 501.1 [M + H]$^+$, RT = 3.47 |

TABLE 22-continued

| Compound | Structure & name | Analytical data |
|---|---|---|
| 38 | 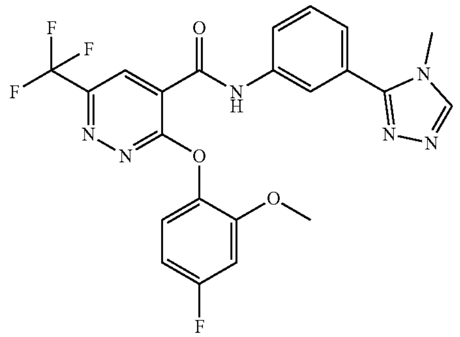 [SMILES: COc1cc(F)ccc1Oc1nnc(C(F)(F)F)cc1C(=O)Nc1cccc(-c2nncn2C)c1] 3-(4-Fluoro-2-methoxyphenoxy)-N-(3-(4-methyl-4H-1,2,4-triazol-3-yl)phenyl)-6-(trifluoromethyl)pyridazine-4-carboxamide | $^{1}H$ NMR (500 MHz, DMSO-$d_6$) δ 11.07 (s, 1H), 8.64 (s, 1H), 8.61 (s, 1H), 8.13 (t, J = 1.8 Hz, 1H), 7.88-7.83 (m, 1H), 7.61-7.53 (m, 2H), 7.39 (dd, J = 8.9, 6.0 Hz, 1H), 7.16 (dd, J = 10.7, 2.9 Hz, 1H), 6.88 (td, J = 8.5, 2.9 Hz, 1H), 3.77 (s, 3H), 3.73 (s, 3H). LC-MS (Method 5): m/z 489.0 $[M + H]^+$, RT = 3.9 |
| 39 | 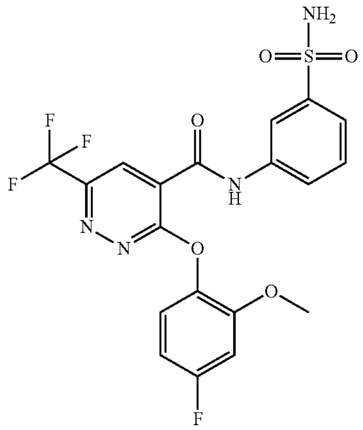 [SMILES: COc1cc(F)ccc1Oc1nnc(C(F)(F)F)cc1C(=O)Nc1cccc(S(N)(=O)=O)c1] 3-(4-Fluoro-2-methoxyphenoxy)-N-(3-sulfamoylphenyl)-6-(trifluoromethyl)pyridazine-4-carboxamide | $^{1}H$ NMR (500 MHz, $CD_3OD$) δ 8.55 (s, 1H), 8.44 (s, 1H), 8.33 (t, J = 1.9 Hz, 1H), 7.91 (ddd, J = 8.1, 2.1, 0.9 Hz, 1H), 7.73 (ddd, J = 7.9, 1.7, 1.0 Hz, 1H), 7.57 (t, J = 8.0 Hz, 1H), 7.37 (dd, J = 8.8, 5.6 Hz, 1H), 6.99 (dd, J = 10.3, 2.8 Hz, 1H), 6.83-6.76 (m, 1H), 3.77 (s, 3H). LC-MS(Method 5): m/z 486.9 $[M + H]^+$, RT = 4.01 |
| 40 | 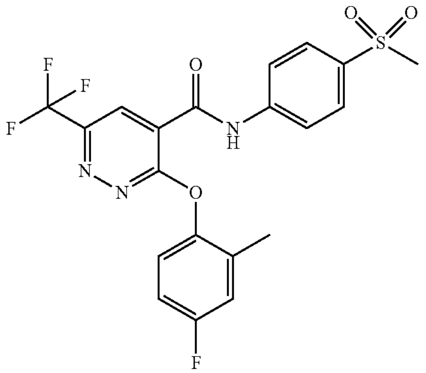 [SMILES: Cc1cc(F)ccc1Oc1nnc(C(F)(F)F)cc1C(=O)Nc1ccc(S(C)(=O)=O)cc1] 3-(4-Fluoro-2-methylphenoxy)-N-(4-(methylsulfonyl)phenyl)-6-(trifluoromethyl)pyridazine-4-carboxamide | $^{1}H$ NMR (400 MHz, DMSO-$d_6$) δ 11.29 (s, 1H), 8.68 (s, 1H), 8.02-7.89 (m, 4H), 7.35 (dd, J = 8.9, 5.1 Hz, 1H), 7.25 (dd, J = 9.4, 3.0 Hz, 1H), 7.15 (td, J = 8.6, 3.2 Hz, 1H), 3.19 (s, 3H), 2.13 (s, 3H). LCMS (Method 5): m/z 470.1 $[M + H]^+$, RT = 4.16 |

TABLE 22-continued

| Compound | Structure & name | Analytical data |
| --- | --- | --- |
| 41 | 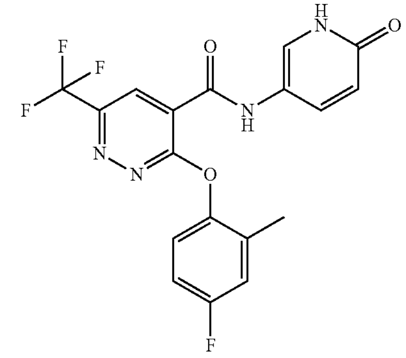 [SMILES: Cc1cc(F)ccc1Oc1nnc(C(F)(F)F)cc1C(=O)Nc1ccc(=O)[nH]c1] 3-(4-Fluoro-2-methylphenoxy)-N-(6-oxo-1,6-dihydropyridin-3-yl)-6-(trifluoromethyl)pyridazine-4-carboxamide | $^1$H NMR (400 MHz, DMSO-$d_6$) δ 11.48 (bs, 1H), 10.62 (s, 1H), 8.59 (s, 1H), 7.97 (d, J = 2.2 Hz, 1H), 7.54 (dd, J = 9.7, 2.8 Hz, 1H), 7.33 (dd, J = 8.9, 5.0 Hz, 1H), 7.25 (dd, J = 9.5, 2.9 Hz, 1H), 7.15 (td, J = 8.5, 3.1 Hz, 1H), 6.43 (d, J = 9.7 Hz, 1H), 2.13 (s, 3H). LCMS (Method 5): m/z 409.1 [M + H]$^+$, RT = 3.6 |
| 42 | 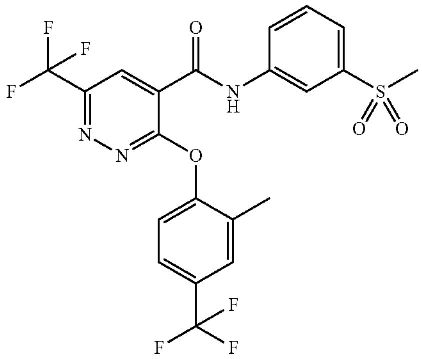 [SMILES: Cc1cc(C(F)(F)F)ccc1Oc1nnc(C(F)(F)F)cc1C(=O)Nc1cccc(S(C)(=O)=O)c1] 3-(2-Methyl-4-(trifluoromethyl)phenoxy)-N-(3-(methylsulfonyl)phenyl)-6-(trifluoromethyl)pyridazine-4-carboxamide | $^1$H NMR (500 MHz, DMSO-$d_6$) δ 11.30 (s, 1H), 8.71 (s, 1H), 8.36 (t, J = 1.8 Hz, 1H), 7.97-7.91 (m, 1H), 7.81 (d, J = 1.9 Hz, 1H), 7.76-7.67 (m, 3H), 7.55 (d, J = 8.5 Hz, 1H), 3.23 (s, 3H), 2.23 (s, 3H). LCMS (Method 4): m/z 520.1 [M + H]$^+$, RT = 3.79 |
| 43 | 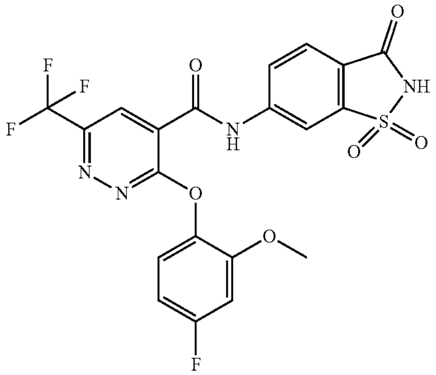 [SMILES: COc1cc(F)ccc1Oc1nnc(C(F)(F)F)cc1C(=O)Nc1ccc2c(c1)S(=O)(=O)NC2=O] N-(1,1-Dioxido-3-oxo-2,3-dihydrobenzo[d]isothiazol-6-yl)-3-(4-fluoro-2-methoxyphenoxy)-6-(trifluoromethyl)pyridazine-4-carboxamide | $^1$H NMR (400 MHz, DMSO-$d_6$) δ 11.55 (s, 1H), 8.67 (s, 1H), 8.36 (s, 1H), 7.98 (s, 2H), 7.37 (dd, J = 8.8, 5.8 Hz, 1H), 7.14 (dd, J = 10.7, 2.9 Hz, 1H), 6.86 (td, J = 8.5, 2.9 Hz, 1H), 3.71 (s, 3H). LC-MS (Method 4): m/z: 513.0 [M + H]$^+$, RT = 3.64 |

TABLE 22-continued

| Compound | Structure & name | Analytical data |
| --- | --- | --- |
| 44 | 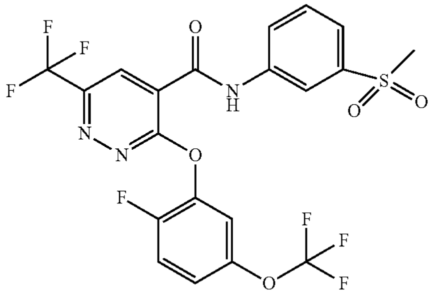 [SMILES: CS(=O)(=O)c1cccc(NC(=O)c2cc(C(F)(F)F)nnc2Oc2cc(OC(F)(F)F)ccc2F)c1] 3-(2-Fluoro-5-(trifluoromethoxy)phenoxy)-N-(3-(methylsulfonyl)phenyl)-6-(trifluoromethyl)pyridazine-4-carboxamide | $^1$H NMR (500 MHz, DMSO-$d_6$) δ 11.27 (s, 1H), 8.75 (s, 1H), 8.36 (t, J = 1.8 Hz, 1H), 7.96 (dt, J = 7.8, 1.6 Hz, 1H), 7.80-7.69 (m, 3H), 7.65 (t, J = 9.5 Hz, 1H), 7.52-7.45 (m, 1H), 3.24 (s, 3H). LC-MS (Method 5): m/z 539.9 $[M + H]^+$, RT = 4.50 |
| 45 | 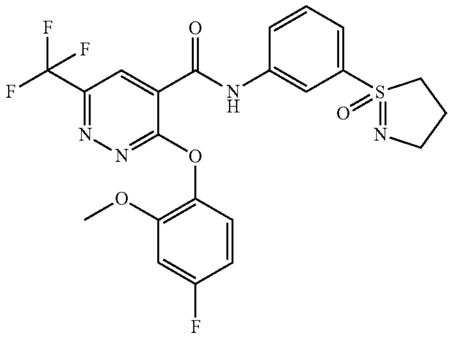 [SMILES: COc1cc(F)ccc1Oc1nnc(C(F)(F)F)cc1C(=O)Nc1cccc(S2(=O)=NCCC2)c1] 3-(4-Fluoro-2-methoxyphenoxy)-N-(3-(1-oxido-4,5-dihydro-3H-1l6-isothiazol-1-yl)phenyl)-6-(trifluoromethyl)pyridazine-4-carboxamide | $^1$H NMR (400 MHz, DMSO-$d_6$) δ 11.19 (s, 1H), 8.64 (s, 1H), 8.32-8.27 (m, 1H), 8.00-7.94 (m, 1H), 7.70-7.61 (m, 2H), 7.38 (dd, J = 8.9, 5.8 Hz, 1H), 7.15 (dd, J = 10.7, 2.9 Hz, 1H), 6.88 (td, J = 8.5, 2.9 Hz, 1H), 3.88-3.79 (m, 1H), 3.73 (s, 3H), 3.71-3.61 (m, 1H), 3.44-3.37 (m, 2H), 2.31-2.13 (m, 2H). LC-MS (Method 5): m/z 510.9 [M + H]+, (ESI+), RT = 3.48 |
| 46 | 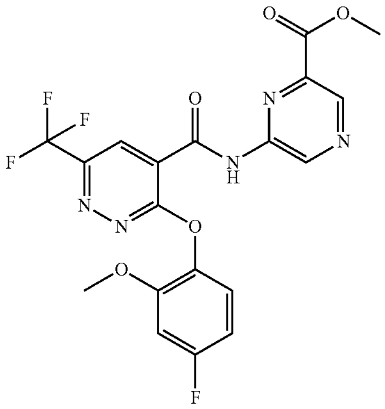 [SMILES: COC(=O)c1cncc(NC(=O)c2cc(C(F)(F)F)nnc2Oc2ccc(F)cc2OC)n1] Methyl 6-(3-(4-fluoro-2-methoxyphenoxy)-6-(trifluoromethyl)pyridazine-4-carboxamido)pyrazine-2-carboxylate | $^1$H NMR (500 MHz, DMSO-$d_6$) δ 12.14 (s, 1H), 9.64 (s, 1H), 9.03 (s, 1H), 8.68-8.57 (m, 1H), 7.47-7.28 (m, 1H), 7.15 (dd, J = 10.7, 2.7 Hz, 1H), 6.87 (td, J = 8.5, 2.8 Hz, 1H), 3.91 (s, 3H), 3.72 (s, 2H). LC-MS (Method 5): m/z 467.9 [M + H]+, (ESI+), RT = 4.28 |

TABLE 22-continued

| Compound | Structure & name | Analytical data |
|---|---|---|
| 47 | 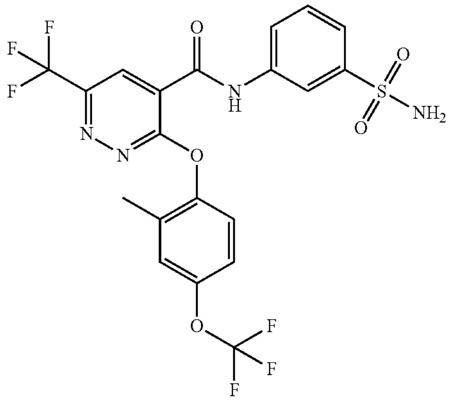 [SMILES: Cc1cc(OC(F)(F)F)ccc1Oc1nnc(C(F)(F)F)cc1C(=O)Nc1cccc(S(N)(=O)=O)c1] 3-(2-Methyl-4-(trifluoromethoxy)phenoxy)-N-(3-sulfamoylphenyl)-6-(trifluoromethyl)pyridazine-4-carboxamide | $^1$H NMR (500 MHz, DMSO-$d_6$) δ 11.15 (s, 1H), 8.67 (s, 1H), 8.30-8.24 (m, 1H), 7.80 (dt, J = 7.2, 1.9 Hz, 1H), 7.64-7.55 (m, 2H), 7.51-7.36 (m, 4H), 7.32 (dd, J = 8.8, 2.6 Hz, 1H), 2.16 (s, 3H). LC-MS (Method 4): m/z 537.1 [M + H]$^+$, (ESI+), RT = 3.64 |
| 48 | 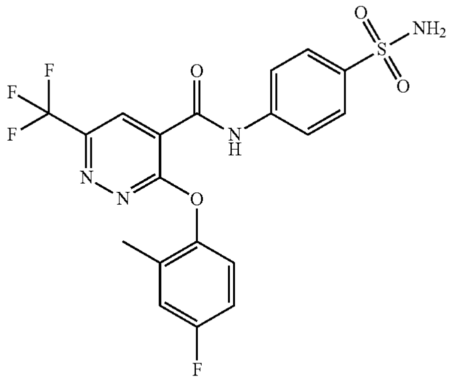 [SMILES: Cc1cc(F)ccc1Oc1nnc(C(F)(F)F)cc1C(=O)Nc1ccc(S(N)(=O)=O)cc1] 3-(4-Fluoro-2-methylphenoxy)-N-(4-sulfamoylphenyl)-6-(trifluoromethyl)pyridazine-4-carboxamide | $^1$H NMR (400 MHz, DMSO-$d_6$) δ 11.19 (s, 1H), 8.67 (s, 1H), 7.91-7.82 (m, 4H), 7.40-7.30 (m, 3H), 7.25 (dd, J = 9.4, 3.0 Hz, 1H), 7.15 (td, J = 8.5, 3.1 Hz, 1H), 2.13 (s, 3H). LC-MS (Method 5): m/z 471.0 [M + H]$^+$, (ESI+), RT = 3.96 |
| 49 | 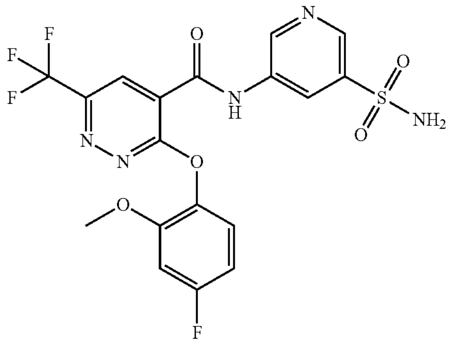 [SMILES: COc1cc(F)ccc1Oc1nnc(C(F)(F)F)cc1C(=O)Nc1cncc(S(N)(=O)=O)c1] 3-(4-Fluoro-2-methoxyphenoxy)-N-(5-sulfamoylpyridin-3-yl)-6-(trifluoromethyl)pyridazine-4-carboxamide | $^1$H NMR (400 MHz, DMSO-$d_6$) δ 11.43 (s, 1H), 8.93 (d, J = 2.3 Hz, 1H), 8.76 (d, J = 2.1 Hz, 1H), 8.69 (t, J = 2.2 Hz, 1H), 8.67 (s, 1H), 7.71 (s, 2H), 7.38 (dd, J = 8.8, 5.9 Hz, 1H), 7.16 (dd, J = 10.7, 2.9 Hz, 1H), 6.88 (td, J = 8.5, 2.9 Hz, 1H), 3.73 (s, 3H). LC-MS (Method 5): m/z 488.1 [M + H]$^+$, (ESI+), RT = 3.71 |

TABLE 22-continued

| Compound | Structure & name | Analytical data |
|---|---|---|
| 50 | 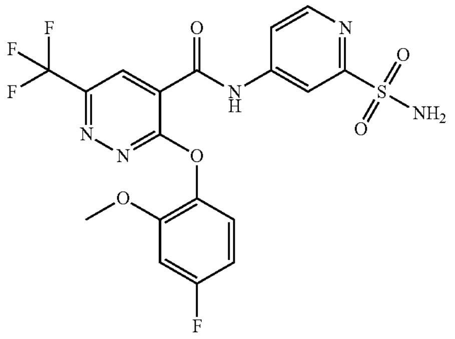 [SMILES: COc1cc(F)ccc1Oc1nnc(C(F)(F)F)cc1C(=O)Nc1ccnc(S(N)(=O)=O)c1] 3-(4-Fluoro-2-methoxyphenoxy)-N-(2-sulfamoylpyridin-4-yl)-6-(trifluoromethyl)pyridazine-4-carboxamide | $^1H$ NMR (400 MHz, DMSO-$d_6$) δ 11.59 (s, 1H), 8.71-8.61 (m, 2H), 8.28 (d, J = 1.8 Hz, 1H), 7.83 (dd, J = 5.4, 2.0 Hz, 1H), 7.49 (s, 2H), 7.38 (dd, J = 8.8, 5.9 Hz, 1H), 7.15 (dd, J = 10.7, 2.9 Hz, 1H), 6.88 (td, J = 8.4, 3.0 Hz, 1H), 3.72 (s, 3H). LC-MS (Method 5): m/z 488.1 $[M + H]^+$, (ESI+), RT = 3.71 |
| 51 | 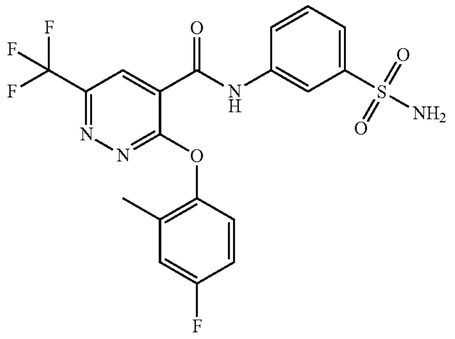 3-(4-Fluoro-2-methylphenoxy)-N-(3-sulfamoylphenyl)-6-(trifluoromethyl)pyridazine-4-carboxamide | $^1H$ NMR (500 MHz, DMSO-$d_6$) δ 11.17 (s, 1H), 8.67 (s, 1H), 8.32-8.26 (m, 1H), 7.82 (dt, J = 7.2, 2.1 Hz, 1H), 7.66-7.57 (m, 2H), 7.45 (s, 2H), 7.35 (dd, J = 8.9, 5.0 Hz, 1H), 7.25 (dd, J = 9.3, 3.1 Hz, 1H), 7.16 (td, J = 8.5, 3.1 Hz, 1H), 2.13 (s, 3H). LC-MS (Method5): m/z 470.9 $[M + H]^+$, (ESI+), RT = 4.07 |
| 52 | 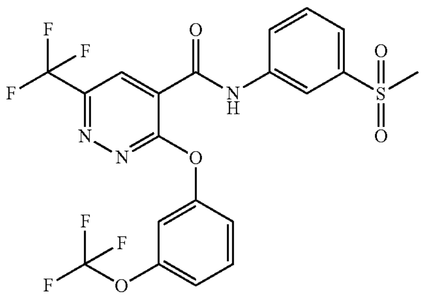 [SMILES: CS(=O)(=O)c1cccc(NC(=O)c2cc(C(F)(F)F)nnc2Oc2cccc(OC(F)(F)F)c2)c1] N-(3-(Methylsulfonyl)phenyl)-3-(3-(trifluoromethoxy)phenoxy)-6-(trifluoromethyl)pyridazine-4-carboxamide | $^1H$ NMR (400 MHz, DMSO-$d_6$) δ 11.22 (s, 1H), 8.66 (s, 1H), 8.35 (t, J = 1.8 Hz, 1H), 7.95 (dt, J = 7.8, 1.7 Hz, 1H), 7.76-7.62 (m, 3H), 7.51-7.48 (m, 1H), 7.46-7.41 (m, 1H), 7.40-7.33 (m, 1H), 3.23 (s, 3H). LC-MS (Method 5): m/z 522.0 $[M + H]^+$, (ESI+), RT = 4.38 |

TABLE 22-continued

| Compound | Structure & name | Analytical data |
|---|---|---|
| 53 | 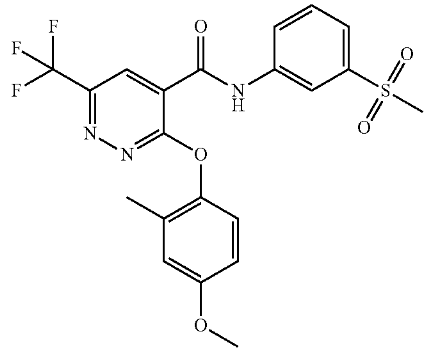 [SMILES: COc1ccc(Oc2nnc(C(F)(F)F)cc2C(=O)Nc2cccc(S(C)(=O)=O)c2)c(C)c1] 3-(4-Methoxy-2-methylphenoxy)-N-(3-(methylsulfonyl)phenyl)-6-(trifluoromethyl)pyridazine-4-carboxamide | $^1H$ NMR (500 MHz, DMSO-$d_6$) δ 11.23 (s, 1H), 8.62 (s, 1H), 8.35 (t, J = 1.8 Hz, 1H), 7.95-7.91 (m, 1H), 7.74-7.65 (m, 2H), 7.18 (d, J = 8.8 Hz, 1H), 6.91 (d, J = 2.9 Hz, 1H), 6.84 (dd, J = 8.8, 3.0 Hz, 1H), 3.75 (s, 3H), 3.22 (s, 3H), 2.08 (s, 3H). LC-MS (Method 5): m/z 481.9 $[M + H]^+$, (ESI+), RT = 4.17 |
| 54 | 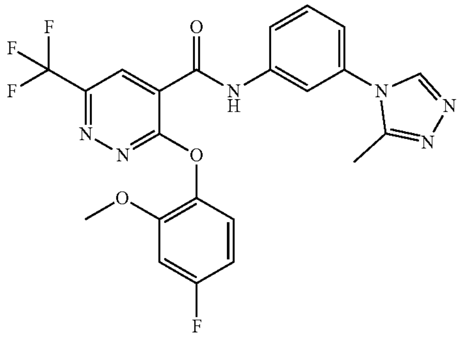 [SMILES: COc1cc(F)ccc1Oc1nnc(C(F)(F)F)cc1C(=O)Nc1cccc(-n2cnnc2C)c1] 3-(4-Fluoro-2-methoxyphenoxy)-N-(3-(3-methyl-4H-1,2,4-triazol-4-yl)phenyl)-6-(trifluoromethyl)pyridazine-4-carboxamide | $^1H$ NMR (400 MHz, DMSO-$d_6$) δ 11.15 (s, 1H), 8.69 (s, 1H), 8.60 (s, 1H), 7.85 (t, J = 1.9 Hz, 1H), 7.78-7.73 (m, 1H), 7.60 (t, J = 8.1 Hz, 1H), 7.36 (dd, J = 8.8, 5.8 Hz, 1H), 7.32 (ddd, J = 8.0, 2.1, 0.9 Hz, 1H), 7.14 (dd, J = 10.7, 2.9 Hz, 1H), 6.86 (td, J = 8.5, 2.9 Hz, 1H), 3.71 (s, 3H), 2.34 (s, 3H). LC-MS (Method 4): m/z 489.2 $[M + H]^+$, (ESI+), RT = 2.98 |
| 55 | 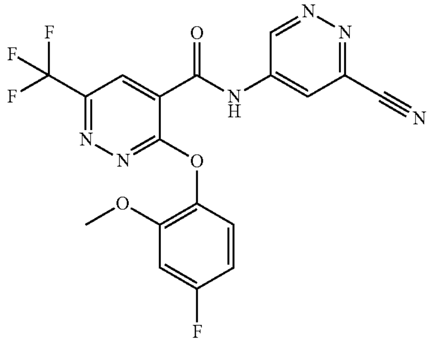 [SMILES: COc1cc(F)ccc1Oc1nnc(C(F)(F)F)cc1C(=O)Nc1cnnc(C#N)c1] N-(6-Cyanopyridazin-4-yl)-3-(4-fluoro-2-methoxyphenoxy)-6-(trifluoromethyl)pyridazine-4-carboxamide | $^1H$ NMR (400 MHz, DMSO-$d_6$) δ 11.90 (s, 1H), 9.55 (d, J = 2.5 Hz, 1H), 8.65 (s, 1H), 8.54 (d, J = 2.6 Hz, 1H), 7.36 (dd, J = 8.8, 5.8 Hz, 1H), 7.14 (dd, J = 10.7, 2.9 Hz, 1H), 6.87 (td, J = 8.5, 2.9 Hz, 1H), 3.71 (s, 3H). LC-MS (Method 5): m/z 434.9 $[M + H]^+$, (ESI+), RT = 4.06 |

TABLE 22-continued

| Compound | Structure & name | Analytical data |
| --- | --- | --- |
| 56 | 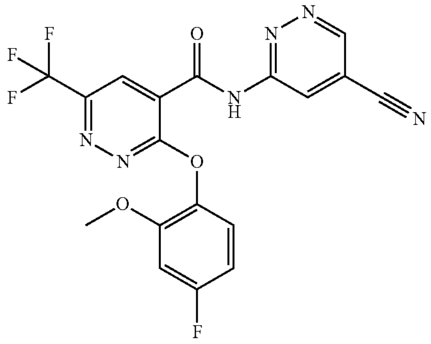 [SMILES: COc1cc(F)ccc1Oc1nnc(C(F)(F)F)cc1C(=O)Nc1cc(C#N)cnn1]<br>N-(5-Cyanopyridazin-3-yl)-3-(4-fluoro-2-methoxyphenoxy)-6-(trifluoromethyl)pyridazine-4-carboxamide | $^1$H NMR (400 MHz, DMSO-$d_6$) δ 12.37 (s, 1H), 9.46 (d, J = 1.7 Hz, 1H), 8.77 (s, 1H), 8.62 (s, 1H), 7.36 (dd, J = 8.7, 6.0 Hz, 1H), 7.14 (dd, J = 10.7, 2.9 Hz, 1H), 6.86 (td, J = 8.5, 2.9 Hz, 1H), 3.71 (s, 3H). LC-MS (Method 5): m/z 434.9 [M + H]$^+$, (ESI+), RT = 4.18 |
| 57 | 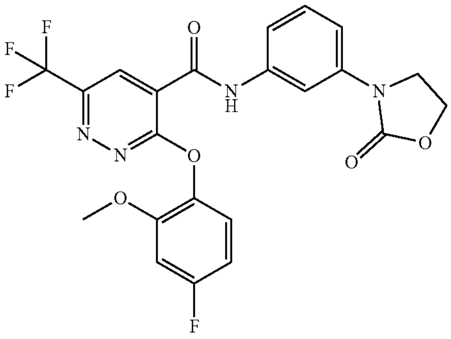 [SMILES: COc1cc(F)ccc1Oc1nnc(C(F)(F)F)cc1C(=O)Nc1cccc(N2CCOC2=O)c1]<br>3-(4-Fluoro-2-methoxyphenoxy)-N-(3-(2-oxooxazolidin-3-yl)phenyl)-6-(trifluoromethyl)pyridazine-4-carboxamide | $^1$H NMR (500 MHz, DMSO-$d_6$) δ 10.95 (s, 1H), 8.60 (s, 1H), 8.04 (t, J = 2.1 Hz, 1H), 7.58-7.53 (m, 1H), 7.44-7.35 (m, 2H), 7.30-7.26 (m, 1H), 7.15 (dd, J = 10.7, 2.9 Hz, 1H), 6.88 (td, J = 8.5, 2.9 Hz, 1H), 4.49-4.38 (m, 2H), 4.10-4.00 (m, 2H), 3.73 (s, 3H). LC-MS (Method 5): m/z 493.1 [M + H]$^+$, (ESI+), RT = 4.27 |
| 58 | 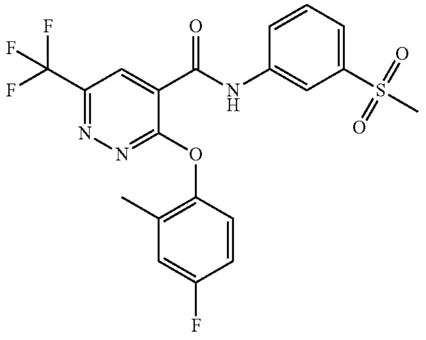 [SMILES: Cc1cc(F)ccc1Oc1nnc(C(F)(F)F)cc1C(=O)Nc1cccc(S(C)(=O)=O)c1]<br>3-(4-Fluoro-2-methylphenoxy)-N-(3-(methylsulfonyl)phenyl)-6-(trifluoromethyl)pyridazine-4-carboxamide | $^1$H NMR (400 MHz, DMSO-$d_6$)) δ 11.26 (s, 1H), 8.67 (s, 1H), 8.39-8.32 (m, 1H), 7.98-7.91 (m, 1H), 7.77-7.66 (m, 2H), 7.34 (dd, J = 8.9, 5.0 Hz, 1H), 7.26 (dd, J = 9.3, 3.1 Hz, 1H), 7.16 (td, J = 8.5, 3.1 Hz, 1H), 3.23 (s, 3H), 2.13 (s, 3H). LC-MS (Method 5): m/z 469.9 [M + H]$^+$, (ESI+), RT = 4.31 |

Example 111

Compound 59: 3-(4-Fluoro-2-methyl-phenoxy)-N-pyridazin-4-yl-6-(trifluoromethyl)pyridazine-4-carboxamide

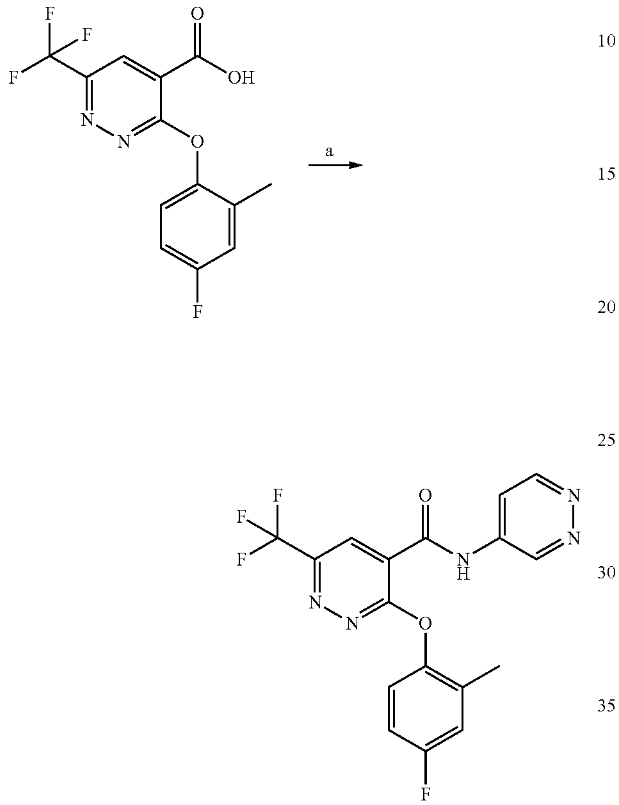

Reagents & conditions: Pyridazin-4-amine, HATU, DIEA, DMF, 25 °C, 1 h;

A mixture of N-[(dimethylamino)(3H-[1,2,3]triazolo[4,5-b]pyridin-3-yloxy)methylidene]-N-methylmethanaminium hexafluorophosphate (0.216 g, 0.569 mmol) and 3-(4-fluoro-2-methyl-phenoxy)-6-(trifluoromethyl)pyridazine-4-carboxylic acid (0.150 g, 0.474 mmol) were dissolved in DMF (1.9 mL) under nitrogen at rt. Then pyridazin-4-amine (0.054 g, 0.569 mmol) was added in one portion followed by N-ethyl-N-isopropyl-propan-2-amine (0.17 mL, 0.949 mmol). The reaction mixture was stirred at rt for 1 h. The reaction was diluted with brine (20 mL) and extracted using EtOAc (2×10 mL), organic layer separated, dried ($Na_2SO_4$), filtered and concentrated in vacuo to obtain the crude residue. Purification by preparative HPLC using Method A afforded the title compound 3-(4-fluoro-2-methyl-phenoxy)-N-pyridazin-4-yl-6-(trifluoromethyl)pyridazine-4-carboxamide (0.139 g, 75%) as an off white solid. $^1H$ NMR (500 MHz, DMSO-$d_6$) δ 11.53 (s, 1H), 9.42-9.32 (m, 1H), 9.22-9.12 (m, 1H), 8.70 (s, 1H), 8.05 (dd, J=6.0, 2.7 Hz, 1H), 7.35 (dd, J=9.0, 5.0 Hz, 1H), 7.26 (dd, J=9.4, 3.0 Hz, 1H), 7.16 (td, J=8.6, 3.2 Hz, 1H), 2.13 (s, 3H). LC-MS (Method 4): m/z 394.2 $[M+H]^+$, (ESI+), RT=2.93

Compound 60: 3-(3-(2,4-Difluorophenoxy)-6-(trifluoromethyl)pyridazine-4-carboxamido) pyridine 1-oxide

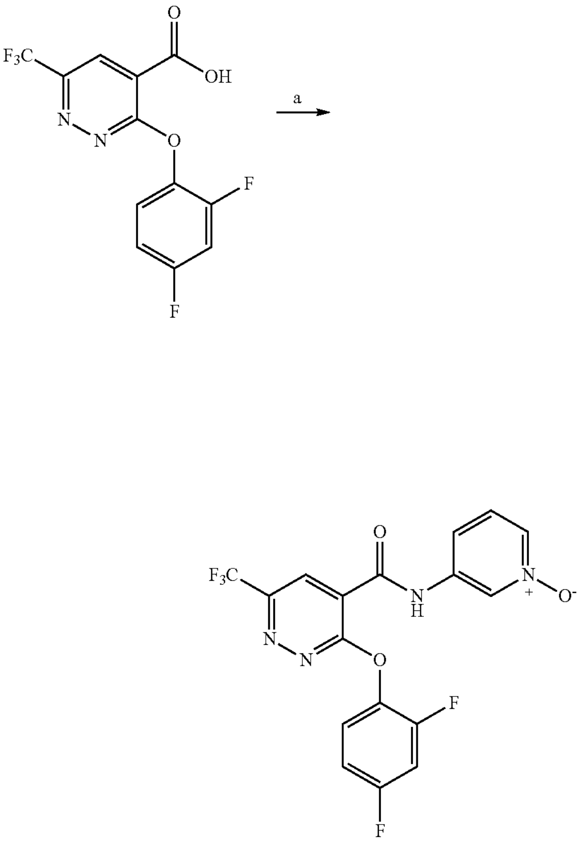

Reagents & condition: 3-aminopyridine 1-oxide, HATU, DIEA, DMF, 25 °C, 16 h;

To a solution of 3-(2,4-difluorophenoxy)-6-(trifluoromethyl)pyridazine-4-carboxylic acid (0.110 g, 0.34 mmol, 1.0 eq), 3-aminopyridine 1-oxide (0.075 g, 0.68 mmol, 2.0 eq) and DIEA (0.222 g, 1.72 mmol, 5.0 eq) in DMF (10 mL) was added HATU (0.196 g, 0.52 mmol, 1.5 eq). The reaction mixture was stirred at 25 °C for 16 h. After reaction, the mixture was quenched with $H_2O$ (40 mL) and extracted with EtOAc (3×50 mL) and the organic layer was concentrated and the residue was purified by preparative HPLC to give 3-(3-(2,4-difluorophenoxy)-6-(trifluoromethyl)pyridazine-4-carboxamido)pyridine-1-oxide (0.0405 g, 28%) as white solid. $^1H$ NMR (400 MHz, DMSO-$d_6$) δ 11.30 (s, 1H), 8.73 (d, J=4.2 Hz, 2H), 8.09 (d, J=6.2 Hz, 1H), 7.70-7.40 (m, 4H), 7.25 (t, J=8.5 Hz, 1H). MS(ESI+): m/z 413.1 $[M+H]^+$.

Compounds 61 to 88 listed in Table 23 were synthesized using the similar method as described for Compound 60 using appropriate carboxylic acids and substituted aryl or heteroaryl aniline.

TABLE 23

| Compound | Structure & Name | Analytical data |
| --- | --- | --- |
| 61 | 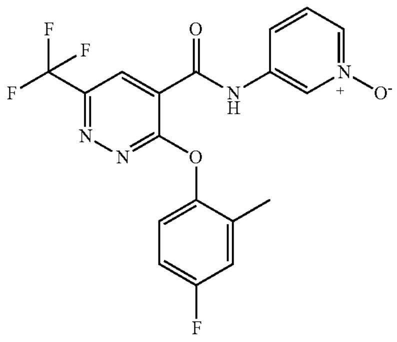 3-(3-(4-Fluoro-2-methylphenoxy)-6-(trifluoromethyl) pyridazine-4-carboxamido) pyridine 1-oxide | $^1$H NMR (400 MHZ, DMSO-$d_6$) δ 11.28 (s, 1H), 8.82-8.58 (m, 2H), 8.17-8.00 (m, 1H), 7.62-7.42 (m, 2H), 7.40-7.11 (m, 3H), 2.13 (s, 3H). MS: m/z 409.1 $[M + H]^+$ |
| 62 | 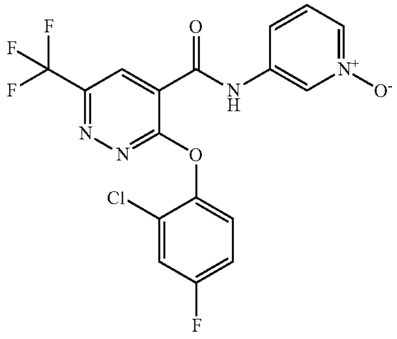 [SMILES: O=C(Nc1ccc[n+]([O-])c1)c1cc(C(F)(F)F)nnc1Oc1ccc(F)cc1Cl] 3-(3-(2-chloro-4-fluorophenoxy)-6-(trifluoromethyl)pyridazine-4-carboxamido)pyridine 1-oxide | $^1$H NMR (400 MHZ, DMSO-$d_6$) δ 11.33 (s, 1H), 8.79-8.65 (m, 2H), 8.16-8.02 (m, 1H), 7.72 (dd, J = 8.4, 3.0 Hz, 1H), 7.64 (dd, J = 9.1, 5.2 Hz, 1H), 7.54 (d, J = 9.1 Hz, 1H), 7.50-7.35 (m, 2H). LC-MS (ESI): m/z found 429.0 $[M + H]^+$ |
| 63 | 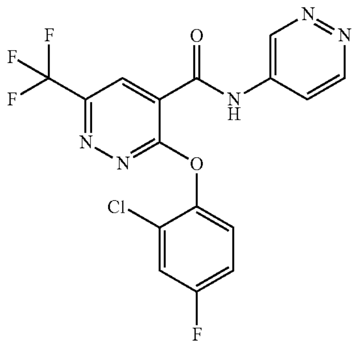 [SMILES: O=C(Nc1ccnnc1)c1cc(C(F)(F)F)nnc1Oc1ccc(F)cc1Cl] 3-(2-Chloro-4-fluorophenoxy)-N-(pyridazin-4-yl)-6-(trifluoromethyl)pyridazine-4-carboxamide | $^1$H NMR (300 MHZ, $CDCl_3$) δ 9.69 (s, 1H), 9.30 (d, J = 2.7 Hz, 1H), 9.19 (d, J = 5.9 Hz, 1H), 8.66 (s, 1H), 8.20 (dd, J = 5.8, 2.8 Hz, 1H), 7.50 (dd, J = 9.1, 4.9 Hz, 1H), 7.37 (dd, J = 7.7, 3.0 Hz, 1H), 7.21 (ddd, J = 9.1, 7.5, 3.0 Hz, 2H), 1.54-1.40 (m, 1H). |

TABLE 23-continued

| Compound | Structure & Name | Analytical data |
| --- | --- | --- |
| 64 | 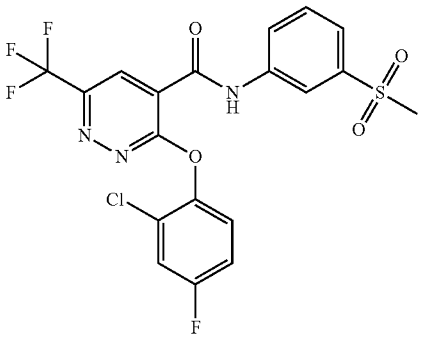 3-(2-Chloro-4-fluorophenoxy)-N-(3-(methylsulfony1)phenyl)-6-(trifluoromethyl)pyridazine-4-carboxamide | $^{1}H$ NMR (300 MHZ, DMSO-$d_6$) δ 11.28 (s, 1H), 8.74 (s, 1H), 8.36 (t, J = 1.9 Hz, 1H), 7.96 (dt, J = 7.6, 1.9 Hz, 1H), 7.80-7.69 (m, 3H), 7.69-7.58 (m, 1H), 7.41 (ddd, J =9.1, 8.1, 3.0 Hz, 1H), 3.24 (s, 3H). LC-MS (Method 2): m/z 488.4[M − H]$^+$ |
| 65 | 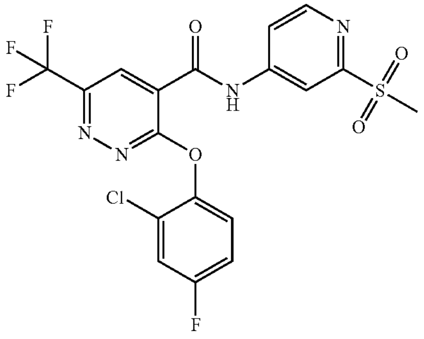 [SMILES: CS(=O)(=O)c1cc(NC(=O)c2cc(C(F)(F)F)nnc2Oc2ccc(F)cc2Cl)ccn1] 3-(2-Chloro-4-fluorophenoxy)-N-(2-(methylsulfonyl)pyridin-4-yl)-6-(trifluoromethyl)pyridazine-4-carboxamide | $^{1}H$ NMR (300 MHz, DMSO-$d_6$) δ 11.70 (s, 1H), 8.83-8.73 (m, 2H), 8.40 (d, J = 2.0 Hz, 1H), 7.92 (dd, J= 5.5, 2.1 Hz, 1H), 7.79-7.56 (m, 2H), 7.41 (ddd, J =9.1, 8.1, 3.0 Hz, 1H), 3.30 (s, 3H). LC-MS (method 2): m/z 491.6[M + H]$^+$ |
| 66 | 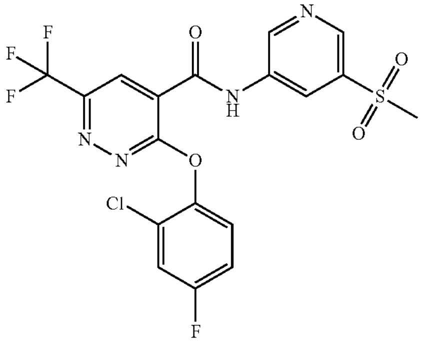 [SMILES: CS(=O)(=O)c1cncc(NC(=O)c2cc(C(F)(F)F)nnc2Oc2ccc(F)cc2Cl)c1] 3-(2-Chloro-4-fluorophenoxy)-N-(5-(methylsulfony1)580yridine-3-y1)-6-(trifluoromethyl)pyridazine-4-carboxamide | $^{1}H$ NMR (300 MHz, $CDCl_3$) δ 9.76 (s, 1H), 9.13 (d, J = 2.5 Hz, 1H), 9.02 (d, J = 2.0 Hz, 1H), 8.78 (t, J = 2.2 Hz, 1H),<br>8.72 (s, 1H), 7.52 (dd, J = 9.1,4.9 Hz, 1H), 7.39 (dd, J = 7.7, 2.9 Hz, 1H), 7.23 (ddd, J = 9.1, 7.5, 3.0 Hz, 2H), 3.19 (s, 3H). LC-MS (Method 2): m/z 489.4[M − H]$^+$ |

TABLE 23-continued

| Compound | Structure & Name | Analytical data |
| --- | --- | --- |
| 67 | 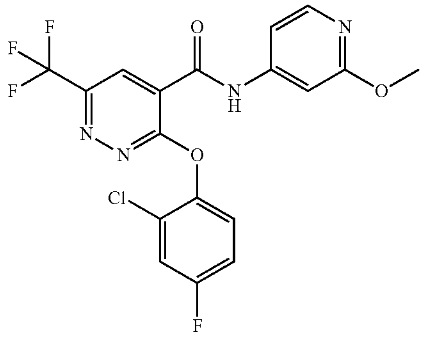 [SMILES: COc1cc(NC(=O)c2cc(C(F)(F)F)nnc2Oc2ccc(F)cc2Cl)ccn1] 3-(2-Chloro-4-fluorophenoxy)-N-(2-methoxypyridin-4-y1)-6-(trifluoromethyl)pyridazine-4-carboxamide | $^{1}H$ NMR (300 MHz, $CDCl_3$) δ 9.52 (s, 1H), 8.67 (s, 1H), 8.16 (d, J = 5.7 Hz, 1H), 7.46 (dd, J =9.1, 4.9 Hz, 1H), 7.35 (dd, J = 7.7, 2.9 Hz, 1H), 7.25-7.10 (m, 3H), 3.96 (s, 3H). LC-MS (Method 2): m/z 443.3 $[M + H]^+$. |
| 68 | 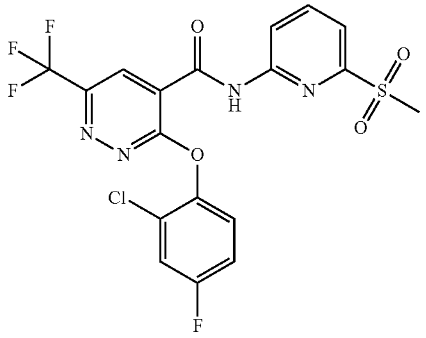 3-(2-Chloro-4-fluorophenoxy)-N-(6-(methylsulfony1)580yridine-2-yl)-6-(trifluoromethyl)pyridazine-4-carboxamide | 1H NMR (300 MHz, $CDCl_3$) δ 10.10 (s, 1H), 8.67 (d, J = 6.7 Hz, 2H), 8.11 (t, J = 8.0 Hz, 1H), 7.95 (dd, J = 7.6, 0.9 Hz, 1H), 7.48 (dd, J = 9.0, 4.9 Hz, 1H), 7.34 (dd, J = 7.8, 2.9 Hz, 1H), 7.19 (ddd, J = 9.0, 7.5, 3.0 Hz, 1H), 3.19 (s, 3H). LC-MS (Method 2): m/z 513.4$[M + Na]^+$ |
| 69 | 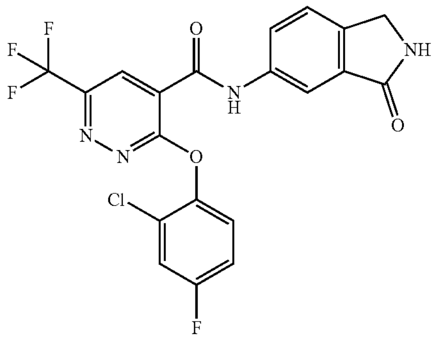 [SMILES: O=C1NCc2ccc(NC(=O)c3cc(C(F)(F)F)nnc3Oc3ccc(F)cc3Cl)cc21] 3-(2-Chloro-4-fluorophenoxy)-N-(3-oxo-2,3-dihydro-1H-isoindol-5-y1)-6-(trifluoromethyl)pyridazine-4-carboxamide | $^{1}H$ NMR (300 MHz, $CDCl_3$) δ 9.69 (s, 1H), 8.72 (s, 1H), 8.25 (dd, J = 8.3, 2.1 Hz, 1H), 7.93 (d, J = 2.1 Hz, 1H), 7.55 (d, J = 8.3 Hz, 1H), 7.46 (dd, J = 9.0, 4.9 Hz, 1H), 7.35 (dd, J = 7.8, 2.9 Hz, 1H), 7.19(ddd, J = 9.0, 7.5, 3.0 Hz, 2H), 6.31 (s, 1H), 4.49 (s, 2H). LC-MS (Method 2): m/z 465.0, 367.0$[M - H]^+$ |

TABLE 23-continued

| Compound | Structure & Name | Analytical data |
|---|---|---|
| 70 | 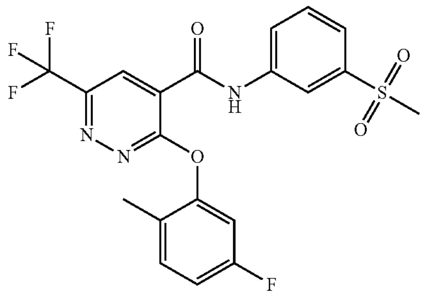 [SMILES: Cc1ccc(F)cc1Oc1nnc(C(F)(F)F)cc1C(=O)Nc1cccc(S(C)(=O)=O)c1] 3-(5-Fluoro-2-methylphenoxy)-N-(3-methanesulfonylphenyl)-6-(trifluoromethyl)pyridazine-4-carboxamide | $^1$H NMR (300 MHZ, DMSO-$d_6$) δ 11.26 (s, 1H), 8.70 (s, 1H), 8.37 (t, J = 1.9 Hz, 1H), 7.95 (dt, J = 7.5, 1.9 Hz, 1H), 7.82-7.62 (m, 2H), 7.50-7.35 (m, 1H), 7.29 (dd, J = 9.5, 2.7 Hz, 1H), 7.14 (td, J = 8.5, 2.7 Hz, 1H), 3.24 (s, 3H), 2.11 (s, 3H). LC-MS (Method 2): m/z 468.4 $[M - H]^+$ |
| 71 | 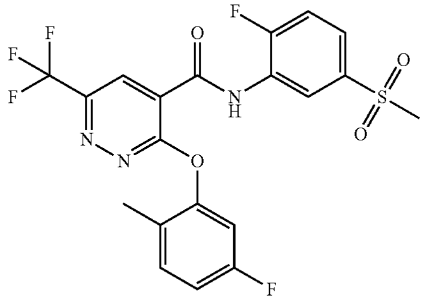 [SMILES: Cc1ccc(F)cc1Oc1nnc(C(F)(F)F)cc1C(=O)Nc1cc(S(C)(=O)=O)ccc1F] 3-(5-Fluoro-2-methylphenoxy)-N-(2-fluoro-5-methanesulfonylphenyl)-6-(trifluoromethyl)pyridazine-4-carboxamide | 1HNMR (300 MHz, DMSO-$d_6$) δ 11.04 (s, 1H), 8.80-8.61 (m, 2H), 7.86 (ddd, J = 8.6, 4.5, 2.4 Hz, 1H), 7.67 (dd, J = 10.5, 8.7 Hz, 1H), 7.49-7.37 (m, 1H), 7.29 (dd, J = 9.5, 2.7 Hz, 1H), 7.14 (td, J = 8.5, 2.7 Hz, 1H), 3.27 (s, 3H), 2.13 (s, 3H). LC-MS (Method 2): m/z 486.4 $[M - H]^+$ |
| 72 | 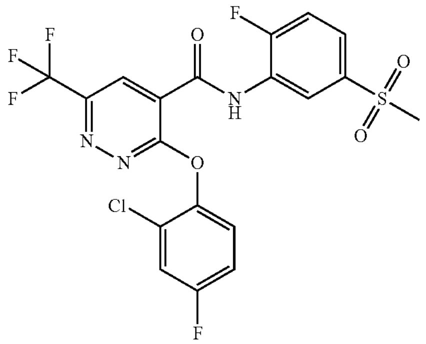 [SMILES: CS(=O)(=O)c1ccc(F)c(NC(=O)c2cc(C(F)(F)F)nnc2Oc2ccc(F)cc2Cl)c1] 3-(2-Chloro-4-fluorophenoxy)-N-(2-fluoro-5-methanesulfonylphenyl)-6-(trifluoromethyl)pyridazine-4-carboxamide | $^1$H NMR (300 MHZ, DMSO-$d_6$) δ 11.09 (s, 1H), 8.73 (d, J =9.4 Hz, 2H), 7.86 (ddd, J = 8.7, 4.6, 2.4 Hz, 1H), 7.76-7.55 (m, 3H), 7.41 (ddd, J = 9.1, 8.1, 3.0 Hz, 1H), 3.27 (s, 3H). LC-MS (Method 2): m/z 506.2$[M - H]^+$ |
| 73 | 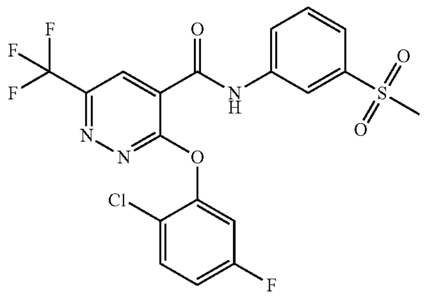 3-(2-Chloro-5-fluorophenoxy)-N-(3-methanesulfonylphenyl)-6-(trifluoromethyl)pyridazine-4-carboxamide | $^1$H NMR (300 MHZ, DMSO-$d_6$) δ 11.28 (s, 1H), 8.77 (s, 1H), 8.37 (t, J = 1.9 Hz, 1H), 7.96 (dt, J = 7.6, 1.8 Hz, 1H), 7.81-7.59 (m, 4H), 7.33 (ddd, J = 9.0, 8.1, 3.0 Hz, 1H), 3.24 (s, 3H). LC-MS (Method 2): m/z 488.3 $[M - H]^+$ |

TABLE 23-continued

| Compound | Structure & Name | Analytical data |
|---|---|---|
| 74 | 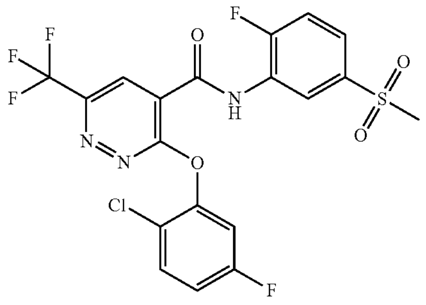 [SMILES: CS(=O)(=O)c1ccc(F)c(NC(=O)c2cc(C(F)(F)F)nnc2Oc2cc(F)ccc2Cl)c1] 3-(2-Chloro-5-fluorophenoxy)-N-(2-fluoro-5-methanesulfonylphenyl)-6-(trifluoromethyl)pyridazine-4-carboxamide | $^1$H NMR (300 MHz, DMSO-$d_6$) δ 11.08 (s, 1H), 8.72 (d, J = 8.6 Hz, 2H), 7.87 (ddd, J = 8.6, 4.5, 2.4 Hz, 1H), 7.80-7.51 (m, 3H), 7.34 (ddd, J = 9.0, 8.1,3.0 Hz, 1H), 3.27 (s, 3H). LC-MS (method 2): m/z 506.2 $[M - H]^+$ |
| 75 | 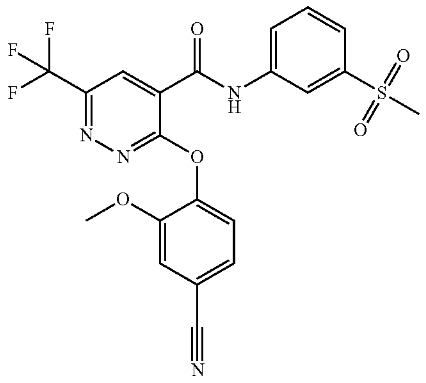 [SMILES: COc1cc(C#N)ccc1Oc1nnc(C(F)(F)F)cc1C(=O)Nc1cccc(S(C)(=O)=O)c1] 3-(4-Cyano-2-methoxyphenoxy)-N-(3-methanesulfonylphenyl)-6-(trifluoromethyl)pyridazine-4-carboxamide | $^1$H NMR (300 MHZ, DMSO-$d_6$) δ 11.29 (s, 1H), 8.72 (s, 1H), 8.36 (t, J = 1.9 Hz, 1H), 7.96 (dt, J = 7.5, 1.9 Hz, 1H), 7.81-7.66 (m, 3H), 7.59 (d, J = 1.1 Hz, 2H), 3.79 (s, 3H), 3.24 (s, 3H). LC-MS (Method 2): m/z 491.3 $[M - H]^+$ |
| 76 | 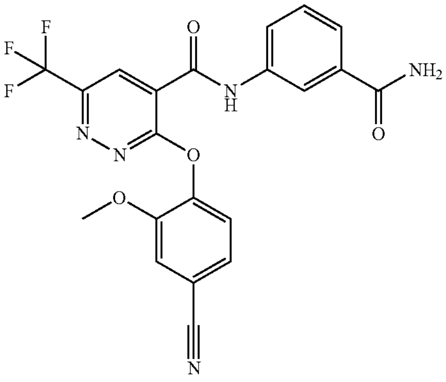 [SMILES: COc1cc(C#N)ccc1Oc1nnc(C(F)(F)F)cc1C(=O)Nc1cccc(C(N)=O)c1] N-(3-Carbamoylphenyl)-3-(4-cyano-2-methoxyphenoxy)-6-(trifluoromethyl)pyridazine-4-carboxamide | $^1$H NMR (300 MHZ, DMSO-$d_6$) δ 11.00 (s, 1H), 8.69 (s, 1H), 8.18 (t, J = 1.9 Hz, 1H), 7.99 (d, J = 20.7 Hz, 1H), 7.87 (ddd, J = 8.0, 2.3, 1.0 Hz, 1H), 7.76 (t, J = 1.1 Hz, 1H), 7.67 (dt, J = 7.8, 1.2 Hz, 1H), 7.59 (d, J = 1.1 Hz, 2H), 7.47 (dd, J = 15.6, 7.7 Hz, 2H), 3.79 (s, 3H), 2.70 (s, 2H). LC-MS (Method 2): m/z 456.3 $[M - H]^+$ |

TABLE 23-continued

| Compound | Structure & Name | Analytical data |
|---|---|---|
| 77 | 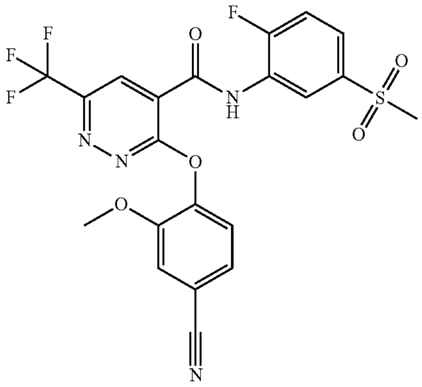 [SMILES: COc1cc(C#N)ccc1Oc1nnc(C(F)(F)F)cc1C(=O)Nc1cc(S(C)(=O)=O)ccc1F] 3-(4-Cyano-2-methoxyphenoxy)-N-(2-fluoro-5-methanesulfonylphenyl)-6-(trifluoromethyl)pyridazine-4-carboxamide | $^1$H NMR (300 MHz, $CDCl_3$) δ 9.93 (d, J = 3.3 Hz, 1H), 9.15 (dd, J = 7.0, 2.3 Hz, 1H), 8.65 (s, 1H), 7.82 (ddd, J = 8.6, 4.8, 2.3 Hz, 1H), 7.56-7.41 (m,2H), 7.40-7.31 (m, 2H), 3.83 (s, 3H), 3.13 (s, 3H). LCMS (Method 2): m/z 509.3 [M − H]$^+$ |
| 78 | 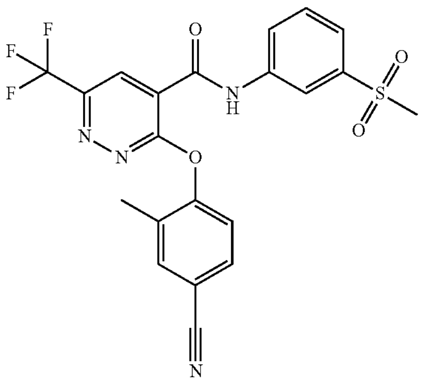 [SMILES: Cc1cc(C#N)ccc1Oc1nnc(C(F)(F)F)cc1C(=O)Nc1cccc(S(C)(=O)=O)c1] 3-(4-Cyano-2-methylphenoxy)-N-(3-methanesulfonylphenyl)-6-(trifluoromethyl)pyridazine-4-carboxamide | $^1$H NMR (300 MHZ, DMSO-$d_6$) δ 11.28 (s, 1H), 8.74 (s, 1H), 8.36 (t, J = 1.9 Hz, 1H), 8.00-7.90 (m, 2H), 7.89-7.76 (m, 1H), 7.76-7.64 (m, 2H), 7.56(d, J = 8.4 Hz, 1H), 3.25 (s, 3H), 2.20 (s, 3H). LC-MS (Method 2): m/z 475.3 [M − H]$^+$ |
| 79 | 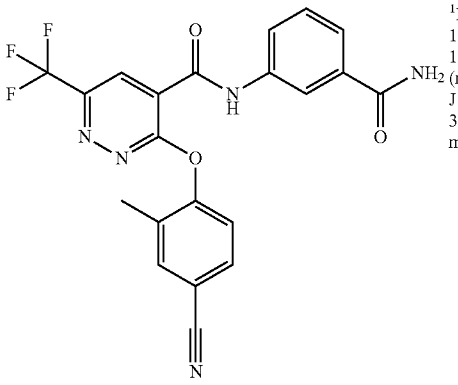 N-(3-Carbamoylphenyl)-3-(4-cyano-2-methylphenoxy)-6-(trifluoromethyl)pyridazine-4-carboxamide | $^1$H NMR (300 MHZ, DMSO-$d_6$) δ 11.00 (s, 1H), 8.72 (s, 1H), 8.18 (t, J = 1.9 Hz, 1H), 8.03 (s, 1H), 7.97-7.92 (m, 1H), 7.90-7.80 (m, 2H), 7.68 (dt, J = 7.9, 1.3 Hz, 1H), 7.62-7.39 (m, 3H), 2.20 (s, 3H). LC-MS (Method 2): m/z 440.3 [M − H]$^+$ |

TABLE 23-continued

| Compound | Structure & Name | Analytical data |
| --- | --- | --- |
| 80 | 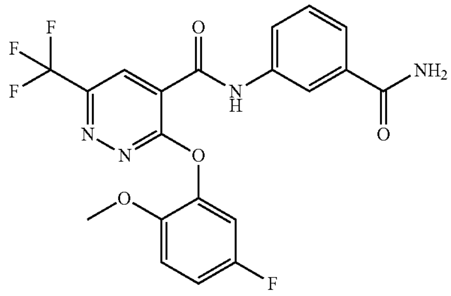 [SMILES: COc1ccc(F)cc1Oc1nnc(C(F)(F)F)cc1C(=O)Nc1cccc(C(N)=O)c1] N-(3-Carbamoylphenyl)-3-(5-fluoro-2-methoxyphenoxy)-6-(trifluoromethyl)pyridazine-4-carboxamide | $^1$H NMR (300 MHz, DMSO-$d_6$) δ 10.96 (s, 1H), 8.65 (s, 1H), 8.18 (t, J = 1.9 Hz, 1H), 8.02 (s, 1H), 7.91-7.83 (m, 1H), 7.71-7.63 (m, 1H), 7.55-7.30(m, 3H), 7.29-7.15 (m, 2H), 3.70 (s, 3H). LC-MS (Method 2): m/z 449.3 $[M - H]^+$ |
| 81 | 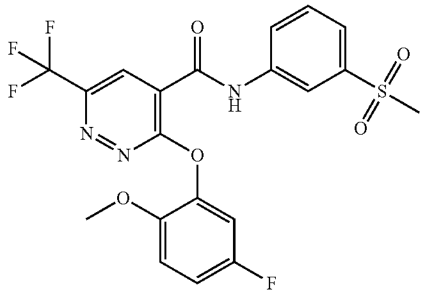 [SMILES: COc1ccc(F)cc1Oc1nnc(C(F)(F)F)cc1C(=O)Nc1cccc(S(C)(=O)=O)c1] 3-(5-Fluoro-2-methoxyphenoxy)-N-(3-methanesulfonylphenyl)-6-(trifluoromethyl)pyridazine-4-carboxamide | $^1$H NMR (300 MHz, DMSO-$d_6$) δ 11.25 (s, 1H), 8.68 (s, 1H), 8.38 (t, J = 1.9 Hz, 1H), 7.97 (dt, J = 7.5, 1.9 Hz, 1H), 7.81-7.66 (m, 2H), 7.36 (dd, J = 8.7,2.7 Hz, 1H), 7.30-7.14 (m, 2H), 3.70 (s, 3H), 3.25 (s, 3H). LC-MS (Method 2): 484.3 $[M - H]^+$ |
| 82 | 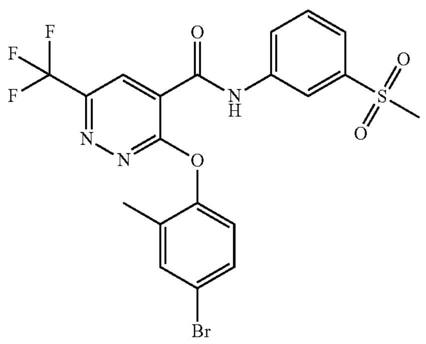 [SMILES: Cc1cc(Br)ccc1Oc1nnc(C(F)(F)F)cc1C(=O)Nc1cccc(S(C)(=O)=O)c1] 3-(4-Bromo-2-methylphenoxy)-N-(3-methanesulfonylphenyl)-6-(trifluoromethyl)pyridazine-4-carboxamide | $^1$H NMR (300 MHZ, DMSO-$d_6$ ) δ 11.27 (s, 1H), 8.70 (s, 1H), 8.37 (t, J = 1.9 Hz, 1H), 7.95 (dt, J = 7.6, 1.8 Hz, 1H), 7.81-7.67 (m, 2H), 7.66-7.60 (m,1H), 7.58-7.47 (m, 1H), 7.29 (d, J = 8.6 Hz, 1H), 3.25 (s, 3H), 2.14 (s, 3H). LC-MS (Method 2): m/z 528.2, 530.2 $[M - H]^+$ |

TABLE 23-continued

| Compound | Structure & Name | Analytical data |
|---|---|---|
| 83 | 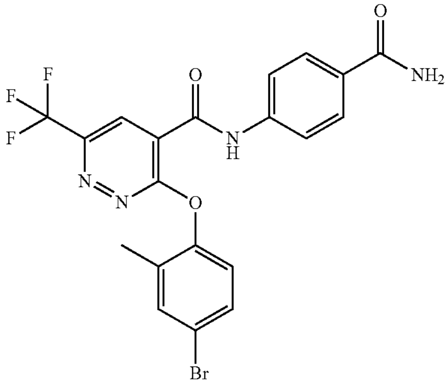 [SMILES: Cc1cc(Br)ccc1Oc1nnc(C(F)(F)F)cc1C(=O)Nc1ccc(C(N)=O)cc1] 3-(4-Bromo-2-methylphenoxy)-N-(4-carbamoylphenyl)-6-(trifluoromethyl)pyridazine-4-carboxamide | $^1$H NMR (300 MHZ, DMSO-$d_6$) δ 11.08 (s, 1H), 8.69 (s, 1H), 7.93 (d, J = 8.7 Hz, 3H), 7.81-7.70 (m, 2H), 7.62 (dd, J = 2.6, 0.8 Hz, 1H), 7.52 (dd, J = 8.9, 2.4 Hz, 1H), 7.31 (t, J = 9.0 Hz, 2H), 2.13 (s, 3H). HPLC purity 100%. LC-MS (Method 2): 495.3, 497.3 $[M + H]^+$ |
| 84 | 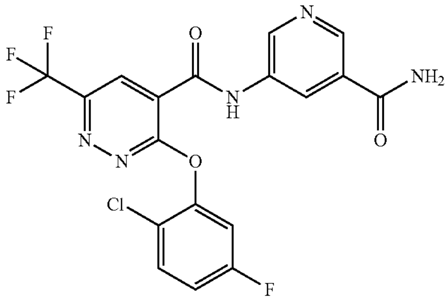 [SMILES: NC(=O)c1cncc(NC(=O)c2cc(C(F)(F)F)nnc2Oc2cc(F)ccc2Cl)c1] N-(5-Carbamoylpyridin-3-yl)-3-(2-chloro-5-fluorophenoxy)-6-(trifluoromethyl)pyridazine-4-carboxamide | $^1$H NMR (300 MHZ, DMSO-$d_6$) δ 11.26 (s, 1H), 8.96 (d, J = 2.5 Hz, 1H), 8.86 (d, J = 1.9 Hz, 1H), 8.78 (s, 1H), 8.58 (t, J = 2.2 Hz, 1H), 8.26 (s, 1H), 7.79-7.57 (m, 3H), 7.34 (ddd, J = 9.0, 8.1, 3.0 Hz, 1H). LC-MS (Method 2): m/z 454.3 $[M + H]^+$ |
| 85 | 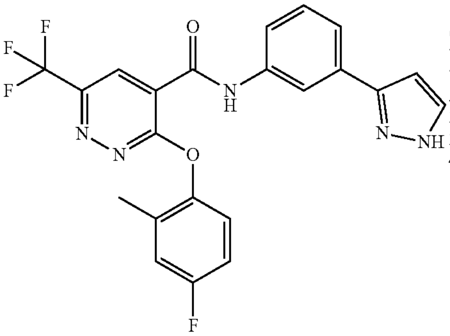 N-(3-(1H-Pyrazol-3-yl)phenyl)-3-(4-fluoro-2-methylphenoxy)-6-(trifluoromethyl)pyridazine-4-carboxamide | $^1$H NMR (400 MHz, $CD_3OD$) δ 8.44 (s, 1H), 8.10 (t, J = 1.8 Hz, 1H), 7.74-7.58 (m, 3H), 7.45 (t, J = 7.9 Hz, 1H), 7.29 (dd, J = 8.9, 4.9 Hz, 1H), 7.11 (dd, J = 9.1, 3.0 Hz, 1H), 7.04 (td, J = 8.4, 3.0 Hz, 1H), 6.68 (d, J = 2.2 Hz, 1H), 2.21 (s, 3H). LC-MS (Method 4): m/z 458.2 $[M + H]^+$, (ESI+), RT = 3.55 |

TABLE 23-continued

| Compound | Structure & Name | Analytical data |
| --- | --- | --- |
| 86 | 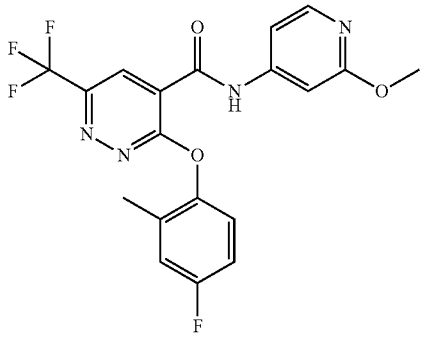 [SMILES: COc1cc(NC(=O)c2cc(C(F)(F)F)nnc2Oc2ccc(F)cc2C)ccn1] 3-(4-Fluoro-2-methylphenoxy)-N-(2-methoxypyridin-4-y1)-6-(trifluoromethyl)pyridazine-4-carboxamide | $^{1}H$ NMR (400 MHZ, DMSO-$d_6$) δ 11.22 (s, 1H), 8.66 (s, 1H), 8.19-8.09 (m, 1H), 7.34 (dd, J = 8.9, 5.1 Hz, 1H), 7.25 (dd, J = 9.5, 3.0 Hz, 1H), 7.21-7.11 (m, 3H), 3.85 (s, 3H), 2.12 (s, 3H). LC-MS (Method 4): m/z 423.2 $[M + H]^+$, (ESI+), RT = 3.63 |
| 87 | 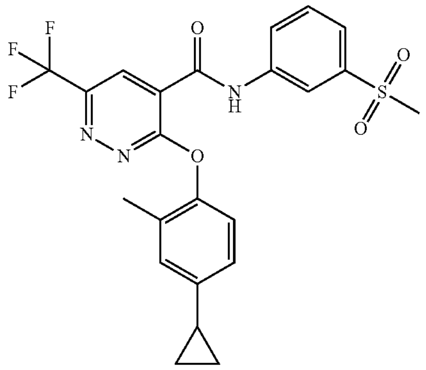 [SMILES: Cc1cc(C2CC2)ccc1Oc1nnc(C(F)(F)F)cc1C(=O)Nc1cccc(S(C)(=O)=O)c1] 3-(4-Cyclopropyl-2-methylphenoxy)-N-(3-(methylsulfonyl)phenyl)-6-(trifluoromethyl)pyridazine-4-carboxamide | $^{1}H$ NMR (400 MHZ, $CD_3OD$) δ 8.43 (s, 1H), 8.41 (t, J = 1.9 Hz, 1H), 8.00-7.95 (m, 1H), 7.78 (ddd, J = 7.8, 1.7, 1.1 Hz, 1H), 7.67 (t, J = 8.0 Hz, 1H), 7.11 (d, J = 8.3 Hz, 1H), 7.07-7.03 (m, 1H), 7.00 (dd, J = 8.4, 2.2 Hz, 1H), 3.15 (s, 3H), 2.15 (s, 3H), 1.97-1.88 (m, 1H), 1.01-0.93 (m, 2H), 0.72-0.64 (m, 2H). m/z 492.2 $[M + H]^+$ |
| 88 | 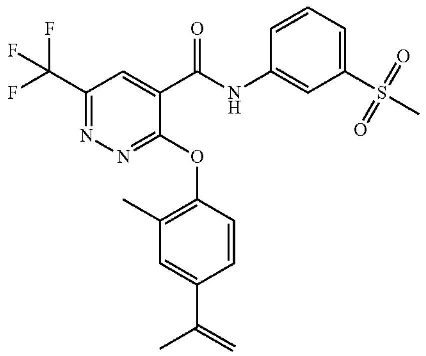 [SMILES: C=C(C)c1ccc(Oc2nnc(C(F)(F)F)cc2C(=O)Nc2cccc(S(C)(=O)=O)c2)c(C)c1] 3-(2-Methyl-4-(prop-1-en-2-yl)phenoxy)-N-(3-(methylsulfony1)phenyl)-6-(trifluoromethyl)pyridazine-4-carboxamide | $^{1}H$ NMR (400 MHZ, $CD_3OD$) δ 8.44 (s, 1H), 8.41 (t, J = 1.9 Hz, 1H), 7.99 (ddd, J = 8.1, 2.1, 1.0 Hz, 1H), 7.78 (ddd, J = 7.8, 1.7, 1.0 Hz, 1H), 7.67 (t, J = 8.0 Hz, 1H), 7.34-7.24 (m, 2H), 7.16 (d, J = 8.3 Hz, 1H), 6.42 (dd, J = 15.7, 1.4 Hz, 1H), 6.35-6.20 (m, 2H), 3.15 (s, 3H), 2.17 (s, 3H), 1.88 (dd, J = 6.5, 1.5 Hz, 3H). m/z 492.2 $[M + H]^+$ |

Example 112

Compound 89: 3-(2-Chloro-4-fluorophenoxy)-N-(2-oxo-1,2-dihydropyridin-4-yl)-6-(trifluoromethyl)pyridazine-4-carboxamide

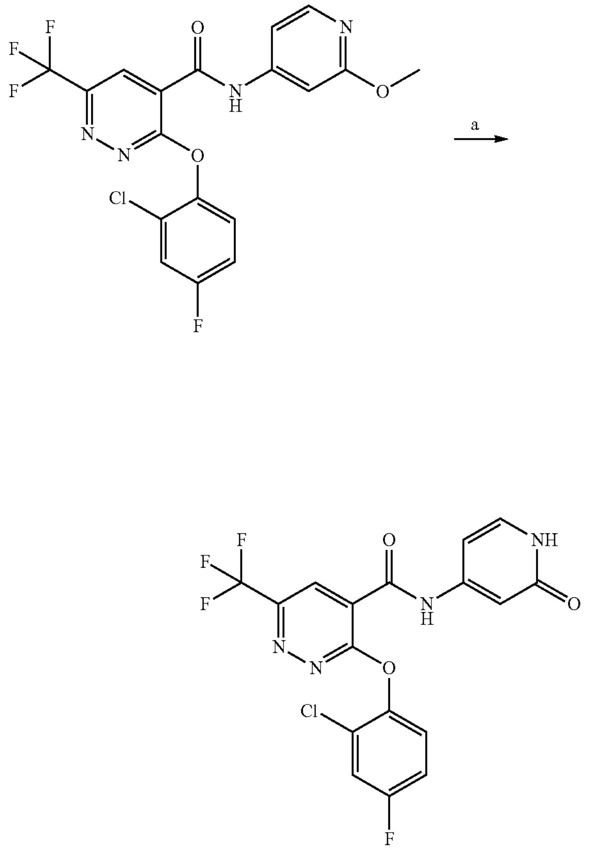

Reagents & conditions: a) iodotrimethylsilane, $CH_3CN$, 60 °C, 24 h

To a solution of 3-(2-chloro-4-fluorophenoxy)-N-(2-methoxypyridin-4-yl)-6-(trifluoromethyl)pyridazine-4-carboxamide (0.117 g, 0.264 mmol) in anhydrous acetonitrile (10 mL) was added iodotrimethylsilane (0.062 mL) at room temperature. After complete addition of iodotrimethylsilane the mixture was stirred at 60 °C for 24 h. At the end of this period mixture was cooled to rt and solvent evaporated to dryness, water was added (15 mL) and extracted with EtOAc (3×20 mL). The EtOAc layers were combined and washed with water (20 ml) and brine (20 mL), the organic layer was dried ($Na_2SO_4$), filtered and the solvent evaporated. The mixture was chromatographed over $SiO_2$ with a gradient of 0-15% EtOAC in DCM to afford 3-(2-chloro-4-fluorophenoxy)-N-(2-oxo-1,2-dihydropyridin-4-yl)-6-(trifluoromethyl)pyridazine-4-carboxamide (0.0416 g, 37%). 1H NMR (300 MHz, DMSO-$d_6$) δ 11.40 (s, 1H), 10.95 (s, 1H), 8.72 (s, 1H), 7.71 (dd, J=8.4, 3.0 Hz, 1H), 7.63 (dd, J=9.1, 5.2 Hz, 1H), 7.47-7.34 (m, 2H), 6.78 (d, J=2.0 Hz, 1H), 6.38 (dd, J=7.2, 2.1 Hz, 1H). LC-MS (Method 2): m/z 427.0 $[M-H]^+$.

Compound 90: 3-(4-Fluoro-2-methylphenoxy)-N-(5-methyl-2-oxo-1,2-dihydropyridin-4-yl)-6-(trifluoromethyl)pyridazine-4-carboxamide

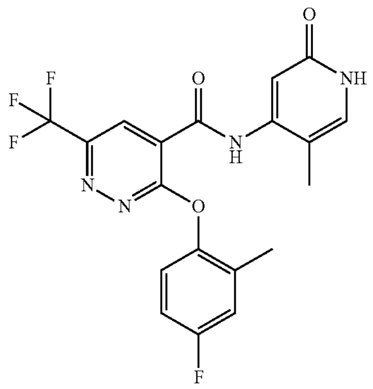 [SMILES: Cc1c[nH]c(=O)cc1NC(=O)c1cc(C(F)(F)F)nnc1Oc1ccc(F)cc1C]

The title compound was prepared by a similar procedure described for Compound 89 using 3-(4-fluoro-2-methylphenoxy)-N-(2-methoxy-5-methylpyridin-4-yl)-6-(trifluoromethyl)pyridazine-4-carboxamide. $^1H$ NMR (400 MHz, DMSO-dr) δ 11.31 (s, 1H), 9.95 (s, 1H), 8.63 (s, 1H), 7.36 (dd, J=8.9, 4.9 Hz, 1H), 7.27 (dd, J=9.5, 3.1 Hz, 1H), 7.24 (s, 1H), 7.17 (td, J=8.6, 3.2 Hz, 1H), 7.11 (s, 1H), 2.15 (s, 3H), 2.00 (s, 3H). LC-MS (Method 5): m/z 422.9 $[M+H]^+$, (ESI+), RT=3.83.

Compound 91: 3-(4-Fluoro-2-methylphenoxy)-N-(3-methyl-2-oxo-1,2-dihydropyridin-4-yl)-6-(trifluoromethyl)pyridazine-4-carboxamide

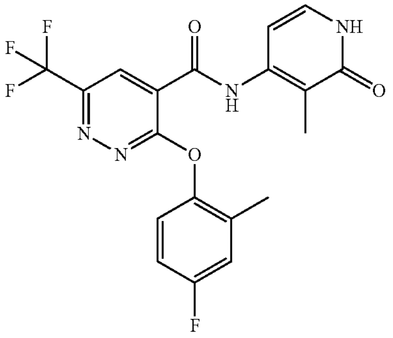 [SMILES: Cc1cc(F)ccc1Oc1nnc(C(F)(F)F)cc1C(=O)Nc1cc[nH]c(=O)c1C]

The title compound was prepared by a similar procedure described for Compound 89 using 3-(4-fluoro-2-methylphenoxy)-N-(2-methoxy-3-methylpyridin-4-yl)-6-(trifluoromethyl)pyridazine-4-carboxamide. $^1H$ NMR (400 MHz, DMSO-$d_6$) δ 11.47 (s, 1H), 10.26 (s, 1H), 8.63 (s, 1H), 7.35 (dd, J=8.6, 5.3 Hz, 1H), 7.30-7.23 (m, 2H), 7.16 (td, J=8.6, 3.1 Hz, 1H), 6.76 (d, J=7.1 Hz, 1H), 2.14 (s, 3H), 1.95 (s, 3H). LC-MS (Method 6): m/z 423.2 $[M+H]^+$, (ESI+), RT=3.05.

Compound 92: 3-(4-Fluoro-2-methylphenoxy)-N-(2-methyl-6-oxo-1,6-dihydropyridin-3-yl)-6-(trifluoromethyl)pyridazine-4-carboxamide

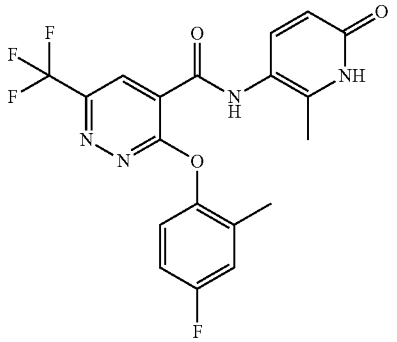 [SMILES: Cc1cc(F)ccc1Oc1nnc(C(F)(F)F)cc1C(=O)Nc1ccc(=O)[nH]c1C]

The title compound was prepared by a similar procedure described for Compound 89 using 3-(4-fluoro-2-methylphenoxy)-N-(6-methoxy-2-methylpyridin-3-yl)-6-(trifluoromethyl)pyridazine-4-carboxamide. $^1$H NMR (400 MHz, DMSO-$d_6$) δ 11.73 (s, 1H), 10.10 (s, 1H), 8.61 (s, 1H), 7.43 (d, J=9.5 Hz, 1H), 7.33 (dd, J=9.0, 5.1 Hz, 1H), 7.26 (dd, J=9.5, 3.0 Hz, 1H), 7.16 (td, J=8.5, 3.2 Hz, 1H), 6.22 (d, J=8.9 Hz, 1H), 2.16 (s, 3H), 2.14 (s, 3H). LC-MS (Method 6): m/z 423.2 $[M+H]^+$, (ESI+), RT=2.85.

Compound 93: 3-(4-Fluoro-2-methyl-phenoxy)-6-methyl-N-[3-(methylsulfonimidoyl)phenyl]pyridazine-4-carboxamide

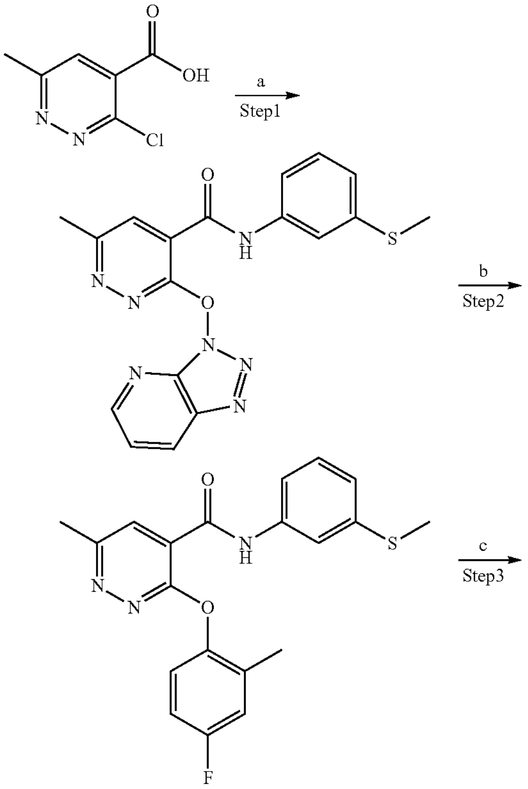

-continued

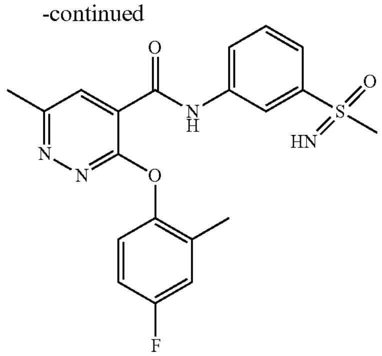

Reagents & conditions: a) HATU, DCM, DIEA, rt 18 h; b) 4-fluoro-2-methyl-phenol, $Cs_2CO_3$, $CH_3CN$, rt, 16 h; c) diacetoxyiodo-benzene, $(NH_4)_2CO_3$, MeOH, rt, 3 h.

Step 1: 6-methyl-N-(3-methylsulfanylphenyl)-3-(triazolo[4,5-b]pyridin-3-yloxy)pyridazine-4-carboxamide. A mixture of 3-(methylsulfanyl)aniline (1.2 mL, 6.95 mmol), 3-chloro-6-methylpyridazine-4-carboxylic acid (1.00 g, 5.79 mmol) were dissolved in DCM (23.179 mL) under an atmosphere of nitrogen at RT °C. Then N-[(dimethylamino)(3H-[1,2,3]triazolo[4,5-b]pyridin-3-yloxy)methylidene]-N-methylmethanaminium hexafluorophosphate (HATU) (2.42 g, 6.37 mmol) was added in one portion. To the above mixture N-ethyl-N-isopropyl-propan-2-amine (2.0 mL, 11.6 mmol) was added dropwise over 2-3 minutes. The reaction mixture was stirred at rt for 18 h. The reaction was diluted with sat. $NaHCO_3$ solution (30 mL) and stirred vigorously for 45 minutes and then extracted with DCM (30 mL×2). The combined organic extracts were dried over $MgSO_4$, filtered and concentrated under reduced pressure to obtain the dark brown crude residue. Purification by chromatography eluting with a gradient of 0 to 50% EtOAc in heptane yields the title compound 6-methyl-N-(3-methylsulfanylphenyl)-3-(triazolo[4,5-b]pyridin-3-yloxy)pyridazine-4-carboxamide (68.0%) (1.29 g, 2.23 mmol, 39% Yield) isolated impure as a beige solid. $^1$H NMR (500 MHz, $CDCl_3$) δ 9.51 (s, 1H), 8.72 (dd, J=4.5, 1.4 Hz, 1H), 8.53 (dd, J=8.4, 1.4 Hz, 1H), 8.10 (s, 1H), 7.71 (t, J=1.9 Hz, 1H), 7.51 (dd, J=8.4, 4.5 Hz, 1H), 7.46 (ddd, J=8.1, 2.0, 0.8 Hz, 1H), 7.30 (t, J=8.0 Hz, 1H), 7.10 (ddd, J=7.9, 1.8, 0.9 Hz, 1H), 2.76 (s, 3H), 2.51 (s, 3H). LC-MS (Method 3): m/z 394.4 $[M+H]^+$, (ESI+), RT=0.76.

Step 2: 3-(4-fluoro-2-methyl-phenoxy)-6-methyl-N-(3-methylsulfanylphenyl)pyridazine-4-carboxamide. 6-methyl-N-(3-methylsulfanylphenyl)-3-(triazolo[4,5-b]pyridin-3-yloxy)pyridazine-4-carboxamide (68%, 0.25 g, 0.432 mmol) and 4-fluoro-2-methyl-phenol (65 mg, 0.519 mmol) were suspended in anhydrous acetonitrile (4.3211 mL) under an atmosphere of nitrogen and treated with cesium carbonate (0.282 g, 0.864 mmol). The resulting mixture was stirred at rt overnight. Reaction diluted with sat. $NH_4Cl$ solution (10 mL) and EtOAc (10 mL) then stirred at rt for 10 minutes. Layers shaken and separated, then aqueous re-extracted with EtOAc (×1). Combined organics dried ($Na_2SO_4$), filtered and concentrated in vacuo to yield a brown gum. The material was purified by column chromatography with a gradient of EtOAc and Heptane (0-100%) to obtain the title compound 3-(4-fluoro-2-methyl-phenoxy)-6-methyl-N-(3-methylsulfanylphenyl)pyridazine-4-carboxamide (0.122 g, 71%) as a yellow/brown solid. $^1$H NMR (400 MHz, $CDCl_3$): δ 9.75 (s, 1H), 8.21 (s, 1H), 7.71 (t, J=1.8 Hz, 1H), 7.36 (m, 1H), 7.29 (t, J=7.9 Hz, 1H), 7.17 (dd, J=8.8, 4.8 Hz, 1H), 7.09 (dt, J=7.7, 1.1 Hz, 2H), 7.05 (dd, J=8.9, 2.9 Hz, 1H), 7.00 (td, J=8.3, 3.1 Hz, 1H), 2.75 (s, 3H), 2.52 (s, 3H), 2.22 (s, 3H). LC-MS (Method 3): m/z 384 $[M+H]^+$, (ESI+), RT=0.89.

Step 3: 3-(4-fluoro-2-methyl-phenoxy)-6-methyl-N-[3 (methylsulfonimidoyl)phenyl]pyridazine-4-carboxamide. 3-(4-fluoro-2-methyl-phenoxy)-6-methyl-N-(3-methylsulfanylphenyl)pyridazine-4-carboxamide (0.122 g, 0.318 mmol) was dissolved in Methanol (3.2 mL) and treated with ammonium carbonate (0.046 g, 0.477 mmol) and diacetoxyiodo-benzene (0.236 g, 0.732 mmol), each added in one portion. After 60 minutes added more ammonium carbonate (0.046 g, 0.477 mmol) and diacetoxyiodo-benzene (0.236 g, 0.732 mmol). After a further 2 hours at rt the mixture was concentrated in vacuo to yield a brown gum. Purified using column chromatography with a gradient of methanol in ethyl acetate yielding the impure title compound. This was purified further using a preparative HPLC (Gilson 6) to yield the title compound (0.064 mg, 47%). $^1H$ NMR (500 MHz, DMSO-$d_6$) δ 11.06 (s, 1H), 8.36 (t, J=1.9 Hz, 1H), 7.90 (ddd, J=8.0, 2.0, 0.9 Hz, 1H), 7.90 (s, 1H), 7.70 (ddd, J=7.8, 1.6, 1.1 Hz, 1H), 7.62 (t, J=7.9 Hz, 1H), 7.25 (dd, J=8.9, 5.1 Hz, 1H), 7.20 (dd, J=9.4, 3.0 Hz, 1H), 7.11 (td, J=8.5, 3.2 Hz, 1H), 4.24 (s, 1H), 3.07-3.05 (m, 3H), 2.61 (s, 3H), 2.10 (s, 3H). LC-MS (Method 6): m/z 415.3 [M+H]+, (ESI+), RT=2.55.

Compound 94: 3-(4-Fluoro-2-methoxyphenoxy)-6-methyl-N-(3-(S-methylsulfonimidoyl)phenyl) pyridazine-4-carboxamide

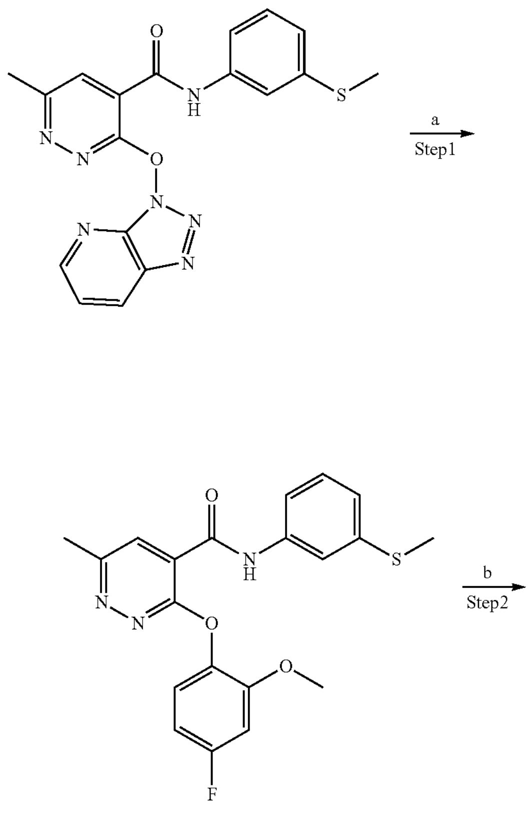

-continued

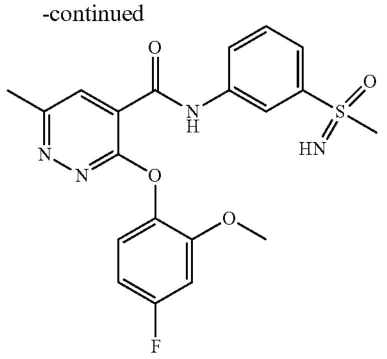

Reagents & conditions: a) 4-fluoro-2-methoxyphenol, $Cs_2CO_3$, acetonitrile, rt, 16 h; b) diacetoxyiodo-benzene, $(NH_4)_2CO_3$, MeOH, rt, 3 h.

Step 1—3-(4-fluoro-2-methoxyphenoxy)-6-methyl-N-(3-(methylthio)phenyl)pyridazine-4-carboxamide. 6-methyl-N-(3-methylsulfanylphenyl)-3-(triazolo[4,5-b]pyridin-3-yloxy)pyridazine-4-carboxamide (68%, 0.500 g, 0.864 mmol) and 4-fluoro-2-methoxyphenol (0.150 g, 1.04 mmol) and cesium carbonate (0.563 g, 1.73 mmol) were suspended in anhydrous acetonitrile (8.6 mL) and the resulting mixture was stirred at rt for 16 h. Reaction diluted with Sat. $NH_4Cl$ solution (20 mL) and DCM (10 mL) then stirred at rt for 10 minutes. Layers separated and the aqueous re-extracted with DCM (10 mL). Combined organics concentrated in vacuo to yield a brown solid that was purified with column chromatography with a gradient of (0-100%) ethyl acetate and heptane to yield the title compound (0.320 g 88%) as a pink crystalline solid $^1H$ NMR (500 MHz, $CDCl_3$): δ 9.84 (s, 1H), 8.18 (s, 1H), 7.71 (t, J=1.9 Hz, 1H), 7.42 (dd, J=8.6, 5.4 Hz, 1H), 7.38 (ddd, J=8.1, 2.0, 0.9 Hz, 1H), 7.29 (t, J=7.9 Hz, 1H), 7.08 (ddd, J=7.8, 1.8, 1.0 Hz, 1H), 6.79 (dt, J=4.6, 2.2 Hz, 1H), 6.78-6.74 (m, 1H), 3.79 (s, 3H), 2.78 (s, 3H), 2.52 (s, 3H). LC-MS (Method 6): m/z 400.5 $[M+H]^+$, (ESI+), RT=4.01.

Step 2—3-(4-fluoro-2-methoxyphenoxy)-N-(3-(S-methylsulfonimidoyl)phenyl)-6-(trifluoromethyl)pyridazine-4-carboxamide. Title compound was prepared by similar procedure as described for step 3 of Compound 93 using 3-(4-fluoro-2-methoxyphenoxy)-6-methyl-N-(3-(methylthio)phenyl)pyridazine-4-carboxamide. $^1H$ NMR (500 MHz, DMSO-$d_6$) δ 11.00 (s, 1H), 8.37 (t, J=1.8 Hz, 1H), 7.94-7.89 (m, 1H), 7.86 (s, 1H), 7.73-7.67 (m, 1H), 7.61 (t, J=7.9 Hz, 1H), 7.31 (dd, J=8.8, 5.9 Hz, 1H), 7.10 (dd, J=10.7, 2.9 Hz, 1H), 6.84 (td, J=8.5, 2.9 Hz, 1H), 4.24 (s, 1H), 3.70 (s, 3H), 3.06 (s, 3H), 2.61 (s, 3H). LC-MS (Method 6): m/z 431.3 [M+H]+, (ESI+), RT=2.43.

Compound 95: 3-(2-Ethoxy-4-fluorophenoxy)-6-methyl-N-(3-(S-methylsulfonimidoyl)phenyl) pyridazine-4-carboxamide

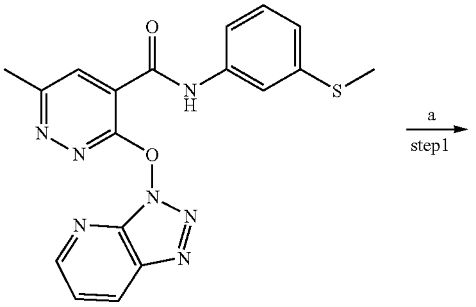

-continued

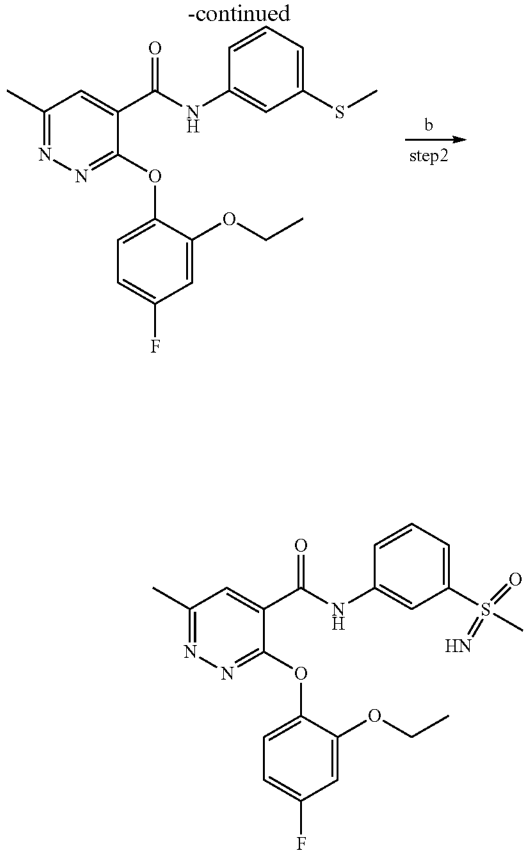

Reagents & conditions: a) 4-fluoro-2-methoxyphenol, $Cs_2CO_3$, acetonitrile, rt, 16 h; b) diacetoxyiodo-benzene, $(NH_4)_2CO_3$, MeOH, rt, 3 h.

Step 1—3-(2-ethoxy-4-fluorophenoxy)-6-methyl-N-(3-(methylthio)phenyl)pyridazine-4-carboxamide. The title compound (0.388 g, 99%) was prepared as an off-white crystalline solid by a similar method as described for step 2 of Compound 93, but using 2-ethoxy-4-fluoro-phenol and 6-methyl-N-(3-methylsulfanylphenyl)-3-(triazolo[4,5-b] pyridin-3-yloxy)pyridazine-4-carboxamide. $^1H$ NMR (500 MHz, $CDCl_3$): δ 9.83 (s, 1H), 8.16 (s, 1H), 7.72 (t, J=1.9 Hz, 1H), 7.39 (dd, J=9.4, 5.7 Hz, 1H), 7.37-7.34 (m, 1H), 7.29 (t, J=7.9 Hz, 1H), 7.08 (ddd, J=7.8, 1.8, 1.0 Hz, 1H), 6.79-6.76 (m, 1H), 6.75 (d, J=2.3 Hz, 1H), 4.00 (q, J=7.0 Hz, 2H), 2.77 (s, 3H), 2.51 (s, 3H), 1.15 (t, J=7.0 Hz, 3H). LC-MS (Method 1): m/z 414.3 $[M+H]^+$, (ESI+), RT=0.90.

Step 2—3-(2-ethoxy-4-fluorophenoxy)-6-methyl-N-(3-(S-methylsulfonimidoyl)phenyl) pyridazine-4-carboxamide. Title compound was prepared by similar procedure as described for step 3 of Compound 93 using 3-(2-ethoxy-4-fluorophenoxy)-6-methyl-N-(3-(methylthio)phenyl) pyridazine-4-carboxamide. $^1H$ NMR (500 MHz, DMSO-$d_6$) δ 10.97 (s, 1H), 8.37 (t, J=1.8 Hz, 1H), 7.96-7.88 (m, 1H), 7.87 (s, 1H), 7.71-7.68 (m, 1H), 7.61 (t, J=7.9 Hz, 1H), 7.32 (dd, J=8.8, 5.9 Hz, 1H), 7.06 (dd, J=10.7, 2.9 Hz, 1H), 6.82 (td, J=8.5, 2.9 Hz, 1H), 4.24 (s, 1H), 3.97 (q, J=7.0 Hz, 2H), 3.06 (s, 3H), 2.61 (s, 3H), 1.05 (t, J=7.0 Hz, 3H). LC-MS (Method 6): m/z 445.3 $[M+H]^+$, (ESI+), RT=2.62.

Compound 96: 3-(2-Chloro-4-fluorophenoxy)-N-(3-(S-methylsulfonimidoyl)phenyl)-6-(trifluoromethyl) pyridazine-4-carboxamide

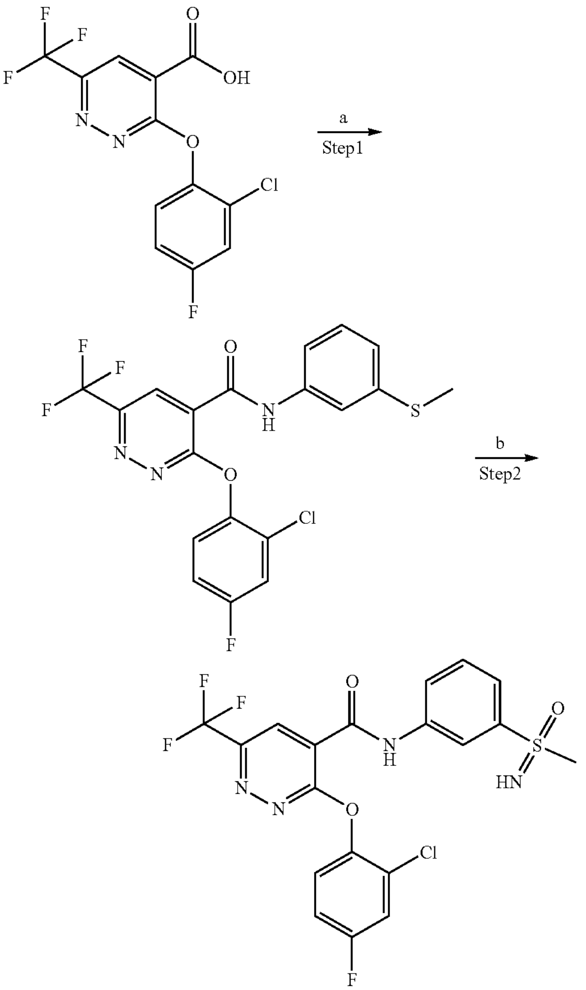

Reagents & conditions: a) 3-(methyltio)aniline, HATU, DMF, DIEA, rt 18 h; b) diacetoxyiodo-benzene, $(NH_4)_2CO_3$, MeOH, rt, 3 h.

Step 1: 3-(2-chloro-4-fluorophenoxy)-N-[3-(methylsulfanyl)phenyl]-6-(trifluoromethyl)pyridazine-4-carboxamide. To a mixture of 3-(2-chloro-4-fluorophenoxy)-6-(trifluoromethyl)pyridazine-4-carboxylic acid (0.100 g, 0.297 mmol), 3-(methylsulfanyl)aniline (0.041 g, 0.356 mmol), HATU (0.226 g, 0.594 mmol) in DMF (3 mL) was added DIEA (0.129 mL, 0.743 mmol) at 25 °C and stirring continue for further 2 h at 25 °C. At the end of this period water (5 mL) was added and extracted with EtOAc (3×25 mL). The organic layers combined and washed with 1M LiCl solution (20 mL) followed by brine (20 mL). The EtOAc layer was dried ($Na_2SO_4$), filtered and the solvent evaporated. The crude mixture was chromatographed over $SiO_2$ with a gradient of 0-60% EtOAc in hexane to provide 3-(2-chloro-4-fluorophenoxy)-N-[3-(methylsulfanyl)phenyl]-6-(trifluoromethyl)pyridazine-4-carboxamide (0.086 g, 63.23%). $^1H$ NMR (300 MHz, DMSO-$d_6$) δ 10.90 (s, 1H), 8.70 (s, 1H), 7.79-7.54 (m, 3H), 7.49-7.22 (m, 3H), 7.07 (ddd, J=7.8, 1.9, 1.1 Hz, 1H), 2.48 (s, 3H). LC-MS (Method 2): m/z 456.3 $[M-H]^+$.

Step 2: 3-(2-chloro-4-fluorophenoxy)-N-(3-(S-methylsulfonimidoyl)phenyl)-6-(trifluoromethyl)pyridazine-4-carboxamide. 3-(2-chloro-4-fluorophenoxy)-N-[3-(methylsulfanyl)phenyl]-6-(trifluoromethyl)pyridazine-4-carboxamide 0.133 g, 0.291 mmol) was dissolved in Methanol (5.0 mL) and treated with ammonium carbonate (0.42 g, 0.436 mmol) and diacetoxyiodo-benzene (0.215 mg, 0.668 mmol), each added in one portion. The reaction mixture was stirred for 3 h at rt. At the end of this period the reaction mixture was concentrated in vacuo and the crude mixture was chromatographed over $SiO_2$ eluting with a gradient of 0-100% EtOAc in DCM to provide 3-(2-chloro-4-fluorophenoxy)-N-(3-(S-methylsulfonimidoyl)phenyl)-6-(trifluoromethyl) pyridazine-4-carboxamide (0.098 g, 69%). $^1$H NMR (300 MHz, DMSO-$d_6$) δ 11.21 (s, 1H), 8.73 (s, 1H), 8.35 (t, J=1.9 Hz, 1H), 7.99-7.87 (m, 1H), 7.79-7.58 (m, 4H), 7.41 (ddd, J=9.1, 8.1, 3.0 Hz, 1H), 4.27 (s, 1H), 3.07 (d, J=1.1 Hz, 3H). LC-MS (Method 2): m/z 489.5 $[M+H]^+$.

Compound 97: 3-(2-Chloro-4-fluorophenoxy)-N-(2-(S-methylsulfonimidoyl)pyridin-4-yl)-6-(trifluoromethyl)pyridazine-4-carboxamide

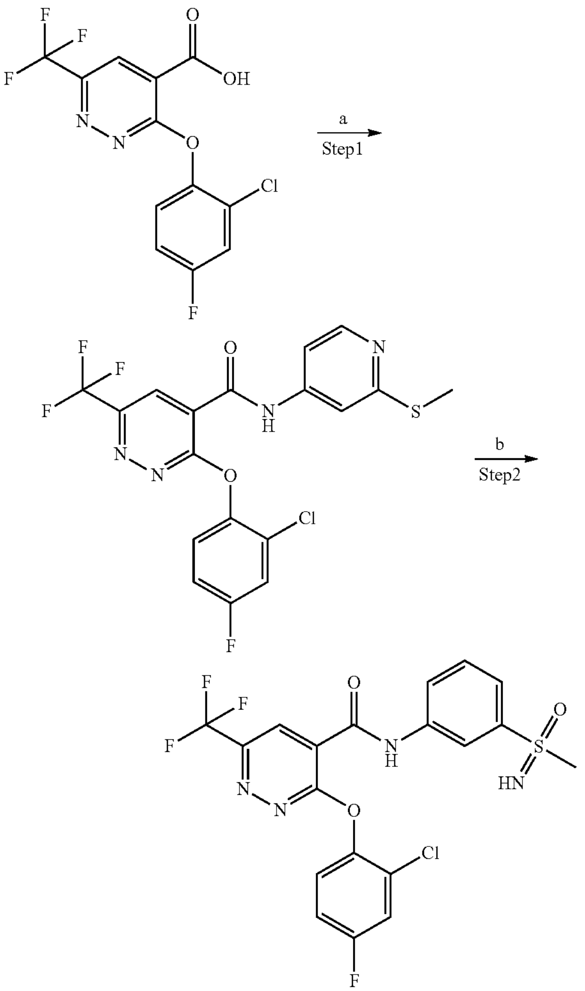

Reagents & conditions: a) 2-(methyltio)pyridin-4-amine, HATU, DMF, DIEA, rt, 18 h; b) diacetoxyiodo-benzene, $(NH_4)_2CO_3$, MeOH, rt, 3 h.

Step 1: 3-(2-chloro-4-fluorophenoxy)-N-(2-(methylthio) pyridin-4-yl)-6-(trifluoromethyl)pyridazine-4-carboxamide. The title compound (0.0913 g, 45%) was prepared by a similar procedure described for step 1 of Compound 96 using 3-(2-chloro-4-fluorophenoxy)-6-(trifluoromethyl) pyridazine-4-carboxylic acid and 2-(methylthio)pyridin-4-amine. H NMR (300 MHz, $CDCl_3$) δ 9.49 (s, 1H) 8.66 (s, 1H), 8.42 (dd, J=5.6, 0.7 Hz, 1H), 7.63 (dd, J=2.1, 0.7 Hz, 1H), 7.47 (dd, J=9.1, 4.9 Hz, 1H), 7.36 (dd, J=7.7, 2.9 Hz, 1H), 7.31-7.15 (m, 3H), 2.59 (s, 3H).

Step 2: 3-(2-chloro-4-fluorophenoxy)-N-(2-(S-methylsulfonimidoyl)pyridin-4-yl)-6-(trifluoromethyl)pyridazine-4-carboxamide. Title compound (0.0366 g, 42%) was prepared by a similar procedure described for step 2 of Compound 96. $^1$H NMR (300 MHz, DMSO-$d_6$) δ 11.62 (s, 1H), 8.77 (s, 1H), 8.69 (d, J=5.4 Hz, 1H), 8.40 (d, J=2.0 Hz, 1H), 7.86 (dd, J=5.4, 2.1 Hz, 1H), 7.76-7.58 (m, 2H), 7.41 (ddd, J=9.1, 8.1, 3.0 Hz, 1H), 4.44 (s, 1H), 3.16 (d, J=1.1 Hz, 3H). LC-MS (Method 2): m/z 490.4 $[M+H]^+$.

Compound 98: 3-(4-Fluoro-2-methylphenoxy)-N-(4-(S-methylsulfonimidoyl)phenyl)-6-(trifluoromethyl) pyridazine-4-carboxamide

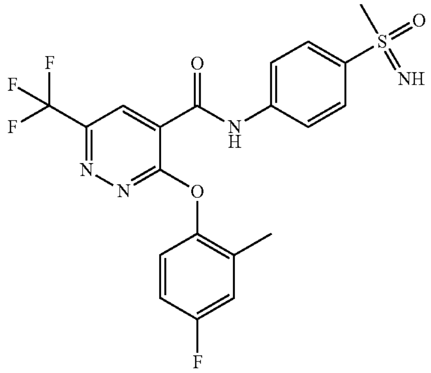 [SMILES: Cc1cc(F)ccc1Oc1nnc(C(F)(F)F)cc1C(=O)Nc1ccc(S(C)(=N)=O)cc1]

The title compound 3-(4-fluoro-2-methylphenoxy)-N-(4-(S-methylsulfonimidoyl)phenyl)-6-(trifluoromethyl) pyridazine-4-carboxamide was prepared by a similar procedure described for step 2 of Compound 96 using 3-(4-fluoro-2-methylphenoxy)-N-(4-(methylthio)phenyl)-6-(trifluoromethyl)pyridazine-4-carboxamide. $^1$H NMR (400 MHz, DMSO-$d_6$) δ 11.21 (s, 1H), 8.67 (s, 1H), 7.99-7.85 (m, 4H), 7.35 (dd, J=8.9, 5.1 Hz, 1H), 7.25 (dd, J=9.4, 2.9 Hz, 1H), 7.15 (td, J=8.6, 3.2 Hz, 1H), 4.17 (s, 1H), 3.08-3.00 (m, 3H), 2.13 (s, 3H). LC-MS (Method 5): m/z 469.1 [M+H]+, (ESI+), RT=3.80.

Compound 99: 3-(4-Fluoro-2-methoxyphenoxy)-N-(3-(S-methylsulfonimidoyl)phenyl)-6-(trifluoromethyl)pyridazine-4-carboxamide

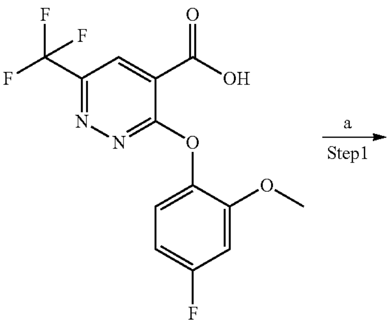

-continued

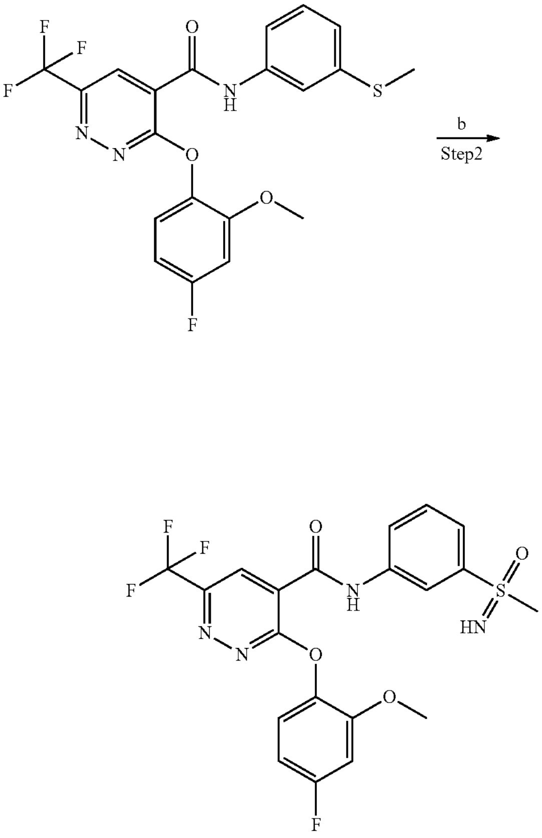

Reagents & conditions: 3-(methyltio)aniline, propylphosphonic anhydride (50% in EtOAc), DMAP, DIEA, DCM, rt, 3 h; b) diacetoxyiodo-benzene, $(NH_4)_2CO_3$, MeOH, rt, 3 h.

Step 1: 3-(4-fluoro-2-methoxyphenoxy)-N-(3-(methylthio)phenyl)-6-(trifluoromethyl)pyridazine-4-carboxamide. Title compound was prepared by a similar procedure described for Compound 1 using 3-(4-fluoro-2-methoxyphenoxy)-6-(trifluoromethyl)pyridazine-4-carboxylic acid and 3-(methylthio)aniline. $^1$H NMR (400 MHz, DMSO-$d_6$) δ 10.85 (s, 1H), 8.60 (s, 1H), 7.67 (t, J=1.9 Hz, 1H), 7.49-7.40 (m, 1H), 7.40-7.28 (m, 2H), 7.15 (dd, J=10.7, 2.8 Hz, 1H), 7.10-6.99 (m, 1H), 6.88 (td, J=8.5, 2.9 Hz, 1H), 3.73 (s, 3H), 2.48 (s, 3H). LC-MS (Method 1) m/z 453.9 [M+H]+, (ESI+), RT=4.87.

Step 2: 3-(4-fluoro-2-methoxyphenoxy)-N-(3-(S-methylsulfonimidoyl)phenyl)-6-(trifluoromethyl)pyridazine-4-carboxamide. Title compound was prepared by similar procedure described for step 2 of Compound 93 using 3-(4-fluoro-2-methoxyphenoxy)-N-(3-(methylthio)phenyl)-6-(trifluoromethyl)pyridazine-4-carboxamide, $(NH_4)_2CO_3$ and diacetoxyiodo-benze to provide 3-(4-fluoro-2-methoxyphenoxy)-N-(3-(S-methylsulfonimidoyl)phenyl)-6-(trifluoromethyl)pyridazine-4-carboxamide as a racemic mixture. $^1$H NMR (500 MHz, DMSO-$d_6$) δ 11.20 (s, 1H), 8.63 (s, 1H), 8.38-8.32 (m, 1H), 7.96-7.88 (m, 1H), 7.77-7.69 (m, 1H), 7.64 (t, J=7.9 Hz, 1H), 7.38 (dd, J=8.8, 5.8 Hz, 1H), 7.15 (dd, J=10.7, 2.9 Hz, 1H), 6.88 (td, J=8.5, 2.9 Hz, 1H), 4.27 (s, 1H), 3.73 (s, 3H), 3.07 (s, 3H). LC-MS (Method 1): m/z 485.0 [M+H]+, (ESI+), RT=3.84.

Compounds 100 & 101: First Eluting Isomer and Second Eluting Isomer

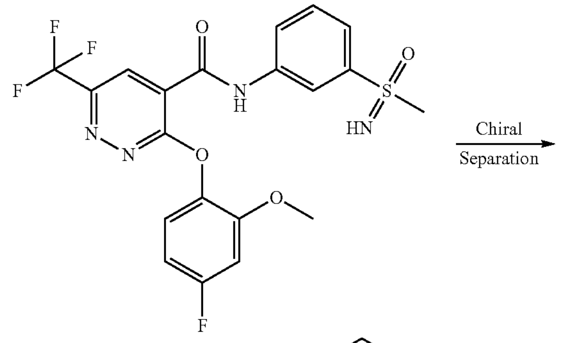

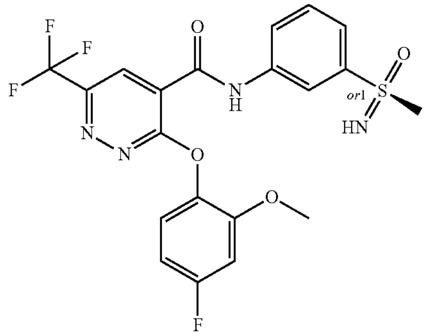

and

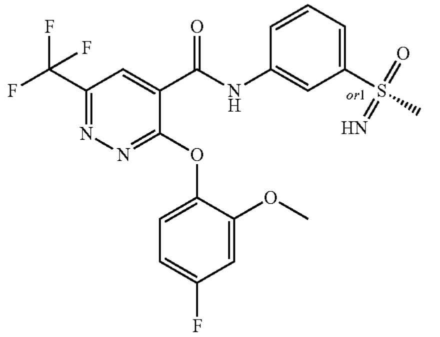

The racemic mixture from Compound 99 was purified by SFC to give the title compounds: first eluting isomer (Compound 100)—$^1$H NMR (500 MHz, DMSO-$d_6$) δ 11.18 (s, 1H), 8.63 (s, 1H), 8.35 (t, J=1.8 Hz, 1H), 7.95-7.90 (m, 1H), 7.72 (dt, J=7.8, 1.1 Hz, 1H), 7.64 (t, J=7.9 Hz, 1H), 7.38 (dd, J=8.8, 5.8 Hz, 1H), 7.16 (dd, J=10.7, 2.9 Hz, 1H), 6.88 (td, J=8.5, 2.9 Hz, 1H), 4.26 (s, 1H), 3.73 (s, 3H), 3.07 (s, 3H). LC-MS (Method 6): m/z 485.3 $[M+H]^+$, (ESI+), RT=3.09 and the second eluting isomer (Compound 101)—$^1$H NMR (500 MHz, DMSO-$d_6$) δ 11.20 (s, 1H), 8.61 (s, 1H), 8.34 (t, J=1.9 Hz, 1H), 7.94-7.89 (m, 1H), 7.74-7.69 (m, 1H), 7.63 (t, J=7.9 Hz, 1H), 7.37 (dd, J=8.8, 5.8 Hz, 1H), 7.15 (dd, J=10.7, 2.9 Hz, 1H), 6.88 (td, J=8.5, 2.9 Hz, 1H), 4.25 (s, 1H), 3.73 (s, 3H), 3.06 (s, 3H). LC-MS (Method 1): m/z 484.9 $[M+H]^+$, (ESI+), RT=3.83.

Compound 102: (R)-3-(4-fluoro-2-methylphenoxy)-N-(3-(S-methylsulfonimidoyl)phenyl)-6-(trifluoromethyl)pyridazine-4-carboxamide

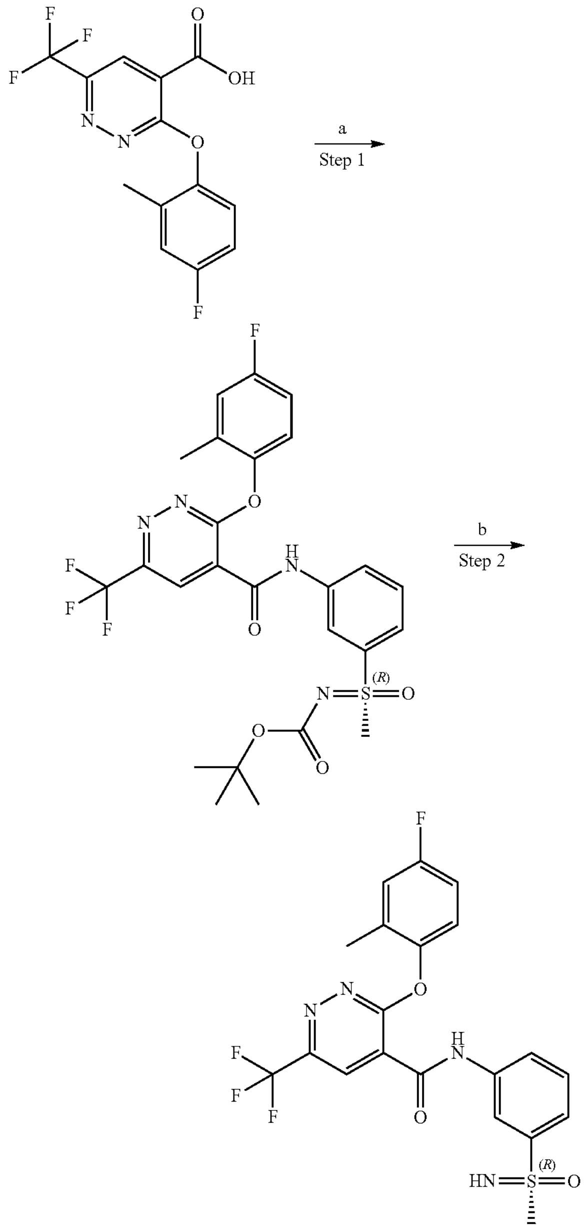

Reagents & conditions: a) tert-butyl (R)-((3-aminophenyl)(methyl)(oxo)-$\lambda^6$-sulfaneylidene)carbamate [Intermediate 72], HATU, DIEA, DMF, rt, 1 h; b) 4M HCl in dioxane, DCM, rt, 2 h.

Step 1: tert-butyl (R)-((3-(3-(4-fluoro-2-methylphenoxy)-6-(trifluoromethyl)pyridazine-4-carboxamido) phenyl)(methyl)(oxo)-$\lambda^6$-sulfaneylidene) carbamate: To a mixture of 3-(4-fluoro-2-methylphenoxy)-6-(trifluoromethyl) pyridazine-4-carboxylic acid (300 mg, 0.95 mmol), tert-butyl (R)-((3-aminophenyl)(methyl)(oxo)-$\lambda^6$-sulfaneylidene)carbamate[Intermediate 72](255 mg, 0.94 mmol) and N,N-Diisopropylethylamine (366 mg, 2.8 mmol) in DMF (5 mL) was added N,N,N',N'-Tetramethyl-O-(7-azabenzotriazol-1-yl)uranium (719 mg, 1.8 mmol) at 25 °C under nitrogen gas. The reaction mixture was stirred at 25 °C for 1 h. The reaction mixture was quenched with ice water and extracted with EA. The combined organic phase was washed with brine, dried over $Na_2SO_4$ and concentrated to give the crude product. The residue was chromatographed over $SiO_2$ with a gradient of 0-60% EtOAc in petroleum ether to afford tert-butyl (R)-((3-(3-(4-fluoro-2-methylphenoxy)-6-(trifluoromethyl)pyridazine-4-carboxamido) phenyl)(methyl)(oxo)-$\lambda^6$-sulfaneylidene) carbamate (510 mg, 94%) as a yellow oil. LC-MS: m/z 591.0 $[M+23]^+$.

Step 2: (R)-3-(4-fluoro-2-methylphenoxy)-N-(3-(S-methylsulfonimidoyl)phenyl)-6-(trifluoromethyl)pyridazine-4-carboxamide. To a mixture of tert-butyl (R)-((3-(3-(4-fluoro-2-methylphenoxy)-6-(trifluoromethyl)pyridazine-4-carboxamido) phenyl)(methyl)(oxo)-$\lambda^6$-sulfaneylidene) carbamate (0.510 g, 0.89 mmol) in DCM (3 mL) was added HCl/1,4-Dioxane (4M, 3 mL) at 25 °C. The reaction mixture was stirred at 25 °C for 2 h. The reaction mixture was concentrated to give the crude product. The residue was purified with reversed phase flash chromatography (eluting with ACN/$H_2O$ (0.1% $NH_3$) 0~45%) to afford (R)-3-(4-fluoro-2-methylphenoxy)-N-(3-(S-methylsulfonimidoyl) phenyl)-6-(trifluoromethyl)pyridazine-4-carboxamide (0.300 g, 71%) as an off-white solid. $^1H$ NMR (400 MHz, DMSO-$d_6$) δ 11.20 (s, 1H), 8.67 (s, 1H), 8.35 (t, J=4 Hz, 1H), 7.98-7.87 (m, 1H), 7.73 (dt, J=8 Hz, 1.2 Hz, 1H), 7. 65 (t, J=8 Hz), 7.35 (dd, J=8 Hz, 4 Hz, 1H), 7.26 (dd, J=8 Hz, 3.2 Hz, 1H), 7.16 (td, J=8.4 Hz, 3.2 Hz, 1H), 4.27 (s, 1H), 3.11-3.02 (s, 3H), 2.13 (s, 3H). LC-MS (ESI): m/z 469.1 $[M+1]^+$.

Compound 103: (S)-3-(4-fluoro-2-methylphenoxy)-N-(3-(S-methylsulfonimidoyl)phenyl)-6-(trifluoromethyl)pyridazine-4-carboxamide

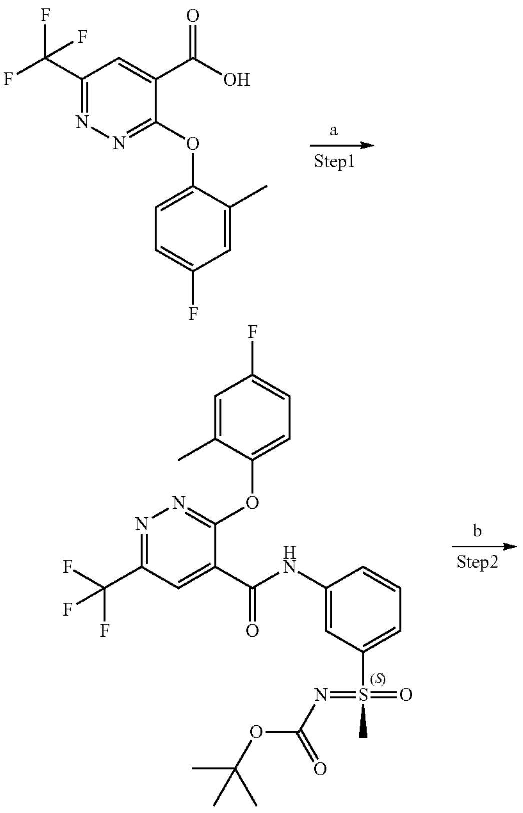

-continued

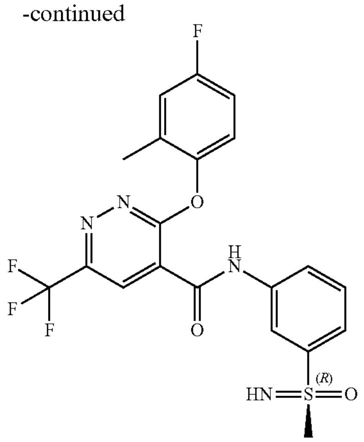

Reagents & conditions: a) tert-butyl (S)-((3-aminophenyl)(methyl)(oxo)-λ$^6$-sulfaneylidene)carbamate [Intermediate 71], HATU, DIEA, DMF, rt, 1 h; b) 4M HCl in dioxane, DCM, rt, 2 h.

Step 1: tert-butyl (S)-((3-(3-(4-fluoro-2-methylphenoxy)-6-(trifluoromethyl)pyridazine-4-carboxamido) phenyl)(methyl)(oxo)-λ$^6$-sulfaneylidene) carbamate. To a mixture of 3-(4-fluoro-2-methylphenoxy)-6-(trifluoromethyl) pyridazine-4-carboxylic acid (0.350 g, 1.1 mmol), tert-butyl (S)-((3-aminophenyl)(methyl)(oxo)-λ$^6$-sulfaneylidene)carbamate (0.298 g, 1.1 mmol) and N,N-Diisopropylethylamine (0.428 g, 3.3 mmol) in DMF (5 mL) was added HATU (0.839 g 2.2 mmol) at 25 °C under nitrogen atmosphere. The reaction mixture was stirred at 25 °C for 1 h. The reaction mixture was quenched with ice water and extracted with EtOAc. The combined organic phase was washed with brine, dried over $Na_2SO_4$ and concentrated to give the crude product which was purified with flash chromatography (eluting with EA/PE 0~60%) to afford tert-butyl (S)-((3-(3-(4-fluoro-2-methylphenoxy)-6-(trifluoromethyl)pyridazine-4-carboxamido) phenyl)(methyl)(oxo)-λ$^6$-sulfaneylidene) carbamate (0.550 g, 87%) as a yellow oil. LC-MS: m/z found 591.0 $[M+23]^+$.

Step 2: (S)-3-(4-fluoro-2-methylphenoxy)-N-(3-(S-methylsulfonimidoyl)phenyl)-6-(trifluoromethyl)pyridazine-4-carboxamide. To a mixture of tert-butyl (S)-((3-(3-(4-fluoro-2-methylphenoxy)-6-(trifluoromethyl)pyridazine-4-carboxamido) phenyl)(methyl)(oxo)-λ$^6$-sulfaneylidene) carbamate (0.550 g, 0.96 mmol) in DCM (3 mL) was added HCl/1,4-Dioxane (4M, 3 mL) at 25 °C. The reaction mixture was stirred at 25 °C for 2 h. The reaction mixture was concentrated to give the crude product. The residue was purified with reversed phase flash chromatography (eluting with $ACN/H_2O$ (0.1% $NH_3$) 0-45%) to afford (S)-3-(4-fluoro-2-methylphenoxy)-N-(3-(S-methylsulfonimidoyl) phenyl)-6-(trifluoromethyl)pyridazine-4-carboxamide (0.305 g, 67%) as an off-white solid. $^1$H NMR (400 MHz, DMSO-$d_6$) δ 11.20 (s, 1H), 8.67 (s, 1H), 8.35 (t, J=4 Hz, 1H), 7.98-7.87 (m, 1H), 7.73 (dt, J=8 Hz, 1.2 Hz, 1H), 7. 65 (t, J=8 Hz), 7.35 (dd, J=8 Hz, 4 Hz, 1H), 7.26 (dd, J=8 Hz, 3.2 Hz, 1H), 7.16 (td, J=8.4 Hz, 3.2 Hz, 1H), 4.27 (s, 1H), 3.11-3.02 (s, 3H), 2.13 (s, 3H). LC-MS: m/z found 469.1 $[M+1]^+$.

Compounds 104 and 105: 3-(4-Fluoro-2-methoxy-phenoxy)-6-methyl-N-(3-methylsulfonylphenyl) pyridazine-4-carboxamide and 3-(4-fluoro-2-methoxy-phenoxy)-6-methyl-N-(3-methylsulfinylphenyl)pyridazine-4-carboxamide

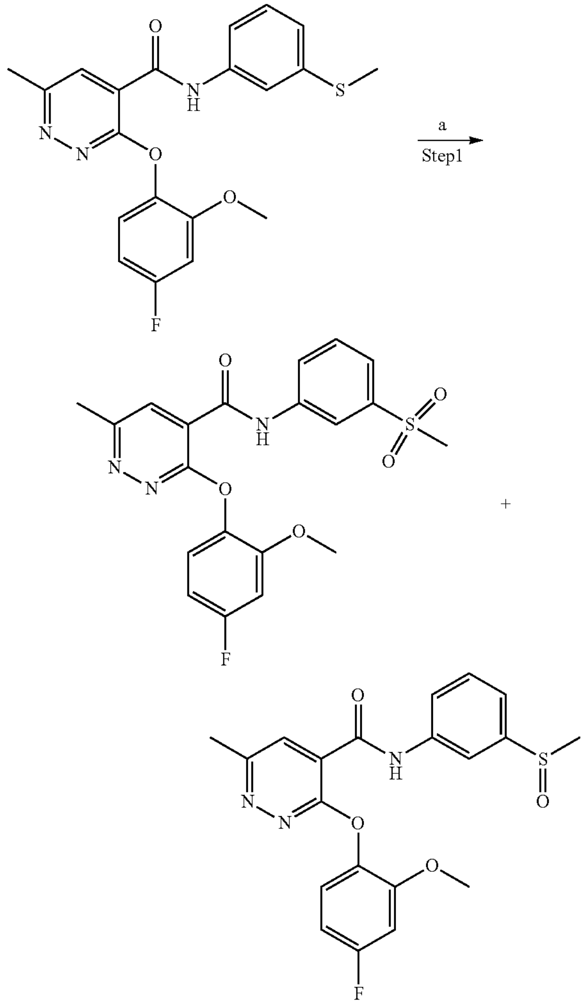

Reagents & conditions: Oxone, MeOH, rt, 16 h

A solution of 3-(4-fluoro-2-methoxy-phenoxy)-6-methyl-N-(3-methylsulfanylphenyl)pyridazine-4-carboxamide (0.130 g, 0.325 mmol) in Methanol (3.25 mL) was treated with Oxone (0.109 g, 0.716 mmol). The resultant mixture stirred at rt overnight. Then more oxone (0.109 g, 0.716 mmol) was added and the mixture stirred at rt for a further 6 h at rt. Diluted the reaction mixture with DCM (25 mL) and sat. $NaHCO_3$ solution (25 mL). Layers were separated and the aqueous re-extracted with DCM (25 mL). Combined organics were concentrated in vacuo to a pale yellow solid. The material was purified using preparative HPLC Method 1 to afford 3-(4-fluoro-2-methoxy-phenoxy)-6-methyl-N-(3-methylsulfonylphenyl)pyridazine-4-carboxamide (0.087 g, 61%) as a white solid, $^1$H NMR (500 MHz, $CDCl_3$) δ 10.10 (s, 1H), 8.18-8.12 (m, 3H), 7.76 (dt, J=7.7, 1.3 Hz, 1H), 7.66-7.57 (m, 1H), 7.47 (dd, J=8.7, 5.6 Hz, 1H), 6.84-6.74 (m, 2H), 3.82 (s, 3H), 3.09 (s, 3H), 2.76 (s, 3H). LC-MS (Method 6): m/z 432.3 $[M+H]^+$, (ESI+), RT=2.78 and the second title compound 3-(4-fluoro-2-methoxy-phenoxy)-6-methyl-N-(3-methylsulfinylphenyl)pyridazine-4-carboxamide (0.015 g, 10%) as an off-white solid. $^1$H NMR (500 MHz, DMSO-$d_6$) δ 10.96 (s, 1H), 8.13 (t, J=1.7 Hz, 1H), 7.86 (s, 1H), 7.81-7.76 (m, 1H), 7.57 (t, J=7.9 Hz, 1H), 7.42 (m, 1H), 7.31 (dd, J=8.8, 5.9 Hz, 1H), 7.09 (dd, J=10.7, 2.9 Hz, 1H), 6.84 (td, J=8.5, 2.9 Hz, 1H), 3.70 (s, 3H), 2.75 (s, 3H), 2.60 (s, 3H). LC-MS (Method 1): m/z 416.0 [M+H]+, (ESI+), RT=3.45.

Compound 106: 3-(4-Fluoro-2-methylphenoxy)-N-(4-methyl-3-(methylsulfonyl)phenyl)-6-(trifluoromethyl)pyridazine-4-carboxamide

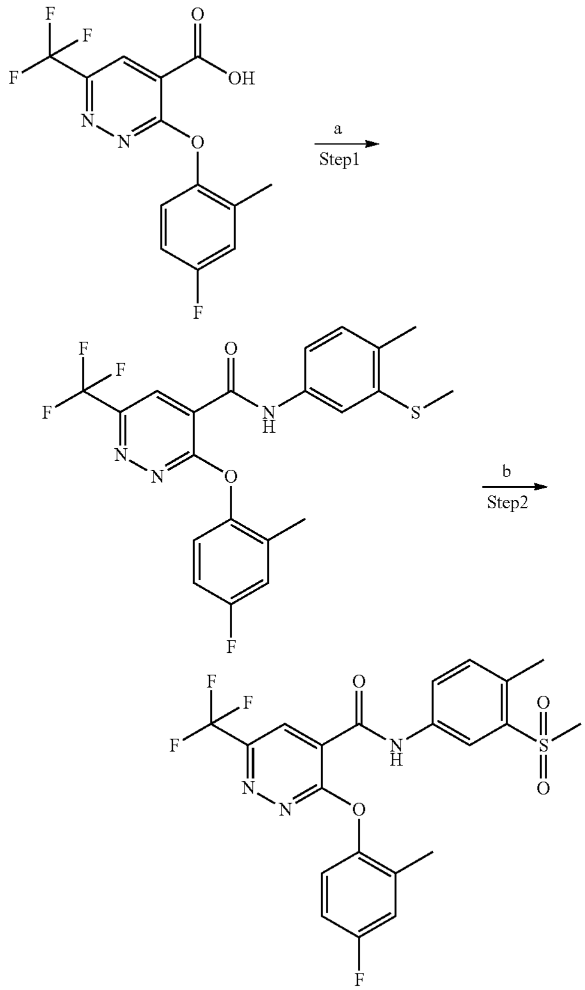

Reagents & conditions: a) 4-methyl-3-(methylthio)aniline, propylphosphonic anyhrdride (50% in EtOAc), DMAP, DIEA, DCM, rt, 3 h; b) Oxone, MeOH, rt, 16 h.

Step 1: 3-(4-fluoro-2-methylphenoxy)-N-(4-methyl-3-(methylthio)phenyl)-6-(trifluoromethyl)pyridazine-4-carboxamide. The title compound was prepared by a similar procedure described for Compound 1 using 3-(4-fluoro-2-methylphenoxy)-6-(trifluoromethyl)pyridazine-4-carboxylic acid and 4-methyl-3-(methylthio)aniline. $^1$H NMR (500 MHz, DMSO-$d_6$) δ 10.83 (s, 1H), 8.63 (s, 1H), 7.57 (d, J=2.0 Hz, 1H), 7.40 (dd, J=8.1, 2.0 Hz, 1H), 7.34 (dd, J=8.9, 5.0 Hz, 1H), 7.25 (dd, J=9.5, 3.0 Hz, 1H), 7.22-7.18 (m, 1H), 7.15 (td, J=8.5, 3.2 Hz, 1H), 2.46 (s, 3H), 2.22 (s, 3H), 2.13 (s, 3H). LC-MS (Method 1): m/z 451.9 [M+H]+, (ESI+), RT=5.05.

Step 2: 3-(4-fluoro-2-methylphenoxy)-N-(4-methyl-3-(methylsulfonyl)phenyl)-6-(trifluoromethyl)pyridazine-4-carboxamide. The title compound was prepared by a similar procedure described for Compounds 104 and 105 using 3-(4-fluoro-2-methylphenoxy)-N-(4-methyl-3-(methylthio)phenyl)-6-(trifluoromethyl)pyridazine-4-carboxamide and excess Oxone. $^1$H NMR (500 MHz, DMSO-$d_6$) δ 11.19 (s, 1H), 8.65 (s, 1H), 8.34 (d, J=2.4 Hz, 1H), 7.90 (dd, J=8.2, 2.4 Hz, 1H), 7.50 (d, J=8.4 Hz, 1H), 7.34 (dd, J=9.0, 5.0 Hz, 1H), 7.25 (dd, J=9.4, 3.0 Hz, 1H), 7.15 (td, J=8.5, 3.1 Hz, 1H), 3.23 (s, 3H), 2.62 (s, 3H), 2.13 (s, 3H). LC-MS (Method 1): m/z 451.9 [M+H]$^+$, (ESI+), RT=5.05.

Compound 107: 3-(4-Fluoro-2-methoxyphenoxy)-N-(4-methyl-3-(methylsulfonyl)phenyl)-6-(trifluoromethyl)pyridazine-4-carboxamide

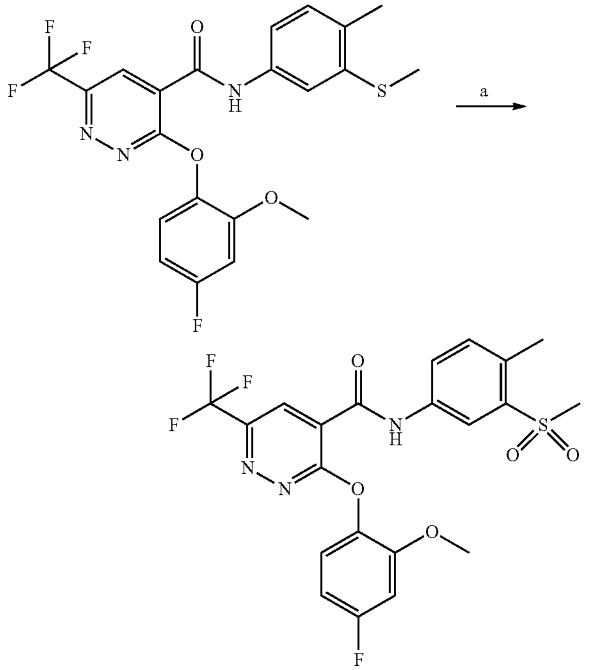

Reagents & conditions: Oxone, MeOH, rt, 16 h 3-(4-fluoro-2-methoxyphenoxy)-N-(4-methyl-3-(methylthio)phenyl)-6-(trifluoromethyl)pyridazine-4-carboxamide was prepared by similar procedure described for Compound 1 using 3-(4-fluoro-2-methoxyphenoxy)-6-(trifluoromethyl)pyridazine-4-carboxylic acid and 4-methyl-3-(methylthio)aniline and was used for the next step. The title compound was prepared by a similar procedure described for Compounds 104 and 105 using 3-(4-fluoro-2-methoxyphenoxy)-N-(4-methyl-3-(methylthio)phenyl)-6-(trifluoromethyl)pyridazine-4-carboxamide. $^1$H NMR (400 MHz, DMSO-$d_6$) δ 11.14 (s, 1H), 8.62 (s, 1H), 8.34 (d, J=2.3 Hz, 1H), 7.91 (dd, J=8.3, 2.3 Hz, 1H), 7.50 (d, J=8.5 Hz, 1H), 7.37 (dd, J=8.8, 5.8 Hz, 1H), 7.15 (dd, J=10.7, 2.9 Hz, 1H), 6.88 (td, J=8.5, 2.9 Hz, 1H), 3.73 (s, 3H), 3.23 (s, 3H), 2.62 (s, 3H). LC-MS (Method 1): m/z 500.1 [M+H]+, (ESI+), RT=4.33.

Compound 108: 3-(2-Ethoxy-4-fluorophenoxy)-6-methyl-N-(3-methylsulfonyl)phenyl)pyridazine-4-carboxamide

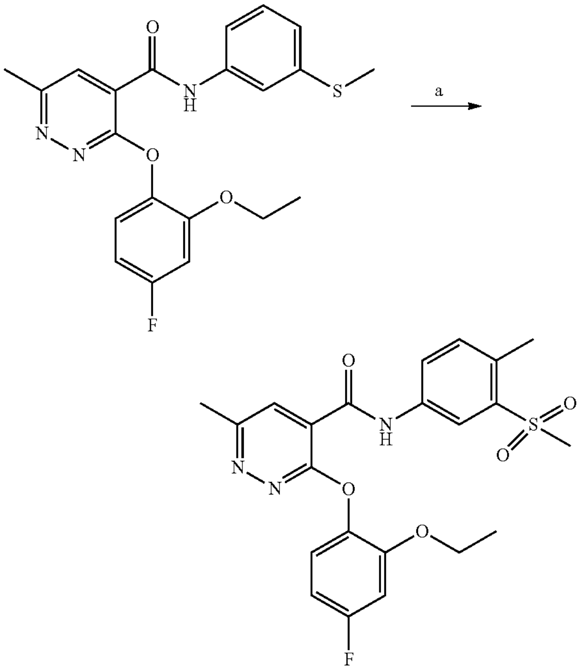

Reagents & conditions: Oxone, MeOH, rt, 16 h

The title compound was prepared by a similar procedure described for Compounds 104 and 105 using 3-(2-ethoxy-4-fluorophenoxy)-6-methyl-N-(3-(methylthio)phenyl) pyridazine-4-carboxamide and excess Oxone. $^1$H NMR (500 MHz, DMSO-$d_6$) δ 11.04 (s, 1H), 8.38 (t, J=1.7 Hz, 1H), 7.95 (dt, J=7.7, 1.5 Hz, 1H), 7.88 (s, 1H), 7.71 (dt, J=7.8, 1.4 Hz, 1H), 7.68 (t, J=7.8 Hz, 1H), 7.32 (dd, J=8.8, 5.9 Hz, 1H), 7.06 (dd, J=10.7, 2.9 Hz, 1H), 6.82 (td, J=8.5, 2.9 Hz, 1H), 3.97 (q, J=7.0 Hz, 2H), 3.22 (s, 3H), 2.61 (s, 3H), 1.04 (t, J=7.0 Hz, 3H). LC-MS (Method 6): m/z 446.3 $[M+H]^+$, (ESI+), RT=2.97.

Compound 109: 3-(4-Fluoro-2-methylphenoxy)-N-(4-methyl-3-(S-methylsulfonimidoyl)phenyl)-6-(trifluoromethyl)pyridazine-4-carboxamide

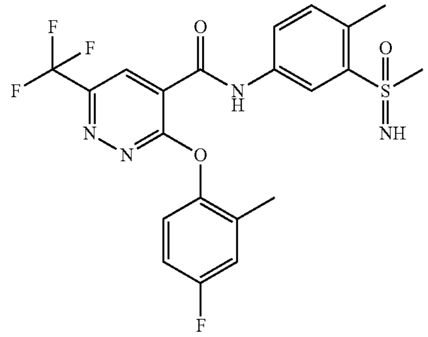 [SMILES: Cc1cc(F)ccc1Oc1nnc(C(F)(F)F)cc1C(=O)Nc1ccc(C)c(S(C)(=N)=O)c1]

The title compound was prepared by a similar procedure described for step 3 of Compound 93 using 3-(4-fluoro-2-methylphenoxy)-N-(4-methyl-3-(methylthio)phenyl)-6-(trifluoromethyl)pyridazine-4-carboxamide. $^1$H NMR (500 MHz, DMSO-$d_6$) δ 11.11 (s, 1H), 8.64 (s, 1H), 8.34 (d, J=2.3 Hz, 1H), 7.89 (dd, J=8.2, 2.4 Hz, 1H), 7.43 (d, J=8.4 Hz, 1H), 7.34 (dd, J=8.9, 5.0 Hz, 1H), 7.25 (dd, J=9.5, 2.9 Hz, 1H), 7.15 (td, J=8.5, 3.2 Hz, 1H), 4.29 (s, 1H), 3.08 (s, 3H), 2.66 (s, 3H), 2.13 (s, 3H). LC-MS (Method 1): m/z: 482.9 [M+H]+, (ESI+), RT=4.01.

Compounds 110 to 113 listed in Table 24 were synthesized using the similar method as described for step 1 of compound 59 using carboxylic acids with appropriate substituted aryl or heteroaryl aniline.

TABLE 24

| Compound | Structure and name | Analytical data |
|---|---|---|
| 110 | 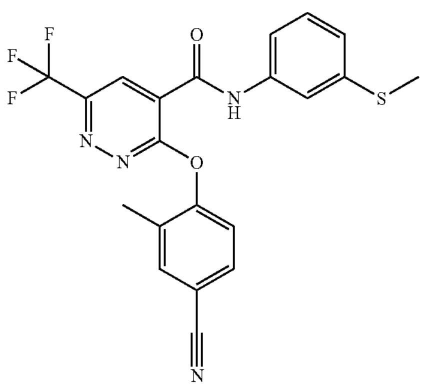 [SMILES: CSc1cccc(NC(=O)c2cc(C(F)(F)F)nnc2Oc2ccc(C#N)cc2C)c1] 3-(4-Cyano-2-methylphenoxy)-N-(3-(methylthio)phenyl)-6-(trifluoromethyl)pyridazine-4-carboxamide | $^1$H NMR (300 MHz, DMSO-$d_6$) δ 10.91 (s, 1H), 8.70 (s, 1H), 7.93 (dd, J = 2.2, 0.9 Hz, 1H), 7.84 (dd, J = 8.3, 2.1 Hz, 1H), 7.66 (t, J = 1.9 Hz, 1H), 7.55 (d, J = 8.4 Hz, 1H), 7.48-7.29 (m, 2H), 7.08 (ddd, J = 7.7, 1.9, 1.1 Hz, 1H), 2.49 (s, 3H), 2.20 (s, 3H). |

TABLE 24-continued

| Compound | Structure and name | Analytical data |
| --- | --- | --- |
| 111 | 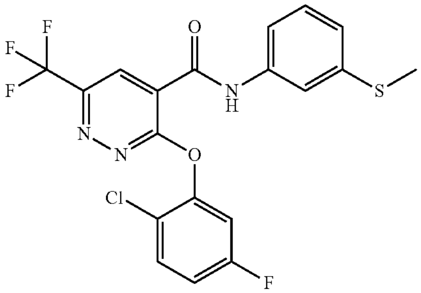 [SMILES: CSc1cccc(NC(=O)c2cc(C(F)(F)F)nnc2Oc2cc(F)ccc2Cl)c1] 3-(2-Chloro-5-fluorophenoxy)-N-(3-(methylthio)phenyl)-6-(trifluoromethyl)pyridazine-4-carboxamide | $^{1}H$ NMR (300 MHz, CDCl3) δ 9.42 (s, 1H), 8.71 (s, 1H), 7.70 (t, J = 1.9 Hz, 1H), 7.56 (dd, J = 9.0, 5.5 Hz, 1H), 7.45-7.27 (m, 3H), 7.17-7.06 (m, 2H), 2.52 (s, 3H). LC-MS (Method 2): m/z 456.2 $[M - H]^{+}$ |
| 112 | 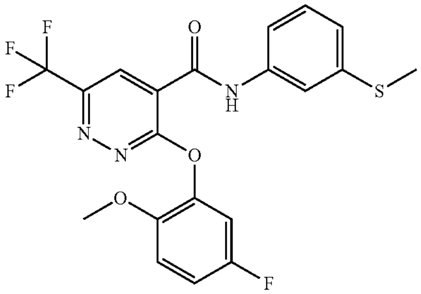 [SMILES: COc1ccc(F)cc1Oc1nnc(C(F)(F)F)cc1C(=O)Nc1cccc(SC)c1] 3-(5-Fluoro-2-methoxyphenoxy)-N-(3-(methylthio)phenyl)-6-(trifluoromethyl)pyridazine-4-carboxamide | $^{1}H$ NMR (300 MHz, CDCl3) δ 9.69 (s, 1H), 8.64 (s, 1H), 7.70 (t, J = 1.9 Hz, 1H), 7.43-7.28 (m, 3H), 7.13-6.94 (m, 3H), 3.80 (s, 3H), 2.52 (s, 3H). |
| 113 | 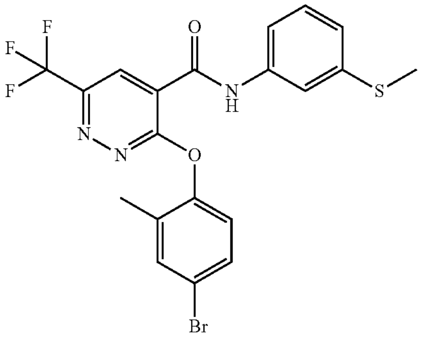 [SMILES: CSc1cccc(NC(=O)c2cc(C(F)(F)F)nnc2Oc2ccc(Br)cc2C)c1] 3-(4-Bromo-2-methylphenoxy)-N-(3-(methylthio)phenyl)-6-(trifluoromethyl)pyridazine-4-carboxamide | $^{1}H$ NMR (300 MHz, DMSO) δ 10.90 (s, 1H), 8.66 (s, 1H), 7.65 (dt, J = 12.5, 2.0 Hz, 2H), 7.56-7.22 (m, 4H), 7.07 (dt, J = 7.9, 1.5 Hz, 1H), 2.49 (s, 3H), 2.13 (s, 3H). |

Compounds 114 to 117 listed in Table 25 were synthesized using the similar method as described for step 3 of Compound 93 using appropriate substituted compounds listed in Table 24.

TABLE 25

| Compound | Structure and name | Analytical data |
|---|---|---|
| 114 | 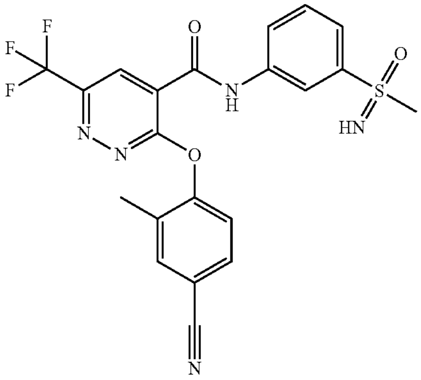 3-(4-Cyano-2-methylphenoxy)-N-(3-(S-methylsulfonimidoyl)phenyl)-6-(trifluoromethyl)pyridazine-4-carboxamide | $^1$H NMR (300 MHz, DMSO-$d_6$) δ 11.22 (s, 1H), 8.73 (s, 1H), 8.34 (t, J = 1.9 Hz, 1H), 7.92 (ddd, J = 9.3, 2.2, 1.1 Hz, 2H), 7.84 (dd, J = 8.5, 2.4 Hz, 1H), 7.74 (dt, J = 7.9, 1.4 Hz, 1H), 7.65 (t, J = 7.9 Hz, 1H), 7.56 (d, J = 8.4 Hz, 1H), 4.29 (s, 1H), 3.08 (d, J = 0.9 Hz, 3H), 2.20 (s, 3H). LC-MS (Method 2): 474.5 $[M - H]^+$ |
| 115 | 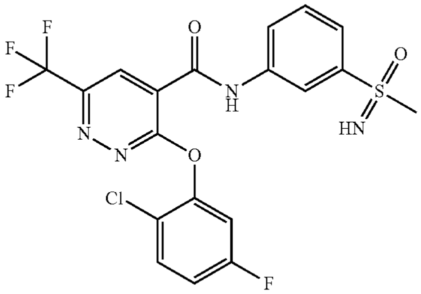 3-(2-Chloro-5-fluorophenoxy)-N-(3-(S-methylsulfonimidoyl)phenyl)-6-(trifluoromethyl)pyridazine-4-carboxamide | $^1$H NMR (300 MHz, DMSO) δ 11.23 (s, 1H), 8.76 (s, 1H), 8.36 (t, J = 1.9 Hz, 1H), 7.94 (ddd, J = 8.0, 2.2, 1.2 Hz, 1H), 7.79-7.70 (m, 2H), 7.69-7.58 (m, 2H), 7.34 (ddd, J = 9.0, 8.1, 3.0 Hz, 1H), 4.29 (d, J = 23.2 Hz, 1H), 3.11 (s, 3H). LC-MS (Method 2): m/z 487.3 $[M - H]^+$ |
| 116 | 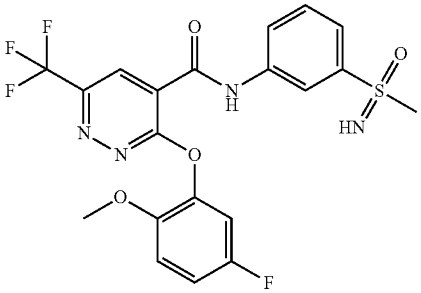 [SMILES: COc1ccc(F)cc1Oc1nnc(C(F)(F)F)cc1C(=O)Nc1cccc(S(C)(=N)=O)c1] | $^1$H NMR (300 MHz, DMSO-$d_6$) δ 11.18 (s, 1H), 8.67 (s, 1H), 8.36 (t, J = 1.9 Hz, 1H), 7.94 (ddd, J = 8.0, 2.2, 1.2 Hz, 1H), 7.77-7.57 (m, 2H), 7.36 (dd, J = 8.7, 2.7 Hz, 1H), 7.30-7.16 (m, 2H), 4.28 (d, J = 1.3 Hz, 1H), 3.70 (s, 3H), 3.08 (d, J = 1.1 Hz, 3H). LC-MS (Method 2): m/z 483.3 $[M - H]^+$ |
| 117 | 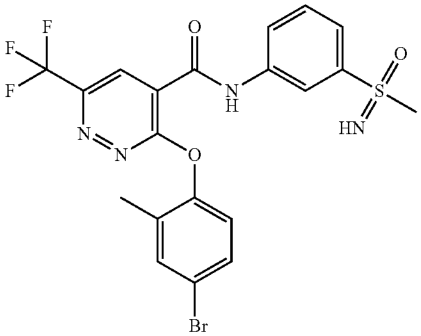 [SMILES: Cc1cc(Br)ccc1Oc1nnc(C(F)(F)F)cc1C(=O)Nc1cccc(S(C)(=N)=O)c1] 3-(4-Bromo-2-methylphenoxy)-N-(3-(S-methylsulfonimidoyl)phenyl)-6-(trifluoromethyl)pyridazine-4-carboxamide | $^1$H NMR (300 MHz, DMSO-$d_6$) δ 11.21 (s, 1H), 8.69 (s, 1H), 8.35 (t, J = 1.9 Hz, 1H), 7.92 (ddd, J = 8.0, 2.2, 1.2 Hz, 1H), 7.74 (dt, J = 7.9, 1.3 Hz, 1H), 7.70-7.60 (m, 2H), 7.52 (ddd, J = 8.6, 2.5, 0.7 Hz, 1H), 7.29 (d, J = 8.6 Hz, 1H), 4.29 (d, J = 1.3 Hz, 1H), 3.07 (d, J = 1.1 Hz, 3H), 2.14 (s, 3H). LC-MS (Method 2): 529.2, 531.3 $[M - H]^+$ |

Example 113

Compound 118: 3-(2-Chloro-5-fluorophenoxy)-N-(3-sulfamoylphenyl)-6-(trifluoromethyl)pyridazine-4-carboxamide

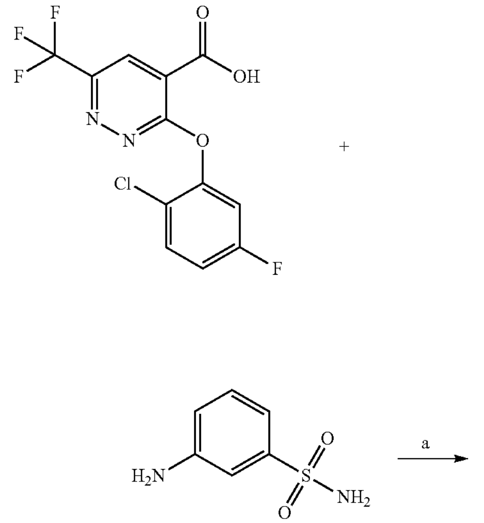

-continued

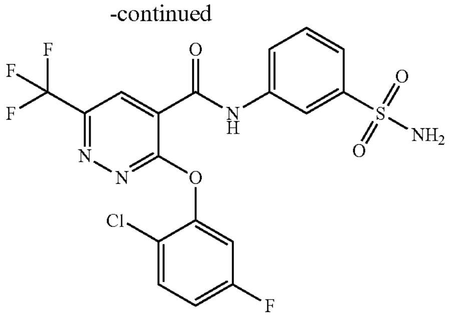

Reagents & conditions: EDC, pyridine, rt, 16 h.

A mixture of 3-(2-chloro-5-fluorophenoxy)-6-(trifluoromethyl)pyridazine-4-carboxylic acid (0.100 g, 0.316 mmol), 3-aminobenzene-1-sulfonamide (0.082 g, 0.481 mmol) and EDC (0.0667 g, 0.348 mmol) in pyridine (4 mL) was stirred at rt for 16 h. The solvent was evaporated and the crude was chromatographed over SiO2 with a gradient of 0-100% EtOAc in hexane to provide 3-(2-chloro-5-fluorophenoxy)-N-(3-sulfamoylphenyl)-6-(trifluoromethyl) pyridazine-4-carboxamide (0.086 g, 55.41%). $^1$H NMR (300 MHz, DMSO-$d_6$) δ 11.18 (s, 1H), 8.76 (s, 1H), 8.30 (t, J=1.5 Hz, 1H), 7.83 (dt, J=6.4, 2.4 Hz, 1H), 7.74 (dd, J=9.0, 5.7 Hz, 1H), 7.67-7.55 (m, 3H), 7.46 (s, 2H), 7.33 (ddd, J=9.0, 8.1, 3.0 Hz, 1H). LC-MS (Method 1): m/z 489.4 $[M-H]^+$.

Compounds 119 to 129 listed in Table 26 were synthesized using the similar method as described for Compound 118 using appropriate carboxylic acids with substituted aryl or heteroaryl aniline.

TABLE 26

| Compound | Structure & name | Analytical data |
|---|---|---|
| 119 | 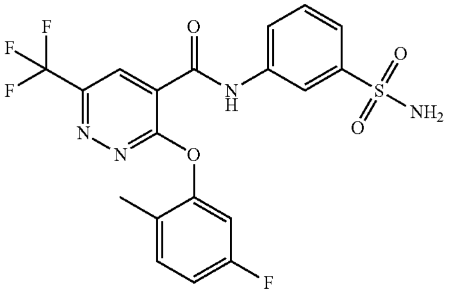 [SMILES: Cc1ccc(F)cc1Oc1nnc(C(F)(F)F)cc1C(=O)Nc1cccc(S(N)(=O)=O)c1] 3-(5-Fluoro-2-methylphenoxy)-N-(3-sulfamoylphenyl)-6-(trifluoromethyl)pyridazine-4-carboxamide | $^1$H NMR (300 MHz, DMSO-$d_6$) δ 11.22 (s, 1H), 8.76 (s, 1H), 8.36 (q, J = 1.4 Hz, 1H), 7.93-7.82 (m, 1H), 7.74-7.61 (m, 2H), 7.51 (d, J = 6.7 Hz, 2H), 7.50-7.42 (m, 1H), 7.35 (dd, J = 9.5, 2.7 Hz, 1H), 7.20 (td, J = 8.5, 2.7 Hz, 1H), 2.17 (s, 3H). LC-MS (Method 1): m/z 469.1 $[M-H]^+$ |
| 120 | 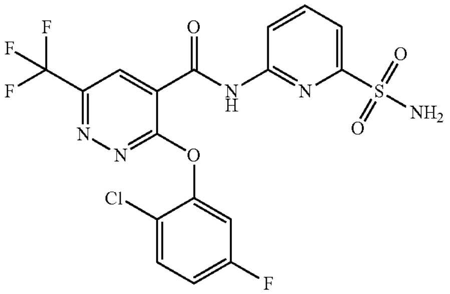 [SMILES: NS(=O)(=O)c1cccc(NC(=O)c2cc(C(F)(F)F)nnc2Oc2cc(F)ccc2Cl)n1] 3-(2-Chloro-5-fluorophenoxy)-N-(6-sulfamoylpyridin-2-yl)-6-(trifluoromethyl)pyridazine-4-carboxamide | $^1$H NMR (300 MHz, DMSO-$d_6$) δ 11.83 (s, 1H), 8.73 (s, 1H), 8.41 (d, J = 8.5 Hz, 1H), 8.19 (t, J = 8.0 Hz, 1H), 7.85-7.65 (m, 2H), 7.56 (d, J = 28.7 Hz, 3H), 7.39-7.25 (m, 1H) |

TABLE 26-continued

| Compound | Structure & name | Analytical data |
| --- | --- | --- |
| 121 | 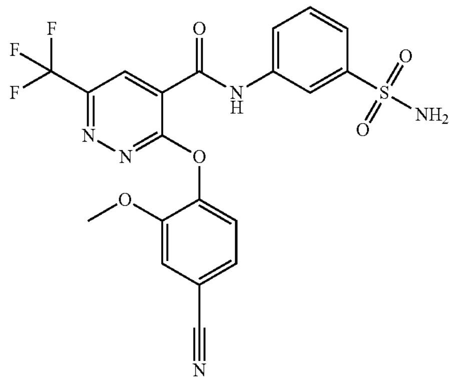 [SMILES: COc1cc(C#N)ccc1Oc1nnc(C(F)(F)F)cc1C(=O)Nc1cccc(S(N)(=O)=O)c1] 3-(4-Cyano-2-methoxyphenoxy)-N-(3-sulfamoylphenyl)-6-(trifluoromethyl)pyridazine-4-carboxamide | $^1H$ NMR (300 MHz, DMSO-$d_6$) δ 11.19 (s, 1H), 8.71 (s, 1H), 8.29 (q, J = 1.4 Hz, 1H), 7.84 (dt, J = 6.1, 2.4 Hz, 1H), 7.77 (t, J = 1.1 Hz, 1H), 7.67-7.56 (m, 4H), 7.46 (s, 2H), 3.78 (s, 3H). LC-MS (Method 2): m/z 492.4 $[M - H]^+$ |
| 122 | 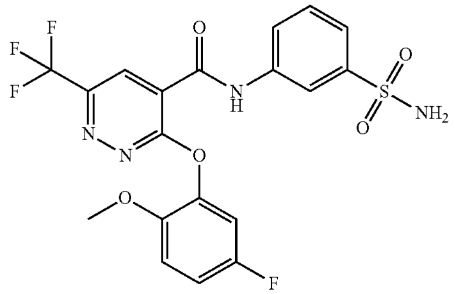 [SMILES: COc1ccc(F)cc1Oc1nnc(C(F)(F)F)cc1C(=O)Nc1cccc(S(N)(=O)=O)c1] 3-(5-Fluoro-2-methoxyphenoxy)-N-(3-sulfamoylphenyl)-6-(trifluoromethyl)pyridazine-4-carboxamide | $^1H$ NMR (300 MHz, DMSO-$d_6$) δ 11.15 (s, 1H), 8.68 (s, 1H), 8.30 (q, J = 1.4 Hz, 1H), 7.90-7.78 (m, 1H), 7.68-7.56 (m, 2H), 7.46 (s, 2H), 7.36 (dd, J = 8.7, 2.7 Hz, 1H), 7.30-7.13 (m, 2H), 3.70 (s, 3H). LC-MS (Method 2): 485.3 $[M - H]^+$ |
| 123 | 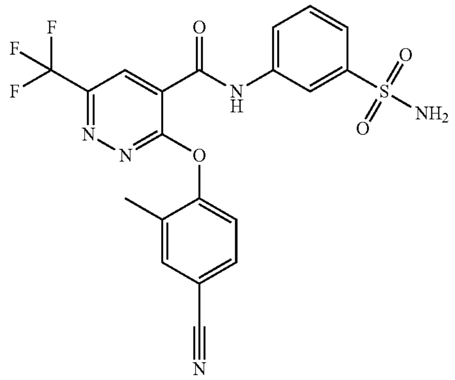 [SMILES: Cc1cc(C#N)ccc1Oc1nnc(C(F)(F)F)cc1C(=O)Nc1cccc(S(N)(=O)=O)c1] 3-(4-Cyano-2-methylphenoxy)-N-(3-sulfamoylphenyl)-6-(trifluoromethyl)pyridazine-4-carboxamide. | $^1H$ NMR (300 MHz, DMSO-$d_6$) δ 11.24 (s, 1H), 8.79 (s, 1H), 8.38-8.33 (m, 1H), 7.99 (dd, J = 2.0, 0.9 Hz, 1H), 7.94-7.84 (m, 2H), 7.74-7.58 (m, 3H), 7.52 (s, 2H), 2.25 (s, 3H). LC-MS (Method 2): m/z 476.3 $[M - H]^+$ |

TABLE 26-continued

| Compound | Structure & name | Analytical data |
|---|---|---|
| 124 | 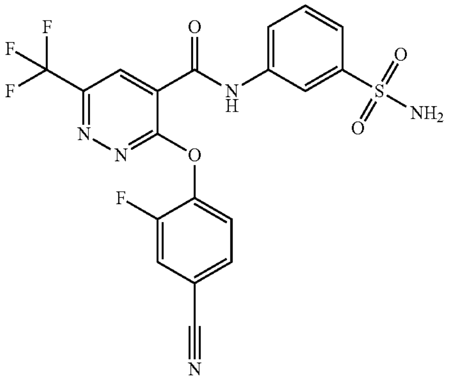 [SMILES: N#Cc1ccc(Oc2nnc(C(F)(F)F)cc2C(=O)Nc2cccc(S(N)(=O)=O)c2)c(F)c1] 3-(4-Cyano-2-fluorophenoxy)-N-(3-sulfamoylphenyl)-6-(trifluoromethyl)pyridazine-4-carboxamide. | $^{1}H$ NMR (300 MHz, DMSO-$d_6$) δ 11.23 (s, 1H), 8.79 (s, 1H), 8.32-8.26 (m, 1H), 8.19 (dd, J = 10.4, 1.9 Hz, 1H), 7.95-7.87 (m, 1H), 7.87-7.75 (m, 2H), 7.68-7.57 (m, 2H), 7.47 (s, 2H). |
| 125 | 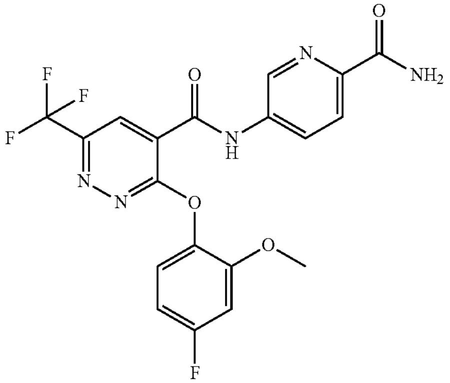 [SMILES: COc1cc(F)ccc1Oc1nnc(C(F)(F)F)cc1C(=O)Nc1ccc(C(N)=O)nc1] N-(6-Carbamoylpyridin-3-yl)-3-(4-fluoro-2-methoxyphenoxy)-6-(trifluoromethyl)pyridazine-4-carboxamide | $^{1}H$ NMR (400 MHz, DMSO-$d_6$) δ 11.35 (s, 1H), 8.89 (d, J = 2.2 Hz, 1H), 8.65 (s, 1H), 8.29 (dd, J = 8.6, 2.4 Hz, 1H), 8.08 (d, J = 8.5 Hz, 1H), 8.04 (d, J = 2.0 Hz, 1H), 7.62-7.52 (m, 1H), 7.37 (dd, J = 8.8, 5.8 Hz, 1H), 7.14 (dd, J = 10.7, 2.9 Hz, 1H), 6.86 (td, J = 8.5, 2.9 Hz, 1H), 3.71 (s, 3H). LC-MS (Method 4): m/z 452.1 $[M + H]^+$, (ESI+), RT = 2.96 |
| 126 | 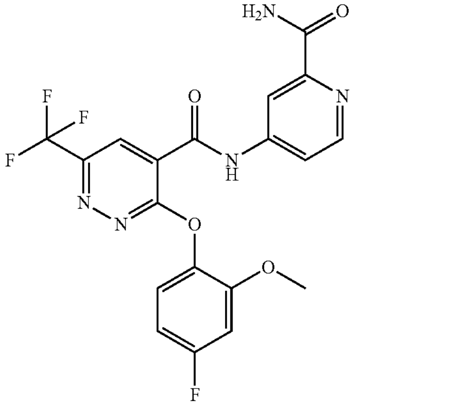 [SMILES: COc1cc(F)ccc1Oc1nnc(C(F)(F)F)cc1C(=O)Nc1ccnc(C(N)=O)c1] N-(2-Carbamoylpyridin-4-yl)-3-(4-fluoro-2-methoxyphenoxy)-6-(trifluoromethyl)pyridazine-4-carboxamide | $^{1}H$ NMR (400 MHz, DMSO-$d_6$) δ 11.39 (s, 1H), 8.65 (s, 1H), 8.58 (d, J = 5.5 Hz, 1H), 8.31 (d, J = 1.8 Hz, 1H), 8.10 (d, J = 2.1 Hz, 1H), 7.86 (dd, J = 5.4, 2.0 Hz, 1H), 7.66 (d, J = 2.1 Hz, 1H), 7.37 (dd, J = 8.8, 5.9 Hz, 1H), 7.14 (dd, J = 10.7, 2.8 Hz, 1H), 6.86 (td, J = 8.5, 2.9 Hz, 1H), 3.71 (s, 3H). LC-MS (Method 4): m/z: 452.1 $[M + H]^+$, (ESI+), RT = 3.03 |

TABLE 26-continued

| Compound | Structure & name | Analytical data |
|---|---|---|
| 127 | 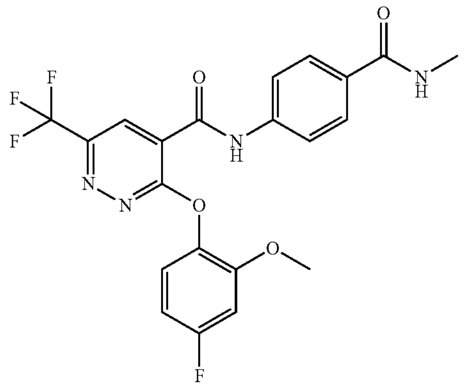 [SMILES: CNC(=O)c1ccc(NC(=O)c2cc(C(F)(F)F)nnc2Oc2ccc(F)cc2OC)cc1] 3-(4-Fluoro-2-methoxyphenoxy)-N-(4-(methylcarbamoyl)phenyl)-6-(trifluoromethyl)pyridazine-4-carboxamide | $^{1}$H NMR (400 MHz, DMSO-$d_6$) δ 11.07 (s, 1H), 8.62 (s, 1H), 8.44-8.35 (m, 1H), 7.94-7.83 (m, 2H), 7.83-7.72 (m, 2H), 7.38 (dd, J = 8.8, 5.8 Hz, 1H), 7.15 (dd, J = 10.7, 2.9 Hz, 1H), 6.88 (td, J = 8.5, 2.9 Hz, 1H), 3.73 (s, 3H), 2.78 (d, J = 4.5 Hz, 3H). LC-MS (Method 5): m/z 464.9 [M + H]$^+$, (ESI+), RT = 3.95 |
| 128 | 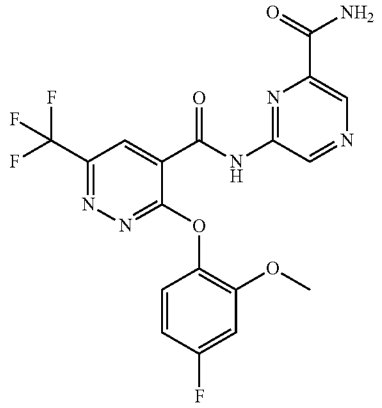 [SMILES: COc1cc(F)ccc1Oc1nnc(C(F)(F)F)cc1C(=O)Nc1cncc(C(N)=O)n1] N-(6-Carbamoylpyrazin-2-yl)-3-(4-fluoro-2-methoxyphenoxy)-6-(trifluoromethyl)pyridazine-4-carboxamide | $^{1}$H NMR (500 MHz, DMSO-$d_6$) δ 9.54 (s, 1H), 8.96, (s, 1H), 8.62, (s, 1H), 8.21 (s, 1H), 7.97 (s, 1H), 7.73 (s, 1H), 7.36 (s, 1H), 7.15 (dd, J = 10.7, 2.8 Hz, 1H), 6.87 (td, J = 8.5, 2.9 Hz, 1H), 3.72 (s, 3H). LC-MS (method 5): m/z 452.9 [M + H]$^+$ RT = 3.80 |
| 129 | 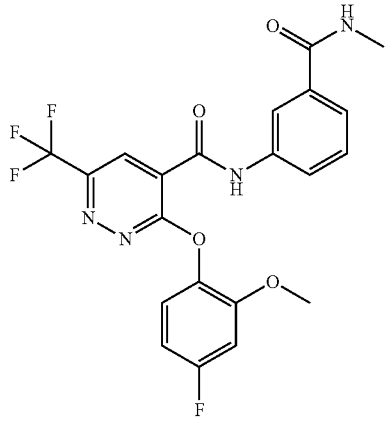 [SMILES: CNC(=O)c1cccc(NC(=O)c2cc(C(F)(F)F)nnc2Oc2ccc(F)cc2OC)c1] 3-(4-Fluoro-2-methoxyphenoxy)-N-(3-(methylcarbamoyl)phenyl)-6-(trifluoromethyl)pyridazine-4-carboxamide | $^{1}$H NMR (500 MHz, DMSO-$d_6$) δ 10.98 (s, 1H), 8.61 (s, 1H), 8.54-8.43 (m, 1H), 8.20-8.13 (m, 1H), 7.90-7.81 (m, 1H), 7.60 (d, J = 7.8 Hz, 1H), 7.48 (t, J = 7.9 Hz, 1H), 7.38 (dd, J = 8.8, 5.8 Hz, 1H), 7.15 (dd, J = 10.7, 2.8 Hz, 1H), 6.88 (td, J = 8.5, 2.9 Hz, 1H), 3.73 (s, 3H), 2.78 (d, J = 4.5 Hz, 3H). LCMS (Method 5): m/z: 464.9 [M + H]$^+$, (ESI+), RT = 3.98 |

Example 114

Compound 130: 3-(4-Fluoro-2-hydroxyphenoxy)-N-(3-(methylsulfonyl)phenyl)-6-(trifluoromethyl)pyridazine-4-carboxamide

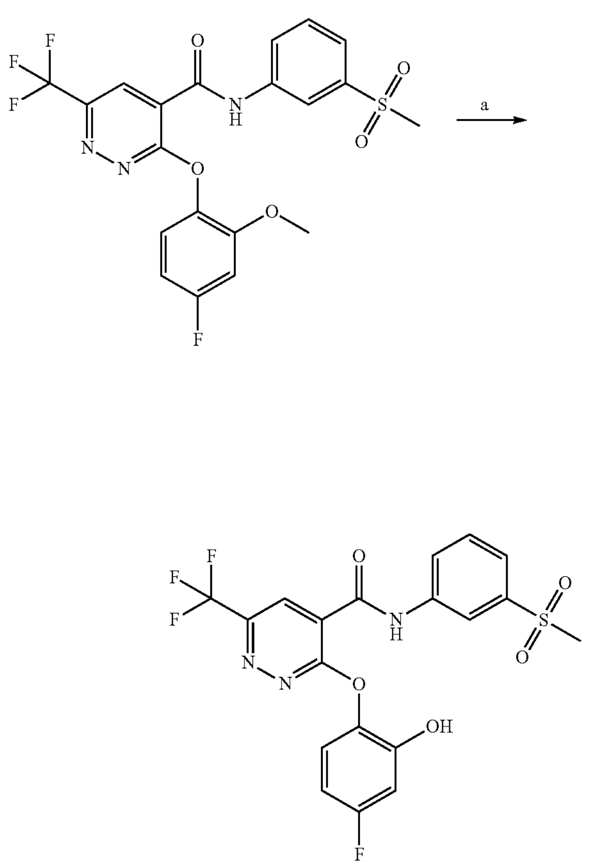

Reagents & conditions: Trichloroborane (1.0M in DCM), tetrabutylammonium iodide, DCM, 0 °C.

Trichloroborane (1.0M in DCM, 1.0 mL, 1.03 mmol), tetrabutylammonium iodide (42 mg, 0.113 mmol) and 3-(4-fluoro-2-methoxy-phenoxy)-N-(3-methylsulfonylphenyl)-6-(trifluoromethyl)pyridazine-4-carboxamide (50 mg, 0.103 mmol) were stirred in dry DCM-Anhydrous (0.515 mL) at 0 °C for 1 h, cooled with ice-water bath. The reaction mixture was then concentrated under vacuum to obtain a crude residue. Purification by chromatography on silica eluting with a gradient of EtOAc in heptane. Fractions with product were combined and concentrated. Purification by chromatography on silica eluting with a gradient of 0 to 100% EtOAc in heptane afforded the title compound (0.014 mg, 28%) as a white solid, and was re-purified by Prep LC. $^{1}$H NMR (400 MHz, DMSO-$d_6$) δ 11.42 (bs, 1H), 10.42 (bs, 1H), 8.58 (s, 1H), 8.41-8.36 (m, 1H), 7.96 (dt, J=7.6, 1.7 Hz, 1H), 7.77-7.66 (m, 2H), 7.30 (dd, J=8.8, 6.0 Hz, 1H), 6.78-6.71 (m, 1H), 6.71-6.63 (m, 1H), 3.23 (s, 3H). (LC-MS (Method 5): m/z 472.0 $[M+H]^+$, (ESI+), RT=3.94.

Compound 131: 3-(4-Fluoro-2-hydroxyphenoxy)-N-(3-sulfamoylphenyl)-6-(trifluoromethyl)pyridazine-4-carboxamide

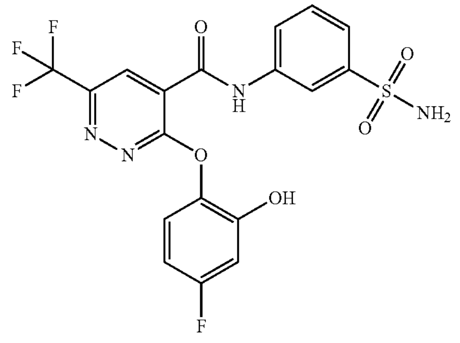 [SMILES: NS(=O)(=O)c1cccc(NC(=O)c2cc(C(F)(F)F)nnc2Oc2ccc(F)cc2O)c1]

The title compound 3-(4-fluoro-2-hydroxyphenoxy)-N-(3-sulfamoylphenyl)-6-(trifluoromethyl)pyridazine-4-carboxamide (0.020 g, 66%) was prepared as a white solid by a similar method described for Compound 130, but starting from 3-(4-fluoro-2-methoxyphenoxy)-N-(3-sulfamoylphenyl)-6-(trifluoromethyl)pyridazine-4-carboxamide $^{1}$H NMR (400 MHz, DMSO-$d_6$) δ 11.15 (bs, 1H), 10.32 (bs, 1H), 8.59 (s, 1H), 8.31-8.28 (m, 1H), 7.84 (dt, J=6.6, 2.2 Hz, 1H), 7.64-7.57 (m, 2H), 7.43 (s, 2H), 7.30 (dd, J=8.8, 5.9 Hz, 1H), 6.77 (dd, J=10.2, 2.8 Hz, 1H), 6.74-6.65 (m, 1H). LC-MS (Method 6): m/z: 473.1$[M+H]^+$.

Compound 132: N-(3-Methanesulfonylphenyl)-3-[2-methyl-4-(1,2-oxazol-4-yl)phenoxy]-6-(trifluoromethyl)pyridazine-4-carboxamide

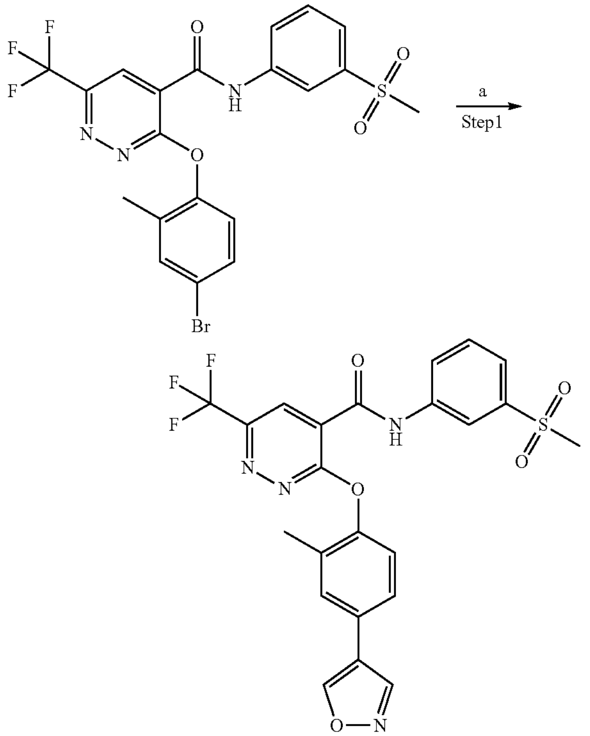

Reagents & conditions: KF, 4-(4,4,5,5-tetramethyl-1,3,2-dioxaborolan-2-yl)-1,2-oxazole, pd(dppf)$Cl_2$. DCM, DMF, 60 °C.

A solution of KF (0.0164 g, 0.283 mmol) in $H_2O$ (0.200 mL) was added to a solution of 3-(4-bromo-2-methylphenoxy)-N-(3-methanesulfonylphenyl)-6-(trifluoromethyl) pyridazine-4-carboxamide (0.050 g, 0.094 mmol) and 4-(4, 4,5,5-tetramethyl-1,3,2-dioxaborolan-2-yl)-1,2-oxazole (0.022 g, 0.113 mmol) in DMF (3 mL) at rt. The mixture was degassed by bubbling nitrogen for 10 min, to the above mixture pd(dppf)$Cl_2$·DCM (0.008 g, 10 mol %) was added and the resulting mixture was heated at 60 °C for 3 h. At the end of this period, it was cooled to rt and water (5 mL) was added and extracted with EtOAc (2×20 mL). The combined organics were washed with water (20 mL) and 1M LiCl (20 mL). The EtOAc layer was dried over $Na_2SO_4$, filtered and the solvent evaporated under reduced pressure. The crude mixture was chromatographed over $SiO_2$ with a gradient of 0-20% EtOAc in DCM to afford N-(3-methanesulfonylphenyl)-3-[2-methyl-4-(1,2-oxazol-4-yl)phenoxy]-6-(trifluoromethyl)pyridazine-4-carboxamide (0.021 g, 44%). $^1H$ NMR (300 MHz, DMSO-$d_6$) δ 11.29 (s, 1H), 9.48 (s, 1H), 9.20 (s, 1H), 8.70 (s, 1H), 8.38 (d, J=2.0 Hz, 1H), 8.01-7.89 (m, 1H), 7.81-7.61 (m, 4H), 7.38 (d, J=8.4 Hz, 1H), 3.25 (s, 3H), 2.18 (s, 3H). LC-MS (Method 2): m/z 517.3 $[M-H]^+$.

Compound 133: 3-[2-Methyl-4-(1H-pyrazol-4-yl) phenoxy]-N-(3-methylsulfonylphenyl)-6-(trifluoromethyl)pyridazine-4-carboxamide

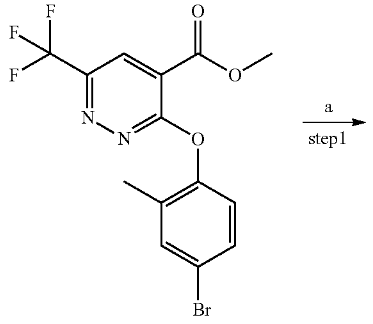

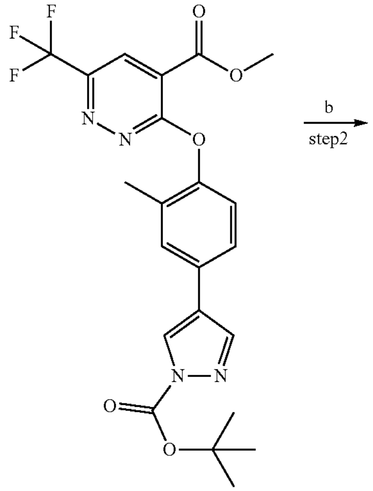

-continued

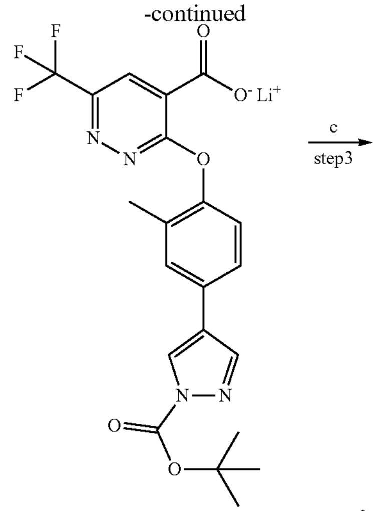

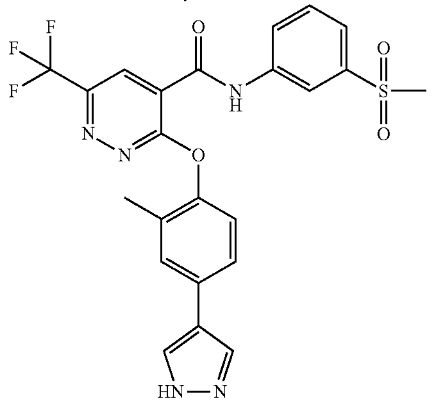

Reagents & conditions: a) tert-butyl 4-(4,4,5,5-tetramethyl-1,3,2-dioxaborolan-2-yl)-1H-pyrazole-1-carboxylate, $Pd_2(dba)_3$, Xphos, 1,4-dioxane, $H_2O$, 40 °C; b) LiOH, THF, $H_2O$, rt; c) (i) DMAP. DIEA, 3-(methylsulfonyl)aniline, 50% Propylphosphonic anyhydride solution in EtOAc, DCM, rt; (ii) 4M HCl in dioxane, rt.

Step 1: methyl 3-[4-(1-tert-butoxycarbonylpyrazol-4-yl)-2-methyl-phenoxy]-6-(trifluoromethyl) pyridazine-4-carboxylate A suspension of methyl 3-(4-bromo-2-methyl-phenoxy)-6-(trifluoromethyl)pyridazine-4-carboxylate (100 mg, 0.256 mmol), tert-butyl 4-(4,4,5,5-tetramethyl-1,3,2-dioxaborolan-2-yl)-1H-pyrazole-1-carboxylate (75 mg, 0.256 mmol), $Pd_2(dba)_3$ (12 mg, 0.0128 mmol) and Xphos (6.1 mg, 0.0128 mmol) in 1,4-Dioxane (2 mL) and Water (0.2 mL) was degassed with nitrogen and stirred at 40 °C for 18.5 h. The reaction mixture was poured into water (20 mL) and extracted with EtOAc (3×20 mL). The organic phases were combined, passed through a phase separator and concentrated in vacuo. The compound was purified by column chromatography over silica USING 0-100% EtOAc in heptane and flushed using 0-60% MeOH in DCM (on a Biotage Sfar 10 g column, compound dry-loaded onto silica using DCM) to afford methyl 3-[4-(1-tert-butoxycarbonylpyrazol-4-yl)-2-methyl-phenoxy]-6-(trifluoromethyl)pyridazine-4-carboxylate (75.0%) (46 mg, 28%) as a pale yellow oil. $^1H$ NMR (400 MHz, DMSO-$d_6$) δ 8.75 (s, 1H), 8.55 (s, 1H), 8.33 (s, 1H), 7.81 (d, J=1.6 Hz, 1H), 7.69 (dd, J=8.3, 2.1 Hz, 1H), 7.27 (d, J=8.4 Hz, 1H), 3.97 (s, 3H), 2.17 (s, 3H), 1.64-1.56 (m, 9H). LC-MS (Method 3): m/z 379.2 [M+H]+, (ESI+), RT=1.03.

Step 2: 3-[4-(1-tert-butoxycarbonylpyrazol-4-yl)-2-methyl-phenoxy]-6-(trifluoromethyl)pyridazine-4-carboxylate, Lithium Salt To a mixture of methyl 3-[4-(1-tert-butoxycarbonylpyrazol-4-yl)-2-methyl-phenoxy]-6-(trifluoromethyl)pyridazine-4-carboxylate (75%, 46 mg, 0.0721 mmol) in THE (0.6 mL):Water (0.1 mL), lithium hydroxide (4.5 mg, 0.180 mmol) was added and the mixture was stirred at rt for 3 h. The reaction was concentrated in vacuo to afford 3-[4-(1-tert-butoxycarbonylpyrazol-4-yl)-2-methyl-phenoxy]-6-(trifluoromethyl)pyridazine-4-carboxylate, lithium salt (85.0%) (40 mg, 0.0723 mmol, 100% Yield) as a pale yellow solid. LC-MS (Method 1): m/z 365.05 [M+H]+, (ESI+), RT=0.97. This material was used for the next step without any further purification.

Step 3. To a stirring solution of 3-[4-(1-tert-butoxycarbonylpyrazol-4-yl)-2-methyl-phenoxy]-6-(trifluoromethyl)pyridazine-4-carboxylate lithium salt (40 mg, 0.0850 mmol), N-ethyl-N-isopropyl-propan-2-amine (0.030 mL, 0.170 mmol) and N,N-dimethylpyridin-4-amine (2.1 mg, 0.0170 mmol) in DCM (0.6 mL), 50% Propylphosphonic anhydride solution in EtOAc (50%, 0.061 mL, 0.102 mmol) was added dropwise at RT and stirred for 10 minutes. 3-(methylsulfonyl)aniline (17 mg, 0.102 mmol) was subsequently added in one portion and stirred for 1 h at RT. The reaction was re-treated with 50% Propylphosphonic anhydride solution in EtOAc (50%, 0.061 mL, 0.102 mmol) and N-ethyl-N-isopropyl-propan-2-amine (0.030 mL, 0.170 mmol) followed by DMF (0.1 mL) to facilitate dissolution. The reaction was stirred at RT for 16 h. The reaction was re-treated with 50% Propylphosphonic anhydride solution in EtOAc (50%, 0.061 mL, 0.102 mmol) and stirred for 2 hr at rt. The reaction was re-treated with N-ethyl-N-isopropyl-propan-2-amine (0.030 mL, 0.170 mmol), N,N-dimethylpyridin-4-amine (2.1 mg, 0.0170 mmol) and 50% Propylphosphonic anhydride solution in EtOAc (50%, 0.061 mL, 0.102 mmol) and stirred at 45 °C for 1 h. The reaction was concentrated in vacuo and 4 M HCl in dioxane (1.0 mL, 4.00 mmol) was added, the reaction was stirred at rt for 18 h. The reaction mixture was poured into water (10 mL) and extracted with DCM (3×20 mL), the combined organic phases were passed through a phase separator and concentrated in vacuo. The compound was purified by Prep Method 1, concentrated in vacuo and freeze-dried overnight to afford the title compound 3-[2-methyl-4-(1H-pyrazol-4-yl)phenoxy]-N-(3-methylsulfonylphenyl)-6-(trifluoromethyl)pyridazine-4-carboxamide (6.0 mg, 14%) as a white solid. $^1$H NMR (400 MHz, DMSO-$d_6$) δ 12.92 (s, 1H), 11.27 (s, 1H), 8.62 (s, 1H), 8.36 (s, 1H), 8.06 (s, 2H), 7.93 (d, J=7.7 Hz, 1H), 7.69 (d, J=7.7 Hz, 2H), 7.61 (d, J=1.7 Hz, 1H), 7.53 (dd, J=8.3, 2.0 Hz, 1H), 7.25 (d, J=8.4 Hz, 1H), 3.22 (s, 3H), 2.15 (s, 3H). LC-MS (Method 6): m/z 518.3 $[M+H]^+$, (ESI+), RT=2.94.

Compound 134: 3-(4-Fluoro-2-methyl-phenoxy)-N-([1,2,4]triazolo[4,3-a]pyridin-5-yl)-6-(trifluoromethyl)pyridazine-4-carboxamide

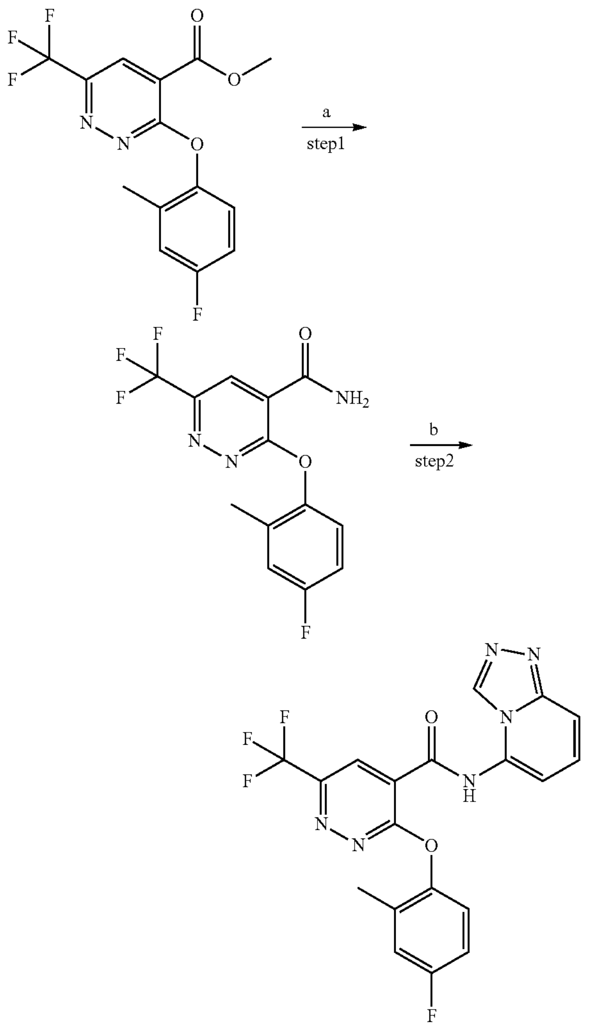

Reagents & conditions: a) ammonium hydroxie (25%), 65 °C; b) BrettPhos Pd G3, 5-bromo[1,2,4]triazolo[4,3-a]pyridine, 1,4-dioxane, cedium carbonate, 90 °C.

Step 1. 3-(4-fluoro-2-methyl-phenoxy)-6-(trifluoromethyl)pyridazine-4-carboxamide A suspension of methyl 3-(4-fluoro-2-methyl-phenoxy)-6-(trifluoromethyl)pyridazine-4-carboxylate (300 mg, 0.908 mmol) in ammonium hydroxide (25%, 1.9 mL, 45.4 mmol) was stirred at 65 °C for 10 min. The mixture was cooled to room temperature and the suspension was filtered and washed with water (5 mL×2), dried under high vacuum at 40 °C for 2 h to obtain the crude product. Purification using Prep method P3 to afford the title compound (175 mg, 61%) as a white solid. $^1$H NMR (400 MHz, DMSO-$d_6$) δ 8.42 (s, 1H), 8.21 (d, J=5.3 Hz, 2H), 7.31 (dd, J=8.9, 5.1 Hz, 1H), 7.25 (dd, J=9.4, 3.0 Hz, 1H), 7.15 (td, J=8.6, 3.1 Hz, 1H), 2.12 (s, 3H). LC-MS (Method 6): m/z 316.1$[M+H]^+$, (ESI+), RT=2.95.

Step 2. 3-(4-fluoro-2-methyl-phenoxy)-N-([1,2,4]triazolo[4,3-a]pyridin-5-yl)-6-(trifluoromethyl)pyridazine-4-carboxamide: A mixture of BrettPhos Pd G3 (29 mg, 0.0317 mmol), 3-(4-fluoro-2-methyl-phenoxy)-6-(trifluoromethyl)pyridazine-4-carboxamide (100 mg, 0.317 mmol) and 5-bromo[1,2,4]triazolo[4,3-a]pyridine (94 mg, 0.476 mmol) were dissolved in anhydrous 1,4-dioxane (3 mL) under nitrogen at RT. The mixture was degassed with nitrogen for 5 minutes, then cesium carbonate (207 mg, 0.634 mmol) was added in one portion. The reaction mixture was stirred at 90 °C for 16 h. The solvent was removed in vacuo and the crude residue purified using Prep LC Method P1 to afford the title compound (95.0%) (13 mg, 9.3%) as a yellow solid. $^1$H NMR (400 MHz, DMSO-$d_6$) δ 11.66 (s, 1H), 9.33 (s, 1H), 8.79 (s, 1H), 7.72 (d, J=9.2 Hz, 1H), 7.49 (dd, J=9.1, 7.3 Hz, 1H), 7.38 (s, 1H), 7.27 (dd, J=9.2, 2.8 Hz, 2H), 7.17 (td, J=8.5, 3.0 Hz, 1H), 2.16 (s, 3H). LC-MS (Method 4): m/z 433.2 $[M+H]^+$, (ESI+), RT=2.89.

Compound 135: 3-(4-Fluoro-2-methylphenoxy)-N-(tetrazolo[1,5-a]pyridin-7-yl)-6-(trifluoromethyl)pyridazine-4-carboxamide

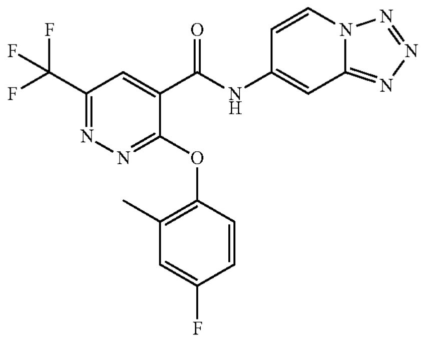 [SMILES: Cc1cc(F)ccc1Oc1nnc(C(F)(F)F)cc1C(=O)Nc1ccn2nnnc2c1]

A mixture of BrettPhos Pd G3 (29 mg, 0.0317 mmol), (100 mg, 0.317 mmol) and 7-bromotetrazolo[1,5-a]pyridine (95 mg, 0.476 mmol) were dissolved in anhydrous 1,4-dioxane (3 mL) under nitrogen at RT. Then cesium carbonate (207 mg, 0.634 mmol) was added in one portion, the suspension was degassed for 5 min. The reaction mixture was stirred at 70 °C for 2 h. The mixture was filtered through celite plug, washed with MeOH (5 mL) and the solvent was removed in vacuo. Purification by Prep LC (Method P1) to afford the desired product (63 mg) with impurities. The material was subsequently re-purified with prep method P3 to afford the title compound (26 mg, 19%) as a pale yellow solid. $^1$H NMR (500 MHz, DMSO-$d_6$) δ 11.67 (s, 1H), 9.30 (d, J=6.9 Hz, 1H), 8.73 (s, 1H), 8.61-8.53 (m, 1H), 7.45 (dd, J=7.4, 2.1 Hz, 1H), 7.36 (dd, J=9.0, 5.0 Hz, 1H), 7.26 (dd, J=9.3, 2.9 Hz, 1H), 7.16 (td, J=8.5, 3.2 Hz, 1H), 2.14 (s, 3H). LCMS (Method 5) m/z 434.1 [M+H]+, (ESI+), RT=4.08.

Compound 136: 3-(3,4-difluoro-2-methoxy-phenoxy)-N-[3-(methylsulfonimidoyl)phenyl]-6-(trifluoromethyl)pyrazine-2-carboxamide

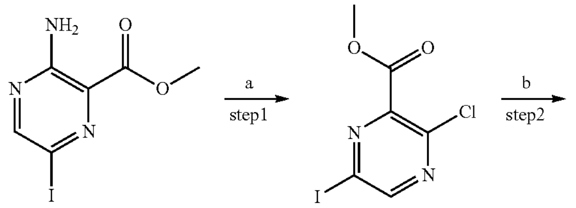

-continued

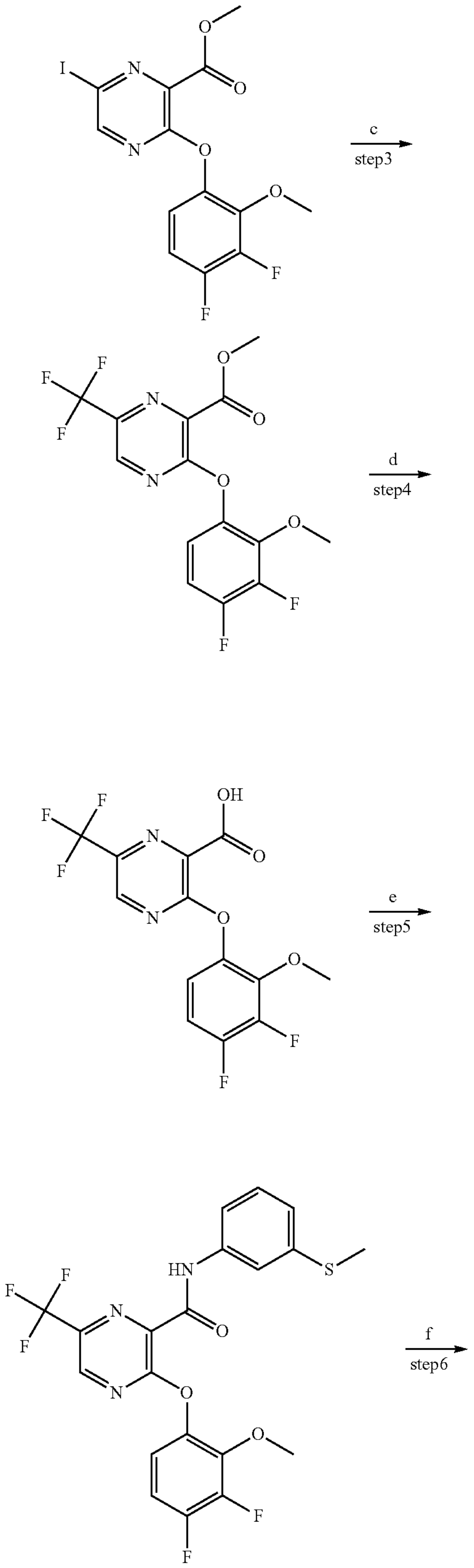

-continued

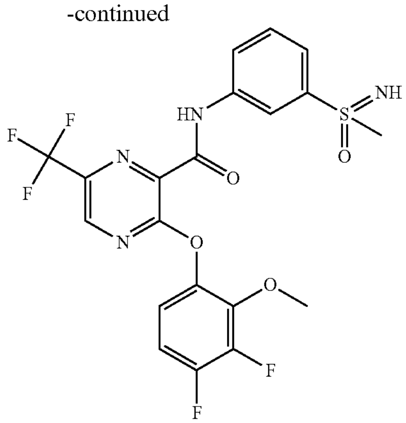

Reagents & conditions: a) titanium tetrachloride, tert-butyl nitrite, DCM, 0 °C; b) 3,4-difluoro-2-mthoxy-phenol, $K_2CO_3$, acetonitrile, 60 °C; c) CuI, TBAI, methyl difluoro(fluorosulfonyl)acetate, DMF, 70 °C; d) LiOH, THF/$H_2O$, rt; e) HATU, DIEA, 3-(methylsulfanyl)aniline, DMF, rt; f) $(NH_4)_2CO_3$, (Diacetoxyiodo)benzene, MeOH, rt Step 1: methyl 3-chloro-6-iodo-pyrazine-2-carboxylate: To a solution of methyl 3-amino-6-iodopyrazine-2-carboxylate (100 mg, 0.358 mmol) in DCM-Anhydrous (1.5 mL) at 0 °C was added titanium tetrachloride (38 uL, 0.358 mmol) and the red solution stirred for 5 minutes before addition of tert-butyl nitrite (90%, 95 uL, 0.717 mmol) the solution was allowed to warm to ambient. After 30 minutes titanium tetrachloride (38 uL, 0.358 mmol) was added and the mixture stirred at ambient for 1 h before analysis by LCMS. Water (~5 mL) was added causiously and the solution extracted with DCM (~3×5 mL). The organics were passed through a phase separator and the solvent removed in vacuo to afford methyl 3-chloro-6-iodo-pyrazine-2-carboxylate (90.0%) (103 mg, 0.311 mmol, 87% Yield) as a pale yellow oil. Material used crude in subsequent step.

Step 2: methyl 3-(3,4-difluoro-2-methoxy-phenoxy)-6-iodo-pyrazine-2-carboxylate: A mixture of 3,4-difluoro-2-methoxy-phenol (62 mg, 0.387 mmol), methyl 3-chloro-6-iodo-pyrazine-2-carboxylate (110 mg, 0.369 mmol) and $K_2CO_3$ (76 mg, 0.553 mmol) in Acetonitrile-Anhydrous (1.5 mL) was stirred at 60 °C overnight. The reaction was filtered through a phase separator and washed with DCM (3×10 mL), concentrated in vacuo and purified by FCC (10 g silica; 0-100% MTBE in Heptanes). Product fractions (single peak on trace) were evaporated in vacuo to afford methyl 3-(3,4-difluoro-2-methoxy-phenoxy)-6-iodo-pyrazine-2-carboxylate (82.0%) (55 mg, 0.107 mmol, 29% Yield) as a colourless oil.

$^1H$ NMR (400 MHz, $CD_3OD$) δ 8.53 (s, 1H), 7.10-6.97 (m, 2H), 4.00 (s, 3H), 3.85-3.83 (m, 3H) m/z: 423.0 $[M+H]^+$, (ESI+), RT=0.95 LCMS Method 2.

Step 3: methyl 3-(3,4-difluoro-2-methoxy-phenoxy)-6-(trifluoromethyl)pyrazine-2-carboxylate: To a mixture of methyl 3-(3,4-difluoro-2-methoxy-phenoxy)-6-iodo-pyrazine-2-carboxylate (55 mg, 0.130 mmol), copper iodide (37 mg, 0.195 mmol) and N,N,N-tributylbutan-1-aminium iodide (TBAI) (19 mg, 0.0521 mmol) in DMF-Anhydrous (0.5 mL) under N2 was added methyl difluoro(fluorosulfonyl)acetate (0.083 mL, 0.651 mmol). The reaction mixture was heated to 70 °C and stirred at this temperature for 3.5 h. The reaction mixture was cooled to rt, filtered, poured into water and extracted with EtOAc (3×). The combined organic phases were washed with brine (5×), dried with MgSO4, filtered and concentrated in vacuo to methyl 3-(3,4-difluoro-2-methoxy-phenoxy)-6-(trifluoromethyl)pyrazine-2-carboxylate (90.0%) (36 mg, 0.0890 mmol, 68% Yield) as a dark brown oily solid. $^1H$ NMR (500 MHz, $CD_3OD$) δ 8.59 (s, 1H), 6.99-6.95 (m, 3H), 3.94 (s, 3H), 3.78-3.74 (m, 3H). $^{19}F$ NMR (471 MHz, $CD_3OD$) δ −68.23, −140.04--141.07 (m), −154.06--155.17 (m).

Step 4: 3-(3,4-difluoro-2-methoxy-phenoxy)-6-(trifluoromethyl)pyrazine-2-carboxylic acid: To a mixture of methyl 3-(3,4-difluoro-2-methoxy-phenoxy)-6-(trifluoromethyl)pyrazine-2-carboxylate (39 mg, 0.106 mmol) in THF (0.3 mL):Water (0.1 mL), LiOH (21 mg, 0.848 mmol) was added and the mixture was stirred at rt for 38 h. The reaction was diluted with water (40 mL) and the pH was adjusted to 1 by dropwise addition of 1M HCl. The aqueous layer was extracted with EtOAc (3×40 mL), passed through a phase separator and concentrated in vacuo. Product was used for the next step without any further purifications.

Step 5: 3-(3,4-difluoro-2-methoxy-phenoxy)-N-(3-methylsulfanylphenyl)-6-(trifluoromethyl)pyrazine-2-carboxamide: A mixture of 3-(3,4-difluoro-2-methoxy-phenoxy)-6-(trifluoromethyl)pyrazine-2-carboxylic acid (28 mg, 0.0800 mmol), N-ethyl-N-isopropyl-propan-2-amine (DIEA) (0.028 mL, 0.160 mmol), HATU (36 mg, 0.0959 mmol) and 3-(methylsulfanyl)aniline (13 mg, 0.0959 mmol) in DMF (0.1969 mL) was stirred at rt for 1 h. The reaction mixture was poured into water (20 mL) and extracted with EtOAc (3×30 mL). The combined organic phases were passed through a phase separator and concentrated in vacuo. The compound was purified by FCC using 0-100% EtOAc in Heptane over silica (on a Biotage Sfar 10 g column, compound wet-loaded using DCM) to afford 3-(3,4-difluoro-2-methoxy-phenoxy)-N-(3-methylsulfanylphenyl)-6-(trifluoromethyl)pyrazine-2-carboxamide (55.0%)(68 mg, 0.0793 mmol, 99%) as a pale yellow solid. m/z: 472.1 $[M+H]^+$, (ESI+), RT=1.07 LCMS Method 2

Step 6: 3-(3,4-difluoro-2-methoxy-phenoxy)-N-[3-(methylsulfonimidoyl)phenyl]-6-(trifluoromethyl)pyrazine-2-carboxamide: To a suspension of 3-(3,4-difluoro-2-methoxy-phenoxy)-N-(3-methylsulfanylphenyl)-6-(trifluoromethyl) pyrazine-2-carboxamide (60%, 68 mg, 0.0866 mmol) in Methanol (1 mL), (Diacetoxyiodo)benzene (64 mg, 0.199 mmol) and $(NH_4)_2CO_3$ (12 mg, 0.130 mmol) were added and the reaction was stirred at rt for 4 h. The reaction was concentrated in vacuo and purified by Prep Method 1. Fractions evaporated in vacuo to afford 3-(3,4-difluoro-2-methoxy-phenoxy)-N-[3-(methylsulfonimidoyl)phenyl]-6-(trifluoromethyl)pyrazine-2-carboxamide (99.0%) (10 mg, 0.0203 mmol, 23% Yield) as an off white solid. $^1H$ NMR (400 MHz, $CD_3OD$) δ 8.75 (s, 1H), 8.54 (t, J=1.9 Hz, 1H), 8.09 (dd, J=8.1, 1.2 Hz, 1H), 7.89-7.82 (m, 1H), 7.69 (t, J=8.0 Hz, 1H), 7.18-7.05 (m, 2H), 3.90 (d, J=1.7 Hz, 3H), 3.20 (s, 3H). m/z: 501.3 $[M-H]^-$, (ESI−), RT=3.07 LCMS Method 4.

Example 115

Compound Profiling on NaV1.8—Human NaV1.8 Cell Line—SyncroPatch384PE Assay

Compounds were tested on recombinant human $Na_V1.8$ stably transfected HEK cells using the SyncroPatch384PE system, an automated patch clamp device. Cells were cultured at 37 °C/5% CO2 in DMEM medium supplemented with GlutaMAX I, NEAA 1%, FBS 10% and seeded in T175 flasks. Cells were cultured at 30 °C one day prior to recording sodium currents. On the day of the recordings, cells were detached with 0.05% Trypsin-EDTA, resuspended in serum free DMEM medium and placed into the SyncroPatch384PE 6 °C pre-cooled cell hotel and shaken at 200 rpm. Intracellular solution (IC) contained, in mM: 10, CsCl; 110, CsF; 20, EGTA; 10, HEPES. Extracellular solution (EC) contained, in mM: 140, NaCl; 4, KCl; 5, Glucose; 10, HEPES; 2, $CaCl_2$; 1, $MgCl_2$. Washing solution contained, in mM: 40, NMDG; 100, NaCl; 4, KCl; 10, Glucose; 10, HEPES; 5, $CaCl_2$; 1, $MgCl_2$.

Compounds were tested in quadruplicates in 0.1% DMSO and 0.030% Pluronic Acid. Compounds were diluted 1:3.33 in EC solution to create a 10-point concentration response curve, spanning a final concentration range from 10-0.0002 µM in the assay plate. Compounds with low nM potency were retested using a lower concentration range (1-0.00002 µM). Each plate contained tetracaine and another tool compound as positive controls. Up to 7 compounds were tested on one plate. 150 µM tetracaine and 0.1% DMSO were used as high and low controls, respectively.

Whole cell patch clamp recordings were conducted according to Nanion's standard procedure for SyncroPatch384PE®. Cells were held at a holding potential of −120 mV. A depolarization step to 10 mV for 30 ms was applied (P1 measurement), followed by a hyperpolarization step to −100 mV for 100 ms. An inactivation step at −40 mV for 10 sec was applied before stepping to −100 mV for 20 ms, followed by a step to 10 mV for 30 ms (P2 measurement) and then back to −100 mV for 30 ms. Sweep interval was 15 sec with a sampling rate of 10 kHz. Following establishment of the whole-cell configuration in EC, two washing steps with reference buffer were performed to stabilize the baseline. Compounds were then applied by the SynchroPatch into each well and the current was recorded for five minutes in EC, followed by application of tetracaine to achieve full block at the end of the experiment. The potency of the compounds was assessed on two read-outs, resting state block (P1 measurement) or inactivated state block (P2 measurement) to obtain IC50 values. Values were normalized to high (tetracaine) and low (DMSO) controls.

Table 27 shows the potency of compounds against human NaV1.8, where "A" represents an IC50 less than or equal to 200 nM, "B" represents an IC50 greater than 201 nM to less than or equal to 500 nM, "C" represents an IC50 greater than 501 nM to less than or equal to 1000 nM, "D" represents an IC50 greater than 1001 nM to less than or equal to 5000 nM, "E" represents an IC50 greater than 5001 nM.

TABLE 27

| Compound | P1 IC50 | P2 IC50 |
|---|---|---|
| 1 | A | A |
| 2 | B | A |
| 3 | B | D |
| 4 | E | E |
| 5 | C | D |
| 6 | D | B |
| 7 | D | C |
| 8 | D | D |
| 9 | E | D |
| 10 | E | E |
| 11 | D | D |
| 12 | D | D |
| 13 | A | A |
| 14 | B | B |
| 15 | E | D |
| 16 | D | D |
| 17 | C | B |
| 18 | D | C |
| 19 | D | D |
| 20 | C | C |
| 21 | C | C |
| 22 | D | D |
| 23 | B | B |

TABLE 27-continued

| Compound | P1 IC50 | P2 IC50 |
|---|---|---|
| 24 | A | A |
| 25 | A | A |
| 26 | A | A |
| 27 | A | A |
| 28 | D | D |
| 29 | E | E |
| 30 | E | E |
| 31 | E | E |
| 32 | E | E |
| 33 | A | A |
| 34 | A | A |
| 35 | A | A |
| 36 | B | C |
| 37 | A | A |
| 38 | D | D |
| 39 | A | A |
| 40 | D | E |
| 41 | D | E |
| 42 | A | A |
| 43 | C | D |
| 44 | B | C |
| 45 | B | B |
| 46 | E | E |
| 47 | A | A |
| 48 | C | D |
| 49 | A | A |
| 50 | A | A |
| 51 | A | A |
| 52 | E | E |
| 53 | A | A |
| 54 | D | D |
| 55 | D | D |
| 56 | E | E |
| 57 | E | E |
| 58 | B | B |
| 59 | C | B |
| 60 | D | D |
| 61 | E | E |
| 62 | E | E |
| 63 | B | C |
| 64 | A | A |
| 65 | C | C |
| 66 | E | D |
| 67 | E | E |
| 68 | E | E |
| 69 | E | E |
| 70 | C | C |
| 71 | E | E |
| 72 | A | A |
| 73 | B | B |
| 74 | A | C |
| 75 | A | A |
| 76 | A | A |
| 77 | B | B |
| 78 | E | E |
| 79 | B | B |
| 80 | C | C |
| 81 | B | D |
| 82 | A | A |
| 83 | A | A |
| 84 | E | E |
| 85 | E | E |
| 86 | C | C |
| 87 | A | A |
| 88 | A | A |
| 89 | D | D |
| 90 | E | E |
| 91 | E | E |
| 92 | E | E |
| 93 | D | E |
| 94 | D | E |
| 95 | E | E |
| 96 | B | C |
| 97 | D | D |
| 98 | E | E |
| 99 | A | A |
| 100 | A | A |
| 101 | A | A |

TABLE 27-continued

| Compound | P1 IC50 | P2 IC50 |
|---|---|---|
| 102 | C | B |
| 103 | E | B |
| 104 | E | E |
| 105 | E | E |
| 106 | B | B |
| 107 | A | A |
| 108 | E | E |
| 109 | B | B |
| 110 | E | E |
| 111 | E | E |
| 114 | A | A |
| 116 | B | B |
| 117 | A | A |
| 118 | A | A |
| 119 | C | C |
| 121 | A | A |
| 122 | C | B |
| 123 | A | A |
| 125 | A | B |
| 126 | A | A |
| 127 | C | C |
| 128 | E | E |
| 129 | B | B |
| 130 | E | D |
| 131 | B | C |
| 132 | B | A |
| 133 | E | E |
| 134 | E | E |
| 135 | A | C |
| 136 | A | A |

D. Examples for Fourth Set of Compounds

Example 116

Methods of making the compounds of the present invention, and intermediates used in their synthesis, are provided in the General Synthetic Schemes and Specific Syntheses Procedures below. Chemicals were purchased from standard commercial vendors and used as received unless otherwise noted. Otherwise, their preparation is facile and known to one of ordinary skill in the art, or it is referenced or described herein. Abbreviations are consistent with those in the ACS Style Guide. “Dry” glassware means oven/desiccator dried. Solvents were ACS grade unless otherwise noted.

All reactions were performed in flame-dried or oven-dried glassware under a positive pressure of dry nitrogen or dry argon and were stirred magnetically unless otherwise indicated. Chemicals were purchased from standard commercial vendors and used as received unless otherwise noted. Yields are not optimized. The chemical names were generated using the ChemDraw Professional 19.1, available from PerkinElmer or chemAxon.

Reactions were monitored by thin layer chromatography (TLC) using 0.25 mm silica gel 60 F254 plates purchased from EMD MILLIPORE™. Purification was performed with CombiFlash NextGen 300 Automated Flash Chromatography System or purified using one of the preparative HPLC methods mentioned below.

Prep Method 1 (P1): Acidic Early Method

Purification (METCR/Prep004) (P1) LC were performed using a Waters Sunfire C18 column (30 mm×100 mm, 5 μm; temperature: room temperature), with an injection volume of 1500 μL at flow rate of 40 mL/min at 100% B (A=0.1% formic acid in water; B=0.1% formic acid in acetonitrile) for 0.55 min then a gradient of 10-95% B over 13.89 min and held for 2.11 min. A second gradient of 95-10% B was then applied over 0.2 min. UV spectra were recorded at 215 nm using a Gilson detector.

Prep Method 2 (P2): Acidic Standard Method

Purification (METCR/Prep001) (P2) LC were performed using a Waters Sunfire C18 column (30 mm×100 mm, 5 μm; temperature: room temperature), with an injection volume of 1500 μL at flow rate of 40 mL/min at 30% B (A=0.10% formic acid in water; B=0.10% formic acid in acetonitrile) for 0.55 min then a gradient of 30-95% B over 10.45 min and held for 2.10 min. A second gradient of 95-30% B was then applied over 0.21 min. UV spectra were recorded at 215 nm using a Gilson detector.

Prep Method 3 (P3): Basic Early Method

Purification (METCR/Prep002) (P3) LC were performed using a Waters X-Bridge C18 column (30 mm×100 mm, 5 μm; temperature: room temperature), with an injection volume of 1500 μL at flow rate of 40 mL/min at 10% B (A=0.2% ammonium hydroxide in water; B=0.2% ammonium hydroxide in acetonitrile) for 0.55 min then a gradient of 10-95% B over 13.89 min and held for 2.11 min. A second gradient of 95-10% B was then applied over 0.2 min. UV spectra were recorded at 215 nm using a Gilson detector.

Prep Method 4 (P4): Basic Standard Method

Purification (METCR/Prep003) (P4) LC were performed using a Waters X-Bridge C18 column (30 mm×100 mm, 5 μm; temperature: room temperature), with an injection volume of 1500 μL at flow rate of 40 mL/min at 300% B (A=0.2% ammonium hydroxide in water; B=0.2% ammonium hydroxide in acetonitrile) for 0.55 min then a gradient of 30-95% B over 10.45 min and held for 2.10 min. A second gradient of 95-30% B was then applied over 0.21 min. UV spectra were recorded at 215 nm using a Gilson detector.

Analytical LCMC were collected using one of following methods.

Method 1 (M1): Acidic IPC Method (METCRI410—MS17, MS18, MS19)

Analytical (MET/CR/1410) (M1) HPLC-MS were performed using a Kinetex Core shell C18 column (2.1 mm×50 mm, 5 μm; temperature: 40 °C), with an injection volume of 3 μL at a flow rate of 1.2 mL/min and a gradient of 5-100% B (A=0.1% formic acid in water; B=0.10% formic acid in acetonitrile) over 1.2 min, then 100% B for 0.1 min. A second gradient of 100-5% B was then applied over 0.01 min and held for 0.39 min. UV spectra were recorded at 215 nm using a SPD-M20A PDA detector, spectrum range: 210-400 nm. Mass spectra were obtained using a 2010EV detector. Data were integrated and reported using Shimadzu LCMS-Solutions and PsiPort software.

Method 2(M2):

Mass spectrometry data were collected using a Waters Acquity H-class ultra-high pressure liquid chromatograph coupled to a Waters Acquity TQD mass spectrometer. An Acquity UPLC BEH C18 column (2.1×50 mm) was used for separation and resolving samples. The compounds were eluted from the column using a 10-minute linear solvent gradient: 0-0.5 min, 5% B; 0.5-6.5 min, 100% B, 6.5-7.5 min; 100% B, 7.5-8.1 min; 5% B, 8.1-10 min; 5% B. The solvent flow rate is 0.45 mL per minute. Solvent A was water and solvent B was acetonitrile. Mass spectra were collected in positive or negative ion mode, with following parameters: 2.5 kV capillary voltage; 25 V sampling cone voltage; 140 C source temperature; 400 C desolvation temperature; nitrogen desolvation at 800 L/hr.

Method 3 (M3): Basic IPC Method (MET-uPLC-AB-2005—MS16, MSQ5)

Analytical (MET/uPLC/AB2005) (M14) uHPLC-MS were performed using a Waters uPLC® BEHTM C18 column (2.1 mm×30 mm, 1.7 μm; temperature 40 °C), with an injection volume of 1 μL at a flow rate of 1.0 mL/min and a gradient of 1-100% B (A=2 mM ammonium bicarbonate in water, buffered to pH 10; B=acetonitrile) over 1.1 min, then 100% B for 0.25 min. A second gradient of 100-1% B was then applied over 0.05 min and held for 0.4 min. UV spectra were recorded at 215 nm using a Waters ACQUITY PDA detector, spectrum range: 200-400 nm. Mass spectra were obtained using a Waters Quattro Premier XE mass detector or a Waters SQD2. Data were integrated and reported using Waters MassLynx and OpenLynx software.

Method 4 (M4): Acidic Final Analysis Method (METCR-uPLC-AB101—MSQ1, MSQ2, MSQ4)

Analytical (MET/uPLC/AB101) (M4) uHPLC-MS were performed using a Phenomenex Kinetex-XB C18 column (2.1 mm×100 mm, 1.7 μm; temperature: 40 °C), with an injection volume of 1 μL at flow rate of 0.6 mL/min and a gradient of 5-100% B (A=0.1% formic acid in water; B=0.1% formic acid in acetonitrile) over 5.3 min, then 100% B for 0.5 min. A second gradient of 100-5% B was then applied over 0.02 min and held for 1.18 min. UV spectra were recorded at 215 nm using a Waters ACQUITY PDA detector, spectrum range: 200-400 nm, ELS data was collected on a Waters ACQUITY ELS detector when reported. Mass spectra were obtained using a Waters SQD or Waters ACQUITY QDA. Data were integrated and reported using Waters MassLynx and OpenLynx software.

Method 5 (M5): Acidic Final Analysis Method (METCR1416—MS18, MS19)

Analytical (MET/CR/1416) (M5) HPLC-MS were performed using a Waters Atlantis dC18 column (2.1 mm×100 mm, 3 μm; temperature: 40 °C), with an injection volume of 3 μL at flow rate of 0.6 mL/min and a gradient of 5-100% B (A=0.1% formic acid in water; B=0.1% formic acid in acetonitrile) over 5 min, then 100% B for 0.4 min. A second gradient of 100-5% B was then applied over 0.02 min and held for 1.58 min. UV spectra were recorded at 215 nm using a SPD-M20A PDA detector, spectrum range: 210-400 nm. Mass spectra were obtained using a 2010EV detector. Data were integrated and reported using Shimadzu LCMS-Solutions and PsiPort software.

Method 6 (M6): Basic Final Analysis Method (MET-uPLC-AB105-MS16, MSQ5)

Analytical (MET/uHPLC/AB105) (M8) uHPLC-MS were performed using a Waters uPLC® BEHTM C18 column (2.1 mm×100 mm, 1.7 μm column; temperature: 40 °C), with an injection volume of 1 μL and at flow rate of 0.6 mL/min and a gradient of 5-100% B (A=2 mM ammonium bicarbonate in water, buffered to pH 10; B=acetonitrile) over 5.3 min, then 100% B for 0.5 min. A second gradient of 100-5% B was then applied over 0.02 min and held for 1.18 min. UV spectra were recorded at 215 nm using a Waters ACQUITY PDA detector, spectrum range: 200-400 nm. Mass spectra were obtained using a Waters Quattro Premier XE mass detector or a Waters SQD2. Data were integrated and reported using Waters MassLynx and OpenLynx software.

SFC chiral resolution was performed using following method: Column: Daicel CHIRALPAK IG, 250 mm×20 mm I.D., 5 μm; Mobile Phase A: $CO_2$/MeOH [0.2% $NH_3$ (7M Solution in MeOH)]=70/30; Flow rate: 60 g/min; 214 nm. Temperature: 35 °C.

Unless otherwise stated, $^1$H nuclear magnetic resonance spectroscopy (NMR) spectra were recorded on a Bruker™ 300 MHz, or 500 MHz, 400 MHz or 250 MHz on either a Bruker Avance III HD 500 MHz spectrometer Bruker Avance III HD 400 MHz spectrometer. Chemical shifts, 6, are quoted in parts per million (ppm) relative to TMS and calibrated using residual un-deuterated solvent as an internal reference. The following abbreviations are used to denote the multiplicities and general assignments: s (singlet), d (doublet), t (triplet), q (quartet), dd (doublet of doublets), ddd (doublet of doublet of doublets), dt (doublet of triplets), dq (doublet of quartets), hep (heptet), m (multiplet), pent (pentet), td (triplet of doublets), qd (quartet of doublets), app. (apparent) and br. (broad). Coupling constants, J, are quoted to the nearest 0.1 Hz.

Example 117

General Synthetic Schemes

Several methods for preparing the compounds of this invention are illustrated in the following Schemes and Examples. The present invention further provides processes for the preparation of compounds of structural Formula I as defined above. In some cases, the order of carrying out the foregoing reaction schemes may be varied to facilitate the reaction or to avoid unwanted reaction products. The following examples are provided for the purpose of illustration only and are not to be construed as limitations on the disclosed invention.

Scheme A

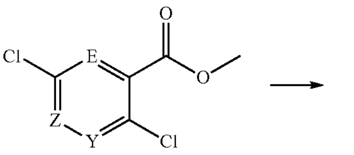

A-1

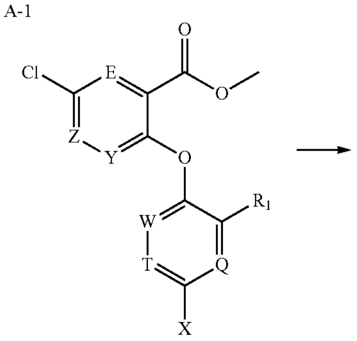

A-2

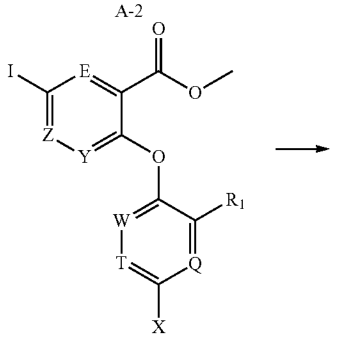

A-3

-continued

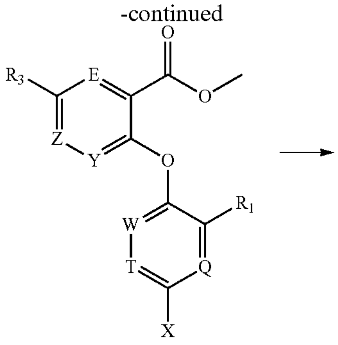

A-4

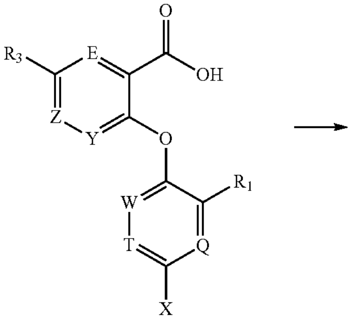

A-5

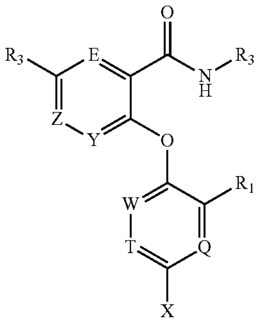

A-6

The compounds of the formula A-6 may be synthesized in five step linear synthesis starting from dichlorocarboxylic acid ester A-1 by nucleophilic displacement of Cl adjacent to the carboxylic acid using various substituted phenols in the presence of base, such as $K_2CO_3$, $Cs_2CO_3$, NaH, KH or other organic bases to provide intermediates of type A-2. Intermediates of type A-2 was further treated with HI (50%), HI (57%) or HI (40%) to furnish intermediates of type A-3. Variously substituted $R_3$ groups can be introduced either by Pd mediated or Cu mediated coupling with intermediates of type A-3. The carboxylic acid of intermediates type A-5 can be prepared by hydrolyzing ester intermediates of type A-4 using a base, such as aqueous NaOH, KOH, or LiOH. Alternatively, intermediates of type A-5 can be prepared by treating intermediates A-4 using aqueous 1 to 6N HCl. The carboxylic acids (A-5) can be activated to the acid chloride and coupled with $R_2NH_2$ or carboxylic acids (A-5) can be coupled with $R_2NH_2$ using standard amide coupling agents, not limited to HATU, TBTU, EDC or $T_3P$ in organic solvents and base, such as DIEA, $Et_3N$, DMAP or pyridine to furnish A-6.

Scheme B

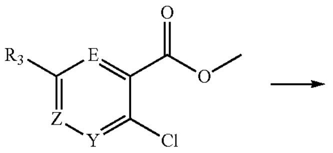

B-1

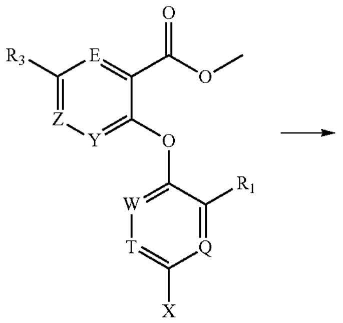

B-2

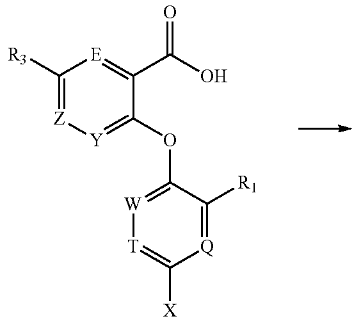

B-3

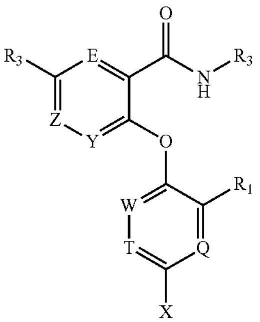

A-6

Alternatively, compounds of the formula A-6 can be prepared nucleophilic displacement of Cl intermediates of type B-1 using various substituted phenols in the presence of base, such as $K_2CO_3$, $Cs_2CO_3$, NaH, KH or other organic bases to provide intermediates of type B-2. The carboxylic acid of intermediates type B-3 can be prepared by hydrolyzing ester intermediates of type B-2 using a base, such as aqueous NaOH, KOH, or LiOH. Alternatively, intermediates of type B-3 can also be prepared by treating intermediates B-2 using aqueous 1 to 6N HCl. The carboxylic acids (B-3) can be activated to the acid chloride and coupled with $R_2NH_2$ or carboxylic acids (B-3) can couple with $R_2NH_2$ using standard amide coupling agents, not limited to HATU, TBTU, EDC or $T_3P$ in organic solvents and base, such as DIEA, $Et_3N$, DMAP or pyridine to furnish A-6.

Scheme C

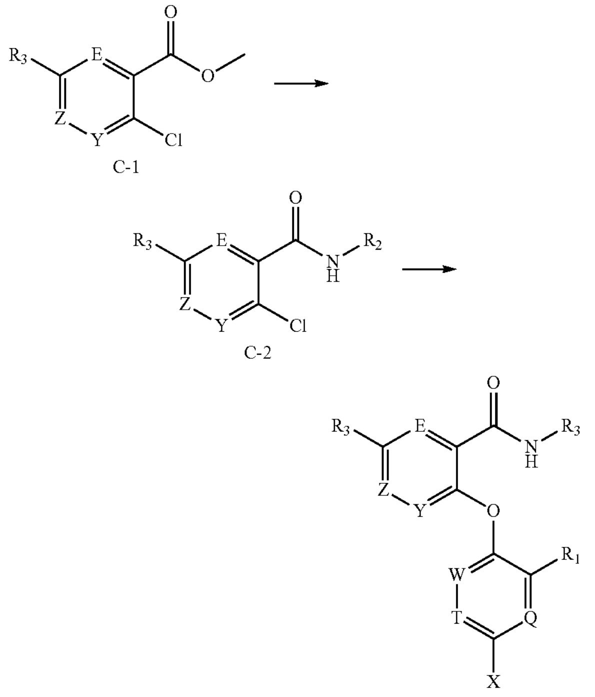

C-1

C-2

A-6

Alternatively, compounds of type A-6 can also be prepared by activating carboxylic acids (C-1) to the acid chloride and coupled with $R_2NH_2$ or carboxylic acids (C-1) can be coupled with $R_2NH_2$ using standard amide coupling agents, not limited to HATU, TBTU, EDC or $T_3P$ in organic solvents and base, such as DIEA, $Et_3N$, DMAP or pyridine to furnish C-2. The compounds of type A-6 can be obtained by treating intermediates of type C-2 with various phenols in the presence of base, such as NaH, $K_2CO_3$, $Cs_2CO_3$, DIEA or $Et_3N$ using organic solvents.

Example 118

Specific Synthesis

Intermediate 1: 3-(4-Fluoro-2-methyl-phenoxy)-6-(trifluoromethyl)pyridazine-4-carboxylic Acid

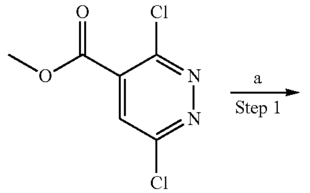

-continued

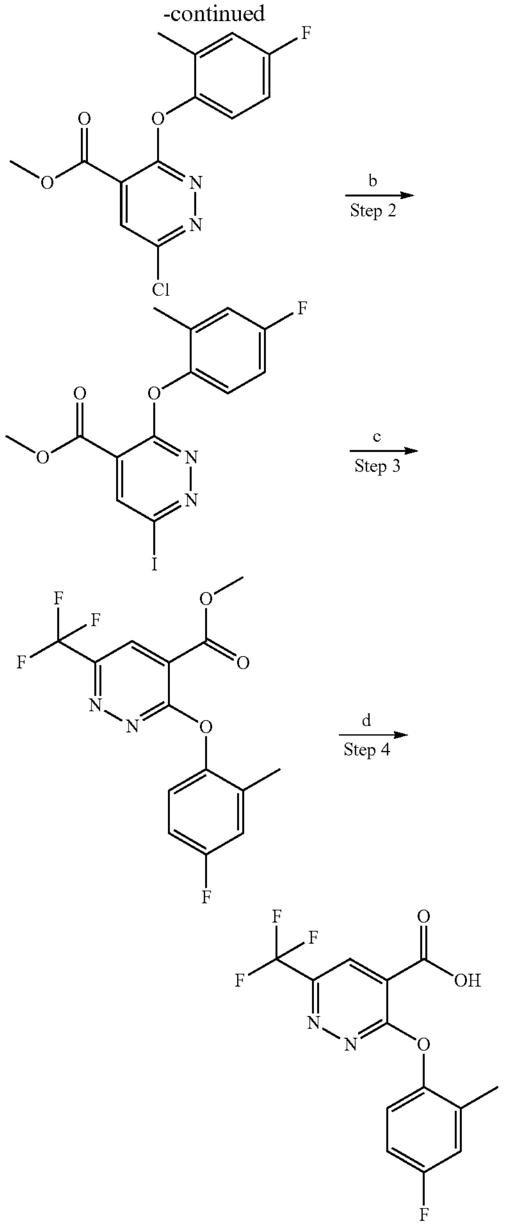

Reagents & conditions: Reagents & conditions: a) 4-fluoro-2-methoxy-phenol, $K_2CO_3$, $CH_3CN$, 60 °C, 7 h; b) HI(55%), 40 °C, 24 h; c) methyl 2,2-difluoro-2-(fluorosulfonyl) acetate, TBAI, CuI, DMF, 90 °C, 2 h; d) LiOH, THF, $H_2O$, rt, 24 h.

Step 1: methyl 6-chloro-3-(4-fluoro-2-methyl-phenoxy)pyridazine-4-carboxylate

A mixture of 4-fluoro-2-methyl-phenol (3.01 g, 23.8 mmol), methyl 3,6-dichloropyridazine-4-carboxylate (4.70 g, 22.7 mmol) and potassium carbonate (4.71 g, 34.1 mmol) in acetonitrile (47 mL) was stirred at 80 °C for 3 h.

The reaction was cooled to room temperature, filtered and washed with MeCN (20 mL). Filtrate was concentrated in vacuo to obtain the crude residue. Purification by chromatography on silica eluting with a gradient of 0 to 15% EtOAc in heptane afforded the title compound methyl 6-chloro-3-(4-fluoro-2-methyl-phenoxy)pyridazine-4-carboxylate (95.0%) (4.10 g, 58%) as a pale yellow oil. $^1H$ NMR (500

MHz, DMSO-$d_6$) δ 8.26 (s, 1H), 7.29-7.20 (m, 2H), 7.16-7.06 (m, 1H), 3.94 (s, 3H), 2.11 (s, 3H). LC-MS: m/z: 297/299 $[M+H]^+$.

Step 2: methyl 3-(4-fluoro-2-methyl-phenoxy)-6-iodo-pyridazine-4-carboxylate A mixture of 6-chloro-3-(4-fluoro-2-methyl-phenoxy) pyridazine-4-carboxylate (95%, 4.10 g, 13.1 mmol) in 55% aqueous hydrogen iodide (50 mL, 0.197 mol) was stirred at 40 °C for 3 h. The mixture was left overnight at RT. The reaction mixture was filtered. The filter cake was washed with water. The solid was re-dissolved in 55% aqueous hydrogen iodide (50 mL, 0.197 mol) and stirred at 40 °C for 24 h. The mixture was cooled to RT and filtered, the solid was washed with water and dried in high vacuum oven at 40 °C overnight to afford methyl 3-(4-fluoro-2-methyl-phenoxy)-6-iodo-pyridazine-4-carboxylate (79.0%) (2.70 g, 42%) as a yellow solid. $^1H$ NMR (400 MHz, DMSO-$d_6$) δ 8.37 (s, 1H), 7.26-7.17 (m, 2H), 7.15-7.05 (m, 1H), 3.91 (s, 3H), 2.09 (s, 3H). MS: m/z: 388.9 $[M+H]^+$.

Step 3: methyl 3-(4-fluoro-2-methyl-phenoxy)-6-(trifluoromethyl)pyridazine-4-carboxylate To a mixture of methyl 3-(4-fluoro-2-methyl-phenoxy)-6-iodo-pyridazine-4-carboxylate (80%, 2.70 g, 5.57 mmol), CuI (1.6 g, 8.35 mmol), tetrabutylammonium; iodide (0.824 g, 2.23 mmol) in DMF (10 mL) (degassed with nitrogen for 5 minutes) methyl difluoro(fluorosulfonyl)acetate (5.34 g, 27.8 mmol) was added and stirred at 90 °C for 2 h. The reaction was cooled to RT, filtered and washed with EtOAc (2×10 mL). The filtrate was washed with brine (50 mL) and dried over $MgSO_4$, filtered, concentrated under reduced pressure to obtain the crude residue. Purification by chromatography on silica eluting with a gradient of 0 to 50% EtOAc in heptane afforded the title compound methyl 3-(4-fluoro-2-methyl-phenoxy)-6-(trifluoromethyl)pyridazine-4-carboxylate (99.0%) (0.770 mg, 41%) as a pale yellow solid. $^1H$ NMR (400 MHz, DMSO-$d_6$) δ 8.54 (s, 1H), 7.32-7.20 (m, 2H), 7.14 (td, J=8.5, 3.2 Hz, 1H), 3.97 (s, 3H), 2.13 (s, 3H). MS: m/z: 316.95 $[M+H]^+$, (ESI+). Unreacted starting material methyl 6-chloro-3-(4-fluoro-2-methyl-phenoxy) pyridazine-4-carboxylate (220 mg, 13%) was recovered as a pale yellow oil.

Step 4: 3-(4-fluoro-2-methyl-phenoxy)-6-(trifluoromethyl)pyridazine-4-carboxylic Acid To a mixture of methyl 3-(4-fluoro-2-methyl-phenoxy)-6-(trifluoromethyl)pyridazine-4-carboxylate (99%, 770 mg, 2.31 mmol) in THF (7.92 mL):Water (1.98 mL), lithium hydroxide (288 mg, 11.5 mmol) was added and the mixture was stirred at rt overnight. The reaction was diluted with water (10 mL) and the pH was adjusted to 1 by dropwise addition of 1M HCl. The solids were filtered, washed with water (2×10 mL), dissolved in EtOAc (20 mL), dried over $Na_2SO_4$ and concentrated under reduced pressure to obtain the title compound 3-(4-fluoro-2-methyl-phenoxy)-6-(trifluoromethyl)pyridazine-4-carboxylic acid (99.0%) (640 mg, 87%) as an off white solid. $^1H$ NMR (400 MHz, DMSO-$d_6$) δ 8.49 (s, 1H), 7.31-7.22 (m, 2H), 7.18-7.09 (m, 1H), 2.12 (s, 3H). LC-MS: m/z 316.95 $[M+H]^+$, (ESI+), RT=1.06 Method METCR1410 Generic 2 min.

Intermediate 2: 3-(4-Fluoro-2-methoxy-phenoxy)-6-(trifluoromethyl)pyridazine-4-carboxylic Acid

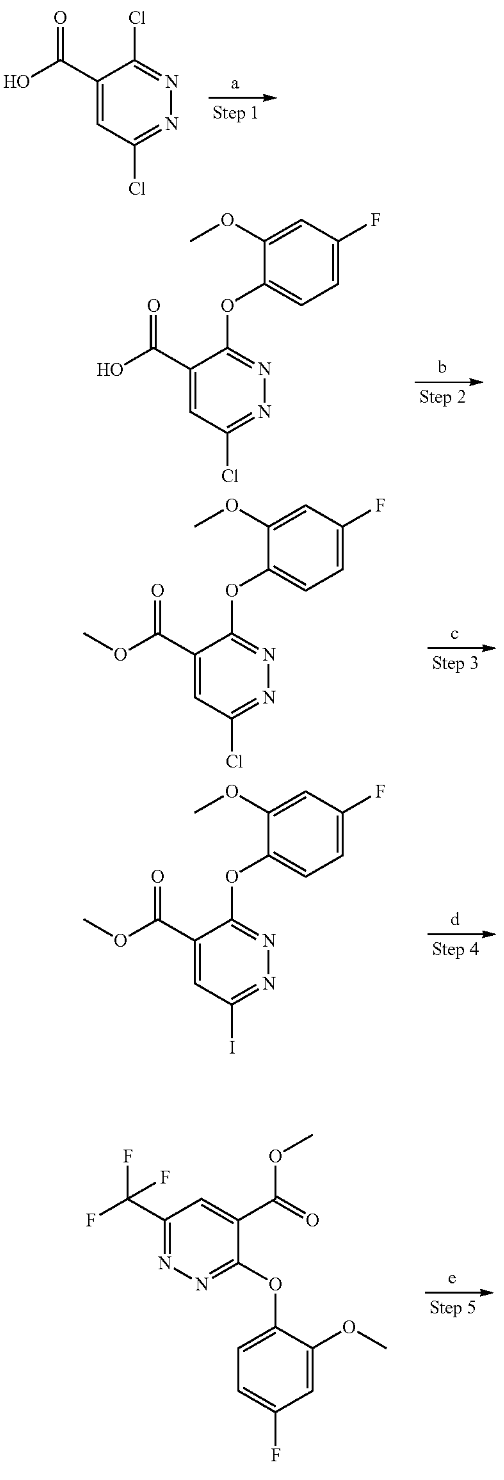

-continued

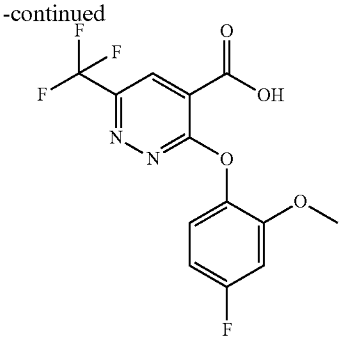

Reagents & conditions: a) 4-fluoro-2-methoxy-phenol, $K_2CO_3$, $CH_3CN$, 60 °C, 7 h; b) $SOCl_2$, MeOH, 50 °C; c) HI (55%), 40 °C, 24 h; d) methyl 2,2-difluoro-2-(fluorosulfonyl) acetate, TBAI, CuI, DMF, 90 °C, 2 h; e) LiOH, THF, $H_2O$, rt, 24 h.

Step 1: 6-chloro-3-(4-fluoro-2-methoxy-phenoxy) pyridazine-4-carboxylic Acid

To solution of 4-fluoro-2-methoxyphenol (1.2 mL, 10.4 mmol) in DMF (20.7 mL) was added sodium hydride (60%) (0.622 g, 15.5 mmol) under nitrogen and the solution was stirred at rt for 30 min. To the resulting mixture 3,6-dichloropyridazine-4-carboxylic acid (1.00 g, 5.18 mmol) was added and stirring continued further at rt for 66 hours. At the end of this period, water (200 mL) was added and adjusted to pH1 with HCl (6N). The mixture was extracted with EtOAc (4×40 mL). The combined extracts were dried over $Na_2SO_4$, filtered and concentrated. The crude mixture was purified by column chromatography over $SiO_2$ with a 0-80% gradient of EtOAc in heptane to afford the title compound 6-chloro-3-(4-fluoro-2-methoxy-phenoxy) pyridazine-4-carboxylic acid (1.211 g, 74%) as a pale red solid. $^1$H NMR (500 MHz, DMSO-$d_6$) δ 8.32 (s, 1H), 7.27 (dd, J=8.8, 5.8 Hz, 1H), 7.12 (dd, J=10.7, 2.9 Hz, 1H), 6.84 (td, J=8.5, 2.9 Hz, 1H), 3.71 (s, 3H). LC-MS: m/z 299.0/301.0 $[M+H]^+$, (ESI+).

Step 2: methyl 6-chloro-3-(4-fluoro-2-methoxy-phenoxy)pyridazine-4-carboxylate 6-chloro-3-(4-fluoro-2-methyl-phenoxy)pyridazine-4-carboxylic acid (500 mg, 1.77 mmol) was dissolved in DCM (12.2 mL), Thionyl chloride (5.1 mL, 70.8 mmol) was added in one portion at rt and the resulting mixture was stirred at 50 °C for 8 h. Additional thionyl chloride (2.5 mL, 35 mmol) was added and the reaction was stirred at 50 °C for a further 1 h. The mixture was allowed to cool to 0 °C, and anhydrous methanol (5.48 mL) was added dropwise. The resulting mixture was stirred at rt for 30 min. The reaction mixture was diluted with water (20 mL) followed by saturated aqueous $Na_2CO_3$ (20 mL) and the layers were separated and the organic layer dried ($MgSO_4$), filtered and concentrated in vacuo. The crude residue was purified by chromatography on silica eluting with a gradient of EtOAc in heptane afforded methyl 6-chloro-3-(4-fluoro-2-methyl-phenoxy) pyridazine-4-carboxylate (335 mg, 64%) as an off white solid. $^1$H NMR (400 MHz, DMSO-$d_6$) δ 8.25 (s, 1H), 7.25-7.18 (m, 2H), 7.10 (td, J=8.6, 3.1 Hz, 1H), 3.92 (s, 3H), 2.09 (s, 3H). LC-MS: m/z 297.3 $[M+H]^+$, (ESI+), RT=1.21 METCR1410 Generic 2 min.

Step 3: methyl 3-(4-fluoro-2-methoxy-phenoxy)-6-iodo-pyridazine-4-carboxylate

A mixture of methyl 6-chloro-3-(4-fluoro-2-methoxy-phenoxy)pyridazine-4-carboxylate (8.10 g, 23.3 mmol) in 55% aqueous hydrogen iodide (18 mL, 0.350 mol) was stirred at 40 °C for 24 h. The mixture was cooled to rt and filtered. The solid was washed with water and dried in high vacuum oven at 40 °C overnight to afford the title compound methyl 3-(4-fluoro-2-methoxy-phenoxy)-6-iodo-pyridazine-4-carboxylate (12.58 g, 88%) as an orange solid. $^1$H NMR (400 MHz, DMSO-$d_6$) δ 8.35 (s, 1H), 7.25 (m, 1H), 7.13-7.09 (m, 1H), 6.84-6.79 (m, 1H), 3.90 (s, 3H), 3.70 (s, 3H). LC-MS: m/z: 404.9 $[M+H]^+$, (ESI+), RT=1.19, METCR1410 Generic 2 min.

Step 4: methyl 3-(4-fluoro-2-methoxy-phenoxy)-6-(trifluoromethyl)pyridazine-4-carboxylate To a mixture of methyl 3-(4-fluoro-2-methoxy-phenoxy)-6-iodo-pyridazine-4-carboxylate (13.34 g, 21.8 mmol), copper iodide (6.26 g, 32.7 mmol), tetrabutylammonium iodide (3.23 g, 8.71 mmol) in DMF (72 mL) (degassed with nitrogen for 5 minutes), methyl difluoro(fluorosulfonyl) acetate (20.92 g, 0.109 mol) was added and stirred at 90 °C for 2 h. The reaction was cooled to rt, poured into water (200 mL) and extracted with EtOAc (4×100 mL). The combined organic layers were washed with water (50 mL) and brine (50 mL), dried over $Na_2SO_4$, filtered and the solvent evaporated under reduced pressure to obtain the crude residue. Purification by chromatography on silica eluting with a gradient of 0 to 50% EtOAc in heptane afforded the title compound (95.0%) (2.85 g, 36%) as a pale orange solid. $^1$H NMR (500 MHz, DMSO-$d_6$) δ 8.53 (s, 1H), 7.32 (dd, J=8.8, 5.8 Hz, 1H), 7.16 (dd, J=10.7, 2.9 Hz, 1H), 6.87 (td, J=8.5, 2.9 Hz, 1H), 3.96 (s, 3H), 3.72 (s, 3H). LC-MS: m/z 347.3 $[M+H]^+$, (ESI+), RT=3.57 MET-uPLC-AB-105 (7 min, high pH).

Step 5: 3-(4-fluoro-2-methoxy-phenoxy)-6-(trifluoromethyl)pyridazine-4-carboxylic Acid To a mixture of methyl 3-(4-fluoro-2-methoxy-phenoxy)-6-(trifluoromethyl)pyridazine-4-carboxylate (2.85 g, 7.82 mmol) in THF:$H_2O$ (4:1; v/v) (40 mL), lithium hydroxide (0.98 g, 39.1 mmol) was added and the mixture was stirred at rt for 24 h. The reaction was diluted with water (40 mL) and the pH was adjusted to 1 by dropwise addition of 1M HCl. The product was extracted with EtOAc (3×60 mL), dried ($MgSO_4$), filtered and the solvent evaporated under reduced pressure to obtain the title compound 3-(4-fluoro-2-methoxy-phenoxy)-6-(trifluoromethyl)pyridazine-4-carboxylic acid (90.0%) (2.35 g, 82%) as an orange solid. $^1$H NMR (500 MHz, DMSO-$d_6$) δ 8.11 (s, 1H), 7.24 (dd, J=8.8, 5.9 Hz, 1H), 7.12 (dd, J=10.7, 2.8 Hz, 1H), 6.84 (dt, J=8.5, 4.2 Hz, 1H), 3.71 (s, 4H). LC-MS: m/z 332.95 $[M+H]^+$, (ESI+), RT=1.03 Method XX METCR1410 Generic 2 min.

Example 119

Compound 1: tert-Butyl (R)-3-(3-(4-fluoro-2-methylphenoxy)-6-(trifluoromethyl)pyridazine-4-carboxamido)piperidine-1-carboxylate

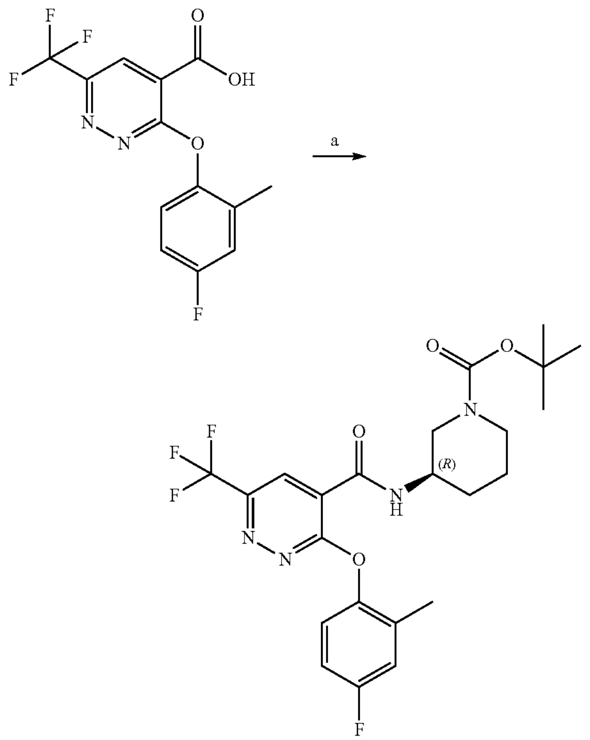

Reagents & conditions: tert-butyl (3R)-3-aminopiperidine-1-carboxylate, HATU, DIEA, DCM, rt, 2 h.

A mixture of N-ethyl-N-isopropyl-propan-2-amine (0.12 mL, 0.696 mmol), 3-(4-fluoro-2-methyl-phenoxy)-6-(trifluoromethyl)pyridazine-4-carboxylic acid (100 mg, 0.316 mmol) and tert-butyl (3R)-3-aminopiperidine-1-carboxylate (76 mg, 0.379 mmol) were dissolved in DCM (5 mL) under nitrogen at rt. N-[(dimethylamino)(3H-[1,2,3]triazolo[4,5-b]pyridin-3-yloxy)methylidene]-N-methylmethanaminium hexafluorophosphate (144 mg, 0.379 mmol) was added in one portion. The reaction mixture was stirred at rt for 2 h. The solvent was reduced to 2 mL in vacuo. Purification by chromatography on silica eluting with a gradient of 0 to 100% EtOAc in heptane afforded tert-butyl (3R)-3-[[3-(4-fluoro-2-methyl-phenoxy)-6-(trifluoromethyl)pyridazine-4-carbonyl]amino]piperidine-1-carboxylate (95.0%) (140 mg, 0.267 mmol, 84% Yield) as an off white solid. $^1$H NMR (500 MHz, DMSO-$d_6$) δ 8.76 (d, J=7.5 Hz, 1H), 8.37 (s, 1H), 7.30 (dd, J=9.0, 5.0 Hz, 1H), 7.25 (dd, J=9.3, 3.1 Hz, 1H), 7.15 (dt, J=8.5, 4.3 Hz, 1H), 3.89-3.77 (m, 2H), 3.60-3.51 (m, 1H), 3.09-2.92 (m, 2H), 2.12 (s, 3H), 1.93-1.84 (m, 1H), 1.73-1.65 (m, 1H), 1.59-1.30 (m, 11H). LC-MS: m/z 496.95 $[M-H]^+$, (ESI−), RT=1.36 METCR1410 Generic 2 min.

Compound 2: (R)-3-(4-Fluoro-2-methylphenoxy)-N-(piperidin-3-yl)-6-(trifluoromethyl)pyridazine-4-carboxamide

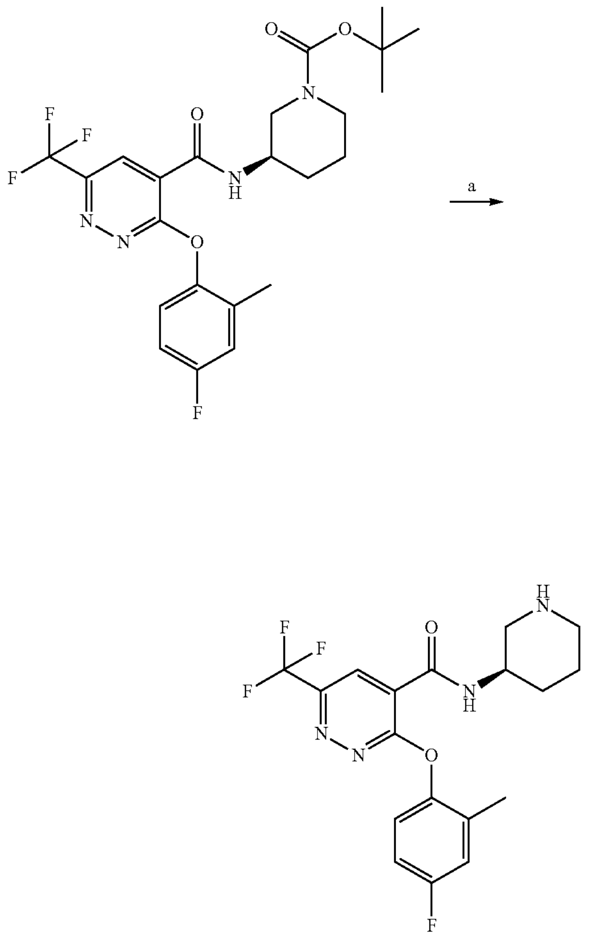

Reagents & conditions: a) 2,2,2-trifluoroacetic acid, DCM, rt, 3 h.

tert-butyl (R)-3-(3-(4-fluoro-2-methylphenoxy)-6-(trifluoromethyl)pyridazine-4-carboxamido)piperidine-1-carboxylate (0.130 g, 0.248 mmol) and 2,2,2-trifluoroacetic acid (0.37 mL, 4.96 mmol) was stirred in DCM (3.92 mL) under nitrogen at rt. The reaction mixture was stirred at rt for 3 h. The solvent was removed in vacuo and the residue was dissolved in DCM (10 mL), washed with sat. $NaHCO_3$ (10 mL) and brine (10 mL). Organic layer separated, dried over sodium sulphate, filtered and concentrated under reduced pressure to afford the title compound (R)-3-(4-fluoro-2-methylphenoxy)-N-(piperidin-3-yl)-6-(trifluoromethyl)pyridazine-4-carboxamide (0.075 g, 72%) as an off white solid. $^1$H NMR (500 MHz, DMSO-$d_6$) δ 8.67 (d, J=7.9 Hz, 1H), 8.41 (s, 1H), 7.31 (dd, J=8.9, 5.0 Hz, 1H), 7.25 (dd, J=9.3, 3.1 Hz, 1H), 7.14 (td, J=8.5, 3.1 Hz, 1H), 3.89-3.79 (m, 1H), 2.96 (dd, J=11.8, 3.4 Hz, 1H), 2.71 (dt, J=12.1, 4.3 Hz, 1H), 2.48-2.42 (m, 2H), 2.31-2.18 (m, 1H), 2.13 (s, 3H), 1.89-1.79 (m, 1H), 1.67-1.56 (m, 1H), 1.52-1.34 (m, 2H). LC-MS: m/z 399.0 $[M+H]^+$, (ESI+), RT=2.95 MET-uPLC-AB-101 (7 min, low pH).

Compound 3: (R)-3-(4-Fluoro-2-methylphenoxy)-N-(1-(methylsulfonyl)piperidin-3-yl)-6-(trifluoromethyl)pyridazine-4-carboxamide

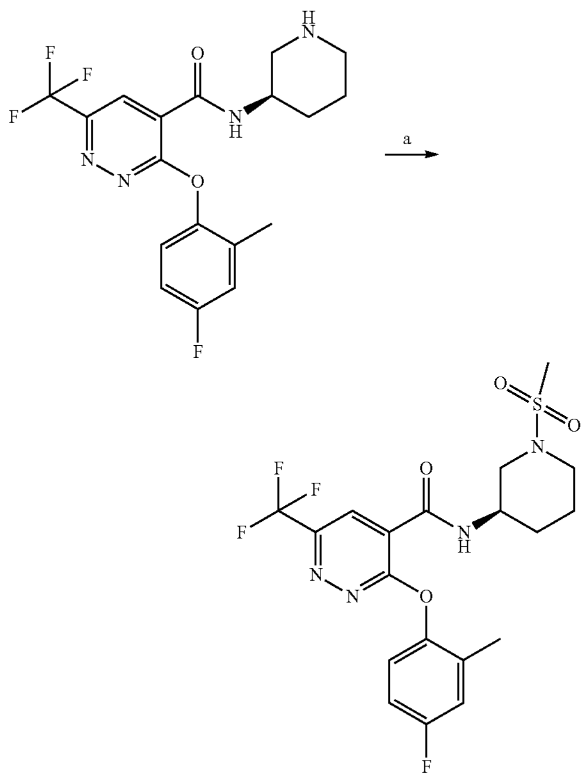

Reagents and conditions: $MeSO_2Cl$, DMAP, $Et_3N$, DCM, rt.

A mixture of triethylamine (0.015 mL, 0.107 mmol), (R)-3-(4-fluoro-2-methylphenoxy)-N-(piperidin-3-yl)-6-(trifluoromethyl)pyridazine-4-carboxamide (0.030 g, 0.0715 mmol) and methanesulfonyl chloride (0.0083 mL, 0.107 mmol) were dissolved in DCM (2 mL) under nitrogen at rt. To the above mixture N,N-dimethylpyridin-4-amine (8.7 mg, 0.0715 mmol) was added and stirring continued for further 1 h at rt. The solvent was removed in vacuo. Purification by preparative LC afforded the title compound (R)-3-(4-fluoro-2-methylphenoxy)-N-(1-(methylsulfonyl)piperidin-3-yl)-6-(trifluoromethyl)pyridazine-4-carboxamide (0.019 g, 57%) as a white solid. $^1H$ NMR (400 MHz, DMSO-$d_6$) δ 8.87 (d, J=7.7 Hz, 1H), 8.41 (s, 1H), 7.30 (dd, J=8.9, 5.1 Hz, 1H), 7.24 (dd, J=9.4, 3.0 Hz, 1H), 7.14 (td, J=8.6, 3.1 Hz, 1H), 4.09-3.96 (m, 1H), 3.56 (dd, J=11.4, 3.7 Hz, 1H), 3.32-3.22 (m, 1H), 2.97-2.89 (m, 1H), 2.87 (s, 3H), 2.82 (dd, J=11.4, 8.3 Hz, 1H), 2.12 (s, 3H), 1.90-1.78 (m, 2H), 1.66-1.46 (m, 2H). LC-MS: m/z 477.0 [M+H]+, (ESI+), RT=4.1 MET-uPLC-AB-101 (7 min, low pH). [Early Elute Method:—Column: Sunfire™ Prep. C18 10 um OBDTM, 30×100 mm; Mobile Phase: 5-95% Acetonitrile (0.1% formic acid) in Water (0.1% formic acid) over 14 minutes, Flow Rate: 40 mL/min UV: 215 and 254 nm)

Compound 4: (R)—N-(1-Acetylpiperidin-3-yl)-3-(4-fluoro-2-methylphenoxy)-6-(trifluoromethyl)pyridazine-4-carboxamide

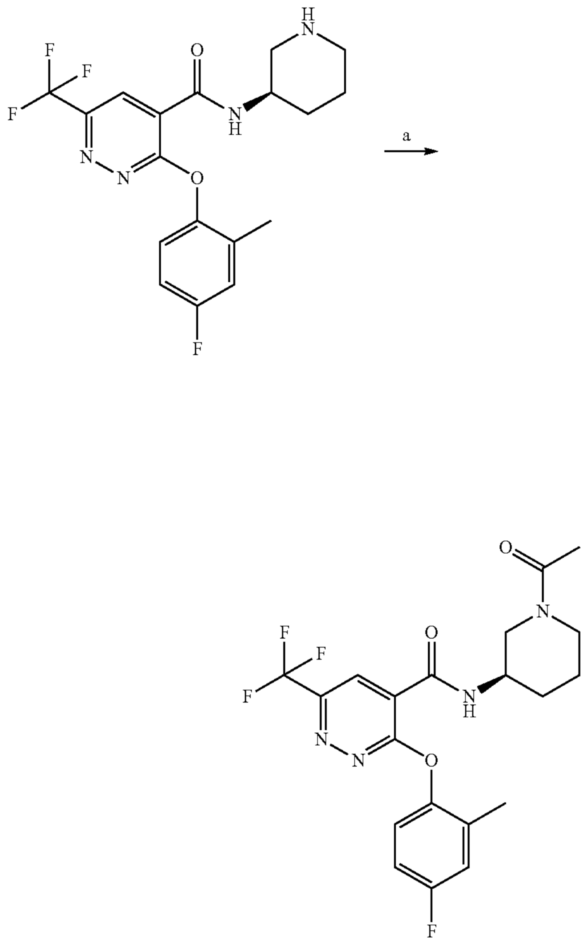

Reagent & conditions: a) $Ac_2O$, $Et_3N$, DCM, DMAP, rt.

A mixture of acetic anhydride (0.0099 mL, 0.107 mmol), (R)-3-(4-fluoro-2-methylphenoxy)-N-(piperidin-3-yl)-6-(trifluoromethyl)pyridazine-4-carboxamide (0.030 g, 0.0715 mmol) and triethylamine (0.015 mL, 0.107 mmol) were dissolved in DCM (2 mL) under nitrogen at rt, DMAP (0.0087 g, 7.15 μmol) was added. The reaction mixture was stirred at rt for 1 h. The solvent was removed in vacuo. Purification by Preparative LC Method A afforded the title compound (R)—N-(1-acetylpiperidin-3-yl)-3-(4-fluoro-2-methylphenoxy)-6-(trifluoromethyl)pyridazine-4-carboxamide (0.015 g, 49%) as a white solid. $^1H$ NMR (400 MHz, DMSO-$d_6$) δ 8.52 (bs, 1H), 8.30 (s, 1H), 7.28 (dd, J=8.9, 5.0 Hz, 1H), 7.20 (dd, J=9.4, 3.1 Hz, 1H), 7.10 (td, J=8.5, 3.1 Hz, 1H), 4.04-3.74 (m, 2H), 3.59-3.49 (m, 1H), 3.40-3.19 (m, 2H), 2.15 (s, 3H), 2.02-1.91 (m, 4H), 1.78-1.61 (m, 2H), 1.59-1.44 (m, 1H). LC-MS: m/z 441.0 [M+H]+, (ESI+), RT=3.94 MET-uPLC-AB-101 (7 min, low pH).

Compound 5: tert-Butyl (S)-3-(3-(4-fluoro-2-methoxyphenoxy)-6-(trifluoromethyl)pyridazine-4-carboxamido)piperidine-1-carboxylate

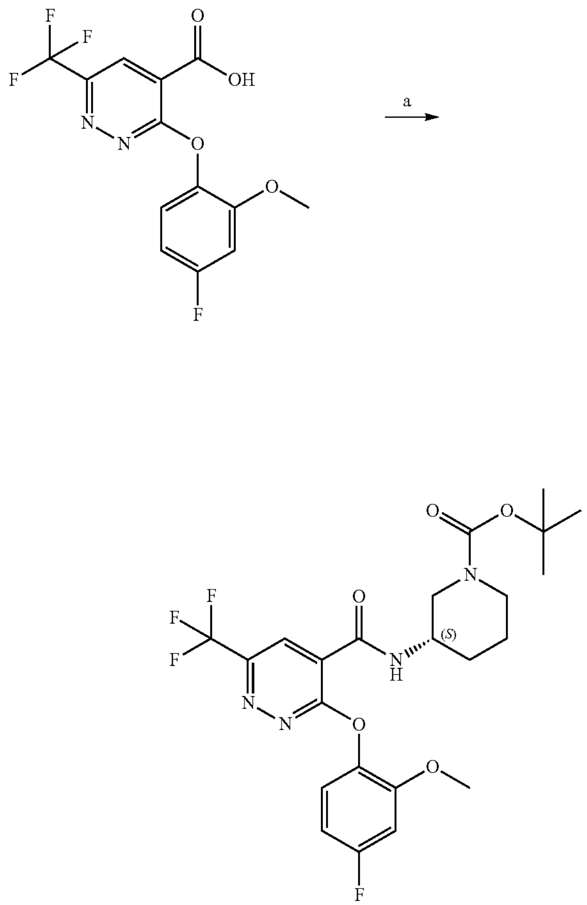

Reagent & conditions: tert-butyl (3S)-3-aminopiperidine-1-carboxylate, DIEA, DCM, rt.

A mixture of, 3-(4-fluoro-2-methoxy-phenoxy)-6-(trifluoromethyl)pyridazine-4-carboxylic acid (140 mg, 0.421 mmol), tert-butyl (3S)-3-aminopiperidine-1-carboxylate (101 mg, 0.506 mmol) and N-ethyl-N-isopropyl-propan-2-amine (0.16 mL, 0.927 mmol) were dissolved in DCM (2.1071 mL) under nitrogen at rt. N-[(dimethylamino)(3H-[1,2,3]triazolo[4,5-b]pyridin-3-yloxy)methylidene]-N-methylmethanaminium hexafluorophosphate (192 mg, 0.506 mmol) was added in one portion. The reaction mixture was stirred at rt for 2 h. IPC1 LCMS showed formation of desired product. The reaction mixture was purified directly by chromatography on silica (Sfar Duo 10 g) eluting with a gradient of 0 to 50% of EtOAc in heptane to afford tert-butyl (3S)-3-[[3-(4-fluoro-2-methoxy-phenoxy)-6-(trifluoromethyl)pyridazine-4-carbonyl]amino]piperidine-1-carboxylate (95.0%) (182 mg, 80%) as a colorless oil. $^1$H NMR (400 MHz, DMSO-$d_6$) δ 8.71 (d, J=7.6 Hz, 1H), 8.34 (s, 1H), 7.34 (dd, J=8.8, 5.9 Hz, 1H), 7.16 (dd, J=10.7, 2.9 Hz, 1H), 6.88 (td, J=8.5, 2.9 Hz, 1H), 3.90-3.76 (m, 2H), 3.73 (s, 3H), 3.58-3.51 (m, 1H), 3.09-2.96 (m, 2H), 1.97-1.84 (m, 1H), 1.77-1.65 (m, 1H), 1.61-1.41 (m, 2H), 1.37 (s, 9H). m/z 513.6 $[M+H]^+$, (ESI+), RT=4.06 MET-uPLC-AB-105 (7 min, high pH).

Compound 6: (S)-3-(4-Fluoro-2-methoxyphenoxy)-N-(piperidin-3-yl)-6-(trifluoromethyl)pyridazine-4-carboxamide

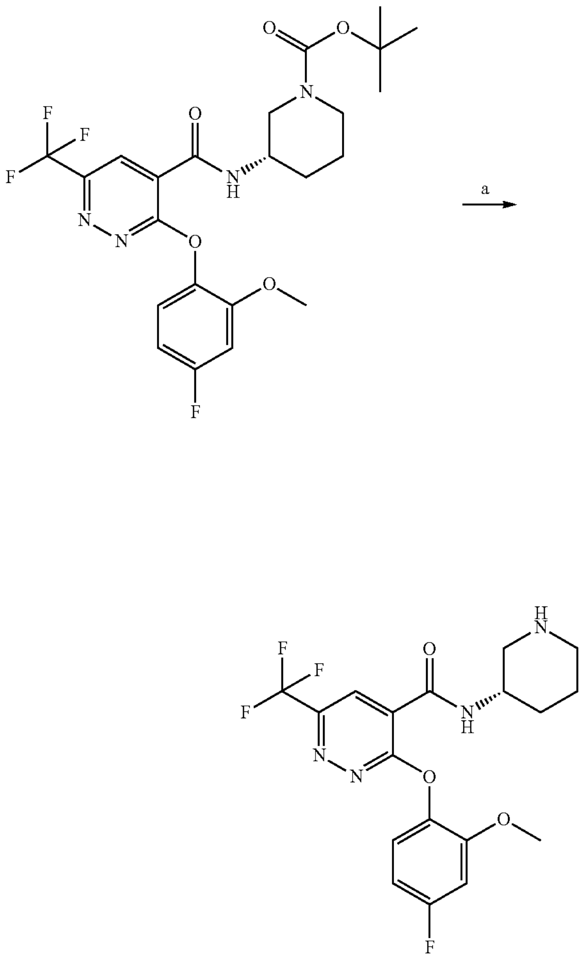

Reagent & conditions: a) 2,2,2-trifluoroacetic acid, DCM, rt, 3 h.

The title compound was prepared by a similar procedure described for Compound 2 using tert-butyl (S)-3-(3-(4-fluoro-2-methoxyphenoxy)-6-(trifluoromethyl)pyridazine-4-carboxamido)piperidine-1-carboxylate. $^1$H NMR (400 MHz, DMSO-$d_6$) δ 8.64 (d, J=7.8 Hz, 1H), 8.37 (s, 1H), 7.35 (dd, J=8.8, 5.9 Hz, 1H), 7.15 (dd, J=10.7, 2.9 Hz, 1H), 6.88 (td, J=8.5, 2.9 Hz, 1H), 3.96-3.76 (m, 2H), 3.73 (s, 3H), 2.99 (m, 2H), 2.75 (m, 1H), 2.46 (m, 1H), 1.84 (m, 1H), 1.63 (s, 1H), 1.56-1.33 (m, 2H). m/z 415.3 $[M+H]^+$, (ESI+), RT=3.09 MET-uPLC-AB-105 (7 min, high pH).

Compound 7: (S)-3-(4-Fluoro-2-methoxyphenoxy)-N-(1-(methylsulfonyl)piperidin-3-yl)-6-(trifluoromethyl)pyridazine-4-carboxamide

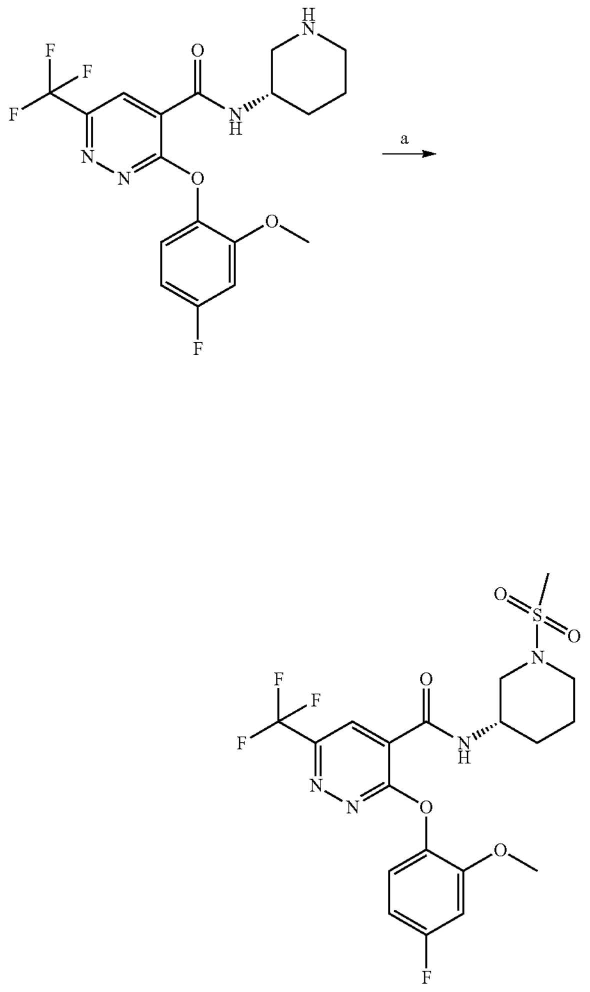

Reagent & conditions: a) $MeSO_2Cl$, DMAP, DCM, rt, 1 h.

The title product was prepared by a similar procedure described for Compound 3 using (S)-3-(4-fluoro-2-methoxyphenoxy)-N-(piperidin-3-yl)-6-(trifluoromethyl) pyridazine-4-carboxamide and methanesulfonyl chloride. $^1H$ NMR (500 MHz, DMSO-$d_6$) δ 8.83 (d, J=7.7 Hz, 1H), 8.38 (s, 1H), 7.34 (dd, J=8.8, 5.8 Hz, 1H), 7.15 (dd, J=10.7, 2.9 Hz, 1H), 6.87 (td, J=8.5, 2.9 Hz, 1H), 4.00 (m, 1H), 3.72 (s, 3H), 3.57 (dd, J=11.2, 3.9 Hz, 2H), 2.94-2.88 (m, 1H), 2.87 (s, 3H), 2.80 (dd, J=11.3, 8.4 Hz, 1H), 1.91-1.76 (m, 2H), 1.65-1.45 (m, 2H). m/z 492.9 [M+H]+, (ESI+), RT=4.06 METCR1416 Hi res 7 min.

Compound 8: (S)—N-(1-Acetylpiperidin-3-yl)-3-(4-fluoro-2-methoxyphenoxy)-6-(trifluoromethyl) pyridazine-4-carboxamide

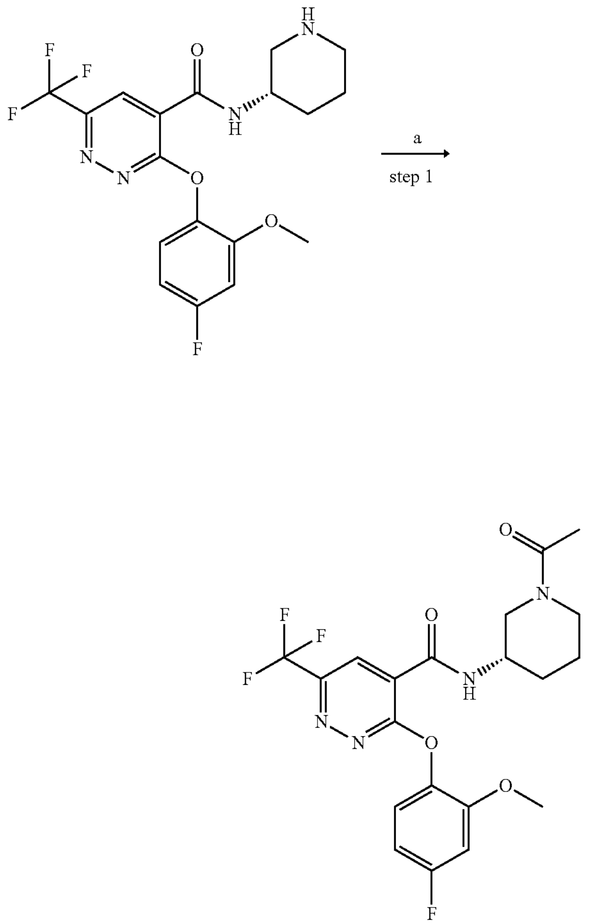

Reagent & conditions: a) $Ac_2O$, $Et_3N$, DCM, DMAP, rt.

The title product was prepared by a similar procedure described for Compound 4 using (S)-3-(4-fluoro-2-methoxyphenoxy)-N-(piperidin-3-yl)-6-(trifluoromethyl) pyridazine-4-carboxamide and acetic anhydride. $^1H$ NMR (400 MHz, DMSO-$d_6$) δ 8.45 (s, 1H), 8.28 (s, 1H), 7.33 (dd, J=8.8, 5.8 Hz, 1H), 7.10 (dd, J=10.6, 2.9 Hz, 1H), 6.86 (td, J=8.5, 2.9 Hz, 1H), 4.03-3.85 (m, 2H), 3.74 (s, 3H), 3.60-3.45 (m, 1H), 3.25 (d, J=34.9 Hz, 2H), 1.97 (s, 3H), 1.95-1.87 (m, 1H), 1.68 (dd, J=11.5, 7.7 Hz, 2H), 1.51 (s, 1H). m/z 457.0 [M+H]+, (ESI+), RT=3.85 METCR1416 Hi res 7 min.

The compounds listed in Table 28 were prepared by a similar procedure described for Compound 1 using appropriate starting materials.

TABLE 28

| Compound | Structure and Name | Analytical data |
|---|---|---|
| 9 | 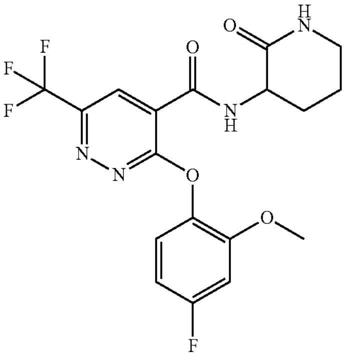 [SMILES: COc1cc(F)ccc1Oc1nnc(C(F)(F)F)cc1C(=O)NC1CCCNC1=O] 3-(4-Fluoro-2-methoxyphenoxy)-N-(2-oxopiperidin-3-yl)-6-(trifluoromethyl)pyridazine-4-carboxamide | $^1$H NMR (500 MHz, DMSO-$d_6$) δ 8.98 (d, J = 7.4 Hz, 1H), 8.32 (s, 1H), 7.72 (s, 1H), 7.36 (dd, J = 8.8, 5.9 Hz, 1H), 7.14 (dd, J = 10.7, 2.9 Hz, 1H), 6.87 (td, J = 8.5, 2.9 Hz, 1H), 4.37 (m, 6.5 Hz, 1H), 3.71 (s, 3H), 3.19-3.12 (m, 2H), 2.22-2.14 (m, 1H), 1.85-1.66 (m, 3H). m/z 429.0 [M + H]+, (ESI+), RT = 3.68 METCR1416 Hi res 7 min |
| 10 | 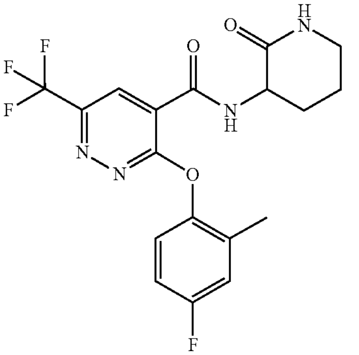 [SMILES: Cc1cc(F)ccc1Oc1nnc(C(F)(F)F)cc1C(=O)NC1CCCNC1=O] 3-(4-Fluoro-2-methylphenoxy)-N-(2-oxopiperidin-3-yl)-6-(trifluoromethyl)pyridazine-4-carboxamide | $^1$H NMR (400 MHz, DMSO-$d_6$) δ 9.04 (d, J = 7.5 Hz, 1H), 8.36 (s, 1H), 7.73 (s, 1H), 7.32 (dd, J = 8.9, 5.0 Hz, 1H), 7.25 (dd, J = 9.4, 3.1 Hz, 1H), 7.15 (td, J = 8.6, 3.1 Hz, 1H), 4.47-4.31 (m, 1H), 3.21-3.12 (m, 2H), 2.26-2.16 (m, 1H), 2.14 (s, 3H), 1.89-1.66 (m, 3H). m/z 413.0 [M + H]+, (ESI+), RT = 3.80 METCR1416 Hi res 7 min |
| 11 | 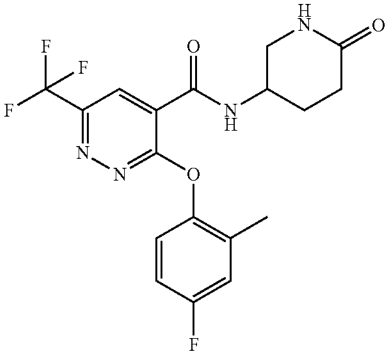 [SMILES: Cc1cc(F)ccc1Oc1nnc(C(F)(F)F)cc1C(=O)NC1CCC(=O)NC1] 3-(4-Fluoro-2-methylphenoxy)-N-(6-oxopiperidin-3-yl)-6-(trifluoromethyl)pyridazine-4-carboxamide | $^1$H NMR (500 MHz, DMSO-$d_6$) δ 8.99 (d, J = 7.3 Hz, 1H), 8.44 (s, 1H), 7.51-7.43 (m, 1H), 7.29 (dd, J = 8.9, 5.1 Hz, 1H), 7.25 (dd, J = 9.5, 3.1 Hz, 1H), 7.14 (td, J = 8.6, 3.2 Hz, 1H), 4.27-4.17 (m, 1H), 3.43-3.40 (m, 1H), 3.11 (dd, J = 10.2, 6.3 Hz, 1H), 2.36-2.20 (m, 2H), 2.11 (s, 3H), 2.01-1.92 (m, 1H), 1.92-1.83 (m, 1H). m/z 412.9 [M + H]+, (ESI+), RT = 3.58 METCR1416 Hi res 7 min |

TABLE 28-continued

| Compound | Structure and Name | Analytical data |
|---|---|---|
| 12 | 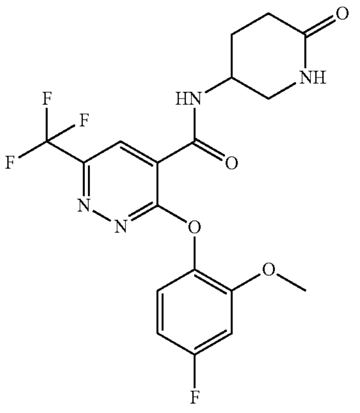 3-(4-Fluoro-2-methoxyphenoxy)-N-(6-oxopiperidin-3-yl)-6-(trifluoromethyl)pyridazine-4-carboxamide | $^1$H NMR (400 MHz, DMSO-$d_6$) δ 8.95 (d, J = 7.3 Hz, 1H), 8.39 (s, 1H), 7.47-7.44 (m, 1H), 7.32 (dd, J = 8.8, 5.9 Hz, 1H), 7.14 (dd, J = 10.7, 2.9 Hz, 1H), 6.87 (td, J = 8.5, 2.9 Hz, 1H), 4.25-4.15 (m, 1H), 3.72 (s, 3H), 3.45-3.40 (m, 1H), 3.15-3.05 (m, 1H), 2.37-2.19 (m, 2H), 2.00-1.80 (m , 2H). m/z 429.0 [M + H]+, (ESI+), RT = 3.49 METCR1416 Hi res 7 min |

Example 120

Compound Profiling on NaV1.8—Human NaV1.8 Cell Line—SyncroPatch384PE Assay

Compounds were tested on recombinant human $Na_V1.8$ stably transfected HELK cells using the SyncroPatch384PE system, an automated patch clamp device. Cells were cultured at 37 °C/5% CO2 in DMEM medium supplemented with GlutaMAX I, NEAA 1%, FBS 10% and seeded in T175 flasks. Cells were cultured at 30 °C one day prior to recording sodium currents. On the day of the recordings, cells were detached with 0.05% Trypsin-EDTA, resuspended in serum free DMEM medium and placed into the SyncroPatch384PE 6 °C pre-cooled cell hotel and shaken at 200 rpm. Intracellular solution (IC) contained, in mM: 10, CsCl; 110, CsF; 20, EGTA; 10, HEPES. Extracellular solution (EC) contained, in mM: 140, NaCl; 4, KCl; 5, Glucose; 10, HEPES; 2, $CaCl_2$; 1, $MgCl_2$. Washing solution contained, in mM: 40, NMDG; 100, NaCl; 4, KCl; 10, Glucose; 10, HEPES; 5, $CaCl_2$; 1, $MgCl_2$.

Compounds were tested in quadruplicates in 0.1% DMSO and 0.030% Pluronic Acid. Compounds were diluted 1:3.33 in EC solution to create a 10-point concentration response curve, spanning a final concentration range from 10-0.0002 μM in the assay plate. Compounds with low nM potency were retested using a lower concentration range (1-0.00002 μM). Each plate contained tetracaine and another tool compound as positive controls. Up to 7 compounds were tested on one plate. 150 μM tetracaine and 0.1% DMSO were used as high and low controls, respectively.

Whole cell patch clamp recordings were conducted according to Nanion's standard procedure for SyncroPatch384PE®. Cells were held at a holding potential of −120 mV. A depolarization step to 10 mV for 30 ms was applied (P1 measurement), followed by a hyperpolarization step to −100 mV for 100 ms. An inactivation step at −40 mV for 10 sec was applied before stepping to −100 mV for 20 ms, followed by a step to 10 mV for 30 ms (P2 measurement) and then back to −100 mV for 30 ms. Sweep interval was 15 sec with a sampling rate of 10 kHz. Following establishment of the whole-cell configuration in EC, two washing steps with reference buffer were performed to stabilize the baseline. Compounds were then applied by the SynchroPatch into each well and the current was recorded for five minutes in EC, followed by application of tetracaine to achieve full block at the end of the experiment. The potency of the compounds was assessed on two read-outs, resting state block (P1 measurement) or inactivated state block (P2 measurement) to obtain IC50 values. Values were normalized to high (tetracaine) and low (DMSO) controls. Table 28 shows the potency of compounds against human NaV1.8.

Table 29 shows the potency of compounds against human NaV1.8, where "A" represents an IC50 less than or equal to 200 nM, "B" represents an IC50 greater than 201 nM to less than or equal to 500 nM, "C" represents an IC50 greater than 501 nM to less than or equal to 1000 nM, "D" represents an IC50 greater than 1001 nM to less than or equal to 5000 nM, "E" represents an IC50 greater than 5001 nM.

TABLE 29

| Compound | P1 IC50 | P2 IC50 |
|---|---|---|
| 1 | E | E |
| 3 | E | E |
| 4 | E | E |
| 5 | E | E |
| 6 | E | E |
| 7 | E | E |
| 8 | E | E |
| 9 | E | E |
| 10 | E | E |
| 11 | E | E |
| 12 | E | E |

E. Examples of Fifth Set of Compounds

Example 121

Synthetic Procedures

Exemplary compounds were prepared via several general synthetic routes set forth in the Examples below. Any of the disclosed compounds of the present invention can be prepared according to one or more of these synthetic routes or specific examples, or via modifications thereof accessible to the person of ordinary skill in the art.

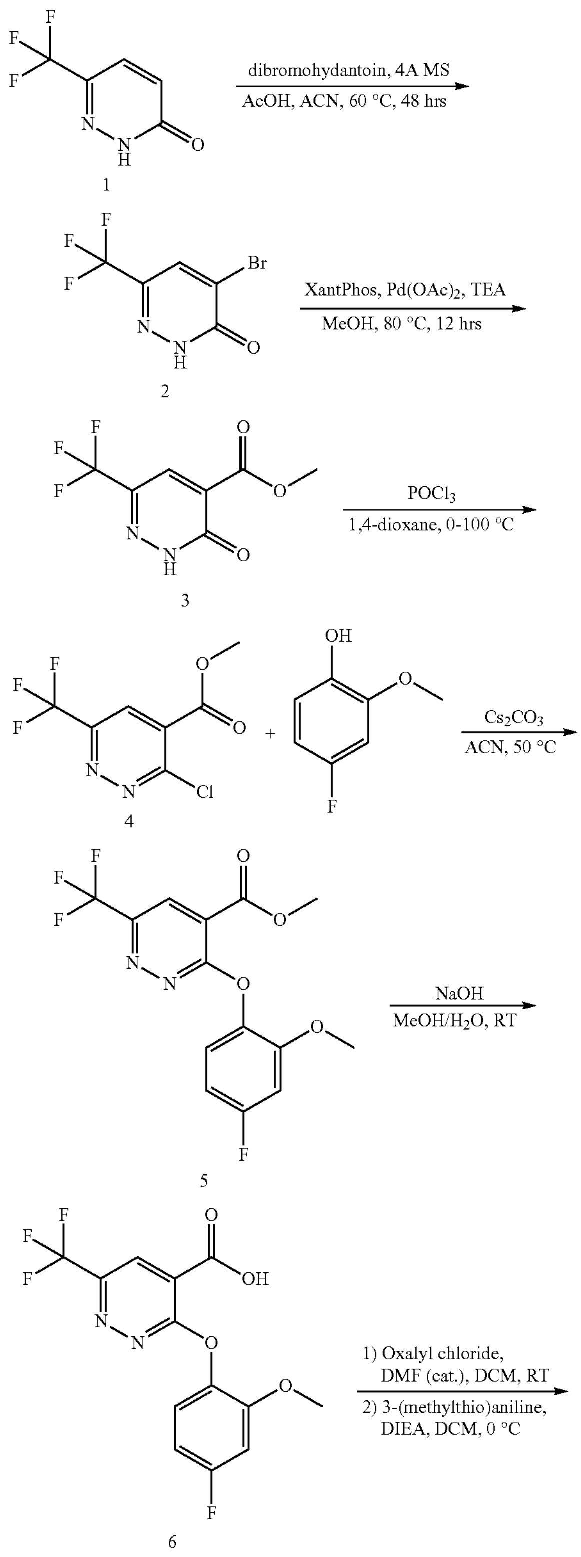

1

2

3

4

+

5

6

-continued

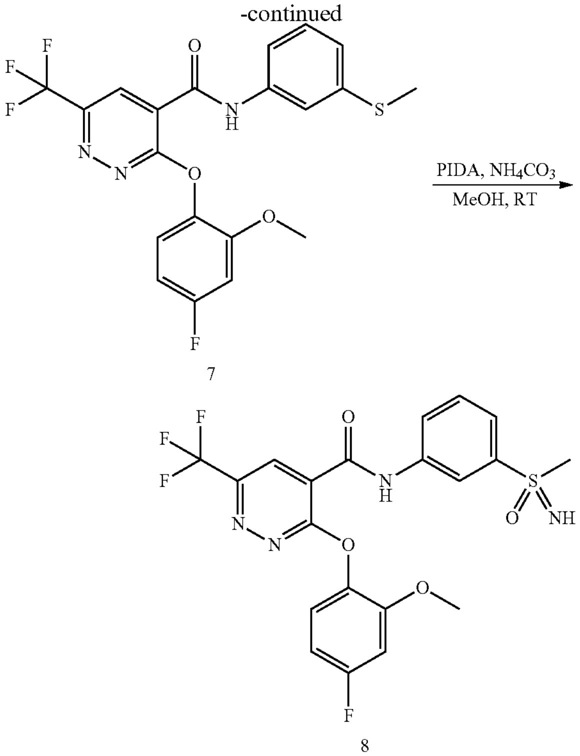

7

8

Method A

Step 1: 4-bromo-6-(trifluoromethyl)pyridazin-3(2H)-one 6-(trifluoromethyl)pyridazin-3(2H)-one (9.00 g, 54.8 mmol, 1.00 eq), 4 Angstrom molecular sieves (18.0 g) and dibromohydantoin (20.3 g, 71.3 mmol, 1.30 eq) were added into acetic acid (37.0 mL) and acetonitrile (863 mL), and the mixture was stirred at 60 °C for 48 hrs. The reaction mixture was diluted with water (1.00 L) and extracted with ethyl acetate (500 mL×3). The combined organic layers were washed with brine (1.50 L), dried over $Na_2SO_4$, filtered and concentrated under reduced pressure to give a residue. The residue was purified by column chromatography ($SiO_2$, Petroleum ether/Ethyl acetate=50/1 to 15/1) to afford the desired product (7.00 g, 28.8 mmol, 52.5% yield) as a yellow solid.

$^1$H NMR: 400 MHz $CDCl_3$δ–12.22 (s, 1H), 7.86 (s, 3H).

MS, ES$^+$ m/z 243 (M+H)$^+$

Step 2: methyl 3-oxo-6-(trifluoromethyl)-2,3-dihydropyridazine-4-carboxylate

To a solution of 4-bromo-6-(trifluoromethyl)pyridazin-3(2H)-one (5.00 g, 20.5 mmol, 1.00 eq) in methanol (100 mL) was added Xantphos (500 mg, 864 μmol, 0.042 eq), $Pd(OAc)_2$ (115 mg, 514 umol, 0.0250 eq) and triethylamine (4.16 g, 41.1 mmol, 5.73 mL, 2.00 eq) to an autoclave, and the mixture was stirred under CO (50 psi) at 80 °C for 12 hrs. The reaction mixture was concentrated under reduced pressure to remove solvent, and the residue was purified by column chromatography ($SiO_2$, Petroleum ether/Ethyl acetate=30/1 to 0/1) to afford the desired compound (2.50 g, 11.2 mmol, 54.7% yield) as a yellow solid.

$^1$H NMR: 400 MHz $CDCl_3$δ 12.54 (s, 1H), 8.11 (s, 1H), 3.99 (s, 3H).

MS, ES$^+$ m/z 223 (M+H)$^+$

Step 3: methyl 3-chloro-6-(trifluoromethyl) pyridazine-4-carboxylate

To a solution of methyl 3-oxo-6-(trifluoromethyl)-2,3-dihydropyridazine-4-carboxylate (1.50 g, 6.75 mmol, 1.00 eq) in 1,4-dioxane (15.0 mL) was added phosphorus oxychloride (10.3 g, 67.5 mmol, 6.28 mL, 10.0 eq) at 0 °C, and the mixture was stirred at 100 °C for 12 hours. The reaction mixture was concentrated under reduced pressure to remove solvent. The residue was diluted with saturated sodium bicarbonate solution (60 mL) and extracted with ethyl acetate (20 mL×3). The combined organic layers were washed with brine (60 mL), dried over sodium sulfate, filtered, and concentrated under reduced pressure to give a residue. The residue was purified by column chromatography ($SiO_2$, Petroleum ether/Ethyl acetate=50/1 to 8/1) to give the desired product (1.00 g, 4.16 mmol, 61.6% yield) as a yellow oil.

$^1$H NMR: 400 MHz $CDCl_3$ δ–8.17 (s, 1H), 4.06 (s, 3H).

MS, $ES^+$ m/z 241 $(M+H)^+$

Step 4: methyl 3-(4-fluoro-2-methoxyphenoxy)-6-(trifluoromethyl)pyridazine-4-carboxylate To a solution of methyl 3-chloro-6-(trifluoromethyl) pyridazine-4-carboxylate (500 mg, 2.1 mmol) in acetonitrile (10 mL) was added 4-fluoro-2-methoxy-phenol (325 mg, 2.3 mmol, 1.1 eq) and cesium carbonate (680 mg, 2.1 mmol, 1.0 eq). The resulting mixture was heated to 50 °C for 2 hours. After cooling to room temperature, the mixture was diluted with water (75 mL) and extracted with ethyl acetate (25 mL×3). The combined organic layers were dried over anhydrous magnesium sulfate, filtered, and concentrated under reduced pressure to afford the desired product. Used without further purification, and assumed quantitative yield.

MS, $ES^+$ m/z 347 $(M+H)^+$

Step 5: 3-(4-fluoro-2-methoxyphenoxy)-6-(trifluoromethyl)pyridazine-4-carboxylic Acid The crude product from step 4 (719 mg, 2.1 mmol) was dissolved in methanol (15 mL) and water (5 mL) and excess solid sodium hydroxide was added. The resulting mixture was stirred at room temperature for 2 hours. The resulting solution was diluted with water (75 mL) and the pH was adjusted to ~2 by careful addition of 6N hydrochloric acid, causing a precipitate to form. This was collected by filtration, rinsed with water and dried under reduced pressure to afford the desired product (350 mg, 1.1 mmol, 51% yield) as a white solid.

MS, $ES^+$ m/z 333 $(M+H)^+$

Step 6: 3-(4-fluoro-2-methoxyphenoxy)-N-(3-(methylthio)phenyl)-6-(trifluoromethyl)pyridazine-4-carboxamide 3-(4-fluoro-2-methoxyphenoxy)-6-(trifluoromethyl) pyridazine-4-carboxylic acid (350 mg, 1.1 mmol) was taken up in dichloromethane (5 mL). Oxalyl chloride (0.1 mL, 1.2 mmol) and N,N-dimethylformamide (1 drop) were added, and the mixture was allowed to stir at room temperature for 1 hour. The mixture was cooled in an ice bath, and 3-methylsulfanylaniline (161 mg, 1.2 mmol) and N,N-diisopropylethylamine (272 mg, 2.1 mmol) were added dropwise as a solution in dichloromethane (5 mL). The mixture was concentrated under reduced pressure, and the resulting residue was purified by column chromatography ($SiO_2$, dichloromethane/methanol, 0-5%) to afford the desired product (355 mg, 0.8 mmol, 74% yield) as a solid.

MS, $ES^+$ m/z 454 $(M+H)^+$

Step 7: 3-(4-fluoro-2-methoxyphenoxy)-N-(3-(S-methylsulfonimidoyl)phenyl)-6-(trifluoromethyl) pyridazine-4-carboxamide To a solution of 3-(4-fluoro-2-methoxyphenoxy)-N-(3-(methylthio)phenyl)-6-(trifluoromethyl)pyridazine-4-carboxamide (355 mg, 0.8 mmol) in methanol (10 mL) was added ammonium carbonate (113 mg, 1.2 mmol, 1.5 eq) and iodobenzene diacetate (580 mg, 1.8 mmol, 2.3 eq). The mixture was allowed to stir at room temperature for 2 hours, and then concentrated under reduced pressure. The resulting residue was purified by column chromatography ($SiO_2$, dichloromethane/methanol, 0-12%) to afford the desired product (189 mg, 0.4 mmol, 50% yield) as a solid.

$^1$H NMR (400 MHz, DMSO-d6) δ ppm 3.07 (d, J=0.76 Hz, 3H) 3.74 (s, 3H) 4.29 (s, 1H) 6.83-6.94 (m, 1H) 7.17 (dd, J=10.74, 2.91 Hz, 1H) 7.39 (dd, J=8.84, 5.81 Hz, 1H) 7.65 (t, J=7.96 Hz, 1H) 7.69-7.77 (m, 1H) 7.93 (ddd, J=8.02, 2.08, 1.01 Hz, 1H) 8.36 (t, J=1.89 Hz, 1H) 8.65 (s, 1H) 11.21 (s, 1H).

MS, $ES^+$ m/z 485 $(M+H)^+$

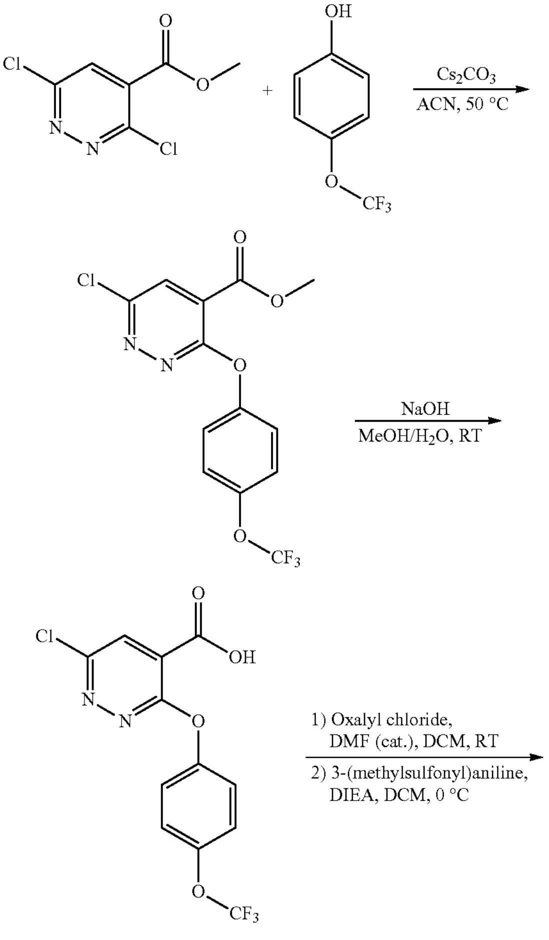

-continued

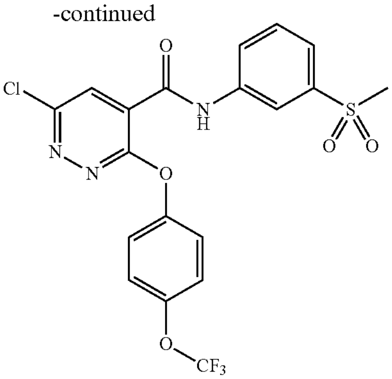

Method B

Step 1: methyl 6-chloro-3-(4-(trifluoromethoxy) phenoxy)pyridazine-4-carboxylate To a solution of methyl 3,6-dichloropyridazine-4-carboxylate (1.5 g, 7.2 mmol) in acetonitrile (15 mL) was added 4-(trifluoromethoxy)phenol (1.4 g, 8.0 mmol) and cesium carbonate (2.4 g, 7.2 mmol). The resulting mixture was stirred at 40 °C for 1 hour, and then diluted with water (100 mL). The mixture was extracted with ethyl acetate (25 mL×3), and the combined organic layers were dried over anhydrous magnesium sulfate, concentrated, and purified by column chromatography ($SiO_2$, heptane/ethyl acetate, 0-50% gradient) to afford the desired product (1.2 g, 3.4 mmol, 47% yield) as an oil which solidified on standing. MS, $ES^+$ m/z 349 $(M+H)^+$ Step 2: 6-chloro-3-(4-(trifluoromethoxy)phenoxy) pyridazine-4-carboxylic Acid To a solution of methyl 6-chloro-3-(4-(trifluoromethoxy) phenoxy)pyridazine-4-carboxylate (1.2 g, 3.4 mmol) in methanol (15 mL) was added water (5 mL) and excess solid sodium hydroxide. The resulting mixture was allowed to stir at room temperature for 1.5 hours, and then diluted with water (75 mL). The pH was adjusted to ~1 by careful addition of 6N hydrochloric acid, causing a precipitate to form. Precipitate was collected by filtration, rinsed with water, and sucked to dryness to afford the desired product (365 mg, 1.1 mmol, 32% yield) as a colorless solid.

MS, $ES^+$ m/z 335 $(M+H)^+$

Step 3: 6-chloro-N-(3-(methylsulfonyl)phenyl)-3-(4-(trifluoromethoxy)phenoxy)pyridazine-4-carboxamide 6-chloro-3-(4-(trifluoromethoxy)phenoxy)pyridazine-4-carboxylic acid (365 mg, 1.1 mmol) was taken up in dichloromethane (5 mL), and oxalyl chloride (0.14 mL, 1.6 mmol) was added, followed by a single drop of N,N-dimethylformamide. The resulting mixture was allowed to stir at room temperature for 1 hour, and then cooled in an ice bath. 3-(methylsulfonyl)aniline (225 mg, 1.3 mmol) and triethylamine (0.15 mL, 1.1 mmol) were added dropwise as a solution in dichloromethane (5 mL), and the mixture was allowed to warm to room temperature. Volatiles were removed under reduced pressure, and the resulting residue was purified by preparative RP-HPLC (water/acetonitrile, 5-95% gradient) to afford the desired product (239 mg, 0.49 mmol, 45% yield) as a colorless solid.

$^1H$ NMR (400 MHz, DMSO-$d_6$): δ ppm 3.24 (s, 3H) 7.41-7.55 (m, 4H) 7.65-7.78 (m, 2H) 7.94 (dt, J=7.83, 1.64 Hz, 1H) 8.31-8.39 (m, 2H) 11.24 (s, 1H)

MS, $ES^+$ m/z 488 $(M+H)^+$

The following compounds of formula (I-IV) could be prepared by the methodology:

TABLE 30

Compounds of Formula (IV-c)

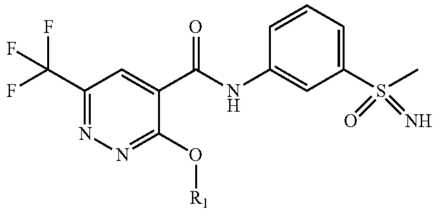

| Example | Name | $R_1$ |
|---|---|---|
| 4 | 3-(4-fluoro-2-methylphenoxy)-N-(3-(S-methylsulfonimidoyl)phenyl)-6-(trifluoromethyl)pyridazine-4-carboxamide | 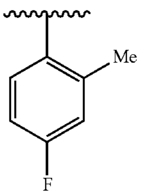 [SMILES: *c1ccc(F)cc1C] |

TABLE 30-continued

Compounds of Formula (IV-c)

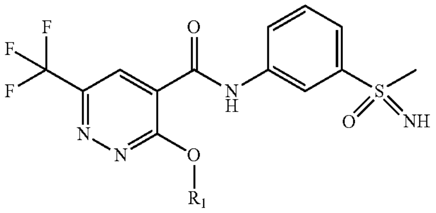

| Example | Name | $R_1$ |
| --- | --- | --- |
| 5 | 3-(2,4-difluorophenoxy)-N-(3-(S-methylsulfonimidoyl)phenyl)-6-(trifluoromethyl)pyridazine-4-carboxamide | 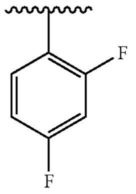 |
| 6 | 3-(2-chloro-4-fluorophenoxy)-N-(3-(S-methylsulfonimidoyl)phenyl)-6-(trifluoromethyl)pyridazine-4-carboxamide | 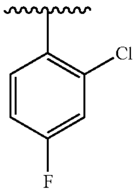 [SMILES: *c1ccc(F)cc1Cl] |
| 7 | 3-(2,4-dichlorophenoxy)-N-(3-(S-methylsulfonimidoyl)phenyl)-6-(trifluoromethyl)pyridazine-4-carboxamide | 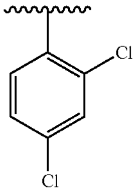 [SMILES: *c1ccc(Cl)cc1Cl] |
| 8 | 3-(2,4-dimethoxyphenoxy)-N-(3-(S-methylsulfonimidoyl)phenyl)-6-(trifluoromethyl)pyridazine-4-carboxamide | 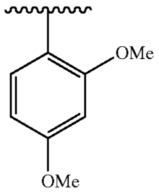 [SMILES: *c1ccc(OC)cc1OC] |
| 9 | 3-(2-chloro-4-trifluoromethoxyphenoxy)-N-(3-(S-methylsulfonimidoyl)phenyl)-6-(trifluoromethyl)pyridazine-4-carboxamide | 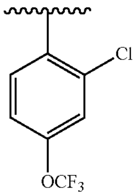 |
| 10 | 3-(2-chloro-4-difluoromethoxyphenoxy)-N-(3-(S-methylsulfonimidoyl)phenyl)-6-(trifluoromethyl)pyridazine-4-carboxamide | 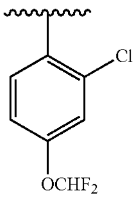 |

TABLE 30-continued

Compounds of Formula (IV-c)

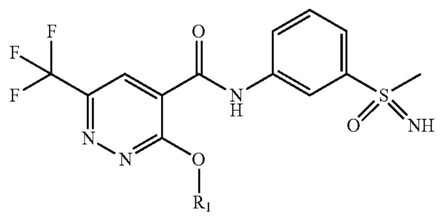

| Example | Name | $R_1$ |
|---|---|---|
| 11 | 3-(2-chloro-4-fluoromethoxyphenoxy)-N-(3-(S-methylsulfonimidoyl)phenyl)-6-(trifluoromethyl)pyridazine-4-carboxamide | 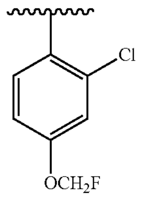 |
| 12 | 3-(4-fluoromethoxyphenoxy)-N-(3-(S-methylsulfonimidoyl)phenyl)-6-(trifluoromethyl)pyridazine-4-carboxamide | 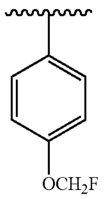 |
| 13 | 3-(4-difluoromethoxyphenoxy)-N-(3-(S-methylsulfonimidoyl)phenyl)-6-(trifluoromethyl)pyridazine-4-carboxamide | 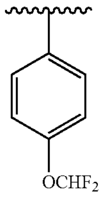 |
| 14 | 3-(4-trifluoromethoxyphenoxy)-N-(3-(S-methylsulfonimidoyl)phenyl)-6-(trifluoromethyl)pyridazine-4-carboxamide | 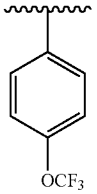 [SMILES: *c1ccc(OC(F)(F)F)cc1] |
| 15 | 3-(4-(2,2,2-trifluoroethoxy)phenoxy)-N-(3-(S-methylsulfonimidoyl)phenyl)-6-(trifluoromethyl)pyridazine-4-carboxamide | 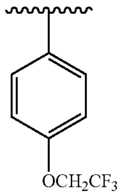 |
| 16 | 3-(2-fluoro-4-(2,2,2-trifluoroethoxy)phenoxy)-N-(3-(S-methylsulfonimidoyl)phenyl)-6-(trifluoromethyl)pyridazine-4-carboxamide | 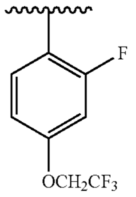 |

TABLE 30-continued

Compounds of Formula (IV-c)

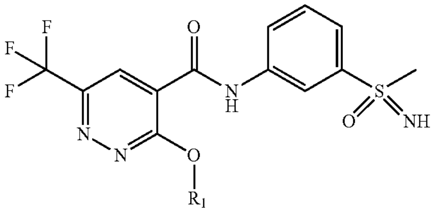

| Example | Name | $R_1$ |
|---|---|---|
| 17 | 3-(2-fluoro-4-trifluoromethoxyphenoxy)-N-(3-(S-methylsulfonimidoyl)phenyl)-6-(trifluoromethyl)pyridazine-4-carboxamide | 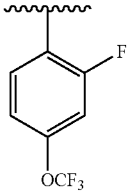 |
| 18 | 3-(2-fluoro-4-difluoromethoxyphenoxy)-N-(3-(S-methylsulfonimidoyl)phenyl)-6-(trifluoromethyl)pyridazine-4-carboxamide | 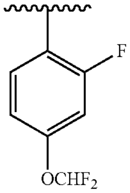 |
| 19 | 3-(2-fluoro-4-fluoromethoxyphenoxy)-N-(3-(S-methylsulfonimidoyl)phenyl)-6-(trifluoromethyl)pyridazine-4-carboxamide | 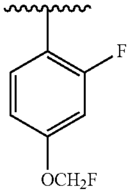 |
| 20 | 3-(2-methyl-4-trifluoromethoxyphenoxy)-N-(3-(S-methylsulfonimidoyl)phenyl)-6-(trifluoromethyl)pyridazine-4-carboxamide | 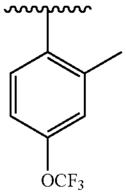 [SMILES: *c1ccc(OC(F)(F)F)cc1C] |
| 21 | 3-(2-methyl-4-difluoromethoxyphenoxy)-N-(3-(S-methylsulfonimidoyl)phenyl)-6-(trifluoromethyl)pyridazine-4-carboxamide | 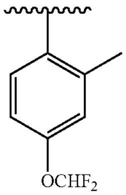 [SMILES: *c1ccc(OC(F)F)cc1C] |
| 22 | 3-(2-methyl-4-fluoromethoxyphenoxy)-N-(3-(S-methylsulfonimidoyl)phenyl)-6-(trifluoromethyl)pyridazine-4-carboxamide | 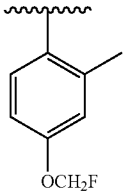 |

TABLE 30-continued

Compounds of Formula (IV-c)

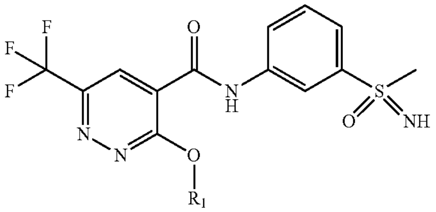

| Example | Name | $R_1$ |
|---|---|---|
| 23 | 3-(2-methyl-4-(2,2,2-trifluoroethoxy)phenoxy)-N-(3-(S-methylsulfonimidoyl)phenyl)-6-(trifluoromethyl)pyridazine-4-carboxamide | 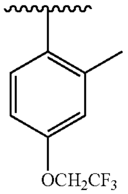 |
| 24 | 3-(3,4-difluorophenoxy)-N-(3-(S-methylsulfonimidoyl)phenyl)-6-(trifluoromethyl)pyridazine-4-carboxamide | 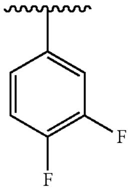 |
| 25 | 3-(3,4,5-trifluorophenoxy)-N-(3-(S-methylsulfonimidoyl)phenyl)-6-(trifluoromethyl)pyridazine-4-carboxamide | 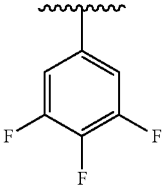 |
| 26 | 3-(3,6-difluorophenoxy)-N-(3-(S-methylsulfonimidoyl)phenyl)-6-(trifluoromethyl)pyridazine-4-carboxamide | 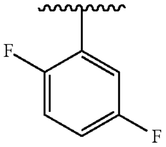 |
| 27 | 3-(2,3-difluorophenoxy)-N-(3-(S-methylsulfonimidoyl)phenyl)-6-(trifluoromethyl)pyridazine-4-carboxamide | 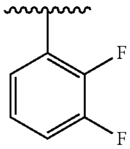 |
| 28 | 3-(2-chloro-3-fluorophenoxy)-N-(3-(S-methylsulfonimidoyl)phenyl)-6-(trifluoromethyl)pyridazine-4-carboxamide | 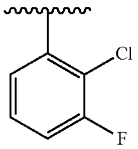 [SMILES: *c1cccc(F)c1Cl] |
| 29 | 3-(3-fluoro-4-trifluoromethoxyphenoxy)-N-(3-(S-methylsulfonimidoyl)phenyl)-6-(trifluoromethyl)pyridazine-4-carboxamide | 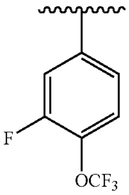 |

TABLE 30-continued

Compounds of Formula (IV-c)

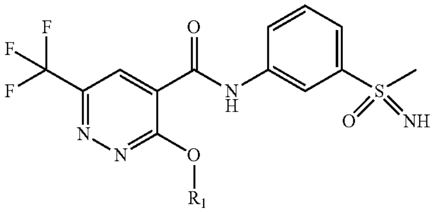

| Example | Name | $R_1$ |
|---|---|---|
| 30 | 3-(3-fluoro-4-difluoromethoxyphenoxy)-N-(3-(S-methylsulfonimidoyl)phenyl)-6-(trifluoromethyl)pyridazine-4-carboxamide | 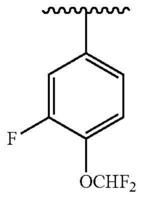 |
| 31 | 3-(3-fluoro-4-fluoromethoxyphenoxy)-N-(3-(S-methylsulfonimidoyl)phenyl)-6-(trifluoromethyl)pyridazine-4-carboxamide | 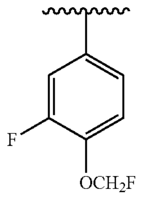 |
| 32 | 3-(4-chloro-2-methoxyphenoxy)-N-(3-(S-methylsulfonimidoyl)phenyl)-6-(trifluoromethyl)pyridazine-4-carboxamide | 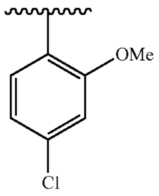 [SMILES: *c1ccc(Cl)cc1OC] |
| 33 | 3-(2-dimethylaminophenoxy)-N-(3-(S-methylsulfonimidoyl)phenyl)-6-(trifluoromethyl)pyridazine-4-carboxamide | 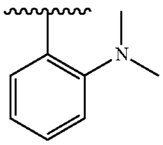 [SMILES: *c1ccccc1N(C)C] |

TABLE 31

Compounds of Formula (IV-d)

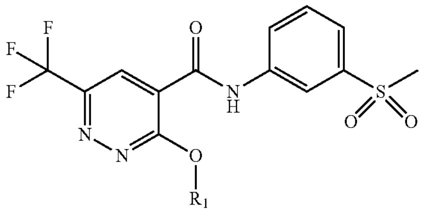

| Example | Name | $R_1$ |
|---|---|---|
| 34 | 3-(4-fluoro-2-methylphenoxy)-N-(3-(methylsulfonyl)phenyl)-6-(trifluoromethyl)pyridazine-4-carboxamide | 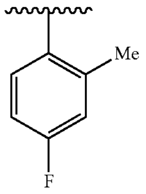 [SMILES: *c1ccc(F)cc1C] |
| 35 | 3-(2,4-difluorophenoxy)-N-(3-(methylsulfonyl)phenyl)-6-(trifluoromethyl)pyridazine-4-carboxamide | 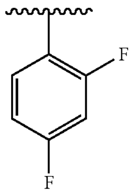 [SMILES: *c1ccc(F)cc1F] |
| 36 | 3-(2-chloro-4-fluorophenoxy)-N-(3-(methylsulfonyl)phenyl)-6-(trifluoromethyl)pyridazine-4-carboxamide | 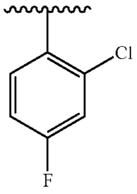 |
| 37 | 3-(2,4-dichlorophenoxy)-N-(3-(methylsulfonyl)phenyl)-6-(trifluoromethyl)pyridazine-4-carboxamide | 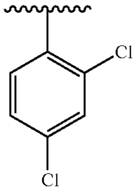 [SMILES: *c1ccc(Cl)cc1Cl] |
| 38 | 3-(2,4-dimethoxyphenoxy)-N-(3-(methylsulfonyl)phenyl)-6-(trifluoromethyl)pyridazine-4-carboxamide | 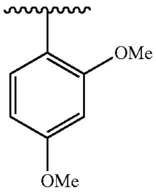 [SMILES: *c1ccc(OC)cc1OC] |
| 39 | 3-(2-chloro-4-(trifluoromethoxy)phenoxy)-N-(3-(methylsulfonyl)phenyl)-6-(trifluoromethyl)pyridazine-4-carboxamide | 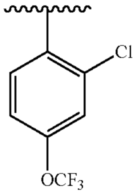 [SMILES: *c1ccc(OC(F)(F)F)cc1Cl] |

TABLE 31-continued

Compounds of Formula (IV-d)

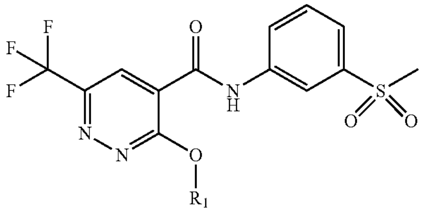

| Example | Name | $R_1$ |
|---|---|---|
| 40 | 3-(2-chloro-4-(difluoromethoxy)phenoxy)-N-(3-(methylsulfonyl)phenyl)-6-(trifluoromethyl)pyridazine-4-carboxamide | 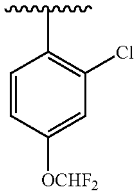 [SMILES: *c1ccc(OC(F)F)cc1Cl] |
| 41 | 3-(2-chloro-4-(fluoromethoxy)phenoxy)-N-(3-(methylsulfonyl)phenyl)-6-(trifluoromethyl)pyridazine-4-carboxamide | 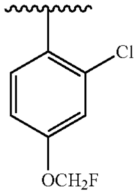 |
| 42 | 3-(4-(fluoromethoxy)phenoxy)-N-(3-(methylsulfonyl)phenyl)-6-(trifluoromethyl)pyridazine-4-carboxamide | 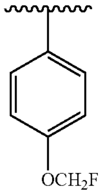 |
| 43 | 3-(4-(difluoromethoxy)phenoxy)-N-(3-(methylsulfonyl)phenyl)-6-(trifluoromethyl)pyridazine-4-carboxamide | 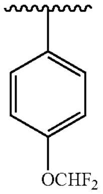 |
| 44 | N-(3-(methylsulfonyl)phenyl)-3-(4-(trifluoromethoxy)phenoxy)-6-(trifluoromethyl)pyridazine-4-carboxamide | 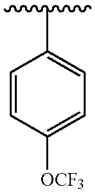 |
| 45 | N-(3-(methylsulfonyl)phenyl)-3-(4-(2,2,2-trifluoroethoxy)phenoxy)-6-(trifluoromethyl)pyridazine-4-carboxamide | 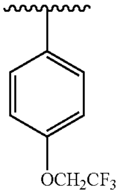 |

TABLE 31-continued

Compounds of Formula (IV-d)

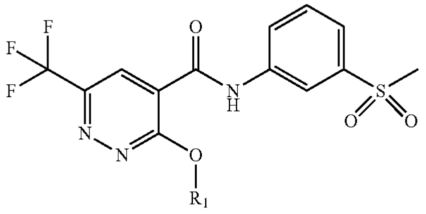

| Example | Name | $R_1$ |
|---|---|---|
| 46 | 3-(2-fluoro-4-(2,2,2-trifluoroethoxy)phenoxy)-N-(3-(methylsulfonyl)phenyl)-6-(trifluoromethyl)pyridazine-4-carboxamide | 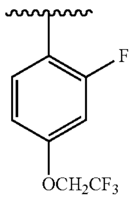 |
| 47 | 3-(2-fluoro-4-(trifluoromethoxy)phenoxy)-N-(3-(methylsulfonyl)phenyl)-6-(trifluoromethyl)pyridazine-4-carboxamide | 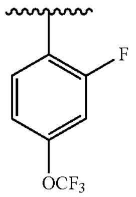 [SMILES: *c1ccc(OC(F)(F)F)cc1F] |
| 48 | 3-(4-(difluoromethoxy)-2-fluorophenoxy)-N-(3-(methylsulfonyl)phenyl)-6-(trifluoromethyl)pyridazine-4-carboxamide | 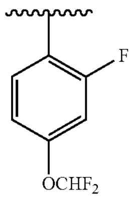 [SMILES: *c1ccc(OC(F)F)cc1F] |
| 49 | 3-(2-fluoro-4-(fluoromethoxy)phenoxy)-N-(3-(methylsulfonyl)phenyl)-6-(trifluoromethyl)pyridazine-4-carboxamide | 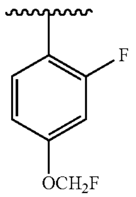 |
| 50 | 3-(2-methyl-4-(trifluoromethoxy)phenoxy)-N-(3-(methylsulfonyl)phenyl)-6-(trifluoromethyl)pyridazine-4-carboxamide | 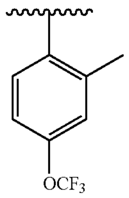 |
| 51 | 3-(4-(difluoromethoxy)-2-methylphenoxy)-N-(3-(methylsulfonyl)phenyl)-6-(trifluoromethyl)pyridazine-4-carboxamide | 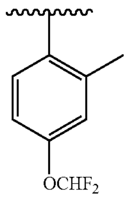 [SMILES: *c1ccc(OC(F)F)cc1C] |

TABLE 31-continued

Compounds of Formula (IV-d)

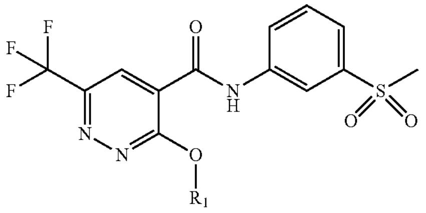

| Example | Name | $R_1$ |
|---|---|---|
| 52 | 3-(4-(fluoromethoxy)-2-methylphenoxy)-N-(3-(methylsulfonyl)phenyl)-6-(trifluoromethyl)pyridazine-4-carboxamide | 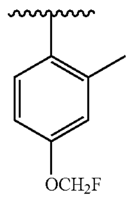 |
| 53 | 3-(2-methyl-4-(2,2,2-trifluoroethoxy)phenoxy)-N-(3-(methylsulfonyl)phenyl)-6-(trifluoromethyl)pyridazine-4-carboxamide | 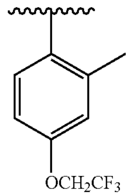 |
| 54 | 3-(3,4-difluorophenoxy)-N-(3-(methylsulfonyl)phenyl)-6-(trifluoromethyl)pyridazine-4-carboxamide | 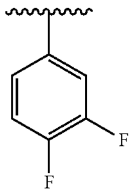 [SMILES: *c1ccc(F)c(F)c1] |
| 55 | N-(3-(methylsulfonyl)phenyl)-6-(trifluoromethyl)-3-(3,4,5-trifluorophenoxy)pyridazine-4-carboxamide | 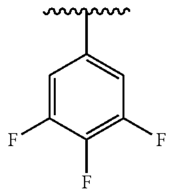 [SMILES: *c1cc(F)c(F)c(F)c1] |
| 56 | 3-(2,5-difluorophenoxy)-N-(3-(methylsulfonyl)phenyl)-6-(trifluoromethyl)pyridazine-4-carboxamide | 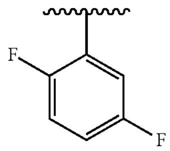 [SMILES: *c1cc(F)ccc1F] |
| 57 | 3-(2,3-difluorophenoxy)-N-(3-(methylsulfonyl)phenyl)-6-(trifluoromethyl)pyridazine-4-carboxamide | 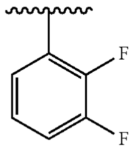 [SMILES: *c1cccc(F)c1F] |
| 58 | 3-(2-chloro-3-fluorophenoxy)-N-(3-(methylsulfonyl)phenyl)-6-(trifluoromethyl)pyridazine-4-carboxamide | 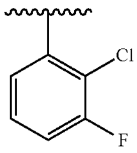 [SMILES: *c1cccc(F)c1Cl] |

TABLE 31-continued

Compounds of Formula (IV-d)

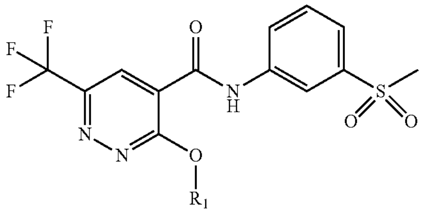

| Example | Name | $R_1$ |
|---|---|---|
| 59 | 3-(3-fluoro-4-(trifluoromethoxy)phenoxy)-N-(3-(methylsulfonyl)phenyl)-6-(trifluoromethyl)pyridazine-4-carboxamide | 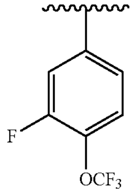 |
| 60 | 3-(4-(difluoromethoxy)-3-fluorophenoxy)-N-(3-(methylsulfonyl)phenyl)-6-(trifluoromethyl)pyridazine-4-carboxamide | 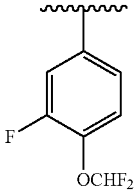 |
| 61 | 3-(3-fluoro-4-(fluoromethoxy)phenoxy)-N-(3-(methylsulfonyl)phenyl)-6-(trifluoromethyl)pyridazine-4-carboxamide | 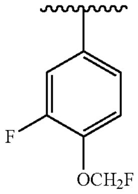 |
| 62 | 3-(4-chloro-2-methoxyphenoxy)-N-(3-(methylsulfonyl)phenyl)-6-(trifluoromethyl)pyridazine-4-carboxamide | 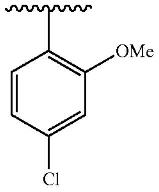 [SMILES: *c1ccc(Cl)cc1OC] |
| 63 | 3-(2-(dimethylamino)phenoxy)-N-(3-(methylsulfonyl)phenyl)-6-(trifluoromethyl)pyridazine-4-carboxamide | 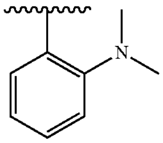 [SMILES: *c1ccccc1N(C)C] |

TABLE 32

Compounds of Formula (IV-a)

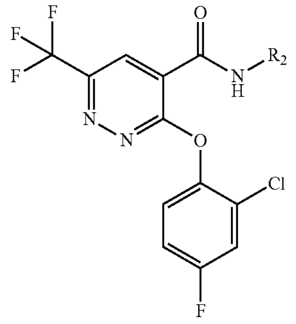

| Example | Name | $R_2$ |
|---|---|---|
| 64 | 3-(2-chloro-4-fluorophenoxy)-N-(3-methylsulfonylphenyl)-6-(trifluoromethyl)pyridazine-4-carboxamide | 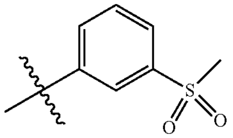 [SMILES: *c1cccc(S(C)(=O)=O)c1] |
| 65 | 3-(2-chloro-4-fluorophenoxy)-N-(3-ethylsulfonylphenyl)-6-(trifluoromethyl)pyridazine-4-carboxamide | 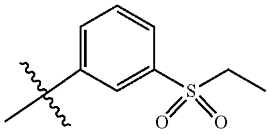 [SMILES: *c1cccc(S(=O)(=O)CC)c1] |
| 66 | 3-(2-chloro-4-fluorophenoxy)-N-(3-methylsulfonyl-6-methyl-phenyl)-6-(trifluoromethyl)pyridazine-4-carboxamide | 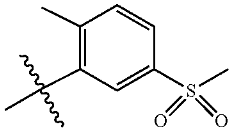 |
| 67 | 3-(2-chloro-4-fluorophenoxy)-N-(3-methylsulfonyl-6-fluoro-phenyl)-6-(trifluoromethyl)pyridazine-4-carboxamide | 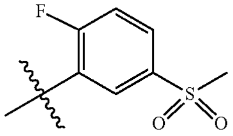 [SMILES: *c1cc(S(C)(=O)=O)ccc1F] |
| 68 | N-(3-acetylphenyl)-3-(2-chloro-4-fluoro-phenoxy)-6-(trifluoromethyl)pyridazine-4-carboxamide | 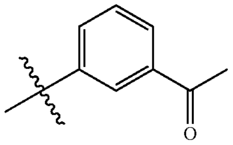 [SMILES: *c1cccc(C(C)=O)c1] |
| 69 | 3-(2-chloro-4-fluoro-phenoxy)-N-[3-(hydroxymethyl)phenyl]-6-(trifluoromethyl)pyridazine-4-carboxamide | 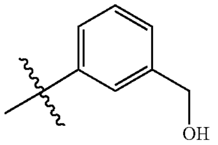 [SMILES: *c1cccc(CO)c1] |
| 70 | 3-(2-chloro-4-fluoro-phenoxy)-N-[3-cyanophenyl]-6-(trifluoromethyl)pyridazine-4-carboxamide | 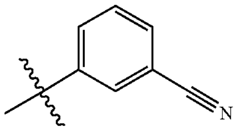 [SMILES: *c1cccc(C#N)c1] |
| 71 | 3-(2-chloro-4-fluoro-phenoxy)-N-(4-pyridyl)-6-(trifluoromethyl)pyridazine-4-carboxamide | 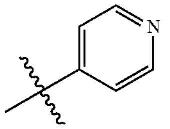 [SMILES: *c1ccncc1] |

TABLE 32-continued

Compounds of Formula (IV-a)

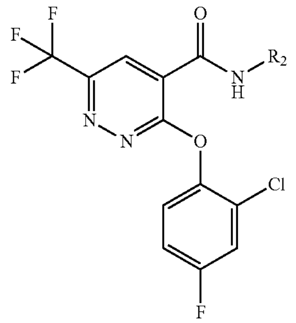

| Example | Name | $R_2$ |
|---|---|---|
| 72 | 3-(2-chloro-4-fluoro-phenoxy)-N-(3-pyridyl)-6-(trifluoromethyl)pyridazine-4-carboxamide | 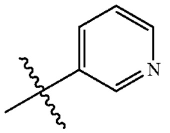 [SMILES: *c1cccnc1] |
| 73 | 3-(2-chloro-4-fluoro-phenoxy)-N-(3-pyridyl-N-oxide)-6-(trifluoromethyl)pyridazine-4-carboxamide | 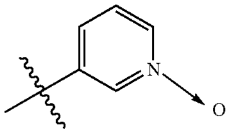 [SMILES: *c1cccnc1 ; O] |
| 74 | 3-(2-chloro-4-fluoro-phenoxy)-N-(4-pyridyl-N-oxide)-6-(trifluoromethyl)pyridazine-4-carboxamide | 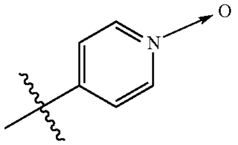 [SMILES: O ; *c1ccncc1] |
| 75 | 3-(2-chloro-4-fluoro-phenoxy)-N-(2-oxo-1H-pyridin-4-yl)-6-(trifluoromethyl)pyridazine-4-carboxamide | 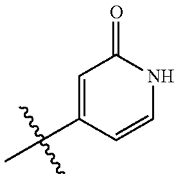 [SMILES: *c1cc[nH]c(=O)c1] |
| 76 | 3-(2-chloro-4-fluoro-phenoxy)-N-(2-fluoro-4-pyridyl)-6-(trifluoromethyl)pyridazine-4-carboxamide | 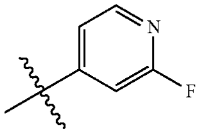 [SMILES: *c1ccnc(F)c1] |
| 77 | 3-(2-chloro-4-fluoro-phenoxy)-N-(2-methyl-4-pyridyl)-6-(trifluoromethyl)pyridazine-4-carboxamide | 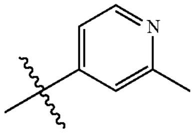 [SMILES: *c1ccnc(C)c1] |
| 78 | 3-(2-chloro-4-fluoro-phenoxy)-N-(6-fluoro-3-pyridyl)-6-(trifluoromethyl)pyridazine-4-carboxamide | 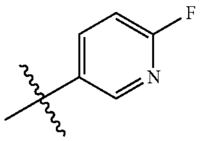 [SMILES: *c1ccc(F)nc1] |
| 79 | 3-(2-chloro-4-fluoro-phenoxy)-N-(6-chloro-3-pyridyl)-6-(trifluoromethyl)pyridazine-4-carboxamide | 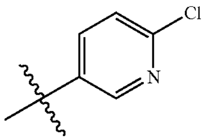 [SMILES: *c1ccc(Cl)nc1] |

TABLE 32-continued

Compounds of Formula (IV-a)

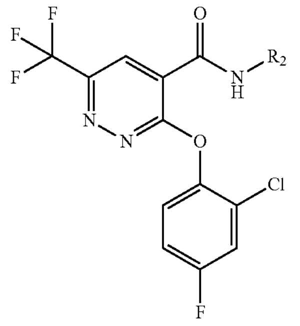

| Example | Name | $R_2$ |
|---|---|---|
| 80 | 3-(2-chloro-4-fluoro-phenoxy)-N-(1-methyl-2-oxo-4-pyridyl)-6-(trifluoromethyl)pyridazine-4-carboxamide | 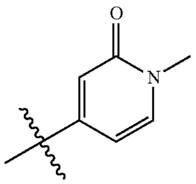 [SMILES: *c1ccn(C)c(=O)c1] |
| 81 | 3-(2-chloro-4-fluoro-phenoxy)-N-pyridazin-4-yl-6-(trifluoromethyl)pyridazine-4-carboxamide | 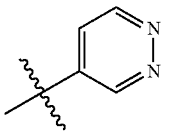 [SMILES: *c1ccnnc1] |
| 82 | 3-(2-chloro-4-fluoro-phenoxy)-N-(2-oxidopyridazin-2-ium-4-yl)-6-(trifluoromethyl)pyridazine-4-carboxamide | 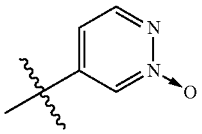 [SMILES: *c1ccn[n+]([O-])c1] |
| 83 | 3-(2-chloro-4-fluoro-phenoxy)-N-pyrimidin-4-yl-6-(trifluoromethyl)pyridazine-4-carboxamide | 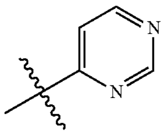 [SMILES: *c1ccncn1] |

TABLE 33

Compounds of Formula (IV-e)

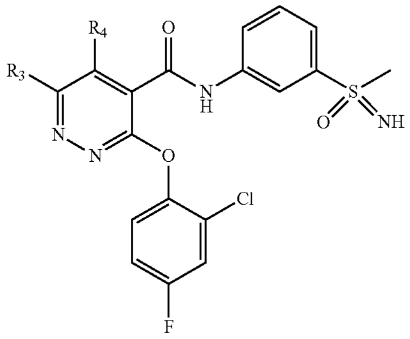

| Example | Name | $R_3$ | $R_4$ |
|---|---|---|---|
| 84 | 3-(2-chloro-4-fluorophenoxy)-N-(3-(S-methylsulfonimidoyl)phenyl)-6-(difluoromethyl)pyridazine-4-carboxamide | $CF_2H$ | H |

TABLE 33-continued

Compounds of Formula (IV-e)

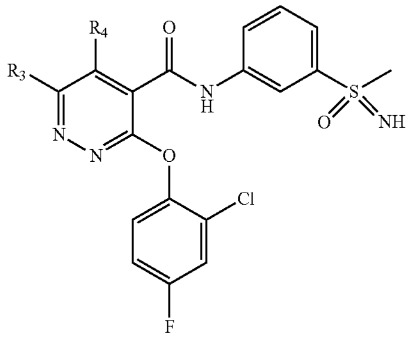

| Example | Name | $R_3$ | $R_4$ |
|---|---|---|---|
| 85 | 3-(2-chloro-4-fluorophenoxy)-N-(3-(S-methylsulfonimidoyl)phenyl)-6-(fluoromethyl)pyridazine-4-carboxamide | $CH_2F$ | H |

TABLE 33-continued

Compounds of Formula (IV-e)

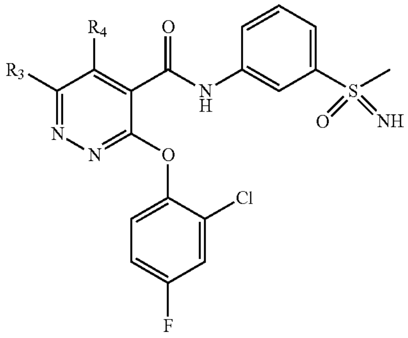

| Example | Name | $R_3$ | $R_4$ |
|---|---|---|---|
| 86 | 3-(2-chloro-4-fluorophenoxy)-N-(3-(S-methylsulfonimidoyl)phenyl)-6-chloro-pyridazine-4-carboxamide | Cl | H |
| 87 | 3-(2-chloro-4-fluorophenoxy)-N-(3-(S-methylsulfonimidoyl)phenyl)-6-(trifluoromethoxy)pyridazine-4-carboxamide | $OCF_3$ | H |
| 88 | 3-(2-chloro-4-fluorophenoxy)-N-(3-(S-methylsulfonimidoyl)phenyl)-6-(difluoromethoxy)pyridazine-4-carboxamide | $OCHF_2$ | H |
| 89 | 3-(2-chloro-4-fluorophenoxy)-N-(3-(S-methylsulfonimidoyl)phenyl)-6-(fluoromethoxy)pyridazine-4-carboxamide | $OCFH_2$ | H |
| 90 | 3-(2-chloro-4-fluorophenoxy)-N-(3-(S-methylsulfonimidoyl)phenyl)-6-bromo-pyridazine-4-carboxamide | Cl | H |
| 91 | 3-(2-chloro-4-fluorophenoxy)-N-(3-(S-methylsulfonimidoyl)phenyl)-6-cyclopropyl-pyridazine-4-carboxamide | 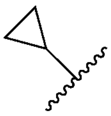 [SMILES: *C1CC1] | H |
| 92 | 3-(2-chloro-4-fluorophenoxy)-N-(3-(S-methylsulfonimidoyl)phenyl)-6-tert-butyl-pyridazine-4-carboxamide | 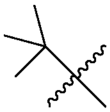 [SMILES: *C(C)(C)C] | H |
| 93 | 3-(2-chloro-4-fluorophenoxy)-N-(3-(S-methylsulfonimidoyl)phenyl)-6-isopropyl-pyridazine-4-carboxamide | 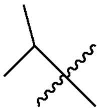 [SMILES: *C(C)C] | H |
| 94 | 3-(2-chloro-4-fluorophenoxy)-N-(3-(S-methylsulfonimidoyl)phenyl)-6-methyl-pyridazine-4-carboxamide | 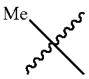 | H |

TABLE 33-continued

Compounds of Formula (IV-e)

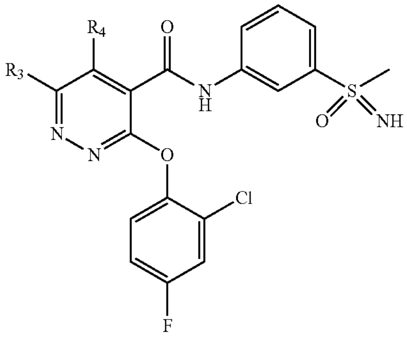

| Example | Name | $R_3$ | $R_4$ |
|---|---|---|---|
| 95 | 3-(2-chloro-4-fluorophenoxy)-N-(3-(S-methylsulfonimidoyl)phenyl)-5,6-dimethyl-pyridazine-4-carboxamide | 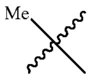 | 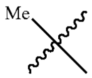 |
| 96 | 3-(2-chloro-4-fluorophenoxy)-N-(3-(S-methylsulfonimidoyl)phenyl)-6-methoxy-pyridazine-4-carboxamide | 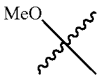 | H |
| 97 | 3-(2-chloro-4-fluorophenoxy)-N-(3-(S-methylsulfonimidoyl)phenyl)-5-methyl-6-methoxy-pyridazine-4-carboxamide | 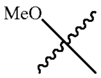 | 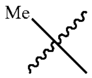 |
| 98 | 3-(2-chloro-4-fluorophenoxy)-N-(3-(S-methylsulfonimidoyl)phenyl)-6-cyano-pyridazine-4-carboxamide | 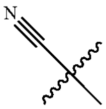 [SMILES: *C#N] | H |
| 99 | 3-(2-chloro-4-fluorophenoxy)-N-(3-(S-methylsulfonimidoyl)phenyl)-6-nitro-pyridazine-4-carboxamide | 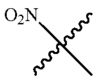 | H |
| 100 | 3-(2-chloro-4-fluorophenoxy)-N-(3-(S-methylsulfonimidoyl)phenyl)-6-((trifluoromethyl)thio)pyridazine-4-carboxamide | $SCF_3$ | H |
| 101 | 3-(2-chloro-4-fluorophenoxy)-N-(3-(S-methylsulfonimidoyl)phenyl)-6-(pentafluoro-l6-sulfaneyl)pyridazine-4-carboxamide | $SF_5$ | H |

TABLE 34
Compounds of Formula (III-g)
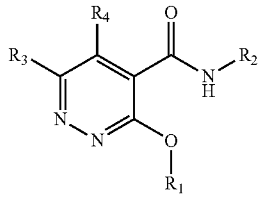
| Example | Name | Structure |
| --- | --- | --- |
| 102 | 3-(3-(4-(trifluoromethoxy)phenoxy)-6-(trifluoromethyl)pyridazine-4-carboxamido)pyridine 1 -oxide | 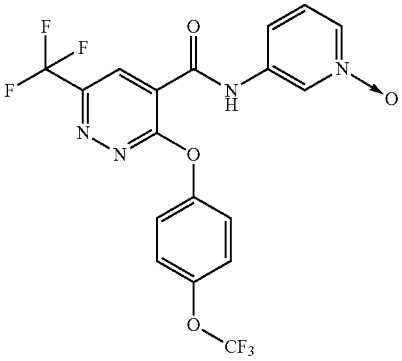 [SMILES: O=C(Nc1ccc[n+]([O-])c1)c1cc(C(F)(F)F)nnc1Oc1ccc(OC(F)(F)F)cc1] |
| 103 | 3-(3-(2,4-dimethoxyphenoxy)-6-(trifluoromethyl)pyridazine-4-carboxamido)pyridine 1-oxide | 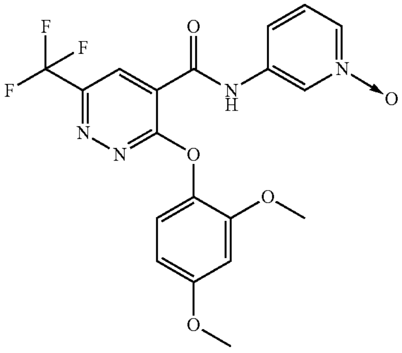 [SMILES: COc1ccc(Oc2nnc(C(F)(F)F)cc2C(=O)Nc2ccc[n+]([O-])c2)c(OC)c1] |
| 104 | 3-(3-(2-chloro-4-(trifluoromethoxy)phenoxy)-6-(trifluoromethyl)pyridazine-4-carboxamido)pyridine 1-oxide | 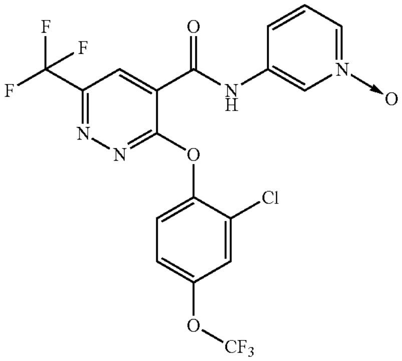 [SMILES: O=C(Nc1ccc[n+]([O-])c1)c1cc(C(F)(F)F)nnc1Oc1ccc(OC(F)(F)F)cc1Cl] |

TABLE 34-continued
Compounds of Formula (III-g)
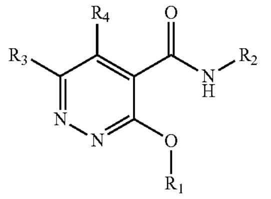
| Example | Name | Structure |
| --- | --- | --- |
| 105 | 3-(2-chloro-4-(trifluoromethoxy)phenoxy)-N-(pyridazin-4-yl)-6-(trifluoromethyl)pyridazine-4-carboxamide | 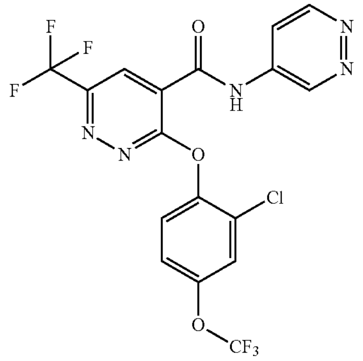 [SMILES: O=C(Nc1ccnnc1)c1cc(C(F)(F)F)nnc1Oc1ccc(OC(F)(F)F)cc1Cl] |
| 106 | 3-(4-fluoro-2-methoxyphenoxy)-N-(pyridazin-4-yl)-6-(trifluoromethyl)pyridazine-4-carboxamide | 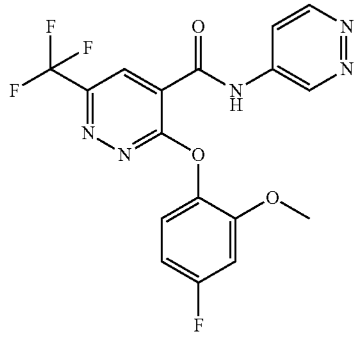 [SMILES: COc1cc(F)ccc1Oc1nnc(C(F)(F)F)cc1C(=O)Nc1ccnnc1] |
| 107 | N-(pyridazin-4-yl)-3-(4-(trifluoromethoxy)phenoxy)-6-(trifluoromethyl)pyridazine-4-carboxamide | 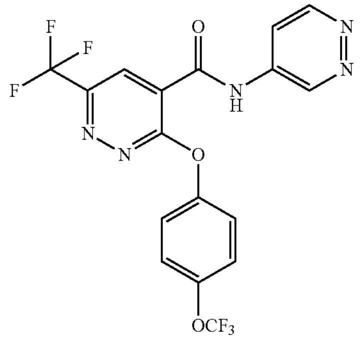 [SMILES: O=C(Nc1ccnnc1)c1cc(C(F)(F)F)nnc1Oc1ccc(OC(F)(F)F)cc1] |

TABLE 34-continued
Compounds of Formula (III-g)
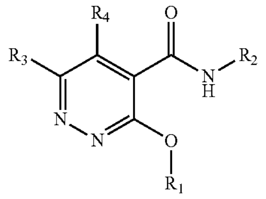
| Example | Name | Structure |
| --- | --- | --- |
| 108 | 3-(2,4-dimethoxyphenoxy)-N-(pyridazin-4-yl)-6-(trifluoromethyl)pyridazine-4-carboxamide | 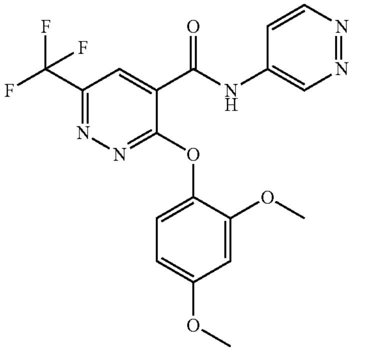 [SMILES: COc1ccc(Oc2nnc(C(F)(F)F)cc2C(=O)Nc2ccnnc2)c(OC)c1] |
| 109 | 5-(3-(2,4-dimethoxyphenoxy)-6-(trifluoromethyl)pyridazine-4-carboxamido)pyridazine 1-oxide | 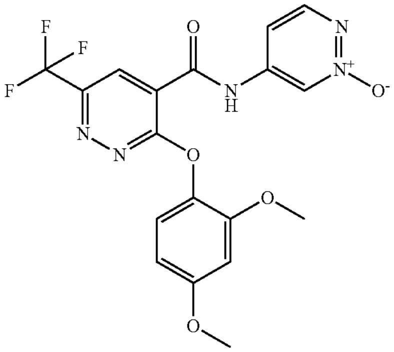 [SMILES: COc1ccc(Oc2nnc(C(F)(F)F)cc2C(=O)Nc2ccn[n+]([O-])c2)c(OC)c1] |
| 110 | 5-(3-(4-(trifluoromethoxy)phenoxy)-6-(trifluoromethyl)pyridazine-4-carboxamido)pyridazine 1-oxide | 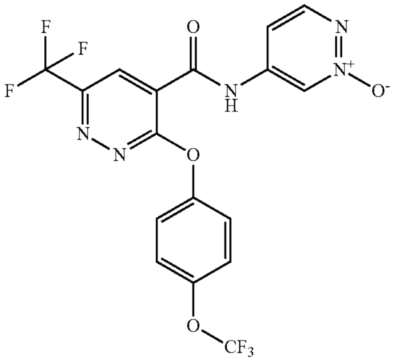 [SMILES: O=C(Nc1ccn[n+]([O-])c1)c1cc(C(F)(F)F)nnc1Oc1ccc(OC(F)(F)F)cc1] |

TABLE 34-continued

Compounds of Formula (III-g)

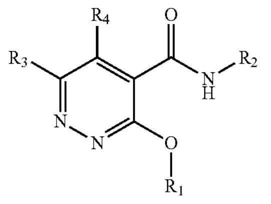

| Example | Name | Structure |
|---|---|---|
| 111 | 5-(3-(4-fluoro-2-methoxyphenoxy)-6-(trifluoromethyl)pyridazine-4-carboxamido)pyridazine 1-oxide | 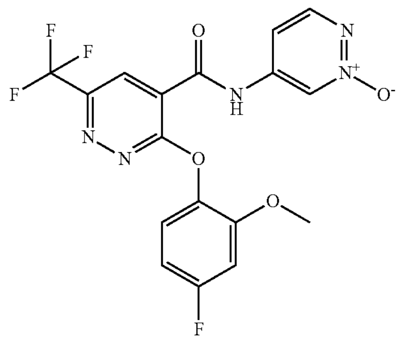 [SMILES: COc1cc(F)ccc1Oc1nnc(C(F)(F)F)cc1C(=O)Nc1ccn[n+]([O-])c1] |
| 112 | 5-(3-(2-chloro-4-(trifluoromethoxy)phenoxy)-6-(trifluoromethyl)pyridazine-4-carboxamido)pyridazine 1-oxide | 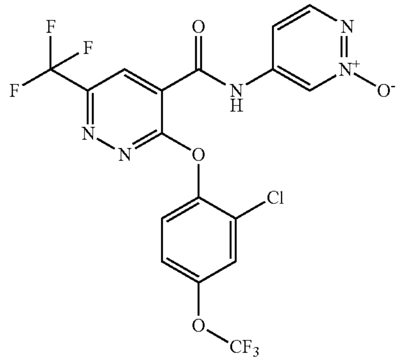 [SMILES: O=C(Nc1ccn[n+]([O-])c1)c1cc(C(F)(F)F)nnc1Oc1ccc(OC(F)(F)F)cc1Cl] |

TABLE 35

Compounds of Formula (VI-f)

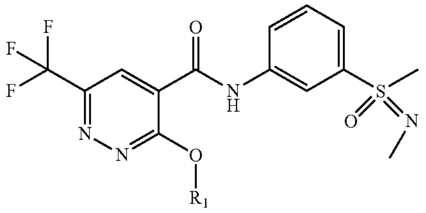

| Example | Name | $R_1$ |
|---|---|---|
| | N-(3-(N,S-dimethylsulfonimidoyl)phenyl)-3-(4-fluoro-2-methylphenoxy)-6-(trifluoromethyl)pyridazine-4-carboxamide | 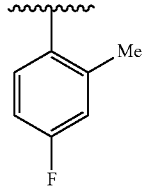 |

TABLE 35-continued

Compounds of Formula (VI-f)

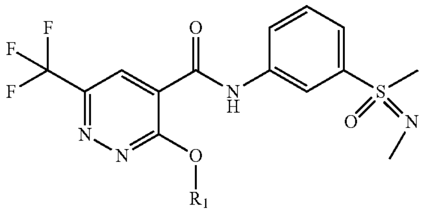

| Example | Name | $R_1$ |
| --- | --- | --- |
| | 3-(2,4-difluorophenoxy)-N-(3-(N,S-dimethylsulfonimidoyl)phenyl)-6-(trifluoromethyl)pyridazine-4-carboxamide | 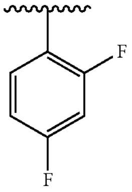 [SMILES: *c1ccc(F)cc1F] |
| | 3-(2-chloro-4-fluorophenoxy)-N-(3-(N,S-dimethylsulfonimidoyl)phenyl)-6-(trifluoromethyl)pyridazine-4-carboxamide | 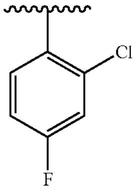 [SMILES: *c1ccc(F)cc1Cl] |
| | 3-(2,4-dichlorophenoxy)-N-(3-(N,S-dimethylsulfonimidoyl)phenyl)-6-(trifluoromethyl)pyridazine-4-carboxamide | 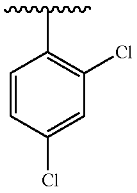 [SMILES: *c1ccc(Cl)cc1Cl] |
| | 3-(2,4-dimethoxyphenoxy)-N-(3-(N,S-dimethylsulfonimidoyl)phenyl)-6-(trifluoromethyl)pyridazine-4-carboxamide | 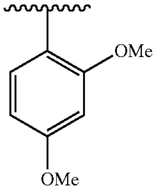 [SMILES: *c1ccc(OC)cc1OC] |
| | 3-(2-chloro-4-(trifluoromethoxy)phenoxy)-N-(3-(N,S-dimethylsulfonimidoyl)phenyl)-6-(trifluoromethyl)pyridazine-4-carboxamide | 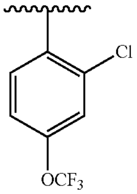 |
| | 3-(2-chloro-4-(difluoromethoxy)phenoxy)-N-(3-(N,S-dimethylsulfonimidoyl)phenyl)-6-(trifluoromethyl)pyridazine-4-carboxamide | 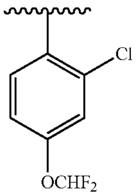 |

TABLE 35-continued

Compounds of Formula (VI-f)

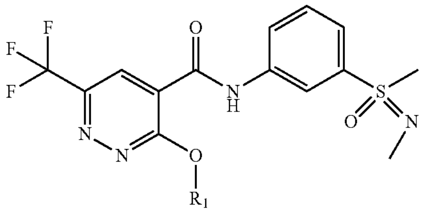

| Example | Name | $R_1$ |
|---|---|---|
| | 3-(2-chloro-4-(fluoromethoxy)phenoxy)-N-(3-(N,S-dimethylsulfonimidoyl)phenyl)-6-(trifluoromethyl)pyridazine-4-carboxamide | 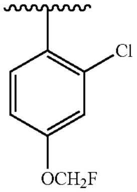 |
| | N-(3-(N,S-dimethylsulfonimidoyl)phenyl)-3-(4-(fluoromethoxy)phenoxy)-6-(trifluoromethyl)pyridazine-4-carboxamide hydrochloride | 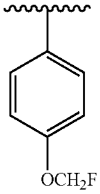 |
| | 3-(4-(difluoromethoxy)phenoxy)-N-(3-(N,S-dimethylsulfonimidoyl)phenyl)-6-(trifluoromethyl)pyridazine-4-carboxamide | 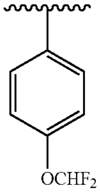 |
| | N-(3-(N,S-dimethylsulfonimidoyl)phenyl)-3-(4-(trifluoromethoxy)phenoxy)-6-(trifluoromethyl)pyridazine-4-carboxamide | 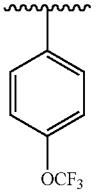 |
| | N-(3-(N,S-dimethylsulfonimidoyl)phenyl)-3-(4-(2,2,2-trifluoroethoxy)phenoxy)-6-(trifluoromethyl)pyridazine-4-carboxamide | 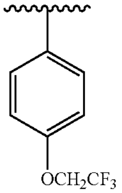 |
| | N-(3-(N,S-dimethylsulfonimidoyl)phenyl)-3-(2-fluoro-4-(2,2,2-trifluoroethoxy)phenoxy)-6-(trifluoromethyl)pyridazine-4-carboxamide | 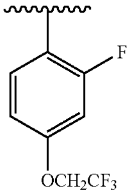 |

TABLE 35-continued

Compounds of Formula (VI-f)

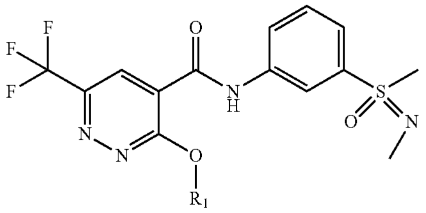

| Example | Name | $R_1$ |
|---|---|---|
| | N-(3-(N,S-dimethylsulfonimidoyl)phenyl)-3-(2-fluoro-4-(trifluoromethoxy)phenoxy)-6-(trifluoromethyl)pyridazine-4-carboxamide | 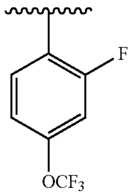 [SMILES: *c1ccc(OC(F)(F)F)cc1F] |
| | 3-(4-(difluoromethoxy)-2-fluorophenoxy)-N-(3-(N,S-dimethylsulfonimidoyl)phenyl)-6-(trifluoromethyl)pyridazine-4-carboxamide | 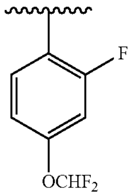 |
| | N-(3-(N,S-dimethylsulfonimidoyl)phenyl)-3-(2-fluoro-4-(fluoromethoxy)phenoxy)-6-(trifluoromethyl)pyridazine-4-carboxamide | 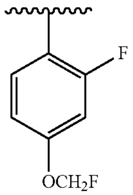 |
| | N-(3-(N,S-dimethylsulfonimidoyl)phenyl)-3-(2-methyl-4-(trifluoromethoxy)phenoxy)-6-(trifluoromethyl)pyridazine-4-carboxamide | 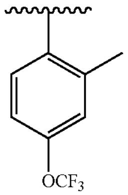 |
| | 3-(4-(difluoromethoxy)-2-methylphenoxy)-N-(3-(N,S-dimethylsulfonimidoyl)phenyl)-6-(trifluoromethyl)pyridazine-4-carboxamide | 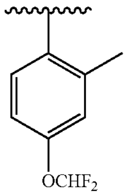 |
| | N-(3-(N,S-dimethylsulfonimidoyl)phenyl)-3-(4-(fluoromethoxy)-2-methylphenoxy)-6-(trifluoromethyl)pyridazine-4-carboxamide | 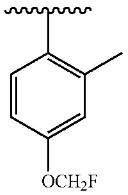 |

TABLE 35-continued

Compounds of Formula (VI-f)

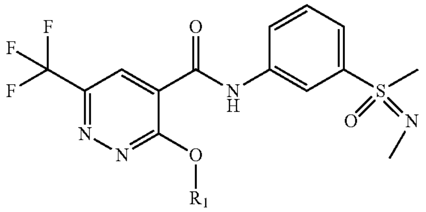

| Example | Name | $R_1$ |
|---|---|---|
| | N-(3-(N,S-dimethylsulfonimidoyl)phenyl)-3-(2-methyl-4-(2,2,2-trifluoroethoxy)phenoxy)-6-(trifluoromethyl)pyridazine-4-carboxamide | 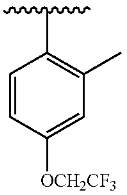 |
| | 3-(3,4-difluorophenoxy)-N-(3-(N,S-dimethylsulfonimidoyl)phenyl)-6-(trifluoromethyl)pyridazine-4-carboxamide | 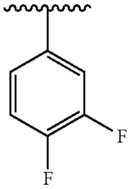 |
| | N-(3-(N,S-dimethylsulfonimidoyl)phenyl)-6-(trifluoromethyl)-3-(3,4,5-trifluorophenoxy)pyridazine-4-carboxamide | 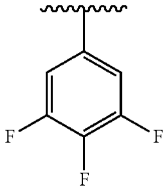 [SMILES: *c1cc(F)c(F)c(F)c1] |
| | 3-(2,5-difluorophenoxy)-N-(3-(N,S-dimethylsulfonimidoyl)phenyl)-6-(trifluoromethyl)pyridazine-4-carboxamide | 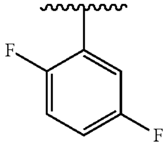 [SMILES: *c1cc(F)ccc1F] |
| | 3-(2,3-difluorophenoxy)-N-(3-(N,S-dimethylsulfonimidoyl)phenyl)-6-(trifluoromethyl)pyridazine-4-carboxamide | 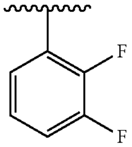 [SMILES: *c1cccc(F)c1F] |
| | 3-(2-chloro-3-fluorophenoxy)-N-(3-(N,S-dimethylsulfonimidoyl)phenyl)-6-(trifluoromethyl)pyridazine-4-carboxamide | 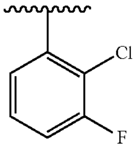 [SMILES: *c1cccc(F)c1Cl] |
| | N-(3-(N,S-dimethylsulfonimidoyl)phenyl)-3-(3-fluoro-4-(trifluoromethoxy)phenoxy)-6-(trifluoromethyl)pyridazine-4-carboxamide | 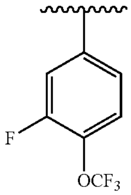 [SMILES: *c1ccc(OC(F)(F)F)c(F)c1] |

TABLE 35-continued

Compounds of Formula (VI-f)

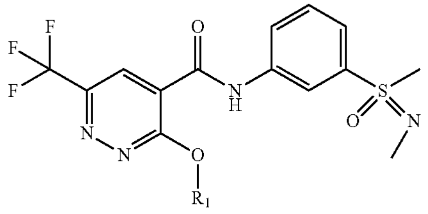

| Example | Name | $R_1$ |
|---|---|---|
| | 3-(4-(difluoromethoxy)-3-fluorophenoxy)-N-(3-(N,S-dimethylsulfonimidoyl)phenyl)-6-(trifluoromethyl)pyridazine-4-carboxamide | 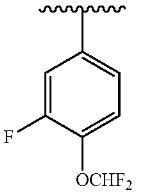 |
| | N-(3-(N,S-dimethylsulfonimidoyl)phenyl)-3-(3-fluoro-4-(fluoromethoxy)phenoxy)-6-(trifluoromethyl)pyridazine-4-carboxamide | 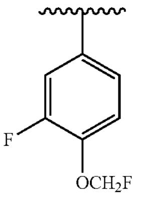 |
| | 3-(4-chloro-2-methoxyphenoxy)-N-(3-(N,S-dimethylsulfonimidoyl)phenyl)-6-(trifluoromethyl)pyridazine-4-carboxamide | 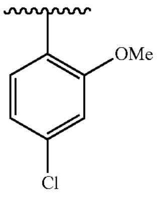 [SMILES: *c1ccc(Cl)cc1OC] |
| | 3-(2-(dimethylamino)phenoxy)-N-(3-(N,S-dimethylsulfonimidoyl)phenyl)-6-(trifluoromethyl)pyridazine-4-carboxamide | 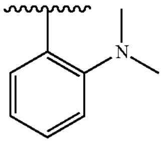 [SMILES: *c1ccccc1N(C)C] |
| | N-(3-(N,S-dimethylsulfonimidoyl)phenyl)-3-(4-fluoro-2-methoxyphenoxy)-6-(trifluoromethyl)pyridazine-4-carboxamide | 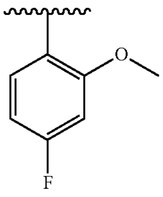 [SMILES: *c1ccc(F)cc1OC] |

Example 122

Assay Methods

The ability of pyridazine carboxamide derivatives exemplified above to inhibit the $Na_V1.8$ channel was determined using one or more of the methods described below.

HEK $Na_V1.8$ β1/β2 Stably Expressing Cell Line

A HEK293 cell line stably expressing the human $Na_V1.8$ ($hNa_V1.8$) ion channel with β1/β2 subunits was constructed. The cell line is suitable for $IC_{50}$ determination in fluorescence and electrophysiological based assays. It is also suitable to form mechanism of action pharmacology studies in electrophysiological assays. HEK293 $Na_V1.8$ cells are grown as adherent monolayers in DMEM/high glucose media, 10% fetal bovine serum, Na pyruvate (2 mM), Hepes (10 mM) with selection agents G418 (400 mg/L) and puromycin (0.5 mg/L) at 37 degrees C., 10% $CO_2$.

$Na_v1.8$ Fluorescence Inhibition Assay

Compounds were made up to or supplied as a 10 mM stock solution using DMSO as the vehicle. Concentration-response curves were generated using a Matrix multichannel pipettor. Compound source plates were made by diluting 10 mM compound stocks to create 500 μM (100×) solutions in DMSO in 96 well v-bottom plates. Compounds were then serially diluted in 100% DMSO to generate a 5 point, 4-fold dilution scheme dose response curve. 2 μl of the 100× dose response curves was then added to preincubation and stimulation assay plates. 100 μl of pre-incubation buffer and 200 μl of stimulation buffer were then added to the plates resulting in a final assay test concentration range of 5 μM to 0.02 μM with a final DMSO concentration of 1%.

On the day of assay, plates were washed to remove cell culture media using 2K EBSS buffer (135 mM NaCl, 2 mM KCl, 5 mM Glucose, 2 mM $CaCl_2$), 1 mM MgCl2, 10 mM HEPES, pH 7.4). The Na-sensitive fluorescent dye, Asante Natrium Green-2 (ANG-2) is incubated for 60 min to allow equilibration and then washed with 2K EBSS. Plates are the transferred to a fluorescence plate reader (FLIPR™, Molecular Devices) for fluorescence measurement using an excitation wavelength of 490 nm and an emission wavelength of 565 nm. Compounds are pre-incubated at for 5 min at final test concentration in the presence of ouabain (30 μM) to inhibit Na+ efflux through Na+/K+ exchanger. Following the pre-incubation phase, $hNa_V1.8$ channels are stimulated with 10 μM of the pyrethroid deltamethrin to prevent channel inactivation. The assay was run for 15 min with vehicle and 30 μM tetracaine serving as negative and positive controls, respectively. The peak change in fluorescence relative to negative and positive control wells was calculated and fit with a logistic equation to determine $IC_{50}$.

PatchXpress $Na_v1.8$ Inhibition Assay

HEK-$Na_V1.8$ β1/β2 cells were recorded in whole cell patch-clamp using the PatchXpress automated patch clamp platforms (Molecular Devices). Cells suspensions were obtained by trypsinization of adherent monolayers, followed by gentle rocking for minimally 30 min. Compounds were prepared from 10 mM DMSO stocks.

$Na_V1.8$ channel variants were evaluated using Protocol 1, depicted in FIG. 1, in which cells were initially voltage clamped at a holding potential of −100 mV to maintain $Na_V1.8$ in a closed resting state. After current amplitude becomes stable, the mid-point voltage of steady state inactivation was determined for each cell using a series of 5 sec conditioning steps to increasingly depolarized voltages (−100 to 0 mV) The holding potential was then reset to a voltage that produces ~50% inactivation ($V_{half}$-set automatically via PatchXpress scripts) so that closed and inactivated channel inhibition can be assessed. Protocol 1 was run at a frequency of 0.1 Hz until current amplitude is steady (automatically determined by PatchXpress scripts). The effect of test reagent on Nav current amplitude was monitored using custom PatchXpress stability scripts which determines the timing of compound addition and washout.

Data were processed and analyzed using DataXpress 2.0 (Molecular Devices). Percent inhibition is calculated using Microsoft Excel such that compound block is normalized to the average of control and washout currents according to the formula, % Inhibition=(((Ctrl+Wash)/2)−Drug)/((Ctrl+Wash)/2)*100. Normalized concentration-response relationships were fit using XLfit software (IDBS) 4 Parameter Logistic Model or Sigmoidal Dose-Response Model.

$hNa_V1.8$ Automated Patch Clamp-IonFlux$^{HT}$ Assay

The IonFlux HT automated whole-cell patch-clamp instrument (Fluxion Biosciences, Inc., Almeda, CA USA) was used to record the inward sodium currents.

Cells: HEK-293 cells were stably transfected with human $Na_V1.8$ cDNA (type X voltage-gated sodium channel alpha subunit, accession #NM_006514) and the human beta subunit 1 (accession #NM_001037). The cells were harvested with trypsin and maintained in serum free medium at room temperature before recording. The cells were washed and re-suspended in the Extracellular Solution before being applied to the instrument.

Test concentrations: Stock solution was prepared in DMSO at 300× the final assay concentrations, and stored at −80 °C until the day of assay. On the day of the assay, an aliquot of the stock solution was thawed and diluted into external solution to make final test concentrations. A final concentration of 0.330% DMSO was maintained for each concentration of the assay compounds and controls.

Recording conditions: Intracellular Solution (mM): 100 CsF, 45 CsCl, 5 NaCl, 10 HEPES, 5 EGTA (pH 7.3, titrated with 1M CsOH).

Extracellular Solution (mM): 150 NaCl, 4 BaCl, 1 $MgCl_2$, 1.8 $CaCl_2$, 10 HEPES, 5 Glucose, (pH 7.4, titrated with 10M NaOH).

When sodium channels are held at a depolarized membrane potential, the channels open and inactivate and remain inactivated until the membrane potential is stepped back to a hyperpolarized membrane potential, when the inactivated channels recover into the closed state. Compounds that show more inhibition at pulse 2 compared to pulse 1 are state-dependent inhibitors. An example is Tetracaine, which is a much more potent inhibitor in the inactivated state than in the tonic or open state.

Cells were held at −120 mV for 50 ms before stepping to −10 mV for 2 s to completely inactivate the sodium channels (pulse 1), and stepped back to −120 mV for 10 ms (to completely recover from inactivation, however, channels that have inhibitors bound to them may not recover from inactivation) before stepping to −10 mV for 50 ms (pulse 2). The sweep interval is 20 s (0.05 Hz). Each concentration of compound was applied for two minutes. The assay was performed at room temperature.

Reference compounds: Tetracaine was used as the positive control and was tested concurrently with the test compound.

Data analysis: Only current amplitudes in excess of 3 nA at the control stage were analyzed. The amplitude of the sodium current was calculated by measuring the difference between the peak inward current on stepping to −10 mV (i.e., peak of the current) and remaining current at the end of the step. The sodium current was assessed in vehicle control conditions and then at the end of each two (2) minute compound application. Individual cell trap results were normalized to the vehicle control amplitude and the mean±SEM calculated for each compound concentration. These values were then plotted and estimated $IC_{50}$ curve fits calculated.

Activity of Representative $Na_V1.8$ Inhibitors

The ability of representative pyridazine carboxamide derivatives exemplified above to inhibit the Nav1.8 channel was determined using one or more of the methods described immediately hereinabove.

| Example | Name | Activity |
|---|---|---|
| 1 | 3-(4-fluoro-2-methoxy-phenoxy)-N-[3-(methylsulfonimidoyl)phenyl]-6-(trifluoromethyl)pyridazine-4-carboxamide | +++ |
| 2 | 3-(4-fluoro-2-methyl-phenoxy)-N-[3-(methylsulfonimidoyl)phenyl]-6-(trifluoromethyl)pyridazine-4-carboxamide | +++ |

-continued

| Example | Name | Activity |
|---|---|---|
| 3 | 6-chloro-N-(3-methylsulfonylphenyl)-3-[4-(trifluoromethoxy)phenoxy]pyridazine-4-carboxamide | +++ |

+ $IC_{50}$ >1 μM
++ $IC_{50}$ 500 nM-1 μM
+++ $IC_{50}$ <500 nM

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

*Pain Medicine: An Essential Review*, Young, R J, Nguyen, M, Nelson, E, Urman, Eds. Springer, Cham, Switzerland. 2017, ISBN 978-3-319-43131-4.

Yekkirala, A. S.; Roberson, D. P.; Bean, B. P.; Woolf, C. J., Breaking barriers to novel analgesic drug development. *Nat Rev Drug Discov* 2017, 16 (8), 544-563.

Skolnick, P., The Opioid Epidemic: Crisis and Solutions. *Annual Review of Pharmacology and Toxicology, Vol* 58 2018, 58, 143-159.

Catterall, W. A., Voltage-gated sodium channels at 60: structure, function and pathophysiology. *J Physiol-London* 2012, 590 (11), 2577-2589.

Ruiz, M. D.; Kraus, R. L., Voltage-Gated Sodium Channels: Structure, Function, Pharmacology, and Clinical Indications. *J Med Chem* 2015, 58 (18), 7093-7118.

Yu, F. H.; Catterall, W. A., Overview of the voltage-gated sodium channel family. *Genome Biol* 2003, 4 (3).

Eijkelkamp, N.; Linley, J. E.; Baker, M. D.; Minett, M. S.; Cregg, R.; Werdehausen, R.; Rugiero, F.; Wood, J. N., Neurological perspectives on voltage-gated sodium channels. Brain 2012, 135, 2585-2612.

Bagal, S. K.; Chapman, M. L.; Marron, B. E.; Prime, R.; Storer, R. I.; Swain, N. A., Recent progress in sodium channel modulators for pain. *Bioorganic & medicinal chemistry letters* 2014, 24 (16), 3690-3699.

Jukic, M.; Kikelj, D.; Anderluh, M., Isoform Selective Voltage-Gated Sodium Channel Modulators and the Therapy of Pain. *Curr Med Chem* 2014, 21 (2), 164-186.

Deuis, J. R.; Mueller, A.; Israel, M. R.; Vetter, I., The pharmacology of voltage-gated sodium channel activators. *Neuropharmacology* 2017, 127, 87-108.

Vetter, I.; Deuis, J. R.; Mueller, A.; Israel, M. R.; Starobova, H.; Zhang, A.; Rash, L. D.; Mobli, M., Na(V)1.7 as a pain target—From gene to pharmacology. *Pharmacology & Therapeutics* 2017, 172, 73-100.

Bennett, D. L. H.; Woods, C. G., Painful and painless channelopathies. *Lancet Neurol* 2014, 13 (6), 587-599.

McCormack, K.; Santos, S.; Chapman, M. L.; Krafte, D. S.; Marron, B. E.; West, C. W.; Krambis, M. J.; Antonio, B. M.; Zellmer, S. G.; Printzenhoff, D.; Padilla, K. M.; Lin, Z. X.; Wagoner, P. K.; Swain, N. A.; Stupple, P. A.; de Groot, M.; Butt, R. P.; Castle, N. A., Voltage sensor interaction site for selective small molecule inhibitors of voltage-gated sodium channels. *P Natl Acad Sci USA* 2013, 110 (29), E2724-E2732.

Donnell, A.; Collins, S.; Ali, Z.; Iavarone, L.; Surujbally, R.; Kirby, S.; Butt, R. P., Efficacy of the $Na_V$1.7 Blocker Pf-05089771 in A Randomised, Placebo-Controlled, Double-Blind Clinical Study in Subjects with Painful Diabetic Peripheral Neuropathy. *Pain* 2018.

Zakrzewska, J. M.; Palmer, J.; Morisset, V.; Giblin, G. M. P.; Obermann, M.; Ettlin, D. A.; Cruccu, G.; Bendtsen, L.; Estacion, M.; Derjean, D.; Waxman, S. G.; Layton, G.; Gunn, K.; Tate, S., Safety and efficacy of a $Na_V$1.7 selective sodium channel blocker in patients with trigeminal neuralgia: a double-blind, placebo-controlled, randomised withdrawal phase 2a trial. *The Lancet Neurology* 2017, 16(4), 291-300.

Han, C. Y.; Huang, J. Y.; Waxman, S. G., Sodium channel Na(v)1.8 Emerging links to human disease. *Neurology* 2016, 86 (5), 473-483.

Akopian, A. N.; Sivilotti, L.; Wood, J. N., A tetrodotoxin-resistant voltage-gated sodium channel expressed by sensory neurons. *Nature* 1996, 379 (6562), 257.

Shields, S. D.; Ahn, H.-S.; Yang, Y.; Han, C.; Seal, R. P.; Wood, J. N.; Waxman, S. G.; Dib-Hajj, S. D., $Na_V$1.8 expression is not restricted to nociceptors in mouse peripheral nervous system. PAIN® 2012, 153 (10), 2017-2030.

Akopian, A. N.; Souslova, V.; England, S.; Okuse, K.; Ogata, N.; Ure, J.; Smith, A.; Kerr, B. J.; McMahon, S. B.; Boyce, S.; Hill, R.; Stanfa, L. C.; Dickenson, A. H.; Wood, J. N., The tetrodotoxin-resistant sodium channel SNS has a specialized function in pain pathways. *Nat Neurosci* 1999, 2, 541.

Dong, X.-W.; Goregoaker, S.; Engler, H.; Zhou, X.; Mark, L.; Crona, J.; Terry, R.; Hunter, J.; Priestley, T., Small interfering RNA-mediated selective knockdown of NaV1.8 tetrodotoxin-resistant sodium channel reverses mechanical allodynia in neuropathic rats. *Neuroscience* 2007, 146(2), 812-821.

Faber, C. G.; Lauria, G.; Merkies, I. S. J.; Cheng, X.; Han, C.; Ahn, H.-S.; Persson, A.-K.; Hoeijmakers, J. G. J.; Gerrits, M. M.; Pierro, T.; Lombardi, R.; Kapetis, D.; Dib-Hajj, S. D.; Waxman, S. G., Gain-of-function Na<sub>v</sub>1.8 mutations in painful neuropathy. *Proceedings of the National Academy of Sciences* 2012, 109 (47), 19444-19449.

Lu, V. B.; Ikeda, S. R.; Puhl, H. L., A 3.7 kb Fragment of the Mouse Scn10a Gene Promoter Directs Neural Crest But Not Placodal Lineage EGFP Expression in a Transgenic Animal. *J Neurosci* 2015, 35 (20), 8021-8034.

Black, J. A.; Dib-Hajj, S.; Baker, D.; Newcombe, J.; Cuzner, M. L.; Waxman, S. G., Sensory neuron-specific sodium channel SNS is abnormally expressed in the brains of mice with experimental allergic encephalomyelitis and humans with multiple sclerosis. *P Natl Acad Sci USA* 2000, 97 (21), 11598-11602.

Damarjian, T. G.; Craner, M. J.; Black, J. A.; Waxman, S. G., Upregulation and colocalization of p75 and Na(v)1.8 in Purkinje neurons in experimental autoimmune encephalomyelitis. *Neurosci Lett* 2004, 369 (3), 186-190.

Shields, S. D.; Cheng, X. Y.; Gasser, A.; Saab, C. Y.; Tyrrell, L.; Eastman, E. M.; Iwata, M.; Zwinger, P. J.; Black, J. A.; Dib-Hajj, S. D.; Waxman, S. G., A channelopathy contributes to cerebellar dysfunction in a model of multiple sclerosis. *Ann Neurol* 2012, 71(2), 186-194.

Shields, S. D.; Butt, R. P.; Dib-Hajj, S. D.; Waxman, S. G., Oral Administration of PF-01247324, a Subtype-Selective $Na_V$1.8 Blocker, Reverses Cerebellar Deficits in a Mouse Model of Multiple Sclerosis. *Plos One* 2015, 10 (3).

Sweatt, J. D., Pitt-Hopkins Syndrome: intellectual disability due to loss of TCF4-regulated gene transcription. *Exp Mol Med* 2013, 45.

Rannals, M. D.; Hamersky, G. R.; Page, S. C.; Campbell, M. N.; Briley, A.; Gallo, R. A.; Phan, B. N.; Hyde, T. M.; Kleinman, J. E.; Shin, J. H.; Jaffe, A. E.; Weinberger, D. R.; Maher, B. J., Psychiatric Risk Gene Transcription Factor 4 Regulates Intrinsic Excitability of Prefrontal Neurons via Repression of SCN10a and KCNQ1. *Neuron* 2016, 90 (1), 43-55.

Bucknill, A. T.; Coward, K.; Plumpton, C.; Tate, S.; Bountra, C.; Birch, R.; Sandison, A.; Hughes, S. P.; Anand, P., Nerve fibers in lumbar spine structures and injured spinal roots express the sensory neuron-specific sodium channels SNS/PN3 and NaN/SNS2. *Spine* 2002, 27(2), 135-140.

Renton, T.; Yiangou, Y.; Plumpton, C.; Tate, S.; Bountra, C.; Anand, P., Sodium channel Na v 1.8 immunoreactivity in painful human dental pulp. *BMC oral health* 2005, 5 (1), 5.

Shembalkar, P. K.; Till, S.; Boettger, M. K.; Terenghi, G.; Tate, S.; Bountra, C.; Anand, P., Increased sodium channel SNS/PN3 immunoreactivity in a causalgic finger. *Eur J Pain* 2001, 5 (3), 319-323.

Beyak, M.; Vanner, S., Inflammation-induced hyperexcitability of nociceptive gastrointestinal DRG neurones: the role of voltage-gated ion channels. *Neurogastroenterology & Motility* 2005, 17 (2), 175-186.

Cestele, S.; Catterall, W. A., Molecular mechanisms of neurotoxin action on voltage-gated sodium channels. *Biochimie* 2000, 82 (9-10), 883-892.

Bagal, S. K.; Bungay, P. J.; Denton, S. M.; Gibson, K. R.; Glossop, M. S.; Hay, T. L.; Kemp, M. I.; Lane, C. A. L.; Lewis, M. L.; Maw, G. N.; Million, W. A.; Payne, C. E.; Poinsard, C.; Rawson, D. J.; Stammen, B. L.; Stevens, E. B.; Thompson, L. R., Discovery and Optimization of Selective Na(v)1.8 Modulator Series That Demonstrate Efficacy in Preclinical Models of Pain. *Acs Med Chem Lett* 2015, 6 (6), 650-654.

Kort, M. E.; Drizin, I.; Gregg, R. J.; Scanio, M. J. C.; Shi, L.; Gross, M. F.; Atkinson, R. N.; Johnson, M. S.; Pacofsky, G. J.; Thomas, J. B.; Carroll, W. A.; Krambis, M. J.; Liu, D.; Shieh, C. C.; Zhang, X. F.; Hernandez, G.; Mikusa, J. P.; Zhong, C. M.; Joshi, S.; Honore, P.; Roeloffs, R.; Marsh, K. C.; Murray, B. P.; Liu, J. R.; Werness, S.; Faltynek, C. R.; Krafte, D. S.; Jarvis, M. F.; Chapman, M. L.; Marron, B. E., Discovery and biological evaluation of 5-aryl-2-furfuramides, potent and selective blockers of the Na(v)1.8 sodium channel with efficacy in models of neuropathic and inflammatory pain. *J Med Chem* 2008, 51 (3), 407-416.

Zhang, X. F.; Shieh, C. C.; Chapman, M. L.; Matulenko, M. A.; Hakeem, A. H.; Atkinson, R. N.; Kort, M. E.; Marron, B. E.; Joshi, S.; Honore, P.; Faltynek, C. R.; Krafte, D. S.; Jarvis, M. F., A-887826 is a structurally novel, potent and voltage-dependent Na(v)1.8 sodium channel blocker that attenuates neuropathic tactile allodynia in rats. Neuropharmacology 2010, 59 (3), 201-207.

Jarvis, M. F.; Honore, P.; Shieh, C. C.; Chapman, M.; Joshi, S.; Zhang, X. F.; Kort, M.; Carroll, W.; Marron, B.; Atkinson, R.; Thomas, J.; Liu, D.; Krambis, M.; Liu, Y.; McGaraughty, S.; Chu, K.; Roeloffs, R.; Zhong, C. M.; Mikusa, J. P.; Hernandez, G.; Gauvin, D.; Wade, C.; Zhu, C.; Pai, M.; Scanio, M.; Shi, L.; Drizin, I.; Gregg, R.; Matulenko, M.; Hakeem, A.; Grosst, M.; Johnson, M.; Marsh, K.; Wagoner, P. K.; Sullivan, J. P.; Faltynek, C. R.; Krafte, D. S., A-803467, a potent and selective Na(v)1.8 sodium channel blocker, attenuates neuropathic and inflammatory pain in the rat. *P Natl Acad Sci USA* 2007, 104 (20), 8520-8525.

Payne, C. E.; Brown, A. R.; Theile, J. W.; Loucif, A. J. C.; Alexandrou, A. J.; Fuller, M. D.; Mahoney, J. H.; Antonio, B. M.; Gerlach, A. C.; Printzenhoff, D. M.; Prime, R. L.; Stockbridge, G.; Kirkup, A. J.; Bannon, A. W.; England, S.; Chapman, M. L.; Bagal, S.; Roeloffs, R.; Anand, U.; Anand, P.; Bungay, P. J.; Kemp, M.; Butt, R. P.; Stevens, E. B., A novel selective and orally bioavailable Na(v)1.8 channel blocker, PF-01247324, attenuates nociception and sensory neuron excitability. *Brit J Pharmacol* 2015, 172 (10), 2654-2670.

U.S. Pat. No. 10,005,768 to Yao et al., for Carboxamide Derivatives and Use Thereof, issued Jun. 26, 2018;

U.S. Pat. No. 10,005,724 to Andrez et al., for Therapeutic Compounds and Methods of Use Thereof, issued Jun. 26, 2018;

U.S. Pat. No. 10,000,475 to Tadesse et al., for Triazine Carboxamides as Sodium Channel Blockers, issued Jun. 19, 2018;

U.S. Pat. No. 9,969,693 to Bogdan et al., for 6-heteroaryloxy- or 6-aryloxy-quinoline-2-Carboxamides and Method of Use, issued May 15, 2018;

U.S. Pat. No. 9,828,397 to Anderson et al., for Prodrugs of Pyridone Amides Useful as Modulators of Sodium Channels, issued Nov. 28, 2017;

U.S. Pat. No. 9,783,501 to Hadida-Ruah et al., for Substituted Quinolines as Modulators of Sodium Channels, issued Oct. 10, 2017;

U.S. Pat. No. 8,536,195 to Termin et al., for Bicylic Derivatives as Modulators of Voltage Gated Ion Channels, issued Sep. 17, 2013;

U.S. Pat. No. 8,492,403 to Kawatkar et al., for Bicylic Derivatives as Modulators of Voltage Gated Ion Channels, issued Jul. 23, 2013;

U.S. Pat. No. 8,314,125 to Termin et al., for Bicyclic Derivatives as Modulators of Ion Channels, issued Nov. 20, 2012;

U.S. Pat. No. 8,309,543 to Gonzalez et al., for Compositions Useful as Inhibitors of Voltage-Gated Sodium Channels, issued Nov. 13, 2012;

U.S. Pat. No. 8,236,833 to Martinborough et al., for Biphenyl Derivatives as Modulators of Voltage Gated Ion Channels, issued Aug. 7, 2012;

U.S. Pat. No. 8,236,829 to Neubert et al., for Bicyclic Derivatives as Modulators of Voltage Gated ION Channels, issued Aug. 7, 2012;

U.S. Pat. No. 7,989,481 to Neubert et al., for Indane Derivatives as Modulators of Sodium Channels, issued Aug. 2, 2011;

U.S. Pat. No. 7,705,031 to Wilson et al., for Benzimidazoles Useful as Modulators of Ion Channels, issued Apr. 28, 2010.

VI. INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

VII. EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification, and guidance that can be adapted to the practice of this invention in its various embodiments and equivalents thereof.

What is claimed is:

1. A compound of Formula (II):

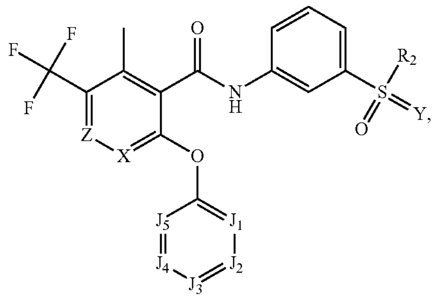

(II)

wherein:

each of $J_1$, $J_2$, $J_4$, and $J_5$ is independently N, N—O, or $CR_6$;

$J_3$ is N, N—O, or $CR_7$;

X is CH or N;

Y is $NR_8$ or O;

Z is CH, N, or N—O, $R_2$ is alkyl, haloalkyl, alkoxy, or haloalkoxy;

each instance of $R_6$ is independently H, halogen, $C_{1-3}$ alkyl, $C_{3-5}$ cycloalkyl, $C_{1-3}$ alkoxy, $CD_3$ or $CT_3$; and $R_7$ is H, halogen, -$CD_3$, alkyl, haloalkyl, alkoxy, haloalkoxy, alkyl sulphonyl, alkyl sulfoximinyl, alkyl sulfonamide, cyano, —$CF_3$, —$OCF_3$, heterocyclyl in which each ring has 5 or 6 members, heteroaryl having 5 or 6 ring members, saturated heterocyclyl, or partially unsaturated heterocyclyl, O-aryl in which each ring has 5 or 6 members, O-heteroaryl in which each ring has 5 or 6 members, O-cycloalkyl, O-cycloheteroalkyl, each of which is optionally substituted where valency permits, $R_8$ is H, $C_{1-3}$ alkyl, or $C_{3-5}$ cycloalkyl, acyl, with the provisos that:

X and Z cannot both be CH; and not more than two of $J_1$, $J_2$, $J_3$, $J_4$, and $J_5$ are N or N—O, or a pharmaceutically acceptable salt thereof.

2. The compound of claim 1, wherein Y is $NR_8$.

3. The compound of claim 1, wherein Y is O.

4. The compound of claim 1, wherein $R_2$ is alkyl.

5. The compound of claim 4, wherein $R_2$ is —$CH_3$.

6. The compound of claim 1, wherein none of $J_1$, $J_2$, $J_3$, $J_4$, and $J_5$ are N or N—O.

7. The compound of claim 1, wherein one of $J_1$, $J_2$, $J_3$, $J_4$, and $J_5$ is N or N—O.

8. The compound of claim 1, wherein two of $J_1$, $J_2$, $J_3$, $J_4$, and $J_5$ are N or N—O.

9. The compound of claim 1, wherein Z is CH.

10. The compound of claim 1, wherein Z is N.

11. A compound of claim 1, wherein the compound is selected from the group consisting of:

3-(4-Fluoro-2-methylphenoxy)-5-methyl-N-(3-(methylsulfonyl)phenyl)-6-(trifluoromethyl)pyridazine-4-carboxamide (Example 7);

5-Methyl-N-(3-methylsulfonylphenyl)-3-[2-methyl-4-(trifluoromethyl)phenoxy]-6-(trifluoromethyl) pyridazine-4-carboxamide (Example 8);

5-Methyl-3-(2-methyl-4-(trifluoromethoxy)phenoxy)-N-(3-(methylsulfonyl)phenyl)-6-(trifluoromethyl) pyridazine-4-carboxamide (Example 9);

3-(4-Cyano-2-methoxyphenoxy)-5-methyl-N-(3-(methylsulfonyl)phenyl)-6-(trifluoromethyl)pyridazine-4-carboxamide (Example 10; compound 4);

3-(4-Chloro-2-methoxyphenoxy)-5-methyl-N-(3-(methylsulfonyl)phenyl)-6-(trifluoromethyl)pyridazine-4-carboxamide (Example 10; compound 5);

3-(4-Chloro-2-fluorophenoxy)-5-methyl-N-(3-(methylsulfonyl)phenyl)-6-(trifluoromethyl)pyridazine-4-carboxamide (Example 10; compound 6);

3-(2-Chloro-6-methylphenoxy)-5-methyl-N-(3-(methylsulfonyl)phenyl)-6-(trifluoromethyl)pyridazine-4-carboxamide (Example 10; compound 7);

3-(4-Fluoro-2-methylphenoxy)-5-methyl-N-(3-(S-methylsulfonimidoyl)phenyl)-6-(trifluoromethyl) pyridazine-4-carboxamide (Example 13; compound 20);

3-(4-Cyanophenoxy)-5-methyl-N-[3-(methylsulfonimidoyl)phenyl]-6-(trifluoromethyl)pyridazine-4-carboxamide (Example 13; compound 21);

3-(4-Chlorophenoxy)-5-methyl-N-[3-(methylsulfonimidoyl)phenyl]-6-(trifluoromethyl)pyridazine-4-carboxamide (Example 13; compound 22);

3-(3,4-Difluoro-2-methoxy-phenoxy)-5-methyl-N-[3-(methylsulfonimidoyl)phenyl]-6-(trifluoromethyl) pyridazine-4-carboxamide (Example 13; compound 23);

3-(4-Cyano-2-methylphenoxy)-5-methyl-N-(3-(S-methylsulfonimidoyl)phenyl)-6-(trifluoromethyl) pyridazine-4-carboxamide (Example 13; compound 24);

3-(4-Cyano-2-methoxyphenoxy)-5-methyl-N-(3-(S-methylsulfonimidoyl)phenyl)-6-(trifluoromethyl) pyridazine-4-carboxamide (Example 13; compound 25);

3-(4-Chloro-2-methoxyphenoxy)-5-methyl-N-(3-(S-methylsulfonimidoyl)phenyl)-6-(trifluoromethyl) pyridazine-4-carboxamide (Example 13; compound 26);

3-(4-Chloro-2-fluorophenoxy)-5-methyl-N-(3-(S-methylsulfonimidoyl)phenyl)-6-(trifluoromethyl)pyridazine-4-carboxamide (Example 13; compound 27);

3-(4-Bromo-2-methylphenoxy)-5-methyl-N-(3-(S-methylsulfonimidoyl)phenyl)-6-(trifluoromethyl) pyridazine-4-carboxamide (Example 13; compound 28);

3-(2-Chloro-6-methylphenoxy)-5-methyl-N-(3-(S-methylsulfonimidoyl)phenyl)-6-(trifluoromethyl) pyridazine-4-carboxamide (Example 13; compound 29);

3-(4-Fluoro-2-methylphenoxy)-5-methyl-N-(3-(S-methylsulfonimidoyl)phenyl)-6-(trifluoromethyl) pyridazine-4-carboxamide (Example 14, compound 30);

3-(4-Fluoro-2-methylphenoxy)-5-methyl-N-(3-(R-methylsulfonimidoyl)phenyl)-6-(trifluoromethyl)pyridazine-4-carboxamide (Example 14, compound 31);

(S)-3-(4-fluoro-2-methylphenoxy)-5-methyl-N-(3-(S-methylsulfonimidoyl)phenyl)-6-(trifluoromethyl)pyridazine-4-carboxamide (Example 15);

(R)-3-(4-fluoro-2-methylphenoxy)-5-methyl-N-(3-(S-methylsulfonimidoyl)phenyl)-6-(trifluoromethyl)pyridazine-4-carboxamide (Example 15);

(S)-5-Methyl-3-(2-methyl-4-(trifluoromethyl)phenoxy)-N-(3-(S-methylsulfonimidoyl)phenyl)-6-(trifluoromethyl)pyridazine-4-carboxamide (Example 16);

(R)-5-Methyl-3-(2-methyl-4-(trifluoromethyl)phenoxy)-N-(3-(S-methylsulfonimidoyl)phenyl)-6-(trifluoromethyl)pyridazine-4-carboxamide (Example 16);

3-[2,3-difluoro-4-(trifluoromethoxy)phenoxy]-5-methyl-N-(3-methylsulfonylphenyl)-6-(trifluoromethyl)pyridazine-4-carboxamide (Example 17; compound 1419);

3-((2,6-dimethylpyridin-3-yl)oxy)-5-methyl-N-(3-(methylsulfonyl)phenyl)-6-(trifluoromethyl)pyridazine-4-carboxamide (Example 17; compound 1420);

3-(4-chloro-3-fluoro-2-methyl-phenoxy)-5-methyl-N-(3-methylsulfonylphenyl)-6-(trifluoromethyl)pyridazine-4-carboxamide (Example 17; compound 1421);

3-[4-(difluoromethoxy)-2,3-difluoro-phenoxy]-5-methyl-N-(3-methylsulfonylphenyl)-6-(trifluoromethyl)pyridazine-4-carboxamide (Example 17; compound 1422);

3-(2,6-difluoro-4-(trifluoromethoxy)phenoxy)-5-methyl-N-(3-(methylsulfonyl)phenyl)-6-(trifluoromethyl)pyridazine-4-carboxamide (Example 17; compound 1423);

3-(2,3-difluoro-4-isopropoxyphenoxy)-5-methyl-N-(3-(methylsulfonyl)phenyl)-6-(trifluoromethyl)pyridazine-4-carboxamide (Example 17; compound 1424);

3-(3,4-difluoro-2-methoxybenzyl)-5-methyl-N-(3-(methylsulfonyl)phenyl)-6-(trifluoromethyl)pyridazine-4-carboxamide (Example 17, compound 1425);

3-(4-cyclobutoxy-2,3-difluorophenoxy)-5-methyl-N-(3-(methylsulfonyl)phenyl)-6-(trifluoromethyl)pyridazine-4-carboxamide (Example 17, compound 1426);

3-(3-fluoro-4-methoxy-2-methyl-phenoxy)-5-methyl-N-(3-methylsulfonylphenyl)-6-(trifluoromethyl)pyridazine-4-carboxamide (Example 17; compound 1427);

3-[(6-methoxy-2-methyl-3-pyridyl)oxy]-5-methyl-N-(3-methylsulfonylphenyl)-6-(trifluoromethyl)pyridazine-4-carboxamide (Example 17; compound 1428);

ethyl 3-(3-(4-fluoro-2-methylphenoxy)-5-methyl-6-(trifluoromethyl)pyridazine-4-carboxamido)-5-(methylsulfonyl)benzoate (Example 17; compound 1429);

3-(4-cyano-2-methylphenoxy)-N-(3-methanesulfonylphenyl)-5-methyl-6-(trifluoromethyl)pyridazine-4-carboxamide (Example 30; compound 1465);

3-[2-fluoro-4-(trifluoromethoxy)phenoxy]-N-(3-methanesulfonylphenyl)-5-methyl-6-(trifluoromethyl)pyridazine-4-carboxamide (Example 32; compound 1467);

N-(3-methanesulfonylphenyl)-5-methyl-3-{[2-methyl-6-(trifluoromethyl)pyridin-3-yl]oxy}-6-(trifluoromethyl)pyridazine-4-carboxamide (Example 33; compound 1468);

3-[(6-bromo-2-methylpyridin-3-yl)oxy]-N-(3-methanesulfonylphenyl)-5-methyl-6-(trifluoromethyl)pyridazine-4-carboxamide (Example 34; compound 1469);

(S)-3-(4-chloro-2-fluorophenoxy)-5-methyl-N-(3-(S-methylsulfonimidoyl)phenyl)-6-(trifluoromethyl)pyridazine-4-carboxamide (Example 36);

(R)-3-(4-fluoro-2-methylphenoxy)-5-methyl-N-(3-(S-methylsulfonimidoyl)phenyl)-6-(trifluoromethyl)pyridazine-4-carboxamide (Example 36);

(S)-3-(3,4-difluoro-2-methoxyphenoxy)-5-methyl-N-(3-(S-methylsulfonimidoyl)phenyl)-6-(trifluoromethyl)pyridazine-4-carboxamide (Example 37);

(R)-3-(3,4-difluoro-2-methoxyphenoxy)-5-methyl-N-(3-(S-methylsulfonimidoyl)phenyl)-6-(trifluoromethyl)pyridazine-4-carboxamide (Example 37);

(S)-3-[2,3-difluoro-4-(trifluoromethoxy)phenoxy]-5-methyl-N-[3-(methylsulfonimidoyl)phenyl]-6-(trifluoromethyl)pyridazine-4-carboxamide (Example 39);

(R)-3-[2,3-difluoro-4-(trifluoromethoxy)phenoxy]-5-methyl-N-[3-(methylsulfonimidoyl)phenyl]-6-(trifluoromethyl)pyridazine-4-carboxamide (Example 39);

(S)-3-(4-cyano-2-methoxyphenoxy)-5-methyl-N-(3-(S-methylsulfonimidoyl)phenyl)-6-(trifluoromethyl)pyridazine-4-carboxamide (Example 40; compound 1479);

(R)-3-(4-cyano-2-methoxyphenoxy)-5-methyl-N-(3-(S-methylsulfonimidoyl)phenyl)-6-(trifluoromethyl)pyridazine-4-carboxamide (Example 40; compound 1480);

(S)-3-(4-chloro-2-methoxyphenoxy)-5-methyl-N-(3-(S-methylsulfonimidoyl)phenyl)-6-(trifluoromethyl)pyridazine-4-carboxamide (Example 41);

(R)-3-(4-chloro-2-methoxyphenoxy)-5-methyl-N-(3-(S-methylsulfonimidoyl)phenyl)-6-(trifluoromethyl)pyridazine-4-carboxamide (Example 41);

3-[(2,6-dimethylpyridin-3-yl)oxy]-N-{3-[imino(methyl)oxo-$\lambda^6$-sulfanyl]phenyl}-5-methyl-6-(trifluoromethyl)pyridazine-4-carboxamide (Example 42; compound 1483);

(S)-3-[(2,6-dimethylpyridin-3-yl)oxy]-N-{3-[imino(methyl)oxo-$\lambda^6$-sulfanyl]phenyl}-5-methyl-6-(trifluoromethyl)pyridazine-4-carboxamide (Example 43);

(R)-3-[(2,6-dimethylpyridin-3-yl)oxy]-N-{3-[imino(methyl)oxo-$\lambda^6$-sulfanyl]phenyl}-5-methyl-6-(trifluoromethyl)pyridazine-4-carboxamide (Example 43);

3-(4-chloro-3-fluoro-2-methyl-phenoxy)-5-methyl-N-[3-(methylsulfonimidoyl)phenyl]-6-(trifluoromethyl)pyridazine-4-carboxamide (Example 44; compound 1486);

(S)-3-(4-chloro-3-fluoro-2-methyl-phenoxy)-5-methyl-N-[3-(methylsulfonimidoyl)phenyl]-6-(trifluoromethyl)pyridazine-4-carboxamide (Example 45);

(R)-3-(4-chloro-3-fluoro-2-methyl-phenoxy)-5-methyl-N-[3-(methylsulfonimidoyl)phenyl]-6-(trifluoromethyl)pyridazine-4-carboxamide (Example 45);

(S)-3-(4-chloro-3-fluoro-2-methoxy-phenoxy)-5-methyl-N-[3-(methylsulfonimidoyl)phenyl]-6-(trifluoromethyl)pyridazine-4-carboxamide (Example 47);

(R)-3-(4-chloro-3-fluoro-2-methoxy-phenoxy)-5-methyl-N-[3-(methylsulfonimidoyl)phenyl]-6-(trifluoromethyl)pyridazine-4-carboxamide (Example 47);

3-(4-cyclobutoxy-2,3-difluorophenoxy)-N-{3-[imino(methyl)oxo-$\lambda^6$-sulfanyl]phenyl}-5-methyl-6-(trifluoromethyl)pyridazine-4-carboxamide (Example 49);

(S)-3-[2-fluoro-4-(trifluoromethoxy)phenoxy]-N-{3-[imino(methyl)oxo-$\lambda^6$-sulfanyl]phenyl}-5-methyl-6-(trifluoromethyl)pyridazine-4-carboxamide (Example 51);

(R)-3-[2-fluoro-4-(trifluoromethoxy)phenoxy]-N-{3-[imino(methyl)oxo-$\lambda^6$-sulfanyl]phenyl}-5-methyl-6-(trifluoromethyl)pyridazine-4-carboxamide (Example 51);

3-((6-cyclobutoxy-2-methylpyridin-3-yl)oxy)-5-methyl-N-(3-(S-methylsulfonimidoyl)phenyl)-6-(trifluoromethyl)pyridazine-4-carboxamide (Example 53);

(S)-3-(2,3-difluoro-4-isopropoxyphenoxy)-5-methyl-N-(3-(S-methylsulfonimidoyl)phenyl)-6-(trifluoromethyl)pyridazine-4-carboxamide (Example 55);

(R)-3-(2,3-difluoro-4-isopropoxyphenoxy)-5-methyl-N-(3-(S-methylsulfonimidoyl)phenyl)-6-(trifluoromethyl)pyridazine-4-carboxamide (Example 55);

(S)-3-(3-fluoro-4-methoxy-2-methylphenoxy)-N-{3-[imino(methyl)oxo-λ$^6$-sulfanyl]phenyl}-5-methyl-6-(trifluoromethyl)pyridazine-4-carboxamide (Example 57);

(R)-3-(3-fluoro-4-methoxy-2-methylphenoxy)-N-{3-[imino(methyl)oxo-λ$^6$-sulfanyl]phenyl}-5-methyl-6-(trifluoromethyl)pyridazine-4-carboxamide (Example 57);

(S)—N-{3-[imino(methyl)oxo-λ$^6$-sulfanyl]phenyl}-3-[(6-methoxy-2-methylpyridin-3-yl)oxy]-5-methyl-6-(trifluoromethyl)pyridazine-4-carboxamide (Example 59);

(R)—N-{3-[imino(methyl)oxo-λ$^6$-sulfanyl]phenyl}-3-[(6-methoxy-2-methylpyridin-3-yl)oxy]-5-methyl-6-(trifluoromethyl)pyridazine-4-carboxamide (Example 59)

3-[4-(difluoromethoxy)-2,3-difluoro-phenoxy]-5-methyl-N-(3-methylsulfonylphenyl)-6-(trifluoromethyl) pyridazine-4-carboxamide (Example 60; compound 1510);

(S)-3-[4-(difluoromethoxy)-2,3-difluorophenoxy]-N-{3-[imino(methyl)oxo-λ$^6$-sulfanyl]phenyl}-5-methyl-6-(trifluoromethyl)pyridazine-4-carboxamide (Example 61);

(R)-3-[4-(difluoromethoxy)-2,3-difluorophenoxy]-N-{3-[imino(methyl)oxo-λ$^6$-sulfanyl]phenyl}-5-methyl-6-(trifluoromethyl)pyridazine-4-carboxamide (Example 61);

3-[2,6-difluoro-4-(trifluoromethoxy)phenoxy]-N-{3-[imino(methyl)oxo-λ$^6$-sulfanyl]phenyl}-5-methyl-6-(trifluoromethyl)pyridazine-4-carboxamide (Example 63);

3-[3-fluoro-2-methyl-4-(trifluoromethoxy)phenoxy]-N-{3-[imino(methyl)oxo-λ$^6$-sulfanyl]phenyl}-5-methyl-6-(trifluoromethyl)pyridazine-4-carboxamide (Example 64; compound 1515);

3-(4-cyano-2-methylphenoxy)-N-{3-[(S)-imino(methyl) oxo-λ$^6$-sulfanyl]phenyl}-5-methyl-6-(trifluoromethyl) pyridazine-4-carboxamide (Example 71; compound 1525);

3-(4-cyano-2-methyl-phenoxy)-5-methyl-6-(trifluoromethyl)pyridazine-4-carboxylic and tert-butyl N—[(R)-(3-aminophenyl)(methyl)oxo-λ$^6$-sulfanylidene]carbamate (Example 72; compound 1526);

3-(4-chloro-3-fluoro-2-methoxy-phenoxy)-5-methyl-N-(3-methylsulfonylphenyl)-6-(trifluoromethyl) pyridazine-4-carboxamide (Example 79; compound 1552);

2-(4-fluoro-2-methylphenoxy)-4-methyl-N-(3-(S-methylsulfonimidoyl)phenyl)-5-(trifluoromethyl)nicotinamide (Example 82; compound 1557);

(R)-2-((6-fluoro-2-methylpyridin-3-yl)oxy)-4-methyl-N-(3-(S-methylsulfonimidoyl)phenyl)-5-(trifluoromethyl)nicotinamide (Example 84; compound 1559);

(S)-2-((6-fluoro-2-methylpyridin-3-yl)oxy)-4-methyl-N-(3-(S-methylsulfonimidoyl)phenyl)-5-(trifluoromethyl)nicotinamide (Example 85; compound 1560);

(R)-3-((6-cyano-2-methoxypyridin-3-yl)oxy)-5-methyl-N-(3-(S-methylsulfonimidoyl)phenyl)-6-(trifluoromethyl)pyridazine-4-carboxamide (Example 101; compound 1736); and (R)-3-((6-cyano-2-methylpyridin-3-yl)oxy)-5-methyl-N-(3-(S-methylsulfonimidoyl)phenyl)-6-(trifluoromethyl)pyridazine-4-carboxamide (Example 101; compound 1737).

12. A compound of claim 1, wherein the compound is selected from the group consisting of:

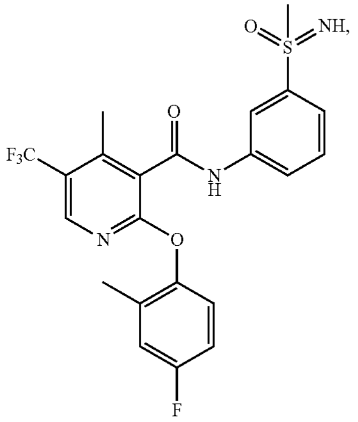

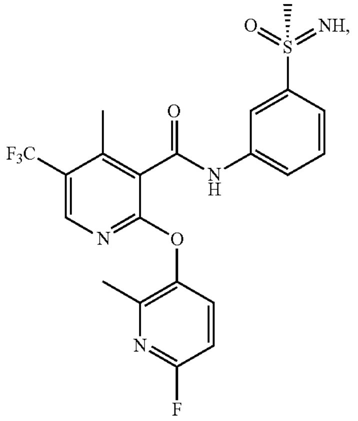

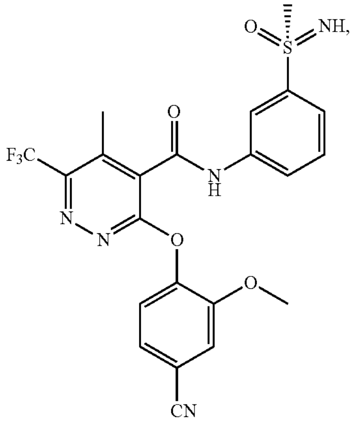

-continued
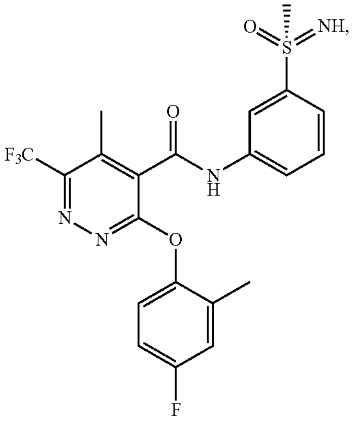
and
-continued
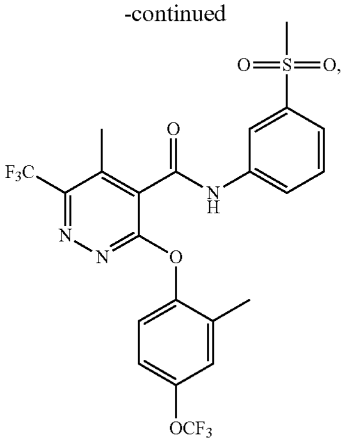
or a pharmaceutically acceptable salt or stereoisomer thereof.
* * * * *